United States Patent
Oalmann et al.

(10) Patent No.: US 11,951,094 B2
(45) Date of Patent: Apr. 9, 2024

(54) TLR2 MODULATOR COMPOUNDS, PHARMACEUTICAL COMPOSITIONS AND USES THEREOF

(71) Applicant: Axial Therapeutics, Inc., Woburn, MA (US)

(72) Inventors: Christopher J. Oalmann, Watertown, MA (US); Dennis S. Yamashita, Cambridge, MA (US); Patrick J. Stern, Needham, MA (US)

(73) Assignee: Axial Therapeutics, Inc., Woburn, MA (US)

( * ) Notice: Subject to any disclaimer, the term of this patent is extended or adjusted under 35 U.S.C. 154(b) by 20 days.

(21) Appl. No.: 17/840,952

(22) Filed: Jun. 15, 2022

(65) Prior Publication Data

US 2023/0051773 A1    Feb. 16, 2023

Related U.S. Application Data

(63) Continuation of application No. PCT/US2021/034346, filed on May 26, 2021.

(60) Provisional application No. 63/030,370, filed on May 27, 2020.

(51) Int. Cl.
  *A61K 31/4025*    (2006.01)
  *A61P 35/00*    (2006.01)
  *A61K 31/40*    (2006.01)

(52) U.S. Cl.
  CPC .......... *A61K 31/4025* (2013.01); *A61K 31/40* (2013.01); *A61P 35/00* (2018.01)

(58) Field of Classification Search
  CPC .. A61K 31/4025; A61K 31/40; C07D 403/10; C07D 207/16; A61P 37/02
  See application file for complete search history.

(56) References Cited

U.S. PATENT DOCUMENTS

| 7,550,487 | B2 | 6/2009 | Anselm et al. |
| 2004/0195550 | A1 | 10/2004 | Debaud et al. |

FOREIGN PATENT DOCUMENTS

| CN | 106892904 A | 6/2017 |
| JP | 2016102079 A | 6/2016 |
| WO | WO 93/14067 A1 | 7/1993 |
| WO | WO 2002/028946 A1 | 4/2002 |
| WO | WO 2005/019236 A1 | 3/2005 |
| WO | WO 2005/019237 A1 | 3/2005 |
| WO | WO 2006/133353 A2 | 12/2006 |
| WO | WO 2009/022171 A1 | 2/2009 |
| WO | WO 2009/025983 A2 | 2/2009 |
| WO | WO 2016/020864 A1 | 2/2016 |
| WO | WO 2017/011279 A1 | 1/2017 |
| WO | WO 2018/005812 A1 | 1/2018 |
| WO | WO-2018005812 A1 * | 1/2018 ............ A61K 31/40 |
| WO | WO 2018/107112 A1 | 6/2018 |
| WO | WO 2018/108086 A1 | 6/2018 |
| WO | WO 2019/126696 A1 | 6/2019 |
| WO | WO 2019/206828 A1 | 10/2019 |
| WO | WO 2020/023872 A1 | 1/2020 |
| WO | WO 2020/028532 A1 | 2/2020 |
| WO | WO-2023091747 A1 * | 5/2023 |

OTHER PUBLICATIONS

So et al. Int. J. Biol. Sci. 2010, 6, 675-681 (Year: 2010).*
Kanzler et al. Nat. Med. 2007, 13, 552-559 (Year: 2007).*
Ghasemi, Cancer's epigenetic drugs: where are they in the cancer medicines? The Pharmacogenomics Journal 2020, 20, 367-379 (published Dec. 10, 2019) (Year: 2019).*
Invitation to Pay Additional Fees dated Aug. 3, 2021, for International Application No. PCT/US2021/034346.
International Search Report and Written Opinion dated Oct. 12, 2021, for Application No. PCT/US2021/034346.
[No Author Listed] PubChem Substance Record; SID 397435447. https://pubchem.ncbi.nlm.nih.gov/substance/397435447#section= External-ID. Last accessed Jul. 19, 2021.
Andrews et al., Concepts Collide: Genomic, Immune, and Microbial Influences on the Tumor Microenvironment and Response to Cancer Therapy. Front Immunol. May 4, 2018;9:946. doi: 10.3389/fimmu. 2018.00946.
Cario et al., Toll-Like Receptor 2 Controls Mucosal Inflammation by Regulating Epithelial Barrier Function. Gastroenterology. 2007;132(4):1359-1374 10.1053/j.gastro.2007.02.056.
Chen et al., Structure-based discovery of a specific TLR1-TLR2 small molecule agonist from the ZINC drug library database. Chem. Comm. 2018 Sep. 2018; 54(81):11411-11414.
de Groot et al., Arteriogenesis requires toll-like receptor 2 and 4 expression in bone-marrow derived cells. J Mol Cell Cardiol. Jan. 2011;50(1):25-32. doi: 10.1016/j.yjmcc.2010.08.006. Epub Aug. 12, 2010.
El-Omar et al., Polymorphisms in Toll-like receptor genes and risk of cancer. Oncogene. Jan. 7, 2008;(27);244-252. doi: 10.1038/sj. onc.1210912.
Gopalakrishnan et al., Gut microbiome modulates response to anti-PD-1 immunotherapy in melanoma patients. Science. Jan. 5, 2018;359(6371):97-103. doi: 10.1126/science.aan4236. Epub Nov. 2, 2017.
Hoebe et al., The interface between innate and adaptive immunity. Nat Immunol. Oct. 2004;5(10):971-4. doi: 10.1038/ni1004-971.
Hua et al., Differential roles of TLR2 and TLR4 in acute focal cerebral ischemia/reperfusion injury in mice. Brain Res. Mar. 25, 2009;1262:100-8. doi: 10.1016/j.brainres.2009.01.018. Epub Jan. 22, 2009.
Huang et al., TLR signaling by tumor and immune cells: a double-edged sword. Oncogene. Jan. 7, 2008;27(2):218-24. doi: 10.1038/ sj.onc.1210904.

(Continued)

*Primary Examiner* — Amanda L. Aguirre
(74) *Attorney, Agent, or Firm* — Wolf, Greenfield & Sacks, P.C.

(57) ABSTRACT

The present disclosure relates to compounds which modulate the activity of Toll-like receptor (TLR) proteins, including agonists or activators, partial agonists, and antagonists. Of particular interest of compounds that modulate the activity of TLR2, as well as methods of using such compounds to treat cancer and other disorders associated with a TLR2 pathway.

18 Claims, 8 Drawing Sheets

(56) References Cited

OTHER PUBLICATIONS

Kanzler et al., Therapeutic targeting of innate immunity with Toll-like receptor agonists and antagonists. Nat Med. May 2007;13(5):552-9. doi: 10.1038/nm1589.
Kawai et al., Toll-like receptors and their crosstalk with other innate receptors in infection and immunity. Immunity. May 27, 2011;34(5):637-50. doi: 10.1016/j.immuni.2011.05.006.
Kutikhin, Association of polymorphisms in TLR genes and in genes of the Toll-like receptor signaling pathway with cancer risk. Hum Immunol. Nov. 2011;72(11):1095-116. doi: 10.1016/j.humimm.2011.07.307. Epub Aug. 3, 2011.
Larue et al., Toll-like receptors in urothelial cells—targets for cancer immunotherapy. Nat Rev Urol. Sep. 2013;10(9):537-45. doi: 10.1038/nrurol.2013.153. Epub Aug. 27, 2013.
Latorre et al., Intestinal Serotonin Transporter Inhibition by Toll-Like Receptor 2 Activation. A Feedback Modulation. PLoS One. Dec. 29, 2016;11(12):e0169303. doi: 10.1371/journal.pone.0169303.
Macleod et al., T cell activation by TLRs: a role for TLRs in the adaptive immune response. Sci STKE. Sep. 4, 2007;2007(402):pe48. doi: 10.1126/stke.4022007pe48.
Mandal et al., Association of Toll-like receptor (TLR) 2, 3 and 9 genes polymorphism with prostate cancer risk in North Indian population. Mol Biol Rep. Jul. 2012;39(7):7263-9. doi: 10.1007/s11033-012-1556-5. Epub Feb. 6, 2012.
Meyer et al., Clinical investigations of Toll-like receptor agonists. Expert Opin Investig Drugs. Jul. 2008;17(7):1051-65. doi: 10.1517/13543784.17.7.1051.
Morin et al., Diprovocims: A New and Exceptionally Potent Class of Toll-like Receptor Agonists. J Am Chem Soc. Oct. 31, 2018;140(43):14440-14454. doi: 10.1021/jacs.8b09223. Epub Oct. 16, 2018.
Muhlradt et al., Isolation, Structure Elucidation, and Synthesis of a Macrophage Stimulatory Lipopeptide from Mycoplasma fermentans Acting at Picomolar Concentration. J. Exp. Med. Jun. 2, 1997;185(11):1951-1958. doi:10.1084/jem.185.11.1951.

Pasare et al., Control of B-cell responses by Toll-like receptors. Nature. Nov. 17, 2005;438(7066):364-8. doi: 10.1038/nature04267.
Richard et al., Toll-like receptor 2 acts as a natural innate immune receptor to clear amyloid beta 1-42 and delay the cognitive decline in a mouse model of Alzheimer's disease. J Neurosci. May 28, 2008;28(22):5784-93. doi: 10.1523/JNEUROSCI.1146-08.2008.
Sato et al., Single Lgr5 stem cells build crypt-villus structures in vitro without a mesenchymal niche. Nature. May 14, 2009;459(7244):262-5. doi: 10.1038/nature07935. Epub Mar. 29, 2009.
So et al., The application of Toll like receptors for cancer therapy. Int J Biol Sci. Nov. 3, 2010;6(7):675-81. doi: 10.7150/ijbs.6.675.
Su et al., Structural Basis of TLR2/TLR1 Activation by the Synthetic Agonist Diprovocim. J. Med. Chem. Mar. 4, 2019;62(6):2938-2949.
Veenstra-Vanderweele et al., Autism gene variant causes hyperserotonemia, serotonin receptor hypersensitivity, social impairment and repetitive behavior. Proc Natl Acad Sci U S A. Apr. 3, 2012;109(14):5469-74. doi: 10.1073/pnas.1112345109. Epub Mar. 19, 2012.
Wang et al., Adjuvant effect of the novel TLR1/TLR2 agonistDiprovocim synergizes with anti-PD-L1 toeliminate melanoma in mice. PNAS. 2018;115(37): E8698-E8706.
Wang et al., Alternative isoform regulation in human tissue transcriptomes. Nature. Nov. 27, 2008;456(7221):470-6. doi: 10.1038/nature07509.
Wang et al., TLR2 Plays a Pivotal Role in Mediating Mucosal Serotonin Production in the Gut. J Immunol. May 15, 2019;202(10):3041-3052. doi: 10.4049/jimmunol.1801034. Epub Apr. 5, 2019.
PCT/US2021/034346, Aug. 3, 2021, Invitation to Pay Additional Fees.
PCT/US2021/034346, Oct. 12, 2021, International Search Report and Written Opinion.
International Preliminary Report on Patentability dated Dec. 8, 2022 for International Application No. PCT/US2021/034346.

* cited by examiner

Scheme 1:

Scheme 2:

Scheme 3:

Scheme 4:

Scheme 5:

Scheme 6:

Scheme 7:

Scheme 8:

Scheme 9:

Scheme 10:

Scheme 11:

Scheme 12:

ORAL DOSING STUDY DESIGN

TLR2 MODULATOR COMPOUNDS, PHARMACEUTICAL COMPOSITIONS AND USES THEREOF

CROSS REFERENCE TO RELATED APPLICATION(S)

The present application is a Continuation application of International Application No. PCT/US21/034346, filed on May 26, 2021, which claims the benefit of U.S. Provisional Application No. 63/030,370, filed May 27, 2020, each of which is herein incorporated by reference in its entirety.

TECHNICAL FIELD

The present disclosure relates to modulators of Toll-like receptor (TLR) proteins, and particularly modulators of TLR2, as well as methods of using such compounds to treat cancer and other disorders associated with a TLR2 pathway. Methods of identifying compounds that modulate the activity of TLR2 are also provided.

BACKGROUND

The innate immune system contains several families of germline-encoded pattern recognition receptors (PRRs), including Toll-like receptors (TLRs), Nod-like receptors (NLRs), RIG-1-like receptors (RLRs), cytosolic DNA sensors (CDSs) and C-type lectins (CLRs) (Newton and Dixit 2012). These receptors recognize microbial components termed pathogen-associated molecular patterns (PAMPs). PAMPs are highly conserved molecular structures on a wide range of pathogens such as bacteria, fungi, parasites and viruses. PAMPs include lipid-based bacterial cell wall components such as lipoproteins and lipopolysaccharides, microbial protein components such as flagellin, and pathogen nucleic acids in the form of double stranded DNA and single or double stranded RNA. In addition, some PRRs also recognize 'self' ligands known as damage-associated molecular patterns (DAMPs) released from damaged or dying cells and tissues. Cells of the innate immune system respond to PAMPs and DAMPs by producing proinflammatory cytokines, chemokines and co-stimulatory molecules that are involved in clearing the pathogens and damaged tissue. Furthermore, innate immune responses essentially shape the downstream adaptive immune responses to generate a more specific and long-lasting immunity (Hoebe et al. 2004; Pasare and Medzhitov 2005). As such, harnessing innate immune signaling pathways is a promising therapeutic strategy to fight infections, immune disorders, as well as in diseases such as cancer.

TLRs are a well-studied class of innate immune receptors recognizing a diverse range of lipid-, protein-, nucleic acid-based PAMPs and DAMPs (Kawai and Akira 2011). The engagement of TLRs with their specific ligands leads to the activation of innate immune responses, and evokes adaptive immune responses through the activation of antigen presenting cells (APCs) and by amplifying B- and T-cell effector cells (Pasare and Medzhitov 2005; MacLeod and Wetzler 2007). Several studies have demonstrated that stimulation of TLRs with specific ligands and combinations of, to fine-tune adaptive immune responses. Moreover, the aberrant TLR expression in cancer cells and several TLR polymorphisms identified in tumors indicate a role for TLRs in cancer (El-Omar et al. 2008; Kutikhin 2011; Mandal et al. 2012). The infiltration of TLR-expressing immune cells into the tumor microenvironment further implies the significance of TLRs and cancer (Bennaceur et al. 2009; Sato et al. 2009). However, the precise contribution of TLRs in cancer remains to be understood. Activation of TLRs can have opposing roles by either promoting cancer cell apoptosis or promoting tumor progression and survival (Huang et al. 2008). Overall, TLRs are promising targets for the development of new and effective therapeutic agents (Kanzler et al. 2007; Wang et al. 2008; So and Ouchi 2010). Several small molecules agonists of TLRs have been identified for use as immune stimulants to boost immunity against cancer (Meyer and Stockfleth 2008).

Among the TLRs, TLR2 requires heterodimerization with either TLR1 or TLR6 for activation with bacterial acylated lipoproteins. A widely-recognized agonist activating TLR1/TLR2 is PAM3CSK4, and bacterial diacylated lipopolypeptides such as MALP-2 stimulate TLR2/TLR6, [Muhlradt et al., J. Exp. Med. 1997, 185:1951]).

SUMMARY

There remains a need for novel modulators of TLR2, methods of identifying novel TLR2 modulators, and related therapeutic methods of treatment. According, in one aspect, provided herein is a compound of Formula (IA):

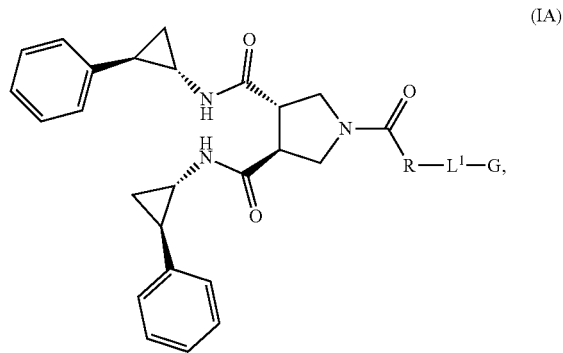

or a pharmaceutically acceptable salt thereof, wherein R, $L^1$, and G are as defined herein.

In another aspect, provided herein is a method for modulating the activity of a Toll-like receptor 2 (TLR2) protein or a TLR2-mediated pathway or system in a subject in need thereof, comprising administering to the subject a compound as described herein, or a pharmaceutically acceptable salt thereof.

In another aspect, provided herein is a method for preventing or treating a TLR2 protein-mediated disorder in a subject in need thereof, comprising administering to the subject a compound as described herein, or a pharmaceutically acceptable salt thereof.

DETAILED DESCRIPTION

Figure 1:
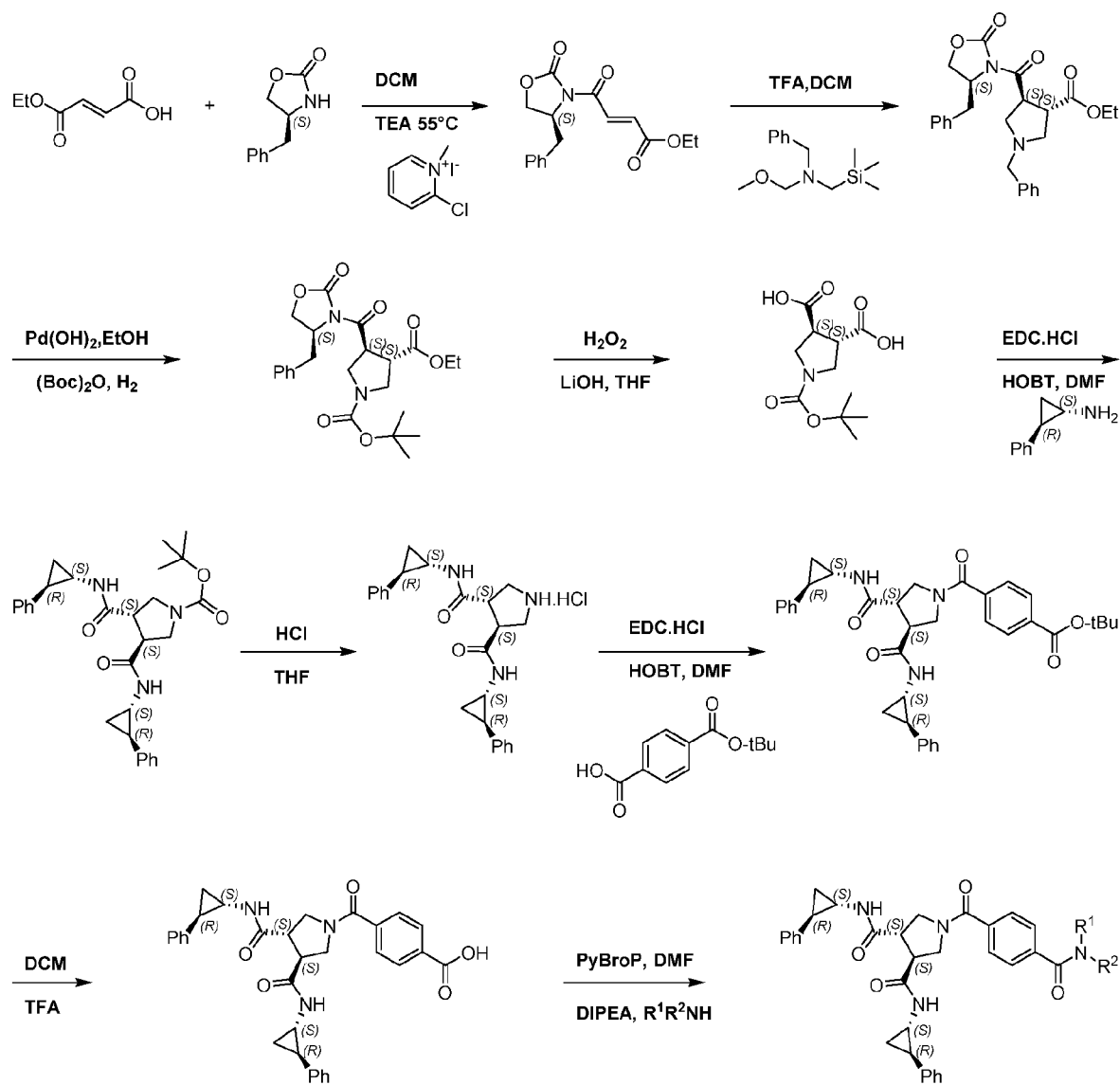
FIG. 1 shows synthesis Schemes 1 and 2.
Figure 1:
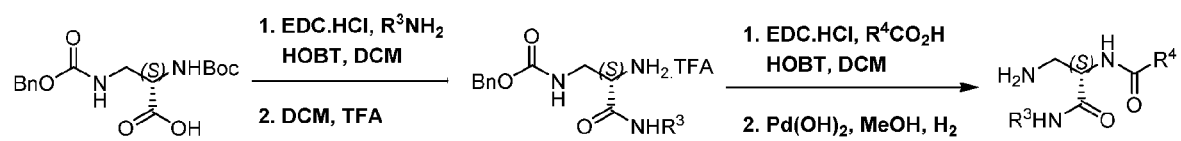
Figure 2:
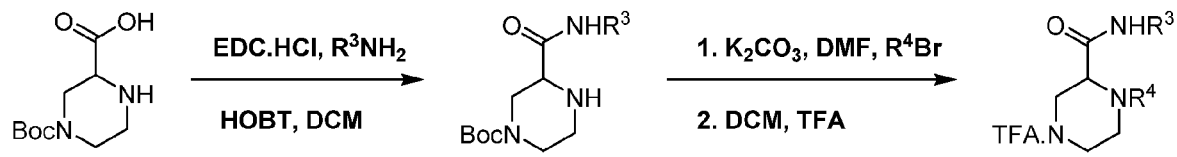
FIG. 2 shows synthesis Schemes 3, 4, 5, and 6.
Figure 2:
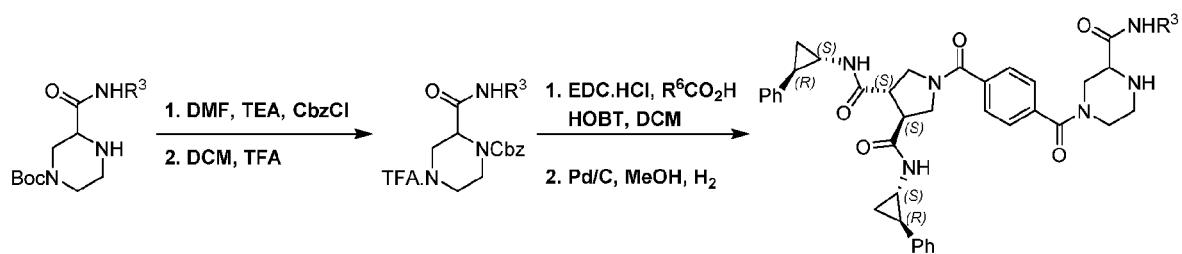
Figure 2:
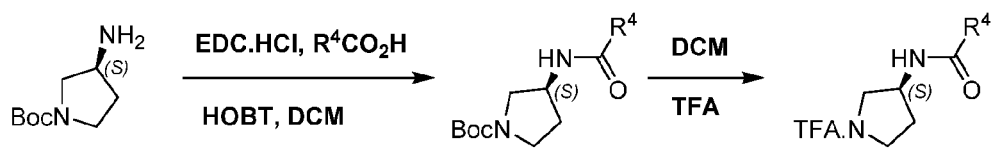
Figure 2:
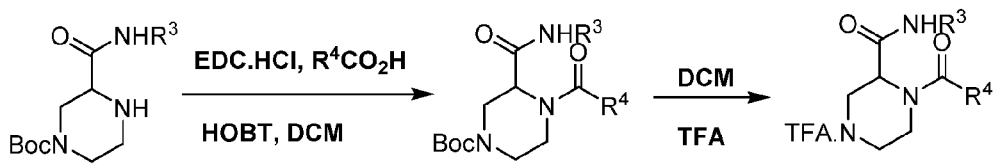
Figure 3:
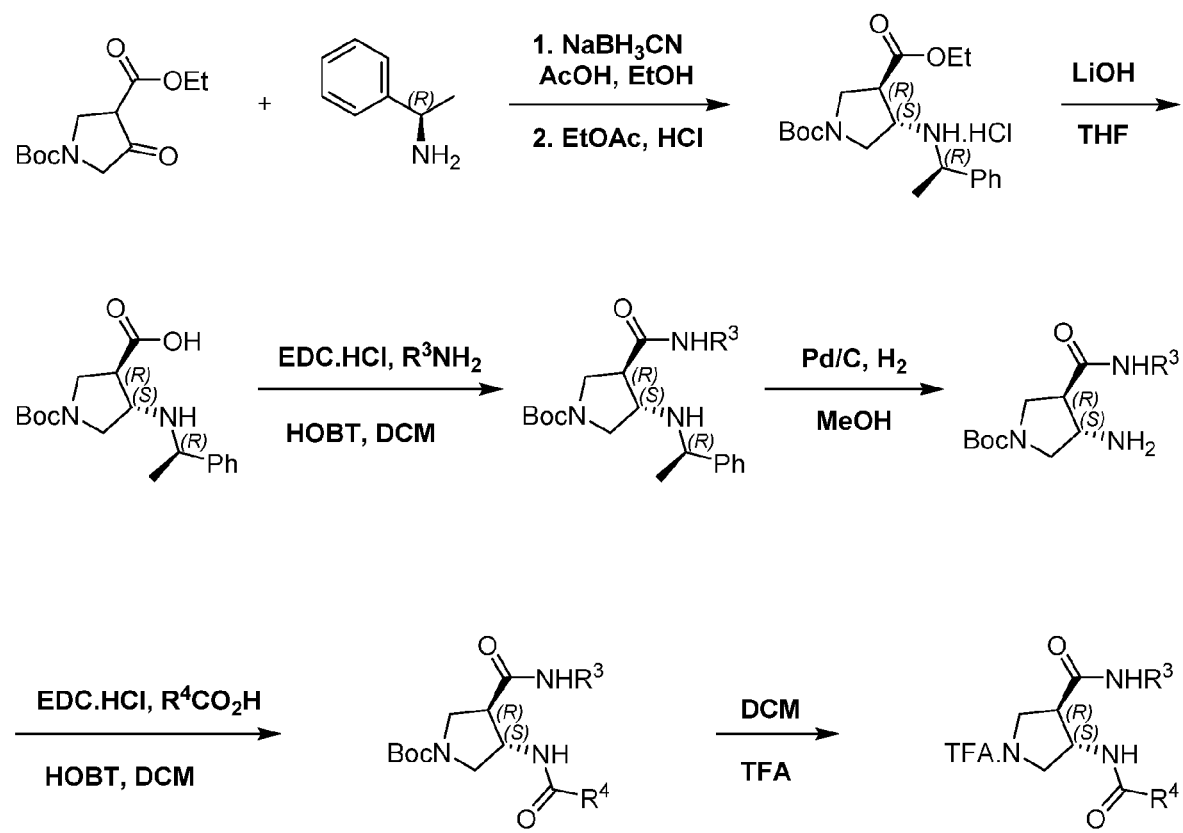
FIG. 3 shows synthesis Scheme 7.
Figure 4:
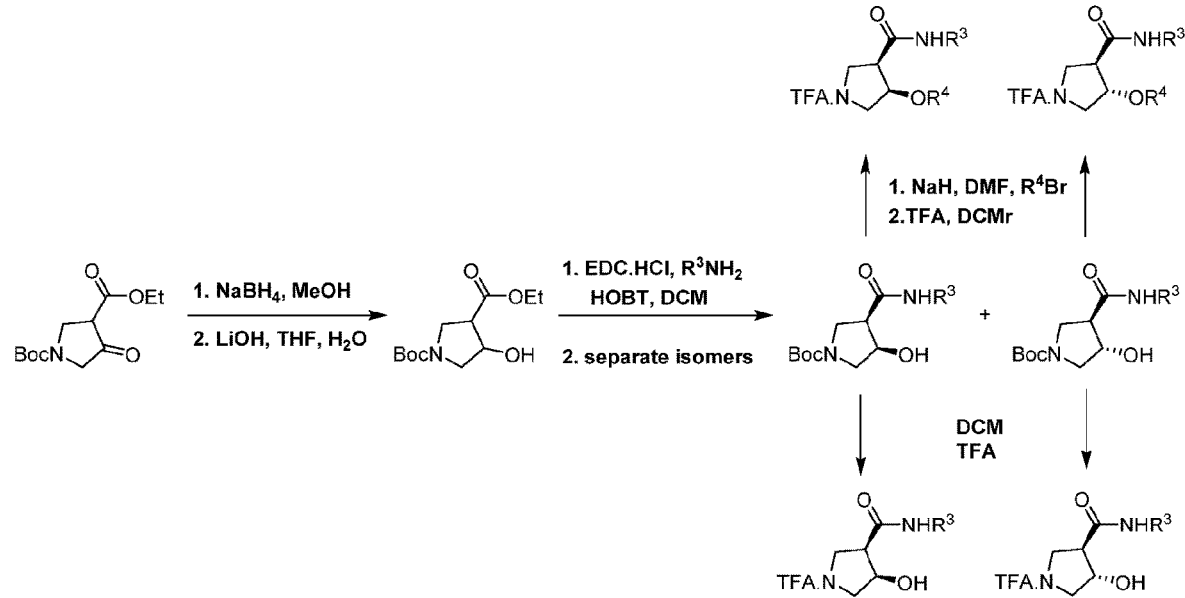
FIG. 4 shows synthesis Schemes 8 and 9.
Figure 4:
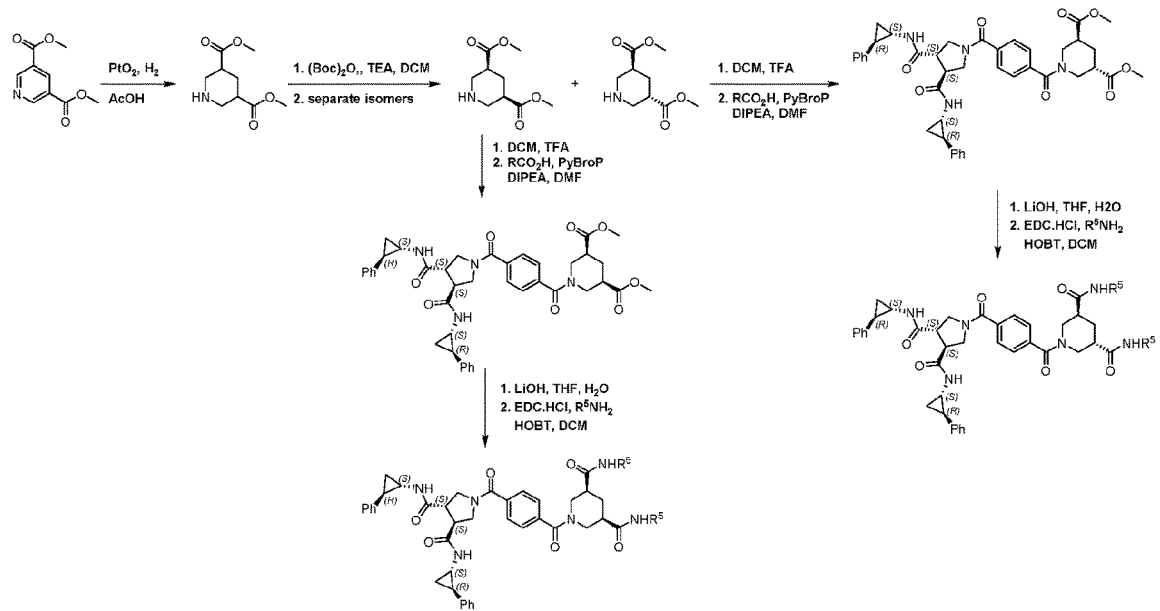
Figure 5:
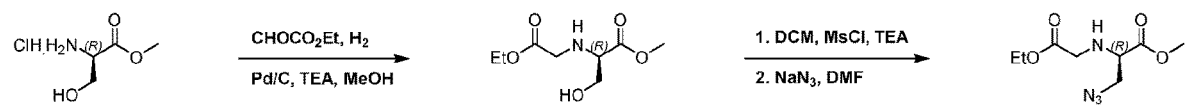
FIG. 5 shows synthesis Schemes 10 and 11.
Figure 5:
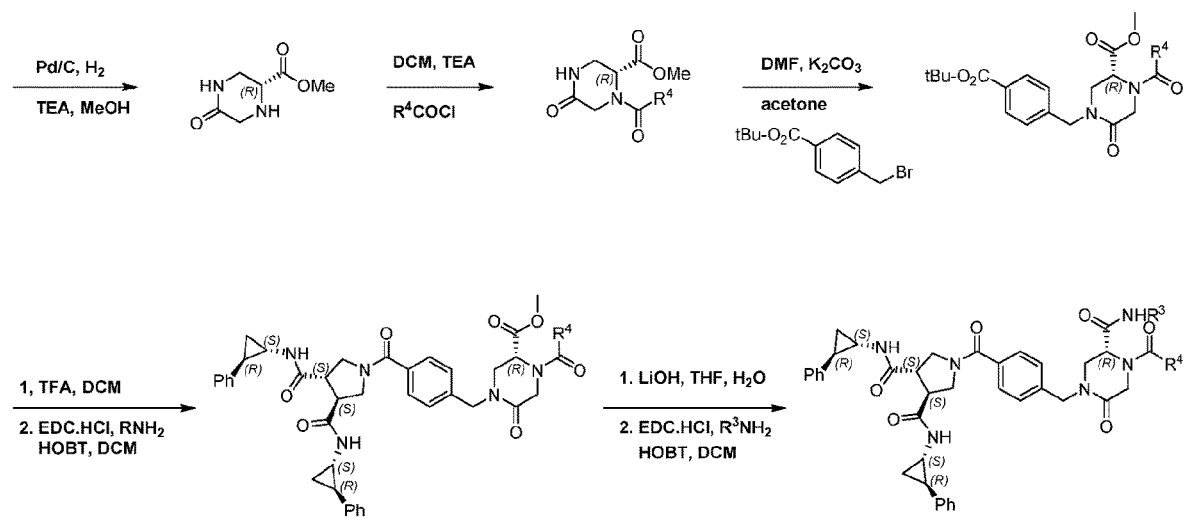
Figure 5:
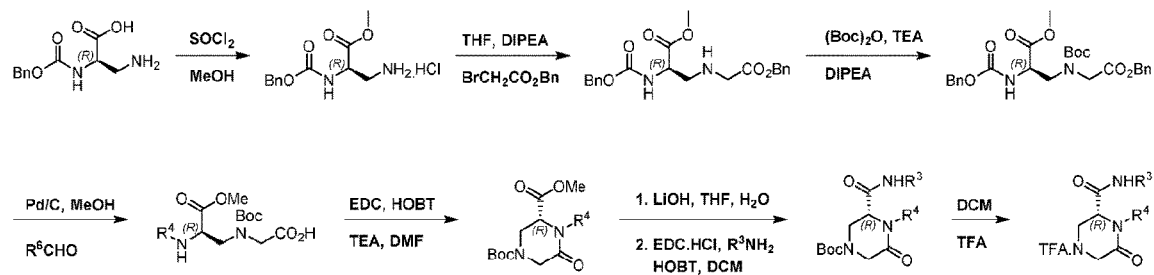
Figure 6:
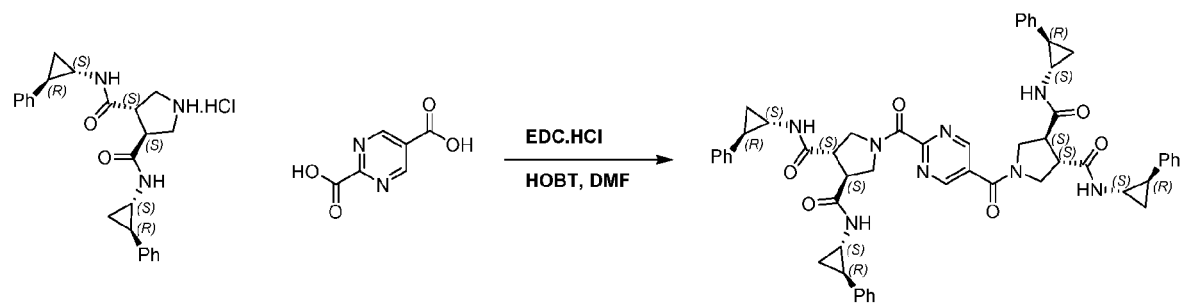
FIG. 6 shows synthesis Scheme 12.
Figure 7:
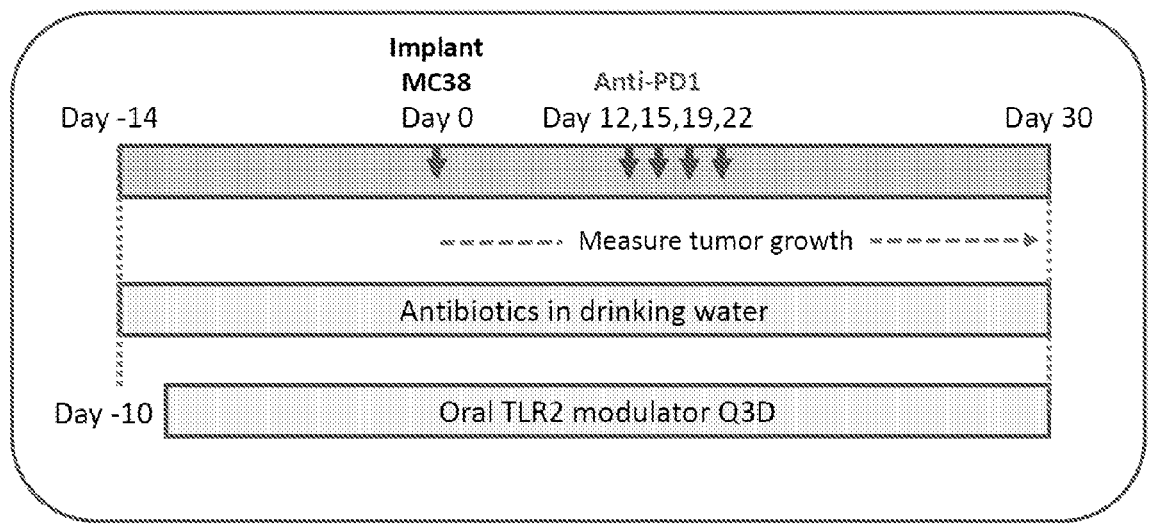
FIG. 7 depicts an outline of an oral dosing study.
Figure 8:
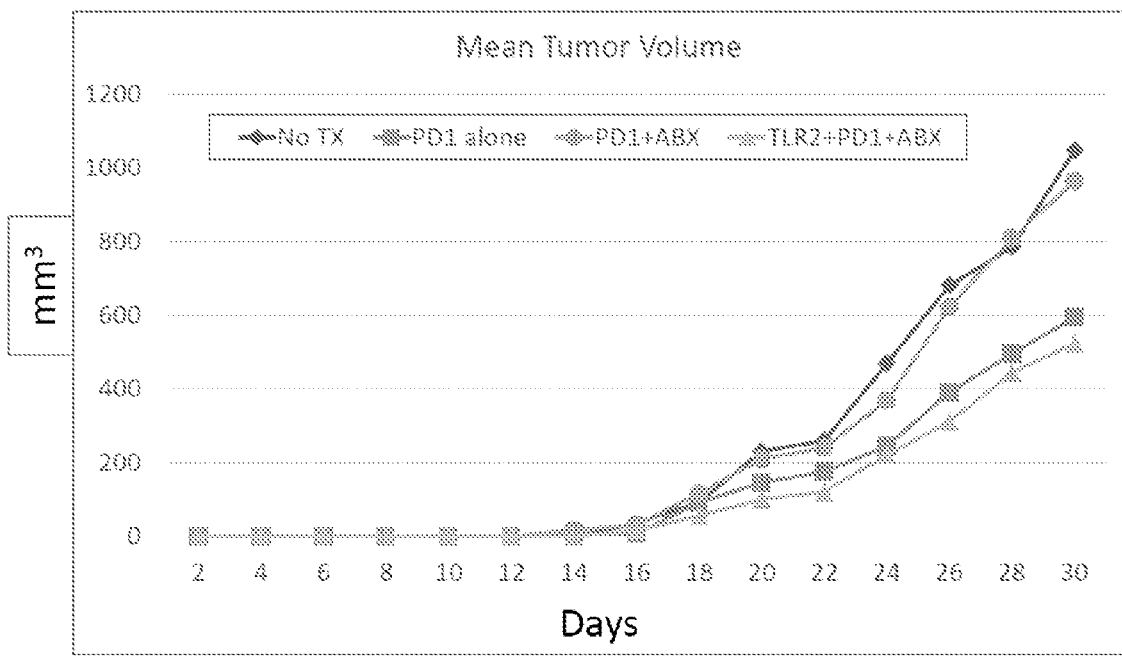
FIG. 8 depicts mean tumor volume in response to checkpoint therapy versus combination antibiotic/checkpoint therapy.

The present disclosure relates to modulators of Toll-like receptor (TLR) proteins, and particularly modulators of TLR2, as well as methods of using such compounds to treat cancer and other disorders associated with a TLR2 pathway. Methods of identifying compositions that activate, or act as agonists, of TLR2 are also provided.

Compounds of the Invention

In one aspect, provided herein is a compound of Formula (I):

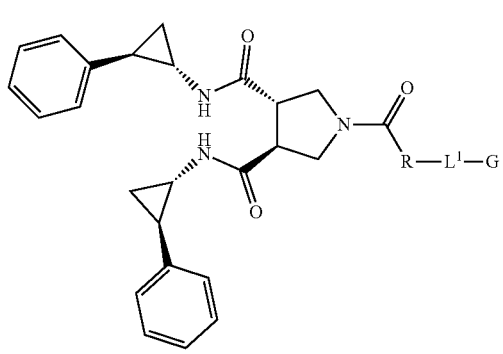

(I)

or a pharmaceutically acceptable salt thereof, wherein:
R is substituted or unsubstituted

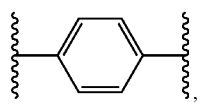

substituted or unsubstituted

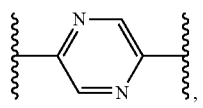

substituted or unsubstituted

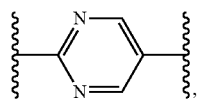 [SMILES: *c1cnc(*)nc1]

substituted or unsubstituted

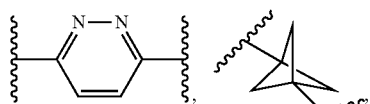

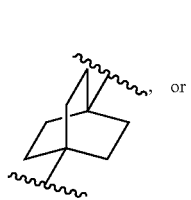 or

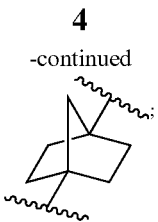

$L^1$ is —CO—, —SO$_2$—, —(CH$_2$)$_m$—, —CH(CF$_3$)—, or —CF$_2$—;

G is:

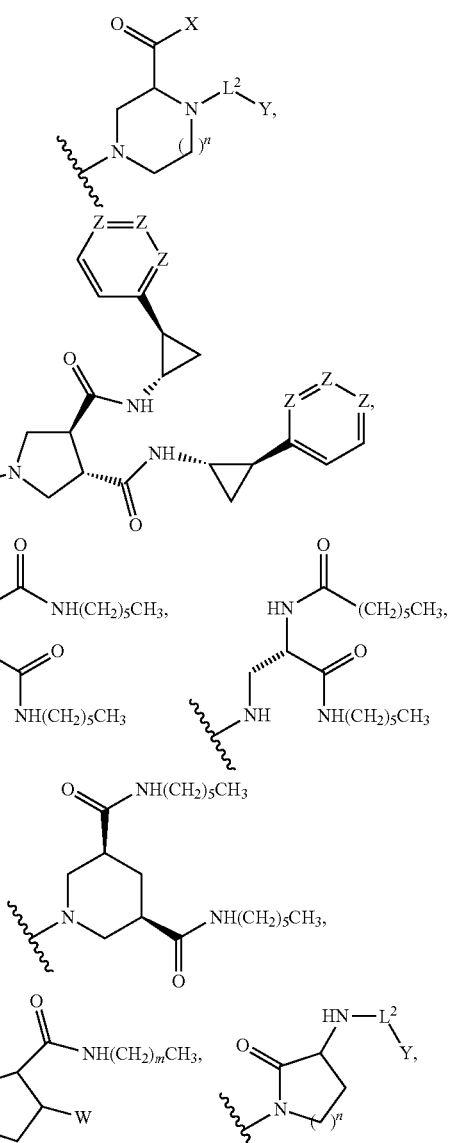

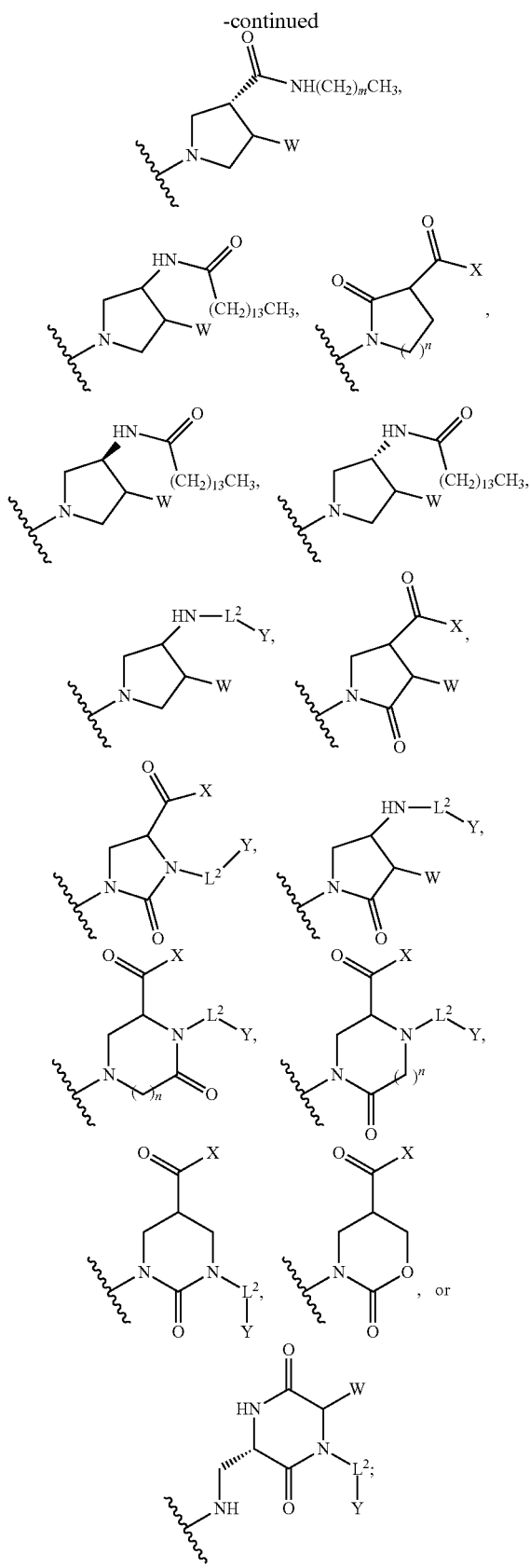

X is —NH(CH₂)ₘ CH₃, —NH(CH₂)ₘ-(substituted or unsubstituted Ph), or

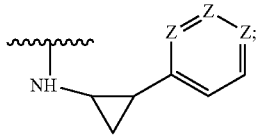

Z is CH or N, provided that no more than one Z on any one ring is N;

L² is a bond, —(CH₂)ₘ—, —CO—, —SO₂— or —(C=O)NH—;

Y is —H, substituted or unsubstituted $C_{1-16}$ alkyl, $C_{1-16}$ alkyl-(substituted or unsubstituted Ph), —NH(CH₂)ₘCH₃, or substituted or unsubstituted $C_{3-10}$ cycloalkyl;

W is H, hydroxyl, —OCH₃, —O(CH₂)ₘCH₃, —NH(C=O)CH₃—NH(C=O)(CH₂)ₘCH₃, —(C=O)—NH(CH₂)ₘCH₃, substituted or unsubstituted $C_{1-16}$ alkyl, $C_{1-16}$ alkyl-(substituted or unsubstituted Ph), —NH(CH₂)ₘCH₃, —N((CH₂)ₘCH₃)₂, or substituted or unsubstituted $C_{3-10}$ cycloalkyl;

each m is independently 1-16; and
each n is independently 1-3;
provided that the compound of Formula (I) is not:

002

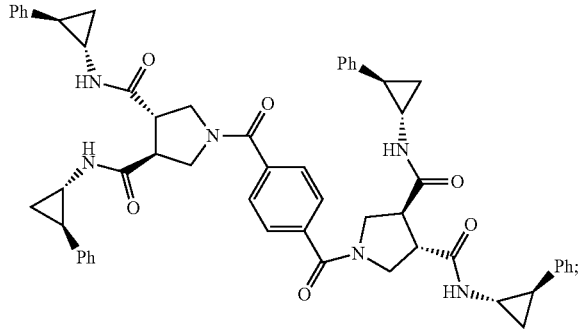

003

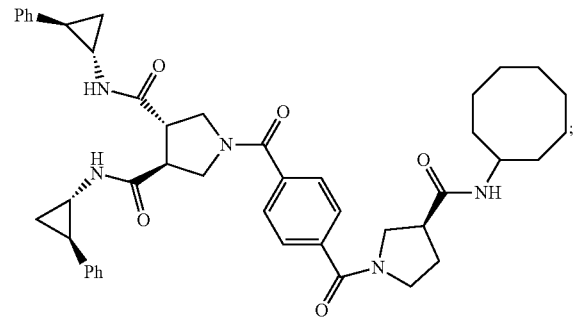

004

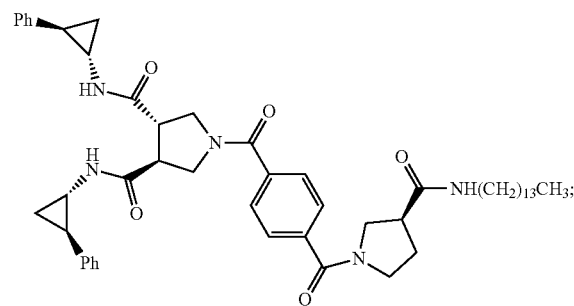

-continued
029
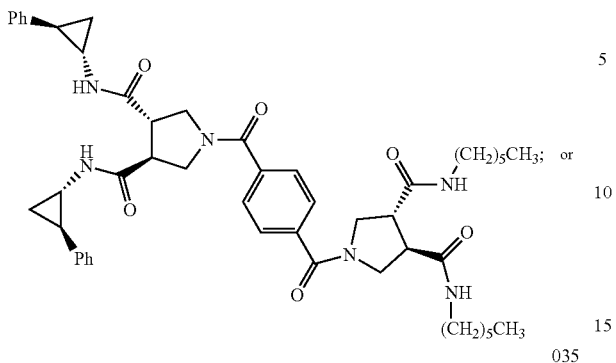
In one aspect, provided herein is a compound of Formula (IA):
(IA)
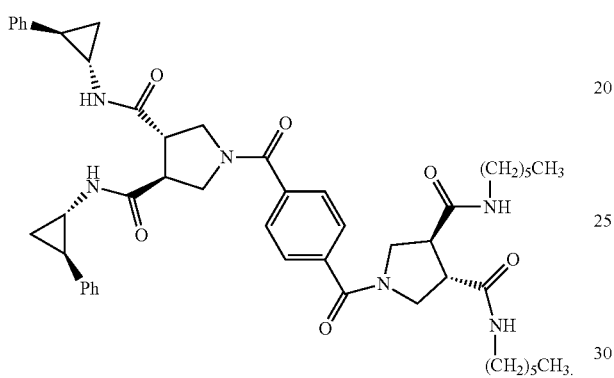
or a pharmaceutically acceptable salt thereof, wherein:
R is substituted or unsubstituted
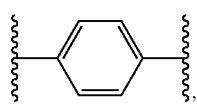
substituted or unsubstituted
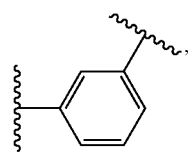 [SMILES: *c1cccc(*)c1]
substituted or unsubstituted
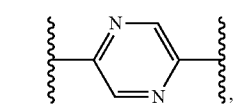
substituted or unsubstituted
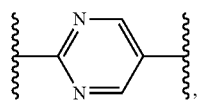
substituted or unsubstituted
 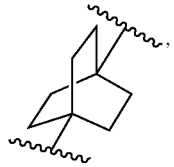
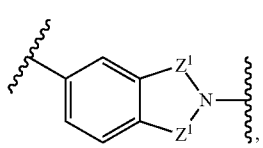
substituted or unsubstituted
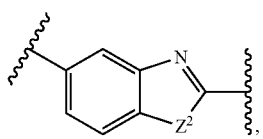
substituted or unsubstituted
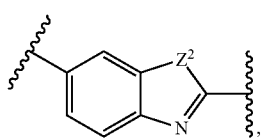

substituted or unsubstituted N

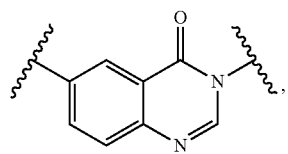

substituted or unsubstituted

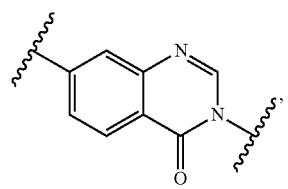 [SMILES: *c1ccc2c(=O)n(*)cnc2c1]

substituted or unsubstituted

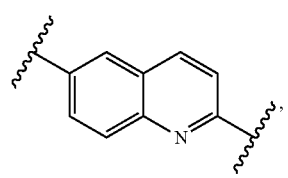 [SMILES: *c1ccc2nc(*)ccc2c1]

substituted or unsubstituted

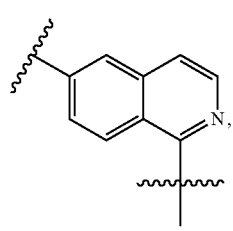 [SMILES: *c1ccc2c(*)nccc2c1]

substituted or unsubstituted

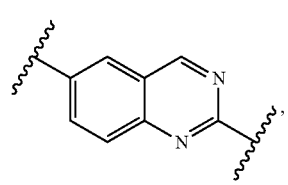

substituted or unsubstituted

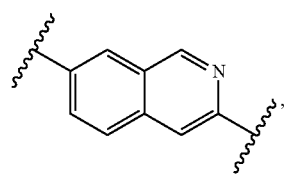

substituted or unsubstituted

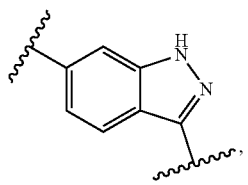 [SMILES: *c1ccc2c(*)n[nH]c2c1]

substituted or unsubstituted

[indazole N-methyl structure]

substituted or unsubstituted

[imidazopyridine structure]

substituted or unsubstituted

[imidazopyridine structure]

or substituted or unsubstituted

[dihydroisoquinolinone structure]

$L^1$ is a bond, —CO—, —SO$_2$—, —(CH$_2$)$_m$—, —CH(CH$_3$)—, —CH(CF$_3$)—, —CF$_2$—, —NHC(=O)—, —NHCH$_2$—, five-membered heterocyclylene, five-membered heteroarylene, or

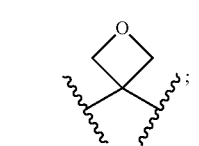 [SMILES: *C1(*)COC1]

G is:
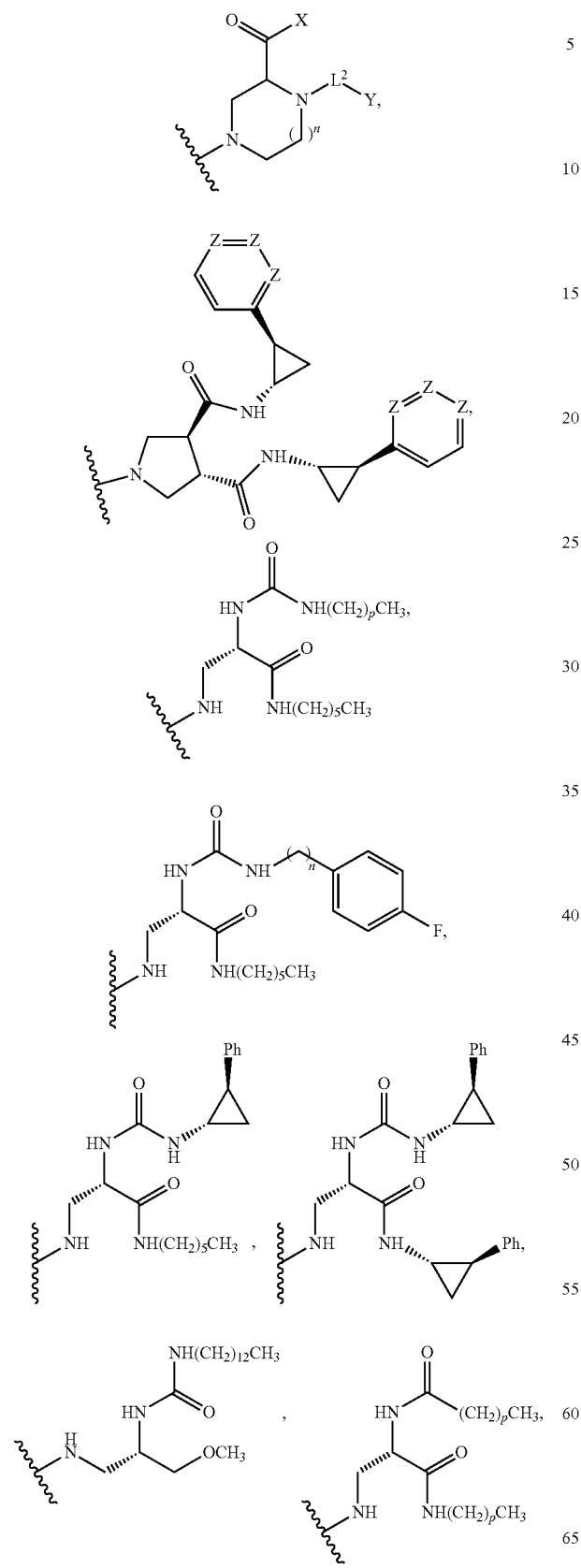
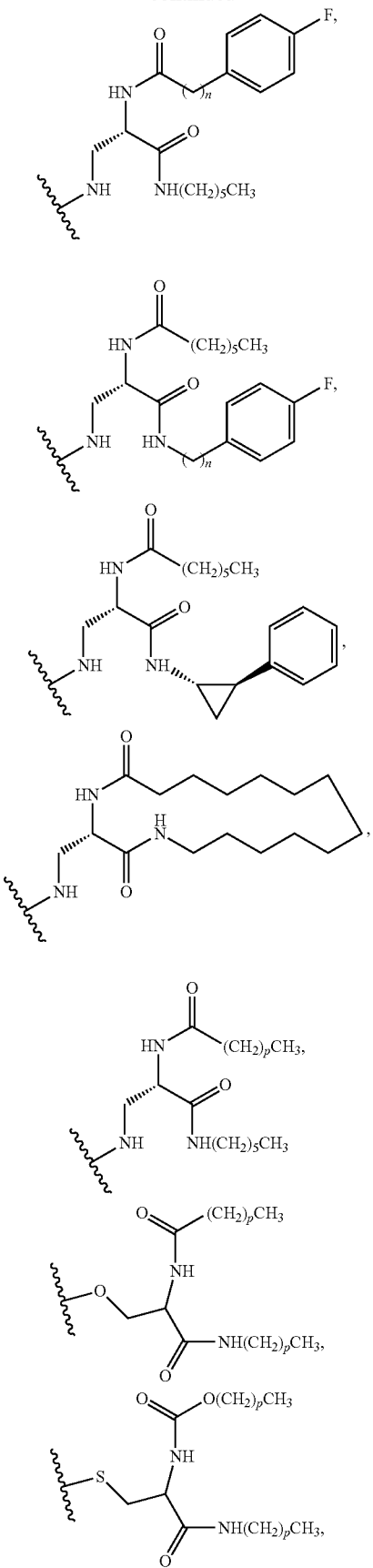

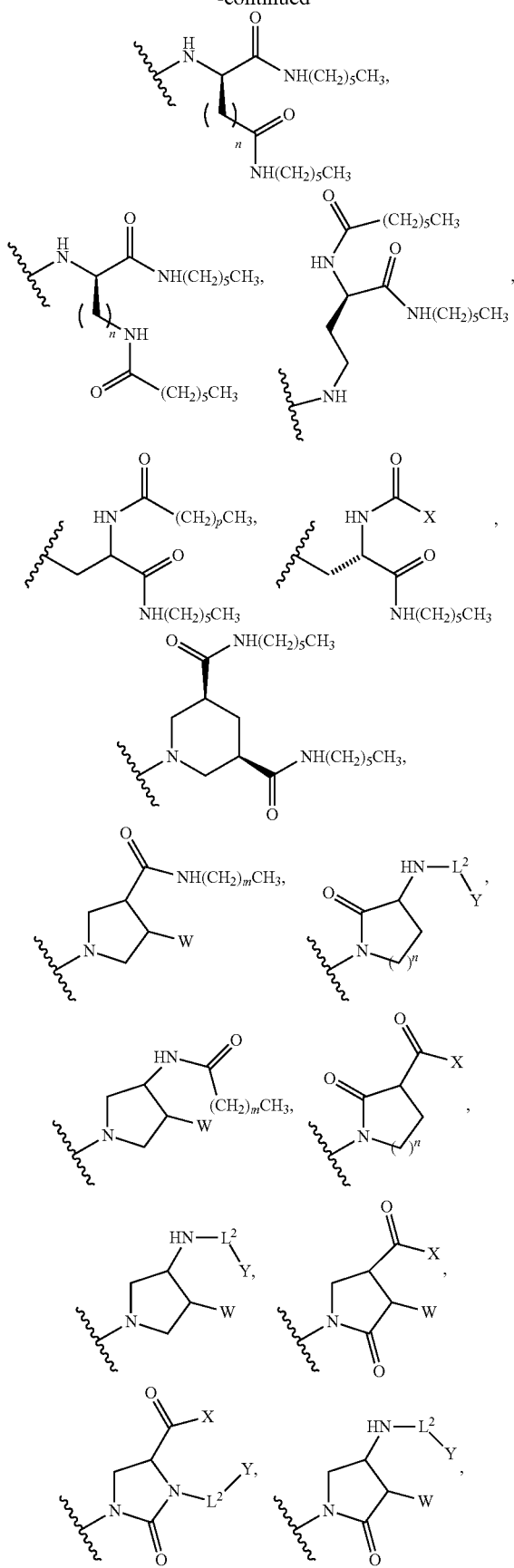
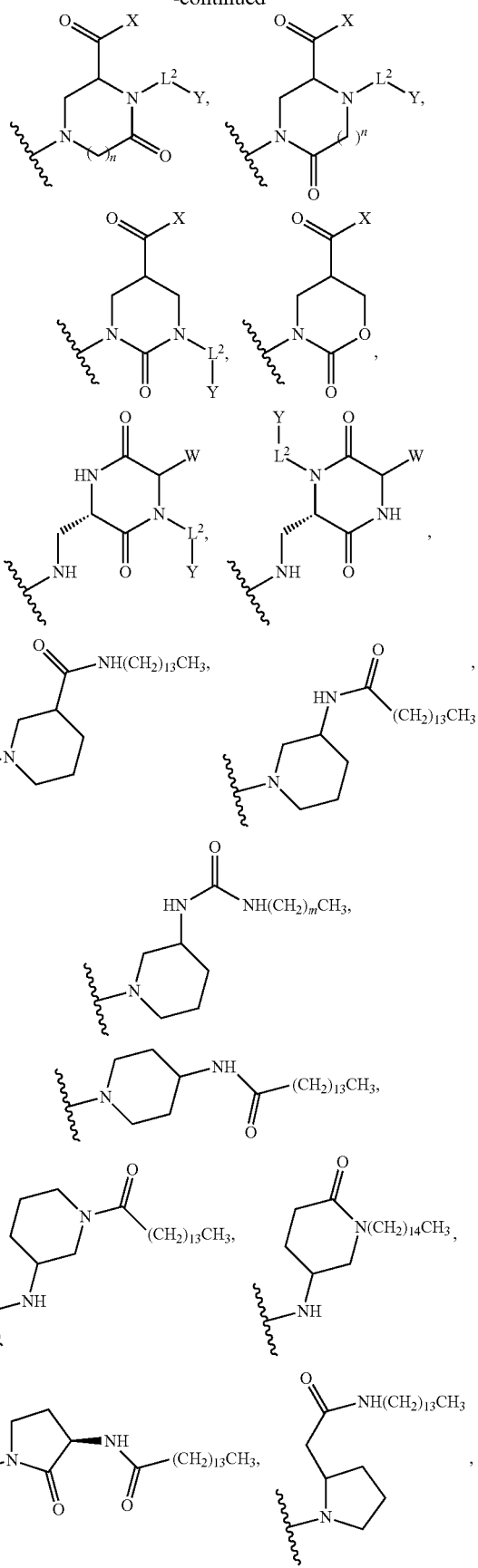

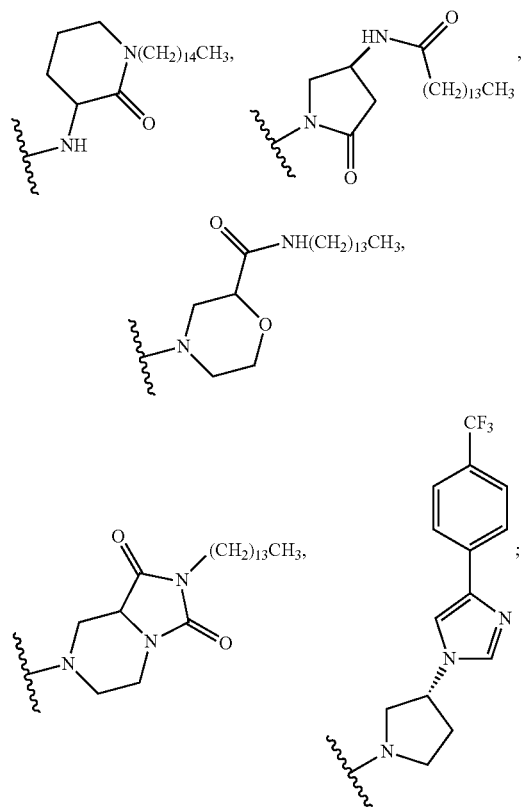

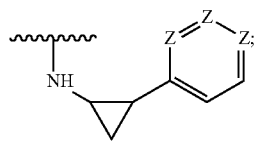

X is —NH(CH₂)ₘCH₃, —NH(CH₂)ₘ-(substituted or unsubstituted Ph), or

[structure showing NH-cyclopropyl-phenyl with Z substituents]

Z is CH or N, provided that no more than one Z on any one ring is N;
each $Z^1$ is independently —CH₂— or —C(=O)—;
each $Z^2$ is independently —O—, —S—, or —NH—;
$L^2$ is a bond, —(CH₂)ₘ—, —CO—, —SO₂—, —(C=O)NH—, or —(C=O)O—;
Y is —H, substituted or unsubstituted $C_{1-16}$ alkyl, $C_{1-16}$ alkyl-(substituted or unsubstituted Ph), —NH(CH₂)ₘCH₃, —SO₂(CH₂)₁₃CH₃, or substituted or unsubstituted $C_{3-10}$ cycloalkyl;
W is H, hydroxyl, —OCH₃, —O(CH₂)ₘCH₃, —NH(C=O)CH₃—NH(C=O)(CH₂)ₘCH₃, —(C=O)—NH(CH₂)ₘCH₃, substituted or unsubstituted $C_{1-16}$ alkyl, $C_{1-16}$ alkyl-(substituted or unsubstituted Ph), —NH(CH₂)ₘCH₃, —N((CH₂)ₘCH₃)₂, —N(CH₃)(Y), or substituted or unsubstituted $C_{3-10}$ cycloalkyl;
each m is independently 1-16;
each n is independently 1-3; and
each p is independently 3-8;

provided that the compound of Formula (I) is not:

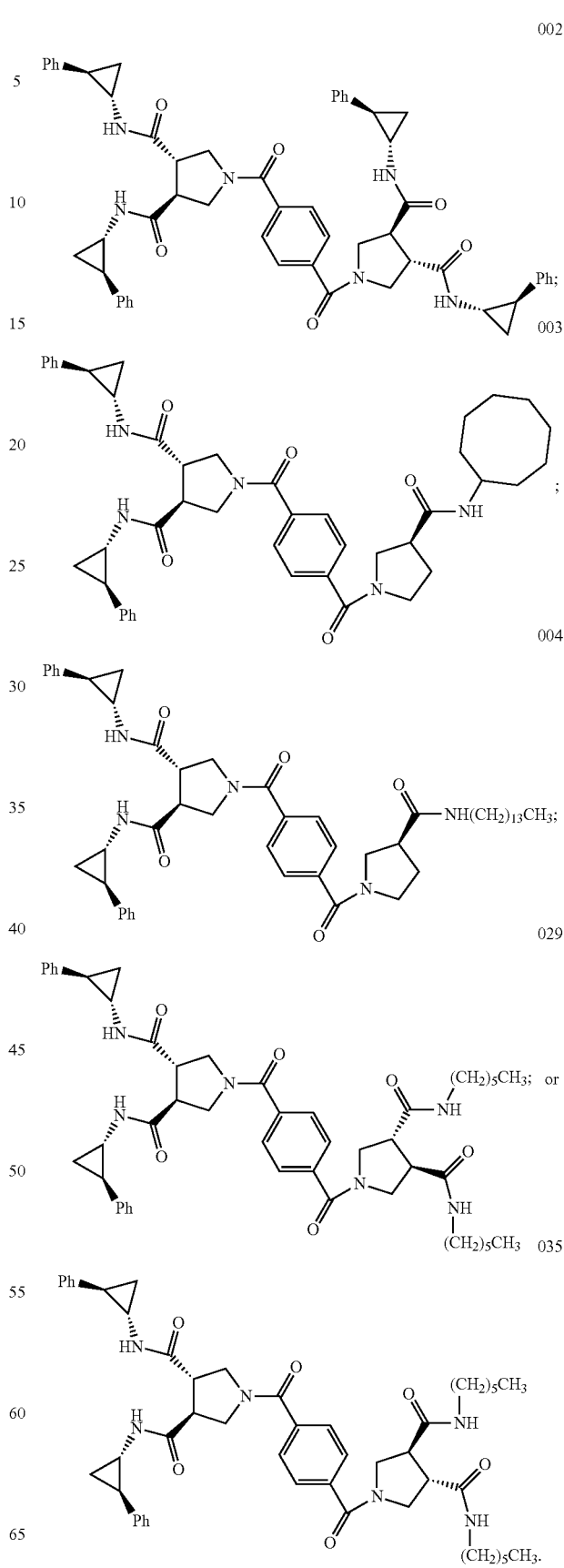

In one aspect, provided herein is a compound of Formula (IB):

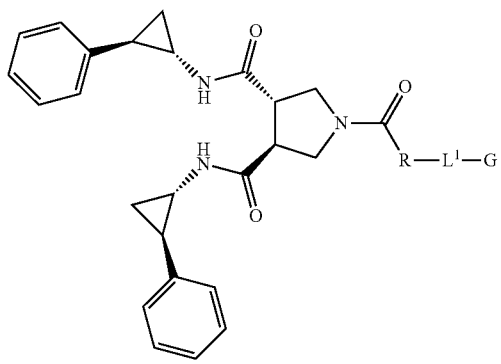
(IB)

or a pharmaceutically acceptable salt thereof, wherein:
R is substituted or unsubstituted

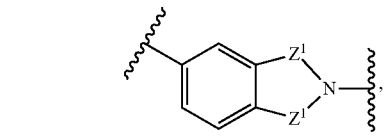, substituted or unsubstituted

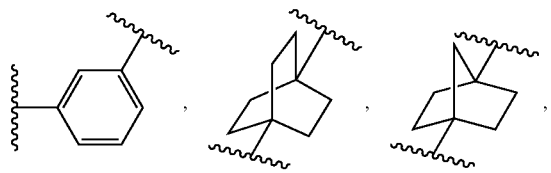 [SMILES: *c1cccc(*)c1 ; *C12CCC(*)(CC1)CC2 ; *C12CCC(*)(CC1)C2], substituted or unsubstituted

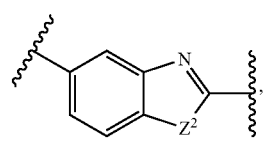, substituted or unsubstituted

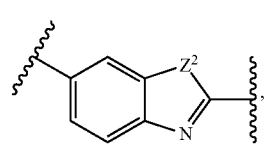, substituted or unsubstituted

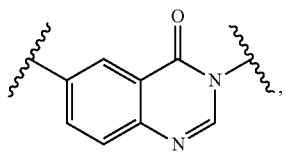 [SMILES: *c1ccc2ncn(*)c(=O)c2c1]

or substituted

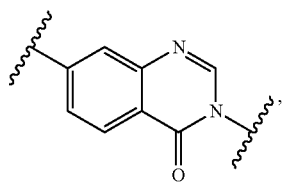 [SMILES: *c1ccc2c(=O)n(*)cnc2c1]

or unsubstituted

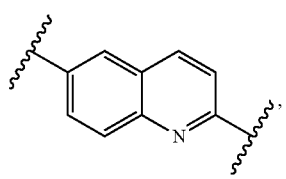 [SMILES: *c1ccc2nc(*)ccc2c1], substituted or unsubstituted

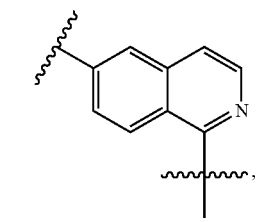 [SMILES: *c1ccc2c(*)nccc2c1], substituted or unsubstituted

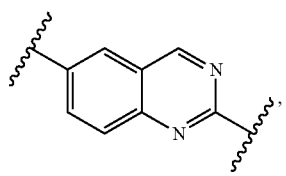 [SMILES: *c1ccc2nc(*)ncc2c1], substituted or unsubstituted

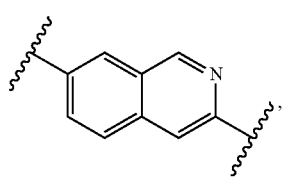 [SMILES: *c1ccc2cc(*)ncc2c1],

| 19 | 20 |
substituted or unsubstituted
G is:
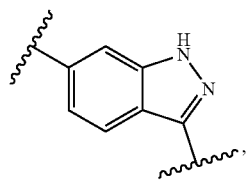 [SMILES: *c1ccc2c(*)n[nH]c2c1]
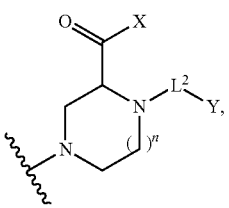
substituted or unsubstituted
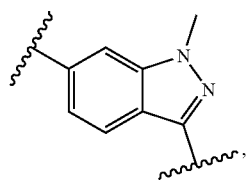 [SMILES: *c1ccc2c(*)nn(C)c2c1]
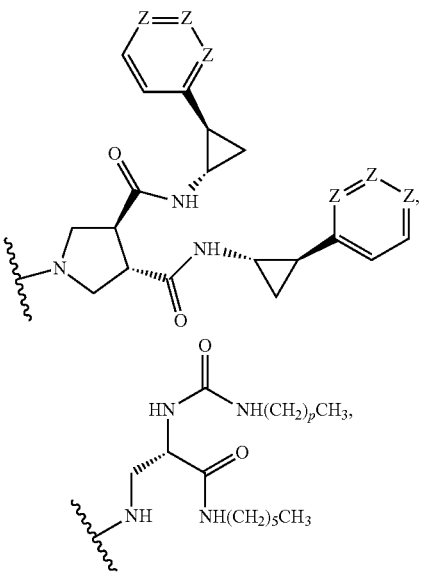
substituted or unsubstituted
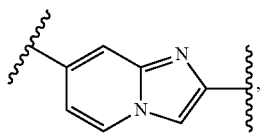 [SMILES: *c1ccn2cc(*)nc2c1]
substituted or unsubstituted
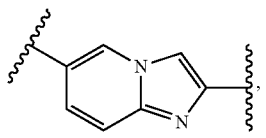 [SMILES: *c1ccc2nc(*)cn2c1]
or substituted or unsubstituted
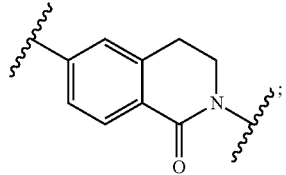 [SMILES: *c1ccc2c(c1)CCN(*)C2=O]
L¹ is a bond, —CO—, —SO$_2$—, —(CH$_2$)$_m$—, —CH(CH$_3$)—, —CH(CF$_3$)—, —NHC(=O)—, —NHCH$_2$—, five-membered heterocyclylene, five-membered heteroarylene, or
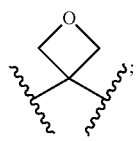 [SMILES: *C1(*)COC1]

-continued
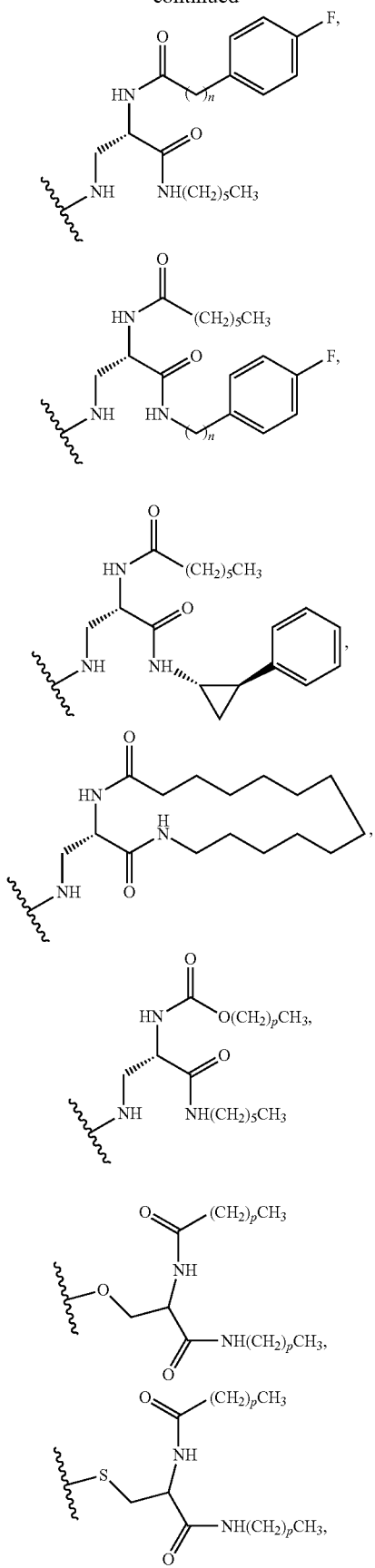
-continued
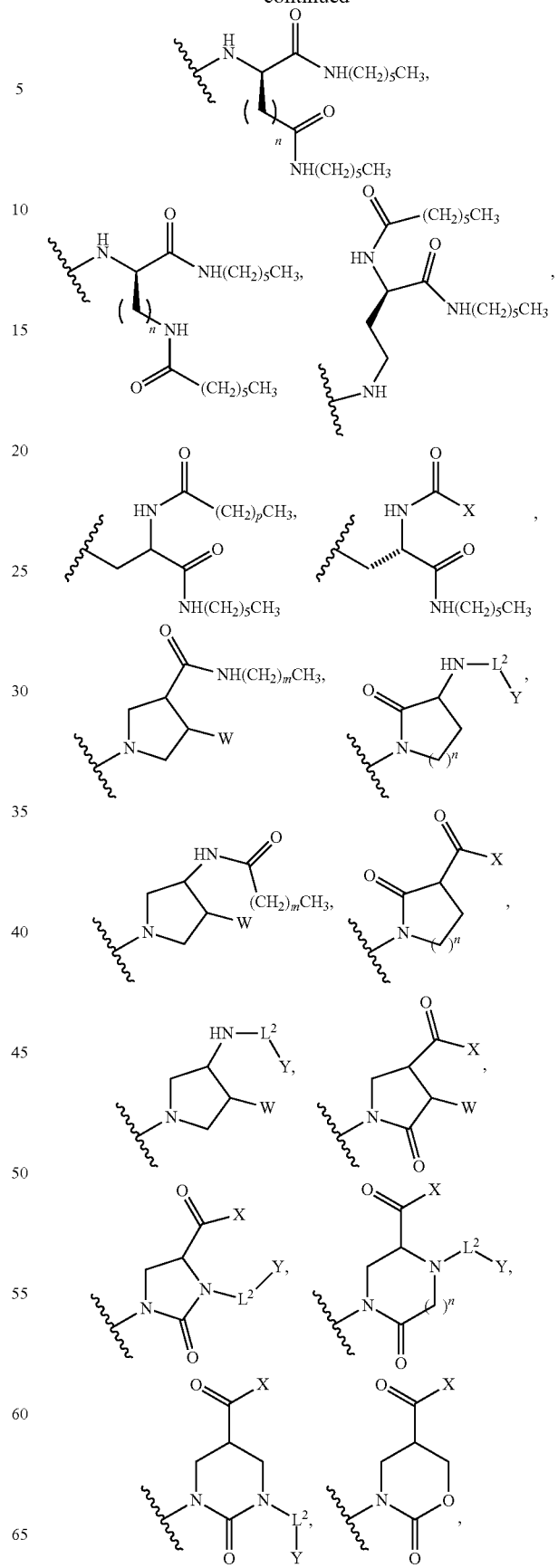

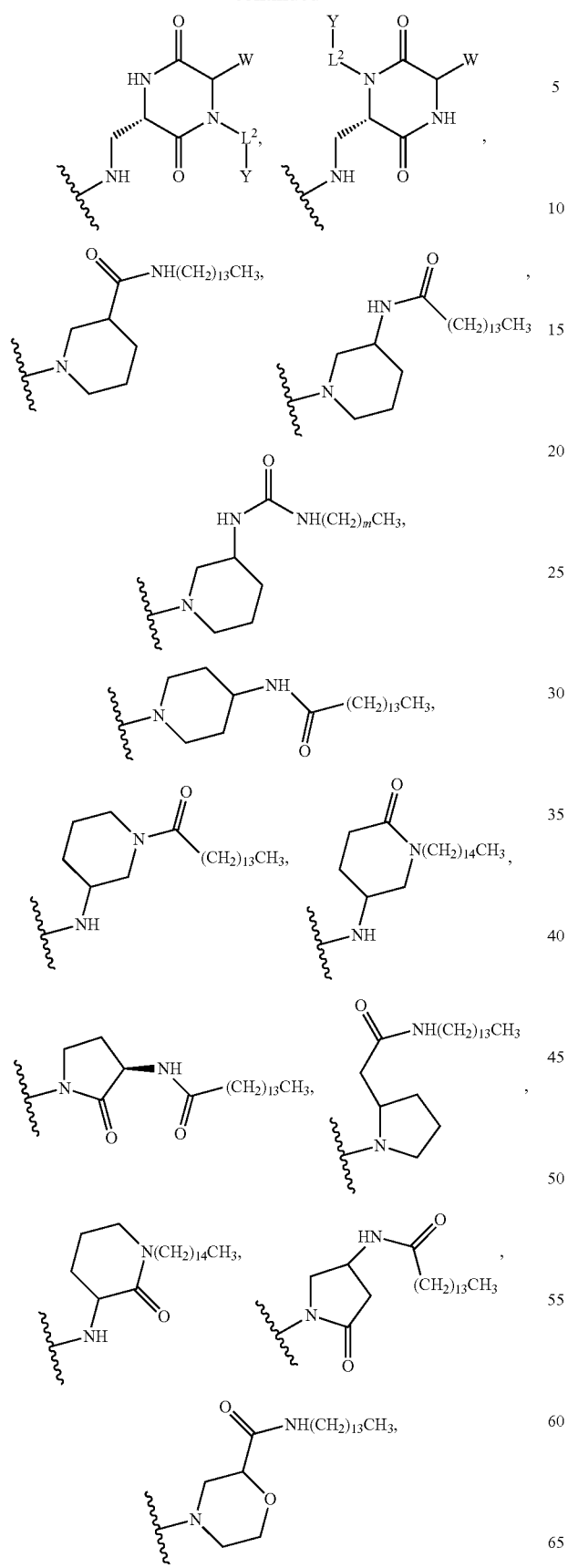

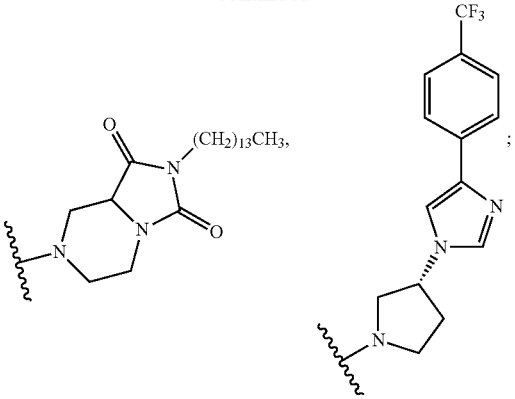

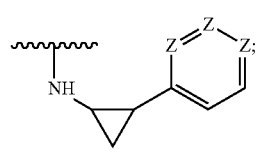

X is —NH(CH$_2$)$_m$CH$_3$, —NH(CH$_2$)$_m$-(substituted or unsubstituted Ph), or Z is CH or N, provided that no more than one Z on any one ring is N;

each Z$^1$ is independently —CH$_2$— or —C(=O)—;

each Z$^2$ is independently —O—, —S—, or —NH—;

L$^2$ is a bond, —(CH$_2$)$_m$—, —CO—, —SO$_2$—, —(C=O)NH—, or —(C=O)O—;

Y is —H, substituted or unsubstituted C$_{1-16}$ alkyl, C$_{1-16}$ alkyl-(substituted or unsubstituted Ph), —NH(CH$_2$)$_m$CH$_3$, —SO$_2$(CH$_2$)$_{13}$CH$_3$, or substituted or unsubstituted C$_{3-10}$ cycloalkyl;

W is —OCH$_3$, —O(CH$_2$)$_m$CH$_3$, —NH(C=O)CH$_3$—NH(C=O)(CH$_2$)$_m$CH$_3$, —(C=O)—NH(CH$_2$)$_m$CH$_3$, substituted or unsubstituted C$_{1-16}$ alkyl, C$_{1-16}$ alkyl-(substituted or unsubstituted Ph), —NH(CH$_2$)$_m$CH$_3$, —N((CH$_2$)$_m$CH$_3$)$_2$, —N(CH$_3$)(Y), or substituted or unsubstituted C$_{3-10}$ cycloalkyl;

each m is independently 1-16;

each n is independently 1-3; and each p is independently 3-8;

provided that the compound is not

002

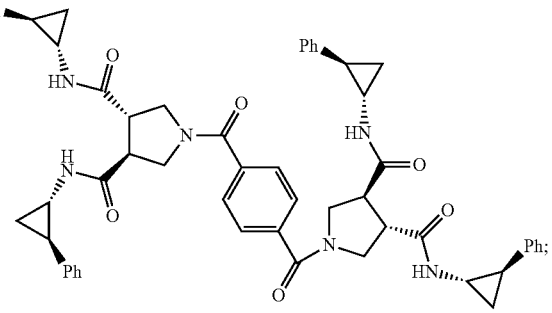

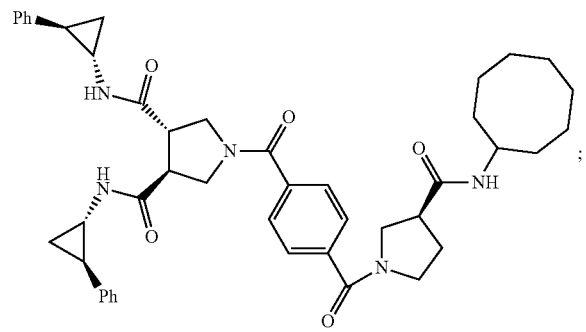
003
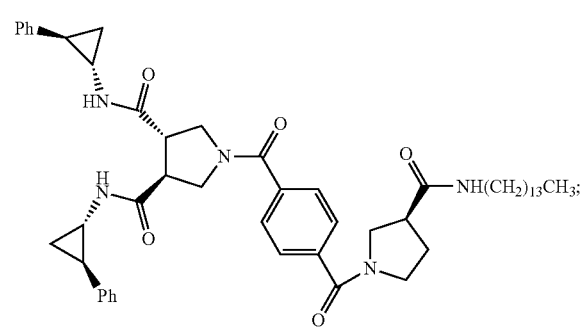
004
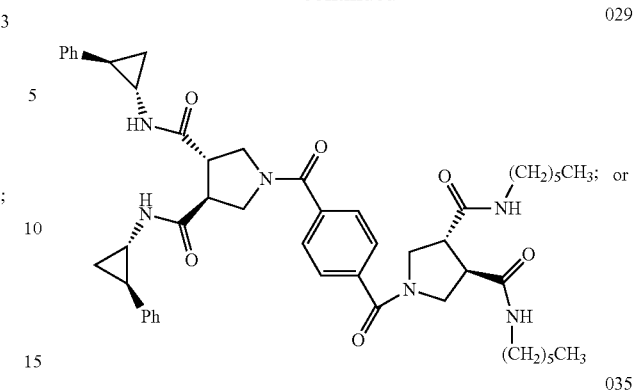
029
035
In certain embodiments, the compound of Formula (I) or (IA) is selected from the compounds of Table 1.
TABLE 1
| Compound | Structure |
|---|---|
| 001 | 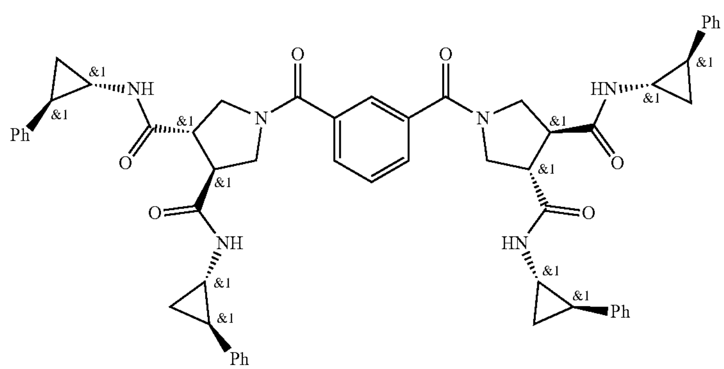 [SMILES: O=C(N[C@H]1C[C@@H]1c1ccccc1)[C@@H]1CN(C(=O)c2cccc(C(=O)N3C[C@@H](C(=O)N[C@H]4C[C@@H]4c4ccccc4)[C@H](C(=O)N[C@H]4C[C@@H]4c4ccccc4)C3)c2)C[C@H]1C(=O)N[C@H]1C[C@@H]1c1ccccc1] |
| 005 | 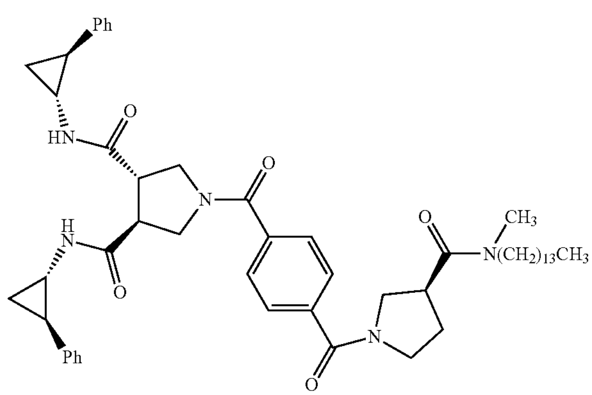 |

TABLE 1-continued
| Compound | Structure |
|---|---|
| 006 | 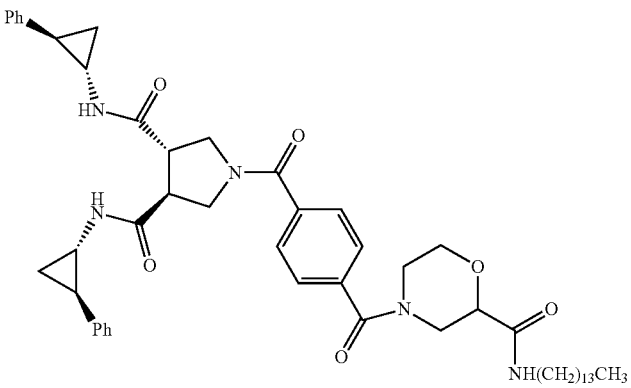 |
| 007 | 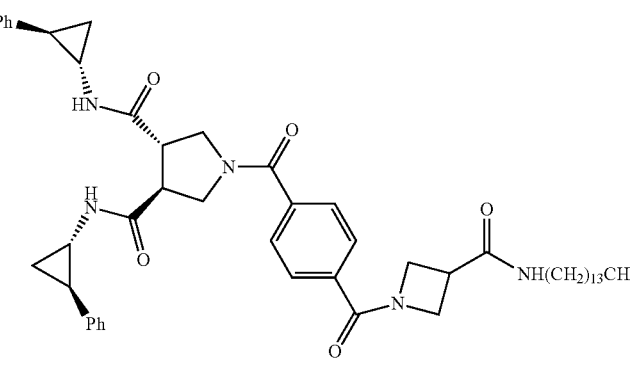 |
| 008 | 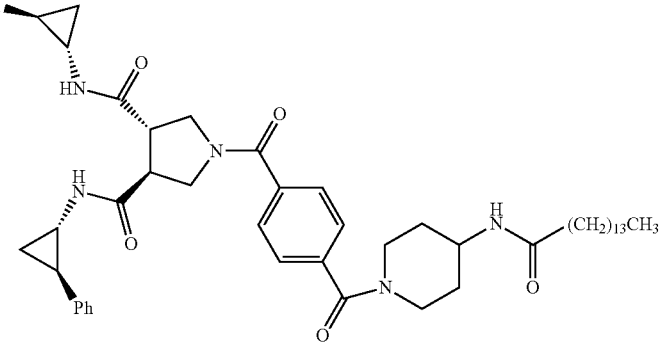 |
| 009 | 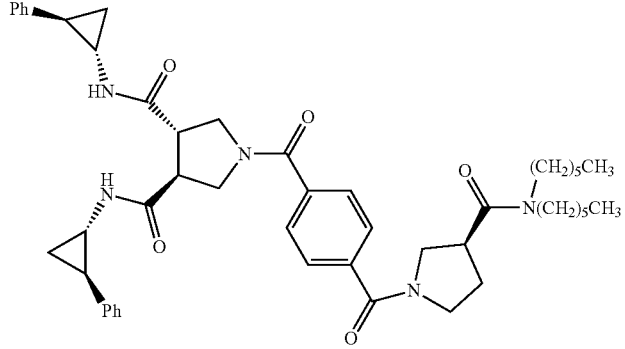 |

TABLE 1-continued

| Compound | Structure |
|---|---|
| 010 | *structure depicting a pyrrolidine with two phenylcyclopropyl carboxamide substituents, N-acylated with a terephthaloyl group connected to a piperidine-4-carboxamide bearing NH(CH₂)₁₃CH₃* |
| 011 | *structure depicting a pyrrolidine with two phenylcyclopropyl carboxamide substituents, N-acylated with a terephthaloyl group linked via amide to a gem-dimethyl-containing chain terminating in NH(CH₂)₁₃CH₃* |
| 012 | *structure similar to 011 with a gem-dimethyl diamine linker bearing NH-C(O)-(CH₂)₁₃CH₃* |
| 013 | *structure depicting a pyrrolidine with two phenylcyclopropyl carboxamide substituents, N-acylated with a terephthaloyl group linked via amide to a glutamine-like residue with two NH(CH₂)₅CH₃ groups* |

TABLE 1-continued

| Compound | Structure |
|---|---|
| 014 | 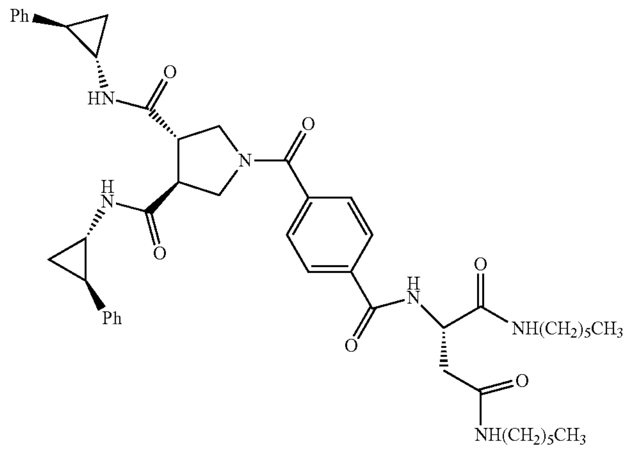 |
| 015 | 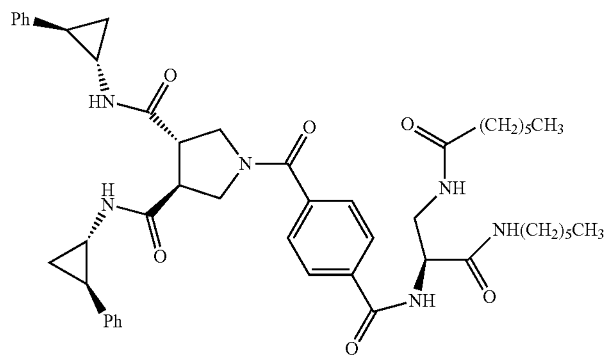 |
| 016 | 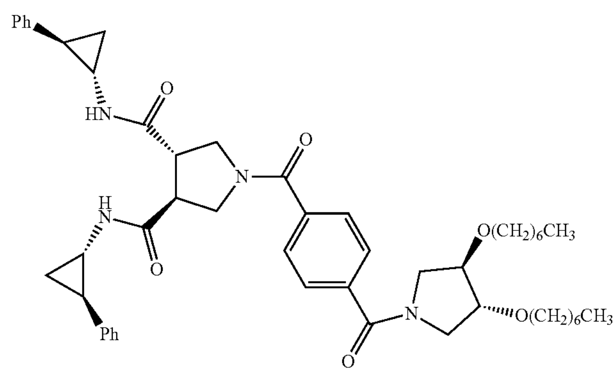 |
| 017 | 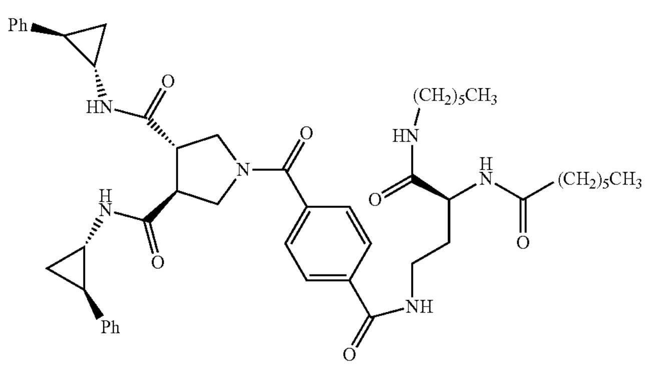 |

TABLE 1-continued

| Compound | Structure |
|---|---|
| 018 | (chemical structure) |
| 019 | (chemical structure) |
| 020 | (chemical structure) |
| 021 | (chemical structure) |

TABLE 1-continued

| Compound | Structure |
|---|---|
| 022 | 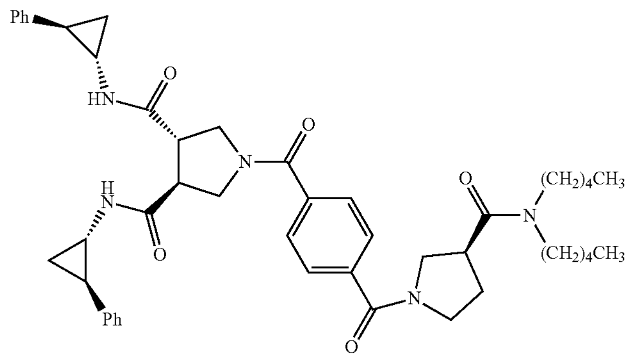 |
| 023 | 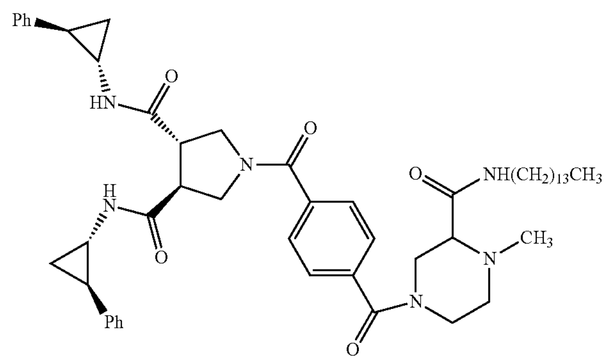 |
| 024 | 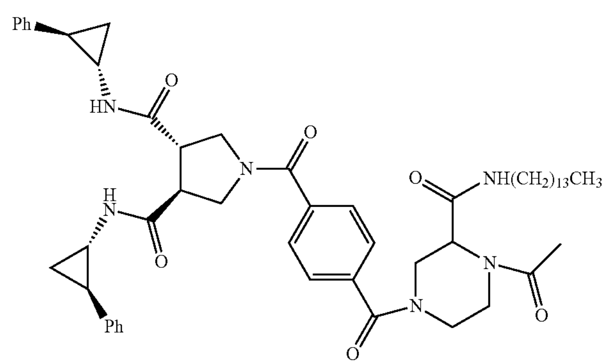 |
| 025 | 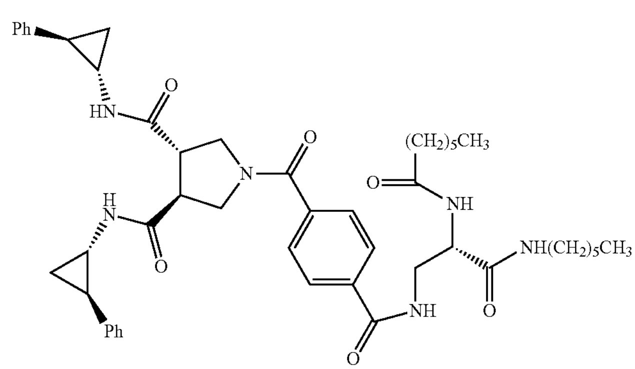 |

TABLE 1-continued

| Compound | Structure |
|---|---|
| 026 | 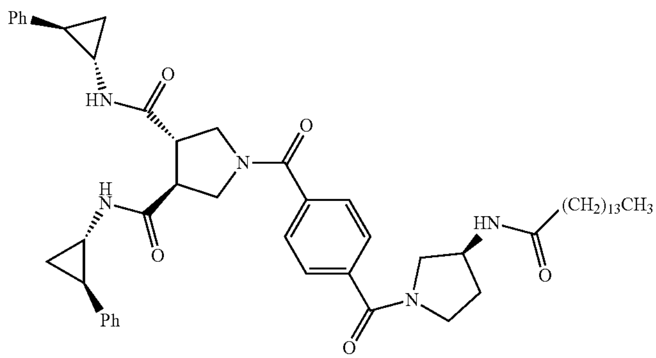 |
| 027 | 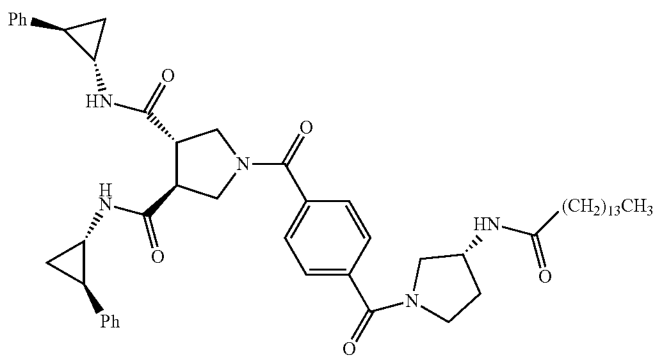 |
| 028 | 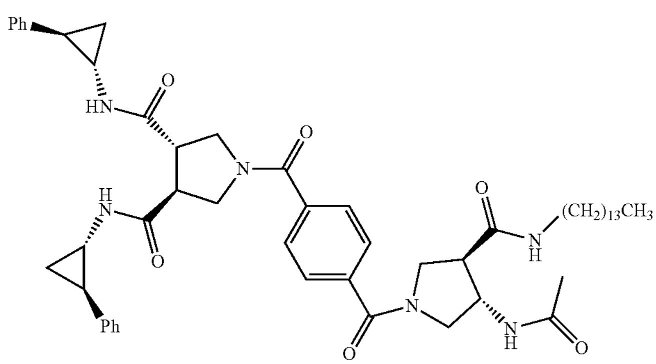 |
| 030 | 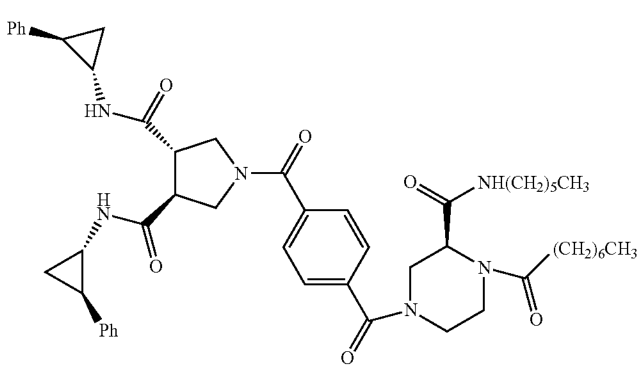 |

TABLE 1-continued

| Compound | Structure |
|---|---|
| 031 | 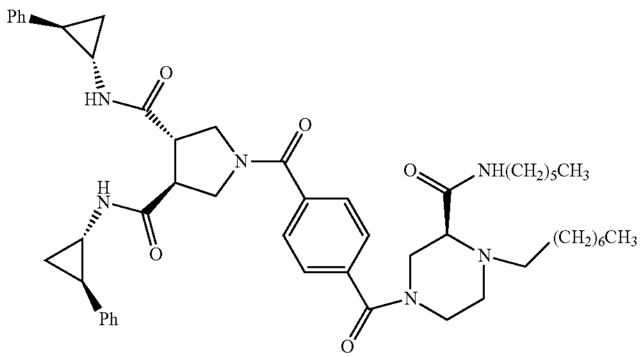 |
| 032 | 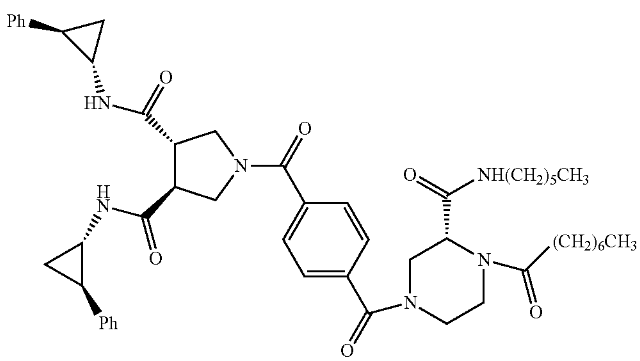 |
| 033 | 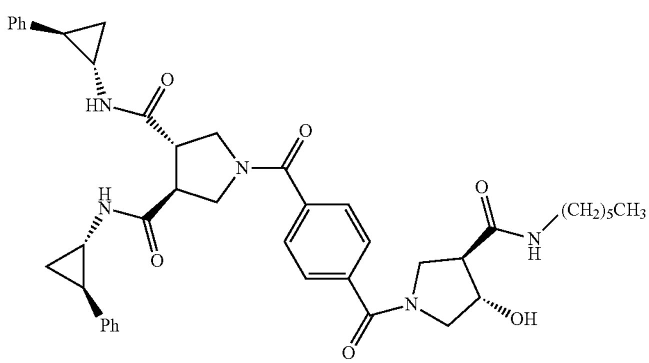 |
| 034 | 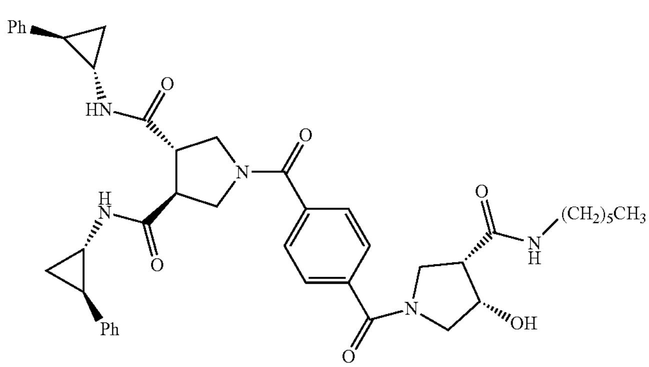 |

TABLE 1-continued

| Compound | Structure |
|---|---|
| 036 | 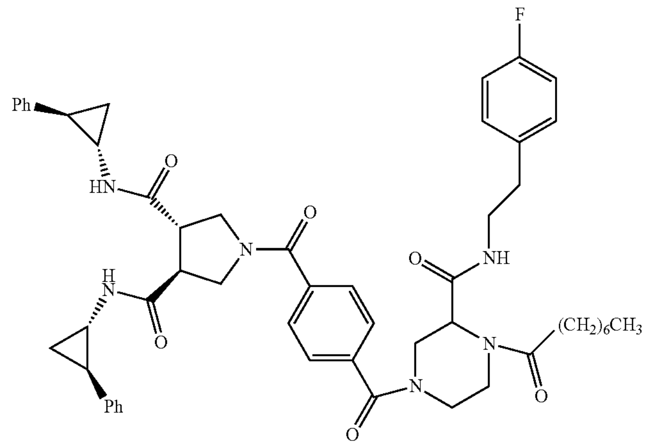 |
| 037 | 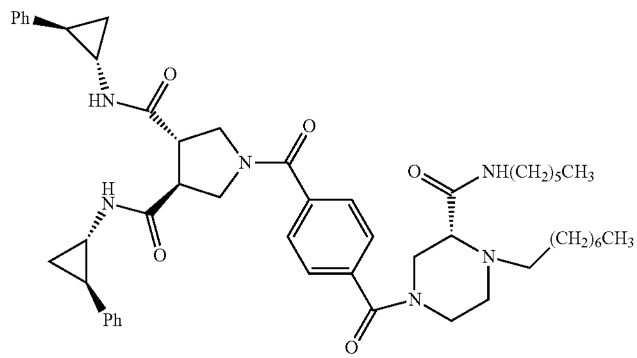 |
| 038 | 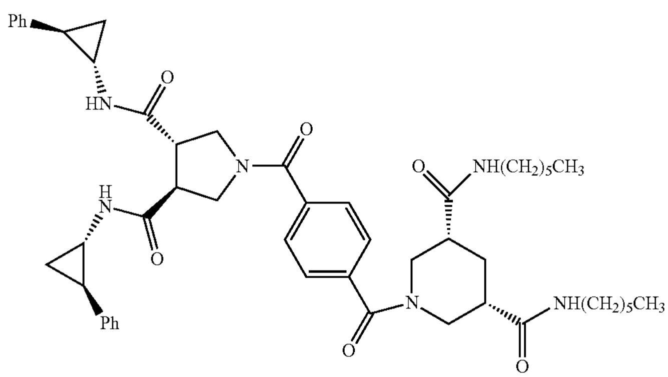 |
| 039 | 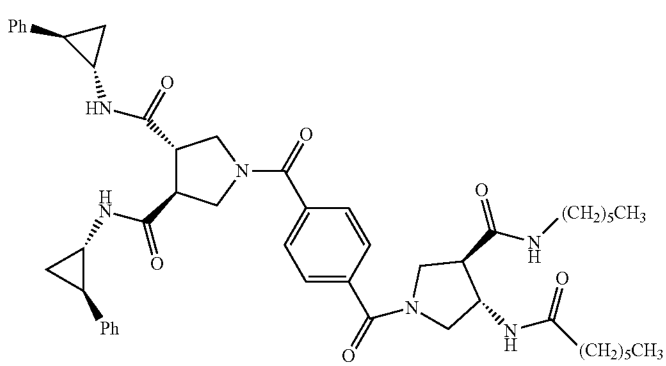 |

TABLE 1-continued

| Compound | Structure |
|---|---|
| 040 | 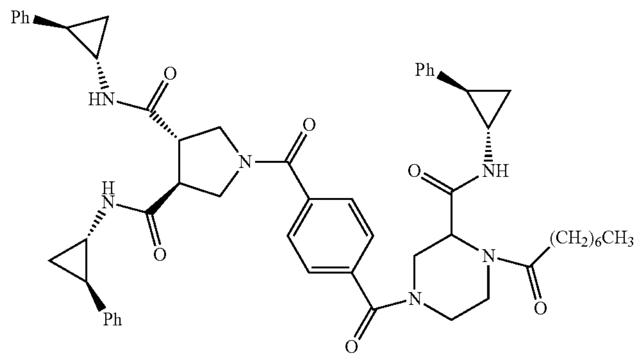 |
| 041 | 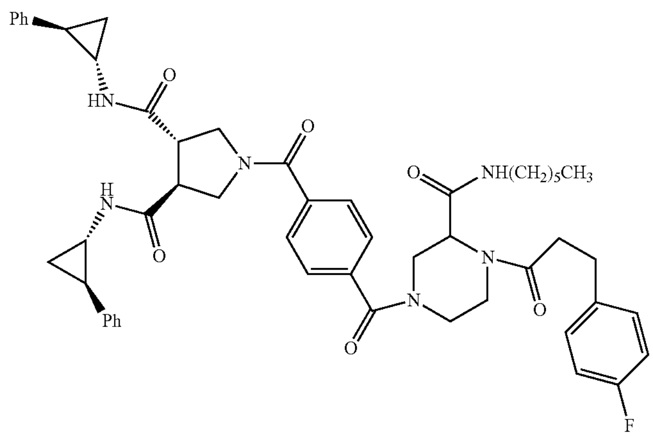 |
| 042 | 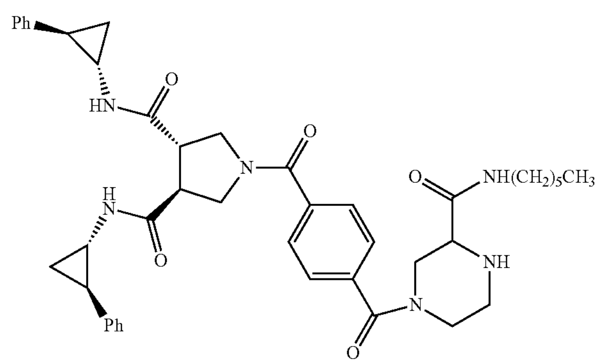 |
| 043 | 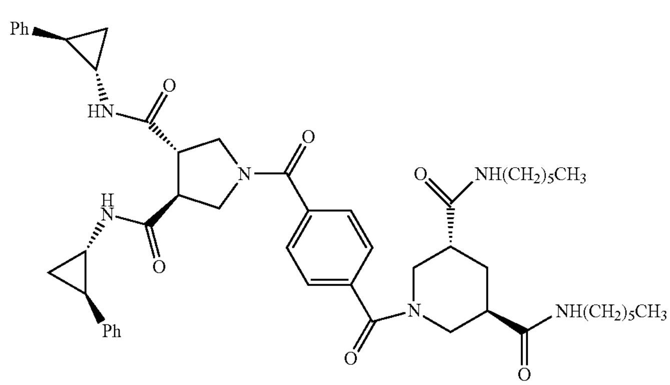 |

TABLE 1-continued
| Compound | Structure |
|---|---|
| 044 | 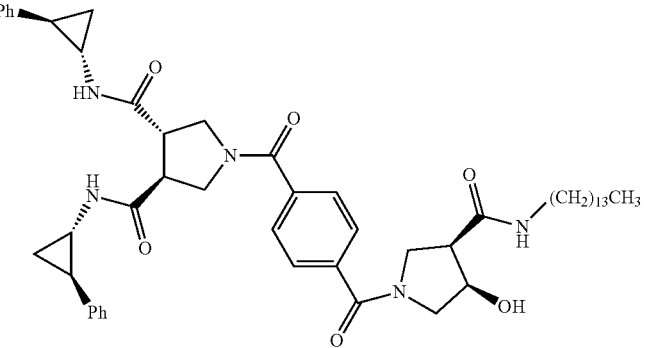 |
| 045 | 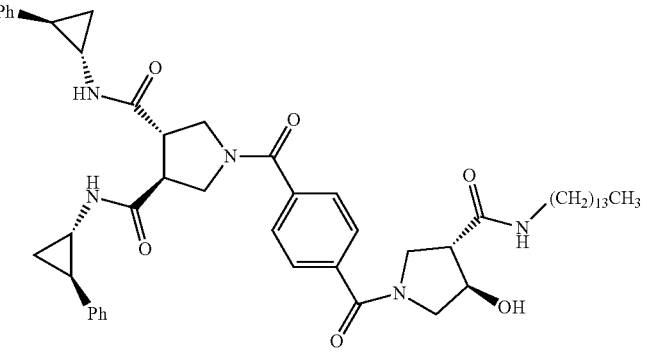 |
| 046 | 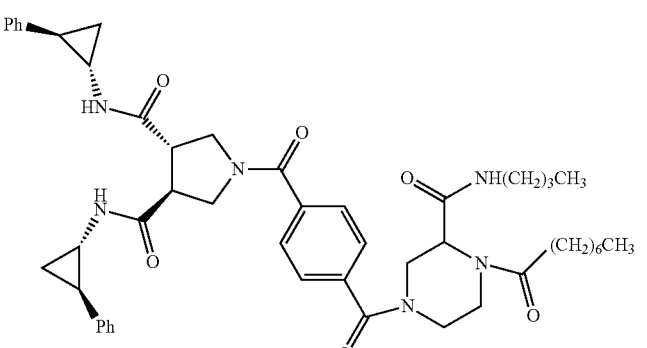 |
| 047 | 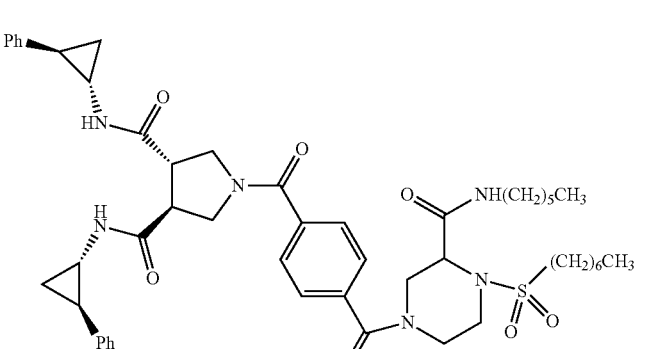 |

TABLE 1-continued

| Compound | Structure |
|---|---|
| 048 | (structure) |
| 049 | (structure) |
| 050 | (structure) |
| 051 | (structure) |

TABLE 1-continued
| Compound | Structure |
|---|---|
| 052 | 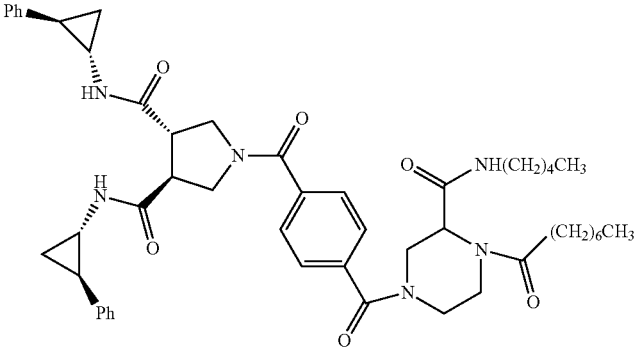 |
| 053 | 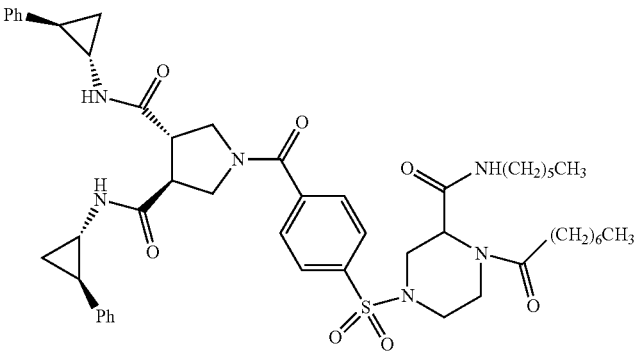 |
| 054 | 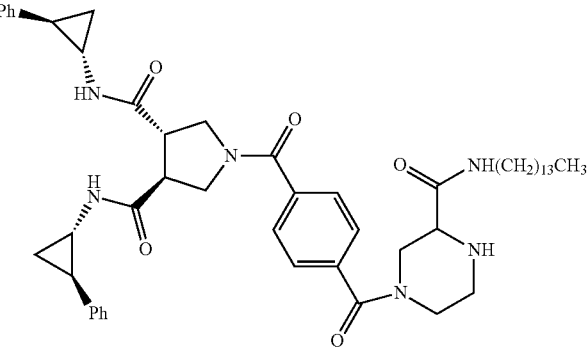 |
| 055 | 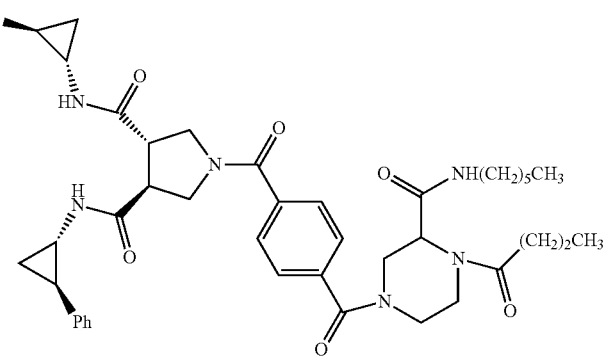 |

TABLE 1-continued

| Compound | Structure |
|---|---|
| 056 | 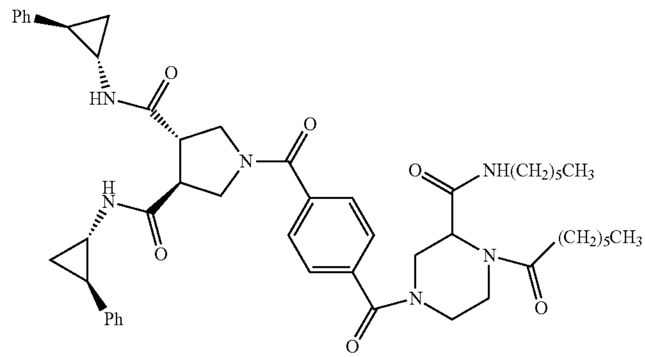 |
| 057 | 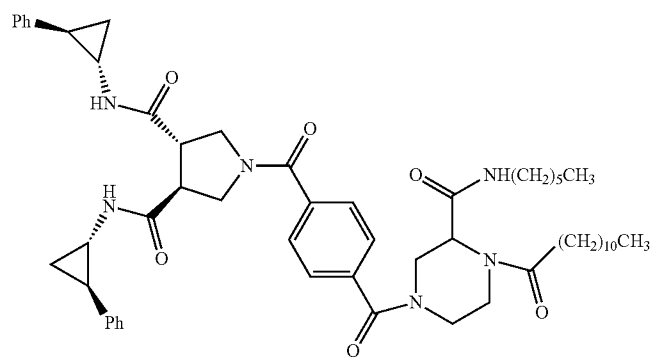 |
| 058 | 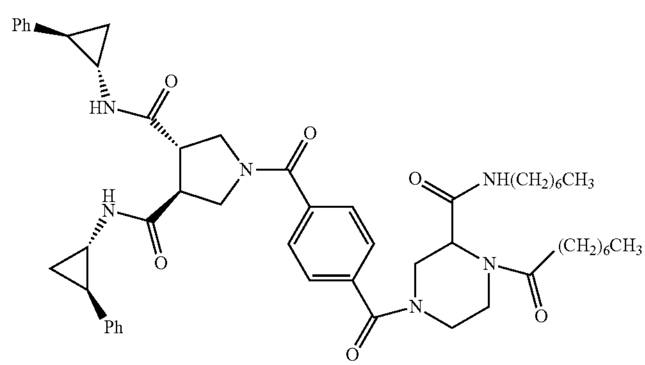 |
| 059 | 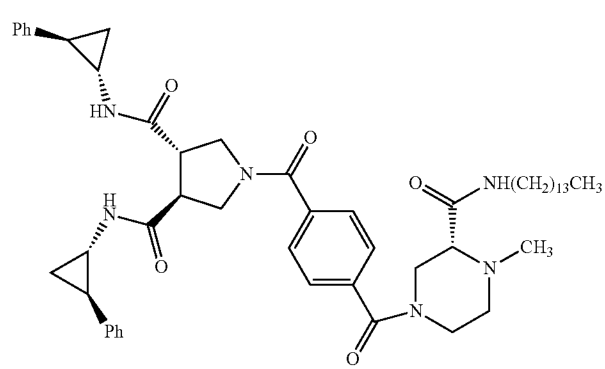 |

TABLE 1-continued

| Compound | Structure |
|---|---|
| 060 | 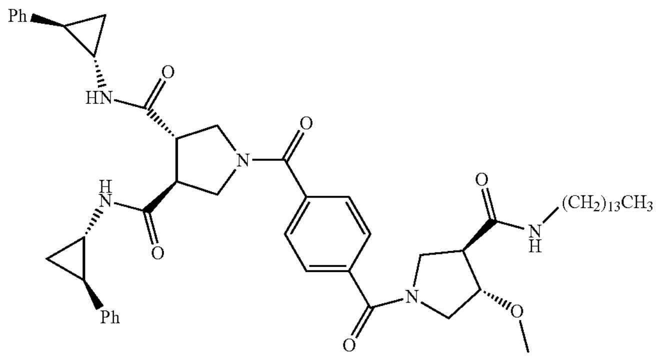 |
| 061 | 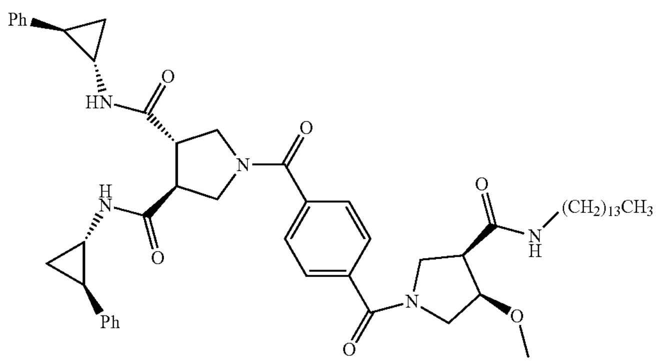 |
| 062 | 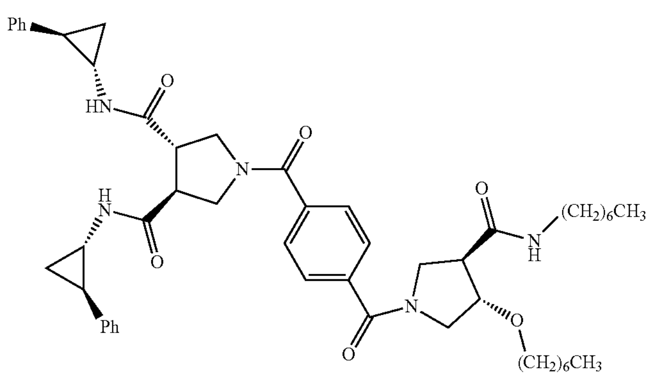 |
| 063 | 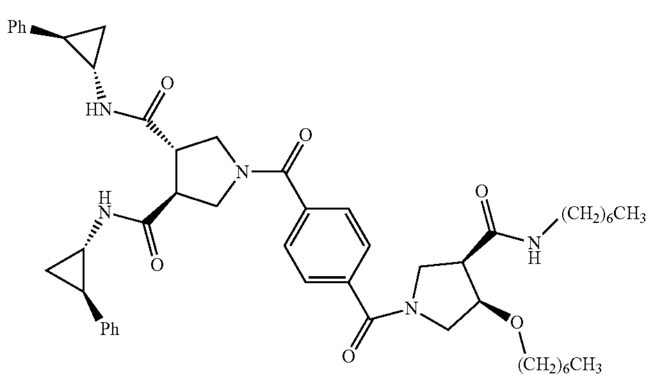 |

TABLE 1-continued

| Compound | Structure |
|---|---|
| 064 | 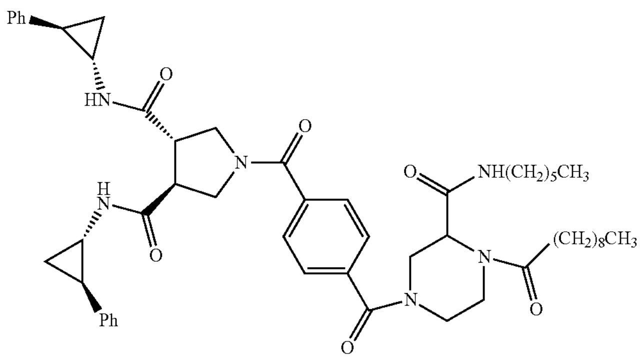 |
| 065 | 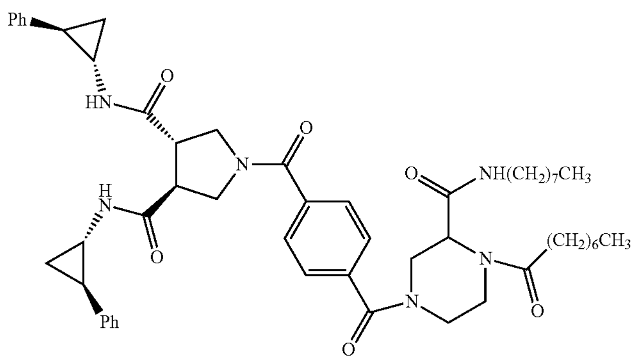 |
| 066 | 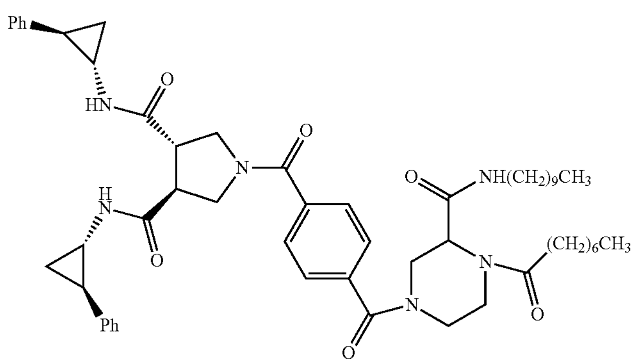 |
| 067 | 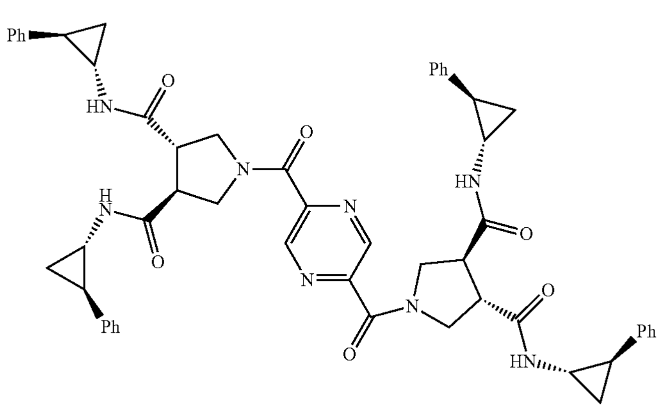 [SMILES: O=C(N[C@H]1C[C@@H]1c1ccccc1)[C@@H]1CN(C(=O)c2cnc(C(=O)N3C[C@@H](C(=O)N[C@H]4C[C@@H]4c4ccccc4)[C@H](C(=O)N[C@H]4C[C@@H]4c4ccccc4)C3)cn2)C[C@H]1C(=O)N[C@H]1C[C@@H]1c1ccccc1] |

TABLE 1-continued

| Compound | Structure |
| --- | --- |
| 068 | 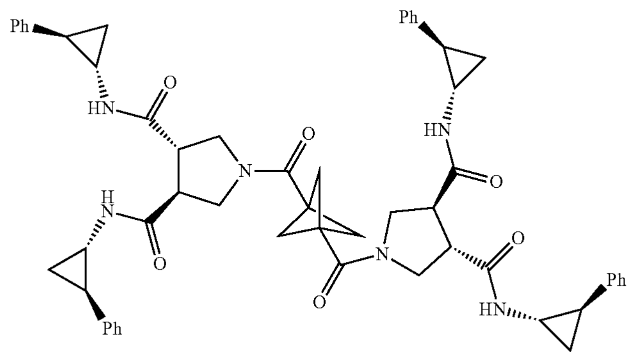 [SMILES: O=C(N[C@H]1C[C@@H]1c1ccccc1)[C@@H]1CN(C(=O)C23CC(C(=O)N4C[C@@H](C(=O)N[C@H]5C[C@@H]5c5ccccc5)[C@H](C(=O)N[C@H]5C[C@@H]5c5ccccc5)C4)(C2)C3)C[C@H]1C(=O)N[C@H]1C[C@@H]1c1ccccc1] |
| 069 | 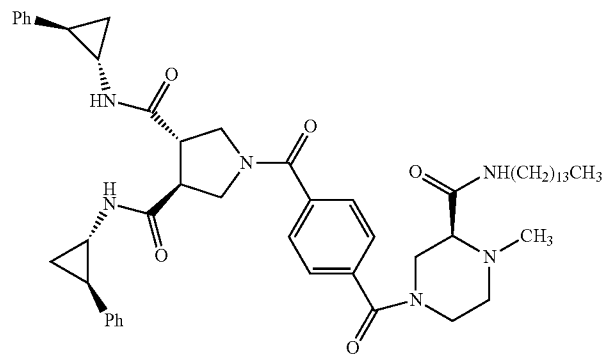 |
| 070 | 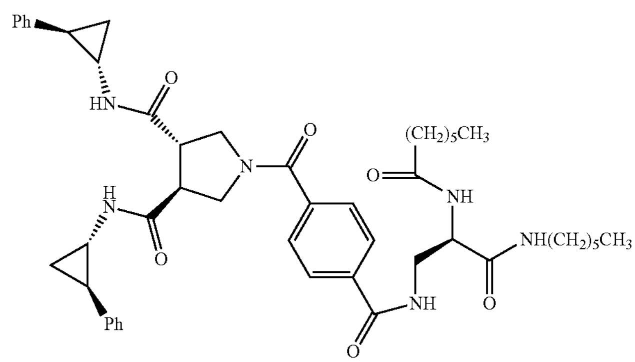 |
| 071 | 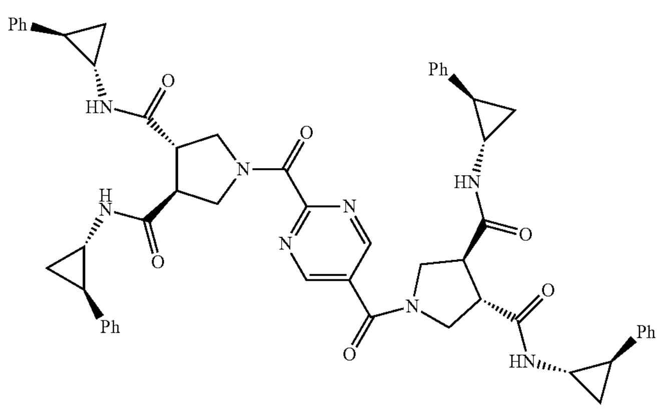 [SMILES: O=C(N[C@H]1C[C@@H]1c1ccccc1)[C@@H]1CN(C(=O)c2cnc(C(=O)N3C[C@@H](C(=O)N[C@H]4C[C@@H]4c4ccccc4)[C@H](C(=O)N[C@H]4C[C@@H]4c4ccccc4)C3)nc2)C[C@H]1C(=O)N[C@H]1C[C@@H]1c1ccccc1] |

TABLE 1-continued

| Compound | Structure |
|---|---|
| 072 | 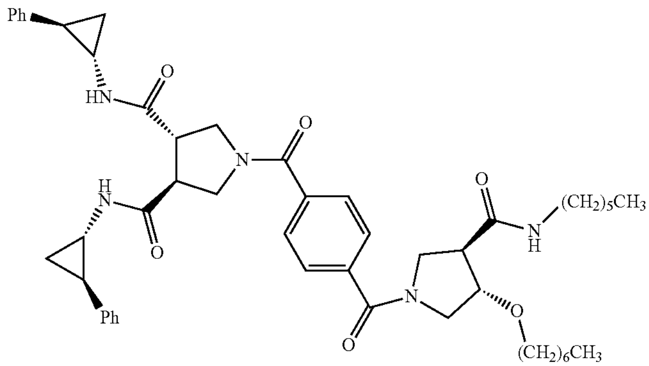 |
| 073 | 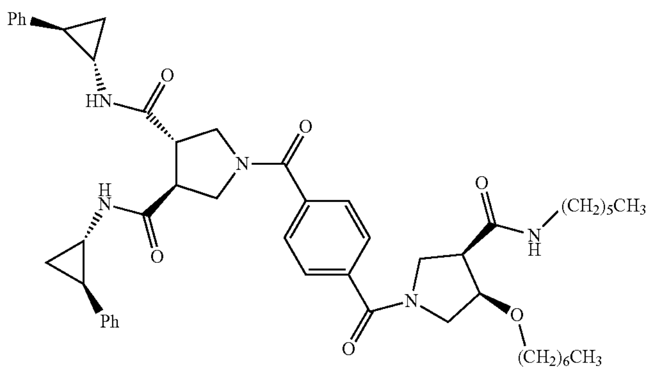 |
| 074 | 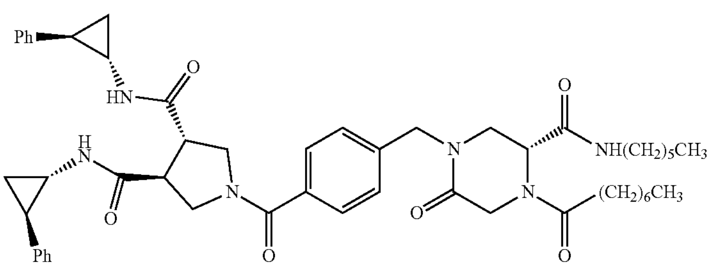 |
| 075 | 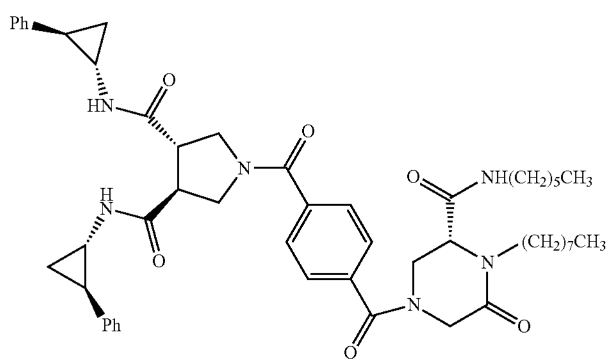 |

TABLE 1-continued

| Compound | Structure |
|---|---|
| 076 | 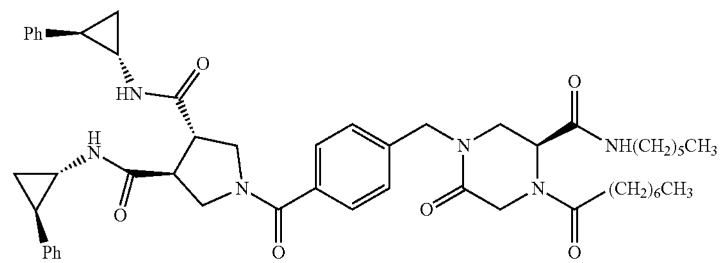 |

In certain embodiments, the compound of Formula (IA) or (TB) is selected from the compounds of Table 2.

TABLE 2

| Compound | Structure |
|---|---|
| 077 | 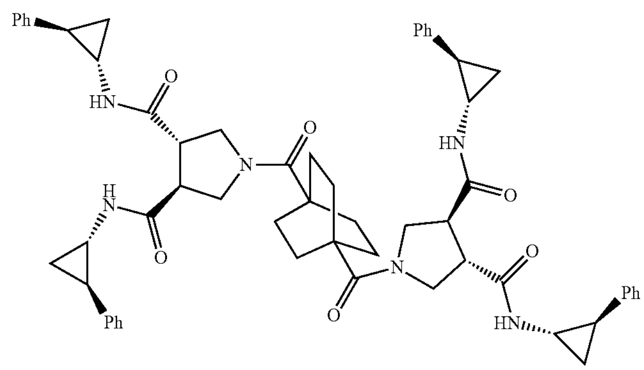 [SMILES: O=C(N[C@H]1C[C@@H]1c1ccccc1)[C@@H]1CN(C(=O)C23CCC(C(=O)N4C[C@@H](C(=O)N[C@H]5C[C@@H]5c5ccccc5)[C@H](C(=O)N[C@H]5C[C@@H]5c5ccccc5)C4)(CC2)CC3)C[C@H]1C(=O)N[C@H]1C[C@@H]1c1ccccc1] |
| 078 | 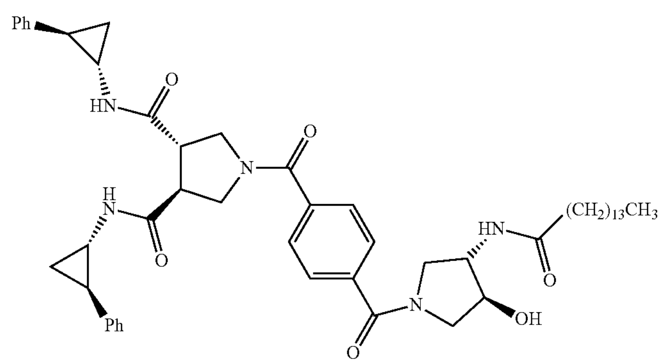 |
| 079 | 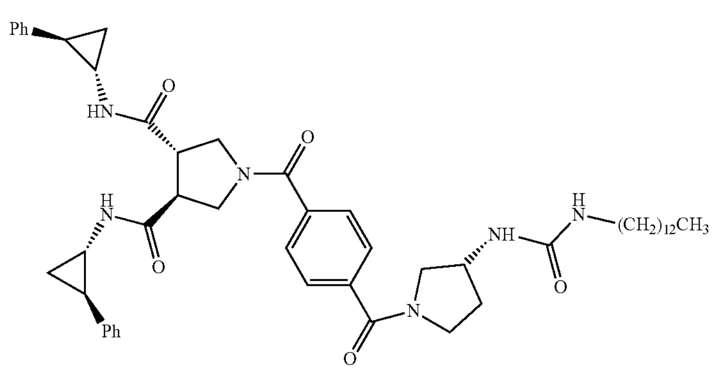 |

TABLE 2-continued

| Compound | Structure |
|---|---|
| 080 | 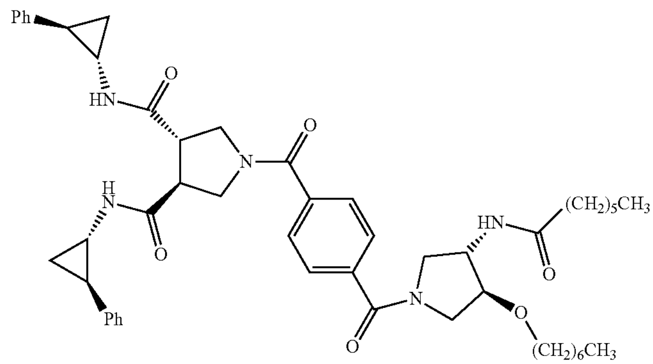 |
| 081 | 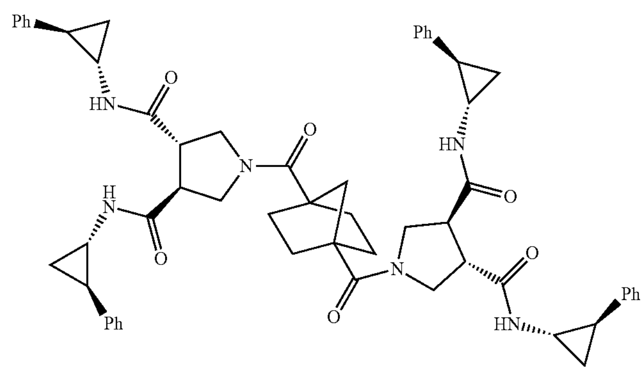 [SMILES: O=C(N[C@H]1C[C@@H]1c1ccccc1)[C@@H]1CN(C(=O)C23CCC(C(=O)N4C[C@@H](C(=O)N[C@H]5C[C@@H]5c5ccccc5)[C@H](C(=O)N[C@H]5C[C@@H]5c5ccccc5)C4)(CC2)C3)C[C@H]1C(=O)N[C@H]1C[C@@H]1c1ccccc1] |
| 082 | 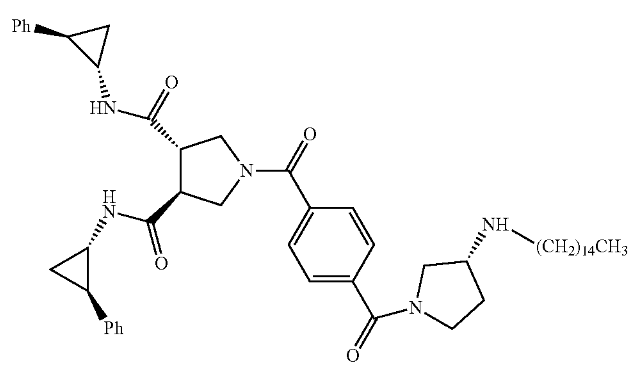 |
| 083 | 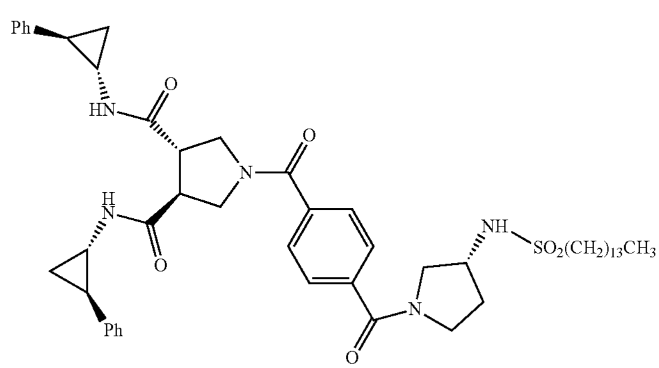 |

TABLE 2-continued

| Compound | Structure |
|---|---|
| 084 | (structure) |
| 085 | (structure) |
| 086 | (structure) |
| 087 | (structure) |

TABLE 2-continued

| Compound | Structure |
|---|---|
| 088 | (structure) |
| 089 | (structure) |
| 090 | (structure) |
| 091 | (structure) |

TABLE 2-continued
| Compound | Structure |
|---|---|
| 092 | 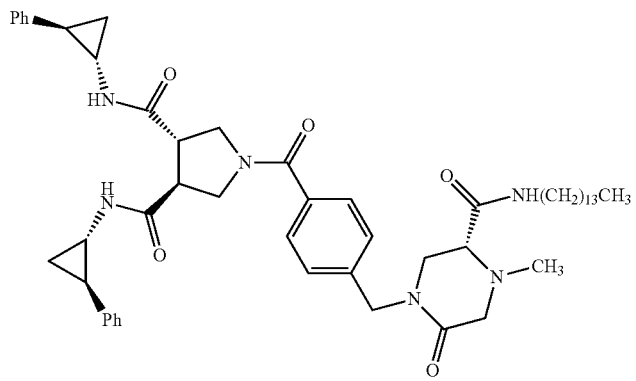 |
| 093 | 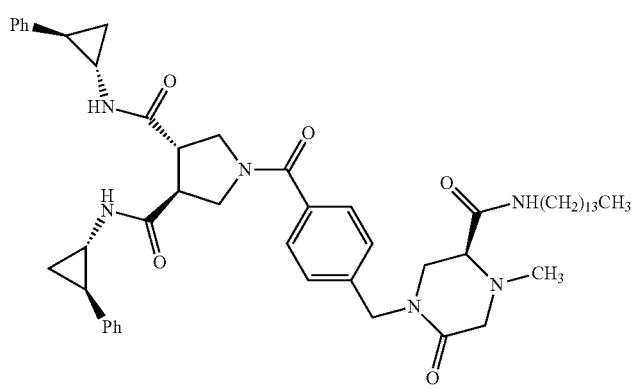 |
| 094 | 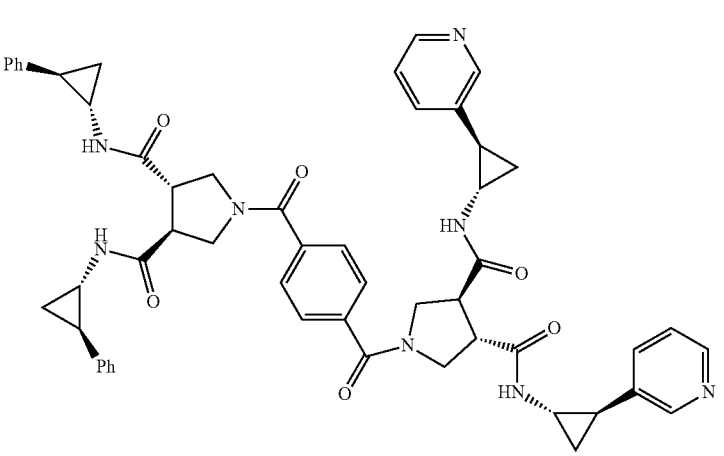 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4cccnc4)[C@H](C(=O)N[C@H]4C[C@@H]4c4cccnc4)C3)cc2)C[C@H]1C(=O)N[C@H]1C[C@@H]1c1ccccc1] |

TABLE 2-continued
| Compound | Structure |
|---|---|
| 095 | 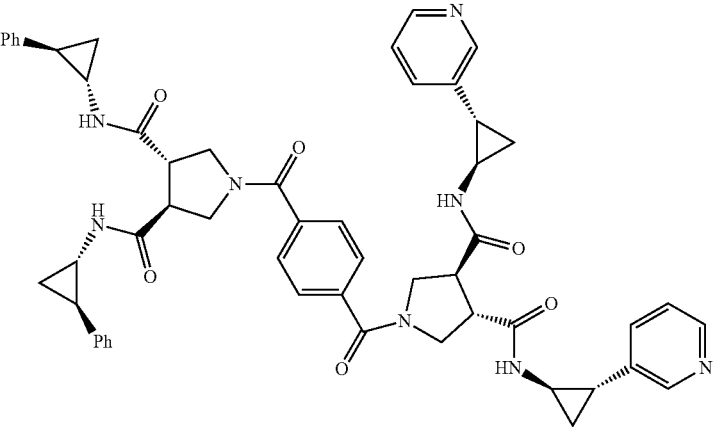 [SMILES: O=C(N[C@H]1C[C@@H]1c1ccccc1)[C@@H]1CN(C(=O)c2ccc(C(=O)N3C[C@@H](C(=O)N[C@@H]4C[C@H]4c4cccnc4)[C@H](C(=O)N[C@@H]4C[C@H]4c4cccnc4)C3)cc2)C[C@H]1C(=O)N[C@H]1C[C@@H]1c1ccccc1] |
| 096 | 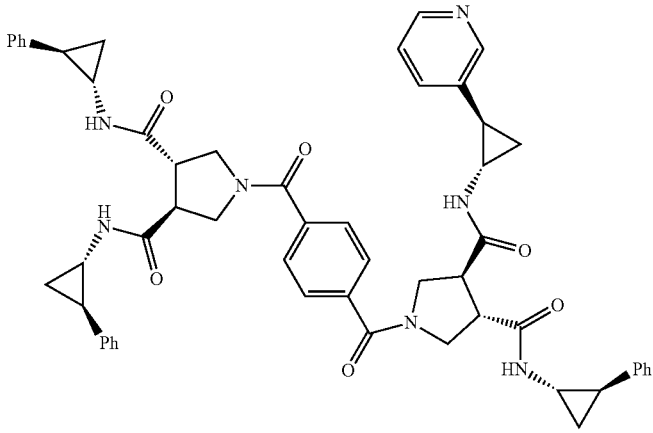 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4cccnc4)C3)cc2)C[C@H]1C(=O)N[C@H]1C[C@@H]1c1ccccc1] |
| 097 | 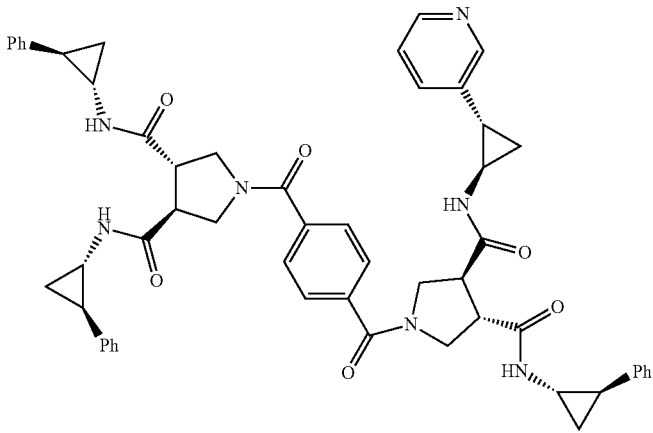 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@@H]4C[C@H]4c4cccnc4)C3)cc2)C[C@H]1C(=O)N[C@H]1C[C@@H]1c1ccccc1] |

TABLE 2-continued
| Compound | Structure |
|---|---|
| 098 | 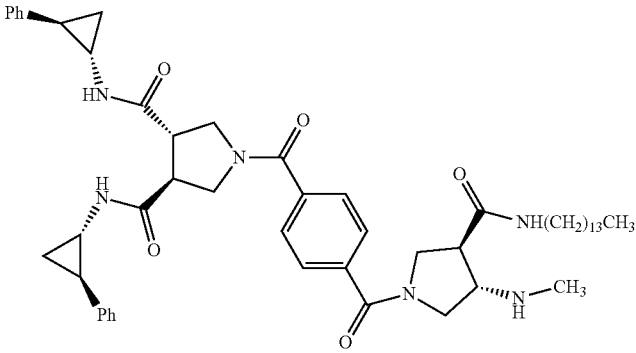 |
| 099 | 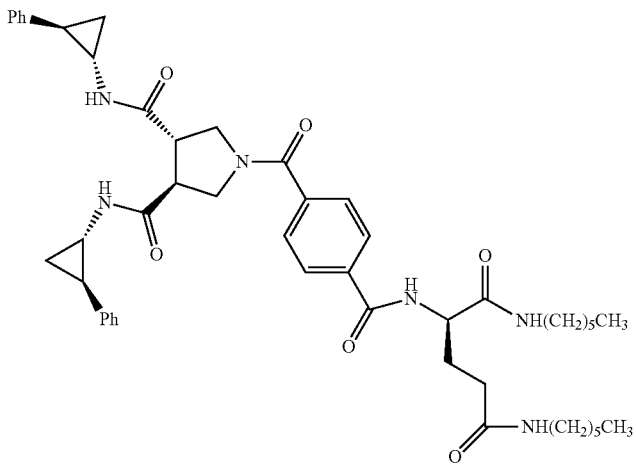 |
| 100 | 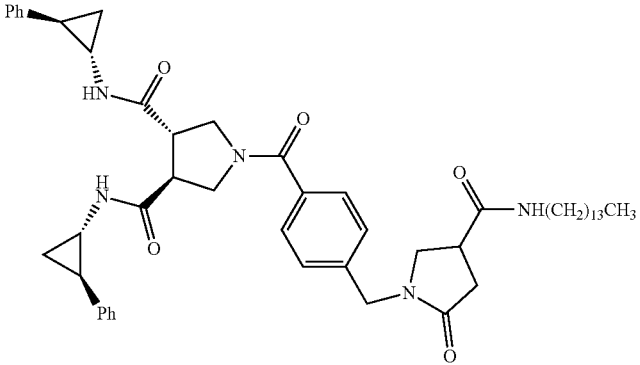 |
| 101 | 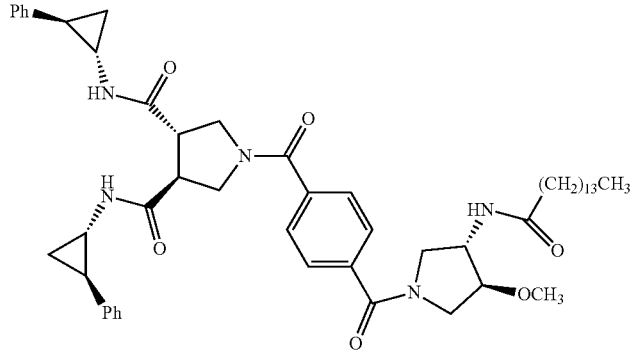 |

TABLE 2-continued

| Compound | Structure |
|---|---|
| 102 | 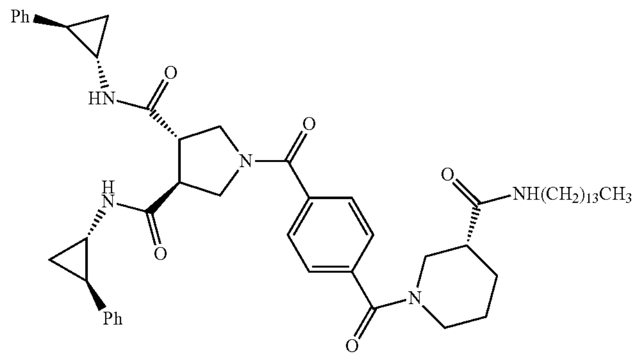 |
| 103 | 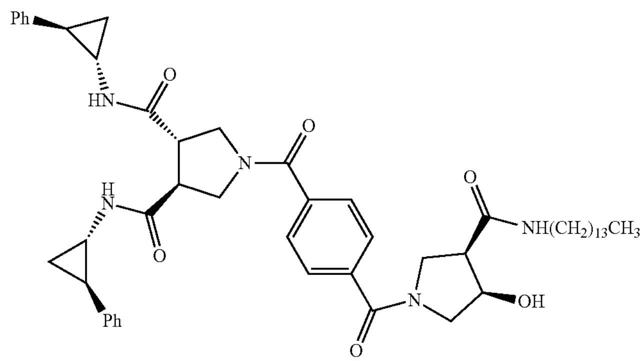 |
| 104 | 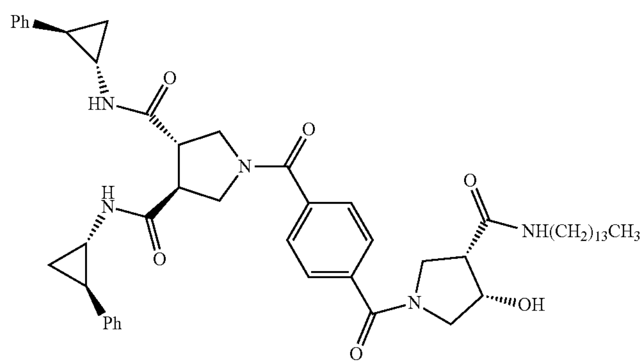 |
| 105 | 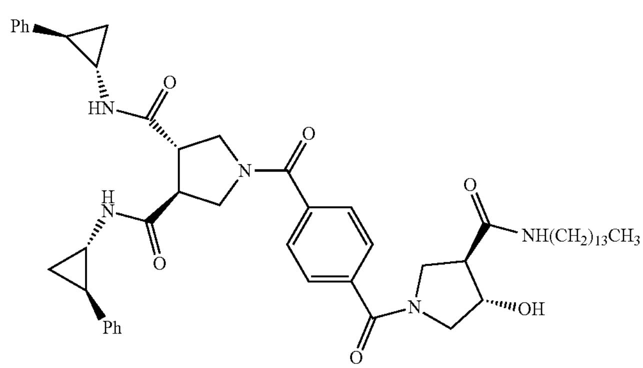 |

TABLE 2-continued

| Compound | Structure |
|---|---|
| 106 | 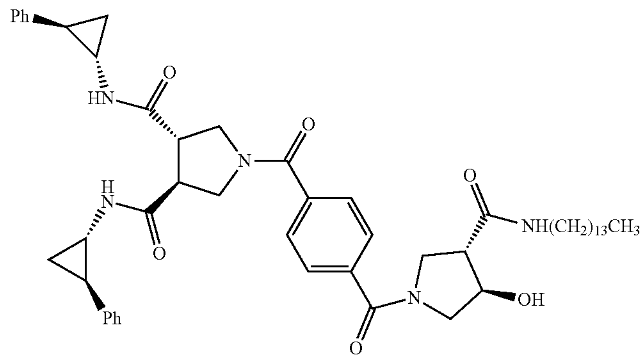 |
| 107 | 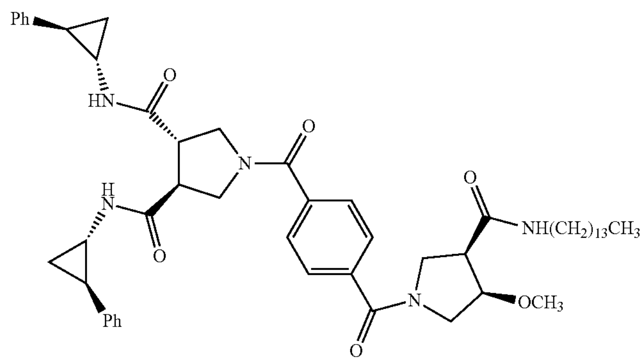 |
| 108 | 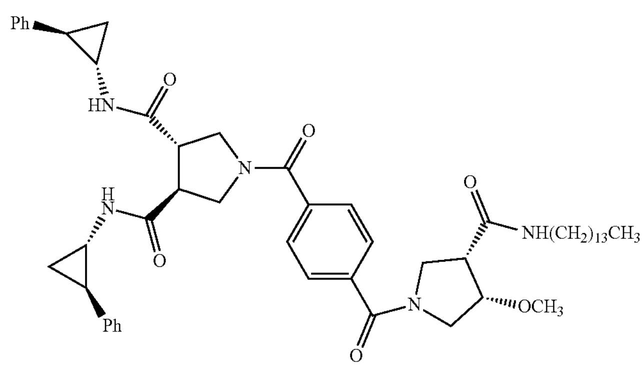 |
| 109 | 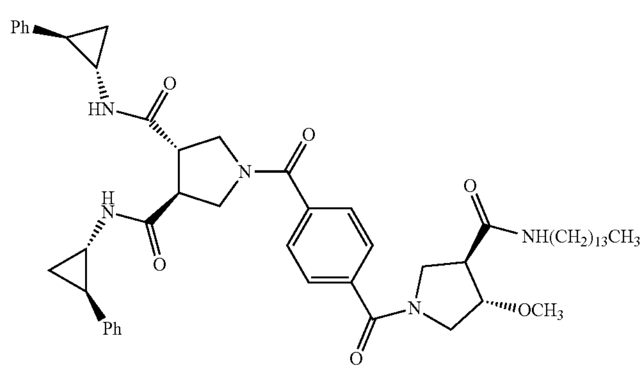 |

TABLE 2-continued

| Compound | Structure |
|---|---|
| 110 | 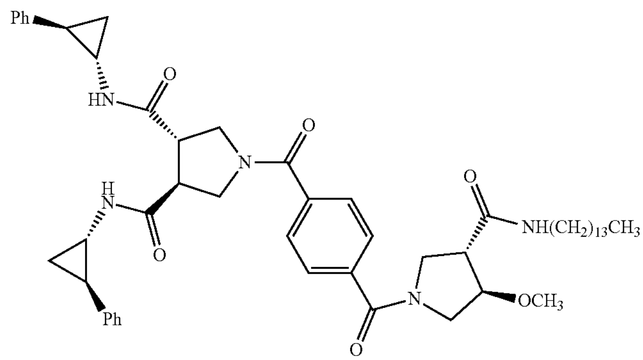 |
| 111 | 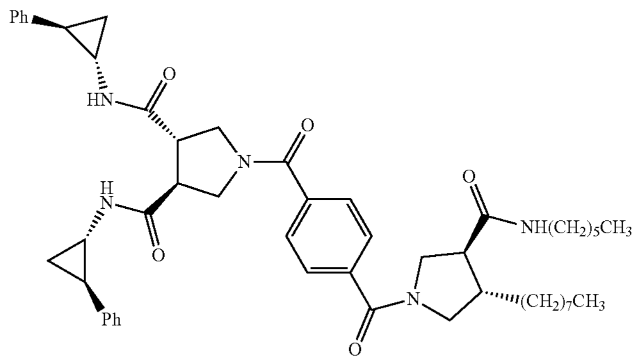 |
| 112 | 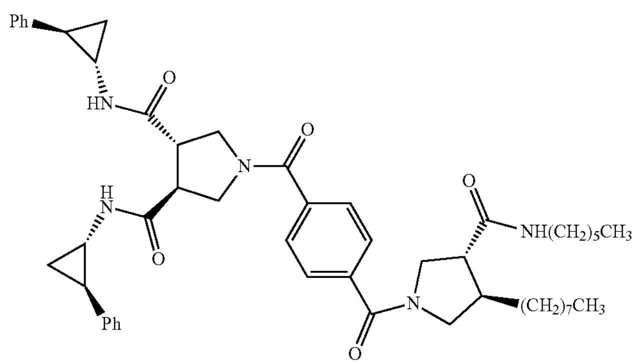 |
| 113 | 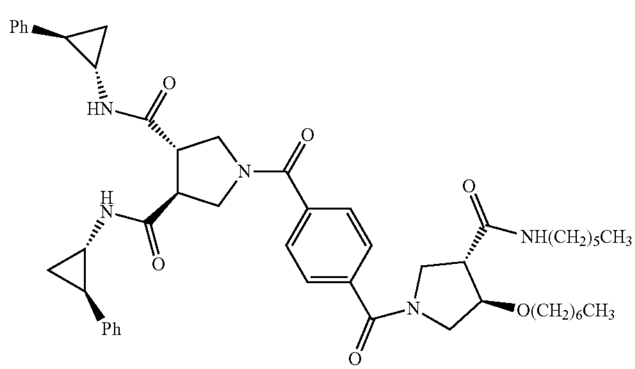 |

TABLE 2-continued

| Compound | Structure |
|---|---|
| 114 | 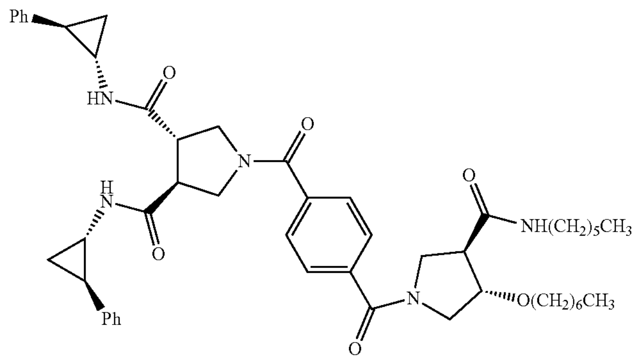 |
| 115 | 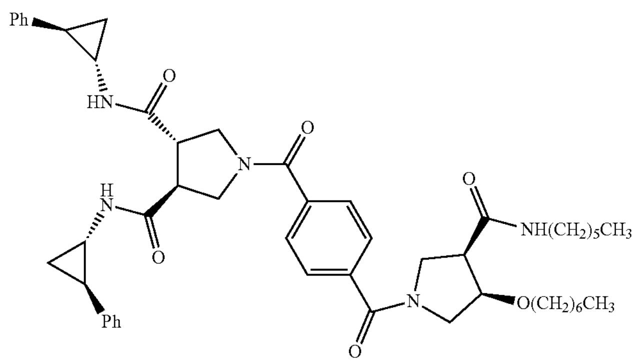 |
| 116 | 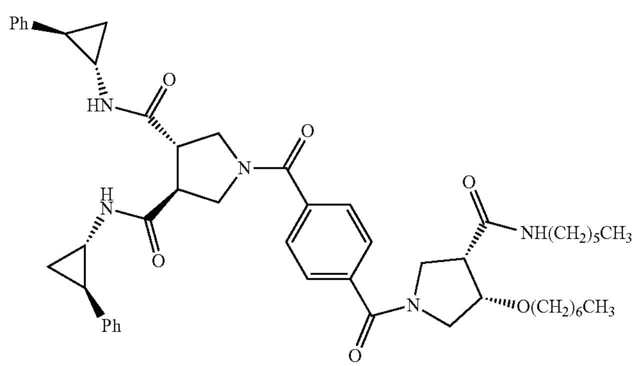 |
| 117 | 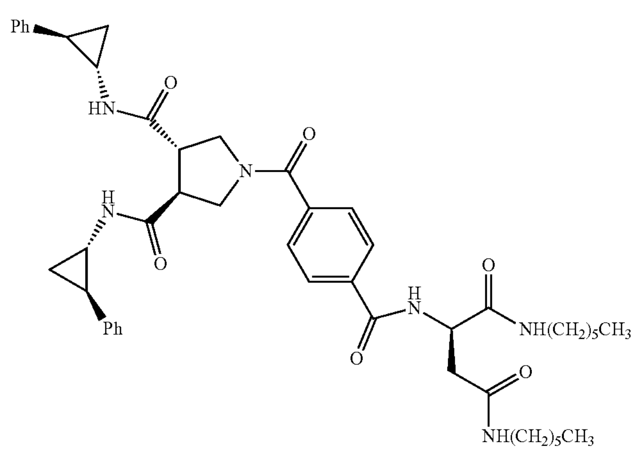 |

TABLE 2-continued
| Compound | Structure |
|---|---|
| 118 | 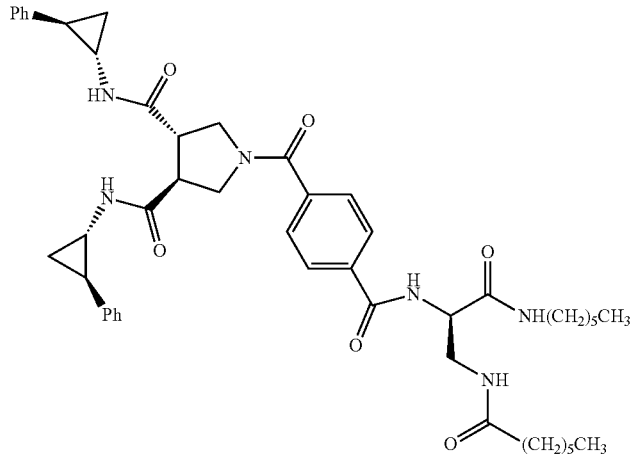 |
| 119 | 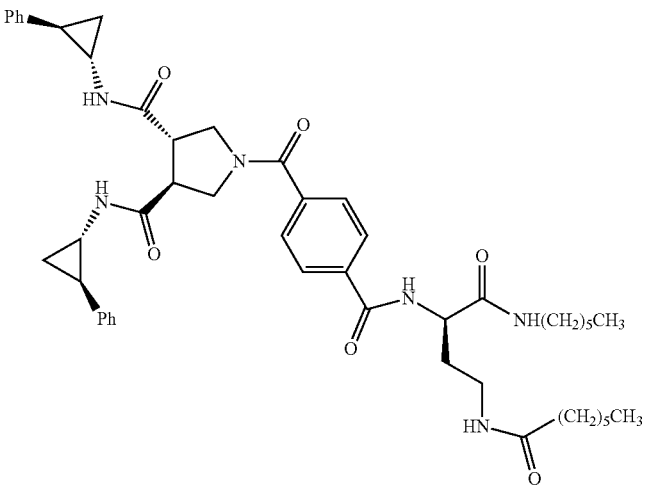 |
| 120 | 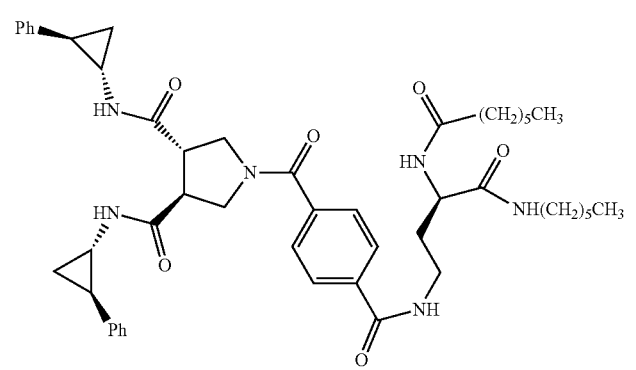 |

TABLE 2-continued

| Compound | Structure |
|---|---|
| 121 | 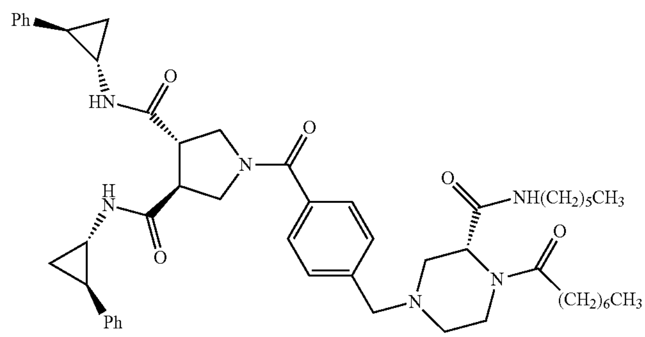 |
| 122 | 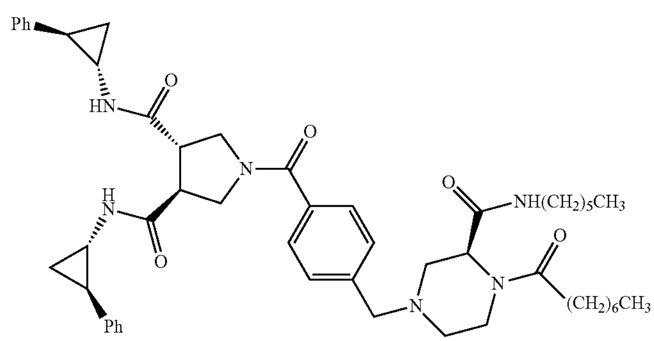 |
| 123 | 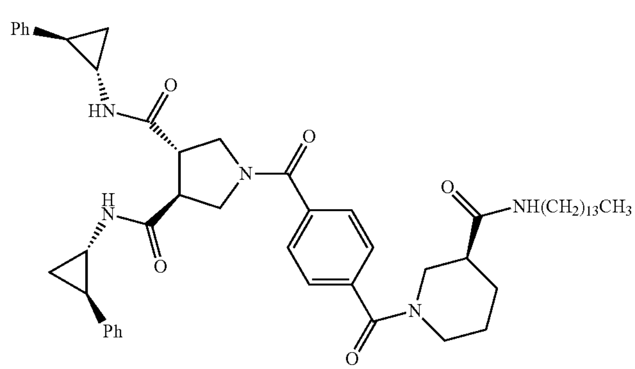 |
| 124 | 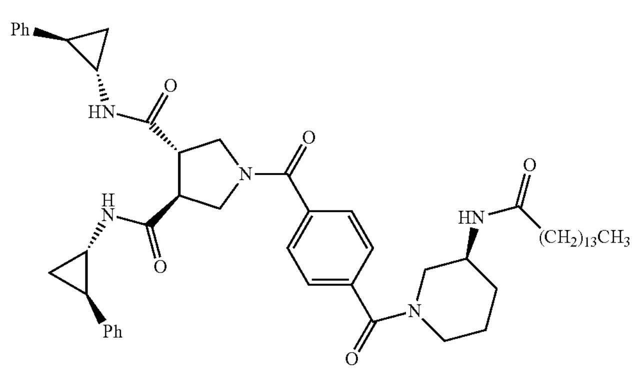 |

TABLE 2-continued
| Compound | Structure |
|---|---|
| 125 | 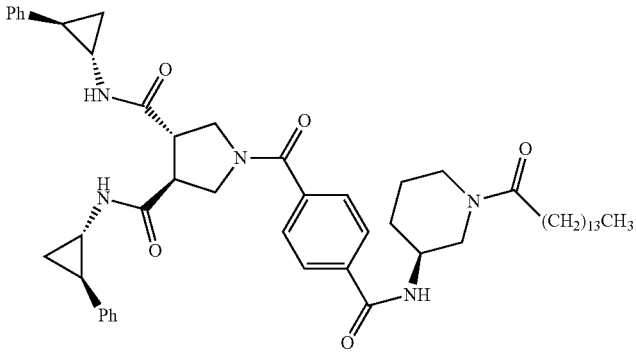 |
| 126 | 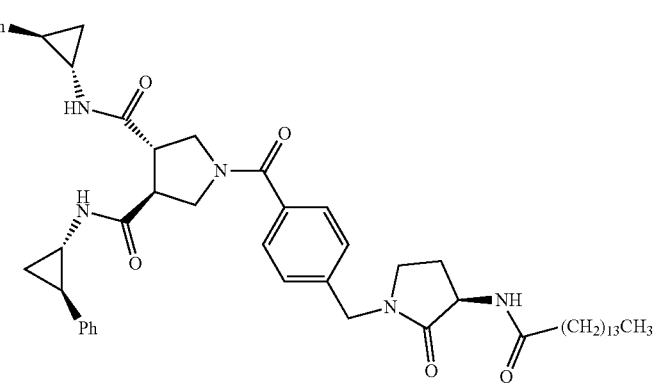 |
| 127 | 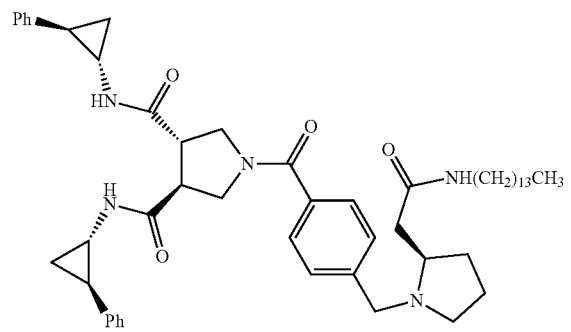 |
| 128 | 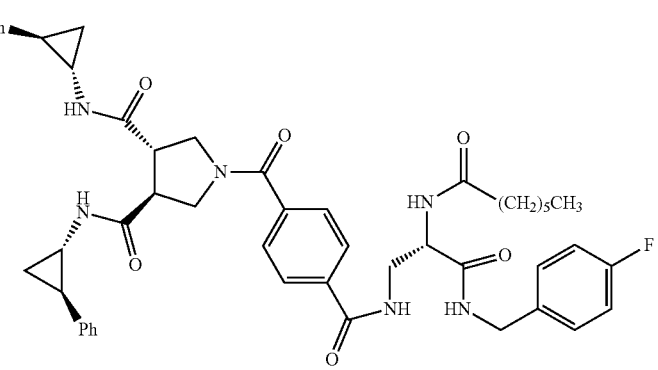 |

TABLE 2-continued

| Compound | Structure |
|---|---|
| 129 | 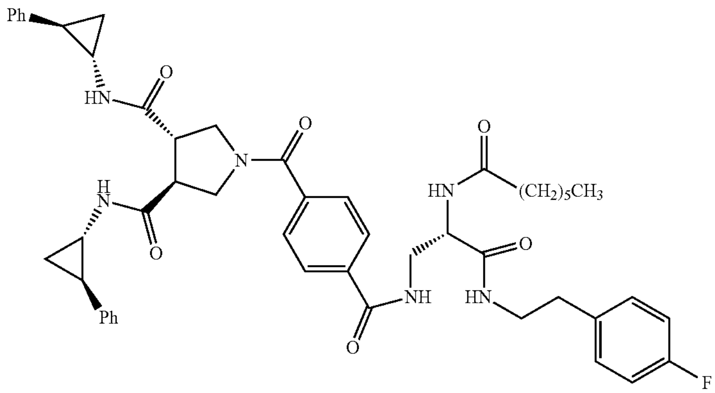 |
| 130 | 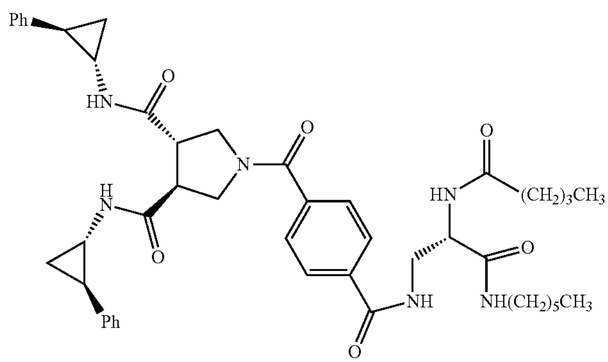 |
| 131 | 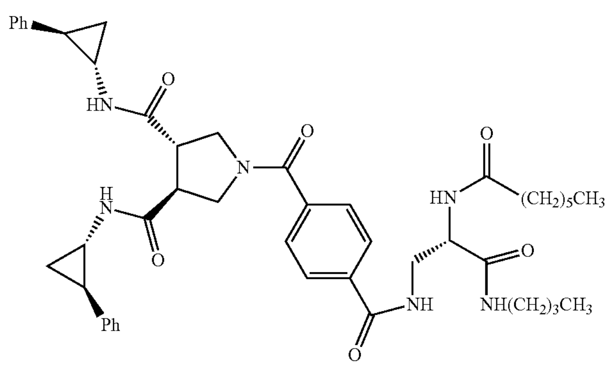 |
| 132 | 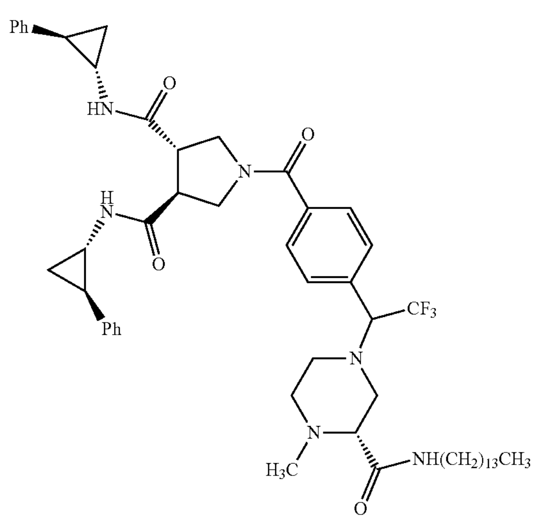 |

TABLE 2-continued

| Compound | Structure |
|---|---|
| 133 | 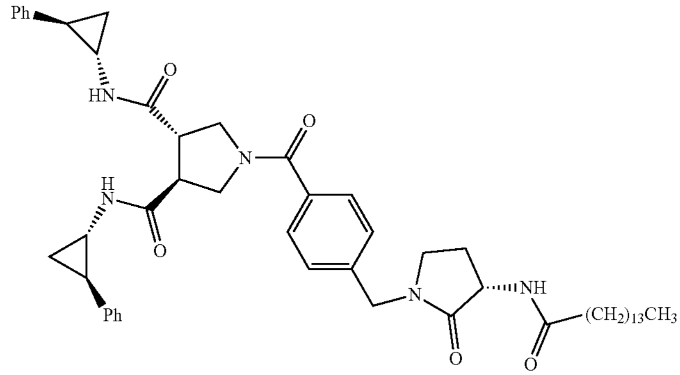 |
| 134 | 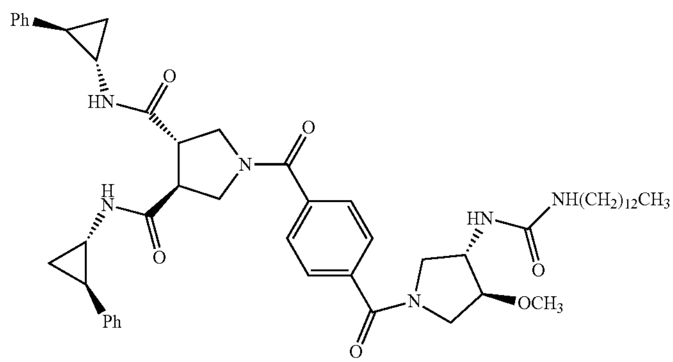 |
| 135 | 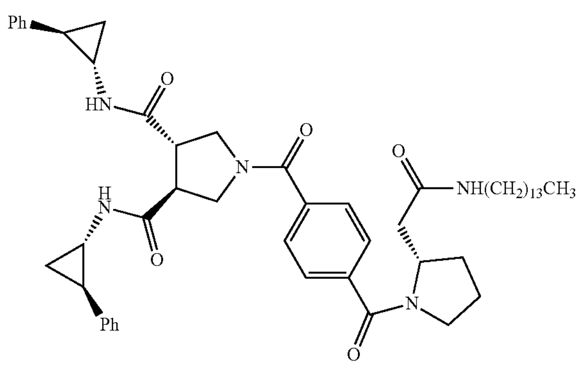 |
| 136 | 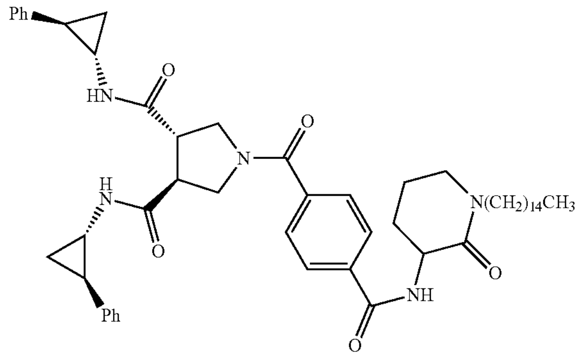 |

TABLE 2-continued

| Compound | Structure |
|---|---|
| 137 | 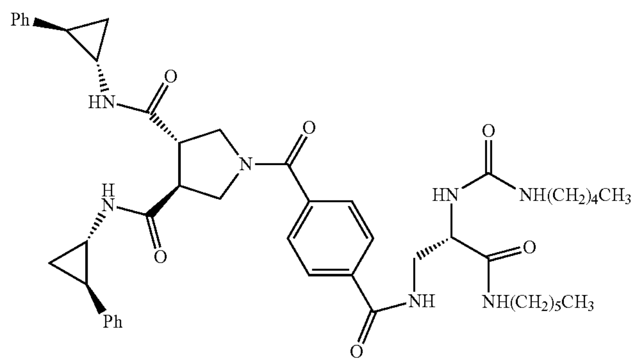 |
| 138 | 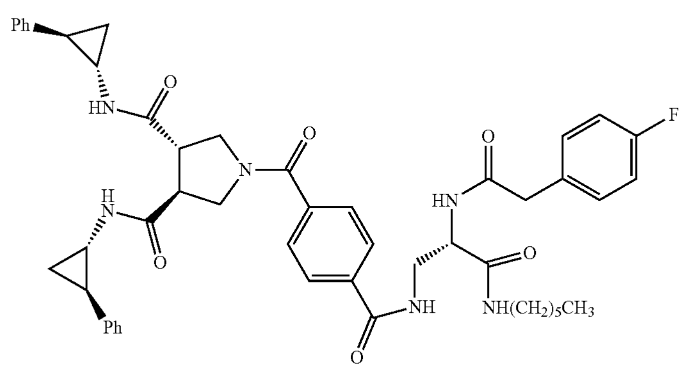 |
| 139 | 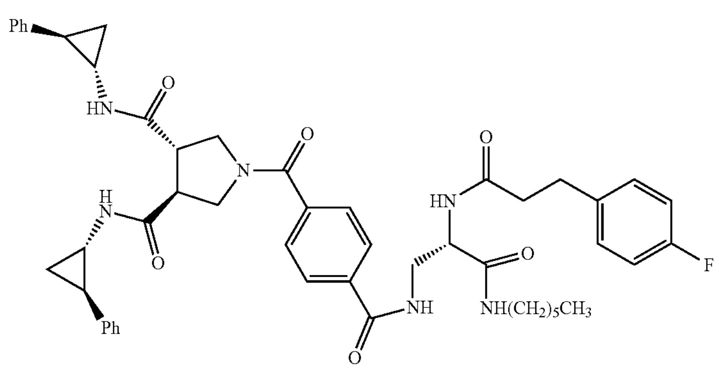 |
| 140 | 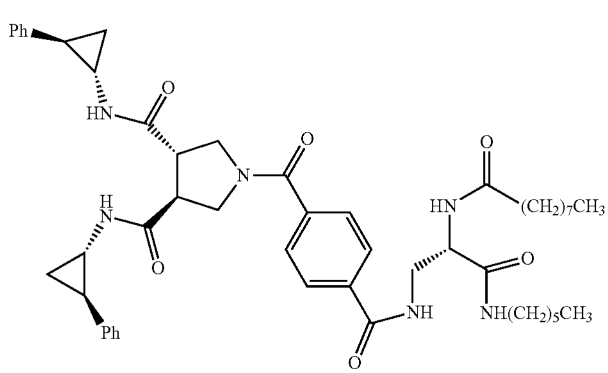 |

TABLE 2-continued
| Compound | Structure |
|---|---|
| 141 | 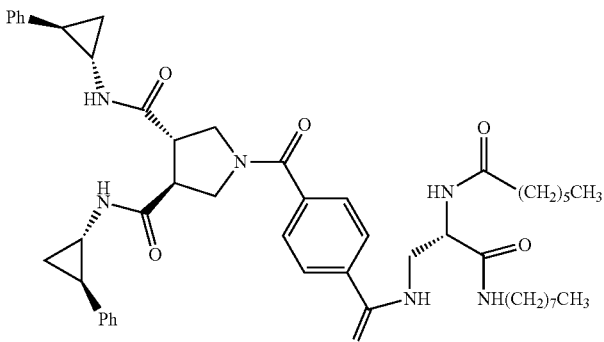 |
| 142 | 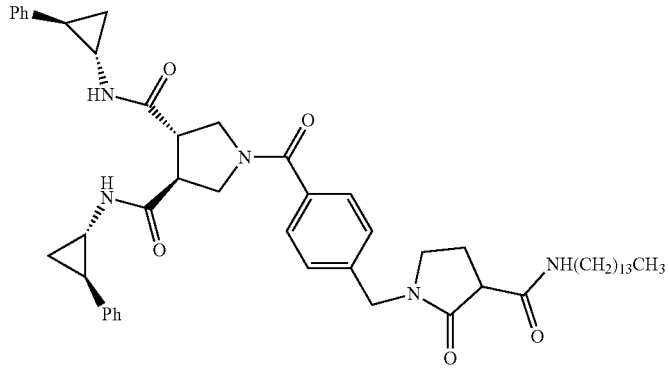 |
| 143 | 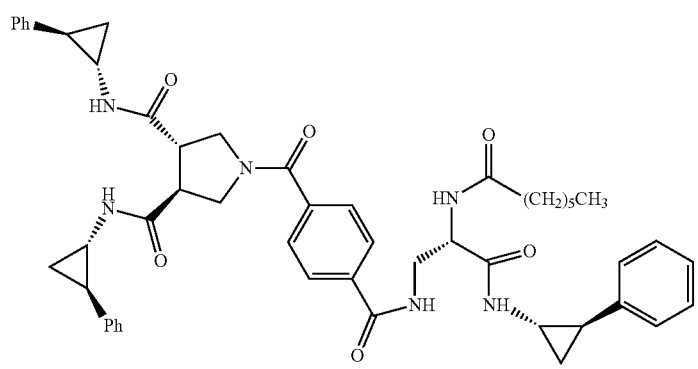 |
| 144 | 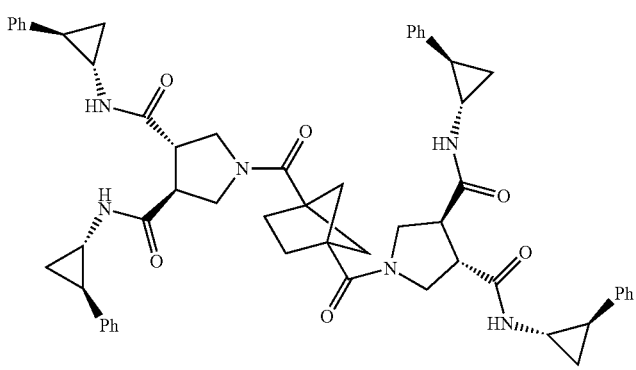 [SMILES: O=C(N[C@H]1C[C@@H]1c1ccccc1)[C@@H]1CN(C(=O)C23CCC(C(=O)N4C[C@@H](C(=O)N[C@H]5C[C@@H]5c5ccccc5)[C@H](C(=O)N[C@H]5C[C@@H]5c5ccccc5)C4)(C2)C3)C[C@H]1C(=O)N[C@H]1C[C@@H]1c1ccccc1] |

TABLE 2-continued
| Compound | Structure |
|---|---|
| 145 | 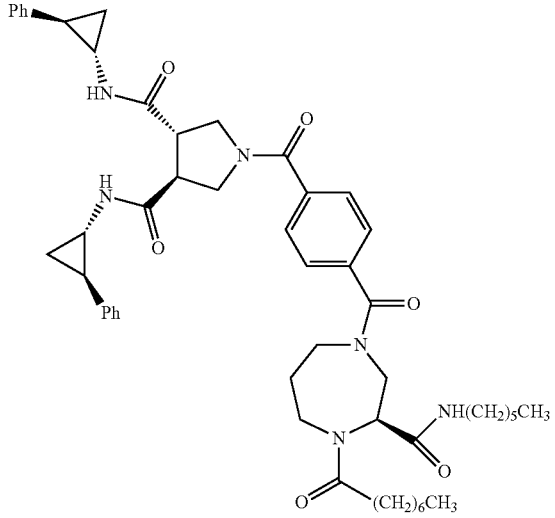 |
| 146 | 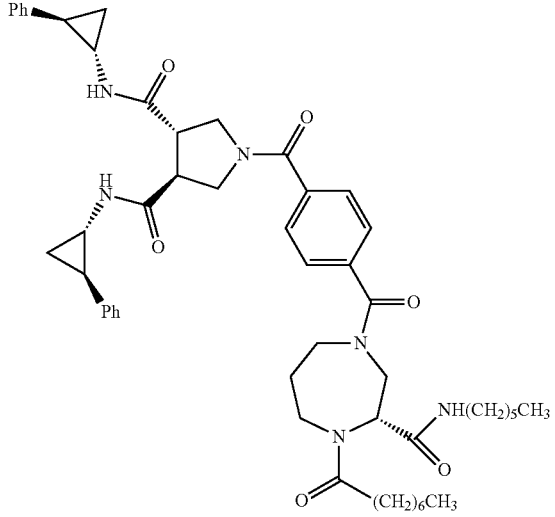 |
| 147 | 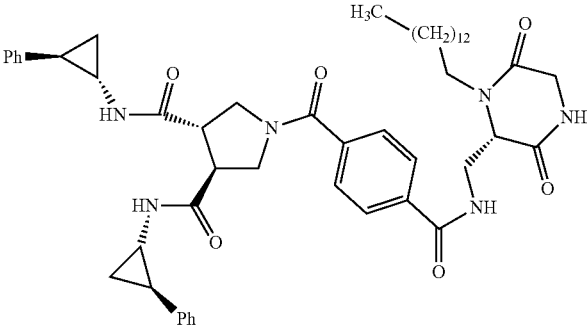 |

TABLE 2-continued

| Compound | Structure |
|---|---|
| 148 | 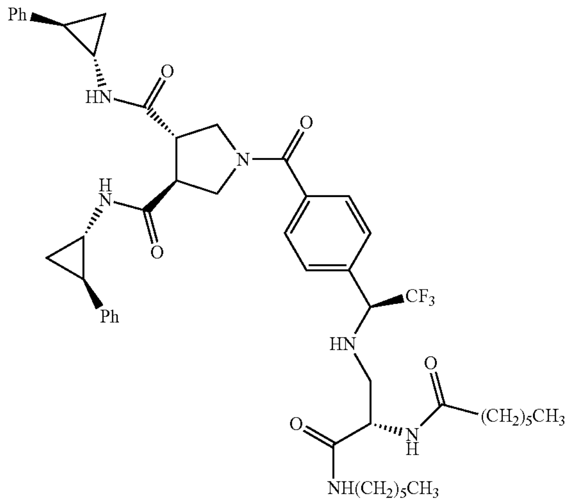 |
| 149 | 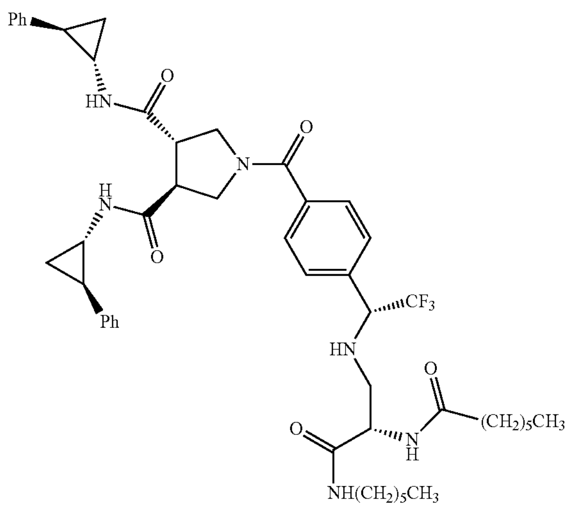 |
| 150 | 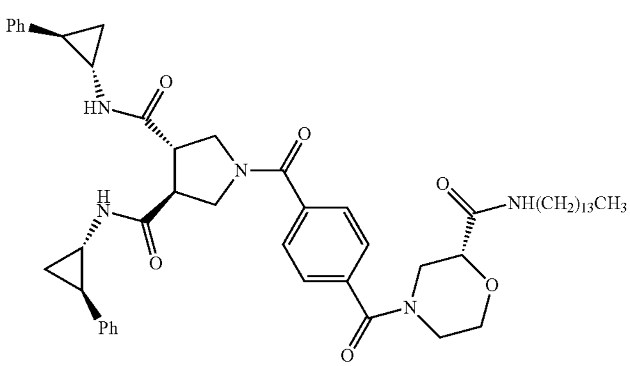 |

TABLE 2-continued

| Compound | Structure |
|---|---|
| 151 | (structure) |
| 152 | (structure) |
| 153 | (structure) |
| 154 | (structure) |

TABLE 2-continued

| Compound | Structure |
|---|---|
| 155 | 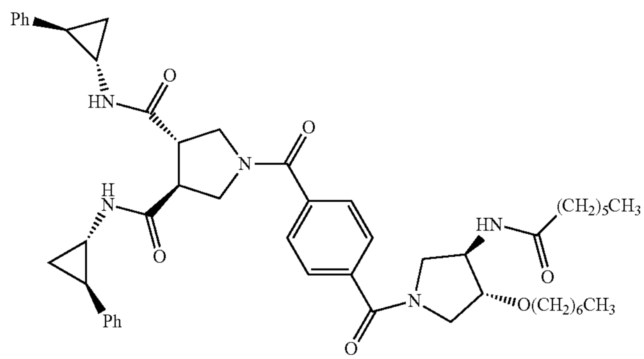 |
| 156 | 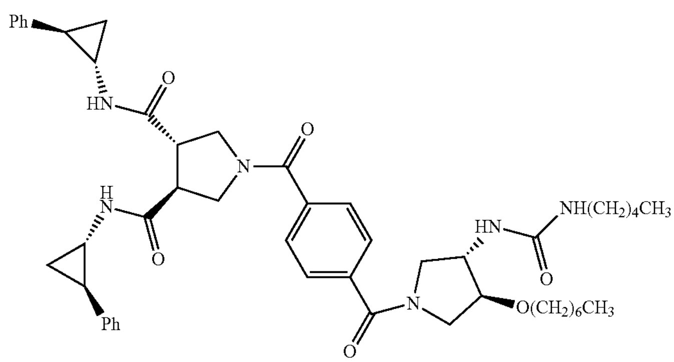 |
| 157 | 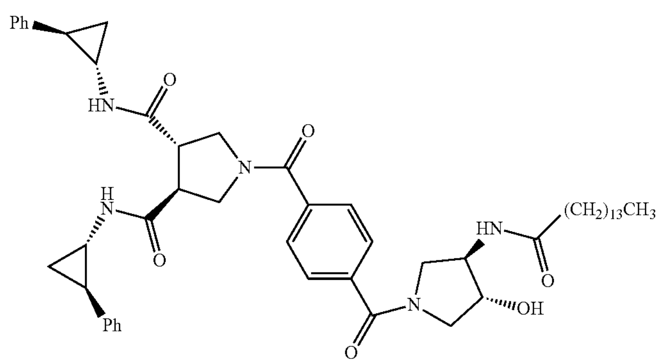 |
| 158 | 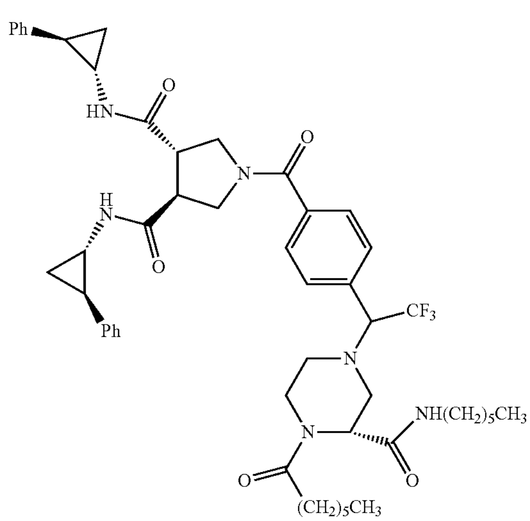 |

TABLE 2-continued

| Compound | Structure |
|---|---|
| 159 | 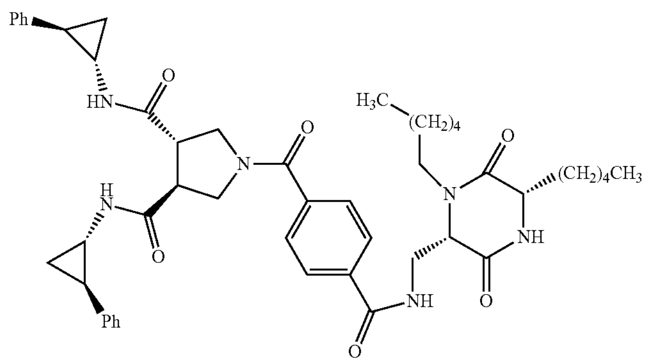 |
| 160 | 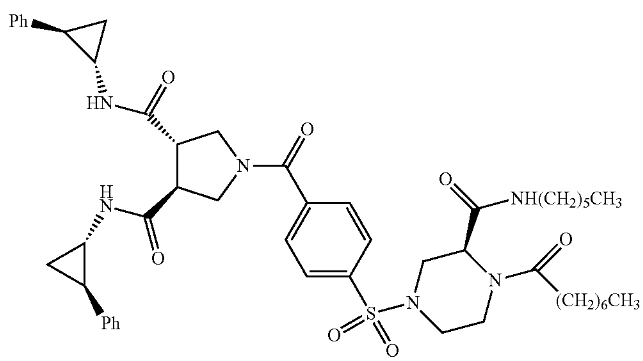 |
| 161 | 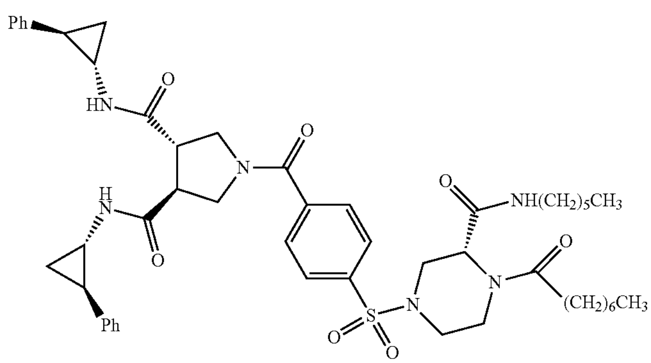 |
| 162 | 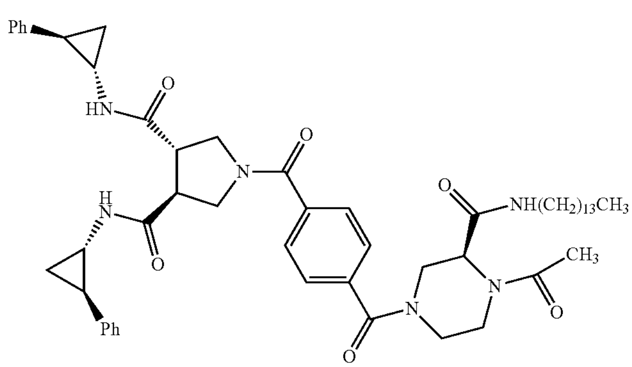 |

TABLE 2-continued

| Compound | Structure |
|---|---|
| 163 | 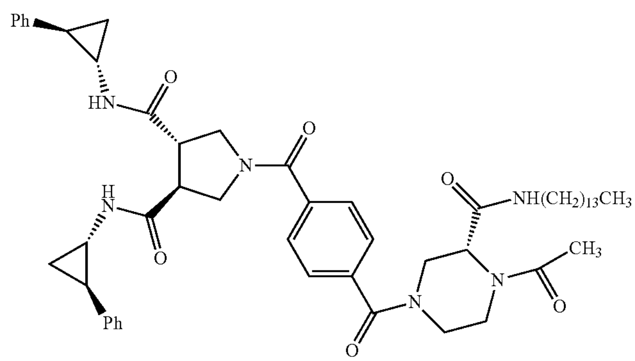 |
| 164 | 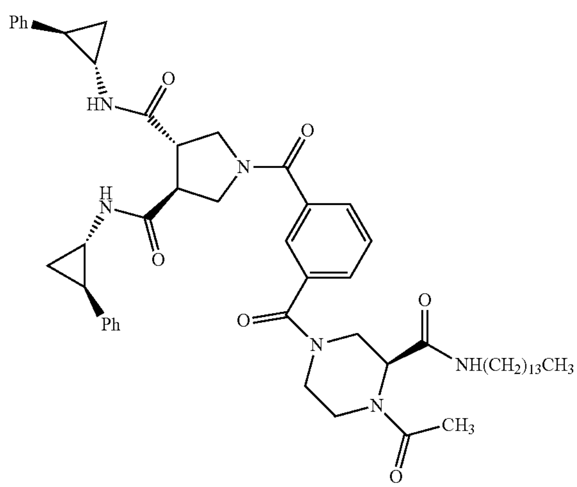 |
| 165 | 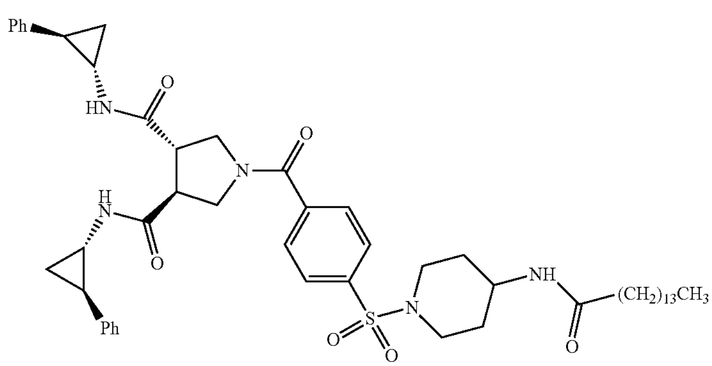 |
| 166 | 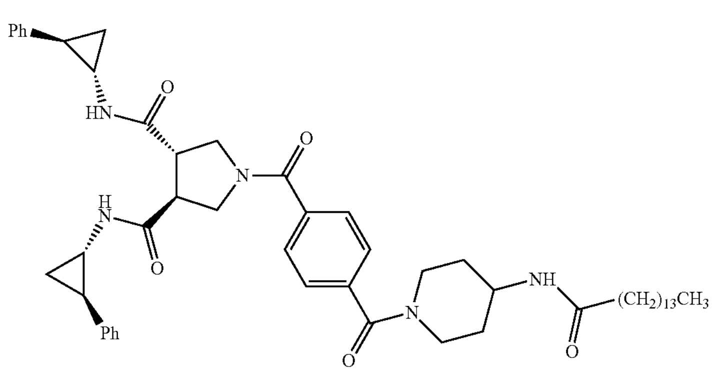 |

TABLE 2-continued
| Compound | Structure |
|---|---|
| 167 | 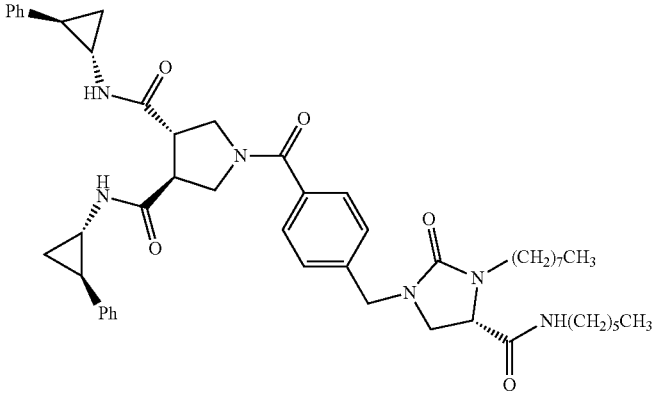 |
| 168 | 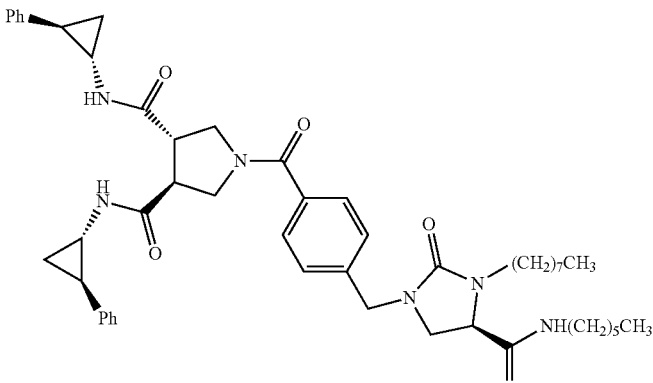 |
| 169 | 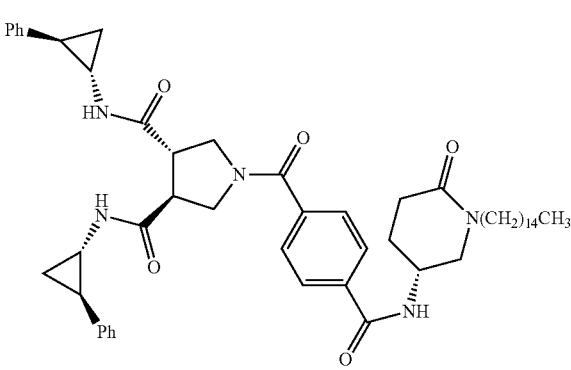 |

| Compound | Structure |
|---|---|
| 170 | 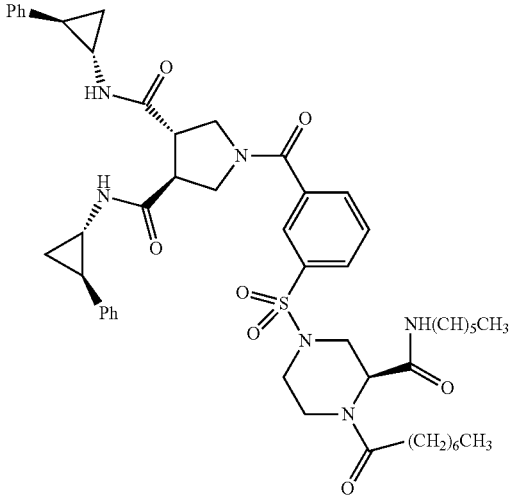 |
| 171 | 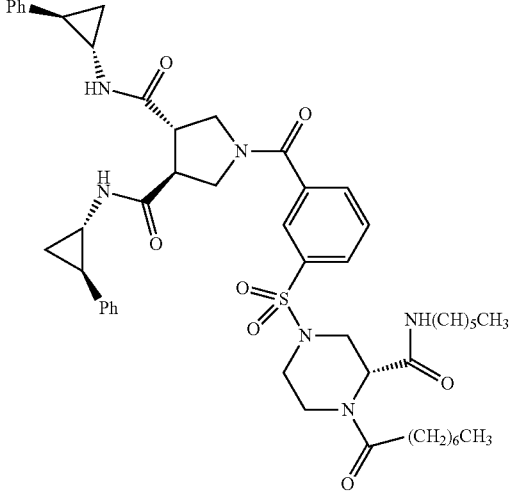 |
| 172 | 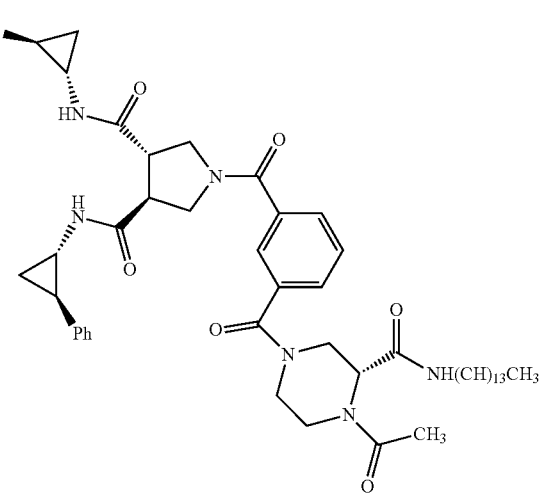 |

TABLE 2-continued

| Compound | Structure |
|---|---|
| 173 | 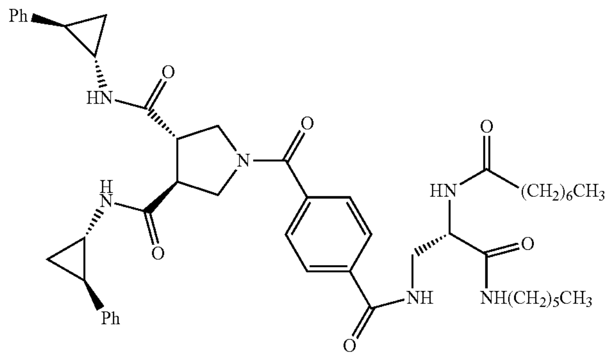 |
| 174 | 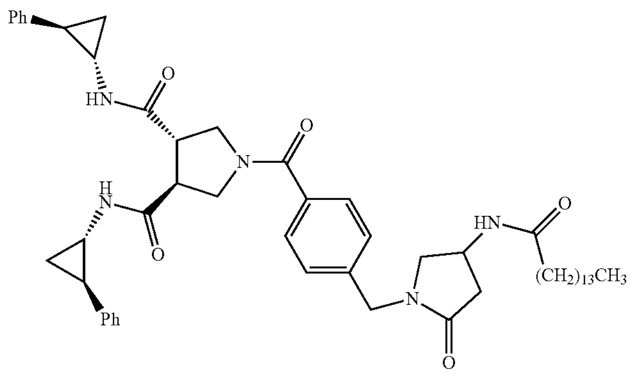 |
| 175 | 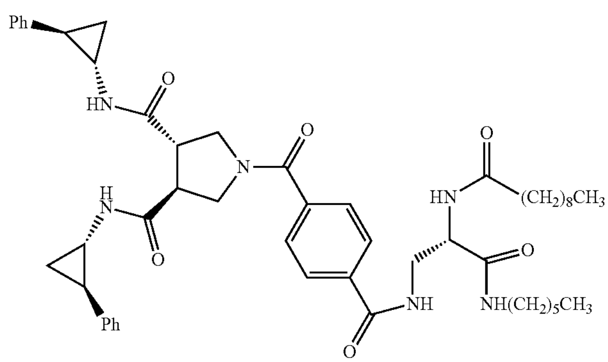 |
| 176 | 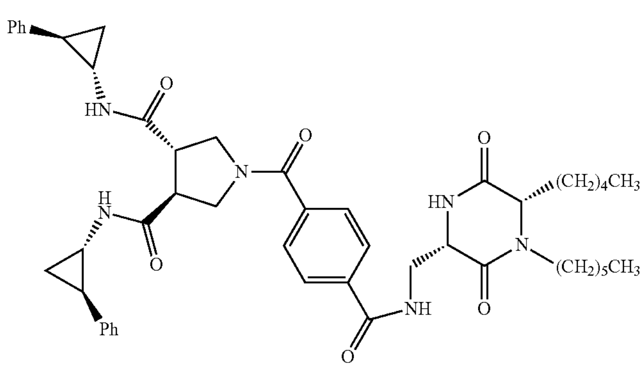 |

TABLE 2-continued

| Compound | Structure |
|---|---|
| 177 | 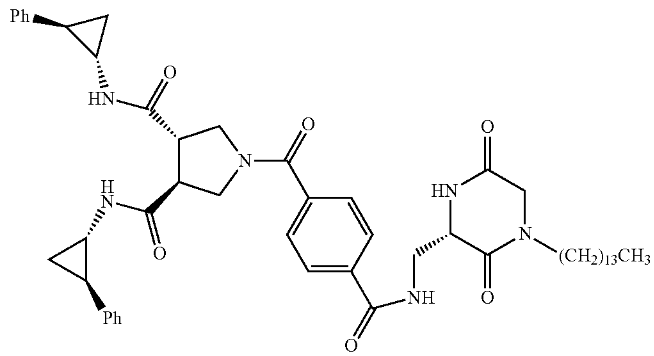 |
| 178 | 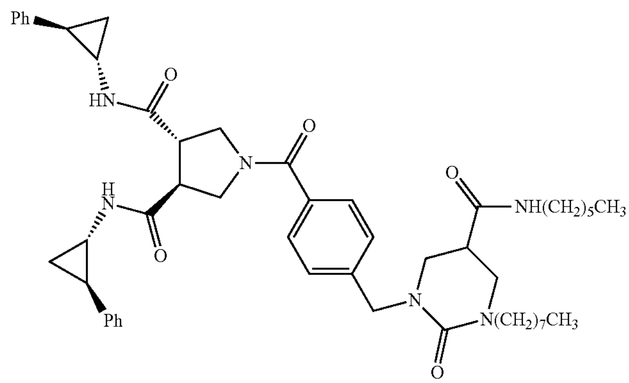 |
| 179 | 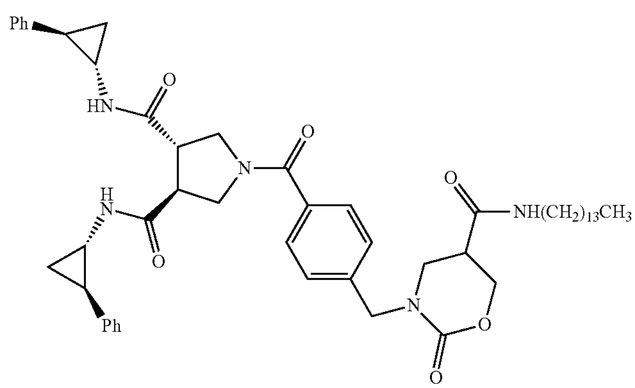 |
| 180 | 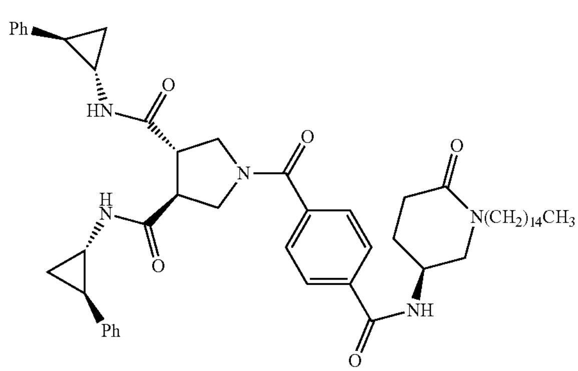 |

TABLE 2-continued
| Compound | Structure |
|---|---|
| 181 | 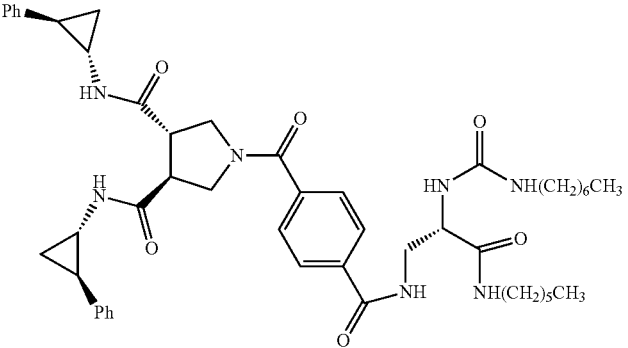 |
| 182 | 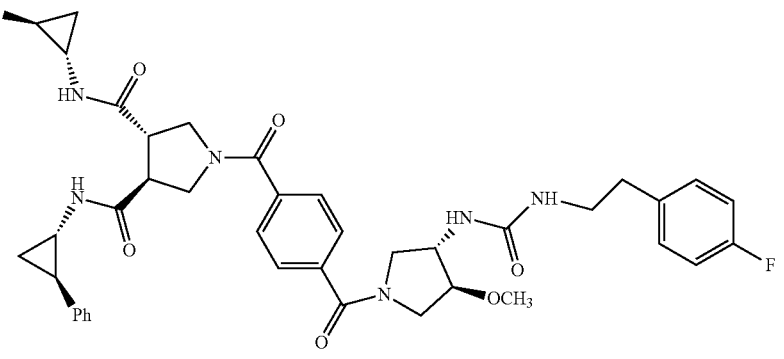 |
| 183 | 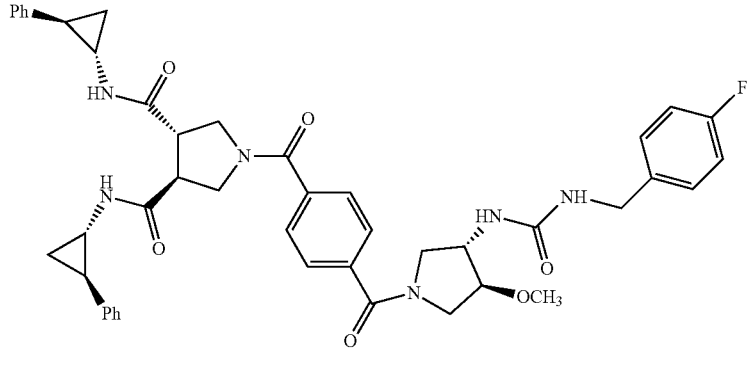 [SMILES: CO[C@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@@H]1NC(=O)NCc1ccc(F)cc1] |
| 184 | 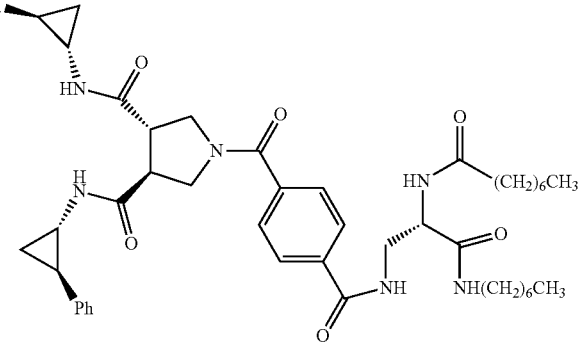 |

TABLE 2-continued

| Compound | Structure |
|---|---|
| 185 | (structure) |
| 186 | (structure) |
| 187 | (structure) |
| 188 | (structure) |

TABLE 2-continued

| Compound | Structure |
| --- | --- |
| 189 | 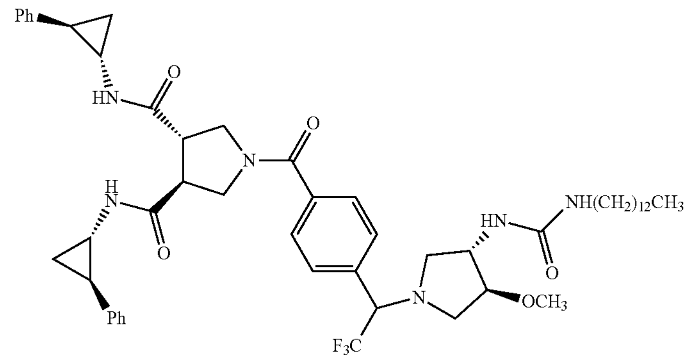 |
| 190 | 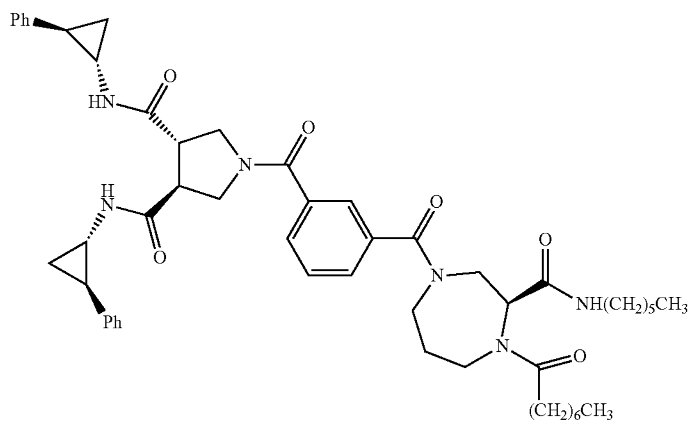 |
| 191 | 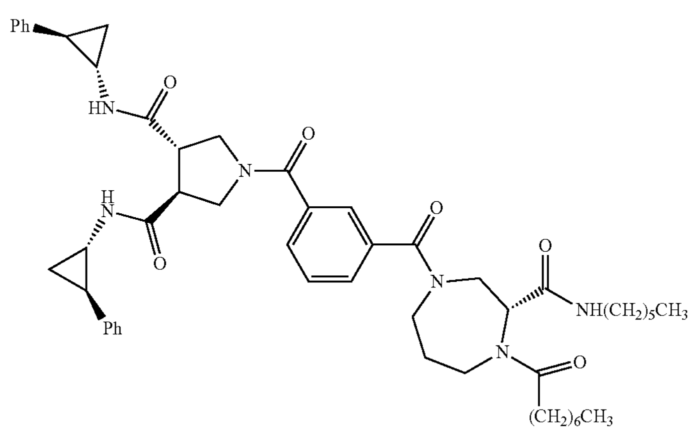 |

TABLE 2-continued
| Compound | Structure |
|---|---|
| 192 | 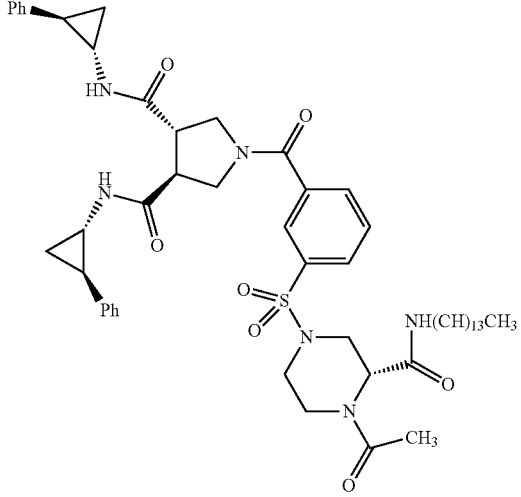 |
| 193 | 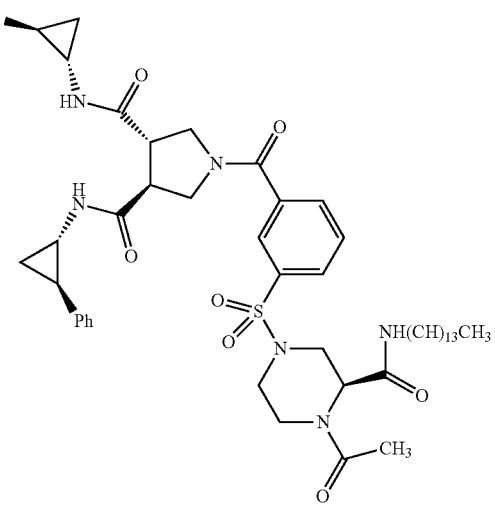 |
| 194 | 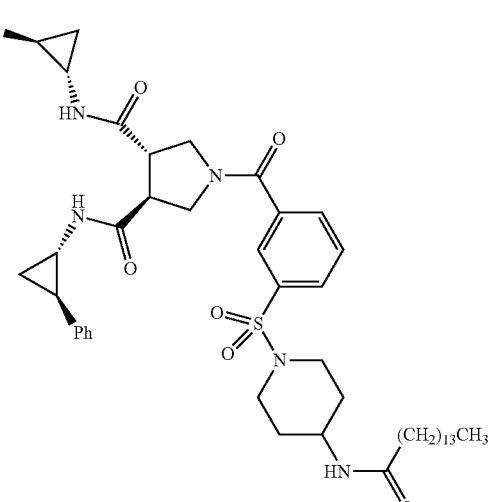 |

TABLE 2-continued
| Compound | Structure |
|---|---|
| 195 | 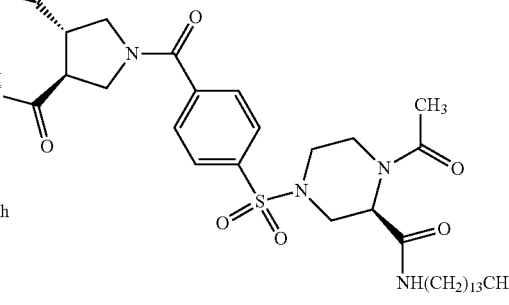 |
| 196 | 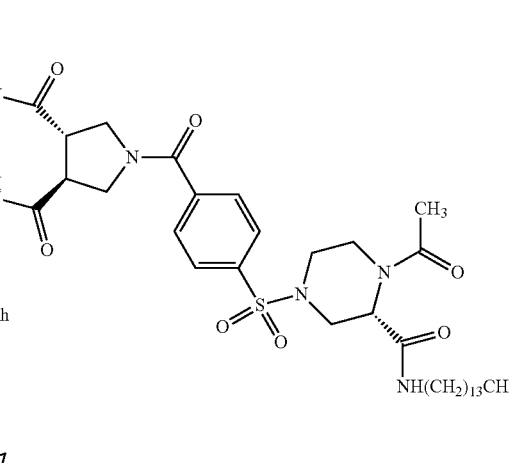 |
| 197 | 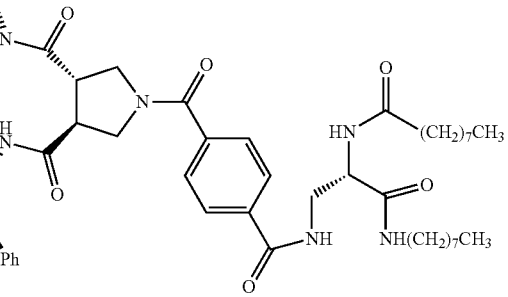 |
| 198 | 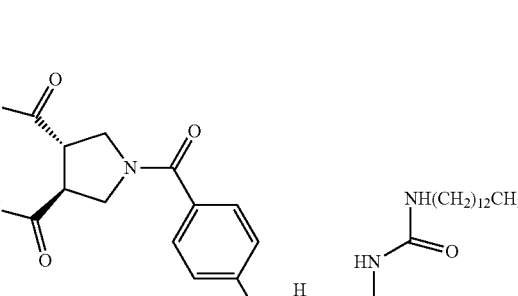 |

TABLE 2-continued

| Compound | Structure |
|---|---|
| 199 | 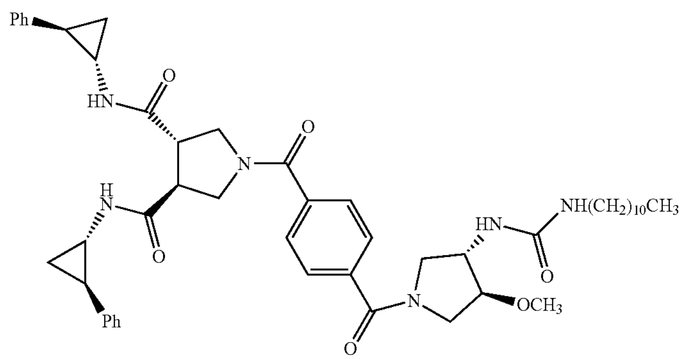 |
| 200 | 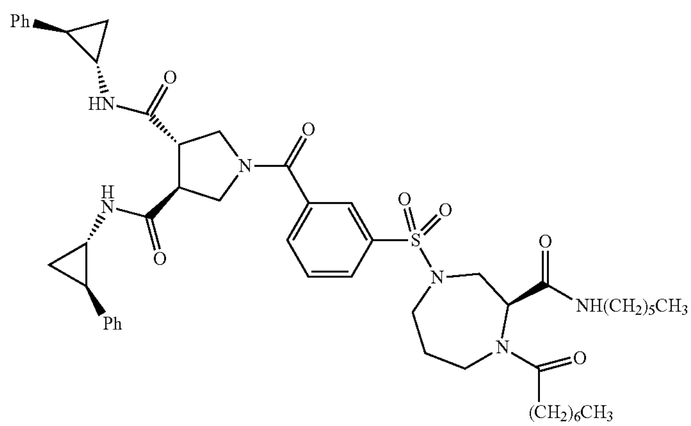 |
| 201 | 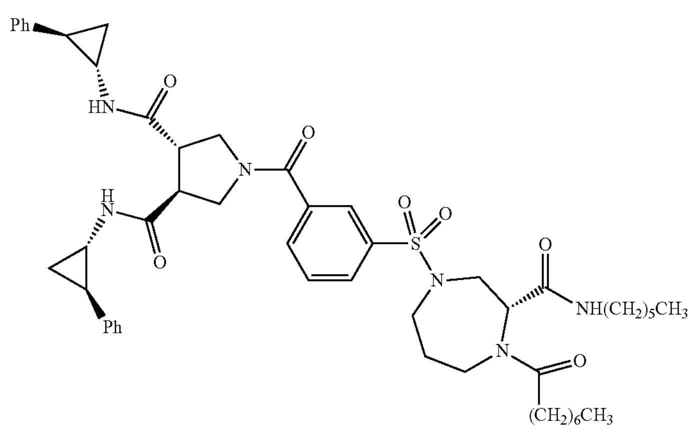 |
| 202 | 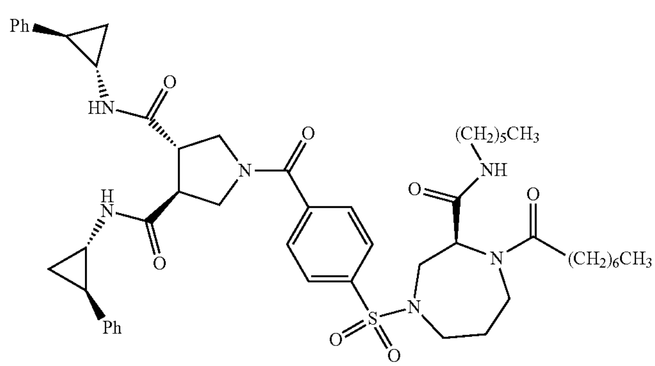 |

TABLE 2-continued
| Compound | Structure |
|---|---|
| 203 | 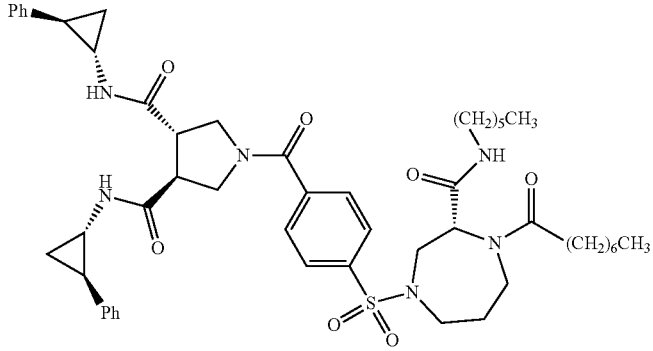 |
| 204 | 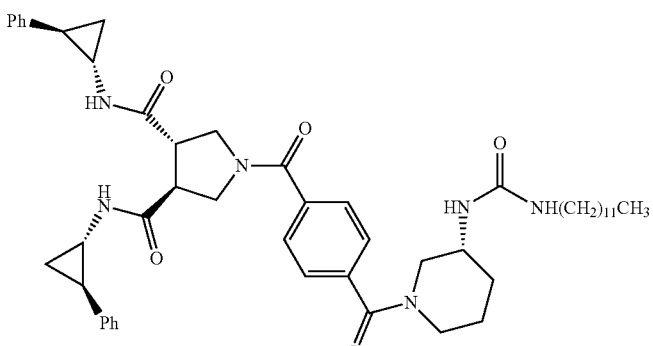 |
| 205 | 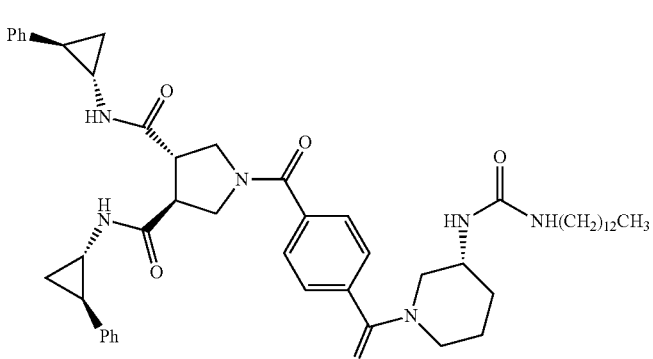 |
| 206 | 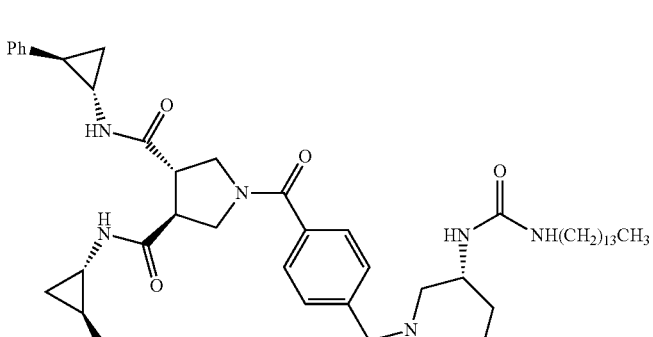 |

TABLE 2-continued

| Compound | Structure |
|---|---|
| 207 | 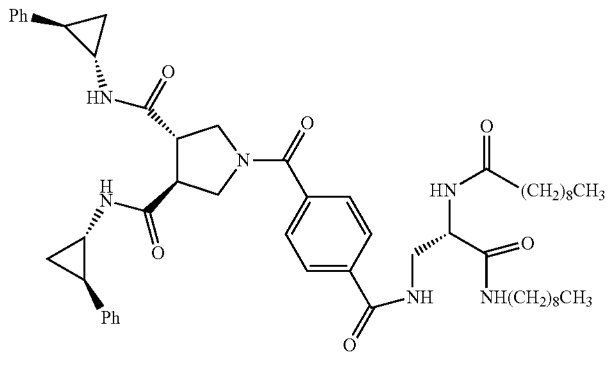 |
| 208 | 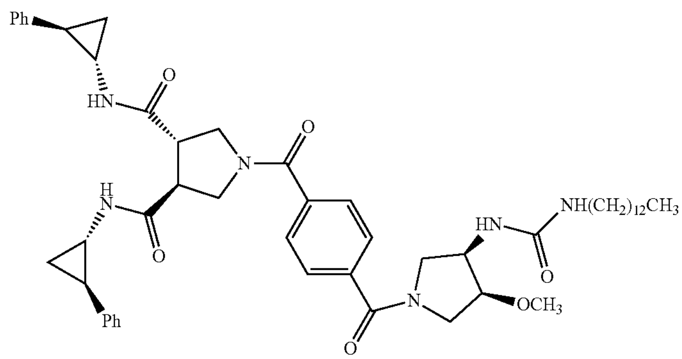 |
| 209 | 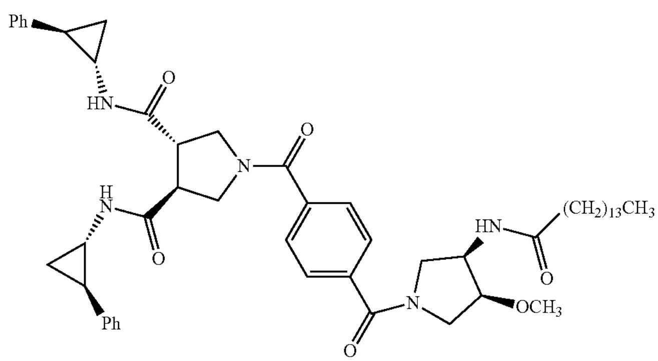 |
| 210 | 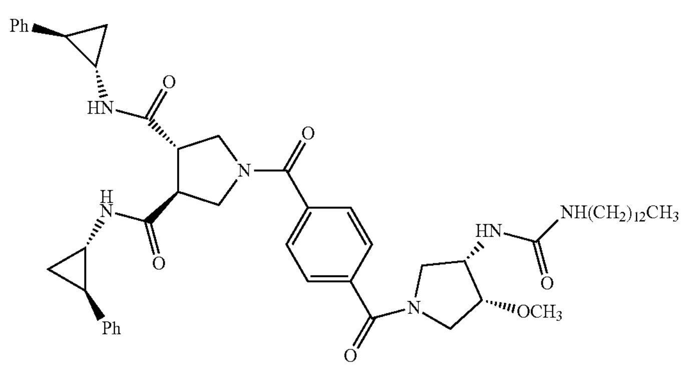 |

TABLE 2-continued

| Compound | Structure |
|---|---|
| 211 | 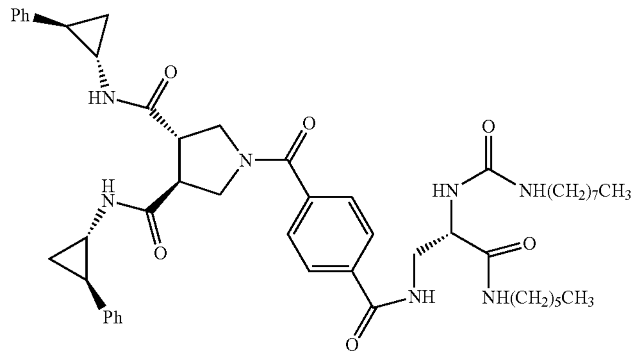 |
| 212 | 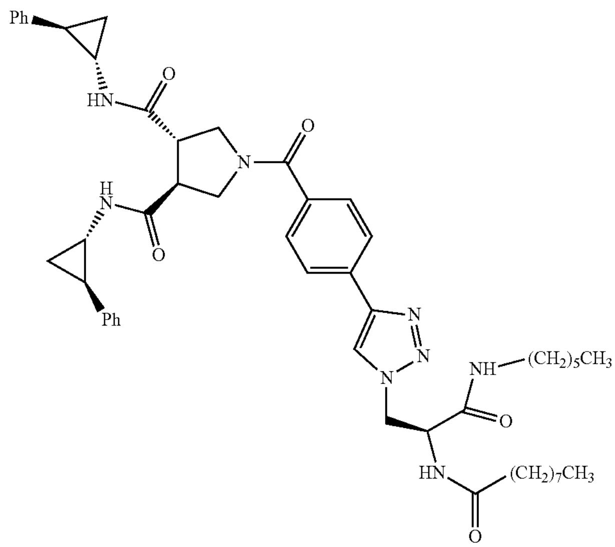 |
| 213 | 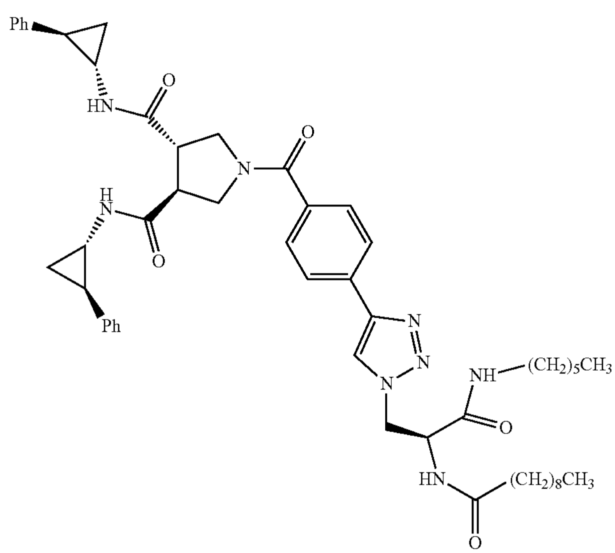 |

TABLE 2-continued

| Compound | Structure |
|---|---|
| 214 | 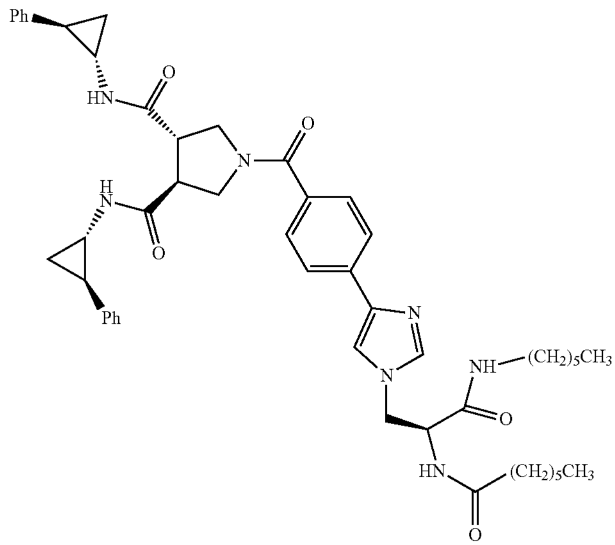 |
| 215 | 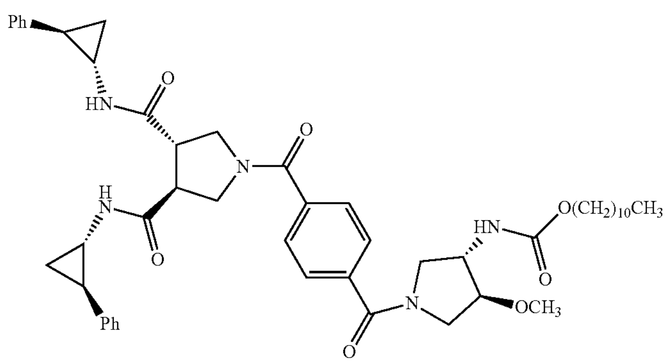 |
| 216 | 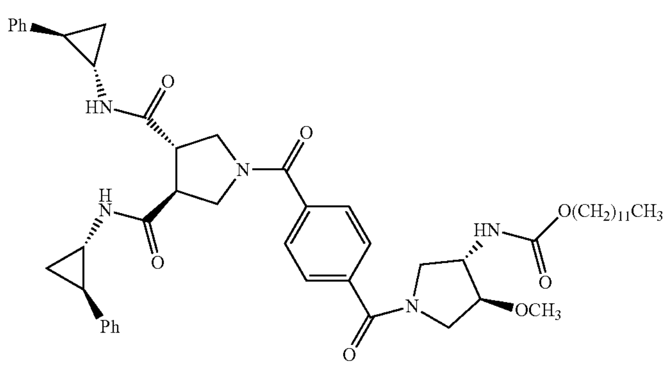 |
| 217 | 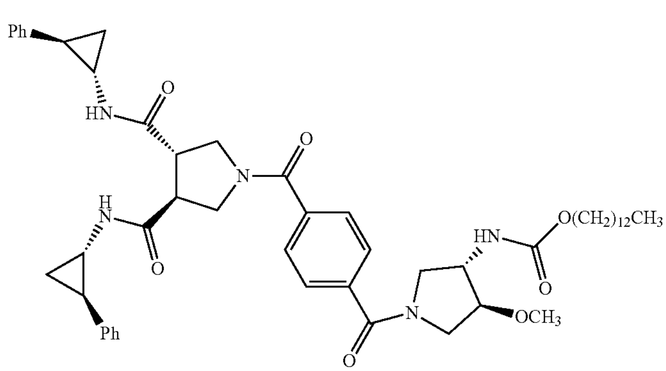 |

//
US 11,951,094 B2
137                                                                                          138
TABLE 2-continued
| Compound | Structure |
|---|---|
| 218 | 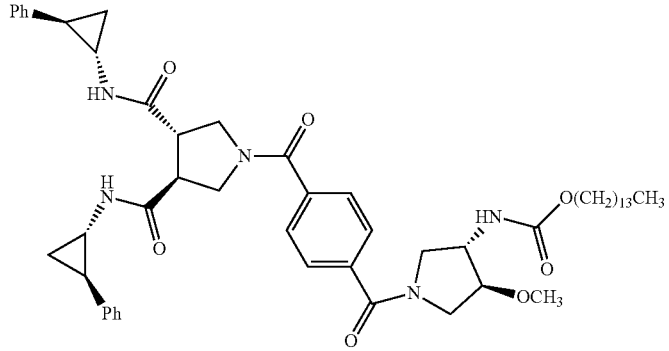 |
| 219 | 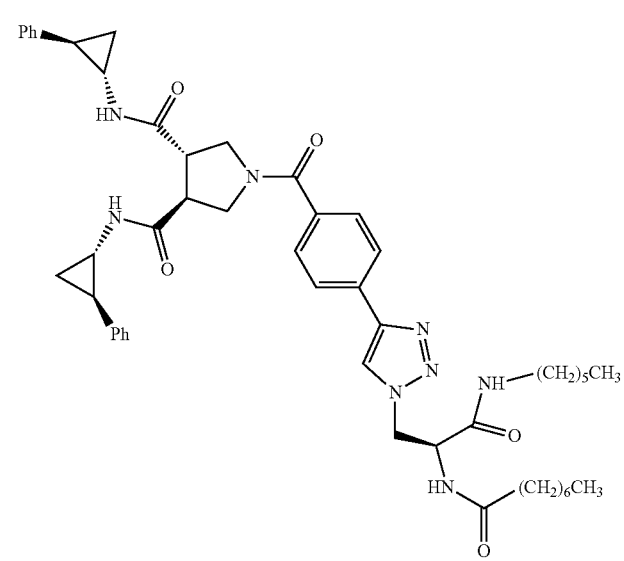 |
| 220 | 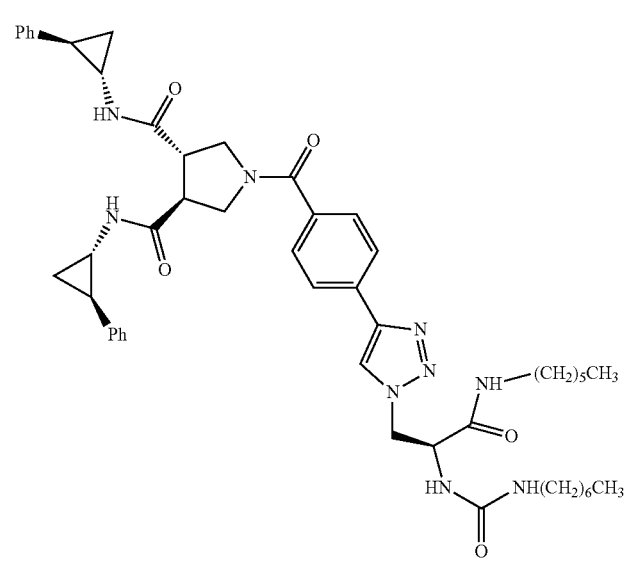 |

TABLE 2-continued

| Compound | Structure |
|---|---|
| 221 | 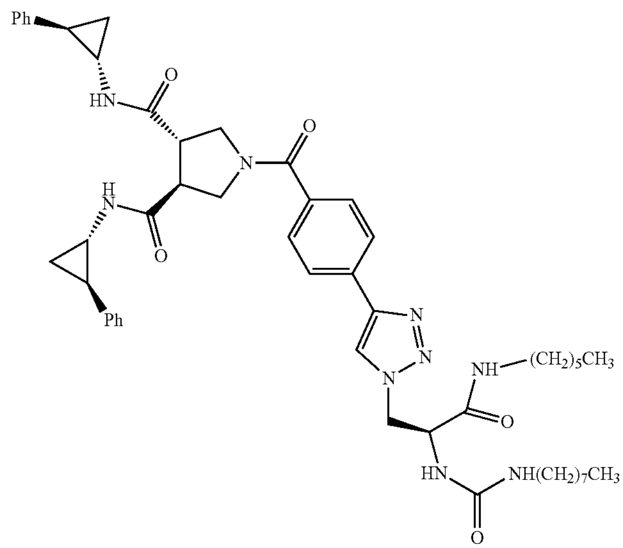 |
| 222 | 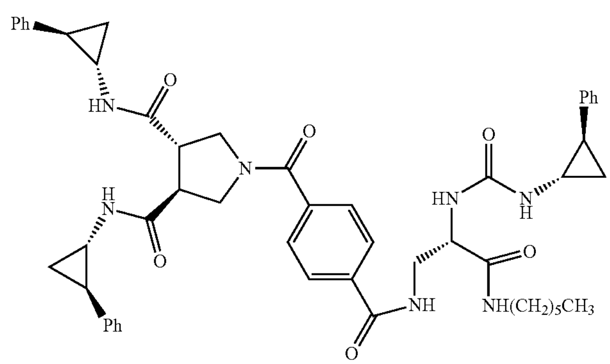 |
| 223 | 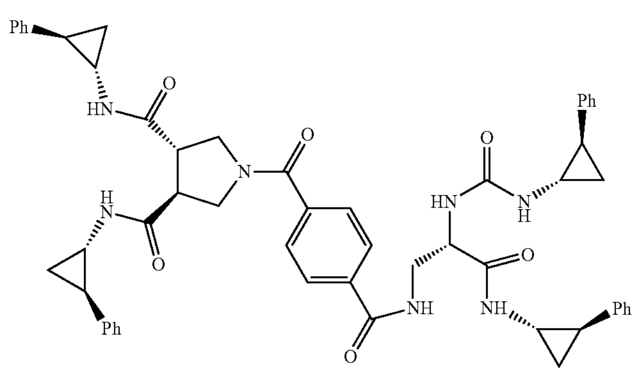 [SMILES: O=C(N[C@@H](CNC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1)C(=O)N[C@H]1C[C@@H]1c1ccccc1)N[C@H]1C[C@@H]1c1ccccc1] |
| 224 | 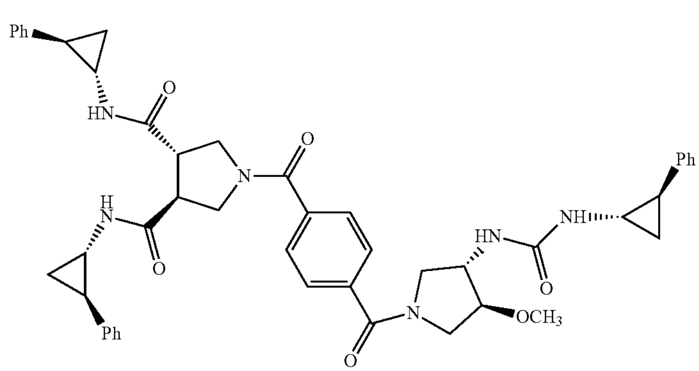 [SMILES: CO[C@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@@H]1NC(=O)N[C@H]1C[C@@H]1c1ccccc1] |

TABLE 2-continued

| Compound | Structure |
| --- | --- |
| 225 | 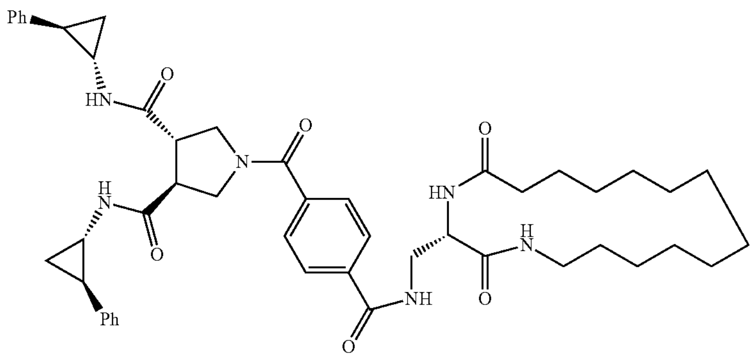 [SMILES: O=C1CCCCCCCCCCCCNC(=O)[C@H](CNC(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)N1] |
| 226 | 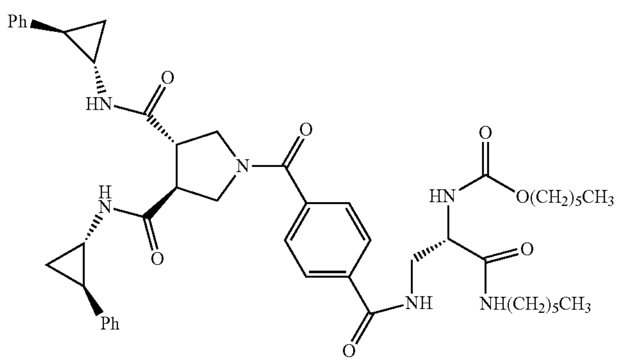 |
| 227 | 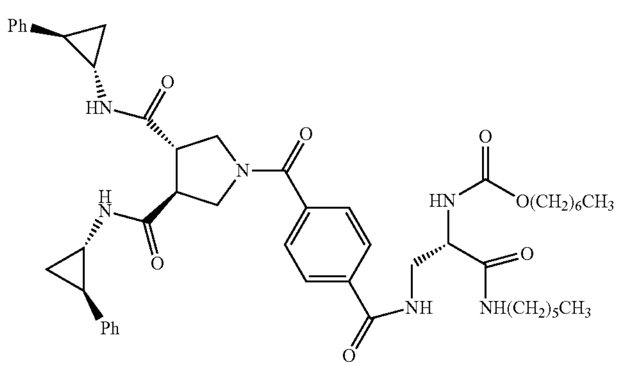 |
| 228 | 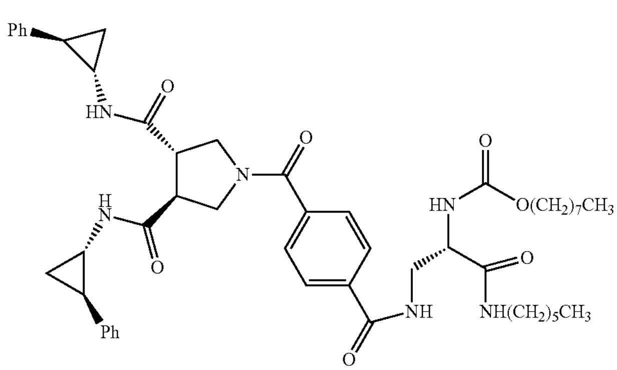 |

TABLE 2-continued
| Compound | Structure |
|---|---|
| 229 | 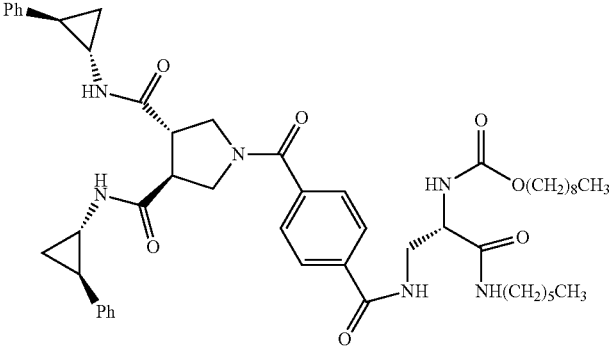 |
| 230 | 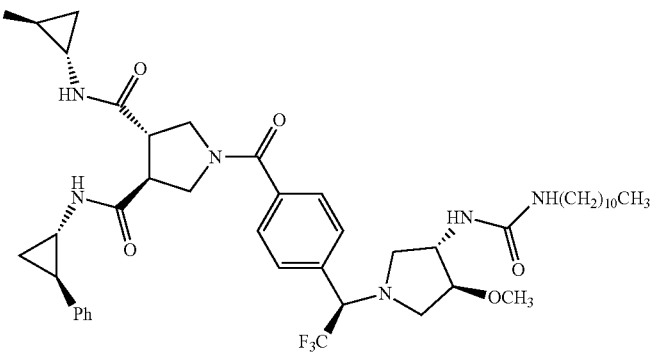 |
| 231 | 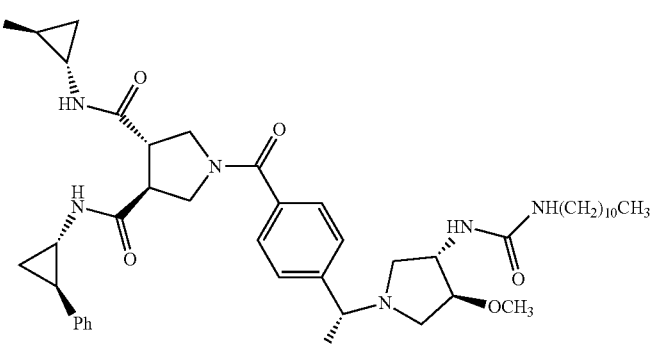 |
| 232 | 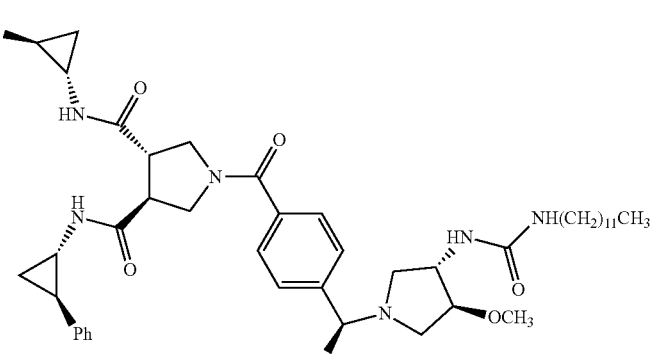 |

TABLE 2-continued

| Compound | Structure |
|---|---|
| 233 | 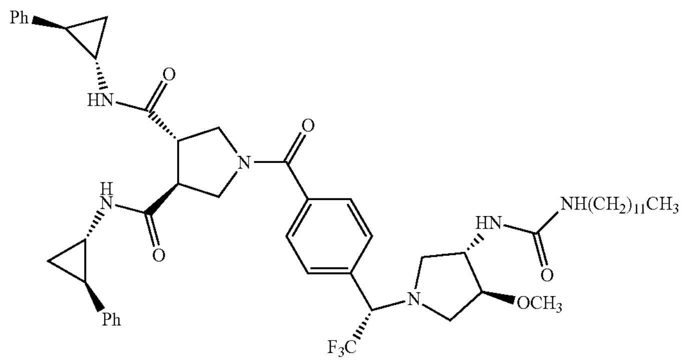 |
| 234 | 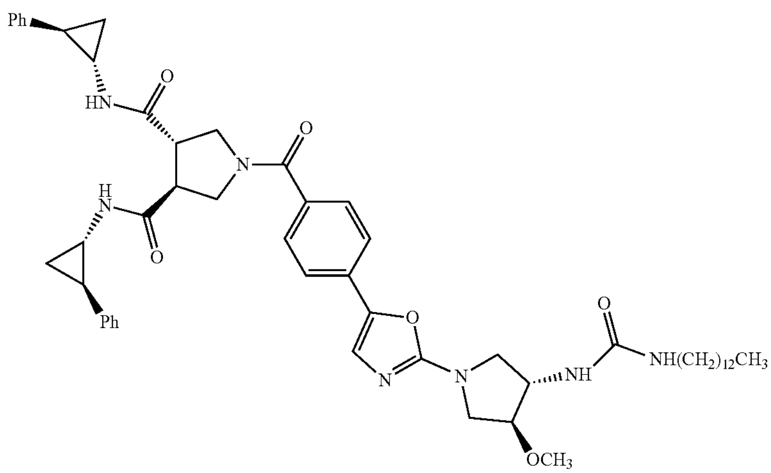 |
| 235 | 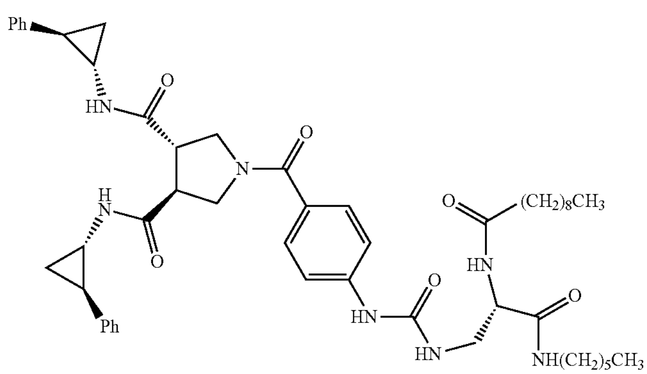 |
| 236 | 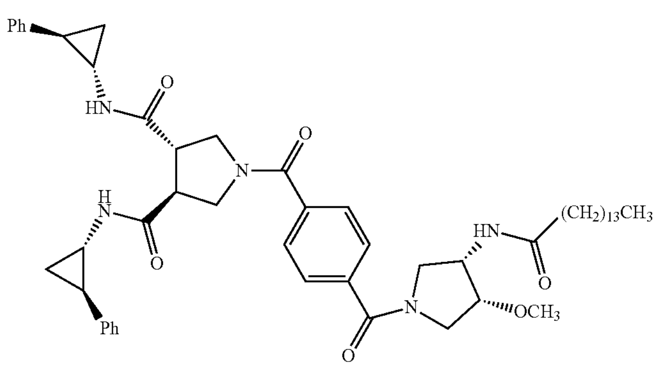 |

TABLE 2-continued

| Compound | Structure |
|---|---|
| 237 | (chemical structure) |
| 238 | (chemical structure) |
| 239 | (chemical structure) |

TABLE 2-continued

| Compound | Structure |
|---|---|
| 240 | 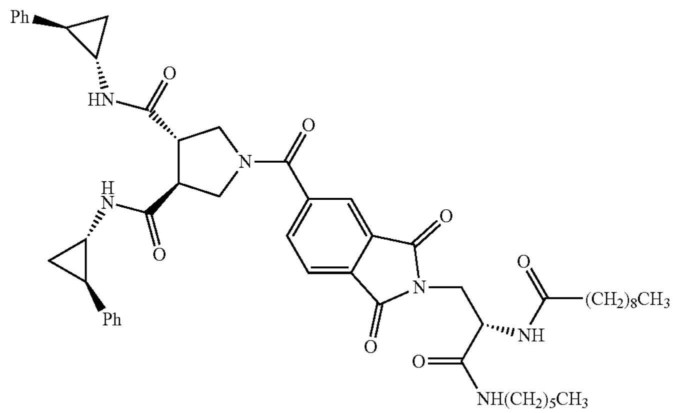 |
| 241 | 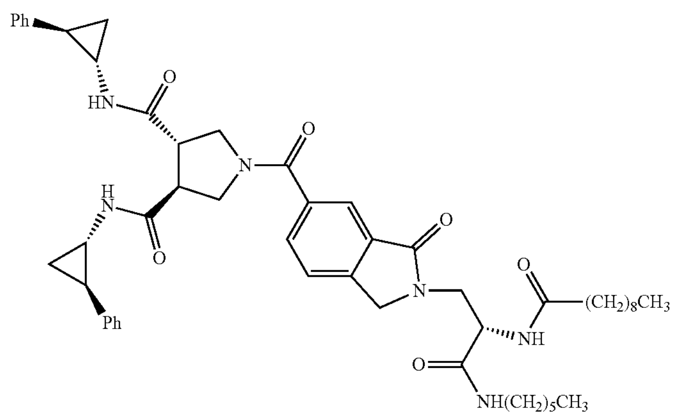 |
| 242 | 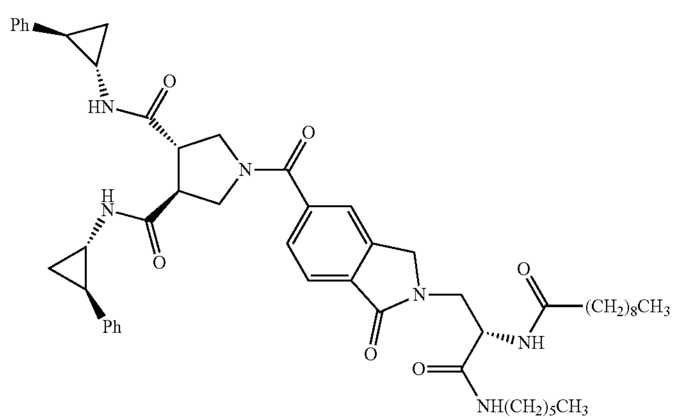 |

TABLE 2-continued
| Compound | Structure |
|---|---|
| 243 | 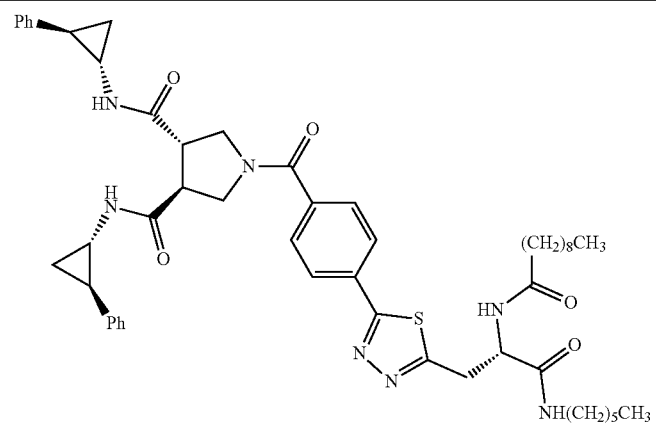 |
| 244 | 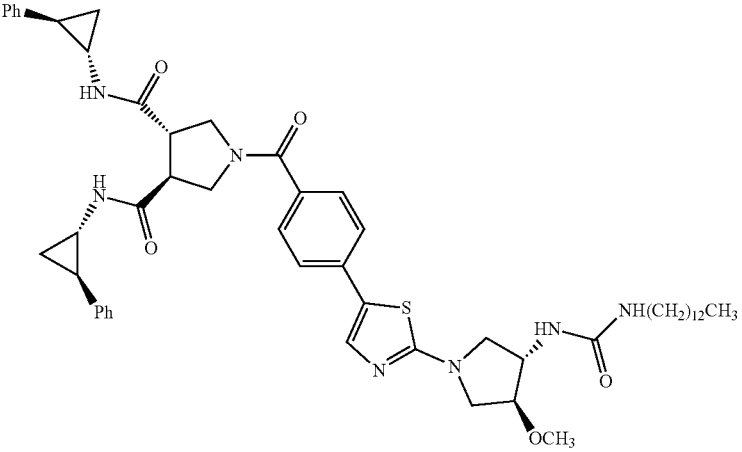 |
| 245 | 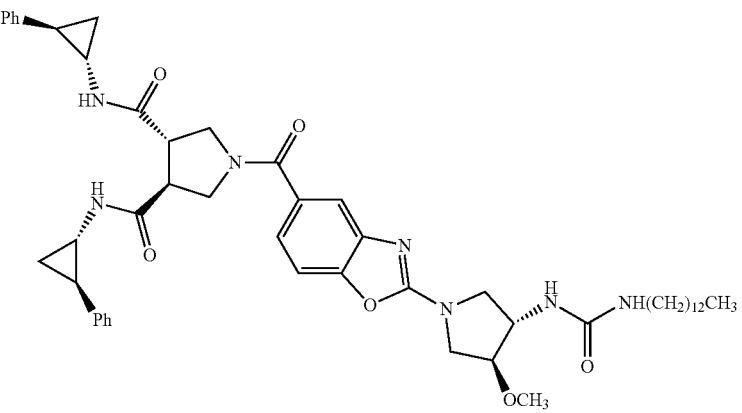 |

TABLE 2-continued

| Compound | Structure |
|---|---|
| 246 | 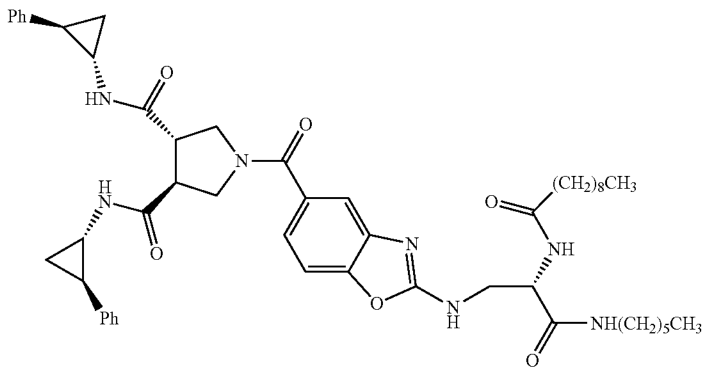 |
| 247 | 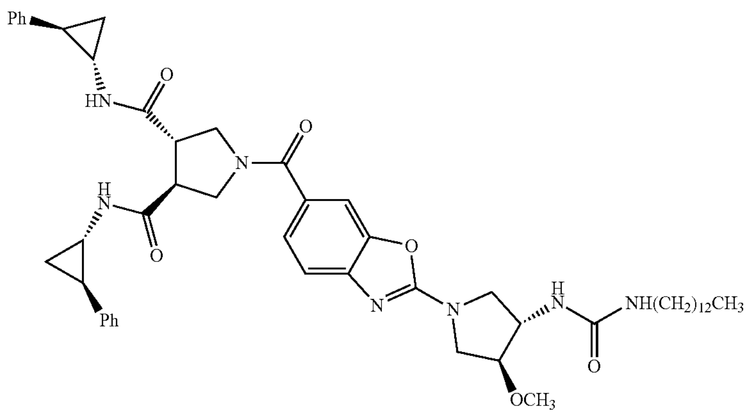 |
| 248 | 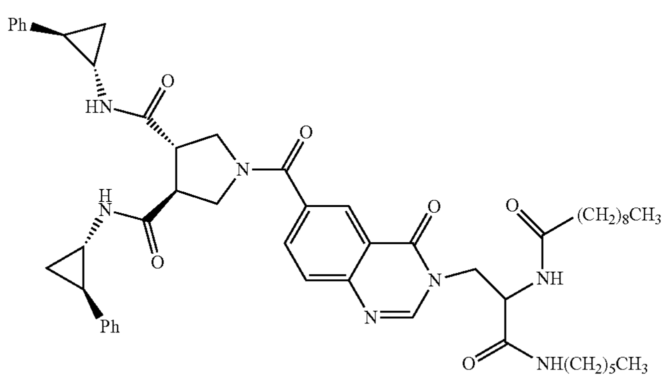 |
| 249 | 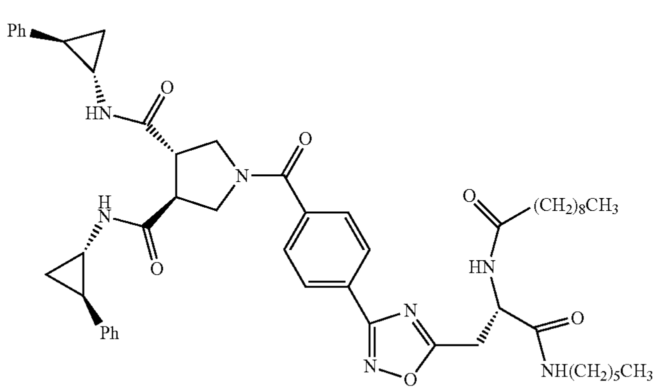 |

TABLE 2-continued

| Compound | Structure |
|---|---|
| 250 | 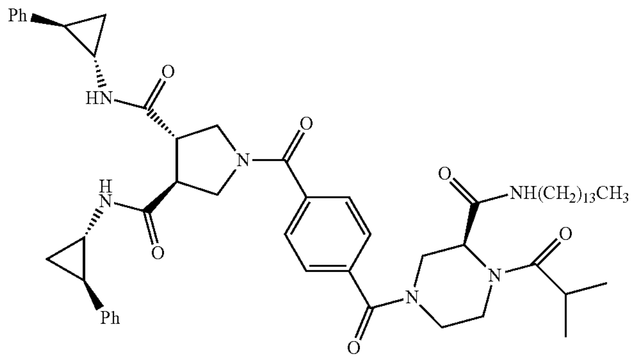 |
| 251 | 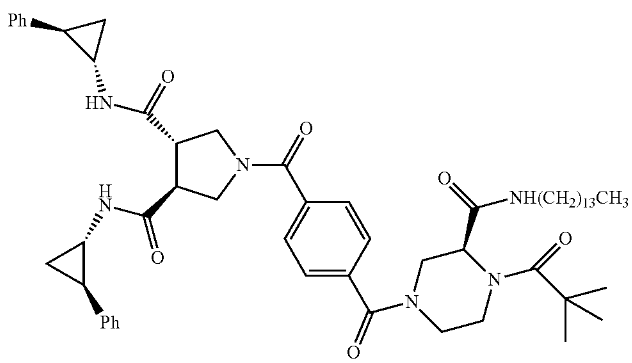 |
| 252 | 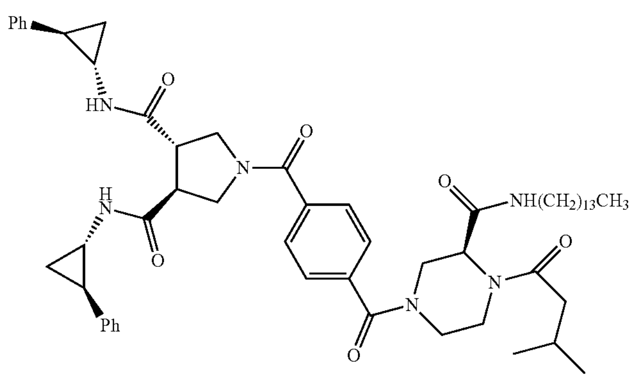 |
| 253 | 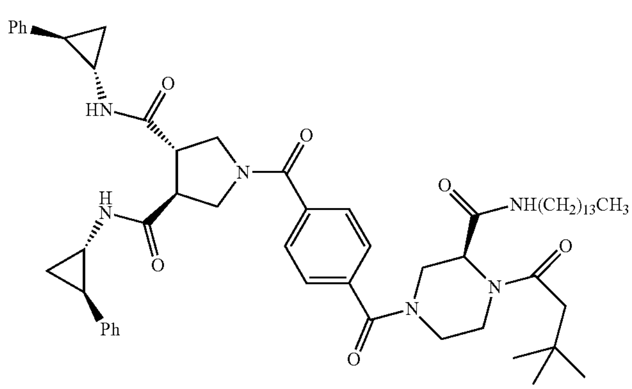 |

TABLE 2-continued

| Compound | Structure |
|---|---|
| 254 | (chemical structure) |
| 255 | (chemical structure) |
| 256 | (chemical structure) |
| 257 | (chemical structure) |

TABLE 2-continued
| Compound | Structure |
|---|---|
| 258 | 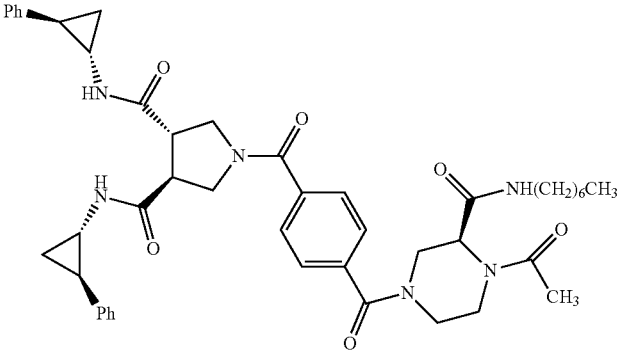 |
| 259 | 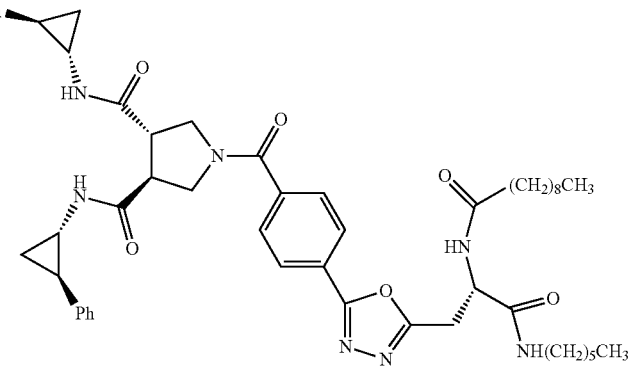 |
| 260 | 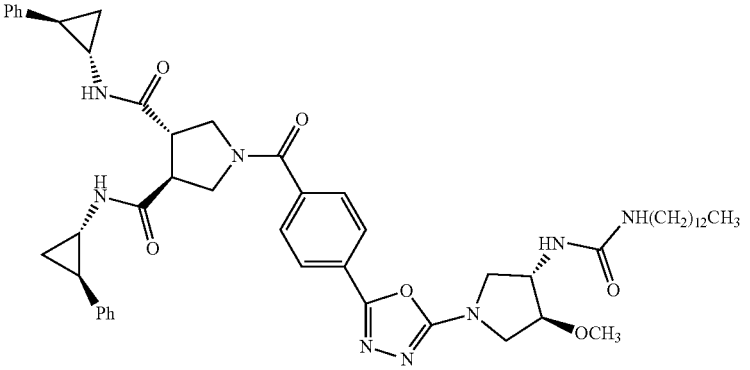 |
| 261 | 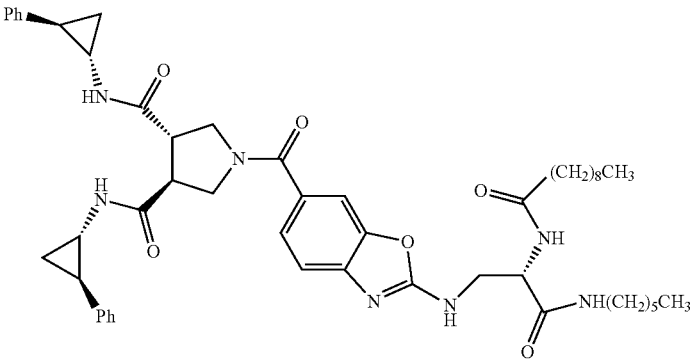 |

| Compound | Structure |
|---|---|
| 262 | 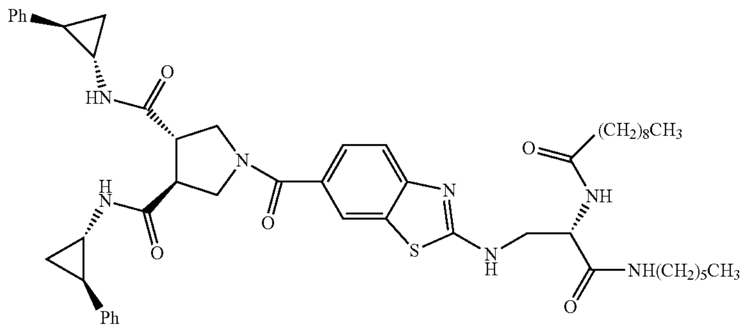 |
| 263 | 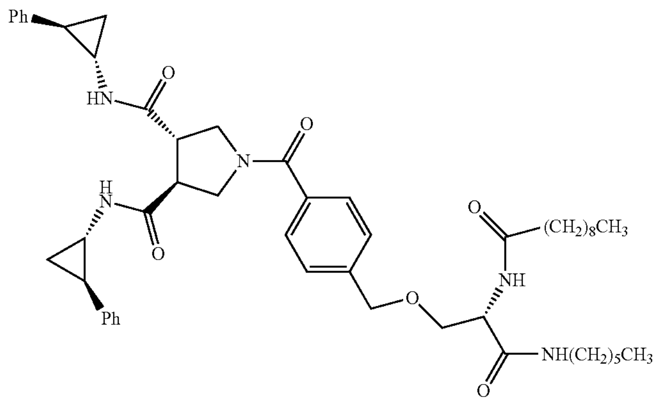 |
| 264 | 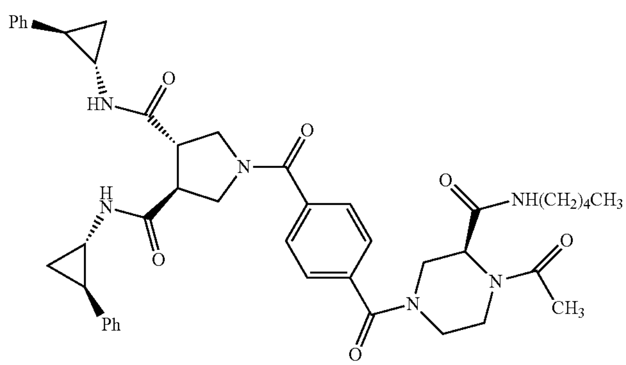 |
| 265 | 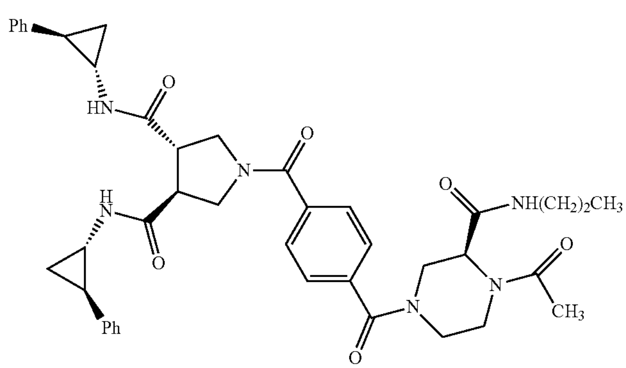 |

TABLE 2-continued
| Compound | Structure |
|---|---|
| 266 | 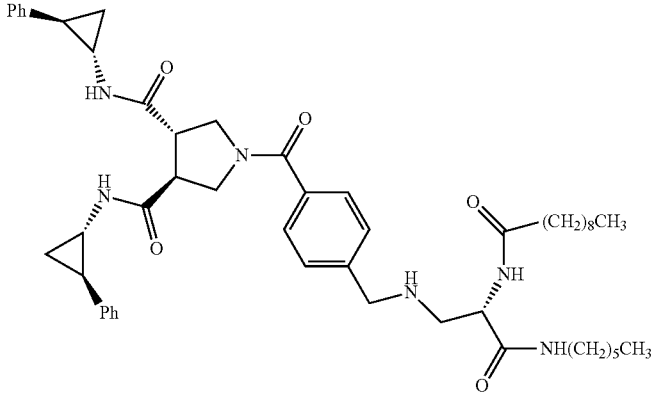 |
| 267 | 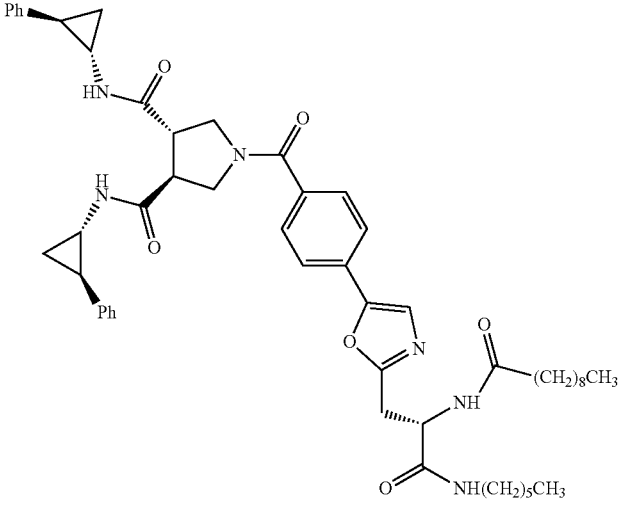 |
| 268 | 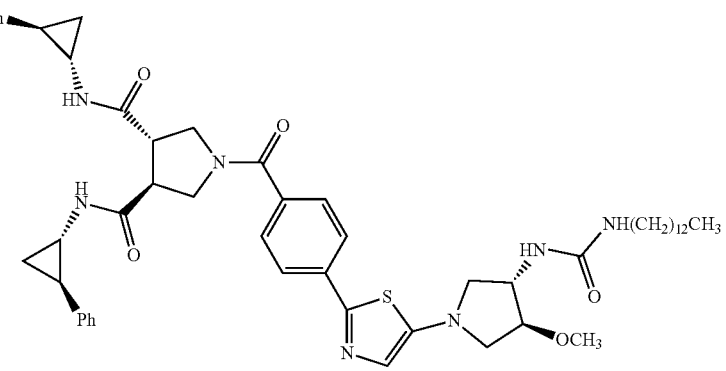 |

TABLE 2-continued

| Compound | Structure |
|---|---|
| 269 | (structure) |
| 270 | (structure) |
| 271 | (structure) |

TABLE 2-continued
| Compound | Structure |
|---|---|
| 272 | 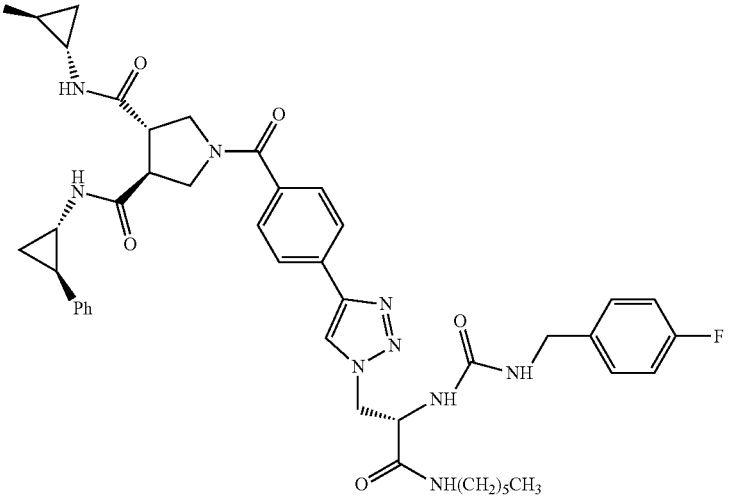 |
| 273 | 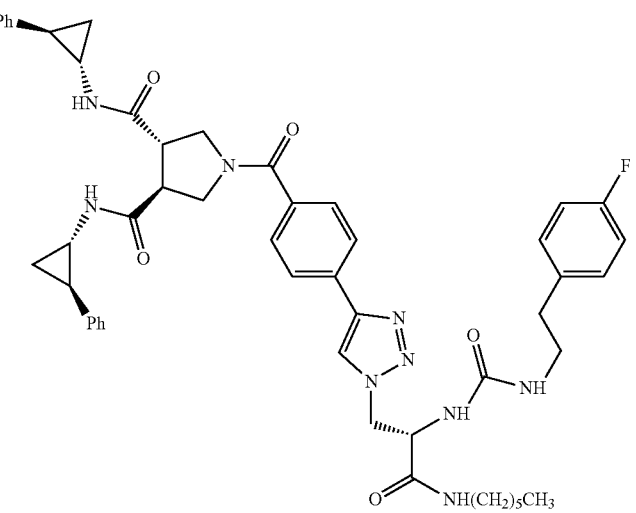 |
| 274 | 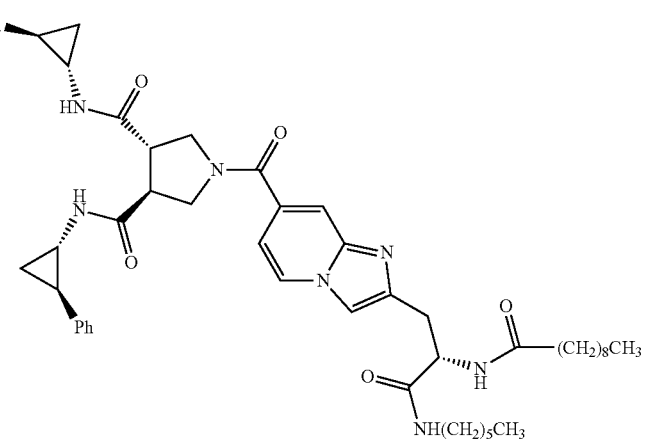 |

TABLE 2-continued
| Compound | Structure |
|---|---|
| 275 | 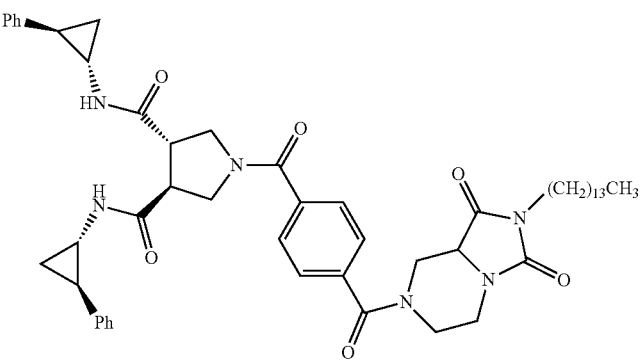 |
| 276 | 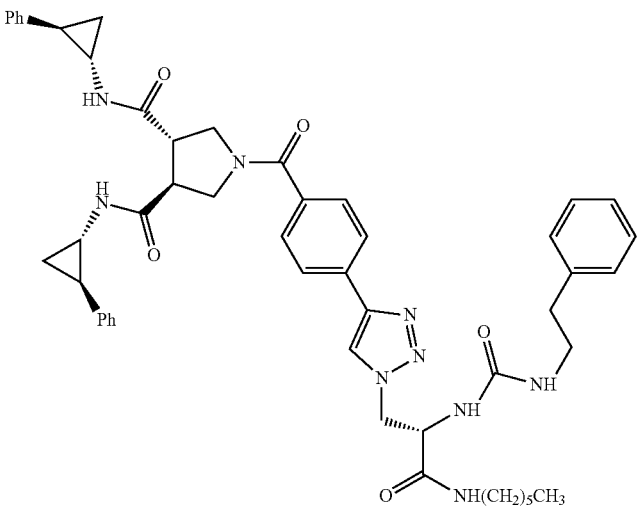 |
| 277 | 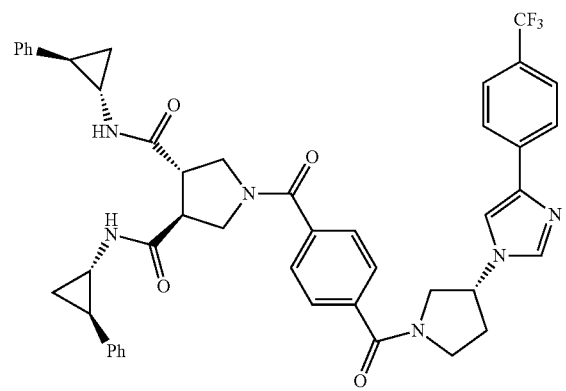 [SMILES: O=C(N[C@H]1C[C@@H]1c1ccccc1)[C@@H]1CN(C(=O)c2ccc(C(=O)N3CC[C@@H](n4cnc(-c5ccc(C(F)(F)F)cc5)c4)C3)cc2)C[C@H]1C(=O)N[C@H]1C[C@@H]1c1ccccc1] |

TABLE 2-continued
| Compound | Structure |
|---|---|
| 278 | 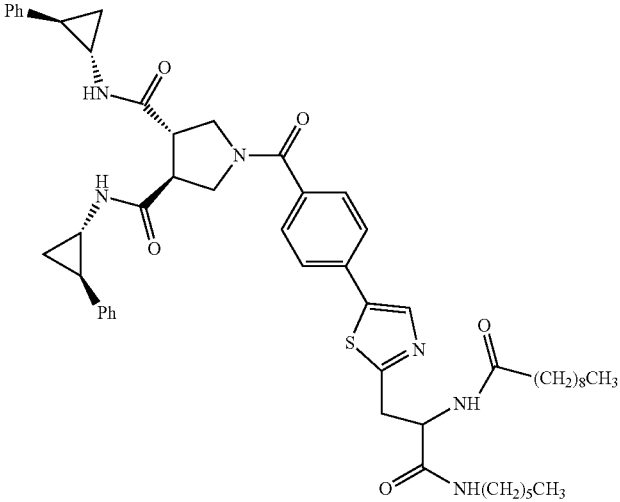 |
| 279 | 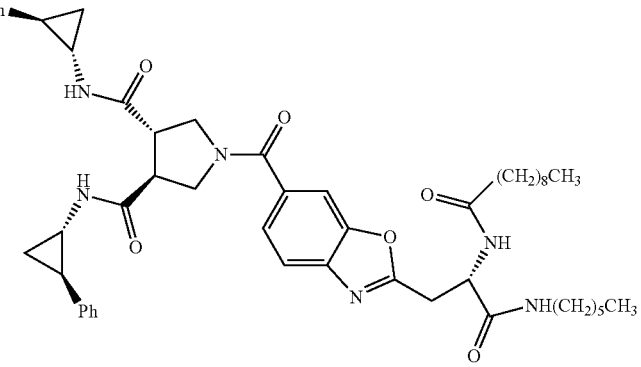 |
| 280 | 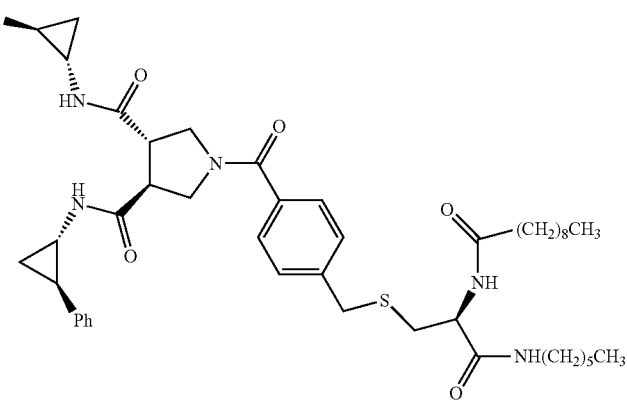 |

TABLE 2-continued

| Compound | Structure |
|---|---|
| 281 | 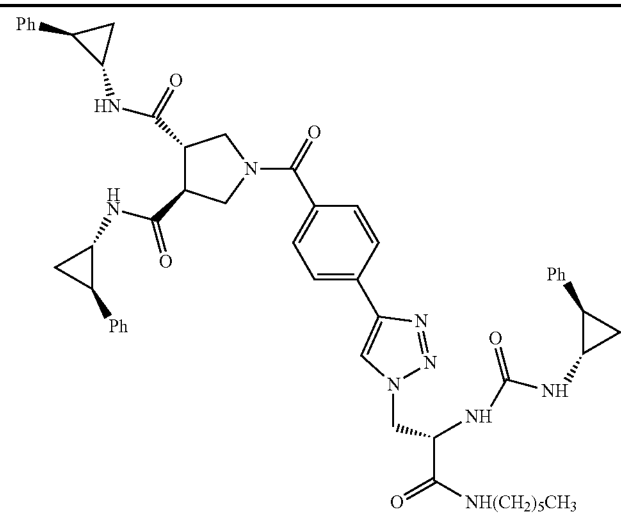 |
| 282 | 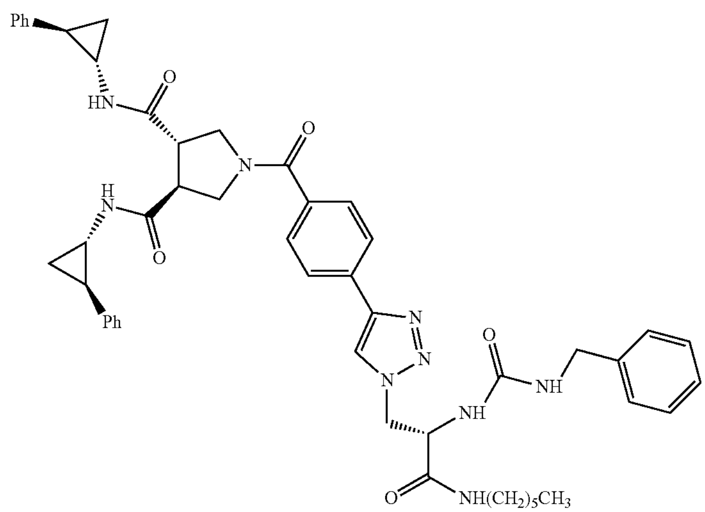 |
| 283 | 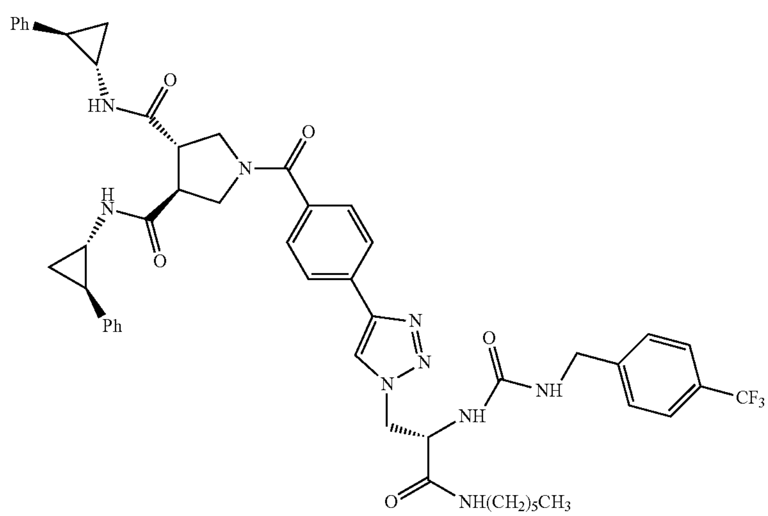 |

TABLE 2-continued
| Compound | Structure |
|---|---|
| 284 | 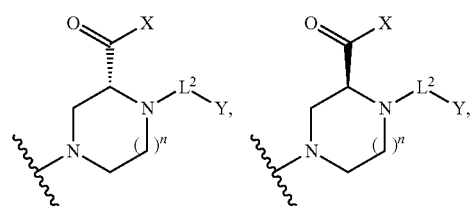 |
| 285 | 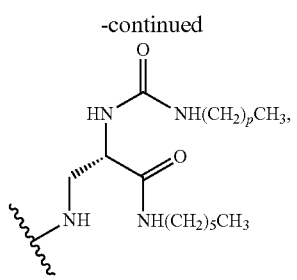 |
In certain embodiments of Formula (IA), G is:
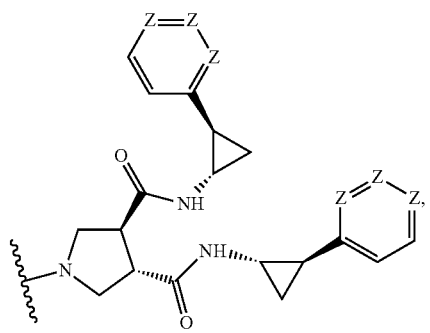
-continued
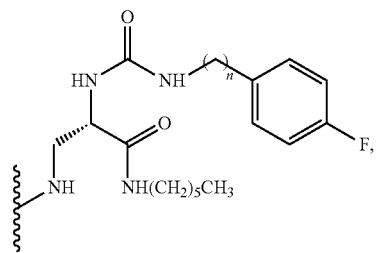

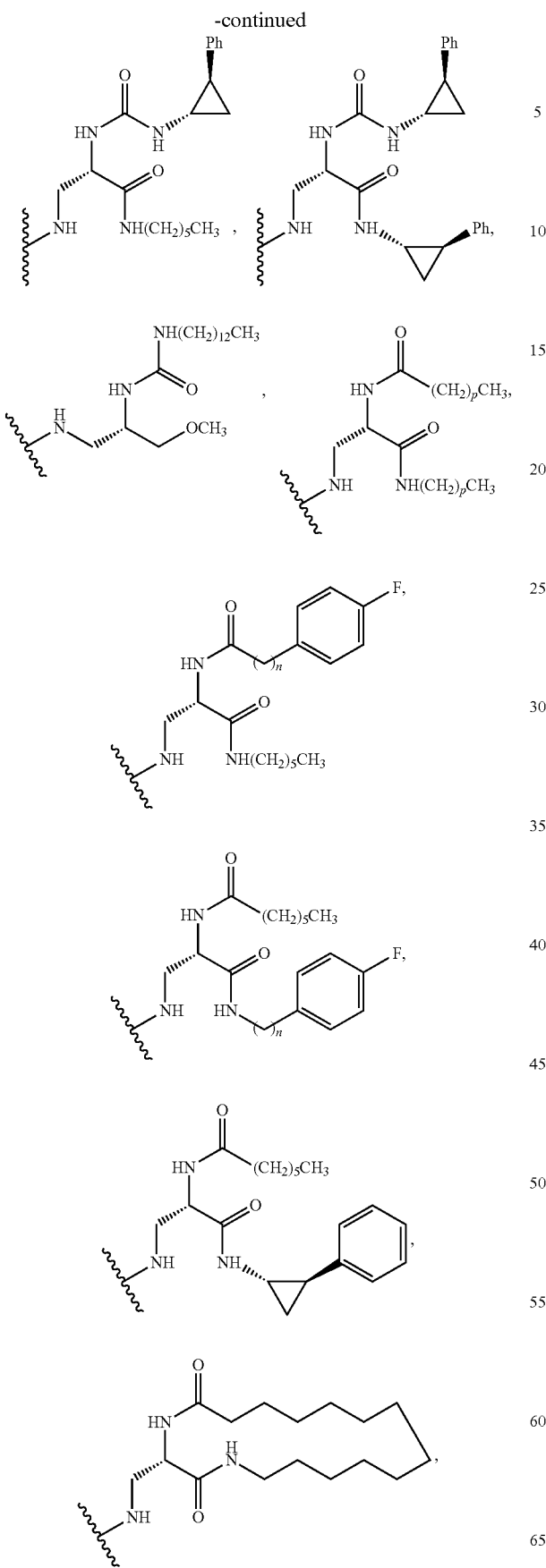
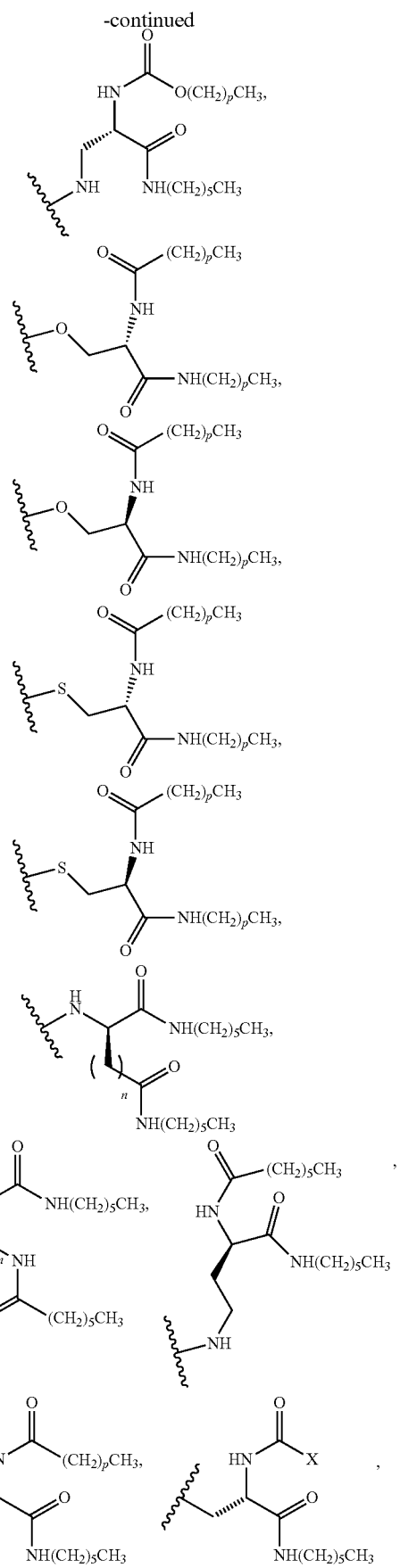

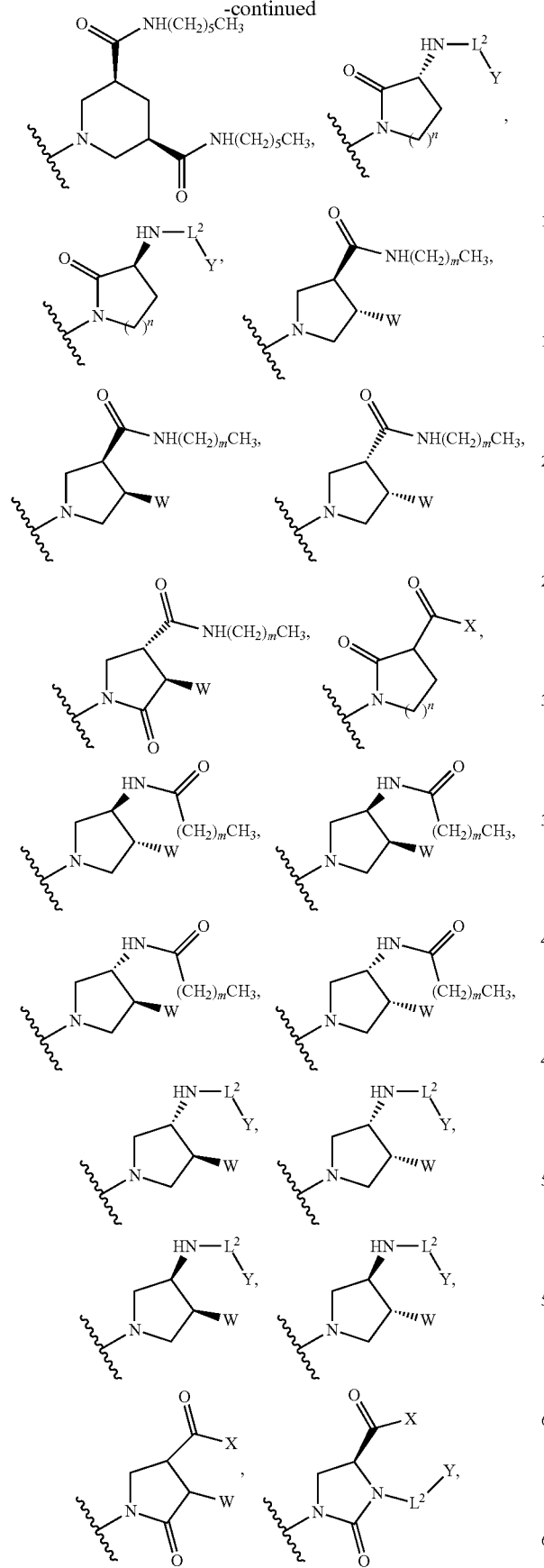
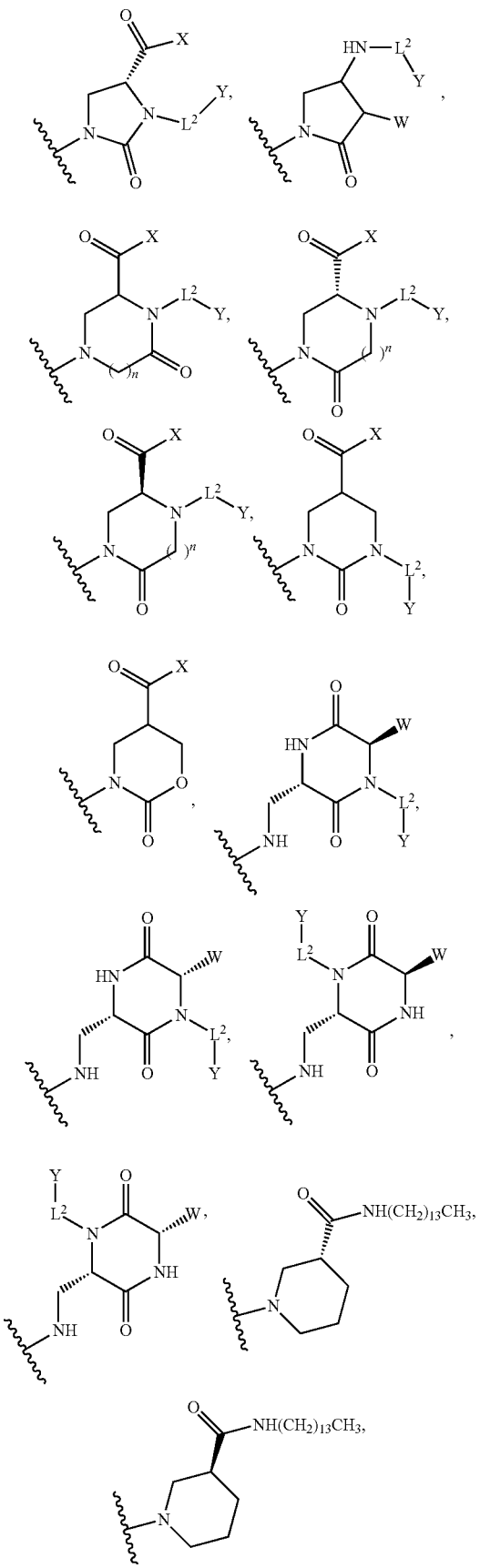

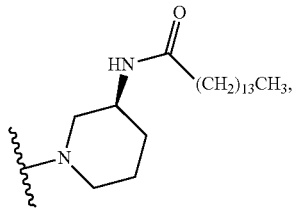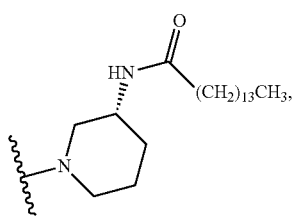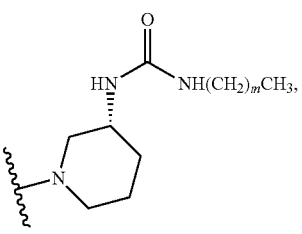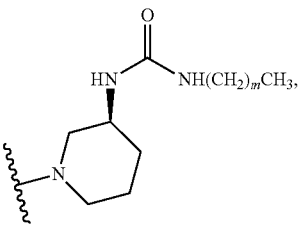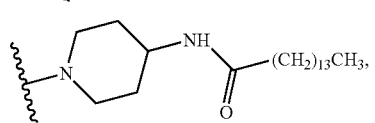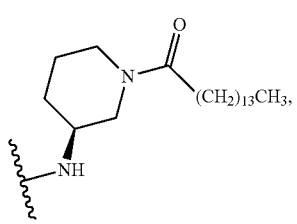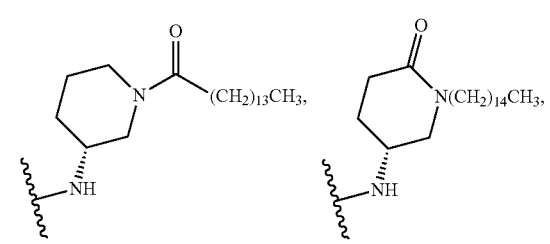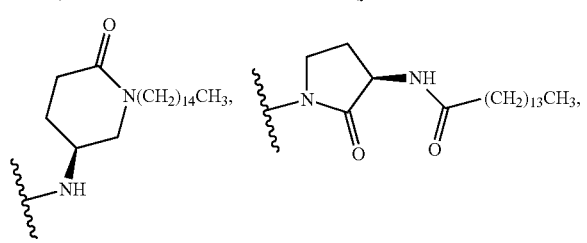
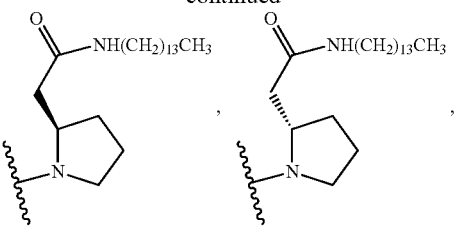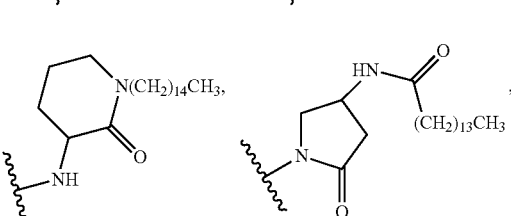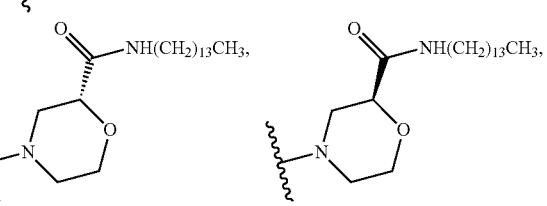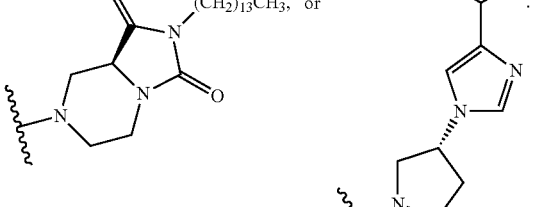
In certain embodiments of Formula (IA) or (IB), G is:
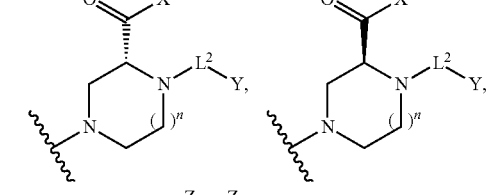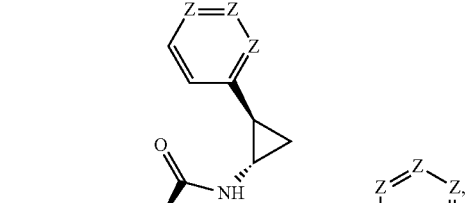

183
-continued
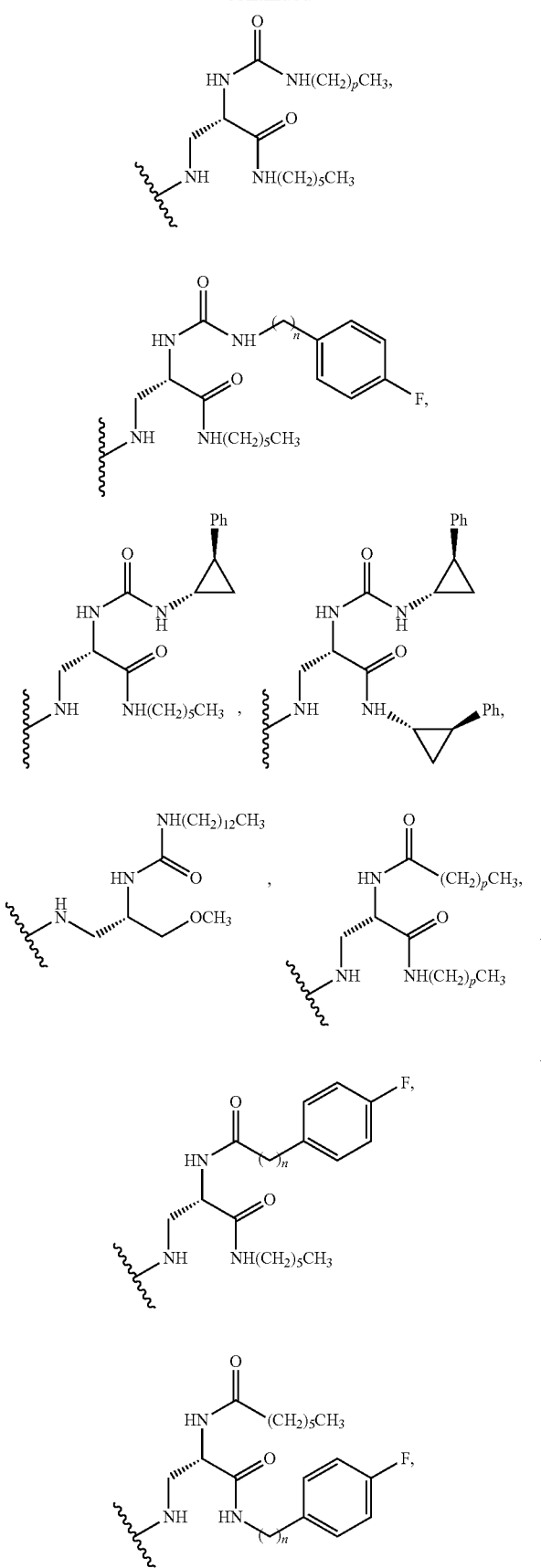
184
-continued
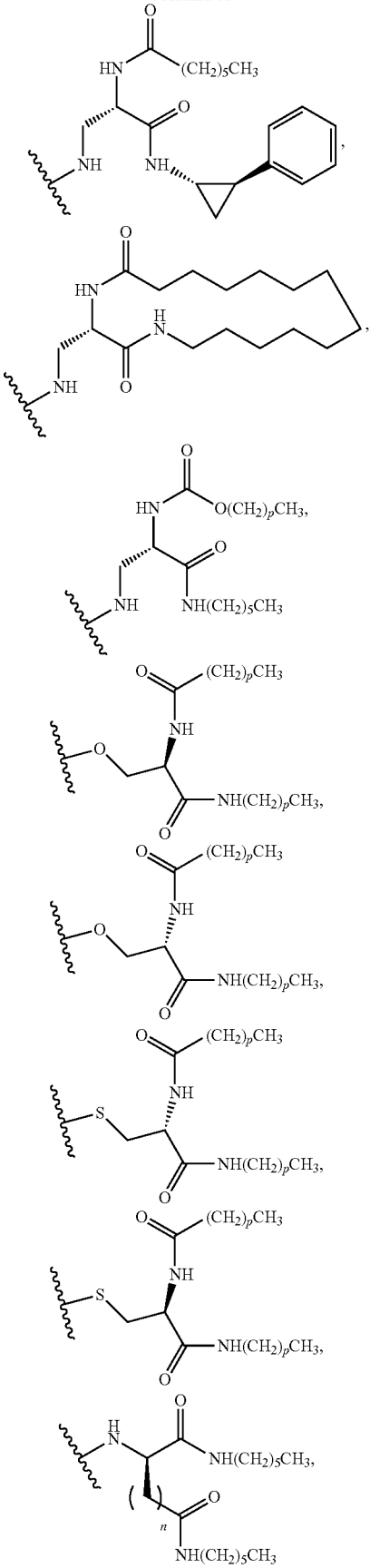

-continued
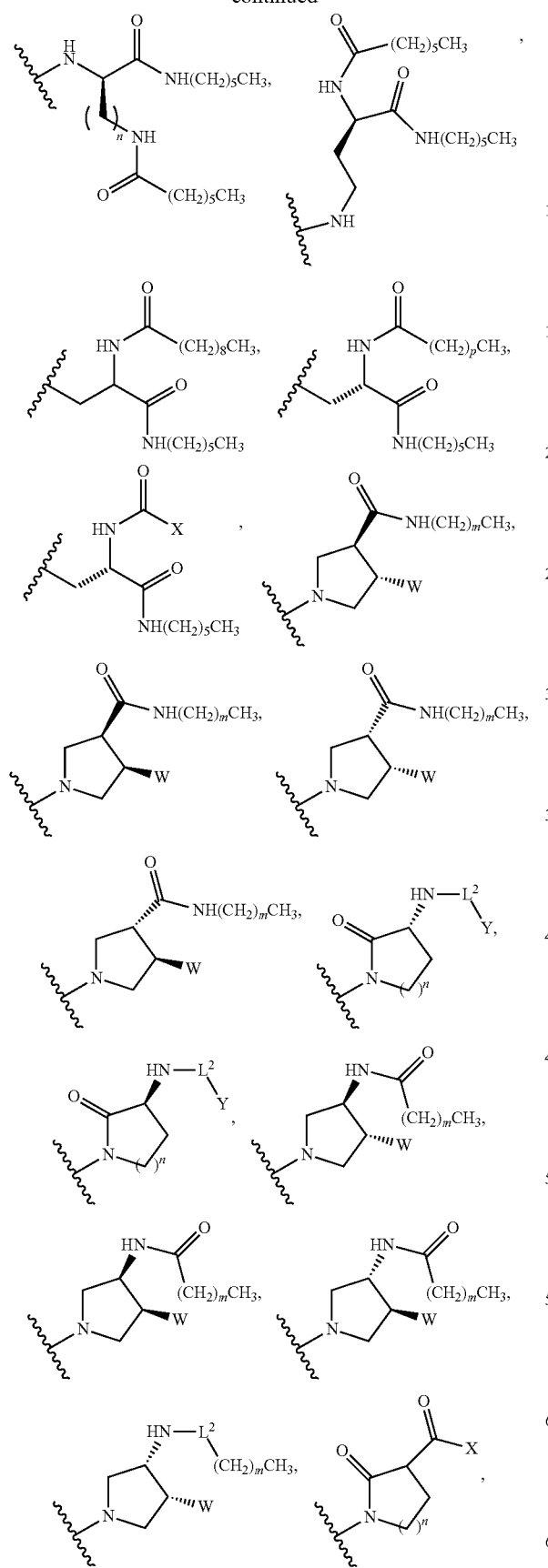
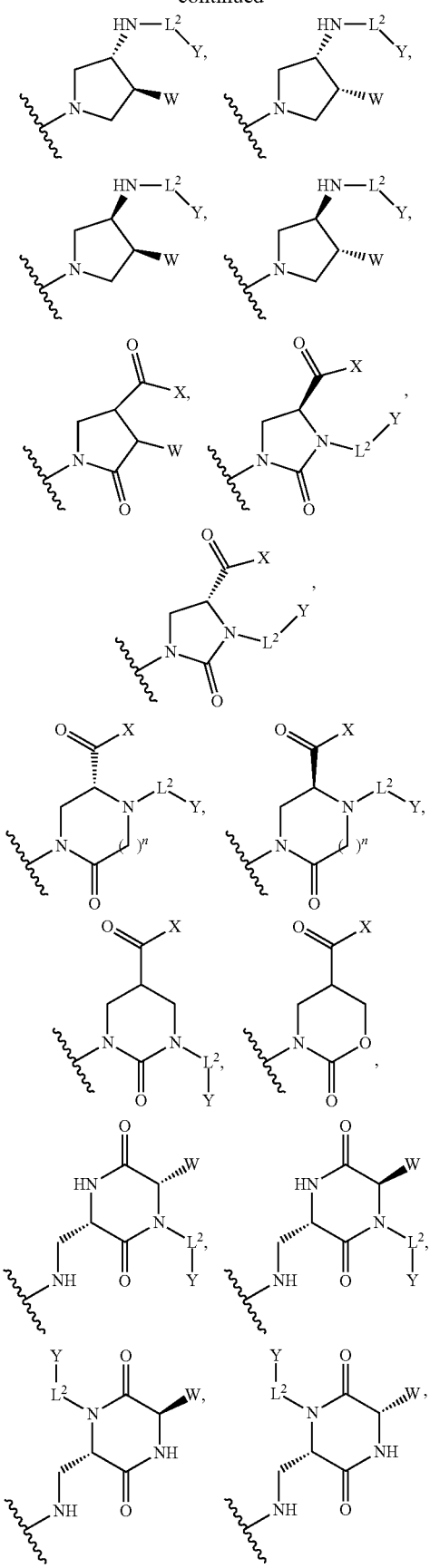

187
-continued
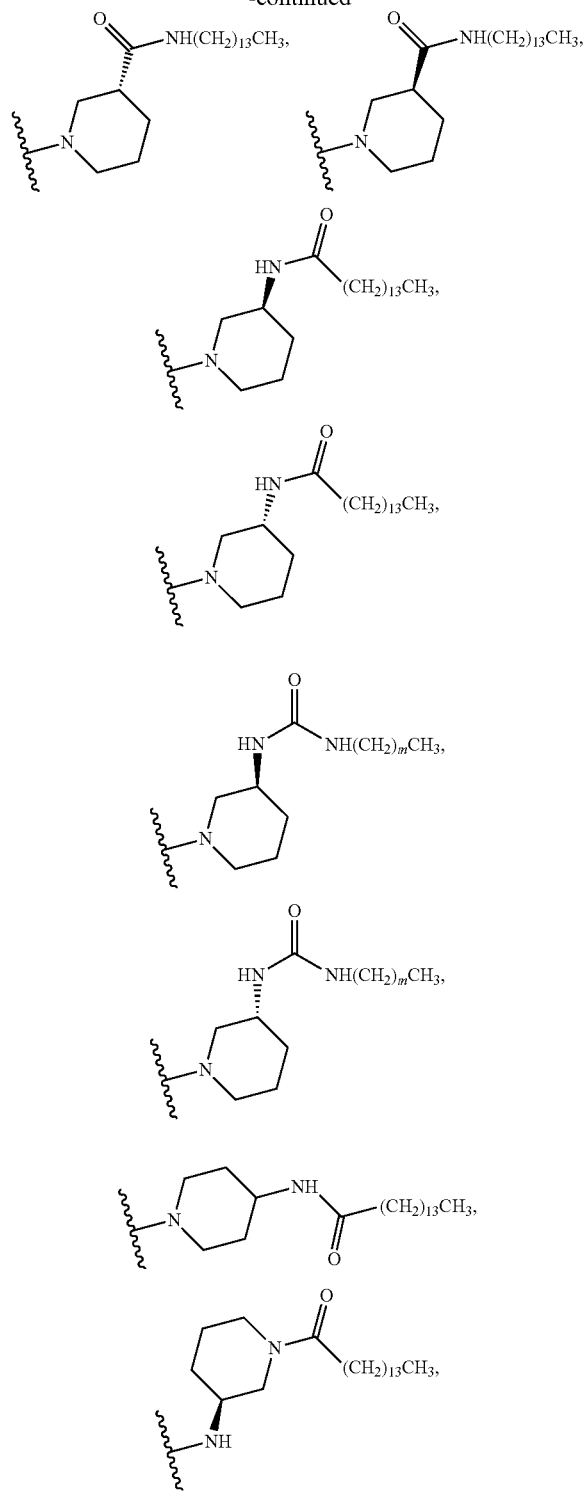
188
-continued
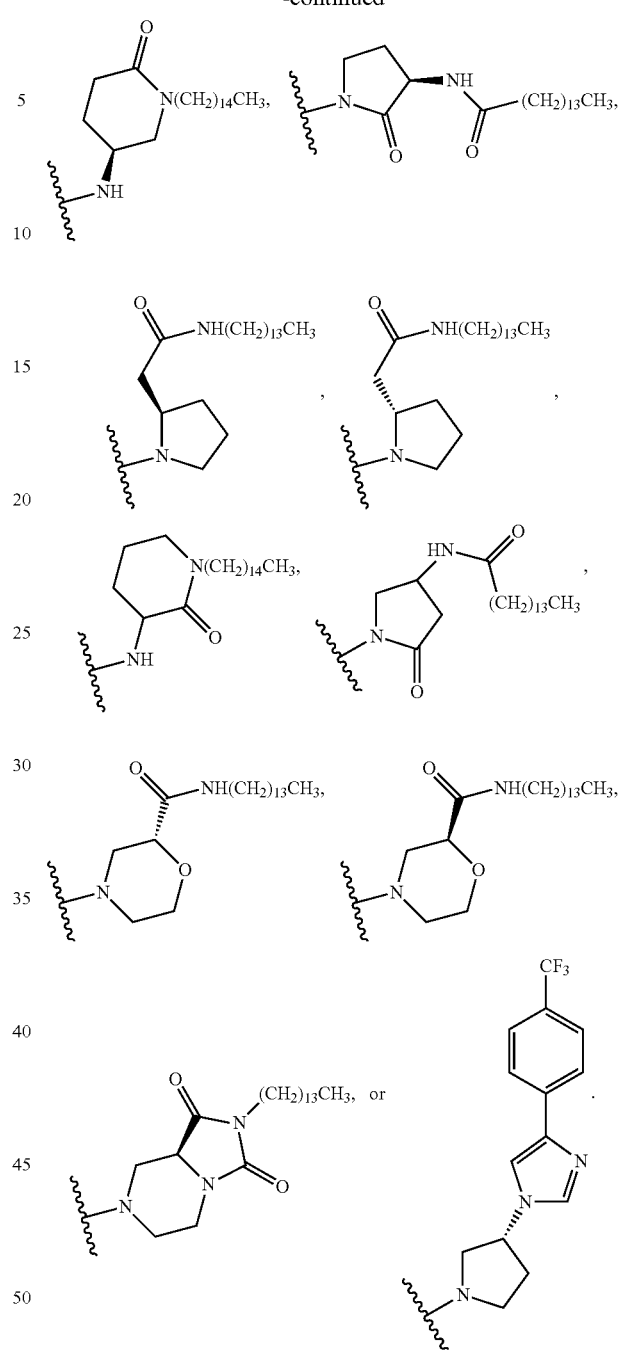
In certain embodiments of Formula (I), or (IA), G is:
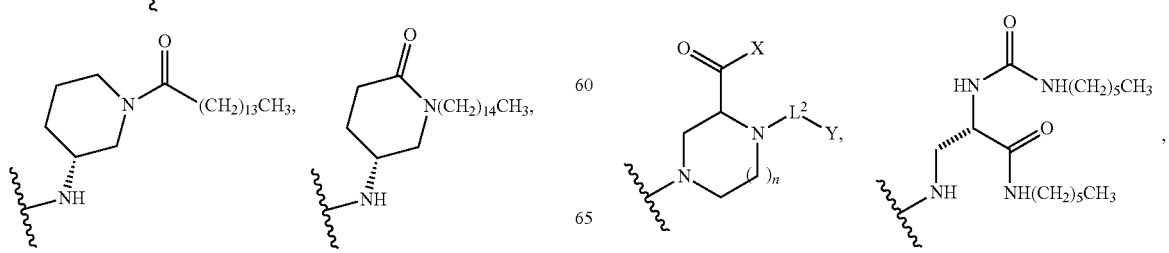

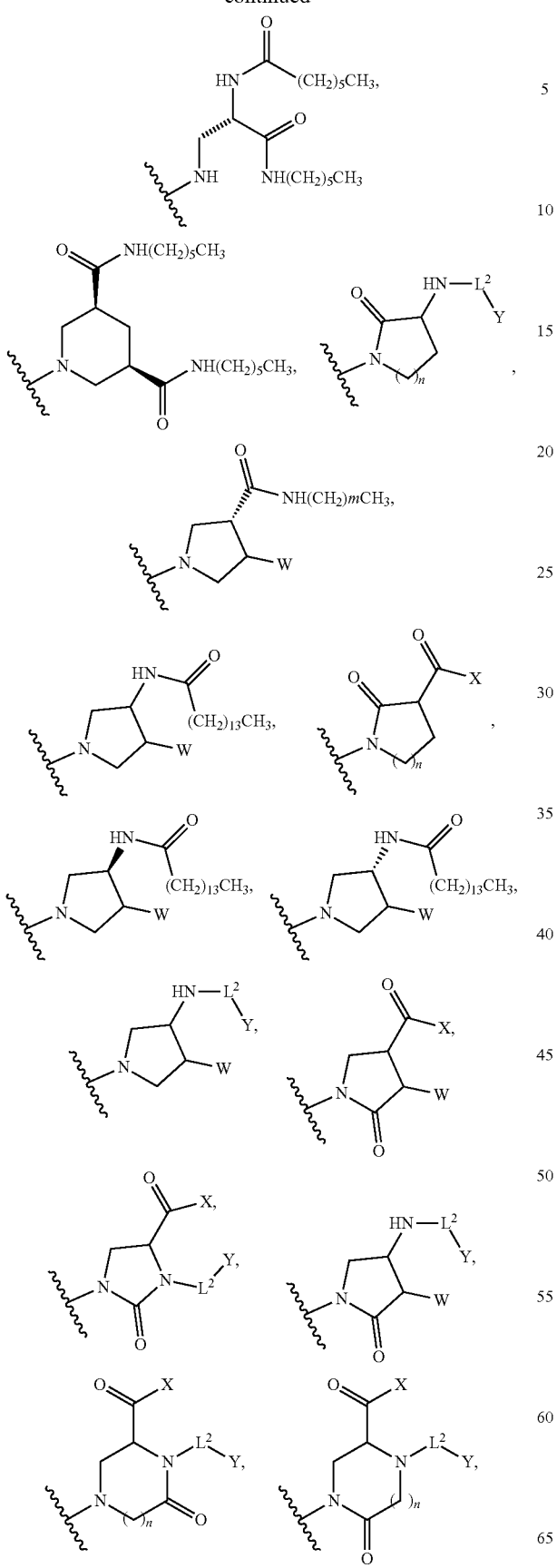
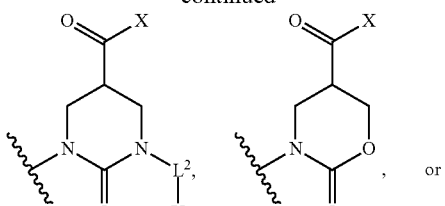
In certain embodiments of Formula (IA), G is:
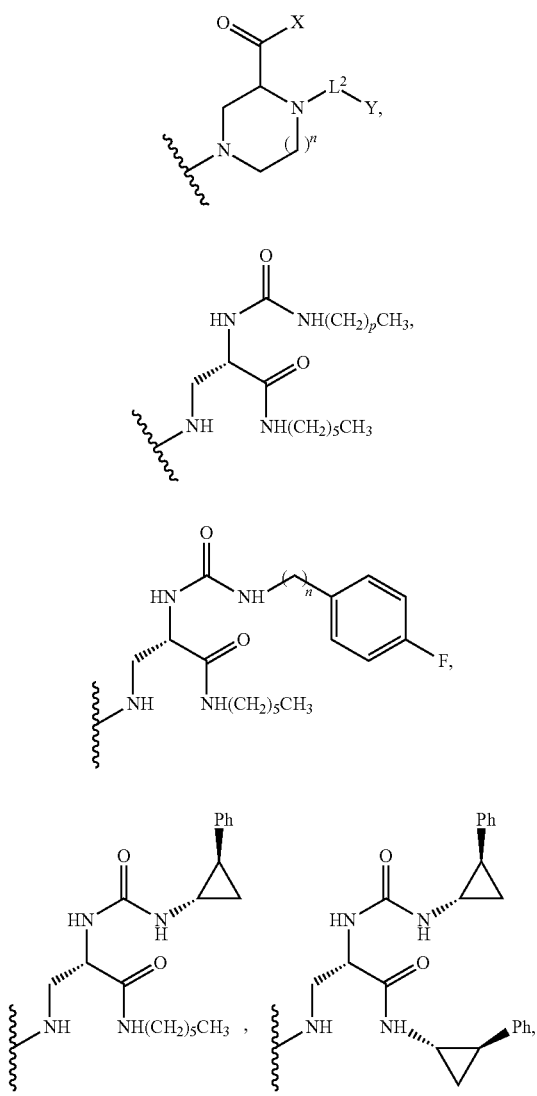

191
-continued
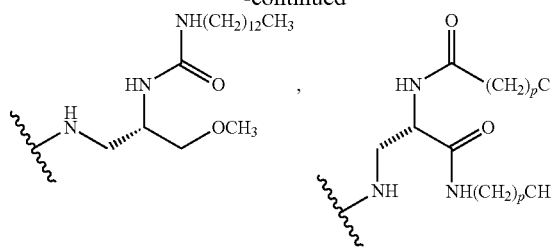
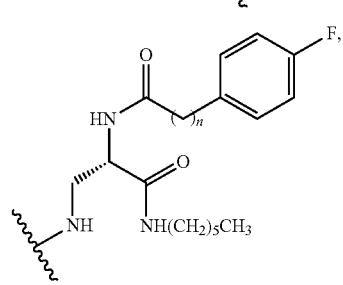
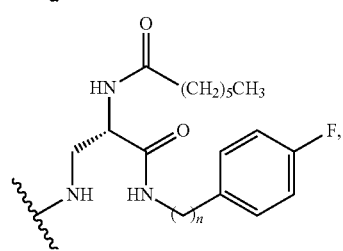
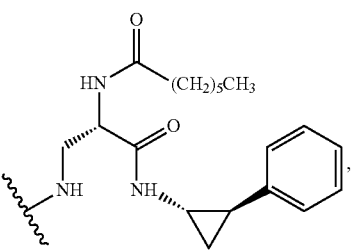
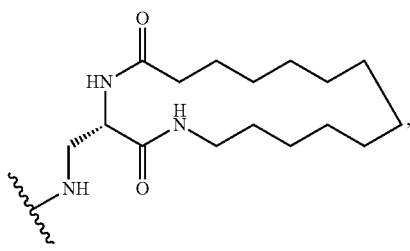
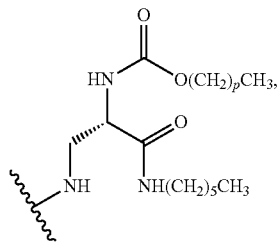
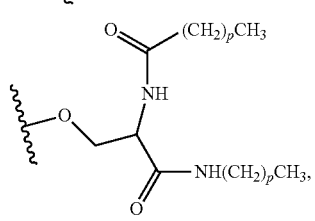
192
-continued
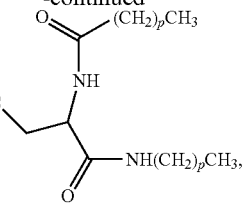
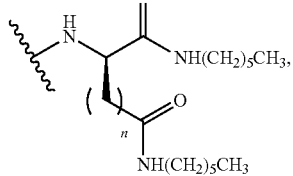
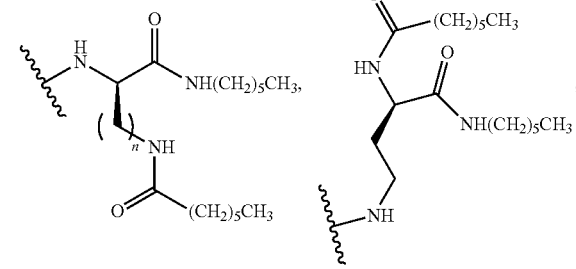
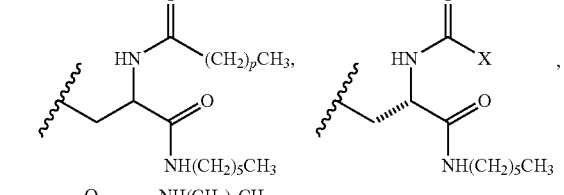
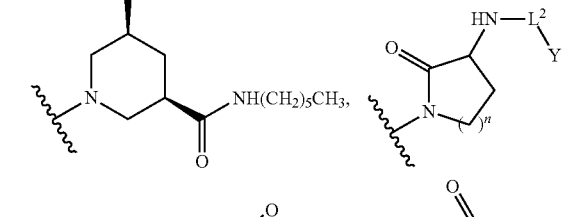
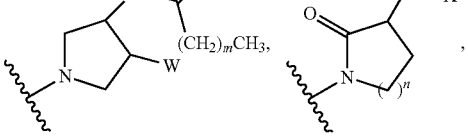
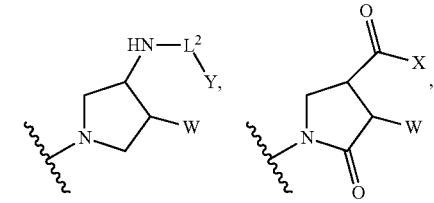
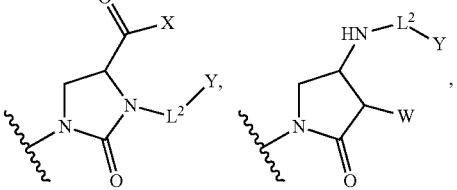

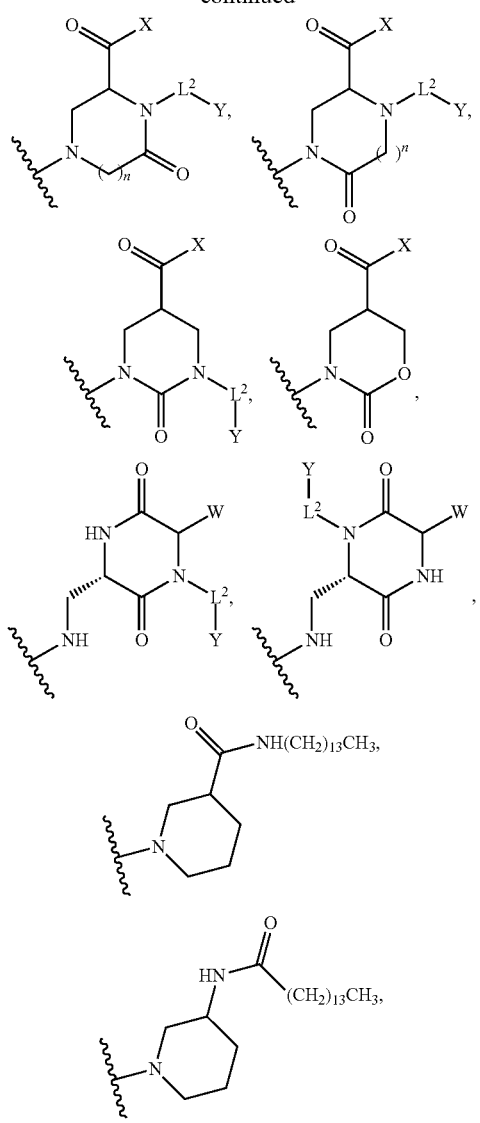
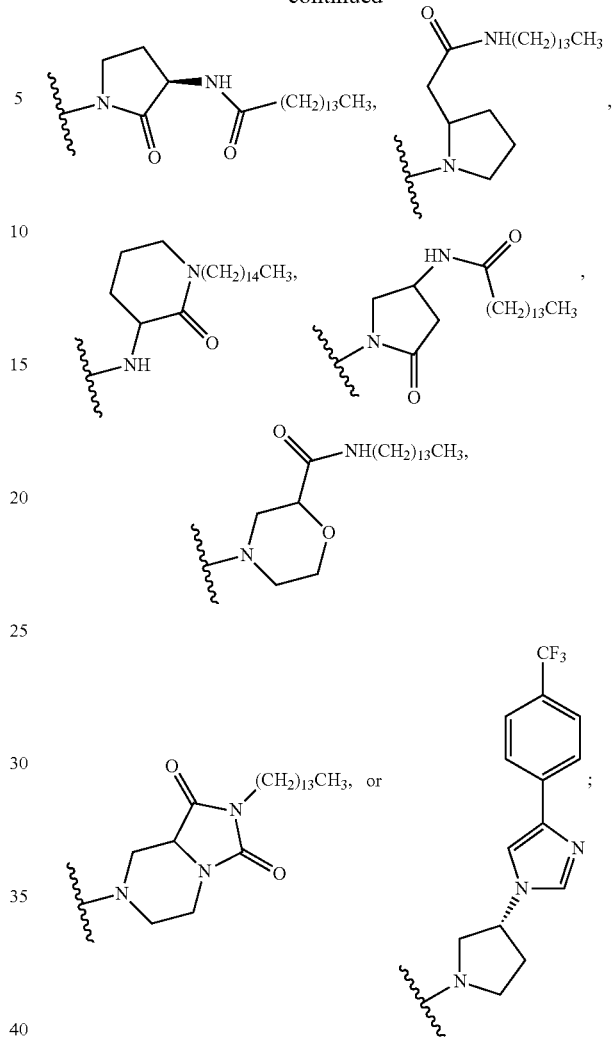
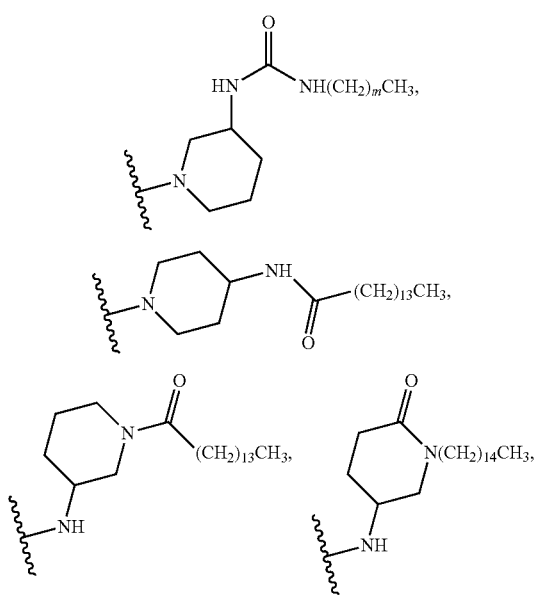
In certain embodiments of Formula (I), (IA), or (IB), G is:
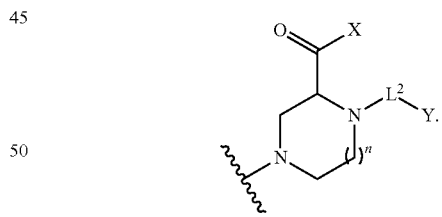
In certain embodiments of Formula (I), (IA), or (IB), G is:
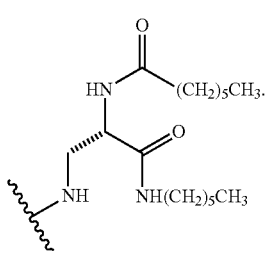

In certain embodiments of Formula (IA) or (IB), G is:

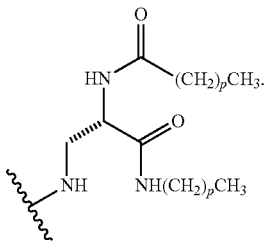

In certain embodiments of Formula (I), (IA), or (IB), G is:

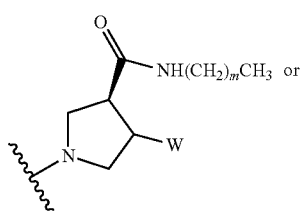

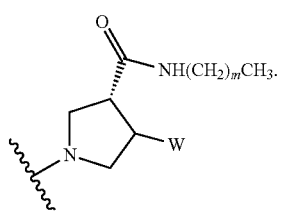

In certain embodiments of Formula (I), (IA), or (IB), G is:

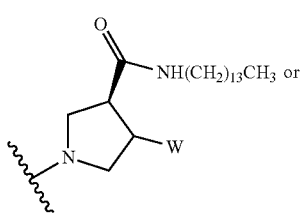

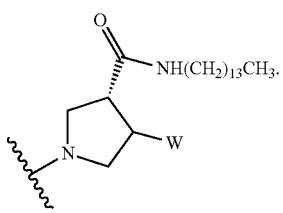

In certain embodiments of Formula (I), (IA), or (IB), G is:

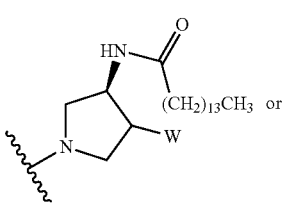

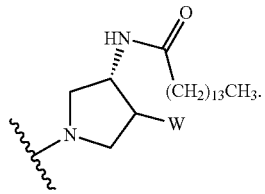

In certain embodiments of Formula (I) or (IA), G is:

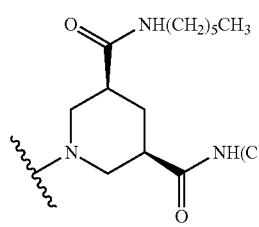

In certain embodiments of Formula (IA) or (IB), G is:

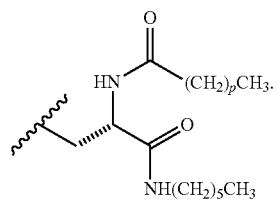

In certain embodiments of Formula (I), (IA), or (IB), G is:

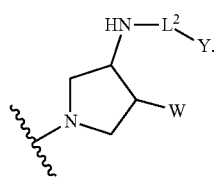

In certain embodiments of Formula (IA) or (IB), G is:

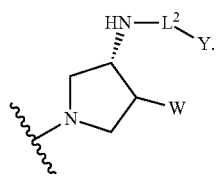

In certain embodiments of Formula (I), (IA), or (IB), if R is substituted or unsubstituted

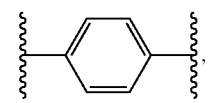

G is not

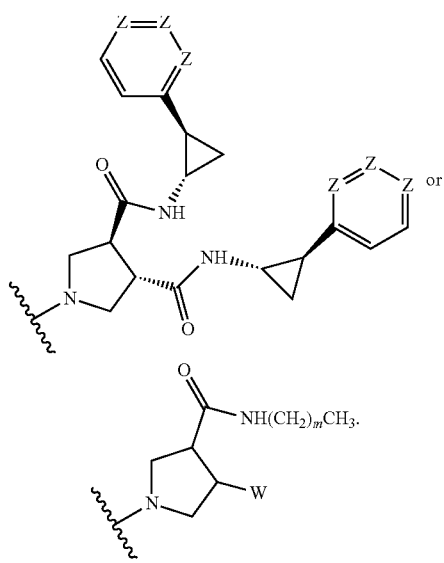 or

In certain embodiments of Formula (I), (IA), or (IB), if R is substituted or unsubstituted

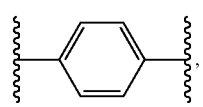

G is not

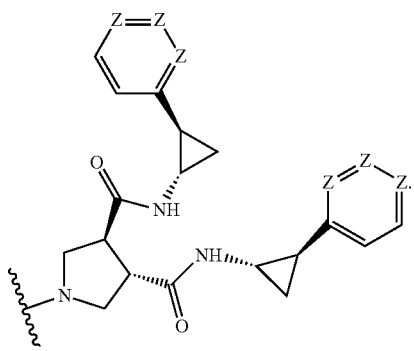

In certain embodiments of Formula (I), (IA), or (IB), if R is substituted

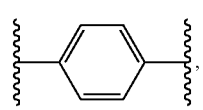

G is not

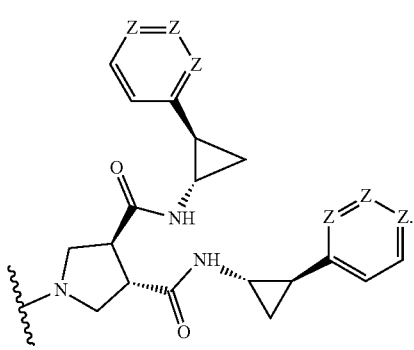

In certain embodiments of Formula (I), (IA), or (IB), G is not

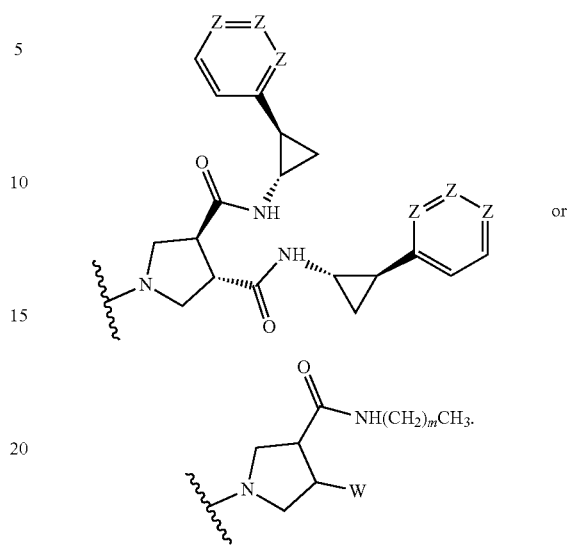 or

In certain embodiments of Formula (I), (IA), or (IB), G is not

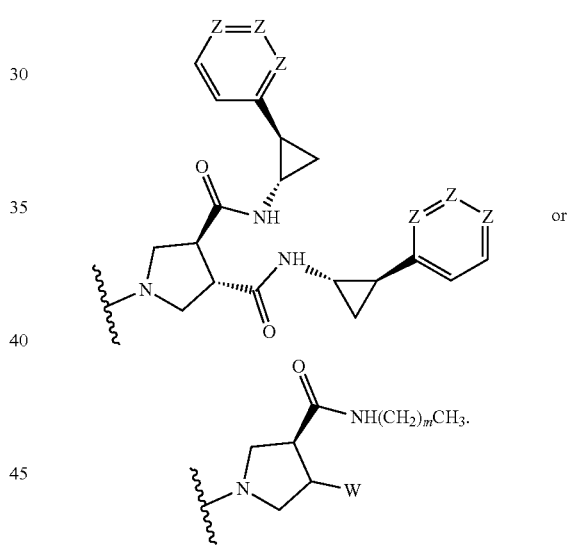 or

In certain embodiments of Formula (I), (IA), or (IB), if R is substituted or unsubstituted

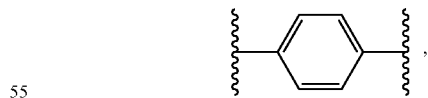

G is not

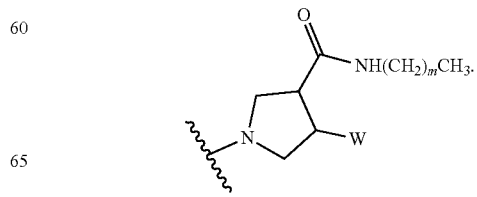

In certain embodiments of Formula (I), (IA), or (IB), if R is unsubstituted

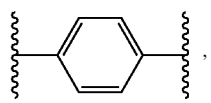,

G is not

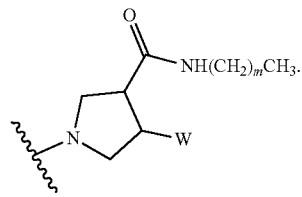.

In certain embodiments of Formula (I), (IA), or (IB), if R is substituted or unsubstituted

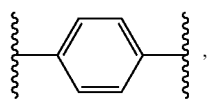 [SMILES: *c1ccc(*)cc1],

G is not

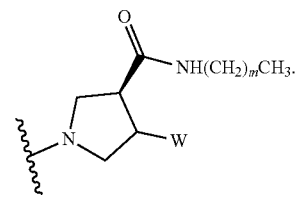.

In certain embodiments of Formula (I), (IA), or (IB), if R is unsubstituted

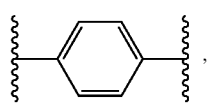 [SMILES: *c1ccc(*)cc1],

G is not

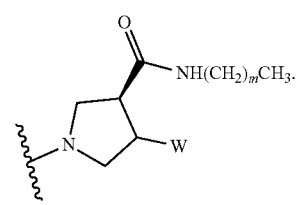.

In certain embodiments of Formula (I), (IA), or (IB), if G is

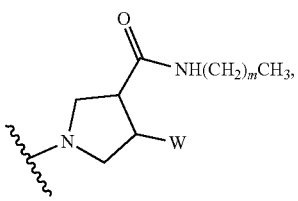

then W is not —(C=O)—NH(CH$_2$)$_m$CH$_3$ or H. In certain embodiments of Formula (I), (IA), or (IB), if G is

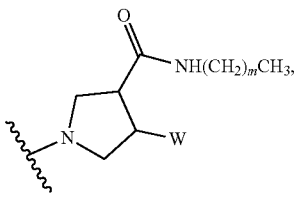

then W is not —(C=O)—NH(CH$_2$)$_m$CH$_3$. In certain embodiments of Formula (I), (IA), or (IB), if G is

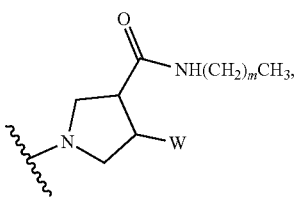

then W is not H.

In certain embodiments of Formula (I), (IA), or (IB), if G is

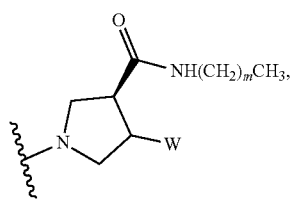

then W is not —(C=O)—NH(CH$_2$)$_m$CH$_3$ or H. In certain embodiments of Formula (I), (IA), or (IB), if G is

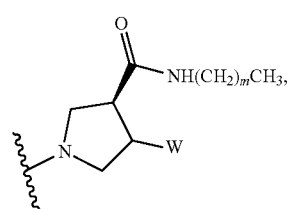

then W is not —(C=O)—NH(CH$_2$)$_m$CH$_3$. In certain embodiments of Formula (I), (IA), or (IB), if G is

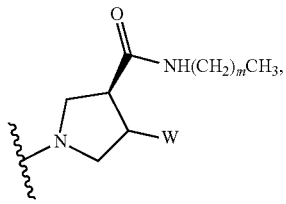

then W is not H.

In certain embodiments of Formula (I), (IA), or (IB), W is H, hydroxyl, —OCH$_3$, —O(CH$_2$)$_m$CH$_3$, —NH(C=O)CH$_3$—NH(C=O)(CH$_2$)$_m$CH$_3$, substituted or unsubstituted C$_{1-16}$ alkyl, C$_{1-16}$ alkyl-(substituted or unsubstituted Ph), —NH(CH$_2$)$_m$CH$_3$, —N((CH$_2$)$_m$CH$_3$)$_2$, or substituted or unsubstituted C$_{3-10}$ cycloalkyl. In certain embodiments of Formula (I), (IA), or (IB), W is not —(C=O)—NH(CH$_2$)$_m$CH$_3$.

In certain embodiments of Formula (IA) or (IB), W is —NH(C=O)CH$_3$, —NH(C=O)(CH$_2$)$_m$, CH$_3$, —NH(CH$_2$)$_m$CH$_3$, —N((CH$_2$)$_m$CH$_3$)$_2$, or —N(CH$_3$)(Y). In certain embodiments of Formula (I), (IA), or (IB), W is —NH(C=O)CH$_3$, —NH(C=O)(CH$_2$)$_m$CH$_3$, —NH(CH$_2$)$_m$CH$_3$, or —N((CH$_2$)$_m$CH$_3$)$_2$. In certain embodiments of Formula (IA) or (IB), W is —NH(CH$_2$)$_m$CH$_3$, —N((CH$_2$)$_m$CH$_3$)$_2$, or —N(CH$_3$)(Y). In certain embodiments of Formula (I), (IA), or (IB), W is —NH(CH$_2$)$_m$CH$_3$, or —N((CH$_2$)$_m$CH$_3$)$_2$. In certain embodiments of Formula (I), (IA), or (IB), W is —NH(C=O)CH$_3$ or —NH(C=O)(CH$_2$)$_m$CH$_3$. In certain embodiments of Formula (I), (IA), or (IB), W is, —NH(C=O)CH$_3$.

In certain embodiments of Formula (I), (IA), or (IB), W is H, substituted or unsubstituted C$_{1-16}$ alkyl, C$_{1-16}$ alkyl-(substituted or unsubstituted Ph), or substituted or unsubstituted C$_{3-10}$ cycloalkyl. In certain embodiments of Formula (I), (IA), or (IB), W is substituted or unsubstituted C$_{1-16}$ alkyl, C$_{1-16}$ alkyl-(substituted or unsubstituted Ph), or substituted or unsubstituted C$_{3-10}$ cycloalkyl. In certain embodiments of Formula (I), (IA), or (IB), W is substituted or unsubstituted C$_{1-16}$ alkyl or C$_{1-16}$ alkyl-(substituted or unsubstituted Ph).

In certain embodiments of Formula (I), (IA), or (IB), W is H, hydroxyl, —OCH$_3$, or —O(CH$_2$)$_m$CH$_3$, In certain embodiments, W is H, hydroxyl, or —OCH$_3$. In certain embodiments, W is H or —OCH$_3$. In certain embodiments, W is hydroxyl or —OCH$_3$. In certain embodiments, W is H. In certain embodiments, W is —OCH$_3$.

In certain embodiments of Formula (IA) or (IB), R is substituted or unsubstituted

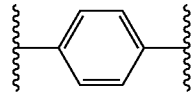

or substituted or unsubstituted

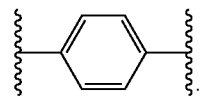

In certain embodiments of Formula (I) or (IA), R is substituted or unsubstituted

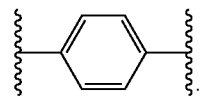

In certain embodiments of Formula (I), (IA), or (IB), R is unsubstituted

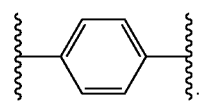 [SMILES: *c1ccc(*)cc1]

In certain embodiments of Formula (I), (IA), or (IB), if R is substituted or unsubstituted

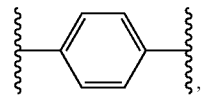 [SMILES: *c1ccc(*)cc1]

at least one Z is N. In certain embodiments of Formula (I), (IA), or (IB), if R is substituted

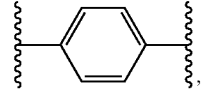

at least one Z is N.

In certain embodiments of Formula (IA) or (IB), R is substituted or unsubstituted

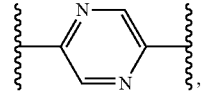

substituted or unsubstituted

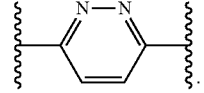

or substituted or unsubstituted

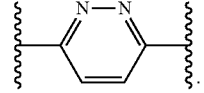

In certain embodiments of Formula (IA) or (IB), R is

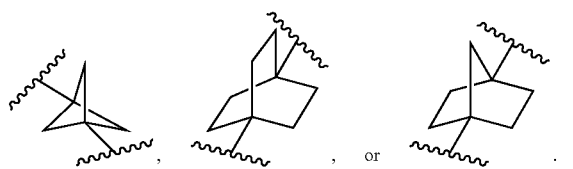 [SMILES: *C12CC(*)(C1)C2 ; *C12CCC(*)(CC1)CC2 ; *C12CCC(*)(CC1)C2]

In certain embodiments of Formula (IA) or (IB), R is substituted or unsubstituted


substituted or unsubstituted

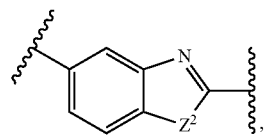

or substituted or unsubstituted

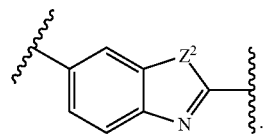

In certain embodiments of Formula (IA) or (IB), R is substituted or unsubstituted

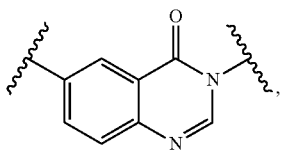 [SMILES: *c1ccc2ncn(*)c(=O)c2c1]

substituted or unsubstituted

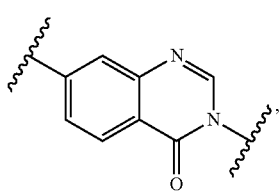 [SMILES: *c1ccc2c(=O)n(*)cnc2c1]

or substituted or unsubstituted

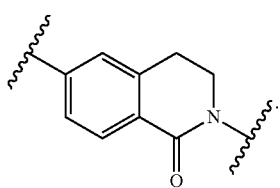 [SMILES: *c1ccc2c(c1)CCN(*)C2=O]

In certain embodiments of Formula (IA) or (IB), R is substituted or unsubstituted

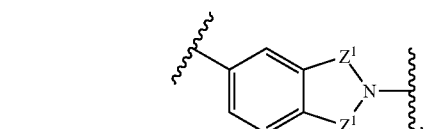

substituted or unsubstituted

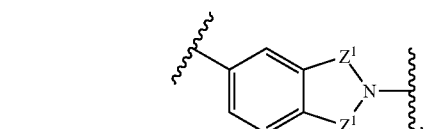

substituted or unsubstituted

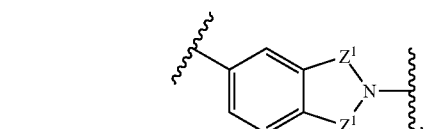

or substituted or unsubstituted

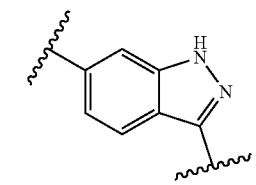 [SMILES: *c1ccc2c(*)n[nH]c2c1]

In certain embodiments of Formula (IA) or (IB), R is substituted or unsubstituted

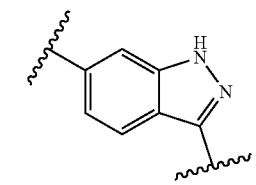 [SMILES: *c1ccc2c(*)n[nH]c2c1]

or substituted or unsubstituted

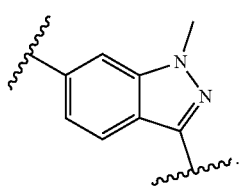 [SMILES: *c1ccc2c(*)nn(C)c2c1]

In certain embodiments of Formula (IA) or (IB), R is substituted or unsubstituted

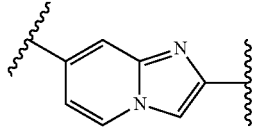 [SMILES: *c1ccn2cc(*)nc2c1]

or substituted or unsubstituted

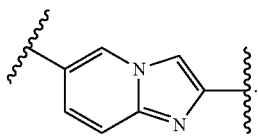 [SMILES: *c1ccc2nc(*)cn2c1]

In certain embodiments of Formula (IA) or (IB), $L^1$ is a bond, —CO—, —SO$_2$—, —(CH$_2$)$_m$—

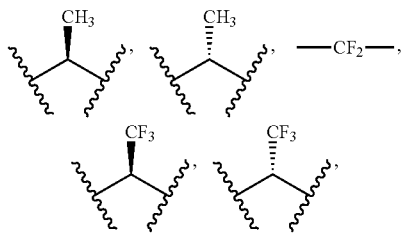

—NHC(=O)—, —NHCH$_2$—, five-membered heterocyclylene, five-membered heteroarylene, or

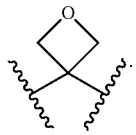 [SMILES: *C1(*)COC1]

In certain embodiments of Formula (IA) or (IB), $L^1$ is $L^1$ is a bond, —CO—, —SO$_2$—, —(CH$_2$)$_m$—

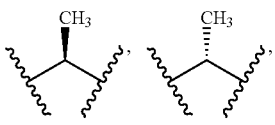

—CF$_2$—,

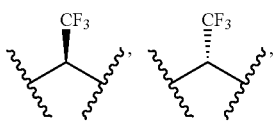

—NHC(=O)—, —NHCH$_2$—,

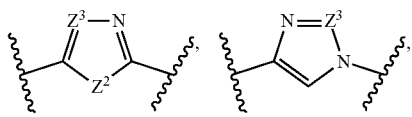

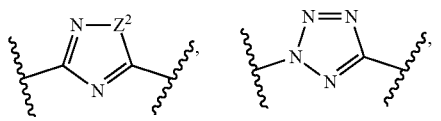

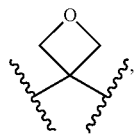

wherein each $Z^3$ is independently —CH— or —N—.

In certain embodiments of Formula (IA) or (IB), $L^1$ is a bond, —CO—, —SO$_2$—, (—CH$_2$—)$_m$,

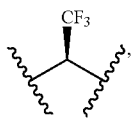 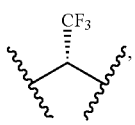

—NHC(=O)—,

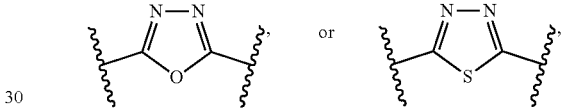

In certain embodiments of Formula (I), $L^1$ is a bond, (—CH$_2$—)$_m$, —CO—, —SO$_2$—,

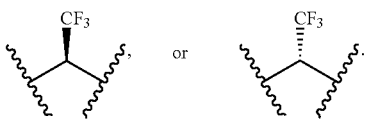

In certain embodiments of Formula (IA), or (IB), $L^1$ is a bond, —CO—, —SO$_2$—, or (—CH$_2$—)$_m$ In certain embodiments of Formula (I), (IA), or (IB), $L^1$ is —CO—, —SO$_2$—, or (—CH$_2$—)$_m$. In certain embodiments of Formula (I), (IA), or (IB), $L^1$ is —CO— or —SO$_2$—. In certain embodiments of Formula (I), (IA), or (IB), $L^2$ is (—CH$_2$—)$_m$ or —CO—. In certain embodiments of Formula (IA) or (TB), $L^1$ is a bond, (—CH$_2$—)$_m$, or —CO—. In certain embodiments of Formula (IA) or (IB), $L^1$ is a bond or —CO—. In certain embodiments of Formula (IA) or (IB), $L^1$ is a bond or (—CH$_2$—)$_m$. In certain embodiments, $L^1$ is a bond.

In certain embodiments of Formula (IA) or (IB), $L^1$ is five-membered heterocyclylene or five-membered heteroarylene. In certain embodiments of Formula (IA) or (IB), $L^1$ is five-membered heterocyclylene. In certain embodiments of Formula (IA) or (IB), $L^1$ is five-membered heteroarylene. In certain embodiments of Formula (IA) or (IB), $L^1$ is

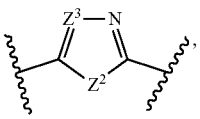 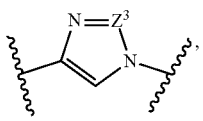

-continued

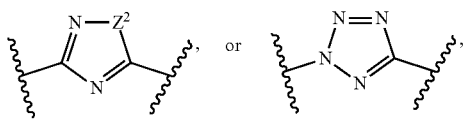

wherein each $Z^3$ is independently —CH— or —N—.

In some embodiments of Formula (IA), $L^1$ is —$(CH_2)_m$—, —$CH(CH_3)$—, —$CH(CF_3)$—, or —$CF_2$—. In some embodiments of Formula (IA), $L^1$ is —$(CH_2)_m$—,

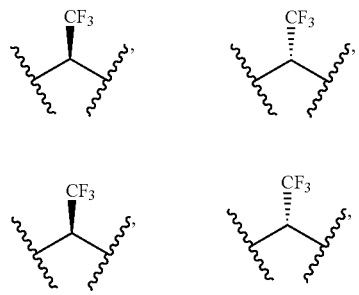

or —$CF_2$—. In some embodiments of Formula (IA), $L^1$ is —$(CH_2)_m$— or —$CH(CH_3)$—. In some embodiments of Formula (IA), $L^1$ is —$(CH_2)_m$—,

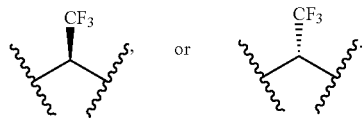

In some embodiments of Formula (IA), $L^1$ is

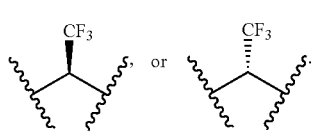

In some embodiments of Formula (IA), $L^1$ is $CH(CF_3)$— or —$CF_2$—. In some embodiments of Formula (IA), $L^1$ is —$CF_2$—,

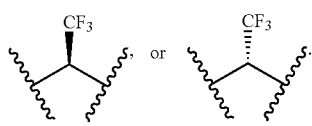

In some embodiments of Formula (IA), $L^1$ is

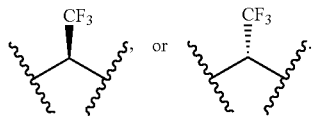

In some embodiments of Formula (IA), $L^1$ is

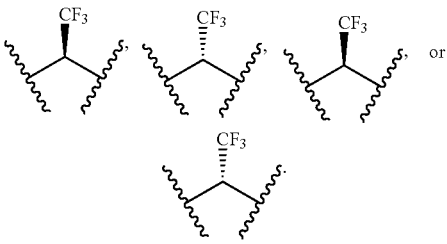

In some embodiments of Formula (IA) or (IB), $L^1$ is —NHC(=O)— or —NHCH$_2$—.

In certain embodiments of Formula (I), (IA), or (IB), n is 1. In certain embodiments of Formula (I), (IA), or (IB), n is 2. In certain embodiments of Formula (I), (IA), or (IB), n is 3. In certain embodiments of Formula (I), (IA), or (IB), n is 1 or 2. In certain embodiments of Formula (I), (IA), or (IB), n is 2 or 3.

In certain embodiments of Formula (I), (IA), or (IB), m is 1. In certain embodiments of Formula (I), (IA), or (IB), m is 5. In certain embodiments of Formula (I), (IA), or (IB), m is 13. In certain embodiments of Formula (I), (IA), or (IB), each m is independently 1-10. In certain embodiments of Formula (I), (IA), or (B), each m is independently 1-5. In certain embodiments of Formula (I), (IA), or (IB), each m is independently 5-16. In certain embodiments of Formula (I), (IA), or (IB), each m is independently 5-13. In certain embodiments of Formula (I), (IA), or (IB), each m is independently 5-10. In certain embodiments of Formula (I), (IA), or (B), each m is independently 10-16.

In certain embodiments of Formula (IA) or (IB), each p is independently 5-8.

In certain embodiments of Formula (I), (IA), or (IB), at least one instance of Z is N. In certain embodiments of Formula (I), (IA), or (IB), each instance of Z is CH.

In certain embodiments of Formula (IA) or (IB), $Z^1$ is —CH$_2$—. In certain embodiments of Formula (IA) or (IB), $Z^1$ is —C(=O)—.

In certain embodiments of Formula (IA) or (TB), each $Z^2$ is independently —O— or —S—. In certain embodiments of Formula (IA) or (IB), each $Z^2$ is independently —O— or —NH—. In certain embodiments of Formula (IA) or (IB), each $Z^2$ is independently —NH— or —S—.

In certain embodiments of Formula (IA) or (IB), $Z^3$ is —CH—. In certain embodiments of Formula (IA) or (IB), $Z^3$ is —N—.

In certain embodiments of Formula (I), (IA), or (IB), X is —NH(CH$_2$)$_m$ CH$_3$ or —NH(CH$_2$)$_m$-(substituted or unsubstituted Ph). In certain embodiments of Formula (I), (IA), or (B), X is —NH(CH$_2$)$_m$-(substituted or unsubstituted Ph) or

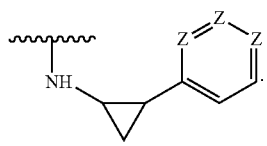

In certain embodiments of Formula (I), (IA), or (IB), X is —NH(CH$_2$)$_m$ CH$_3$ or

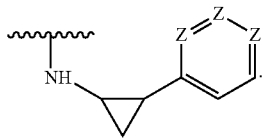

In certain embodiments of Formula (I), (IA), or (IB), X is —NH(CH$_2$)$_m$-(substituted or unsubstituted Ph), In certain embodiments of Formula (I), (IA), or (IB), X is —NH (CH$_2$)$_m$ CH$_3$. In certain embodiments of Formula (I), (IA), or (IB), X is

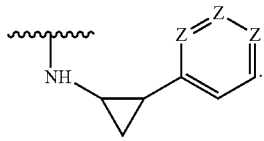

In certain embodiments of Formula (I), (IA), or (IB), Y is —H, substituted or unsubstituted C$_{1-16}$ alkyl, C$_{1-16}$ alkyl-(substituted or unsubstituted Ph), —NH(CH$_2$)$_m$CH$_3$, or substituted or unsubstituted C$_{3-10}$ cycloalkyl. In certain embodiments of Formula (I), (IA), or (IB), Y is —H, substituted or unsubstituted C$_{1-16}$ alkyl, C$_{1-16}$ alkyl-(substituted or unsubstituted Ph), or substituted or unsubstituted C$_{3-10}$ cycloalkyl. In certain embodiments of Formula (I), (IA), or (IB), Y is —H, substituted or unsubstituted C$_{1-16}$ alkyl, or C$_{1-16}$ alkyl-(substituted or unsubstituted Ph). In certain embodiments of Formula (IA) or (IB), Y is —NH(CH$_2$)$_m$CH$_3$ or —SO$_2$(CH$_2$)$_{13}$CH$_3$. In certain embodiments of Formula (I), (IA), or (IB), Y is —NH(CH$_2$)$_m$CH$_3$. In certain embodiments of Formula (IA) or (IB), Y is —SO$_2$(CH$_2$)$_{13}$CH$_3$.

In certain embodiments, the compound of Formula (I), (IA), or (IB) has the structure of Formula (II), (III), (IV), or (V).

(II)

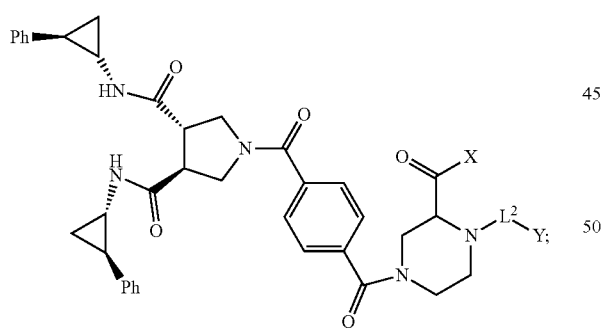

(III)

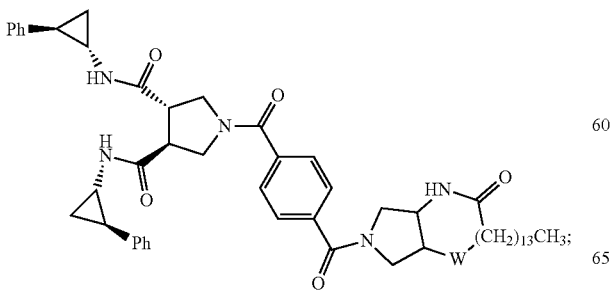

(IV)

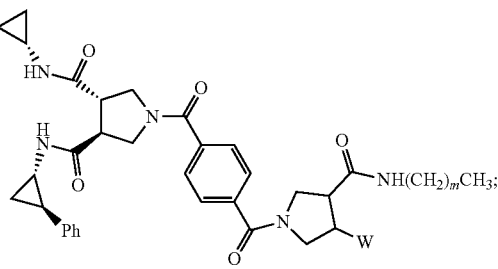

(V)

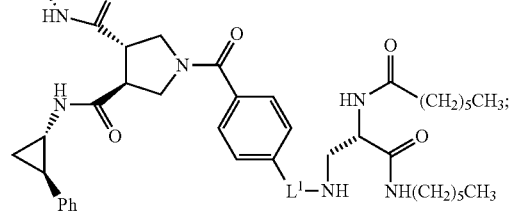

or a pharmaceutically acceptable salt thereof, wherein X, Y, W, L$^1$, and L$^2$ are as defined above.

In certain embodiments, the compound of Formula (IA) or (IB) has the structure of Formula (VI), VII) or (VIII):

(VI)

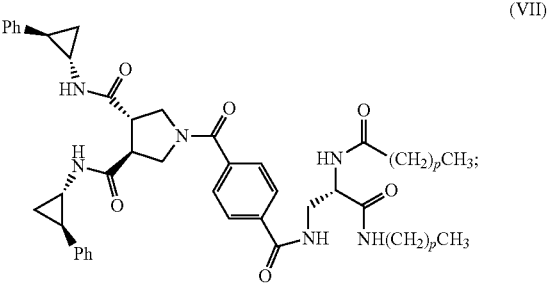

(VII)

(VIII)
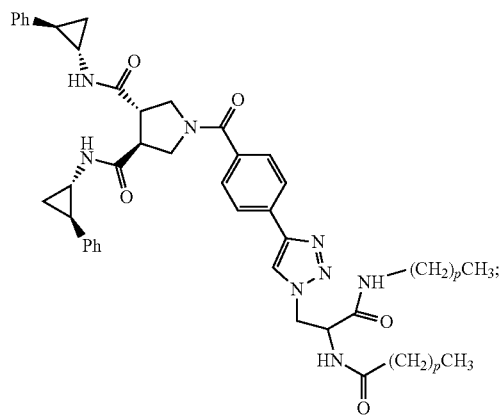
or a pharmaceutically acceptable salt thereof, wherein W, L¹, p, and m are as defined above.
In certain embodiments of Formula (II), L² is —(CH₂)ₘ—, —SO₂—, or —CO—. In certain embodiments, the compound of Formula (II) is selected from compounds:
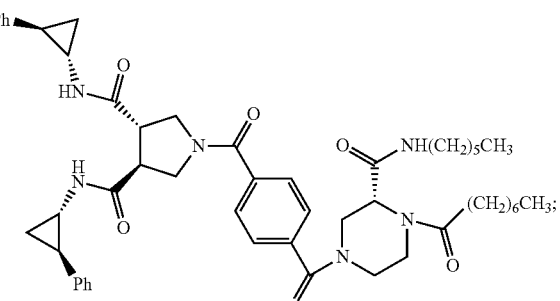
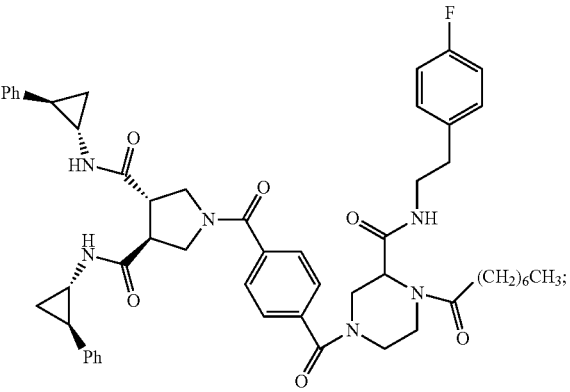
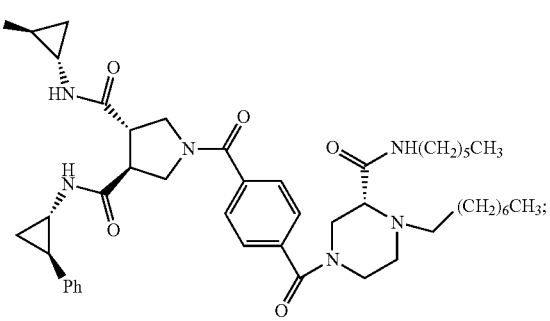
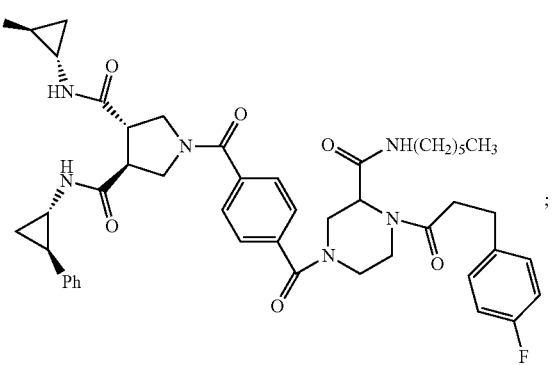

213
-continued
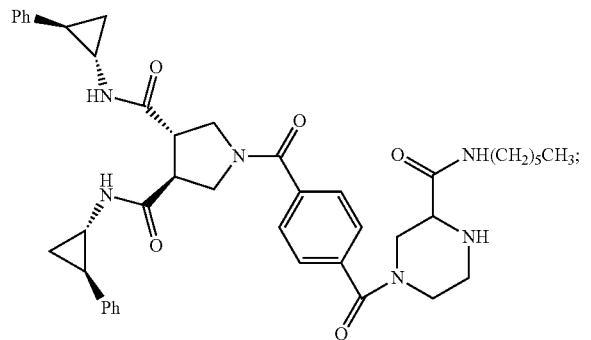
042
214
-continued
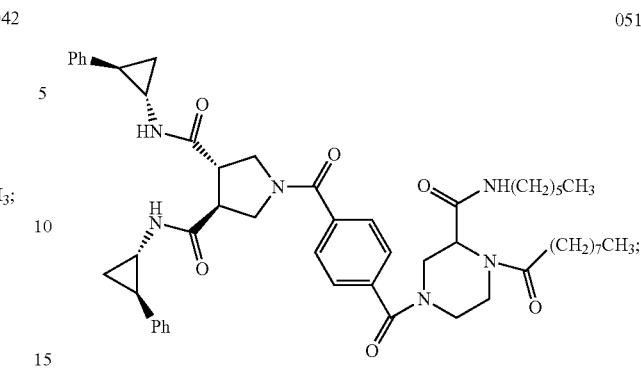
051
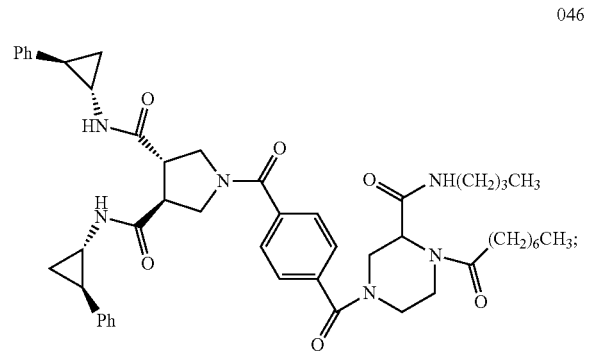
046
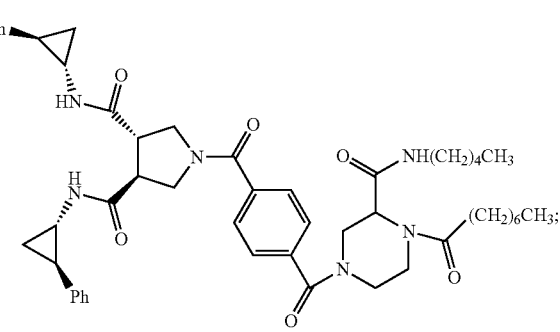
052
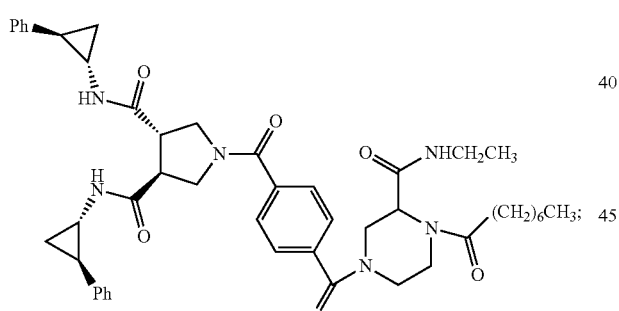
048
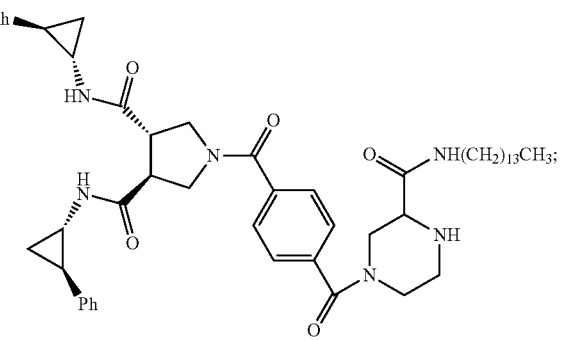
054
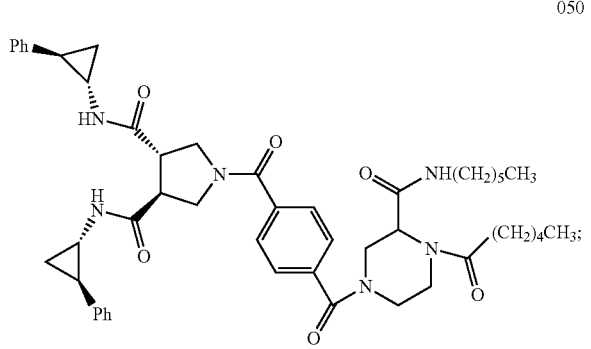
050
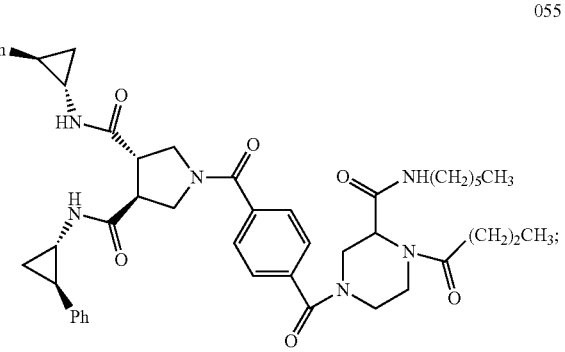
055

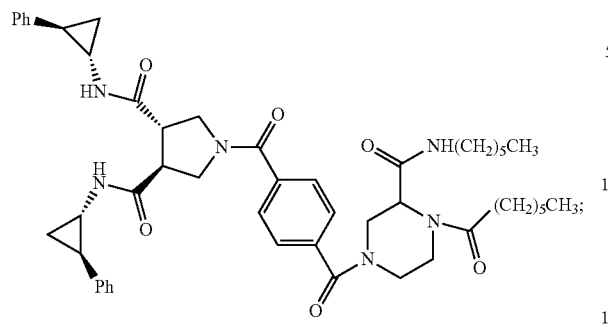
056
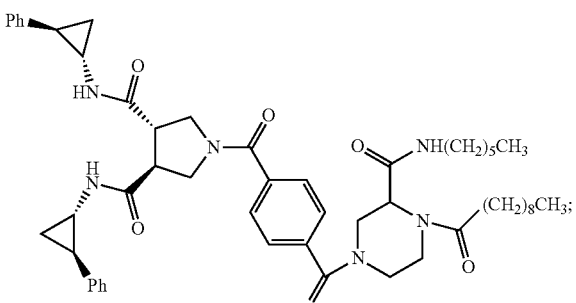
064
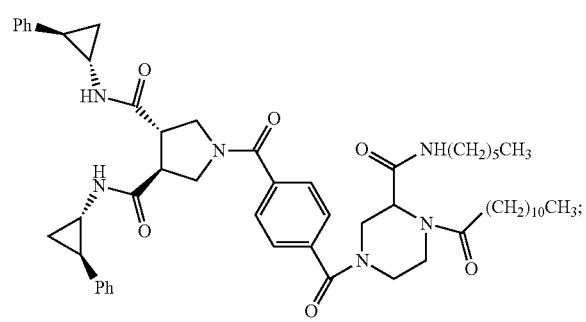
057
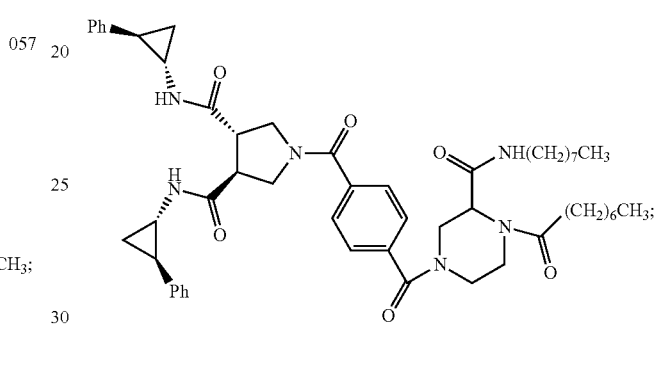
065
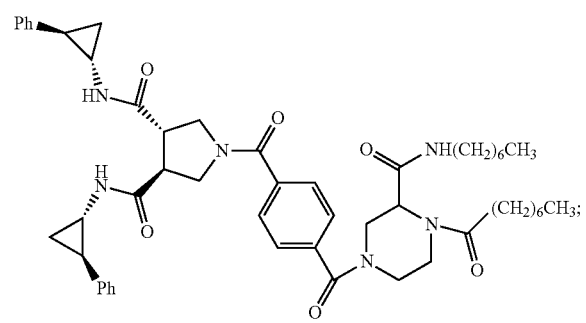
058
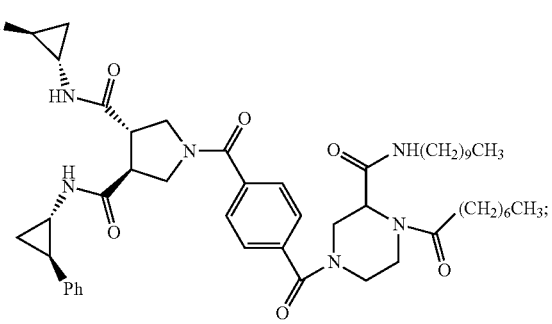
066
and pharmaceutically acceptable salts thereof.
In certain embodiments, Formula (I) has the structure of Formula (III), wherein W is H. In certain embodiments, the compound of Formula (III) is selected from compounds:
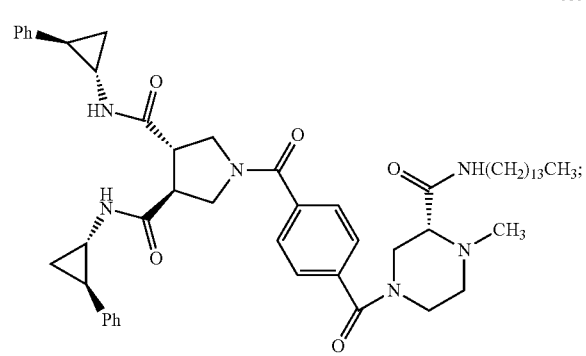
059
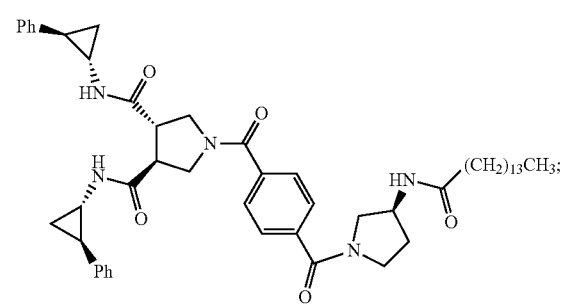
026

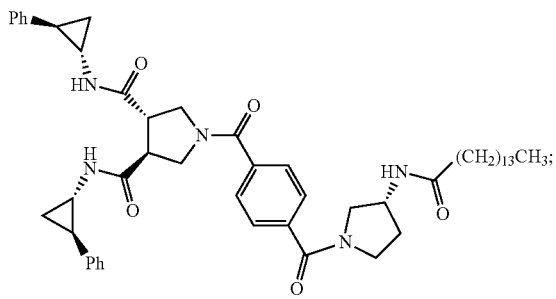

027 and pharmaceutically acceptable salts thereof.

In certain embodiments, the compound of Formula (III) is selected from compounds:

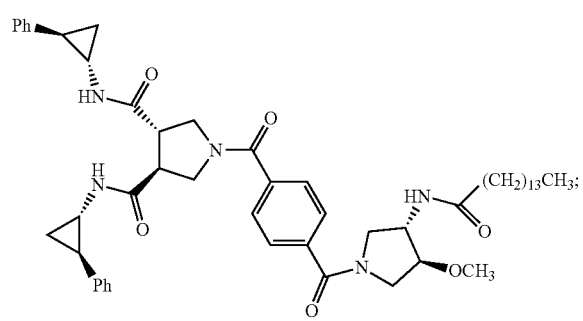

101

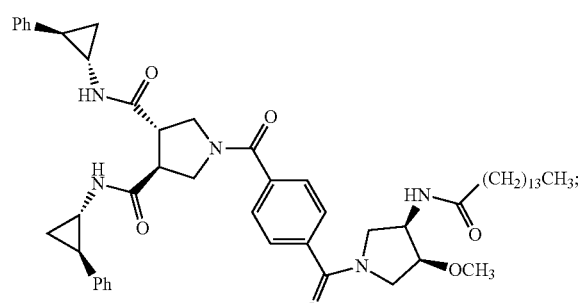

209

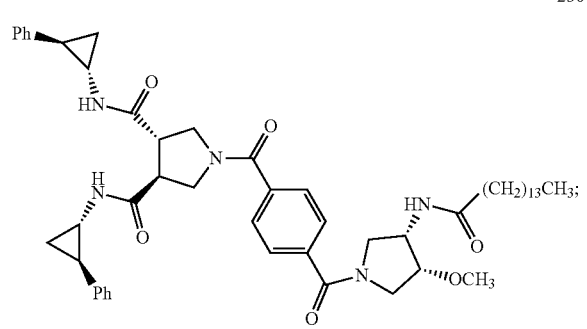

236 and pharmaceutically acceptable salts thereof.

In certain embodiments, Formula (I) has the structure of Formula (IV), wherein: W is —OH, —OCH$_3$, —O(CH$_2$)$_m$CH$_3$, —NH(C═O)CH$_3$, or H(C═O)(CH$_2$)$_m$CH$_3$, and each m is independently 4-15. In certain embodiments, the compound of Formula (IV) is selected from compounds:

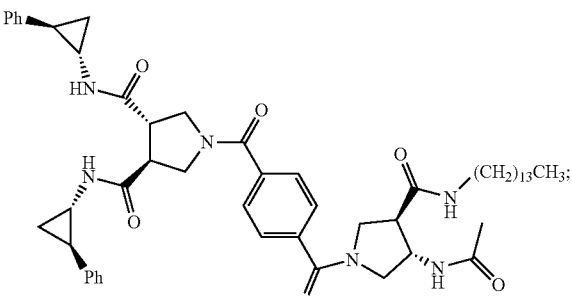

028

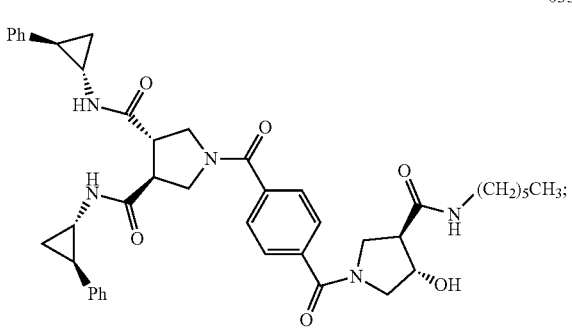

033

034

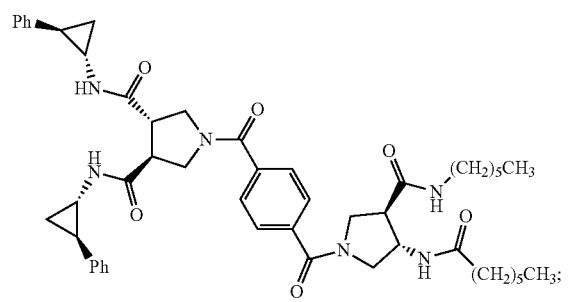

039

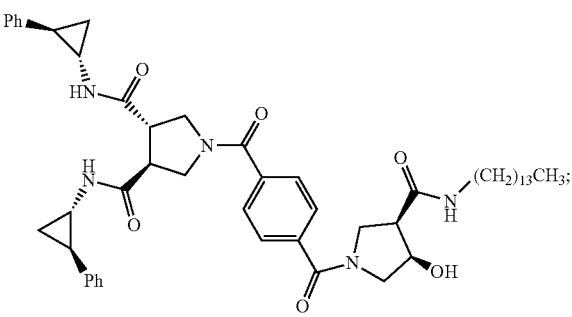

044

045
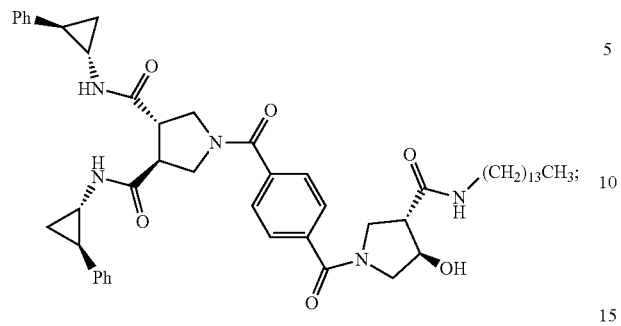
060
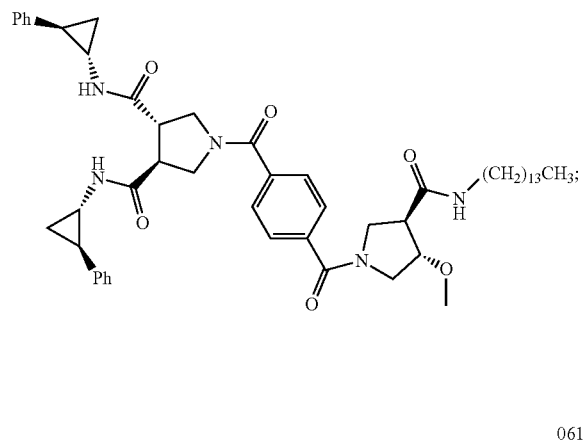
061
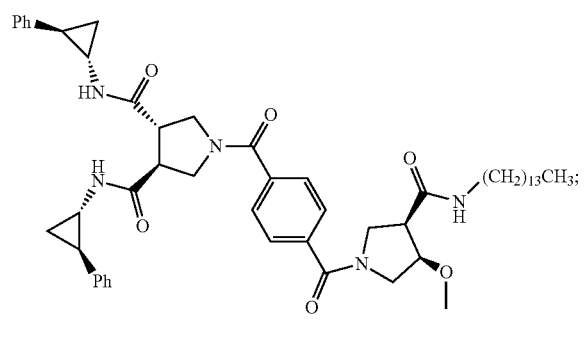
062
063
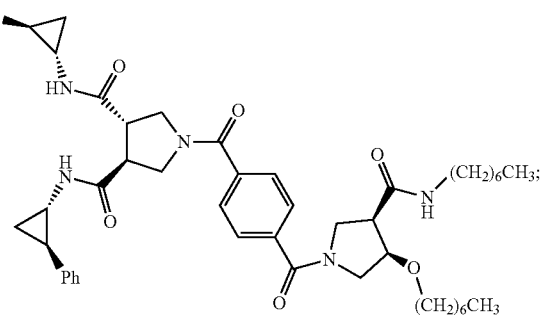
and pharmaceutically acceptable salts thereof.
In certain embodiments, the compound of Formula (IV) is selected from compounds:
098
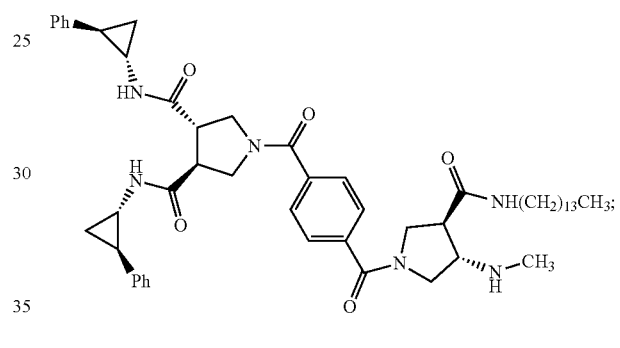
104
108
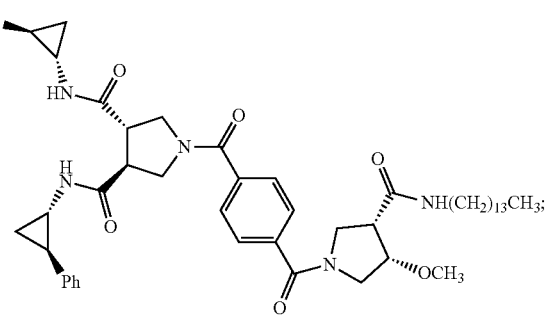

109

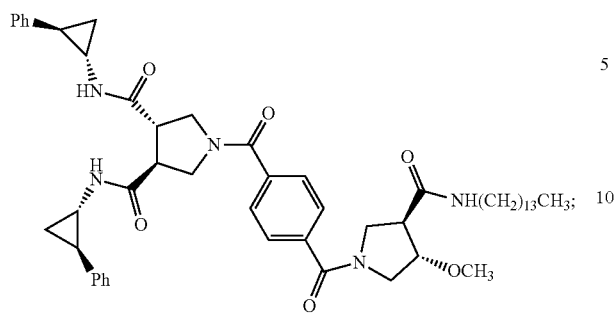

110

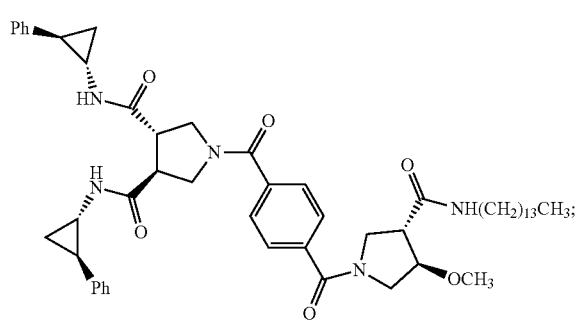

and pharmaceutically acceptable salts thereof.

In certain embodiments, Formula (I) or (IA) has the structure of Formula (V), wherein $L^1$ is —CO—, —SO$_2$—, —(CH$_2$—)$_m$ or —(CF$_2$)—. In certain embodiments, the compound of Formula (V) has the structure:

025

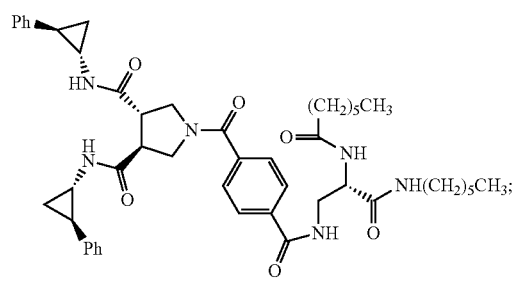

or a pharmaceutically acceptable salt thereof.

In certain embodiments, Formula (IA) or (IB) has the structure of Formula (VI), wherein m is 10, 11, or 12. In certain embodiments, the compound of Formula (VI) is selected from compounds:

079

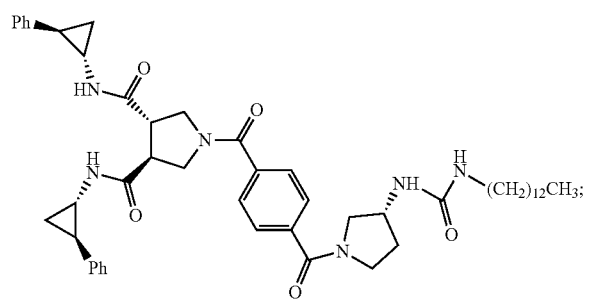

134

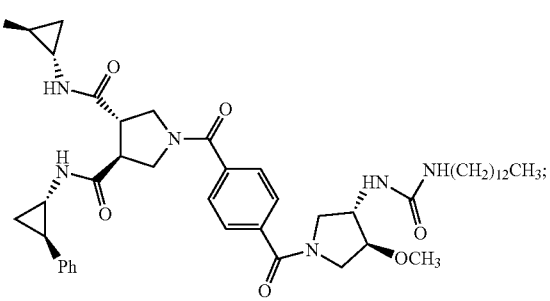

188

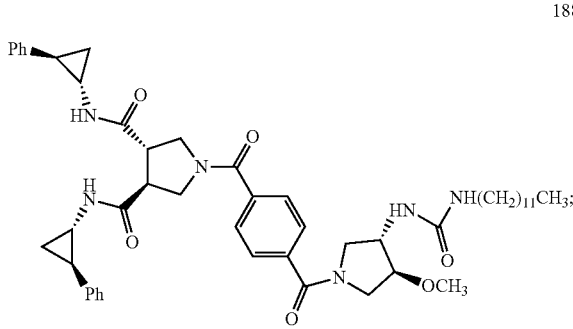

189

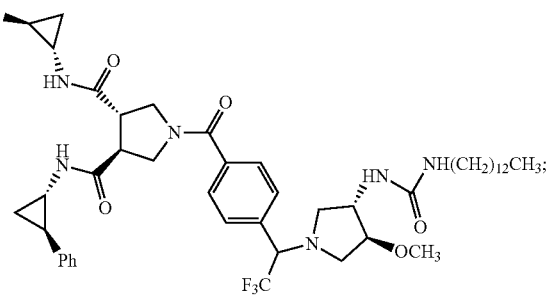

199

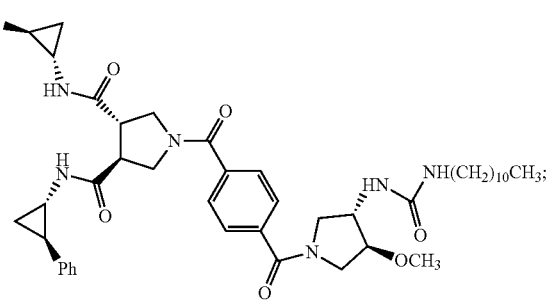

208

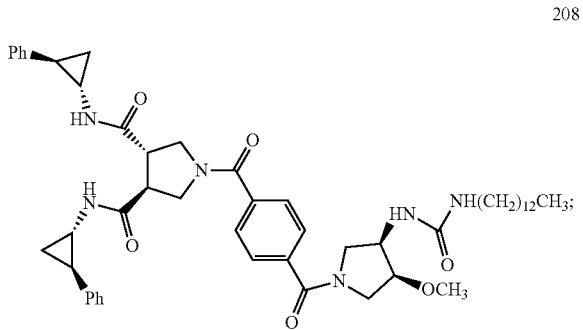

-continued
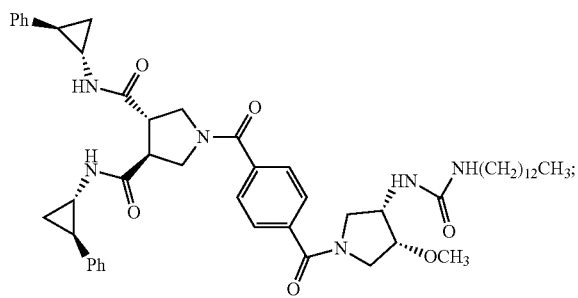
210
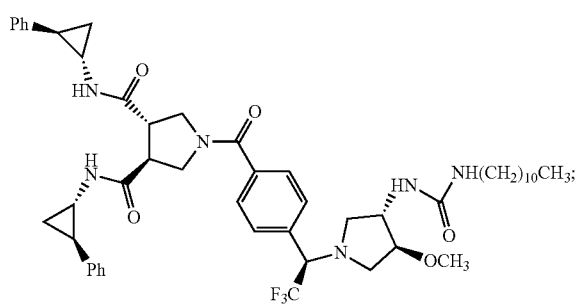
230
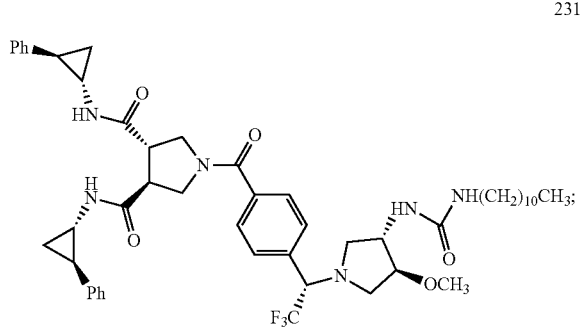
231
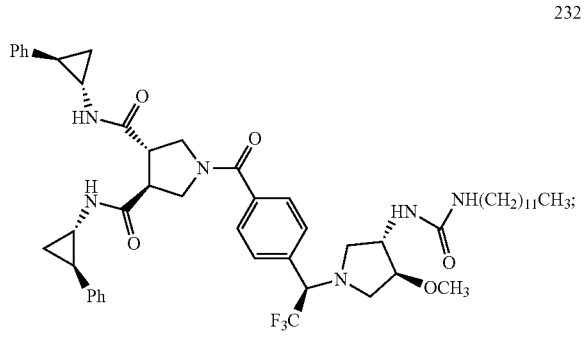
232
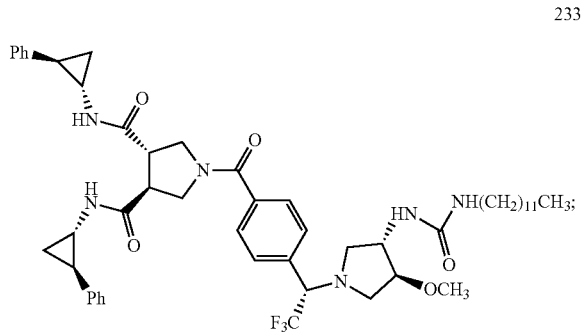
233
and pharmaceutically acceptable salts thereof.
In certain embodiments, Formula (IA) or (IB) has the structure of Formula (VII), wherein p is 5, 6, 7, or 8. In certain embodiments, the compound of Formula (VII) is selected from compounds:
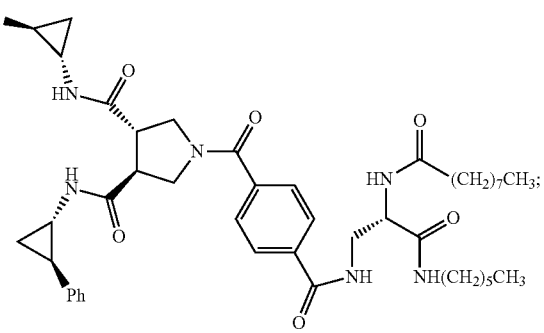
140
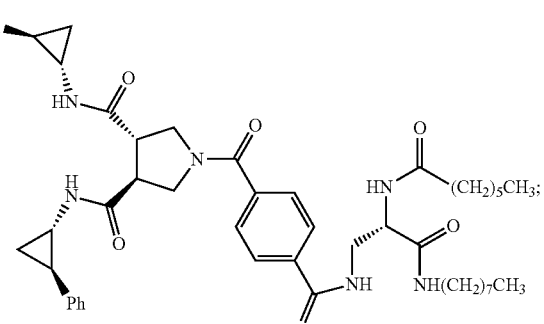
141
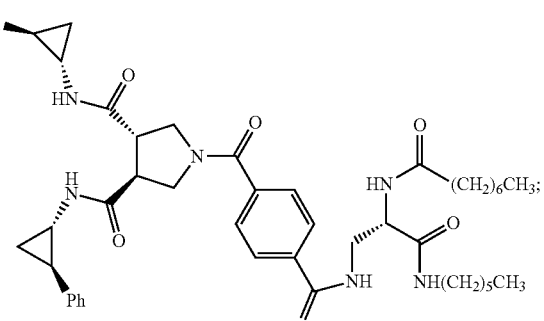
173
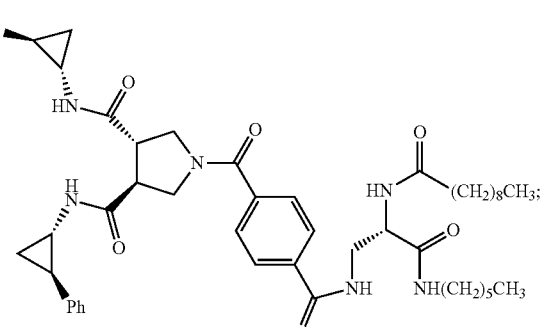
175

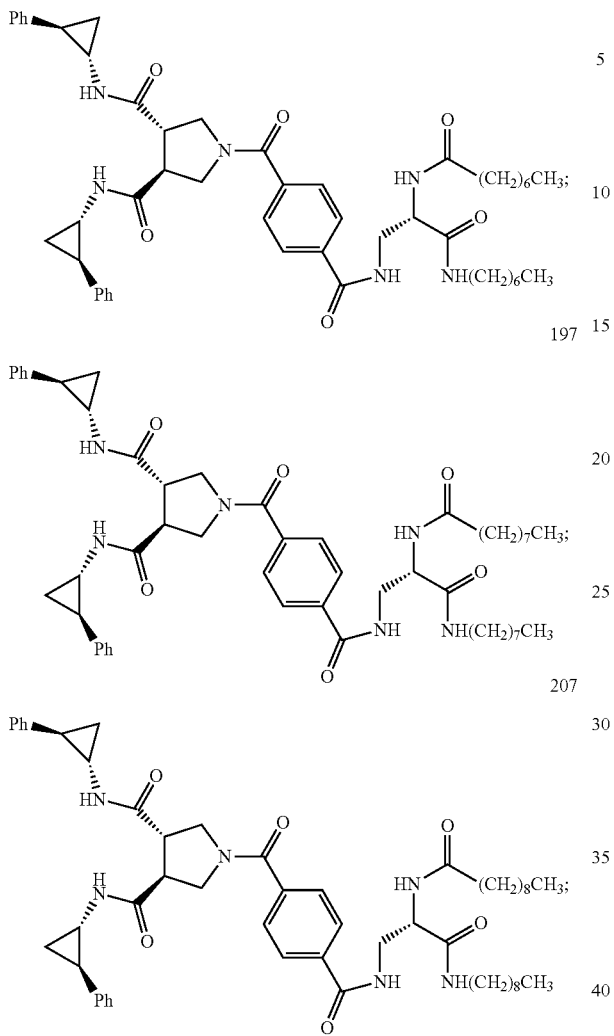
and pharmaceutically acceptable salts thereof.
In certain embodiments, Formula (IA) or (TB) has the structure of Formula (VIII), wherein p is 5, 6, 7, or 8. In certain embodiments, the compound of Formula (VIII) is selected from compounds:
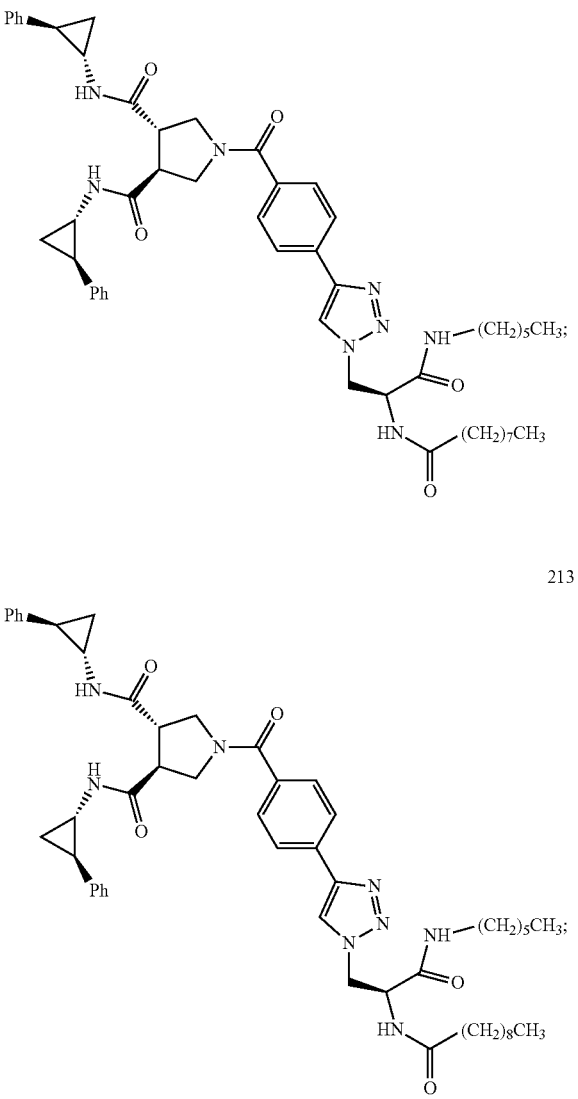

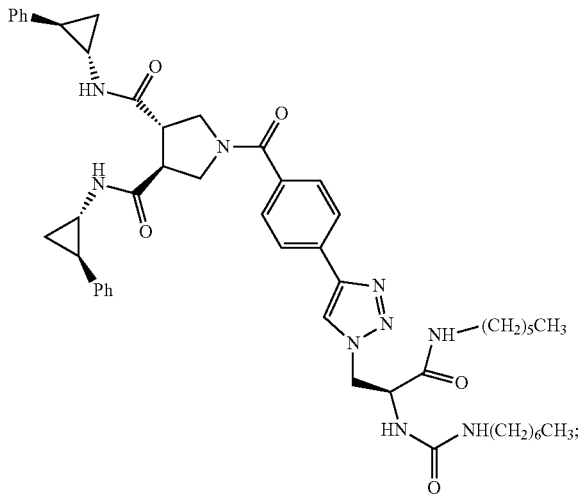

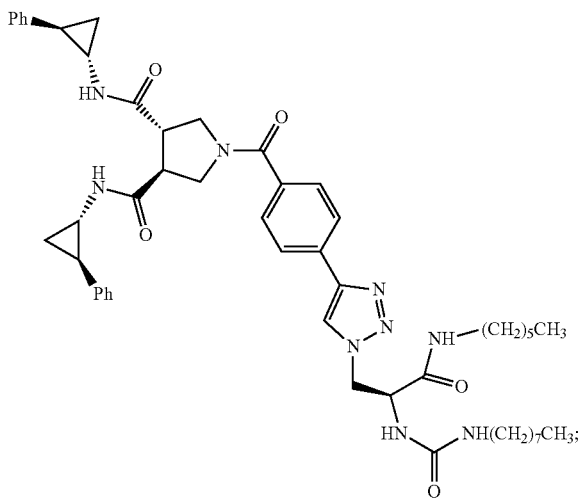

and pharmaceutically acceptable salts thereof.

Pharmaceutical Compositions, Formulations, Administration and Dosing

In another aspect, provided herein is a pharmaceutical composition comprising a compound or pharmaceutically acceptable salt as described herein, and a pharmaceutically acceptable carrier.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

In certain embodiments, the pharmaceutical composition is formulated for oral administration. Solid dosage forms for oral administration include capsules, tablets, pills, powders, and granules. In certain embodiments, the pharmaceutical composition is formulated for enteric delivery.

In certain embodiments, the pharmaceutical composition is formulated for administration by an injection. In certain embodiments, the injection is intravenous, subcutaneous, intramuscular, intraperitoneal, intrathecal, intracranial, intratumoral or peritumoral. Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, the pharmaceutical composition is formulated for controlled release within the lower intestine or colon of a subject. Such a pharmaceutical composition may be further formulated for enteric delivery.

In certain embodiments, the pharmaceutical composition is formulated for delivery outside of the systemic circulation of a subject. In certain embodiments, the pharmaceutical composition is formulated for topical or intravesical delivery.

In certain embodiments, the pharmaceutical composition is formulated for delivery by inhalation. Inhalation may be by nose or mouth. In certain embodiments, a vaporizer, nebulizer, or similar device may be used in connection with delivery by inhalation.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

In one embodiment, dosing Q3D (every third day) generates a tumor-suppressive response and enhances the growth-inhibiting effects of checkpoint therapy. In certain embodiments, the TLR2 modulator is a compound or composition disclosed herein. In certain embodiments, the TLR2 modulator is diprovocim.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Combinations

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Therapeutic Methods

T Cell Activation

The human microbiome can have a profound impact on the efficacy of anti-cancer checkpoint therapies. The enhancement or diminution of immune-therapies is due in part to changes in T cell activation, with enhancement of T cell activation leading to enhancement of immune-oncology therapeutic efficacy (Gut microbiome modulates response to anti-PD-1 immunotherapy in melanoma patients. Gopalakrishnan V, et al. *Science*. 2018 Jan. 5; 359(6371): 97-103). Interestingly, administration of antibiotics has been shown to severely diminish the efficacy of checkpoint therapies in preclinical models and in clinical cancer treatment. The mechanism mediating this enhancement (or suppression) remains to be fully elucidated. Gut microbes can stimulate a range of TLR immune receptors, including TLR2. A developed preclinical model system that addresses the impact of gut TLR2 modulation on T cell activation and acquisition of effector function is described herein.

Methods of Use

In another aspect, provided herein is a method for preventing or treating a TLR2 protein-mediated disorder in a subject in need thereof, comprising administering to the subject a compound or pharmaceutically acceptable salt, or a pharmaceutical composition thereof, as described herein.

Provided herein in one aspect is a method for modulating the activity of a Toll-like receptor 2 (TLR2) protein or a TLR2-mediated pathway or system in a subject in need thereof, comprising administering to the subject a compound or pharmaceutically acceptable salt, or a pharmaceutical composition thereof, as described herein.

In certain embodiments of the methods, the TLR2 protein-mediated disorder is an autoimmune disease, a cancer, a viral infection, a bacterial infection, or a combination thereof.

In certain embodiments, the cancer is a solid cancer, bladder cancer, breast cancer, cervical cancer, colon and rectal cancer, endometrial cancer, kidney cancer, lip and oral cancer, liver cancer, melanoma, mesothelioma, non-small cell lung cancer, non-melanoma skin cancer, oral cancer, ovarian cancer, pancreatic cancer, prostate cancer, sarcoma, small cell lung cancer or thyroid cancer.

In certain embodiments of the methods, the compound or pharmaceutically acceptable salt, or a pharmaceutical composition thereof, is co-administered with one or more oncolytic agents. In certain embodiments, the oncolytic agents are selected from selected from checkpoint inhibitors (e.g., pembrolizumab, nivolumab, ipilmumab, atezolizumab, durvalumab, avelumab, and tremelimumab), immuno-oncology (IO) agents such as (e.g., STING agonists or IDO inhibitors), targeted therapies such as protein kinase inhibitors, PARP inhibitors, nuclear receptor antagonists/degraders/hormone therapies (e.g., imatinib, erlotinib, olaparib, tamoxifen, and fulvestrant), cytotoxic agents (e.g., cyclophosphamide, carboplatin, paclitaxel, doxorubicin, epothilone, irinotecan, etoposide, azacytidine, vinblastine, and bleomycin), epigenetic therapies (e.g., vorinostat, and romidepsin), and cellular therapies (e.g., CAR-T).

In certain embodiments, the compound or pharmaceutically acceptable salt, or a pharmaceutical composition thereof, is administered as an adjuvant in a vaccination therapy selected from adenovirus vaccination, anthrax vaccination (e.g., AVA (BioThrax)), cholera vaccination (e.g., Vaxchora), diphtheria vaccination, DTaP vaccination (e.g., Daptacel, Infanrix), Tdap vaccination (e.g., Adacel, Boostrix), DT vaccination (e.g., Tenivac), DTaP-IPV vaccination (e.g., Kinrix, Quadracel), DTaP-HepB-IPV vaccination (e.g., Pediarix), DTaP-IPV/Hib vaccination (e.g., Pentacel), Hepatitis A (HepA) vaccination (e.g., Havrix, Vaqta), HepA-HepB vaccination (e.g., Twinrix), Hepatitis B (HepB) vaccination (e.g., Engerix-B, Recombivax HB, Heplisav-B), DTaP-HepB-IPV vaccination, (e.g., Pediarix), *Haemophilus influenzae* type b (Hib) vaccination, (e.g., ActHIB, PedvaxHIB, Hiberix), DTaP-IPV/Hib vaccination (e.g., Pentacel), Human Papillomavirus (HPV) vaccination (e.g., Gardasil 9), inactivated influenza vaccination (e.g., Afluria, Fluad, Flublok, Flucelvax, FluLaval, Fluarix, Fluvirin, Fluzone, Fluzone High-Dose, Fluzone Intradermal, FluMist), Japanese Encephalitis vaccination (e.g., Ixiaro), measles vaccination, MMR vaccination (e.g., M-M-R II), MMRV vaccination (e.g., ProQuad), meningitis vaccinations such as MenACWY (e.g., Menactra, Menveo) and MenB (e.g., Bexsero, Trumenba), pneumonia vaccinations such as PCV13 (e.g., Prevnar13) and PPSV23 (e.g., Pneumovax 23), polio vaccination (e.g., Ipol), rabies vaccination (e.g., Imovax Rabies, RabAvert), rotavirus vaccination such as RV1 (e.g., Rotarix) and RV5 (e.g., RotaTeq), shingles vaccination such as ZVL (e.g., Zostavax) and RZV (e.g., Shingrix), smallpox vaccination such as Vaccinia (e.g., ACAM2000), tuberculosis vaccination, typhoid fever vaccination (e.g., Vivotif, Typhim Vi), varicella vaccination (e.g., Varivax), and yellow fever vaccination (e.g., YF-Vax).

In certain embodiments, the method further comprises administration of one or more vaccine adjuvants selected from aluminum, MPL (3-O-desacyl-4'-monophosphoryl lipid A), MF59 (an oil in water emulsion comprising squalene), ASO1B (monophosphoryl lipid A and QS-21, a natural compound extracted from the Chilean soapbark tree), and CpG 1018 (cytosine phosphoguanine (CpG) motifs, which are synthetic forms of DNA that mimics bacterial and viral genetic material).

In certain embodiments, the methods are for treatment of an autoimmune disease, and the autoimmune disease is systemic lupus erythematosus (SLE), ulcerative colitis, or Crohn's disease.

In another aspect, provided herein is a method of enhancing immune function by orally administering a TLR2 modulator (e.g., an agonist or partial agonist) In certain embodiments, the TLR2 modulator is a compound, pharmaceutically acceptable salt thereof, or a pharmaceutical composition thereof, as described herein. In certain embodiments, the TLR2 modulator is diprovocim.

Methods to Identify Compounds

The in vitro TLR2 assay consists of a cell line that responds to TLR2 engagement by producing a factor that elicits a color change in the culture media and can be readily measured by various colorimetric detection methods. This assay enables the identification of existing and novel compounds that engage TLR2 and, by virtue of compound dilution, to approximate the binding affinity of these compounds for eliciting a TLR2 signal.

Provided herein is an assay to identify TLR2 modulators and/or characterize the binding affinities of TLR2 modulators. See, e.g., Example 44.

In certain embodiments, the method comprises the steps:
(1) culturing HEK-Blue TLR2 cells for 16-24 hours;
(2) replacing the culture medium with HEK-Blue Detection media;
(3) contacting the cultured cells with candidate TLR2 modulator compounds; and
(4) measuring the absorbance of the contacted cells at 600 nm.

In certain embodiments, step (3) comprises contacting the cultured cells with candidate TLR2 modulator compounds for a period of 8-16 hours, or for a period of 16-24 hours.

In certain embodiments, the method comprises comparing the absorbance measured in step (4) to absorbances measured under the same conditions using TLR2 modulator compounds of known binding affinities. For example, for determining compound affinities, control or test compounds are assessed in a 7 point dilution scheme, comprising a top concentration of 10 μM and diluted 10-fold to 10 μM.

Definitions

The following definitions are more general terms used throughout the present application.

As used herein, and unless defined otherwise, the term "alkyl" refers to a radical of a straight-chain or branched saturated hydrocarbon group having from 1 to 20 carbon atoms ("$C_{1-20}$ alkyl"). In some embodiments, an alkyl group has 1 to 16 carbon atoms ("$C_{1-16}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl (C), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

As used herein, and unless defined otherwise, the term "cycloalkyl" refers to a radical of a saturated, non-aromatic cyclic hydrocarbon group having from 3 to 10 ring carbon atoms ("$C_{3-10}$ cycloalkyl") and zero heteroatoms in the non-aromatic ring system. In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cyclooctyl ($C_8$), bicyclo[2.2.1]heptanyl ($C_7$), bicyclo[2.2.2]octanyl ($C_8$), and the like. Exemplary $C_{3-10}$ cycloalkyl groups include, without limitation, the aforementioned $C_{3-8}$ cycloalkyl groups as well as cyclononyl ($C_9$), cyclodecyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged. or spiro ring system such as a bicyclic system ("bicyclic cycloalkyl"). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-TH-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

When a range of values ("range") is listed, it is intended to encompass each value and sub-range within the range. A range is inclusive of the values at the two ends of the range unless otherwise provided. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$—C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$—NR$^{bb}$C(=NR$^{bb}$)N(R$^{bb}$)$_2$—C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$—NR$^{bb}$P(=O)(OR$^{cc}$)$_2$—NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$ or =NO$R^{cc}$;

each instance of $R^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of Rb is, independently, selected from hydrogen, —OH, —O$R^{aa}$, —N($R^{cc}$)$_2$—CN, —C(=O)$R^{aa}$, C(=O)N($R^{cc}$)$_2$, —CO$_2$$R^{aa}$, —SO$_2$$R^{aa}$, —C(=N$R^4$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, wherein X$^-$ is a counterion;

each instance of $R^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ff}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, or two geminal Rd substituents can be joined to form =O or =S; wherein X$^-$ is a counterion;

each instance of $R^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-16}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{99}$ substituents can be joined to form =O or =S; wherein X is a counterion.

In certain embodiments, the carbon atom substituents are independently halogen, substituted or unsubstituted C$_{1-6}$ alkyl, —O$R^{aa}$, —S$R^{aa}$, —N($R^{bb}$)$_2$, —CN, —SCN, —NO$_2$, —C(=O)$R^{aa}$, —CO$_2$$R^{aa}$, —C(=O)N($R^{bb}$)$_2$, —OC(=O)$R^{aa}$, —OCO$_2$$R^{aa}$, —OC(=O)N($R^{bb}$)$_2$, —N$R^{bb}$C(=O)$R^{aa}$, —N$R^{bb}$CO$_2$$R^{aa}$, or —N$R^{bb}$C(=O)N($R^{bb}$)$_2$. In certain embodiments, the carbon atom substituents are independently halogen, substituted or unsubstituted C$_{1-6}$ alkyl, —O$R^{aa}$, —S$R^{aa}$, —N($R^{bb}$)$_2$, —CN, —SCN, or —NO$_2$.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Unless otherwise provided, a formula includes compounds that do not include isotopically enriched atoms (e.g., isotopes of hydrogen, nitrogen, and oxygen) and hand also compounds that do include isotopically enriched atoms. Compounds that include isotopically enriched atoms may be useful, for example, as analytical tools and/or probes in biological assays.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "modulator" as used herein the context of the TLR2 protein refers to a compound that modulates the activity of the protein. For example, a modulator may be an agonist, a partial-agonist, or an antagonist.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

A "microbial infection" refers to an infection with a microorganism, such as a fungus, bacteria or virus. In certain embodiments, the microbial infection is an infection with a fungus, i.e., a fungal infection. In certain embodiments, the microbial infection is an infection with a virus, i.e., a viral infection. In certain embodiments, the microbial infection is an infection with a bacterium, i.e., a bacterial infection. Various microbial infections include, but are not limited to, skin infections, GI infections, urinary tract infections, genito-urinary infections, sepsis, blood infections, and systemic infections.

EXAMPLES

Example 1

Synthesis of (3S,4b)-1-(4-(((5)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide, Compound 025

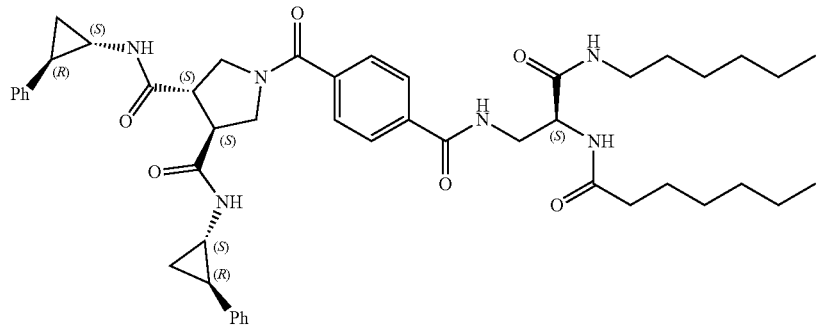

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Step 1: Preparation of ethyl (S,E)-4-(4-benzyl-2-oxooxazolidin-3-yl)-4-oxobut-2-enoate

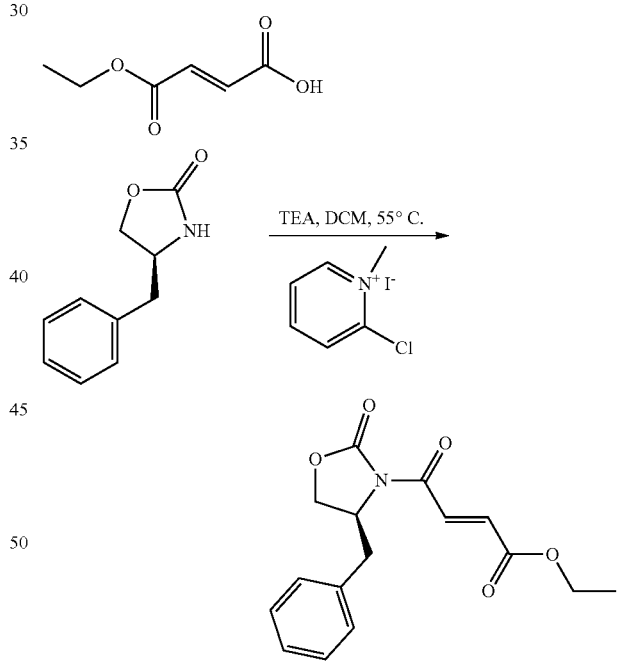

(S)-4-benzyloxazolidin-2-one (33.84 g, 190.97 mmol), 2-chloro-1-methylpyridin-1-ium iodide (53.22 g, 208.32 mmol) and triethylamine (60 mL) were added to a solution of monoethyl fumarate (25.0 g, 173.61 mmol) in dichloromethane (250 mL). The reaction mixture was stirred for 2 hrs at 55° C. then concentrated under reduce pressure. The crude product was purified using column chromatography eluting with DCM to give ethyl (S,E)-4-(4-benzyl-2-oxooxazolidin-3-yl)-4-oxobut-2-enoate (30.0 gm, 57.02%). LCMS (Method-$C_3$): 97.34% (RT: 0.994, 235.0 nm) (MS: ESI +ve 304.28 [M+1]).

Step 2: Preparation of ethyl (3S,4S)-1-benzyl-4-((S)-4-benzyl-2-oxooxazolidine-3-carbonyl)pyrrolidine-3-carboxylate

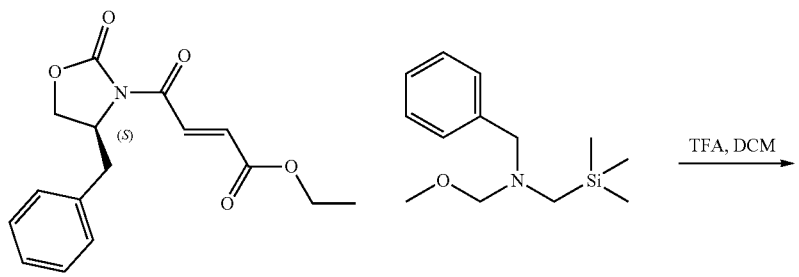

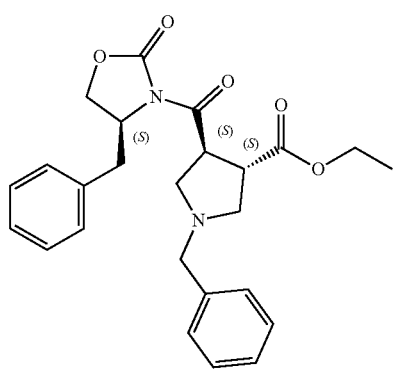

N-benzyl-1-methoxy-N-(trimethylsilyl)methyl)methanamine (24.81 g, 104.6 mmol) and trifluoracetic acid (3.5 mL) were added to a solution of ethyl (S,E)-4-(4-benzyl-2-oxooxazolidin-3-yl)-4-oxobut-2-enoate (30.0 g, 98.68 mmol) in dichloromethane (250 mL) at 0° C. After 18 hrs, the reaction mixture was diluted with water (300 mL) and extracted with DCM (3×100 mL). The combined organic layers were washed with brine, NaHCO$_3$ (2×100 mL) then dried over sodium sulphate. The mixture was concentrated under reduced pressure and the crude product was purified using column chromatography eluting with 10-20% Ethyl acetate/Hexane to give ethyl (3S,4S)-1-benzyl-4-((S)-4-benzyl-2-oxooxazolidine-3-carbonyl)pyrrolidine-3-carboxylate (12 g, 27.79%). LCMS (Method-C$_3$): 91.03% (RT: 18.66, 220.0 nm) (MS: ESI +ve 437.2 [M+1]).

Step 3: Preparation of 1-(tert-butyl) 3-ethyl (3S, 4S)-4-((S)-4-benzyl-2-oxooxazolidine-3-carbonyl)pyrrolidine-1,3-dicarboxylate

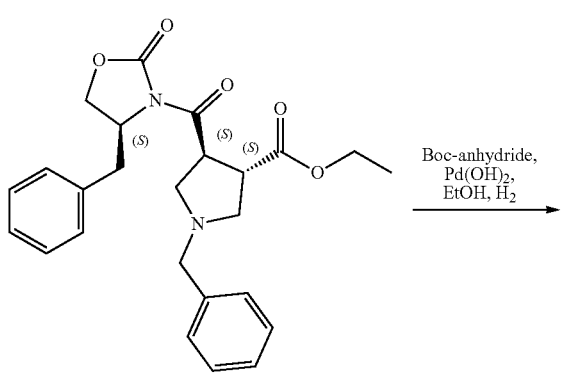

-continued

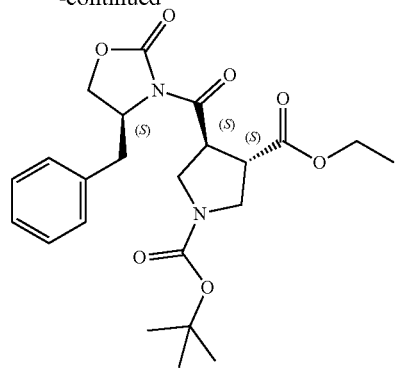

Ethyl (3S,4S)-1-benzyl-4-((S)-4-benzyl-2-oxooxazolidine-3-carbonyl) pyrrolidine-3-carboxylate (12.0 g, 27.45 mmol), Boc-anhydride (6.28 g, 28.83 mmol) were dissolved in Ethanol (150 mL) and palladium hydroxide (2.25 g) was added in an autoclave. The reaction mixture was purged with Hydrogen gas and stirred for 16 hrs. The reaction mixture was filtered through celite and the filtrate was concentrated under reduced pressure to give 1-(tert-butyl) 3-ethyl(3S,4S)-4-((S)-4-benzyl-2-oxooxazolidine-3-carbonyl) pyrrolidine-1,3 dicarboxylate (12.0 g, 97.76%). LCMS (Method-C3): 87.82% (RT: 1.880, 225.0 nm) (MS: ESI +ve 446.69 [M+H−100]).

Step 4: Preparation of (3S,4S)-1-(tert-butoxycarbonyl)pyrrolidine-3,4-dicarboxylic acid

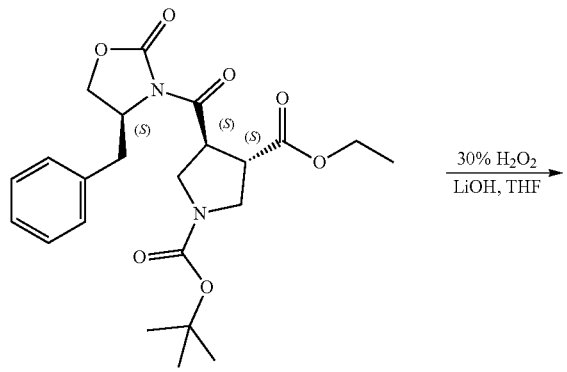

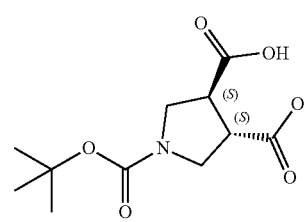

A solution of 1-(tert-butyl) 3-ethyl (3S,4S)-4-((S)-4-benzyl-2-oxooxazolidine-3-carbonyl)pyrrolidine-1,3-dicarboxylate (12.0 g, 26.84 mmol) in THF (100 mL) was cooled to 0° C. Hydrogen peroxide (15.0 mL) was added dropwise. After 5 min, LiOH·H₂O (2.75 g, 67.11 mmol) was added. After 2 hrs, additional Lithium hydroxide (2.64 g, 64.42 mmol), water (50 mL) and THF (30 mL) were added. The reaction mixture was stirred for 3 hrs more at room temperature. Saturated aqueous sodium sulphite (50 mL) was added and the volatiles were removed under a nitrogen stream. The resulting mixture was poured into water (300 mL) and extracted with DCM (100×3 mL). The aqueous phase was adjusted to pH 2 by the addition of 1 N HCL (200 mL) then extracted with ethyl acetate (100×3 mL). The combined organic layers were dried over anhydrous sodium sulphate and concentrated under reduced pressure to give (3S,4S)-1-(tert-butoxycarbonyl)pyrrolidine-3,4-dicarboxylic acid (6.0 g, 86.11%). ¹H NMR: 1.39 (s, 9H), 3.23-3.25 (d, J=9.2 Hz, 2H), 3.35-3.37 (d, J=7.2 Hz, 3H), 3.53 (s, 2H), 12.75 (s, 2H).

Step 5: Preparation of tert-butyl (3S,4S)-3,4-bis(((1S,2R)-2-phenylcyclopropyl)carbamoyl)pyrrolidine-1-carboxylate

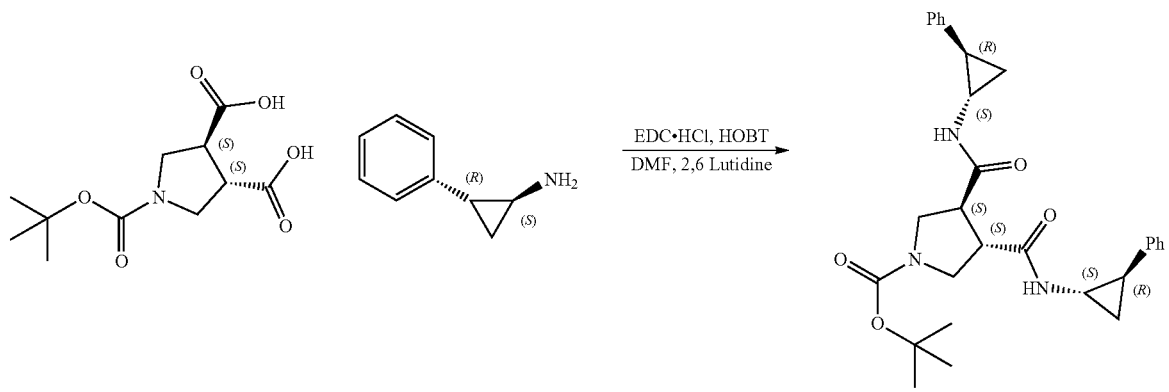

EDC.HCl (11.10 g, 57.91 mmol) and HOBT (6.88 g, 50.96 mmol) were added to a stirred solution of (3S,4S)-1-(tert-butoxycarbonyl)pyrrolidine-3,4-dicarboxylic acid (6.0 g, 23.16 mmol) and (1S,2R)-2-phenylcyclopropan-1-amine (7.7 g, 57.9 mmol) in DMF (30 mL). After 10 minutes, 2,6 Lutidine (13.39 mL, 115.83 mmol) was added and the reaction mixture was stirred for 16 hrs at room temperature. The reaction was quenched into ice cold water and the resulting precipitate was collected by filtration and dissolved in DCM. The mixture was dried over sodium sulphate and concentrated under reduced pressure. The crude residue was purified using column chromatography eluting with 3-5% methanol-DCM to give tert-butyl (3S,4S)-3,4-bis(((1S,2R)-2-phenylcyclopropyl)carbamoyl)pyrrolidine-1-carboxylate (7.0, 61.78%). LCMS (Method-C3): 95.01% (RT: 1.021, 254.0 nm) (MS: ESI +ve 490.5 [M+H−100]).

Step 6: Preparation of (3S,4S)—N3,N4-bis((1S,2R)-2-phenylcyclopropyl)pyrrolidine-3,4-dicarboxamide hydrogen chloride. (Intermediate S-10)

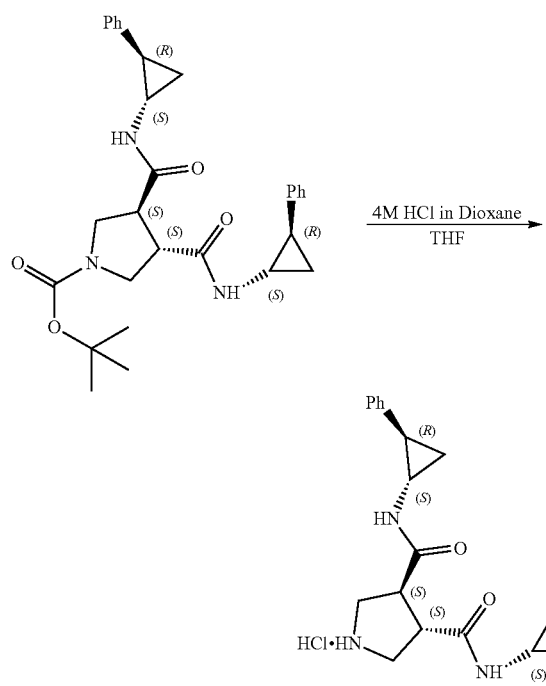

tert-Butyl (3S,4S)-3,4-bis(((1S,2R)-2-phenylcyclopropyl) carbamoyl) pyrrolidine-1-carboxylate (7.0 g, 14.31 mmol) was suspended in THF (40 mL). 4M HCL in Dioxane (60 mL) was added dropwise to the stirred solution over for 3 hours. The solvent was removed under reduce pressure and the crude residue was titrated with N-pentane to give (3S, 4S)—N3,N4-bis((1S,2R)-2-phenylcyclopropyl)pyrrolidine-3,4-dicarboxamide hydrogen chloride (5.5 g, 98.77%). LCMS (Method-C3): 98.56% (RT: 0.864, 230.0 nm) (MS: ESI +ve 390.39 [M+H+1]).

Step 7: Preparation of tert-butyl 4-((3S,4S)-3,4-bis (((1S,2R)-2-phenylcyclopropyl) carbamoyl pyrrolidine-1-carbonyl)benzoate

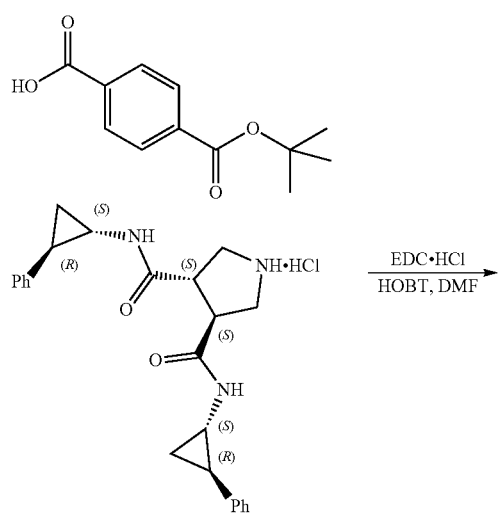

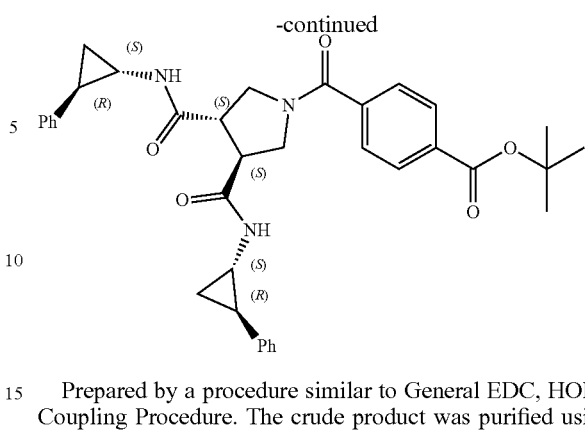

Prepared by a procedure similar to General EDC, HOBT Coupling Procedure. The crude product was purified using column chromatography eluting with 3-5% methanol in DCM to give tert-butyl 4-((3S,4S)-3,4-bis(((1S,2R)-2-phenylcyclopropyl) carbamoyl) pyrrolidine-1-carbonyl)benzoate (0.035 g, 8.75%). LCMS (Method-C3): 100% (RT: 1.870, 226.00 nm) (MS: ESI +ve 594.33 [M+1]). $^1$H NMR: 1.09-1.17 (m, 4H), 1.55 (s, 9H), 1.84 (s, 1H), 1.96 (s, 1H), 2.76 (s, 1H), 2.85 (s, 1H), 3.07-3.20 (m, 2H), 3.42-3.62 (m, 3H), 3.79-3.84 (t, J=10.8 Hz, 1H), 7.06-7.28 (m, 10H), 7.61-7.63 (d, J=7.6 Hz, 2H) 7.94-7.96 (d, J=8 Hz, 2H), 8.29 (s, 1H), 8.44 (s, 1H)

Step 8: Preparation of 4-((3S,4S)-3,4-bis(((1S,2R)-2-phenylcyclopropyl) carbamoyl) pyrrolidine-1-carbonyl)benzoic acid

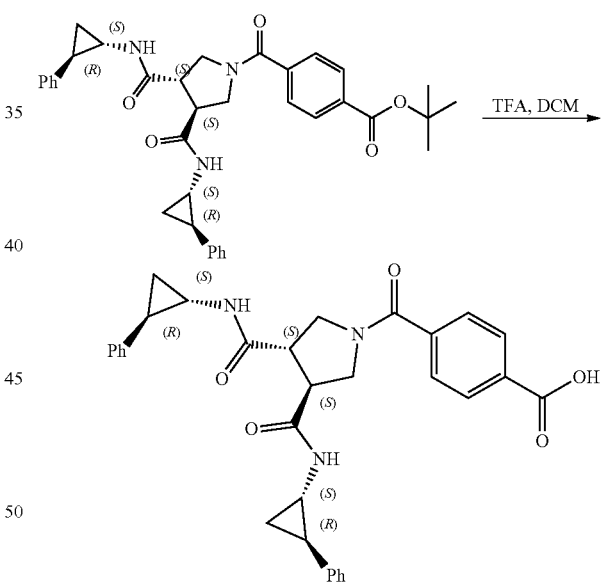

Prepared by a procedure similar to General Boc Deprotection Procedure to give 4-((3S,4S)-3,4-bis(((1S,2R)-2-phenylcyclopropyl) carbamoyl) pyrrolidine-1-carbonyl)benzoic acid (2.2 g, crude). LCMS (Method-C3): 91.45% (RT: 0.934, 230.0 nm) (MS: ESI +ve 538.69[M+1]). The material could be further purified using Prep HPLC Method 4 to give 4-((3S,4S)-3,4-bis(((1S,2R)-2-phenylcyclopropyl) carbamoyl) pyrrolidine-1-carbonyl)benzoic acid (0.030 g, 33.13%). LCMS (Method-C3): 100% (RT 1.610, 226.0 nm) (MS: ESI +ve 538.31 [M+H]). $^1$H NMR:–1.09-1.01 (d, J=4.8 Hz, 2H), 1.17-1.18 (d, J=5.2 Hz, 2H), 1.85 (s, 1H), 1.96 (s, 1H), 2.77 (s, 1H), 2.84 (s, 1H), 3.09-3.20 (m, 2H), 3.44-3.62 (m, 3H), 3.79-3.81 (d, J=8.8 Hz, 1H), 7.06-7.28 (m, 10H), 7.61-7.63 (d, J=8 Hz, 2H), 7.98-8.00 (d, J=8 Hz, 2H), 8.30 (s, 1H), 8.44 (s, 1H), 13.15 (s, 1H).

Step-9: Preparation of benzyl tert-butyl (3-(hexylamino)-3-oxopropane-1,2-diyl)-(S)-dicarbamate

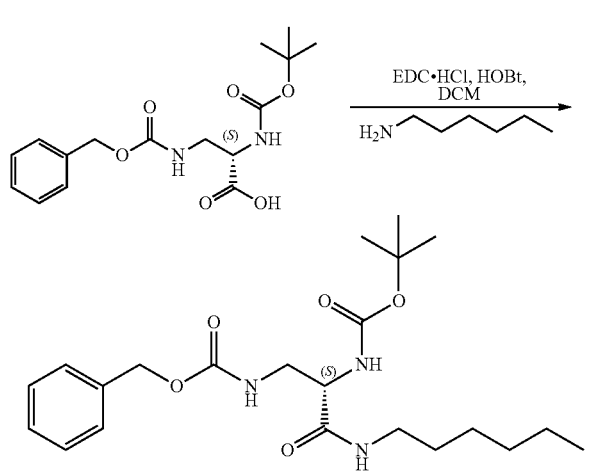

Prepared by a procedure similar to General EDC, HOBT Coupling Procedure to afford benzyl tert-butyl (3-(hexylamino)-3-oxopropane-1,2-diyl) (S)-dicarbamate (600 mg, 96.32%). LCMS (Method-C3): 85.49% (RT: 1.82, 202.00 nm) (MS: ESI +ve 423.31 [M+H]).

Step 10: Preparation of benzyl (S)-(2-amino-3-(hexylamino)-3-oxopropyl)carbamate TFA salt

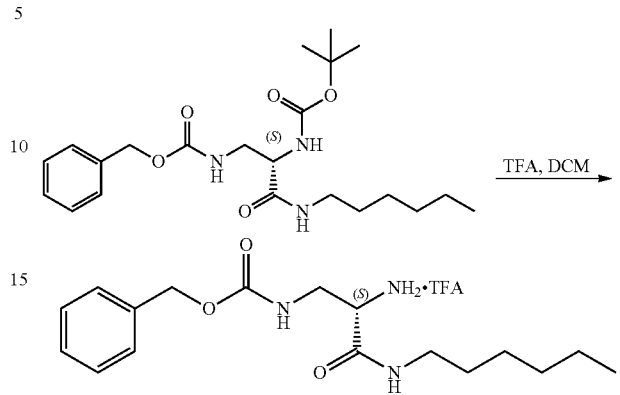

Prepared by a procedure similar to General Boc Deprotection Procedure to afford the TFA salt of benzyl (S)-(2-amino-3-(hexylamino)-3-oxopropyl)carbamate (450 mg, 98%). LCMS (Method-C3): 68.94% (RT: 1.85, 202.4 nm) (MS: ESI +ve 322.2 [M+H]).

Step-11: Preparation of benzyl (S)-(2-heptanamido-3-(hexylamino)-3-oxopropyl) carbamate

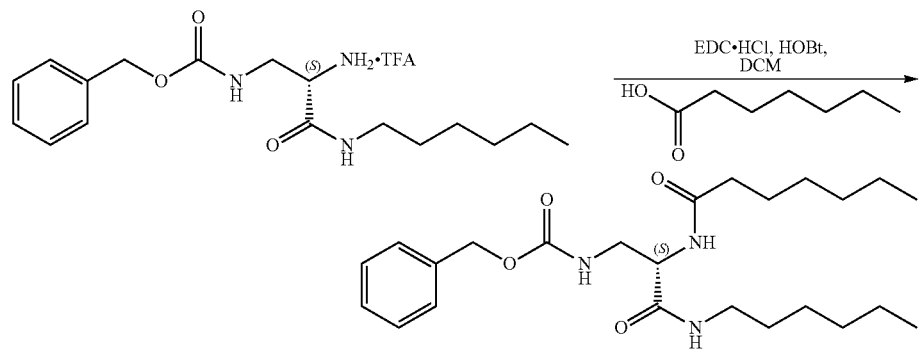

Prepared by a procedure similar to General EDC, HOBT Coupling Procedure. The crude residue was purified by column chromatography (Stationary Phase: Basic Alumina and Eluent: 15% Ethyl acetate & Hexane) to afford benzyl (S)-(2-heptanamido-3-(hexylamino)-3-oxopropyl)carbamate (300 mg, 49.42%). LCMs (Method-C3): 80.96% (RT 1.92, 202.02 nm) (MS: ESI +ve 434.14 [M+H]).

Step-12: Preparation of (S)—N-(3-amino-1-(hexylamino)-1-oxopropan-2-yl)heptanamide

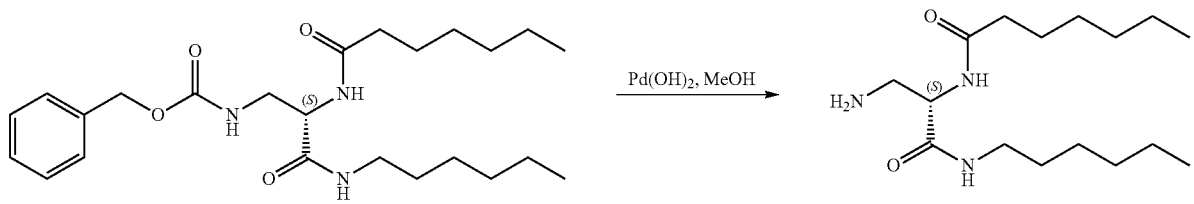

To a stirred solution of benzyl (S)-(2-heptanamido-3-(hexylamino)-3-oxopropyl) carbamate in methanol was added palladium hydroxide (10% by weight). The reaction mixture was stirred at room temperature under hydrogen balloon pressure for 16 hrs. The mixture was filtered through celite and the filtrate was concentrated to give (S)—N-(3-amino-1-(hexylamino)-1-oxopropan-2-yl) heptanamide (200 mg, 96.53%). LCMS (Method-C3): 55.53% (RT 1.45, 202.0 nm) (MS: ESI +ve 300.2 [M+H]).

Step-13: Preparation of (3S,4S)-1-(4-(((S)-2-heptanamido-3-(hexylamino)-3-oxopropyl) carbamoyl) benzoyl)-N3,N4-bis((1S,2R)-2-phenylcyclopropyl) pyrrolidine-3,4-dicarboxamide, Compound 025

((1S,2R)-2-phenylcyclopropyl)pyrrolidine-3,4-dicarboxamide, Compound 025 (13.068 mg, 8.87%). LCMS: (Method-C3) RT-1.93 min; 100%; (M+1)=820.7. $^1$H NMR: (400 MHz, DMSO) δ ppm: 0.80-0.81 (q, 6H J=4 Hz), 1.095-1.22 (m, 16H), 1.29-1.33 (q, 2H), 1.23 (t, 3H), 1.84 (q, 1H), 1.97 (q, 1H), 2.04-2.12 (m, 3H), 2.67 (t, 1H), 2.77 (m, 1H), 2.85 (m 2H), 3.45-3.54 (m, 4H), 3.63-3.77 (m, 1H), 3.79-3.12 (m, 1H), 4.44-4.46 (s, 1H) 7.05-7.13 (d, 2H J=8 Hz), 7.16-7.22 (m, 4H J=6.8 Hz), 7.23-7.28 (m, 4H, J=8 Hz), 7.56-7.61 (m, 2H), 7.85-7.91 (m, 3H), 8.04-8.06 (d, 1H) 8.37-8.38 (s, 1H), 8.52 (s, 2H), 8.65 (s, 1H).

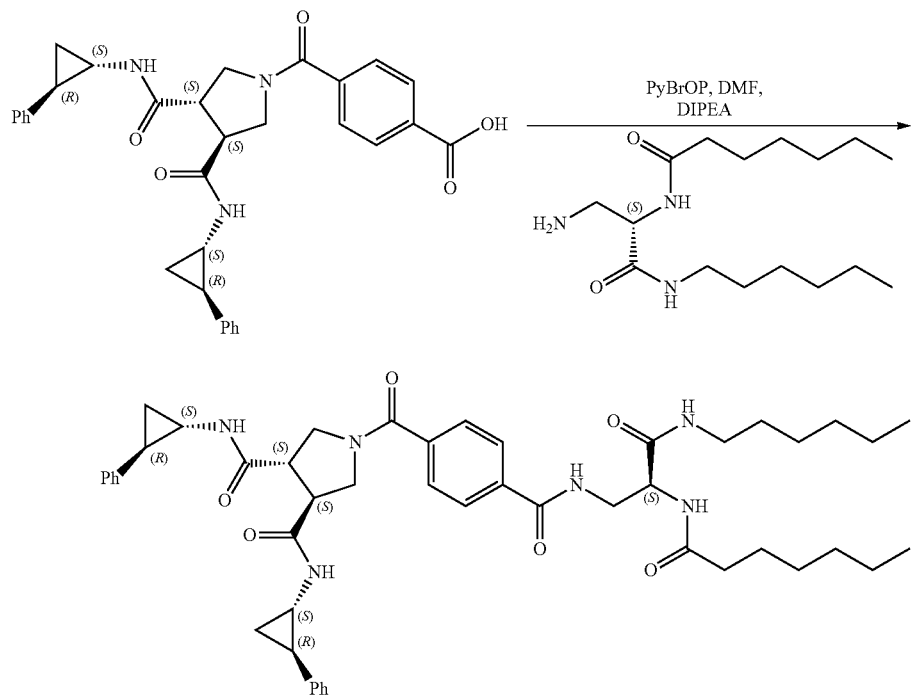

To a stirred solution of 4-((3S,4S)-3,4-bis(((1S,2R)-2-phenylcyclopropyl) carbamoyl) pyrrolidine-1-carbonyl)benzoic acid (100 mg, 0.186 mmol) and (S)—N-(3-amino-1-(hexylamino)-1-oxopropan-2-yl) heptanamide (55 mg, 0.186 mmol) in DMF (5 mL) was added DIPEA (0.1 mL, 0.55 mmol). The reaction was stirred at room temperature for 5 minutes and PyBroP (104 mg, 0.021 mmol) was added and stirring continued for 16 hrs. Ice water was added to reaction mixture and the resulting precipitate was collected by filtration, dissolved in DCM and dried over sodium sulphate. The crude residue was purified using Prep HPLC Method 1 to give (3S,4S)-1-(4-(((S)-2-heptanamido-3-(hexylamino)-3-oxopropyl) carbamoyl) benzoyl)-N3,N4-bis Example 2

Synthesis of (3S,4S)-1-(4-(((R)-2-heptanamido-3-(hexylamino)-3-oxopropyl)carbamoyl)benzoyl)-N3,N4-bis((1S,2R)-2-phenylcyclopropyl)pyrrolidine-3,4-dicarboxamide, Compound 070

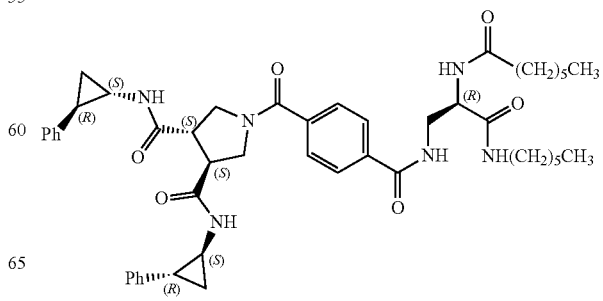

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide, Compound 025 substituting (R)-3-(((benzyloxy)carbonyl)amino)-2-((tert-butoxycarbonyl)amino)propanoic acid in step 9. The final product was purified using Prep HPLC Method 10 to give (3S,4S)-1-(4-(((R)-2-heptanamido-3-(hexylamino)-3-oxopropyl)carbamoyl)benzoyl)-N3,N4-bis((1S,2R)-2-phenylcyclopropyl)pyrrolidine-3,4-dicarboxamide, Compound 070, as a white solid (0.005 g, 1.09%). LCMS (Method-C3): 100% (RT: 1.879, 226 nm) (MS: ESI +ve 819.46 [M+H]).

¹H NMR: (400 MHz, DMSO) δ ppm: 0.78-0.84 (m, 4H), 1.15-1.23 (m, 16H), 1.38-1.44 (m, 4H), 1.84 (m, 1H), 1.97 (t, 1H), 2.68-2.77 (m, 2H), 2.85 (m, 2H), 3.03 (m, 4H), 3.12 (m, 2H), 3.21 (m, 4H), 3.49-3.51 (m, J=8.8 Hz, 4H), 3.62 (m, 1H), 3.83 (m, 1H), 4.46 (q, 1H), 7.05-7.07 (m, J=7.6 Hz, 2H), 7.12-7.16 (q, 4H), 7.61-7.63 (d, 2H), 7.90-7.92 (m, 3H), 8.03 (m, 1H), 8.31 (m, 1H), 8.45 (s, 1H), 8.55-8.57 (d, 1H).

Synthesis of (3S,4S)-1-(4-(((S)-3-((4-fluorophenethyl)amino)-2-heptanamido-3-oxopropyl)carbamoyl)benzoyl)-N3,N4-bis((1S,2R)-2-phenylcyclopropyl)pyrrolidine-3,4-dicarboxamide, Compound 129

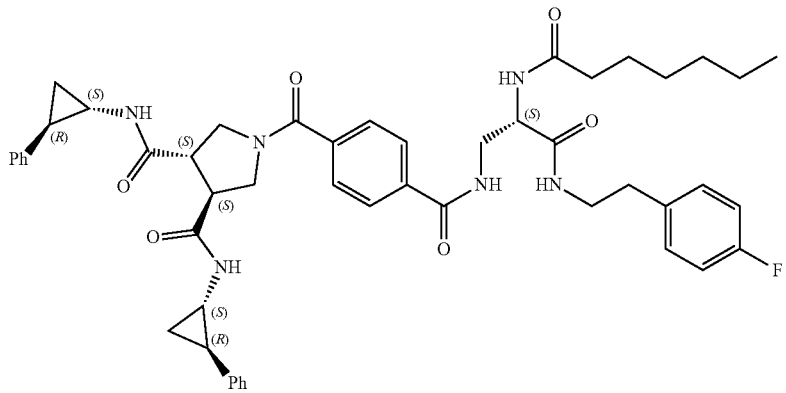

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025) substituting the applicable amine in step 1. The crude final product was purified using Prep HPLC Method 1 to give Compound 129 (0.025 g, 9.84%). LCMS (Method-J): 100% (RT 5.215, 220.0 nm) (MS: ESI +ve 858.3 [M+1]. ¹H NMR: (400 MHz, DMSO-d₆) δ 0.78-0.80 (d, J=6.8 Hz, 3H), 1.08-1.25 (m, 10H), 1.44 (s, 2H), 1.85 (s, 1H), 1.98-2.12 (m, 3H), 2.61-2.86 (m, 4H), 3.10-3.29 (m, 4H), 3.49-3.84 (m, 5H), 4.42-4.48 (m, 1H), 7.04-7.29 (m, 14H), 7.58-7.60 (d, J=8.4 Hz, 2H), 7.91-7.95 (d, J=8.4 Hz, 2H), 7.95-8.03 (m, 2H), 8.33-8.31 (d, J=4 Hz, 1H), 8.47-8.48 (d, J=3.6 Hz, 1H), 8.53 (s, 1H), 8.59 (s, 1H).

Synthesis of (3S,4S)-1-(4-(((S)-3-((4-fluorobenzyl)amino)-2-heptanamido-3-oxopropyl) carbamoyl) benzoyl)-N3,N4-bis((1S,2R)-2-phenylcyclopropyl)pyrrolidine-3,4-dicarboxamide, Compound 128

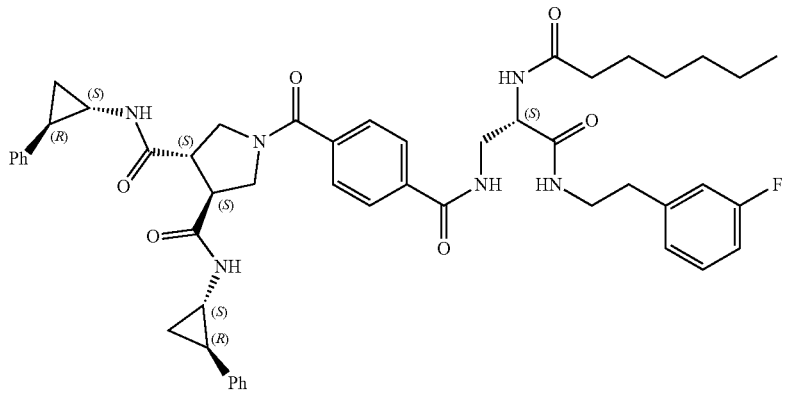

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025) substituting the applicable amine in step 1. The crude final product was purified using Prep HPLC Method 7 to give (3S,4S)-1-(4-(((S)-3-((4-fluorobenzyl)amino)-2-heptanamido-3-oxopropyl)carbamoyl)benzoyl)-N3,N4-bis((1S,2R)-2-phenylcyclopropyl)pyrrolidine-3,4-dicarboxamide (Compound 128) (0.103 g). LCMS (Method-H): 100% (RT 3.370, 202.0 nm) (MS: ESI +ve 843.5[m+1]). $^1$H NMR (400 MHz, DMSO) δ ppm: 0.78-0.79 (d, J=4, 4H), 1.09-1.23 (m, 10H), 1.44 (s, 2H), 1.84 (s, 1H), 1.84 (s, 1H), 2.10-2.14 (t, J=6, 2H), 2.77 (s, 1H), 2.85 (s, 1H), 3.09-3.11 (d, J=8, 1H), 3.16-3.21 (m, 1H), 3.41-3.43 (m, 1H), 3.49-3.54 (m, 4H), 3.60-3.62 (m, 1H), 3.78-3.83 (d, J=4, 1H), 4.24-4.25 (d, J=4, 2H), 4.51-4.53 (d, J=8, 1H), 7.00-7.06 (m, 4H), 7.11-7.18 (m, 4H), 7.21-7.28 (m, 5H), 7.58-7.6 (d, J=8, 2H), 7.84-7.86 (d, J=8, 2H), 8.02-8.04 (d, J=8, 1H), 8.31-8.32 (d, J=8, 1H), 8.46-8.48 (d, J=8, 2H), 8.60 (s, 1H).

Synthesis of (3S,4S)-1-(4-(((S)-3-(hexylamino)-3-oxo-2-pentanamidopropyl) carbamoyl) benzoyl)-N3,N4-bis((1S,2R)-2-phenylcyclopropyl)pyrrolidine-3,4-dicarboxamide, Compound 130

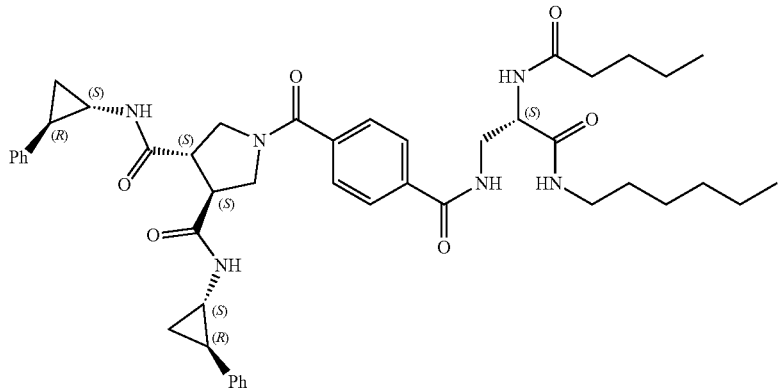

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 7 to give (3S,4S)-1-(4-(((S)-3-(hexylamino)-3-oxo-2-pentanamidopropyl)carbamoyl)benzoyl)-N3,N4-bis((1S,2R)-2-phenylcyclopropyl)pyrrolidine-3,4-dicarboxamide (Compound 130) (0.07 g, 20%). LCMS (Method-C2): 99.25% (RT 1.843, 254 nm) (MS: ESI +ve 791.35 [M+1]). $^1$H NMR: (400 MHz, DMSO) δ ppm: 0.81-0.85 (m, 6H), 1.07-1.23 (m, 12H), 1.29-1.33 (m, 2H), 1.38-1.44 (m, 2H), 1.83 (s, 1H), 1.95-1.96 (m, 1H), 2.09-2.13 (m, 2H), 2.67 (s, 1H), 2.76-2.77 (m, 1H), 2.85-3.06 (m, 3H), 3.08-3.20 (m, 1H), 3.45-3.53 (m, 4H), 3.59-3.64 (m, 1H), 3.78-3.83 (m, 1H), 4.43-4.49 (m, 1H), 7.05-7.07 (d, J=7.2 Hz, 2H), 7.11-7.18 (m, 4H), 7.22-7.28 (m, 4H), 7.57-7.60 (d, J=8.4 Hz, 2H), 7.84-7.91 (m, 4H), 8.30-8.31 (d, J=4 Hz, 1H), 8.44-8.45 (d, J=4 Hz, 1H), 8.50-8.51 (m, 1H).

Synthesis of (3S,4S)-1-(4-(((S)-3-(butylamino)-2-heptanamido-3-oxopropyl)carbamoyl) benzoyl)-N3,N4-bis((1S,2R)-2-phenylcyclopropyl)pyrrolidine-3,4-dicarboxamide, Compound 131

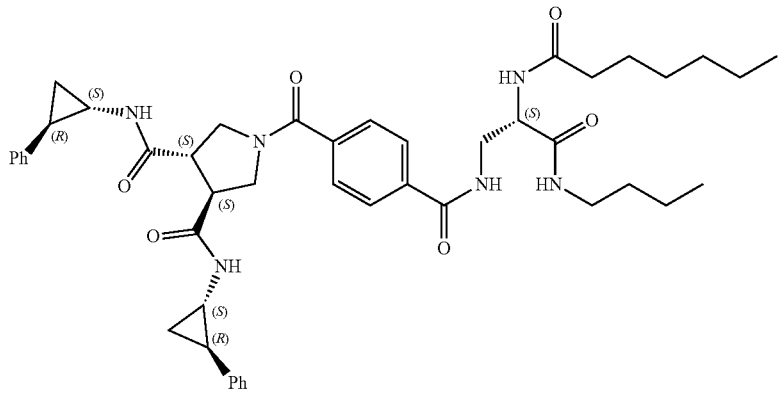

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 7 to give (3S,4S)-1-(4-(((S)-3-(butylamino)-2-heptanamido-3-oxopropyl)carbamoyl) benzoyl)-N3,N4-bis((1S,2R)-2-phenylcyclopropyl)pyrrolidine-3,4-dicarboxamide (Compound 131) (0.034 g, 23.33%). LCMS (Method-H): 99.35% (RT: 3.313, 220.00 nm) (MS: ESI +ve 791.06 [M+1]). ¹H NMR: (400 MHz, DMSO) δ ppm: 0.81-0.86 (m, 6H), 1.086-1.24 (m, 12H), 1.30-1.35 (m, 2H), 1.43-1.45 (d, J=6.8 Hz, 2H), 1.84 (s, 1H), 2.10 (s, 1H), 2.10-2.13 (t, J=7.2 Hz, 2H), 2.68-2.78 (m, 2H), 2.98-3.24 (m, 4H), 3.34-3.51 (s, 4H), 3.54-3.52 (m, 1H), 3.65-3.85 (m, 1H), 4.44-4.4.49 (m, 1H), 7.066-7.29 (m, 10H), 7.58-7.60 (d, J=8 Hz, 2H), 7.85-7.91 (m, 4H), 8.29-8.30 (d, J=4 Hz, 1H), 8.44-8.51 (m, 2H).

Synthesis of (3S,4S)-1-(4-(((S)-2-(2-(4-fluorophenyl) acetamido)-3-(hexylamino)-3-oxopropyl) carbamoyl) benzoyl)-N3,N4-bis((1S,2R)-2-phenylcyclopropyl) pyrrolidine-3,4-dicarboxamide, Compound 138

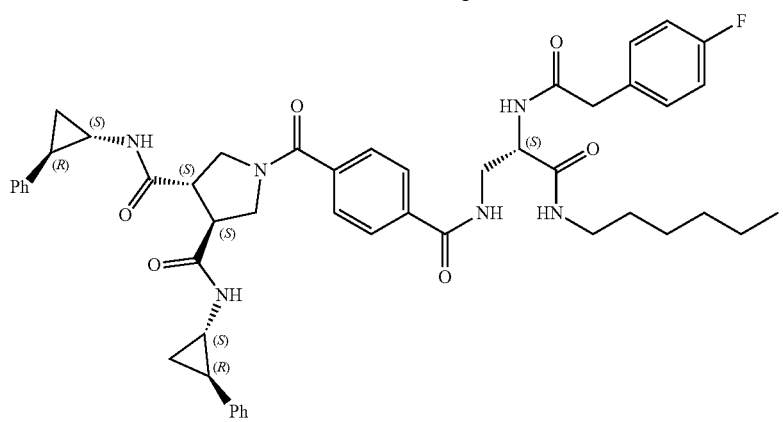

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 1 to give (3S,4S)-1-(4-(((S)-2-(2-(4-fluorophenyl) acetamido)-3-(hexylamino)-3-oxopropyl) carbamoyl) benzoyl)-N3,N4-bis((1S,2R)-2-phenylcyclopropyl) pyrrolidine-3,4-dicarboxamide (Compound 138), as a white solid (0.040 g, 16.74%). LCMS (Method-J): 100% (RT 5.124, 202.0 nm) (MS: ESI +ve 844 [M+H]). ¹H NMR: (400 MHz, DMSO) δ ppm: 0.81-0.84 (t, 3H); 1.09 (s, 2H); 1.10-1.14 (m, 8H); 1.32-1.34 (d, J=6.4, 2H); 1.86 (s, 1H); 1.99-2.00 (d, J=5.2, 1H); 2.68 (s, 2H); 2.98-3.06 (m, 4H); 3.08-3.18 (m, 1H); 3.41-3.49 (m, 5H); 3.56-3.63 (m, 1H); 3.80-3.82 (m, 1H); 4.46-4.48 (d, J=6.4, 1H); 7.00-7.06 (m, 4H); 7.13-7.19 (m, 4H); 7.25-7.30 (m, 5H); 7.57-7.59 (d, J=8, 2H); 7.82-7.84 (d, J=8.4, 2H); 7.95-7.98 (m, 1H); 8.35-8.37 (d, J=8, 2H); 8.54 (s, 2H).

Synthesis of (3S,4S)-1-(4-(((S)-2-(3-(4-fluorophenyl) propanamido)-3-(hexylamino)-3-oxopropyl) carbamoyl) benzoyl)-N3,N4-bis ((1S,2R)-2-phenylcyclopropyl) pyrrolidine-3,4-dicarboxamide, Compound 139

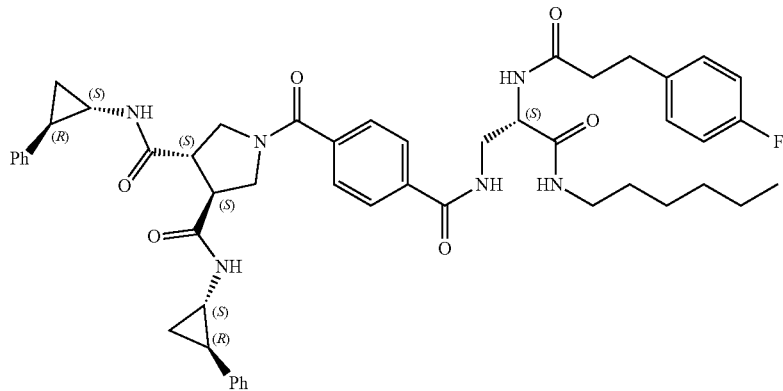

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 1 to give (3S,4S)-1-(4-(((S)-2-(3-(4-fluorophenyl) propanamido)-3-(hexylamino)-3-oxopropyl) carbamoyl) benzoyl)-N3,N4-bis((1S,2R)-2-phenylcyclopropyl) pyrrolidine-3,4-dicarboxamide (Compound 139), as a white solid (0.033 g, 14.21%). LCMS (Method-J): 100% (RT 5.210, 202.0 nm) (MS: ESI +ve 858[M+H]). $^1$H NMR: (400 MHz, DMSO) δ ppm: 0.79-0.82 (t, 3H); 1.10-1.22 (d, J=6.8, 2H); 1.16 (s, 7H); 1.30-1.32 (d, J=6.8, 2H); 1.84 (s, 1H); 1.97 (s, 1H); 2.36-2.50 (m, 3H); 2.79-2.96 (m, 3H); 2.98 (s, 1H); 3.00-3.05 (m, 2H); 3.06 (m, 1H); 3.09-3.13 (m, 1H); 3.23-3.43 (m, 4H); 3.45-3.51 (m, 1H); 3.54-3.77 (m, 1H); 4.43-4.78 (m, 1H); 7.00-7.06 (m, 4H); 7.11-7.28 (m, 9H); 7.57-7.59 (d, J=8.4, 2H); 7.85-7.87 (d, J=8, 2H); 7.89-7.92 (t, 1H); 8.17-8.19 (d, J=8, 1H); 8.36 (s, 1H); 8.51 (s, 2H); 8.63 (s, 1H).

Synthesis of (3S,4S)-1-(4-(((S)-3-(hexylamino)-2-nonanamido-3-oxopropyl) carbamoyl)benzoyl)-N3,N4-bis((1S,2R)-2-phenylcyclopropyl)pyrrolidine-3,4-dicarboxamide, Compound 140

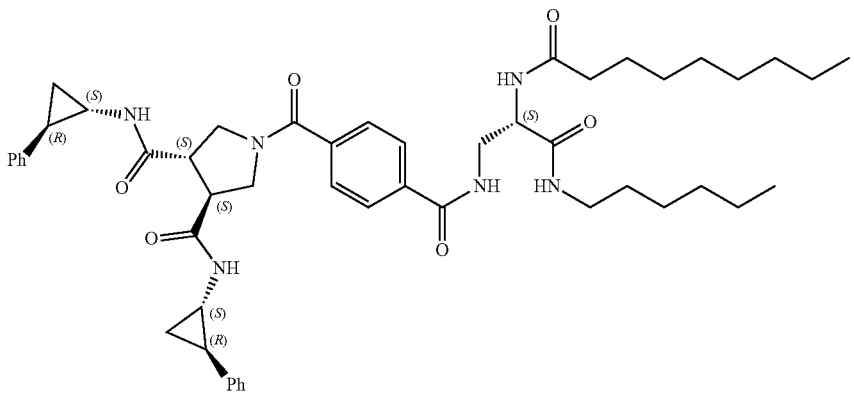

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 7 to give (3S,4S)-1-(4-(((S)-3-(hexylamino)-2-nonanamido-3-oxopropyl)carbamoyl)benzoyl)-N3,N4-bis((1S,2R)-2-phenylcyclopropyl)pyrrolidine-3,4-dicarboxamide (Compound 140), as an off white solid (0.31 g, 18.24%). LCMS (Method-C3): 100% (RT 2.036, 223.0 nm) (MS: ESI +ve 848.21 [M+H]). $^1$H NMR: (400 MHz, DMSO) δ ppm: 0.81-0.86 (m, 6H), 1.08-1.19 (m, 18H), 1.33-1.35 (m, 2H), 1.45 (s, 2H), 1.85 (s, 1H), 1.98 (m, 1H), 2.10-2.13 (m, 2H), 2.68-2.79 (m, 2H), 2.85-3.23 (m, 4H), 3.50-3.55 (m, 4H), 3.61-3.65 (m, 1H), 3.80-3.85 (m, 1H), 4.44-4.49 (m, 1H), 7.06-7.08 (d, J=7.2 Hz, 2H), 7.12-7.19 (m, 4H), 7.23-7.29 (m, 4H), 7.58-7.60 (d, J=8 Hz, 2H), 7.85-7.91 (m, 4H), 8.29-8.30 (d, J=4 Hz, 1H), 8.43-8.44 (d, J=4 Hz, 1H), 8.50 (m, 1H).

Synthesis of (3S,4S)-1-(4-(((S)-3-(hexylamino)-2-octanamido-3-oxopropyl) carbamoyl) benzoyl)-N3,N4-bis((1S,2R)-2-phenylcyclopropyl)pyrrolidine-3,4-dicarboxamide, Compound 173

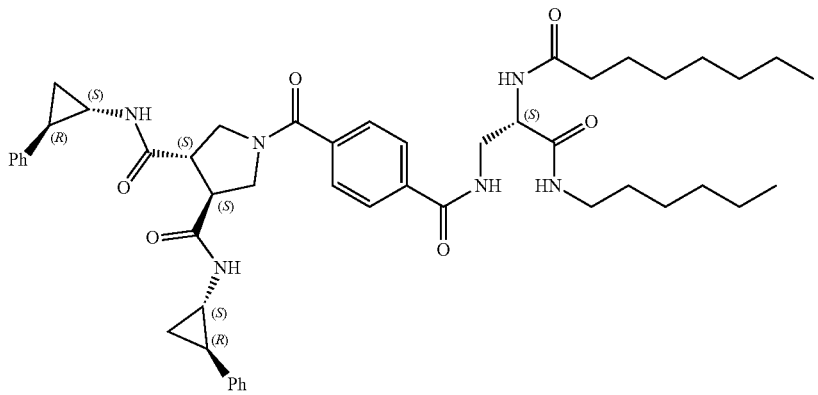

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 3 to give (3S,4S)-1-(4-(((S)-3-(hexylamino)-2-octanamido-3-oxopropyl) carbamoyl) benzoyl)-N3,N4-bis((1S,2R)-2-phenylcyclopropyl) pyrrolidine-3,4-dicarboxamide (Compound 173), as a white solid (0.03 g, 14.2%). LCMS (Method-H): 100% (RT: 3.642, 202.0 nm) (MS: ESI +ve 834.0 [M+H]). $^1$H NMR: (400 MHz, DMSO) δ ppm: 0.81-0.85 (m, 6H); 1.08-1.12 (m, 3H); 1.23 (s, 15H); 1.33-1.34 (d, J=6.8, 2H); 1.45 (s, 2H); 1.85 (s, 1H); 1.96-2.00 (m, 1H); 2.12-2.34 (t, 2H); 2.68 (s, 1H); 2.78-2.85 (m, 1H); 2.99-3.07 (m, 2H); 3.08-3.14 (m, 1H); 3.17-3.21 (m, 1H); 3.35-3.48 (m, 4H); 3.51-3.60 (m, 1H); 3.81-3.84 (m, 1H); 4.45-4.47 (d, J=8, 1H); 7.06-7.08 (d, J=7.2, 2H); 7.12-7.19 (m, 4H); 7.25-7.29 (m, 4H); 7.58-7.60 (d, J=8, 2H); 7.85-7.87 (d, J=8, 3H); 7.92-7.94 (d, J=8.4, 1H); 8.31 (s, 1H); 8.45 (s, 1H); 8.52 (s, 1H).

Synthesis of (3S,4S)-1-(4-(((S)-2-decanamido-3-(hexylamino)-3-oxopropyl) carbamoyl) benzoyl)-N3,N4-bis ((1S,2R)-2-phenylcyclopropyl) pyrrolidine-3,4-dicarboxamide, Compound 175

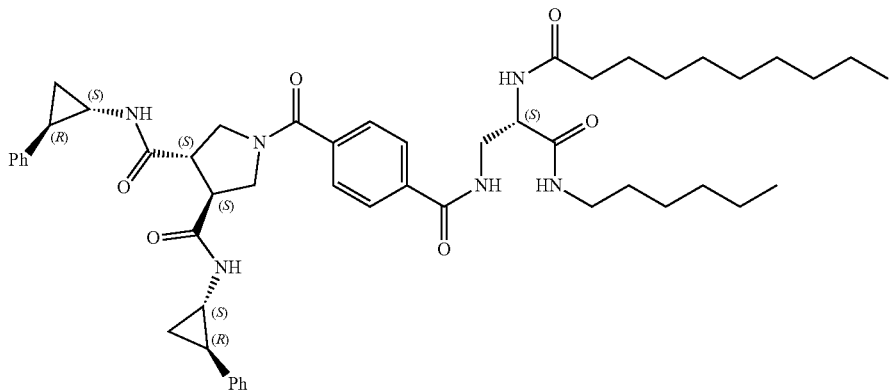

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 3 to give (3S,4S)-1-(4-(((S)-2-decanamido-3-(hexylamino)-3-oxopropyl) carbamoyl) benzoyl)-N3,N4-bis ((1S, 2R)-2-phenylcyclopropyl) pyrrolidine-3,4-dicarboxamide (Compound 175), (0.03 g, 10.3%). LCMS (Method-H): 100% (RT: 3.935, 202.0 nm) (MS: ESI +ve 860.0 [M−H]). $^1$H NMR: (400 MHz, DMSO) δ ppm: 0.67-0.80 (m, 8H); 1.07-1.10 (m, 2H); 1.18 (s, 26H); 1.32-1.33 (d, J=6.4, 3H); 1.81 (s, 2H); 1.95-1.99 (t, 1H); 2.0-2.12 (t, 2H); 2.76 (s, 1H); 2.85 (s, 1H); 3.01 (s, 5H); 3.05-3.09 (m, 2H); 3.44-3.48 (m, 4H); 3.64-3.81 (m, 1H); 4.42 (m, 1H); 4.44-4.48 (m, 1H); 7.05-7.07 (d, J=7.6, 3H); 7.11-7.16 (m, 4H); 7.23-7.28 (m, 4H); 7.57-7.59 (d, J=8, 2H); 7.84-7.86 (d, J=8.4, 3H); 7.92-7.94 (d, J=8, 1H); 8.30 (s, 1H); 8.55 (s, 1H).

Synthesis of (3S,4S)-1-(4-(((S)-3-(heptylamino)-2-octanamido-3-oxopropyl) carbamoyl)benzoyl)-N3,N4-bis((1S,2R)-2-phenylcyclopropyl)pyrrolidine-3,4-dicarboxamide, Compound 184

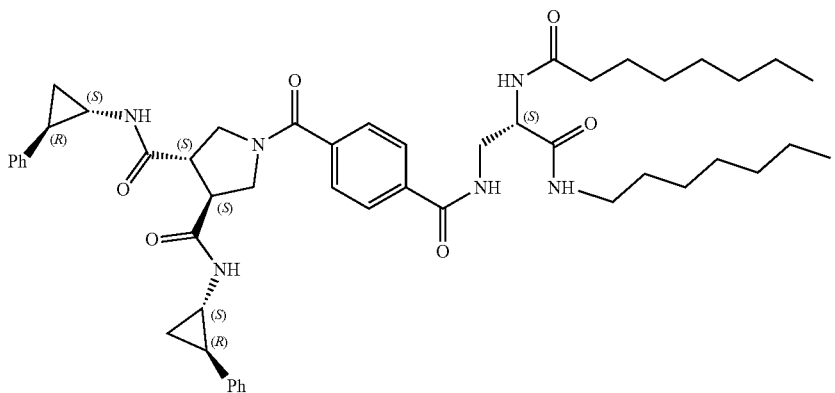

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 1 to give to give (3S,4S)-1-(4-(((S)-3-(heptylamino)-2-octanamido-3-oxopropyl) carbamoyl)benzoyl)-N3,N4-bis((1S,2R)-2-phenylcyclopropyl)pyrrolidine-3,4-dicarboxamide (Compound 184), as an off white solid (0.030 g, 12.69%). LCMS (Method-J): 100% (RT: 4.155, 202 nm) (MS: ESI +ve 848.3[M+1]). $^1$H NMR: (400 MHz, DMSO) δ ppm: 0.80-0.84 (m, 6H), 1.07-1.23 (m, 20H), 1.34 (s, 2H), 1.447 (s, 2H), 1.84 (s, 1H), 1.97-1.99 (d, J=8.8 Hz, 1H), 2.09-2.12 (t, J=7.2 Hz, 2H), 2.78 (s, 1H), 2.85 (s, 1H), 2.98-3.22 (m, 4H), 3.46-3.53 (m, 4H), 3.59-3.64 (t, J=10 Hz, 1H), 3.78-3.84 (t, J=8.4 Hz, 1H), 4.44-4.46 (d, J=7.6 Hz, 1H), 7.05-7.28 (m, 10H), 7.57-7.59 (d, J=8.4 Hz, 2H), 7.84-7.94 (m, 4H), 8.31-8.32 (d, J=4 Hz, 1H), 8.45-8.46 (d, J=4 Hz, 1H), 8.52-8.53 (d, J=6 Hz, 1H).

Synthesis of (3S,4S)-1-(4-(((S)-2-nonanamido-3-(octylamino)-3-oxopropyl) carbamoyl)benzoyl)-N3,N4-bis((1S,2R)-2-phenylcyclopropyl)pyrrolidine-3,4-dicarboxamide, Compound 197

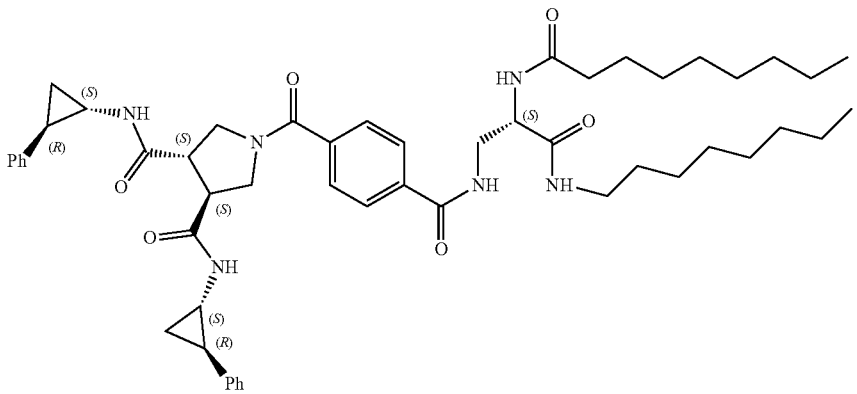

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 7 to give (3S,4S)-1-(4-(((S)-2-nonanamido-3-(octylamino)-3-oxopropyl) carbamoyl)benzoyl)-N3,N4-bis((1S,2R)-2-phenylcyclopropyl)pyrrolidine-3,4-dicarboxamide (Compound 197) (0.033 g, 13.51%). LCMS (Method-H): 97.06% (RT: 4.068, 202 nm) (MS: ESI +ve 876.7[M+2]). $^1$H NMR: (400 MHz, DMSO) δ ppm: 0.81-0.85 (m, 6H), 1.07-1.23 (m, 27H), 1.34 (s, 3H), 1.447 (s, 3H), 1.84 (s, 1H), 1.97 (s, 1H), 2.08-2.12 (t, J=7.2 Hz, 3H), 2.67 (s, 1H), 2.78 (s, 1H), 2.85-3.20 (m, 6H), 3.48-3.53 (t, J=12.8 Hz, 4H), 3.60-3.64 (t, J=10 Hz, 1H), 3.78-3.83 (t, J=11.6 Hz, 1H), 4.44-4.46 (d, J=7.6 Hz, 1H), 7.05-7.28 (m, 10H), 7.57-7.59 (d, J=8.4 Hz, 2H), 7.83-7.91 (m, 4H), 8.29-8.30 (d, J=4.4 Hz, 1H), 8.43-8.44 (d, J=4 Hz, 1H), 8.05 (s, 1H).

Synthesis of (3S,4S)-1-(4-(((S)-2-decanamido-3-(nonylamino)-3-oxopropyl)carbamoyl)benzoyl)-N3,N4-bis((1S,2R)-2-phenylcyclopropyl)pyrrolidine-3,4-dicarboxamide, Compound 207

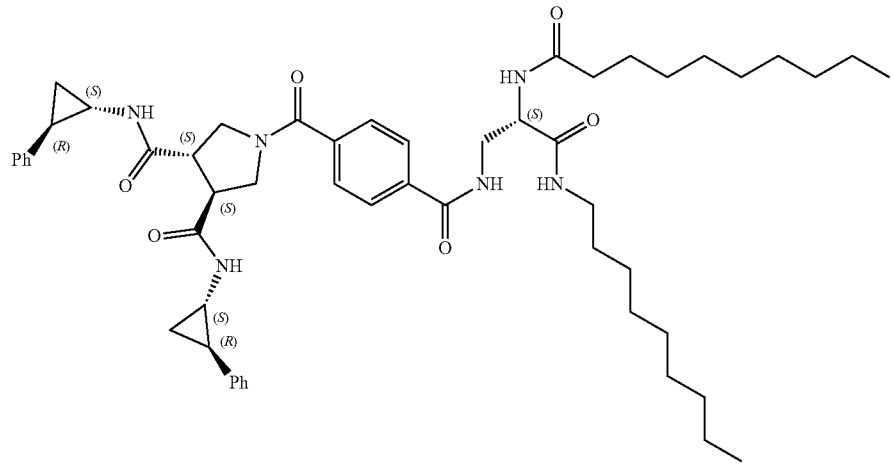

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 12 to give Compound 207 as an off white solid (0.004 g, 1.98%). LCMS (Method-J): 100% (RT 2.42, 202.0 nm) (MS: ESI +ve 904.7 [M+1]. $^1$H NMR: (400 MHz, DMSO-$d_6$) δ 0.84-0.87 (m, 6H), 1.08-1.20 (m, 30H), 1.35 (s, 2H), 1.46 (s, 2H), 1.85 (s, 1H), 1.98 (s, 1H), 2.10-2.13 (t, J=4 Hz, 2H), 2.79 (s, 1H), 2.86 (s, 1H), 3.02-3.05 (t, J=4 Hz, 2H), 3.10-3.12 (t, J=8 Hz, 1H), 3.17-3.22 (t, J=4 Hz, 1H), 3.50-3.55 (m, 4H), 3.63 (s, 1H), 3.82 (s, 1H), 4.45-4.47 (d, J=7.6 Hz, 1H), 7.06-7.19 (m, 6H), 7.23-7.29 (m, 4H), 7.58-7.60 (d, J=8 Hz, 2H), 7.85-7.91 (m, 4H), 8.29-8.50 (m, 3H).

Synthesis of (3S,4S)-1-(4-(((S)-2-heptanamido-3-(octylamino)-3-oxopropyl) carbamoyl) benzoyl)-N3,N4-bis((1S,2R)-2-phenylcyclopropyl)pyrrolidine-3,4-dicarboxamide, Compound 141

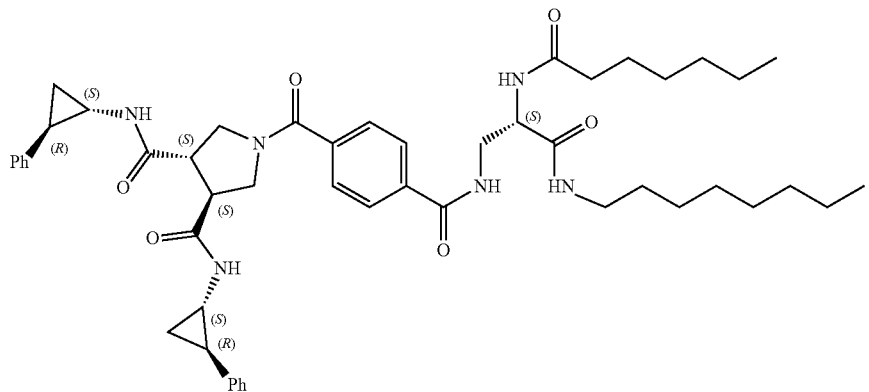

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 1 to give (3S,4S)-1-(4-(((S)-2-heptanamido-3-(octylamino)-3-oxopropyl)carbamoyl)benzoyl)-N3,N4-bis((1S,2R)-2-phenylcyclopropyl)pyrrolidine-3,4-dicarboxamide (Compound 141) (0.056 g). LCMS (Method-J): 100% (RT 5.679, 214.4 nm) (MS: ESI +ve 847.5[m+1]). $^1$H NMR (400 MHz, DMSO) δ ppm: 0.8-0.84 (m, 6H), 1.11-1.18 (m, 20H), 1.33 (s, 2H), 1.44 (s, 1H), 1.83 (s, 1H), 1.97 (s, 1H), 2.10 (s, 2H), 2.77 (s, 1H), 2.85 (s, 1H), 3.02 (s, 2H), 3.08-3.10 (d, J=8, 1H), 3.18-3.20 (s, J=8, 1H), 3.42-3.48 (d, J=24, 5H), 3.62 (s, 1H), 3.81-3.83 (d, J=8, 1H), 4.46 (s, 1H), 7.07 (s, 2H), 7.14-7.16 (d, J=8, 4H), 7.24-7.26 (d, J=8, 4H), 7.57-7.59 (d, J=8, 2H), 7.83-7.92 (m, 4H), 8.31 (s, 1H), 8.45 (s, 1H), 8.52 (S, 1H).

Synthesis of (3S,4S)-1-(4-(((R)-3-heptanamido-4-(hexylamino)-4-oxobutyl) carbamoyl) benzoyl)-N3,N4-bis((1S,2R)-2-phenylcyclopropyl)pyrrolidine-3,4-dicarboxamide, Compound 120

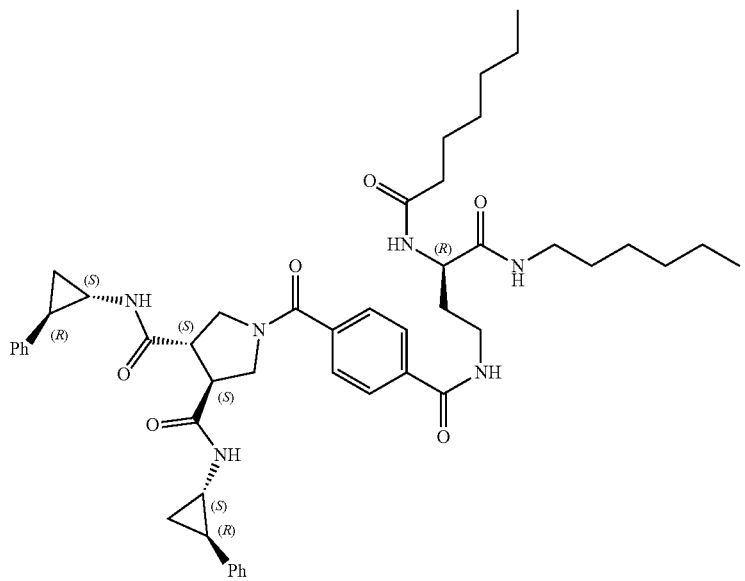

Prepared by a procedure similar to that reported for (3S,4S)-1-(4-(((S)-2-heptanamido-3-(hexylamino)-3-oxopropyl) carbamoyl) benzoyl)-N3,N4-bis((1S,2R)-2-phenylcyclopropyl)pyrrolidine-3,4-dicarboxamide (Compound 025), substituting the applicable amine and carboxylic acid. The crude final product was purified using Prep HPLC Method 1 to give (3S,4S)-1-(4-(((R)-3-heptanamido-4-(hexylamino)-4-oxobutyl)carbamoyl)benzoyl)-N3,N4-bis((1S,2R)-2-phenylcyclopropyl)pyrrolidine-3,4-dicarboxamide (Compound 120)(0.013 g, 8%). LCMS (Method-J2): 100% (RT 5.370, 202.0 nm) (MS: ESI+ve 833.5 [M+H]). $^1$H NMR: (400 MHz, DMSO) δ ppm: 0.84-0.87 (m, 6H), 1.08-1.12 (m, 2H), 1.15-1.27 (m, 14H), 1.37-1.38 (m, 2H), 1.46-1.50 (m, 2H), 1.71-1.73 (m, 2H), 1.84-1.97 (m, 4H), 2.12-2.16 (m, 2H), 2.77-2.79 (m, 1H), 2.84-2.87 (m, 1H), 3.02-3.08 (m, 4H), 3.10-3.19 (m, 2H), 3.49-3.81 (m, 2H), 3.60-3.65 (m, 1H), 3.30-3.35 (m, 1H), 4.30-4.35 (m, 1H), 7.06-7.08 (m, 2H), 7.12-7.19 (m, 4H), 7.22-7.29 (m, 4H), 7.59-7.61 (m, 2H), 7.87-7.92 (m, 3H), 8.00-8.03 (m, 1H), 8.30-8.31 (d, J=4.0 Hz, 1H), 8.45-8.50 (d, 2H).

Synthesis of (3S,4S)-1-(4-(((S)-2-heptanamido-3-oxo-3-(((1S,2R)-2-phenylcyclopropyl) amino)propyl)carbamoyl)benzoyl)-N3,N4-bis((1S,2R)-2-phenylcyclopropyl)pyrrolidine-3,4-dicarboxamide, Compound 143

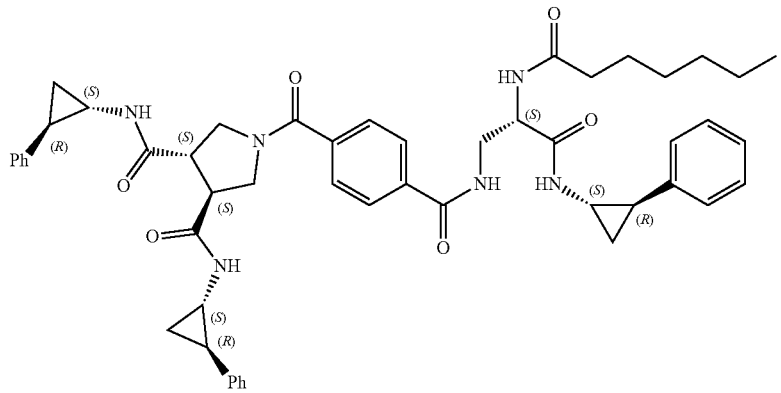

Step-1: Preparation of methyl (S)-3-amino-2-((tert-butoxycarbonyl)amino)propanoate

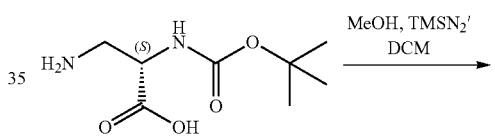

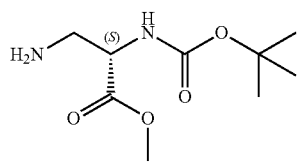

(S)-3-amino-2-((tert-butoxycarbonyl)amino)propanoic acid (1 g, 0.0048 mmol) was dissolved in DCM (16.6 mL). MeOH (1.6 mL) was added followed by Diazomethyltrimethylsilane (5.5 mL) dropwise. After 2 hr. MeOH (10 mL) was added, the mixture was concentrated and the crude product was purified using flash chromatography eluting with 0-10% DCM in MeOH to give methyl (S)-3-amino-2-((tert-butoxycarbonyl)amino)propanoate (0.250 g, 25% yield). LCMS (Method-H): 30% (RT: 2.443, 202.0 nm) (MS: ESI +ve 219.0[M+1]).

Step-2: Preparation of methyl (S)-3-(4-((3S,4S)-3,4-bis(((1S,2R)-2-phenylcyclopropyl) carbamoyl)pyrrolidine-1-carbonyl)benzamido)-2-((tert-butoxycarbonyl)amino)propanoate

Step-3: Preparation of methyl (S)-2-amino-3-(4-((3S,4S)-3,4-bis(((1S,2R)-2-phenylcyclopropyl) carbamoyl)pyrrolidine-1-carbonyl)benzamido)propanoate

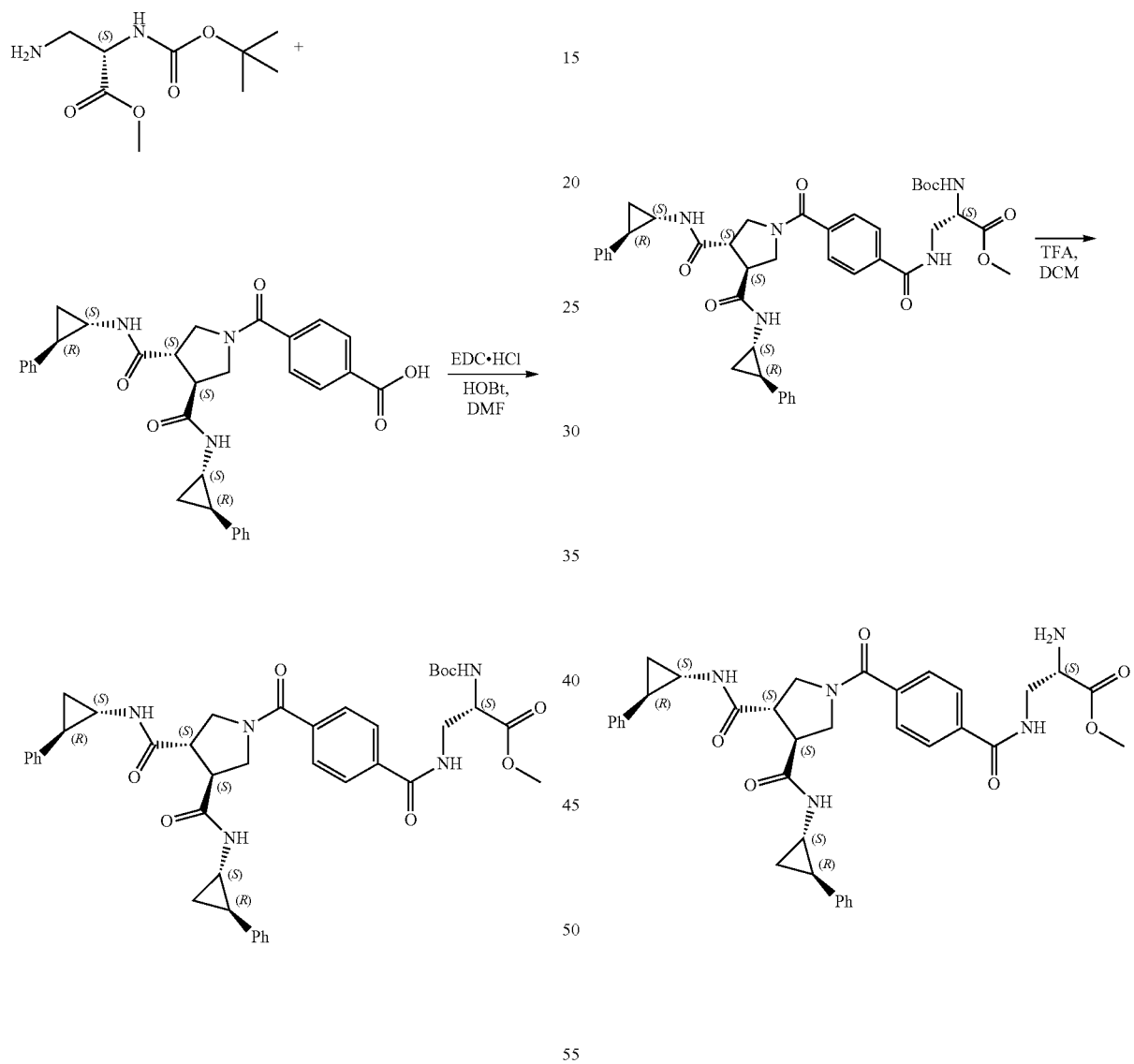

Prepared using General EDC, HOBT Coupling Procedure. The crude was purified using flash chromatography eluting with 0-10% MeOH in DCM to give methyl (S)-3-(4-((3S,4S)-3,4-bis(((1S,2R)-2-phenylcyclopropyl)carbamoyl)pyrrolidine-1-carbonyl)benzamido)-2-((tert-butoxycarbonyl) amino)propanoate (0.330 g, 96.2% yield). LCMS (Method-C3): 32% (RT: 1.333, 254.0 nm) (MS: ESI – ve 639.0 [M–100]).

Prepared using General BOC Deprotection Procedure to give (S)-2-amino-3-(4-((3S,4S)-3,4-bis(((1S,2R)-2-phenylcyclopropyl)carbamoyl)pyrrolidine-1-carbonyl)benzamido) propanoate (0.435 g crude). LCMS (Method-C3): 54.9% (RT: 1.142, 226.0 nm) (MS: ESI +ve 638.6 [M+1]).

Step-4: Preparation of methyl (S)-3-(4-((3S,4S)-3,4-bis(((1S,2R)-2-phenylcyclopropyl) carbamoyl)pyrrolidine-1-carbonyl)benzamido)-2-heptanamidopropanoate

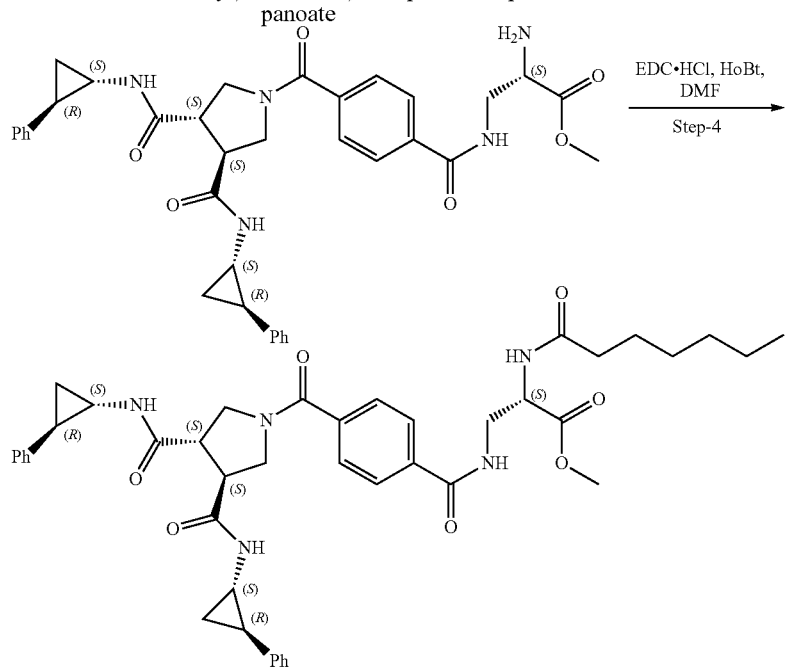

Prepared using General EDC, HOBT Coupling Procedure to give methyl (S)-3-(4-((3S,4S)-3,4-bis(((1S,2R)-2-phenylcyclopropyl)carbamoyl)pyrrolidine-1-carbonyl)benzamido)-2-heptanamidopropanoate. (0.147 g, 35.5% yield). LCMS (Method-H): 72.9% (RT: 3.217, 230.0 nm) (MS: ESI +ve 638. [M+1]).

Step-5: Preparation of (S)-3-(4-((3S,4S)-3,4-bis(((1S,2R)-2-phenylcyclopropyl) carbamoyl)pyrrolidine-1-carbonyl)benzamido)-2-heptanamidopropanoic acid

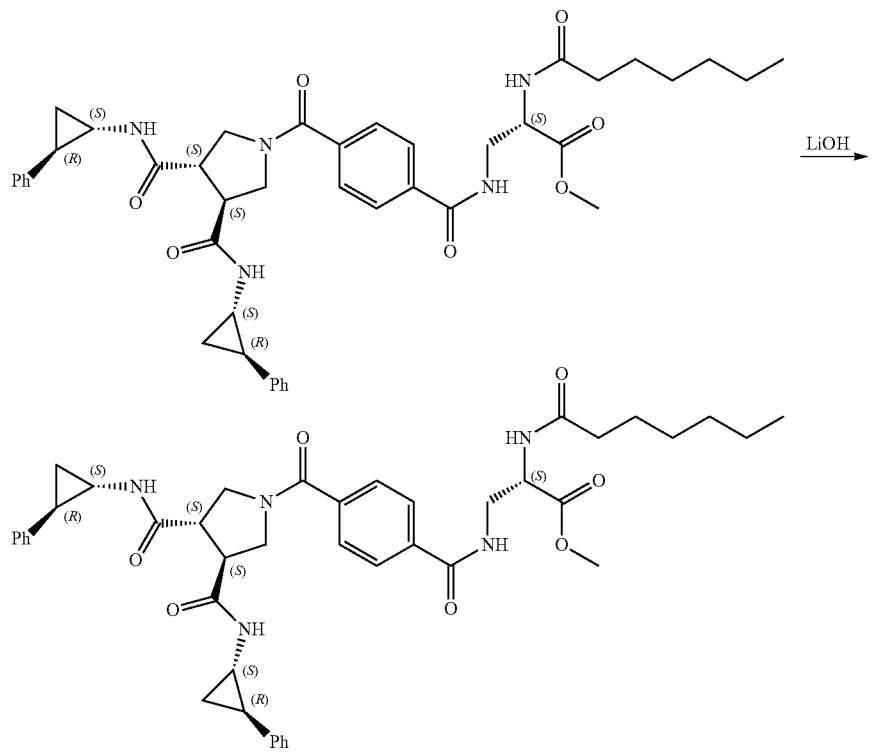

Prepared using General EDC, HOBT Coupling Procedure to give methyl (S)-3-(4-((3S,4S)-3,4-bis(((1S,2R)-2-phenylcyclopropyl)carbamoyl)pyrrolidine-1-carbonyl)benzamido)-2-heptanamidopropanoate. (0.147 g, 35.5% yield). LCMS (Method-H): 72.9% (RT: 3.217, 230.0 nm) (MS: ESI [M+1]).68.7% (RT: 2.545, 214.0 nm) (MS: ESI −ve 734.6 [M−1]).

Step-6: Preparation of (3S,4S)-1-(4-(((S)-2-h

Step-1: Preparation of methyl (S)-3-amino-2-((tert-butoxycarbonyl)amino)propanoate

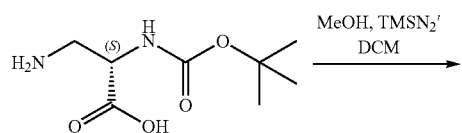

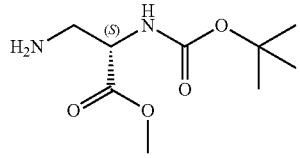

(S)-3-amino-2-((tert-butoxycarbonyl)amino)propanoic acid (1 g, 0.0048 mmol) was dissolved in DCM (16.6 mL). MeOH (1.6 mL) was added followed by Diazomethyltrimethylsilane (5.5 mL) dropwise. After 2 hr. MeOH (10 mL) was added, the mixture was concentrated and the crude product was purified using flash chromatography eluting with 0-10% DCM in MeOH to give methyl (S)-3-amino-2-((tert-butoxycarbonyl)amino)propanoate (0.250 g, 25% yield). LCMS (Method-H): 30% (RT: 2.443, 202.0 nm) (MS: ESI +ve 219.0[M+1]).

Septanamido-3-oxo-3-(((1S,2R)-2-phenylcyclopropyl)amino)propyl)carbamoyl)benzoyl)-N3,N4-bis((1S,2R)-2-phenylcyclopropyl)pyrrolidine-3,4-dicarboxamide, Compound 143

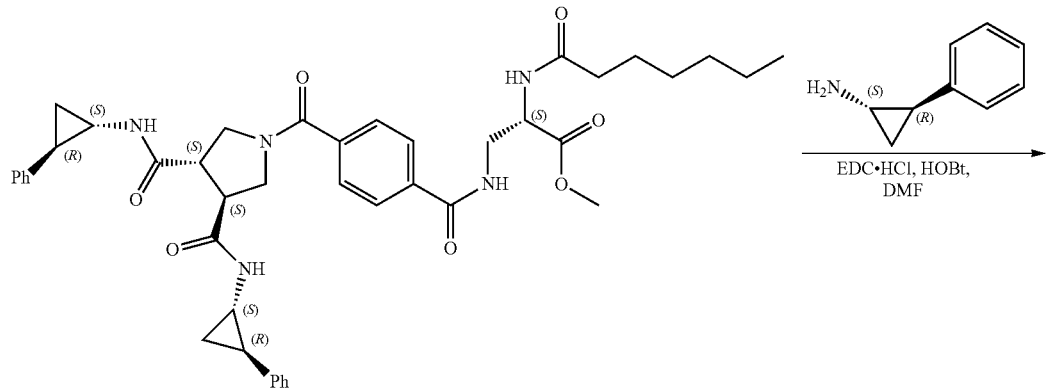

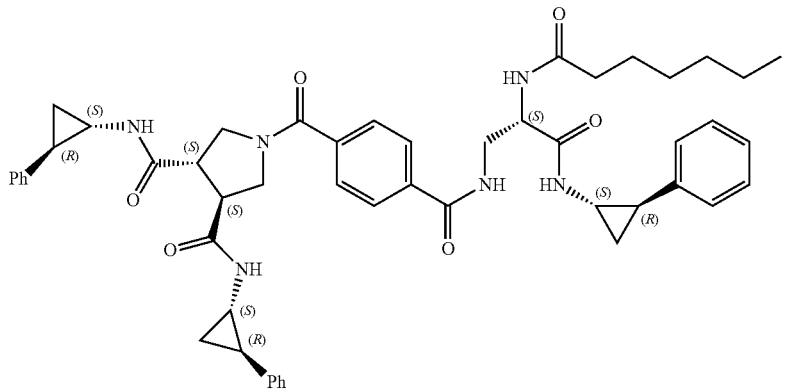

Prepared using General EDC, HOBT Coupling Procedure. The crude final product was purified using Prep HPLC Method to give (3S,4S)-1-(4-(((S)-2-heptanamido-3-oxo-3-(((1S,2R)-2-phenylcyclopropyl)amino)propyl)carbamoyl)benzoyl)-N3,N4-bis((1S,2R)-2-phenylcyclopropyl)pyrrolidine-3,4-dicarboxamide (Compound 143) (0.014 g, 11%). LCMS (Method-C3): 100% (RT: 1.828, 202.0 nm) (MS: ESI +ve 852.4 [M+1]). ¹H NMR: (400 MHz, DMSO) δ ppm: 0.799-0.816 (m, 3H), 1.108-1.191 (m, 13H), 1.437-1.453 (t, J=6.4 Hz, 2H), 1.825-1.877 (m, 2H), 1.972 (s, 1H), 2.100-2.137 (t, J=14.8 Hz, 2H), 2.676 (s, 1H), 2.856 (s, 2H), 3.095 (s, 1H), 3.095-3.115 (m, 1H), 3.135-3.168 (m, 1H), 3.188-3.209 (m, 1H), 3.440 (m, 1H), 3.471-3.543 (m, 4H), 3.575-3.648 (m, 1H), 3.794-3.845 (m, 1H), 4.414-4.449 (m, 1H), 7.008-7.068 (m, 4H), 7.136-7.288 (m, 11H), 7.587-7.607 (d, 2H), 7.854-7.911 (m, 3H), 8.252-8.291 (t, J=15.6 Hz, 2H), 8.434-8.444 (d, J=4 Hz, 1H), 8.526 (s, 1H).

Synthesis of (3S,4S)-1-(4-(((S)-2-(3-heptylureido)-3-(hexylamino)-3-oxopropyl) carbamoyl) benzoyl)-N3,N4-bis ((1S,2R)-2-phenylcyclopropyl) pyrrolidine-3,4-dicarboxamide, Compound 181

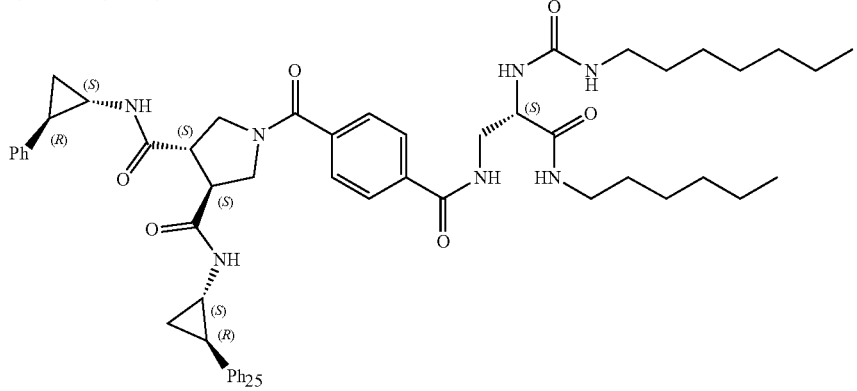

Step-1: Preparation of benzyl phenyl (3-(hexylamino)-3-oxopropane-1,2-diyl) (S)-dicarbamate

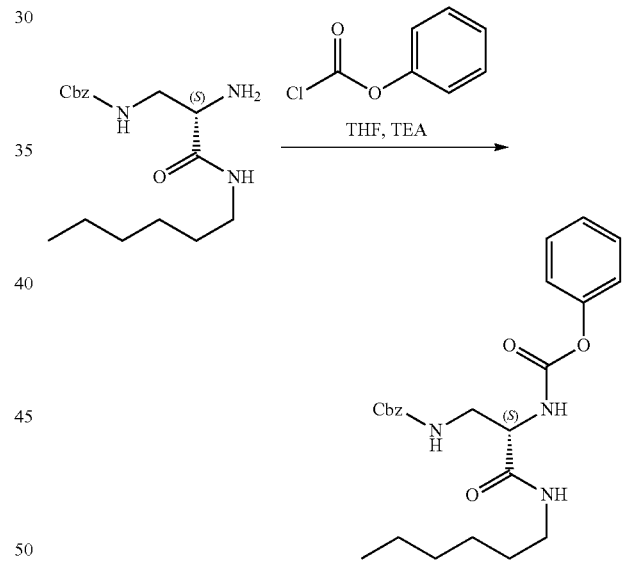

To a stirred solution of phenyl chloroformate (0.25 g, 1.59 mmol) in THF (10 mL), was added benzyl (S)-(2-amino-3-(hexylamino)-3-oxopropyl)carbamate (0.61 mg, 1.91 mmol) at 0° C. followed by the addition of TEA (0.92 mL, 6.38 mmol) after 5 min. The reaction mixture was stirred for 16 hrs at room temperature. The mixture was diluted with ice-cold water (25 mL) the resulting precipitate was collected by filtration and dried under vacuum. The crude product was purified using flash chromatography, eluting with 0-10% MeOH/DCM, to give benzyl phenyl (3-(hexylamino)-3-oxopropane-1,2-diyl) (S)-dicarbamate as a white solid (0.2 g, 28.3%). LCMS (Method-C-Fast): 43.8% (RT: 1.463, 202.0 nm) (MS: ESI +ve 442.5 [M+H]).

285

Step-2: Preparation of benzyl (S)-(2-(3-heptylu-reido)-3-(hexylamino)-3-oxopropyl) carbamate

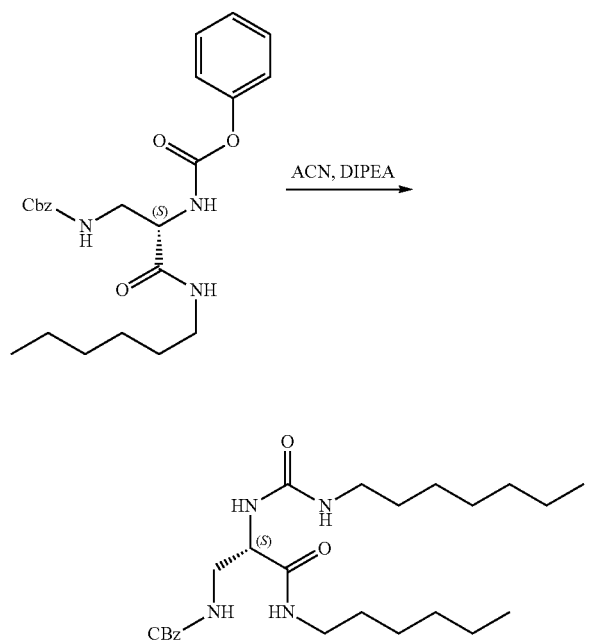

A mixture of benzyl phenyl (3-(hexylamino)-3-oxopropane-1,2-diyl) (S)-dicarbamate (0.2 g, 0.45 mmol) in acetonitrile (5 mL), heptylamine (0.05 g, 0.45 mmol) and DIPEA (0.23 mL, 1.35 mmol) was stirred for 16 hrs at room temperature. The mixture was diluted with ice-cold water (25 mL), the resulting precipitate was collected by filtration and dried under vacuum to give benzyl (S)-(2-(3-heptylureido)-3-(hexylamino)-3-oxopropyl) carbamate as a white solid (0.25 g, 100%). LCMS (Method-C-Fast): 72.74% (RT: 1.795, 202.0 nm) (MS: ESI +ve 463.9 [M+H]).

286

Step-3: Preparation of (S)-3-amino-2-(3-heptylureido)-N-hexylpropanamide

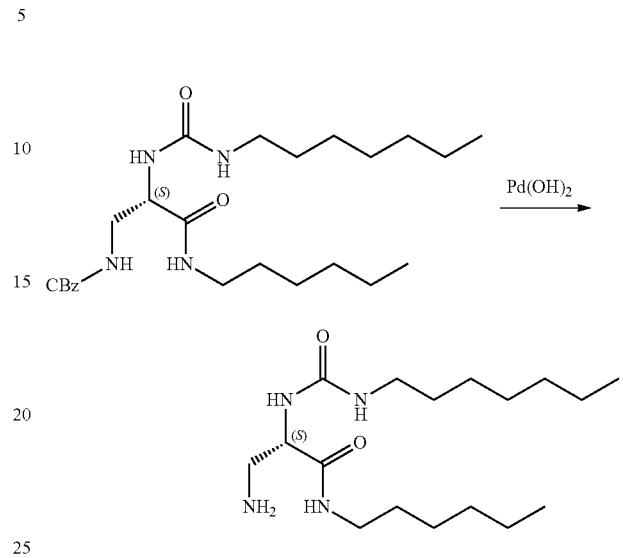

A mixture of benzyl (S)-(2-(3-heptylureido)-3-(hexylamino)-3-oxopropyl) carbamate (0.25 g, 0.54 mmol) and palladium hydroxide (0.3 g) in MeOH:DCM (2:1, 15 mL) was hydrogenated under a balloon of hydrogen for 16 h. The reaction mixture was filtered through celite and the filtrate was concentrated to give (S)-3-amino-2-(3-heptylureido)-N-hexylpropanamide as an off white solid (0.16 g, 82.2%). LCMS (Method-C2): 73.4% (RT: 1.143, 202.0 nm) (MS: ESI +ve 329.0 [M+H]).

Step-4: Synthesis of (3S,4S)-1-(4-(((S)-2-(3-heptylureido)-3-(hexylamino)-3-oxopropyl) carbamoyl) benzoyl)-N3,N4-bis ((1S,2R)-2-phenylcyclopropyl) pyrrolidine-3,4-dicarboxamide, Compound 181

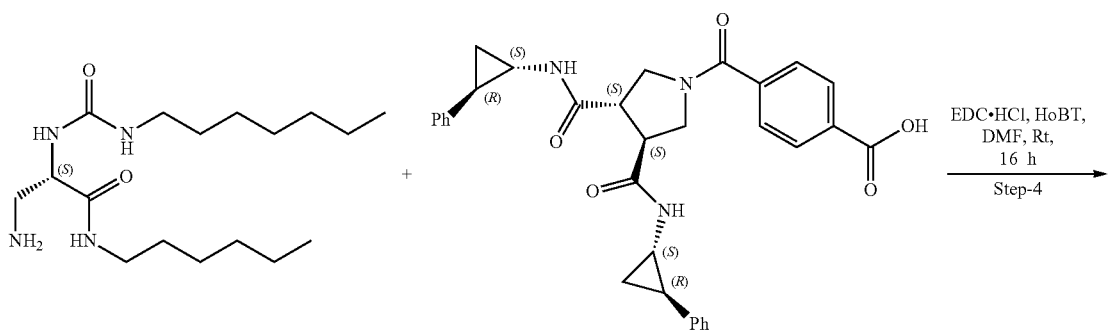

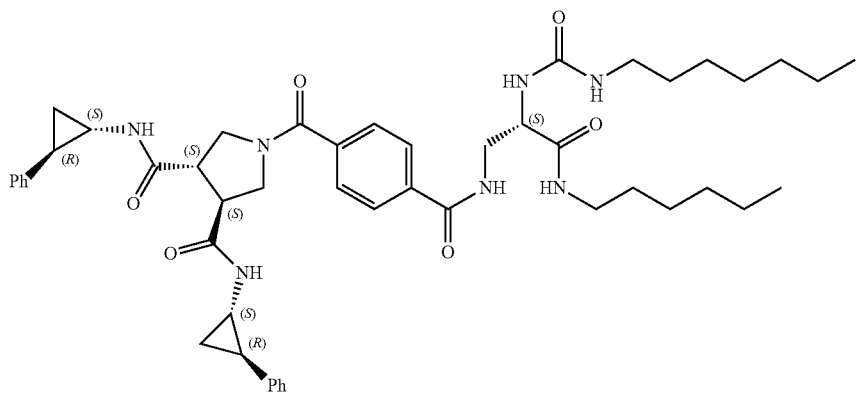

Prepared using General EDC, HOBT Coupling Procedure. The crude was purified using Prep HPLC Method 3 to give (3S,4S)-1-(4-(((S)-2-(3-heptylureido)-3-(hexylamino)-3-oxopropyl) carbamoyl) benzoyl)-N3,N4-bis ((1S, 2R)-2-phenylcyclopropyl) pyrrolidine-3,4-dicarboxamide (Compound 181), as a white solid (0.02 g, 6.6%). LCMS (Method-H): 97.2% (RT: 3.601, 202.0 nm) (MS: ESI +ve 847.0 [M−H]). $^1$H NMR: (400 MHz, DMSO) δ ppm: 0.81-0.86 (m, 6H); 1.09-1.13 (m, 2H); 1.97 (s, 12H); 1.33 (s, 4H); 1.98 (s, 2H); 2.86 (s, 4H); 3.03-3.10 (m, 8H); 3.61-3.66 (m, 5H); 3.80-3.82 (d, J=8.4, 2H); 4.33-4.37 (t, 2H); 6.13-6.15 (d, J=7.6, 1H); 6.22 (s, 1H); 7.07-7.30 (m, 10H); 7.57-7.59 (d, J=8, 2H); 7.86-7.88 (d, J=8, 2H); 7.93-7.95 (d, J=5.2, 1H); 8.29 (s, 1H); 8.43 (s, 1H); 8.54 (s, 1H).

Synthesis of (3S,4S)-1-(4-(((S)-3-(hexylamino)-3-oxo-2-(3-pentylureido) propyl)carbamoyl)benzoyl)-N3,N4-bis((1S,2R)-2-phenylcyclopropyl)pyrrolidine-3,4-dicarboxamide, Compound 137

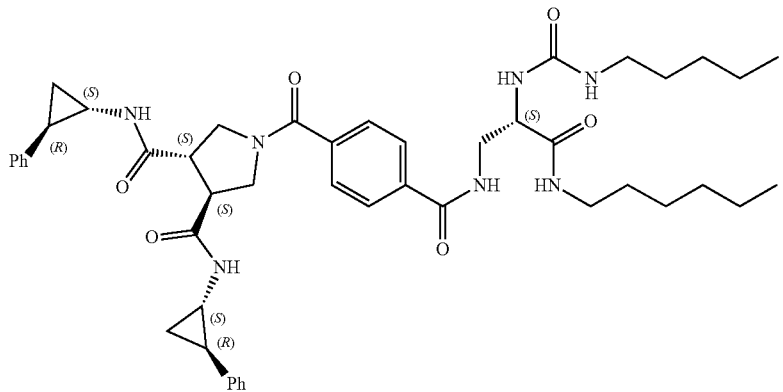

Prepared by a procedure similar to that reported for (3S,4S)-1-(4-(((S)-2-(3-heptylureido)-3-(hexylamino)-3-oxopropyl) carbamoyl) benzoyl)-N3,N4-bis ((1S, 2R)-2-phenylcyclopropyl) pyrrolidine-3,4-dicarboxamide (Compound 181), substituting the applicable amine and carboxylic acid. The crude final product was purified using Prep HPLC Method 7 to give (3S,4S)-1-(4-(((S)-3-(hexylamino)-3-oxo-2-(3-pentylureido)propyl)carbamoyl)benzoyl)-N3,N4-bis((1S,2R)-2-phenylcyclopropyl)pyrrolidine-3,4-dicarboxamide (Compound 137) as an off white solid (0.033 g, 6%). LCMS (Method-C3): 100% (RT 1.937, 202.0 nm) (MS: ESI +ve 820.56 [M+H]). $^1$H NMR: (400 MHz, DMSO) δ ppm: 0.80-0.83 (m, 6H), 1.07-1.12 (m, 2H), 1.16-1.21 (m, 12H), 1.27-1.34 (m, 4H), 1.83-1.87 (t, 1H), 1.941.97 (m, 1H), 2.67-2.77 (m, 2H), 2.83-2.85 (m, 2H), 2.86-2.91 (m, 3H), 3.03-3.21 (m, 1H), 3.36-3.60 (m, 4H), 3.60-3.63 (m, 1H), 3.76-3.79 (m, 1H), 4.30 (m, 1H), 6.34-6.36 (t, 1H), 7.05-7.18 (m, 6H), 7.23-7.28 (m, 4H), 7.56-7.58 (d, J=8 Hz, 2H), 7.86-7.88 (d, J=8 Hz, 2H), 7.96-7.98 (m, 1H), 7.39-7.40 (d, J=4 Hz, 1H), 8.50-8.54 (m, 2H), 8.65-8.66 (t, 1H).

Synthesis of (3S,4S)-1-(4-(((S)-3-(hexylamino)-2-(3-octylureido)-3-oxopropyl)carbamoyl)benzoyl)-N3,N4-bis((1S,2R)-2-phenylcyclopropyl)pyrrolidine-3,4-dicarboxamide, Compound 211

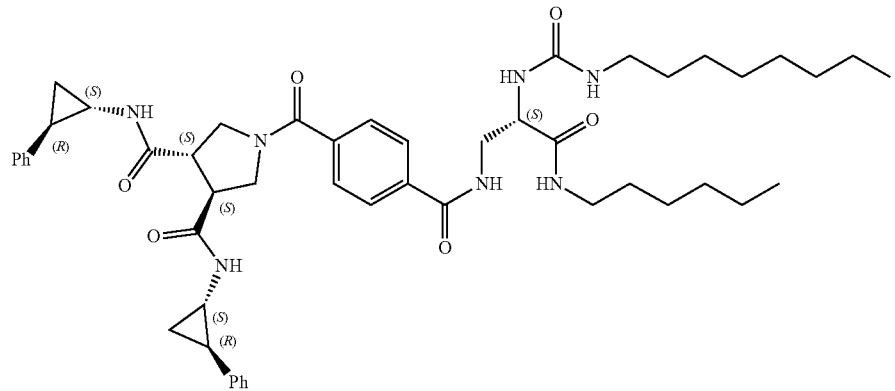

Prepared by a procedure similar to that reported for (3S,4S)-1-(4-(((S)-2-(3-heptylureido)-3-(hexylamino)-3-oxopropyl) carbamoyl) benzoyl)-N3,N4-bis ((1S,2R)-2-phenylcyclopropyl) pyrrolidine-3,4-dicarboxamide (Compound 181), substituting the applicable amine and carboxylic acid. The crude final product was purified using Prep HPLC Method 13 to give (3S,4S)-1-(4-(((S)-3-(hexylamino)-2-(3-octylureido)-3-oxopropyl)carbamoyl)benzoyl)-N3,N4-bis((1S,2R)-2-phenylcyclopropyl)pyrrolidine-3,4-dicarboxamide (Compound 211), as an off white solid (0.072 g, 23.84%). LCMS (Method-J): 100% (RT 4.629, 202.4 nm) (MS: ESI +ve 862.6 [M+H]). $^1$H NMR: (400 MHz, DMSO) δ ppm: 0.80-0.86 (m, 7H), 1.11-1.32 (m, 21H), 1.84 (m, 1H), 1.97 (m, 1H), 2.50-2.67 (m, 3H), 2.77-2.85 (m, 2H), 2.94-3.09 (m, 5H), 3.11-3.22 (m, 1H), 3.33-3.53 (m, 4H), 3.60-3.81 (m, 2H), 4.32-4.34 (m, 1H), 6.11-6.13 (d, J=7.6 Hz, 1H), 6.21 (m, 1H), 7.057.07 (d, J=7.2 Hz, 2H), 7.11-7.22 (m, 4H), 7.24-7.28 (m, 4H), 7.56-7.58 (d, J=8 Hz, 2H), 7.84-7.86 (d, J=8 Hz, 2H), 7.93 (s, 1H), 8.29-8.30 (d, J=4 Hz, 1H), 8.43-8.44 (d, J=3.6 Hz, 1H), 8.53 (s, 1H).

Synthesis of (3S,4S)-1-(4-(((S)-3-oxo-3-(((1S,2R)-2-phenylcyclopropyl) amino)-2-(3-((1S,2R)-2-phenylcyclopropyl)ureido)propyl)carbamoyl)benzoyl)-N3,N4-bis((1S,2R)-2-phenylcyclopropyl) pyrrolidine-3,4-dicarboxamide, Compound 222

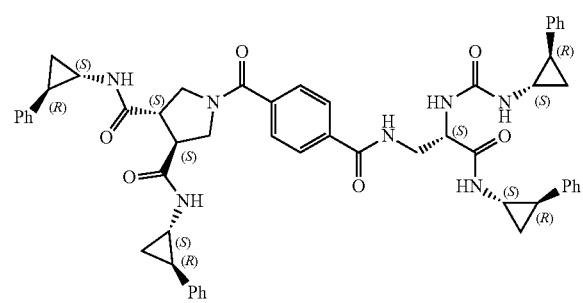

Prepared by a procedure similar to that reported for (3S,4S)-1-(4-(((S)-2-(3-heptylureido)-3-(hexylamino)-3-oxopropyl) carbamoyl) benzoyl)-N3,N4-bis ((1S,2R)-2-phenylcyclopropyl) pyrrolidine-3,4-dicarboxamide (Compound 181), substituting the applicable amine and carboxylic acid. The crude final product was purified using Prep HPLC Method 1 to give (3S,4S)-1-(4-(((S)-2-(3-(4-fluorobenzyl)ureido)-3-(hexylamino)-3-oxopropyl)carbamoyl)benzoyl)-N3,N4-bis((1S,2R)-2-phenylcyclopropyl)pyrrolidine-3,4-dicarboxamide (Compound 186) (0.050 g, 23.55%). LCMS (Method-J): 100% (RT 4.190, 254.0 nm) (MS: ESI +ve 859.5 [M+H]). $^1$H NMR: (400 MHz, DMSO) δ ppm: 0.79-0.81 (t, J=6.8 Hz, 3H), 1.07-1.34 (m, 13H), 1.84 (s, 1H), 1.97-1.99 (m, 2H), 2.65 (s, 1H), 2.65 (s, 1H), 2.77 (s, 1H), 2.99-3.330 (m, 5H), 3.33-3.51 (m, 6H), 3.59 (s, 1H), 3.78-3.80 (m, 1H), 4.12-4.28 (m, 2H), 4.25 (s, 1H), 6.30-6.32 (m, 1H), 6.74 (s, 1H), 7.04-7.18 (m, 8H), 7.21-7.26 (m, 6H), 7.56-7.58 (m, 2H), 7.84-7.86 (m, 2H), 7.97 (s, 1H), 8.29-8.30 (m, 1H), 8.43-8.55 (m, 3H).

Synthesis of nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate, Compound 229

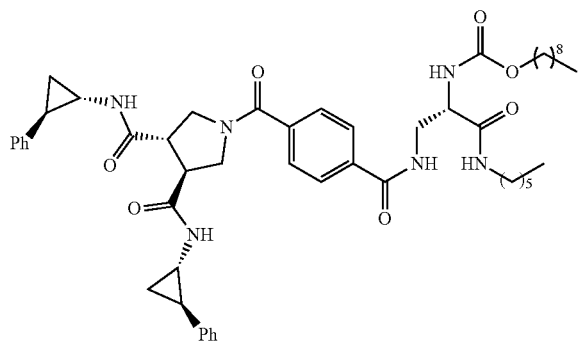

Step-1: Preparation of 4-nitrophenyl nonyl carbonate

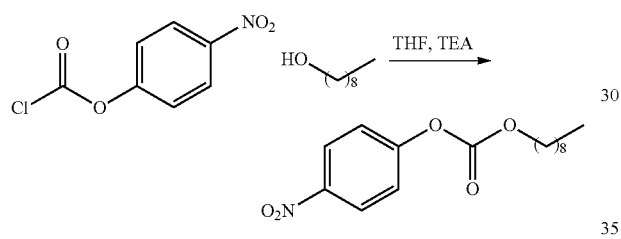

A mixture of nonan-1-ol (1.0 g, 6.93 mmol), 4-nitrophenyl chloroformate (1.67 g, 8.31 mmol) and TEA (1 ml) in THF (0.5 ml) was stirred at room temperature for 16 h. The reaction mixture was concentrated and the crude product was purified using flash chromatography to give 4-nitrophenyl nonyl carbonate (2.1 g, 99%). ¹H NMR: (400 MHz, DMSO) (62575) 6 ppm: 0.901 (t, 3H), 1.29 (m, 9H), 1.37 (s, 2H), 1.79 (m, 2H), 7.41 (d, J=9.2 Hz, 2H), 8.305 (d, J=9.2 Hz, 2H).

Step-2: Preparation of benzyl nonyl (3-(hexylamino)-3-oxopropane-1,2-diyl)(S)-dicarbamate

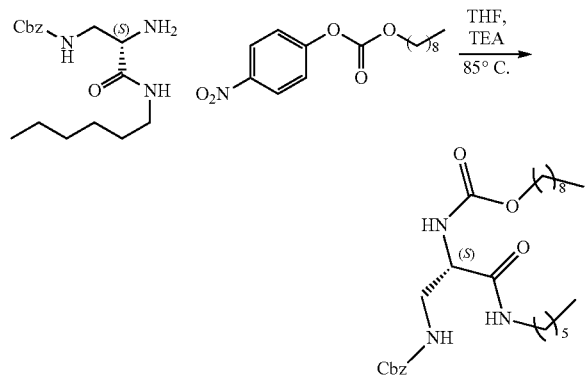

4-nitrophenyl nonyl carbonate (0.800 g, 2.50 mmol) and benzyl (S)-(2-amino-3-(hexylamino)-3-oxopropyl)carbamate (0.995 g, 3.09 mmol) was dissolved in THF (20 mL). DMAP (0.03 g, 0.2 mmol) followed by TEA (1.0 mL) was added to the reaction mixture which was stirred at 85° C. for 16 h. The reaction mixture was quenched with ice cold water and extracted with EtOAc. The organic layer was dried over sodium sulfate and concentrated. The crude product was purified using flash chromatography to give benzyl nonyl (3-(hexylamino)-3-oxopropane-1,2-diyl)(S)-dicarbamate (0.4 g, 34%). LCMS (Method H): 87.9% (RT: 4.357, 202.0 nm) (MS: ESI +ve 492.4 [M+H]).

Step-3: Preparation of nonyl (S)-(3-amino-1-(hexylamino)-1-oxopropan-2-yl)carbamate

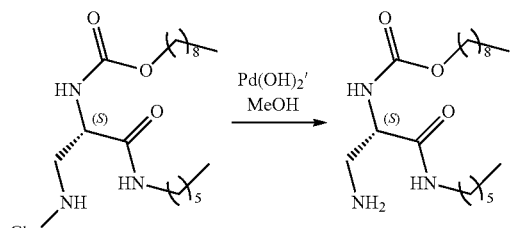

Benzyl nonyl (3-(hexylamino)-3-oxopropane-1,2-diyl)(S)-dicarbamate (0.400 g, 0.813 mmol) and Pd(OH)₂ (0.400 g, 45% wt %) were suspended in MDC:MeOH (1:2, 30 ml) and stirred under hydrogen at room temperature for 16 h. The reaction mixture was filtered through celite, washed with MeOH and the filtrate was concentrated to give nonyl (S)-(3-amino-1-(hexylamino)-1-oxopropan-2-yl)carbamate (0.289 g, 89.6%). MS: ESI +ve 358.07 [M+H].

Step-4: Preparation of nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate, Compound 229

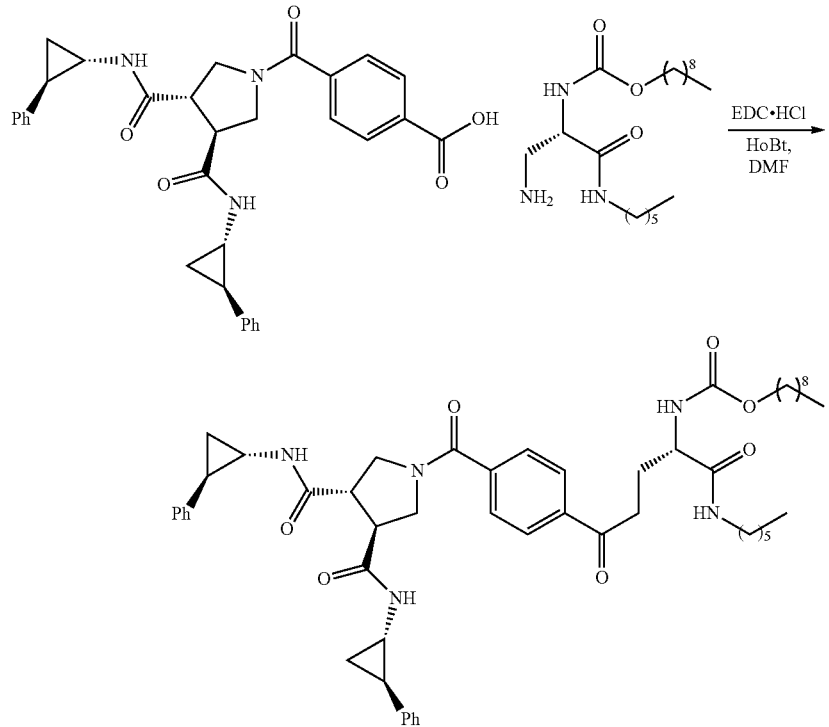

Prepared using General EDC, HOBT Procedure. The crude was purified using Prep HPLC Method 1 to give nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 229) (0.069 g, 33.340%). LCMS (Method H) 99.19% (RT: 4.158, 202.0 nm) (MS: ESI +ve 877.6[M+H]). $^1$H NMR (400 MHz, DMSO) (71749) δ ppm: 0.826 (m, 6H), 1.24 (m, 18H), 1.34 (s, 2H), 1.50 (s, 2H), 1.85 (s, 1H), 1.98 (s, 1H), 2.78 (s, 1H), 2.86 (s, 1H), 2.98 (s, 4H), 3.17 (m, 1H), 3.46 (m, 4H), 3.63 (t, 1H), 3.82 (t, 1H), 3.9 (m, 2H), 4.19 (s, 1H), 7.19 (m, 10H), 7.60 (d, J=8 Hz, 2H), 7.87 (t, 3H), 8.31 (1H, J=4 Hz, d), 8.46 (br, 2H), 8.54 (s, 1H).

Synthesis of octyl ((S)-3-(4-((3S,4S)-3,4-bis(((1S,2R)-2-phenylcyclopropyl) carbamoyl)pyrrolidine-1-carbonyl)benzamido)-1-(hexylamino)-1-oxopropan-2-yl)carbamate, Compound 228

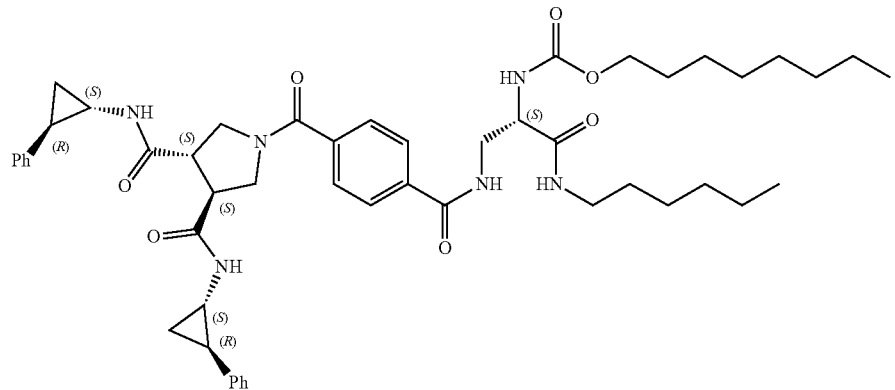

Prepared by a procedure similar to that reported for nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 229), substituting the applicable starting materials. The crude product was purified using Prep HPLC Method 12 to give octyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 228)(0.110 g, 34.2%), as a white solid. LCMS (Method-C-fast): 95.7 (RT: 2.034, 202.0 nm) (MS: ESI +ve 864.7 [M+1]). ¹H NMR: (400 MHz, DMSO) δ ppm: 0.796-0.864 (m, 6H), 1.076-1.111 (m, 3H), 1.128-1.229 (m, 17H), 1.336 (m, 2H), 1.503 (s, 2H), 1.841 (s, 1H), 1.968 (s, 1H), 2.603 (s, 1H), 2.677 (s, 1H), 2.991-3.090 (m, 4H), 3.111-3.229 (m, 2H), 3.458-3.536 (m, 4H), 3.602-3.622 (m, 1H), 3.785-3.835 (m, 2H), 3.895-3.927 (t, J=12.8 Hz, 2H), 4.164-4.181 (d, J=6.8 Hz, 1H), 7.055-7.073 (d, 2H), 7.116-7.184 (m, 4H), 7.220-7.288 (m, 4H), 7.581-7.601 (d, 2H), 7.841-7.909 (m, 4H), 8.298-8.308 (d, J=4 Hz, 1H), 8.445-8.455 (d, J=4 Hz, 1H), 8.537 (s, 1H).

Prepared by a procedure similar to that reported for nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 229), substituting the applicable starting materials. The crude product was purified using Prep HPLC Method 12 to give heptyl ((S)-3-(4-((3S,4S)-3,4-bis(((1S,2R)-2-phenylcyclopropyl) carbamoyl)pyrrolidine-1-carbonyl)benzamido)-1-(hexylamino)-1-oxopropan-2-yl)carbamate (Compound 227) (0.080 g, 33.34%). LCMS (Method C): 100% (RT: 1.5, 225.0 nm) (MS: ESI +ve 849.6[M−H]). ¹H NMR: (400 MHz, DMSO) (71749) δ ppm: 0.829 (m, 6H), 1.12 (m, 18H), 1.33 (s, 2H), 1.50 (s, 2H), 1.8 (s, 1H), 1.9 (s, 1H), 1.99 (s, 1H), 2.08 (s, 1H), 2.77 (s, 1H), 2.88 (s, 1H), 3.02 (m, 4H), 3.18 (m, 1H), 3.46 (m, 4H), 3.54 (m, 1H), 3.8 (t, 1H), 3.9 (m, 2H), 4.18 (s, 1H), 7.16 (m, 10H), 7.60 (d, J=8 Hz, 2H), 7.863 (t, 3H), 8.29 (1H, J=4 Hz, d), 8.44 (br, 2H).

Synthesis of heptyl ((S)-3-(4-((3S,4S)-3,4-bis(((1S,2R)-2-phenylcyclopropyl) carbamoyl)pyrrolidine-1-carbonyl)benzamido)-1-(hexylamino)-1-oxopropan-2-yl)carbamate, Compound 227

Synthesis of hexyl ((S)-3-(4-((3S,4S)-3,4-bis(((1S,2R)-2-phenylcyclopropyl) carbamoyl)pyrrolidine-1-carbonyl)benzamido)-1-(hexylamino)-1-oxopropan-2-yl)carbamate, Compound 226

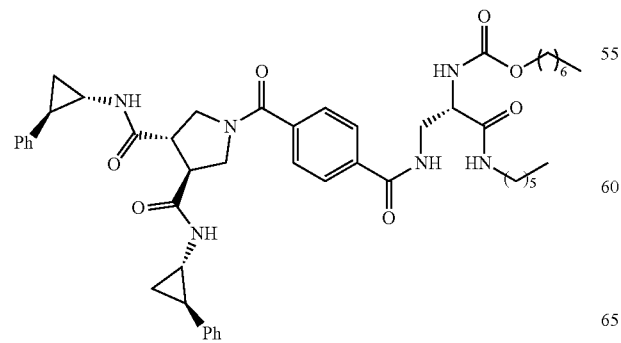

Prepared by a procedure similar to that reported for nonyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 229), substituting the applicable starting materials. The crude product was purified using Prep HPLC Method 10 to give hexyl ((S)-3-(4-((3S,4S)-3,4-bis(((1S,2R)-2-phenylcyclopropyl)carbamoyl)pyrrolidine-1-carbonyl)benzamido)-1-(hexylamino)-1-oxopropan-2-yl)carbamate (Compound 226) (0.124 g, 40% yield), as a white solid. LCMS (Method-C-fast): 100% (RT: 1.819, 202.0 nm) (MS: ESI +ve 836.4 [M+1]). $^1$H NMR: (400 MHz, DMSO) δ ppm: 0.799-0.859 (m, 6H), 1.077-1.341 (m, 17H), 1.504 (s, 3H), 1.844 (s, 2H), 1.971 (s, 2H), 3.012 (s, 3H), 3.044-3.209 (m, 4H), 3.458-3.505 (m, 3H), 3.483-3.539 (m, 2H), 3.788-3.839 (m, 2H), 3.898-3.931 (t, J=13.2 Hz, 2H), 4.171 (m, 2H), 7.056-7.075 (m, 3H), 7.117-7.165 (m, 4H), 7.221-7.288 (m, 4H), 7.580-7.600 (d, 2H), 7.842-7.898 (m, 3H), 8.288-8.298 (d, J=4 Hz, 1H), 8.432-8.443 (d, J=4.4 Hz, 1H), 8.496-8.526 (m, 2H).

Synthesis of (3S,4S)-1-(4-(((((S)-3,17-dioxo-1,4-diazacycloheptadecan-2-yl)methyl)carbamoyl)benzoyl)-N3,N4-bis((1S,2R)-2-phenylcyclopropyl)pyrrolidine-3,4-dicarboxamide, Compound 225

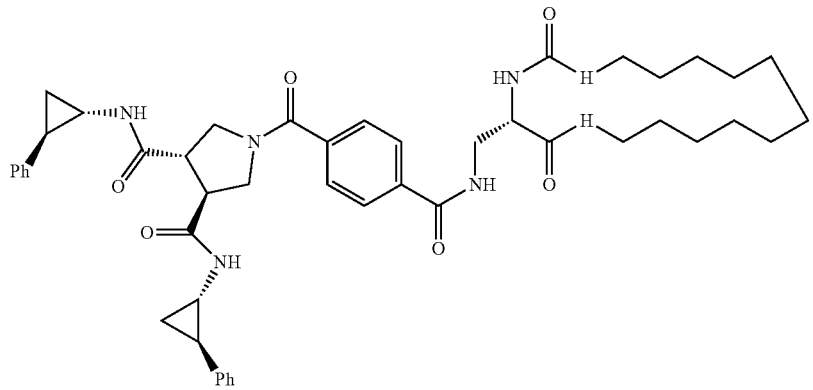

Step-1: Preparation of methyl (S)-3-((tert-butoxycarbonyl)amino)-2-(undec-10-enamido)propanoate

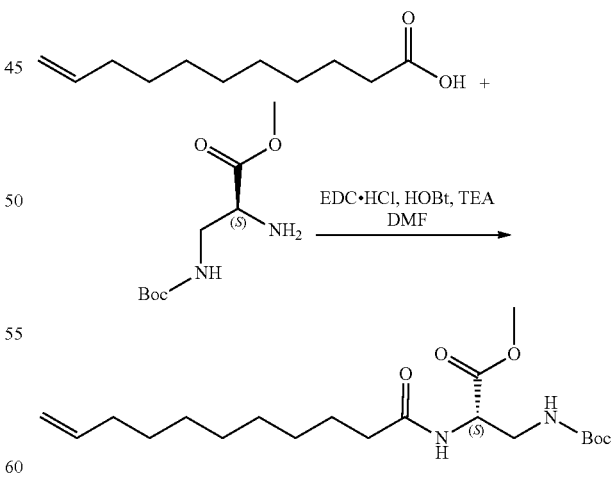

Prepared using a procedure similar to General EDC, HOBT Coupling Procedure. The crude product was purified using flash chromatography, eluting with 5-10% MeOH:DCM to give methyl (S)-3-((tert-butoxycarbonyl)amino)-2-(undec-10-enamido)propanoate (3.5 g, 83.87%). LC-MS (Method-C2): 95.17% (RT 1.496, 202.0 nm) (MS: ESI +ve 385.1 [M+1]).

Step 2: Preparation of (S)-3-((tert-butoxycarbonyl)amino)-2-(undec-10-enamido)propanoic acid

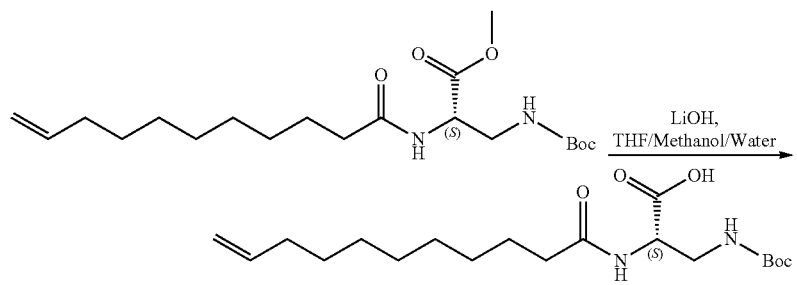

Prepared using General Ester Hydrolysis Procedure to give (S)-3-((tert-butoxycarbonyl)amino)-2-(undec-10-enamido)propanoic acid as a white solid (3 g, 88%). LCMS (Method-C2): 94.21% (RT: 1.418, 202.0 nm) (MS: ESI +ve 371.4[M+1]).

Step-3: Preparation of tert-butyl (S)-(3-(but-3-en-1-ylamino)-3-oxo-2-(undec-10-enamido)propyl)carbamate

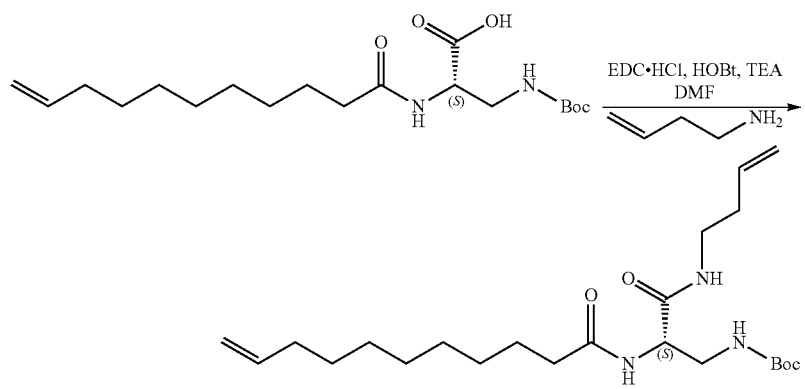

Prepared using a procedure similar to General EDC, HOBT Coupling Procedure. The crude product was purified using flash chromatography, eluting with 5-10% MeOH: DCM to give tert-butyl (S)-(3-(but-3-en-1-ylamino)-3-oxo-2-(undec-10-enamido)propyl)carbamate (0.900 g, 78.72%). LC-MS (Method-C2): 81.94% (RT 1.463, 202.0 nm) (MS: ESI +ve 424.7 [M+1])

Step-4: Preparation of tert-butyl (S,Z)-((3,17-dioxo-1,4-diazacycloheptadec-9-en-2-yl)methyl)carbamate

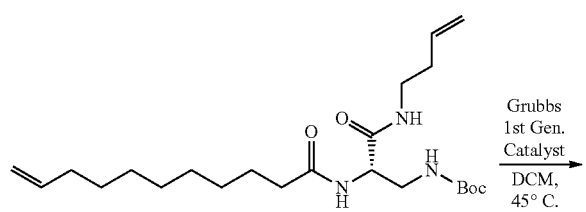

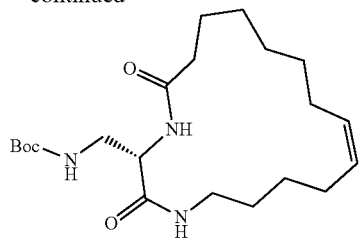

-continued

A mixture of tert-butyl (S)-(3-(but-3-en-1-ylamino)-3-oxo-2-(undec-10-enamido)propyl)carbamate (0.800 g, 1.76 mmol) and Grubbs 1rst Generation Catalyst (benzylidenebis(tricyclohexylphosphino)-dichlororuthenium) (0.160 g) was stirred at 45° C. for 20 h. The volatiles were removed to give tert-butyl (S,Z)-((3,17-dioxo-1,4-diazacycloheptadec-9-en-2-yl)methyl)carbamate (0.125 g, 98.53%). LC-MS (Method-C2): 75.87% (RT 1.33, 202.0 nm) (MS: ESI +ve 396.6[M+1]).

301

Step-5: Preparation of tert-butyl (S)-((3,17-dioxo-1,4-diazacycloheptadecan-2-yl)methyl)carbamate

302

Step 6: Preparation of (S)-3-(aminomethyl)-1,4-diazacycloheptadecane-2,5-dione

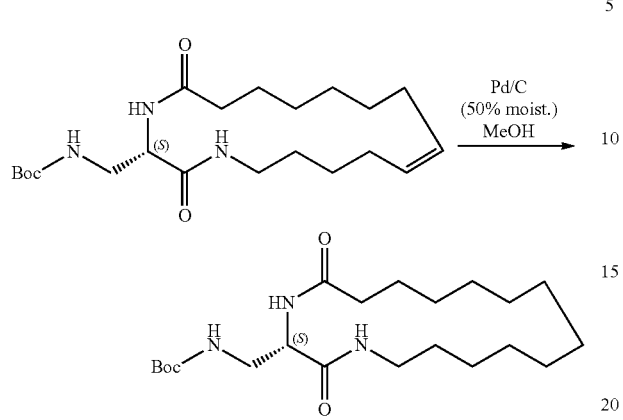

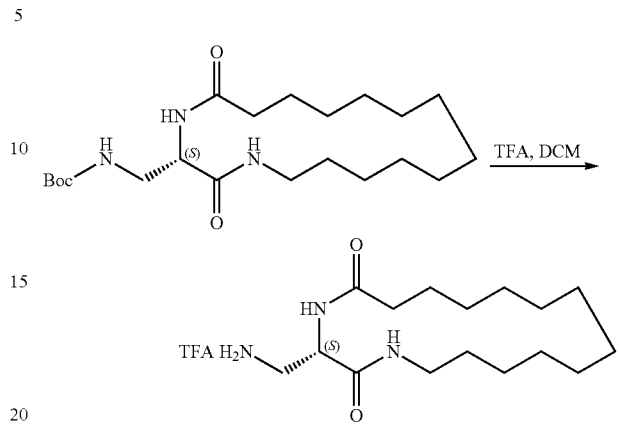

A mixture of tert-butyl (S,Z)-((3,17-dioxo-1,4-diazacycloheptadec-9-en-2-yl)methyl)carbamate (0.125 g, 0.31 mmol) and palladium on carbon (50% moisture) (0.125 g) in MeOH (30 mL) was hydrogenated under balloon pressure for 6-7 h. The mixture was filtered through celite and the filtrate was concentrated to give tert-butyl (S)-((3,17-dioxo-1,4-diazacycloheptadecan-2-yl)methyl)carbamate (0.085 g, 67.66%) LC-MS (Method-J): 75.55% (RT 4.198, 202.0 nm) (MS: ESI +ve 398.2[M+1]).

Prepared using General BOC Deprotection Procedure to give the TFA salt of (S)-3-(aminomethyl)-1,4-diazacycloheptadecane-2,5-dione (0.100 g, 78.28%). LC-MS (Method-C2): 79.64% (RT 1.115, 202.0 nm) (MS: ESI +ve 298.2[M+1]).

Step 7: Preparation (3S,4S)-1-(4-((((S)-3,17-dioxo-1,4-diazacycloheptadecan-2-yl)methyl)carbamoyl)benzoyl)-N3,N4-bis((1S,2R)-2-phenylcyclopropyl)pyrrolidine-3,4-dicarboxamide, Compound 225

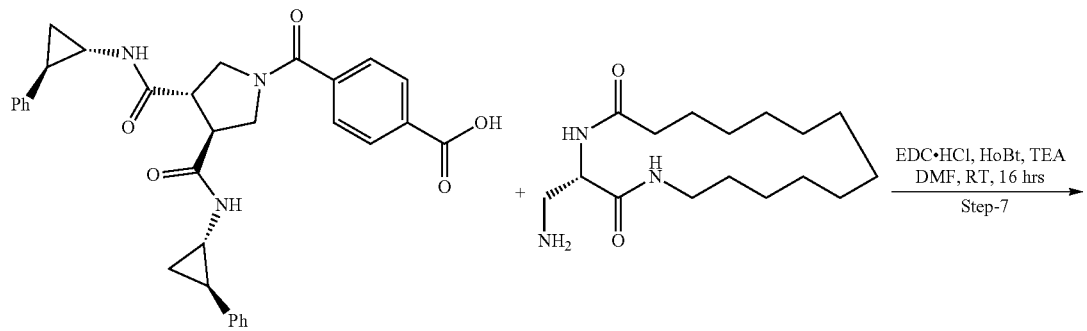

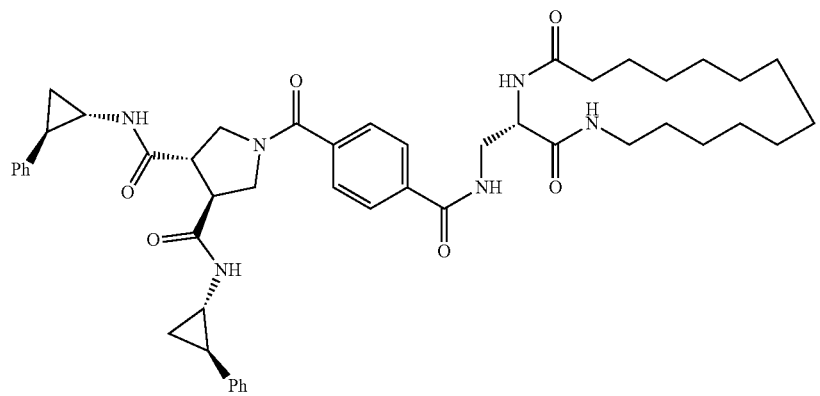

Prepared using a procedure similar to General EDC, HOBT Coupling Procedure. The crude product was purified using Prep HPLC Method 10 to give (3S,4S)-1-(4-((((S)-3,17-dioxo-1,4-diazacycloheptadecan-2-yl)methyl)carbamoyl)benzoyl)-N3,N4-bis((1S,2R)-2-phenylcyclopropyl)pyrrolidine-3,4-dicarboxamide (Compound 225)(0.024 g, 12.50%). LCMS (Method-J): 99.32% (RT 4.318, 254.0 nm) (MS: ESI +ve 817.4 [M+1]. 1H NMR: (400 MHz, DMSO) δ ppm: 1.83-1.10 (t, J=4 Hz, 2H), 1.12-1.39 (m, 16H), 1.39 (s, 3H), 1.64 (s, 1H), 1.85 (s, 1H), 1.97-2.07 (m, 2H), 2.19-2.21 (m, 1H), 2.78-2.86 (m, 2H), 3.09-3.21 (m, 2H), 3.43-3.53 (m, 4H), 3.61-3.65 (t, J=2.4 Hz, 1H), 3.78-3.80 (m, 1H), 4.48-4.49 (m, 1H), 7.06-7.28 (m, 10H), 7.58-7.60 (d, J=8 Hz, 2H), 7.83-7.85 (d, J=8.4 Hz, 3H), 7.98-8.00 (d, J=8.4 Hz, 1H), 8.30-8.31 (d, J=3.6 Hz, 1H), 8.45-8.46 (d, J=4 Hz, 1H), 8.59 (s, 1H).

Synthesis of (3S,4S)-1-(4-(((R)-1,5-bis(hexylamino)-1,5-dioxopentan-2-yl)carbamoyl) benzoyl)-N3,N4-bis((1S,2R)-2-phenylcyclopropyl)pyrrolidine-3,4-dicarboxamide, Compound 099

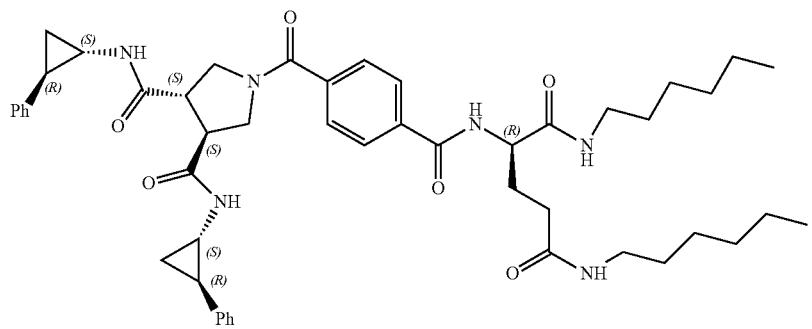

Step-1: Preparation of methyl N2-(tert-butoxycarbonyl)-N5-hexyl-D-glutaminate

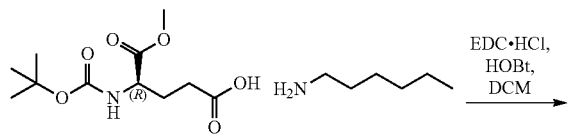

Prepared using a procedure similar to General EDC, HOBT Coupling Procedure. The crude product was purified using flash chromatography, eluting with 0-5% DCM in MeOH. (0.455 g, 69% yield). LCMS (Method-C3): 79.7% (RT: 1.308, 202.0 nm) (MS: ESI +ve 345.4 [M+1]).

Step-2: Preparation of N2-(tert-butoxycarbonyl)-N5-hexyl-D-glutamine

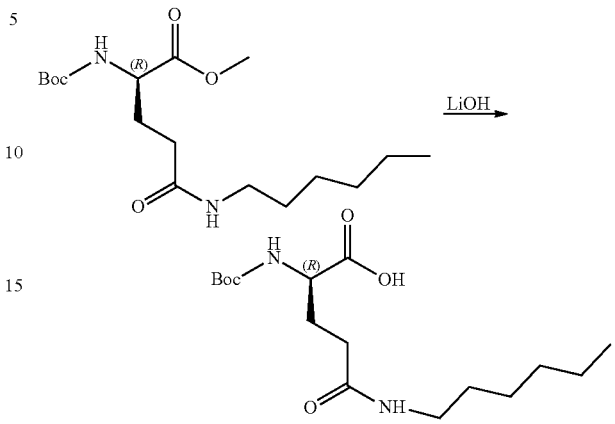

Prepared using a procedure similar to General Ester Hydrolysis Procedure to give N2-(tert-butoxycarbonyl)-N5-hexyl-D-glutamine (0.38 g, 88.5% yield). LCMS (Method-C3): 70.1% (RT: 1.661, 202.0 nm) (MS: ESI +ve 331.7 [M+1]).

Step-3: Preparation of tert-butyl (R)-(1,5-bis(hexylamino)-1,5-dioxopentan-2-yl)carbamate

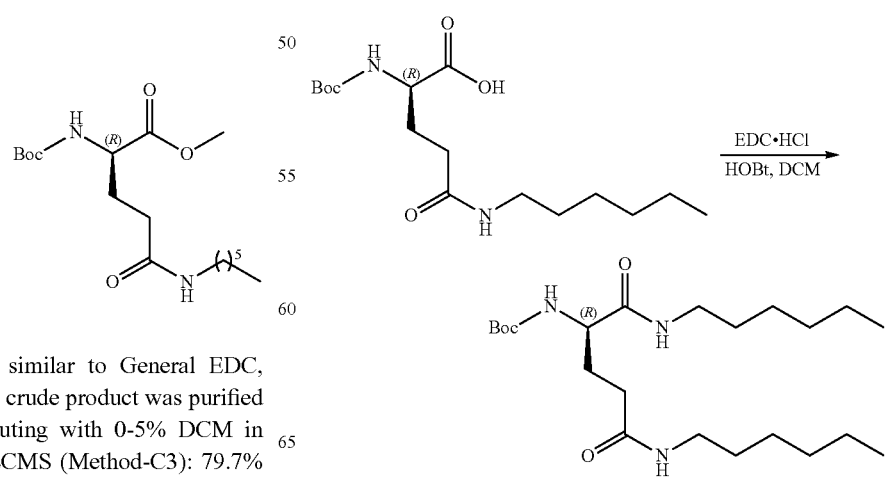

Prepared using a procedure similar to General EDC, HOBT Coupling Procedure to give (tert-butyl (R)-(1,5-bis(hexylamino)-1,5-dioxopentan-2-yl)carbamate (0.385 g, 79.7%). LCMS (Method-C3): 100% (RT: 1.394, 210.0 nm) (MS: ESI +ve 414.0 [M+1]).

Step-4: Preparation of (R)-2-amino-N1,N5-dihexylpentanediamide

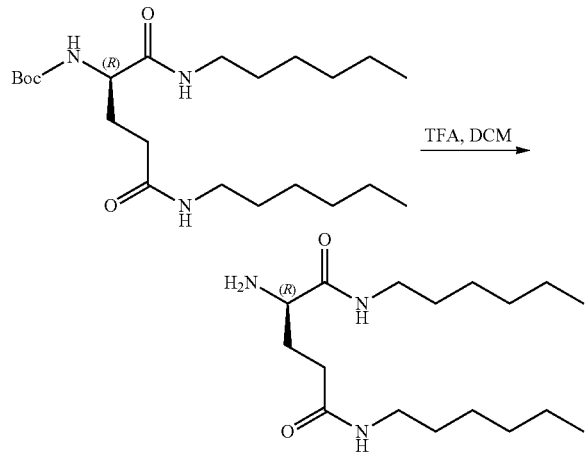

Prepared using a procedure similar to General BOC Deprotection Procedure to give (R)-2-amino-N1,N5-dihexylpentanediamide (0.52 g crude). LCMS (Method-C3): 91.6% (RT: 1.160, 202 nm) (MS: ESI +ve 314.0[M+1]).

Step-5: Preparation of (3S,4S)-1-(4-(((R)-1,5-bis(hexylamino)-1,5-dioxopentan-2-yl)carbamoyl)benzoyl)-N3,N4-bis((1S,2R)-2-phenylcyclopropyl)pyrrolidine-3,4-dicarboxamide, Compound 099

Prepared using a procedure similar to General EDC, HOBT Coupling Procedure. The crude product was purified using Prep HPLC Method 12 to give (3S,4S)-1-(4-(((R)-1,5-bis(hexylamino)-1,5-dioxopentan-2-yl)carbamoyl)benzoyl)-N3,N4-bis((1S,2R)-2-phenylcyclopropyl)pyrrolidine-3,4-dicarboxamide (Compound 099)(0.0.38 g, 16.3% yield), as a white solid. LCMS (Method-C3): 100% (RT: 1.955, 222.0 nm) (MS: ESI +ve 834.4 [M+1]). $^1$H NMR: (400 MHz, DMSO) δ ppm: 0.843 (m, 6H), 1.108 (s, 2H), 1.211-1.235 (m, 13H), 1.385 (m, 4H), 1.846 (s, 2H), 1.973 (s, 2H), 2.334 (m, 2H), 2.676 (s, 2H), 2.988-3.050 (m, 4H), 3.099-3.120 (m, 1H), 3.191-3.211 (m, 2H), 3.490-3.539 (m, 2H), 3.618 (m, 1H), 3.790-3.818 (m, 1H), 4.349 (s, 1H), 7.057-7.076 (m, 2H), 7.118-7.219 (m, 4H), 7.237-7.270 (m, 4H), 7.590-7.610 (d, J=8 Hz, 2H), 7.807 (s, 1H), 7.922-7.958 (m, 3H), 8.336 (s, 1H), 8.472 (s, 1H), 8.598-8.617 (d, J=7.6 Hz, 1H).

Synthesis of (3S,4S)-1-(4-(((R)-1,4-bis(hexylamino)-1,4-dioxobutan-2-yl) carbamoyl) benzoyl)-N3,N4-bis((1S,2R)-2-phenylcyclopropyl) pyrrolidine-3,4-dicarboxamide, Compound 117

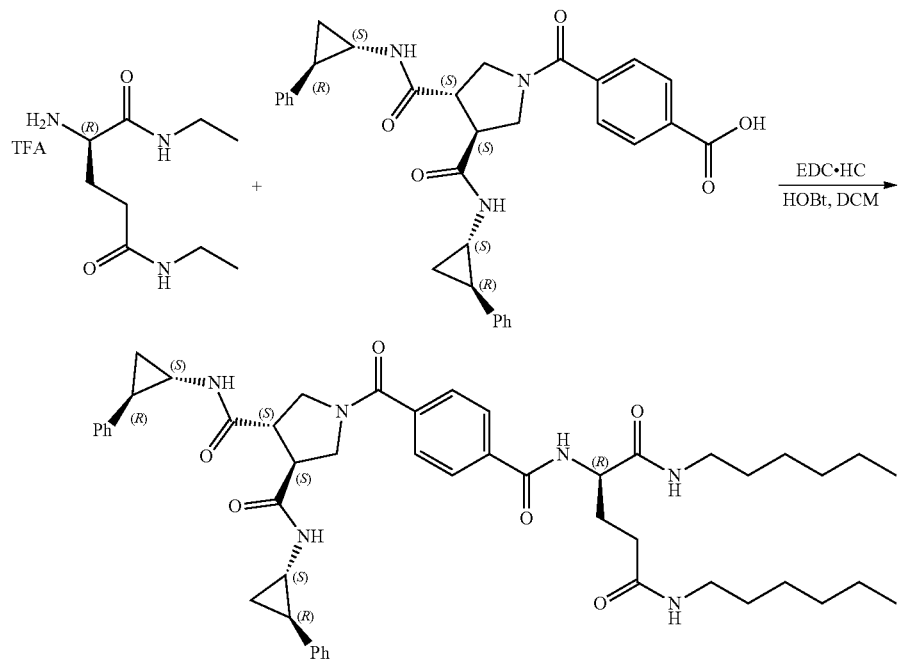

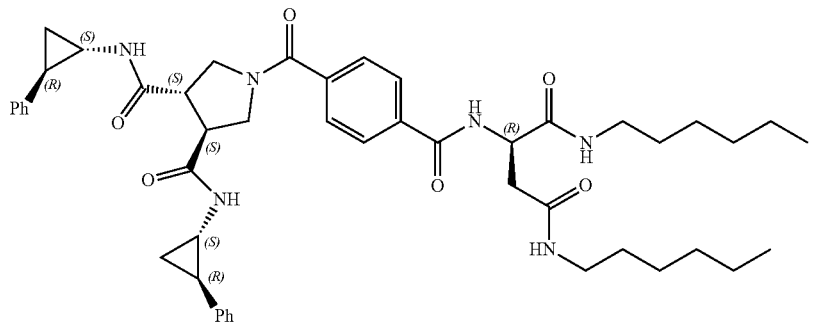

Prepared by a procedure similar to that reported for (3S,4S)-1-(4-(((R)-1,5-bis(hexylamino)-1,5-dioxopentan-2-yl)carbamoyl)benzoyl)-N3,N4-bis((1S,2R)-2-phenylcyclopropyl)pyrrolidine-3,4-dicarboxamide (Compound 099), substituting the applicable starting materials. The crude final product was purified using Prep HPLC Method 10 to give (3S,4S)-1-(4-(((R)-1,4-bis(hexylamino)-1,4-dioxobutan-2-yl) carbamoyl) benzoyl)-N3,N4-bis((1S,2R)-2-phenylcyclopropyl) pyrrolidine-3,4-dicarboxamide (Compound 117) (0.007 g, 3.06%). LCMS (Method-J): 100% (RT 5.381, 202.0 nm) (MS: ESI +ve 820 [M+H]). $^1$H NMR: (400 MHz, DMSO) δ ppm: 0.79-0.86 (m, 7H); 1.13-1.22 (m, 16H); 1.31-1.37 (m, 4H); 1.85 (s, 2H); 1.98 (s, 2H); 2.77 (s, 1H); 2.85 (s, 2H); 2.99 (s, 4H); 3.03-3.10 (m, 1H); 3.12-3.22 (m, 2H); 3.46-3.54 (m, 3H); 3.62 (s, 2H); 3.82 (s, 2H); 7.06-7.12 (m, 2H); 7.14-7.19 (m, 4H); 7.24-7.29 (m, 4H); 7.60-7.62 (d, J=8.4, 2H); 7.87-7.93 (m, 4H); 8.33-8.34 (d, J=4, 1H); 8.48-8.49 (d, J=4.4, 2H); 8.67-8.69 (d, J=8, 1H).

Synthesis of (3S,4S)-1-(4-(((R)-3-heptanamido-1-(hexylamino)-1-oxopropan-2-yl) carbamoyl) benzoyl)-N3,N4-bis((1S,2R)-2-phenylcyclopropyl) pyrrolidine-3,4-dicarboxamide, Compound 118

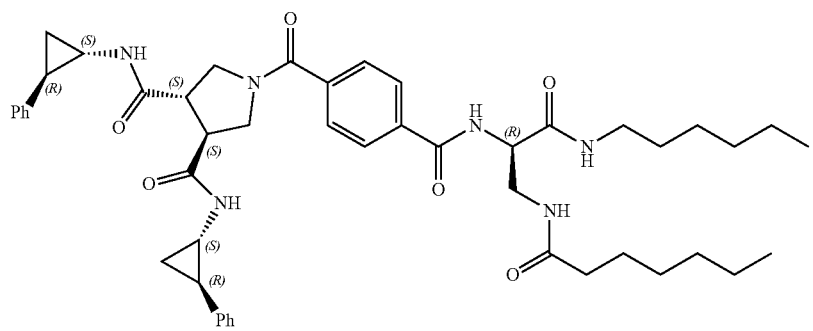

Step 1: Preparation of benzyl tert-butyl (3-(hexylamino)-3-oxopropane-1,2-diyl) (R)-dicarbamate

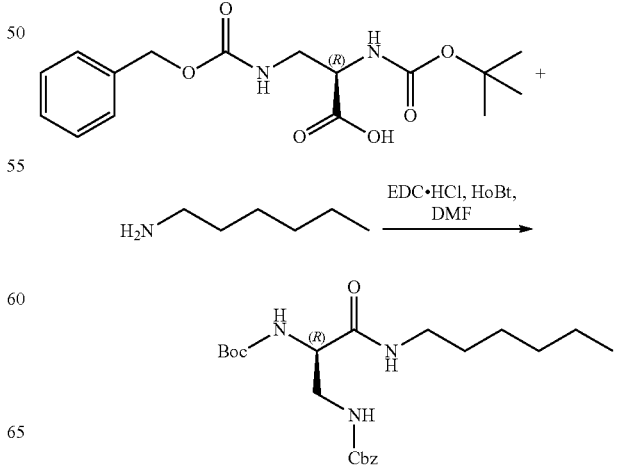

Prepared using a procedure similar to General EDC, HOBT Coupling Procedure to give crude benzyl tert-butyl (3-(hexylamino)-3-oxopropane-1,2-diyl) (R)-dicarbamate (1.2 g, 96.3%). LCMS (Method-C2): 100% (RT: 1.381, 202.0 nm) (MS: ESI +ve 422.0 [M+H]).

Step-2: Preparation of tert-butyl (R)-(3-amino-1-(hexylamino)-1-oxopropan-2-yl) carbamate

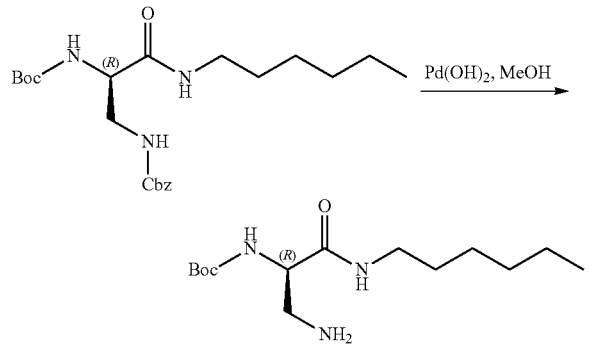

Tert-butyl (3-(hexylamino)-3-oxopropane-1,2-diyl) (R)-dicarbamate (1.2 g, 2.85 mmol) was dissolved in MeOH:DCM (2:1, 30 mL). Palladium hydroxide (1.2 g) was added and the reaction was hydrogenated at room temperature for 4 hrs. The reaction mixture was filtered through a pad of celite and concentrated to yield tert-butyl (R)-(3-amino-1-(hexylamino)-1-oxopropan-2-yl) carbamate as a yellow oil (0.7 g, 85.5%). LCMS (Method-C2): 94.08% (RT: 1.421, 202.0 nm) (MS: ESI +ve 288.0 [M+H]).

Step-3: Preparation of tert-butyl (R)-(3-heptanamido-1-(hexylamino)-1-oxopropan-2-yl) carbamate

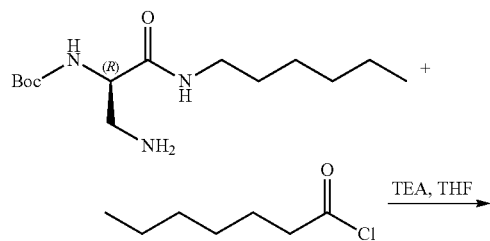

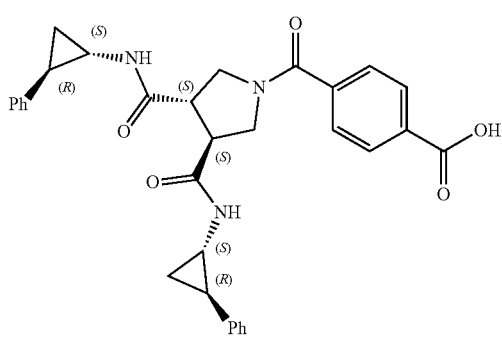

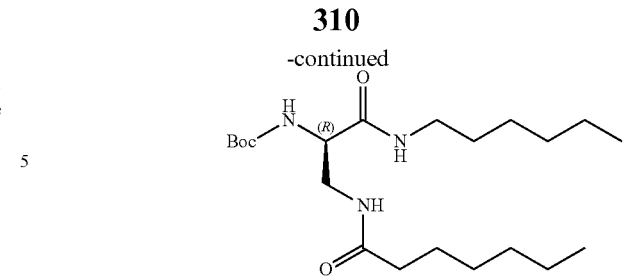

To a stirred solution of heptanoyl chloride (0.22 g, 1.67 mmol) in tetrahydrofuran (10 mL) was added tert-butyl (R)-(3-amino-1-(hexylamino)-1-oxopropan-2-yl) carbamate (0.46 g, 1.3 mmol) at 0° C. followed by TEA. The reaction mixture was stirred at room temperature for 16 hrs and diluted with ice-cold water (25 mL). The resulting precipitate was collected by filtration, and dried under vacuum to give crude tert-butyl (R)-(3-heptanamido-1-(hexylamino)-1-oxopropan-2-yl) carbamate as an off white solid (0.55 g, 86.7%). LCMS (Method-C2): 92.62% (RT: 1.466, 202.0 nm) (MS: ESI +ve 400 [M+H]).

Step-4: Preparation of (R)—N-(2-amino-3-(hexylamino)-3-oxopropyl) heptanamide TFA Salt

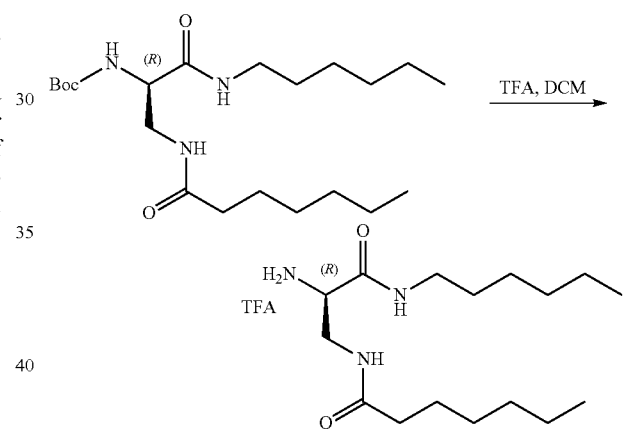

Prepared using a procedure similar to General BOC Deprotection Procedure to give crude (R)—N-(2-amino-3-(hexylamino)-3-oxopropyl) heptanamide TFA Salt (0.67 g). LCMS (Method-H): 88.17% (RT 3.092, 202.0 nm) (MS: ESI +ve 300 [M+H]).

Step-5: Preparation of (3S,4S)-1-(4-(((R)-3-heptanamido-1-(hexylamino)-1-oxopropan-2-yl) carbamoyl) benzoyl)-N3,N4-bis((1S,2R)-2-phenylcyclopropyl) pyrrolidine-3,4-dicarboxamide, Compound 118

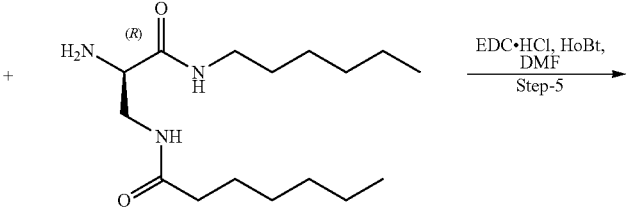

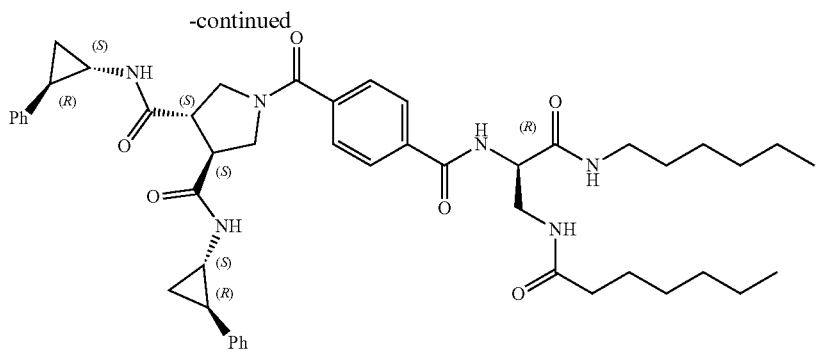

Prepared using a procedure similar to General EDC, HOBT Coupling Procedure. The crude final product was purified using Prep HPLC Method 1 to give (3S,4S)-1-(4-(((R)-3-heptanamido-1-(hexylamino)-1-oxopropan-2-yl)carbamoyl) benzoyl)-N3,N4-bis((1S,2R)-2-phenylcyclopropyl) pyrrolidine-3,4-dicarboxamide (Compound 118) (0.045 g, 14.77%). LCMS (Method-J): 100% (RT 5.347, 202.0 nm) (MS: ESI +ve 820 [M+H]). $^1$H NMR: (400 MHz, DMSO) δ ppm: 0.77-0.86 (m, 7H); 1.09-1.23 (m, 18H); 1.38-1.44 (m, 5H); 1.83-1.84 (d, J=5.6, 2H); 1.95-1.98 (m, 2H); 2.00-2.07 (m, 2H); 2.77-2.85 (m, 1H); 2.85-2.87 (m, 1H); 3.02-3.07 (m, 3H); 3.11-3.18 (m, 1H); 3.43-3.47 (m, 5H); 3.47-3.54 (m, 2H); 3.62-3.83 (m, 1H); 4.46-4.45 (d, J=5.2, 2H); 7.06-7.08 (d, J=7.2, 2H); 7.12-7.19 (m, 4H); 7.24-7.29 (m, 4H); 7.63-7.61 (d, J=8.4, 2H); 7.93-7.91 (d, J=8.4, 3H); 8.06 (s, 1H); 8.34 (s, 1H); 8.48-8.51 (m, 1H); 8.58-8.60 (d, J=8, 1H).

Synthesis of (3S,4S)-1-(4-(((R)-4-heptanamido-1-(hexylamino)-1-oxobutan-2-yl) carbamoyl)benzoyl)-N3,N4-bis((1S,2R)-2-phenylcyclopropyl)pyrrolidine-3,4-dicarboxamide, Compound 119

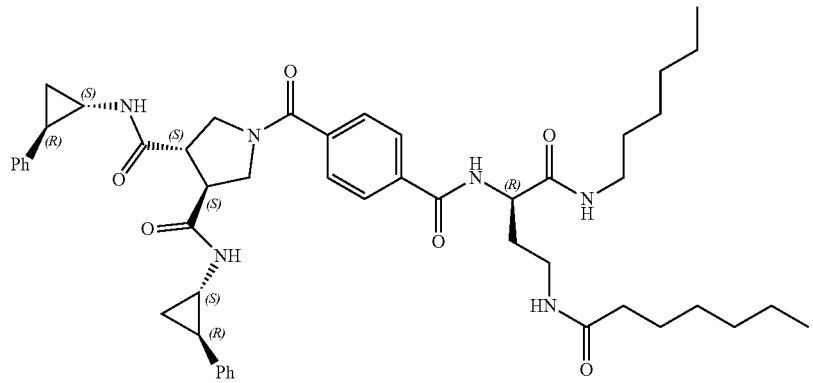

Prepared by a procedure similar to that reported for (3S,4S)-1-(4-(((R)-3-heptanamido-1-(hexylamino)-1-oxopropan-2-yl) carbamoyl) benzoyl)-N3,N4-bis((1S,2R)-2-phenylcyclopropyl) pyrrolidine-3,4-dicarboxamide (Compound 118), substituting the applicable starting materials. The crude final product was purified using flash chromatography, eluting with 0-5% MeOH in DCM to give (3S,4S)-1-(4-(((R)-4-heptanamido-1-(hexylamino)-1-oxobutan-2-yl)carbamoyl)benzoyl)-N3,N4-bis((1S,2R)-2-phenylcyclopropyl)pyrrolidine-3,4-dicarboxamide (Compound 119), as a white solid (0.075 g, 48%). LCMS (Method-J): 99.19% (RT: 5.338, 254.0 nm) (MS: ESI +ve 833.5[M+H]. 1H NMR: (400 MHz, DMSO) δ ppm: 0.83-0.86 (m, 6H), 1.09-1.11 (m, 2H), 1.15-1.24 (m, 13H), 1.38-1.47 (m, 4H), 1.79-1.85 (m, 3H), 1.87-1.95 (m, 1H), 1.98-2.34 (m, 2H), 2.68-1.78 (m, 1H), 2.84-2.87 (m, 1H), 3.03-3.2 (m, 5H), 3.13-3.22 (m, 1H), 3.35-3.52 (m, 2H), 3.54-3.62 (m, 1H), 3.80-3.83 (m, 1H), 4.39 (m, 1H), 7.06-7.08 (m, 2H), 7.12-7.22 (m, 4H), 7.24-7.29 (m, 4H), 7.60-7.62 (d, J=8.4 Hz, 2H), 7.77-7.80 (m, 1H), 7.93-7.97 (m, 3H), 8.30-8.31 (d, J=4.0 Hz, 1H), 8.45-8.46 (d, J=4.0 Hz, 1H), 8.57-8.59 (m, 1H).

Synthesis of (3S,4S)-1-(4-(((S)-3-methoxy-2-(3-tridecylureido) propyl) carbamoyl)benzoyl)-N3,N4-bis((1S,2R)-2-phenylcyclopropyl)pyrrolidine-3,4-dicarboxamide, Compound 198

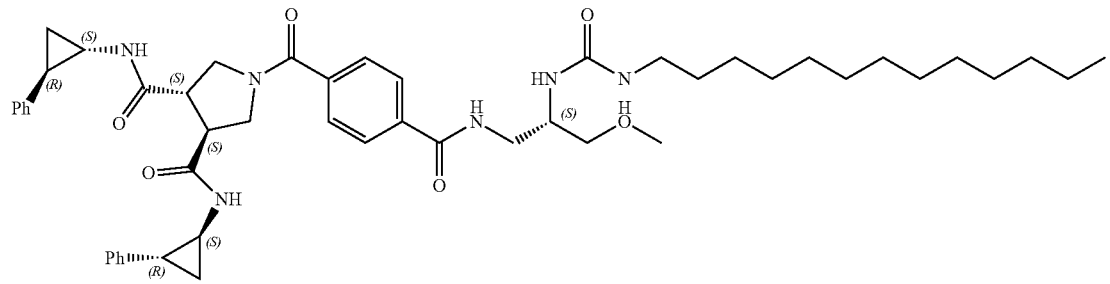

Step-1: Preparation of benzyl tert-butyl (3-methoxypropane-1,2-diyl)(S)-dicarbamate

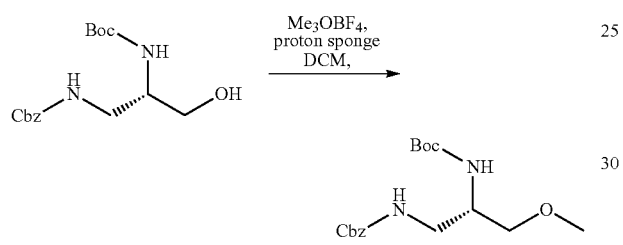

Benzyl tert-butyl (3-hydroxypropane-1,2-diyl)(S)-dicarbamate (0.5 g, 1.54 mmol) was dissolved in dry DCM (15 mL). Proton sponge (0.802 g) was added followed by triethyl oxonium tetrafluoro borate (0.555 g) after 5 min. The reaction mixture was stirred at room temperature for 72 h then extracted in CHCl₃ (2×50 mL) and washed with sat. aq sodium carbonate (50 mL). The organic layer was dried, concentrated and purified using flash chromatography on basic alumina, eluting with 20% EtOAc in hexane, to give benzyl tert-butyl (3-methoxypropane-1,2-diyl)(S)-dicarbamate (0.45 g, 86.27%). LCMS (Method-H): 59.90% (RT 3.096, 202.4 nm) (MS: ESI +ve 239.0 [M−100].

Step-2: Preparation of benzyl (S)-(2-amino-3-methoxypropyl)carbamate

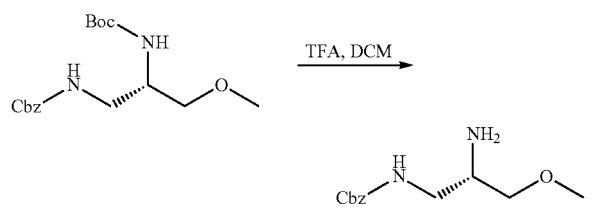

Prepared using General BOC Deprotection Procedure to give benzyl (S)-(2-amino-3-methoxypropyl)carbamate as the TFA salt, as a brown gum (0.39 g, Crude). Mass: (MS: ESI +ve 239.51 [M+1]).

Step-3: Preparation of benzyl (S)-(3-(hexylamino)-2-(3-hexylureido)-3-oxopropyl) carbamate

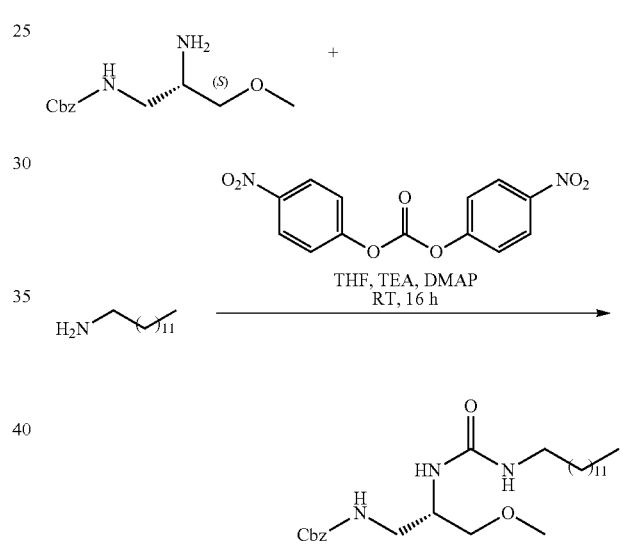

To a stirred solution of bis(4-nitrophenyl) carbonate (0.4974 g, 1635 mmol) in THF (15 mL) at room temperature was added TEA (0.68 mL, 4.905 mmol), DMAP (0.020 g, 0.215 mmol) and tridecan-1-amine (0.325 g, 1.635 mmol). The mixture was stirred for 3 hrs, benzyl (S)-(2-amino-3-methoxypropyl)carbamate (0.39 g, 1.635 mmol) was added, and the mixture was stirred at room temperature for 16 h. The reaction mixture was concentrated under vacuum then diluted with water (50 mL) and extracted using ethyl acetate (3×50 mL). The organic layer was dried over sodium sulfate and concentrated. The crude product was purified using flash chromatography on basic alumina, eluting with 0-2% MeOH: DCM, to give benzyl (S)-(3-methoxy-2-(3-tridecylureido)propyl)carbamate as a white solid (0.34 g, 54%). LCMS (Method-H): 84.79% (RT: 4.549, 202.0 nm) (MS: ESI +ve 464.4 [M+H]).

Step-4: Preparation of (S)-3-amino-N-hexyl-2-(3-pentylureido)propanamide

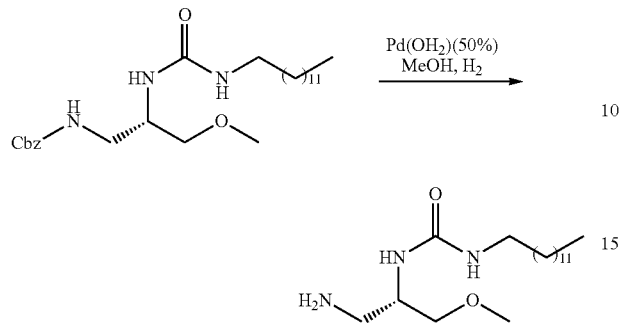

A mixture of benzyl (S)-(3-methoxy-2-(3-tridecylureido)propyl)carbamate (0.34 g, 1.05 mmol) and palladium hydroxide (0.2 g) in MeOH (15 mL) was hydrogenated at room temperature for 2 h. The reaction mixture was filtered through celite and the filtrate was concentrated to yield (S)-1-(1-amino-3-methoxypropan-2-yl)-3-tridecylurea as a brown gum (0.22 g, Crude). LCMS (Method-H): 61.23% (RT: 4.074, 202.4 nm) (MS: ESI +ve 330.0 [M+H]).

Step-5: Preparation of (3S,4S)-1-(4-(((S)-3-methoxy-2-(3-tridecylureido)propyl)carbamoyl)benzoyl)-N3,N4-bis((1S,2R)-2-phenylcyclopropyl)pyrrolidine-3,4-dicarboxamide, Compound 198

Prepared using General EDC, HOBT Coupling Procedure. The crude product was purified using Prep HPLC Method 1 to give (3S,4S)-1-(4-(((S)-3-methoxy-2-(3-tridecylureido)propyl)carbamoyl)benzoyl)-N3,N4-bis((1S,2R)-2-phenylcyclopropyl)pyrrolidine-3,4-dicarboxamide (Compound 198), as an off white solid (0.125 g, 39.76%). LCMS (Method-J2): 99.67% (RT 4.978, 254.0 nm) (MS: ESI +ve 849.6 [M+H]). $^1$H NMR: (400 MHz, DMSO) δ ppm: 0.83-0.86 (m, 3H), 1.08-1.30 (m, 26H), 1.85 (s, 1H), 1.97 (m, 1H), 2.67-2.77 (m, 2H), 2.85-2.96 (m, 2H), 3.08-3.28 (m, 5H), 3.38-3.54 (m, 6H), 3.60-3.64 (m, 1H), 3.78-3.84 (m, 1H), 4.070 (m, 1H), 5.97-5.98 (d, J=4.4 Hz, 2H), 7.05-7.07 (d, J=7.6 Hz, 2H), 7.11-7.18 (m, 4H), 7.22-7.28 (m, 4H), 7.57-7.59 (d, J=8 Hz, 2H), 7.88-7.90 (d, J=8 Hz, 2H), 8.29-8.30 (d, J=4 Hz, 1H), 8.43-8.44 (d, J=7.6 Hz, 1H), 8.52 (s, 1H).

Synthesis of (3S,4S)-1-(4-((3S,4S)-3,4-bis(((1S*,2R*)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide, Compound 094

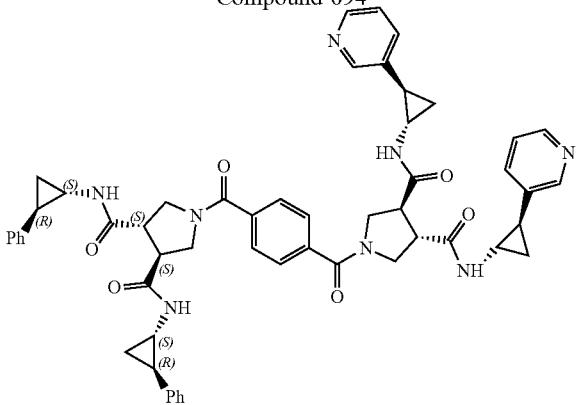

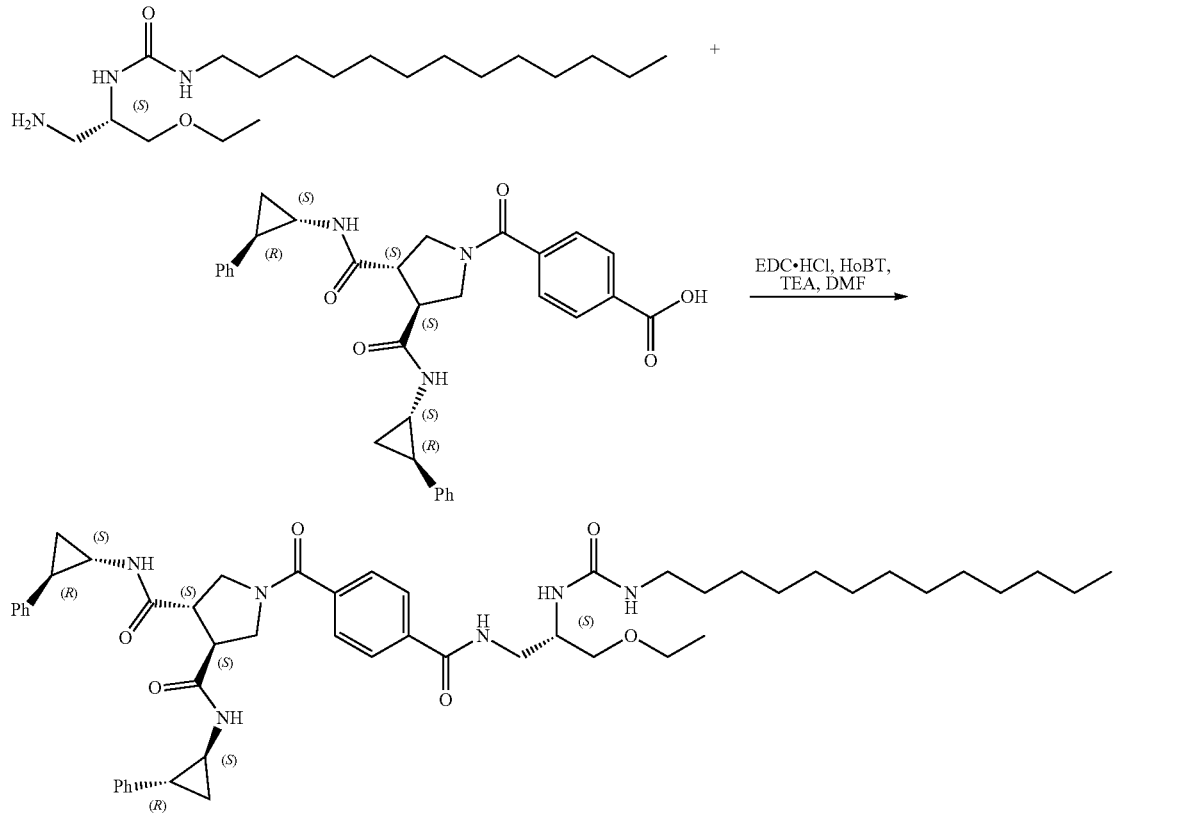

Step 1: Preparation of ethyl (1R,2R)-2-(pyridin-3-yl) cyclopropane-1-carboxylate

Step 3: Preparation of tert-butyl ((1R*,2S&)-2-(pyridin-3-yl) cyclopropyl) carbamate. (Intermediate) (Racemic)

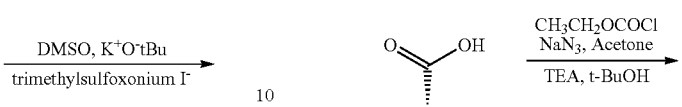

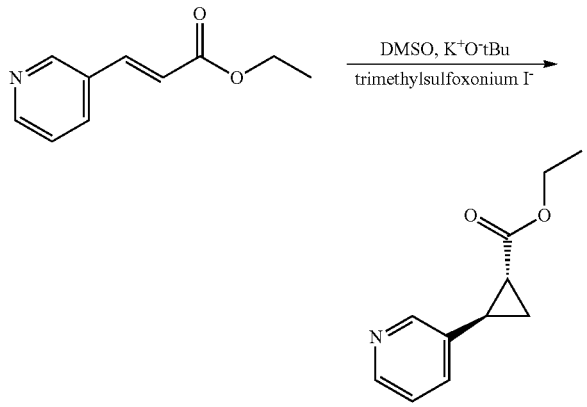

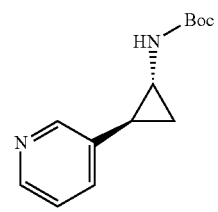

To a stirred solution of ethyl (E)-3-(pyridin-3-yl) acrylate (5.0 g, 28.2 mmol), in dimethyl sulfoxide (50 mL) was added trimethyl sulfoxonium iodide (15.5 g 70.6 mmol) followed by potassium tertiary butoxide (7.9 g, 70.6 mmol). The reaction mixture was stirred at 60° C. for 30 minutes. Ice cold water was added and the mixture was extracted with ethyl acetate (3×60 mL), washed with brine (2×100 mL), dried over sodium sulfate and evaporated. The crude product was purified using flash chromatography eluting with 0-70% ethyl acetate in hexane to give ethyl (1R*,2R*)-2-(pyridin-3-yl) cyclopropane-1-carboxylate (1.5 g, 27.8%) as product. LCMS (Method-X): 78.6% (RT 0.500, 264 nm) (MS: ESI +ve 192 [M+H]).

Step 2: Preparation of (1R*,2R*)-2-(pyridin-3-yl) cyclopropane-1-carboxylic acid Ethyl chloroformate (3.5 mL, 33.4 mmol) was added to a solution of (1R,2R)-2-(pyridin-3-yl) cyclopropane-1-carboxylic acid (4.2 g, 25.7 mmol) and triethylamine (5.6 mL, 38.6 mmol) in acetone (40 mL) at −20° C. and stirred for 1 hour. A solution of sodium azide (2.5 g, 38.6 mmol) in water (12 mL) was added and stirring continued for 30 min. The solvent was evaporated and the crude residue was dissolved in ethyl acetate (3×40 mL), washed with water (3×30 mL), brine (2×30 mL), dried over sodium sulfate and evaporated. The resulting crude (1R*,2R*)-2-(pyridin-3-yl) cyclopropane-1-carbonyl azide (1.0 g) was dissolved in tert-butanol (10 mL) and heated at 90° C. for 16 hrs. The volatiles were removed and the crude residue was purified by flash chromatography, eluting with 0-70% ethyl acetate in hexane to give tert-butyl ((1R*,2S*)-2-(pyridin-3-yl) cyclopropyl) carbamate (1.1 g, 30%). LCMS (30 min): 93.6% (RT 14.34, 214 nm) (MS: ESI +ve 235 [M+H]). Chiral HPLC (Racemic): 49.1% (RT: 3.33), 50.6%, (RT: 3.87).

Step-4: SFC Separation of racemic tert-butyl ((1R*, 2S*)-2-(pyridin-3-yl) cyclopropyl) carbamate

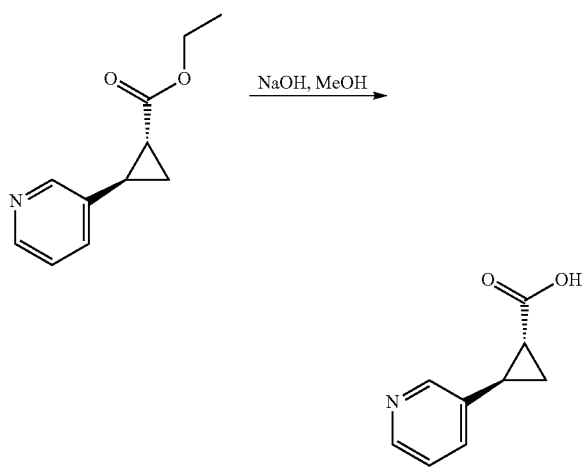

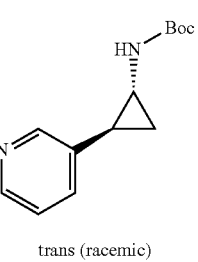

trans (racemic)

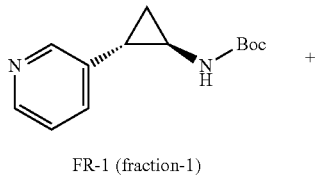

FR-1 (fraction-1)

Prepared using a procedure similar to General Ester Hydrolysis Procedure. The crude product was triturated with MeOH to obtain (1R*,2R*)-2-(pyridin-3-yl) cyclopropane-1-carboxylic acid as free salt (1.0 g, 78.13%). LCMS (Method-G): 20.2% (RT 4.373, 254 nm) (MS: ESI +ve 164 [M+H]).

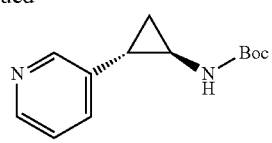

FR-2 (fraction-2)

tert-butyl ((1R*,2S*)-2-(pyridin-3-yl) cyclopropyl) carbamate (1.1 g). (trans racemic) was resolved using a Waters SFC 200 and UV detector. The column used was a Chiralpak IH (250*21.0) mm, 5 microns, column flow was 80.0 ml/min and ABPR was 100 bar. Mobile phase; (A) Liquid Carbon dioxide (Liq. CO2) and (B) 0.1% DEA in IPA: acetonitrile (50:50). to give;

Fraction 1; tert-butyl ((1R,2S)-2-(pyridin-3-yl) cyclopropyl) carbamate (0.48 g) absolute stereochemistry is arbitrarily assigned LCMS FR-1: 100% (RT 15.116, 214.0 nm) (MS: ESI +ve 235.4 [M+1]). ¹H NMR FR-1: (400 MHz, DMSO) δ ppm: 1.03-1.05 (d, J=6.4, 6H), 1.15-1.18 (m, 3H), 1.38 (s, 12H), 1.89-1.95 (m, 1H), 2.66 (s, 1H), 3.76-3.79 (t, 1H), 4.36 (s, 1H), 5.76 (s, 1H), 7.25-7.28 (m, 2H), 7.42-7.44 (d, J=7.6, 1H), 8.35 (s, 1H), 8.41 (s, 1H). Chiral HPLC (Fr-1): 100% (RT: 3.33 min).

Fraction 2; tert-butyl ((1S,2R)-2-(pyridin-3-yl) cyclopropyl) carbamate (0.48 g) absolute stereochemistry is arbitrarily assigned LCMS FR-2: 99.23% (RT 14.564, 214.0 nm) (MS: ESI +ve 235.4 [M+1]). ¹H NMR FR-2: (400 MHz, DMSO) δ ppm: 1.00-1.03 (t, 2H), 1.15-1.18 (m, 4H), 1.38 (s, 17H), 1.90-1.92 (d, J=6.4, 2H), 2.66 (s, 2H), 7.25-7.28 (m, 2H), 7.32 (s, 1H), 7.42-7.44 (d, J=7.6, 2H), 8.41 (s, 4H). Chiral HPLC (Fr-1): 100% (RT: 3.85 min).

Step-5: Synthesis of (1R*,2S*)-2-(pyridin-3-yl) cyclopropan-1-amine

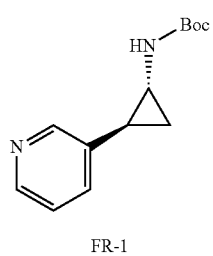

FR-1

To a stirred solution of tert-butyl ((1R*,2S*)-2-(pyridin-3-yl) cyclopropyl) carbamate FR-1 (0.5 g, 2.35 mmol) in dioxane (2 mL) was added 4N HCl in dioxane (3 mL). The reaction was stirred for 3 hrs and concentrated to give (1R*,2S*)-2-(pyridin-3-yl) cyclopropan-1-amine (0.38 g, crude). LCMS (Method-G): 97.35% (RT: 4.349, 214 nm) (MS: ESI +ve 135 [M+H]).

Step-6: Synthesis of tert-butyl (3S,4S)-3,4-bis(((1S,2R)-2-(pyridin-3-yl) cyclopropyl) carbamoyl) pyrrolidine-1-carboxylate

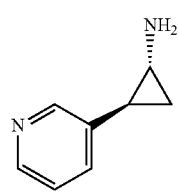

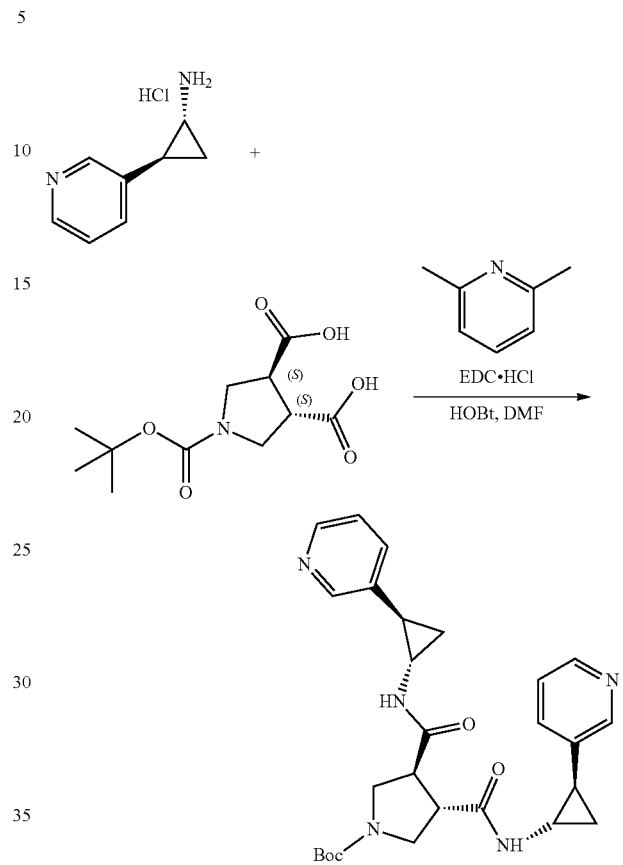

Prepared using a procedure similar to General EDC, HOBT coupling Procedure and used with further purification. tert-butyl (3S,4S)-3,4-bis(((1S*,2R*)-2-(pyridin-3-yl) cyclopropyl) carbamoyl) pyrrolidine-1-carboxylate (0.38 g, Crude) LCMS (Method-C2): 37.3% (RT: 0.921, 231.0 nm) (MS: ESI +ve 492[M+H]).

Step-7: Synthesis of (3S,4S)—N3,N4-bis((1S*,2R*)-2-(pyridin-3-yl) cyclopropyl) pyrrolidine-3,4-dicarboxamide

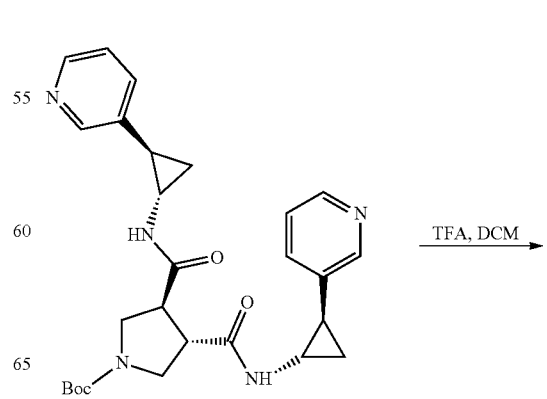

321

-continued

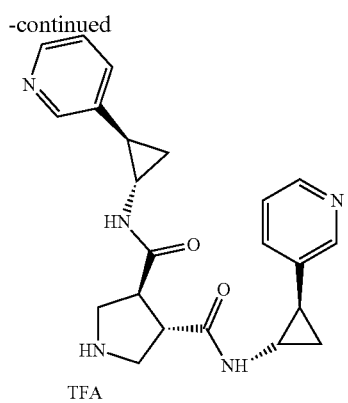

TFA

Prepared by a procedure similar to General BOC Deprotection Procedure. The crude residue was triturated in pentane to give (3S,4S)—N3,N4-bis((1S*,2R*)-2-(pyridin-3-yl) cyclopropyl) pyrrolidine-3,4-dicarboxamide. (0.8 g). LCMS (Method-C2): 38.14% (RT: 0.239, 254.0 nm) (MS: ESI +ve 392[M+H]).

Step-8: Preparation of (3S,4S)-1-(4-((3S,4S)-3,4-bis(((1S,2R)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide, Compound 094

322

Prepared using a procedure similar to General EDC, HOBT coupling Procedure. The crude product was purified using Prep HPLC Method 1 to give (3S,4S)-1-(4-((3S,4S)-3,4-bis(((1S,2R)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide (Compound 094), as a white solid (0.057 g, 3.67%). LCMS (Method-J): 100% (RT 3.792, 202.0 nm) (MS: ESI +ve 910 [M−H]). $^1$H NMR: (400 MHz, DMSO) δ ppm: 1.10-1.26 (m, 8H); 1.86-1.99 (m, 4H); 2.80-2.86 (m, 4H); 3.11-3.21 (m, 4H); 3.42-3.48 (m, 4H); 3.63-3.68 (s, 2H); 3.78-3.83 (m, 2H); 7.05-7.07 (d, J=7.6, 2H); 7.11-7.18 (m, 4H); 7.21-7.30 (m, 6H); 7.42-7.49 (m, 2H); 7.56 (s, 4H) 8.30-8.50 (m, 8H).

Synthesis of (3S,4S)-1-(4-((3S,4S)-3,4-bis(((1S*, 2R*)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide, Compound 095

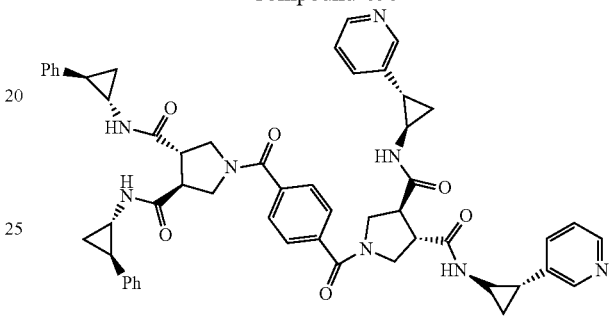

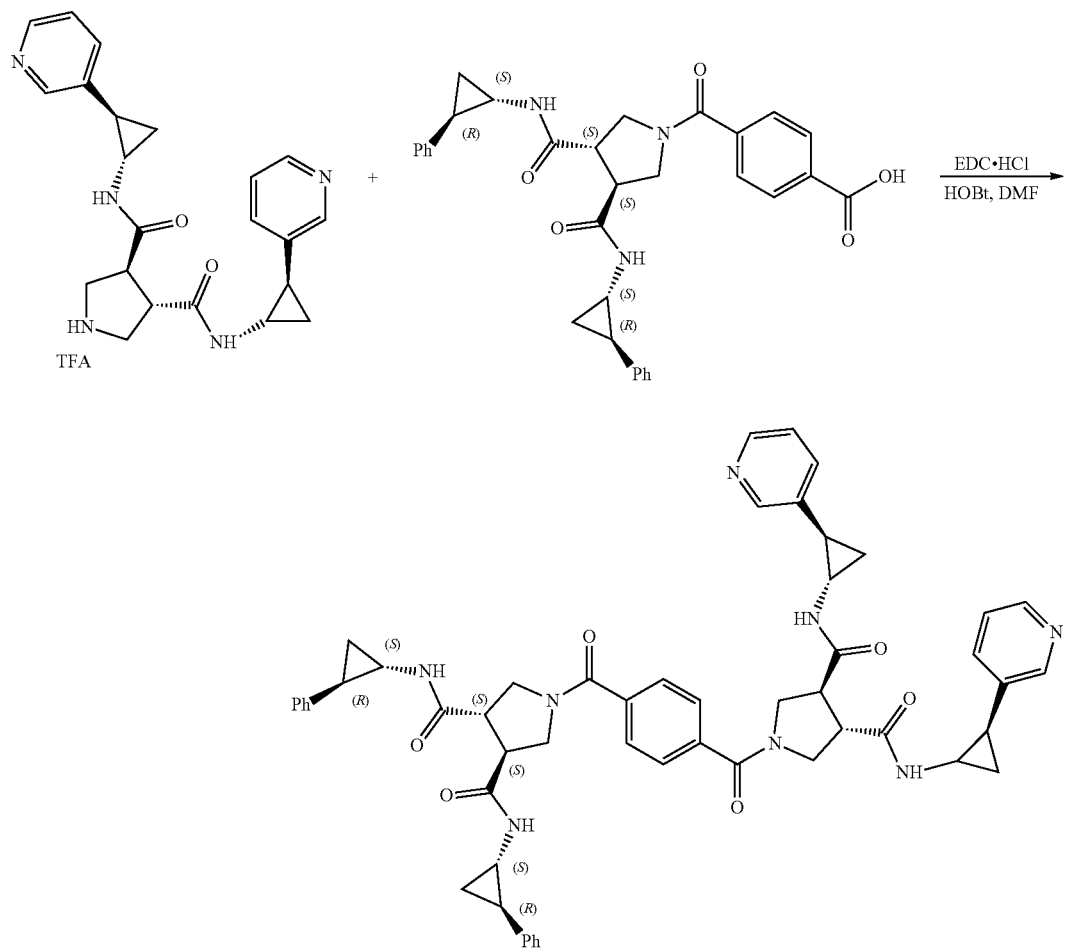

Prepared by a procedure similar to that reported for (3S,4S)-1-(4-((3S,4S)-3,4-bis(((1S,2R)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide (Compound 094), using Fraction 2 from Step-4. The crude product was purified using Prep HPLC Method 1 to give (3S,4S)-1-(4-((3S,4S)-3,4-bis(((1S*,2R*)-2-(pyridin-3-yl) cyclopropyl) carbamoyl) pyrrolidine-1-carbonyl) benzoyl)-N3,N4-bis((1S,2R)-2-phenylcyclopropyl) pyrrolidine-3,4-dicarboxamide (Compound 095)(0.055 g, 3.67%). LCMS (Method-J): 100% (RT 3.823, 202.0 nm) (MS: ESI +ve 912 [M+H]). ¹H NMR: (400 MHz, DMSO) δ ppm: 1.09-1.26 (m, 8H); 1.95 (s, 4H); 2.83 (s, 4H); 3.09-3.20 (m, 4H); 3.48-3.52 (m, 4H); 3.65-3.67 (d, J=8.4, 2H); 3.78 (s, 2H); 7.06-7.08 (d, J=7.6, 2H); 7.11-7.18 (m, 4H); 7.21-7.28 (m, 6H); 7.42-7.47 (m, 2H); 7.56 (s, 4H) 8.37-8.43 (m, 6H); 8.50-8.58 (m, 2H).

Synthesis of (3S,4S)—N3-((1S)-2-phenylcyclopropyl)-N4-(2-phenylcyclopropyl)-1-(4-((3S,4S)-3-(((1S,2R)-2-phenylcyclopropyl)carbamoyl)-4-(((1S*,2R*)-2-(pyridin-3-yl)cyclopropyl)carbamoyl) pyrrolidine-1-carbonyl)benzoyl)pyrrolidine-3,4-dicarboxamide, Compound 096

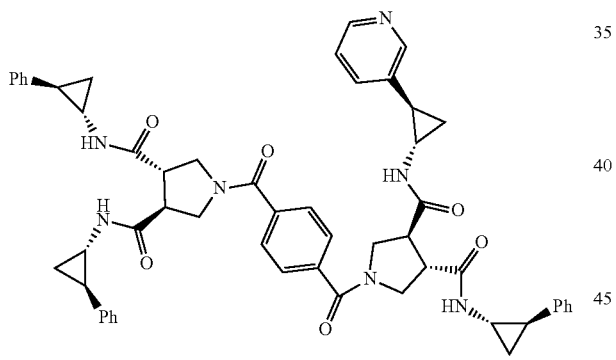

Step 1: Synthesis of (3S,4S)-1-(tert-butoxycarbonyl)-4-(ethoxycarbonyl)pyrrolidine-3-carboxylic acid

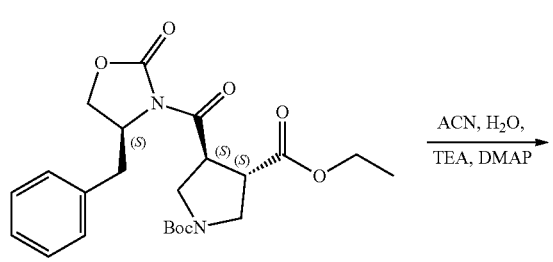

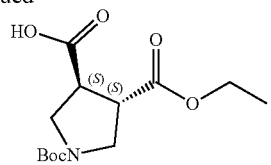

1-(tert-butyl) 3-ethyl (3S,4S)-4-((S)-4-benzyl-2-oxooxazolidine-3-carbonyl) pyrrolidine-1,3-dicarboxylate (1.0 g, 2.2 mmol) was dissolved in acetonitrile (5 mL) and water (2.5 mL). Triethylamine (1.2 mL) and DMAP (0.005 g) were added and the mixture was stirred for 1.5 hr at 80° C., then allowed to warm to room temperature over 16 hr. The mixture was then heated at 80° C. for 3 hr. Saturated aq. Na₂CO₃ solution was added and THF was removed, in vacuo. The resulting mixture was poured into water (600 mL) and extracted with DCM (200 mL×3). The aqueous phase was acidified with 1 N HCL to pH 2 (200 mL) and extracted with ethyl acetate (200 mL×3), dried over anhydrous sodium sulfate and concentrated under reduced pressure to give (3S,4S)-1-(tert-butoxycarbonyl)-4-(ethoxycarbonyl) pyrrolidine-3-carboxylic acid as an off white solid (0.3 g, 46.62%) LCMS (Method-C): 93.86% (RT: 1.187, 202.0 nm) (MS: ESI +ve 188 [M+H−100]).

Step 2: Synthesis of 1-(tert-butyl) 3-ethyl (3S,4S)-4-(((1S*,2S*)-2-(pyridin-2-yl) cyclopropyl) carbamoyl) pyrrolidine-1,3-dicarboxylate

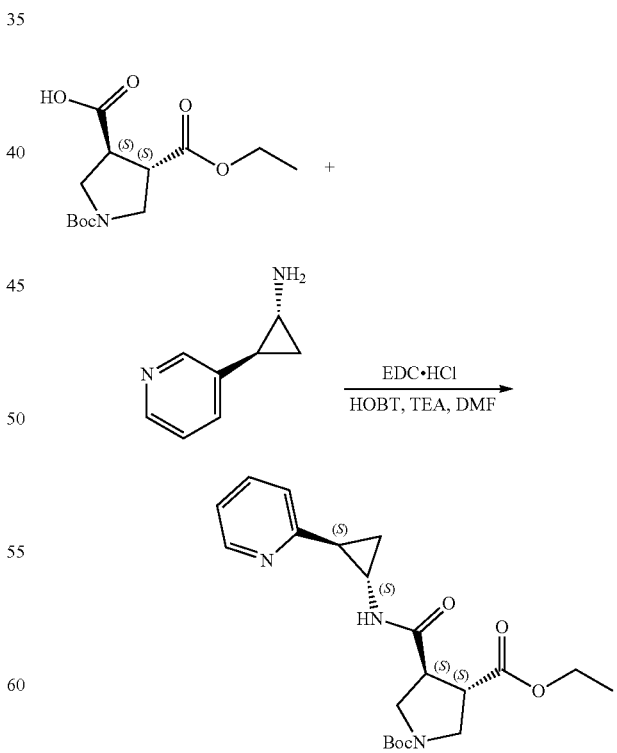

Prepared using a procedure similar to General EDC, HOBT Coupling Procedure. The crude product was purified using flash chromatography eluting with 3-5% MeOH in DCM to give 1-(tert-butyl) 3-ethyl (3S,4S)-4-(((1S,2S)-2-(pyridin-2-yl) cyclopropyl) carbamoyl) pyrrolidine-1,3-dicarboxylate liquid (0.13 g, 61.71%). LCMS (Method-C2): 96.36% (RT: 1.037, 225.00 nm) (MS: ESI +ve 404.4 [M+1]).

Step 3: Synthesis of (3S,4S)-1-(tert-butoxycarbonyl)-4-(((1S*,2S*)-2-(pyridin-2-yl) cyclopropyl) carbamoyl)pyrrolidine-3-carboxylic acid

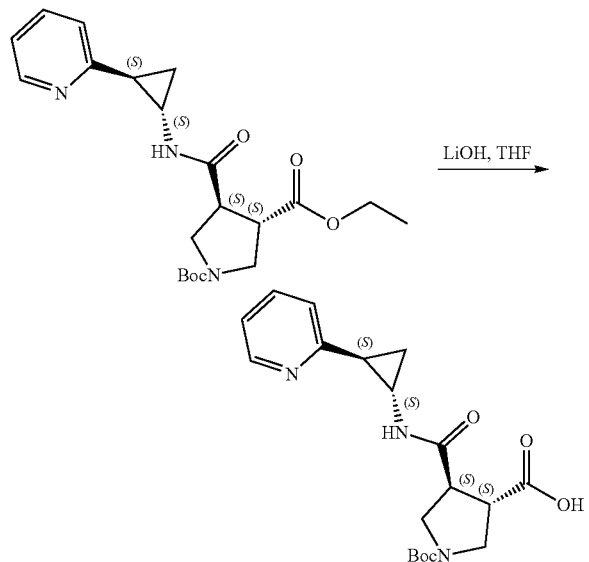

Prepared using a procedure similar to General Ester Hydrolysis Procedure. The crude product was used without further purification. (3S,4S)-1-(tert-butoxycarbonyl)-4-(((1S*,2S*)-2-(pyridin-2-yl)cyclopropyl)carbamoyl)pyrrolidine-3-carboxylic acid (0.1 g, 82.67) LCMS (Method-C2): 91.22% (RT: 0.969, 225.00 nm) (MS: ESI +ve 376.36 [M+2]).

Step 4: Synthesis of tert-butyl (3S,4S)-3-(((1S*,2R*)-2-phenylcyclopropyl)carbamoyl)-4-(((1S,2R)-2-(pyridin-3-yl)cyclopropyl)carbamoyl)pyrrolidine-1-carboxylate

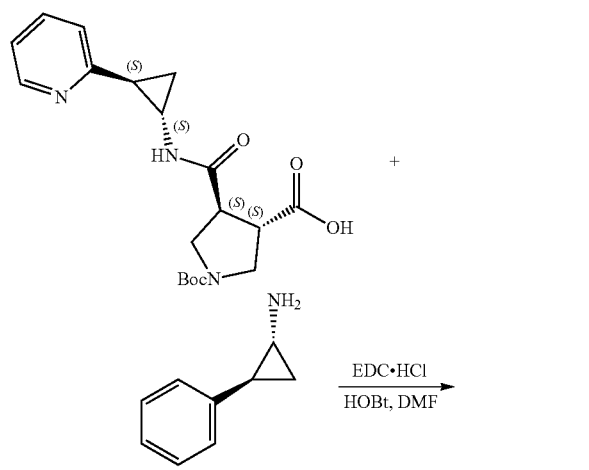

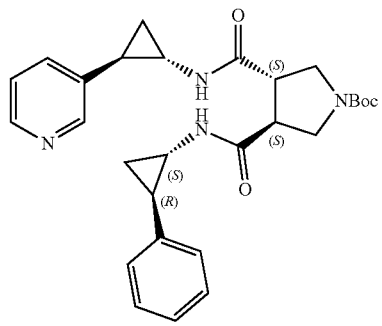

Prepared using a procedure similar to General EDC, HOBT Coupling Procedure. The crude product was purified using flash chromatography eluting with 3-5% MeOH in DCM to give tert-butyl (3S,4S)-3-(((1S,2R)-2-phenylcyclopropyl)carbamoyl)-4-(((1S*,2R*)-2-(pyridin-3-yl)cyclopropyl)carbamoyl) pyrrolidine-1-carboxylate as an off white solid (0.07 g, 53.57%). LCMS (Method-C2): 100.0% (RT: 1.121, 222.00 nm) (MS: ESI +ve 491.4 [M+1]).

Step 5: Synthesis of (3S,4S)—N3-((1S,2R)-2-phenylcyclopropyl)-N4-((1S*,2R*)-2-(pyridin-3-yl) cyclopropyl)pyrrolidine-3,4-dicarboxamide

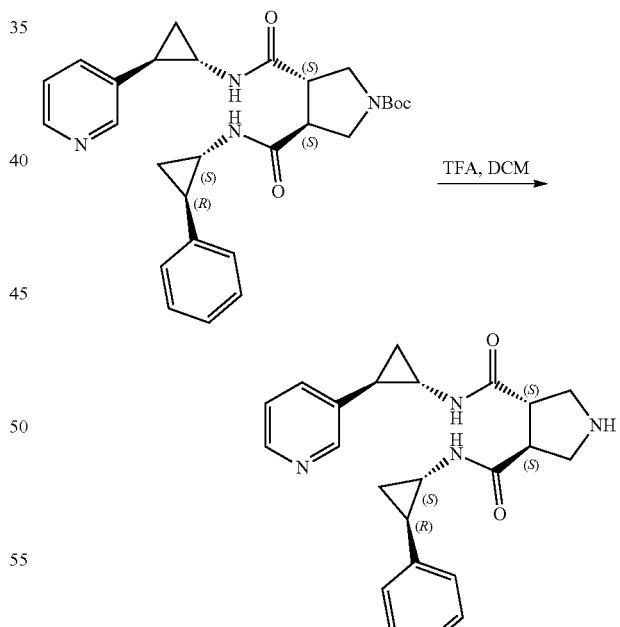

Prepared using General BOC Deprotection Procedure. Used without further purification. (3S,4S)—N3-((1S,2R)-2-phenylcyclopropyl)-N4-((1S,2R)-2-(pyridin-3-yl) cyclopropyl) pyrrolidine-3,4-dicarboxamide. (0.1 g). LCMs (Method-C2): 97.56% (RT: 0.939, 222.0 nm) (MS: ESI +ve 391.44 [M+1]).

Step 6: Synthesis of (3S,4S)—N3-((1S)-2-phenyl-cyclopropyl)-N4-(2-phenylcyclopropyl)-1-(4-((3S,4S)-3-(((1S,2R)-2-phenylcyclopropyl)carbamoyl)-4-(((1S*,2R*)-2-(pyridin-3-yl)cyclopropyl)carbamoyl)pyrrolidine-1-carbonyl)benzoyl)pyrrolidine-3,4-dicarboxamide, Compound 096

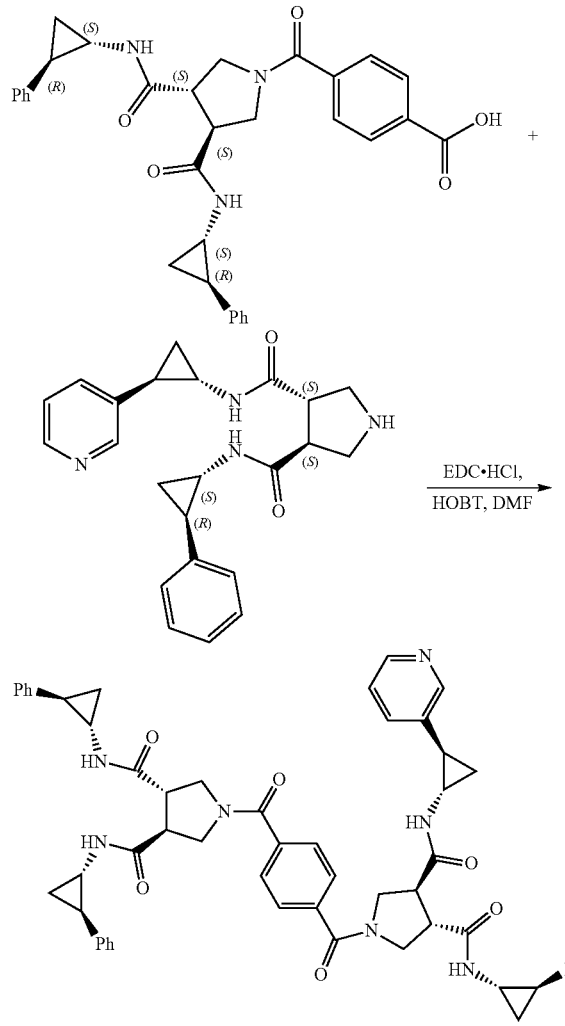

Prepared using a procedure similar to General EDC, HOBT Coupling Procedure. The crude product was purified using Prep HPLC Method 6 to give (3S,4S)—N3-((1S)-2-phenylcyclopropyl)-N4-(2-phenylcyclopropyl)-1-(4- ((3S,4S)-3-(((1S,2R)-2-phenylcyclopropyl)carbamoyl)-4-(((15S*,2R*)-2-(pyridin-3-yl)cyclopropyl)carbamoyl) pyrrolidine-1-carbonyl)benzoyl)pyrrolidine-3,4-dicarboxamide (Compound 096), (34 mg, 20.08%). LCMs (Method-C3): 100% (RT 1.604, 202.0 nm) (MS: ESI +ve 910.65 [M+H]). ¹H NMR (400 MHz, DMSO) δ ppm: 1.85-1.98 (t, J=39.2 Hz, 9H), 2.34-2.54 (d, J=68 4H), 2.64-3.12 (m, 7H), 3.19-3.83 (m, 12H), 7.07-7.43 (m, 13H), 7.45-7.57 (m, 4H), 8.34-8.53 (m, 6H).

Synthesis of (3S,4S)—N3-((1S)-2-phenylcyclopropyl)-N4-(2-phenylcyclopropyl)-1-(4-((3S,4S)-3-(((1S,2R)-2-phenylcyclopropyl)carbamoyl)-4-(((1S*,2R*)-2-(pyridin-3-yl)cyclopropyl)carbamoyl)pyrrolidine-1-carbonyl)benzoyl)pyrrolidine-3,4-dicarboxamide, Compound 097

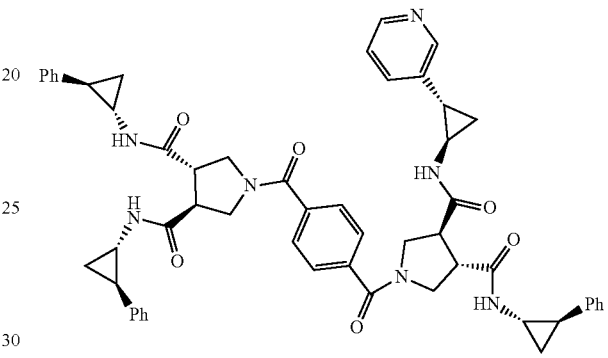

Prepared by a procedure similar to that reported for give (3S,4S)—N3-((1S)-2-phenylcyclopropyl)-N4-(2-phenylcyclopropyl)-1-(4-((3S,4S)-3-(((1S,2R)-2-phenylcyclopropyl)carbamoyl)-4-(((1S*,2R*)-2-(pyridin-3-yl)cyclopropyl)carbamoyl) pyrrolidine-1-carbonyl)benzoyl)pyrrolidine-3,4-dicarboxamide (Compound 096) using Fraction 2 of ((1R*,2S*)-2-(pyridin-3-yl) cyclopropyl) carbamate. The crude final product was purified using Prep HPLC Method 1 to give (3S,4S)—N3-((1S)-2-phenylcyclopropyl)-N4-(2-phenylcyclopropyl)-1-(4-((3S,4S)-3-(((1S,2R)-2-phenylcyclopropyl)carbamoyl)-4-(((1S*,2R*)-2-(pyridin-3-yl)cyclopropyl)carbamoyl)pyrrolidine-1-carbonyl)benzoyl)pyrrolidine-3,4-dicarboxamide (Compound 097)(34 mg, 10.04%). LCMs (Method-J): 100% (RT 4.383, 220 nm) (MS: ESI +ve 910.65 [M+H]). (400 MHz, DMSO) δ ppm: 1.09-1.26 (m, 8H), 1.86-1.97 (d, J=56.4 4H), 2.33 (s, 2H), 2.50 (s, 2H), 2.67-2.92 (m, 4H), 3.08-3.20 (m, 4H), 3.50-3.79 (m, 6H), 7.06-7.26 (m, 13H), 7.43-7.56 (m, 4H), 8.37-8.57 (m, 6H).

Synthesis of (3S,4S)-1-(4-(3-(hexylcarbamoyl)-4-octylpiperazine-1-carbonyl)benzoyl)-N3,N4-bis((1S,2R)-2-phenylcyclopropyl)pyrrolidine-3,4-dicarboxamide formate, Compound 018

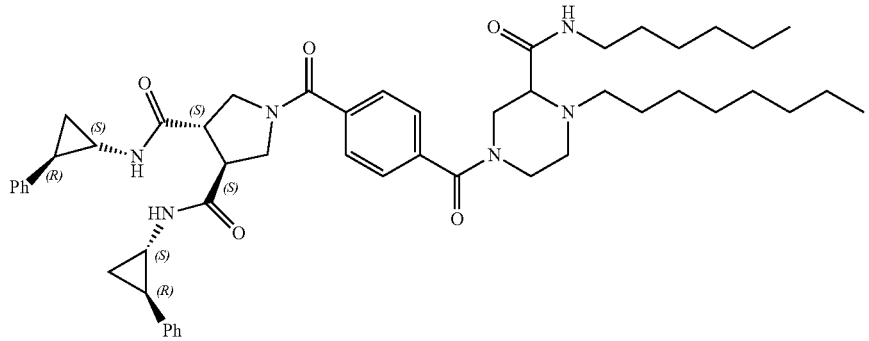

Step-1: preparation of tert-butyl 3-(hexylcarbamoyl) piperazine-1-carboxylate

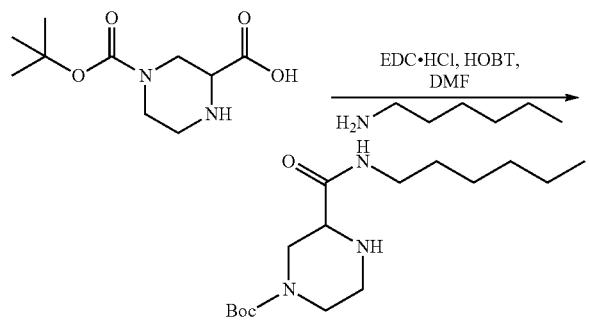

Prepared by a procedure similar to General EDC, HOBT Coupling PGP Procedure. The crude residue was purified by column chromatography (Stationary phase-Basic alumina ($Al_2O_3$)) eluting with 70% ethyl acetate in hexane to afford tert-butyl 3-(hexylcarbamoyl)piperazine-1-carboxylate (1 g, 73.45%). LCMS (Method-C): 86.46% (RT: 1.489, 202.0 nm) (MS: ESI +ve 314.4 [M+1]).

Step-2: Preparation of tert-butyl 3-(hexylcarbamoyl)-4-octylpiperazine-1-carboxylate

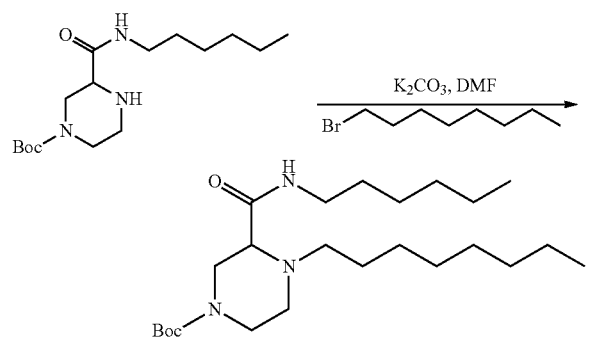

Tert-butyl3-(hexylcarbamoyl)piperazine-1-carboxylate (0.5 g, 1.59 mmol) was dissolved in DMF (5 mL) along with 1-bromooctane (0.379 g, 1.96 mmol) and potassium carbonate was added (0.264 g, 1.96 mmol). The resulting mixture was stirred at 50° C. for 12 hrs. The reaction was quenched with ice cold water and the mixture was extracted with ethyl acetate (3×12 mL). The organic layer was dried over sodium sulphate. The crude product was purified by column chromatography (Stationary phase-Basic alumina ($Al_2O_3$)) eluting with 60% ethyl acetate in hexane to afford tert-butyl 3-(hexylcarbamoyl)-4-octylpiperazine-1-carboxylate (0.35 g, 51.5%). LCMS (Method-C3): 61.54% (RT 1.951, 202.0 nm) (MS: ESI +ve 426.6 [M+H]).

Step 3: Preparation of N-hexyl-1-octylpiperazine-2-carboxamide

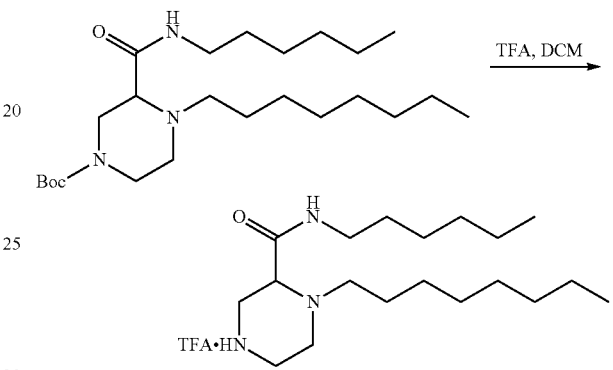

Prepared by a procedure similar to General Boc Deprotection Procedure. The crude residue was triturated with pentane to give N-hexyl-1-octylpiperazine-2-carboxamide trifluoroacetate (320 mg). LCMS (Method-C3): 53.7% (RT: 1.75 min, 202 nm) (MS: ESI +ve 326.4 [M+1]). Step-4: Preparation of (3S,4S)-1-(4-(3-(hexylcarbamoyl)-4-octylpiperazine-1-carbonyl)benzoyl)-N3,N4-bis((1S,2R)-2-phenylcyclopropyl)pyrrolidine-3,4-dicarboxamide formate, Compound 018.

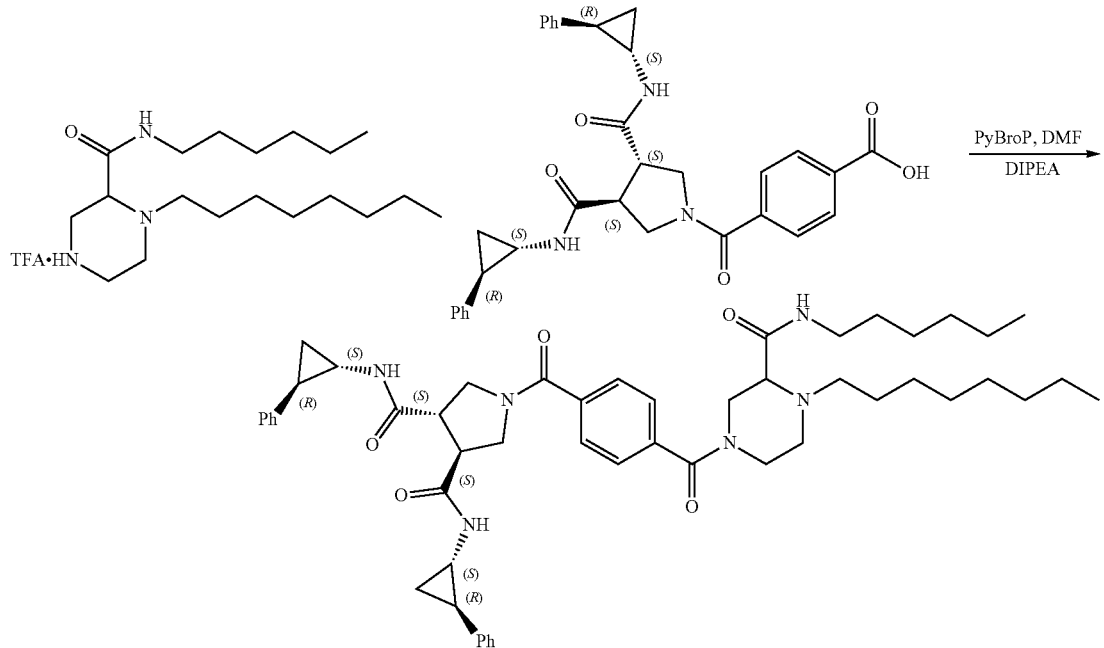

To a stirred solution of 4-((3S,4S)-3,4-bis(((1S,2R)-2-phenylcyclopropyl) carbamoyl) pyrrolidine-1-carbonyl)benzoic acid (100 mg, 0.18 mmol) and N-hexyl-1-octylpiperazine-2-carboxamide (60 mg, 0.18 mmol) in DMF (3 mL) was added DIPEA (60 mg, 0.54 mmol). The reaction was stirred at room temperature for 5 minutes. PyBroP (0.080 mg, 0.18 mmol) was added and the mixture was stirred at room temperature for 16 hrs. The reaction was quenched ice cold water and the resulting precipitate was dissolved in DCM and dried over sodium sulphate then The crude residue was purified using Prep HPLC Method 1 to give (3S,4S)-1-(4-(3-(hexylcarbamoyl)-4-octylpiperazine-1-carbonyl) benzoyl)-N3,N4-bis((1S,2R)-2-phenylcyclopropyl)pyrrolidine-3,4-dicarboxamide formate, Compound 018 (30 mg, 19.26%) LCMS (Method-C): 100% (RT 2.12, 202 nm) (MS: ESI +ve 846.6 [M+H]). ¹H NMR: (400 MHz, DMSO) δ ppm: 0.86 (m, 6H), 1.24 (m, 21H), 1.42 (m, 3H), 1.87 (s, 2H), 1.97 (m, 1H), 2.34 (m, 2H), 2.84 (m, 4H), 3.00 (m, 2H), 3.10-3.11 (m, 3H), 3.19-3.21 (m, 2H), 3.52 (m, 3H), 3.66 (m, 1H), 3.81 (m, 1H), 7.07-7.17 (m, 6H), 7.25-7.27 (m, 4H), 7.43-7.45 (m, 2H), 7.57-7.58 (d, J=4 Hz, 2H), 7.82-7.94 (m, 1H), 8.31 (s, 1H), 8.46 (s, 1H).

Example 3

Synthesis of (3S,4S)-1-(4-((R)-3-(hexylcarbamoyl)-4-octylpiperazine-1-carbonyl) benzoyl)-N3,N4-bis((1S,2R)-2-phenylcyclopropyl)pyrrolidine-3,4-dicarboxamide formate, Compound 037

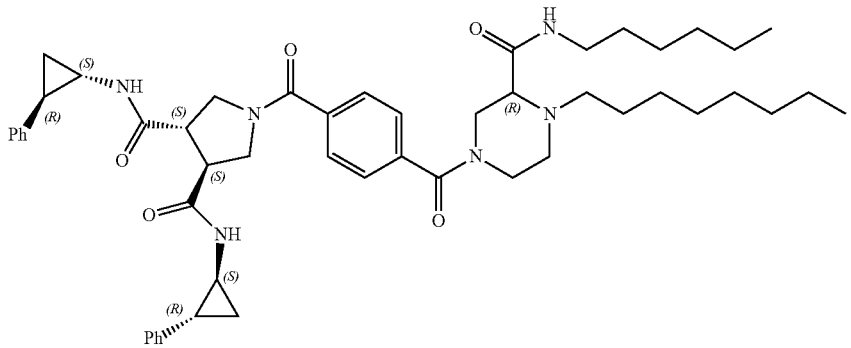

Prepared by a procedure similar to that reported for (3S,4S)-1-(4-(3-(hexylcarbamoyl)-4-octylpiperazine-1-carbonyl)benzoyl)-N3,N4-bis((1S,2R)-2-phenylcyclopropyl) pyrrolidine-3,4-dicarboxamide formate (30 mg, 19.26%), Compound 018 substituting (R)-4-(tert-butoxycarbonyl)piperazine-2-carboxylic acid in the first step. The crude final product was purified using Prep HPLC Method 2 to give (3S,4S)-1-(4-((R)-3-(hexylcarbamoyl)-4-octylpiperazine-1-carbonyl)benzoyl)-N3,N4-bis((1S,2R)-2-phenylcyclopropyl)pyrrolidine-3,4-dicarboxamide formate (0.028 g, 17.17%), Compound 037. LCMS (Method-C): 100% (RT 2.19, 202 nm) (MS: ESI +ve 846.0 [M+H]). ¹H NMR: (400 MHz, DMSO) δ ppm: 0.86 (m, 6H), 1.12 (m, 2H), 1.24 (m, 21H), 1.42 (m, 3H), 1.87 (m, 1H), 1.98 (m, 1H), 2.07 (m, 1H), 2.23 (m, 2H), 2.51 (m, 1H), 2.78-2.84 (m, 3H), 3.00 (m, 2H), 3.17 (m, 2H), 3.21 (q, J=4 Hz, 1H), 3.49-3.55 (m, 2H), 3.64-3.69 (m, 1H), 3.78-3.83 (m, 1H), 3.96-4.11 (m, 1H), 7.07-7.19 (m, 6H), 7.23-7.29 (m, 4H), 7.45-7.43 (d, J=8 Hz, 2H), 7.57-7.59 (d, J=8 Hz, 2H), 7.82-7.94 (m, 1H), 8.31-8.32 (d, J=4 Hz, 1H), 8.44-8.45 (d, J=4 Hz, 1H).

Example 4

Synthesis of (3S,4S)-1-(4-(4-methyl-3-(tetradecylcarbamoyl)piperazine-1-carbonyl) benzoyl)-N3,N4-bis((1S,2R)-2-phenylcyclopropyl)pyrrolidine-3,4-dicarboxamide formate, Compound 023

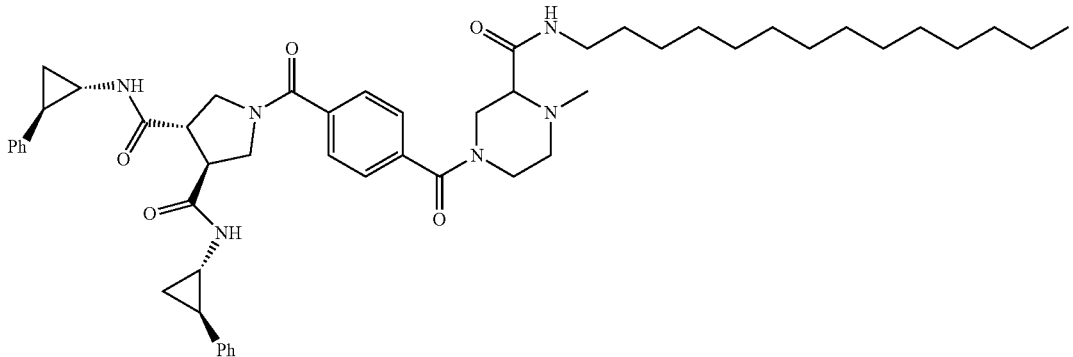 [SMILES: CCCCCCCCCCCCCCNC(=O)C1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)CCN1C]

Prepared by a procedure similar to that reported for (3S,4S)-1-(4-(3-(hexylcarbamoyl)-4-octylpiperazine-1-carbonyl)benzoyl)-N3,N4-bis((1S,2R)-2-phenylcyclopropyl)pyrrolidine-3,4-dicarboxamide formate (30 mg, 19.26%), Compound 018, substituting tetradecylamine in step 1 and methyl iodide in step 2. The crude final product was purified using Prep HPLC Method 2 to give (3S,4S)-1-(4-(4-methyl-3-(tetradecylcarbamoyl)piperazine-1-carbonyl)benzoyl)-N3,N4-bis((1S,2R)-2-phenylcyclopropyl)pyrrolidine-3,4-dicarboxamide formate, Compound 023 (0.040 g, 26%). LCMS (Method-C3): 100% (RT 2.454, 202.0 nm) (MS: ESI +ve 859.9 [M+H]). $^1$H NMR: (400 MHz, DMSO) δ ppm: 0.86-0.83 (t, 3H), 1.11 (t, 3H), 1.39-1.23 (m, 28H), 1.86 (s, 1H), 1.97 (s, 1H), 2.15 (s, 3H), 2.55 (s, 2H), 2.97-2.85 (d, 2H), 3.09 (s, 2H), 3.13-3.11 (m, 1H), 3.18-3.16 (m, 1H), 3.53-3.50 (m, 2H), 3.65 (t, 1H), 3.79 (t, 1H), 4.26-4.18 (s, 1H), 7.18-7.06 (m, 6H), 7.28-7.22 (m, 5H), 7.45-7.43 (d, 2H), 7.58-7.56 (d, 2H), 7.96 (s, 1H), 8.33 (s, 1H), 8.46-8.43 (s, 1H).

Example 5

Synthesis of (3S,4S)-1-(4-((R)-4-methyl-3-(tetradecylcarbamoyl)piperazine-1-carbonyl)benzoyl)-N3,N4-bis((1S,2R)-2-phenylcyclopropyl)pyrrolidine-3,4-dicarboxamide formate, Compound 059

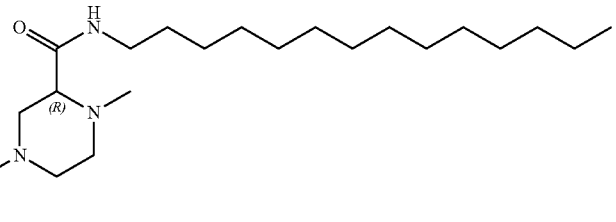
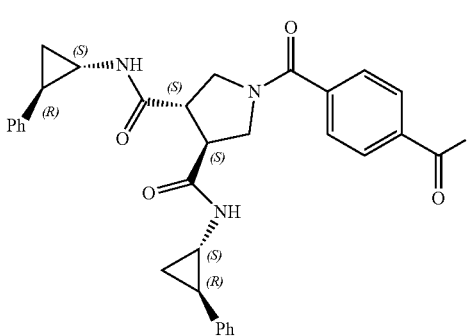

Prepared by a procedure similar to that reported for (3S,4S)-1-(4-(3-(hexylcarbamoyl)-4-octylpiperazine-1-carbonyl)benzoyl)-N3,N4-bis((1S,2R)-2-phenylcyclopropyl)pyrrolidine-3,4-dicarboxamide formate (30 mg, 19.26%), Compound 018, substituting tetradecylamine and (R)-4-(tert-butoxycarbonyl)piperazine-2-carboxylic acid in step 1 and methyl iodide in step 2. The crude final product was purified using Prep HPLC Method 9 to give (3S,4S)-1-(4-((R)-4-methyl-3-(tetradecylcarbamoyl) piperazine-1-carbonyl) benzoyl)-N3,N4-bis((1S,2R)-2-phenylcyclopropyl)pyrrolidine-3,4-dicarboxamide, Compound 059, as a white solid (0.030 g, 23.7%). LCMS (Method-C3): 100% (RT 2.522, 202.0 nm) (MS: ESI +ve 860 [M+H]). $^1$H NMR: (400 MHz, DMSO) δ ppm: 0.86 (s, 3H); 1.11 (s, 2H); 1.24 (s, 24H); 1.5 (s, 2H); 1.87 (s, 1H); 1.98 (s, 1H); 2.15 (s, 4H); 2.85 (s, 1H); 3.10 (s, 2H); 3.19 (s, 2H); 3.51 (s, 3H); 3.67 (s, 2H); 3.81 (s, 1H); 4.26 (s, 2H); 7.09 (s, 6H); 7.25-7.27 (d, J=7.2, 4H); 7.46-7.45 (d, J=4.8, 2H); 7.58 (s, 2H); 7.91 (s, 1H) 8.31 (s, 1H); 8.44 (s, 1H).

Example 6

Synthesis of (3S,4S)-1-(4-((S)-4-methyl-3-(tetradecylcarbamoyl) piperazine-1-carbonyl) benzoyl)-N3,N4-bis ((1S,2R)-2-phenylcyclopropyl) pyrrolidine-3,4-dicarboxamide formate, Compound 069

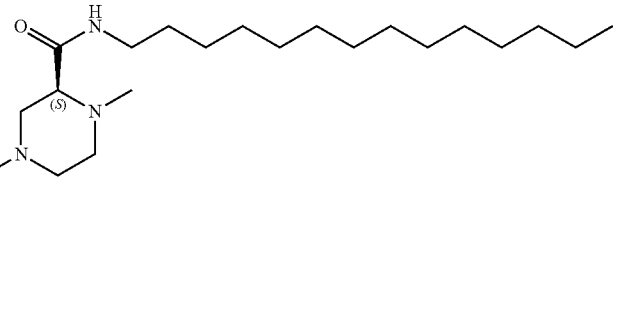

Prepared by a procedure similar to that reported for (3S,4S)-1-(4-(3-(hexylcarbamoyl)-4-octylpiperazine-1-carbonyl)benzoyl)-N3,N4-bis((1S,2R)-2-phenylcyclopropyl) pyrrolidine-3,4-dicarboxamide formate (30 mg, 19.26%), Compound 018, substituting tetradecylamine and (S)-4-(tert-butoxycarbonyl)piperazine-2-carboxylic acid in step 1 and methyl iodide in step 2. The crude final product was purified using Prep HPLC Method 9 to give (3S,4S)-1-(4-((S)-4-methyl-3-(tetradecylcarbamoyl) piperazine-1-carbonyl) benzoyl)-N3,N4-bis ((1S,2R)-2-phenylcyclopropyl) pyrrolidine-3,4-dicarboxamide formate, Compound 069 (0.016 g, 6.6%). LCMS (Method-C3): 100% (RT 6.118, 202.0 nm) (MS: ESI +ve 860 [M+H]). $^1$H NMR: (400 MHz, DMSO) δ ppm: 0.58 (s, 3H); 1.11-1.23 (m, 27H); 1.39 (s, 1H); 1.75 (s, 1H); 1.86 (s, 1H); 2.14 (s, 3H); 2.33 (s, 2H); 2.78 (s, 3H); 2.96 (s, 2H); 3.16-3.20 (t, 2H); 3.29 (s, 2H); 3.44 (s, 1H); 3.49 (s, 2H); 3.63-3.66 (d, J=9.2, 1H); 3.77 (s, 1H); 4.27 (s, 1H); 7.06-7.08 (d, J=7.6, 2H); 7.11-7.18 (m, 4H); 7.22-7.26 (m, 4H); 7.43-7.45 (d, J=7.6, 2H); 7.56-7.58 (d, J=8, 2H); 7.91 (s, 1H) 8.32 (s, 1H); 8.45 (s, 1H).

Example 7

Synthesis of (3S,4S)—N3,N4-bis ((1S,2R)-2-phenylcyclopropyl)-1-(4-(3-(tetradecylcarbamoyl) piperazine-1-carbonyl) benzoyl) pyrrolidine-3,4-dicarboxamide, Compound 054

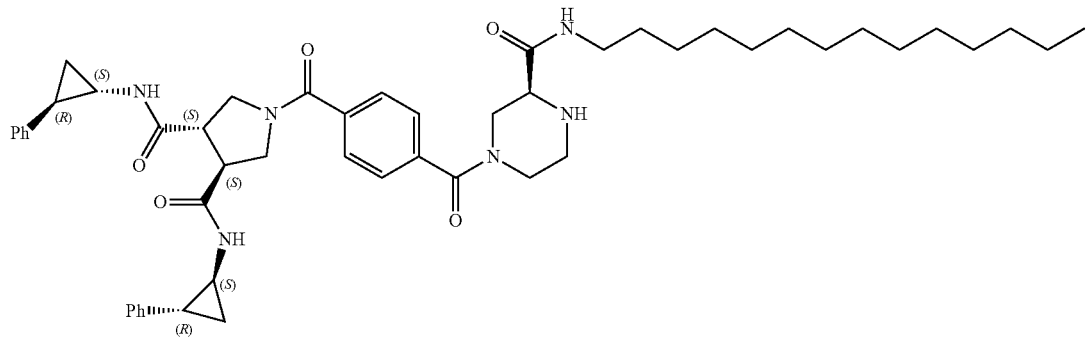

Step-1: Preparation of tert-butyl 3-(tetradecylcarbamoyl) piperazine-1-carboxylate

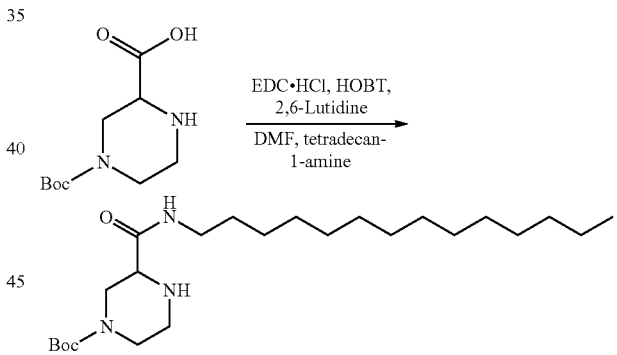

Prepared using a procedure similar to General EDC, HOBT Coupling Procedure. The crude product was purified column chromatography on basic alumina eluting with 0.5% Dichloromethane: Methanol. (0.986 g, 54.7% yield). LCMS (Method-C3): 91.5% (RT: 2.038, 202 nm) (MS: ESI +ve 426.5[M+1]).

Step-2: Preparation of 1-benzyl 4-(tert-butyl) 2-(tetradecylcarbamoyl)piperazine-1,4-dicarboxylate

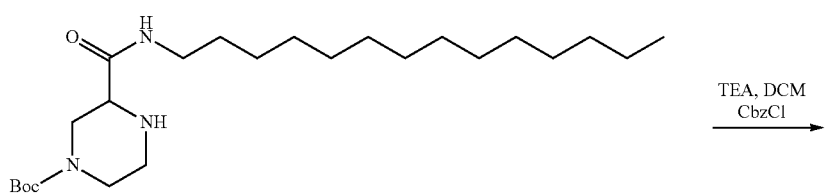

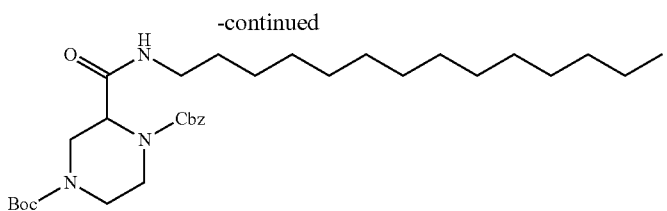

tert-Butyl 3-(tetradecylcarbamoyl) piperazine-1-carboxylatelate (0.936 g, 2.198 mmol) was dissolved in Dichloromethane (10 mL), cooled to 0° C. Triethylamine was added dropwise (0.667 g, 6.596 mmol) followed by benzyl chloroformate (0.450 g, 2.638 mmol). The reaction mixture was stirred at room temperature for 16 hrs. It was extracted in Dichloromethane (2×20 mL) washed with water (2×20 mL) then concentrated. The crude product was purified using column chromatography eluting with 0.5% (MS: ESI +ve 560.4[M+1]).

Step-3: Preparation of benzyl 2-(tetradecylcarbamoyl)piperazine-1-carboxylate trifluoroacetate

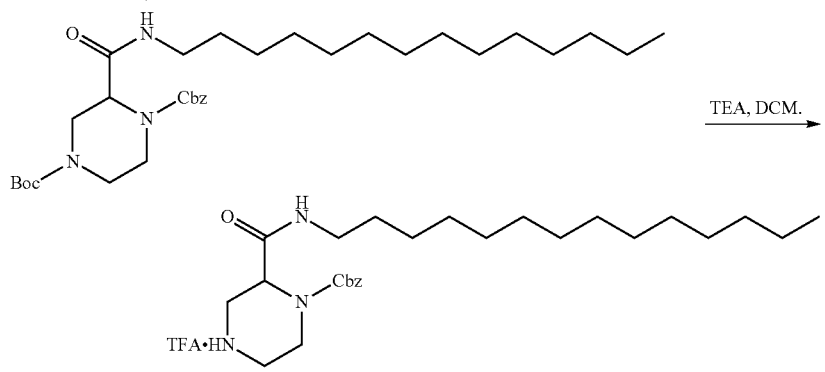

Prepared using a procedure similar to General Boc Deprotection Procedure. The crude residue was chased with dichloromethane (2×10 mL) to give benzyl 2-(tetradecylcarbamoyl)piperazine-1-carboxylate (1.1 g, crude). LCMS (Method-C3): 100% (RT: 1.989, 210 nm) (MS: ESI +ve 460.5[M+1]).

Step-4: Preparation of benzyl 4-(4-((3S,4S)-3,4-bis(((1S,2R)-2-phenylcyclopropyl) carbamoyl)pyrrolidine-1-carbonyl)benzoyl)-2-(tetradecylcarbamoyl)piperazine-1-carboxylate

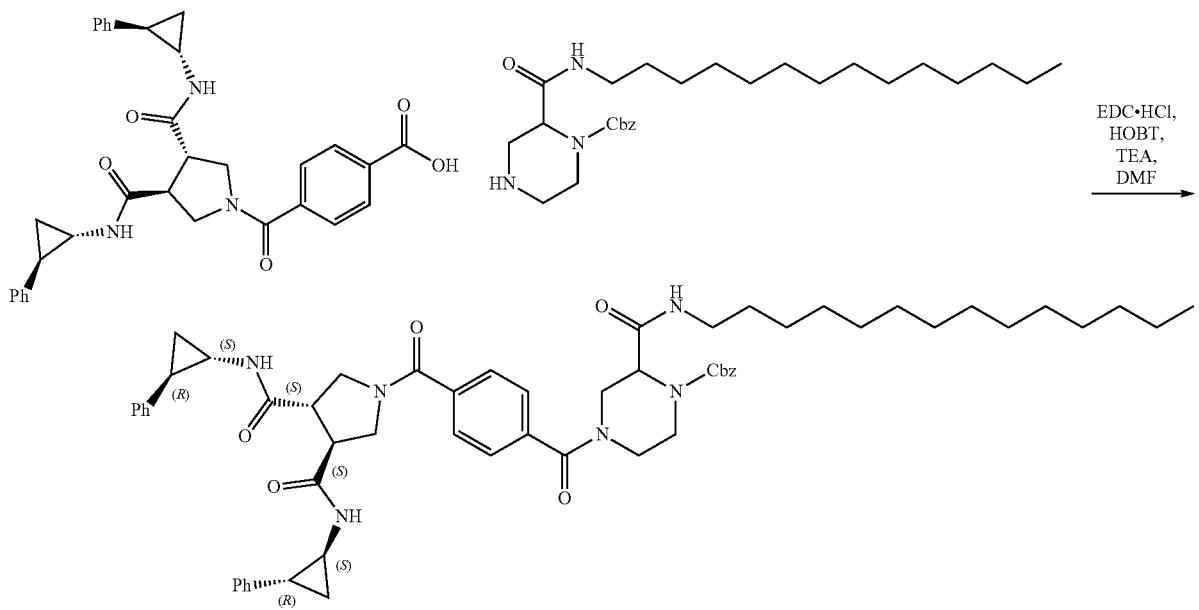

Prepared using a procedure similar to General EDC, HOBT Coupling Procedure. The crude product was purified using column chromatography eluting with Dichloromethane: Methanol (0-3%). (0.459 g, 63% yield). LCMS (Method-C3): 83.5% (RT: 2.694, 230 nm) (MS: ESI +ve 980.0 [M+1]).

Step-5: Preparation of (3S,4S)—N3,N4-bis((1S,2R)-2-phenylcyclopropyl)-1-(4-(3-(tetradecylcarbamoyl)piperazine-1-carbonyl)benzoyl)pyrrolidine-3,4-dicarboxamide, Compound 054

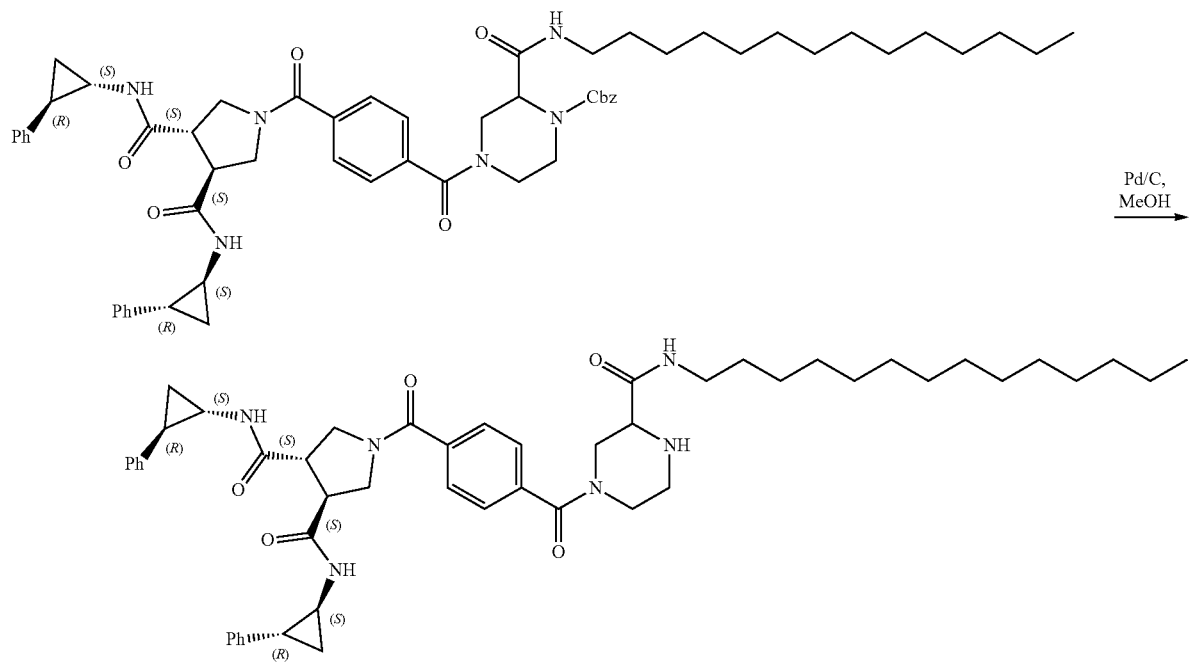

Benzyl-4-(4-((3S,4S)-3,4-bis(((1S,2R)-2-phenylcyclopropyl)carbamoyl)pyrrolidine-1-carbonyl)benzoyl)-2-(tetradecylcarbamoyl)piperazine-1-carboxylate (0.459 g, 0.468 mmol) was dissolved in methanol (7 mL). Pd/C (0.230 g) was added and the mixture was stirred under a hydrogen atmosphere for 5 hrs at room temperature. The reaction mixture was filtered through celite and rinsed with methanol. The combined filtrate was concentrated, and the crude residue was purified using column chromatography eluting with 0-10% dichloromethane in methanol to give (3S,4S)—N3,N4-bis((1S,2R)-2-phenylcyclopropyl)-1-(4-(3-(tetradecylcarbamoyl)piperazine-1-carbonyl)benzoyl)pyrrolidine-3,4-dicarboxamide, Compound 054, (0.108 g, 27.4% yield) as a mixture of diastereomers. LCMS (Method-J): 100% (RT: 5.247, 225.0 nm) (MS: ESI +ve 846.0 [M+1]). $^1$H NMR: (400 MHz, DMSO) δ ppm: 0.845-0.861 (m, 4H), 1.119-1.135 (m, 4H), 1.243 (s, 20H), 1.350 (s, 3H), 1.876-1.977 (m, 3H), 2.789-2.854 (m, 4H), 3.084-3.123 (m, 5H), 3.216 (s, 2H), 3.526 (s, 2H), 3.652-3.674 (m, 1H), 3.788-3.838 (m, 1H), 3.968 (s, 1H), 7.703-7.190 (m, 6H), 7.229-7.276 (m, 4H), 7.460 (s, 2H), 7.572-7.592 (m, 2H), 7.806-7.890 (d, J=33.6 Hz, 2H), 8.324-8.452 (m, 2H).

Example 8

Synthesis of (3S,4S)-1-(4-(3-(hexylcarbamoyl)piperazine-1-carbonyl)benzoyl)-N3,N4-bis((1S,2R)-2-phenylcyclopropyl)pyrrolidine-3,4-dicarboxamide formate, Compound 042

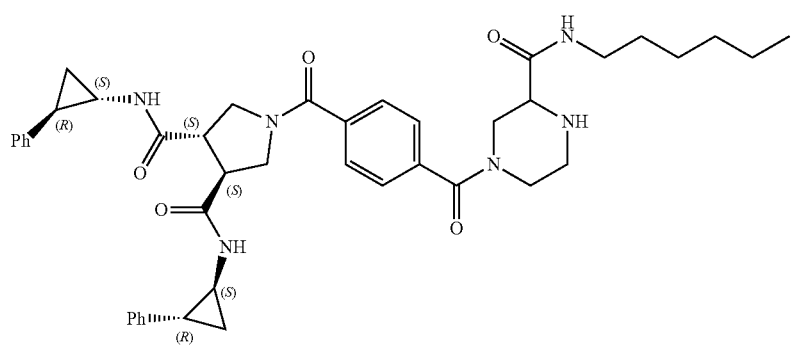

Prepared by a procedure similar to that reported for 3S,4S)—N3,N4-bis((1S,2R)-2-phenylcyclopropyl)-1-(4-(3-(tetradecylcarbamoyl)piperazine-1-carbonyl)benzoyl)pyrrolidine-3,4-dicarboxamide, Compound 054, substituting hexyl amine in step 1. The crude final product was purified using Prep HPLC Method 6 to give (3S,4S)-1-(4-(3-(hexylcarbamoyl)piperazine-1-carbonyl)benzoyl)-N3,N4-bis((1S,2R)-2-phenylcyclopropyl)pyrrolidine-3,4-dicarboxamide formate, Compound 042, as a mixture of diastereomers. LCMS (Method-C3): 100% (RT: 1.561, 222.0 nm) (MS: ESI +ve 733.86 [M+H]), $^1$H NMR: (400 MHz, DMSO) δ ppm: 0.8-0.9 (s, 3H), 1.05-1.15 (J=6 Hz, t, 3H), 1.15-1.35 (t, 8H), 1.84-1.91 (s, 1H), 1.94-2.01 (s, 1H), 2.78-2.88 (d, 2H), 2.95-3.15 (t, 5H), 3.15-3.23 (s, 2H), 3.48-3.56 (t, 2H), 3.62-3.70 (t, 1H), 3.78-3.88 (t, 1H), 3.91-4.00 (s, 1H), 4.32-4.46 (s, 1H), 7.05-7.32 (m, 10H), 7.4-7.52 (s, 2H), 7.55-7.62 (d, 2H), 7.78-7.91 (s, 1H), 8.3-8.38 (d, 1H), 8.42-8.49 (J=4 Hz, d, 1H).

Example 9

Synthesis of (3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019

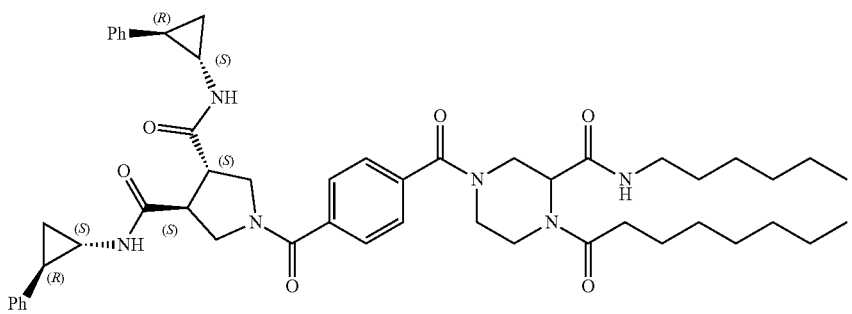

Step-1: Preparation of tert-butyl 3-(hexylcarbamoyl)-4-octanoylpiperazine-1-carboxylate

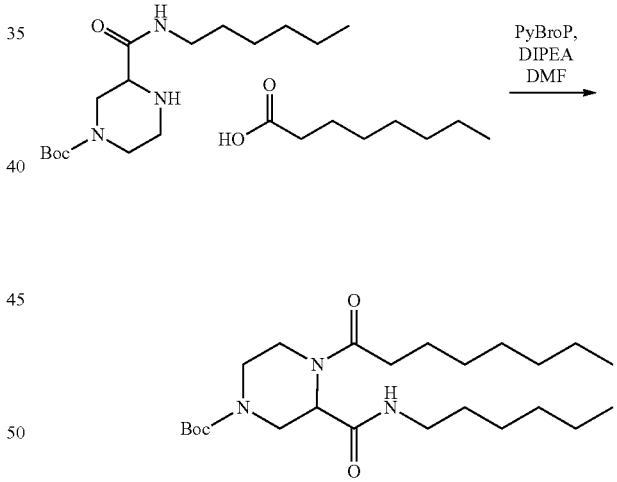

Prepared by a procedure similar to General PyBroP Coupling Procedure. The crude product was purified by column chromatography (Stationary phase-Basic alumina ($Al_2O_3$)) eluting at 55% ethyl acetate in hexane to give 3-(hexylcarbamoyl)-4-octanoylpiperazine-1-carboxylate (0.9 g, 64.17%). LCMS (Method-C3): 86.46% (RT: 2.106, 202.0 nm) (MS: ESI +ve 442.5 [M+1]). This step could also be achieved using the appropriate acid chloride, TEA and DMF.

Step 2: Synthesis of N-hexyl-1-octanoylpiperazine-2-carboxamide

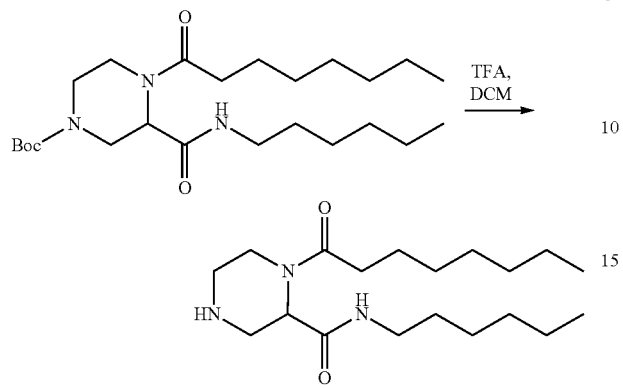

Prepared by a procedure similar to General Boc Deprotection Procedure. The crude residue was triturated with pentane to give N-hexyl-1-octanoylpiperazine-2-carboxamide (920 mg, crude). LCMS (Method-C3): 50.3% (RT: 1.625 min, 202 nm) (MS: ESI +ve 340.7 [M+1]).

Step-3: Preparation of ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019

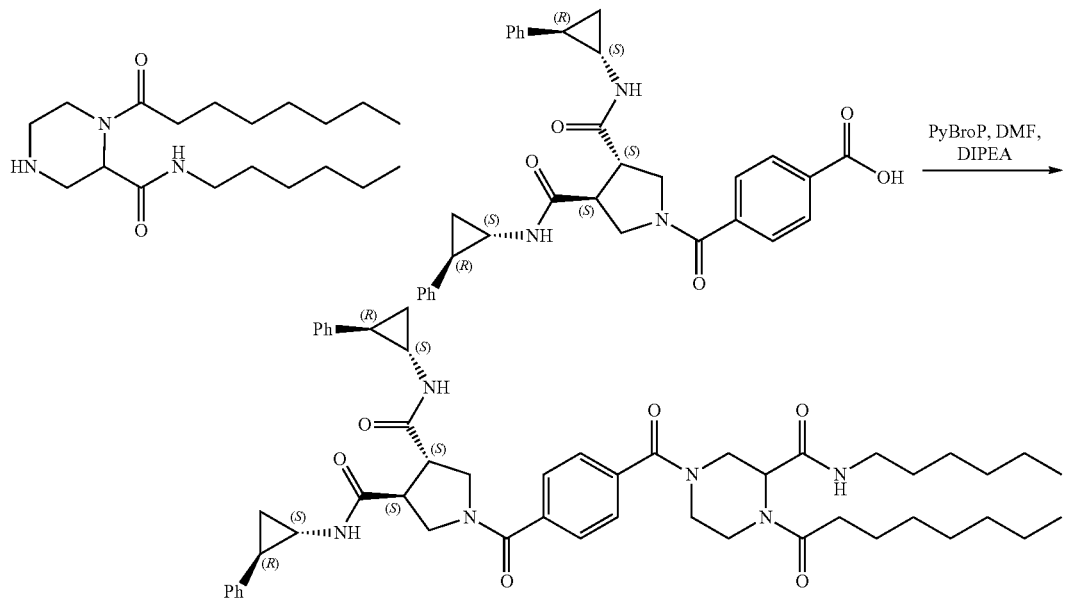

Prepared by a procedure similar to General PyBroP Coupling Procedure. The crude product was purified using Prep HPLC Method 1 to give ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (0.019 g, 11.92%), Compound 019. LCMS (Method-C3): 100% (RT 2.07, 202 nm) (MS: ESI +ve 860.6 [M+H]).
$^1$H NMR: (400 MHz, DMSO) δ ppm: 0.86 (m, 6H), 1.17 (s, 2H), 1.24 (m, 19H), 1.48 (s, 2H), 1.86-1.97 (m, 2H), 2.78 (m, 3H), 3.09-3.22 (m, 6H), 3.55 (m, 3H), 3.65 (m, 1H), 3.81 (m, 2H), 4.19 (m, 1H), 4.68 (m, 1H), 7.01-7.14 (m, 7H), 7.28 (m, 3H), 7.37-7.38 (d, J=4 Hz, 2H), 7.56-7.58 (d, J=8 Hz, 2H), 7.99 (m, 1H), 8.31 (m, 1H), 8.44 (m, 1H).

Example 10

Synthesis of (3S,4S)-1-(4-((R)-3-(hexylcarbamoyl)-4-octanoylpiperazine-1-carbonyl) benzoyl)-N3,N4-bis((1S,2R)-2-phenylcyclopropyl)pyrrolidine-3,4-dicarboxamide, Compound 032

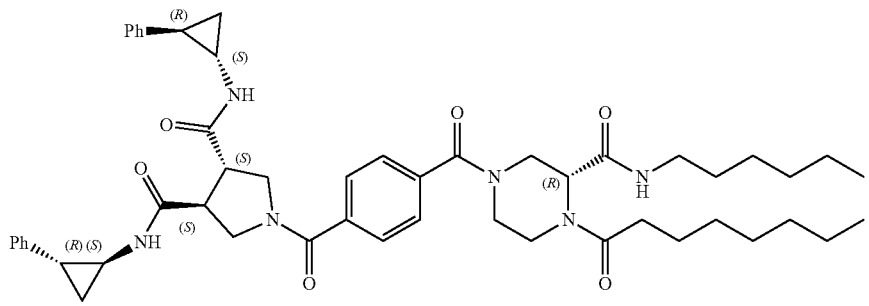

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting (R)-4-(tert-butoxycarbonyl)piperazine-2-carboxylic acid in the first step. The crude final product was purified using Prep HPLC Method 2 to give (3S,4S)-1-(4-((R)-3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 032, as a white solid (0.060 g, 37.64%). LCMS (Method-C3): 100% (RT 2.045, 226 nm) (MS: ESI +ve 860.8 [M+H]). $^1$H NMR: (400 MHz, DMSO) δ ppm: 0.86 (m, 6H), 1.09 (m, 2H), 1.20 (m, 19H), 1.49 (m, 2H), 1.87 (m, 1H), 1.98 (m, 1H), 2.34-2.39 (m, 1H), 2.79-2.86 (m, 2H), 3.08-3.23 (m, 6H), 3.51 (m, 3H), 3.66 (m, 1H), 3.79 (m, 1H), 3.82-3.84 (m, 1H), 4.19 (m, 1H), 4.39 (m, 1H), 4.70 (m, 1H), 7.07-7.08 (d, J=4 Hz, 2H), 7.12-7.19 (m, 4H), 7.23-7.29 (m, 4H), 7.37-7.39 (d, J=8 Hz, 2H), 7.57-7.59 (d, J=8 Hz, 2H), 7.73-8.01 (m, 1H), 8.32-8.33 (d, J=4 Hz, 1H), 8.45-8.46 (d, J=4 Hz, 1H).

Example 11

Synthesis of (3S,4S)-1-(4-(4-(3-(4-fluorophenyl)propanoyl)-3-(hexylcarbamoyl) piperazine-1-carbonyl)benzoyl)-N3,N4-bis((1S,2R)-2-phenylcyclopropyl)pyrrolidine-3,4-dicarboxamide, Compound 041

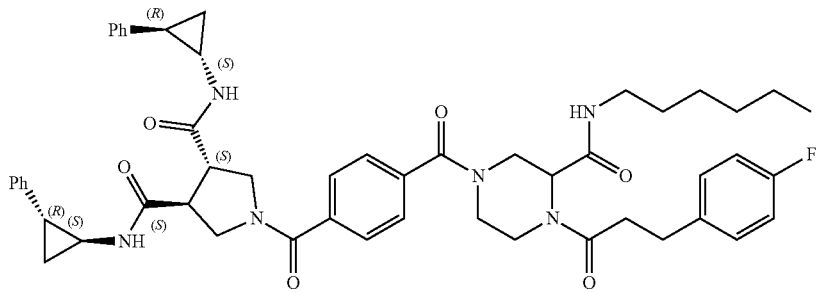

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting 3-(4-fluorophenyl)propanoic acid in step 1. The crude compound was purified on Stationary Phase-Basic alumina; Eluent-3% Methanol: Dichloromethane to give (3S,4S)-1-(4-(4-(3-(4-fluorophenyl)propanoyl)-3-(hexylcarbamoyl) piperazine-1-carbonyl)benzoyl)-N3,N4-bis((1S,2R)-2-phenylcyclopropyl)pyrrolidine-3,4-dicarboxamide, Compound 041. LCMS (Method-C3) 100% (RT 1.91, 308 nm) (MS: ESI +ve 883.5 [M+H]). $^1$H NMR: (400 MHz, DMSO) δ ppm: 0.835 (t, 4H), 1.11-1.23 (m, 12H), 1.56 (s, 1H), 1.86 (t, 1H), 1.97 (t, 1H), 2.67-2.84 (m, 6H), 2.89-3.22 (m, 6H), 3.51 (m, 3H), 3.52-3.54 (t, 3H), 3.78 (t, 1H), 4.18 (s, 1H), 4.7 (s, 1H), 7.06-7.09 (m, 3H), 7.11-7.16 (m, 4H), 7.18-7.28 (m, 6H), 7.36-7.38 (d, 2H J=8 Hz), 7.56-7.58 (d, 2H J=8 Hz), 7.75 (s, 1 Hz), 8.00 (s, 1H), 8.32 (s, 1H), 8.44-8.45 (d, 1H).

Example 12

Synthesis of (3S,4S)-1-(4-(4-butyryl-3-(hexylcarbamoyl)piperazine-1-carbonyl)benzoyl)-N3,N4-bis((1S,2R)-2-phenylcyclopropyl)pyrrolidine-3,4-dicarboxamide, Compound 055

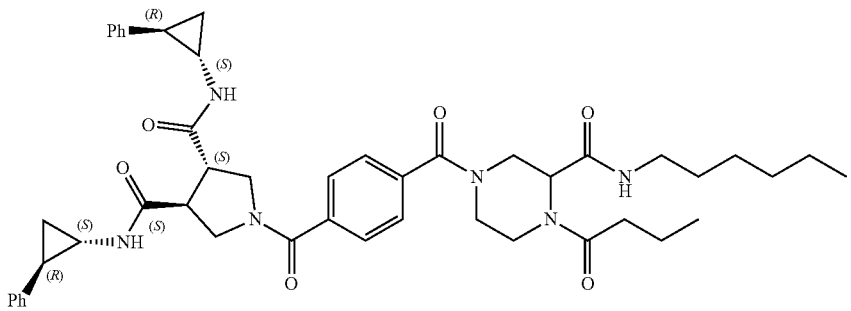

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting butyryl chloride in step 1. The crude final product was purified using Prep HPLC Method 1 to afford (3S,4S)-1-(4-(4-butyryl-3-(hexylcarbamoyl)piperazine-1-carbonyl)benzoyl)-N3,N4-bis((1S,2R)-2-phenylcyclopropyl)pyrrolidine-3,4-dicarboxamide, Compound 055, as a mixture of diastereomers (0.010 g, 06%). LCMS (Method-C3): 100% (RT 1.716, 202.0 nm) (MS: ESI +ve 803.8 [M+H]). $^1$H NMR: (400 MHz, DMSO) δ ppm: 0.86-0.84 (m, 6H), 1.20-1.04 (m, 14H), 1.53-1.50 (t, 2H), 1.95 (s, 1H), 1.99 (s, 1H), 2.86 (m, 4H), 3.18-3.12 (m, 6H), 3.64 (t, 3H), 3.66-3.64 (t, 2H), 3.92-3.79 (m, 3H), 4.13 (s, 1H), 7.23-7.01 (m, 6H), 7.29-7.25 (m, 4H), 7.37 (d, 2H), 8.01-7.74 (br s, 1H), 8.34 (d, 1H), 8.46 (d, 1H).

Example 13

Synthesis of (3S,4S)-1-(4-(4-hexanoyl-3-(hexylcarbamoyl)piperazine-1-carbonyl) benzoyl)-N3,N4-bis((1S,2R)-2-phenylcyclopropyl)pyrrolidine-3,4-dicarboxamide, Compound 050

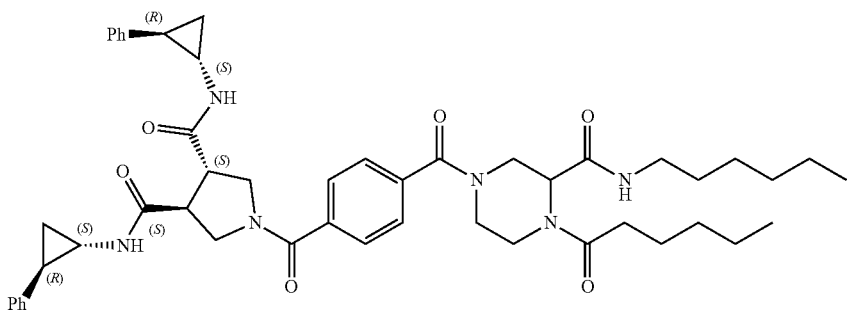

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting hexanoyl chloride in step 1. The crude final product was purified using Prep HPLC Method 6 to afford (3S,4S)-1-(4-(4-hexanoyl-3-(hexylcarbamoyl)piperazine-1-carbo- nyl)benzoyl)-N3,N4-bis((1S,2R)-2-phenylcyclopropyl)pyrrolidine-3,4-dicarboxamide, Compound 050, (19.67 mg, 12.73%) as a mixture of diastereomers. LCMS: RT-1.95, 100%, 230 nm (MS: ESI +ve 832.5 [M+H]. $^1$H NMR: (400 MHz, DMSO) δ ppm: 0.85 (m, 6H), 1.11-1.49 (m, 17H), 1.86 (t, 1H), 1.97 (t, 2H), 2.67-2.85 (m, 3H), 3.09-3.22 (m, 5H), 3.33 (s, 1H) 3.50-3.52 (d, 3H J=8 Hz), 3.65 (m, 2H), 3.81 (t, 2H), 7.06-7.16 (m, 5H), 7.24-7.26 (m, 3H, J=6.8 Hz), 7.37-7.39 (d, 3H), 7.90-8.0 (s, 1H) 8.31 (s, 1H), 8.42 (s, 1H).

Example 14

Synthesis of (3S,4S)-1-(4-(4-heptanoyl-3-(hexylcarbamoyl)piperazine-1-carbonyl) benzoyl)-N3,N4-bis ((1S,2R)-2-phenylcyclopropyl)pyrrolidine-3,4-dicarboxamide, Compound 056

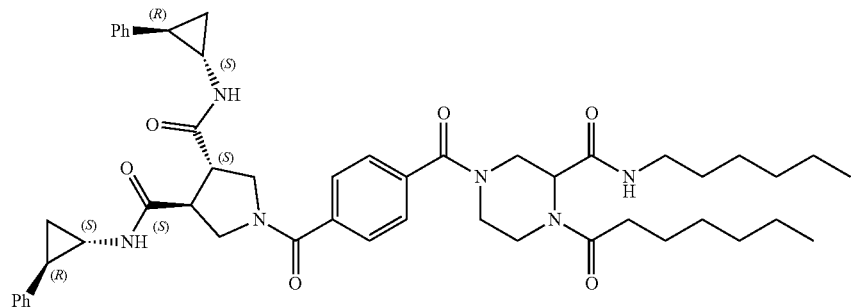

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting heptanoyl chloride in step 1. The crude final product was purified using Prep HPLC Method 2 to afford (3S,4S)-1-(4-(4-heptanoyl-3-(hexylcarbamoyl)piperazine-1-carbonyl)benzoyl)-N3,N4-bis((1S,2R)-2-phenylcyclopropyl)pyrrolidine-3,4-dicarboxamide, Compound 056, as a mixture of diastereomers (0.023 g, 15%). LCMS (Method-C3): 100% (RT 1.996, 230.0 nm) (MS: ESI +ve 845.0 [M+H]). $^1$H NMR: (400 MHz, DMSO) δ ppm: 0.85-0.67 (m, 8H), 1.26-1.11 (m, 20H), 1.47 (s, 2H), 1.86 (s, 1H), 1.97 (s, 1H), 2.33 (s, 1H), 2.89-2.73 (m, 3H), 3.11 (d, 3H), 3.20-3.17 (d, 1H), 3.50 (s, 2H), 3.65 (t, 1H), 3.83-3.78 (t, 2H), 4.04 (s, 1H), 4.69 (s, 1H), 7.18-7.06 (m, 6H), 7.26-7.25 (m, 4H), 7.38-7.37 (d, 2H), 7.58-7.56 (d, 2H), 7.95-7.72 (br s, 1H), 8.32 (s, 1H), 8.44 (s, 1H).

Example 15

Synthesis of (3S,4S)-1-(4-(4-octanoyl-3-(pentylcarbamoyl)piperazine-1-carbonyl)benzoyl)-N3,N4-bis ((1S,2R)-2-phenylcyclopropyl)pyrrolidine-3,4-dicarboxamide, Compound 052

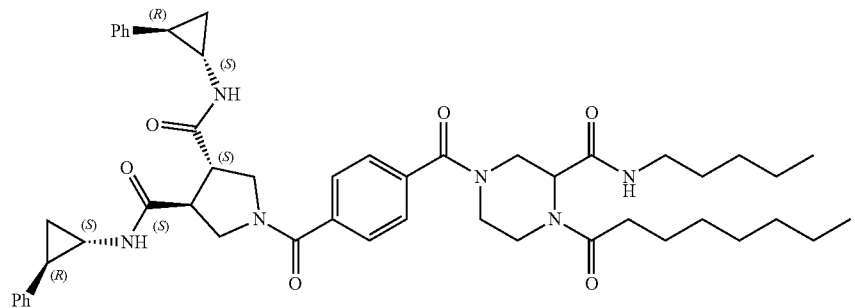

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting octanoyl chloride in step 1. The crude final product was purified using Prep HPLC Method 8 to afford (3S,4S)-1-(4-(4-octanoyl-3-(pentylcarbamoyl)piperazine-1-carbonyl)benzoyl)-N3,N4-bis((1S,2R)-2-phenylcyclopropyl)pyrrolidine-3,4-dicarboxamide, Compound 052, as a mixture of diastereomers (0.010 g, 06%). LCMS (Method-C3): 100% (RT 1.716, 202.0 nm) (MS: ESI +ve 803.8 [M+H]) $^1$H NMR: (400 MHz, DMSO) δ ppm: 0.814-0.866 (m, 7H), 1.115-1.125 (m, 19H), 1.4-1.58 (s, 4H), 1.84-2.02 (s, 2H), 2.78-2.92 (s, 3H), 3.05-3.25 (m, 5H), 3.48-3.85 (m, 4H), 4.15-4.25 (s, 1H), 4.65-4.75 (s, 1H), 7.05-7.31 (m, 1 OH), 7.32-7.42 (d, 2H), 7.5-7.65 (d, 2H), 7.72-7.78 (s, 1H), 8.3-8.5 (s, 1H)

Example 16

Synthesis of (3S,4S)-1-(4-(3-(hexylcarbamoyl)-4-nonanoylpiperazine-1-carbonyl) benzoyl)-N3,N4-bis ((1S,2R)-2-phenylcyclopropyl)pyrrolidine-3,4-dicarboxamide, Compound 051

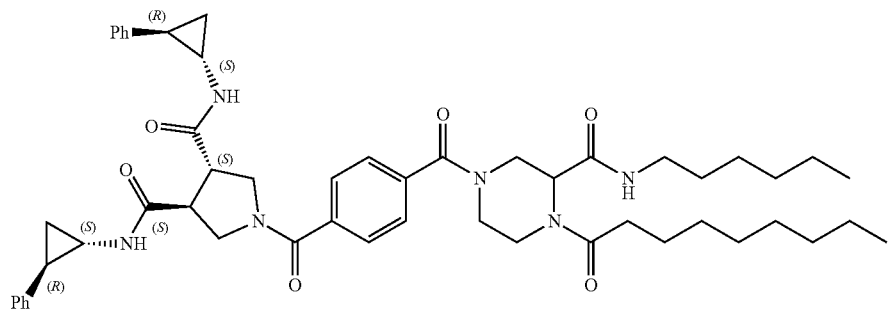

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting nonanoyl chloride in step 1. The crude final product was purified using Prep HPLC Method 6 to afford (3S,4S)-1-(4-(3-(hexylcarbamoyl)-4-nonanoylpiperazine-1-carbonyl)benzoyl)-N3,N4-bis((1S,2R)-2-phenylcyclopropyl) pyrrolidine-3,4-dicarboxamide, Compound 051, (19.67 mg, 12.73%). LCMS: RT-2.11, 100%, 230 nm (MS: ESI +ve 874.1 [M+H]. $^1$H NMR: (400 MHz, DMSO) δ ppm: 0.84-0.86 (m, 6H), 1.11-1.25 (m, 27H), 1.48 (s, 2H) 1.86 (s, 1H), 1.97 (s, 1H), 2.33-2.38 (s, 1H) 2.78-2.85 (m, 3H), 3.09-3.22 (m, 5H), 3.33 (s, 1H) 3.50-3.55 (m, 3H J=8.6 Hz), 3.63-3.67 (m, 2H), 3.78-3.92 (t, 1H), 4.18 (s, 1H), 4.69 (s, 1H) 7.06-7.08 (d, 2H J=7.2 Hz), 7.11-7.18 (q, 4H) 7.22-7.28 (q, 4H) 7.37-7.38 (d, 2H), 7.56-7.58 (d, 2H) 7.28-8.01 (s, 1H) 8.34 (s, 1H), 8.45 (d, 1H).

Example 17

Synthesis of (3S,4S)-1-(4-(4-decanoyl-3-(hexylcarbamoyl)piperazine-1-carbonyl)benzoyl)-N3,N4-bis ((1S,2R)-2-phenylcyclopropyl)pyrrolidine-3,4-dicarboxamide, Compound 064

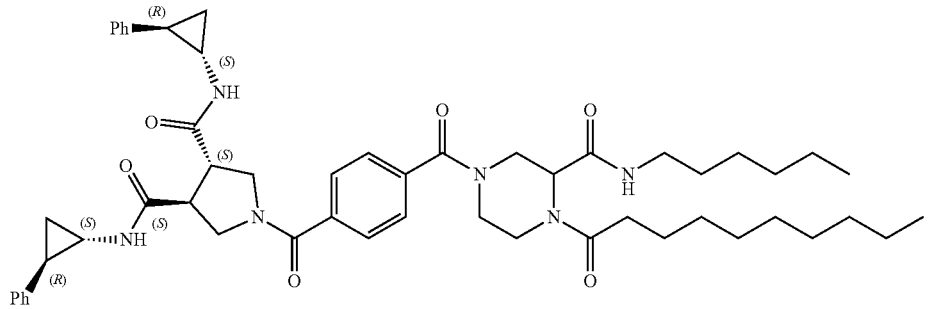

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting decanoyl chloride in step 1. The crude final product was purified using Prep HPLC Method 6 to afford (3S,4S)-1-(4-(4-decanoyl-3-(hexylcarbamoyl) piperazine-1-carbonyl) benzoyl)-N3,N4-bis((1S,2R)-2-phenylcyclopropyl)pyrrolidine-3,4-dicarboxamide, Compound 064, as a mixture of diastereomers (0.04 g, 18.2%). LCMS (Method-C3): 96.7% (RT 6.051, 202.0 nm) (MS: ESI +ve 888 [M+H]). $^1$H NMR: (400 MHz, DMSO) δ ppm: 0.86 (s, 6H); 1.12-1.14 (d, J=6, 3H); 1.26 (s, 21H); 1.87 (s, 3H); 2.79 (s, 3H); 3.10-3.12 (d, J=7.6, 3H); 3.19-3.21 (d, J=8.8, 2H); 3.53 (s, 3H); 3.65 (s, 2H); 3.78-3.83 (m, 1H); 4.69 (s, 1H); 7.07-7.09 (d, J=7.6, 2H); 7.12-7.19 (m, 4H); 7.23-7.29 (m, 4H); 7.37-7.39 (d, J=6.4, 2H); 7.57-7.59 (d, J=6.4, 2H); 8.009 (s, 1H); 8.44 (s, 1H).

Example 18

Synthesis of (3S,4S)-1-(4-(4-dodecanoyl-3-(hexylcarbamoyl)piperazine-1-carbonyl) benzoyl)-N3,N4-bis((1S,2R)-2-phenylcyclopropyl)pyrrolidine-3,4-dicarboxamide, Compound 057

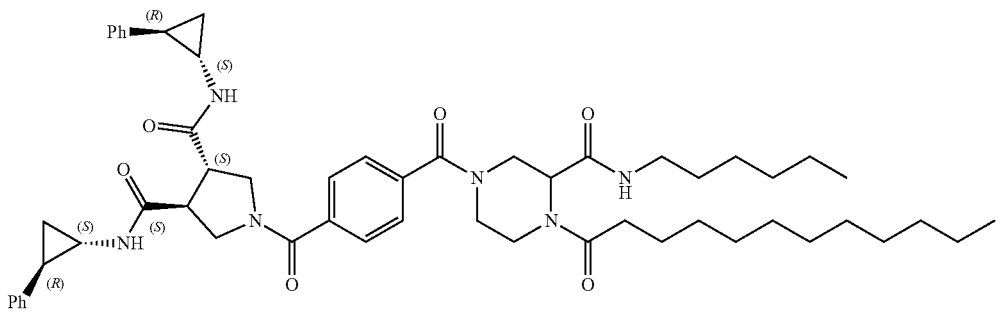

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 019, substituting dodecanoyl chloride in step 1. The crude final product was purified using Prep HPLC Method 6 to afford (3S,4S)-1-(4-(4-dodecanoyl-3-(hexylcarbamoyl)piperazine-1-carbonyl)benzoyl)-N3,N4-bis((1S,2R)-2-phenylcyclopropyl)pyrrolidine-3,4-dicarboxamide, Compound 057, as a white solid (0.026 g, 16.06%). LCMS (Method-C): 95.71% (RT 2.508, 202 nm) (MS: ESI +ve 916.7 [M+H]). $^1$H NMR: (400 MHz, DMSO) δ ppm: 0.84 (m, 6H), 1.24 (m, 31H), 1.47 (m, 3H), 1.89 (s, 1H), 1.98 (s, 2H), 2.78 (m, 1H), 2.85 (m, 2H), 3.09-3.11 (m, 3H), 3.18-3.20 (m, 2H), 3.51 (m, 1H), 3.50 (m, 2H), 4.21 (m, 1H), 4.71 (m, 1H), 7.06-7.08 (m, 2H), 7.11-7.18 (m, 4H), 7.22-7.28 (m, 4H), 7.36-7.38 (d, J=8 Hz, 2H), 7.56-7.58 (d, J=8 Hz, 2H), 8.40 (s, 1H), 8.51 (s, 2H).

Synthesis of (3S,4S)—N3,N4-bis((1S,2R)-2-phenylcyclopropyl)-1-(4-((S)-4-pivaloyl-3-(tetradecylcarbamoyl)piperazine-1-carbonyl)benzoyl)pyrrolidine-3,4-dicarboxamide, Compound 251

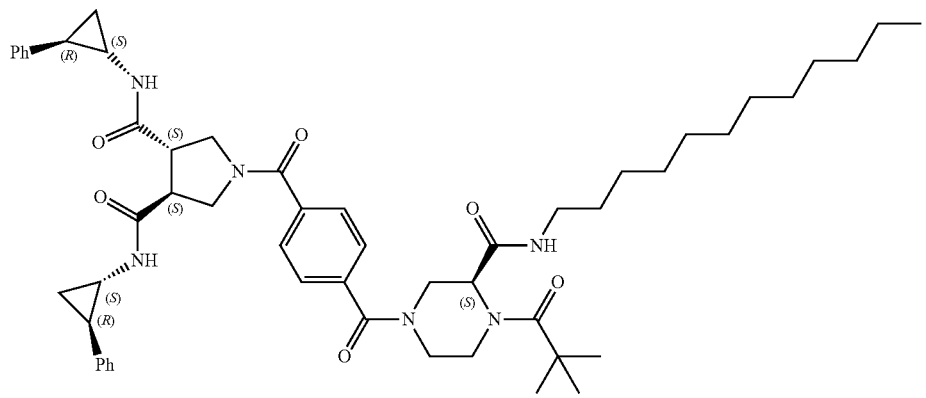

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 10 to give (3S,4S)—N3,N4-bis((1S,2R)-2-phenylcyclopropyl)-1-(4-((S)-4-pivaloyl-3-(tetradecylcarbamoyl)piperazine-1-carbonyl)benzoyl)pyrrolidine-3,4-dicarboxamide (Compound 251) (0.050 g, 19%) as an off white solid. LCMS (Method-J): 97.14% (RT 5.302, 222.0 nm) (MS: ESI +ve 930.6 [M+H]). ¹H NMR: (400 MHz, DMSO) δ ppm: 0.85-0.87 (m, 3H), 1.12-1.22 (m, 36H), 1.88 (s, 1H), 1.97 (s, 1H), 2.79 (s, 1H), 2.85 (s, 1H), 3.02 (bs, 2H), 3.12 (m, 2H), 3.18-3.20 (m, 2H), 3.53 (bs, 3H), 3.64 (bs, 2H), 3.79 (s, 1H), 3.99 (s, 1H), 4.17 (s, 1H), 4.67 (s, 1H), 7.06-7.08 (m, 2H), 7.12-7.16 (m, 4H), 7.22-7.27 (m, 4H), 7.37-7.39 (m, 2H), 7.56-7.58 (m, 2H), 7.80-8.00 (bs, 1H), 8.44 (bs, 1H), 8.51 (s, 1H).

Synthesis of (3S,4S)-1-(4-((S)-4-isobutyryl-3-(tetradecylcarbamoyl)piperazine-1-carbonyl)benzoyl)-N3,N4-bis((1S,2R)-2-phenylcyclopropyl)pyrrolidine-3,4-dicarboxamide, Compound 250

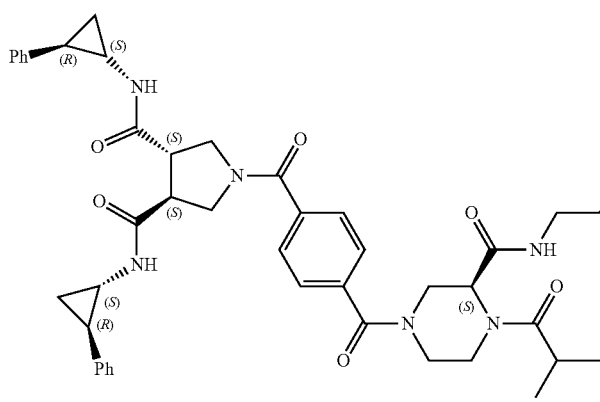
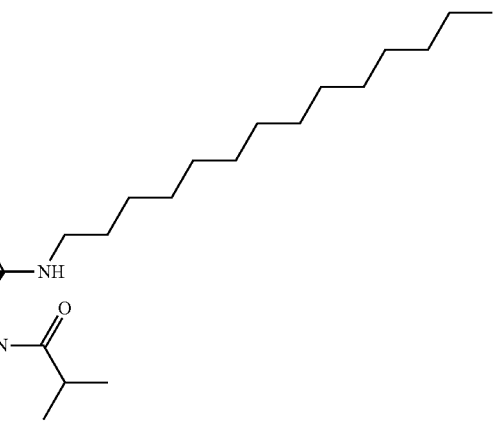

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 13 to give (3S,4S)-1-(4-((S)-4-isobutyryl-3-(tetradecylcarbamoyl)piperazine-1-carbonyl)benzoyl)-N3,N4-bis((1S,2R)-2-phenylcyclopropyl)pyrrolidine-3,4-dicarboxamide (Compound 250) (0.030 g, 11.75%), as an off white solid. LCMS (Method-J): 100% (RT 4.848, 202.0 nm) (MS: ESI +ve 915.23[M+H]). ¹H NMR: (400 MHz, DMSO) δ ppm: 0.83-1.22 (m, 37H), 2.85 (s, 3H), 3.09-3.20 (m, 4H), 3.51-3.93 (m, 8H), 4.69 (s, 1H), 7.06-7.26 (m, 12H), 7.37-7.38 (d, J=7.2 Hz, 2H), 7.56-7.58 (d, J=6.8 Hz, 2H), 8.42-8.52 (m, 3H).

Synthesis of (3S,4S)-1-(4-((S)-4-(3-methylbutanoyl)-3-(tetradecylcarbamoyl)piperazine-1-carbonyl)benzoyl)-N3,N4-bis((1S,2R)-2-phenylcyclopropyl)pyrrolidine-3,4-dicarboxamide, Compound 252

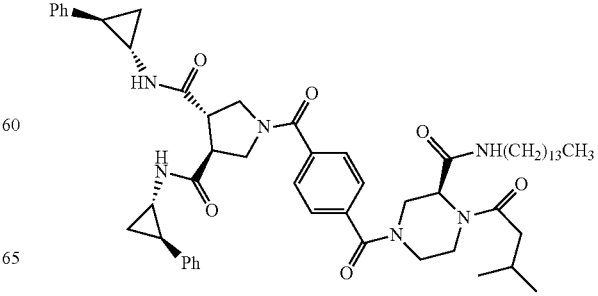

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 13 to give (3S,4S)-1-(4-((S)-4-(3-methylbutanoyl)-3-(tetradecylcarbamoyl)piperazine-1-carbonyl)benzoyl)-N3,N4-bis((1S,2R)-2-phenylcyclopropyl)pyrrolidine-3,4-dicarboxamide (Compound 252)(0.028 g, 10.96%), as an off white solid. LCMS (Method-J): 100% (RT 4.961, 235.0 nm) (MS: ESI +ve 929.7[M+H]). $^1$H NMR: (400 MHz, DMSO) δ ppm: 0.86-0.92 (d, J=22.8 Hz, 9H), 1.29-1.23 (m, 32H), 1.88 (s, 1H), 1.99 (s, 2H), 2.28 (s, 2H), 2.80-2.86 (d, J=26 Hz, 2H), 3.05-3.33 (m, 3H), 3.54 (s, 2H), 3.64-3.66 (d, J=7.6 Hz, 1H), 3.80-3.85 (t, J=11.6 Hz, 2H), 4.19-4.21 (t, J=2.8 Hz, 1H), 4.70-4.71 (d, J=6.8 Hz, 1H), 7.08-7.28 (m, 6H), 7.38-7.40 (d, J=7.2 Hz, 10H), 7.57-7.59 (d, J=6.4 Hz, 2H), 8.31-8.43 (m, 2H).

Synthesis of (3S,4S)-1-(4-((S)-4-(3,3-dimethylbutanoyl)-3-(tetradecylcarbamoyl)piperazine-1-carbonyl)benzoyl)-N3,N4-bis((1S,2R)-2-phenylcyclopropyl)pyrrolidine-3,4-dicarboxamide, Compound 253

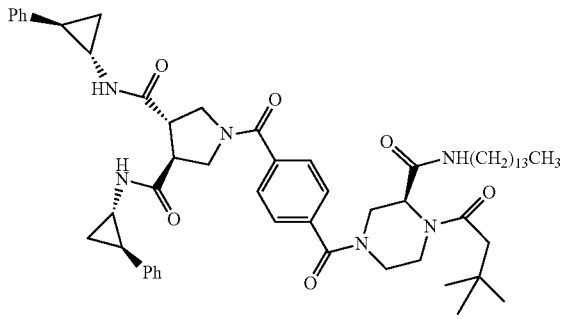

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 10 to give (3S,4S)-1-(4-((S)-4-(3,3-dimethylbutanoyl)-3-(tetradecylcarbamoyl)piperazine-1-carbonyl)benzoyl)-N3,N4-bis((1S,2R)-2-phenylcyclopropyl)pyrrolidine-3,4-dicarboxamide (Compound 253) (0.080 g, 30%), as an off white solid. LCMS (Method-J): 100% (RT 5.089, 220.0 nm) (MS: ESI +ve 943.8 [M+H]). $^1$H NMR: (400 MHz, DMSO) δ ppm: 0.84-0.86 (m, 3H), 1.00 (s, 9H), 1.12-1.23 (m, 32H), 1.86-1.88 (m, 1H), 1.97-1.98 (m, 1H), 2.32-2.34 (m, 2H), 2.79-2.80 (m, 1H), 2.86 (bs, 1H), 3.06-3.13 (m, 3H), 3.17-3.23 (m, 1H), 3.52-3.54 (m, 2H), 3.66 (bs, 2H), 3.79-3.84 (m, 2H), 3.91 (s, 1H), 4.19 (s, 1H), 4.73 (s, 1H), 7.07-7.09 (m, 2H), 7.13-7.19 (m, 4H), 7.23-7.30 (m, 4H), 7.37-7.39 (m, 2H), 7.57-7.59 (m, 2H), 7.70-8.00 (bs, 1H), 8.35 (s, 1H), 8.47 (s, 1H).

Synthesis of (3S,4S)-1-(4-((S)-4-acetyl-3-(heptylcarbamoyl)piperazine-1-carbonyl) benzoyl)-N3,N4-bis((1S,2R)-2-phenylcyclopropyl)pyrrolidine-3,4-dicarboxamide, Compound 258

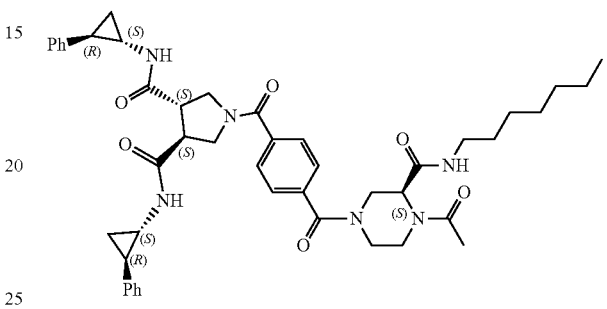

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 12 to give (3S,4S)-1-(4-((S)-4-acetyl-3-(heptylcarbamoyl)piperazine-1-carbonyl)benzoyl)-N3,N4-bis((1S,2R)-2-phenylcyclopropyl)pyrrolidine-3,4-dicarboxamide (Compound 258) (0.032 g, 10.2%), as a white solid. LCMS (Method-C fast): 98.3% (RT: 1.234, 225.0 nm) (MS: ESI +ve 789.5 [M+1]). $^1$H NMR: (400 MHz, DMSO) δ ppm: 0.834 (s, 3H), 1.098-1.212 (m, 14H), 1.576 (s, 3H), 1.869 (s, 1H), 1.929-1.976 (m, 2H), 2.079 (s, 2H), 2.675 (s, 1H), 2.787 (s, 4H), 3.078-3.118 (m, 3H), 3.137-3.209 (m, 2H), 3.509-3.556 (m, 4H), 3.627-3.671 (m, 2H), 3.773-3.960 (t, J=74.8 Hz, 2H), 4.187 (s, 2H), 4.703 (s, 1H), 7.065-7.183 (m, 5H), 7.224-7.287 (m, 4H), 7.377-7.396 (d, 2H), 7.562-7.581 (d, J=7.6 Hz, 2H), 7.785 (s, 1H), 8.389-8.501 (m, 3H).

Synthesis of (3S,4S)-1-(4-((S)-4-acetyl-3-(tridecylcarbamoyl)piperazine-1-carbonyl) benzoyl)-N3,N4-bis((1S,2R)-2-phenylcyclopropyl)pyrrolidine-3,4-dicarboxamide, Compound 254

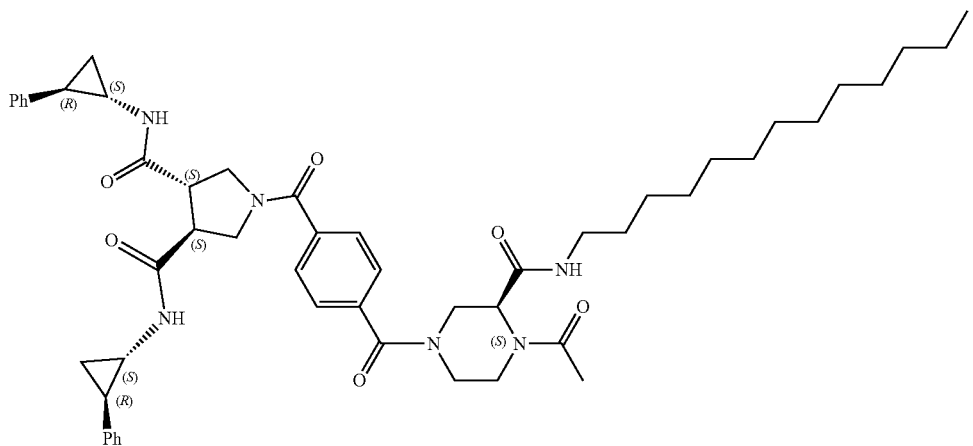

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 12 to give (3S,4S)-1-(4-((S)-4-acetyl-3-(tridecylcarbamoyl)piperazine-1-carbonyl)benzoyl)-N3,N4-bis((1S,2R)-2-phenylcyclopropyl)pyrrolidine-3,4-dicarboxamide (Compound 254) (0.058 g, 20.2%), as a white solid. LCMS (Method-H): 100% (RT: 4.148, 202.0 nm) (MS: ESI +ve 874.5 [M+1]). $^1$H NMR: (400 MHz, DMSO) δ ppm: 0.837-0.868 (m, 2H), 1.182-1.251 (m, 18H), 1.782 (s, 1H), 1.875 (m, 3H), 1.937-1.981 (m, 3H), 2.089 (s, 4H), 2.684 (s, 2H), 2.790 (s, 2H), 3.070-3.104 (m, 4H), 3.190-3.211 (m, 2H), 3.512-3.532 (m, 3H), 3.640-3.662 (m, 2H), 3.791-3.975 (m, 2H), 4.190 (m, 3H), 4.703 (s, 2H), 7.072-7.091 (m, 2H), 7.126-7.172 (m, 4H), 7.231-7.277 (m, 4H), 7.383-7.402 (m, 2H), 7.569-7.587 (m, 2H), 7.776 (s, 1H), 7.988 (s, 1H), 8.327-8.445 (dd, 3H).

Synthesis of (3S,4S)-1-(4-((S)-4-acetyl-3-(dodecylcarbamoyl)piperazine-1-carbonyl)benzoyl)-N3,N4-bis((1S,2R)-2-phenylcyclopropyl)pyrrolidine-3,4-dicarboxamide, Compound 255

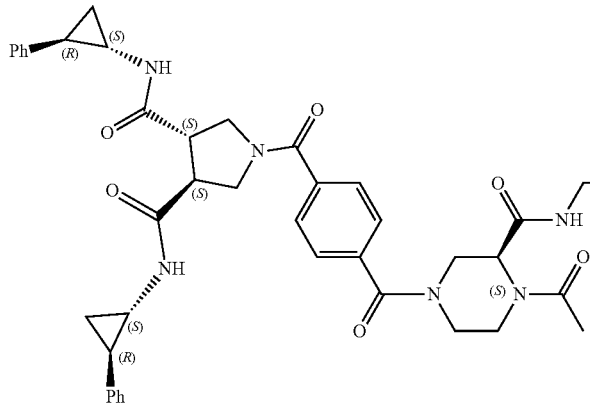
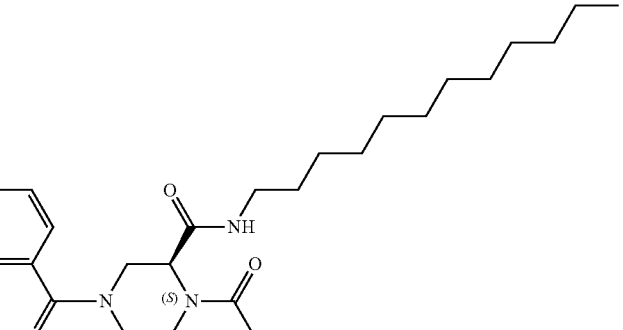

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 12 to give (3S,4S)-1-(4-((S)-4-acetyl-3-(dodecylcarbamoyl)piperazine-1-carbonyl)benzoyl)-N3,N4-bis((1S,2R)-2-phenylcyclopropyl)pyrrolidine-3,4-dicarboxamide (Compound 255), as an off white solid (0.16 g, 31.6%). LCMS (Method-C2): 100% (RT 1.520, 202.0 nm) (MS: ESI +ve 859.7 [M+H]). $^1$H NMR: (400 MHz, DMSO) δ ppm: 0.83-0.87 (m, 6H), 1.12-1.35 (m, 21H), 1.78-2.08 (m, 4H), 2.67-2.86 (m, 2H), 3.10-3.21 (m, 5H), 3.46-3.56 (m, 4H), 3.64-3.68 (m, 2H), 3.79-3.84 (m, 2H), 3.98 (bs, 1H), 4.19 (bs, 1H), 4.70 (bs, 1H), 7.07-7.09 (d, J=7.2 Hz, 2H), 7.12-7.19 (m, 4H), 7.23-7.29 (m, 4H), 7.38-7.40 (d, J=7.6 Hz, 2H), 7.57-7.59 (d, J=7.6 Hz, 2H), 7.78-8.03 (m, 1H), 8.33 (m, 1H), 8.44-8.45 (d, J=3.6 Hz, 1H).

Synthesis of (3S,4S)-1-(4-((S)-4-acetyl-3-(undecylcarbamoyl) piperazine-1-carbonyl) benzoyl)-N3,N4-bis((1S,2R)-2-phenylcyclopropyl) pyrrolidine-3,4-dicarboxamide, Compound 256

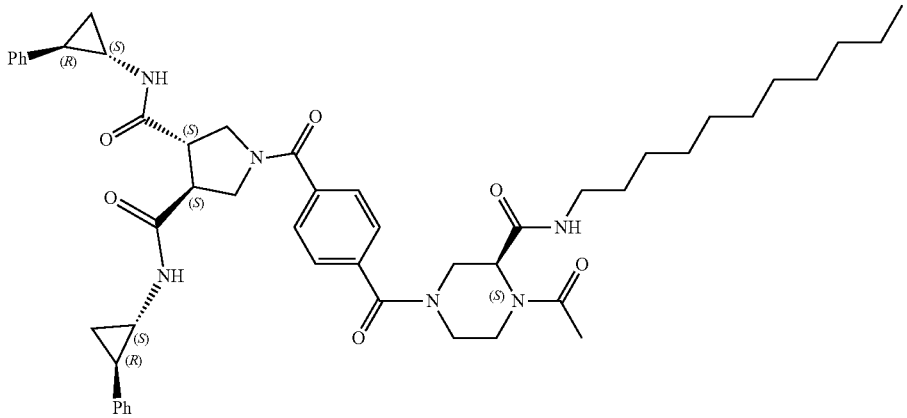

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 13 to give (3S,4S)-1-(4-((S)-4-acetyl-3-(undecylcarbamoyl) piperazine-1-carbonyl) benzoyl)-N3,N4-bis((1S,2R)-2-phenylcyclopropyl) pyrrolidine-3,4-dicarboxamide (Compound 256), as a white solid (0.041 g, 13.5%). LCMS (Method-C-Fast): 98.5% (RT: 1.884, 222.0 nm) (MS: ESI +ve 846.0 [M+H]). $^1$H NMR: (400 MHz, DMSO) δ ppm: 0.83-0.85 (d, J=6.8, 3H); 1.22 (s, 21H); 1.88 (s, 1H); 1.94 (s, 2H); 2.08 (s, 2H); 2.86 (s, 4H); 3.10-3.12 (d, J=8, 3H); 3.17-3.21 (t, 2H); 3.51-3.56 (m, 3H); 3.64-3.65 (d, J=7.6, 2H); 3.78-3.83 (t, 2H); 3.97 (s, 1H); 4.18 (s, 1H); 4.70 (s, 1H); 7.07-7.14 (m, 3H); 7.17-7.19 (m, 4H); 7.23-7.29 (m, 4H); 7.38-7.40 (d, J=7.2, 2H); 7.57-7.59 (d, J=7.2, 2H); 8.38 (s, 1H); 8.49 (s, 1H).

Synthesis of (3S,4S)-1-(4-((S)-4-acetyl-3-(nonylcarbamoyl)piperazine-1-carbonyl)benzoyl)-N3,N4-bis ((1S,2R)-2-phenylcyclopropyl)pyrrolidine-3,4-dicarboxamide, Compound 257

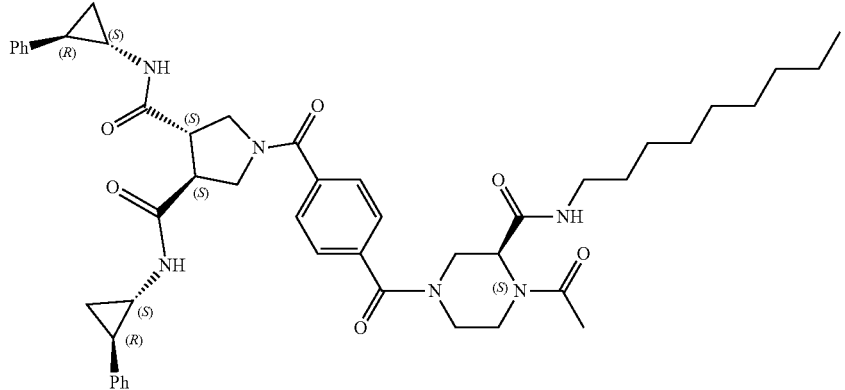

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 10 to give (3S,4S)-1-(4-((S)-4-acetyl-3-(nonylcarbamoyl)piperazine-1-carbonyl)benzoyl)-N3,N4-bis((1S,2R)-2-phenylcyclopropyl)pyrrolidine-3,4-dicarboxamide (Compound 257), as an off white solid (0.075 g, 21%). LCMS (Method-C2): 100% (RT 1.386, 222.0 nm) (MS: ESI +ve 817.81 [M+H]). $^1$H NMR: (400 MHz, DMSO) δ ppm: 0.82-0.84 (m, 3H), 1.11-1.21 (m, 18H), 1.87-2.09 (m, 5H), 2.78-2.85 (m, 2H), 3.07-3.20 (m, 5H), 3.50-3.55 (m, 2H), 3.63-3.65 (m, 2H), 3.66-3.97 (m, 3H), 4.18 (bs, 1H), 4.69 (s, 2H), 7.06-7.08 (d, J=7.2 Hz, 2H), 7.11-7.18 (m, 4H), 7.22-7.28 (m, 4H), 7.37-7.96 (d, J=7.2 Hz, 2H), 7.56-7.58 (d, J=7.6 Hz, 2H), 7.92 (bs, 1H), 8.32-8.33 (d, J=2.8 Hz, 1H), 8.44 (d, J=3.6 Hz, 1H).

Synthesis of (3S,4S)-1-(4-((S)-4-acetyl-3-(tetradecylcarbamoyl) piperazine-1-carbonyl) benzoyl)-N3,N4-bis((1S,2R)-2-phenylcyclopropyl) pyrrolidine-3,4-dicarboxamide, Compound 162

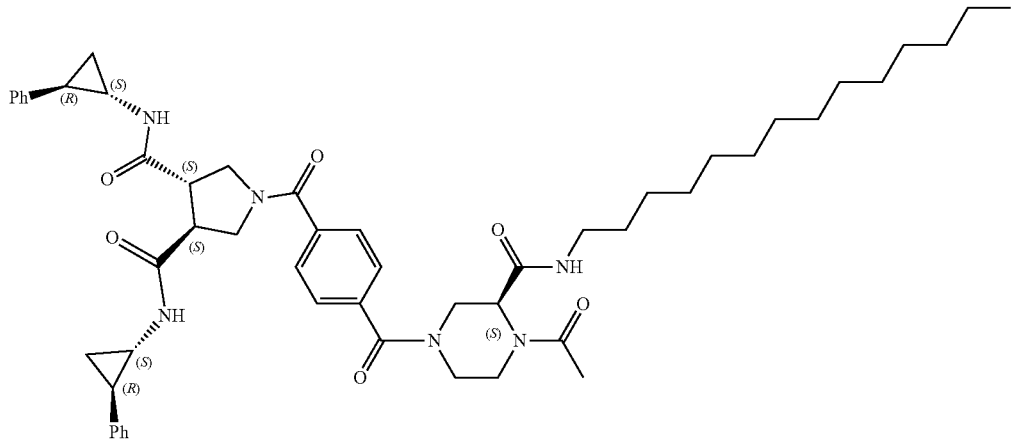

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 1 to give (3S,4S)-1-(4-((S)-4-acetyl-3-(tetradecylcarbamoyl) piperazine-1-carbonyl) benzoyl)-N3,N4-bis ((1S,2R)-2-phenylcyclopropyl) pyrrolidine-3,4-dicarboxamide (Compound 162), as a white solid (0.035 g, 15.57%). LCMS (Method-C): 100% (RT 2.340, 202.0 nm) (MS: ESI +ve 888[M+H]). $^1$H NMR: (400 MHz, DMSO) δ ppm: 0.84-0.86 (d, J=6.8, 3H); 1.01 (s, 2H); 1.18 (s, 26H); 1.23 (s, 2H); 1.88 (s, 1H); 1.94-1.98 (t, 2H); 2.09 (s, 2H); 2.86 (s, 2H); 3.11-3.17 (m, 6H); 3.51-3.56 (m, 3H); 3.64-3.69 (m, 1H); 3.76-3.81 (m, 2H); 3.96 (s, 1H); 4.19 (s, 1H); 4.71 (s, 1H); 7.07-7.09 (d, J=7.2, 2H); 7.13-7.17 (m, 4H); 7.23-7.30 (m, 4H); 7.38-7.40 (d, J=7.2, 2H); 7.57-7.59 (d, J=7.6, 2H); 7.90 (s, 1H); 8.32 (s, 1H); 8.43 (s, 1H).

Synthesis of (3S,4S)-1-(4-((R)-4-acetyl-3-(tetradecylcarbamoyl)piperazine-1-carbonyl)benzoyl)-N3,N4-bis((1S,2R)-2-phenylcyclopropyl)pyrrolidine-3,4-dicarboxamide, Compound 163

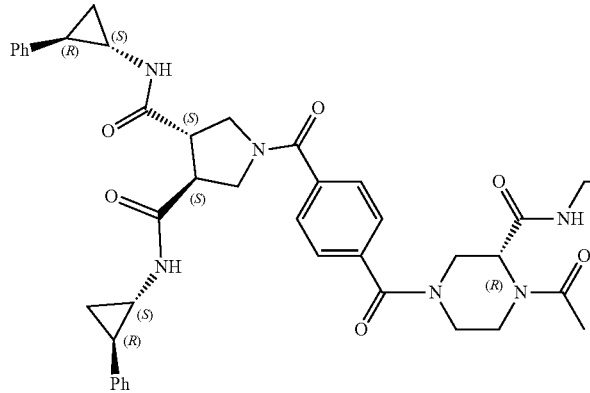
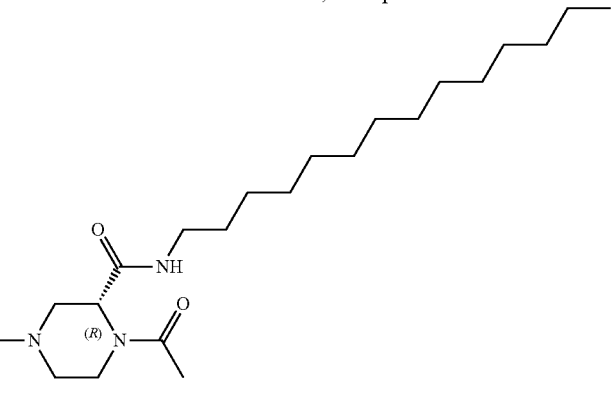

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 10 to give (3S,4S)-1-(4-((R)-4-acetyl-3-(tetradecylcarbamoyl)piperazine-1-carbonyl)benzoyl)-N3,N4-bis((1S,2R)-2-phenylcyclopropyl)pyrrolidine-3,4-dicarboxamide (Compound 163) (0.020 g, 12.2%). LCMS (Method-J): 100% (RT 5.81, 202.0 nm) (MS: ESI +ve 888.4 [M+1]. 1H NMR: (400 MHz, DMSO) δ ppm: 0.83-0.86 (t, J=4 Hz, 3H), 1.09-1.22 (m, 32H), 1.86-2.07 (m, 5H), 2.78-3.20 (m, 7H), 3.63-3.65 (d, J=8 Hz, 2H), 3.78-3.83 (t, J=3.2 Hz, 2H), 4.11 (s, 2H), 4.66 (s, 1H), 7.06-7.28 (m, 10H), 7.37-7.57 (m, 4H), 7.99 (s, 1H), 8.30-8.43 (m, 2H).

Synthesis of (3S,4S)-1-(3-((S)-4-acetyl-3-(tetradecylcarbamoyl) piperazine-1-carbonyl) benzoyl)-N3,N4-bis ((1S,2R)-2-phenylcyclopropyl) pyrrolidine-3,4-dicarboxamide, Compound 164

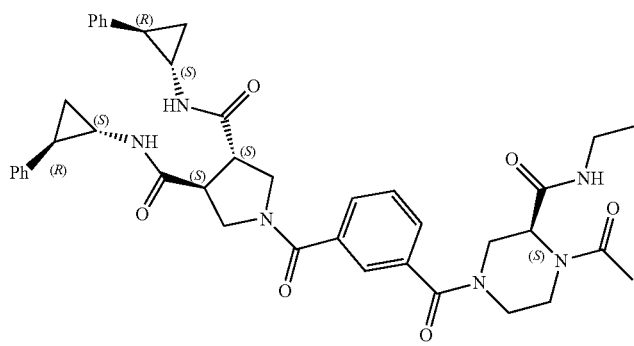

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 1 to give (3S,4S)-1-(3-((S)-4-acetyl-3-(tetradecylcarbamoyl) piperazine-1-carbonyl) benzoyl)-N3,N4-bis ((1S,2R)-2-phenylcyclopropyl) pyrrolidine-3,4-dicarboxamide (Compound 164), as a white solid (0.080 g, 24.2%). LCMS (Method-C): 96.6% (RT 2.452, 202.0 nm) (MS: ESI +ve 888 [M+H]). ¹H NMR: (400 MHz, DMSO) δ ppm: 0.83-0.86 (m, 4H); 1.10-1.12 (d, J=8, 32H); 1.86 (s, 1H); 1.92-1.99 (m, 2H); 2.07 (s, 2H); 2.78 (s, 3H); 3.08-3.14 (m, 2H); 3.16-3.20 (m, 1H); 3.49-3.54 (t, 2H); 3.65-3.67 (d, J=8, 1H); 3.74-3.83 (m, 1H); 4.06 (s, 1H); 4.57 (s, 1H); 7.06-7.18 (m, 6H); 7.22-7.28 (m, 4H); 7.41-7.43 (d, J=8, 2H); 7.49-7.53 (t, 1H); 7.59-7.61 (d, J=7.6, 1H); 7.98 (s, 1H); 8.29 (s, 1H); 8.41 (s, 1H).

Synthesis of (3S,4S)-1-(3-((R)-4-acetyl-3-(tetradecylcarbamoyl)piperazine-1-carbonyl)benzoyl)-N3,N4-bis((1S,2R)-2-phenylcyclopropyl)pyrrolidine-3,4-dicarboxamide, Compound 172

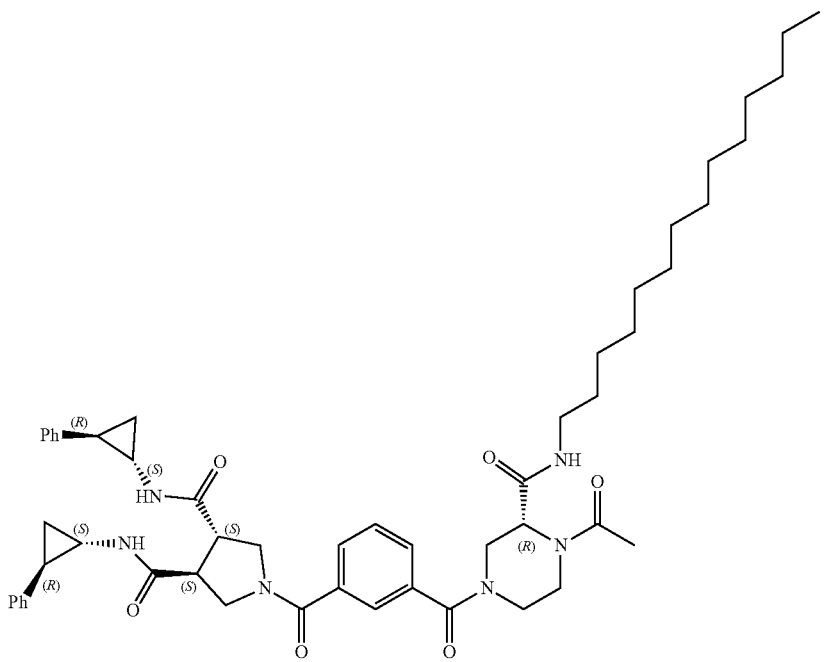

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 13 to give (3S,4S)-1-(3-((R)-4-acetyl-3-(tetradecylcarbamoyl)piperazine-1-carbonyl)benzoyl)-N3,N4-bis((1S,2R)-2-phenylcyclopropyl)pyrrolidine-3,4-dicarboxamide (Compound 172) (0.019 g, 9.59%). LCMS (Method-C): 100% (RT 1.72, 225.0 nm) (MS: ESI +ve 888.9 [M+1]. 1H NMR: (400 MHz, DMSO) δ ppm: 0.84-0.87 (t, J=4 Hz, 3H), 1.10-1.13 (t, J=1.2 Hz, 3H), 1.22-1.23 (m, 28H), 1.86-2.09 (m, 5H), 2.68-3.23 (m, 9H), 3.51-3.55 (m, 4H), 3.65-3.83 (m, 6H), 4.70 (s, 1H), 7.06-7.29 (m, 10H), 7.41-7.44 (d, J=12 Hz, 2H), 7.49-7.53 (t, J=4 Hz, 1H), 7.60-7.61 (d, J=7.2 Hz, 1H), 7.75-8.51 (m, 3H).

367

Synthesis of (3S,4S)-1-(4-((S)-4-acetyl-3-(pentylcarbamoyl) piperazine-1-carbonyl) benzoyl)-N3,N4-bis((1S,2R)-2-phenylcyclopropyl) pyrrolidine-3,4-dicarboxamide, Compound 264

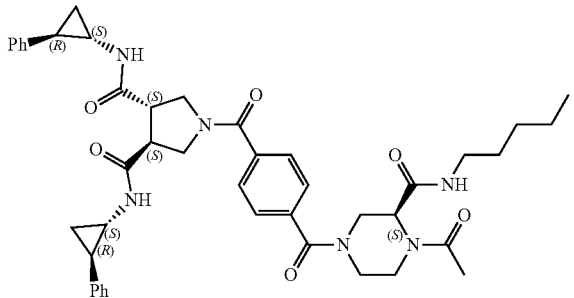

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 19), substituting the applicable starting materials. The crude final product was purified using Prep HPLC Method 13 to give (3S,4S)-1-(4-((S)-4-acetyl-3-(pentylcarbamoyl) piperazine-1-carbonyl) benzoyl)-N3,N4-bis((1S,2R)-2-phenylcyclopropyl) pyrrolidine-3,4-dicarboxamide (Compound 264) (0.020 g, 7.05%). LCMS (Method-J2): 94.19% (RT: 3.837, 230.0 nm) (MS: ESI +ve 761.0 [M+H]). $^1$H NMR: (400 MHz, DMSO) δ ppm: 0.82-0.86 (t, 3H); 1.11-1.26 (m, 11H); 1.88 (s, 1H); 1.94 (s, 2H); 2.09 (s, 2H); 2.69 (s, 1H); 2.80 (s, 1H); 3.11-3.15 (t, 3H); 3.20-3.24 (t, 2H); 3.49-3.54 (t, 3H); 3.63-3.68 (t, 1H); 3.78-3.83 (t, 2H); 3.95 (s, 1H); 4.21 (s, 1H); 4.70 (s, 1H); 7.07-7.09 (d, J=7.6, 2H); 7.13-7.19 (m, 4H); 7.23-7.30 (m, 4H); 7.38-7.40 (d, J=7.2, 2H); 7.57-7.59 (d, J=7.2, 2H); 8.43 (s, 1H); 8.50 (s, 1H), 8.53 (s, 1H).

368

Synthesis of (3S,4S)-1-(4-((S)-4-acetyl-3-(propylcarbamoyl) piperazine-1-carbonyl) benzoyl)-N3,N4-bis((1S,2R)-2-phenylcyclopropyl) pyrrolidine-3,4-dicarboxamide, Compound 265

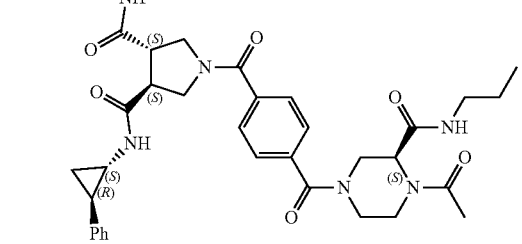

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 019), substituting the applicable starting materials. The crude final product was purified using Prep HPLC Method 13 to give (3S,4S)-1-(4-((S)-4-acetyl-3-(propylcarbamoyl) piperazine-1-carbonyl) benzoyl)-N3,N4-bis((1S,2R)-2-phenylcyclopropyl) pyrrolidine-3,4-dicarboxamide (Compound 265) (0.025 g, 9.19%). LCMS (Method-J2): 100% (RT: 3.641, 202.0 nm) (MS: ESI +ve 733.0 [M+H]). $^1$H NMR: (400 MHz, DMSO) δ ppm: 0.78 (s, 3H); 1.11-1.16 (m, 2H); 1.18-1.28 (m, 2H); 1.32 (s, 3H); 1.88 (s, 1H); 1.94-1.98 (t, 2H); 2.09 (s, 2H); 2.80 (s, 1H); 2.87 (s, 2H); 3.02 (s, 3H); 3.09-3.23 (m, 2H); 3.51-3.53 (d, J=7.2, 3H); 3.64-3.68 (t, 2H); 3.79-3.84 (t, 3H); 4.70 (s, 1H); 7.07-7.09 (d, J=7.2, 2H); 7.13-7.19 (m, 4H); 7.23-7.30 (m, 4H); 7.38-7.40 (d, J=7.6, 2H); 7.58-7.59 (d, J=7.2, 2H); 8.40 (s, 1H); 8.51 (s, 1H).

Synthesis of (3S,4S)-1-(3-(4-pentadecanamidopiperidine-1-carbonyl)benzoyl)-N3,N4-bis((1S,2R)-2-phenylcyclopropyl)pyrrolidine-3,4-dicarboxamide, Compound 166

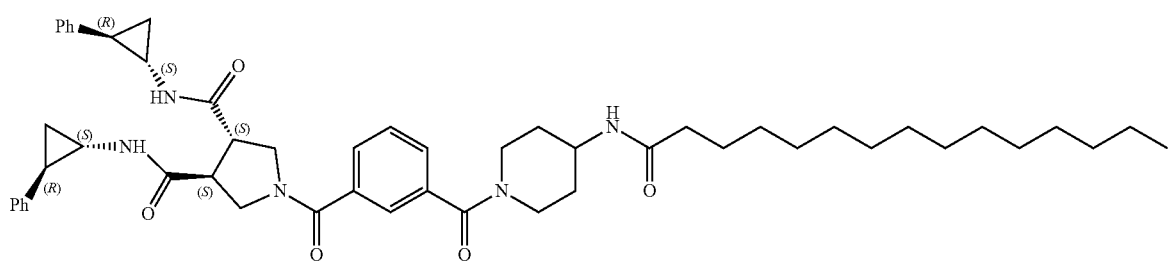

Prepared by a procedure similar to that reported for ((3S,4S)-1-(4-(3-(hexylcarbamoyl)-4-octanoylpiperazine-1-carbonyl)benzoyl)-N3,N4-bis((1S,2R)-2-phenylcyclopropyl)pyrrolidine-3,4-dicarboxamide (Compound 166), substituting the applicable starting materials. The crude final product was purified using Prep HPLC Method 12 to give (3S,4S)-1-(3-(4-pentadecanamidopiperidine-1-carbonyl) benzoyl)-N3,N4-bis((1S,2R)-2-phenylcyclopropyl)pyrrolidine-3,4-dicarboxamide (Compound 166) (0.037 g, 6.8% yield), as a white solid. LCMS (Method-H): 100% (RT: 4.753, 202.0 nm) (MS: ESI +ve 844.6 [M+1]). $^1$H NMR: (400 MHz, DMSO) δ ppm: 0.853 (s, 3H), 1.105 (s, 3H), 1.232 (m, 28H), 1.464 (s, 4H), 1.855 (s, 2H), 2.025-2.116 (m, 2H), 2.777 (s, 1H), 2.848 (s, 1H), 3.117-3.183 (m, 2H), 3.508 (m, 2H), 3.664 (s, 1H), 3.803 (s, 2H), 4.500 (s, 1H), 7.079-7.135 (m, 6H), 7.247 (m, 4H), 7.462 (s, 2H), 7.520-7.583 (m, 2H), 7.735 (m, 1H), 8.296-8.430 (d, 2H).

Example 19

Synthesis of (3S,4S)-1-(4-((S)-3-pentadecanamidopyrrolidine-1-carbonyl)benzoyl)-N3,N4-bis((1S,2R)-2-phenylcyclopropyl)pyrrolidine-3,4-dicarboxamide, Compound 026

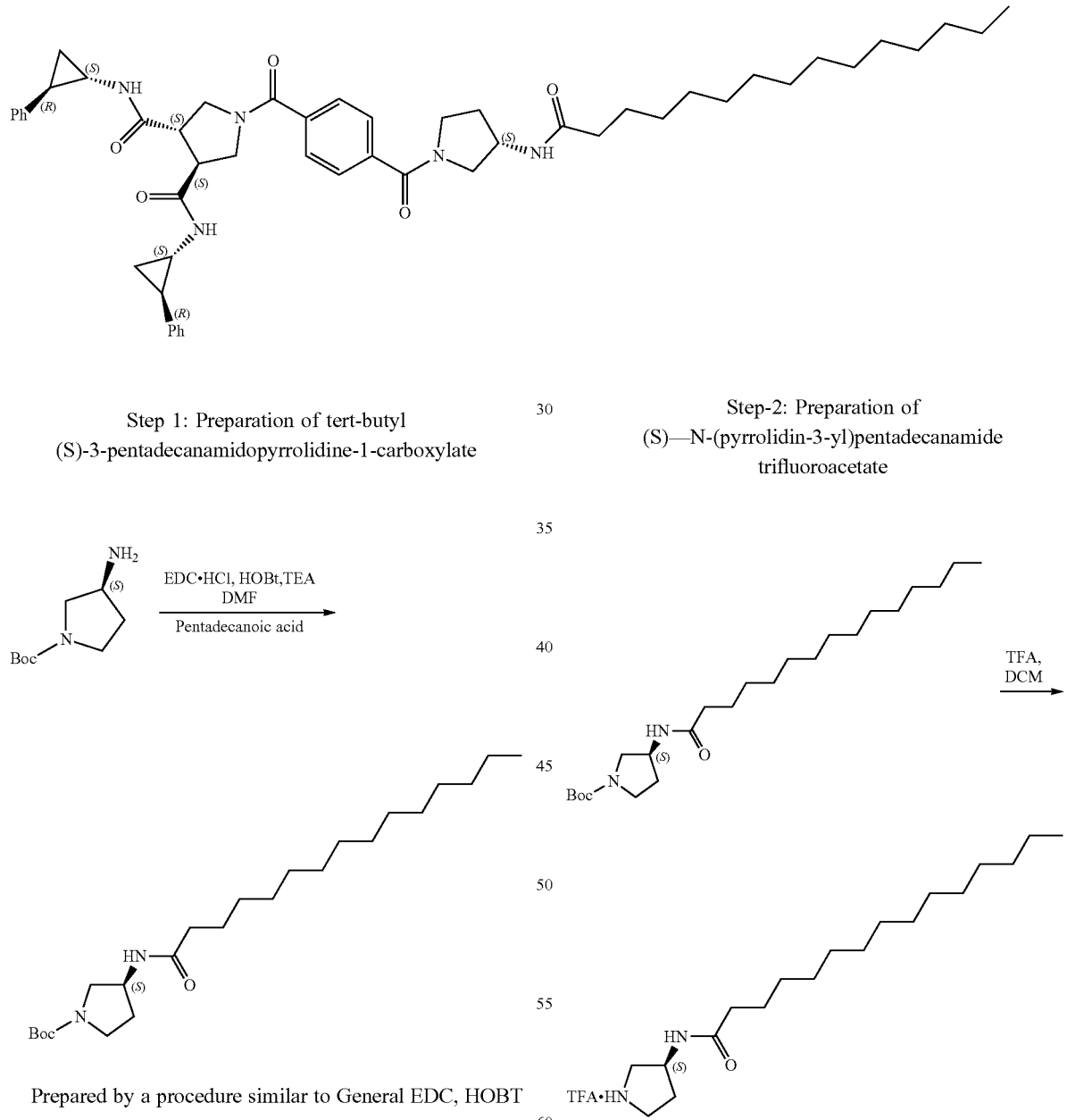

Step 1: Preparation of tert-butyl (S)-3-pentadecanamidopyrrolidine-1-carboxylate Prepared by a procedure similar to General EDC, HOBT Coupling Procedure. The crude product was purified by column chromatography eluting with 0-2% Methanol in Dichloromethane to give tert-butyl (S)-3-pentadecanamidopyrrolidine-1-carboxylate (1.5 g, 60%). LCMS (Method-C3): 100% (RT 2.840, 202.0 nm) (MS: ESI +ve 411.6 [M+H]).

Step-2: Preparation of (S)—N-(pyrrolidin-3-yl)pentadecanamide trifluoroacetate

Prepared by a procedure similar to General Boc Deprotection Procedure to give (S)—N-(pyrrolidin-3-yl)pentadecanamide trifluoroacetste as colourless liquid (0.3 g, 96%). LCMS: 93.82% (RT: 4.302, 202.0 nm) (MS: ESI +ve 311.2[M+H]).

Step-3: Preparation of (3S,4S)-1-(4-((S)-3-pentade-canamidopyrrolidine-1-carbonyl)benzoyl)-N3,N4-bis((1S,2R)-2-phenylcyclopropyl)pyrrolidine-3,4-dicarboxamide, Compound 026

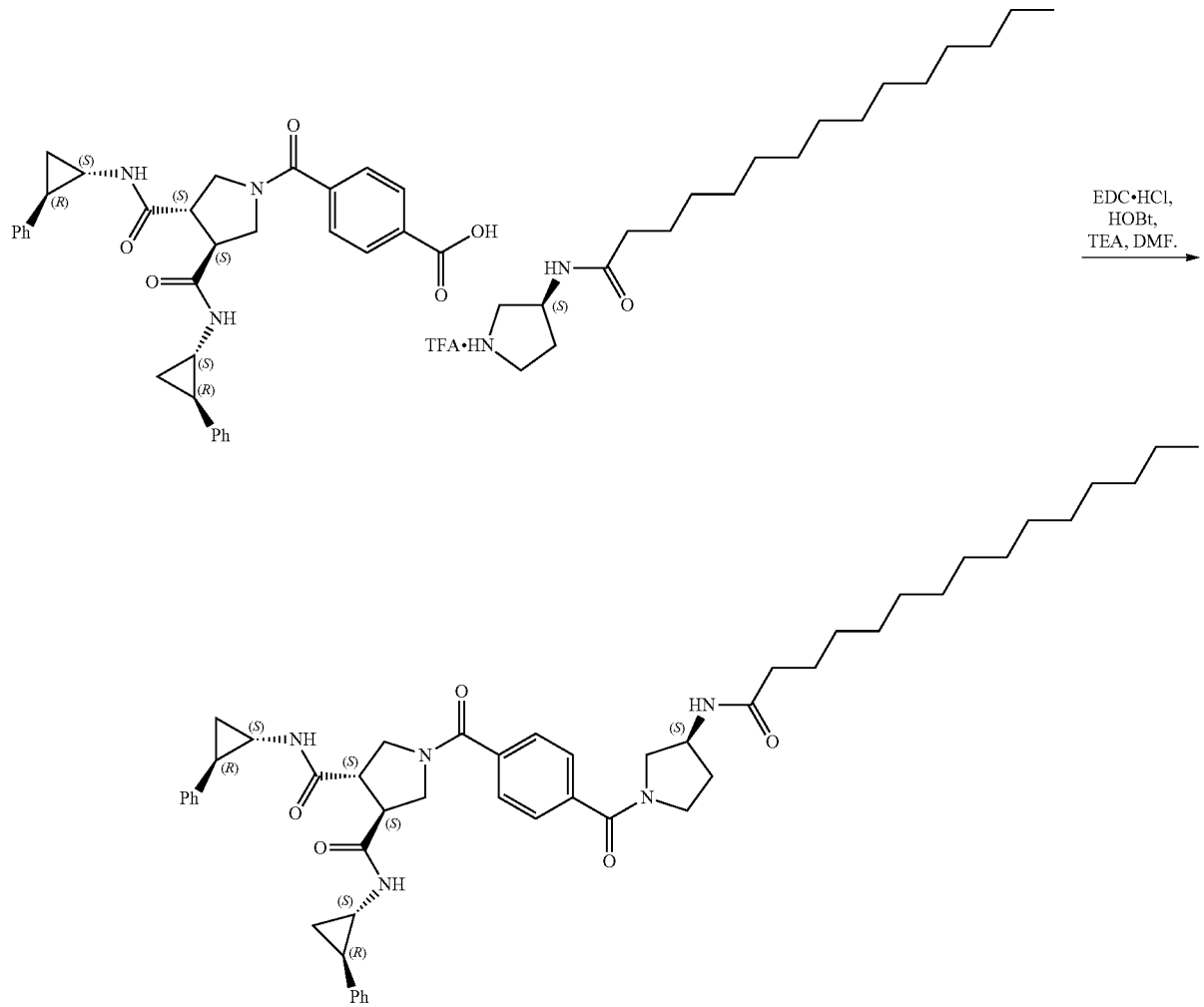

Prepared by a procedure similar to General EDC, HOBT Coupling Procedure. The crude product was purified using Prep HPLC Method 3 to give (3S,4S)-1-(4-((S)-3-pentade-canamidopyrrolidine-1-carbonyl)benzoyl)-N3,N4-bis((1S, 2R)-2-phenylcyclopropyl)pyrrolidine-3,4-dicarboxamide, Compound 026 (0.055 g, 23.55%). LCMS (Method-H2): 100% (RT 4.758, 202.0 nm) (MS: ESI +ve 830.0 [M+H]). $^1$H NMR: (400 MHz, DMSO) δ ppm: 0.83-0.86 (t, J=6.8 Hz, 3H), 1.10-1.23 (m, 26H), 1.42-1.49 (m, 2H), 1.86 (s, 2H), 1.96-2.09 (m, 4H), 2.77-2.85 (m, 2H), 3.09-3.20 (m, 3H), 3.44-3.51 (m, 3H), 3.63-3.65 (m, 3H), 3.78-3.80 (m, 1H), 4.12-4.28 (m, 1H), 7.06-7.18 (m, 6H), 7.22-7.28 (m, 4H), 7.54-7.57 (m, 4H), 8.04-8.10 (m, 1H), 8.30 (s, 1H), 8.44 (s, 2H).

Example 20

Synthesis of (3S,4S)-1-(4-((R)-3-pentadecanami-dopyrrolidine-1-carbonyl)benzoyl)-N3,N4-bis((1S, 2R)-2-phenylcyclopropyl)pyrrolidine-3,4-dicarbox-amide, Compound 027

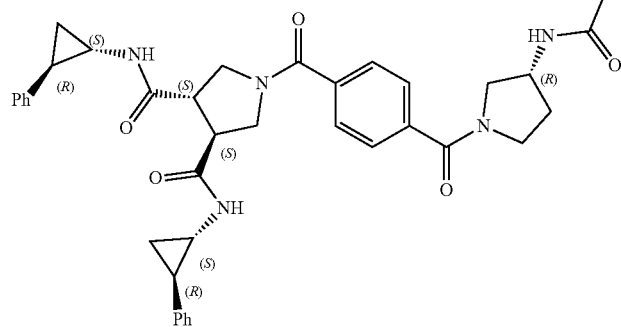

Prepared by a procedure similar to that reported for (3S,4S)-1-(4-((S)-3-pentadecanamidopyrrolidine-1-carbonyl)benzoyl)-N3,N4-bis((1S,2R)-2-phenylcyclopropyl)pyrrolidine-3,4-dicarboxamide, Compound 026, substituting (R)-3-aminopyrrolidine-1-carboxylate in step 1. The final product was purified using Prep HPLC Method 3 to give (3S,4S)-1-(4-((R)-3-pentadecanamidopyrrolidine-1-carbonyl)benzoyl)-N3,N4-bis((1S,2R)-2-phenylcyclopropyl)pyrrolidine-3,4-dicarboxamide, Compound 027, (0.050 g, 21.59%). LCMS (Method-H2): 100% (RT 4.768, 202.0 nm) (MS: ESI +ve 830.45 [M+H]). $^1$H NMR: (400 MHz, DMSO) δ ppm: 0.83-0.86 (t, J=6.8 Hz, 3H), 1.10-1.23 (m, 26H), 1.42-1.49 (m, 2H), 1.85 (s, 2H), 1.98-2.09 (m, 4H), 2.78-2.84 (m, 2H), 3.09-3.21 (m, 3H), 3.50-3.52 (m, 3H), 3.63-3.65 (m, 3H), 3.77-3.80 (m, 1H), 4.10-4.20 (m, 1H), 7.06-7.07 (m, 2H), 7.11-7.18 (m, 4H), 7.23-7.28 (m, 4H), 7.55-7.57 (m, 4H), 8.03-8.04 (m, 1H), 8.33 (s, 1H), 8.46 (s, 2H).

Example 21

Synthesis of (3S,4S)-1-(4-((3S,4R)-3-acetamido-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 028

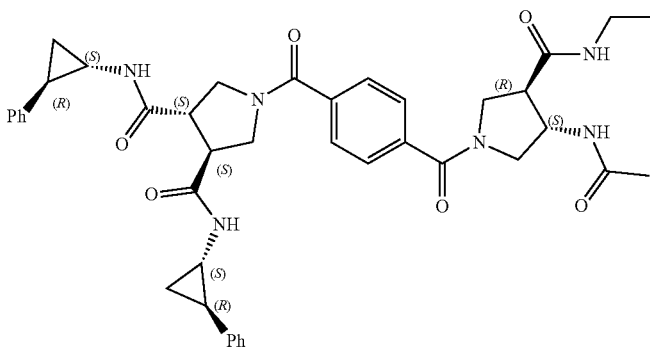

Step 1: Preparation of 1-(tert-butyl) 3-ethyl (3R,4S)-4-(((R)-1-phenylethyl)amino)pyrrolidine-1,3-dicarboxylate

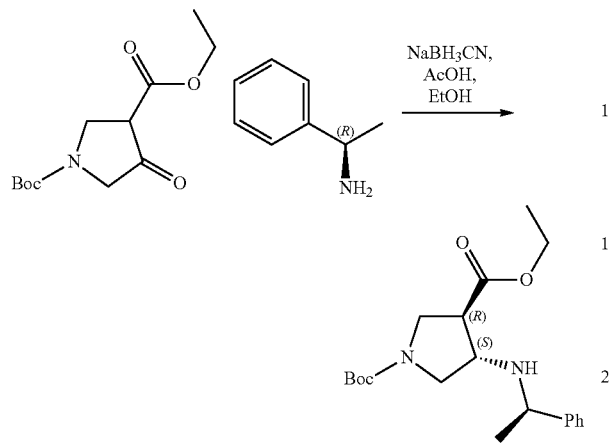

(R)-(+)-α-Methylbenzylamine (2.82 g, 23.33 mmol) was added to a solution of 1-(tert-butyl) 3-ethyl 4-oxopyrrolidine-1,3-dicarboxylate (3.0 g, 11.66 mmol) in ethanol (30 mL) and acetic acid (1.33 mL, 23.32 mmol). After 4 hours, sodium cyanoborohydride (2.93 g, 46.64 mmol) was added and the reaction mixture was stirred at 75° C. for 16 hours. The mixture was concentrated and the residue partitioned between water (150 mL) and ethyl acetate (150 mL). The aqueous phase extracted with ethyl acetate (2×150 mL). The combined organic layers were dried over sodium sulfate and concentrated. The crude product was purified using column chromatography eluting with 20-30% EtOAc in hexane. The resulting product was dissolved in EtOAc (45 mL) and treated with 4M hydrogen chloride in dioxane (3 mL). The resulting precipitate was collected by filtration and recrystallized from acetonitrile (20 mL) to give 1-(tert-butyl) 3-ethyl (3R,4S)-4-(((R)-1-phenylethyl)amino)pyrrolidine-1,3-dicarboxylate (1.0 g, 23.66%). LCMS (Method-DEV.M): 100% (RT 18.206, 202.0 nm) (MS: ESI +ve 363.2 [M+H]).

Step-2: Preparation of (3R,4S)-1-(tert-butoxycarbonyl)-4-(((R)-1-phenylethyl)amino)pyrrolidine-3-carboxylic acid

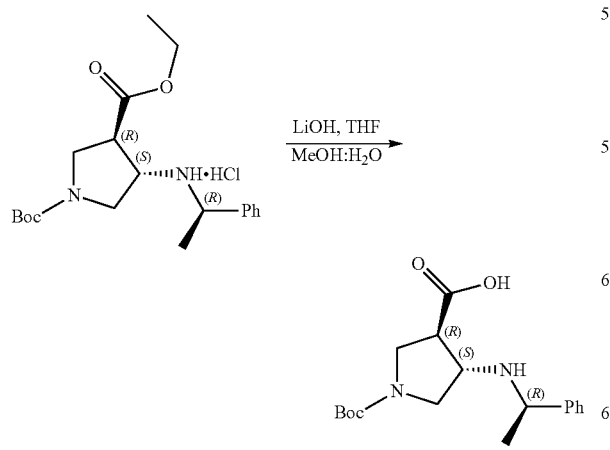

Lithium hydroxide monohydrate (297 mg, 12.41 mmol) was added to a solution of 1-(tert-butyl) 3-ethyl (3R,4S)-4-(((R)-1-phenylethyl)amino)pyrrolidine-1,3-dicarboxylate (900 mg, 2.48 mmol) in THF/methanol/water (6:3:1, 20 mL) at 0° C. The reaction was stirred for 16 hours and then concentrated. The crude residue was acidified with aqueous citric acid. The mixture was extracted with ethyl acetate (3×100 mL), dried over sodium sulphate and concentrated to give (3R,4S)-1-(tert-butoxycarbonyl)-4-(((R)-1-phenylethyl)amino)pyrrolidine-3-carboxylic acid (750 mg, 90%). LCMS (Method-C3): 100% (RT: 1.346, 202.0 nm) (MS: ESI +ve 279.2[M−56+H]).

Step-3: Preparation of tert-butyl (3S,4R)-3-(((R)-1-phenylethyl)amino)-4-(tetradecylcarbamoyl)pyrrolidine-1-carboxylate

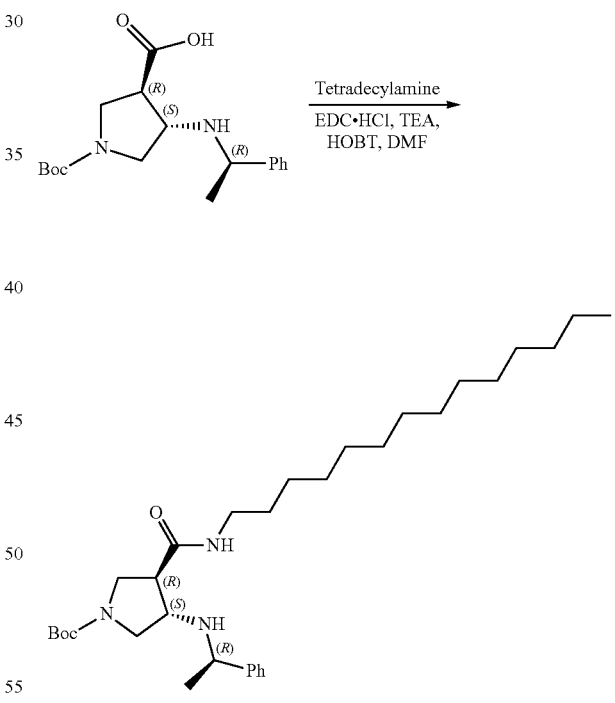

Prepared by a procedure similar to General EDC, HOBT Coupling Procedure. The crude product was purified using column chromatography eluting with 0-2% methanol in dichloromethane to give tert-butyl (3S,4R)-3-(((R)-1-phenylethyl)amino)-4-(tetradecylcarbamoyl)pyrrolidine-1-carboxylate (0.8 g, 67%) LCMS (Method-DEV_M): 96.01% (RT 26.709, 202.0 nm) (MS: ESI +ve 530.4 [M+H]).

Step-4: Preparation of tert-butyl (3S,4R)-3-amino-4-(tetradecylcarbamoyl)pyrrolidine-1-carboxylate

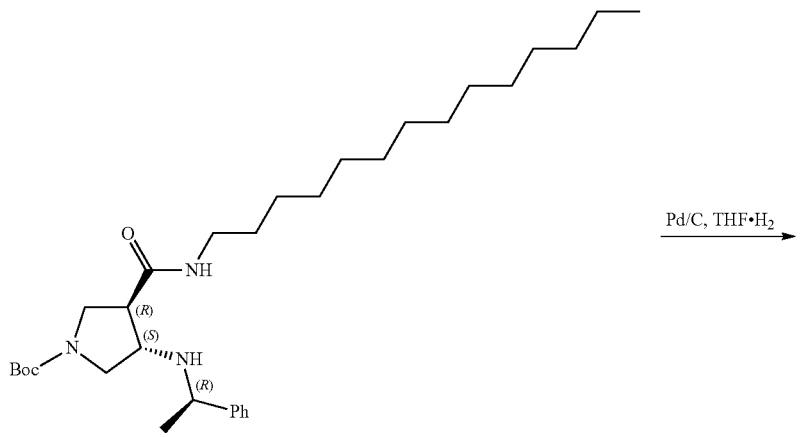

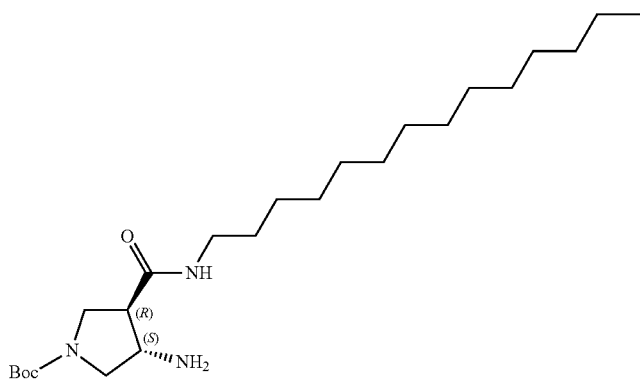

tert-butyl (3S,4R)-3-(((R)-1-phenylethyl)amino)-4-(tetradecylcarbamoyl)pyrrolidine-1-carboxylate (0.8 g, 1.51 mmol) was dissolved in THF (20 mL), Pd/C (0.80 g, 10% with 50% moisture) was added. The mixture was stirred under hydrogen at balloon pressure at room temperature for 16 hrs. The mixture was filtered through celite, rinsed with methanol (10 mL) and the combined organics were concentrated to give tert-butyl (3S,4R)-3-amino-4-(tetradecylcarbamoyl)pyrrolidine-1-carboxylate (0.6 g, 93%). LCMS (Method-C3): 64.27% (RT 2.646, 202 nm) (MS: ESI +ve 426.4 [M+H]).

Step-5: Preparation of tert-butyl (3S,4R)-3-acetamido-4-(tetradecylcarbamoyl)pyrrolidine-1-carboxylate

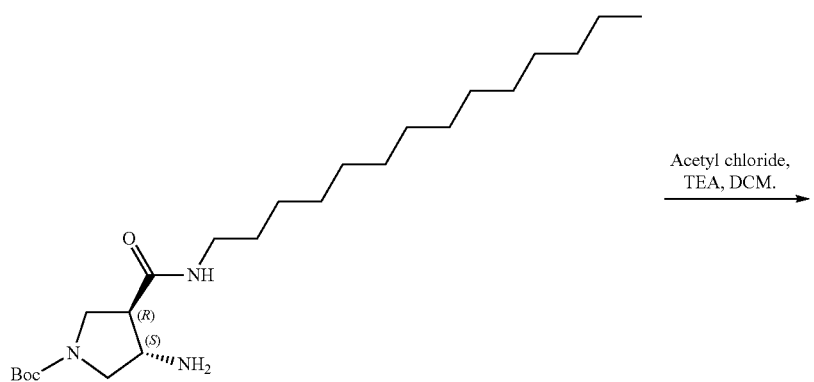

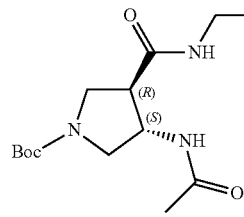

tert-butyl (3S,4R)-3-amino-4-(tetradecylcarbamoyl)pyrrolidine-1-carboxylate (0.5 g, 1.17 mmol) was dissolved in dichloromethane (20 mL) and cooled to 0° C. Triethylamine (0.5 mL, 3.84 mmol) and acetyl chloride (0.1 g, 1.28 mmol) were added and the reaction mixture was stirred at room temperature for 16 hrs. The mixture was diluted with ethyl acetate (50 mL) then washed with saturated aq. sodium bicarbonate (2×25 mL) and brine (2×25 mL). The organic layer was dried over sodium sulphate and concentrated under reduced pressure. The crude residue was purified using column chromatography eluting with 0-2% methanol in dichloromethane to give tert-butyl (3S,4R)-3-amino-4-(tetradecylcarbamoyl)pyrrolidine-1-carboxylate (0.400 g, 72%) LCMS (Method-C3): 100% (RT-2.47, 202.0 nm) (MS: ESI +ve 468.6 [M+H]).

Step-6: Preparation of (3R,4S)-4-acetamido-N-tetradecylpyrrolidine-3-~carboxamide trifluoroacetate

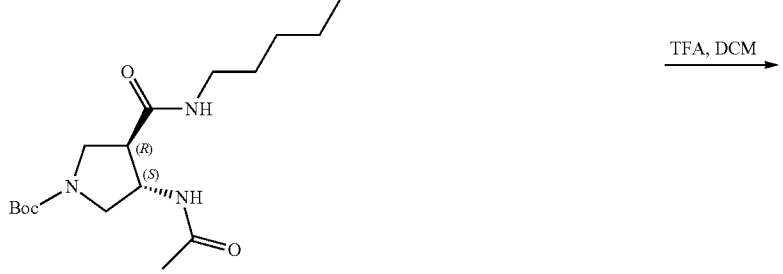

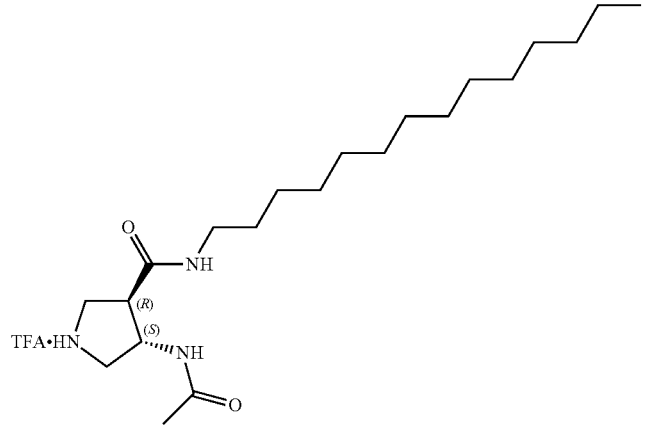

381

Prepared by a procedure similar to General Boc Deprotection Procedure to give (3R,4S)-4-acetamido-N-tetradecylpyrrolidine-3-carboxamide (0.2 g, 99%). LCMS (Method-C3): 91.24% (RT: 1.891, 202.0 nm) (MS: ESI +ve 368.5[M+H]).

382

Step-7: Preparation of (3S,4S)-1-(4-((3S,4R)-3-acetamido-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 028

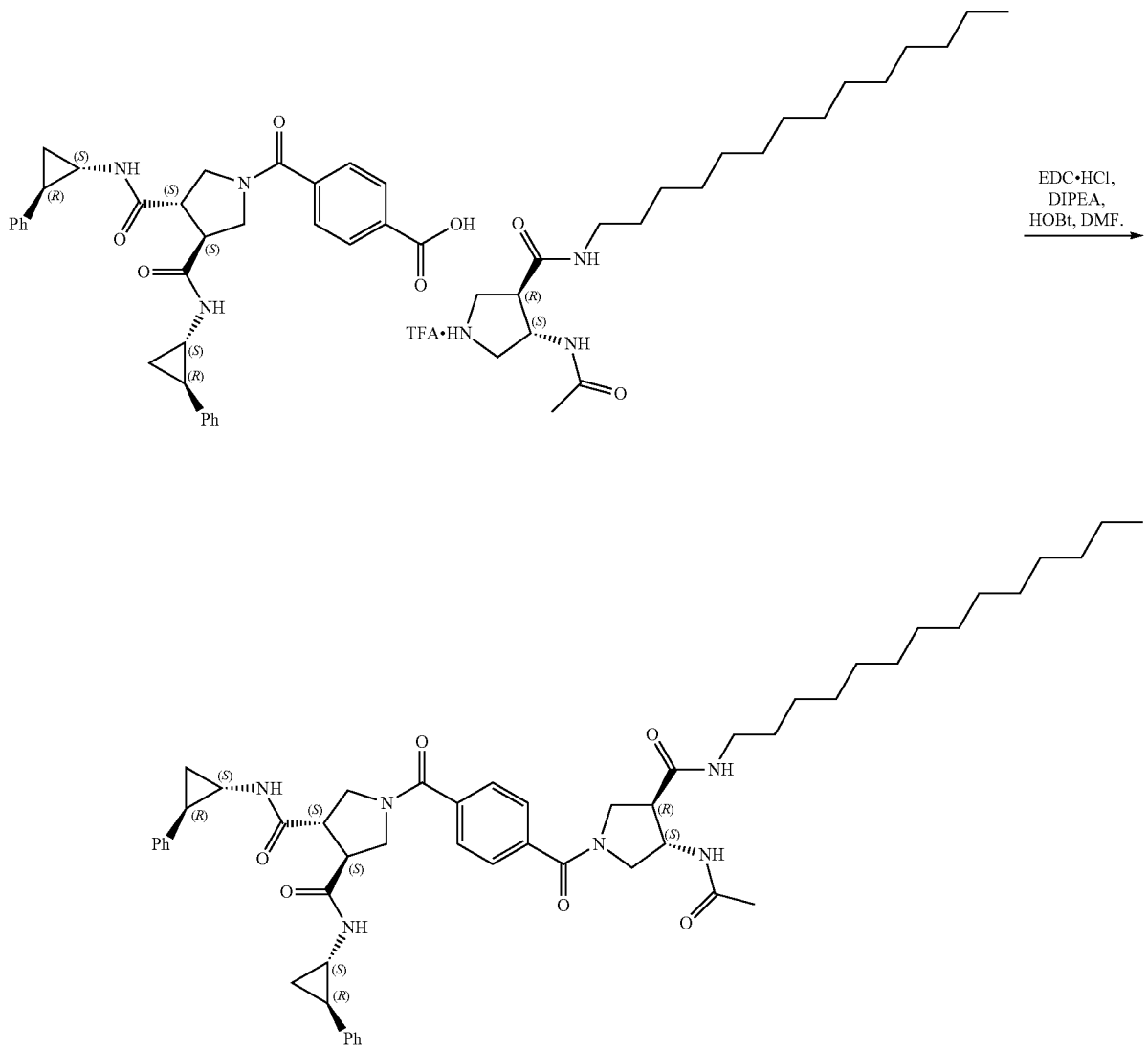

Prepared using a procedure similar to General EDC, HOBT Coupling Procedure. The final product was purified using Prep HPLC Method 4 to give (3S,4S)-1-(4-((3S,4R)-3-acetamido-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 028, (0.040 g, 16%). LCMS (Method-C3): 100% (RT 2.410, 223.0 nm) (MS: ESI +ve 888.7 [M+H]). $^1$H NMR: (400 MHz, DMSO) δ ppm: 0.83-0.86 (t, J=6.0 Hz, 3H), 1.10-1.39 (m, 26H), 1.76 (s, 3H), 1.83 (s, 1H), 1.96 (s, 1H), 2.67 (s, 3H), 2.84-2.92 (m, 1H), 2.94-2.97 (m, 3H), 3.19-3.21 (m, 2H), 3.48-3.54 (m, 3H), 3.57-3.65 (m, 3H), 3.71-3.77 (m, 2H), 4.21-4.39 (m, 1H), 7.06-7.18 (m, 6H), 7.22-7.28 (m, 4H), 7.53-7.56 (m, 4H), 7.87-8.00 (m, 1H), 8.18-8.22 (m, 1H), 8.31 (s, 1H), 8.49 (s, 2H).

Synthesis of (3S,4S)-1-(4-((3S,4R)-3-(methyl-amino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 098

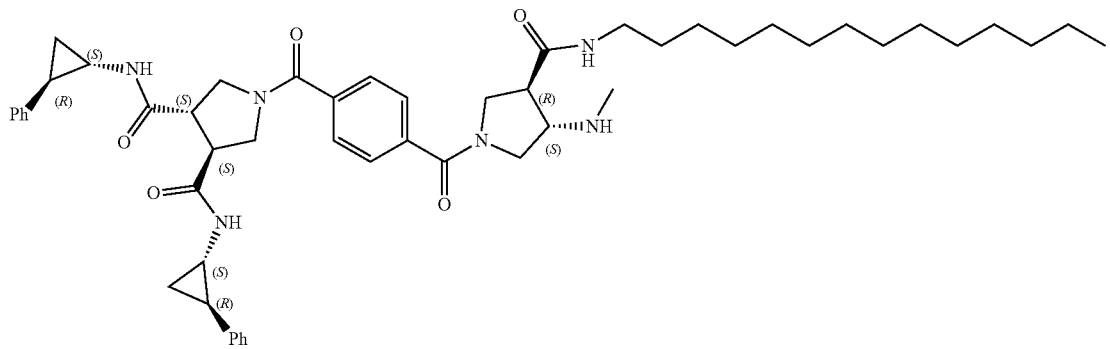

Step-1: Preparation of 1-(tert-butyl) 3-ethyl (3R,4S)-4-(methyl((R)-1-phenylethyl) amino)pyrrolidine-1,3-dicarboxylate Step-2: Preparation of (3R,4S)-1-(tert-butoxycarbonyl)-4-(methyl((R)-1-phenylethyl) amino)pyrrolidine-3-carboxylic acid

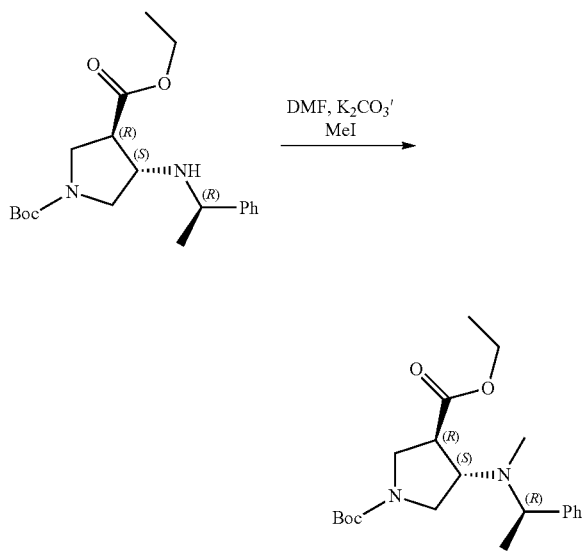

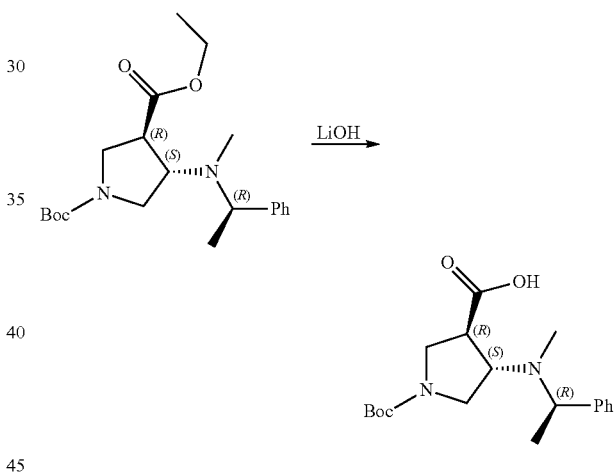

1-(tert-buty) 3-ethyl (R,4S)-4-(((R)-1-phenylethyl)amino)pyrrolidine-1,3-dicarboxylate (1 g, 2.500 mmol) was dissolved in DMF (15 mL) and cooled to 0° C. Potassium carbonate (1 g, 7.5 mmol) was added followed by methyl iodide (1 g, 7.5 mmol). The reaction mixture was heated at 60° C. for 48 hr. The mixture was extracted in ethyl acetate (3×30 mL), washed with brine (3×30 mL) dried and concentrated. The crude product was purified using flash chromatography, eluting with 0-15% hexane in ethyl acetate, to give 1-(tert-butyl) 3-ethyl (3R,4S)-4-(methyl((R)-1-phenylethyl)amino)pyrrolidine-1,3-dicarboxylate (1.0 g, crude). LCMS (Method-C3): 91.8% (RT: 4.243, 220 nm) (MS: ESI +ve 377.0 [M+1]).

Prepared using General Ester Hydrolysis Procedure to give (3R,4S)-1-(tert-butoxycarbonyl)-4-(methyl((R)-1-phenylethyl)amino)pyrrolidine-3-carboxylic acid (0.86 g, 93.5% yield). LCMS (Method-C3): 85.03% (RT: 1.053, 202.0 nm) (MS: ESI +ve 349.4 [M+1]).

Step-3: Preparation of tert-butyl (3S,4R)-3-(methyl((R)-1-phenylethyl)amino)-4-(tetradecylcarbamoyl)pyrrolidine-1-carboxylate

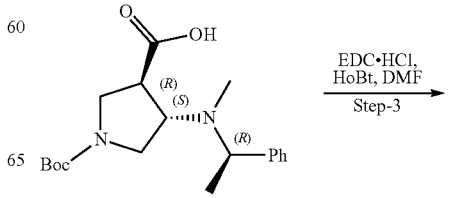

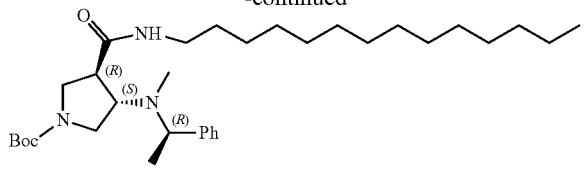

Prepared using General EDC, HOBT Coupling Procedure. The crude product was purified using flash chromatography, eluting with 0-10% DCM in MeOH, to give tert-butyl (3S,4R)-3-(methyl((R)-1-phenylethyl)amino)-4-(tetradecylcarbamoyl)pyrrolidine-1-carboxylate. (1.1 g, 84.6% yield). LCMS (Method-J): 73.6%, 20.9% (RT: 7.140, 7.222, 230.0 nm) (MS: ESI +ve 544.4 [M+1]).

Step-4: Preparation of tert-butyl (3S,4R)-3-(methylamino)-4-(tetradecylcarbamoyl) pyrrolidine-1-carboxylate

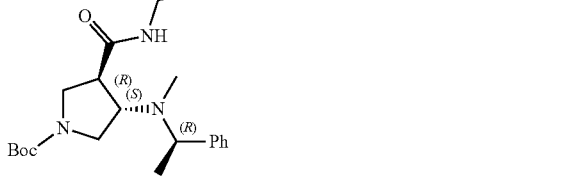

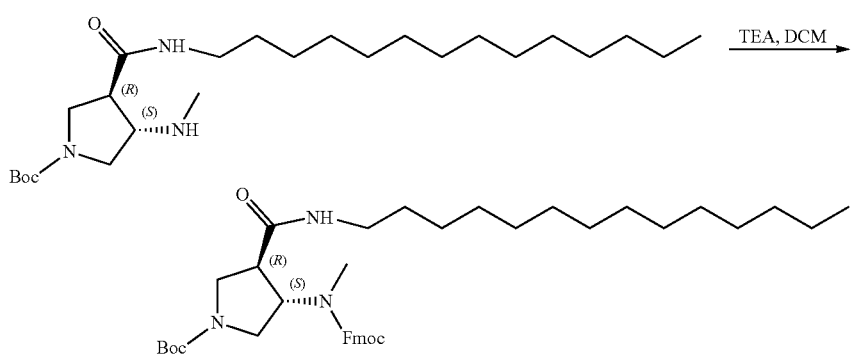

Tert-butyl (3S,4R)-3-(methyl((R)-1-phenylethyl)amino)-4-(tetradecylcarbamoyl)pyrrolidine-1-carboxylate (1.1 g, 2.00 mmol) and palladium on carbon (1.1 g) in MeOH (20 mL) was stirred under hydrogen (balloon) for 16 hrs at room temperature. The mixture was filtered through celite and the filtrate was concentrated to give (tert-butyl (3S,4R)-3-(methylamino)-4-(tetradecylcarbamoyl)pyrrolidine-1-carboxylate (0.762 g, 85.7% yield). LCMS (Method-C3): 94.2% (RT: 1.496, 202.0 nm) (MS: ESI +ve 440.7 [M+1]).

Step-5: Preparation of tert-butyl (3S,4R)-3-((((9H-fluoren-9-yl)methoxy) carbonyl)(methyl)amino)-4-(tetradecylcarbamoyl)pyrrolidine-1-carboxylate Tert-butyl (3S,4R)-3-(methylamino)-4-(tetradecylcarbamoyl)pyrrolidine-1-carboxylate (0.200 g, 0.454 mmol) was dissolved in DCM (10 mL) and cooled to 0° C. Triethylamine (0.19 mL, 1.365 mmol) and Fmoc chloride was added portion wise (0.141 g, 0.545 mmol) and stirred at room temperature for 16 hrs. The mixture was extracted in DCM (2×10 mL), washed with water (2×10 mL) and dried over sodium sulfate. The crude was purified using combi-flash chromatography, eluting with 0-20% DCM in ethyl acetate (0.146 g, 38.8% yield). Crude product was carried forwarded to next step. MS: ESI +ve 662 [M+1]).

Step-6: Preparation of (9H-fluoren-9-yl)methyl methyl((3S,4R)-4-(tetradecylcarbamoyl) pyrrolidin-3-yl)carbamate

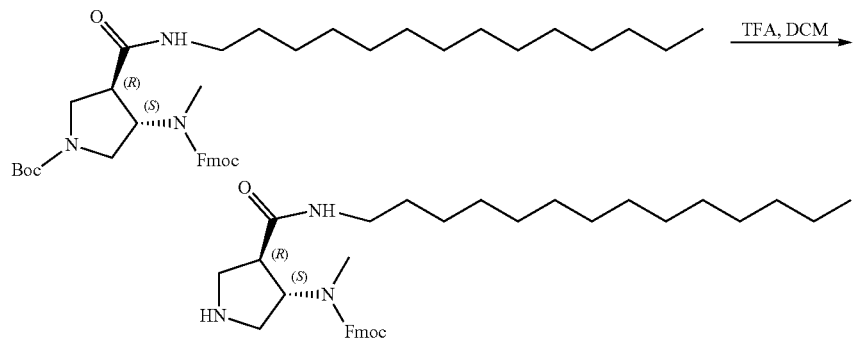

Prepared using General BOC Deprotection Procedure to give (9H-fluoren-9-yl)methyl methyl((3S,4R)-4-(tetradecylcarbamoyl)pyrrolidin-3-yl)carbamate (0.12 g crude). MS: ESI +ve 562 [M+1]).

Step-7: Preparation of (9H-fluoren-9-yl)methyl ((3S,4R)-1-(4-((3S,4S)-3,4-bis(((1S,2R)-2-phenylcyclopropyl)carbamoyl)pyrrolidine-1-carbonyl)benzoyl)-4-(tetradecylcarbamoyl) pyrrolidin-3-yl)(methyl)carbamate

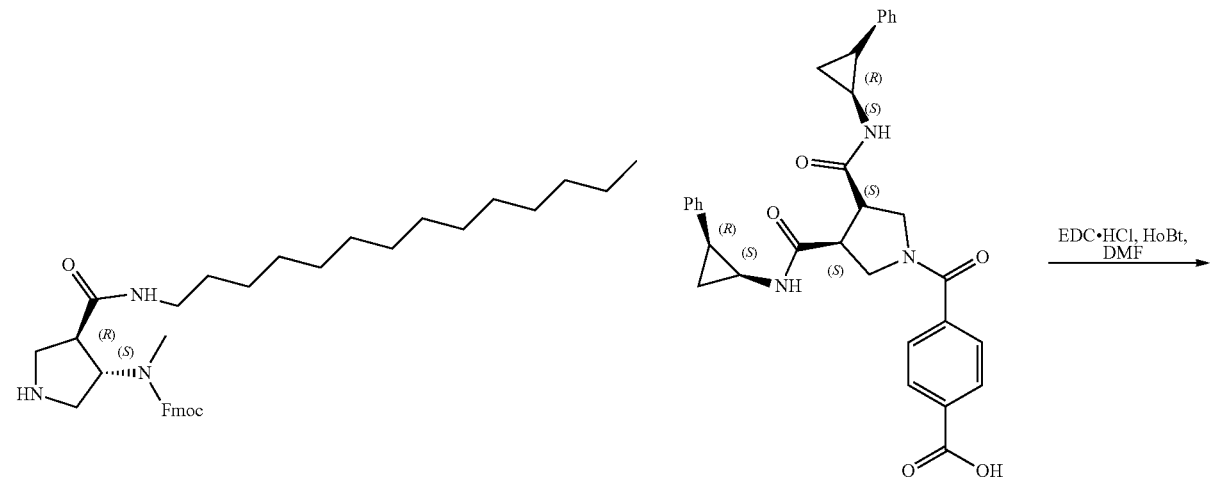

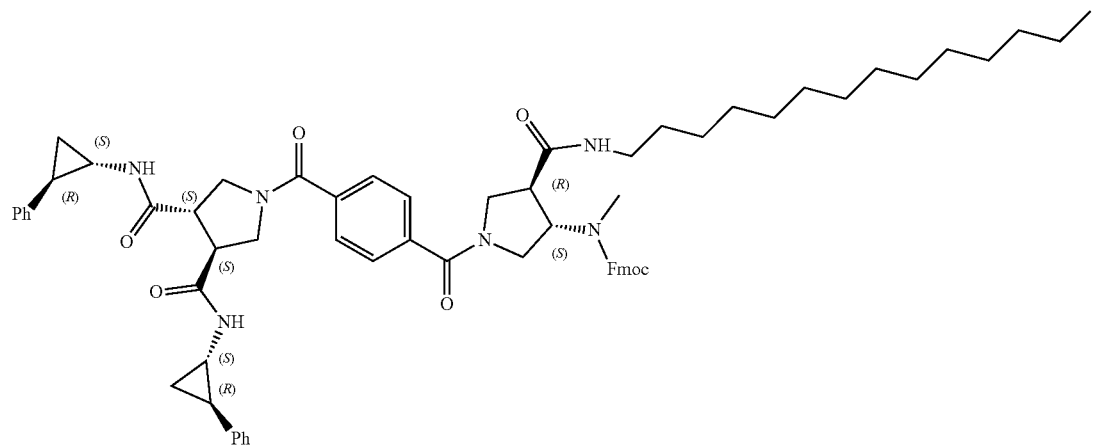

Prepared using General EDC, HOBT Coupling Procedure to give (9H-fluoren-9-yl)methyl ((3S,4R)-1-(4-((3S,4S)-3,4-bis(((1S,2R)-2-phenylcyclopropyl)carbamoyl)pyrrolidine-1-carbonyl)benzoyl)-4-(tetradecylcarbamoyl)pyrrolidin-3-yl)(methyl)carbamate. (0.156 g, 77.6% yield). LCMS (Method-H): 19.3% (RT: 6.084, 220.0 nm) (MS: ESI +ve 1082.0 [M+1]).

Step-8: Preparation of (3S,4S)-1-(4-((3S,4R)-3-(methylamino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 098

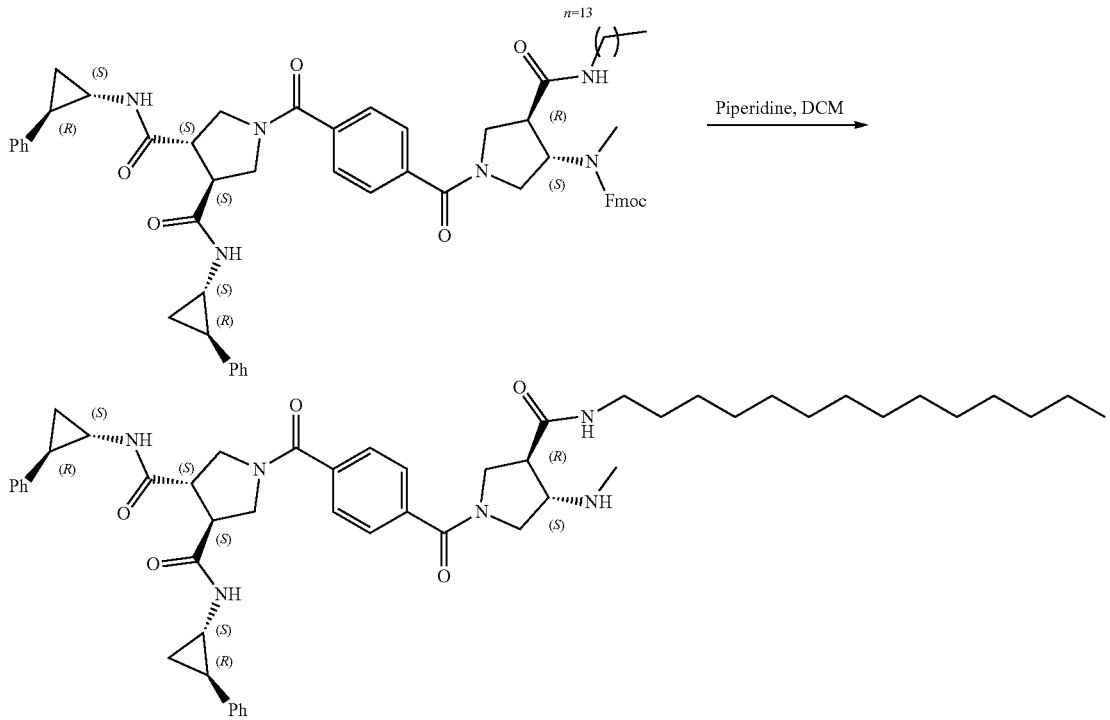

(9H-fluoren-9-yl)methyl ((3S,4R)-1-(4-((3S,4S)-3,4-bis(((1S,2R)-2-phenylcyclopropyl) carbamoyl)pyrrolidine-1-carbonyl)benzoyl)-4-(tetradecylcarbamoyl)pyrrolidin-3-yl)(methyl)carbamate (0.136 g, 0.125 mmol) was dissolved in DMF (5 mL). Piperidine (0.010 g, 0.125 mmol) was added to the reaction mixture at room temperature and stirred for 16 hrs. The mixture was extracted in EtOAc (2×10 mL) then washed with brine (2×10 mL) and concentrated. The crude product was purified Prep HPLC Method 12 to give (3S, 4S)-1-(4-((3S,4R)-3-(methylamino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 098 (0.012 g, 11.5%), as a white solid. LCMS (Method-H): 97.1% (RT: 4.915, 202.0 nm) (MS: ESI +ve 860.0 [M+1]). $^1$H NMR: (400 MHz, DMSO) δ ppm: 0.836-0.853 (m, 3H), 1.108 (s, 2H), 1.239 (m, 25H), 1.401 (s, 2H), 1.859-1.970 (m, 4H), 2.186 (s, 2H), 2.296-2.334 (m, 2H), 2.776 (s, 1H), 2.851 (s, 1H), 3.068-3.111 (m, 2H), 3.188-3.207 (m, 1H), 3.188-3.207 (m, 2H), 3.249-3.276 (m, 2H), 3.636-3.698 (m, 3H), 3.698-3.826 (m, 3 H), 7.061-7.079 (m, 2H), 7.117-7.182 (m, 4H), 7.221-7.287 (m, 4H), 7.551 (s, 4H), 7.970-8.068 (d, J=39.2 Hz, 1H), 8.320 (s, 1H), 8.450 (s, 1H).

Synthesis of (3S,4S)-1-(4-((3S,4R)-3-(dimethyl-amino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 091

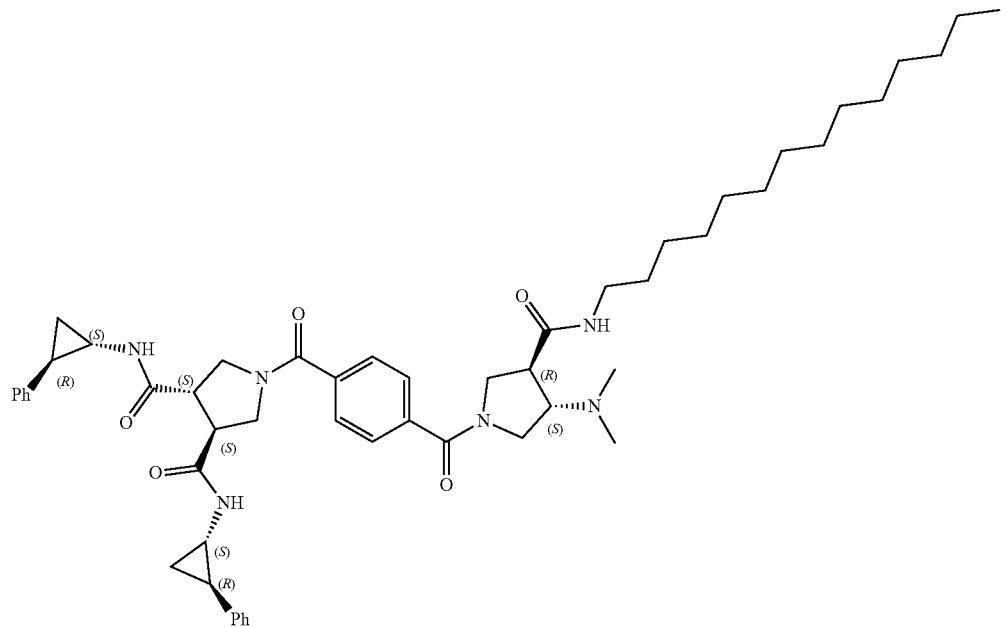

Step-1: Preparation of 1-(tert-butyl) 3-ethyl (3R, 4S)-4-aminopyrrolidine-1,3-dicarboxylate Step-2: Preparation of 1-(tert-butyl) 3-ethyl (3R, 4S)-4-(dimethylamino)pyrrolidine-1,3-dicarboxylate

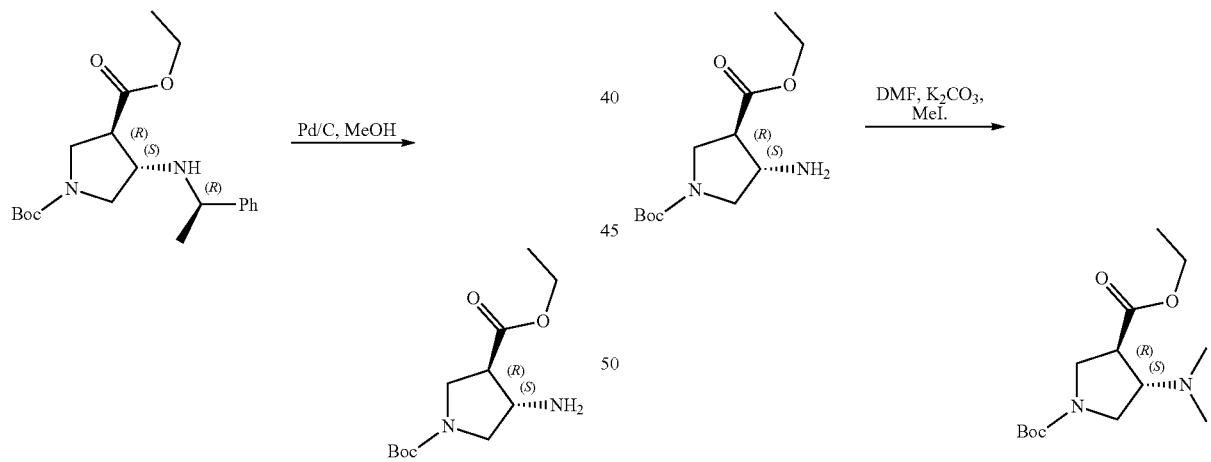

A mixture of 1-(tert-butyl) 3-ethyl (3R,4S)-4-(((R)-1-phenylethyl)amino)pyrrolidine-1,3-dicarboxylate (0.5 g, 1.37 mmol) and Pd/C (0.5 g, 10% with 50% moisture) in MeOH (10 mL), was hydrogenated at balloon pressure for 16 h. The reaction mixture was filtered through celite, rinsed with MeOH (10 mL), and the filtrate was concentrated to give 1-(tert-butyl) 3-ethyl (3R,4S)-4-aminopyrrolidine-1,3-dicarboxylate as a colorless solid (0.387 g, 93%). LCMS (Method-C2): 100% (RT 0.960, 202 nm) (MS: ESI +ve 259.4 [M+H]).

1-(tert-butyl) 3-ethyl (3R,4S)-4-aminopyrrolidine-1,3-dicarboxylate (0.387 g, 1.49 mmol) was dissolved in DMF (10 mL). Potassium carbonate (0.828 g, 5.99 mmol) and methyl iodide (0.425 g, 2.99 mmol) were added and the reaction mixture was stirred for 4 h. The mixture was diluted with water and extracted with EtOAc (3×50 mL). The combined organic layers were dried over anhydrous sodium sulfate and concentrated. The crude product was purified by flash chromatography on basic alumina, eluting with 0-1% MeOH: DCM, to give 1-(tert-butyl) 3-ethyl (3R,4S)-4-(dimethylamino)pyrrolidine-1,3-dicarboxylate (0.127 g, 29.6%) as a semisolid material. LCMS (Method-C2): 85.91% (RT: 1.317, 202.0 nm) (MS: ESI +ve 186.2[M−100]).

Step-3: Preparation of (3R,4S)-1-(tert-butoxycarbonyl)-4-(dimethylamino)pyrrolidine-3-carboxylic acid

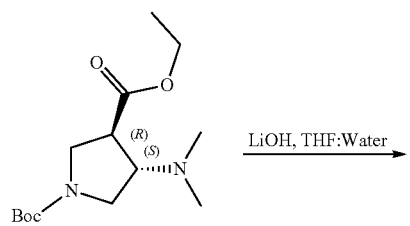

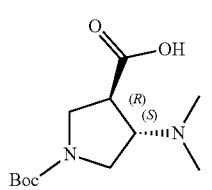

Prepared using General Ester Hydrolysis Procedure to give (3R,4S)-1-(tert-butoxycarbonyl)-4-(dimethylamino) pyrrolidine-3-carboxylic acid as a white solid (0.1 g, 87.3%). LCMS (Method-C2): 98.60% (RT: 1.144, 238.0 nm) (MS: ESI +ve 199.1[M–56]).

Step-4: Preparation of tert-butyl (3S,4R)-3-(dimethylamino)-4-(tetradecylcarbamoyl)pyrrolidine-1-carboxylate

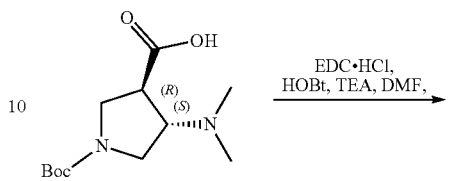

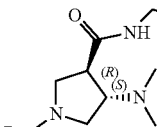

Prepared using General EDC, HOBT Coupling Procedure. The crude solid was purified by flash chromatography, eluting with 0-5% MeOH:DCM, to give tert-butyl (3S,4R)-3-(dimethylamino)-4-(tetradecylcarbamoyl)pyrrolidine-1-carboxylate (0.105 g, 59%) as a white solid. MS: (MS: ESI +ve 353.16[M–100]).

Step-5: Preparation of (3R,4S)-4-(dimethylamino)-N-tetradecylpyrrolidine-3-carboxamide TFA salt

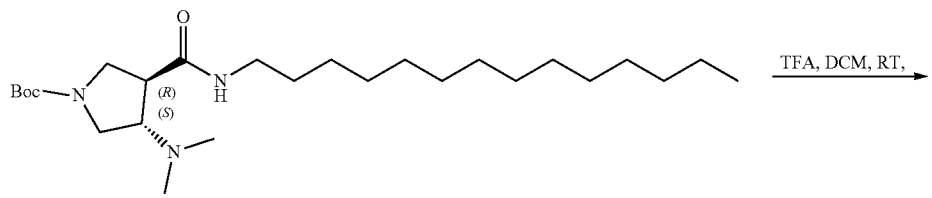

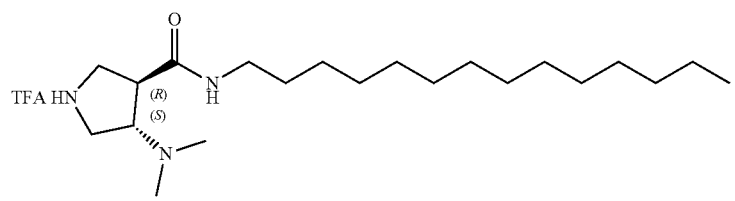

Prepared using General BOC Deprotection Procedure to give (3R,4S)-4-(dimethylamino)-N-tetradecylpyrrolidine-3-carboxamide TFA salt (0.1 g). LCMS (Method-C2): 100% (RT: 1.478, 230.0 nm) (MS: ESI +ve 617[M+H]).

Step-6: Preparation of (3S,4S)-1-(4-((3S,4R)-3-(dimethylamino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 091

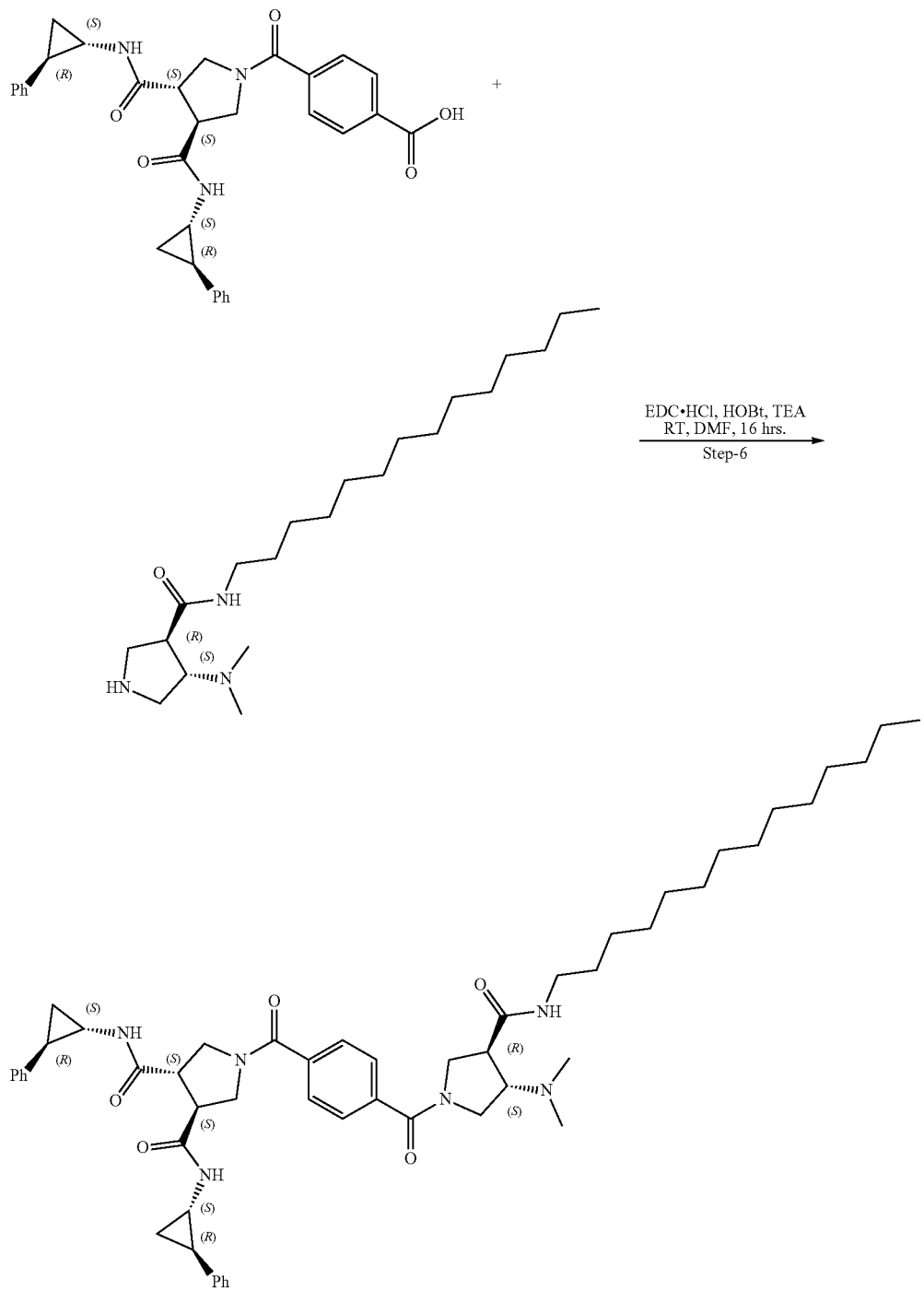

Prepared using General EDC, HOBT Coupling Procedure. The crude solid was purified by Prep HPLC Method 10 to give (3S,4S)-1-(4-((3S,4R)-3-(dimethylamino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 091) (0.03 g, 12%), as an off white solid. LCMS (Method-J): 100% (RT 6.112, 202.0 nm) (MS: ESI +ve 873.3 [M+H]). ¹H NMR: (400 MHz, DMSO) δ ppm: 0.76-0.85 (m, 3H), 1.09-1.22 (m, 25H), 1.38-1.42 (m, 2H), 2.86 (s, 1H), 1.98 (s, 1H), 2.77 (s, 1H), 2.83 (s, 1H), 3.04-3.21 (m, 5H), 3.50-3.65 (m, 2H), 3.75-3.81 (m, 1H), 4.33 (s, 2H), 4.44 (s, 2H), 6.49-6.61 (m, 1H), 7.06-7.08 (m, 2H), 7.11-7.18 (m, 4H), 7.22-7.28 (m, 4H), 7.56-7.63 (m, 4H), 8.09-8.12 (m, 1H), 8.31 (m, 1H), 8.43-8.44 (m, 1H).

Synthesis of (3S,4S)-1-(4-((3S,4R)-3-(methyl((R)-1-phenylethyl)amino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 090

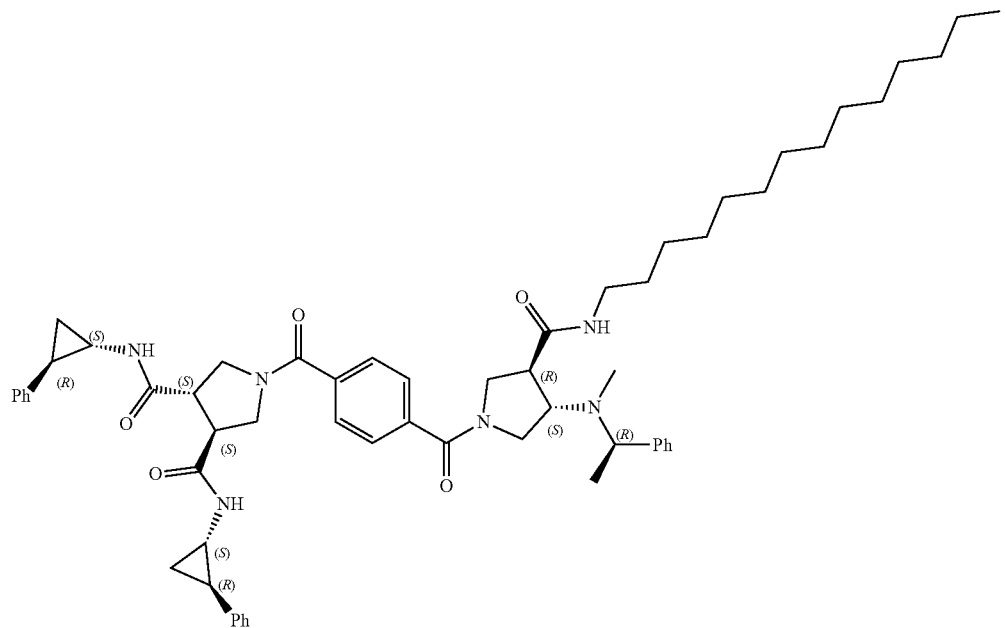

Step-1: Preparation of tert-butyl (3S,4R)-3-(methylamino)-4-(tetradecylcarbamoyl) pyrrolidine-1-carboxylate

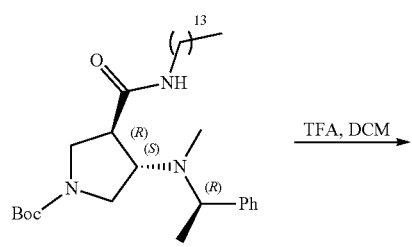

-continued

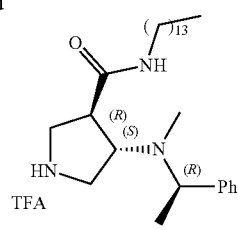

Prepared using General BOC Deprotection Procedure to give (3R,4S)-4-(methyl((R)-1-phenylethyl)amino)-N-tetradecylpyrrolidine-3-carboxamide TFA salt, as a brown gum (0.7 g, Crude) LCMS (Method-DEV): 82.93% (RT 5.100, 214.0 nm) (MS: ESI +ve 444.4 [M+1]).

Step-2: Preparation of (3S,4S)-1-(4-((3S,4R)-3-(methyl((R)-1-phenylethyl)amino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 090

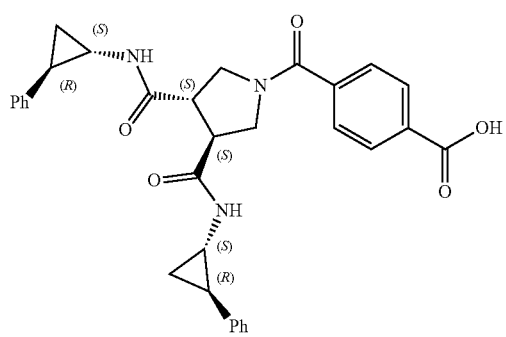

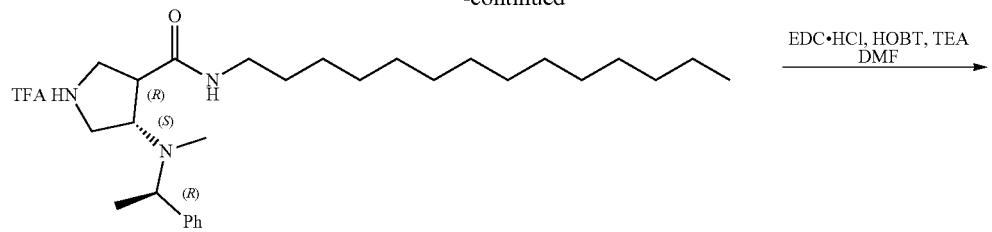

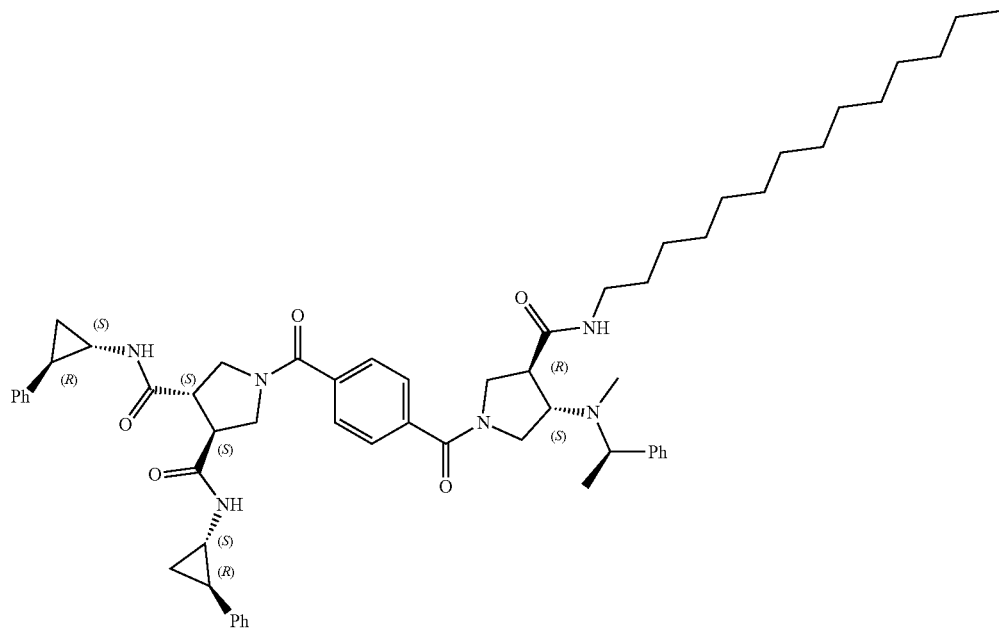

Prepared using General EDC, HOBT Coupling Procedure. The crude was purified using Prep HPLC Method 9 to give (3S,4S)-1-(4-((3S,4R)-3-(methyl((R)-1-phenylethyl)amino)-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 090) (0.017 g, 17%). LCMS (Method-J): 100% (RT 7.177, 202.0 nm) (MS: ESI +ve 963.57 [M+H]). $^1$H NMR: (400 MHz, DMSO) δ ppm: 0.84-0.87 (m, 3H), 1.11-1.45 (m, 34H), 1.86 (s, 1H), 1.98 (s, 1H), 2.15-2.20 (m, 3H), 2.79-2.86 (m, 2H), 2.92-3.24 (m, 3H), 3.39-3.49 (m, 2H), 3.52-3.55 (m, 2H), 3.60-3.69 (m, 3H), 3.71-3.79 (m, 2H), 7.06-7.08 (d, J=7.2 Hz, 2H), 7.13-7.19 (m, 4H), 7.21-7.29 (m, 7H), 7.32-7.33 (d, J=3.6 Hz, 2H), 7.51-7.56 (m, 4H), 7.98-8.11 (m, 1H), 8.28-8.32 (m, 1H), 8.43 (s, 1H).

Example 22

Synthesis of (3S,4S)-1-(4-((3R*,4S*)-3-(hexylcarbamoyl)-4-hydroxypyrrolidine-1-carbonyl)benzoyl)-N3,N4-bis((1S,2R)-2-phenylcyclopropyl)pyrrolidine-3,4-dicarboxamide, Compound 033 (Trans-Racemic)

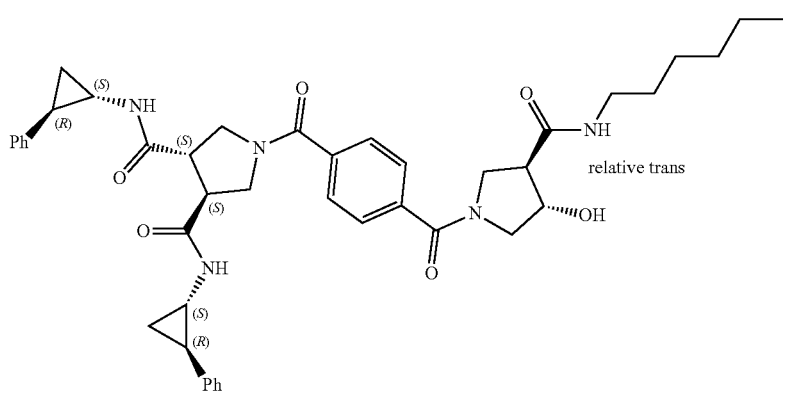

Step 1: Preparation of 1-(tert-butyl) 3-ethyl 4-hydroxypyrrolidine-1,3-dicarboxylate

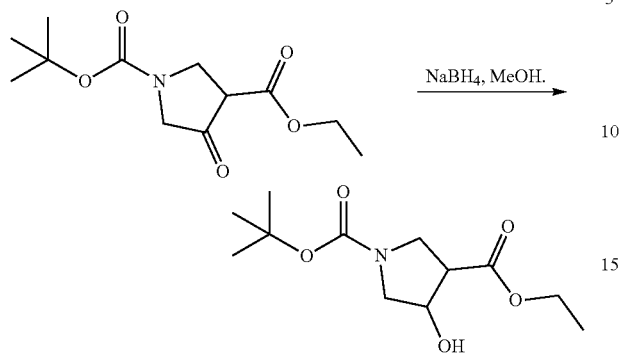

A solution of (S)-4-(tert-butoxycarbonyl) piperazine-2-carboxylic acid (6.0 g, 23.34 mmol) in methanol (30 mL) was cooled to 0° C. and NaBH$_4$ (0.430 g, 11.67 mmol) was added in portions. The reaction mixture was stirred for 2 hrs at room temperature then quenched by the addition of 20% acetic acid, concentrated and portioned between water (50) and ethyl acetate (3×100 mL). The combined organic layers were washed with brine, NaHCO$_3$ (2×100 mL) and dried over sodium sulphate then concentrated under reduced pressure to give 1-(tert-butyl) 3-ethyl 4-hydroxypyrrolidine-1,3-dicarboxylate as a mixture of isomers (5.1 g, 85%). LCMS (Method-C3): 82.39% (RT: 1.866, 202.0 nm) (MS: ESI +ve 260.2[M+H]).

Step-2: Preparation of 1-(tert-butoxycarbonyl)-4-hydroxypyrrolidine-3-carboxylic acid

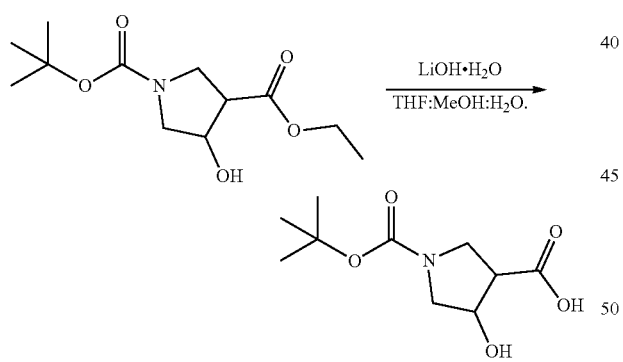

LiOH·H$_2$O (3.36 g, 134.97 mmol) was added to a stirred solution of 1-(tert-butyl) 3-ethyl 4-hydroxypyrrolidine-1,3-dicarboxylate (7.0 g, 26.99 mmol) in THF:MeOH:Water (4:2:1, 87.5 mL). The reaction mixture was stirred for 16 hrs at room temperature. The reaction mixture was concentrated then diluted in water (100 mL) and extracted with ethyl acetate (3×100 mL). The aqueous layer was acidified to ~pH 4 with citric acid and extracted with ethyl acetate (2×100 mL). The combined organics were dried over anhydrous sodium sulphate and concentrated under reduced pressure to give 1-(tert-butoxycarbonyl)-4-hydroxypyrrolidine-3-carboxylic acid as a mixture of isomers (4.2 g, 67%). LCMS (Method-C3): 93.87% (RT: 1.744, 202 nm) (MS: ESI +ve 176.0[(M−56)+H]).

Step 3: Preparation of tert-butyl (3R,4S)-3-(hexylcarbamoyl)-4-hydroxypyrrolidine-1-carboxylate (Fraction-1) and tert-butyl (3R,4R)-3-(hexylcarbamoyl)-4-hydroxypyrrolidine-1-carboxylate

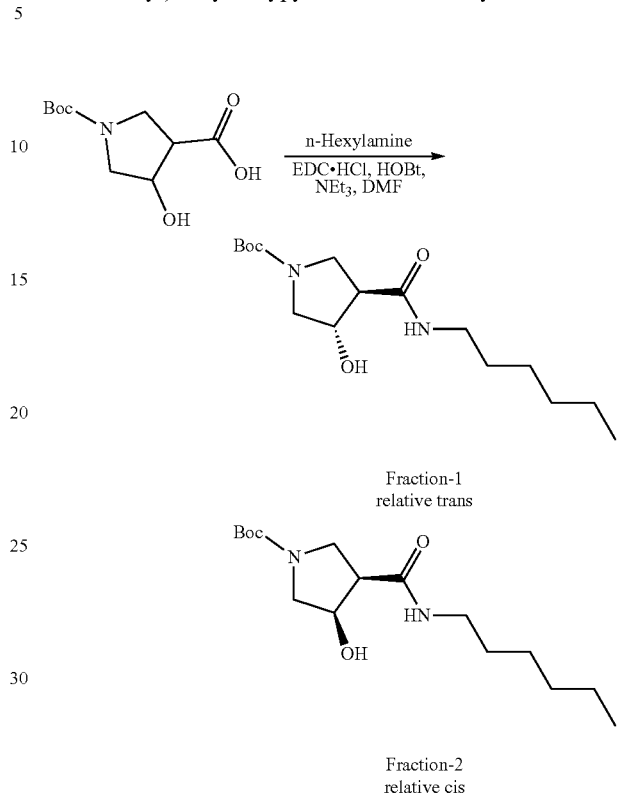

Prepared by a procedure similar to General EDC, HOBT Coupling Procedure. The crude mixture was purified/separated using Prep HPLC Method 4 to give:

Fraction-1, tert-butyl (3R*,4S*)-3-(hexylcarbamoyl)-4-hydroxypyrrolidine-1-carboxylate (0.330 g, 24.27%) assigned trans-relative stereochemistry. LCMS (Method-DEV_M): 100% (RT 15.838, 214.0 nm) (MS: ESI−ve 359.2[(M−H)+ACN]).

Fraction-2, tert-butyl (3R*,4R*)-3-(hexylcarbamoyl)-4-hydroxypyrrolidine-1-carboxylate (0.3 g, 22.6%) assigned cis-relative stereochemistry LCMS (Method-DEV_M): 100% (RT 16.620, 214 nm) (MS: ESI−ve 359.2[(M−H)+ACN]).

Step-4: Preparation of (3R*,4S*)—N-hexyl-4-hydroxypyrrolidine-3-carboxamide trifluoroacetate

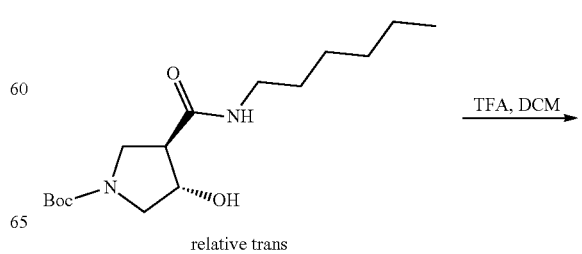

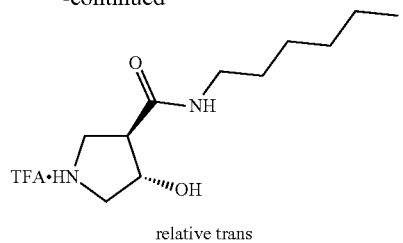

relative trans

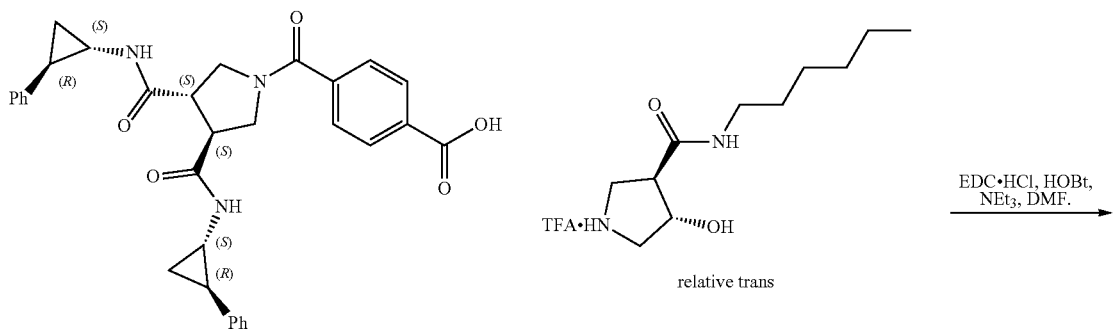

relative trans

Prepared by a procedure similar to General Boc Deprotection Procedure to give (3R*,4S*)—N-hexyl-4-hydroxypyrrolidine-3-carboxamide trifluoroacetate (0.3 g). LCMS (Method-C3): 100% (RT: 1.280, 202.0 nm) (MS: ESI +ve 215.3[M+H]).

Step-5: Preparation of (3S,4S)-1-(4-((3R*,4S*)-3-(hexylcarbamoyl)-4-hydroxypyrrolidine-1-carbonyl)benzoyl)-N3,N4-bis((1S,2R)-2-phenylcyclopropyl) pyrrolidine-3,4-dicarboxamide, Compound 033 (Trans-Racemic)

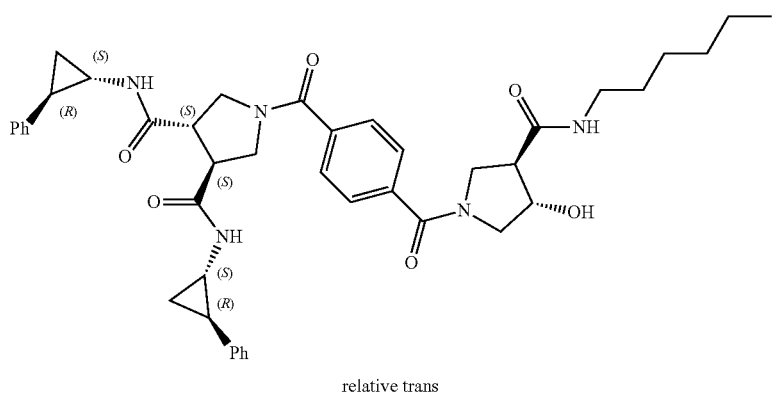

relative trans

Prepared by a procedure similar to General EDC, HOBT Coupling Procedure. The crude residue was purified using Prep HPLC Method 5 to give (3S,4S)-1-(4-((3R*,4S*)-3-(hexylcarbamoyl)-4-hydroxypyrrolidine-1-carbonyl)benzoyl)-N3,N4-bis((1S,2R)-2-phenylcyclopropyl)pyrrolidine-3,4-dicarboxamide, Compound 033 (Trans-Racemic) a mixture of diastereomers (0.016 g, 7.81%). LCMS (Method-C3): 100% (RT 1.718, 254 nm) (MS: ESI +ve 735.31 [M+H]). $^1$H NMR: (400 MHz, DMSO) δ ppm: 0.82-0.86 (t, J=8.8 Hz, 3H), 1.10 (S, 2H), 1.17-1.33 (m, 8H), 1.40 (s, 2H), 1.86 (s, 1H), 1.97 (s, 1H), 2.67 (s, 1H), 2.78 (s, 1H), 2.85-2.97 (m, 1H), 2.98-3.06 (m, 2H), 3.16-3.26 (m, 2H), 3.48-3.54 (m, 4H), 3.60-3.67 (m, 2H), 3.74-3.83 (m, 2H), 4.22-4.35 (m, 1H), 5.36-5.42 (m, 1H), 7.06-7.08 (d, J=7.2, 1H), 7.11-7.18 (m, 4H), 7.22-7.28 (m, 4H), 7.56 (s, 4H), 7.94-8.06 (m, 1H), 8.30 (s, 1H), 8.44 (s, 1H).

Example 23

Synthesis of (3S,4S)-1-(4-((3R*,4R*)-3-(hexylcarbamoyl)-4-hydroxypyrrolidine-1-carbonyl)benzoyl)-N3,N4-bis((1S,2R)-2-phenylcyclopropyl)pyrrolidine-3,4-dicarboxamide, Compound 034 (Cis-Racemic)

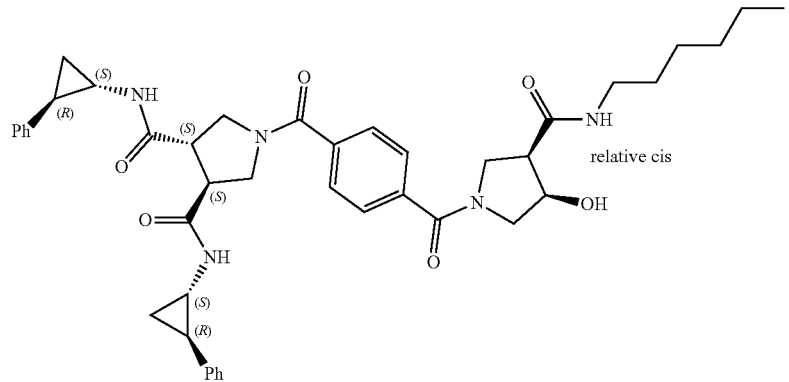

Prepared by a procedure similar to that reported for (3S,4S)-1-(4-((3R*,4S*)-3-(hexylcarbamoyl)-4-hydroxypyrrolidine-1-carbonyl)benzoyl)-N3,N4-bis((1S,2R)-2-phenylcyclopropyl)pyrrolidine-3,4-dicarboxamide, Compound 033 (Trans-Racemic) substituting tert-butyl (3R*,4R*)-3-(hexylcarbamoyl)-4-hydroxypyrrolidine-1-carboxylate (relative cis) in step 4. The final product was purified using column chromatography eluting with 0-6% Methanol in Dichloromethane to give (3S,4S)-1-(4-((3R*,4R*)-3-(hexylcarbamoyl)-4-hydroxypyrrolidine-1-carbonyl)benzoyl)-N3,N4-bis((1S,2R)-2-phenylcyclopropyl)pyrrolidine-3,4-dicarboxamide, Compound 034 (Cis-Racemic), (0.055 g, 27%) as a mixture of diastereomers. LCMS (Method-C3): 100% (RT 1.730, 225 nm) (MS: ESI +ve 735.3 [M+H]). $^1$H NMR: (400 MHz, DMSO) δ ppm: 0.84-0.86 (t, J=6.4 Hz, 3H), 1.11-1.25 (m, 10H), 1.34-1.41 (m, 2H), 1.87 (s, 1H), 1.89 (s, 1H), 2.78 (s, 1H), 2.84 (s, 1H), 2.92-3.00 (m, 4H), 3.09-3.24 (m, 2H), 3.42-3.54 (m, 6H), 3.65-3.83 (m, 2H), 4.37-4.47 (m, 1H), 5.14-5.23 (m, 1H), 7.06-7.08 (d, J=7.2, 1H), 7.11-7.18 (m, 4H), 7.22-7.28 (m, 4H), 7.56-7.57 (d, J=7.6 Hz, 4H), 7.81-7.87 (m, 1H), 8.30-8.31 (d, J=3.6 Hz, 1H), 8.43-8.44 (d, J=3.6 Hz, 1H).

Example 24

Synthesis of (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 044

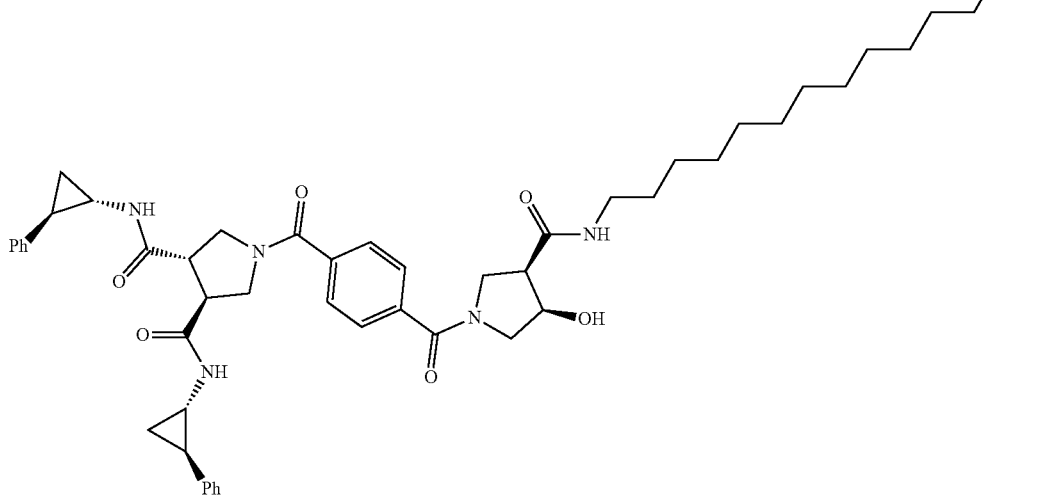

Step 1: Preparation of tert-butyl (3R*, 4R*)-3-hydroxy-4-(tetradecylcarbamoyl) pyrrolidine-1-carboxylate

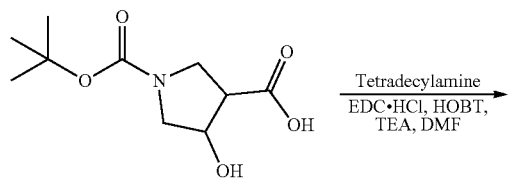

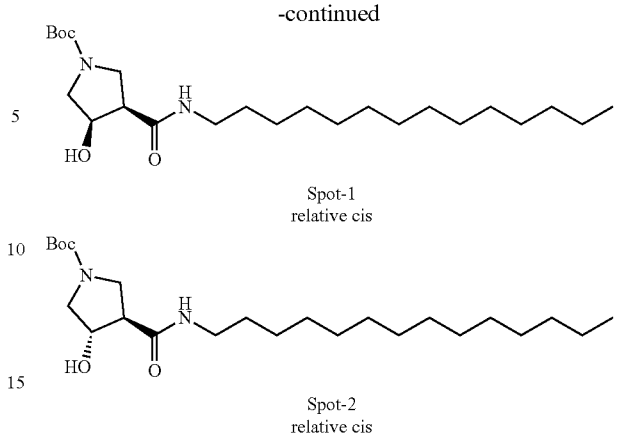

Spot-1
relative cis

Spot-2
relative cis

Prepare by a procedure similar to General EDC, HOBT Coupling Procedure. The crude product was purified/separated using column chromatography eluting with 0-10% MeOH in DCM to give:

Spot 1, tert-butyl (3R*,4R*)-3-hydroxy-4-(tetradecylcarbamoyl)pyrrolidine-1-carboxylate (0.4 g, 21%) assigned relative cis stereochemistry. LCMS (Method-C3): 100% (RT: 2.582, 202.4 nm) (MS: ESI +ve 427.5[M+H]).

Spot-2 tert-butyl (3S*,4R*)-3-hydroxy-4-(tetradecylcarbamoyl)pyrrolidine-1-carboxylate (0.2 g, 10%). LCMS (Method-C3): 100% (RT: 2.523, 202.4 nm) (MS: ESI +ve 427.5[M+H]).

Step-2: Preparation of (3R*, 4R*)-4-hydroxy-N-tetradecylpyrrolidine-3-carboxamide trifluoroacetate

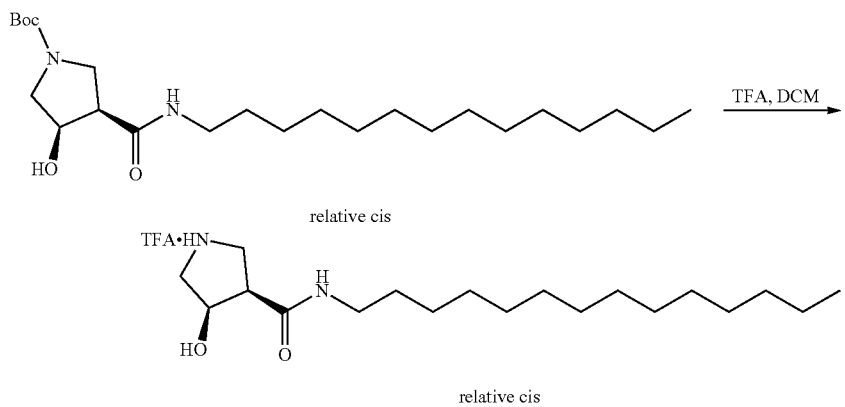

relative cis

Prepared by a procedure similar to General Boc Deprotection Procedure. The crude product was triturated in pentane to give (3R*, 4R*)-4-hydroxy-N-tetradecylpyrrolidine-3-carboxamide trifluoroacetate (0.1 g, 66%). LCMS (Method-C3): 100% (RT: 1.915, 202.0 nm) (MS: ESI +ve 327.4 [M+H]).

Step-3: Preparation of (3S,4S)-1-(4-((3R,4R)-3-hydroxy-4-(tetradecylcarbamoyl) pyrrolidine-1-carbonyl) benzoyl)-N3,N4-bis ((1S,2R)-2-phenylcyclopropyl) pyrrolidine-3,4-dicarboxamide, Compound 044

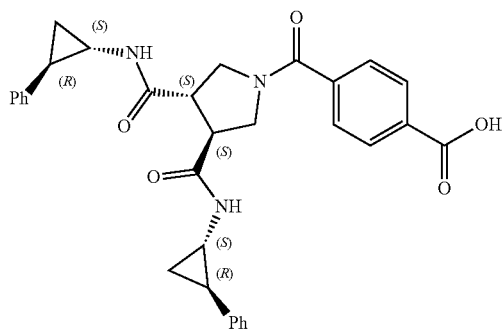

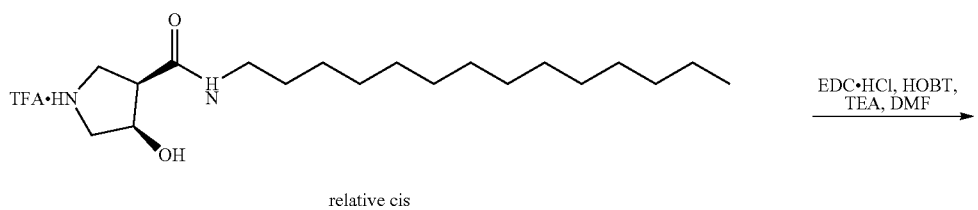

relative cis

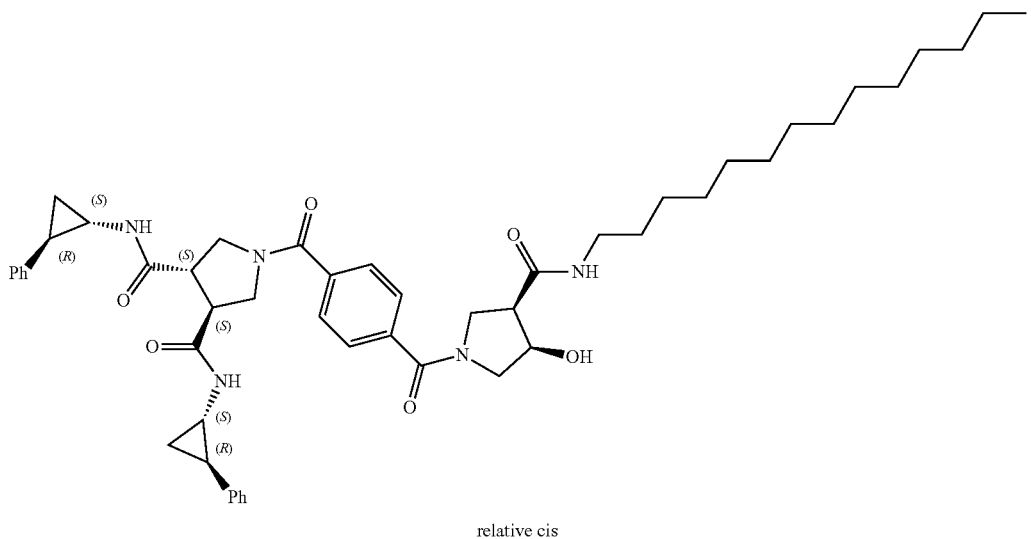

relative cis

Prepared by a procedure similar to General EDC, HOBT Coupling Procedure. The crude product was purified using Prep HPLC Method to give (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 044, as a mixture of diastereomers (0.006 g, 0.3%). LCMS (Method-C3): 100% (RT 2.418, 202.4 nm) (MS: ESI +ve 847.0 [M+H]). $^1$H NMR: (400 MHz, DMSO) δ ppm: 0.86 (t, 3H), 1.36-1.11 (m, 27H), 1.78 (s, 1H), 1.97-1.87 (d, 2H), 2.85-2.68 (d, 2H), 3.11-2.93 (m, 5H), 3.21 (s, 1H), 3.51-3.43 (t, 3H), 3.55 (s, 2H), 3.83-3.80 (d, 2H), 4.48-4.38 (s, 1H), 5.24-5.16 (s, 1H), 7.18-7.09 (m, 6H), 7.27-7.25 (d, 4H), 7.58-7.56 (d, 4H), 7.89 (s, 1H), 8.33 (s, 1H), 8.46 (s, 1H).

Step-4: Chiral SFC Separation of (3S,4S)-1-(4-((3R*,4R*)-3-hydroxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide

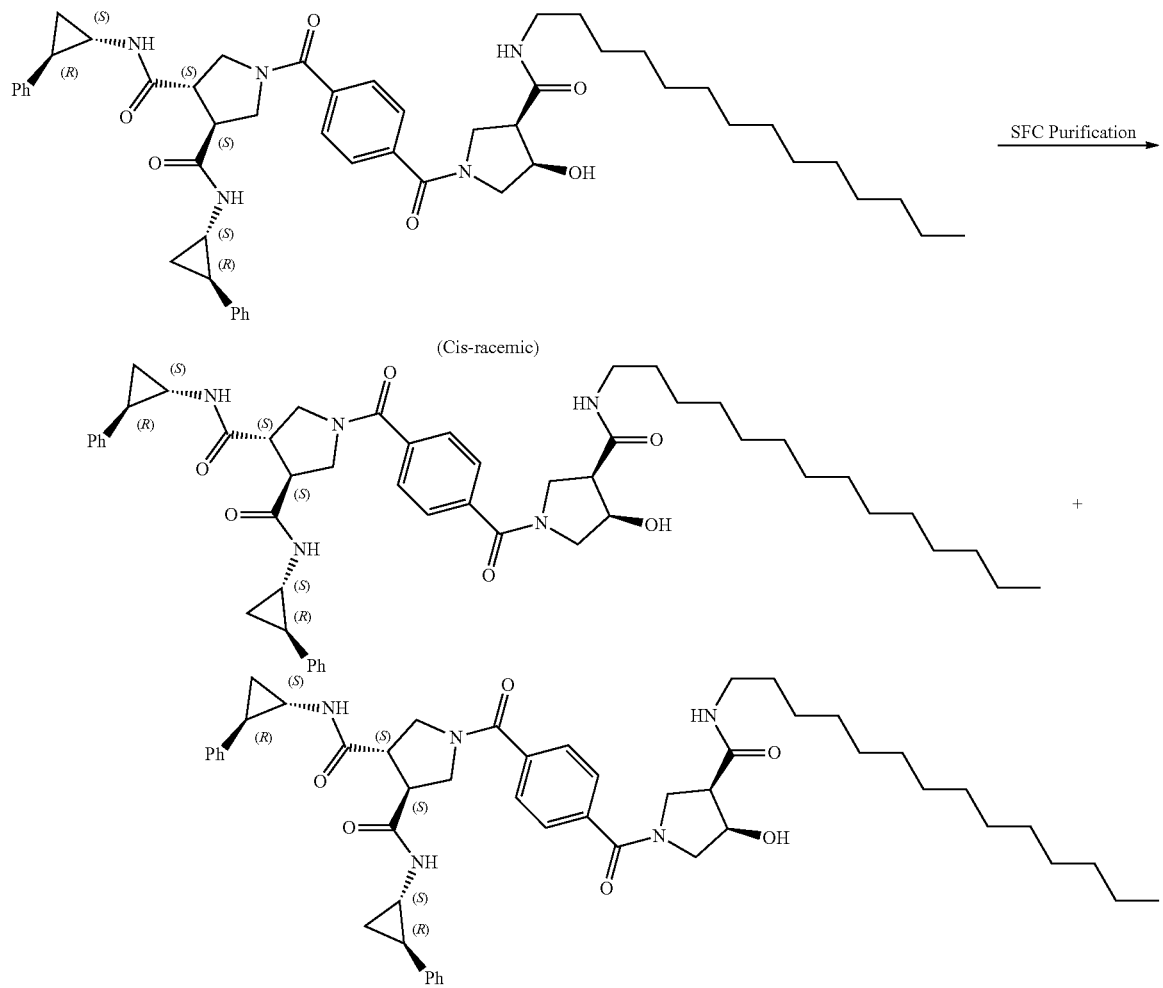

The diastereomers of (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 044) were separated on a Shimadzu LC-20AP chromatography system with UV detector. The column used was CHIRALPAK IC (250*21.0) mm, 5 micron, column flow was 20 ml/min. Mobile phase; (A) 0.1% DEA in hexane, (B) 0.1% DEA in propan-1-ol: acetonitrile (70:30) to give;

Fraction 1; (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl) pyrrolidine-3,4-dicarboxamide, Compound 103 (absolute stereochemistry was arbitrarily assigned) (0.044 g, 13.98%) LCMS (Method-J): 87.68% (RT 6.410, 224.0 nm) (MS: ESI +ve 846.4 [M+H]). The product was re-purified using Prep HPLC Method 1 to give Compound 103 (0.005 g, 1.6%) LCMS (Method-C2): 100% (RT 1.745, 202.0 nm) (MS: ESI +ve 846.87 [M+H]). $^1$H NMR: (400 MHz, DMSO) δ ppm: 0.83-0.85 (d, J=6.4 Hz, 4H), 1.11-1.36 (m, 31H), 1.86 (s, 1H), 2.67 (s, 2H), 3.01-3.82 (m, 14H), 4.36 (s, 1H), 5.14 (s, 1H), 7.06-7.26 (m, 10H), 7.55-7.57 (d, J=4.8 Hz, 4H), 7.81 (s, 1H), 8.30 (s, 1H), 8.43 (s, 1H). Chiral HPLC (Fr-1): 97.76% (RT: 12.78)

Fraction 2; (3S,4S)-1-(4-((3S*,4S*)-3-hydroxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide, Compound 104 (absolute stereochemistry was arbitrarily assigned) (0.054 g, 17.2%) LCMS (Method-J): 93.86% (RT 6.407, 202.0 nm) (MS: ESI +ve 846.4 [M+H]). The product was purified by Reverse Phase Prep HPLC. The compound was further purified using Prep HPLC Method 1 to give Compound 104 (0.006 g, 2.22%) LCMS (Method-J): 100% (RT 6.099, 220.0 nm) (MS: ESI +ve 846.38 [M+H]). $^1$H NMR: (400 MHz, DMSO) δ ppm: 0.83-0.85 (d, J=6.8 Hz, 2H), 1.11-1.36 (m, 27H), 1.97 (s, 3H), 2.67-3.83 (m, 17H), 4.36 (s, 1H), 5.14-5.23 (dd, J=34 Hz, 1H), 7.06-7.28 (m, 10H), 7.56-7.58 (d, J=8.4 Hz, 4H), 7.87 (s, 1H), 8.30 (s, 1H), 8.43 (s, 1H). Chiral HPLC (Fr-2): 100% (RT: 14.41).

Synthesis of (3S,4S)-1-(4-(((3R*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 107 and (3S,4S)-1-(4-(((3S*,4S*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 108
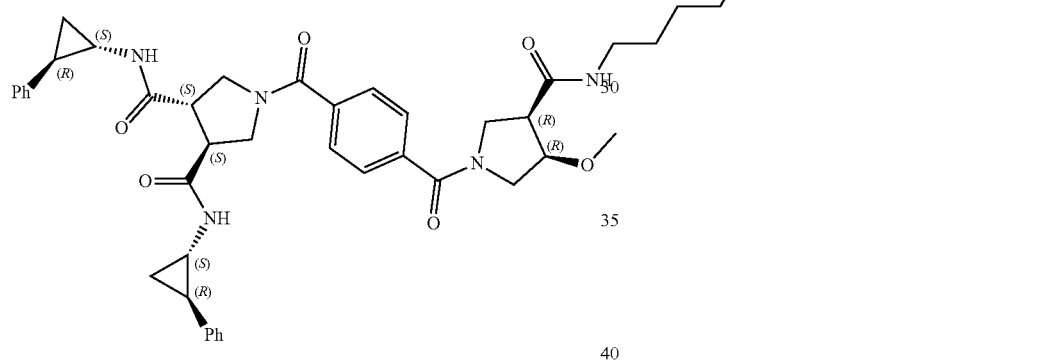
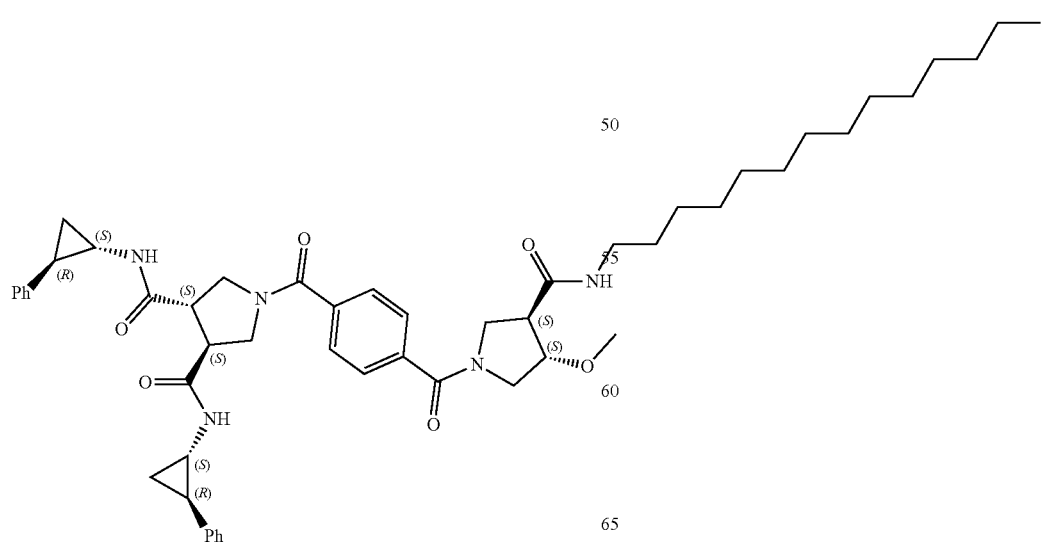

Step-1: Preparation of tert-butyl (3R,4R)-3-methoxy-4-(tetradecylcarbamoyl) pyrrolidine-1-carboxylate

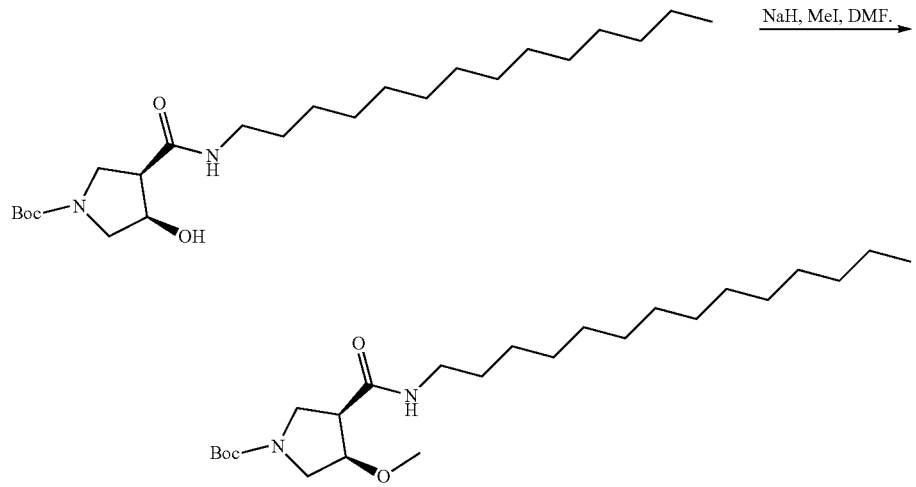

A solution of tert-butyl (3R*,4R*)-3-hydroxy-4-(tetradecylcarbamoyl)pyrrolidine-1-carboxylate (4.0 g, 9.38 mmol) in DMF (80 mL) was cooled to 0° C. and sodium hydride (0.375 g, 9.38 mmol) was added. After 15 min, methyl iodide (0.58 g, 9.38 mmol) was added and the reaction mixture was stirred for 3.0 h at room temperature. The mixture was quenched with water then extracted with EtOAc (3×50 mL). The combined organic layers were dried over sodium sulfate and concentrated. The crude product was purified by flash chromatography eluting, with 0-1.5% MeOH/DCM, to give racemic tert-butyl (3R*,4R*)-3-methoxy-4-(tetradecylcarbamoyl)pyrrolidine-1-carboxylate as a white solid (2.9 g, 70%). LCMS (Method-J2): 100% (RT: 5.762, 202.0 nm) (MS: ESI +ve 385.2[(M−56)+H]).

Step-2: Preparation of (3R*,4R*)-4-methoxy-N-tetradecylpyrrolidine-3-carboxamide TFA Salt

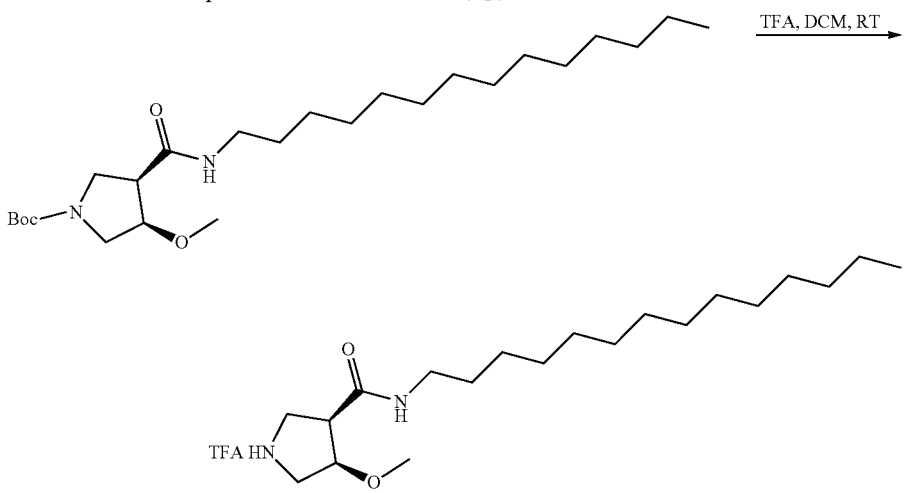

Prepared using General BOC Deprotection Procedure to give racemic (3R*,4R*)-4-methoxy-N-tetradecylpyrrolidine-3-carboxamide TFA salt (2.5 g), which was used without further purification.

Step-3: Preparation of (3S,4S)-1-(4-((3R*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 107 and (3S*,4S*)-1-(4-((3S,4S)-3-methoxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide, Compound 108

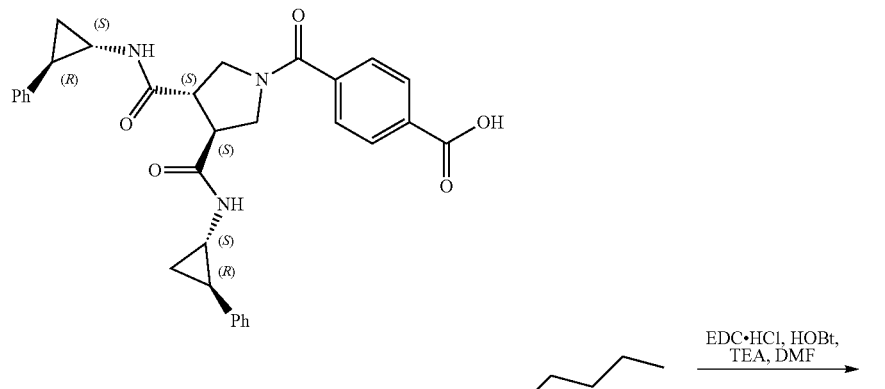

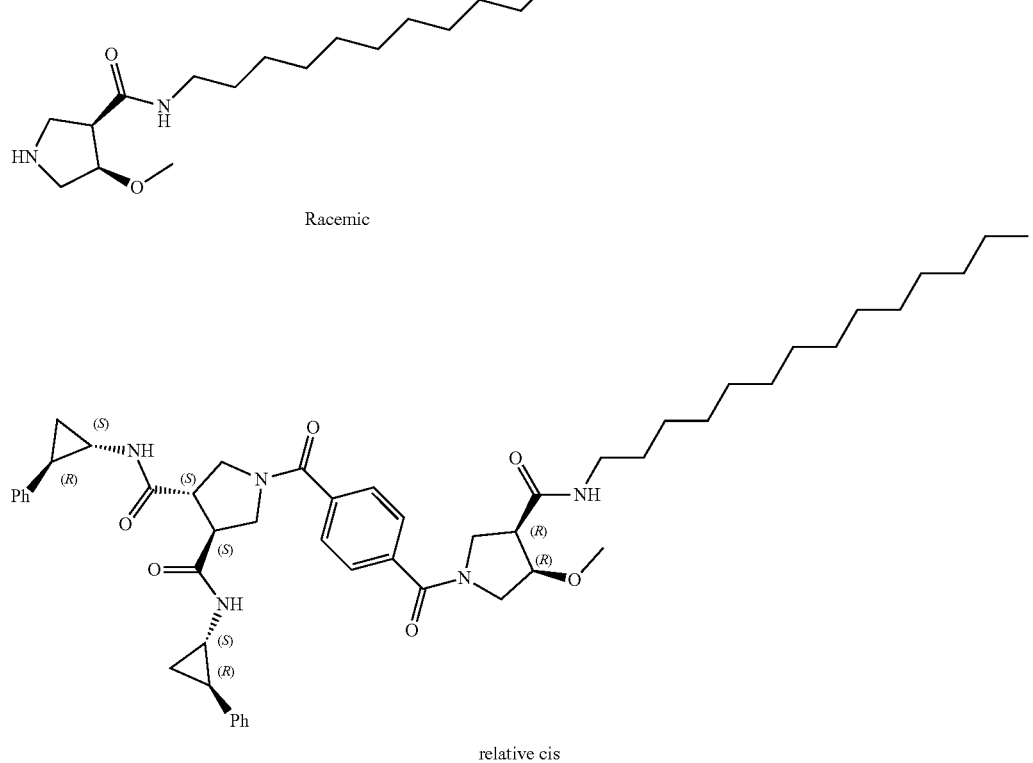

Prepared using General EDC, HOBT Coupling Procedure. The crude product was purified using reverse phase flash chromatography, eluting with 0.1% formic acid in water/acetonitrile, to give 2.1 g as a mixture of diastereomers. LCMS (Method-J2): 100% (RT 4.889, 228.0 nm) (MS: ESI +ve 861.3 [M+H]). Chiral HPLC: (45.44%, RT 14.06 and 53.41% RT 45.44, at 248.0 nm) (0.1 g) The mixture was separated using chiral HPLC on a Shimadzu LC-20AP chromatography system with UV detector. The column was CHIRALPAK IC (250*21.0) mm, 5 micron, column flow was 20.0 ml/min. Mobile phase; (A) 0.1% DEA in n-hexane (B) 0.1% DEA in propane-2-ol:acetonitrile (70:30) to give;

Fraction 1; (3S,4S)-1-(4-((3R*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 107 (0.02 g, 20%) (absolute stereochemistry of pyrrolidine is arbitrary). LCMS (Method-C): 100% (RT 2.617, 225.0 nm) (MS: ESI +ve 860.4 [M+H]). Chiral HPLC: 97.91% (RT 14.01, 248.0 nm) $^1$H NMR: (400 MHz, DMSO) δ ppm: 0.85 (m, 3H), 1.10-1.38 (m, 26H), 1.85-2.07 (m, 2H), 2.78-2.85 (m, 2H), 3.11-3.17 (m, 7H), 3.26 (s, 2H), 3.44-3.59 (m, 5H), 3.68-3.81 (m, 4H), 4.08-4.19 (m, 1H), 7.06-7.26 (m, 10H), 7.56 (s, 4H), 7.82-7.88 (m, 1H), 8.29-8.43 (m, 2H).

Fraction 2; (3S,4S)-1-(4-((3S*,4S*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 108 (0.022 g, 22%) (absolute stereochemistry of pyrrolidine is arbitrary). LCMS (Method-C): 100% (RT 4.889, 235.0 nm) (MS: ESI +ve 860.3 [M+H]). Chiral HPLC: 99.51% (RT 15.87, 248.0 nm)$^1$H NMR: (400 MHz, DMSO) δ ppm: 0.83-0.87 (m 3H), 1.09-1.11 (m, 2H), 1.15-1.24 (m, 23H), 1.36-1.39 (m, 2H), 1.86-1.87 (m, 1H), 1.95-1.97 (m, 1H), 2.77-2.78 (m, 1H), 2.84-2.86 (m, 1H), 3.06-3.09 (m, 1H), 3.12-3.18 (m, 4H), 3.20-3.26 (m, 1H), 3.44 (m, 2H), 3.47-3.55 (m, 4H), 3.55-3.69 (m, 2H), 3.77-3.80 (m, 1H), 4.10-4.20 (m, 1H), 7.06-7.08 (d, 2H), 7.08-7.18 (m, 4H), 7.22-7.29 (m, 4H), 7.54-7.59 (m, 4H), 7.81-7.90 (m, 1H), 8.30-8.32 (m, 1H), 8.44 (s, 1H).

Synthesis of (3S,4S)-1-(4-((3R*,4S*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 113 and (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 114

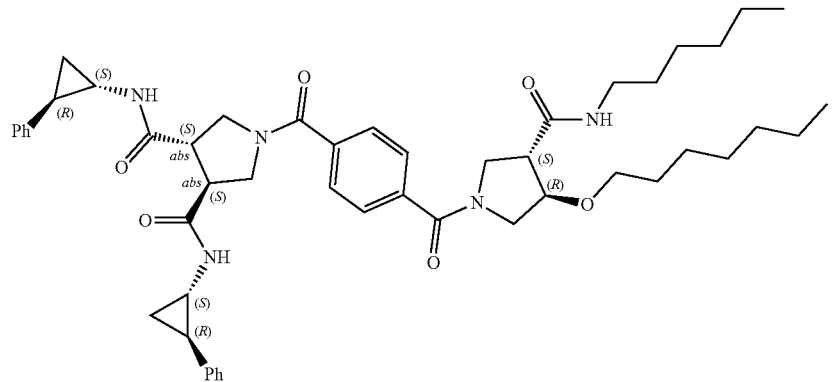

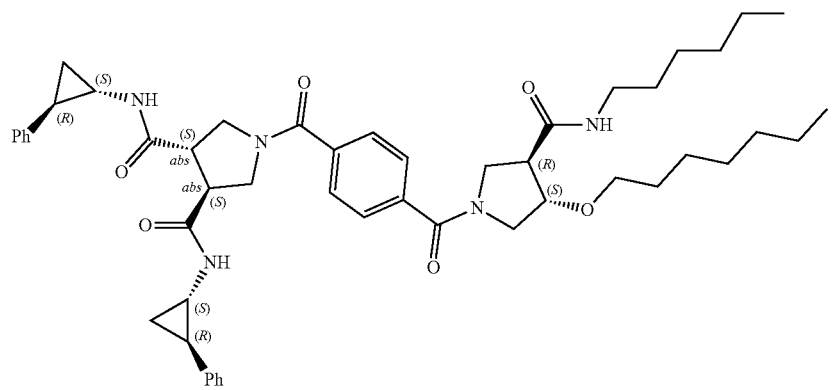

Step-1: Preparation of (3S,4S)-1-(4-((3R*,4S*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 113 and (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 114

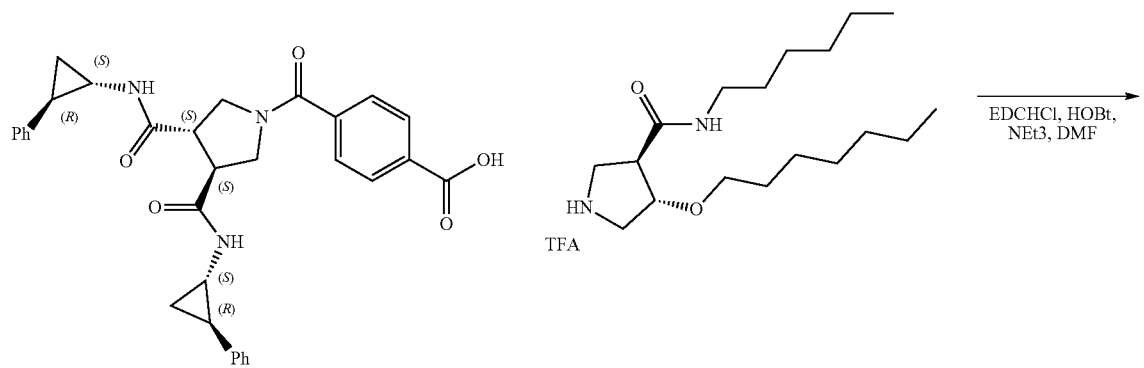

-continued

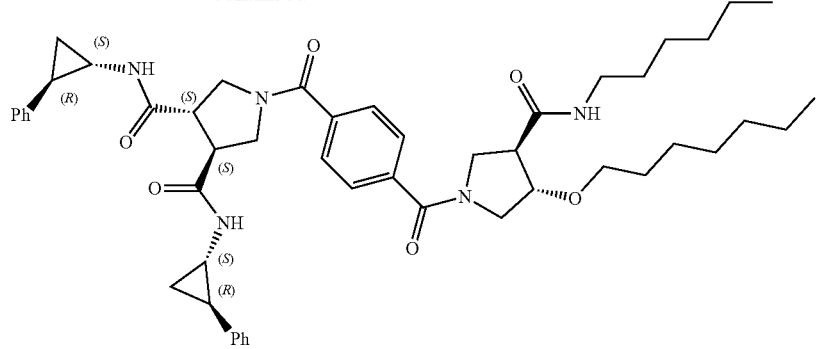

relative trans

Prepared using General EDC, HOBT Coupling Procedure using (3R,4S)-4-(heptyloxy)-N-hexylpyrrolidine-3-carboxamide TFA salt (0.174 g, 0.558 mmol) prepared by a similar method reported for (3R*,4R*)-4-methoxy-N-tetradecylpyrrolidine-3-carboxamide TFA salt to give (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide (0.020 g, 5.1%) as an off white solid. LCMS (Method-J): 96.1% (RT 5.959, 202.0 nm) (MS: ESI +ve 832.5 [M+H]). $^1$H NMR: (400 MHz, DMSO) δ ppm: 0.837-0.871 (m, 6H), 1.097-1.131 (m, 2H), 1.207-1.266 (m, 16H), 1.413 (s, 2H), 1.500 (s, 1H), 1.862-1.977 (m, 2H), 2.786-2.982 (m, 2H), 3.031-3.216 (m, 7H), 3.454-3.470 (m, 5H), 3.533-3.771 (m, 4H), 4.157-4.167 (d, J=4 Hz, 1H), 7.064-7.083 (d, J=7.6 Hz, 1H), 7.121-7.225 (m, 4H), 7.244-7.292 (m, 4H), 7.564 (s, 4H), 8.055-8.188 (d, J=53.2 Hz, 1H), 8.363 (s, 1H), 8.493-8.503 (d, J=16 Hz, 1H).

Step-2: SFC separation of (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide

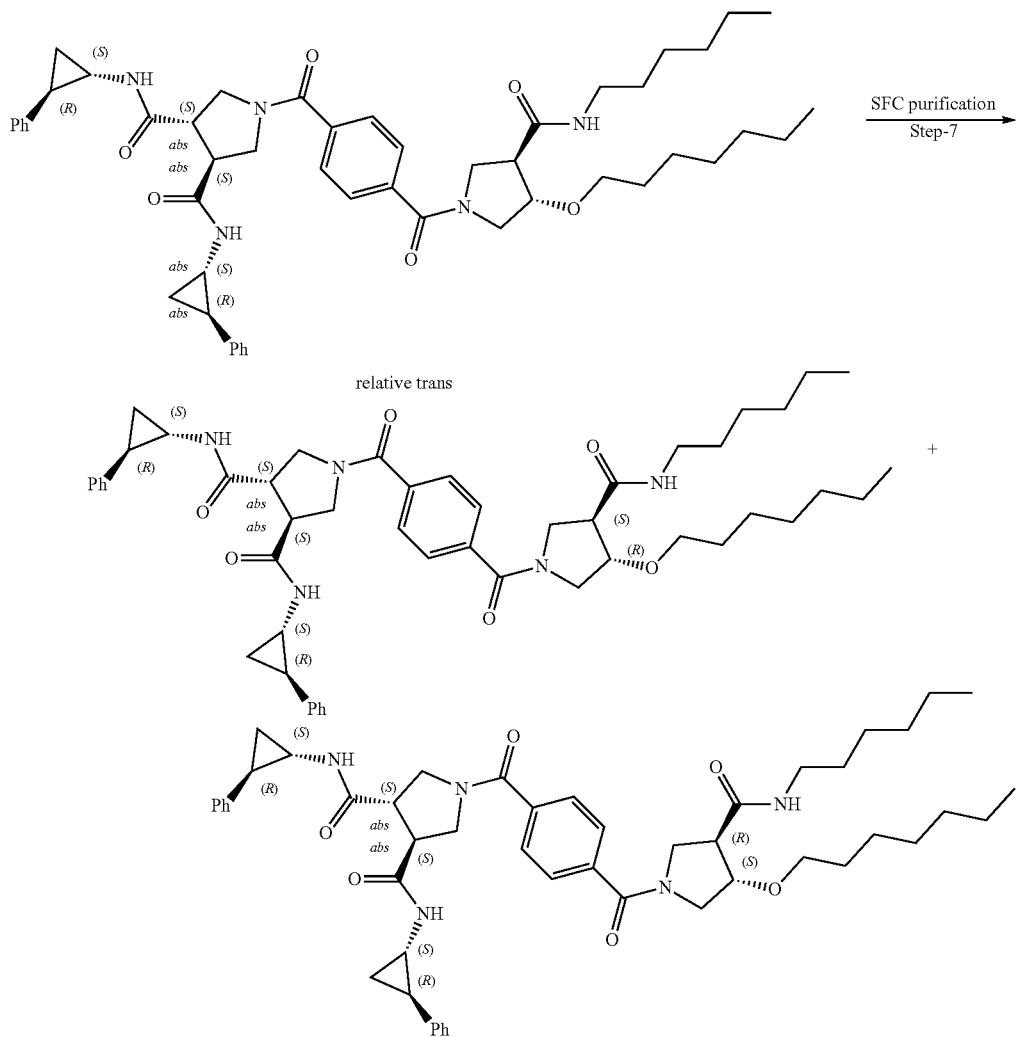

Separated on Waters SFC 20AP chromatography system with UV detector. The column was ChiralPAK IC (250*21.0) mm, 5 micron, column flow was 20.0 ml/min. Mobile phase; (A) 0.1% DEA in hexane and (B) 0.1% DEA in Propan-1-ol: Acetonitrile (70:30) The UV to give;

Fraction 1; (3S,4S)-1-(4-((3R*,4S*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 113 (0.0023 g, 2.13%) (absolute stereochemistry of pyrrolidine is arbitrary). LCMS (Method-J): 98.6% (RT: 5.610, 202.0 nm) (MS: ESI +ve 833.5 [M+H]). ¹H NMR: (400 MHz, DMSO) δ ppm: 0.832-0.884 (m, 6H), 1.111-1.513 (m, 21H), 1.875 (s, 1H), 1.989 (s, 1H), 3.011-3.039 (d, 3H), 3.091-3.132 (m, 3H), 3.185-3.248 (m, 4H), 3.468-3.494 (m, 4H), 3.566-3.711 (m, 4H), 4.059-4.071 (d, J=4.8 Hz, 1H), 7.078-7.305 (m, 11H), 7.574 (s, 4H), 8.028 (s, 1H), 8.161 (s, 1H), 8.300-8.308 (d, J=3.2 Hz, 1H), 8.437-8.445 (d, J=3.2 Hz, 1H). Chiral HPLC (Fr-1): 100% (RT: 10.34), (3S,4S)-1-(4-Fraction 2; (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl) pyrrolidine-3,4-dicarboxamide, Compound 114 (0.018 g, 20.50%) (absolute stereochemistry of pyrrolidine is arbitrary). LCMS (Method-C3): 100% (RT: 5.614, 202.0 nm) (MS: ESI +ve 833.5 [M+H]). ¹H NMR: (400 MHz, DMSO) δ ppm: 0.820-0.867 (m, 6H), 1.109-1.407 (m, 20H), 1.4197 (s, 1H), 1.858-1.970 (m, 3H), 2.943-2.993 (m, 2H), 3.026-3.206 (m, 6H), 3.340 (s, 1H), 3.435 (s, 1H), 3.498-3.691 (m, 4H), 3.711-3.834 (m, 4H), 4.049-4.152 (m, 1H), 7.061-7.080 (d, 2H), 7.117-7.221 (m, 4H), 7.240-7.288 (m, 4H), 7.558 (s, 4H), 8.023-8.153 (d, J=52 Hz, 1H), 8.300 (s, 1H), 8.432-8.441 (d, J=3.6 Hz, 1H). Chiral HPLC (Fr-2): 97.71% (RT: 12.05).

Synthesis of (3S,4S)-1-(4-((3R*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 115 and (3S,4S)-1-(4-((3S*,4S*)-3-(heptyloxy)-4-(hexylcarbamoyl) pyrrolidine-1-carbonyl)benzoyl)-N3,N4-bis ((1S,2R)-2-phenylcyclopropyl)pyrrolidine-3,4-dicarboxamide, Compound 116

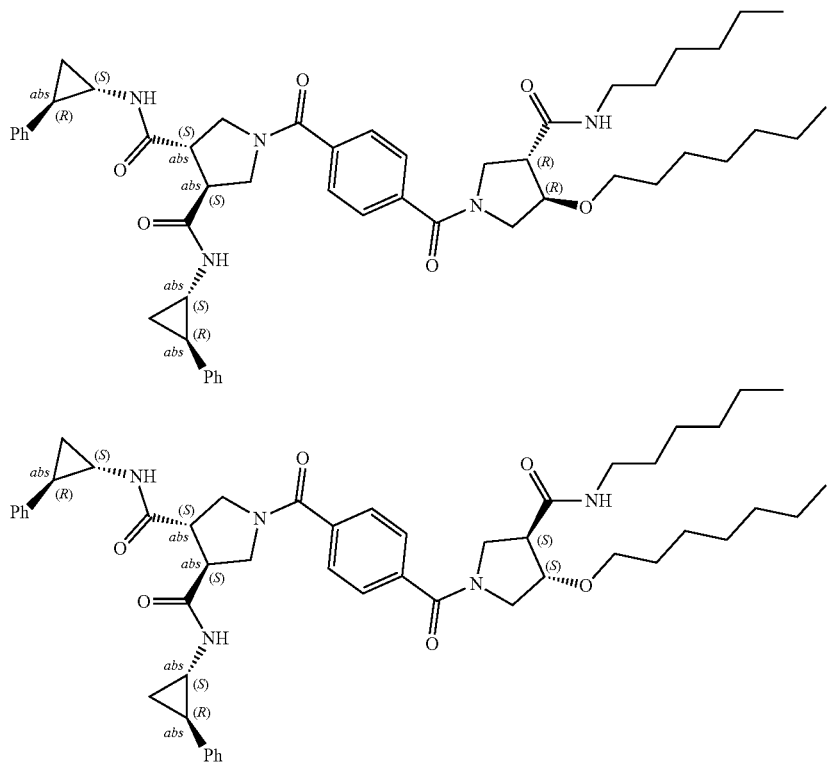

Step-1: Preparation of (3S,4S)-1-(4-((3R*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 115 and (3S,4S)-1-(4-((3S*,4S*)-3-(heptyloxy)-4-(hexylcarbamoyl) pyrrolidine-1-carbonyl)benzoyl)-N3, N4-bis((1S,2R)-2-phenylcyclopropyl)pyrrolidine-3, 4-dicarboxamide, Compound 116

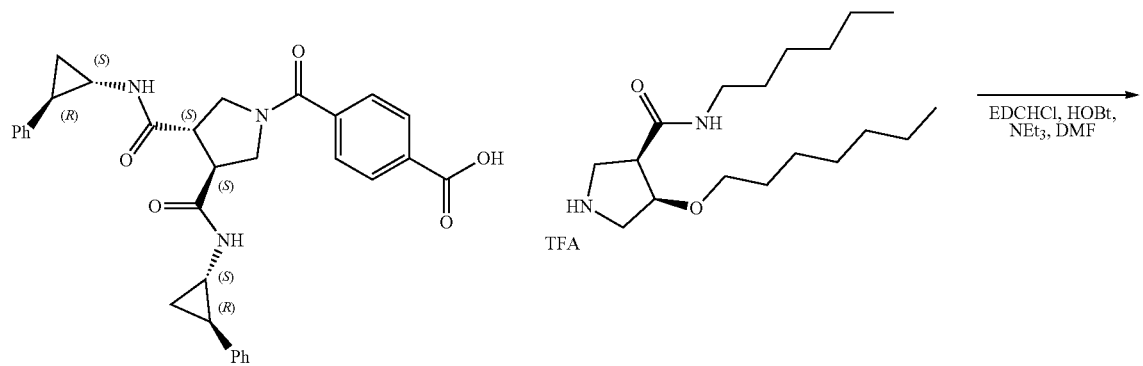

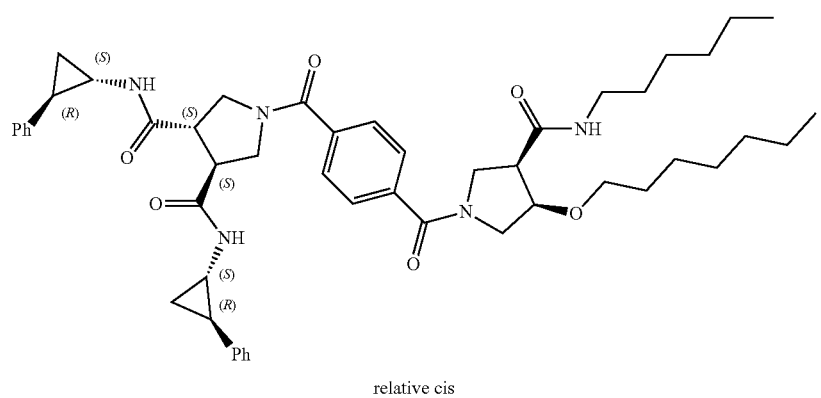

relative cis

Prepared using General EDC, HOBT Coupling Procedure using (3R*,4R*)-4-(heptyloxy)-N-hexylpyrrolidine-3-carboxamide (prepared by a similar method reported for (3R*,4R*)-4-methoxy-N-tetradecylpyrrolidine-3-carboxamide TFA salt. The crude was purified using Prep HPLC Method 2 to give (3S,4S)-1-(4-((3R*,4R*)-3-(heptyloxy)-4-(hexylcarbamoyl)pyrrolidine-1-carbonyl) benzoyl)-N3,N4-bis((1S,2R)-2-phenylcyclopropyl)pyrrolidine-3,4-dicarboxamide (0.153 g, 32.9%) as a mixture of diastereomers. LCMS (Method-J): 100% (RT: 5.869, 214.0 nm) (MS: ESI +ve 833.5 [M+H]). ¹H NMR: (400 MHz, DMSO) δ ppm: 0.851-0.859 (s, 6H), 1.109-1.249 (m, 18H), 1.3639 (s, 4H), 1.858-1.970 (d, 2H), 2.676-2.783 (d, 2H), 2.959 (s, 1H), 3.097-3.114 (m, 3H), 3.194 (s, 1H), 3.284 (s, 2H), 3.429-3.551 (m, 4H), 3.666 (s, 2H), 3.786-3.811 (d, J=10 Hz, 1H), 4.161-4.270 (m, 1H), 7.063-7.182 (m, 6H), 7.221-7.268 (m, 4H), 7.562 (s, 4H), 7.814-7.870 (d, J=22.4 Hz, 1H), 8.309 (s, 1H), 8.444 (s, 1H).

Step-2: SFC Purification of Racemic (3S,4S)-1-(4-((3R*,4R*)-3-(heptyloxy)-4-(hexylcarbamoyl)pyrrolidine-1-carbonyl) benzoyl)-N3,N4-bis((1S,2R)-2-phenylcyclopropyl)pyrrolidine-3,4-dicarboxamide

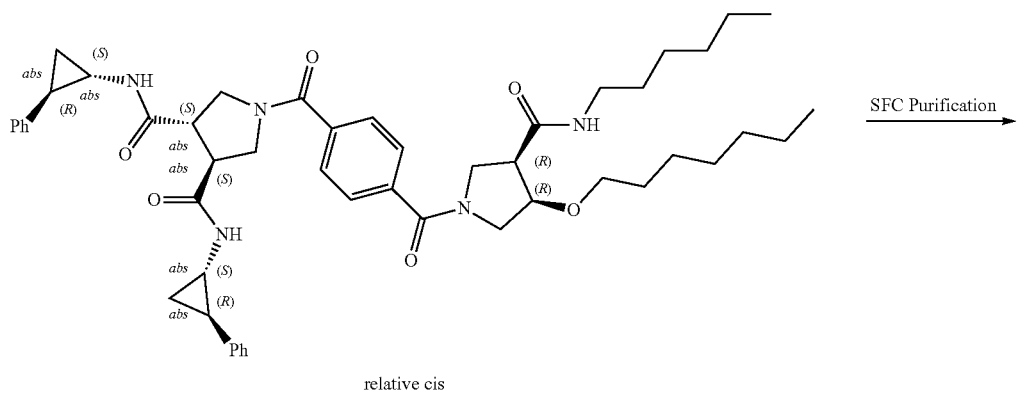

relative cis

-continued

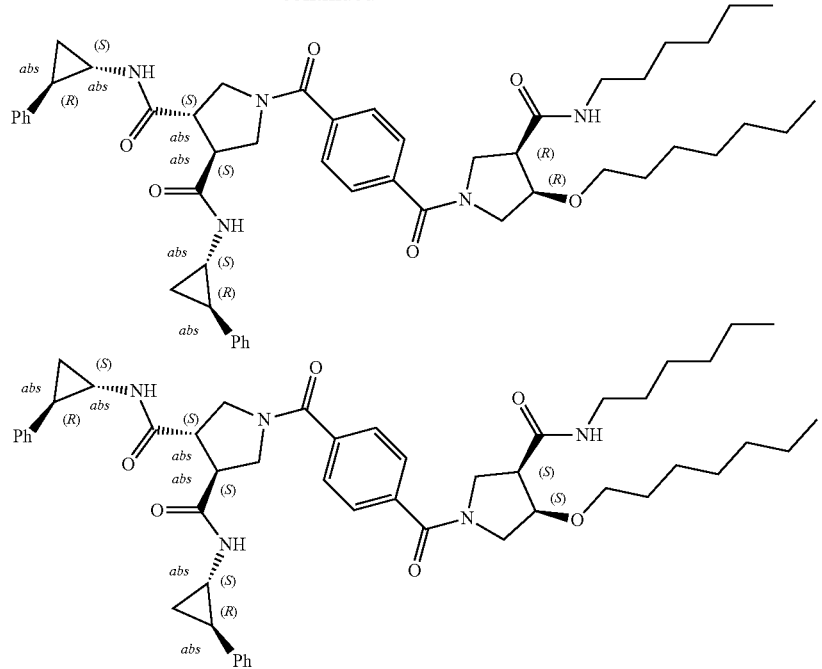

Separated on Waters SEC 20AP and UV detector. The column was used ChiralPAK IH (250*21.0) mm, 5 micron, column flow was 20.0 ml/min. Mobile phase; (A) 0.10% DEA in hexane and (B) 0.1% DEA in Propan-1-ol: Acetonitrile (70:30) to give;

Fraction 1; (3S,4S)-1-(4-((3*,4R*-3-(heptyloxy)-4-(hexylcarbamoyl)pyrrolidine-1-carbonyl)benzoyl)-N3,N4-bis ((1S,2R)-2-phenylcyclopropyl)pyrrolidine-3,4-dicarboxamide, Compound 115 (0.016 g, 21.5%) (absolute stereochemistry of pyrrolidine is arbitrary). LCMS (Method-J): 100% (RT: 5.875, 254.0 nm) (MS: ESI +ve 833.5 [M+H]). $^1$H NMR: (400 MHz, DMSO) δ ppm: 0.825-0.875 (m, 6H), 1.117-1.257 (m, 19H), 1.359-1.411 (m, 4H), 1.880 (s, 1H), 1.979 (s, 1H), 2.862-2.954 (m, 2H), 3.086-3.121 (m, 1H), 3.171-3.293 (m, 4H), 3.442 (m, 1H), 3.483-3.539 (m, 4H), 3.558-3.589 (m, 2H), 3.620-3.660 (m, 2H), 4.166-4.274 (d, J=43.2 Hz, 1H), 7.074-7.191 (m, 6H), 7.229-7.295 (m, 4H), 7.562-7.582 (m, 4H), 7.812-7.873 (m, 1H), 8.307 (s, 1H), 8.439 (s, 1H). Chiral HPLC (Fr-1): 100% (RT: 6.39).

Fraction 2; (3S,4S)-1-(4-((3S*,4S*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 116 (0.021 g, 22.3%). LCMS (Method-J): 100% (RT: 5.862, 254.0 nm) (MS: ESI +ve 833.5 [M+H]). $^1$H NMR: (400 MHz, DMSO) δ ppm: 0.820-0.875 (m, 6H), 1.090-1.258 (m, 18H), 1.349-1.411 (m, 5H), 1.860 (s, 1H), 1.978-1.993 (m, 1H), 2.935 (s, 1H), 2.953 (s, 1H), 2.979 (m, 1H), 3.102-3.076 (m, 4H), 3.121-3.174 (m, 1H), 3.344-3.533 (m, 4H), 3.559-3.693 (m, 2H), 3.693-3.792 (m, 2H), 4.168-4.279 (d, J=44.4 Hz, 1H), 7.067-7.191 (m, 6H), 7.226-7.296 (m, 4H), 7.558-7.578 (m, 4H), 7.818-7.871 (m, 1H), 8.303 (s, 1H), 8.434-8.444 (d, J=4 Hz, 1H). Chiral HPLC (Fr-2): 98.34% (RT: 8.81).

Example 25

Synthesis of (3S,4S)-1-(4-((3S*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 045

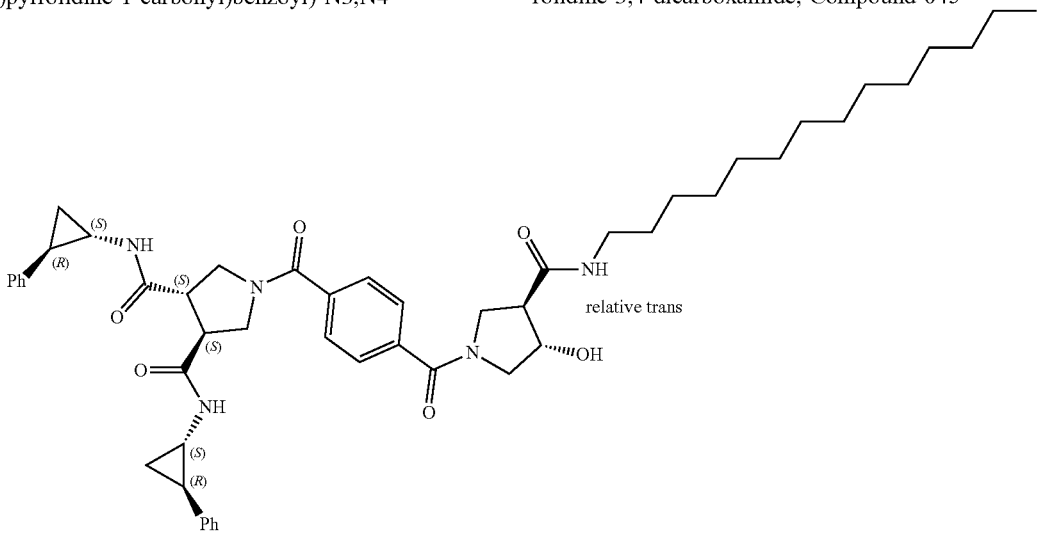

Prepared by a procedure similar to that reported for (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 044, substituting tert-butyl (3S*,4R*)-3-hydroxy-4-(tetradecylcarbamoyl)pyrrolidine-1-carboxylate in step 2. The crude product was purified Prep HPLC Method 1 to give (3S,4S)-1-(4-((3S*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 045, as a mixture of diastereomers (0.005 g, 3%). LCMS (Method-C3): 100% (RT 2.375, 202.4 nm) (MS: ESI +ve 846.9 [M+H]). ¹H NMR: (400 MHz, DMSO) δ ppm: 0.86 (t, 3H), 1.36-1.11 (m, 27H), 1.78 (s, 1H), 1.97-1.87 (d, 2H), 2.85-2.68 (d, 2H), 3.11-2.93 (m, 5H), 3.21 (s, 1H), 3.51-3.43 (t, 3H), 3.55 (s, 2H), 3.83-3.80 (d, 2H), 4.48-4.38 (s, 1H), 5.24-5.16 (s, 1H), 7.18-7.09 (m, 6H), 7.27-7.25 (d, 4H), 7.58-7.56 (d, 4H), 7.89 (s, 1H), 8.33 (s, 1H), 8.46 (s, 1H).

Step-1: Chiral SFC separation of (3S,4S)-1-(4-((3S*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 045

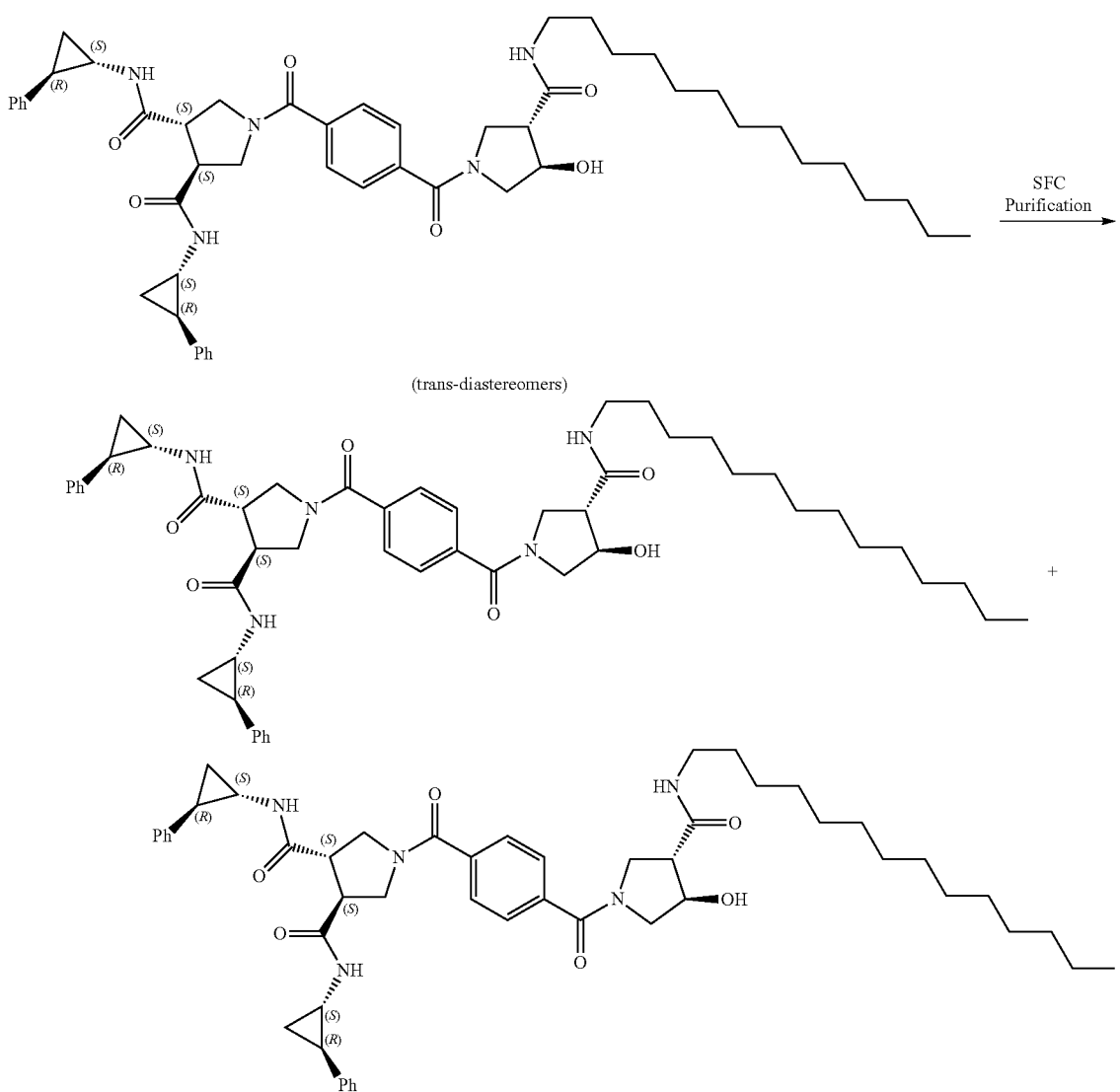

The diastereomers of (3S,4S)-1-(4-((3S*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 045) were separated on a Shimadzu LC-20AP chromatography system with UV detector. The column used was CHIRALPAK IC (250*21.0) mm, 5 micron, column flow was 20 ml/min. Mobile phas; (A) 0.1% DEA in hexane (B) 0.1% DEA in propan-1-ol:acetonitrile (70:30) To give:

Fraction 1; (3S,4S)-1-(4-((3R*,4S*)-3-hydroxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide, Compound 105 (absolute stereochemistry arbitrarily assigned) (0.036 g, 43%) LCMS (Method-C3): 97.80% (RT 6.034, 223.0 nm) (MS: ESI +ve 847.5 [M+H]). The product was re-purified using Prep HPLC Method 1 to give (0.012 g, 3.8%) LCMS (Method-C2): 100% (RT 1.745, 202.0 nm) (MS: ESI-+ve 846.87 [M+H]). ¹H NMR: (400 MHz, DMSO) δ ppm: 0.83-0.85 (d, J=6.8 Hz, 4H), 1.10-1.40 (m, 31H), 1.86 (s, 2H), 1.97 (s, 4H), 2.67-3.20 (m, 10H), 3.34-3.80 (m, 7H), 4.21 (s, 1H), 4.32 (s, 1H), 7.06-7.26 (m, 10H), 7.55 (s, 4H), 7.93 (s, 1H), 8.30 (s, 1H), 8.43 (s, 1H). Chiral HPLC (Fr-1): 99.40% (RT: 13.37)

Fraction 2; (3S,4S)-1-(4-((3S*,4R*)-3-hydroxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide, Compound 106 (absolute stereochemistry arbitrarily assigned) (0.040 g, 48%) LCMS (Method-J): 100% (RT 6.027, 202.0 nm) (MS: ESI +ve 847.5 [M+H]). The compound was repurified using Prep HPLC Method 1 to give (0.007 g, 2.22%) LCMS (Method-J): 100% (RT 6.027, 202.0 nm) (MS: ESI +ve 847.5 [M+H]). ¹H NMR: (400 MHz, DMSO) δ ppm: 0.83-0.85 (d, J=6.8 Hz, 3H), 1.10-1.10 (m, 29H), 1.86 (s, 1H), 1.96 (s, 1H), 2.67-3.80 (m, 16H), 4.11 (s, 1H), 4.21 (s, 1H), 4.3 (s, 1H), 5.34 (s, 1H), 7.06-7.26 (m, 10H), 7.55 (s, 4H), 7.93 (s, 1H), 8.06 (s, 1H), 8.30 (s, 1H), (s, 1H). Chiral HPLC (Fr-2): 100% (RT: 17.17).

Example 26

Synthesis of (3S,4S)-1-(4-((3S*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 060

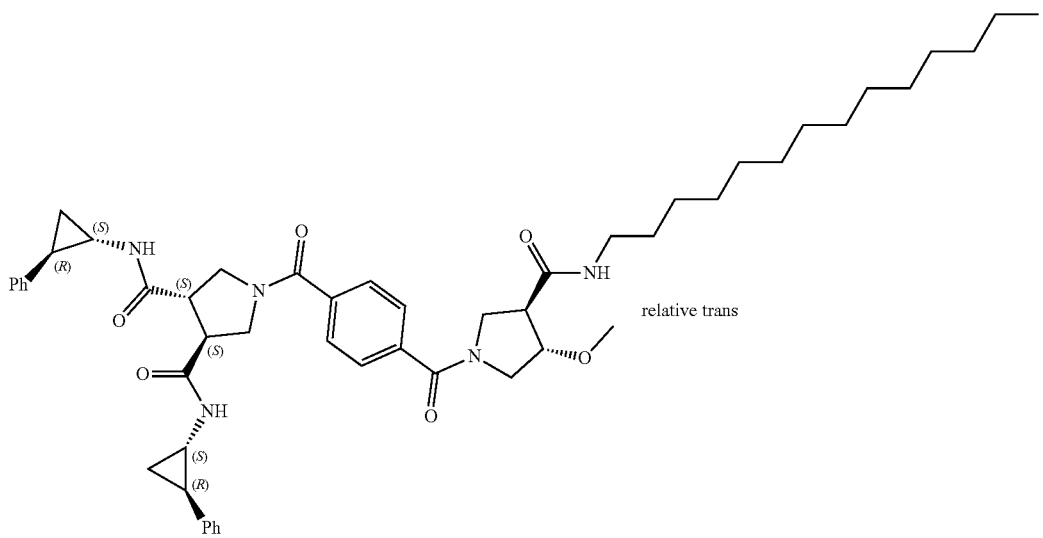

Step-1: Preparation of (3S,4S)-1-(4-((3S*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 060

A solution of (3S,4S)-1-(4-((3S*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide (0.2 g, 0.236 mmol) in DMF (2 mL) was cooled to 0° C. and sodium hydride (0.038 g, 0.945 mmol) was added in portion. After 15 min, methyl iodide (0.036 g, 0.259 mmol) was added. The reaction mixture was stirred for 3.0 hrs at room temperature, then quenched by water and extracted with ethyl acetate (3×50 mL). The combined organic layers were dried over anhydrous sodium sulphate and concentrated under reduced pressure. The compound was purified using Prep HPLC Method 1 to give (3S,4S)-1-(4-((3S*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 060, as a mixture of diastereomers (0.013 g, 6.64%). LCMS (Method-C3): 100% (RT 2.614, 202.0 nm) (MS: ESI +ve 861.1 [M+H]). ¹H NMR: (400 MHz, DMSO) δ ppm: 0.83-0.86 (t, J=7.2 Hz, 3H), 1.10-1.12 (m, 2H), 1.23 (s, 26H), 1.33-1.40

(m, 2H), 1.86 (s, 1H), 2.77 (s, 1H), 2.85 (s, 1H), 2.91-3.00 (m, 4H), 3.09-3.13 (m, 2H), 3.30 (s, 1H), 3.45-3.54 (m, 4H), 3.63-3.68 (m, 2H), 3.80-3.94 (m, 1H), 3.94-4.06 (m, 1H), 7.06-7.08 (d, J=7.6, 1H), 7.11-7.18 (m, 4H), 7.22-7.28 (m, 4H), 7.55 (s, 4H), 8.03-8.17 (m, 1H), 8.31 (s, 1H), 8.44 (s, 1H).

Synthesis of (3S,4S)-1-(4-((3S,4R)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 109 vinylpyrrolidine-1-carboxylate (2.4 g, 53%). The racemic mixture was resolved using a Waters SFC 200 chromatography system with UV detector. The column used was Chiral Pak AD-H (250*21.0) mm, 5 micron, column flow was 80.0 ml/min and ABPR was 100 bar. Mobile phase; (A) Liquid Carbon dioxide (Liq. $CO_2$) and (B) 0.1% Diethylamine in MeOH. Isolated:

Fraction-1; benzyl (3S,4R)-3-hydroxy-4-vinylpyrrolidine-1-carboxylate (0.8 g) Chiral HPLC of Fraction-1: 100% (RT 4.06, 215.0 nm). (Stereochemistry was assigned based on U.S. Pat. No. 8,748,626 B2).

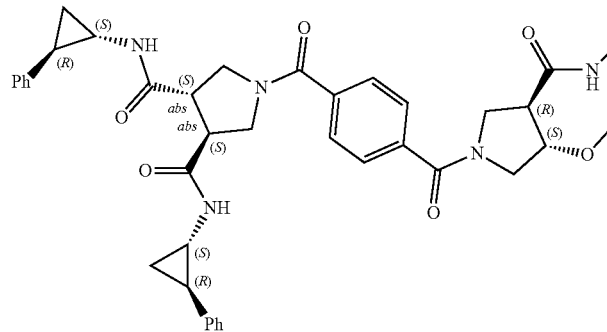

Step-1: Preparation of benzyl (3S,4R)-3-hydroxy-4-vinylpyrrolidine-1-carboxylate (Fraction-1) and benzyl (3R,4S)-3-hydroxy-4-vinylpyrrolidine-1-carboxylate (Fraction-2). (Prepared and assigned stereochemistry as in U.S. Pat. No. 8,748,626 B2

Fraction 2; benzyl (3R,4S)-3-hydroxy-4-vinylpyrrolidine-1-carboxylate (0.8 g). Chiral HPLC of Fraction-2: 99.86% (RT 5.00, 215.0 nm). (Stereochemistry was assigned based on U.S. Pat. No. 8,748,626 B2).

Step-2: Preparation of benzyl (3S,4R)-3-methoxy-4-vinylpyrrolidine-1-carboxylate

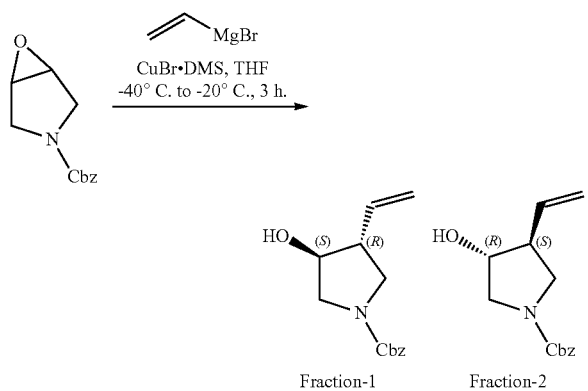

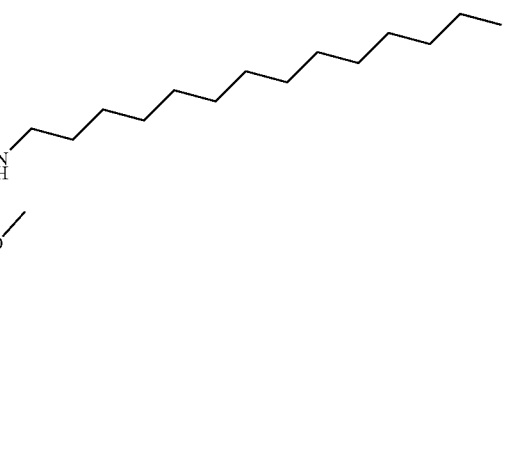

Benzyl 6-oxa-3-azabicyclo [3.1.0]hexane-3-carboxylate (4.0 g, 18.24 mmol) and CuBr.DMS (3.74 g, 18.24 mmol) were dissolved in THF (80 mL) and cooled to −40° C. A solution of vinyl magnesium bromide 1M in THF (73.0 mL, 73.0 mmol) was added dropwise at −40° C. over 10 min and stirring at −20° C. was continued for 3 h. The reaction was quenched with aqueous $KHSO_4$ and the mixture was extracted with ethyl acetate (2×100 mL). The combined organic layers were dried over sodium sulfate and concentrated under reduced pressure. The crude product was purified by flash chromatography, eluting with 0.8-2% MeOH in DCM, to give a racemic mixture of trans 3-hydroxy-4-

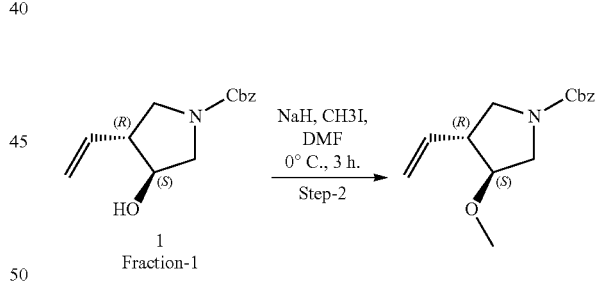

(3S,4R)-3-hydroxy-4-vinylpyrrolidine-1-carboxylate (Fraction-1) (0.4 g, 1.61 mmol) was dissolved in DMF (10 mL) and cooled to 0° C. Sodium hydride (0.077 g, 1.94 mmol) was added portion-wise. After 15 min, methyl iodide (0.12 g, 1.94 mmol) was added and the reaction mixture was stirred for 3.0 hr at 0° C. The reaction mixture was quenched with water and extracted with ethyl acetate (3×50 mL). The organic layer was dried over anhydrous sodium sulfate and concentrated under reduced pressure. The crude product was purified using flash chromatography, eluting with 0-2% MeOH in DCM, to give benzyl (3S,4R)-3-methoxy-4-vinylpyrrolidine-1-carboxylate (0.45 g). LCMS (Method-C3): 96.28% (RT: 1.294, 218.0 nm) (MS: ESI +ve 261.4[M+H]).

Step-3: Preparation of (3R,4S)-1-((benzyloxy)carbonyl)-4-methoxypyrrolidine-3-carboxylic acid

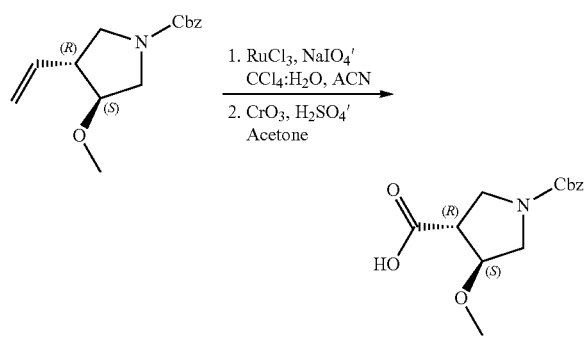

Benzyl (3S,4R)-3-methoxy-4-vinylpyrrolidine-1-carboxylate (0.45 g, 1.72 mmol) was dissolved in a mixture of acetonitrile: carbon tetrachloride: water (1:1:1, 12 mL). RuCl₃ (0.357 g, 1.72 mmol), and NaIO₄ (1.74 g, 6.88 mmol) were added portion-wise. The reaction mixture was stirred at room temperature under a nitrogen atmosphere for 16 h. The mixture was diluted with DCM (50 mL) and washed with brine (2×50 mL). The organic layer was dried over sodium sulfate and concentrated under reduced pressure. The crude solid was dissolved in acetone and a solution of chromium trioxide (0.275 g, 2.75 mmol) and 1N H₂SO₄ (6 mL) were added dropwise. After stirring for 4 h, the reaction mixture was diluted with water (50 mL) and extracted in DCM. The organic layer was washed with brine (2×50 mL) and dried over sodium sulfate then concentrated under reduced pressure. The crude product was purified using flash chromatography eluting with 0-5% MeOH in DCM to give (3R,4S)-1-((benzyloxy)carbonyl)-4-methoxypyrrolidine-3-carboxylic acid (0.32 g, 66%). LCMS (Method-C3): 48.23% (RT: 1.140, 220.0 nm) (MS: ESI +ve 280.3[M+H]).

Step-4: Preparation of benzyl (3S,4R)-3-methoxy-4-(tetradecylcarbamoyl)pyrrolidine-1-carboxylate

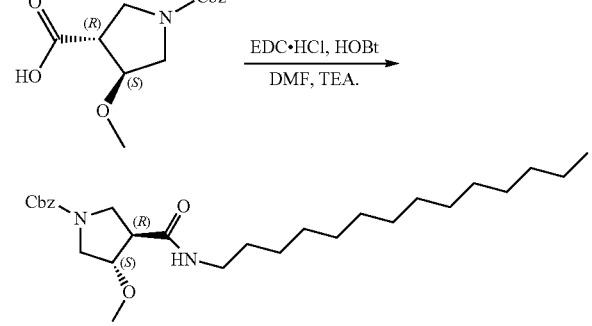

Prepared using a procedure similar to General EDC, HOBT Coupling Procedure. The crude product was purified using flash chromatography, eluting with 0-2% MeOH in DCM, to give benzyl (3S,4R)-3-methoxy-4-(tetradecylcarbamoyl)pyrrolidine-1-carboxylate (0.35 g, 64%) LCMS (Method-C3): 84.06% (RT: 7.204, 202.0 nm) (MS: ESI +ve 475[M+H]).

Step-5: Preparation of (3R,4S)-4-methoxy-N-tetradecylpyrrolidine-3-carboxamide

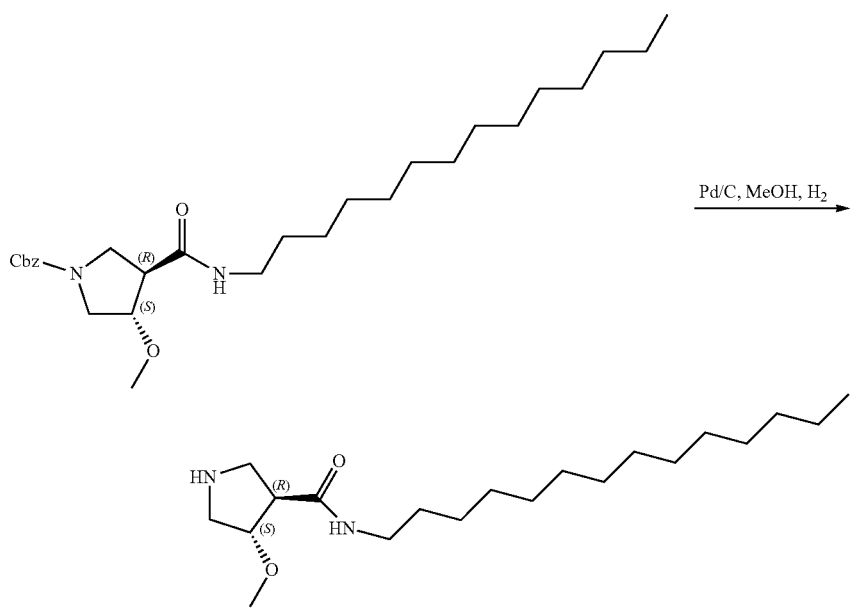

Benzyl (3S,4R)-3-methoxy-4-(tetradecylcarbamoyl)pyrrolidine-1-carboxylate (0.350 g) was dissolved in MeOH (10 mL), and Pd/C (0.2 g, 10% with 50% moisture) was added. The reaction mixture was stirred under hydrogen (balloon-pressure) at room temperature for 16 hr. The reaction mixture was filtered through celite and concentrated. The crude product was purified using flash chromatography, eluting with 0-5% MeOH in DCM, to give (3R,4S)-4-methoxy-N-tetradecylpyrrolidine-3-carboxamide as a white solid (0.2 g, 87%). LCMS (Method-C3): 100% (RT 1.568, 202 nm) (MS: ESI +ve 341.2 [M+H]).

Step-5: Preparation of (3S,4S)-1-(4-((3S,4R)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 109

Prepared using a procedure similar to General EDC, HOBT Coupling Procedure. The crude product was purified using Prep HPLC Method 1 to give (3S,4S)-1-(4-((3S,4R)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide (Compound 109)(0.036 g, 18.%). LCMS (Method-C3): 100% (RT 2.595, 225.0 nm) (MS: ESI +ve 861.3 [M+H]). $^1$H NMR: (400 MHz, DMSO) δ ppm: 0.84-0.87 (m, 3H), 1.10-1.24 (m, 24H), 1.35 (s, 1H), 1.41 (s, 1H), 1.87 (s, 1H), 1.98 (s, 1H), 2.79 (s, 1H), 2.85 (s, 1H), 2.98-3.05 (m, 2H), 3.09-3.12 (m, 2H), 3.20 (s, 1H), 3.31 (s, 3H), 3.46-3.54 (m, 4H), 3.60-3.79 (m, 4H), 3.96-4.08 (m, 1H), 7.07-7.09 (m, 2H), 7.12-7.19 (m, 4H), 7.24-7.29 (m, 4H), 7.56 (s, 3H), 8.07-8.19 (m, 1H), 8.40-8.41 (m, 1H), 8.53 (s, 2H).

Synthesis of (3S,4S)-1-(4-((3R,4S)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 110

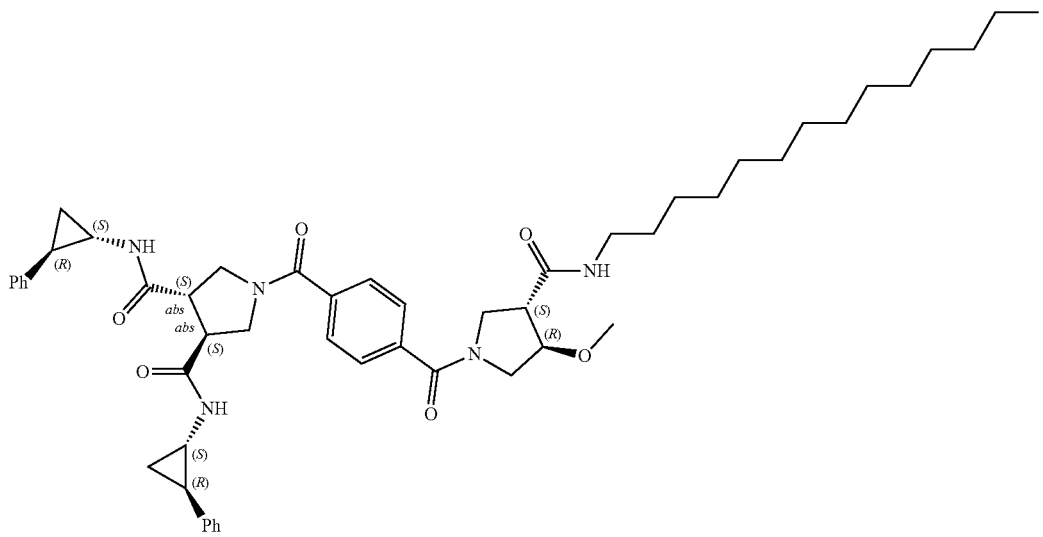

Prepared by the method described for (3S,4R)-1-(4-((3S,4R)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 109 to give (3S,4S)-1-(4-((3R,4S)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 110 (0.034 g, 17%). LCMS (Method-J): 100% (RT 6.178, 220.0 nm) (MS: ESI +ve 861.1 [M+H]). $^1$H NMR: (400 MHz, DMSO) δ ppm: 0.83-0.86 (m, 3H), 1.10-1.12 (m, 2H), 1.23-1.40 (m, 26H), 1.86 (s, 1H), 1.97 (s, 1H), 1.67 (s, 1H), 2.78 (s, 1H), 2.99-3.00 (m, 2H), 3.07-3.11 (m, 2H), 3.19 (m, 2H), 3.30 (s, 2H), 3.43-3.55 (m, 5H), 3.53-3.59 (m, 2H), 3.78-3.83 (m, 1H), 3.95-4.06 (m, 1H), 7.06-7.08 (m, 2H), 7.11-7.18 (m, 4H), 7.22-7.28 (m, 4H), 7.55 (s, 4H), 8.03-8.16 (m, 1H), 8.29 (m, 1H), 8.42-8.43 (s, 2H).

Example 27

Synthesis of (3S,4S)-1-(4-((3R*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 061

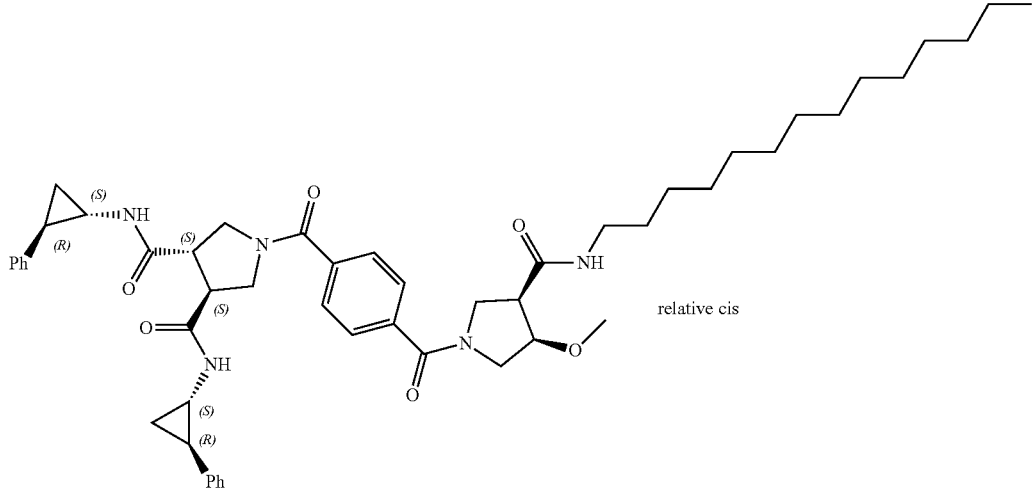

relative cis

Step-1: Preparation of (3S,4S)-1-(4-((3R,4R)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 061

Prepared by a method similar to that reported for (3S,4S)-1-(4-((3S*,4R*)-3-methoxy-4-(tetradecylcarbamoyl) pyrrolidine-1-carbonyl)benzoyl)-N3,N4-bis((1S,2R)-2-phenylcyclopropyl)pyrrolidine-3,4-dicarboxamide, Compound 060, substituting (3S,4S)-1-(4-((3R*,4R*)-3-hydroxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide to give (3S,4S)-1-(4-((3R*,4R*)-3-methoxy-4-(tetradecylcarbamoyl)pyrrolidine-1-carbonyl)benzoyl)-N3,N4-bis((1S,2R)-2-phenylcyclopropyl)pyrrolidine-3,4-dicarboxamide, Compound 061, as a mixture of diastereomers (0.0167 g, 8.21%). LCMS (Method-C3): 100% (RT 2.572, 202.0 nm) (MS: ESI +ve 861.5 [M+H]).
1H NMR: (400 MHz, DMSO) δ ppm: 0.83-0.85 (t, J=6.4 Hz, 3H), 1.10 (S, 2H), 1.23 (s, 26H), 1.38 (s, 2H), 1.86 (s, 1H), 1.96 (s, 1H), 2.77 (s, 1H), 2.85 (s, 1H), 2.98-3.02 (m, 1H), 3.11-3.17 (m, 4H), 3.26 (s, 1H), 3.47-3.59 (m, 4H), 3.66-3.74 (m, 2H), 3.78-3.83 (m, 11H), 4.08-4.18 (m, 1H), 7.06-7.08 (d, J=7.6, 1H), 7.11-7.18 (m, 4H), 7.22-7.26 (m, 4H), 7.56 (s, 4H), 7.83-7.89 (m, 1H), 8.30 (s, 1H), 8.44 (s, 1H).

Example 28

Synthesis of (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 063

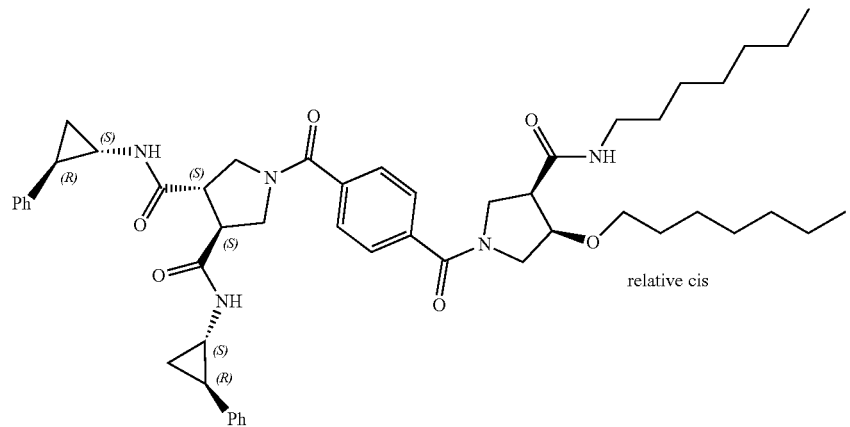

Step-1: Preparation of tert-butyl 3-(heptylcarbamoyl)-4-hydroxypyrrolidine-1-carboxylate

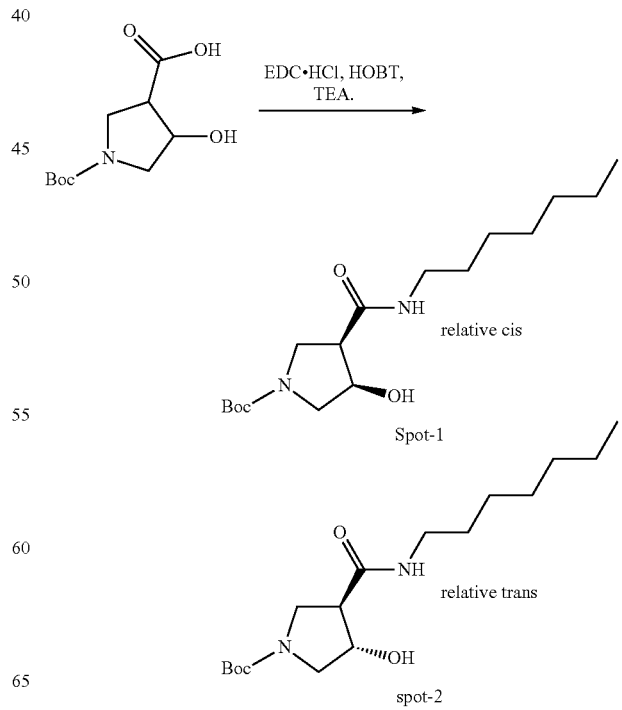

Prepared using a method similar to General EDC, HOBT Coupling Procedure. The crude product was purified using column chromatography eluting with 0-1% Methanol in Dichloromethane to give:

Spot-1, tert-butyl (3R*,4R*)-3-(heptylcarbamoyl)-4-hydroxypyrrolidine-1-carboxylate (1.24 g, 32%) assigned relative cis. LCMS (Method-C): 100% (RT 1.707, 202.0 nm) (MS: ESI +ve 329.3[(M+H])

Spot-2, tert-butyl (3R*,4S*)-3-(heptylcarbamoyl)-4-hydroxypyrrolidine-1-carboxylate (1.0 g, 29%) assigned relative trans. LCMS (Method-C): 100% (RT 1.668, 202.0 nm) (MS: ESI +ve 329.3[+H]).

Step-2: Preparation of tert-butyl (3R,4R)-3-(heptylcarbamoyl)-4-(heptyloxy)pyrrolidine-1-carboxylate

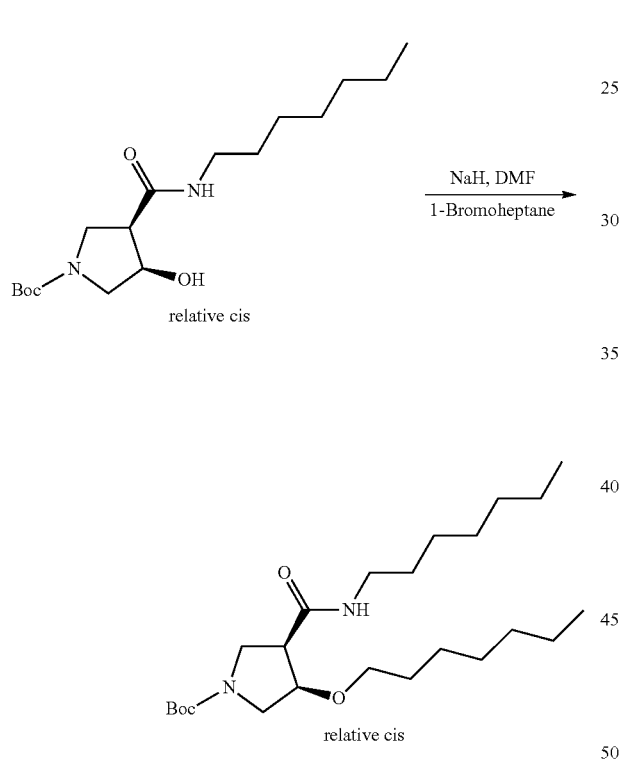

tert-butyl (3R*,4R*)-3-(heptylcarbamoyl)-4-hydroxypyrrolidine-1-carboxylate (1.24 g, 3.77 mmol) was dissolved in dry DMF (10 mL) and cooled to 0° C. Sodium hydride (0.150 g, 3.77 mmol) was added. After 15 min, 1-bromoheptane (0.8 g, 4.14 mmol) was added. The reaction mixture was stirred for 3.0 hrs at 0° C. The reaction mixture was quenched by water and extracted with ethyl acetate (3×50 mL). The combined organic layers were dried over anhydrous sodium sulphate and concentrated under reduced pressure to give tert-butyl (3R*,4R*)-3-(heptylcarbamoyl)-4-(heptyloxy)pyrrolidine-1-carboxylate (0.8 g, 49%). LCMS (Method-C3): 88.56% (RT: 2.468, 202.0 nm) (MS: ESI +ve 427.6[M+H]).

Step-3: Preparation of (3R*,4R*)—N-heptyl-4-(heptyloxy)pyrrolidine-3-carboxamide trifluoroacetate

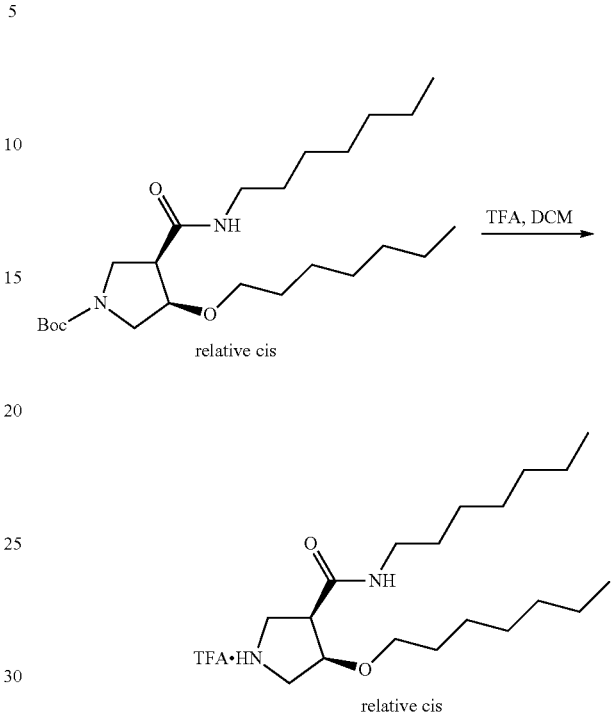

Prepared using a procedure similar to General Boc Deprotection Procedure to give (3R*,4R*)—N-heptyl-4-(heptyloxy)pyrrolidine-3-carboxamide trifluoroacetate (0.450 g). LCMS (Method-C3): 95.73% (RT: 1.692, 202.0 nm) (MS: ESI +ve 327.5[M+H]).

Step-4: Preparation of (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide Prepared by a procedure similar to General EDC, HOBT Coupling Procedure. The crude compound was purified using Prep HPLC Method 6 to give (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 063, (0.040 g, 17%) as a mixture of diastereomers. LCMS (Method-C3): 99.24% (RT 2.307, 254.0 nm) (MS: ESI +ve 847.8 [M+H]). $^1$H NMR: (400 MHz, DMSO) δ ppm: 0.83-0.86 (t, J=6.8 Hz, 6H), 1.09-1.12 (t, J=6.4 Hz, 2H), 1.24 (s, 19H), 1.37 (bs, 4H), 1.85 (s, 1H), 1.97 (s, 1H), 2.78 (s, 1H), 2.85 (s, 1H), 2.94 (bs, 111), 3.09-3.11 (m, 3H), 3.17 (s, 1H), 3.28 (s, 1H), 3.42-3.52 (m, 4H), 3.52-3.58 (m, 2H), 3.77-3.79 (d, J=8.4 Hz, 2H), 4.14-4.27 (m, 1H), 7.06-7.07 (d, J=7.2, 1H), 7.11-7.18 (m, 4H), 7.21-7.28 (m, 4H), 7.56 (s, 4H), 7.83-7.79 (m, 1H), 8.38 (s, 1H), 8.51 (s, 1H).

Example 29

Synthesis of (3S,4S)-1-(4-((3R*,4S*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 062

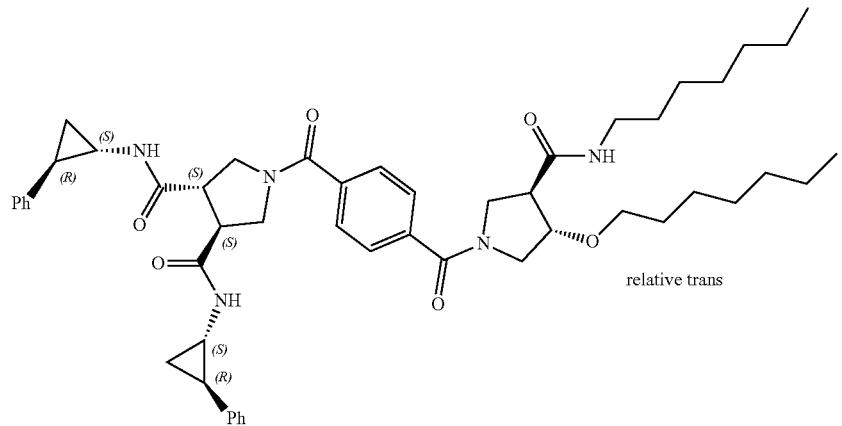

relative trans

Prepared by a method similar to that reported for (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 063, substituting tert-butyl (3R*,4S*)-3-(heptylcarbamoyl)-4-hydroxypyrrolidine-1-carboxylate in step 2. The crude final product was purified using Prep HPLC Method 6 to give (3S,4S)-1-(4-((3R*,4S*)-3-(heptylcarbamoyl)-4-(heptyloxy)pyrrolidine-1-carbonyl) benzoyl)-N3,N4-bis((1S,2R)-2-phenylcyclopropyl)pyrrolidine-3,4-dicarboxamide, Compound 062, (0.040 g, 17%), as a mixture of diastereomers. LCMS (Method-C3): 100% (RT 2.310, 254.0 nm) (MS: ESI +ve 847.8 [M+H]). ¹H NMR: (400 MHz, DMSO) δ ppm: 0.82-0.86 (m, 6H), 1.09-1.12 (t, J=6.4 Hz, 2H), 1.20-1.49 (m, 24H), 1.86 (s, 1H), 1.97 (s, 1H), 2.67 (s, 1H), 2.78 (s, 1H), 2.84-2.91 (m, 2H), 2.93-2.96 (m, 2H), 3.17-3.20 (m, 2H), 3.43-3.50 (m, 5H), 3.69-3.81 (m, 4H), 4.03-4.15 (m, 1H), 7.05-7.07 (d, J=7.6, 1H), 7.11-7.18 (m, 4H), 7.21-7.28 (m, 4H), 7.56 (s, 4H), 8.04-8.17 (m, 1H), 8.38 (s, 1H), 8.50 (s, 1H).

Example 30

Synthesis of (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 072

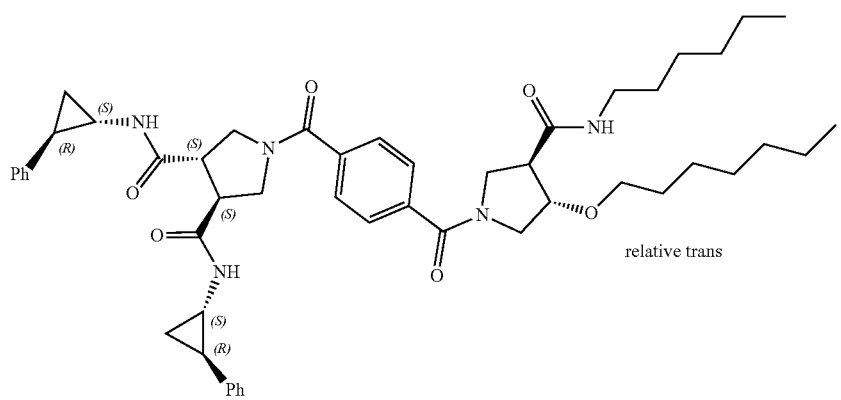

relative trans

Prepared by a procedure similar to that reported for (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 063, substituting hexylamine in step 1 and tert-butyl (3R*,4S*)-3-(hexylcarbamoyl)-4-hydroxypyrrolidine-1-carboxylate in step 2. The crude final product was purified using Prep HPLC Method 1 to give (3S,4S)-1-(4-((3S*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 072, (0.043 g, 18.5%) as an off white solid. LCMS (Method-J): 100% (RT 5.944, 254.0 nm) (MS: ESI +ve 833.6 [M+H]). $^1$H NMR: (400 MHz, DMSO) δ ppm: 0.83-0.87 (m, 6H), 1.11-1.50 (m, 20H), 1.86 (s, 1H), 1.97 (s, 1H), 2.78 (s, 1H), 2.85 (s, 1H), 2.85-2.98 (m, 4H), 3.09-3.16 (m, 2H), 3.19-3.21 (m, 1H), 3.45-3.55 (m, 6H), 3.66-3.71 (m, 2H), 3.78-3.83 (m, 2H), 4.04-4.15 (m, 1H), 7.06-7.08 (d, J=7.6, 2H), 7.12-7.18 (m, 4H), 7.22-7.29 (m, 4H), 7.56 (s, 4H), 8.03-8.16 (m, 1H), 8.30 (s, 1H), 8.44 (s, 1H).

Example 31

Synthesis of (3S,4S)-1-(4-((3R*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 073

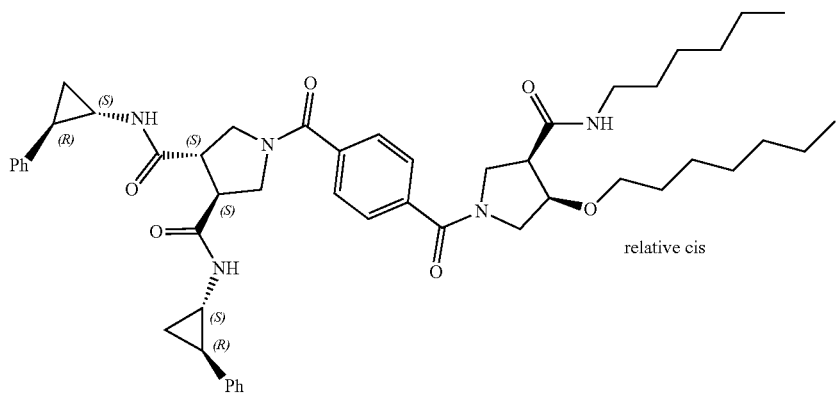

relative cis

Prepared by a procedure similar to that reported for (3S,4S)-1-(4-((3R*,4R*)-3-(heptylcarbamoyl)-4-(heptyloxy)pyrrolidine-1-carbonyl)benzoyl)-N3,N4-bis((1S,2R)-2-phenylcyclopropyl)pyrrolidine-3,4-dicarboxamide, Compound 063, substituting hexylamine in step 1 and tert-butyl (3R*,4R*)-3-(hexylcarbamoyl)-4-hydroxypyrrolidine-1-carboxylate in step 2. The crude final product was purified using Prep HPLC Method 1 to give (3S,4S)-1-(4-((3R*,4R*)-3-(heptyloxy)-4-(hexylcarbamoyl)pyrrolidine-1-carbonyl)benzoyl)-N3,N4-bis((1S,2R)-2-phenylcyclopropyl)pyrrolidine-3,4-dicarboxamide, Compound 073, (0.050 g, 21.54%) as an off white solid. LCMS (Method-J): 100% (RT 5.864, 254.0 nm) (MS: ESI +ve 833.6 [M+H]). $^1$H NMR: (400 MHz, DMSO) δ ppm: 0.858 (s, 6H), 1.11-1.35 (m, 20H), 1.86 (s, 1H), 1.96 (s, 1H), 2.78 (s, 1H), 2.85 (s, 1H), 2.96 (s, 1H), 3.11 (m, 4H), 3.28 (s, 1H), 3.40-3.55 (m, 6H), 3.66 (s, 2H), 3.78 (m, 2H), 4.16-4.27 (m, 1H), 7.08 (s, 2H), 7.12-7.16 (m, 4H), 7.24 (s, 4H), 7.56 (s, 4H), 7.81-7.87 (m, 1H), 8.30 (s, 1H), 8.44 (s, 1H).

Synthesis of (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 134

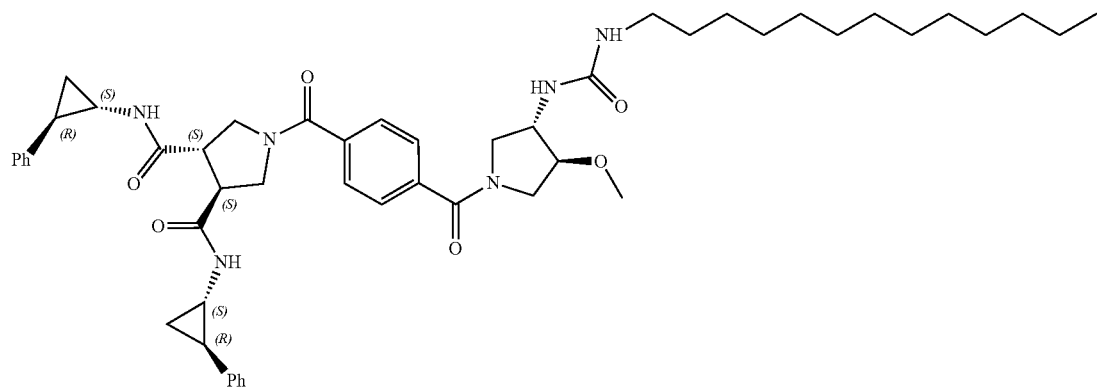

Step-1: Preparation of tert-butyl (3S,4S)-3-methoxy-4-(3-tridecylureido)pyrrolidine-1-carboxylate

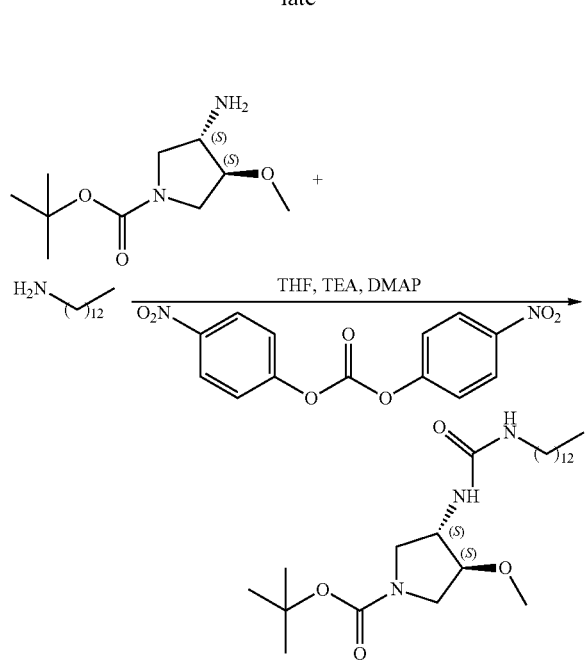

To a stirred solution of bis(4-nitrophenyl) carbonate (0.703 g, 2.312 mmol) in THF (20 mL) was added TEA (0.96 mL, 6.935 mmol), DMAP (0.012 g, 0.0983 mmol) and tridecan-1-amine (0.460 g, 2.312 mmol). The mixture was stirred for 3 hrs. t-Butyl (3S,4S)-3-amino-4-methoxypyrrolidine-1-carboxylate (0.5 g, 2.312 mmol) was added and the mixture was stirred for 16 hrs. The mixture was diluted with water (50 mL), extracted using ethyl acetate (3×50 mL), and the combined organic extracts were dried over sodium sulfate and concentrated under vacuum. The crude product was purified using flash chromatography on basic aluminium oxide, eluting with 0-2% MeOH: DCM, to give tert-butyl (3S,4S)-3-methoxy-4-(3-tridecylureido)pyrrolidine-1-carboxylate as a white solid (1.0 g, 97.9%) LCMS (Method-CFast): 89.34% (RT: 2.502, 202.0 nm) (MS: ESI +ve 386.7 [M−56H]).

Step-2: Preparation of 1-((3S,4S)-4-methoxypyrrolidin-3-yl)-3-tridecylurea

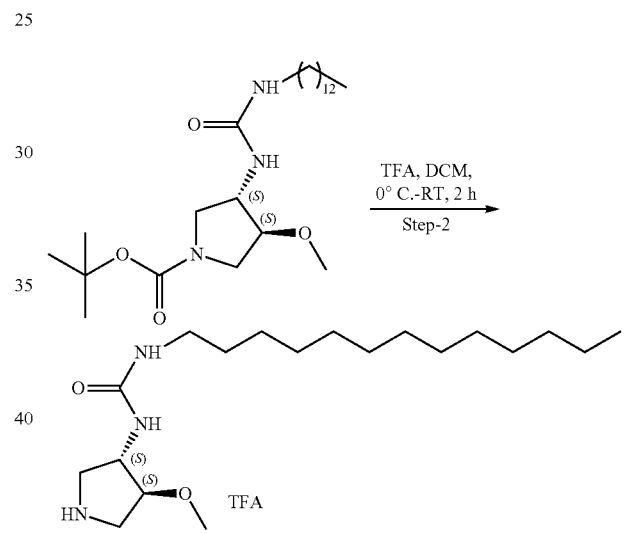

Prepared using General BOC Deprotection Procedure to give crude 1-((3S,4S)-4-methoxypyrrolidin-3-yl)-3-tridecylurea (0.65 g, 84%) As TFA Salt. LCMS (Method-Dev): 58.69% (RT: 6.434, 202.0 nm) (MS: ESI +ve 342.3 [M+H]).

Step-3: Preparation of (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 134

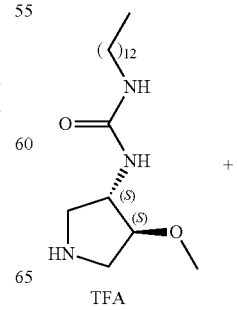

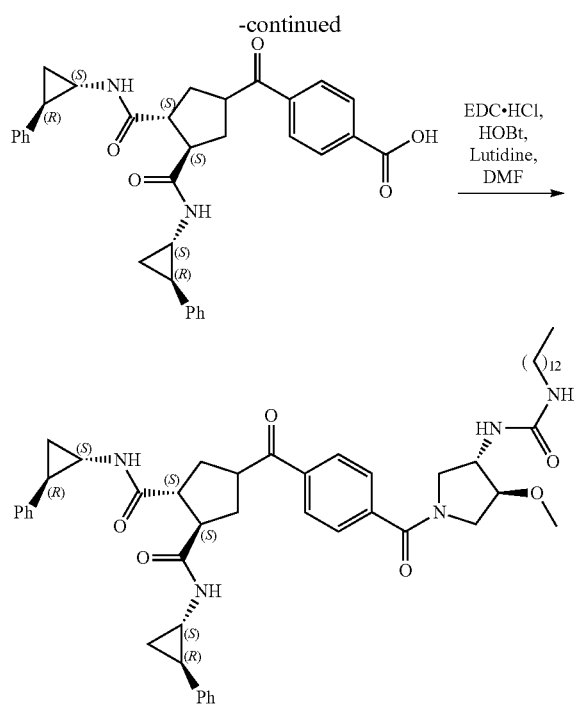

Prepared using a procedure similar to General EDC, HOBT Coupling Procedure. The crude product was purified using reverse phase flash chromatography, eluting with 93% Acetonitrile in 0.1% formic acid in water, to give (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 134, as a white solid (0.580 g, 41.15%). LCMS (Method-J2): 100% (RT 5.647, 202.0 nm) (MS: ESI +ve 861.6 [M+H]). $^1$H NMR: (400 MHz, DMSO) δ ppm: 0.83-0.86 (m, 3H), 1.10 (s, 2H), 1.17-1.36 (m, 26H), 1.86 (s, 1H), 1.97 (s, 1H), 2.67 (s, 1H), 2.77 (s, 1H), 2.85-2.98 (m, 2H), 3.09-3.19 (m, 3H), 3.43-3.55 (m, 3H), 3.64-3.83 (m, 6H), 4.01-4.13 (m, 1H), 5.69-5.74 (m, 1H), 6.13-6.25 (m, 1H), 7.06-7.07 (d, J=7.6 Hz, 2H), 7.11-7.18 (m, 4H), 7.21-7.28 (m, 4H), 7.56 (s, 4H), 8.29 (s, 1H), 8.42 (s, 1H).

Synthesis of (3S,4S)-1-(4-((3S,4S)-3-(3-dodecylureido)-4-methoxypyrrolidine-1-carbonyl) benzoyl)-N3,N4-bis((1S,2R)-2-phenylcyclopropyl)pyrrolidine-3,4-dicarboxamide, Compound 188

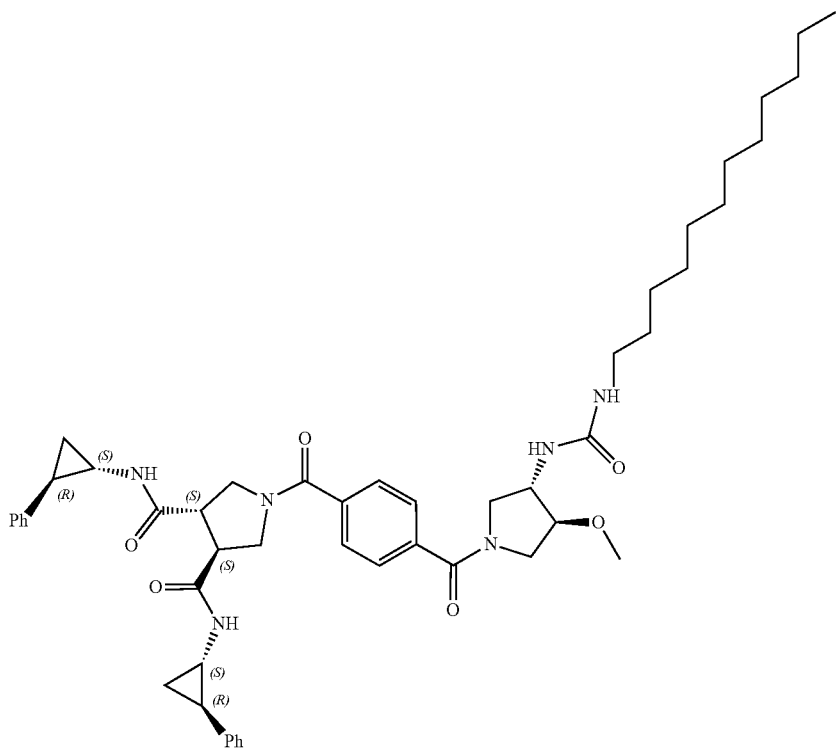

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 13 to give (3S,4S)-1-(4-((3S,4S)-3-(3-dodecylureido)-4-methoxypyrrolidine-1-carbonyl) benzoyl)-N3,N4-bis((1S,2R)-2-phenylcyclopropyl)pyrrolidine-3,4-dicarboxamide, Compound 188 (0.022 g, 13.26%). LCMS (Method-C2): 100% (RT 4.549, 202.0 nm) (MS: ESI +ve 876.16 [M−H]. $^1$H NMR: (400 MHz, DMSO) δ ppm: 0.85-0.88 (t, J=6.4 Hz, 3H), 1.12-1.37 (m, 23H), 1.87 (s, 1H), 1.98 (s, 1H), 2.61-3.24 (m, 9H), 3.45-3.56 (m, 3H), 3.65-3.84 (m, 5H), 4.02-4.069 (d, J=29.6 Hz, 1H), 5.73-5.79 (t, J=19.6 Hz, 1H), 6.17-6.30 (dd, J=6.8 Hz, 1H), 7.07-7.30 (m, 10H), 7.58 (s, 4H), 8.31 (s, 1H), 8.44 (s, 1H), 8.51 (s, 1H).

Synthesis of (3S,4S)-1-(4-((3S,4S)-3-(3-(4-fluorophenethyl)ureido)-4-methoxypyrrolidine-1-carbonyl)benzoyl)-N3,N4-bis((1S,2R)-2-phenylcyclopropyl)pyrrolidine-3,4-dicarboxamide, Compound 182

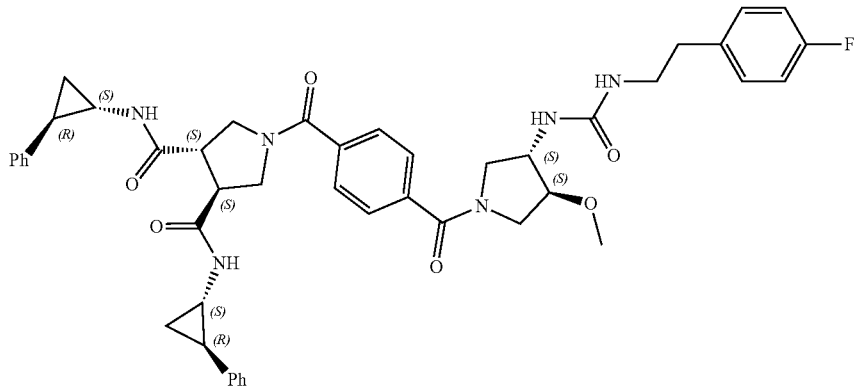

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 12 to give (3S,4S)-1-(4-((3S,4S)-3-(3-(4-fluorophenethyl)ureido)-4-methoxypyrrolidine-1-carbonyl)benzoyl)-N3,N4-bis((1S,2R)-2-phenylcyclopropyl)pyrrolidine-3,4-dicarboxamide, Compound 182 (0.040 g, 11.4% yield), as a white solid. LCMS (Method-H): 98.8% (RT: 3.057, 202.0 nm) (MS: ESI +ve 801.4 [M+1]). $^1$H NMR: (400 MHz, DMSO) δ ppm: 1.100-1.240 (m, 4H), 1.848 (s, 1H), 1.971 (s, 1H), 2.607-2.625 (m, 3H), 2.778 (s, 1H), 2.849 (s, 1H), 3.092-3.275 (m, 7H), 3.438-3.531 (m, 3H), 3.666-3.803 (m, 5H), 4.008-4.084 (d, J=30.4, 1H), 5.733-5.798 (d, J=26 Hz, 1H), 6.266-6.406 (dd, 1H), 7.078-7.287 (m, 14H), 7.570 (s, 4H), 8.312 (s, 1H), 8.447 (s, 1H).

Synthesis of (3S,4S)-1-(4-((3S,4S)-3-methoxy-4-(3-undecylureido)pyrrolidine-1-carbonyl)benzoyl)-N3,N4-bis((1S,2R)-2-phenylcyclopropyl)pyrrolidine-3,4-dicarboxamide, Compound 199

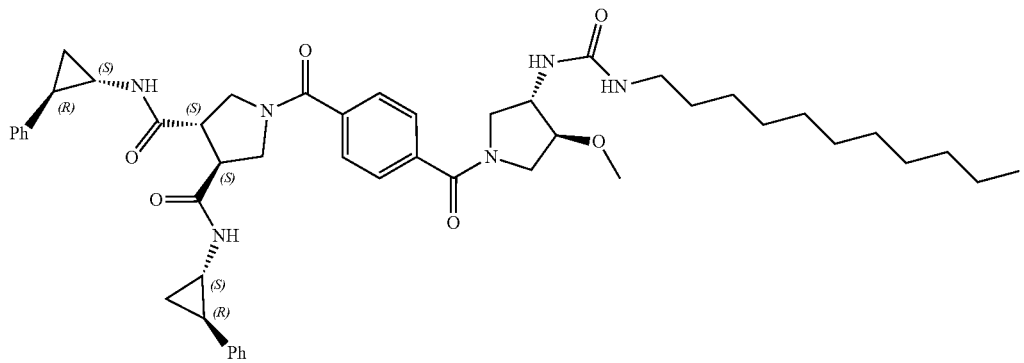

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using flash chromatography, eluting with 0-5% MeOH:DCM, to give (3S,4S)-1-(4-((3S,4S)-3-methoxy-4-(3-undecylureido)pyrrolidine-1-carbonyl)benzoyl)-N3,N4-bis((1S,2R)-2-phenylcyclopropyl)pyrrolidine-3,4-dicarboxamide, Compound 199 (0.075 g, 48%). LCMS (Method-J): 99.50% (RT 4.273, 220.0 nm) (MS: ESI +ve 834.3 [M+H]). $^1$H NMR: (400 MHz, DMSO) δ ppm: 0.85-0.88 (m, 3H), 1.12-1.37 (m, 27H), 1.87 (s, 1H), 1.97 (s, 1H), 2.62 (s, 1H), 2.69 (m, 1H), 2.93-3.00 (m, 2H), 3.11-3.20 (m, 5H), 3.39-3.56 (m, 3H), 3.65-3.84 (m, 5H), 4.02 (bs, 1H), 4.08-4.09 (m, 1H), 5.70-5.75 (m, 1H), 6.14-6.26 (m, 1H), 7.06-7.09 (m, 2H), 7.13-7.19 (m, 4H), 7.23-7.30 (m, 4H), 7.58 (s, 4H), 8.29 (s, 1H), 8.42-8.43 (m, 1H).

Synthesis of (3S,4S)-1-(4-((3S,4R)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 208

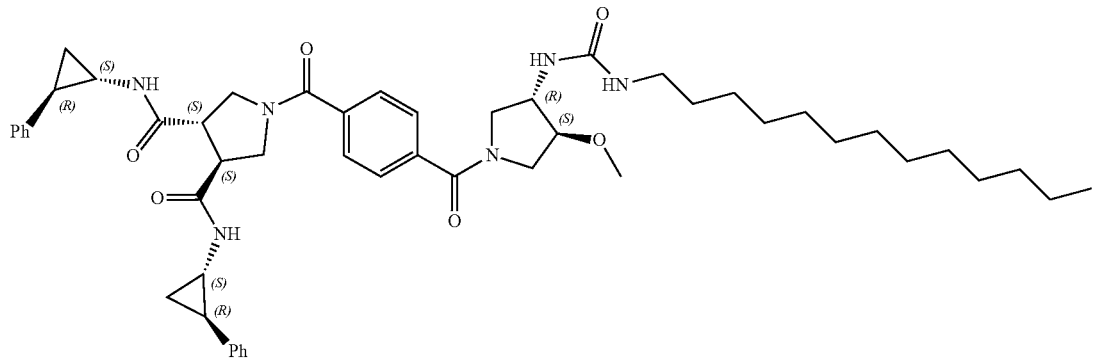

Step 1: Preparation of tert-butyl (3R*,4R*)-3-hydroxy-4-methoxypyrrolidine-1-carboxylate

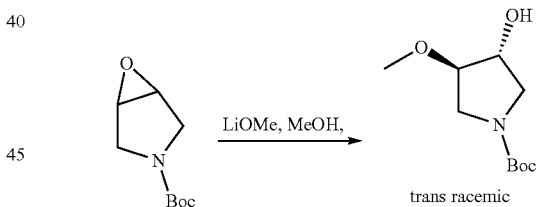

tert-Butyl 6-oxa-3-azabicyclo[3.1.0]hexane-3-carboxylate (5.0 g, 26.997 mmol) was added dropwise, at room temperature, to a solution of lithium methoxide in MeOH and stirred for 72 hrs. The mixture was diluted with acetic acid (50 mL) until a neutral pH was obtained. Potassium hydrogen phosphate solution (200 mL) was added and the mixture was extracted with DCM (2×200 mL). The combined organic layers were dried over sodium sulfate and concentrated to give tert-butyl (3R*,4R*)-3-hydroxy-4-methoxypyrrolidine-1-carboxylate (5.5 g, 93.78%) as a white solid. LCMS (Method-C2): 98.85% (RT 1.052, 202.0 nm) (MS: ESI +ve 218.18[(M+H]).

Step 2: Preparation of tert-butyl (3R*,4R*)-3-methoxy-4-((methylsulfonyl)oxy) pyrrolidine-1-carboxylate

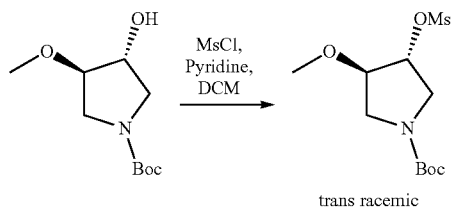 [SMILES: CO[C@@H]1CN(C(=O)OC(C)(C)C)C[C@H]1O ; CO[C@@H]1CN(C(=O)OC(C)(C)C)C[C@H]1OS(C)(=O)=O]

trans racemic tert-Butyl (3R*,4R*)-3-hydroxy-4-methoxypyrrolidine-1-carboxylate (5.5 g, 25.316 mmol) was dissolved in DCM (30 mL) and cooled to 0° C. Pyridine (15 mL) was added followed by methane sulfonyl chloride (3.45 g, 30.271 mmol) after 5 min. The reaction mixture was stirred for 16 h. The mixture was diluted with ethyl acetate (200 mL), washed with 1N HCL (2×100 mL) then brine (2×100 mL). The organic layer was dried over sodium sulfate and concentrated. The resulting solid was purified by flash chromatography, eluting with 1-3% MeOH:DCM, to give tert-butyl (3R*,4R*)-3-methoxy-4-((methylsulfonyl)oxy) pyrrolidine-1-carboxylate (6.9 g, 92.29%) as a semisolid material. LCMS (Method-C2): 84.30% (RT 1.204, 202.0 nm) (MS: ESI +ve 296.3[(M+H]).

Step 3: Preparation of tert-butyl (3S*,4R*)-3-azido-4-methoxypyrrolidine-1-carboxylate

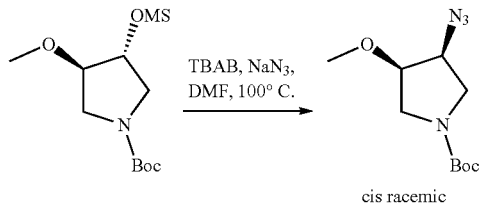

cis racemic tert-Butyl (3R*,4R*)-3-methoxy-4-((methylsulfonyl)oxy) pyrrolidine-1-carboxylate (6.9 g, 23.364 mmol) was dissolved in DMF (50 mL). Tetrabutylammonium bromide and sodium azide were added and the reaction mixture was stirred for 20 h at 100° C. The mixture was diluted with ice water (100 mL) and extracted with EtOAc (2×200 mL). The organic layer was dried over sodium sulfate and concentrated to give tert-butyl (3S,4R)-3-azido-4-methoxypyrrolidine-1-carboxylate (5.5 g, 99%) as a solid. LCMS (Method-C2): 80.64% (RT 1.223, 202.0 nm) (MS: ESI +ve 242.3 [(M+H]).

Step 4: Preparation of tert-butyl (3S,4R)-3-amino-4-methoxypyrrolidine-1-carboxylate

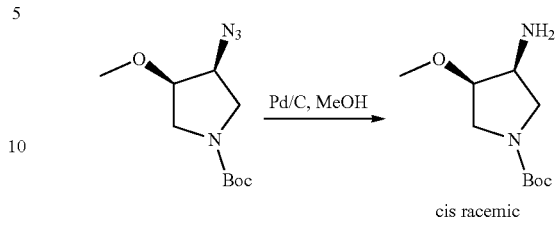

cis racemic

A mixture of tert-butyl (3S,4R)-3-azido-4-methoxypyrrolidine-1-carboxylate (5.5 g, 22.727 mmol) and palladium on carbon (2.0 g) in MeOH (50 mL) was hydrogenated (hydrogen balloon) for 3 hrs. The mixture was filtered through a celite pad and the filtrate was concentrated. The crude product was purified by flash chromatography on basic alumina, eluting with 1-3% MeOH:DCM, to give tert-butyl (3S,4R)-3-amino-4-methoxypyrrolidine-1-carboxylate (3.2 g, 65.18%). LCMs (Method-C2): 94.01% (RT: 0.905, 202.00 nm) (MS: ESI +ve 217.0 [M+1]).

Step 5: Preparation of tert-butyl (3R,4S)-3-amino-4-methoxypyrrolidine-1-carboxylate Salt

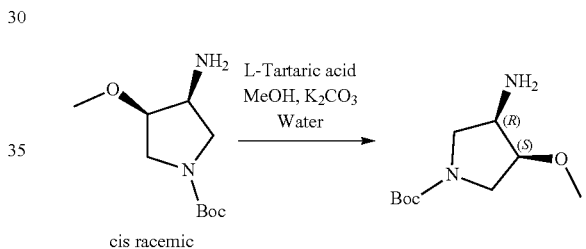

cis racemic

A mixture of tert-butyl (3R,4S)-3-amino-4-methoxypyrrolidine-1-carboxylate (3.2 g, 14.746 mmol) and L-tartaric acid (3.0 g, 20.644 mmol) in MeOH (15 mL) was stirred at room temperature for 3 h. The resulting solid was collected by filtration, washed with MeOH (20 mL) and re-crystallized from MeOH to give the L-tartaric acid salt (1.7 g, 53.1%) as a white solid. The salt was diluted with water (5 mL) and neutralized using potassium carbonate (0.1 g). The aqueous was extracted with EtOAc (2×30 mL) and the organic layer was dried over sodium sulfate and concentrated to give tert-butyl (3R,4S)-3-amino-4-methoxypyrrolidine-1-carboxylate, as a brown oil (0.22 g, 44%). SOR (salt) $[\alpha]D^{25}$+31.68 (C=1.00, MeoH), SOR$[\alpha]_D^{25}$+26.30 (C=1.41, MeOH).

Step 6: Preparation of tert-butyl (3S,4R)-3-methoxy-4-(3-tridecylureido)pyrrolidine-1-carboxylate

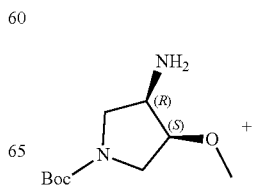
+

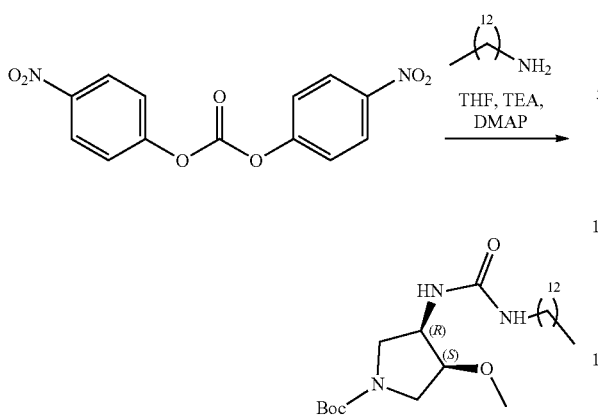

tert-Butyl (3R,4S)-3-amino-4-methoxypyrrolidine-1-carboxylate. (0.2 g, 1.08 mmol) in THF (5 mL) was added dropwise over 30 min. to a stirred solution of bis(4-nitrophenyl) carbonate (0.334 g, 2.752 mmol), TEA (0.3 mL) and DMAP (0.01 g, 0.091 mmol) in THF (10 mL) at 0° C. The reaction mixture was stirred for 4-5 h at 0° C. then tridecan-1-amine (0.21 g, 0.100 mmol) in THF (5 mL) was added dropwise. The mixture was stirred for 16 h then diluted with EtOAc (200 mL), washed with 1N aq sodium hydroxide (5×100 mL) and brine (2×100 mL). The organic layer was dried over sodium sulfate and concentrated under reduced pressure. The resulting solid was purified by flash chromatography, eluting with 1-3% MeOH:DCM, to give tert-butyl (3S,4R)-3-methoxy-4-(3-tridecylureido)pyrrolidine-1-carboxylate (0.35 g, 85.70%). LCMS (Method-C2): 91.59% (RT 1.8336, 220.0 nm) (MS: ESI +ve 386.5[(M−56]).

Step 7: Preparation of 1-((3R,4S)-4-methoxypyrrolidin-3-yl)-3-tridecylurea TFA salt

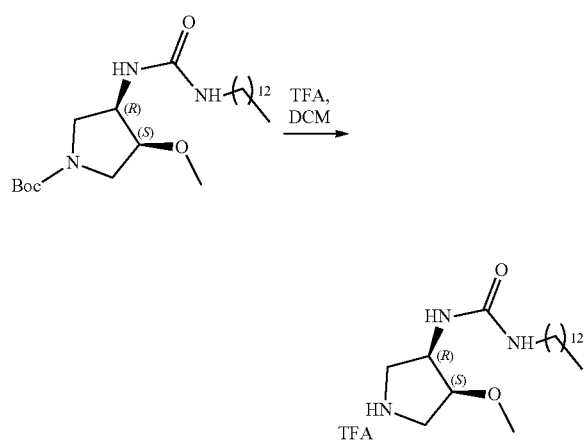

Prepared using General BOC Deprotection Procedure to give 1-((3R,4S)-4-methoxypyrrolidin-3-yl)-3-tridecylurea TFA salt. (0.4 g, crude) as a liquid. LCMS (Method-C2): 100% (RT: 0.939, 202.0 nm) (MS: ESI +ve 342.6[M+H]).

Step 8: Preparation of (3S,4S)-1-(4-((3S,4R)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 208

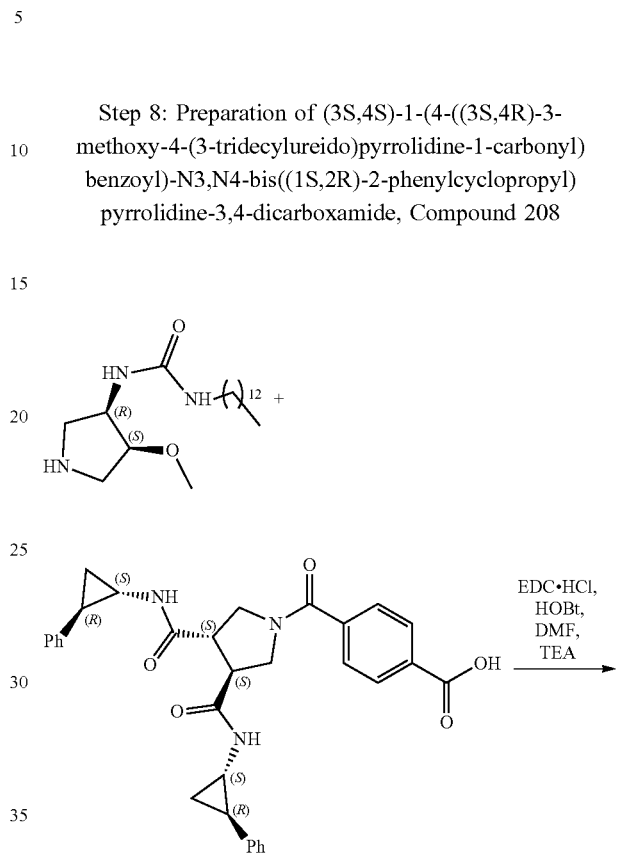

Prepared using General EDC, HOBT Coupling Procedure. The crude product was purified using Prep HPLC Method 12 to give (3S,4S)-1-(4-((3S,4R)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 208)(0.032 g, 20%). LCMS (Method-C-fast): 100% (RT 2.381, 225.0 nm) (MS: ESI +ve 861.85 [M+H]). $^1$H NMR: (400 MHz, DMSO) δ ppm: 0.83-0.85 (d, J=5.2 Hz, 3H), 1.10-1.24 (m, 27H), 1.87 (s, 1H), 1.99 (s, 1H), 2.78-3.21 (m, 9H), 3.51-3.55 (t, J=9.6 Hz, 3H), 3.62-3.87 (m, 5H), 5.96-6.032 (dd, J=18.8 Hz, 1H), 6.15 (s, 1H), 7.06-7.28 (m, 10H), 7.55-7.56 (d, J=4.4 Hz, 4H), 8.34-8.39 (dd, J=15.6 Hz, 1H), 8.50 (s, 2H).

Synthesis of (3S,4S)-1-(4-((3R,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 210

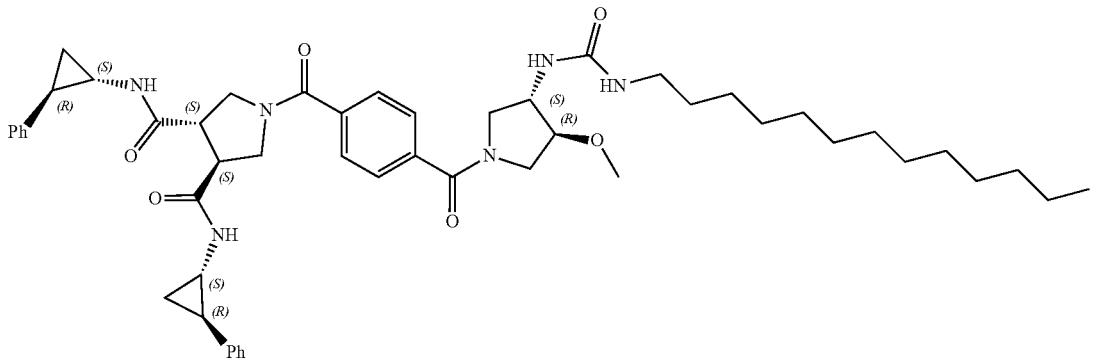

Prepared by a procedure similar to that reported for (3S,4S)-1-(4-((3S,4R)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 208). The final product was purified using Prep HPLC Method 12 to give (3S,4S)-1-(4-((3R,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide, Compound 210 (0.032 g, 19.95%), as an off white solid. LCMS (Method-C-fast): 100% (RT 2.380, 225.0 nm) (MS: ESI +ve 861.14 [M+H]). $^1$H NMR: (400 MHz, DMSO) δ ppm: 0.83-0.85 (d, J=6 Hz, 3H), 1.10-1.36 (m, 24H), 1.86 (s, 1H), 1.97 (s, 1H), 2.78-3.21 (m, 9H), 3.53-3.88 (m, 11H), 4.09-4.16 (t, J=21.6 Hz, 2H), 4.30 (s, 1H), 5.92-5.98 (m, 1H), 6.11 (s, 1H), 7.06-7.28 (m, 10H), 7.55-7.57 (d, J=5.6 Hz, 4H), 8.28 (s, 1H), 8.42 (s, 1H).

Synthesis of (3S,4S)-1-(4-((3S,4S)-3-(3-(4-fluorobenzyl)ureido)-4-methoxypyrrolidine-1-carbonyl)benzoyl)-N3,N4-bis((1S,2R)-2-phenylcyclopropyl)pyrrolidine-3,4-dicarboxamide, Compound 183

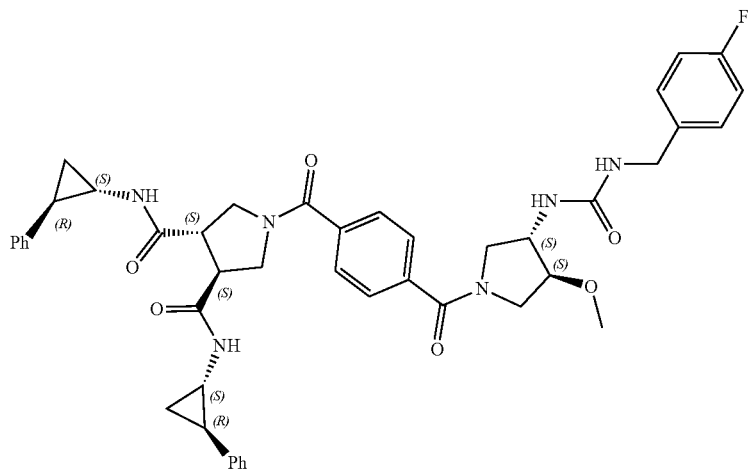

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 12 to give (3S,4S)-1-(4-((3S,4S)-3-(3-(4-fluorobenzyl)ureido)-4-methoxypyrrolidine-1-carbonyl)benzoyl)-N3,N4-bis((1S,2R)-2-phenylcyclopropyl)pyrrolidine-3,4-dicarboxamide (Compound 183)(0.023 g, 9.6% yield), as a white solid. LCMS (Method-H): 96.3% (RT: 3.018, 214.0 nm) (MS: ESI +ve 787.4 [M+1]). $^1$H NMR: (400 MHz, DMSO) δ ppm: 1.110-1.241 (m, 4H), 1.860 (s, 1H), 1.949-1.995 (m, 1H), 2.782 (s, 1H), 2.856-2.865 (m, 1H), 3.114-3.166 (m, 1H), 3.188-3.238 (m, 3H), 3.447-3.483 (m, 1H), 3.408-3.554 (m, 2H), 3.641-3.736 (m, 4H), 3.752-3.832 (m, 2H), 3.881-4.191 (m, 3H), 6.230-6.373 (m, 1H), 6.471-6.488 (d, J=6.8 Hz, 1H), 7.061-7.184 (m, 8H), 7.223-7.314 (m, 6H), 7.571 (s, 4H), 8.302 (s, 1H), 8.431-8.440 (d, J=3.6 Hz, 1H).

Synthesis of (3S,4S)-1-(4-((3S,4S)-3-methoxy-4-(3-((1S,2R)-2-phenylcyclopropyl)ureido) pyrrolidine-1-carbonyl)benzoyl)-N3,N4-bis((1S,2R)-2-phenylcyclopropyl)pyrrolidine-3,4-dicarboxamide, Compound 224

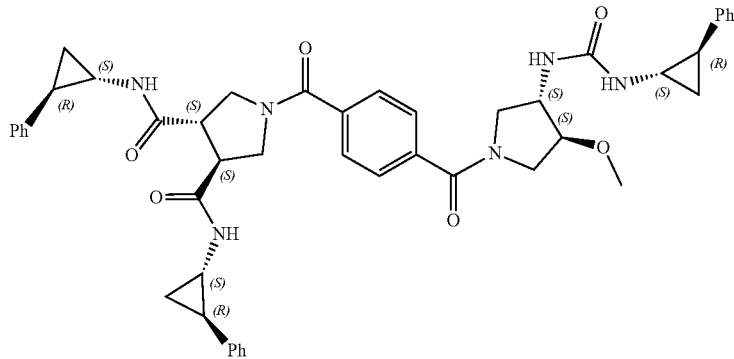

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 10 to give (3S,4S)-1-(4-((3S,4S)-3-methoxy-4-(3-((1S,2R)-2-phenylcyclopropyl)ureido) pyrrolidine-1-carbonyl)benzoyl)-N3,N4-bis((1S,2R)-2-phenylcyclopropyl)pyrrolidine-3,4-dicarboxamide (Compound 224) (0.021 g, 9.13%), as an off white solid. LCMS (Method-J): 100% (RT 1.532, 222.0 nm) (MS: ESI +ve 868.11 [M+H]). $^1$H NMR: (400 MHz, DMSO) δ ppm: 102-1.24 (m, 6H), 1.83-1.91 (m, 2H), 1.95-1.98 (t, J=5.6 Hz, 1H), 2.68 (s, 1H), 2.85-2.87 (s, 2H), 3.10-3.54 (m, 10H), 3.64-3.83 (m, 5H), 4.04-4.12 (m, 1H), 6.27-6.29 (d, J=7.6 Hz, 1H), 6.40-6.44 (m, 1H), 7.05-7.29 (m, 14H), 7.54-7.60 (m, 4H), 8.32 (s, 1H), 8.46 (s, 1H).

Synthesis of (3S,4S)—N3,N4-bis((1S,2R)-2-phenylcyclopropyl)-1-(4-((R)-3-(3-tridecy lureido)pyrrolidine-1-carbonyl)benzoyl)pyrrolidine-3,4-dicarboxamide, Compound 079

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 6 to give (3S,4S)—N3,N4-bis((1S,2R)-2-phenylcyclopropyl)-1-(4-((R)-3-(3-tridecylureido) pyrolidine-1-carbonyl)benzoyl)pyrrolidine-3,4-dicarboxamide (Compound 079) (0.055 g, 36.05%). LCMS (Method-J): 100% (RT 6.17, 202 nm) (MS: ESI +ve 832.5 [M+H]). $^1$H NMR: (400 MHz, DMSO) δ ppm: 0.86 (t, J=8 Hz, 3H), 1.11 (m, 3H), 1.23-1.25 (m, 21H), 1.36 (m, 2H), 1.77-1.79 (m, 1H), 1.87 (m, 1H), 1.97 (m, 1H), 2.07-2.09 (m, 1H), 2.68 (m, 1H), 1.79-1.91 (m, 2H), 2.97-2.99 (m, 1H), 3.10-3.24 (m, 3H), 3.52-3.57 (m, 3H), 3.61-3.65 (m, 3H), 3.67-3.80 (m, 1H), 4.01-4.15 (m, 1H), 5.77-5.84 (m, 1H), 6.16-6.24 (m, 1H), 7.06-7.08 (m, 2H), 7.12-7.18 (m, 4H), 7.22-7.29 (m, 4H), 7.57 (s, 4H), 8.34 (s, 1H), 8.48 (s, 1H).

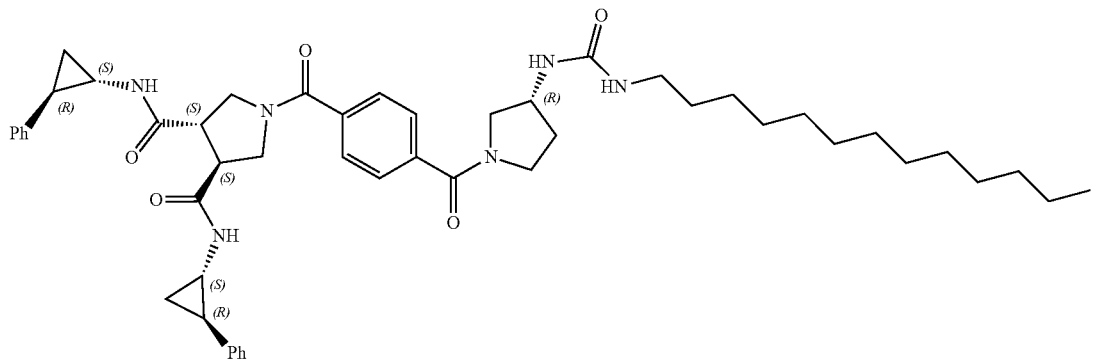

Synthesis of (3S,4S)-1-(4-((3S,4S)-3-(heptyloxy)-4-(3-pentylureido)pyrrolidine-1-carbonyl)benzoyl)-N3, N4-bis((1S,2R)-2-phenylcyclopropyl)pyrrolidine-3, 4-dicarboxamide, Compound 156

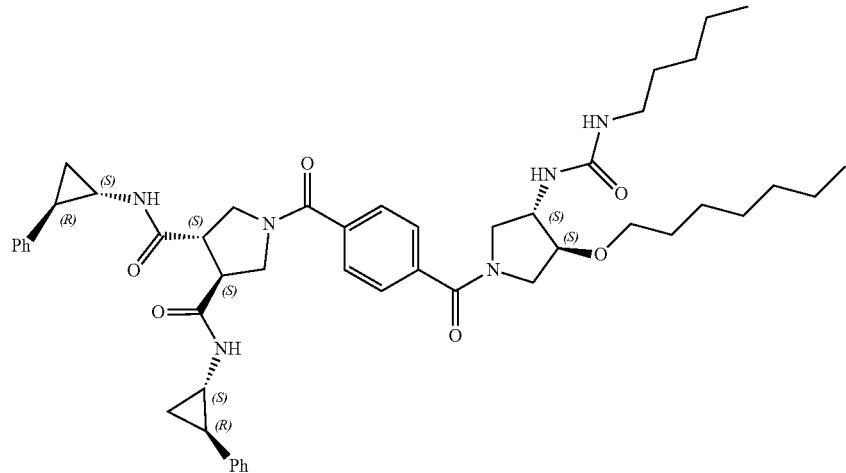

Step-1: Preparation tert-butyl (3S,4S)-3-hydroxy-4-(3-pentylureido)pyrrolidine-1-carboxylate Step-2: Preparation of tert-butyl (3S,4S)-3-(heptyloxy)-4-(3-pentylureido)pyrrolidine-1-carboxylate

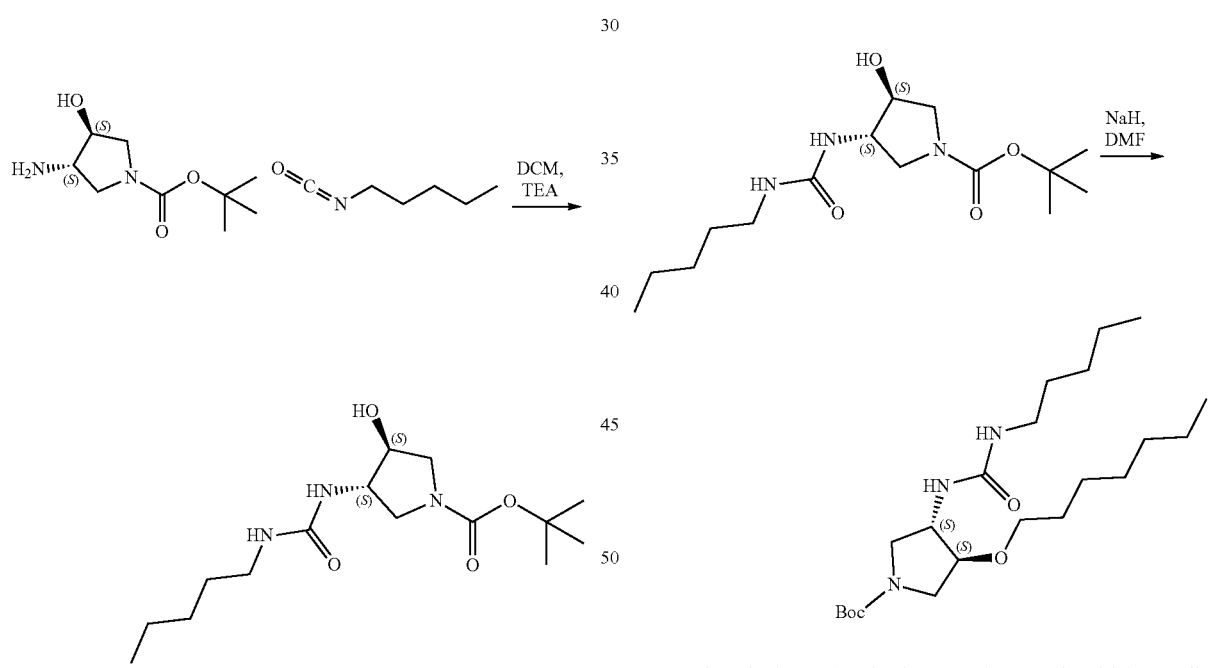

Tert-butyl (3S,4S)-3-amino-4-hydroxypyrrolidine-1-carboxylate (0.700 g, 3.461 mmol) was dissolved in DCM (5 mL) and cooled to 0° C. Pentyl isocyanate (0.391 g, 3.461 mmol) was added and the reaction mixture was stirred at room temperature for 16 hrs. The mixture was concentrated to give tert-butyl (3S,4S)-3-hydroxy-4-(3-pentylureido)pyrrolidine-1-carboxylate (1.1 g, crude). LCMS (Method-H): 98.2% (RT: 2.663, 202.0 nm) (MS: ESI +ve 314.2 [M−1]).

Tert-butyl (3S,4S)-3-hydroxy-4-(3-pentylureido)pyrrolidine-1-carboxylate (1.0 g, 1.585 mmol) was dissolved in DMF (10 mL) and cooled to 0° C. Sodium hydride (0.091 g, 1.902 mmol) was added and the reaction mixture was stirred at 0° C. for 15 mins. 1-Bromoheptane (0.681 g, 1.902 mmol) was added and stirring was continued at 0° C. for 3 hrs. The mixture was diluted with EtOAc (2×20 mL) washed with brine (2×20 mL), dried and concentrated. The crude product was purified using flash chromatography, eluting with 0-30% ethyl acetate in hexane, to give tert-butyl (3S,4S)-3-(heptyloxy)-4-(3-pentylureido)pyrrolidine-1-carboxylate. (0.768 g, 59% yield). LCMS (Method-H): 93.3% (RT: 4.108, 202.0 nm) (MS: ESI +ve 414.3 [M+1])

467
Step-3: Preparation of 1-((3S,4S)-4-(heptyloxy) pyrrolidin-3-yl)-3-pentylurea
468
Prepared using General BOC Deprotection Procedure to give 1-((3S,4S)-4-(heptyloxy)pyrrolidin-3-yl)-3-pentylurea (0.170 g, crude). LCMS (Method-C3): 86.9% (RT: 4.431, 202 nm) (MS: ESI +ve 314.3 [M+1]).
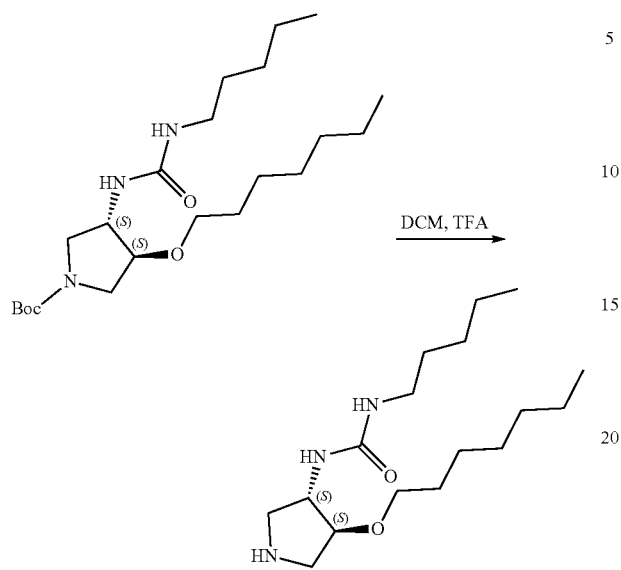
Step-4: Preparation of (3S,4S)-1-(4-((3S,4S)-3-(heptyloxy)-4-(3-pentylureido) pyrrolidine-1-carbonyl) benzoyl)-N3,N4-bis((1S,2R)-2-phenylcyclopropyl) pyrrolidine-3,4-dicarboxamide, Compound 156
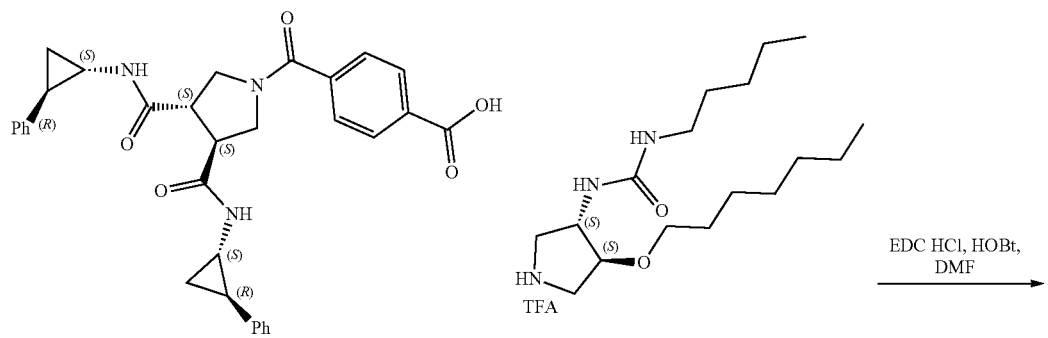
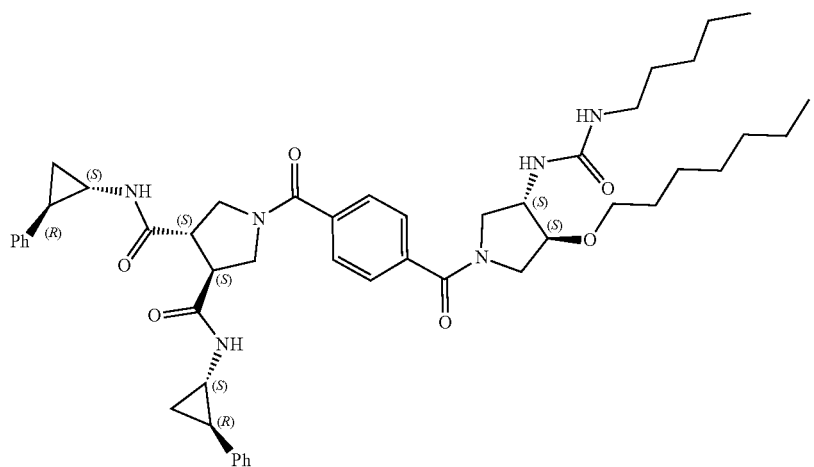

Prepared using General EDC, HOBT Coupling Procedure. The crude product was purified using Prep HPLC 12 to give (3S,4S)-1-(4-((3S,4S)-3-(heptyloxy)-4-(3-pentylureido)pyrrolidine-1-carbonyl)benzoyl)-N3,N4-bis((1S,2R)-2-phenylcyclopropyl)pyrrolidine-3,4-dicarboxamide (Compound 156)(0.066 g, 28.700 yield), as a white solid. LCMS (Method-H): 100% (RT: 3.616, 202.0 nm) (MS: ESI +ve 834.5 [M+1]). ¹H NMR: (400 MHz, DMSO) δ ppm: 0.849-0.969 (in, 6H), 1.097-1.109 (m, 2H), 1.122-1.356 (m, 17H), 1.391-1.513 (m, 2H), 1.655-1.706 (m, 2H), 1.857 (s, 1H), 2.094 (s, 1H), 2.676-2.855 (m, 3H), 2.915-2.973 (m, 3H), 3.075-3.134 (m, 1H), 3.134-3.240 (m, 2H), 3.427-3.551 (in, 4H), 3.638-3.776 (m, 6H), 3.843-4.135 (m, 1H), 5.722-5.802 (d, J=32 Hz, 1H), 6.155-6.297 (dd, 1H), 7.059-7.183 (m, 6H), 7.219-7.288 (m, 4H), 7.568 (s, 4H), 8.103-8.554 (d, 2H).

Synthesis of undecyl ((3S,4S)-1-(4-((3S,4S)-3,4-bis(((1S,2R)-2-phenylcyclopropyl) carbamoyl)pyrrolidine-1-carbonyl)benzoyl)-4-methoxypyrrolidin-3-yl) carbamate, Compound 215

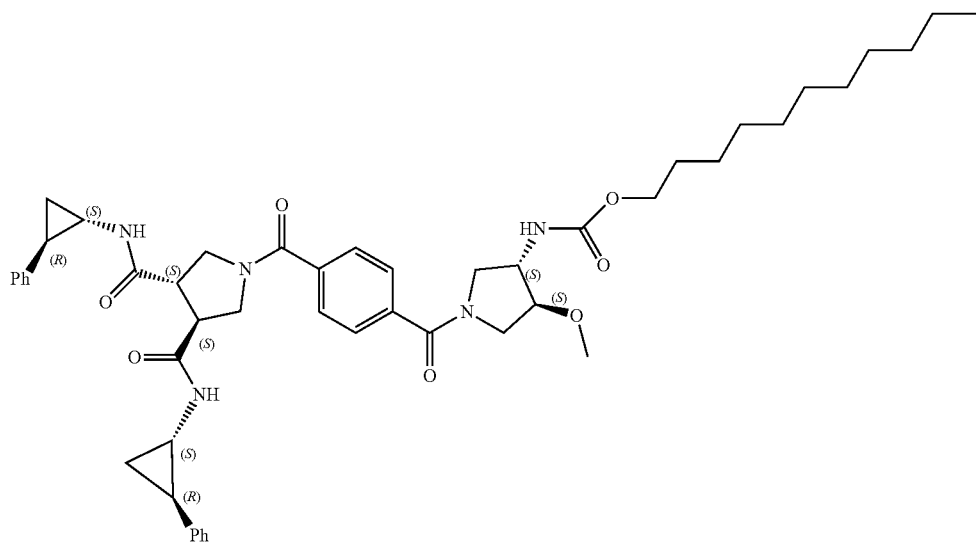

Step 1: Preparation of 4-nitrophenyl undecyl carbonate

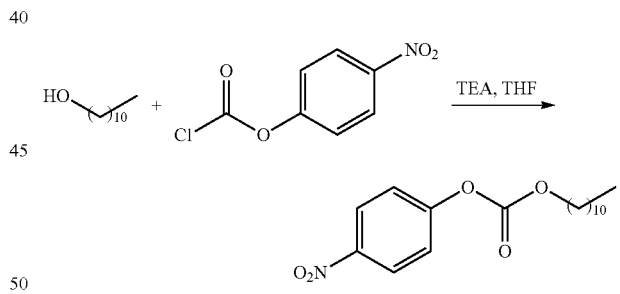

Undecan-1-ol (0.3 g, 1.741 mmol) was dissolved in THF (20 mL) and cooled to 0° C. TEA was added (0.7 mL, 5.223 mmol) followed by 4-nitrophenyl chloroformate (0.462, 2.089 mmol). The reaction mixture was stirred at room temperature for 16 h, extracted with EtOAc (3×30 mL), washed with brine (30 mL) and concentrated. The crude product was purified using flash chromatography, eluting with 5-10% MeOH:DCM, to give 4-nitrophenyl undecyl carbonate. (0.55 g, 93.62%). ¹H NMR: (400 MHz, DMSO) δ ppm: 0.84-0.88 (t, J=1.2 Hz, 1H). 1.26-1.35 (m, 8H), 1.65-1.70 (m, 1H), 3.34 (s, 1H), 4.23-4.26 (t, J=6.8 Hz, 1H), 7.56-7.58 (m, 1H), 8.31-8.33 (m 1H).

Step 2: Preparation tert-butyl (3S,4S)-3-methoxy-4-(((undecyloxy) carbonyl)amino) pyrrolidine-1-carboxylate

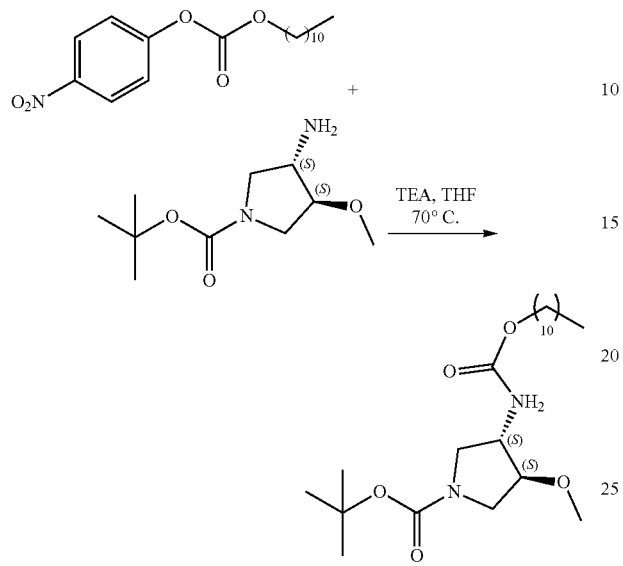

4-Nitrophenyl undecyl carbonate (0.55 g, 1.566 mmol) and tert-butyl (3S,4S)-3-amino-4-methoxypyrrolidine-1-carboxylate (0.406 g, 1.880 mmol) were dissolved in THF (15 mL). TEA (0.4 mL) was added and the mixture was stirred at 70° C. for 6 hrs. The reaction mixture was extracted in EtOAc (3×30 mL) and washed with brine (30 mL). The organic layer was concentrated and the residue was purified using flash chromatography, eluting with 1-2% MeOH:DCM, to give tert-butyl (3S,4S)-3-methoxy-4-(((undecyloxy)carbonyl)amino)pyrrolidine-1-carboxylate (0.2 g, 29.59%). LCMS (Method-C2): 67.27% (RT 1.856, 202.0 nm) (MS: ESI +ve 315.46 [M+1]).

Step 3: Preparation of undecyl ((3S,4S)-4-methoxypyrrolidin-3-yl)carbamate TFA salt

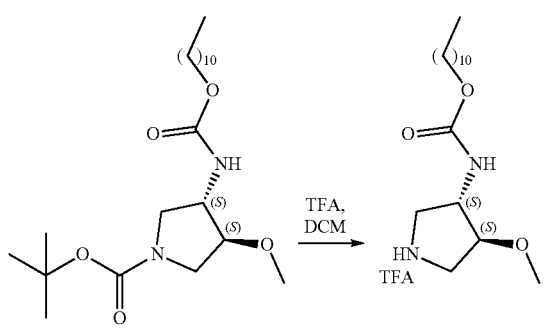

Prepared using General BOC Deprotection Procedure to give undecyl ((3S,4S)-4-methoxypyrrolidin-3-yl)carbamate TFA salt (0.3 g, crude). LCMS (Method-C2): 100% (RT 1.127, 202.0 nm) (MS: ESI +ve 315.46 [M+1]).

Step 4: Preparation undecyl ((3S,4S)-1-(4-((3S,4S)-3,4-bis(((1S,2R)-2-phenylcyclopropyl)carbamoyl) pyrrolidine-1-carbonyl)benzoyl)-4-methoxypyrrolidin-3-yl)carbamate, Compound 215

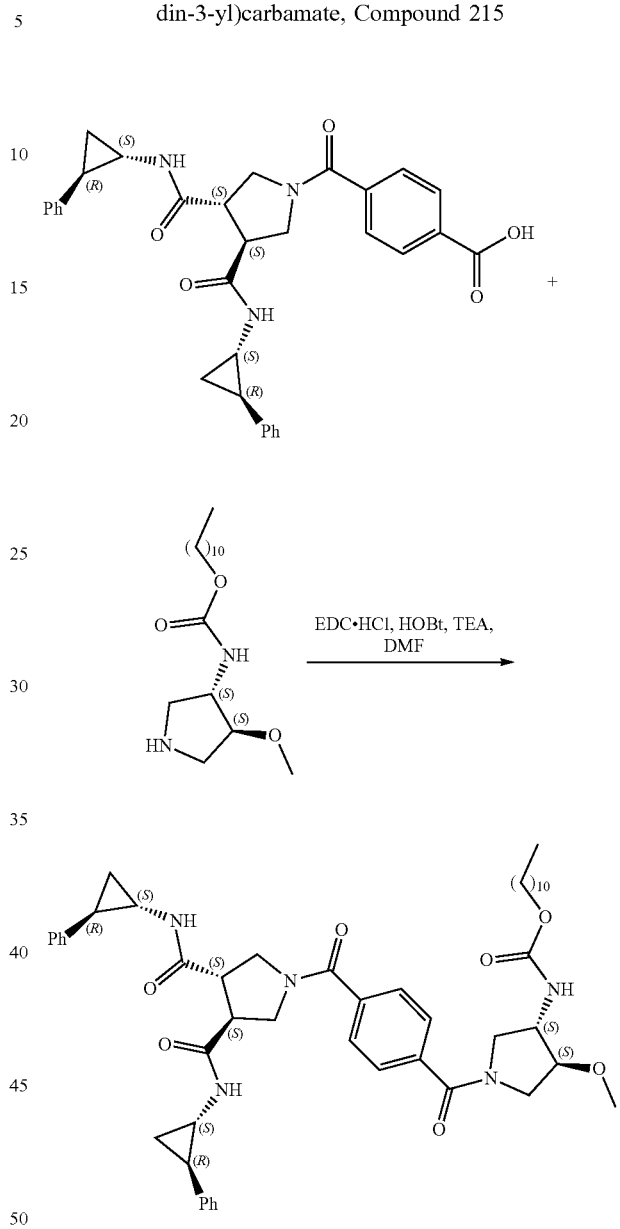

Prepared using General EDC, HOBT Coupling Procedure. The crude final product was purified using Prep HPLC Method 10 to give undecyl ((3S,4S)-1-(4-((3S,4S)-3,4-bis (((1S,2R)-2-phenylcyclopropyl)carbamoyl)pyrrolidine-1-carbonyl) benzoyl)-4-methoxypyrrolidin-3-yl)carbamate (Compound 215)(0.031 g, 13.32%). LCMS (Method-J): 100% (RT: 5.005, 202 nm) (MS: ESI +ve 834.5[M+1]). $^1$H NMR: (400 MHz, DMSO) δ ppm: 0.84-0.87 (t, J=6.8, 3H), 1.12-1.25 (m, 20H), 1.50-1.56 (m, 2H), 1.87-1.98 (m, 2H), 2.85-2.87 (t, J=3.6, 2H), 3.10-3.34 (m, 4H), 3.39-3.55 (s, 3H), 3.69-3.81 (m, 6H), 3.91-3.97 (m, 2H), 7.07-7.29 (m, 10H), 7.56-7.58 (d, J=5.6 Hz, 5H), 8.31-8.31 (d, J=2.8 Hz, 1H), 8.44-8.45 (d, J=4 Hz, 1H).

Synthesis of dodecyl ((3S,4S)-1-(4-((3S,4S)-3,4-bis
(((1S,2R)-2-phenylcyclopropyl) carbamoyl)pyrroli-
dine-1-carbonyl)benzoyl)-4-methoxypyrrolidin-3-yl)
carbamate, Compound 216

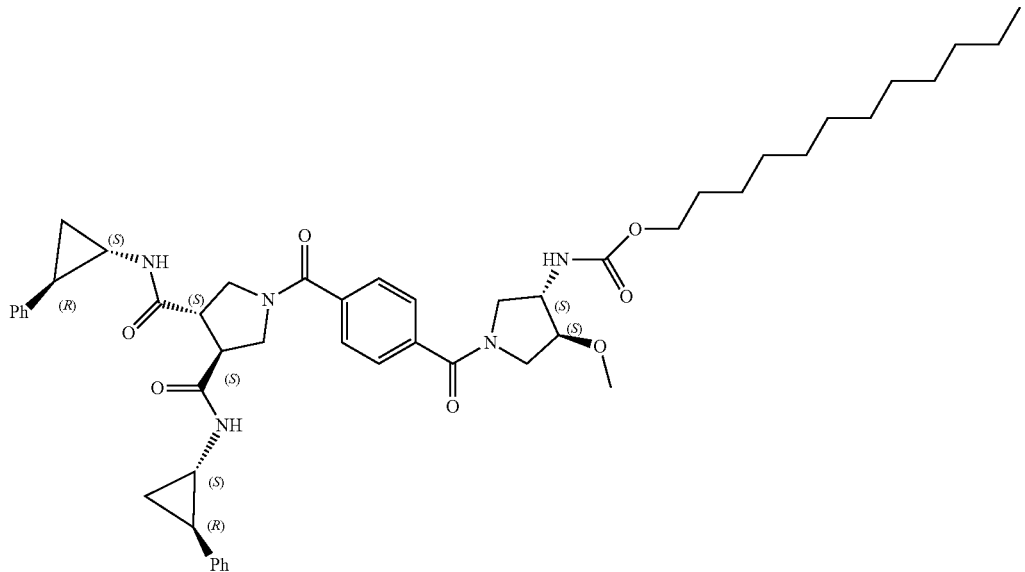

Prepared by a Procedure similar to that reported for undecyl ((3S,4S)-1-(4-((3S,4S)-3,4-bis(((1S,2R)-2-phenyl-cyclopropyl)carbamoyl)pyrrolidine-1-carbonyl)benzoyl)-4-methoxypyrrolidin-3-yl)carbamate (Compound 215). The crude final product was purified using Prep HPLC Method 10 to give dodecyl ((3S,4S)-1-(4-((3S,4S)-3,4-bis(((1S,2R)-2-phenylcyclopropyl)carbamoyl)pyrrolidine-1-carbonyl)benzoyl)-4-methoxypyrrolidin-3-yl)carbamate (Compound 216)(0.030 g, 14.63%). LCMS (Method-J): 100% (RT: 5.521, 254 nm) (MS: ESI +ve 849.6[M+1]). $^1$H NMR: (400 MHz, DMSO) δ ppm: 0.85 (s, 3H), 1.10-1.22 (m, 23H), 1.49-(s, 2H), 1.85 (s, 1H), 1.96 (s, 1H), 2.78-2.84 (m, 2H), 3.09-3.33 (m, 5H), 3.45-3.90 (m, 13H), 7.07-7.26 (m, 10H), 7.56 (s, 5H), 8.35 (s, 1H), 8.48 (s, 1H).

Synthesis of tridecyl ((3S,4S)-1-(4-((3S,4S)-3,4-bis
(((1S,2R)-2-phenylcyclopropyl) carbamoyl)pyrroli-
dine-1-carbonyl)benzoyl)-4-methoxypyrrolidin-3-yl)
carbamate, Compound 217

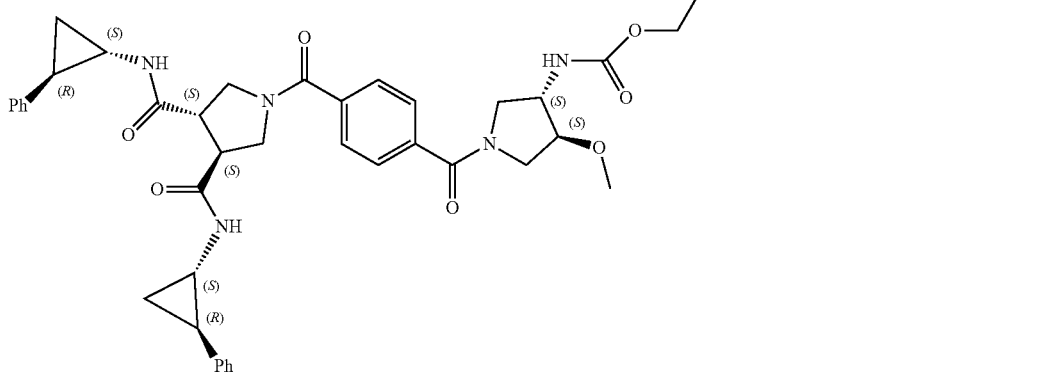

Prepared by a Procedure similar to that reported for undecyl ((3S,4S)-1-(4-((3S,4S)-3,4-bis(((1S,2R)-2-phenyl-cyclopropyl)carbamoyl)pyrrolidine-1-carbonyl)benzoyl)-4-methoxypyrrolidin-3-yl)carbamate (Compound 215). The crude final product was purified using Prep HPLC Method 10 to give tridecyl ((3S,4S)-1-(4-((3S,4S)-3,4-bis(((1S,2R)-2-phenylcyclopropyl)carbamoyl)pyrrolidine-1-carbonyl)benzoyl)-4-methoxypyrrolidin-3-yl)carbamate (Compound 217) (0.030 g, 14.39%). LCMS (Method-J): 100% (RT: 5.521, 254 nm) (MS: ESI +ve 849.6[M+1]). $^1$H NMR: (400 MHz, DMSO) δ ppm: 0.84-0.87 (t, J=6.8 Hz, 3H), 1.10-1.25 (m, 28H), 1.50-1.56 (m, 3H), 1.86-2.00 (m, 2H), 2.79-2.87 (m, 2H), 3.10-3.29 (m, 4H), 3.46 (s, 3H), 3.50-3.55 (m, 3H), 3.64-3.97 (m, 5H), 7.07-7.29 (m, 10H), 7.56-7.58 (d, J=5.6, 5H), 8.31-8.32 (d, J=3.2 Hz, 1H), 8.44-8.45 (d, J=4 Hz, 1H).

Synthesis Tetradecyl ((3S,4S)-1-(4-((3S,4S)-3,4-bis (((1S,2R)-2-phenylcyclopropyl)carbamoyl)pyrrolidine-1-carbonyl)benzoyl)-4-methoxypyrrolidin-3-yl) carbamate, Compound 218

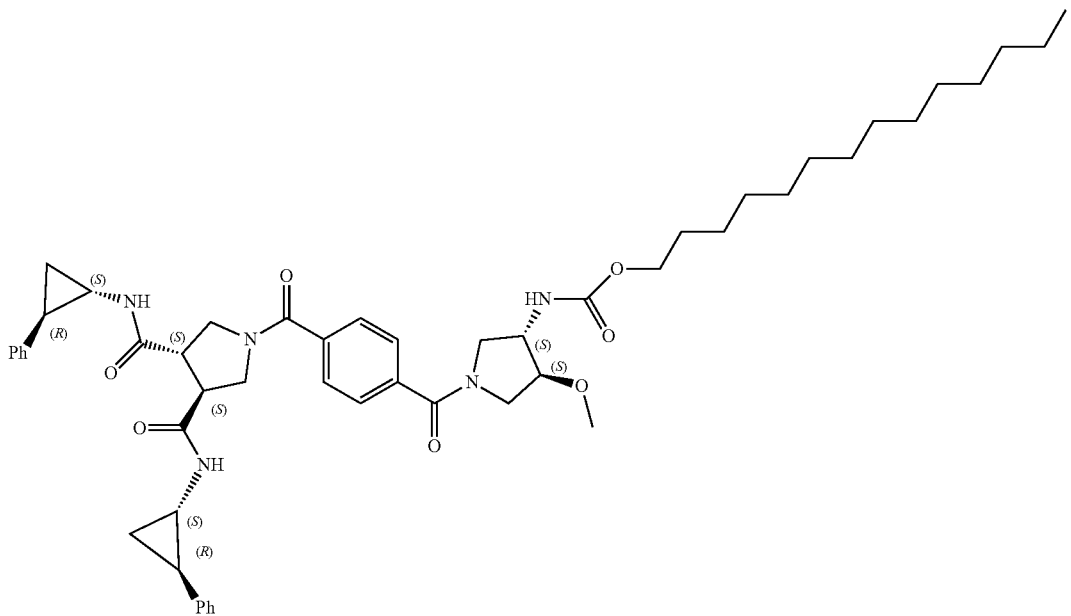

Prepared by a Procedure similar to that reported for undecyl ((3S,4S)-1-(4-((3S,4S)-3,4-bis(((1S,2R)-2-phenyl-cyclopropyl)carbamoyl)pyrrolidine-1-carbonyl)benzoyl)-4-methoxypyrrolidin-3-yl)carbamate (Compound 215). The crude final product was purified using Prep HPLC Method 10 to give tetradecyl ((3S,4S)-1-(4-((3S,4S)-3,4-bis(((1S,2R)-2-phenylcyclopropyl)carbamoyl)pyrrolidine-1-carbonyl)benzoyl)-4-methoxypyrrolidin-3-yl)carbamate (Compound 218), as a white solid (0.050 g, 23.08%). LCMS (Method J): 100% (RT 5.068, 225.0 nm) (MS: ESI +ve 877.6 [M+1]. $^1$H NMR: (400 MHz, DMSO) δ ppm: 0.83-0.86 (m, 3H), 1.10 (s, 2H), 1.17-1.36 (m, 26H), 1.49-1.55 (m, 2H), 1.85 (s, 1H), 1.97 (s, 1H), 2.67-2.85 (m, 2H), 3.07-3.13 (m, 1H), 3.16-3.28 (m, 4H), 3.63-3.68 (m, 3H), 3.78-3.83 (t, J=1.6 Hz, 1H), 3.90-4.05 (m, 3H), 7.06-7.18 (m, 4H), 7.21-7.28 (m, 4H), 7.55-7.57 (d, J=5.6 Hz, 5H), 8.31 (s, 1H), 8.43-8.44 (d, J=3.2 Hz, 1H).

Synthesis of (3S,4S)-1-(4-((R)-3-(3-dodecylureido)piperidine-1-carbonyl)benzoyl)-N3,N4-bis((1S,2R)-2-phenylcyclopropyl)pyrrolidine-3,4-dicarboxamide, Compound 204

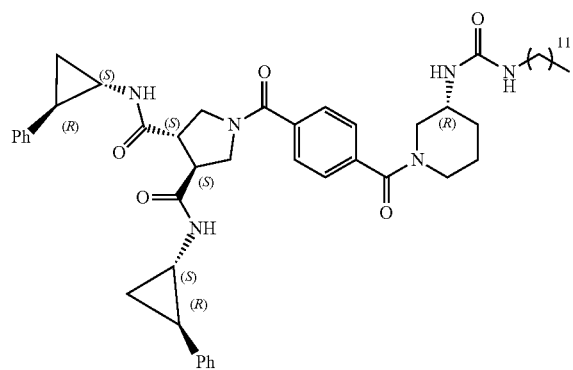

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 13 to give Compound 204, as an off white solid (0.033 g, 17.79%). LCMS (Method-J): 100% (RT 4.946, 202.0 nm) (MS: ESI +ve 832.6 [M+H]). $^1$H NMR: (400 MHz, DMSO) δ ppm: 0.849-0.882 (t, J=1.2 Hz, 3H), 1.10-1.24 (m, 25H), 1.45 (s, 2H), 1.70 (s, 1H), 1.82-1.98 (m, 3H), 2.79-3.25 (m, 8H), 3.53-3.79 (m, 6H), 4.12 (s, 1H), 5.81 (s, 1H), 5.98 (s, 1H), 7.07-7.29 (m, 10H), 7.43 (s, 2H), 7.54 (s, 2H), 8.35-8.36 (d, J=3.6 Hz, 1H), 8.49-8.53 (m, 1H).

Synthesis of (3S,4S)—N3,N4-bis((1S,2R)-2-phenylcyclopropyl)-1-(4-((R)-3-(3-tridecylureido)piperidine-1-carbonyl)benzoyl)pyrrolidine-3,4-dicarboxamide, Compound 205

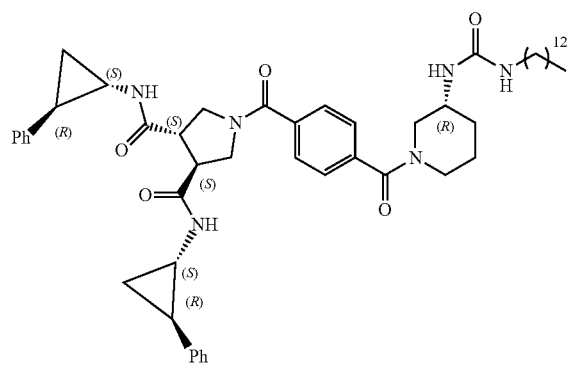

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using Prep HPLC Method 13 to give Compound 205 (0.033 g, 17.49%). LCMS (Method-J): 100% (RT 4.639, 254.0 nm) (MS: ESI +ve 846.2 [M+H]). 1H NMR: (400 MHz, DMSO) δ ppm: 0.849-0.882 (t, J=1.2 Hz, 3H), 1.11-1.24 (m, 25H), 1.45-1.69 (m, 3H), 1.82-1.98 (m, 3H), 2.79-3.24 (m, 7H), 3.53-3.80 (m, 6H), 4.12 (s, 1H), 5.76 (s, 1H), 5.93 (s, 1H), 7.07-7.29 (m, 10H), 7.43 (s, 2H), 7.54 (s, 2H), 8.31-8.32 (d, J=4 Hz, 1H), 8.43-8.44 (d, J=3.6 Hz, 1H).

Synthesis of (3S,4S)—N3,N4-bis((1S,2R)-2-phenylcyclopropyl)-1-(4-((R)-3-(3-tetradecylureido)piperidine-1-carbonyl)benzoyl)pyrrolidine-3,4-dicarboxamide, Compound 206

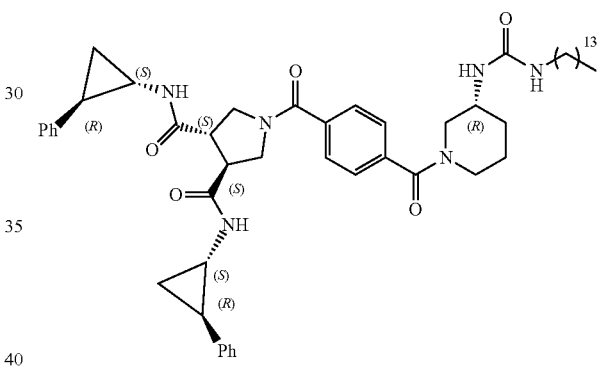

Prepared by a procedure similar to that reported for (3S,4S)-1-(4-((3S,4S)-3-methoxy-4-(3-tridecylureido)pyrrolidine-1-carbonyl)benzoyl)-N3,N4-bis((1S,2R)-2-phenylcyclopropyl)pyrrolidine-3,4-dicarboxamide (Compound 134), substituting the applicable starting materials. The crude product was purified using flash chromatography, eluting with 0-2% MeOH:DCM, to give (3S,4S)—N3,N4-bis((1S,2R)-2-phenylcyclopropyl)-1-(4-((R)-3-(3-tetradecylureido)piperidine-1-carbonyl)benzoyl)pyrrolidine-3,4-dicarboxamide (Compound 206)(0.100 g, 52.14%) LCMS (Method J): 100% (RT 4.824, 222.0 nm) (MS: ESI +ve 860.2 [M+1]. $^1$H NMR: (400 MHz, DMSO) δ ppm: 0.849-0.882 (t, J=1.2 Hz, 3H), 1.11-1.34 (t, J=6 Hz, 2H), 1.18-1.37 (m, 29H), 1.45-1.69 (m, 4H), 1.82-1.88 (t, J=9.2 Hz, 2H), 1.96-1.98 (d, J=6.4 Hz, 1H), 2.79-3.24 (m, 7H), 3.52-3.80 (m, 7H), 4.11-4.12 (d, J=5.2 Hz, 1H), 5.76 (s, 1H), 5.93 (s, 1H), 7.07-7.29 (m, 10H), 7.43 (s, 2H), 7.54 (s, 2H), 8.31-8.32 (d, J=4 Hz, 1H), 8.43-8.44 (d, J=3.6 Hz, 1H).

Example 32

Synthesis of (3R*,5S*)-1-(4-((3S,4S)-3,4-bis(((1S,2R)-2-phenylcyclopropyl) carbamoyl) pyrrolidine-1-carbonyl)benzoyl)-N3,N5-dihexylpiperidine-3,5-dicarboxamide, Compound 038

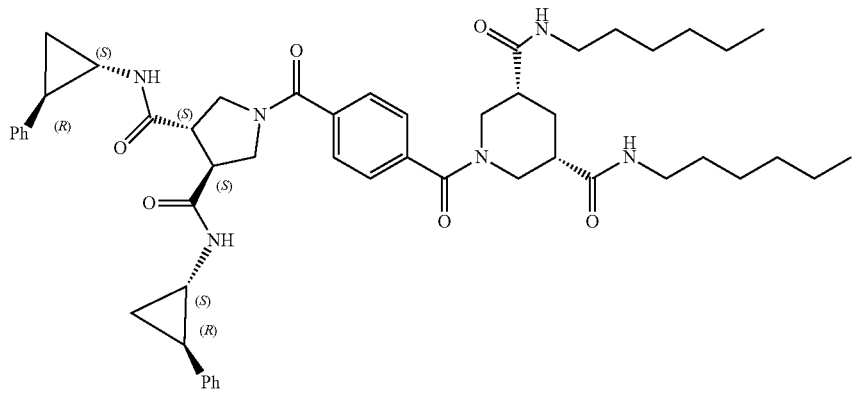

Step-1: Preparation of dimethyl piperidine-3,5-dicarboxylate cis/trans mixture

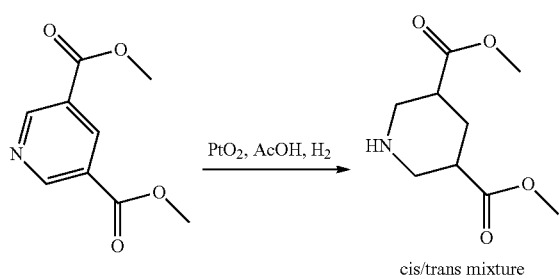

Dimethyl pyridine-3,5-dicarboxylate (1 g, 0.306 mmol) was dissolved in acetic acid (10 mL). Pd/C (0.1 g) was added and the mixture was stirred under hydrogen pressure in an autoclave at room temperature for 12 hrs. The reaction mixture was filtered through cellite then rinsed with methanol (20 mL). The combined filtrate was concentrated to give dimethyl piperidine-3,5-dicarboxylate (cis/trans mixture) and used with no further purification (0.99 g, crude). LCMS (Method-C): 41.2%, 58.7% (RT 1.34, 1.25, 202 nm) (MS: ESI +ve 201.9 [M+H]).

Step-2: Preparation of 1-(tert-butyl) 3,5-dimethyl piperidine-1,3,5-tricarboxylate

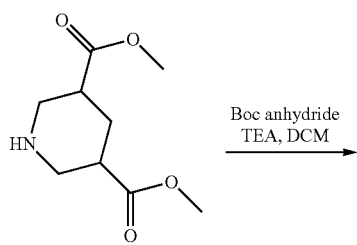

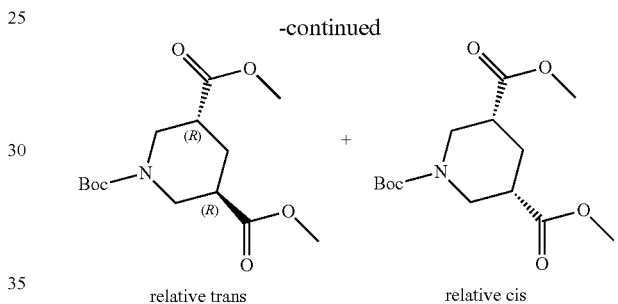

A mixture of dimethyl piperidine-3,5-dicarboxylate (1.4 g, 6.9 mmol), Boc anhydride (1.6 g, 7.6 mmol) and TEA (2.11 g, 20.6 mmol) in $CH_2Cl_2$ was stirred for 16 hrs. Ice cold water was added and the mixture was extracted with $CH_2Cl_2$ (3×10 mL). The organic layers were dried over sodium sulphate and concentrated under reduced pressure. The crude product was purified using column chromatography eluting with 50% ethyl acetate in hexane.

Spot-1, (0.24 g, 11.45%) assigned relative trans stereochemistry. 1-(tert-butyl) 3,5-dimethyl (3R*,5S*)-piperidine-1,3,5-tricarboxylate. LCMS (Method-C): 98.77% (RT: 1.651, 202.0 nm) (MS: ESI +ve 302.4[M+1]). $^1$H NMR: (400 MHz, DMSO) δ ppm: 1.48 (s, 9H), 1.69 (m, 1H), 2.49 (m, 3H), 2.27 (bs, 2H), 3.71 (s, 6H), 4.37 (bs, 2H).

Spot-2 (0.38 g, 18.12%). Assigned relative cis stereochemistry. 1-(tert-butyl) 3,5-dimethyl (3R*,5S*)-piperidine-1,3,5-tricarboxylate. LCMS (Method-C): 96.55% (RT: 1.619, 202.0 nm) (MS: ESI +ve 302.4[M+1]). $^1$H NMR: (400 MHz, DMSO) δ ppm: 1.48 (s, 9H), 2.08 (bs, 2H), 2.87 (m, 2H), 3.52 (m, 4H), 3.71 (s, 6H).

Step-3: Preparation of dimethyl (3R*,5S*)-piperidine-3,5-dicarboxylate trifluoroacetate

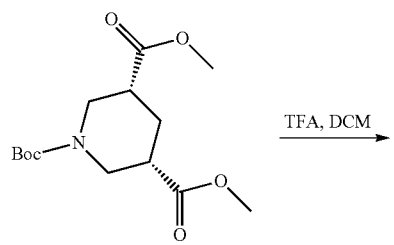

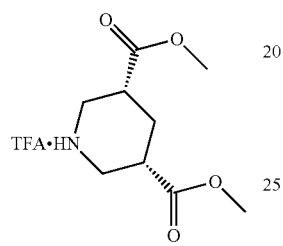

Prepared by a procedure similar to General Boc Deprotection Procedure. The crude product was triturated with pentane (3X) to give dimethyl (3R*,5S*)-piperidine-3,5-dicarboxylate (0.35 g). LC-MS (MS: ESI +ve 201.8[M+1]).

Step-4: Preparation of dimethyl (3R*,5R*)-1-(4-((3S,4S)-3,4-bis(((1S,2R)-2-phenylcyclopropyl)carbamoyl)pyrrolidine-1-carbonyl)benzoyl)piperidine-3,5-dicarboxylate Prepared using a procedure similar to General PyBroP Coupling Procedure. The crude product was purified using column chromatography (Stationary phase-Basic alumina (Al$_2$O$_3$)) eluting with 80% ethyl acetate in hexane to afford dimethyl (3R*,5R*)-1-(4-((3S,4S)-3,4-bis(((1S,2R)-2-phenylcyclopropyl)carbamoyl)pyrrolidine-1-carbonyl)benzoyl) piperidine-3,5-dicarboxylate (0.50 g, 69.79%). LCMS (Method-C3): 79.8% (RT: 1.64 min, 232 nm) (MS: ESI +ve 721.7 [M+1]).

Step-5: Preparation of (3R*,5R*)-1-(4-((3S,4S)-3,4-bis(((1S,2R)-2-phenylcyclopropyl) carbamoyl)pyrrolidine-1-carbonyl)benzoyl)piperidine-3,5-dicarboxylic acid

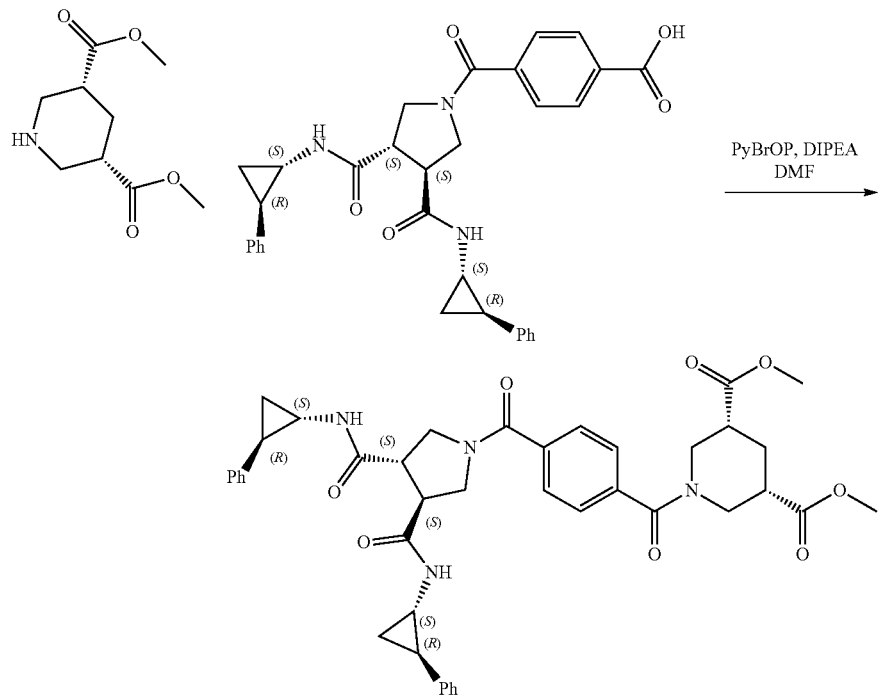

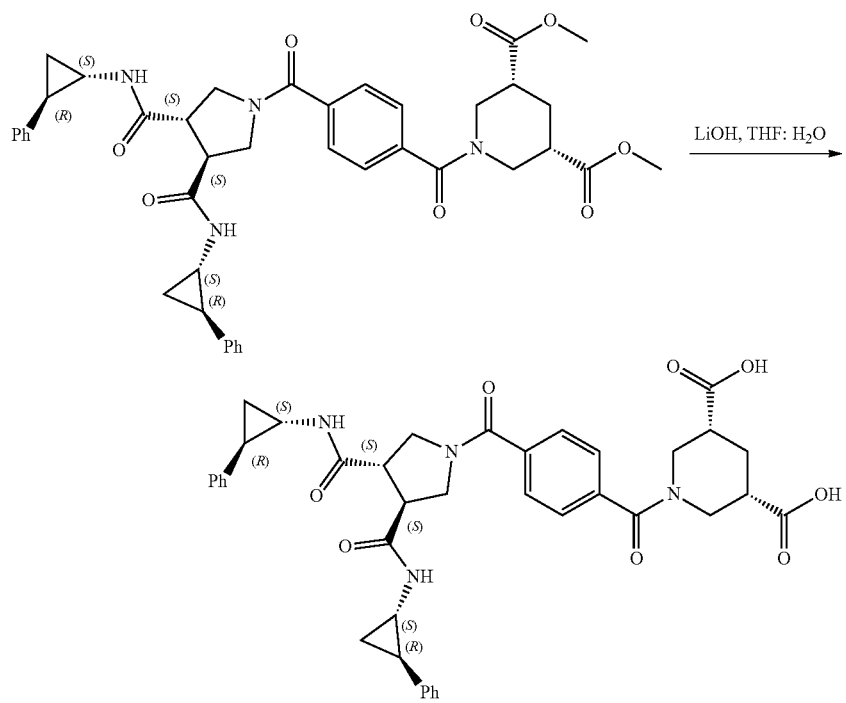

A solution of dimethyl (3R*,5S*)-1-4 (3S,4S)-3,4-bis (((1S,2R)-2-phenylcyclopropyl) carbamoyl)pyrolidine-1-carbonyl)benzoyl)piperidine-3,5-dicarboxylate (0.50 g, 0.69 mmol) and LiOH (0.022 g, 5.3 mmol) in THF:H₂O (1:1, 8 mL) was stirred for 2 hrs. The reaction mixture quenched by addition of 1N HCl (10 mL). The resulting precipitate was collected by filtration, rinsed with water and dried to give (3R*,5S*)-1-(4-((3S,4S)-3,4-bis(((1S,2R)-2-phenylcyclopropyl) carbamoyl) pyrrolidine-1-carbonyl)benzoyl)piperidine-3,5-dicarboxylic acid as a white solid (0.35 g). LCMS (Method-C3): 25.3% (RT: 1.54 min, 240 nm) (MS: ESI +ve 691.6 [M+1]).

Step-6: Preparation of (3R*,5S*)-1-(4-((3S,4S)-3,4-bis(((1S,2R)-2-phenylcyclopropyl) carbamoyl)pyrrolidine-1-carbonyl)benzoyl)-N3,N5-dihexylpiperidine-3,5-dicarboxamide, Compound 038

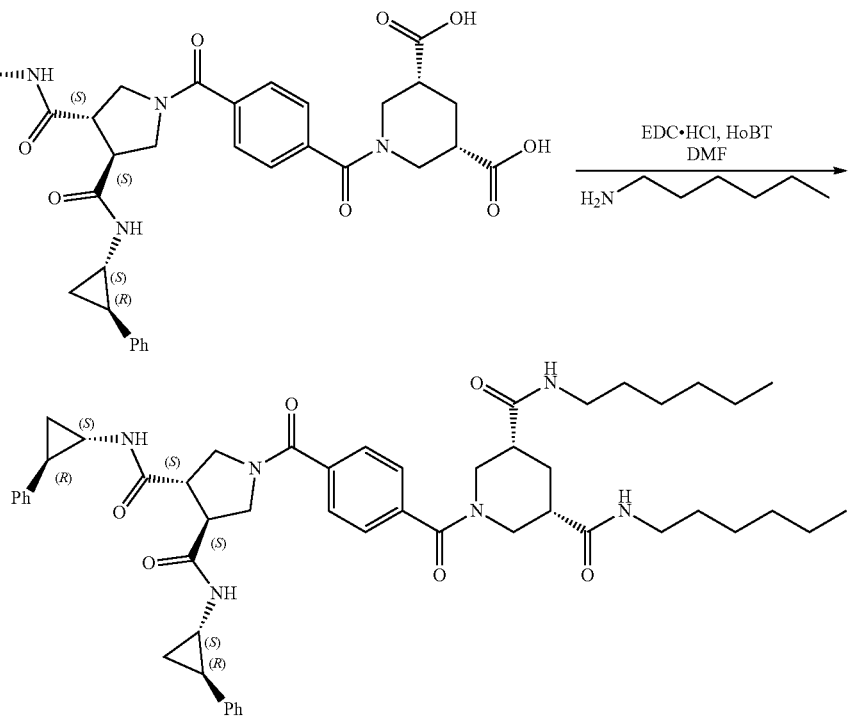

Prepared using a procedure similar to General EDC.HCl, HOBT Coupling Procedure. The crude compound was purified using Prep HPLC Method 7 to give (3R*,5S*)-1-(4-((3S,4S)-3,4-bis(((1S,2R)-2-phenylcyclopropyl)carbamoyl)pyrrolidine-1-carbonyl)benzoyl)-N3,N5-dihexylpiperidine-3,5-dicarboxamide, Compound 038, as a white solid (0.012 g, 2.76%). LCMS (Method-C): 100% (RT: 1.948, 202.0 nm) (MS: ESI +ve 860.6 [M+1]). ¹H NMR: (400 MHz, DMSO) δ ppm: 0.87 (m, 6H), 1.27 (m, 15H), 1.40 (m, 2H), 1.74-1.78 (m, 1H), 1.86 (m, 3H), 1.97 (m, 2H), 2.34 (s, 2H), 2.68 (m, 1H), 2.86 (m, 3H), 3.03-3.22 (m, 7H), 3.51-3.53 (m, 3H), 3.67 (m, 1H), 3.77-3.79 (m, 1H), 4.55 (m, 1H), 7.07-7.19 (m, 6H), 7.25 (m, 4H), 7.44-7.46 (d, J=8 Hz, 2H), 7.56-7.58-7.60 (d, J=8 Hz, 2H), 7.85 (bs, 1H), 8.02 (bs, 1H), 8.36 (s, 1H), 8.48 (m, 1H).

Example 33

Synthesis of (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036

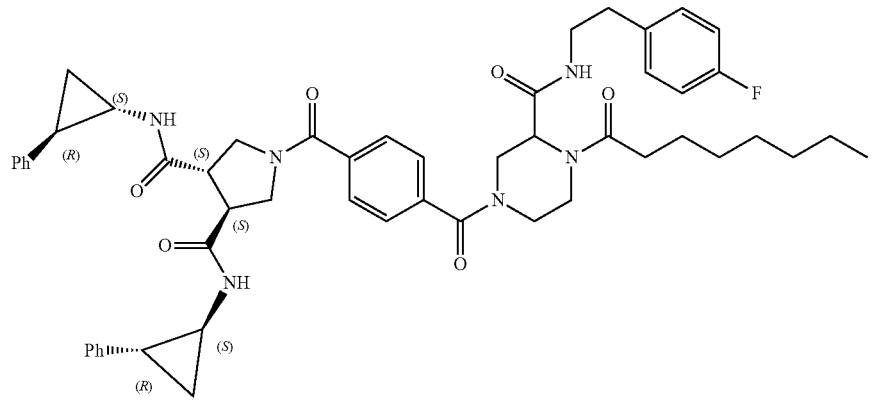

Step-1: Preparation of tert-butyl 3-((4-fluorophenethyl)carbamoyl)piperazine-1-carboxylate

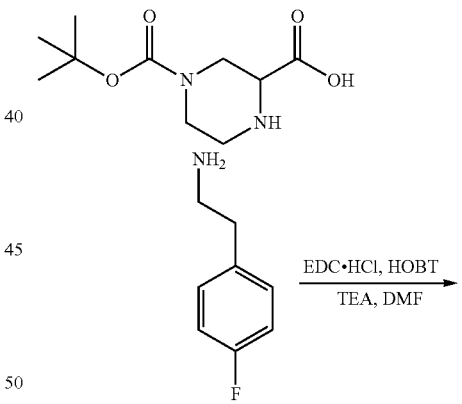

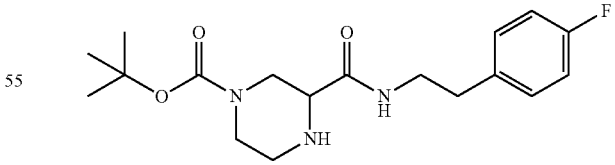

Prepared using a procedure similar to General EDC, HOBT Coupling Procedure. The crude product was purified using column chromatography eluting with 3-5% MeOH in DCM to give tert-butyl 3-((4-fluorophenethyl) carbamoyl)piperazine-1-carboxylate (0.5 g, 46%). LCMS (Method-C3): 95.88% (RT: 1.375, 214 nm) (MS: ESI +ve 352.3[M−H]).

Step 2: Preparation of tert-butyl 3-((4-fluorophen-ethyl)carbamoyl)-4-octanoylpiperazine-1-carboxylate

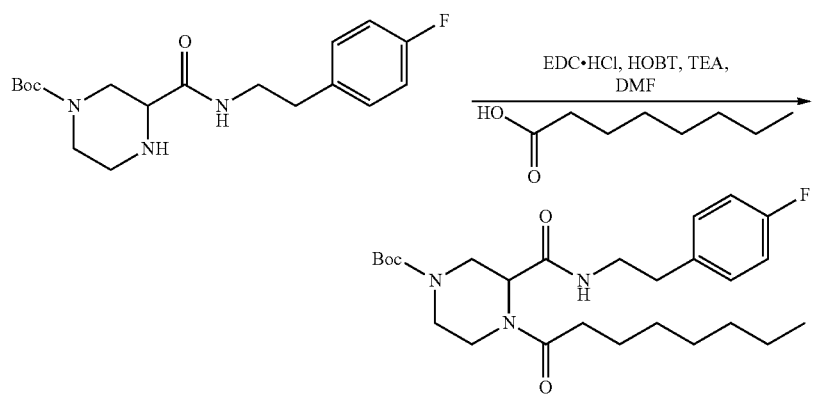

Prepared using a procedure similar to General EDC, HOBT Coupling Procedure. The crude product was purified using column chromatography eluting with 0-2% MeOH in DCM to give tert-butyl 3-((4-fluorophenethyl)carbamoyl)-4-octanoylpiperazine-1-carboxylate (0.6 g, 88%). LCMS (Method-C3): 95.71% (RT: 1.956 min, 225 nm) (MS: ESI +ve 478.5 [M+1]). Can also be prepared by reaction of appropriate acid chloride and $K_2CO_3$ in DMF.

Step 3: Preparation of N-(4-fluorophenethyl)-1-octanoylpiperazine-2-carboxamide trifluoroacetate

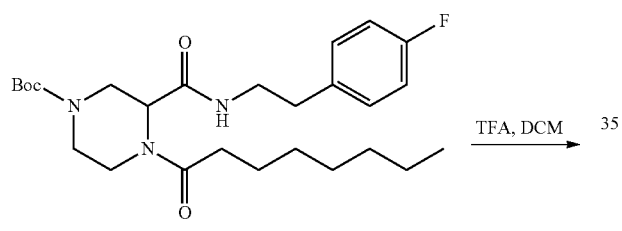

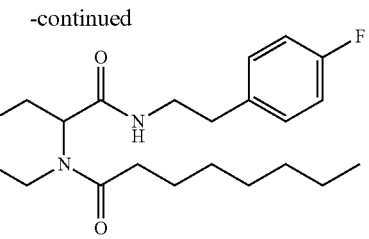

Prepared using a procedure similar to General Boc Deprotection Procedure. The crude product was triturated with pentane (3X) to afford N-(4-fluorophenethyl)-1-octanoylpiperazine-2-carboxamide trifluororacetate (0.45 g, crude).

Step-4: Preparation of (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl) pyrrolidine-3,4-dicarboxamide, Compound 036

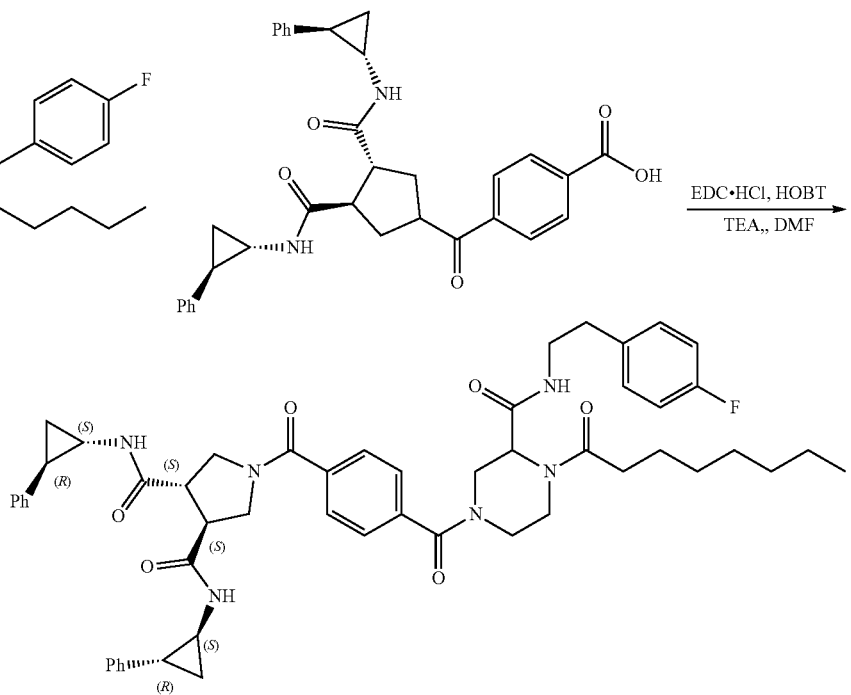

Prepared using a procedure similar to General EDC, HOBT Coupling Procedure. The crude product was purified using Prep HPLC Method 8 to give (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, (80 mg, 24%) as a mixture of diastereomers. LCMS (Method-C): 100% (RT 1.990, 254 nm) (MS: ESI −ve 896.50 [M+H]). $^1$H NMR: (400 MHz, DMSO) δ ppm: 0.87 (s, 3H), 1.12-1.27 (m, 14H), 1.50 (s, 2H), 1.87-1.98 (m, 2H), 2.34-2.39 (m, 4H), 2.79-2.86 (m, 2H), 3.10-3.21 (m, 4H), 3.53-3.66 (m, 4H), 3.79-3.84 (t, 2H), 3.94-4.36 (m, 2H), 4.72-4.92 (m, 1H), 7.07-7.27 (m, 14H), 7.39-7.41 (m, 2H), 7.58-7.59 (m, 2H), 7.84-8.08 (m, 1H), 8.32-8.4 (m, 2H).

Example 34

Synthesis of (3S,4S)-1-(4-(3-(ethylcarbamoyl)-4-octanoylpiperazine-1-carbonyl) benzoyl)-N3,N4-bis ((1S,2R)-2-phenylcyclopropyl) pyrrolidine-3,4-dicarboxamide, Compound 048

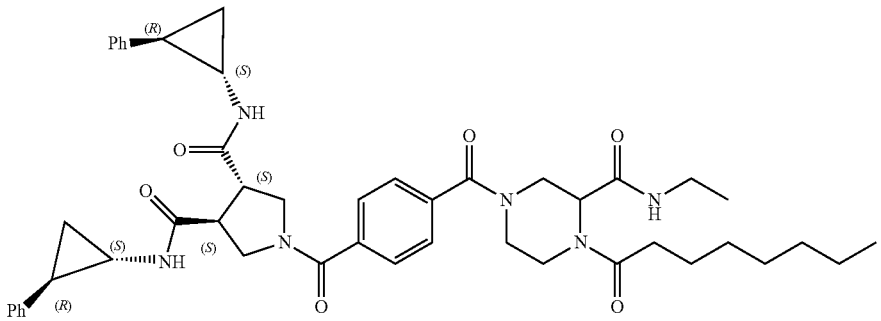

Prepared by a procedure similar to that reported for (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, substituting ethyl amine in step 1. The crude final product was purified using Prep HPLC Method 6 to afford (3S,4S)-1-(4-(3-(ethylcarbamoyl)-4-octanoylpiperazine-1-carbonyl) benzoyl)-N3,N4-bis ((1S,2R)-2-phenylcyclopropyl) pyrrolidine-3,4-dicarboxamide, Compound 048, as a white solid (0.05 g, 36.6%). LCMS (Method-C3): 100% (RT 1.830, 222.0 nm) (MS: ESI +ve 804[M+H]). $^1$H NMR: (400 MHz, DMSO) δ ppm: 0.86-0.87 (d, J=5.6, 4H); 1.12-1.14 (d, J=6.4, 5H); 1.27 (s, 9H); 1.49 (s, 3H); 1.87 (s, 1H); 1.98 (s, 1H); 2.34 (s, 1H); 2.68 (s, 1H); 2.86 (s, 1H); 3.05-3.10 (m, 5H); 3.14-3.21 (m, 1H); 3.49-3.54 (m, 3H); 3.66 (s, 2H); 3.82 (s, 2H); 3.93 (s, 1H); 4.22 (s, 1H); 4.69 (s, 1H); 7.07-7.09 (d, J=7.6, 2H); 7.12-7.19 (m, 4H); 7.23-7.29 (m, 4H); 7.38-7.39 (d, J=6.4, 2H); 7.76 (s, 11); 8.33 (s, 1H), 8.34 (s, 1H), 8.44 (s, 1H).

Example 35

Synthesis of (3S,4S)-1-(4-(3-(butylcarbamoyl)-4-octanoylpiperazine-1-carbonyl) benzoyl)-N3,N4-bis ((1S,2R)-2-phenylcyclopropyl)pyrrolidine-3,4-dicarboxamide, Compound 046

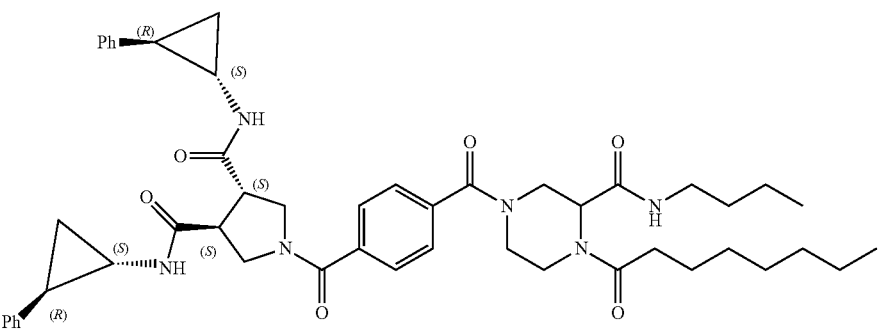

Prepared by a procedure similar to that reported for (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, substituting butan-1-amine in step 1. The crude final product was purified using Prep HPLC Method 3 to afford (3S,4S)-1-(4-(3-(butylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 046, (40.38 mg, 26.12%) as a mixture of diastereomers. LCMS: RT-1.94, 100%, 221 nm (MS: ESI +ve 831.4 [M+H]; $^1$H NMR: (400 MHz, DMSO) δ ppm: 0.82-0.86 (m, 3H), 1.11-1.26 (m, 14H), 1.48 (s, 2H), 1.86 (s, 1H) 1.97. (p, 1H), 2.33-2.38 (m, 2H), 2.67-2.85 (m, 3H), 3.07-3.22 (m, 5H), 3.44-3.65 (m, 5H), 3.78-3.83 (m 3H J=12 Hz), 4.05 (t, 3H), 4.18 (s, 1H), 4.69 (bs, 1H), 7.06-7.08 (d, 6H J=7.6 Hz), 7.11-7.18 (q, 4H), 7.37-7.38 (d, 2H), 7.72-7.99 (s, 1H), 8.32 (s, 1H), 8.43-8.44 (d, 1H).

Example 36

Synthesis of (3S,4S)-1-(4-((3-(heptylcarbamoyl)-4-octanoylpiperazin-1-yl) methyl) benzoyl)-N3,N4-bis ((1S,2R)-2-phenylcyclopropyl) pyrrolidine-3,4-dicarboxamide, Compound 058

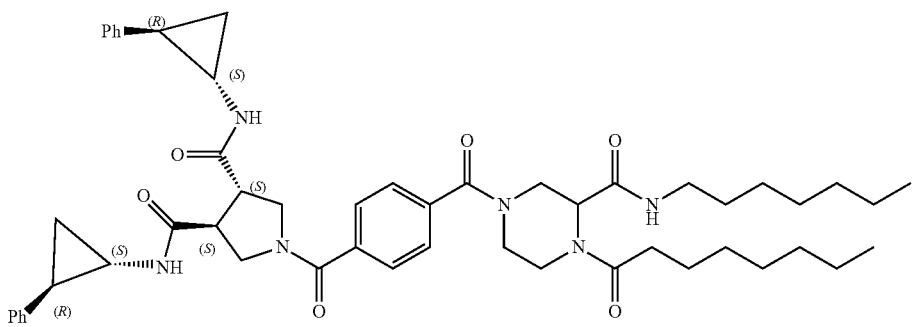

Prepared by a procedure similar to that reported for (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, substituting heptan-1-amine in step 1. The crude final product was purified using Prep HPLC Method 6 to afford (3S,4S)-1-(4-(3-(heptylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 058, as a mixture of diastereomers (0.010 g, 04%). LCMS (Method-C3): 100% (RT 2.090, 202.0 nm) (MS: ESI +ve 874 [M+H]). $^1$H NMR: (400 MHz, DMSO) δ ppm: 0.85-0.87 (d, J=5.6, 6H), 1.12-1.13 (d, J=6, 3H), 1.21-1.24 (d, J=12, 18H), 1.49 (s, 2H), 1.87 (s, 1H), 1.98 (s, 1H), 2.08 (s, 2H), 2.79 (s, 2H), 3.11-3.21 (m, 5H), 3.51-3.59 (d, J=9.6, 5H), 3.79-3.84 (t, 3H), 4.18 (s, 1H), 4.70 (s, 1H), 7.07-7.18 (m, 6H), 7.23-7.27 (s, 5H), 7.38-7.40 (d, J=7.2, 2H) 7.57-7.58 (d, J=6.4, 2H), 7.73 (s, 1H), 7.99 (s, 1H), 8.34 (s, 1H), 8.46 (s, 1H).

Example 37

Synthesis of (3S,4S)-1-(4-(4-octanoyl-3-(octylcarbamoyl) piperazine-1-carbonyl) benzoyl)-N3,N4-bis ((1S,2R)-2-phenylcyclopropyl)pyrrolidine-3,4-dicarboxamide, Compound 065

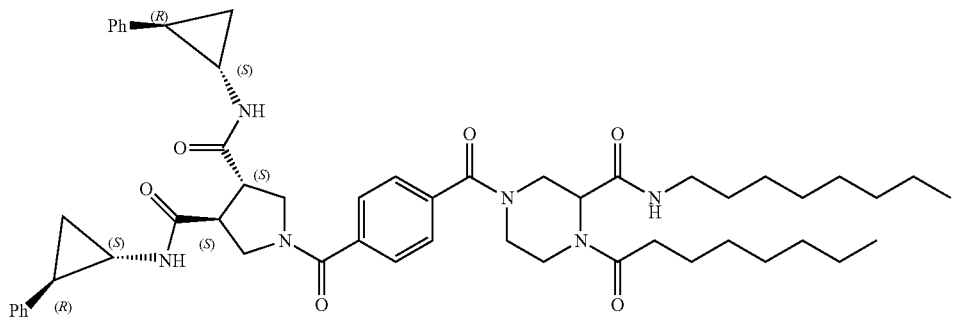

Prepared by a procedure similar to that reported for (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, substituting octan-1-amine in step 1. The crude final product was purified using Prep HPLC Method 2 to afford (3S,4S)-1-(4-(4-octanoyl-3-(octylcarbamoyl)piperazine-1-carbonyl)benzoyl)-N3,N4-bis((1S,2R)-2-phenylcyclopropyl) pyrrolidine-3,4-dicarboxamide, Compound 065, (0.036 g, 9.94%) as a mixture of diastereomers LCMS (Method-C3): 100% (RT 2.604, 222.0 nm) (MS: ESI +ve 845.18 [M+H]). ¹H NMR:−0.86 (s, 6H), 1.12-1.49 (m, 27H), 1.98 (s, 2H), 2.34-2.39 (d, J=19.2 Hz, 1H), 2.86 (s, 3H), 3.10-3.21 (m, 5H), 3.53 (s, 3H), 3.66 (s, 1H), 3.93 (s, 3H), 4.18 (s, 1H), 4.70 (s, 1H), 7.07-7.27 (m, 10H), 7.39 (s, 2H), 7.57 (s, 2H), 7.27-8.02 (m, 1H), 8.34 (s, 1H), 8.46 (s, 1H).

Example 38

Synthesis of (3S,4S)-1-(4-(3-(decylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 066

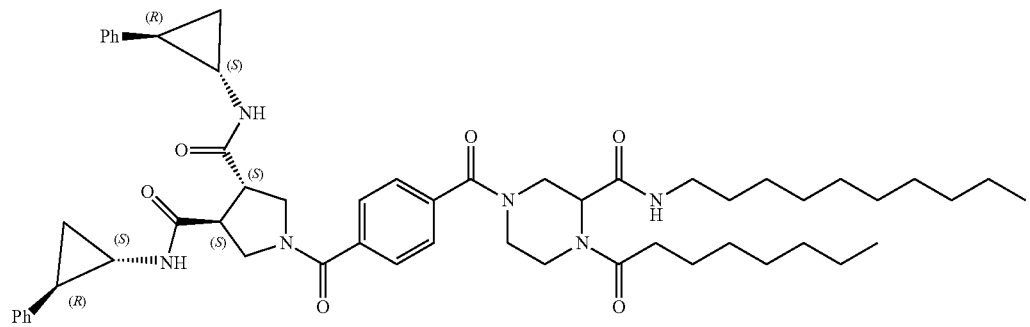

Prepared by a procedure similar to that reported for (3S,4S)-1-(4-(3-((4-fluorophenethyl)carbamoyl)-4-octanoylpiperazine-1-carbonyl)benzoyl)-N3,N4-bis((1S,2R)-2-phenylcyclopropyl)pyrrolidine-3,4-dicarboxamide, Compound 036, substituting decan-1-amine in step 1. The crude final product was purified using Prep HPLC Method 2 to afford (3S,4S)-1-(4-(3-(decylcarbamoyl)-4-octanoylpiperazine-1-carbonyl)benzoyl)-N3,N4-bis((1S,2R)-2-phenylcyclopropyl)pyrrolidine-3,4-dicarboxamide, Compound 066, as a mixture of diastereomers. LCMS (Method-C3): 100% (RT 2.319, 202.0 nm) (MS: ESI +ve 916.6 [M+H]); ¹H NMR: (400 MHz, DMSO) δ ppm: 0.85-0.86 (m, 7H), 1.12-1.22 (m, 22H), 1.49 (s, 3H), 1.87 (s, 1H), 1.98 (s, 1H), 2.68-2.86 (m, 5H), 3.10-3.12 (m, 4H), 3.16-3.21 (m, 2H), 3.53 (s, 4H), 3.64-3.66 (m, 2H), 3.79-3.93 (m, 2H), 4.19 (s, 1H), 4.69 (s, 1H), 7.07-7.93 (m, 13H), 7.57-7.59 (d, J=8 Hz, 2H), 7.73 (s, 2H), 8.33 (s, 1H), 8.45 (s, 1H).

Example 39

Synthesis of (3S,4S)-1-(4-(((R)-5-(hexylcarbamoyl)-4-octanoyl-2-oxopiperazin-1-yl)methyl)benzoyl)-N3,N4-bis((1S,2R)-2-phenylcyclopropyl)pyrrolidine-3,4-dicarboxamide, Compound 074

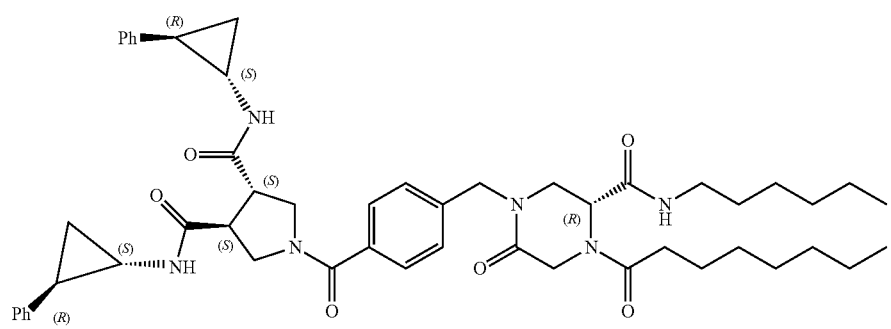

Step-1: Preparation of methyl (2-ethoxy-2-oxoethyl)-D-serinate

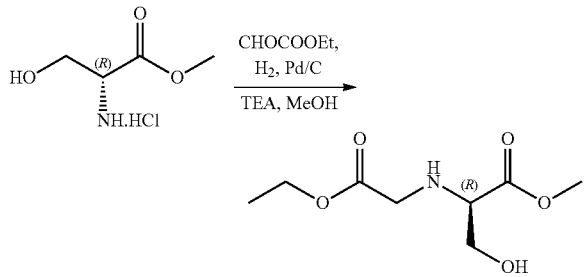

To a stirred solution of D-Serine methyl ester hydrochloride (6.0 g, 32 mmol) in methanol was added triethylamine (5.36 mL, 38 mmol), palladium/carbon 10% (0.6 g) and ethyl oxaloacetate (11.82 mL, 57.84 mmol, 50% solution in toluene). The reaction was stirred at room temperature under a hydrogen gas atmosphere for 24 hrs. The volatiles were removed under reduced pressure and the crude residue was purified by column chromatography eluting with 2% Methanol:Dichloromethane to afford methyl (2-ethoxy-2-oxoethyl)-D-serinate (3.9 g, 49.28%). LC-MS (Method-C3): 92.23% (RT 0.79, 202.0 nm) (MS: ESI +ve 206.3 [M+H]).

Step-2: Preparation of methyl N-(2-ethoxy-2-oxoethyl)-O-(methylsulfonyl)-D-serinate

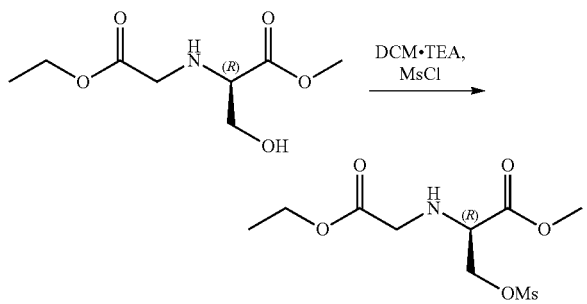

To a stirred solution of methyl (2-ethoxy-2-oxoethyl)-D-serinate (2.0 g, 9.7 mmol) in DCM (25 mL) at 0° C. was added triethylamine (2.71 mL, 19.4 mmol). After 10 minutes, methane sulfonyl chloride (1.3 g, 11.6 mmol) was added and the mixture was stirred for 1 hour warming to room temperature. The reaction mixture was quenched with water, extracted with DCM. The organic layer was washed with sodium bicarbonate, then brine, dried over sodium sulphate and concentrated to afford methyl N-(2-ethoxy-2-oxoethyl)-O-(methylsulfonyl)-D-serinate. (2.7 g, 97.7%).

Step-3: Preparation of methyl (R)-3-azido-2-((2-ethoxy-2-oxoethyl)amino)propanoate

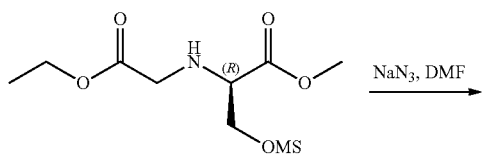

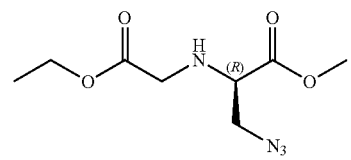

To a stirred solution of methyl N-(2-ethoxy-2-oxoethyl)-O-(methylsulfonyl)-D-serinate (2.7 g, 9.5 mmol) in DMF (25 mL) was added sodium azide (3.09 g, 4.75 mmol). The reaction mixture was heated at 70° C. for 3 hrs, cooled to room temperature, quenched with water and extracted with ethyl acetate. The organic layer was washed with cold water then brine, dried over sodium sulphate and concentrated to afford methyl (R)-3-azido-2-((2-ethoxy-2-oxoethyl)amino)propanoate (2.0 g, 91.15%).

Step-4: Preparation of methyl (R)-5-oxopiperazine-2-carboxylate

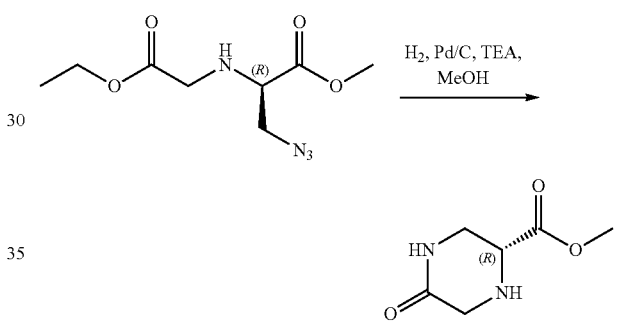

To a stirred solution of methyl (R)-3-azido-2-((2-ethoxy-2-oxoethyl)amino)propanoate (2.0 g, 8.6 mmol) in methanol was added triethylamine (3.6 mL) followed by 10% palladium/carbon (1 g). The reaction mixture was stirred under a hydrogen atmosphere for 48 hrs then filtered through celite. The filtrate was concentrated and the residue was purified using column chromatography (Basic alumina; eluting with 3% methanol: DCM) to give methyl (R)-5-oxopiperazine-2-carboxylate (0.29 g, 21.11%). LC-MS (Method-G): 90.94% (RT 3.73, 230.0 nm) (MS: ESI +ve 159.2 [M+H]).

Step-5: Preparation of methyl (R)-1-octanoyl-5-oxopiperazine-2-carboxylate

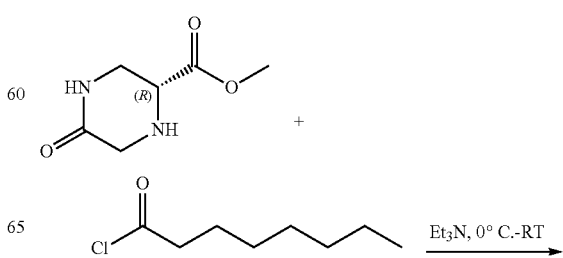

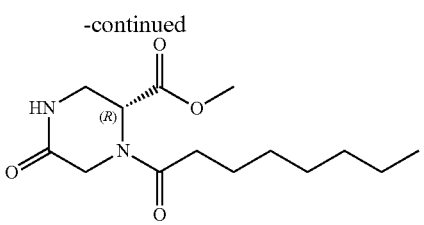

A solution of methyl (R)-5-oxopiperazine-2-carboxylate (0.27 g, 1.7 mmol) was treated with triethylamine (0.71 mL, 5.1 mmol) then octanoyl chloride (0.277 g, 1.7 mmol). The reaction mixture was stirred for 1 hr then quenched with water and extracted with ethyl acetate. The organic layer was washed with sodium bicarbonate, dried over sodium sulphate and concentrated. The crude residue was purified by column chromatography (Basic alumina; eluting with 3% Methanol:DCM) to afford methyl (R)-1-octanoyl-5-oxopiperazine-2-carboxylate (0.22 g, 45%). LCMS (Method-X): 97.41% (RT 0.91, 220.0 nm) (MS: ESI +ve 285.3 [M+H]).

Step-6: Preparation of methyl (R)-4-(4-(tert-butoxycarbonyl)benzyl)-1-octanoyl-5-oxopiperazine-2-carboxylate

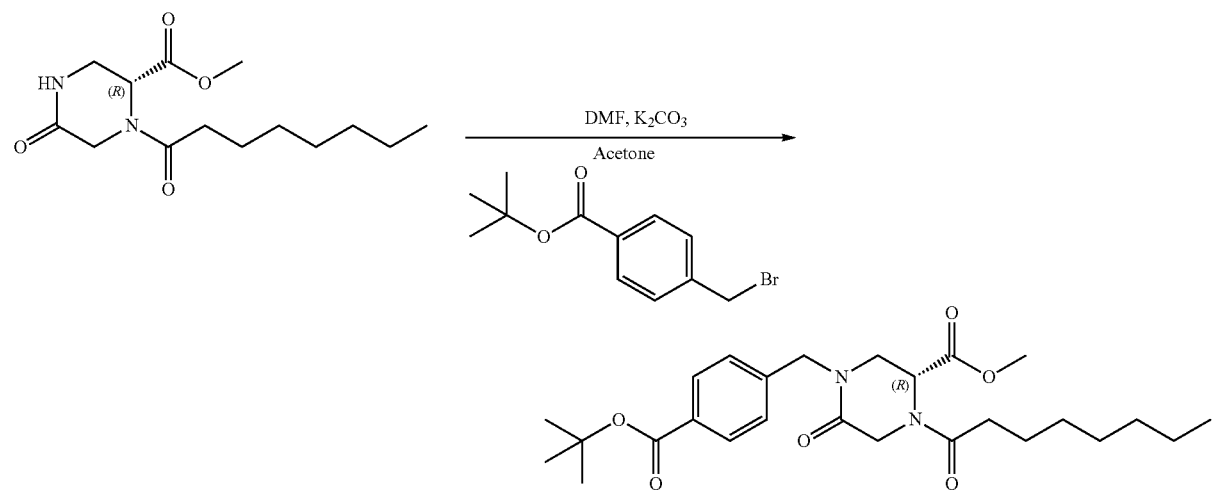

A solution of methyl (R)-1-octanoyl-5-oxopiperazine-2-carboxylate (0.30 g, 1.0 mmol) in acetone was treated with potassium carbonate (0.291 g, 2.0 mmol) then tert-butyl 4-(bromomethyl)benzoate (0.343 g, 1.2 mmol). The reaction mixture heated at 80° C. for 16 hrs, quenched with water then extracted with ethyl acetate. The organic layer was dried over sodium sulphate then concentrated to dryness. The crude compound was purified using column chromatography eluting with 10% Ethyl acetate:Hexane to afford methyl (R)-4-(4-(tert-butoxycarbonyl)benzyl)-1-octanoyl-5-oxopiperazine-2-carboxylate. LCMS (Method-X): 78.52% (RT 1.09, 225.0 nm) (MS: ESI +ve 475.5 [M+H])

Step-7: Preparation of (R)-4-((5-(methoxycarbonyl)-4-octanoyl-2-oxopiperazin-1-yl)methyl)benzoic acid

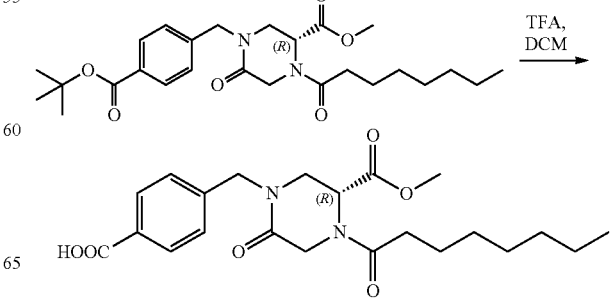

Trifluroaceticacid (1.5 mL) was added to a solution of methyl (R)-4-(4-(tert-butoxycarbonyl)benzyl)-1-octanoyl-5-oxopiperazine-2-carboxylate (0.20 g, 0.42 mmol) in DCM (5 mL) at 0° C. The reaction was stirred for 3 hours warming to room temperature. The mixture was concentrated then chased with DCM (3 X). The crude residue was triturated with pentane to afford (R)-4-((5-(methoxycarbonyl)-4-octanoyl-2-oxopiperazin-1-yl) methyl) benzoic acid (0.17 g, 96.40%). LCMS (Method-X): 100% (RT 0.94, 235.0 nm) (MS: ESI +ve 419.42 [M+H]).

Step-8: Preparation of methyl (R)-4-(4-((3S,4S)-3,4-bis(((1S,2R)-2-phenylcyclopropyl) carbamoyl) pyrrolidine-1-carbonyl)benzyl)-1-octanoyl-5-oxopiperazine-2-carboxylate

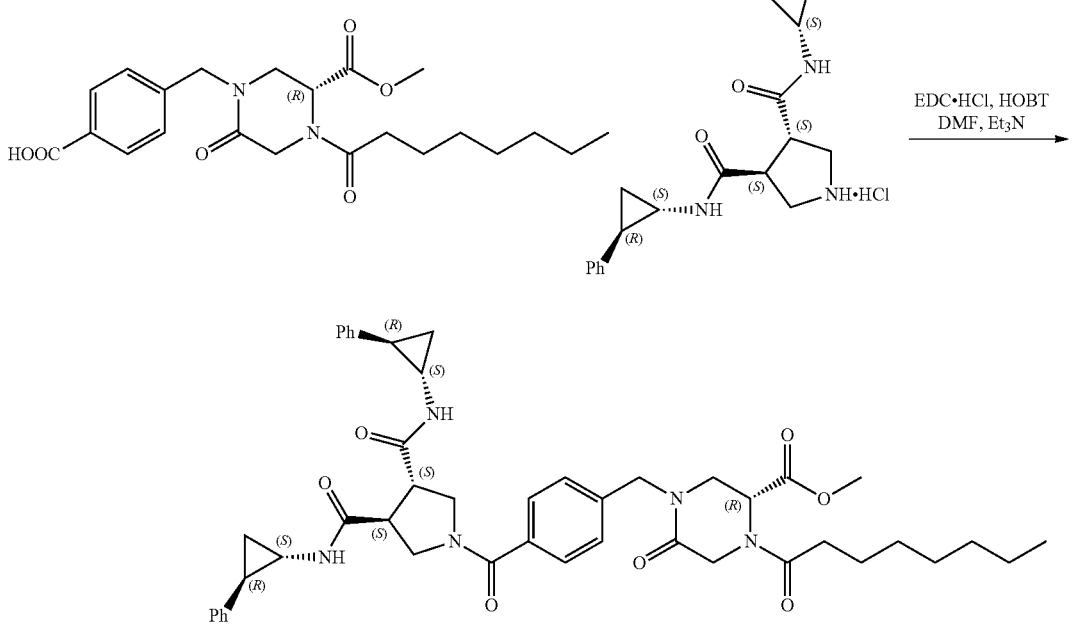

Prepared by a procedure similar to General EDC, HOBT Coupling Procedure. The crude product was purified using column chromatography (Basic Alumina eluting with 2% Methanol:DCM) to afford methyl (R)-4-(4-((3S,4S)-3,4-bis(((1S,2R)-2-phenylcyclopropyl) carbamoyl)pyrrolidine-1-carbonyl)benzyl)-1-octanoyl-5-oxopiperazine-2-carboxylate (0.15 g, 46.74%) LCMS (Method-X): 90.94% (RT 1.04, 225.0 nm) (MS: ESI +ve 790.9 [M+H])

Step-9: Synthesis of (R)-4-(4-((3S,4S)-3,4-bis(((1S,2R)-2-phenylcyclopropyl) carbamoyl) pyrrolidine-1-carbonyl)benzyl)-1-octanoyl-5-oxopiperazine-2-carboxylic acid

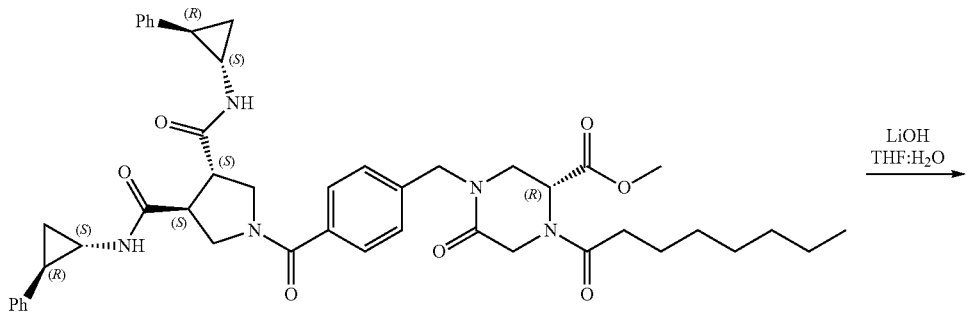

-continued

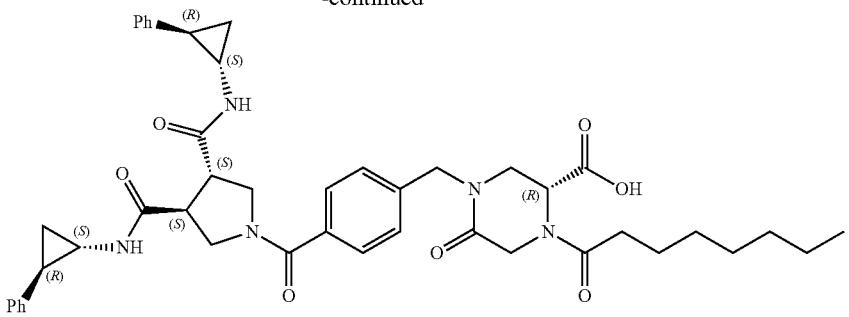

Lithium hydroxide (0.016 g in 4 mL water, 0.38 mmol) was added to a solution of methyl (R)-4-(4-((3S,4S)-3,4-bis(((1S,2R)-2-phenylcyclopropyl) carbamoyl)pyrrolidine-1-carbonyl)benzyl)-1-octanoyl-5-oxopiperazine-2-carboxylate (0.15 g, 0.18 mmol) in THF (8 mL) at 0° C. The reaction was stirred for 1 hour then acidified with citric acid and extracted with ethyl acetate. The organic layer was dried over sodium sulphate and concentrated to afford (R)-4-(4-((3S,4S)-3,4-bis(((1S,2R)-2-phenylcyclopropyl)carbamoyl)pyrrolidine-1-carbonyl)benzyl)-1-octanoyl-5-oxopiperazine-2-carboxylic acid (0.1 g, 66.67%). LCMS (Method-X): 78.48% (RT 1.00, 223.0 nm) (MS: ESI +ve 774.8 [M−H]).

Step-10: Preparation of (3S,4S)-1-(4-(((R)-5-(hexylcarbamoyl)-4-octanoyl-2-oxopiperazin-1-yl)methyl)benzoyl)-N3,N4-bis((1S,2R)-2-phenylcyclopropyl) pyrrolidine-3,4-dicarboxamide, Compound 074

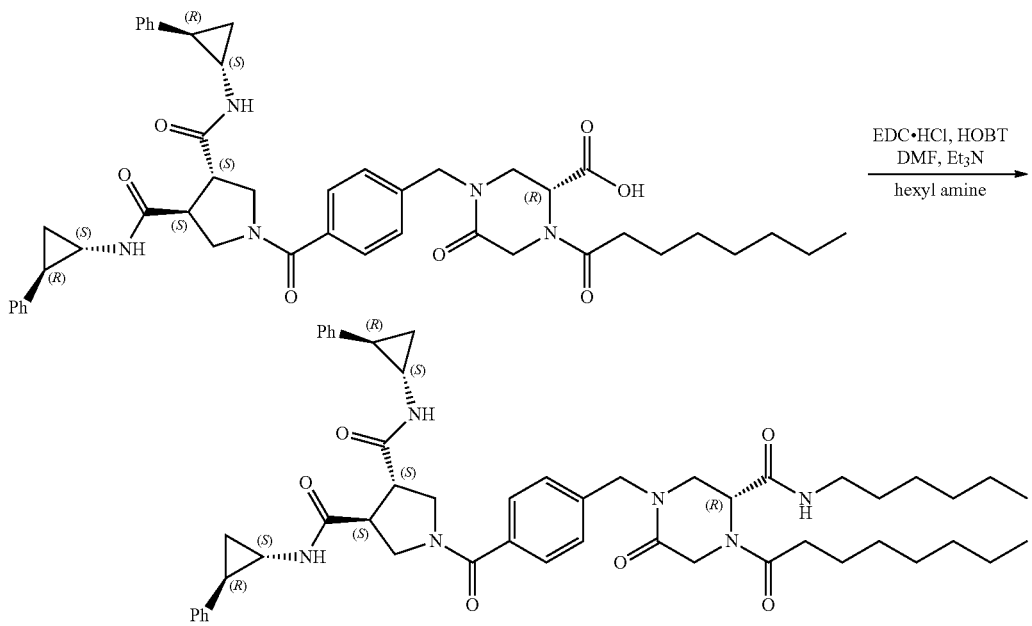

Prepared using a procedure similar to General EDC, HOBT Coupling Procedure. The crude product was purified using Prep HPLC Method 7 to give (3S,4S)-1-(4-(((R)-5-(hexylcarbamoyl)-4-octanoyl-2-oxopiperazin-1-yl)methyl)benzoyl)-N3,N4-bis((1S,2R)-2-phenylcyclopropyl)pyrrolidine-3,4-dicarboxamide, Compound 074, (0.011 g, 10.06%) LCMS (Method-J): 95.60% (RT 5.63, 230.0 nm) (MS: ESI +ve 860.6 [M+H]). $^1$H NMR: (400 MHz, DMSO) δ ppm: 0.83-0.86 (q, 6H J=12 Hz), 1.11-1.27 (m, 21H), 1.48 (s, 2H), 1.85 (s, 1H), 2.03-2.07 (s, 1H), 2.34-2.36 (m, 2H), 2.78-2.84 (m, 2H), 3.07-3.09 (m, 3H), 3.49 (m, 3H), 3.55-3.64 (m 4H), 4.18 (s, 1H), 4.30-4.34 (s, 1H), 4.56-4.63 (m, 2H), 7.06-7.16 (m, 6H J=6.8 Hz) 7.24 (m, 6H), 7.45-7.47 (d, 2H J=6.8 Hz), 7.86-8.084 (bs, 1H), 8.31 (s, 1H), 8.43 (s, 1H).

Example 40

Synthesis of (3S,4S)-1-(4-(((S)-5-(hexylcarbamoyl)-4-octanoyl-2-oxopiperazin-1-yl) methyl)benzoyl)-N3,N4-bis((1S,2R)-2-phenylcyclopropyl)pyrrolidine-3,4-dicarboxamide, Compound 076

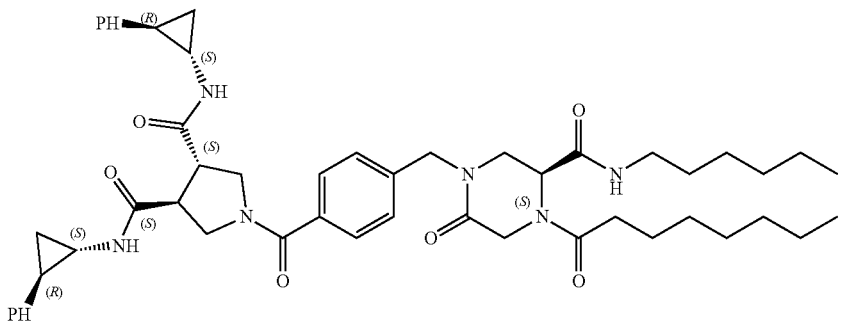

Prepared by a procedure similar to that reported for (3S,4S)-1-(4-(((R)-5-(hexylcarbamoyl)-4-octanoyl-2-oxopiperazin-1-yl)methyl) benzoyl)-N3,N4-bis((1S,2R)-2-phenylcyclopropyl)pyrrolidine-3,4-dicarboxamide, Compound 074, substituting L-Serine methyl ester hydrochloride in step 1. The crude final product was purified using Prep HPLC Method 7 to afford (3S,4S)-1-(4-(((S)-5-(hexylcarbamoyl)-4-octanoyl-2-oxopiperazin-1-yl)methyl)benzoyl)-N3,N4-bis((1S,2R)-2-phenylcyclopropyl)pyrrolidine-3,4-dicarboxamide, Compound 076, (0.025 g, 18.82%). LCMS (Method-C3): 100% (RT 2.02, 225.0 nm) (MS: ESI +ve 860.4 [M+H]). $^1$H NMR: (400 MHz, DMSO) δ ppm: 0.84-0.87 (m, 6H), 1.11-1.28 (m, 20H), 1.50 (s, 2H), 1.87 (s, 1H), 1.97-2.085 (s, 1H), 2.34-2.36 (m, J=7.2 Hz, 2H), 2.68-2.86 (m, 3H), 3.01-3.20 (m, 3H), 3.49-3.60 (m, 5H), 3.79-3.99 (m 1H), 4.19-4.34 (s, 1H), 4.48-4.54 (s, 1H), 4.56-4.91 (m, 2H), 7.07-7.18 (m, 6H) 7.25-7.26 (m, 6H), 7.46-7.48 (d, 2H J=7.6 Hz), 7.86-8.08 (bs, 1H), 8.31 (s, 1H), 8.43 (s, 1H).

Example 41

Synthesis of (3S,4S)-1-(4-((R)-3-(hexylcarbamoyl)-4-octyl-5-oxopiperazine-1-carbonyl)benzoyl)-N3,N4-bis((1S,2R)-2-phenylcyclopropyl)pyrrolidine-3,4-dicarboxamide, Compound 075

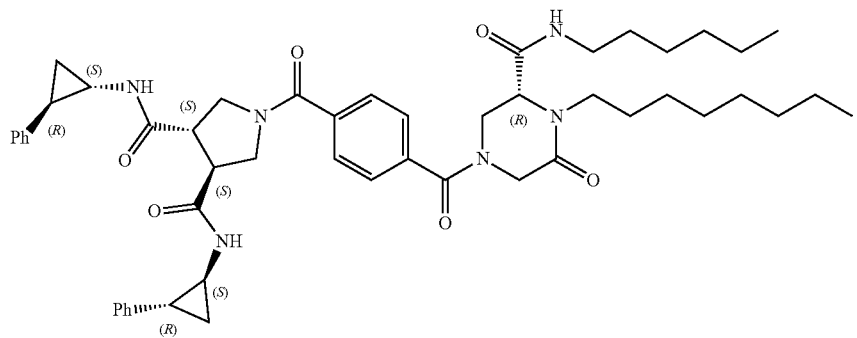

Step 1: Preparation of methyl (R)-3-amino-2-(((benzyloxy)carbonyl)amino)propanoate hydrochloride

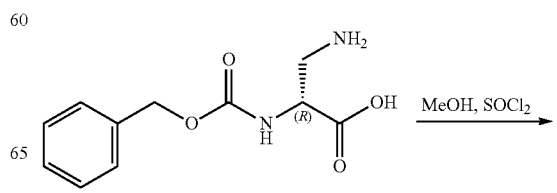

-continued

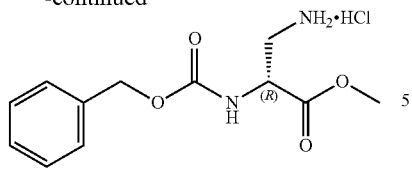

To a stirred solution of MeOH (50 mL) was added thionyl chloride (20 mL) dropwise. The mixture was stirred for 30 minutes. (R)-3-amino-2-(((benzyloxy)carbonyl)amino)propanoic acid (10 g, 41.9 mmol) was added. The reaction mixture was warmed to room temperature and stirring continued for 16 hrs. The mixture was concentrated under reduced pressure to give methyl (R)-3-amino-2-(((benzyloxy)carbonyl)amino)propanoate hydrochloride (12.4 g, 100%). LCMS (Method-X): 100% (RT: 0.734, 215.0 nm) (MS: ESI +ve 253.27[M+H]).

Step-2: Synthesis of methyl (R)-3-((2-(benzyloxy)-2-oxoethyl) amino)-2-(((benzyloxy) carbonyl)amino)propanoate

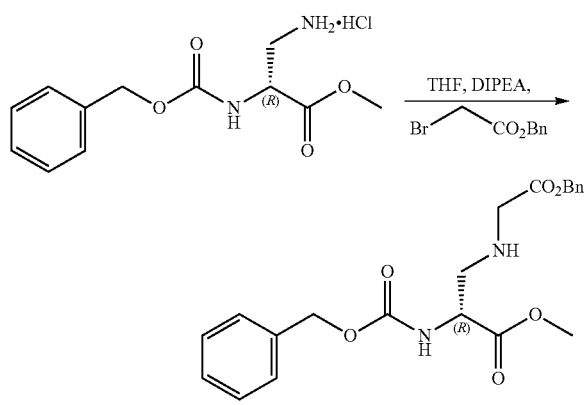

Methyl (R)-3-amino-2-(((benzyloxy) carbonyl) amino) propanoate hydrochloride (12.4 g, 49.1 mmol) was dissolved in THF (50 mL). DIPEA (25.4 mL, 147.4 mmol) was added and the mixture was stirred for 10 min. Benzyl 2-bromoacetate (22.5 g, 98.3 mmol) was added and the reaction mixture was stirred for 16 hrs at room temperature. Water (50 mL) was added the mixture was extracted with ethyl acetate (3×100 mL). The combined organic layers were washed with brine, NaHCO$_3$ (2×100 mL) then dried over anhydrous sodium sulphate and concentrate under reduced pressure. The crude product was purified using column chromatography eluting with 0-30% EtOAC in hexane to give methyl (R)-3-((2-(benzyloxy)-2-oxoethyl) amino)-2-(((benzyloxy)carbonyl)amino)propanoate (11.1 g, 56.6%). LCMS (Method-C3): 76.80% (RT: 0.900, 202.0 nm) (MS: ESI +ve 401.37 [M+H]).

Step-3: Preparation of methyl (R)-3-((2-(benzyloxy)-2-oxoethyl) (tert-butoxycarbonyl) amino)-2-((((benzyloxy)carbonyl)amino)propanoate

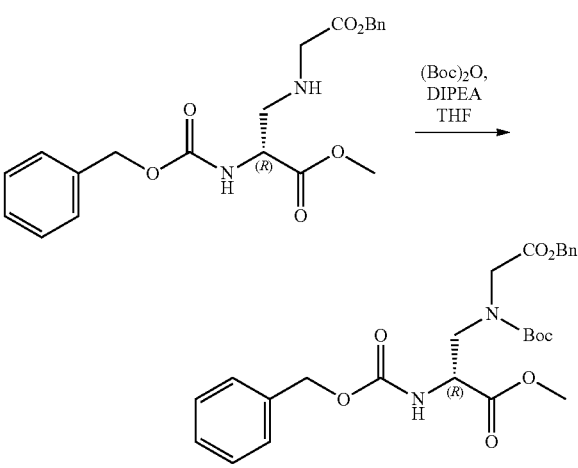

A solution of methyl (R)-3-((2-(benzyloxy)-2-oxoethyl) amino)-2 (((benzyloxy)carbonyl)amino)propanoate (2.6 g, 6.44 mmol) and DIPEA (2.5 g, 19.4 mmol) in THF (20 mL) was stirred for 10 min. Boc-anhydride (2.8 g, 12.9 mmol) was added and the reaction mixture was stirred for 16 hrs slowly warming to room temperature. The reaction mixture was diluted in water (50 mL) and extracted with ethyl acetate (3×100 mL). The combined organic layers were washed with brine, NaHCO$_3$ (2×100 mL) then dried over anhydrous sodium sulphate and concentrated under reduced pressure. The crude product was purified using column chromatography eluting with 0-50% EtOAC in hexane to give methyl (R)-3-((2-(benzyloxy)-2-oxoethyl)(tert-butoxycarbonyl)amino)-2-(((benzyloxy)carbonyl)amino)propanoate. (1.9 g, 59.3%). LCMS (Method-C3): 100% (RT: 1.076 min, 202.0 nm) (MS: ESI +ve 501.47 [M+H]).

Step-4: Preparation of ((R)—N-(tert-butoxycarbonyl)-N-(3-methoxy-2-(octylamino)-3-oxopropyl) glycine

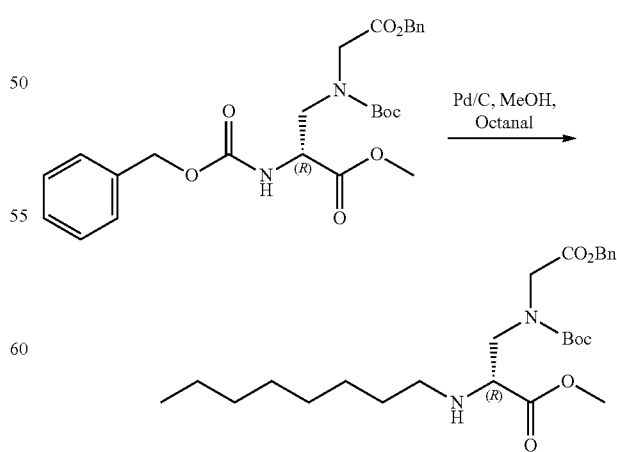

Palladium on carbon (50% wet) (2.2 g) was added to a solution of ethyl (R)-3-((2-(benzyloxy)-2-oxoethyl)(tert-butoxycarbonyl)amino)-2-(((benzyloxy)carbonyl)amino)propanoate (2.2 g, 4.39 mmol) and octanal (0.563 g, 4.39 mmol) in methanol (50 mL). The reaction mixture was stirred at room temperature for 48 hrs under a H₂ atmosphere. The reaction mixture WAS filtered through celite and the filtrate was concentrated to give (R)—N-(tert-butoxycarbonyl)-N-(3-methoxy-2-(octylamino)-3-oxopropyl)glycine (1.75 g) LCMS (Method-X): 76.93% (RT: 0.914 min, 202.0 nm) (MS: ESI +ve 387.41) [M+H]).

Step-5: Preparation of 1-(tert-butyl) 3-methyl (R)-4-octyl-5-oxopiperazine-1,3-dicarboxylate

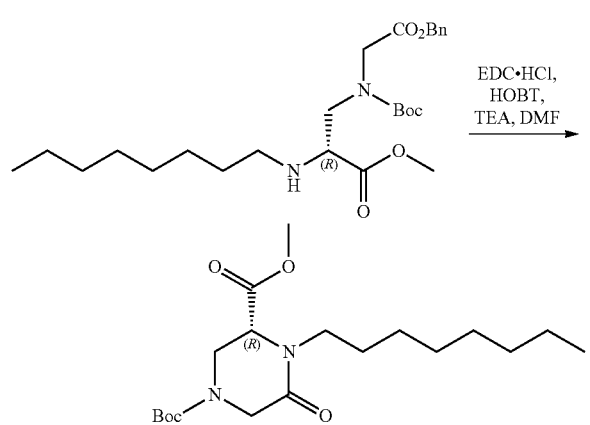

(R)—N-(tert-butoxycarbonyl)-N-(3-methoxy-2-(octylamino)-3-oxopropyl)glycine (1.75 g, 4.504 mmol) was dissolved in DMF (17 mL). HOBT (0.912 g, 6.75 mmol), EDC.HCl (1.29 g, 6.75 mmol) and TEA (1.87 g, 1.35 mmol) were added and the mixture was stirred at room temperature for 16 hrs. The mixture was diluted with water and extracted with Dichloromethane (2×50 mL). The combined organic layers were dried and concentrated. The crude product was purified using combi flash chromatography eluting with 50% Ethyl acetate in Hexane to give 1-(tert-butyl) 3-methyl (R)-4-octyl-5-oxopiperazine-1,3-dicarboxylate (1 g, 61.68%). LCMS (Method-X): 100% (RT 1.108, 202.0 nm) (MS: ESI +ve 315.30 [M+1]).

Step 6: Preparation of (R)-4-(tert-butoxycarbonyl)-1-octyl-6-oxopiperazine-2-carboxylic acid

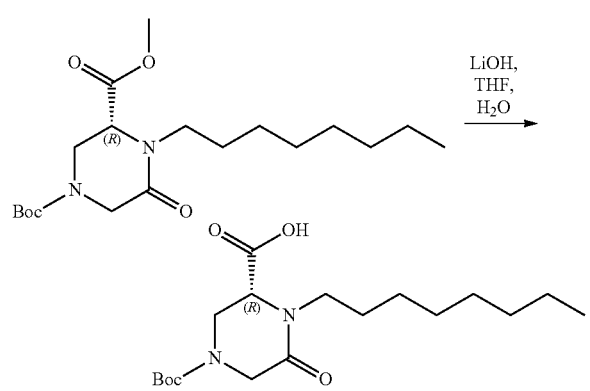

1-(tert-butyl) 3-methyl (R)-4-octyl-5-oxopiperazine-1,3-dicarboxylate (1.0 g, 2.69 mmol) was dissolved in THF·H₂O (1:1, 10 mL). LiOH (0.226 g, 0.539 mmol) was added and the mixture was stirred at room temperature for 2 hrs. The mixture was concentrated and add ice cold water (10 mL) and aq. 1N HCl (3-4 mL) were added. The resulting precipitate was collected by filtration and dried under vacuum to give (R)-4-(tert-butoxycarbonyl)-1-octyl-6-oxopiperazine-2-carboxylic acid (0.8 g, 83.15%) LCMS (Method-X): 100% (RT 1.011, 202 nm) (MS: ESI +ve 357.43 [M+H]).

Step-7: Preparation of tert-butyl (R)-3-(hexylcarbamoyl)-4-octyl-5-oxopiperazine-1-carboxylate

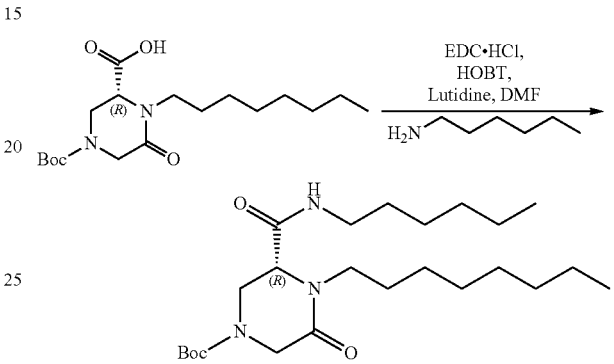

Prepare by a procedure similar to General EDC, HOBT Coupling Procedure. The crude product was purified using combi flash chromatography eluting with 5% methanol in dichloromethane to give tert-butyl (R)-3-(hexylcarbamoyl)-4-octyl-5-oxopiperazine-1-carboxylate. (0.9 g, 91.22%). LCMS (Method-X): 95.64% (RT 1.149, 202.0 nm) (MS: ESI +ve 384.4 [M−56]).

Step-8: Preparation of (R)—N-hexyl-1-octyl-6-oxopiperazine-2-carboxamide trifluoroacetate

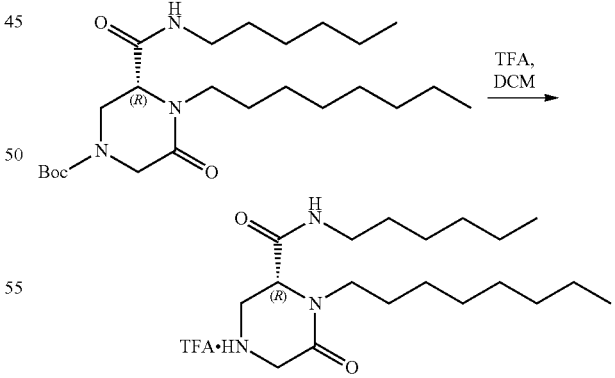

Prepared by a procedure similar to General Boc Deprotection Procedure. The crude product was purified using combi flash chromatography eluting with 5% methanol in dichloromethane to give (R)—N-hexyl-1-octyl-6-oxopiperazine-2-carboxamide. (0.180 g, 93.23%). LCMS (Method-X): 98.05% (RT 1.591, 202.0 nm) (MS: ESI +ve 340.2 [M+1]).

Step-9: Preparation of (3S,4S)-1-(4-((R)-3-(hexyl-carbamoyl)-4-octyl-5-oxopiperazine-1-carbonyl) benzoyl)-N3,N4-bis((1S,2R)-2-phenylcyclopropyl) pyrrolidine-3,4-dicarboxamide, Compound 075

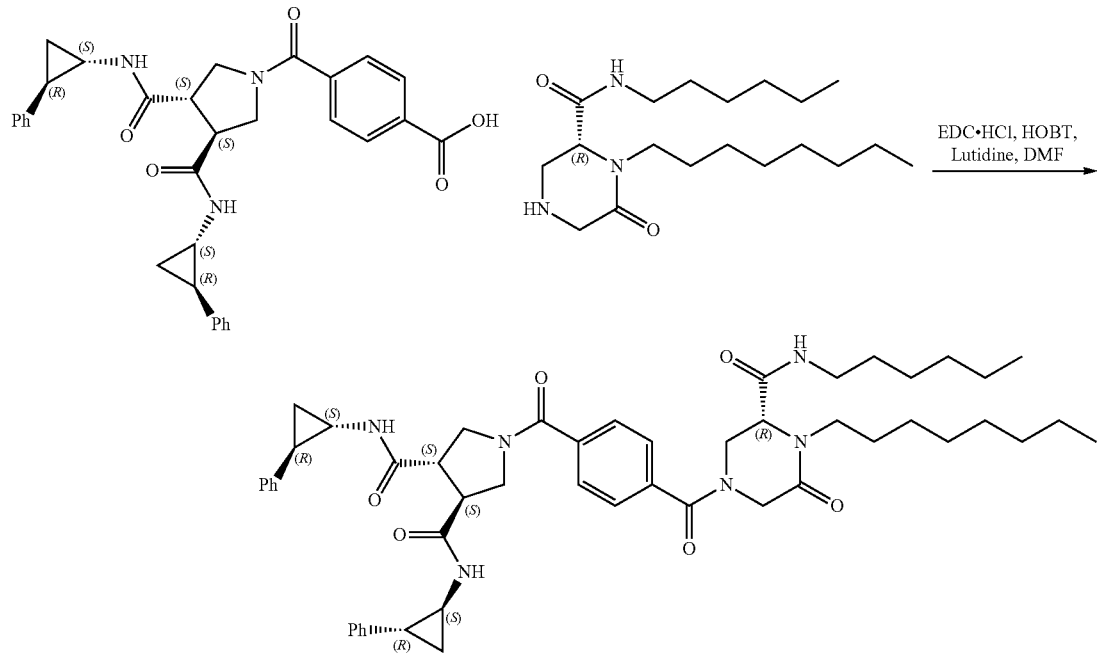

Prepare by a procedure similar to General EDC, HOBT Coupling Procedure. The crude product was purified using combi flash chromatography eluting with 5% Methanol in DCM to give (3S,4S)-1-(4-((R)-3-(hexylcarbamoyl)-4-octyl-5-oxopiperazine-1-carbonyl)benzoyl)-N3,N4-bis((1S, 2R)-2-phenylcyclopropyl)pyrrolidine-3,4-dicarboxamide, Compound 075, (0.11 g, 45.89%). LCMS (Method-J): 100% (RT 5.348, 202.0 nm) (MS: ESI +ve 860.09 [M+1]). $^1$H NMR: (400 MHz, DMSO) δ ppm: 0.83-0.85 (m, 6H), 1.11 (s, 3H), 1.23 (m, 18H), 1.40 (s, 1H), 1.86 (s, 1H), 1.97 (s, 1H), 2.78-2.85 (m, 4H), 3.09-3.20 (m, 4H), 3.50-3.52 (m, 3H), 3.64 (m, 1H), 3.72-3.86 (m, 4H), 3.92-4.08 (m, 2H), 4.47-4.63 (m, 1H), 7.06-7.18 (m, 6H), 7.22-7.41 (m, 6H), 7.58 (m, 2H), 8.02-8.25 (m, 1H), 8.32 (s, 1H), 8.44-8.45 (d, J=3.6 Hz, 1H).

Example 42

Synthesis of (3S,3'S,4S,4'S)-1,1'-(pyrimidine-2,5-dicarbonyl)bis(N3,N4-bis((1S,2R)-2-phenylcyclo-propyl)pyrrolidine-3,4-dicarboxamide), Compound 071

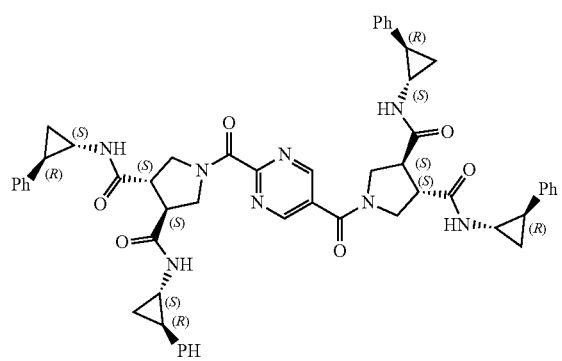

Pyrimidine-2,5-dicarboxylic acid (0.050 g, 0.297 mmol) was dissolved in N,N-Dimethylformamide (5 mL). EDC.HCl (0.142 g, 0.743 mmol) and HOBT (0.088 g, 0.654 mmol) were added followed by (3S,4S)—N3,N4-bis ((1S, 2R)-2-phenylcyclopropyl) pyrrolidine-3,4-dicarboxamide hydrochloride (0.253 g, 0.594 mmol). Triethylamine (0.12 mL, 0.892 mmol) was added dropwise and the reaction mixture was stirred at room temperature for 48 hrs. The mixture was poured into ice water and the resulting precipitate was collected by filtration. The precipitate was dissolved in Dichloromethane (20 mL), dried and concentrated. The crude product was purified by using Prep HPLC Method 9 to give (3S,3'S,4S,4'S)-1,1'-(pyrimidine-2,5-dicarbonyl)bis (N3,N4-bis((1S,2R)-2-phenylcyclopropyl)pyrrolidine-3,4-dicarboxamide), Compound 071, (0.065 g, 24%). LCMS (Method-J): 100% (RT: 5.163, 254.0 nm) (MS: ESI +ve 912.6[M+1]). $^1$H NMR: (400 MHz, DMSO) δ ppm: 1.104-1.191 (m, 8H), 1.855-1.976 (m, 4H), 2.677-3.104 (m, 4H), 3.125-3.238 (m, 4H), 3.352-3.440 (m, 11H), 3.461-3.571 (m, 2H), 3.606-3.708 (m, 2H), 3.728-3.902 (m, 3H), 7.062-7.117 (m, 4H), 7.137-7.215 (m, 8H), 7.234-7.287 (m, 8H), 8.337-8.374 (m, 2H), 8.466-8.476 (m, 2H), 9.076 (s, 2H).

Synthesis of (3S,3'S,4S,4'S)-1,1'-(bicyclo [2.2.1]
heptane-1,4-dicarbonyl) bis (N3,N4-bis((1S,2R)-2-
phenylcyclopropyl) pyrrolidine-3,4-dicarboxamide),
Compound 081

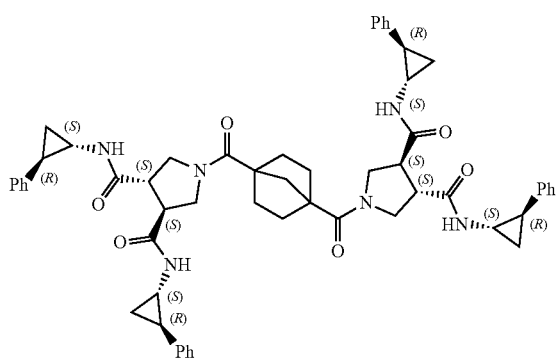

Prepared by a procedure similar to that reported for (3S,3'S,4S,4'S)-1,1'-(pyrimidine-2,5-dicarbonyl)bis(N3, N4-bis((1S,2R)-2-phenylcyclopropyl)pyrrolidine-3,4-dicarboxamide) (Compound 071), using the applicable amides and dicarboxylic acid. The crude product was purified using Prep HPLC Method 1 to give (3S,3'S,4S,4'S)-1,1'-(bicyclo [2.2.1]heptane-1,4-dicarbonyl) bis (N3,N4-bis((1S,2R)-2-phenylcyclopropyl) pyrrolidine-3,4-dicarboxamide)(Compound 081), as a white solid (0.10 g, 20.46%). LCMS (Method-J): 100% (RT 5.191, 202.0 nm) (MS: ESI +ve 928 [M+H]). $^1$H NMR: (400 MHz, DMSO) δ ppm: 1.16 (s, 8H); 1.79 (s, 8H); 1.92-1.94 (d, J=8.8, 6H); 2.83 (s, 4H); 3.01-3.03 (d, J=8, 2H); 3.14-3.16 (d, J=8, 2H); 3.26-3.35 (m, 2H); 3.49 (s, 2H); 3.63-3.65 (d, J=8.8, 2H); 3.88 (s, 2H); 7.10-7.18 (m, 12H); 7.24-7.28 (t, 8H); 8.38 (s, 4H).

Synthesis of (3S,3'S,4S,4'S)-1,1'-(bicyclo [2.2.2] octane-1,4-dicarbonyl) bis (N3,N4-bis((1S,2R)-2-phenylcyclopropyl) pyrrolidine-3,4-dicarboxamide), Compound 077

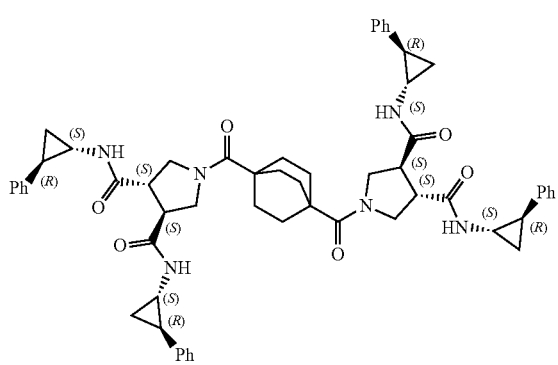

Prepared by a procedure similar to that reported for (3S,3'S,4S,4'S)-1,1'-(pyrimidine-2,5-dicarbonyl)bis(N3, N4-bis((1S,2R)-2-phenylcyclopropyl)pyrrolidine-3,4-dicarboxamide) (Compound 071) using the applicable amides and dicarboxylic acid. The crude product was purified using Prep HPLC Method 1 to give (3S,3'S,4S,4'S)-1,1'-(bicyclo [2.2.2]octane-1,4-dicarbonyl) bis (N3,N4-bis((1S,2R)-2-phenylcyclopropyl) pyrrolidine-3,4-dicarboxamide (Compound 077), as a white solid (0.02 g, 20.46%). LCMS (Method-J): 100% (RT 1.849, 226.0 nm) (MS: ESI +ve 942 [M+H]). $^1$H NMR: (400 MHz, DMSO) δ ppm: 0.97 (s, 8H); 1.76 (s, 12H); 1.94 (s, 4H); 2.83 (s, 4H); 3.09 (s, 3H); 4.00 (s, 1H); 3.26-3.35 (m, 2H); 7.11-7.17 (m, 12H); 7.26-7.27 (m, 8H); 8.10 (s, 4H).

Synthesis of (3S,3'S,4S,4'S)-1,1'-(bicyclo[2.1.1] hexane-1,4-dicarbonyl)bis(N3,N4-bis((1S,2R)-2-phenylcyclopropyl)pyrrolidine-3,4-dicarboxamide), Compound 144

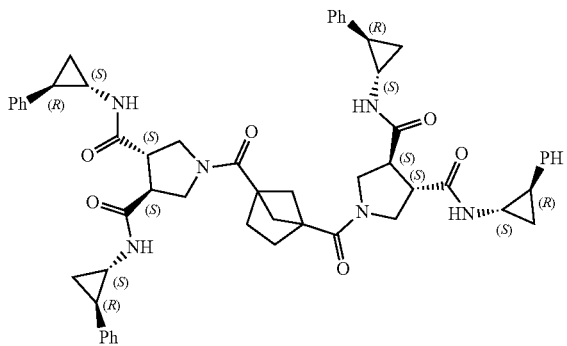

Prepared by a procedure similar to that reported for (3S,3'S,4S,4'S)-1,1'-(pyrimidine-2,5-dicarbonyl)bis(N3, N4-bis((1S,2R)-2-phenylcyclopropyl)pyrrolidine-3,4-dicarboxamide) (Compound 071), using the applicable amides and dicarboxylic acid. The crude product was purified using Prep HPLC Method to give (3S,3'S,4S,4'S)-1,1'-(bicyclo [2.1.1]hexane-1,4-dicarbonyl)bis(N3,N4-bis((1S,2R)-2-phenylcyclopropyl)pyrrolidine-3,4-dicarboxamide) (Compound 144)(34.58 mg, 12.89%). LCMS (Method-H): 100.00% (RT 3.378, 202.0 nm) (MS: ESI +ve 913.5 [M+H]). $^1$H NMR (400 MHz, DMSO) δ ppm: 1.14-1.18 (t, J=1.2, 4H), 1.77 (s, 1H), 1.88-1.97 (m, 5H), 2.84 (s, 2H), 3.02-3.04 (m, 2H), 3.30-3.42 (m, 4H), 3.66-3.67 (m, 2H), 7.11-7.18 (m, 6H), 7.28 (m, 4H)', 8.38 (s, 1H).

Synthesis of (3S,4S)-1-(4-((R)-3-(pentadecylamino) pyrrolidine-1-carbonyl)benzoyl)-N3,N4-bis((1S,2R)-2-phenylcyclopropyl)pyrrolidine-3,4-dicarboxamide, Compound 082

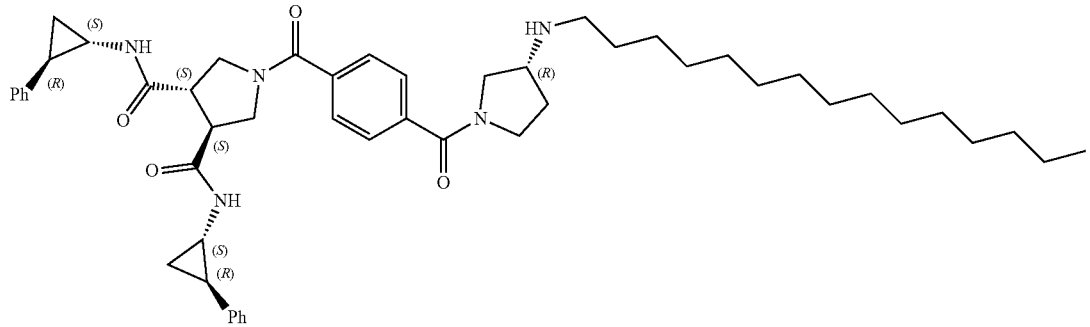

Step-1: Preparation of tert-butyl (R)-3-(pentadecylamino) pyrrolidine-1-carboxylate

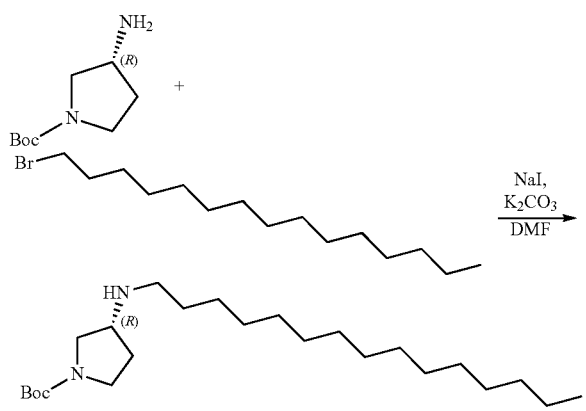

To a stirred suspension, at room temperature, of tert-butyl (R)-3-aminopyrrolidine-1-carboxylate (1.0 g, 5.36 mmol), potassium carbonate (1.47 g, 10.72 mmol) and sodium iodide (0.080 g, 0.536 mmol) in DMF (20 mL) was added 1-bromotridecane (1.25 g, 4.28 mmol). The reaction was stirred for 16 hr. Ice cold water was added and the mixture was extracted with ethyl acetate (3×10 mL). The organic layer was dried over sodium sulfate and concentrated under reduced pressure. The crude product was purified using flash chromatography (Stationary phase-Basic alumina ($Al_2O_3$)), eluting with 0-5% MeOH in DCM, to afford tert-butyl (R)-3-(pentadecylamino)pyrrolidine-1-carboxylate (0.81 g, 38%). LCMS (Method-C): 100% (RT: 17.773, 202.4 nm) (MS: ESI +ve 397.4 [M+1]).

Step-2: Preparation of tert-butyl (R)-3-(((benzyloxy) carbonyl) (pentadecyl) amino) pyrrolidine-1-carboxylate

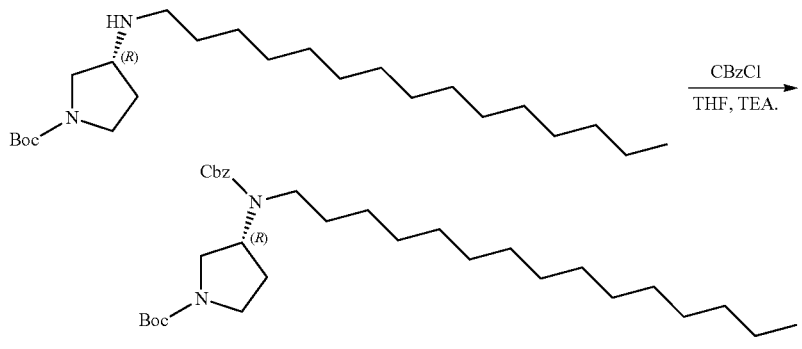

To a stirred solution of tert-butyl (R)-3-(pentadecylamino)pyrrolidine-1-carboxylate (0.7 g 1.769 mmol) and triethylamine (0.74 ml, 5.292 mmol) at 0° C. in THF (9 mL) was added CBzCl (0.9 ml, 2.64 mmol). The reaction mixture was stirred for 16 hr, slowly warming to room temperature, then quenched with ice cold water. The mixture was extracted with ethyl acetate (3×100 mL). The organic layer was dried over sodium sulfate. The crude product was purified by flash chromatography (Stationary phase-Basic alumina ($Al_2O_3$)), eluting with 0-3% MeOH in DCM to afford tert-butyl (R)-3-(((benzyloxy)carbonyl)(pentadecyl) amino)pyrrolidine-1-carboxylate (0.550 g, 58.72%).

Step-3: Preparation of benzyl (R)-pentadecyl(pyrrolidin-3-yl)carbamate

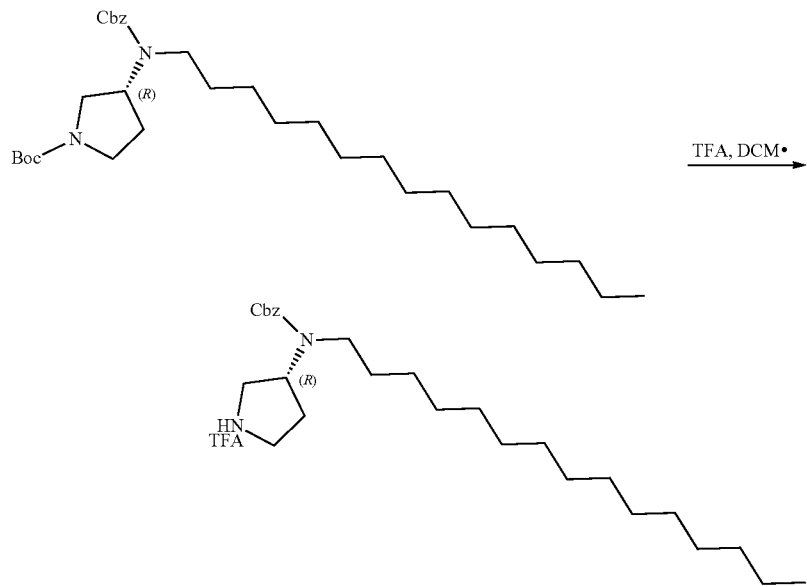

Prepared by a procedure similar to General Boc Deprotection Procedure to afford benzyl (R)-pentadecyl(pyrrolidin-3-yl)carbamate trifluoroacetate salt (0.510 g, crude). LCMS (Method-H2): 12.99% (RT: 2.522 min, 202 nm) (MS: ESI +ve 429.1 [M−1]).

Step-4: Preparation of (benzyl ((R)-1-(4-((3S,4S)-3,4-bis(((1S,2R)-2-phenylcyclopropyl) carbamoyl) pyrrolidine-1-carbonyl)benzoyl)pyrrolidin-3-yl)(pentadecyl)carbamate

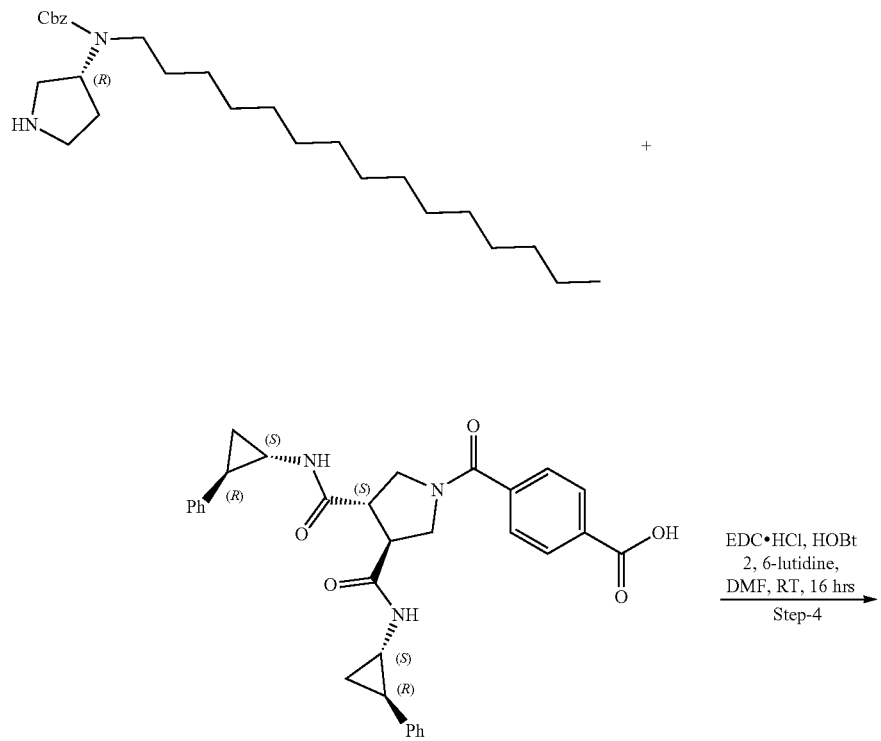

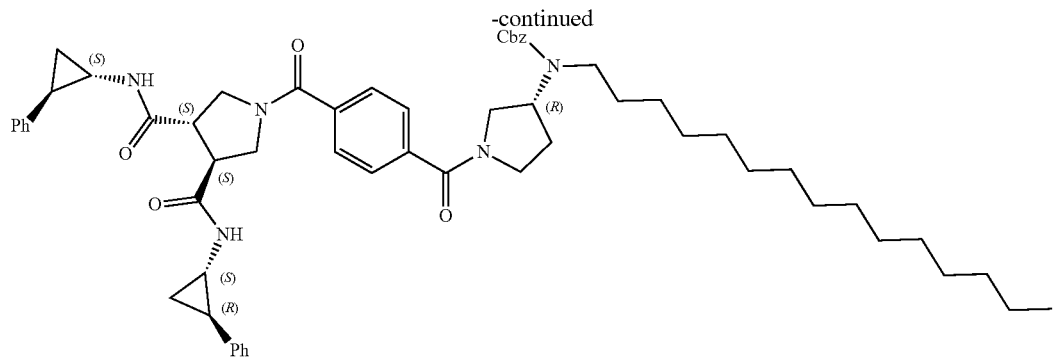

Prepared by a procedure similar to General EDC, HOBT Coupling Procedure. The crude product was purified by flash chromatography (Stationary phase-Basic alumina (Al$_2$O$_3$)), eluting with 0-3% MeOH in DCM to give benzyl ((R)-1-(4-((3S,4S)-3,4-bis(((1S, 2R)-2-phenyl cyclopropyl)carbamoyl)pyrrolidine-1-carbonyl)benzoyl)pyrrolidin-3-yl)(pentadecyl)carbamate (0.14 g, 26%). (MS: ESI +ve 450.55 [M+1]).

Step-5: Preparation of (3S,4S)-1-(4-((R)-3-(pentadecylamino)pyrrolidine-1-carbonyl)benzoyl)-N3,N4-bis((1S,2R)-2-phenylcyclopropyl)pyrrolidine-3,4-dicarboxamide, Compound 082

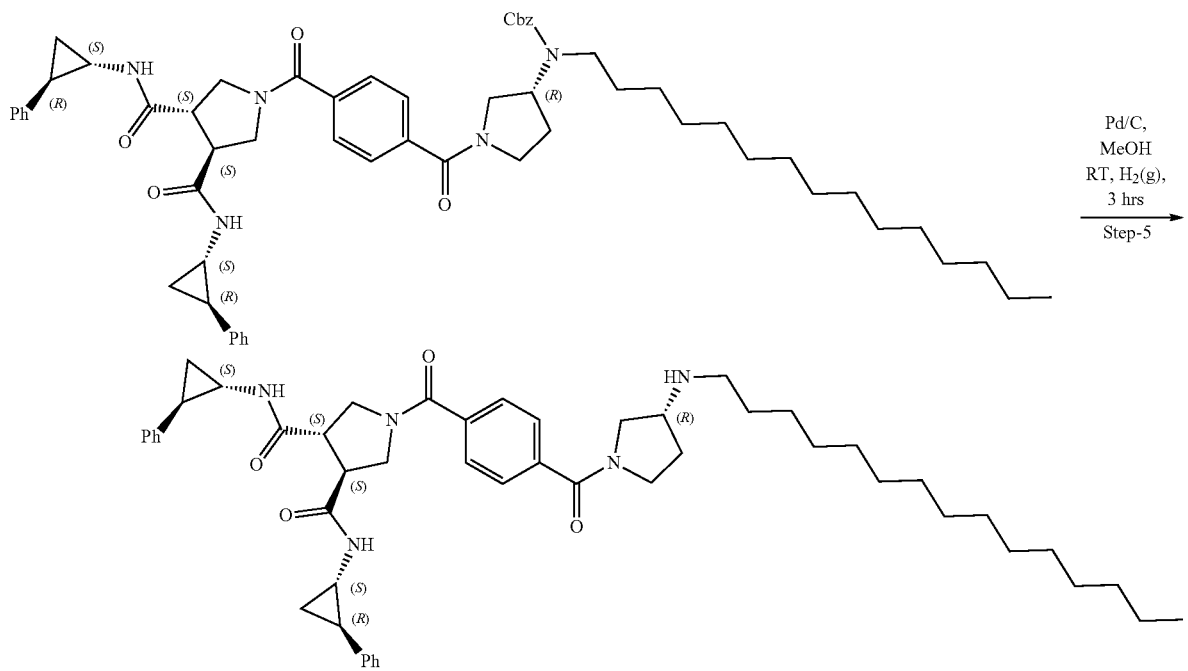

Benzyl ((R)-1-(4-((3S,4S)-3,4-bis(((1S,2R)-2-phenylcyclopropyl)carbamoyl)pyrrolidine-1-carbonyl)benzyl)pyrrolidi-3-yl)(pentadecyl)carbamate (0.13 g, 0.13 mmol) was dissolved in MeOH (10 mL), and 10% Pd/C (50% moisture) (0.130 g) was added. The mixture was stirred under hydrogen (balloon) for 3 hrs then filtered through a pad of celite and concentrated. The crude product was purified using Prep HPLC Method 12. The gradient solvent B was 45-80% over 22 min, and 80-80% over 10 min, 100% over 2 min then 100-45% over 6 min. to give (3S,4S)-1-(4-((R)-3-(pentadecylamino)pyrrolidine-1-carbonyl)benzoyl)-N3,N4-bis((1S,2R)-2-phenylcyclopropyl)pyrrolidine-3,4-dicarboxamide (Compound 082)(0.040 g, 35.83%). LCMS (Method-J): 100% (RT 5.998, 214.4 nm)(MS: ESI +ve 816.5 [M+H]). $^1$H NMR: (400 MHz, DMSO) δ ppm: 0.674 (s, 3H), 1.024-1.40 (m, 30H), 1.72 (s, 1H), 1.85-1.97 (m, 3H), 2.77-2.84 (m, 2H), 3.20-3.50 (m, 9H), 3.80-3.95 (m, 4H), 7.07-7.26 (m, 10H), 7.55 (s, 4H), 7.86-8.05 (m, 1H), 8.28-8.32 (d, J=15.6 Hz, 1H), 8.46 (s, 1H).

Synthesis of (3S,4S)—N3,N4-bis((1S,2R)-2-phenyl-cyclopropyl)-1-(4-((R)-3-(tetradecylsulfonamido)pyrrolidine-1-carbonyl)benzoyl)pyrrolidine-3,4-dicarboxamide, Compound 083

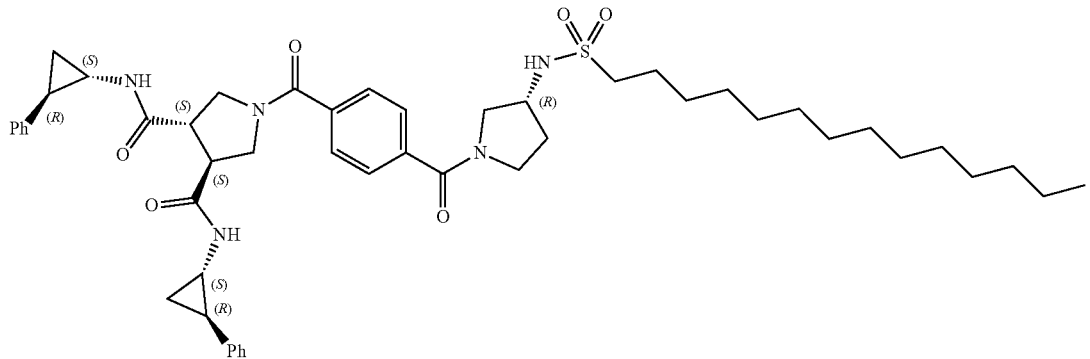

Step 1: Preparation of tetradecane-1-sulfonyl chloride

Step-2: Preparation of tert-butyl (R)-3-(tetradecylsulfonamido)pyrrolidine-1-carboxylate

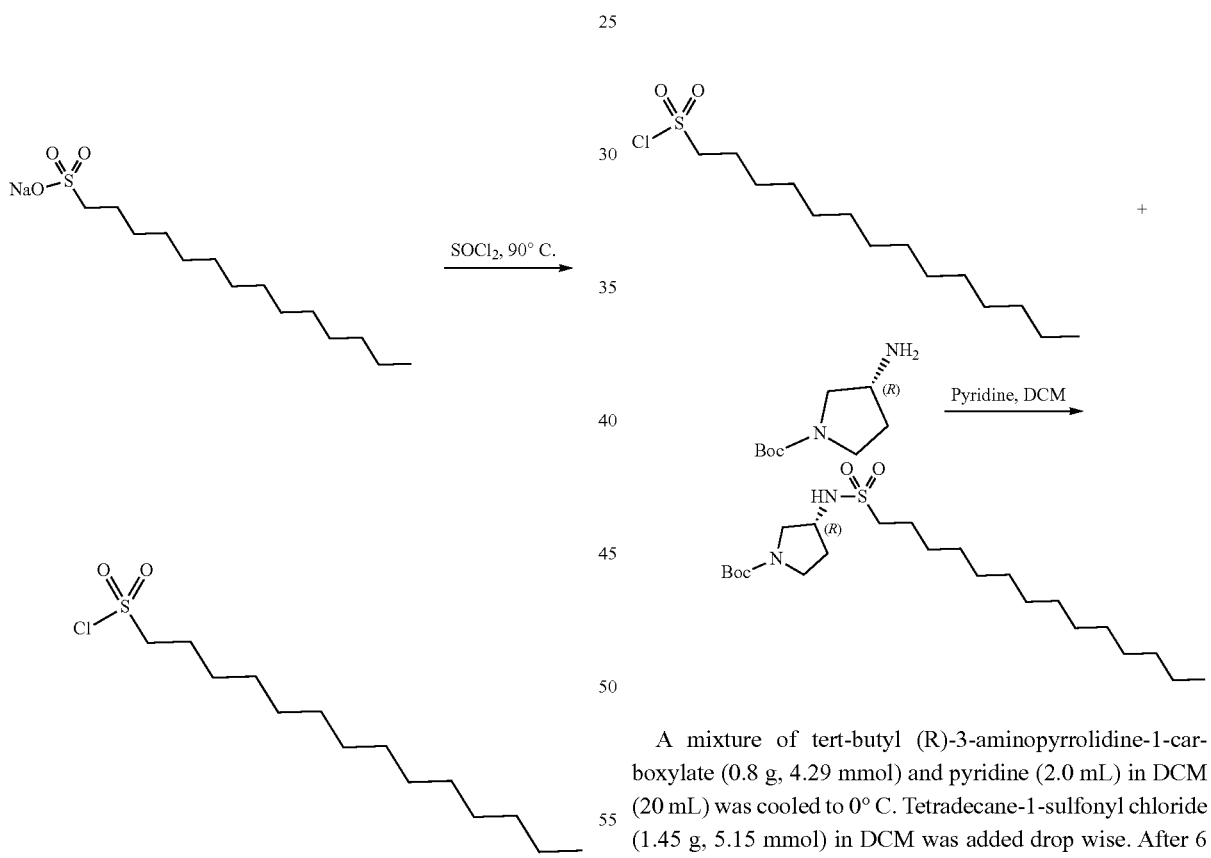

Sodium tetradecane-1-sulfonate (0.8 g) and thionyl chloride (10 mL) were heated at 90° C. for 16 hr. Thionyl chloride was removed under vacuum to give tetradecane-1-sulfonyl chloride (1.2 g) as a colorless liquid. The resulting product was used further without purification.

A mixture of tert-butyl (R)-3-aminopyrrolidine-1-carboxylate (0.8 g, 4.29 mmol) and pyridine (2.0 mL) in DCM (20 mL) was cooled to 0° C. Tetradecane-1-sulfonyl chloride (1.45 g, 5.15 mmol) in DCM was added drop wise. After 6 hours. The reaction mixture was diluted with DCM (50 mL), washed with saturated aq. sodium bicarbonate (2×100 mL) and then brine solution (2×100 mL). The organic layer was dried over sodium sulfate and concentrated under reduced pressure. The crude product was purified by flash chromatography, eluting with 0-2% MeOH in DCM, to give tert-butyl (R)-3-(tetradecylsulfonamido) pyrrolidine-1-carboxylate as a white solid (0.7 g, 36%). LCMS (Method-C3): 87.63% (RT: 2.757, 202.0 nm) (MS: ESI − ve 445.0[M+H]).

Step-3: Preparation of (R)—N-(pyrrolidin-3-yl)tetradecane-1-sulfonamide trifluoroacetate salt

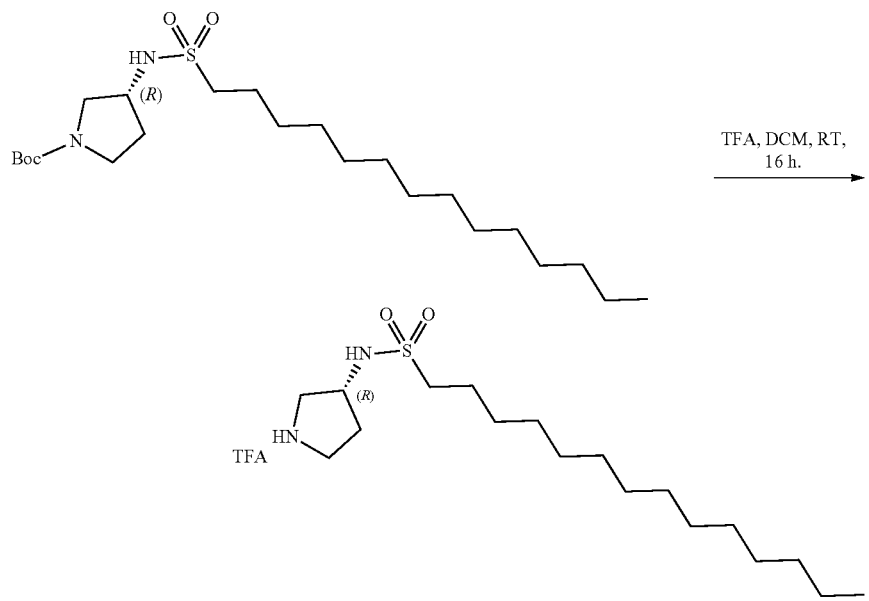

Prepared using a procedure similar to General Boc Deprotection Procedure to give (R)—N-(pyrrolidin-3-yl)tetradecane-1-sulfonamide TFA salt (0.380 g) LCMS (Method-X): 100% (RT: 1.081 202.0 nm) (MS: ESI +ve 347.5[M+H]).

Step-4: Preparation of (3S,4S)—N3,N4-bis((1S, 2R)-2-phenylcyclopropyl)-1-(4-((R)-3-(tetradecylsulfonamido)pyrrolidine-1-carbonyl)benzoyl) pyrrolidine-3,4-dicarboxamide

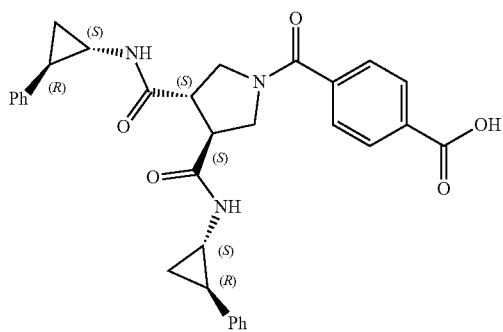

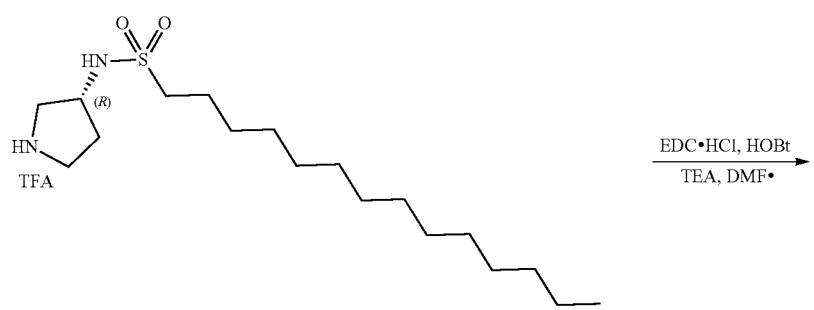

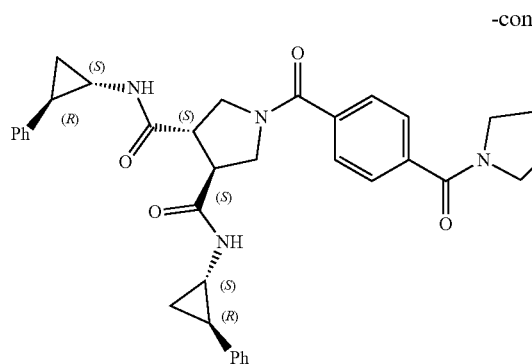
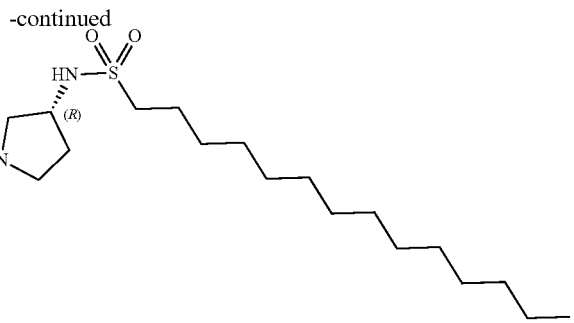

Prepared using a procedure similar to General EDC, HOBT Coupling Procedure. The crude product was purified using flash chromatography, eluting with 3-4% MeOH in DCM to give (3S,4S)—N3,N4-bis((1S,2R)-2-phenylcyclopropyl)-1-(4-((R)-3-(tetradecylsulfonamido)pyrrolidine-1-carbonyl)benzoyl)pyrrolidine-3,4-dicarboxamide (Compound 083)(0.070 g, 28%). LCMS (Method-C3): 100% (RT 2.664, 222.0 nm) (MS: ESI +ve 866.4 [M+H]). $^1$H NMR: (400 MHz, DMSO) δ ppm: 0.84-0.86 (m, 3H), 1.11 (bs, 2H), 1.24-1.34 (m, 25H), 1.57 (bs, 1H), 1.63 (s, 1H), 1.87 (s, 2H), 1.97 (s, 1H), 2.09-2.14 (m, 1H), 2.51 (s, 1H), 2.79 (s, 1H), 2.85 (s, 1H), 2.97-2.98 (m, 1H), 3.04-3.14 (m, 2H), 3.38 (m, 2H), 3.51-3.55 (m, 2H), 3.81-3.88 (m, 1H), 3.98 (m, 1H), 7.07-7.08 (m, 2H), 7.12-7.18 (m, 4H), 7.22-7.29 (m, 4H), 7.42-7.51 (m, 1H), 7.57 (m, 4H), 8.29 (s, 1H), 8.42 (s, 1H).

Synthesis of (3S,4S)-1-(4-((3S,4S)-3-hydroxy-4-(pentadecylamino)pyrrolidine-1-carbonyl)benzoyl)-N3,N4-bis((1S,2R)-2-phenylcyclopropyl)pyrrolidine-3,4-dicarboxamide, Compound 087

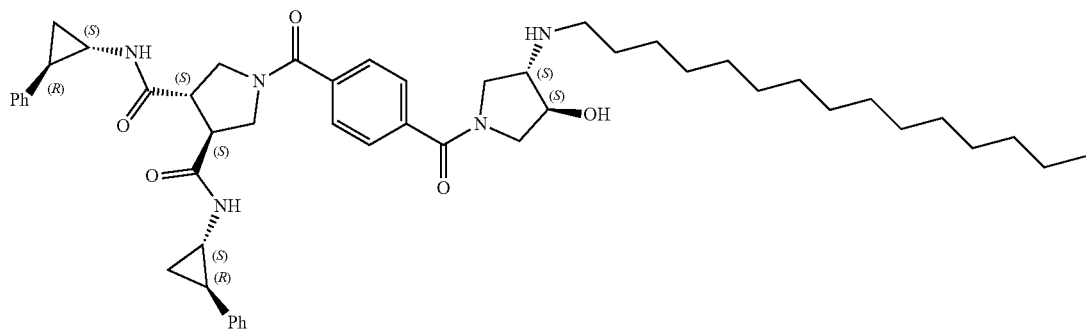

Step-1: Preparation of tert-butyl (3S,4S)-3-hydroxy-4-(pentadecylamino)pyrrolidine-1-carboxylate

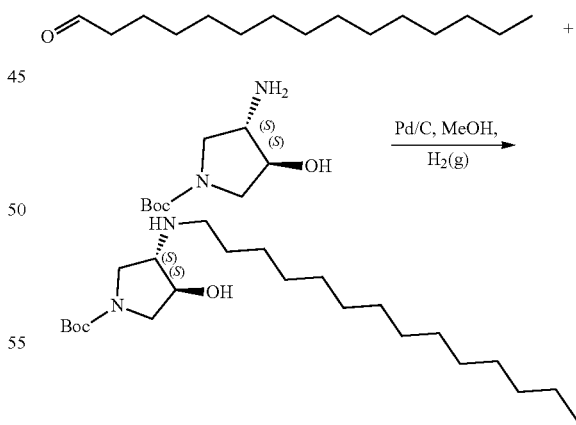

tert-butyl (3S,4S)-3-amino-4-hydroxypyrrolidine-1-carboxylate (0.1 g, 0.495 mmol) and pentadecanal (0.111 g, 0.495) were dissolved in MeOH (10 mL). Palladium on carbon (50% moisture) (0.1 g) was added, and the mixture was stirred for 16 hr under hydrogen (balloon). The reaction mixture was filtered through a pad of celite and concentrated to give tert-butyl (3S,4S)-3-hydroxy-4-(pentadecylamino)pyrrolidine-1-carboxylate (0.15 g, 73.52%). LCMS (Method-X): 77.10% (RT 1.123, 202.0 nm) (MS: ESI +ve 413.6 [M+1]).

Step-5: Preparation of (3S,4S)-1-(4-((3S,4S)-3-hydroxy-4-(pentadecylamino)pyrrolidine-1-carbonyl)benzoyl)-N3,N4-bis((1S,2R)-2-phenylcyclopropyl)pyrrolidine-3,4-dicarboxamide

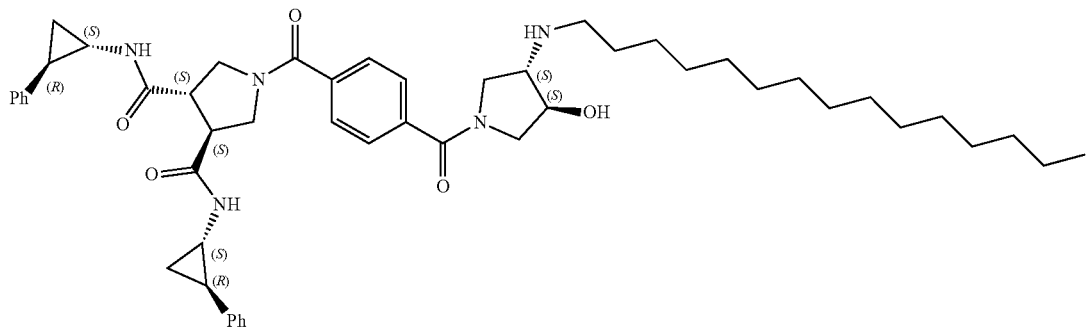

Prepared by a procedure similar to that reported for (3S,4S)-1-(4-((R)-3-(pentadecylamino)pyrrolidine-1-carbonyl)benzoyl)-N3,N4-bis((1S,2R)-2-phenylcyclopropyl)pyrrolidine-3,4-dicarboxamide (Compound 082), using the applicable amine and carboxylic acid. The crude product was purified using Prep HPLC Method 1 to give (3S,4S)-1-(4-((3S,4S)-3-hydroxy-4-(pentadecylamino)pyrrolidine-1-carbonyl)benzoyl)-N3,N4-bis((1S,2R)-2-phenylcyclopropyl)pyrrolidine-3,4-dicarboxamide (Compound 087)(0.011 g, 13%). LCMS (Method-J): 100% (RT 5.980, 202.4 nm) (MS: ESI +ve 833.5 [M+H]). $^1$H NMR: (400 MHz, DMSO) δ ppm: 0.85 (s, 3H), 1.02-1.38 (m, 30H), 1.50-1.86 (m, 2H), 1.86-2.21 (m, 2H), 2.95-3.15 (m, 6H), 3.34-3.68 (m, 6H), 3.95-4.01 (m, 2H), 5.14 (m, 1H), 7.07-7.26 (m, 10H), 7.39-7.71 (m, 5H), 7.73-8.18 (m, 1H), 8.19-8.88 (m, 1H).

Synthesis of (3S,4S)-1-(4-((3S,4S)-3-(heptylamino)-4-(heptyloxy)pyrrolidine-1-carbonyl)benzoyl)-N3,N4-bis((1S,2R)-2-phenylcyclopropyl)pyrrolidine-3,4-dicarboxamide, Compound 089

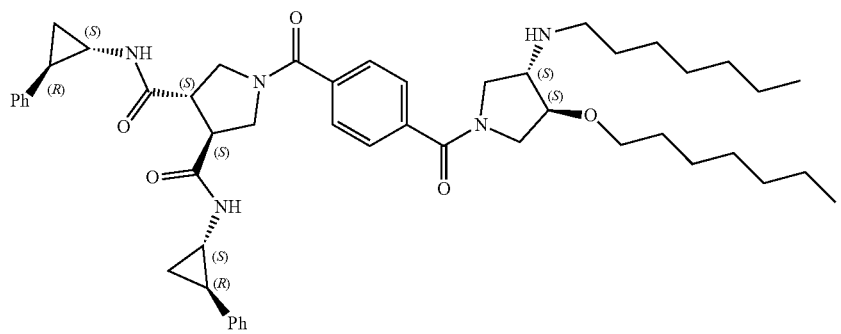

Step-1: Preparation of tert-butyl (3S,4S)-3-(heptylamino)-4-(heptyloxy)pyrrolidine-1-carboxylate

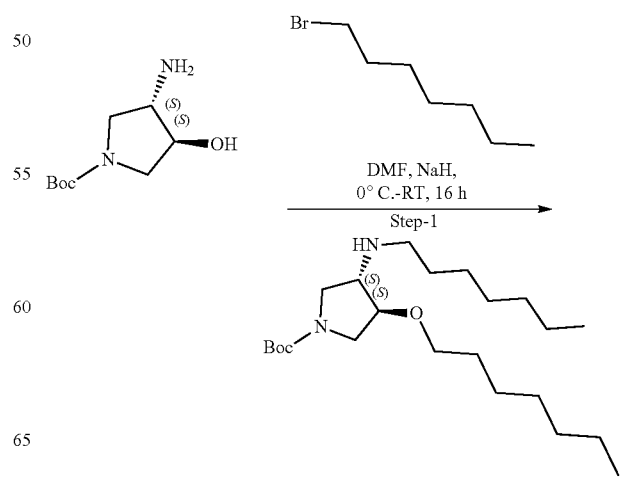

tert-butyl (3S,4S)-3-amino-4-hydroxypyrrolidine-1-carboxylate (0.5 g, 2.472 mmol) was dissolved in dry DMF (10 mL). Sodium hydride (60% in mineral oil) (0.346 g, 8.652 mmol) was added at 0° C. After 5 min, 1-bromoheptane (1.54 g, 8.652 mmol) was added and the reaction mixture was stirred at room temperature for 16 hr. The mixture was extracted with ethyl acetate (2×50 mL), washed with ice-water (50 mL), dried and concentrated. The crude product was purified using flash chromatography, eluting with 1% MeOH in DCM, to give tert-butyl (3S,4S)-3-(heptylamino)-4-(heptyloxy)pyrrolidine-1-carboxylate. (0.74 g, 56.5%). LCMS (Method-J): 64.96% (RT 4.726, 202.0 nm) (MS: ESI +ve 399.4 [M+1]).

Step-5: Preparation of (3S,4S)-1-(4-((3S,4S)-3-(heptylamino)-4-(heptyloxy)pyrrolidine-1-carbonyl)benzoyl)-N3,N4-bis((1S,2R)-2-phenylcyclopropyl)pyrrolidine-3,4-dicarboxamide

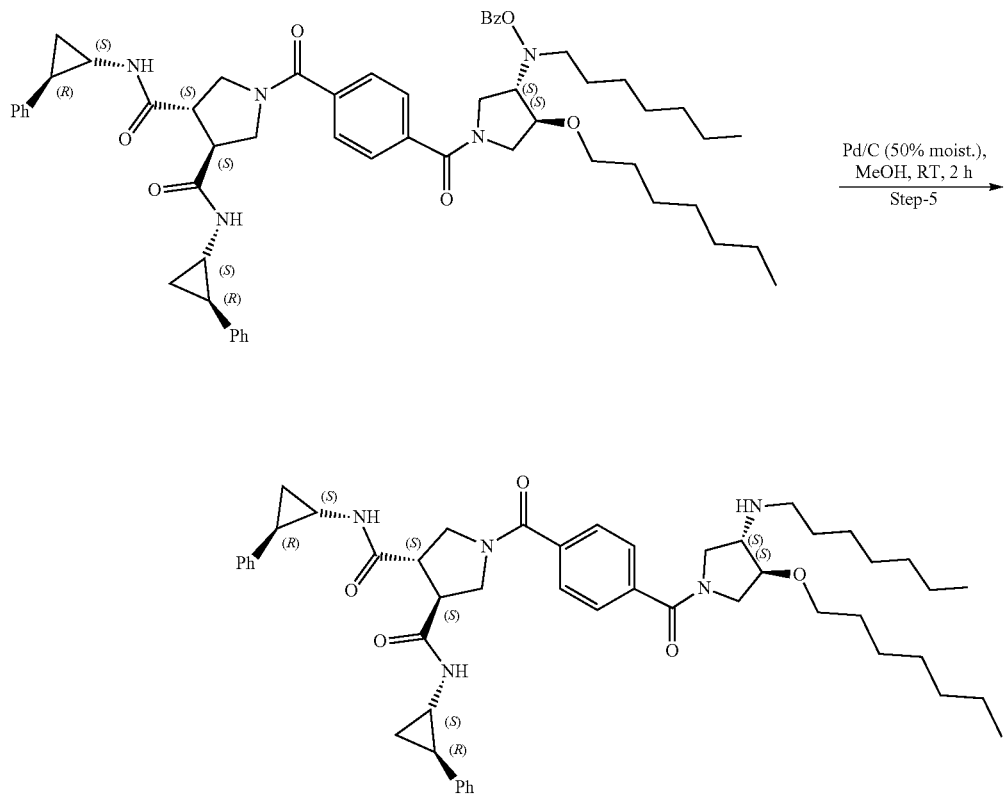

Prepared by a procedure similar to that reported for (3S,4S)-1-(4-((R)-3-(pentadecylamino)pyrrolidine-1-carbonyl)benzoyl)-N3,N4-bis((1S,2R)-2-phenylcyclopropyl)pyrrolidine-3,4-dicarboxamide (Compound 082), using the applicable amine and carboxylic acid. The crude product was purified using Prep HPLC Method 1 to give (3S,4S)-1-(4-((3S,4S)-3-(heptylamino)-4-(heptyloxy)pyrrolidine-1-carbonyl)benzoyl)-N3,N4-bis((1S,2R)-2-phenylcyclopropyl)pyrrolidine-3,4-dicarboxamide (Compound 089), as an off white solid (0.03 g, 26.86%). LCMS (Method-J): 100% (RT 5.788, 202.4 nm) (MS: ESI +ve 818.6 [M+H]). $^1$H NMR: (400 MHz, DMSO) δ ppm: 0.83-0.86 (m, 6H), 1.26-1.37 (m, 26H), 1.50 (m, 1H), 1.85-1.97 (m, 3H), 2.78-2.84 (m, 2H), 3.10-3.23 (m, 4H), 3.42-3.69 (m, 8H), 7.05-7.07 (d, J=7.6 Hz, 2H), 7.11-7.18 (m, 4H), 7.21-7.26 (m, 4H), 7.55 (s, 4H), 8.37 (s, 1H), 8.50 (s, 2H).

Synthesis of (3S,4S)-1-(4-((3R,4R)-3-heptanamido-4-(heptyloxy)pyrrolidine-1-carbonyl) benzoyl)-N3,N4-bis((1S,2R)-2-phenylcyclopropyl)pyrrolidine-3,4-dicarboxamide, Compound 155

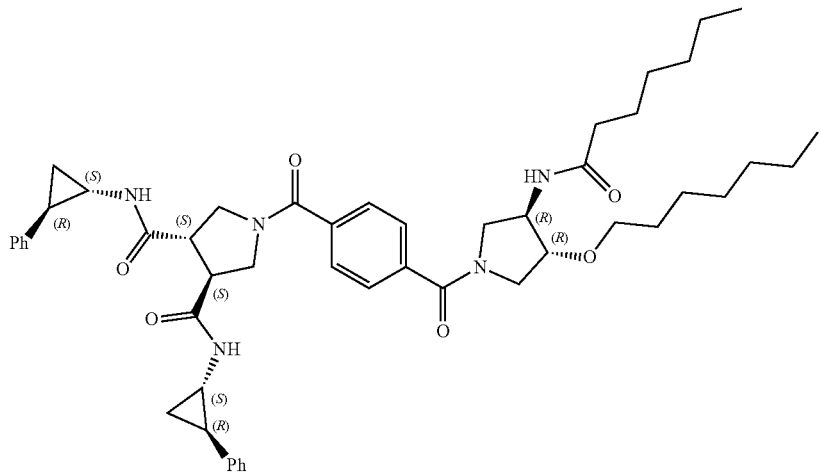

Step-1: Preparation of tert-butyl (3R,4R)-3-heptanamido-4-hydroxypyrrolidine-1-carboxylate Step-2: Preparation of tert-butyl (3R,4R)-3-heptanamido-4-(heptyloxy)pyrrolidine-1-carboxylate

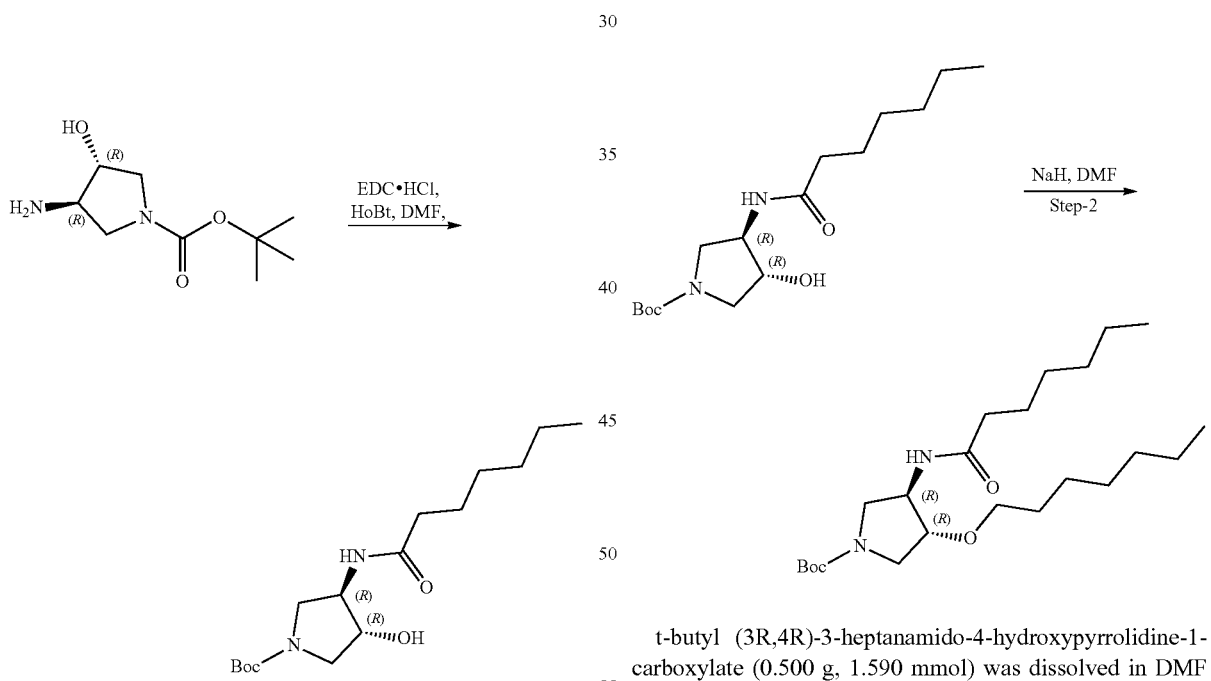

Prepared using General EDC, HOBT Coupling Procedure. The crude product was purified using flash chromatography, eluting with 0-1% MeOH in DCM, to give tert-butyl (3R,4R)-3-heptanamido-4-hydroxypyrrolidine-1-carboxylate. (0.915 g, 100% yield) which was used directly in the next step. LCMS (Method-C3): 96.3% (RT: 1.218, 202.0 nm) (MS: ESI +ve 315.4 [M+1]).

t-butyl (3R,4R)-3-heptanamido-4-hydroxypyrrolidine-1-carboxylate (0.500 g, 1.590 mmol) was dissolved in DMF (10 mL) and cooled to 0° C. Sodium hydride (0.045 g, 1.908 mmol) was added and the mixture was stirred for 15 mins. 1-Bromoheptane (0.341 g, 1.908 mmol) was added and the reaction was stirred for 3 hrs. The mixture was extracted with ethyl acetate (2×20 mL) washed with brine (2×20 mL), dried and concentrated. The crude product was purified using flash chromatography, eluting with 0-10% MeOH in DCM, to give tert-butyl (3R,4R)-3-heptanamido-4-(heptyloxy)pyrrolidine-1-carboxylate. (0.646 g, 98.4% yield). LCMS (Method-H): 84.04% (RT: 4.436, 202.0 nm) (MS: ESI +ve 411.4 [M−1]).

Step-3: Preparation of N—((3R,4R)-4-(heptyloxy) pyrrolidin-3-yl)heptanamide

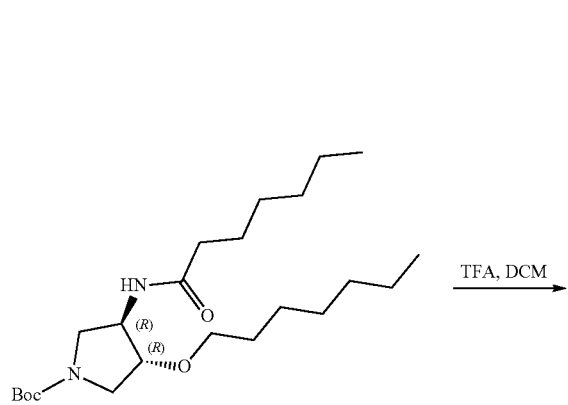

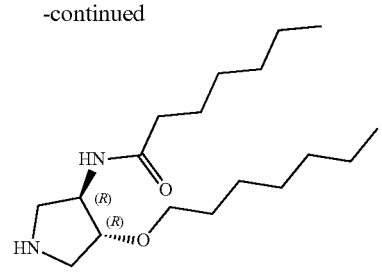

Prepared using General BOC Deprotection Procedure to give N—((3R,4R)-4-(heptyloxy)pyrrolidin-3-yl)heptanamide (0.433 g, 88.5% yield). LCMS (Method-C3): 42.6%, 32.5% (RT: 4.564, 4.880, 202 nm) (MS: ESI +ve 313.3[M+1]).

Step-4: Preparation of (3S,4S)-1-(4-((3R,4R)-3-heptanamido-4-(heptyloxy)pyrrolidine-1-carbonyl) benzoyl)-N3,N4-bis((1S,2R)-2-phenylcyclopropyl) pyrrolidine-3,4-dicarboxamide, Compound 155

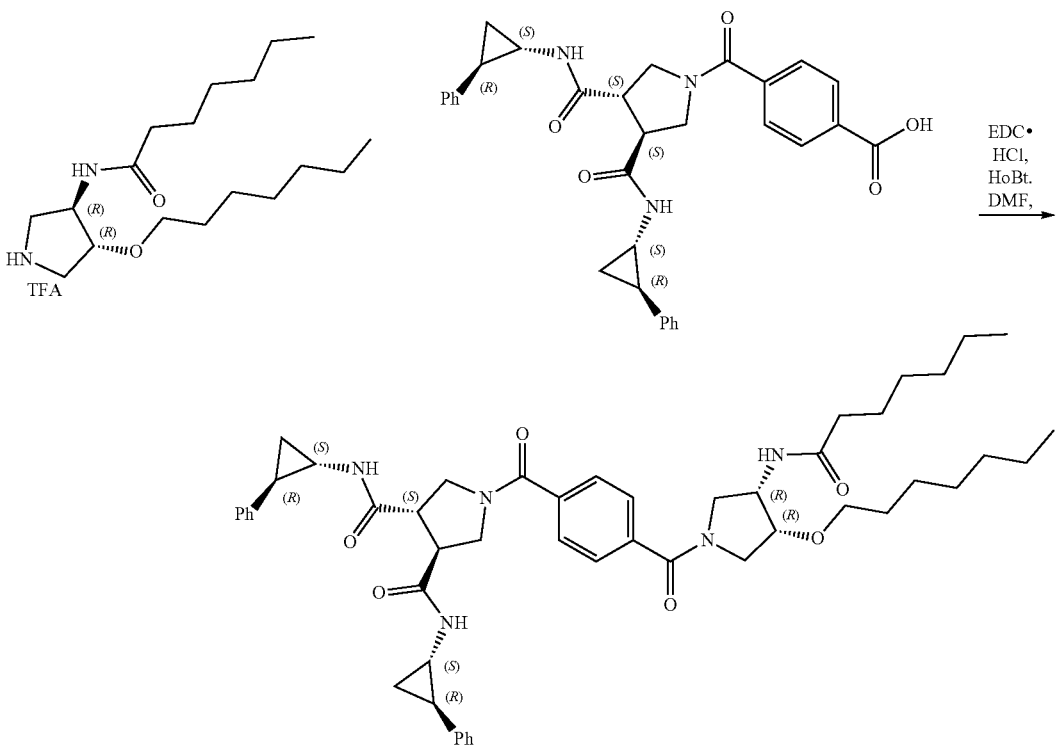

Prepared using General EDC, HOBT Coupling Procedure. The crude product was purified using Prep HPLC Method 12 to give (3S,4S)-1-(4-((3R,4R)-3-heptanamido-4-(heptyloxy)pyrrolidine-1-carbonyl)benzoyl)-N3,N4-bis((1S,2R)-2-phenylcyclopropyl)pyrrolidine-3,4-dicarboxamide (Compound 155) (0.040 g, 17.2% yield), as a white solid. LCMS (Method-H): 100% (RT: 3.912, 202.0 nm) (MS: ESI +ve 833.6 [M+1]). $^1$H NMR: (400 MHz, DMSO) δ ppm: 0.756-0.878 (m, 6H), 1.127-1.456 (m, 19H), 1.442-1.518 (m, 5H), 1.793 (s, 1H), 2.027-2.123 (m, 3H), 2.798-3.043 (m, 2H), 3.112-3.262 (m, 4H), 3.420-3.548 (m, 5H), 3.567-3.751 (m, 4H), 3.826-4.022 (m, 2H), 4.135-4.279 (d, 1H), 7.079-7.197 (m, 6H), 7.237-7.302 (m, 4H), 8.065-8.198 (dd, 1H), 8.317 (s, 1H), 8.450 (s, 1H).

Synthesis of (3S,4S)-1-(4-((3S,4S)-3-heptanamido-4-(heptyloxy)pyrrolidine-1-carbonyl) benzoyl)-N3,N4-bis((1S,2R)-2-phenylcyclopropyl)pyrrolidine-3,4-dicarboxamide, Compound 080

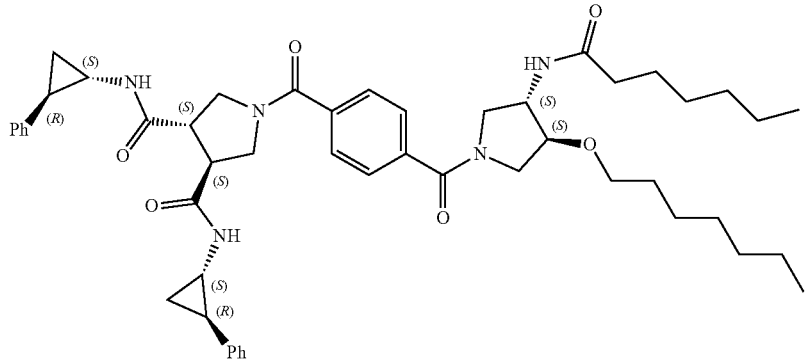

Prepared by a procedure similar to that reported for (3S,4S)-1-(4-((3R,4R)-3-heptanamido-4-(heptyloxy)pyrrolidine-1-carbonyl)benzoyl)-N3,N4-bis((1S,2R)-2-phenylcyclopropyl)pyrrolidine-3,4-dicarboxamide (Compound 155), using the applicable starting materials. The final product was purified using Prep HPLC Method 1 to give (3S,4S)-1-(4-((3S,4S)-3-heptanamido-4-(heptyloxy) pyrolidine-1-carbonyl)benzoyl)-N3,N4-bis((1S,2R)-2-phenylcyclopropyl)pyrrolidine-3,4-dicarboxamide (Compound 080)(0.020 g, 8.63%). LCMS (Method-C): 100% (RT 2.29, 210 nm) (MS: ESI +ve 833.4 [M+H]). $^1$H NMR: (400 MHz, DMSO) δ ppm: 0.85 (t, J=4 Hz, 6H), 1.11-1.44 (m, 18H), 1.26-1.51 (m, 4H), 1.86-2.11 (m, 4H), 2.85-2.68 (m, 2H), 3.10-3.28 (m, 3H), 3.33-3.51 (m, 5H), 3.66-3.74 (m, 3H), 3.84-3.79 (m, 2H), 4.13-4.22 (m, 1H), 7.06-7.08 (m, 2H), 7.18-7.12 (m, 4H), 7.22-7.29 (m, 4H), 7.57 (m, 4H), 8.05-8.15 (m, 1H), 8.29 (s, 1H), 8.43 (s, 1H).

Synthesis of (3S,4S)-1-(4-((3S*,4S*)-3-(hexylcarbamoyl)-4-octylpyrrolidine-1-carbonyl)benzoyl)-N3,N4-bis((1S,2R)-2-phenylcyclopropyl)pyrrolidine-3,4-dicarboxamide, Compound 085

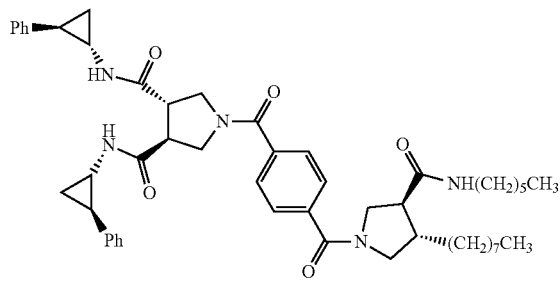

Step 1: Preparation of 1-(tert-butyl) 3-ethyl 4-(((trifluoromethyl)sulfonyl)oxy)-2,5-dihydro-1H-pyrrole-1,3-dicarboxylate

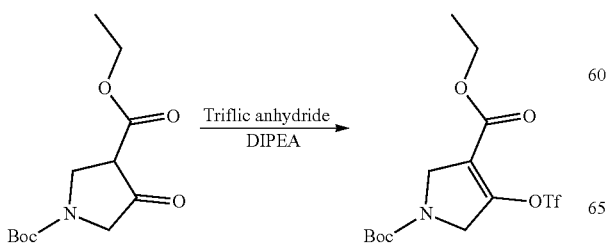

1-(tert-butyl) 3-ethyl 4-oxopyrrolidine-1,3-dicarboxylate (5.0 g, 19.41 mmol) and diisopropylethylamine (5.1 mL, 29.72 mmol) in toluene (90 mL) were cooled to 0° C. Trifluoromethanesulphonic anhydride (3.8 mL, 23.32 mmol) was added drop wise and the reaction mixture was allowed to warm to room temperature over 16 hours. The reaction mixture was diluted with ethyl acetate (150 mL) and washed with saturated aq. sodium bicarbonate (2×100 mL) then brine (2×100 mL). The organic layer was dried over sodium sulfate and concentrated under reduced pressure. The crude product was purified using flash chromatography, eluting with 0-20% ethyl acetate in hexane, to give 1-(tert-butyl) 3-ethyl 4-(((trifluoromethyl)sulfonyl)oxy)-2,5-dihydro-1H-pyrrole-1,3-dicarboxylate as a white solid (6.0 g, 79%). $^1$H NMR: (400 MHz, DMSO) δ ppm: 1.32-1.37 (q, J=6.8 Hz, 3H), 1.49 (s, 9H), 4.28-4.33 (q, J=6.8 Hz, 2H), 4.35-4.40 (m, 4H).

Step-2: Preparation of 1-(tert-butyl) 3-ethyl 4-octyl-2,5-dihydro-1H-pyrrole-1,3-dicarboxylate

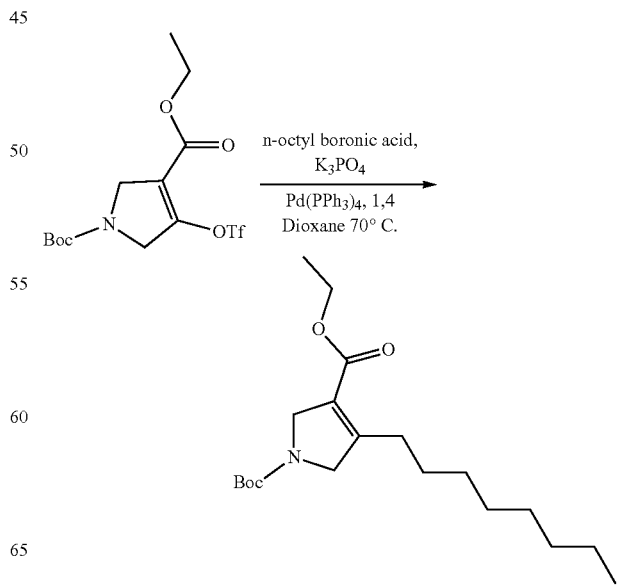

A mixture of 1-(tert-butyl) 3-ethyl 4-(((trifluoromethyl)sulfonyl)oxy)-2,5-dihydro-1H-pyrrole-1,3-dicarboxylate (2.4 g, 2.31 mmol), n-octyl boronic acid (1.94 g, 12.32 mmol) and $K_3PO_4$ (3.92 g, 18.48 mmol) in 1,4 dioxane (50 mL) was purged with nitrogen gas for 10 min. $Pd(PPh_3)_4$ (0.616 g, 0.616 mmol) was added, the mixture was again purged with nitrogen gas for 10 min, and then heated at 70° C. for 16 hours. The reaction mixture was diluted with ethyl acetate (100 mL), washed with saturated aq. sodium bicarbonate (2×100 mL) and brine (2×100 mL). The organic layer was dried over sodium sulfate and concentrated under reduced pressure. The crude product was purified using flash chromatography, eluting with 0-20% ethyl acetate, in hexane to give 1-(tert-butyl) 3-ethyl 4-octyl-2,5-dihydro-1H-pyrrole-1,3-dicarboxylate (0.75 g, 34%). LCMS (Method-C3): 94.23% (RT: 2.735, 244.0 nm) (MS: ESI +ve 298.2[M−56]).

Step-3: Preparation of 1-(tert-butyl) 3-ethyl 4-octylpyrrolidine-1,3-dicarboxylate

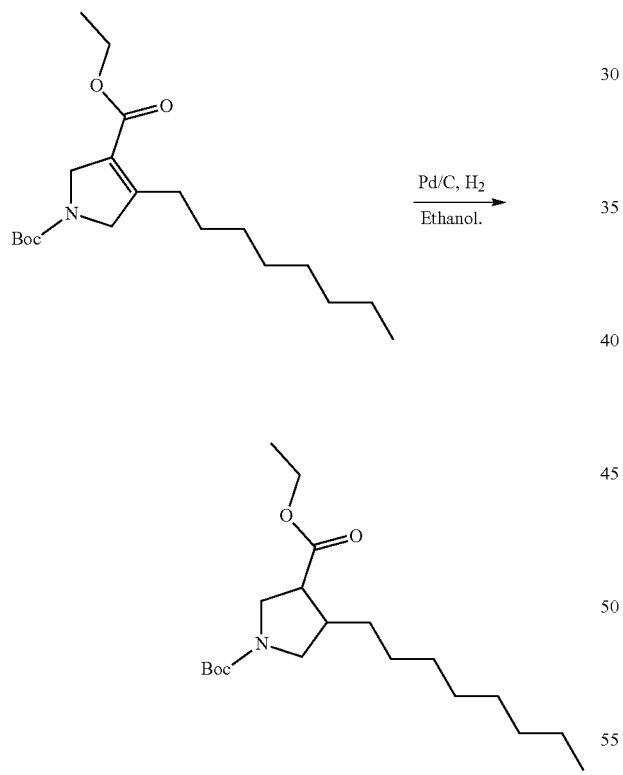

A mixture of 1-(tert-butyl) 3-ethyl 4-octyl-2,5-dihydro-1H-pyrrole-1,3-dicarboxylate (0.7 g) and Pd/C (0.5 g) was suspended in ethanol (20 mL). The mixture was stirred at room temperature under hydrogen gas atmosphere (balloon) for 16 h. The reaction mixture was filtered through celite and concentrated under reduced pressure to give 1-(tert-butyl) 3-ethyl 4-octylpyrrolidine-1,3-dicarboxylate (0.7 g) and used directly in Step-4.

Step-4: Preparation of 1-(tert-butoxycarbonyl)-4-octylpyrrolidine-3-carboxylic acid

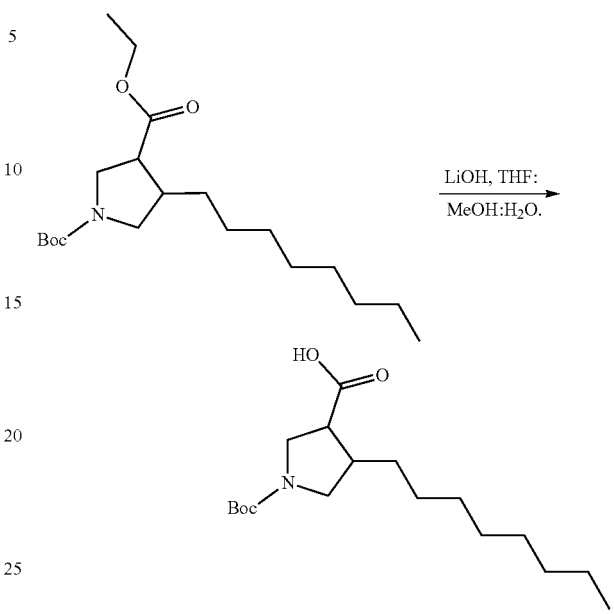

Prepared using a procedure similar to General Ester Hydrolysis Procedure. to give 1-(tert-butoxycarbonyl)-4-octylpyrrolidine-3-carboxylic acid as a white solid (0.5 g, 77%). LCMS (Method-C3): 59.99+19.97% (RT: 2.616 & 2.671, 202.0 nm) (MS: ESI +ve 378[ ]).

Step-5: Preparation of tert-butyl (3S,4S)-3-(hexylcarbamoyl)-4-octylpyrrolidine-1-carboxylate (trans isomer) and tert-butyl (3S,4R)-3-(hexylcarbamoyl)-4-octylpyrrolidine-1-carboxylate (cis isomer)

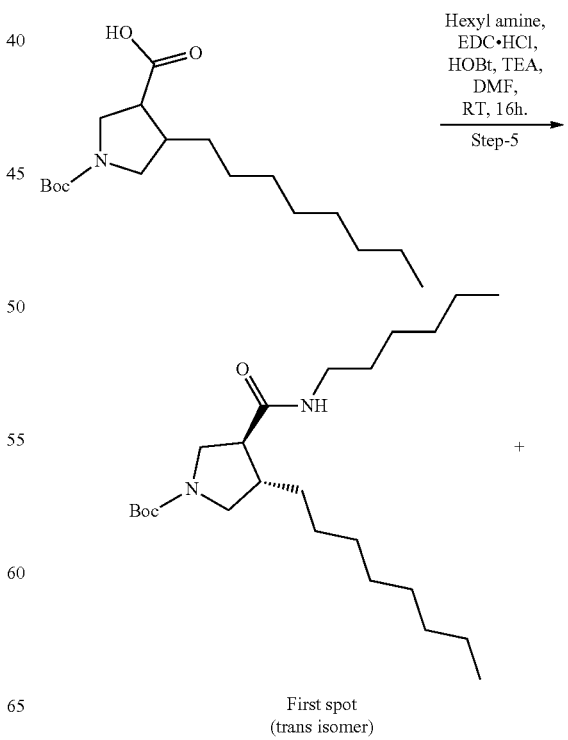

First spot
(trans isomer)

537
-continued

538
Step-6: Preparation of (3S*,4S*)—N-hexyl-4-oc-tylpyrrolidine-3-carboxamide TFA Salt

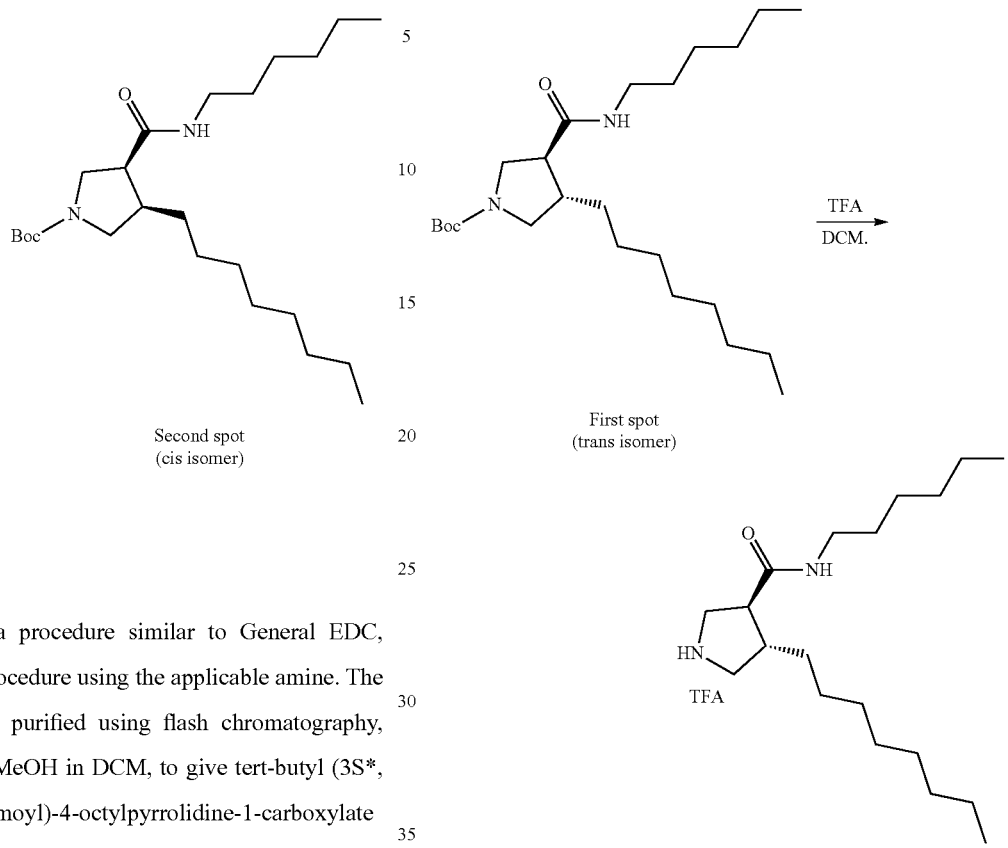

Second spot
(cis isomer)

First spot
(trans isomer)

Prepared using a procedure similar to General EDC, HOBT Coupling Procedure using the applicable amine. The crude mixture was purified using flash chromatography, eluting with 0-2% MeOH in DCM, to give tert-butyl (3S*,4S*)-3-(hexylcarbamoyl)-4-octylpyrrolidine-1-carboxylate (first spot, trans isomer) (0.25 g) (racemic) LCMS (Method-H2): 84.65% (RT 5.116, 202.0 nm) (MS: ESI – ve 409.2 [M–H]) and tert-butyl (3S*,4R*)-3-(hexylcarbamoyl)-4-octylpyrrolidine-1-carboxylate (second spot, cis isomer) (0.25 g). (racemic) LCMS (Method-H2): 88.28% (RT 5.139, 202.0 nm) (MS: ESI – ve 409.2 [M–H]).

Prepared using a procedure similar to General BOC Deprotection Procedure to give (3S*,4S*)—N-hexyl-4-octylpyrrolidine-3-carboxamide TFA Salt (0.25 g). LCMS (Method-C3): 85% (RT: 1.665, 202.0 nm) (MS: ESI +ve 312.1[M+H]).

Step-7: Preparation of ((3S,4S)-1-(4-((3S*,4S*)-3-(hexylcarbamoyl)-4-octylpyrrolidine-1-carbonyl)benzoyl)-N3,N4-bis((1S,2R)-2-phenylcyclopropyl)pyrrolidine-3,4-dicarboxamide, Compound 085

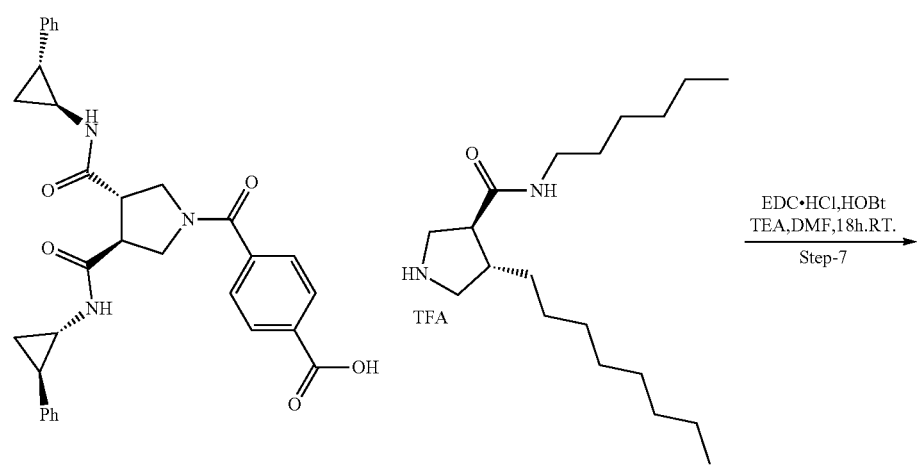

EDC•HCl, HOBt
TEA, DMF, 18h, RT.
Step-7

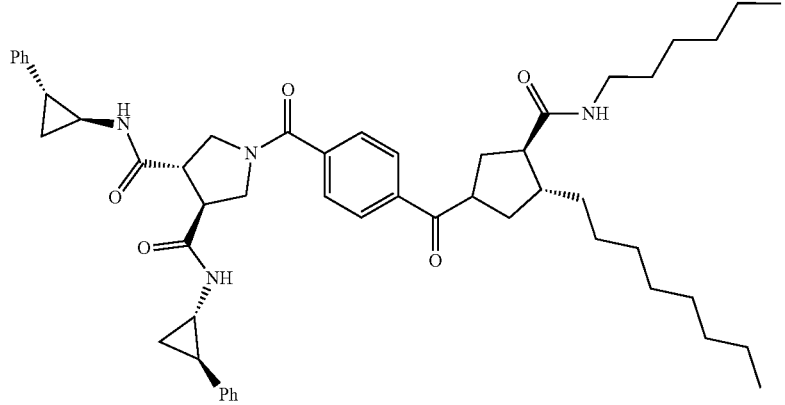

Prepared using a procedure similar to General EDC, HOBT Coupling Procedure. The crude product was purified using flash chromatography, eluting with 0-2% MeOH in DCM, to give ((3S,4S)-1-(4-((3S*,4S*)-3-(hexylcarbamoyl)-4-octylpyrrolidine-1-carbonyl)benzoyl)-N3,N4-bis ((1S,2R)-2-phenylcyclopropyl)pyrrolidine-3,4-dicarboxamide as 1:1 mixture of diastereomers (0.140 g) LCMS (Method-C3): 98.42% (RT 2.254, 222.0 nm) (MS: ESI +ve 830.3 [M+H]). The compound was further purified using Prep HPLC Method 1 to give ((3S,4S)-1-(4-((3S*,4S*)-3-(hexylcarbamoyl)-4-octylpyrrolidine-1-carbonyl)benzoyl)-N3,N4-bis((1S,2R)-2-phenylcyclopropyl)pyrrolidine-3,4-dicarboxamide (Compound 085)(1:1 mixture of diastereomers) (0.050 g, 21%). LCMS (Method-C3): 100% (RT 2.284, 202.0 nm) (MS: ESI +ve 830.5 [M+H]). ¹H NMR: (400 MHz, DMSO) δ ppm: 0.82-0.86 (m, 6H), 1.10-1.38 (m, 28H), 1.85 (s, 3H), 1.96 (s, 1H), 1.78 (s, 1H), 1.84 (s, 1H), 3.09-3.20 (m, 4H), 3.49-3.56 (m, 5H), 3.66-3.68 (m, 1H), 3.78-3.80 (m, 1H), 7.05-7.07 (m, 2H), 7.11-7.18 (m, 4H), 7.22-7.26 (m, 4H), 7.55-7.56 (m, 4H), 7.98-8.12 (m, 1H), 8.31 (s, 1H), 8.45 (s, 1H).

Step-8: Chiral SFC Separation to give (3S,4S)-1-(4-((3S,4S)-3-(hexylcarbamoyl)-4-octylpyrrolidine-1-carbonyl) benzoyl)-N3,N4-bis ((1S, 2R)-2-phenylcyclopropyl) pyrrolidine-3,4-dicarboxamide (Compound 111) and (3S,4S)-1-(4-((3R,4R)-3-(hexylcarbamoyl)-4-octylpyrrolidine-1-carbonyl) benzoyl)-N3,N4-bis ((1S,2R)-2-phenylcyclopropyl) pyrrolidine-3,4-dicarboxamide (Compound 112)

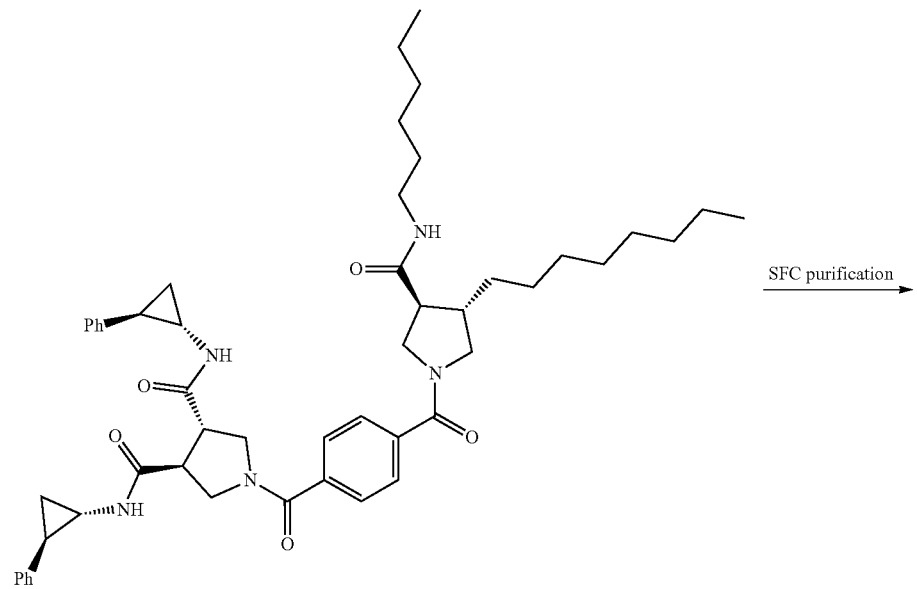

SFC purification →

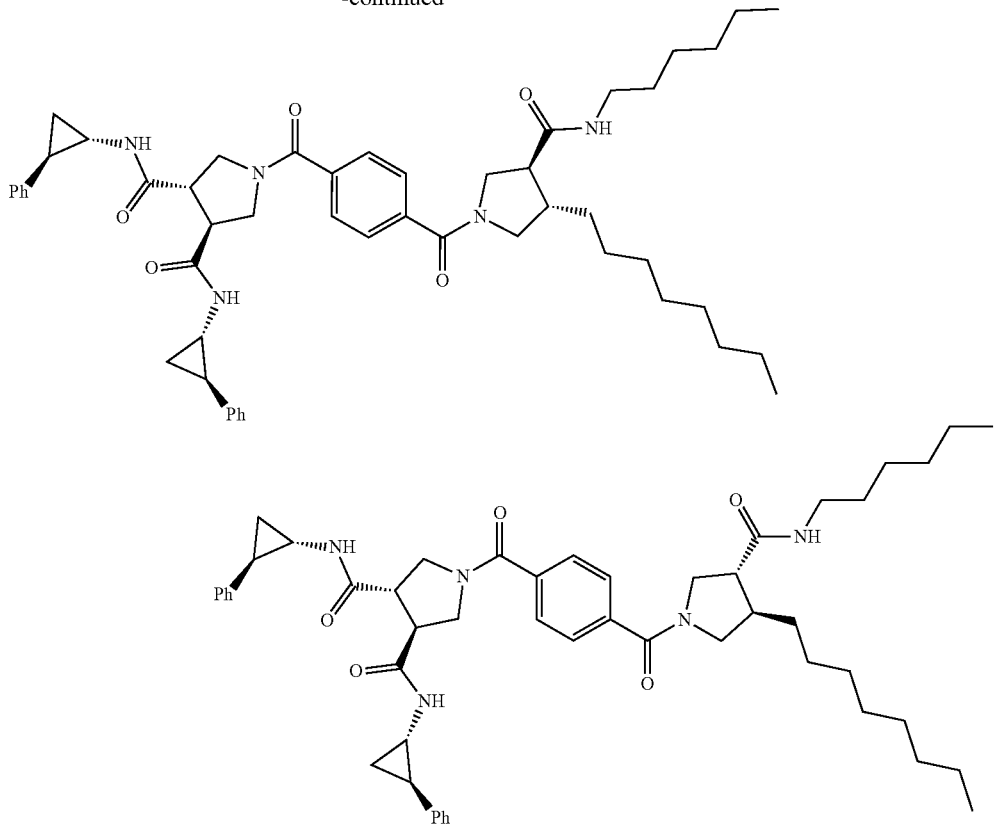

(3S,4S)-1-(4-((3S*, 4S*)-3-(hexylcarbamoyl)-4-octylpyrrolidine-1-carbonyl) benzoyl)-N3,N4-bis ((I S, 2R)-2-phenylcyclopropyl) pyrrolidine-3,4-dicarboxamide (0.09 g) (Compound 085) was separated on a Shimadzu LC-20AP chromatography system with UV detector. The column used was CHIRALCEL OX-H (250*21.0) mm, 5 micron, column flow was 20.0 ml/min. Mobile phase were(A) 0.1% DEA in hexane (B) 0.1% DEA in propan-1-ol: acetonitrile (70:30);

Fraction1; (0.041 g) LCMS (Method-J): 100% (RT 5.817, 202.0 nm) (MS: ESI +ve 830.4 [M+1]). This material was re-purified using Prep HPLC Method 4 to remove DEA to give (3S,4S)-1-(4-((3S,4S)-3-(hexylcarbamoyl)-4-octylpyrrolidine-1-carbonyl) benzoyl)-N3,N4-bis ((1S,2R)-2-phenylcyclopropyl) pyrrolidine-3,4-dicarboxamide (Compound 111) (0.009 g) [absolute stereochemistry of the pyrrolidine was arbitrarily assigned (S,S)]. LCMS (Method-J): 100% (RT 5.817, 202.0 nm) (MS: ESI +ve 830.4 [M+1]) 1H NMR: (400 MHz, DMSO) δ ppm: 0.82-0.89 (m, 6H), 1.10-1.12 (m, 25H), 1.84-1.86 (d, J=6, 1H), 1.98 (s, 1H), 2.28 (s, 1H), 2.79 (s, 2H), 2.86 (s, 1H), 2.90 (s, 1H), 2.99-3.19 (m, 4H), 3.50 (s, 4H), 3.58-3.70 (m, 2H), 3.73-3.81 (m, 2H), 7.07-7.17 (m, 5H), 7.23-7.29 (m, 4H), 7.56-7.57 (d, J=6, 4H), 7.98 (s, 1H), 8.12 (s, 1H), 8.30 (s, 1H), 8.44 (s, 1H)
Chiral HPLC (Fraction-1): 95.19% (RT: 5.52)

Fraction 2; (0.065 g). LCMS (Method-J): 100% (RT 5.817, 202.0 nm) (MS: ESI +ve 830.4 [M+1]). This material was re-purified using Prep HPLC Method 4 to remove DEA to give (3S,4S)-1-(4-((3R,4R)-3-(hexylcarbamoyl)-4-octylpyrrolidine-1-carbonyl) benzoyl)-N3,N4-bis((1S,2R)-2-phenylcyclopropyl) pyrrolidine-3,4-dicarboxamide (Compound 112) (0.009 g) [absolute stereochemistry of the pyrrolidine was arbitrarily assigned (R,R)]. LCMS (Method-J): 100% (RT 5.817, 202.0 nm) (MS: ESI-+ve 830.4 [M+1])
1H NMR: (400 MHz, DMSO) δ ppm: 0.81-0.85 (m, 6H), 1.10-1.26 (m, 25H), 1.87 (s, 1H), 1.98 (s, 1H), 2.34 (s, 1H), 2.68 (s, 2H), 2.86 (s, 4H), 3.18-3.22 (m, 4H), 3.51-3.53 (d, J=8, 4H), 3.65-3.70 (m, 1H), 3.79 (s, 1H), 7.07-7.17 (m, 5H), 7.23-7.29 (m, 4H), 7.56-7.57 (d, J=6, 4H), 8.01 (s, 1H), 8.14 (s, 1H), 8.37 (s, 1H), 8.51 (s, 1H)
Chiral HPLC (Fraction-2): 100% (RT: 5.09)

Synthesis of (3S,4S)-1-(4-((3S*,4R*)-3-(hexylcarbamoyl)-4-octylpyrrolidine-1-carbonyl)benzoyl)-N3, N4-bis((1S,2R)-2-phenylcyclopropyl)pyrrolidine-3, 4-dicarboxamide, Compound 086

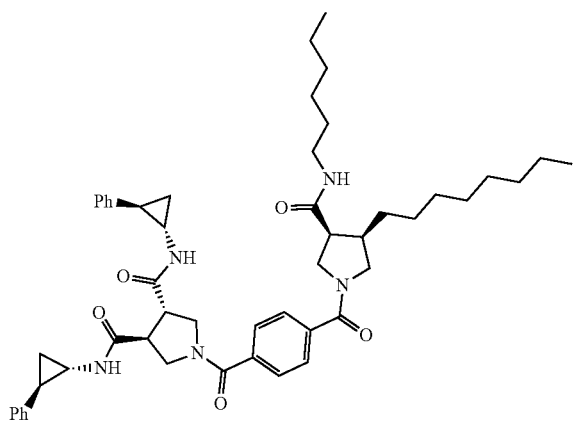 [SMILES: CCCCCCCC[C@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCC]

543

Prepared by a procedure similar to that described for (3S,4S)-1-(4-((3S*,4S*)-3-(hexylcarbamoyl)-4-octylpyrrolidine-1-carbonyl)benzoyl)-N3,N4-bis((1S,2R)-2-phenylcyclopropyl)pyrrolidine-3,4-dicarboxamide (Compound 085) using tert-butyl (3S*,4R*)-3-(hexylcarbamoyl)-4-octylpyrrolidine-1-carboxylate (Second spot, cis isomer) isolated in Step-5. The crude product was purified using Prep HPLC Method 1 to give (3S,4S)-1-(4-((3S*,4R*)-3-(hexylcarbamoyl)-4-octylpyrrolidine-1-carbonyl)benzoyl)-N3,N4-bis((1S,2R)-2-phenylcyclopropyl)pyrrolidine-3,4-dicarboxamide (Compound 086) (1:1 mixture of diastereomers) (0.070 g, 21%). LCMS (Method-C3): 100% (RT 2.273, 202.0 nm)

544

(MS: ESI +ve 830.6 [M+H]). $^1$H NMR: (400 MHz, DMSO) δ ppm: 0.82-0.88 (m, 6H), 1.11-1.40 (m, 28H), 1.86 (s, 3H), 1.97 (s, 1H), 2.34-2.51 (m, 2H), 2.79-2.95 (m, 3H), 3.10-3.24 (m, 4H), 3.28-3.34 (m, 1H), 3.49-3.57 (m, 4H), 3.59-3.67 (m, 1H), 3.59-3.81 (bs, 1H), 7.06-7.08 (m, 2H), 7.12-7.19 (m, 4H), 7.22-7.29 (m, 4H), 7.51-7.59 (m, 4H), 7.93-8.03 (m, 1H), 8.30 (s, 1H), 8.43-8.44 (s, 1H).

Synthesis of (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide, Compound 101

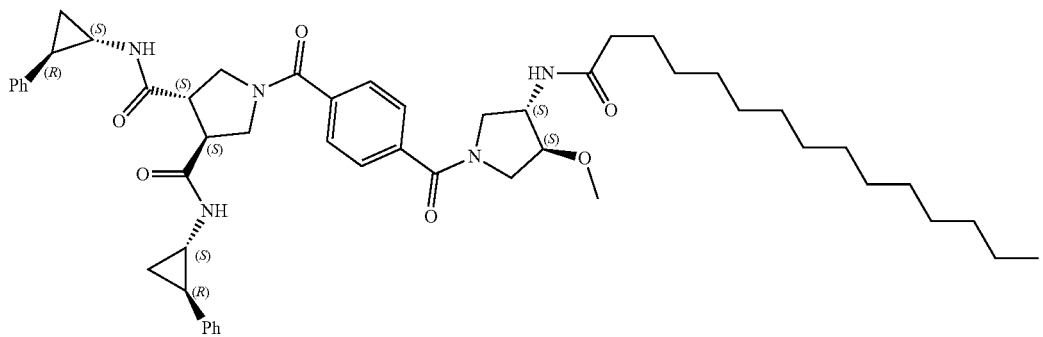

Step-2: Preparation of N—((3S,4S)-4-methoxypyrrolidin-3-yl) pentadecanamide

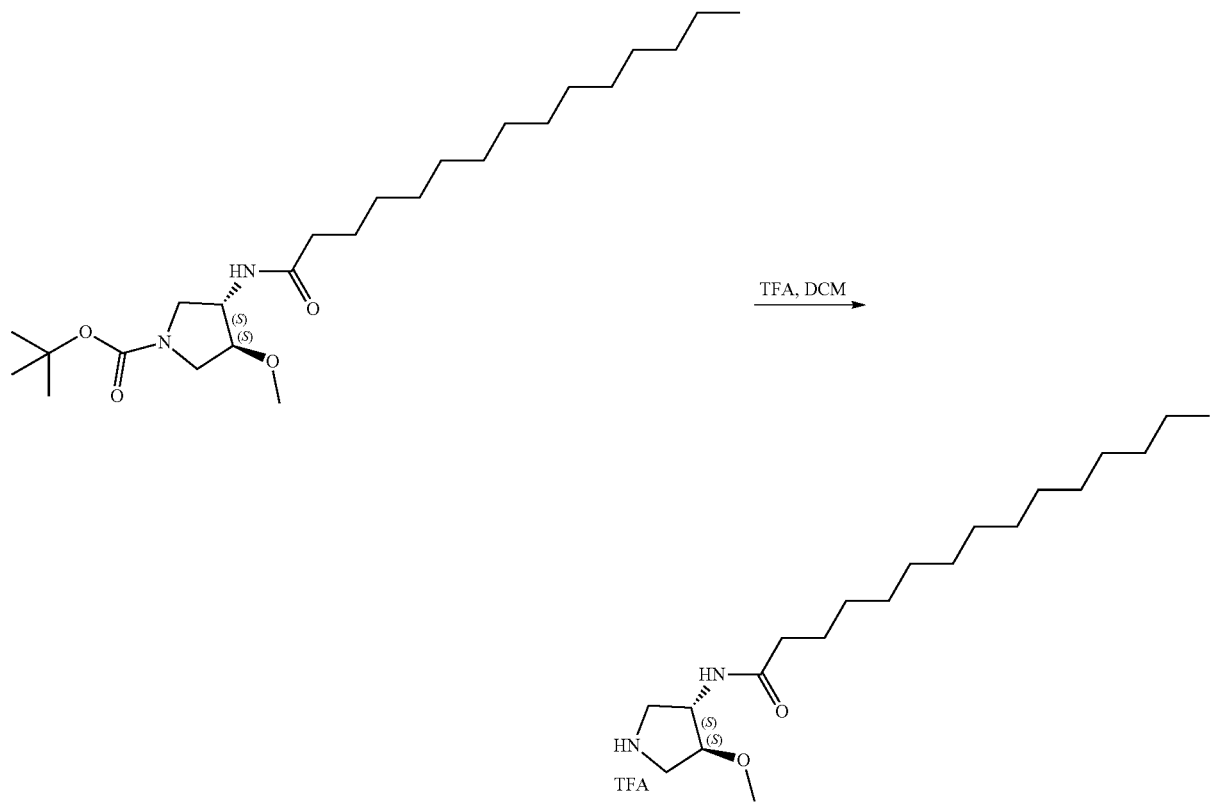

Prepared using a procedure similar to General EDC, HOBT Coupling Procedure. The crude product was collected by filtration from the quenched reaction mixture and used without further purification (0.1.2 g, 98%). LCMS (Method-C-Fast): 97.6% (RT: 2.849, 202.0 nm) (MS: ESI +ve 385.7 [M−56H]).

Prepared using a procedure similar to General BOC Deprotection Procedure to give N—((3S,4S)-4-methoxypyrrolidin-3-yl) pentadecanamide (0.75 g, 98.8%). LCMS (Method-DEV): 100% (RT 6.690, 202.0 nm) (MS: ESI +ve 341.4 [M+H]).

Step-3: Preparation of (3S,4S)-1-(4-((3S,4S)-3-methoxy-4-pentadecanamidopyrrolidine-1-carbonyl) benzoyl)-N3,N4-bis ((1S,2R)-2-phenylcyclopropyl) pyrrolidine-3,4-dicarboxamide, Compound 101

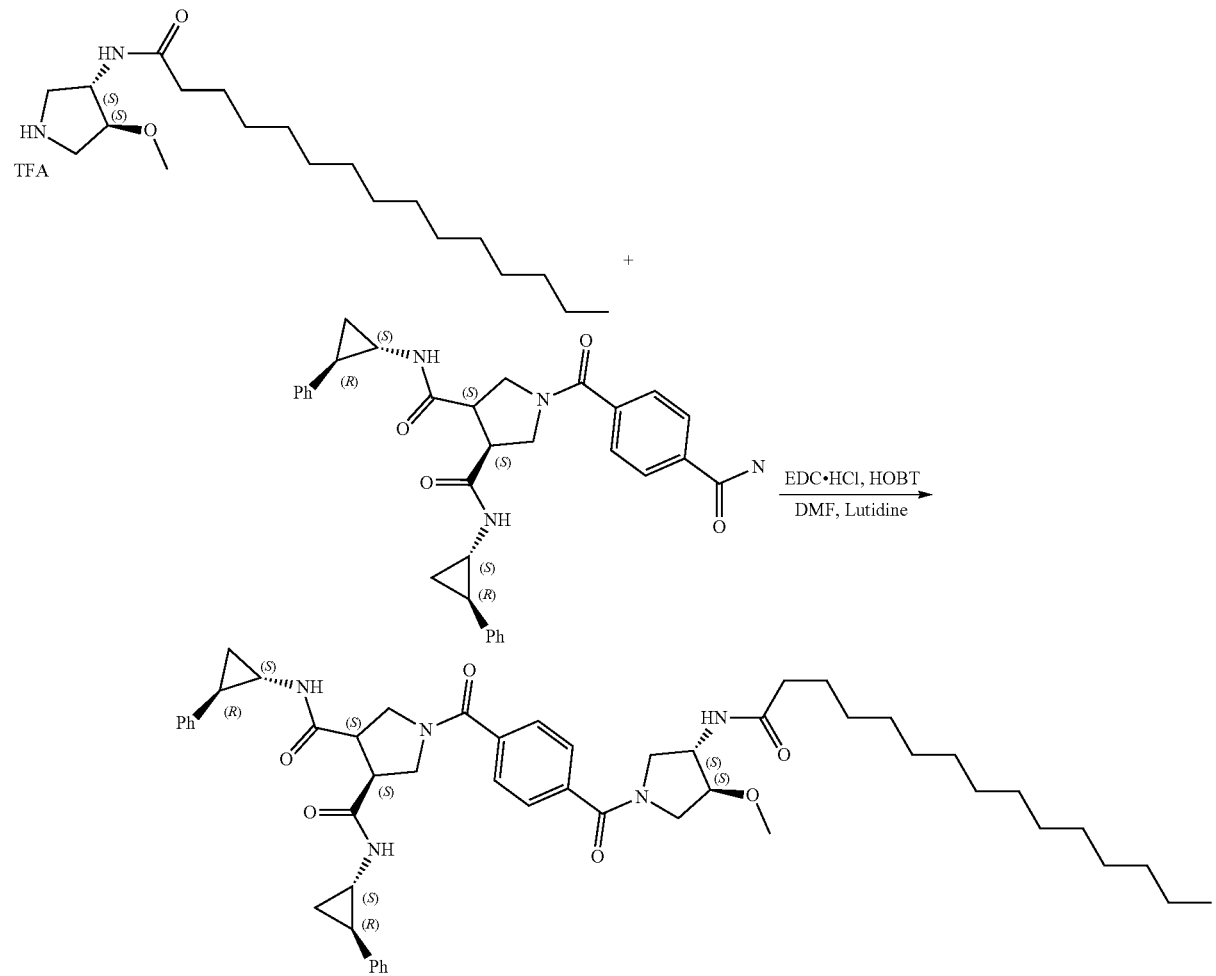

Prepared using a procedure similar to General EDC, HOBT Coupling Procedure. The crude product was purified using Reverse Phase Flash chromatography, eluting with 93% acetonitrile+0.1% formic acid and water, to give (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101) (0.610 g, 43.9%). LCMS (Method-J2): 100% (RT 5.189, 202.0 nm) (MS: ESI +ve 860.6 [M+H]). $^1$H NMR: (400 MHz, DMSO) δ ppm: 0.83-0.86 (m, 3H), 1.11 (s, 2H), 1.23 (s, 25H), 1.43-150 (m, 2H), 1.85 (s, 1H), 1.97-2.10 (m, 3H), 2.78 (s, 1H), 2.85 (s, 1H), 3.09-3.28 (m, 4H), 3.41-3.51 (m, 3H), 3.66-3.83 (m, 6H), 4.15-4.25 (m, 1H), 7.06-7.07 (d, J=7.2 Hz, 2H), 7.11-7.18 (m, 4H), 7.22-7.28 (m, 4H), 7.57 (s, 4H), 8.05-8.15 (m, 1H), 8.29 (s, 1H), 8.43 (s, 1H).

Synthesis of (3S,4S)-1-(4-((3R,4R)-3-methoxy-4-pentadecanamidopyrrolidine-1-carbonyl) benzoyl)-N3,N4-bis((1S,2R)-2-phenylcyclopropyl) pyrrolidine-3,4-dicarboxamide, Compound 154

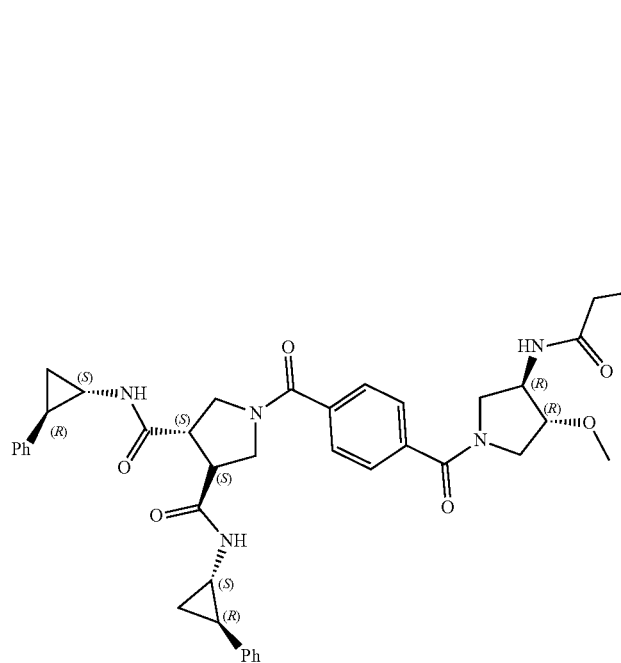

Prepared by a procedure similar to that reported for (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101). The final product was purified using Prep HPLC Method 1 to give (3S,4S)-1-(4-((3R,4R)-3-methoxy-4-pentadecanamidopyrrolidine-1-carbonyl) benzoyl)-N3,N4-bis ((1S,2R)-2-phenylcyclopropyl) pyrrolidine-3,4-dicarboxamide (Compound 154), as a white solid (0.050 g, 20.84%). LCMS (Method-C3): 100% (RT 2.516, 220.0 nm) (MS: ESI +ve 861[M+H]). $^1$H NMR: (400 MHz, DMSO) δ ppm: 0.83-0.86 (t, 3H); 1.23 (s, 29H); 1.40-1.49 (m, 2H); 1.85-1.86 (d, J=5.2, 1H); 1.97 (s, 1H); 2.04 (s, 1H); 2.07-2.14 (m, 1H); 2.78 (s, 2H); 3.09-3.13 (m, 1H); 3.23 (s, 4H); 3.52 (s, 2H); 3.65 (s, 4H); 4.15 (s, 1H); 7.06-7.08 (d, J=7.2, 6H); 7.22-7.28 (m, 4H); 7.57 (s, 4H); 8.06-8.15 (m, 1H); 8.43 (s, 2H).

Synthesis of (3S,4S)-1-(4-((3S,4R)-3-methoxy-4-pentadecanamidopyrrolidine-1-carbonyl)benzoyl)-N3,N4-bis((1S,2R)-2-phenylcyclopropyl)pyrrolidine-3,4-dicarboxamide, Compound 209

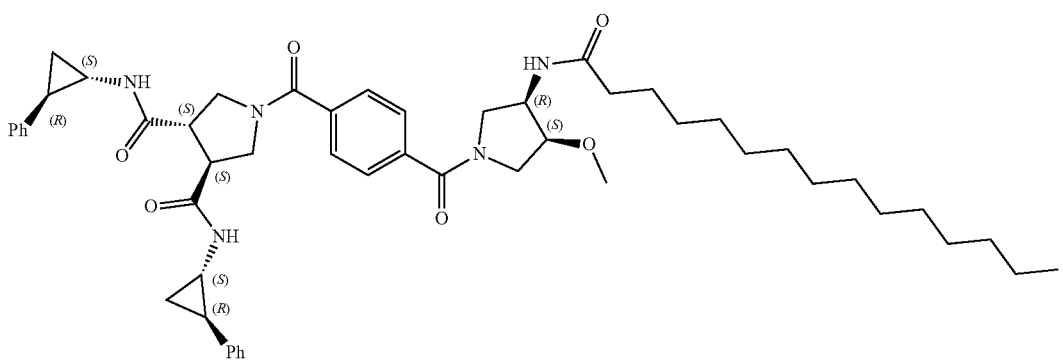

Prepared by a procedure similar to that reported for (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101). The final product was purified using Prep HPLC Method 10 to give (3S,4S)-1-(4-((3S,4R)-3-methoxy-4-pentadecanamidopyrrolidine-1-carbonyl)benzoyl)-N3,N4-bis((1S,2R)-2-phenylcyclopropyl)pyrrolidine-3,4-dicarboxamide (Compound 209)(0.032 g, 19.95%). LCMS (Method-C2): 100% (RT 2.582, 225.0 nm) (MS: ESI +ve 861.9 [M+H]). $^1$H NMR: (400 MHz, DMSO) δ ppm: 0.83-0.86 (d, J=6.4 Hz, 3H), 1.09-1.24 (m, 30H), 1.43.1.50 (dd, J=20.4 Hz, 3H), 1.86 (s, 1H), 1.97 (s, 1H), 2.08-2.15 (m, 3H), 2.78-2.85 (d, J=28 Hz, 2H), 3.09-3.68 (m, 10H), 3.80 (s, 2H), 7.06-7.28 (m, 10H), 7.51-7.57 (m, 4H), 8.32 (s, 1H), 8.45-8.51 (d, J=22.8 Hz, 1H).

Synthesis of (3S,4S)-1-(4-((3R,4S)-3-methoxy-4-pentadecanamidopyrrolidine-1-carbonyl) benzoyl)-N3,N4-bis ((1S,2R)-2-phenylcyclopropyl) pyrrolidine-3,4-dicarboxamide, Compound 236

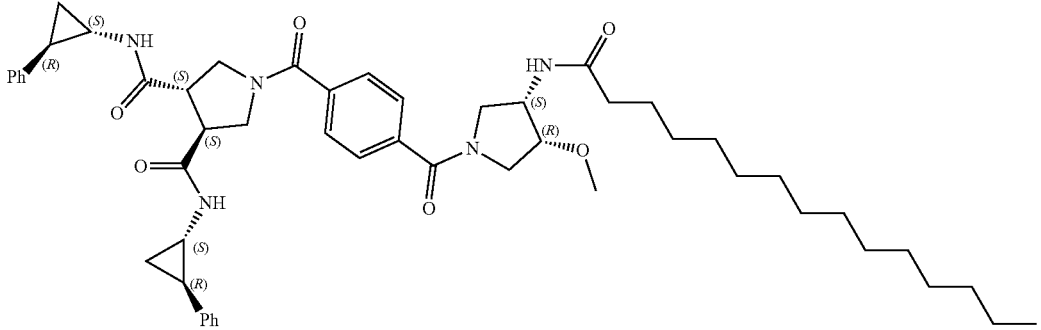

Prepared by a procedure similar to that reported for (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101). The final product was purified using Prep HPLC Method 10 to give (3S,4S)-1-(4-((3R,4S)-3-methoxy-4-pentadecanamidopyrrolidine-1-carbonyl) benzoyl)-N3,N4-bis ((1S,2R)-2-phenylcyclopropyl) pyrrolidine-3,4-dicarboxamide (Compound 236), as a white solid (0.09 g, 37.51%). LCMS (Method-J2): 100% (RT 4.820, 202.0 nm) (MS: ESI +ve 861[M+H]). $^1$H NMR: (400 MHz, DMSO) δ ppm: 0.83-0.86 (t, 3H); 1.10 (s, 3H); 1.17-1.23 (t, 19H); 1.50 (s, 2H); 1.85 (s, 2H); 2.12-2.15 (t, 3H); 2.78 (s, 2H); 3.08-3.11 (d, J=8.4, 1H); 3.18-3.20 (d, J=8, 3H); 3.34 (s, 3H); 3.50-3.52 (d, J=8.8, 3H); 3.60-3.65 (m, 3H); 3.65-3.67 (d, J=8, 2H); 3.80 (s, 1H); 3.90 (s, 2H); 7.06-7.08 (d, J=7.6, 2H); 7.11-7.18 (m, 4H); 7.22-7.28 (m, 4H); 7.52-7.57 (m, 4H); 7.84-7.96 (m, 1H); 8.32 (s, 1H); 8.45 (s, 1H).

Synthesis of (3S,4S)-1-(4-((3R,4R)-3-hydroxy-4-pentadecanamidopyrrolidine-1-carbonyl) benzoyl)-N3,N4-bis ((1S,2R)-2-phenylcyclopropyl) pyrrolidine-3,4-dicarboxamide, Compound 157

Prepared by a procedure similar to that reported for (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101), using the applicable starting materials The final product was purified using Prep HPLC Method 10 to give (3S,4S)-1-(4-((3R,4R)-3-hydroxy-4-pentadecanamidopyrrolidine-1-carbonyl) benzoyl)-N3,N4-bis((1S,2R)-2-phenylcyclopropyl) pyrrolidine-3,4-dicarboxamide (Compound 157), as a white solid (0.039 g, 15.57%). LCMS (Method-C3): 100% (RT 2.383, 222.0 nm) (MS: ESI +ve 847[M+H]). $^1$H NMR: (400 MHz, DMSO) δ ppm: 0.84-0.86 (d, J=6.8, 3H); 1.10-1.12 (d, J=8, 2H); 1.18 (s, 28H); 1.44-1.46 (d, J=7.6, 2H); 1.87-1.89 (d, J=6.8, 1H); 1.98-2.05 (m, 2H); 2.07-2.11 (m, 1H); 2.68 (s, 1H); 2.85 (s, 1H); 3.12-3.18 (m, 1H); 3.20-3.24 (m, 2H); 3.52-3.54 (d, J=8, 2H); 3.65-3.69 (m, 2H); 3.76-3.81 (m, 2H); 3.94 (s, 1H); 4.06 (s, 1H); 5.46 (s, 1H); 7.07-7.09 (d, J=7.2, 6H); 7.23-7.29 (m, 4H); 7.57 (s, 4H); 7.99-8.07 (m, 1H); 8.34 (s, 2H); 8.54 (s, 1H).

Synthesis of (3S,4S)-1-(4-((3S,4S)-3-hydroxy-4-pentadecanamidopyrrolidine-1-carbonyl) benzoyl)-N3,N4-bis((1S,2R)-2-phenylcyclopropyl)pyrrolidine-3,4-dicarboxamide, Compound 078

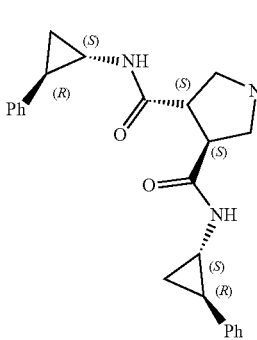
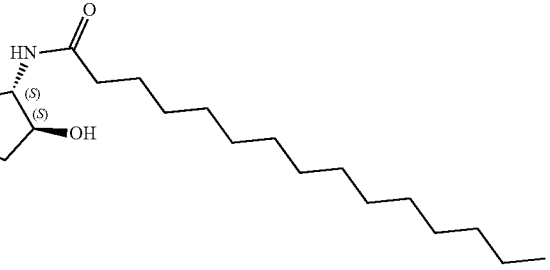

Prepared by a procedure similar to that reported for (3S,4S)-1-(4-((3S,4S)-3-methoxy-4-pentadecanamidopyrrolidine-1-carbonyl) benzoyl)-N3,N4-bis((1S,2R)-2-phenylcyclopropyl) pyrrolidine-3,4-dicarboxamide (Compound 101), using the applicable starting materials. The final product was purified using Prep HPLC Method 10 to give (3S,4S)-1-(4-((3S,4S)-3-hydroxy-4-pentadecanamidopyrrolidine-1-carbonyl)benzoyl)-N3,N4-bis((1S,2R)-2-phenylcyclopropyl)pyrrolidine-3,4-dicarboxamide (Compound 078), (0.034 g, 38%) as an off white solid. LCMS (Method-C): 100% (RT 2.401, 224.0 nm) (MS: ESI +ve 846.7 [M+H]). $^1$H NMR: (400 MHz, DMSO) δ ppm: 0.83-0.86 (q, J=6.8 Hz, 3H), 1.10 (s, 3H), 1.11-1.23 (m, 15H), 1.42 (s, 1H), 1.49 (s, 1H), 1.86 (s, 2H), 1.97-2.08 (m, 4H), 2.78 (s, 1H), 2.84 (s, 1H), 3.09-3.20 (m, 4H), 3.51 (s, 3H), 3.63-3.68 (m, 4H), 3.78-3.80 (m, 4H), 3.92-4.04 (m, 3H), 5.35-5.45 (m, 1H), 7.06-7.07 (m, J=6.8 Hz, 2H), 7.11-7.18 (m, 4H), 7.21-7.28 (m, 4H), 7.57 (m, 4H), 7.97-8.07 (m, 1H), 8.31 (s, 1H), 8.44 (s, 1H).

Synthesis of (3S,4S)-1-(4-(((R)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide, Compound 092

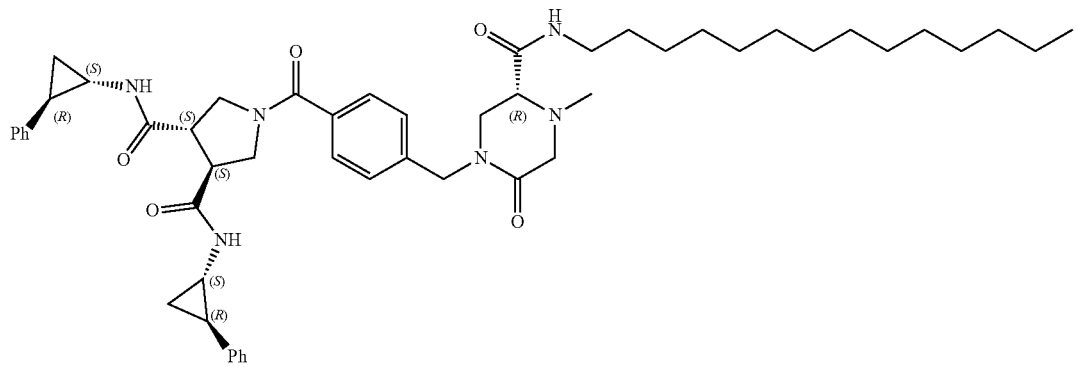

Step-1: Preparation of methyl (2-ethoxy-2-oxoethyl)-D-serinate

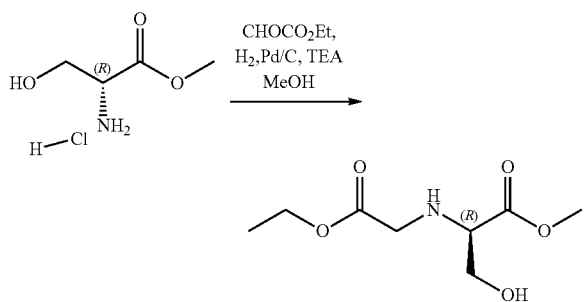

Ethyl oxoacetate (50%) (9.84 g, 48.20 mmol), Triethyl amine (5.36 mL, 38.56 mmol) and Pd/C (50% moisture) (0.6 g) was added to a solution of methyl D-serinate hydrochloride (5.0 g, 32.13 mmol) in MeOH (50 mL) and hydrogenated (balloon) at room temperature for 48 hrs. The reaction mixture was filtered through a pad of celite and concentrated. The crude product was purified using flash chromatography, eluting with 0.8% MeOH in DCM, to yield methyl (2-ethoxy-2-oxoethyl)-D-serinate as a colorless gum (3.84 g, 58.2%). LCMS (Method-H): 72.65% (RT: 1.671, 202.0 nm) (MS: ESI +ve 206.25 [M+H]).

Step-2: Preparation of methyl N-(2-ethoxy-2-oxoethyl)-O-(methylsulfonyl)-D-serinate

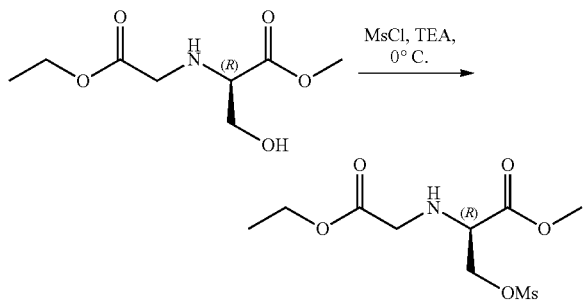

To a stirred solution of methyl (2-ethoxy-2-oxoethyl)-D-serinate (3.84 g, 18.71 mmol) in DCM (80 mL) was added triethyl amine (5.2 mL, 37.42 mmol) at 0° C. Mesylchloride (2.55 g, 22.45 mmol) was added, and the reaction was stirred at 0° C. for 1 hr. The mixture was diluted with water (150 mL) and extracted with DCM (3×150 mL), dried over sodium sulfate and concentrated under vacuum. The crude methyl N-(2-ethoxy-2-oxoethyl)-O-(methylsulfonyl)-D-serinate was used directly in the next step without further purification (5.3 g).

Step-3: Preparation of methyl (R)-3-azido-2-((2-ethoxy-2-oxoethyl)amino)propanoate

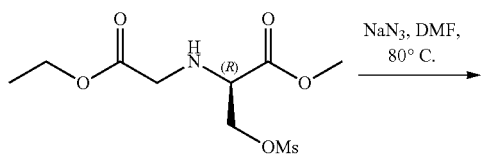

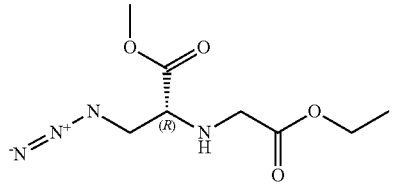

Sodium azide (6.08 mL, 93.63 mmol) was added to a solution of methyl N-(2-ethoxy-2-oxoethyl)-O-(methylsulfonyl)-D-serinate (5.3 g, 18.71 mmol) in DMF (80 mL) and heated at 80° C. for 3.5 hr. The mixture was diluted with water (150 mL) and extracted with ethyl acetate (3×150 mL), dried over sodium sulfate and concentrated under vacuum to give methyl (R)-3-azido-2-((2-ethoxy-2-oxoethyl)amino)propanoate, which was used directly in the next step (4.3 g, Crude).

Step-4: Preparation of methyl (R)-5-oxopiperazine-2-carboxylate

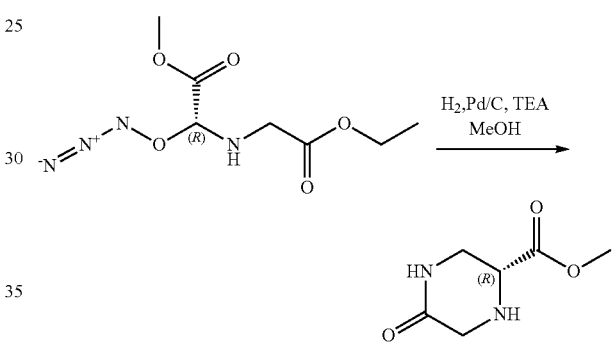

To a stirred solution of methyl (R)-3-azido-2-((2-ethoxy-2-oxoethyl)amino)propanoate (4.3 g, 18.72 mmol) dissolved in MeOH (50 mL) was added TEA(5.36 mL, 38.56 mmol) and Pd/C (50% moisture) (2.25 g). The reaction mixture was hydrogenated (balloon) at room temperature for 48 hr. The mixture was filtered through a pad of celite then concentrated. The crude product was purified using flash chromatography on basic alumina, eluting with 1.5% MeOH in DCM, to yield methyl (R)-5-oxopiperazine-2-carboxylate (0.52 g, 17.3%). LCMS (Method-G): 91.29% (RT: 3.706, 202.4 nm) (MS: ESI +ve 159.2 [M+H]).

Step-5: Preparation of methyl (R)-1-methyl-5-oxopiperazine-2-carboxylate

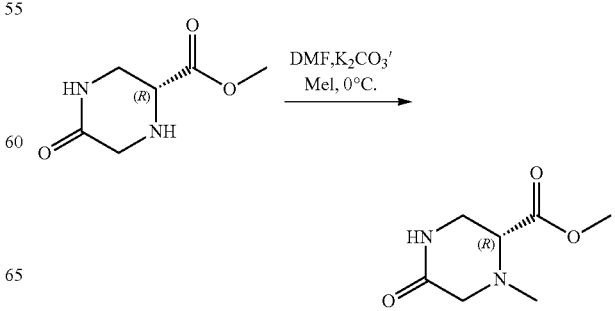

To a stirred solution of methyl (R)-5-oxopiperazine-2-carboxylate (0.16 g, 3.291 mmol) in DMF (10 mL) was added potassium carbonate (0.908 g, 6.582 mmol) at 0° C. Methyl iodide (0.514 g, 3.620 mmol) was added, and the mixture was stirred at room temperature for 16 hr. The mixture was diluted with water (50 mL), extracted with ethyl acetate (3×50 mL), dried over sodium sulfate and concentrated under vacuum. The crude product was purified using flash chromatography on basic alumina, eluting with 1.3% MeOH in DCM, to yield methyl (R)-1-methyl-5-oxopiperazine-2-carboxylate as a yellow solid (0.22 g, 50.52%) LCMS (Method-G): 78.34% (RT: 4.588, 210.0 nm) (MS: ESI +ve 173.2 [M+H]).

Step-6: Preparation of methyl (R)-4-(4-(tert-butoxycarbonyl)benzyl)-1-methyl-5-oxopiperazine-2-carboxylate

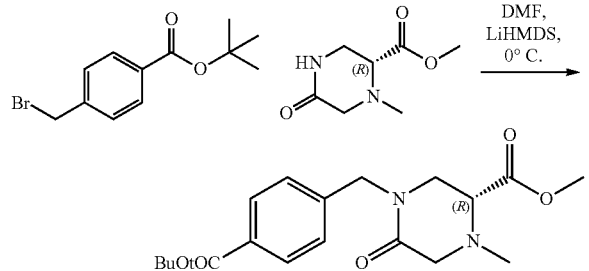

To a stirred solution of methyl (R)-1-methyl-5-oxopiperazine-2-carboxylate (0.22 g, 1.279 mmol) in DMF (5 mL) was added LiHMDS (1M in THF) (1.66 mL, 1.662 mmol) at 0° C. tert-butyl 4-(bromomethyl)benzoate (0.381 g, 1.406 mmol) was added and the mixture was stirred at room temperature for 4 hrs. The mixture was diluted with water (50 mL), extracted using ethyl acetate (3×50 mL), dried over sodium sulfate and concentrated under vacuum. The crude product was purified using flash chromatography, eluting with 1.0% MeOH in DCM, to yield methyl (R)-4-(4-(tert-butoxycarbonyl)benzyl)-1-methyl-5-oxopiperazine-2-carboxylate as a yellow solid (0.2 g, 43.19%) LCMS (Method-C2): 80.24% (RT: 1.241, 238.0 nm) (MS: ESI +ve 363.36 [M+H]).

Step-7: Preparation of (R)-4-((5-(methoxycarbonyl)-4-methyl-2-oxopiperazin-1-yl)methyl)benzoic acid

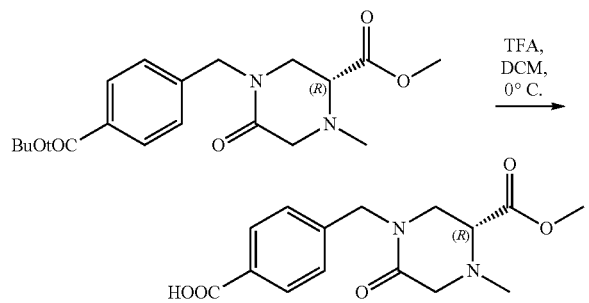

Methyl (R)-4-(4-(tert-butoxycarbonyl)benzyl)-1-methyl-5-oxopiperazine-2-carboxylate (0.2 g, 0.551 mmol) was dissolved in DCM (5 mL). Trifloroacetic acid (0.5 mL) was added dropwise at 0° C. The mixture was stirred at room temperature for 4 hrs then concentrated to give (R)-4-((5-(methoxycarbonyl)-4-methyl-2-oxopiperazin-1-yl)methyl)benzoic acid as a TFA salt (0.23 g) LCMS (Method-G): 79.80% (RT 4.690, 230.0 nm) (MS: ESI +ve 307.2 [M+1]).

Step 8: Preparation of methyl (R)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylate

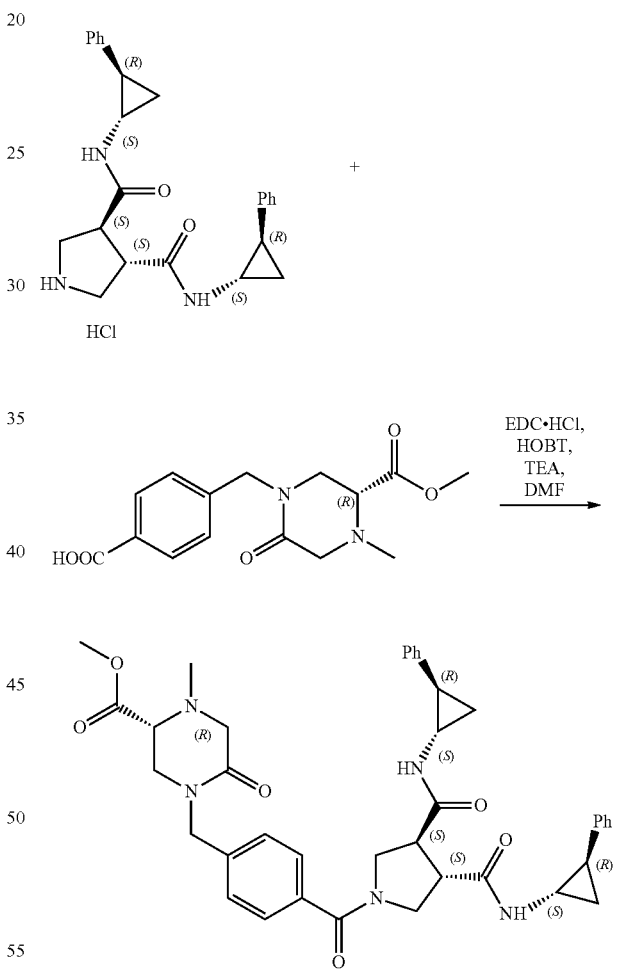

Prepared using a procedure similar to General EDC, HOBT Coupling Procedure. The crude was purified using flash chromatography, eluting with 3% MeOH in DCM, to give methyl (R)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylate (0.16 g, 43.2%). LCMS (Method-G): 77.36% (RT 9.622, 225.0 nm) (MS: ESI +ve 678.2 [M+1]).

557

Step 9: Preparation of (R)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylic acid

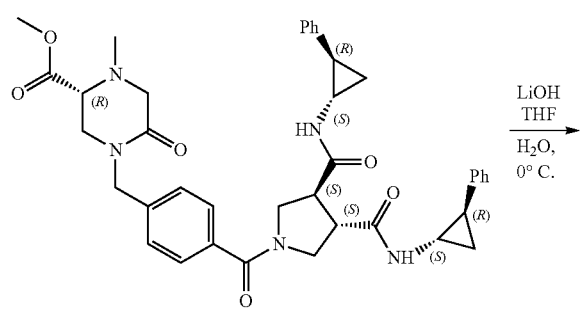

558

-continued

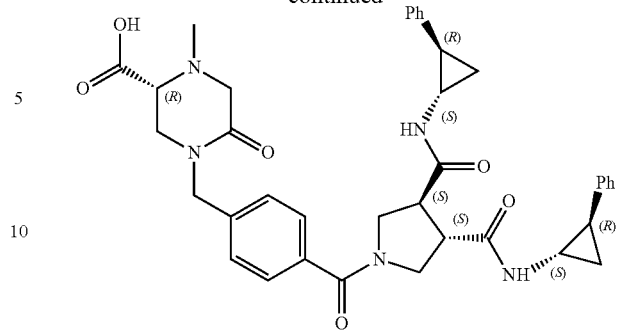

Prepared using a procedure similar to General Ester Hydrolysis Procedure to give (R)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylic acid (0.14 g, 89%) LCMS (Method-C3): 84.14% (RT 1.516, 230 nm) (MS: ESI +ve 664.36 [M+H]).

Step-10: Preparation of (3S,4S)-1-(4-(((R)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide, Compound 092

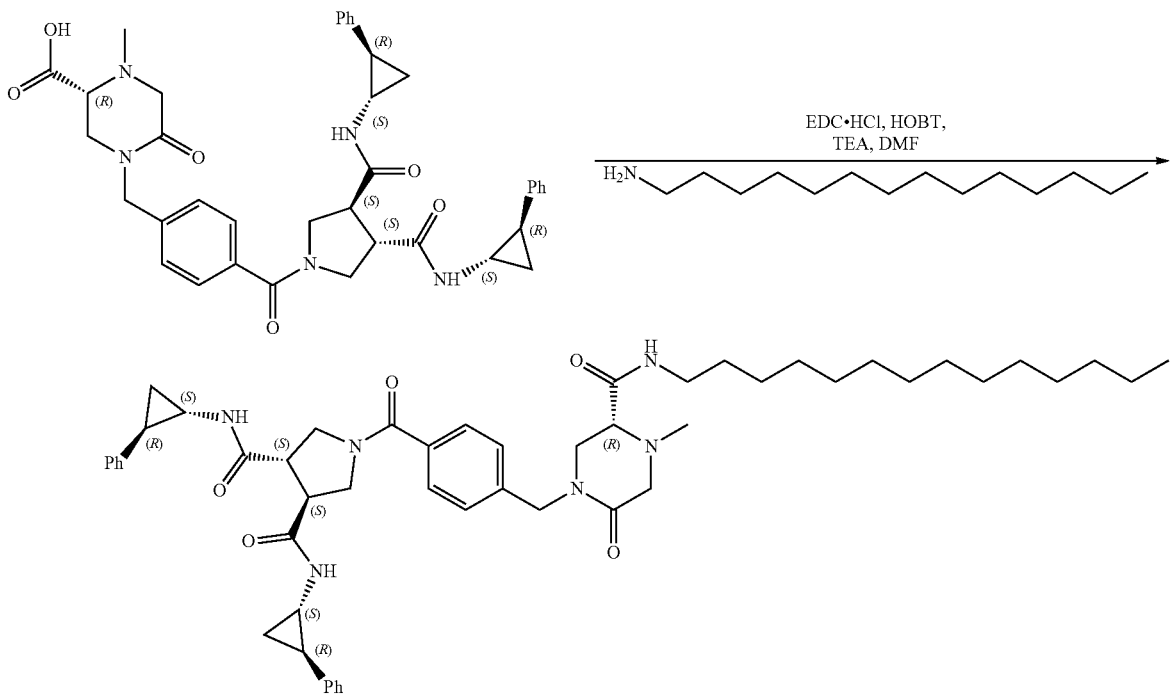

Prepared using a procedure similar to General EDC, HOBT Coupling Procedure. The crude product was purified using Prep HPLC Method 1 to give (3S,4S)-1-(4-(((R)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide (Compound 092)(0.03 g, 16.5%). LCMS (Method-C-Fast): 100% (RT 2.770, 222.0 nm) (MS: ESI +ve 859.65 [M+H]). $^1$H NMR: (400 MHz, DMSO) δ ppm: 0.83-0.85 (m, 3H), 1.10-1.35 (m, 28H), 1.86 (s, 1H), 1.96 (s, 1H), 2.21 (s, 3H), 2.67 (m, 1H), 2.78-2.84 (m, 2H), 2.98-3.07 (m, 4H), 3.18 (s, 2H), 3.34 (m, 2H), 3.42-3.50 (m, 2H), 3.66 (m, 1H), 3.78 (m, 1H), 4.44-4.51 (s, 1H), 4.59-4.65 (m, 1H), 7.06-7.30 (m, 12H), 7.48-7.50 (d, J=8 Hz, 2H), 8.08 (s, 1H), 8.29 (s, 1H), 8.43 (s, 1H).

Synthesis of (3S,4S)-1-(4-(((S)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide, Compound 093

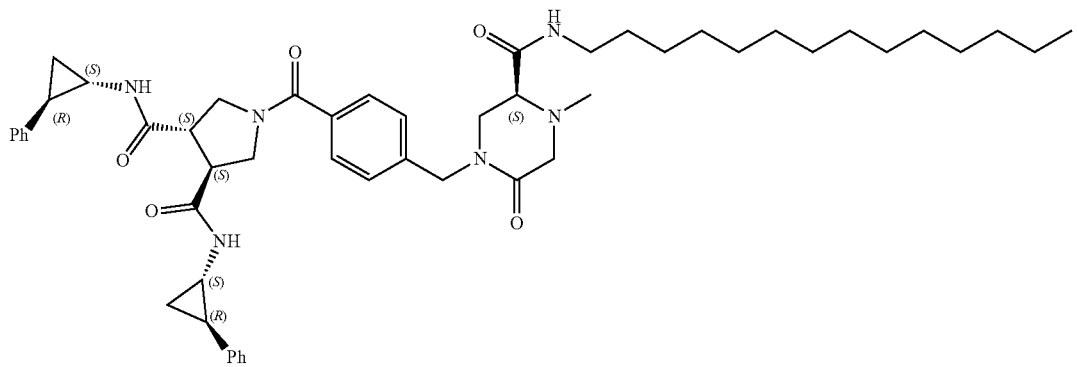

Prepared by a procedure similar to that reported for (3S,4S)-1-(4-(((R)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide (Compound 092), substituting the applicable amine in step 1. The final product was purified using Prep HPLC Method 6 to give (3S,4S)-1-(4-(((S)-4-methyl-2-oxo-5-(tetradecylcarbamoyl)piperazin-1-yl)methyl)benzoyl)-N3,N4-bis((1S,2R)-2-phenylcyclopropyl)pyrrolidine-3,4-dicarboxamide (Compound 093)(0.03 g, 11.59%). LCMS (Method-J): 100% (RT 6.563, 202.0 nm) (MS: ESI +ve 860.0 [M+H]). $^1$H NMR: (400 MHz, DMSO) δ ppm: 0.83-0.85 (m, 3H), 1.10-1.32 (m, 2H), 1.22 (bs, 24H), 1.35 (bs, 2H), 1.86 (s, 1H), 1.96 (s, 1H), 2.21 (s, 3H), 2.67 (m, 1H), 2.77 (m, 1H), 2.84 (m, 1H), 3.46-3.52 (m, 3H), 3.63-3.66 (s, 1H), 3.77-3.80 (m, 1H), 3.44-3.51 (m, 1H), 4.59-4.65 (m, 1H), 7.06-7.30 (m, 12H), 7.48-7.49 (m, 2H), 8.09 (s, 1H), 8.32 (s, 1H), 8.45 (s, 1H), 8.45 (s, 1H).

Synthesis of (3S,4S)-1-(4-(((S)-4-methyl-3-(tetradecylcarbamoyl) piperazin-1-yl) methyl) benzoyl)-N3,N4-bis((1S,2R)-2-phenylcyclopropyl) pyrrolidine-3,4-dicarboxamide, Compound 088

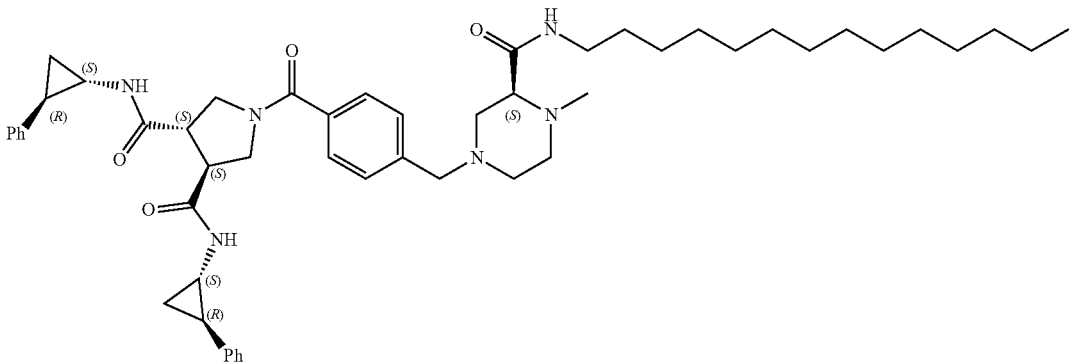

Step-1: Preparation of (3S,4S)-1-(4-(chloromethyl)benzoyl)-N3,N4-bis((1S,2R)-2-phenylcyclopropyl)pyrrolidine-3,4-dicarboxamide

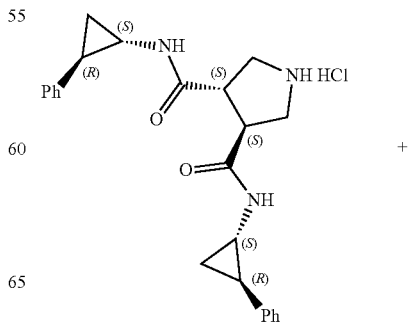

561

-continued

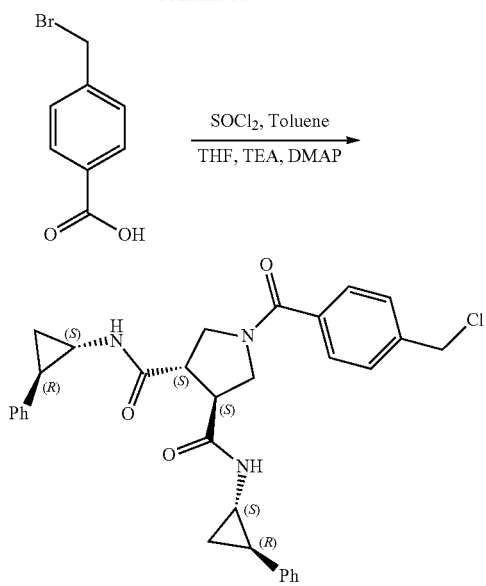

562

To a stirred solution of 4-(bromomethyl) benzoic acid (0.2 g, 0.93 mmol) dissolved in toluene (2 mL), was added thionyl chloride (0.07 mL, 0.93 mmol), and the reaction mixture was stirred at 80° C. for 16 hours. Toluene and excess thionyl chloride were evaporated in vacuo and replaced with tetrahydrofuran (3 mL). To this solution was added (3S,4S)—N3,N4-bis((1S,2R)-2-phenylcyclopropyl) pyrrolidine-3,4-dicarboxamide-1-methane (1/1) hydrochloride (0.27 g, 0.65 mmol), triethylamine (0.15 mL, 1.02 mmol) and 4-dimethylaminopyridine (0.009 g, 0.074 mmol). The reaction mixture was stirred at 65° C. for 4 hours. Ice cold water was added, and the mixture was extracted using ethyl acetate (3×30 mL). The organic layer was washed with brine (2×20 mL), dried over anhydrous sodium sulfate and concentrated under reduced pressure. The crude product was purified using flash chromatography, eluting with 0-10% MeOH in DCM, to give (3S,4S)-1-(4-(chloromethyl) benzoyl)-N3,N4-bis((1S,2R)-2-phenylcyclopropyl) pyrrolidine-3,4-dicarboxamide (0.09 g, 25.7%) LCMS (Method-X): 100% (RT: 1.001, 235.0 nm) (MS: ESI +ve 542[M+H]).

Step-2: Preparation of (3S,4S)-1-(4-(((S)-4-methyl-3-(tetradecylcarbamoyl) piperazin-1-yl) methyl) benzoyl)-N3,N4-bis((1S,2R)-2-phenylcyclopropyl) pyrrolidine-3,4-dicarboxamide, Compound 088

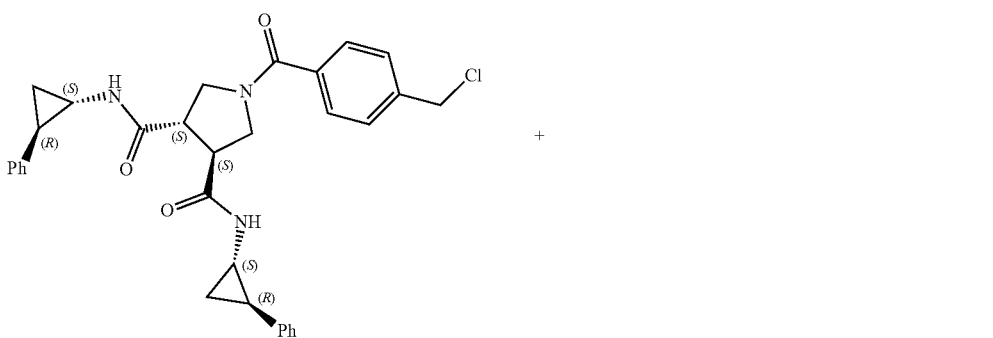

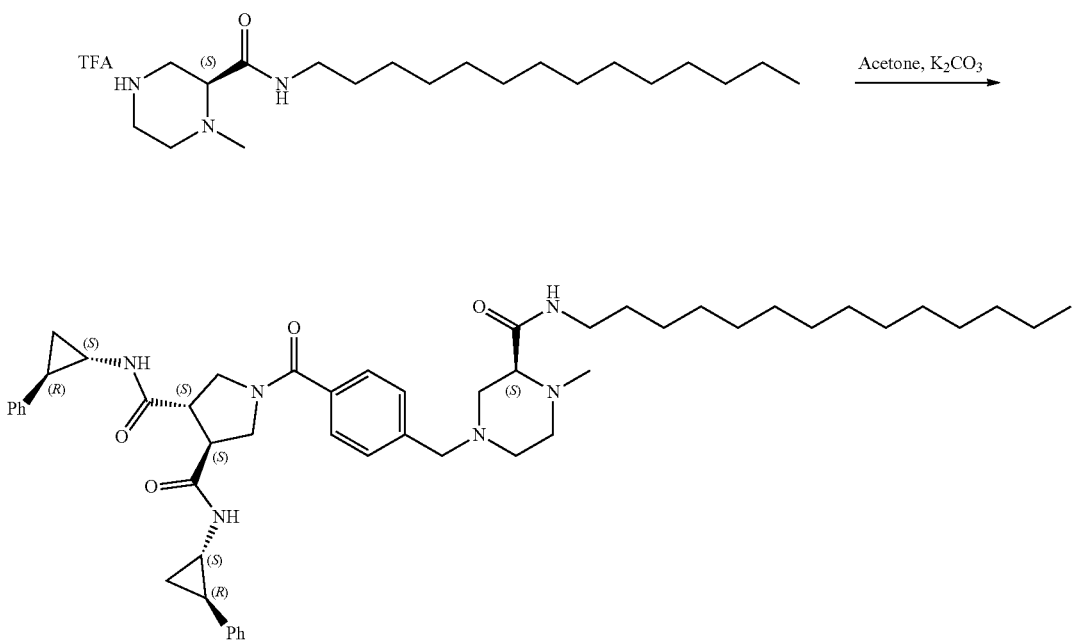

To a stirred solution of (3S,4S)-1-(4-(chloromethyl) benzoyl)-N3,N4-bis((1S,2R)-2-phenylcyclopropyl) pyrrolidine-3,4-dicarboxamide (0.05 g, 0.095 mmol) in DMF (2 mL) was added (S)-1-Methyl-N-tetradecylpiperazine-2-carboxamide (0.049 g, 0.014 mmol) followed by potassium carbonate (0.04 g, 0.28 mmol). The reaction mixture was stirred at room temperature for 16 hr. Ice cold water was added and the resulting precipitate was collected by filtration, dried, and purified using Prep HPLC Method 10 to give (3S,4S)-1-(4-(((S)-4-methyl-3-(tetradecylcarbamoyl) piperazin-1-yl) methyl) benzoyl)-N3,N4-bis((1S,2R)-2-phenylcyclopropyl) pyrrolidine-3,4-dicarboxamide (Compound 088)(0.007 g, 8.6%). LCMS (Method-H): 100% (RT 5.520, 220.0 nm) (MS: ESI +ve 846 [M+H]). $^1$H NMR: (400 MHz, DMSO) δ ppm: 0.84-0.86 (d, J=6.8, 3H); 1.24 (s, 30H); 1.37 (s, 3H); 1.87 (s, 1H); 1.97 (s, 1H); 2.18 (s, 6H); 2.68 (s, 4H); 2.78 (s, 3H); 3.09-3.11 (d, J=8, 3H); 3.18-3.20 (d, J=8.4, 1H); 3.49-3.54 (t, 3H); 3.67 (s, 1H); 3.79 (s, 1H); 7.07-7.17 (m, 6H); 7.23-7.27 (t, 4H); 7.34-7.36 (d, J=7.6, 2H); 7.47-7.49 (d, J=8, 2H); 7.77 (s, 1H); 8.30 (s, 1H); 8.43 (s, 1H).

Synthesis of (3S,4S)-1-(4-(((R)-4-methyl-3-(tetradecylcarbamoyl) piperazin-1-yl) methyl) benzoyl)-N3,N4-bis((1S,2R)-2-phenylcyclopropyl) pyrrolidine-3,4-dicarboxamide, Compound 084

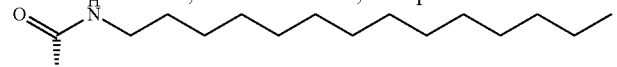
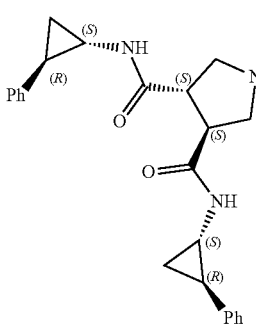

Prepared by a procedure similar to that reported for (3S,4S)-1-(4-(((S)-4-methyl-3-(tetradecylcarbamoyl) piperazin-1-yl) methyl) benzoyl)-N3,N4-bis((1S,2R)-2-phenylcyclopropyl) pyrrolidine-3,4-dicarboxamide (Compound 088), using the applicable starting materials. The crude product was purified by flash chromatography, eluting with 1-2% of MeOH:DCM, to give (3S,4S)-1-(4-(((R)-4-methyl-2-oxo-5-(tetradecylcarbamoyl) piperazin-1-yl)methyl)benzoyl)-N3,N4-bis((1S,2R)-2-phenylcyclopropyl)pyrrolidine-3,4-dicarboxamide (Compound 084)(0.035 g, 9.65%), as an off white solid. LCMS (Method-H2): 99.66% (RT 5.692, 202.0 nm) (MS: ESI − ve 843.65 [M−H]). $^1$H NMR: (400 MHz, DMSO) δ ppm: 0.84 (s, 3H), 1.10-1.35 (m, 31H), 1.85 (s, 1H), 1.96-2.04 (m, 2H), 2.09 (s, 3H), 2.15-2.17 (d, J=6.4 Hz, 2H), 2.33 (s, 1H), 2.67 (s, 3H), 2.77 (s, 2H), 2.84 (s, 1H), 3.01-3.20 (m, 5H), 3.45-3.52 (m, 4H), 3.66 (s, 1H), 3.78 (s, 1H), 7.06-7.16 (m, 6H), 7.24-7.26 (d, J=7.6 Hz, 4H), 7.33-7.35 (d, J=7.6 Hz, 2H), 7.46-7.48 (d, J=7.6 Hz, 2H), 7.75 (s, 1H), 8.29 (s, 1H), 8.43 (s, 1H).

Synthesis of (3S,4S)-1-(4-(((R)-3-(hexylcarbamoyl)-4-octanoylpiperazin-1-yl)methyl) benzoyl)-N3,N4-bis((1S,2R)-2-phenylcyclopropyl)pyrrolidine-3,4-dicarboxamide, Compound 121

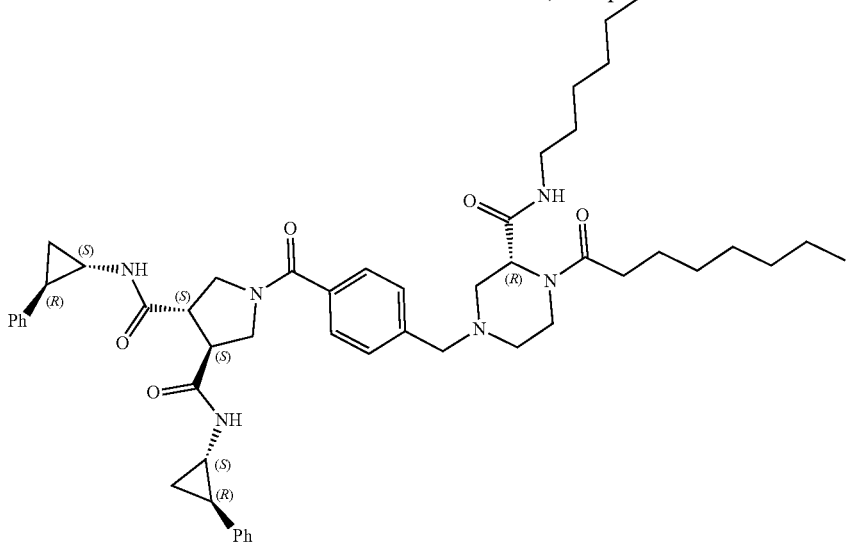

Step-1: Preparation of tert-butyl (R)-4-((3-(hexyl-carbamoyl)-4-octanoylpiperazin-1-yl)methyl)benzoate

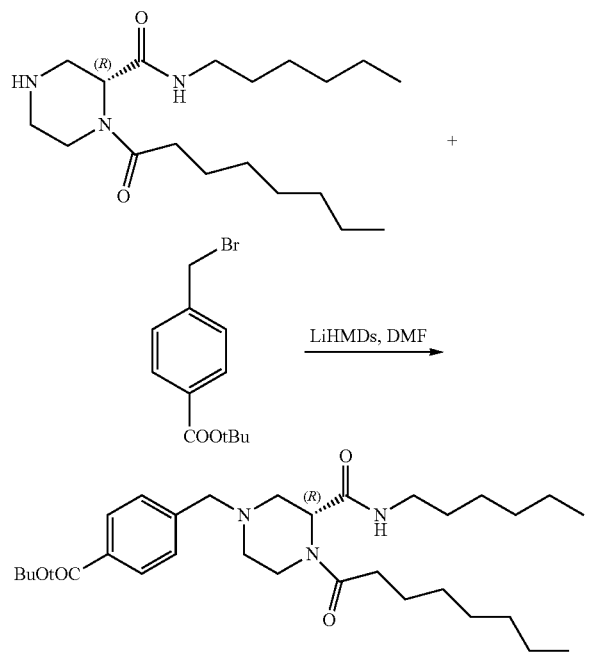

(R)—N-hexyl-1-octanoylpiperazine-2-carboxamide (1.0 g, 2.900 mmol) was dissolved in DMF (10 mL) and cooled to 0° C. LiHMDs (3.82 mL, 3.800 mmol) was added dropwise and the mixture was stirred for 5-10 mins. t-butyl 4-(bromomethyl)benzoate (0.878 g, 3.200 mmol) was added. After 3 hr, the mixture was extracted with ethyl acetate (2×20 mL), washed with water (2×20 mL) and concentrated to dryness. The crude product was purified using flash chromatography, eluting with 0-10% DCM in MeOH, (0.70 g, 47.2%). LCMS (Method-C3): 85.2% (RT: 1.665, 235 nm) (MS: ESI +ve 530.4 [M+1]).

Step-2: Preparation of (R)-4-((3-(hexylcarbamoyl)-4-octanoylpiperazin-1-yl)methyl) benzoic acid

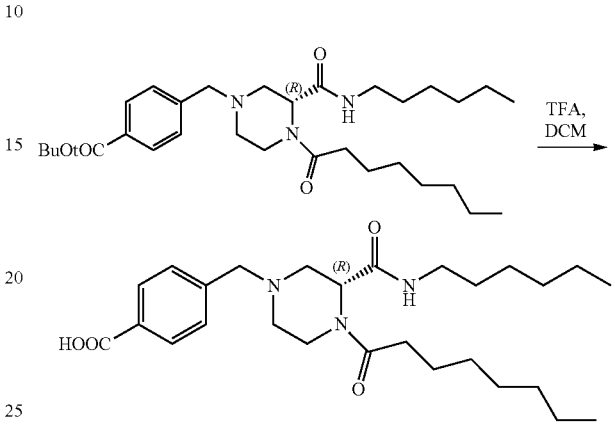

Prepared using General BOC Deprotection Procedure to give (R)-4-((3-(hexylcarbamoyl)-4-octanoylpiperazin-1-yl)methyl)benzoic acid (0.89 g crude). LCMS (Method-C3): 57.9% (RT: 1344, 202 nm) (MS: ESI +ve 474.6 [M+1])

Step-6: Preparation of (3S,4S)-1-(4-(((R)-3-(hexyl-carbamoyl)-4-octanoylpiperazin-1-yl)methyl)benzoyl)-N3,N4-bis((1S,2R)-2-phenylcyclopropyl)pyrrolidine-3,4-dicarboxamide, Compound 121

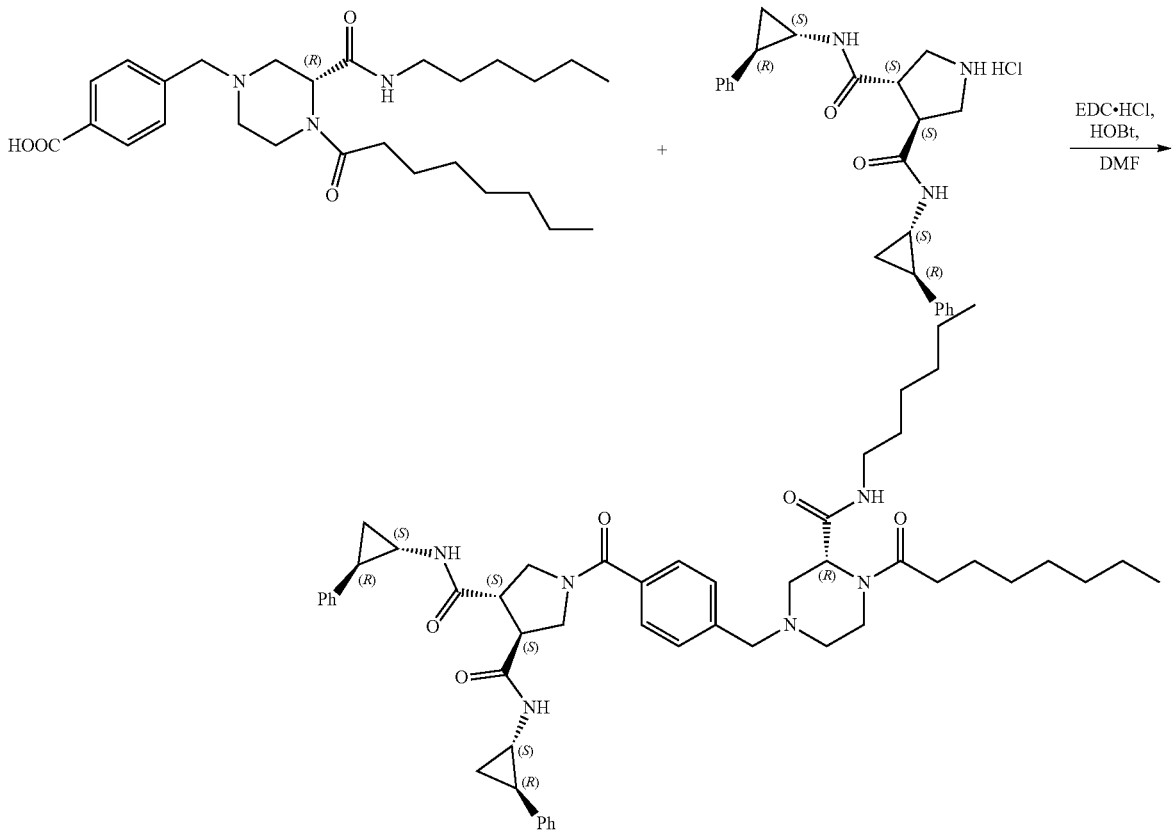

Prepared using General EDC, HOBT Coupling Procedure. The crude product was purified using Prep HPLC Method 12 to give (3S,4S)-1-(4-(((R)-4-heptyl-3-(hexylcarbamoyl)piperazin-1-yl)methyl)benzoyl)-N3,N4-bis((1S,2R)-2-phenylcyclopropyl)pyrrolidine-3,4-dicarboxamide (Compound 121)(0.030 g, 9.3%), as a white solid. LCMS (Method-H): 100% (RT: 4.246, 220.0 nm) (MS: ESI +ve 844.6 [M−1]). $^1$H NMR: (400 MHz, DMSO) δ ppm: 0.828-0.875 (m, 5H), 1.089-1.250 (m, 13H), 1.358-1.485 (m, 6H), 1.862 (s, 3H), 1.979 (s, 3H), 2.774-2.785 (m, 3H), 2.739 (s, 2H), 3.041-3.109 (m, 3H), 3.181-3.203 (m, 3H), 3.401-3.438 (m, 2H), 3.465-3.593 (m, 4H), 3.657-3.777 (m, 3H), 3.798-3.829 (m, 2H), 7.070-7.190 (m, 5H), 7.232-7.296 (m, 4H), 7.450-7.470 (m, 3H), 7.635-7.649 (m, 2H), 7.816 (m, 1H), 8.306-8.318 (d, J=4.8 Hz, 2H), 8.433-8.442 (m, 2H).

Synthesis of (3S,4S)-1-(4-(((S)-3-(hexylcarbamoyl)-4-octanoylpiperazin-1-yl) methyl) benzoyl)-N3,N4-bis((1S,2R)-2-phenylcyclopropyl) pyrrolidine-3,4-dicarboxamide, Compound 122

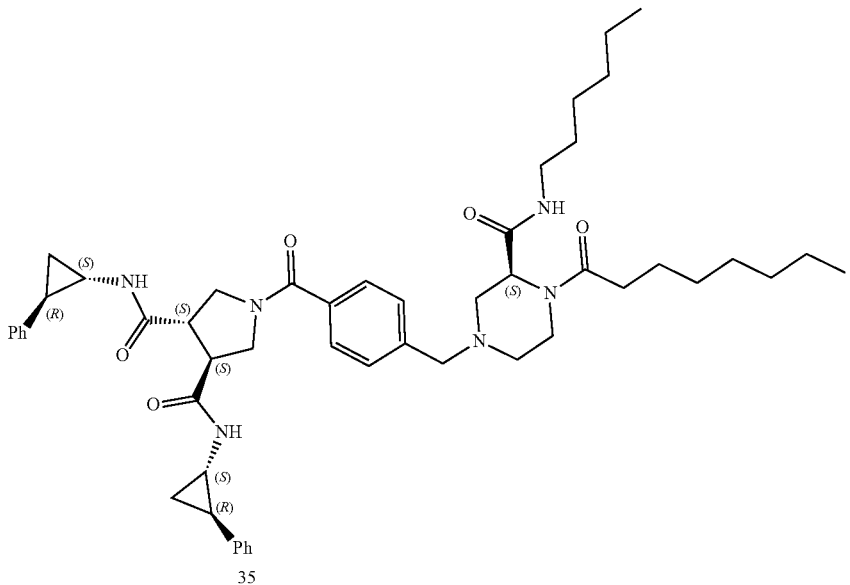

Prepared by a procedure similar to that reported for (3S,4S)-1-(4-(((R)-4-heptyl-3-(hexylcarbamoyl)piperazin-1-yl)methyl)benzoyl)-N3,N4-bis((1S,2R)-2-phenylcyclopropyl)pyrrolidine-3,4-dicarboxamide (Compound 121), using the applicable amine and carboxylic acid. The crude final product was purified using Prep HPLC Method 3 to give (3S,4S)-1-(4-(((S)-3-(hexylcarbamoyl)-4-octanoylpiperazin-1-yl) methyl) benzoyl)-N3,N4-bis((1S,2R)-2-phenylcyclopropyl) pyrrolidine-3,4-dicarboxamide (Compound 122), as a white solid (0.102 g, 19.06%). LCMS (Method-J): 100% (RT 5.460, 202.0 nm) (MS: ESI +ve 846 [M+H]). $^1$H NMR: (400 MHz, DMSO) δ ppm: 0.85-0.87 (m, 6H); 1.09-1.14 (m, 16H); 1.46-1.48 (m, 4H); 1.86-1.97 (m, 1H); 1.97-2.03 (m, 3H); 2.13 (s, 1H); 2.28-2.41 (m, 3H); 2.68 (s, 1H); 2.77-2.79 (m, 2H); 2.86-2.87 (m, 2H); 3.05-3.08 (m, 3H); 3.10-3.16 (m, 1H); 3.18-3.26 (m, 1H); 3.29-3.54 (m, 3H); 3.55-3.64 (m, 2H); 3.66-3.79 (m, 1H); 3.822 (s, 2H); 4.37 (s, 1H); 7.02-7.14 (m, 2H); 7.15-7.19 (m, 3H); 7.23-7.29 (m, 2H); 7.62-7.64 (d, J=5.6, 2H); 8.31 (s, 1H); 8.45 (s, 1H).

Synthesis of (3S,4S)-1-(4-((2-oxo-4-(tetradecylcarbamoyl)pyrrolidin-1-yl)methyl)benzoyl)-N3,N4-bis((1S,2R)-2-phenylcyclopropyl)pyrrolidine-3,4-dicarboxamide, Compound 100

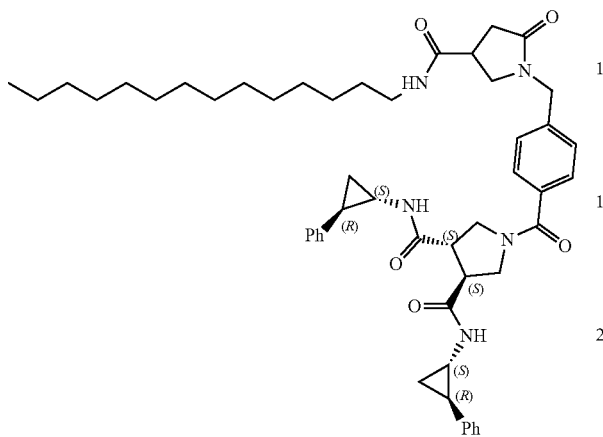

Step 1: Preparation of tert-butyl 4-cyanobenzoate

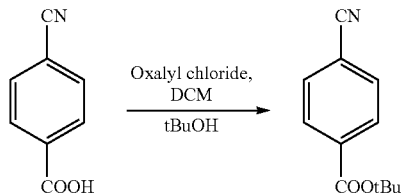

4-cyanobenzoic acid (3.0 g, 20.4 mmol) was dissolved in DCM (10 mL) and cooled to 0° C. Oxalyl chloride (3.86 g, 30.61 mmol) and DMF (1 mL) were added, with stirring continued for 3 hr. The mixture was concentrated then pyridine (10 mL) and t-butanol (10 mL) were added. After 16 h, the reaction was quenched with water (50 mL) and extracted with ethyl acetate (3×100 mL), washed with 10% $KHSO_4$ (50 mL), dried over sodium sulfate and concentrated. The crude product was purified using flash chromatography, eluting with 0.5-1% of MeOH in DCM, to give tert-butyl 4-cyanobenzoate. (2.5 g, 60.33%) $^1$H NMR (400 MHz, DMSO) δ ppm: 1.569 (s, 9H), 7.99-8.068 (m, 4H).

Step 2: Preparation of tert-butyl 4-(aminomethyl)benzoate

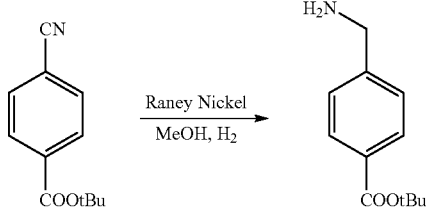

tert-butyl 4-cyanobenzoate (2.5 g, 12.2) was dissolved in MeOH (30 mL). Raney nickel (0.25 g) was added, and the reaction mixture was stirred under hydrogen (balloon) at room temperature for 16 hours. The solids were removed by filtration through celite and the filtrate was concentrated under reduced pressure. The crude product was purified using flash chromatography, eluting with 1-5% MeOH in DCM, to give tert-butyl 4-(aminomethyl)benzoate. (1.5 g, 58.83%). LCMS (Method-C2): 98.95% (RT: 1.002, 238.00 nm) (MS: ESI +ve 208.26 [M+1]).

Step 3: Preparation of (1-(4-(tert-butoxycarbonyl)benzyl)-5-oxopyrrolidine-3-carboxylic acid

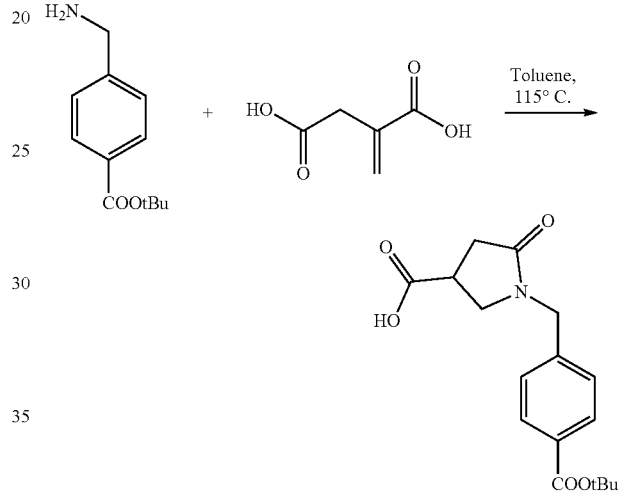

tert-butyl 4-(aminomethyl)benzoate (0.5 g, 2.40 mmol) and 2-methylenesuccinic acid (0.375 g, 2.88 mmol) were dissolved in toluene. The reaction mixture was stirred for 16 hours at 150° C. then concentrated under reduced pressure to give (1-(4-(tert-butoxycarbonyl)benzyl)-5-oxopyrrolidine-3-carboxylic acid. (0.85 g, crude). LCMS (Method-C2): 67.79% (RT: 1.173, 237.00 nm) (MS: ESI +ve 320.38 [M+1]).

Step 4: Preparation of tert-butyl 4-((4-(ethylcarbamoyl)-2-oxopyrrolidin-1-yl)methyl)benzoate

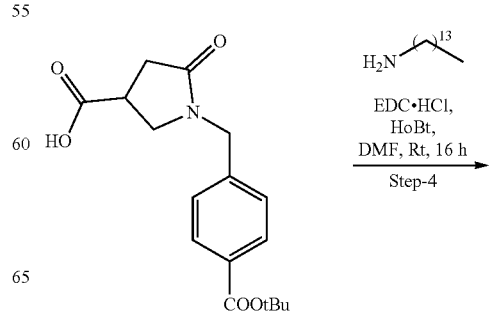

571

-continued

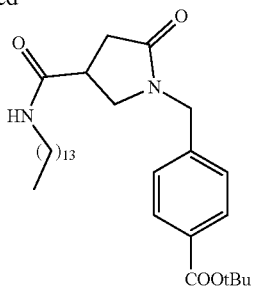

Prepared using General EDC, HOBT Coupling Procedure to give tert-butyl 4-((2-oxo-4-(tetradecylcarbamoyl)pyrrolidin-1-yl)methyl)benzoate. (0.9 g, 97.61%) LCMS (Method-C): 50.7% (RT: 3.066, 235.00 nm) (MS: ESI +ve 515.3 [M+1]).

Step 5: Preparation of 4-((2-oxo-4-(tetradecylcarbamoyl)pyrrolidin-1-yl)methyl)benzoic acid

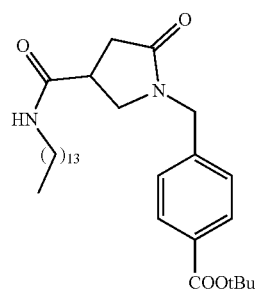

TFA, DCM

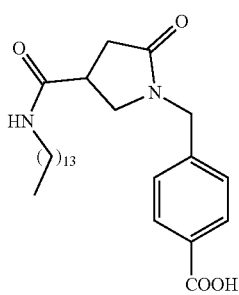

Prepared using General BOC Deprotection Procedure to give 4-((2-oxo-4-(tetradecylcarbamoyl)pyrrolidin-1-yl)methyl)benzoic acid. (0.2 g, 39.78%) LCMs (Method-C2): 46.53% (RT: 1.592, 235.0 nm) (MS: ESI +ve 459.29 [M+1]).

Step 6: Preparation of (3S,4S)-1-(4-((2-oxo-4-(tetradecylcarbamoyl)pyrrolidin-1-yl)methyl)benzoyl)-N3,N4-bis((1S,2R)-2-phenylcyclopropyl)pyrrolidine-3,4-dicarboxamide, Compound 100

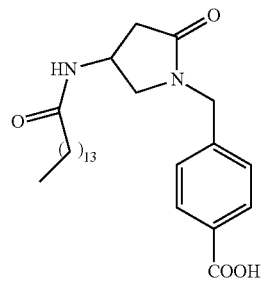

+

572

-continued

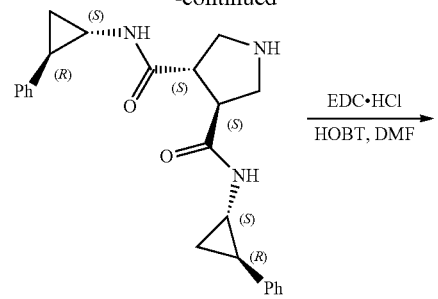

EDC·HCl
HOBT, DMF

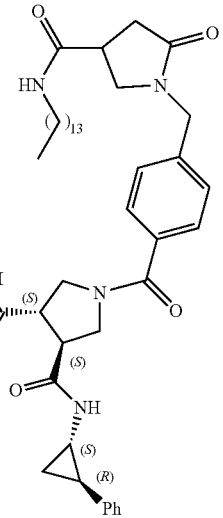

Prepared using General EDC, HOBT Coupling Procedure. The crude was purified Prep-HPLC Method 6 to give (3S,4S)-1-(4-((2-oxo-4-(tetradecylcarbamoyl)pyrrolidin-1-yl)methyl)benzoyl)-N3,N4-bis((1S,2R)-2-phenylcyclopropyl)pyrrolidine-3,4-dicarboxamide (Compound 100)(35 mg, 7.47%). LCMS (Method-J): 99.05% (RT 6.253, 202.0 nm) (MS: ESI +ve 830.43 [M+2]). (400 MHz, DMSO) δ ppm: 0.83-0.85 (d, J=8, 3H), 1.10-1.35 (m, 30H), 1.86-1.96 (d, J=40, 2H), 2.67-2.84 (m, 3H), 3.00-3.24 (m, 9H), 3.33-3.50 (m, 5H), 3.78-3.81 (d, J=12, 2H), 4.10-4.11 (d, J=4, 1H), 4.404 (s, 2H), 7.06-7.29 (m, 12H), 7.48-7.50 (d, J=8, 2H), 7.96 (s, 1H), 8.30-8.42 (d, J=48, 2H).

Synthesis of (3S,4S)-1-(4-((2-oxo-4-tetradecanamidopyrrolidin-1-yl)methyl)benzoyl)-N3,N4-bis((1S, 2R)-2-phenylcyclopropyl)pyrrolidine-3,4-dicarboxamide, Compound 174

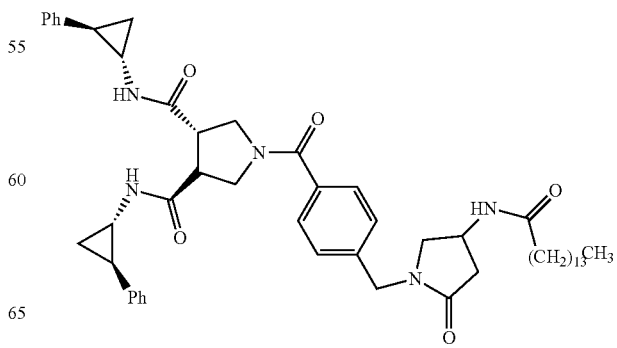

Step-1: Preparation of tert-butyl 4-((4-carbamoyl-2-oxopyrrolidin-1-yl)methyl)benzoate

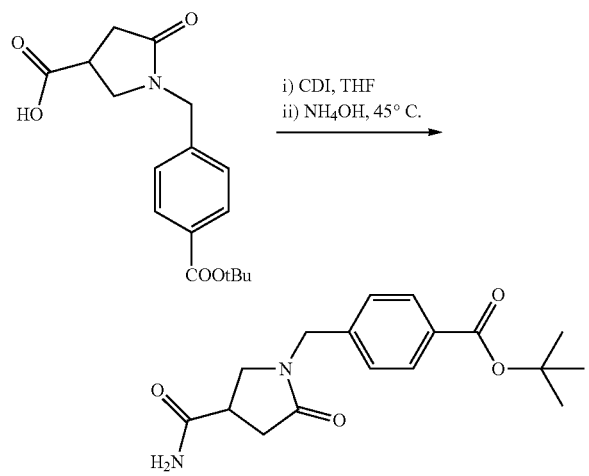

1,1'-Carbonyldiimidazole (CDI) (0.279 g, 1.72 mmol) was added to a solution of 1-(4-(tert-butoxycarbonyl)benzyl)-5-oxopyrrolidine-3-carboxylic acid (0.5 g, 1.56 mmol) in THF (20 mL). Ammonium hydroxide (0.25 mL) was added drop wise and the reaction mixture was stirred at 45° C. for 2 hrs. The mixture was diluted in ethyl acetate (3×30 mL), washed with brine (30 mL), dried and concentrated. The crude product was purified using flash chromatography, eluting with MeOH/DCM, to give tert-butyl 4-((4-carbamoyl-2-oxopyrrolidin-1-yl)methyl)benzoate (0.380 g, 76.23%). LC-MS (Method-C2): 99.08% (RT 1.128, 240.0 nm) (MS: ESI +ve 319.4 [M+1]).

Step-2: Preparation of tert-butyl 4-((4-amino-2-oxopyrrolidin-1-yl)methyl)benzoate

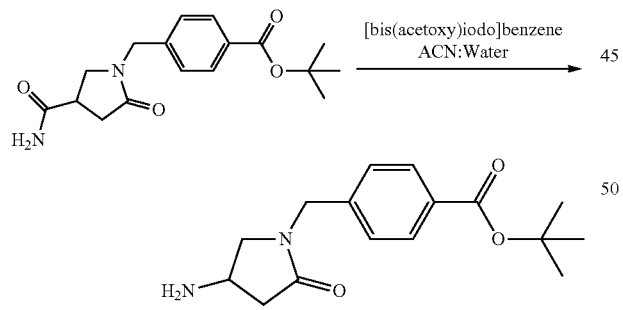

Tert-butyl 4-((4-carbamoyl-2-oxopyrrolidin-1-yl)methyl)benzoate (0.320 g, 1.00 mmol) was dissolved in a mixture of water and acetonitrile (1:1 10 mL) at room temperature. [bis(Acetoxy)iodo]benzene (0.421 g, 1.30 mmol) was added and the mixture was stirred at room temperature for 16 h. The mixture was diluted with ethyl acetate (3×30 mL), washed, and purified by flash chromatography, eluting with 5-10% MeOH/DCM, to give tert-butyl 4-((4-amino-2-oxopyrrolidin-1-yl)methyl)benzoate (0.280 g, 95.94%). LC-MS (Method-H): 83.87% (RT 2.458, 237.0 nm) (MS: ESI +ve 291.1 [M+1]).

Step-3: Preparation of tert-butyl 4-((2-oxo-4-pentadecanamidopyrrolidin-1-yl)methyl)benzoate

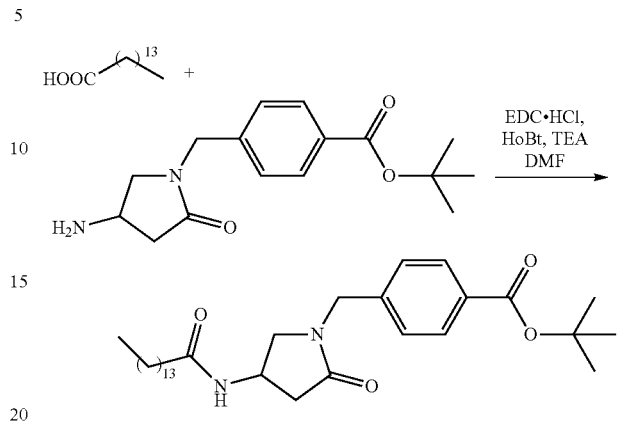

Prepare using General EDC, HOBT Coupling Procedure. The crude product was purified by flash chromatography, eluting with 5-10% MeOH/DCM, to give tert-butyl 4-((2-oxo-4-pentadecanamidopyrrolidin-1-yl)methyl)benzoate as a white solid (0.230 g, 64%). LCMS (Method-J): 93.54% (RT 5.12, 235.0 nm) (MS: ESI +ve 515.9 [M+1].

Step-4: Preparation of 4-((2-oxo-4-pentadecanamidopyrrolidin-1-yl)methyl)benzoic acid

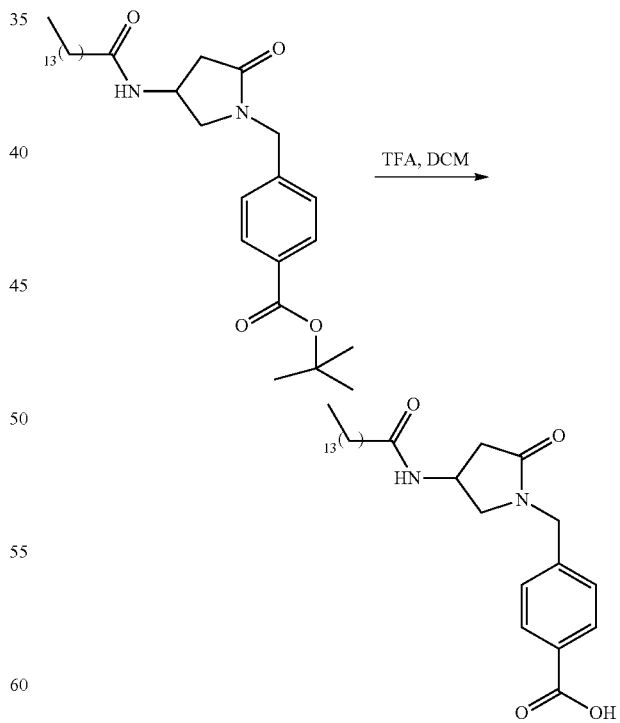

Prepared using General BOC Deprotection Procedure to give 4-((2-oxo-4-pentadecanamidopyrrolidin-1-yl)methyl) benzoic acid (0.150 g, 73%). Confirmed by TLC and the product was used directly in the next step.

Step-5: Preparation of (3S,4S)-1-(4-((2-oxo-4-pentadecanamidopyrrolidin-1-yl)methyl)benzoyl)-N3, N4-bis((1S,2R)-2-phenylcyclopropyl)pyrrolidine-3,4-dicarboxamide, Compound 174

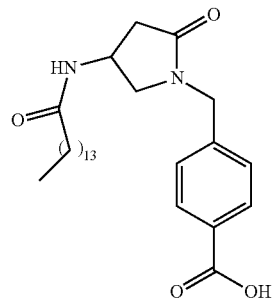

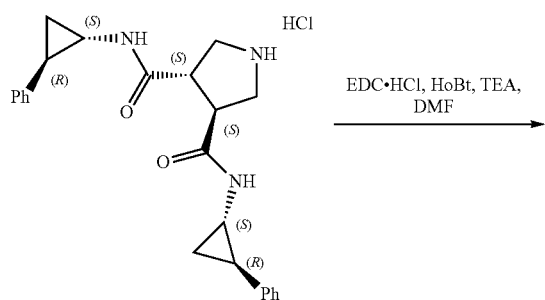

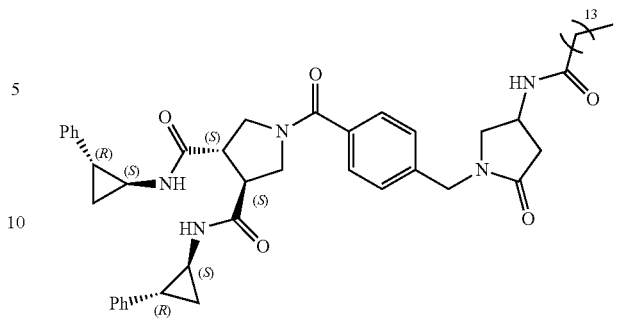

4-Prepared using General EDC, HOBT Coupling Procedure. The crude product was purified Prep HPLC Method 7 to give (3S,4S)-1-(4-((2-oxo-4-pentadecanamidopyrrolidin-1-yl)methyl)benzoyl)-N3,N4-bis((1S,2R)-2-phenylcyclopropyl)pyrrolidine-3,4-dicarboxamide (Compound 174), as an off white solid (0.032 g, 11.79%). LCMS (Method-J): 98.24% (RT 5.178, 214.0 nm) (MS: ESI +ve 831.6 [M+1]. $^1$H NMR: (400 MHz, DMSO) δ ppm: 0.84-0.87 (m, 3H), 1.10-1.24 (m, 19H), 1.44 (s, 2H), 1.87 (s, 1H), 1.87-2.04 (m, 3H), 2.20-2.25 (m, 1H), 2.61-3.22 (m, 6H), 3.49-3.53 (m, 3H), 3.64-3.68 (t, J=0.8 Hz, 1H), 3.77-3.82 (t, J=2.4 Hz, 1H), 4.28 (s, 1H), 4.36-4.48 (m, 2H), 7.07-7.19 (m, 6H), 7.23-7.30 (m, 6H), 7.49-7.51 (d, J=8 Hz, 2H), 8.21-8.22 (d, J=5.2 Hz, 2H), 8.28-8.43 (m, 1H).

Synthesis of (3S,4S)-1-(4-(((R)-2-oxo-3-pentadecanamidopyrrolidin-1-yl)methyl)benzoyl)-N3,N4-bis((1S,2R)-2-phenylcyclopropyl)pyrrolidine-3,4-dicarboxamide, Compound 126

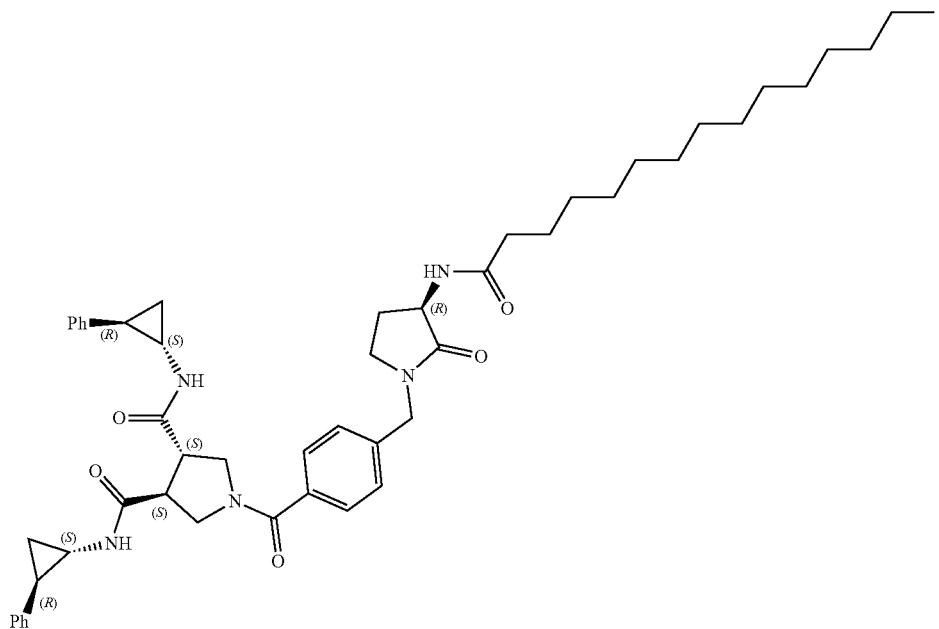

Step-1: Preparation of methyl (R)-4-((2-((tert-butoxycarbonyl)amino)-4-methylthio)butanamido)methyl)benzoate

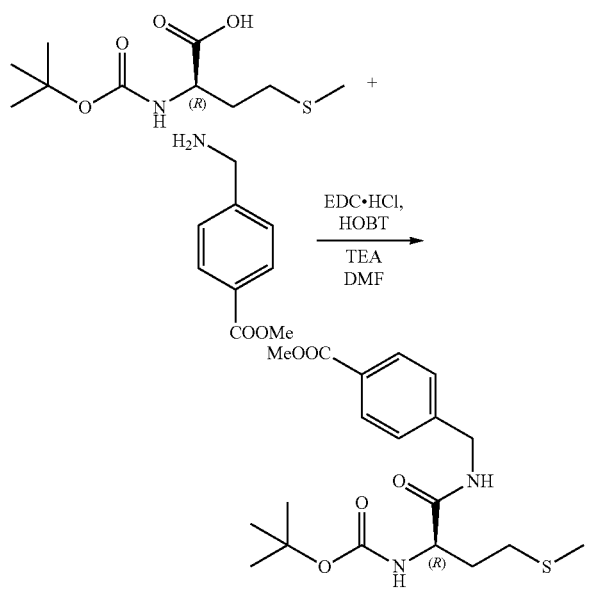

Prepared using General EDC, HOBT Coupling Procedure. The crude product was purified by flash chromatography, eluting in 0-2% MeOH in DCM, to give methyl (R)-4-((2-((tert-butoxycarbonyl)amino)-4-(methylthio)butanamido)methyl)benzoate (1.2 g, 75%). LCMS (Method-C2): 75.64% (RT 1.249, 202.0 nm) (MS: ESI +ve 397.3 [(M+H]).

Step-2: Preparation of methyl (R)-4-((2-((tert-butoxycarbonyl)amino)-4-(iododimethyl-14-sulfaneyl)butanamido)methyl)benzoate

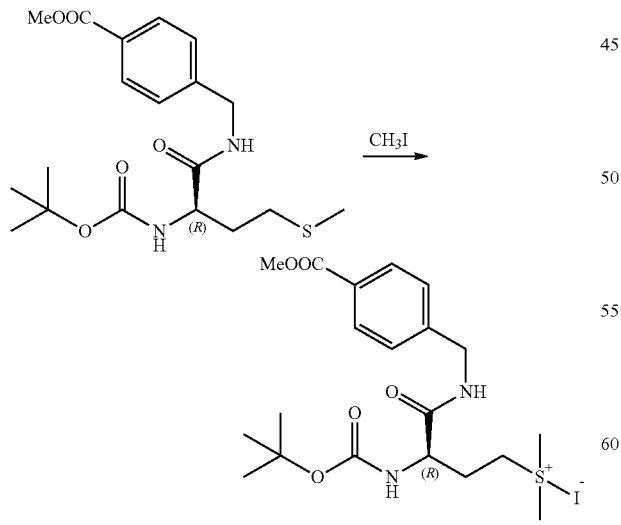

Methyl (R)-4-((2-((tert-butoxycarbonyl) amino)-4-(methylthio)butanamido)methyl)benzoate (0.9 g, 2.26 mmol) was dissolved DCM (10 mL) and methyl iodide (24 g, 172.50 mmol) was added. The reaction mixture was stirred at room temperature for 48 hrs. The solvent was removed under reduced pressure to give methyl (R)-4-((2-((tert-butoxycarbonyl)amino)-4-(iododimethyl-14-sulfaneyl)butanamido)methyl) benzoate (1.2 g), which was used directly in the next step.

Step-3: Preparation of methyl (R)-4-((3-((tert-butoxycarbonyl)amino)-2-oxopyrrolidin-1-yl)methyl)benzoate

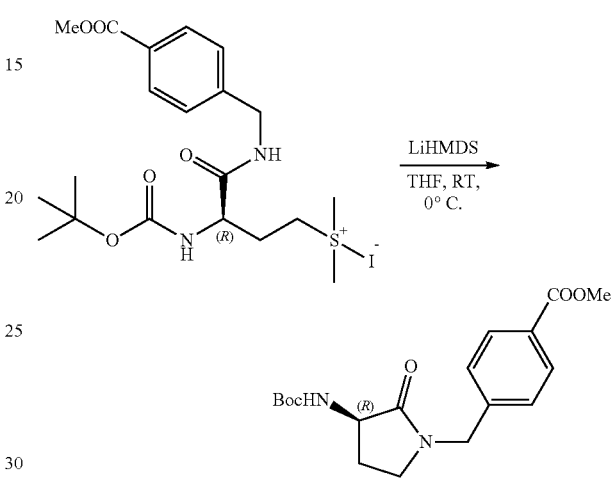

Methyl (R)-4-((2-((tert-butoxycarbonyl)amino)-4-(iododimethyl-14-sulfaneyl)butanamido) methyl) benzoate (1.21 g, 2.23 mmol) was dissolved in THF (30 mL) and cooled to 0° C. 1M LHMDS in THF (2.23 mL, 2.23 mmol) was added and the reaction mixture was stirred at room temperature for 4 hrs. The mixture was extracted with ethyl acetate (3×50 mL), washed with brine (3×30 mL), dried over sodium sulfate and concentrated under reduced pressure. The crude product was purified by flash chromatography, eluting with 10-30% ethyl acetate in hexane, to give methyl (R)-4-((3-((tert-butoxycarbonyl)amino)-2-oxopyrrolidin-1-yl)methyl)benzoate (0.5 g, 64%) as a white solid. LCMS (Method-C2): 100% (RT 1.205, 236.0 nm) (MS: ESI +ve 349.4[(M+H]).

Step-4: Preparation of methyl (R)-4-((3-amino-2-oxopyrrolidin-1-yl)methyl)benzoate TFA salt

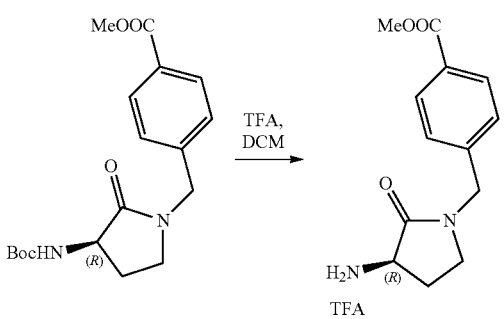

Prepared using General BOC Deprotection Procedure to give methyl (R)-4-((3-amino-2-oxopyrrolidin-1-yl)methyl)benzoate (0.5 g). LC-MS (Method-C2): 100% (RT 0.912, 236.0 nm) (MS: ESI +ve 249.3 [M+1]).

Step 5: Preparation of methyl (R)-4-((2-oxo-3-pentadecanamidopyrrolidin-1-yl)methyl)benzoate

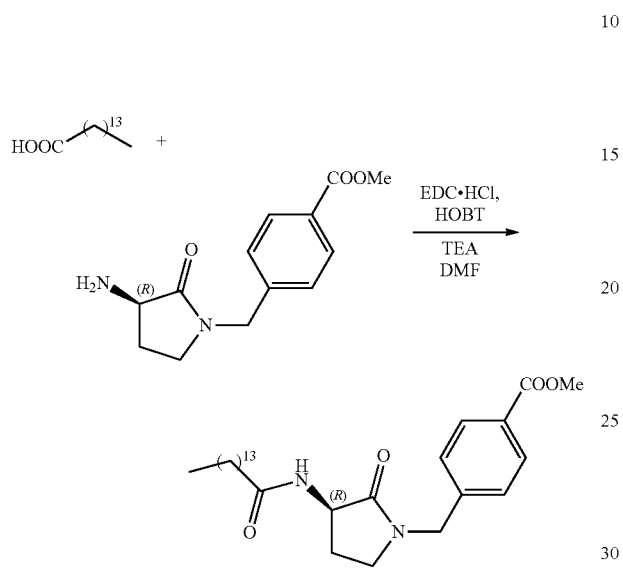

Prepared using General EDC, HOBT Coupling Procedure. The crude product was purified by flash chromatography, eluting with 0-2% MeOH in DCM, to give (R)-4-((2-oxo-3-pentadecanamidopyrrolidin-1-yl)methyl)benzoate (0.5 g, 52%) and was used directly in the next step.

Step 6: Preparation of (R)-4-((2-oxo-3-pentadecanamidopyrrolidin-1-yl)methyl)benzoic acid

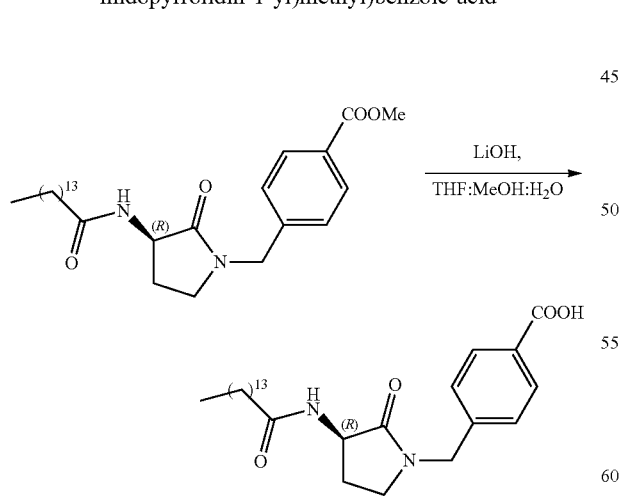

Prepared using General Ester Hydrolysis Procedure to give (R)-4-((2-oxo-3-pentadecanamidopyrrolidin-1-yl)methyl)benzoic acid (0.4 g, 82%). LCMS (Method-C2): 87.75% (RT: 1.649, 235.0 nm) (MS: ESI +ve 459.6[M+1]).

Step 7: Preparation of (3S,4S)-1-(4-(((R)-2-oxo-3-pentadecanamidopyrrolidin-1-yl)methyl)benzoyl)-N3,N4-bis((1S,2R)-2-phenylcyclopropyl)pyrrolidine-3,4-dicarboxamide, Compound 126

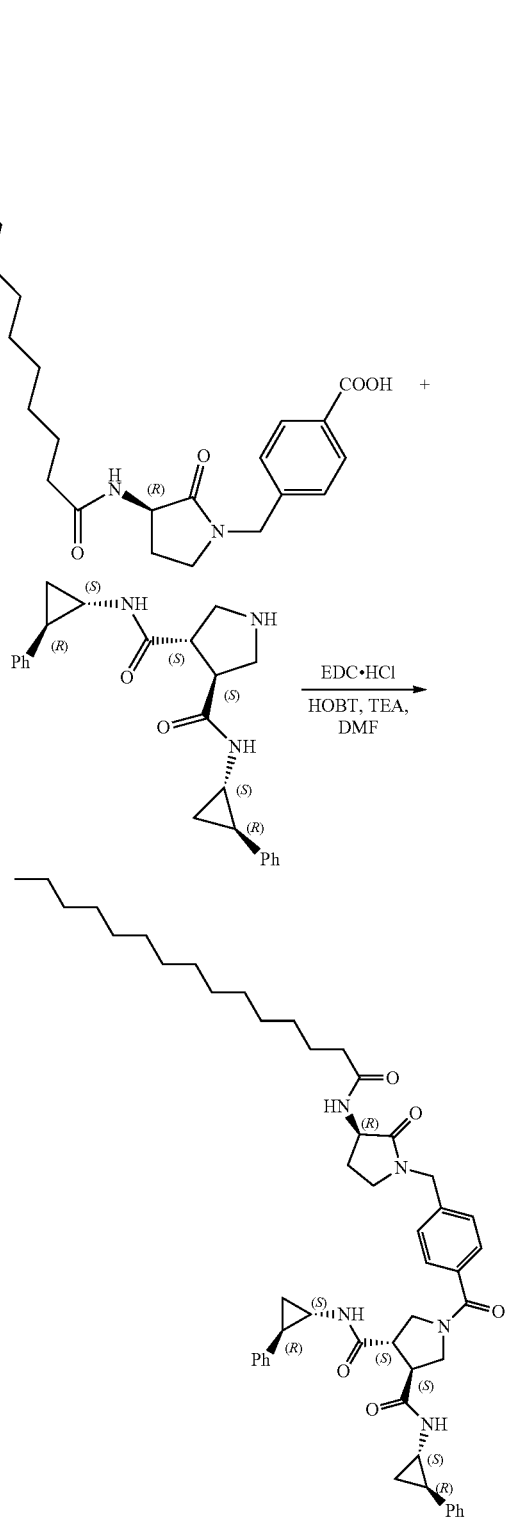

Prepared using General EDC, HOBT Coupling Procedure. Purified using Prep HPLC Method 7 to give (3S,4S)-1-(4-(((R)-2-oxo-3-pentadecanamidopyrrolidin-1-yl)methyl)benzoyl)-N3,N4-bis((1S,2R)-2-phenylcyclopropyl)pyrrolidine-3,4-dicarboxamide (Compound 126)(0.065 g, 24%). LCMS (Method-J): 100% (RT 6.244, 225.0 nm) (MS: ESI +ve 830.6 [M+1]). $^1$H NMR: (400 MHz, DMSO-$d_6$): 0.83-0.85 (m, 3H), 1.10 (s, 2H), 1.24 (s, 24H), 1.49 (s, 2H), 1.74-1.89 (m, 1H), 1.86 (s, 1H), 1.96 (s, 1H), 2.07-2.11 (m, 2H), 2.26 (bs, 1H), 2.78 (s, 1H), 2.84 (s, 1H), 3.08-3.10 (m, 1H), 3.20 (m, 3H), 3.48-3.53 (m, 2H), 3.66 (m, 1H), 3.76-3.81 (m, 1H), 3.35-3.49 (m, 3H), 7.06-7.08 (m, 2H), 7.11-7.18 (m, 4H), 7.22-7.31 (m, 6H), 7.49-7.51 (d, J=8 Hz, 1H), 8.15-8.17 (m, 1H) 8.29 (s, 1H), 8.42 (s, 1H).

Synthesis of (3S,4S)-1-(4-(((S)-2-oxo-3-pentadecanamidopyrrolidin-1-yl)methyl) benzoyl)-N3,N4-bis((1S,2R)-2-phenylcyclopropyl)pyrrolidine-3,4-dicarboxamide, Compound 133

Prepared using a procedure similar to that reported for (3S,4S)-1-(4-(((R)-2-oxo-3-pentadecanamidopyrrolidin-1-yl)methyl)benzoyl)-N3,N4-bis((1S,2R)-2-phenylcyclopropyl)pyrrolidine-3,4-dicarboxamide (Compound 126), substituting the applicable amino acid in step 1. Purified using Prep HPLC Method 1 to give Compound 133 (0.037 g, 13.63%). LCMS (Method-J): 100% (RT 6.546, 202.0 nm) (MS: ESI +ve 831.5 [M+1]). $^1$H NMR: (400 MHz, DMSO-$d_6$) 0.84-0.88 (t, J=6.7 Hz, 3H), 1.21-1.25 (m, 26H), 1.51 (s, 2H), 1.75-1.98 (m, 3H), 2.09-2.12 (t, J=7.2 Hz, 3H), 2.25-2.34 (m, 1H), 2.68-2.86 (m, 2H), 3.09-3.22 (m, 4H), 3.49-3.54 (t, J=8.8 Hz, 2H), 3.65-3.69 (t, J=1.2 Hz, 1H), 3.77-3.82 (t, J=2.8 Hz, H), 4.36-4.51 (m, 3H), 1.07-1.33 (m, 12H), 7.50-7.52 (d, J=8.0 Hz, 2H), 8.15-8.18 (d, J=8.4 Hz, 1H), 8.30-8.31 (d, J=4 Hz, 1H), 8343-8.44 (d, J=4 Hz, 1H).

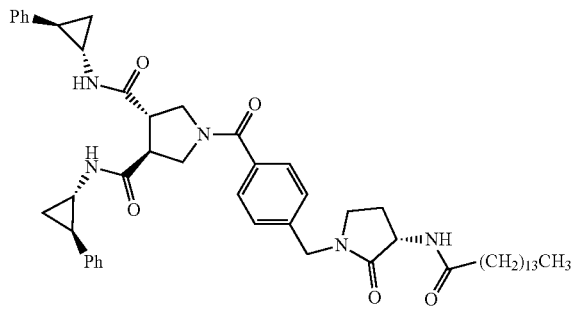

Synthesis of (3S,4S)-1-(4-((R)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide, Compound 127

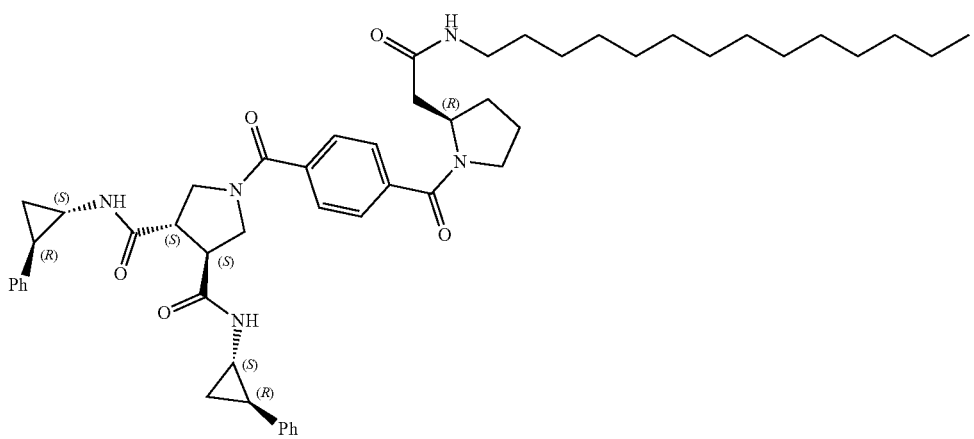

Step 1: Preparation of tert-butyl (R)-2-(2-oxo-2-(tetradecylamino) ethyl) pyrrolidine-1-carboxylate
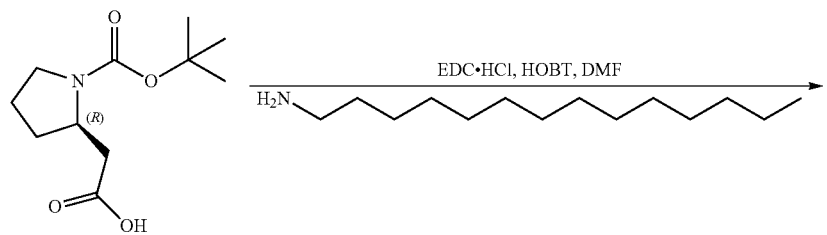
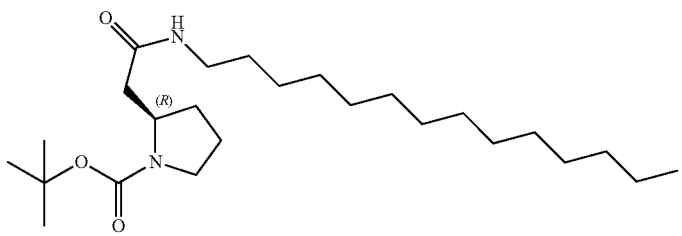
Prepared using General EDC, HOBT Coupling Procedure to give tert-butyl (R)-2-(2-oxo-2-(tetradecylamino) ethyl) pyrrolidine-1-carboxylate as an off white solid (0.9 g, 97.1%) which was used directly in the next step.
Step-2: Preparation of (R)-2-(pyrrolidin-2-yl)-N-tetradecylacetamide
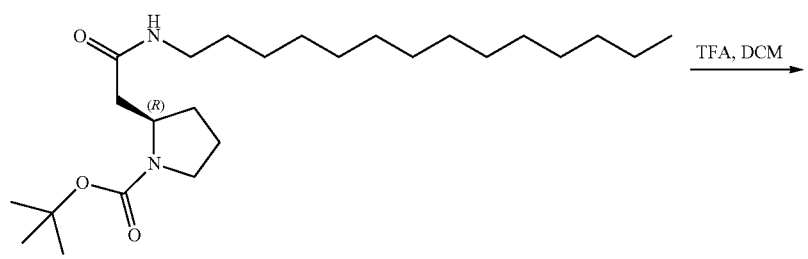
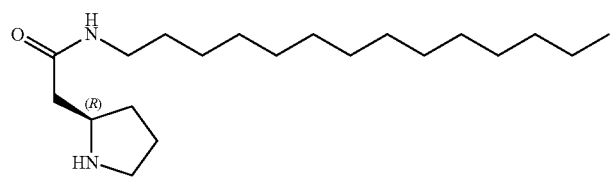

Prepared using General BOC Deprotection Procedure to give (R)-2-(pyrrolidin-2-yl)-N-tetradecylacetamide (0.22 g, 95.9%). LCMS (Method-C): 52.9% (RT 9.097, 202.0 nm) (MS: ESI +ve 325 [M+H]).

Step-3: Preparation of (3S,4S)-1-(4-((R)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide, Compound 127

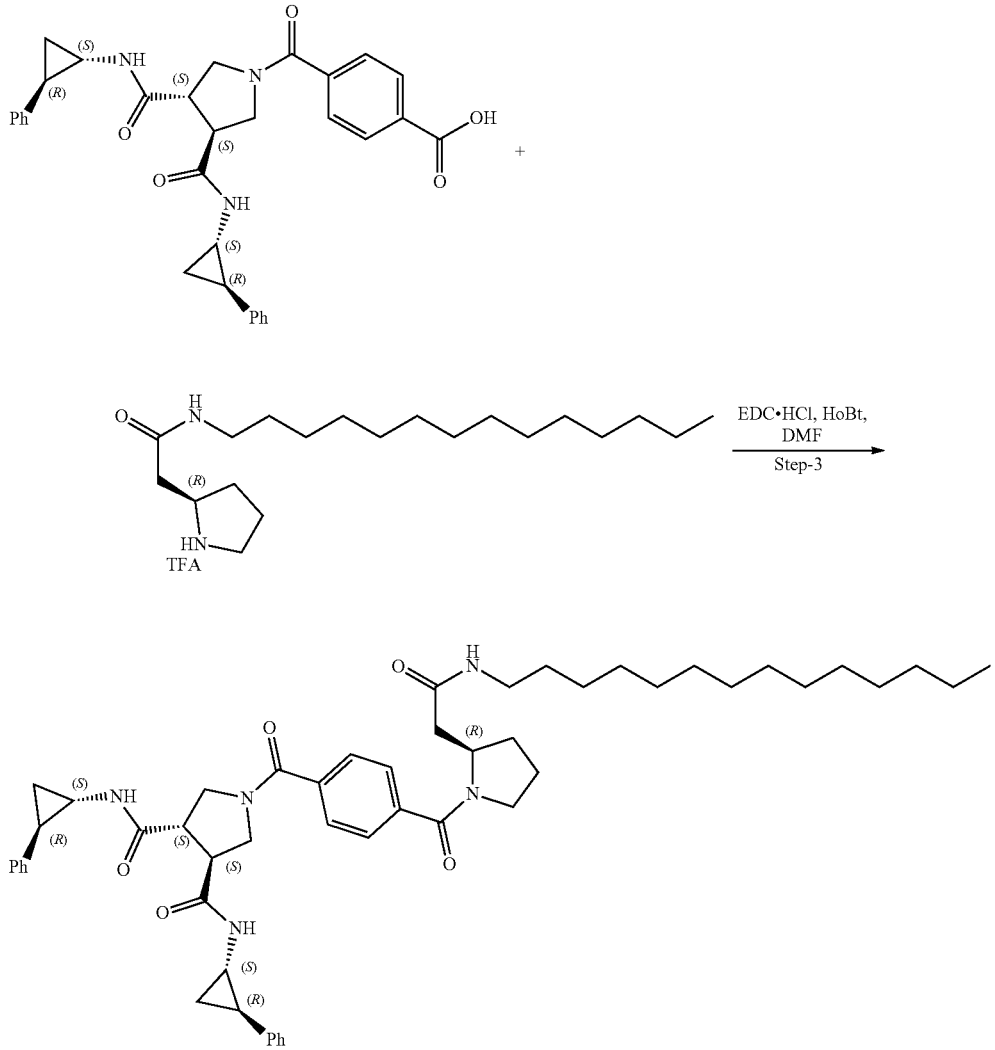

Prepared using General EDC, HOBT Coupling Procedure. Purified using Prep HPLC Method 1 to give (3S,4S)-1-(4-((R)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide (Compound 127)(0.055 g, 23.3%). LCMS (Method-J): 100% (RT 6.623, 202.0 nm) (MS: ESI +ve 844 [M+H]). $^1$H NMR: (400 MHz, DMSO) δ ppm: 0.84-0.88 (t, 3H); 1.10-1.13 (m, 2H); 1.19 (s, 26H); 1.39 (s, 2H); 1.73 (s, 2H); 1.87 (s, 2H); 1.98 (s, 2H); 2.21-2.34 (m, 1H); 2.68-2.77 (m, 2H); 3.04-3.12 (m, 3H); 3.14-3.21 (m, 1H); 3.42-3.46 (d, J=9.6, 1H); 3.49 (s, 2H); 3.64-3.66 (d, J=8.4, 1H); 3.79-3.84 (m, 1H); 4.37 (s, 1H); 7.07-7.17 (m, 6H); 7.23-7.30 (m, 4H); 7.52-7.58 (m, 4H); 7.87 (s, 1H); 8.33 (s, 1H); 8.45 (s, 1H).

Synthesis of (3S,4S)-1-(4-((S)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide, Compound 135

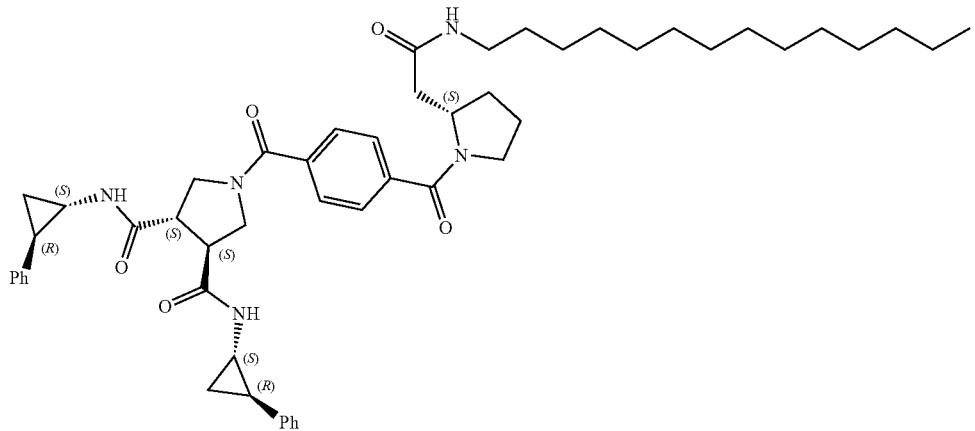

Prepared by a procedure similar to that reported for (3S,4S)-1-(4-((R)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide (Compound 127), substituting the applicable amino acid. The final product was purified using Prep HPLC Method 3 to give (3S,4S)-1-(4-((S)-2-(2-oxo-2-(tetradecylamino) ethyl) pyrrolidine-1-carbonyl) benzoyl)-N3,N4-bis((1S,2R)-2-phenylcyclopropyl) pyrrolidine-3,4-dicarboxamide (Compound 135)(0.055 g, 23.3%). LCMS (Method-J): 98.3% (RT 6.606, 202.0 nm) (MS: ESI +ve 843 [M–H]). $^1$H NMR: (400 MHz, DMSO) δ ppm: 0.83-0.85 (d, J=7.2, 3H); 1.10 (s, 2H); 1.23 (s, 23H); 1.38 (s, 3H); 1.71 (s, 2H); 1.88 (s, 2H); 1.97 (s, 3H); 2.12-2.13 (d, J=7.2, 1H); 2.20-2.33 (m, 1H); 2.72 (s, 1H); 2.85 (s, 1H); 3.03 (s, 1H); 3.09-3.13 (m, 1H); 3.16-3.20 (m, 1H); 3.34 (s, 1H); 3.40 (s, 1H); 3.47-3.50 (d, J=9.2, 2H); 3.64-3.66 (d, J=10, 1H); 3.77-3.83 (m, 1H); 4.35 (s, 1H); 7.06-7.13 (m, 2H), 7.16-7.22 (m, 4H); 7.23-7.28 (m, 4H); 7.53-7.56 (t, 4H); 7.87 (s, 1H); 8.31 (s, 1H); 8.44 (s, 1H).

Synthesis of (3S,4S)-1-(4-((2-oxo-3-(tetradecylcarbamoyl)pyrrolidin-1-yl)methyl)benzoyl)-N3,N4-bis ((1S,2R)-2-phenylcyclopropyl)pyrrolidine-3,4-dicarboxamide, Compound 142

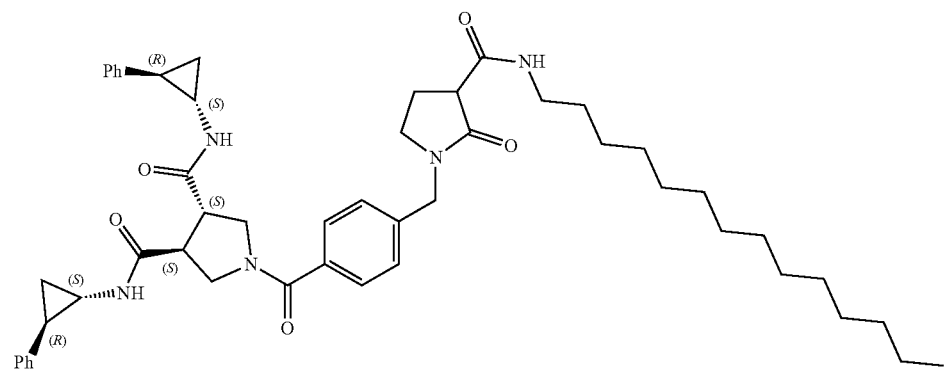

Step 1: Preparation of 1-(4-(tert-butoxycarbonyl)benzyl)-2-oxopyrrolidine-3-carboxylic acid

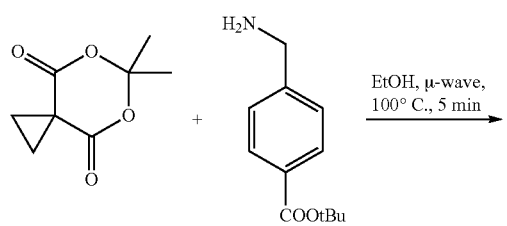

Tert-butyl 4-(aminomethyl)benzoate (1.0 g, 4.8 mmol) and 6,6-dimethyl-5,7-dioxaspiro[2.5]octane-4,8-dione (1.6 g, 9.6 mmol) were dissolved in EtOH (6 mL) and heated for 5 minutes in a microwave reactor at 100° C. The reaction mixture was then concentrated to give 1-(4-(tert-butoxycarbonyl)benzyl)-2-oxopyrrolidine-3-carboxylic acid (0.6 g, 19.98%). LCMS (Method C3): 82.81% (RT: 1.193, 254.0 nm) (MS: ESI +ve 320.1 [M+1]).

Step 2: Preparation of tert-butyl 4-((2-oxo-3-(tetradecylcarbamoyl)pyrrolidin-1-yl)methyl)benzoate

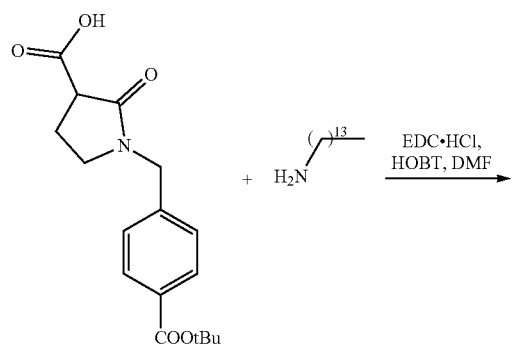

Prepared using General EDC, HOBT Coupling Procedure. The crude product was purified using flash chromatography, eluting with 1-3% MeOH in DCM, to give tert-butyl 4-((2-oxo-3-(tetradecylcarbamoyl)pyrrolidin-1-yl)methyl)benzoate (0.45 g, 82.97%). MASS: (MS: ESI +ve 515.51 [M+1]).

Step 3: Preparation of 4-((2-oxo-3-(tetradecylcarbamoyl)pyrrolidin-1-yl)methyl)benzoic acid

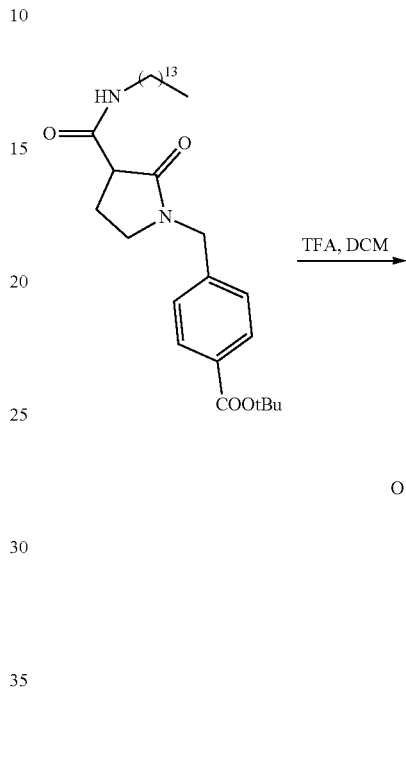

Prepared using General BOC Deprotection Procedure to give 4-((2-oxo-3-(tetradecylcarbamoyl)pyrrolidin-1-yl)methyl)benzoic acid (0.3 g, 71.60%). LCMS (Method-C2): 94.34% (RT: 1.697, 202.00 nm) (MS: ESI +ve 459.85 [M+1]).

Step 4: Preparation of (3S,4S)-1-(4-((2-oxo-3-(tetradecylcarbamoyl)pyrrolidin-1-yl)methyl)benzoyl)-N3,N4-bis((1S,2R)-2-phenylcyclopropyl)pyrrolidine-3,4-dicarboxamide, Compound 142

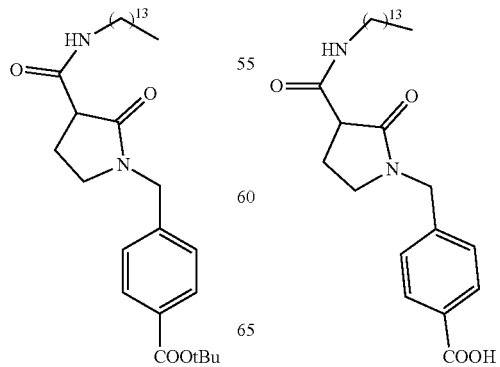

591

-continued

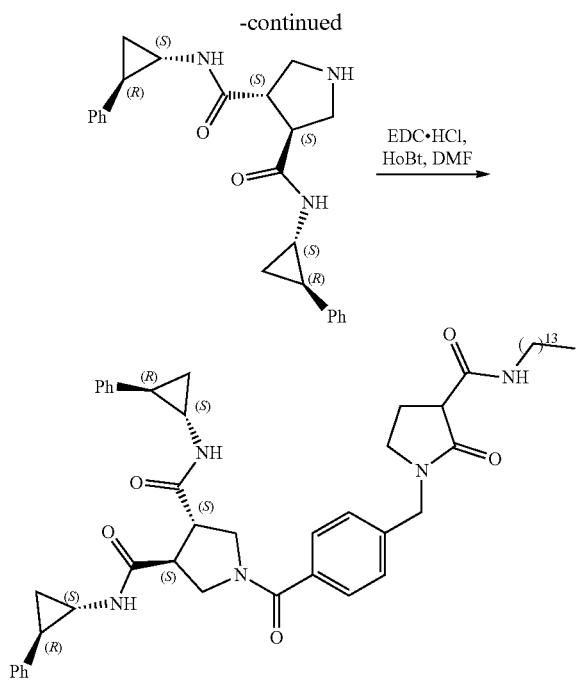

EDC·HCl,
HoBt, DMF
→

Prepared using General EDC, HOBT Coupling Procedure. The crude product was purified using Prep HPLC Method 1 to give (3S,4S)-1-(4-((2-oxo-3-(tetradecylcarbamoyl)pyrrolidin-1-yl)methyl)benzoyl)-N3,N4-bis((1S,2R)-2-phenylcyclopropyl)pyrrolidine-3,4-dicarboxamide (Compound 142)(34 mg, 18.78%). LCMS (Method-J): 100.00% (RT 6.707, 202.0 nm) (MS: ESI +ve 830.5 [M+H]). ¹H NMR (400 MHz, DMSO) δ ppm: 0.83-0.84 (d, J=4 Hz, 3H), 1.10-1.23 (d, J=52 Hz, 21H), 1.38 (s, 2H), 1.86-1.96 (d, J=40 Hz, 2H), 2.77-2.83 (d, J=24 Hz, 2H), 3.06-3.22 (m, 6H), 3.47-3.50 (d, J=12 Hz, 2H), 3.63-3.65 (m, 2H), 4.38-4.47 (m, 2H)', 7.06-7.15 (m, 5H), 7.24-7.28 (m, 4H), 7.48-7.50 (d, J=8 Hz, 2H), 8.07 (s, 1H), 8.29 (s, 1H), 8.42 (s, 1H).

Synthesis of (3S,4S)-1-(4-(((S)-4-(hexylcarbamoyl)-3-octyl-2-oxoimidazolidin-1-yl)methyl)benzoyl)-N3,N4-bis((1S,2R)-2-phenylcyclopropyl)pyrrolidine-3,4-dicarboxamide, Compound 167

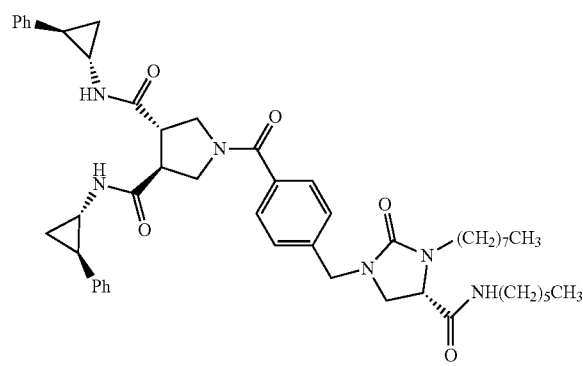

592

Step 1: Preparation of benzyl tert-butyl (3-(hexylamino)-3-oxopropane-1,2-diyl)(S)-dicarbamate

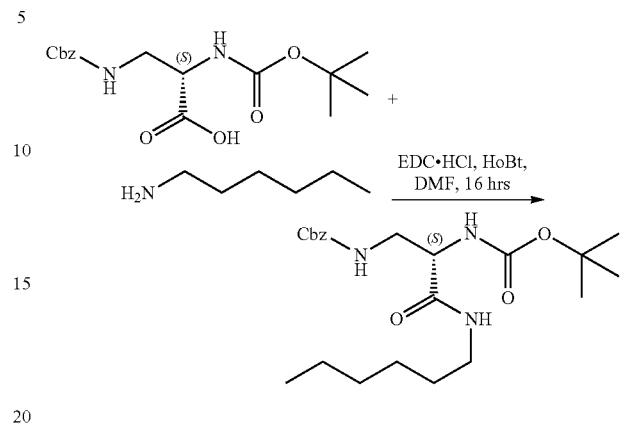

Prepared using General EDC, HOBT Coupling Procedure. The crude product was purified by flash chromatography eluting, with 1-2% MeOH in DCM, to give benzyl tert-butyl (3-(hexylamino)-3-oxopropane-1,2-diyl)(S)-dicarbamate. (3.0 g, 48.16%). LCMS (Method-C2): 100% (RT: 1.360, 202.00 nm) (MS: ESI +ve 422.48[M+1]).

Step 2: Preparation of benzyl (S)-(2-amino-3-(hexylamino)-3-oxopropyl)carbamate

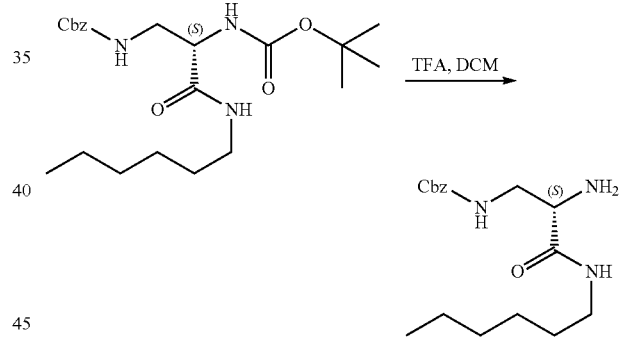

Prepared using General BOC Deprotection Procedure to give benzyl (S)-(2-amino-3-(butylamino)-3-oxopropyl)carbamate, as a white solid (2.3 g, 99%). LCMs(Method-C2): 100% (RT: 1.162, 202.00 nm) (MS: ESI +ve 322.45 [M+1]).

Step 3: Preparation of benzyl (S)-(3-(hexylamino)-2-(octylamino)-3-oxopropyl) carbamate

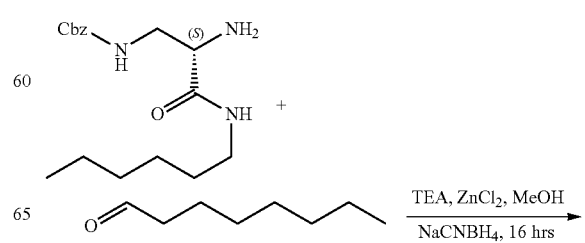

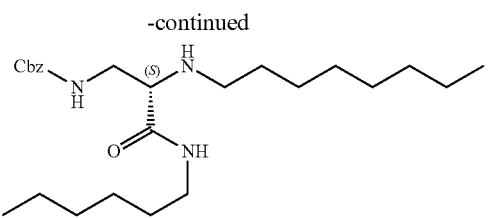

To a stirred solution of benzyl (S)-(2-amino-3-(butylamino)-3-oxopropyl)carbamate (2.6 g, 8.074 mmol) and octanal (1.0 g, 8.074 mmol) in MeOH (30 mL) at 0° C. was added TEA (6.1 mL) followed by zinc chloride (8.6 mL). The reaction mixture was stirred for 4 hrs warming to room temperature. Sodium cyanoborohydride (2.0 g, 32.298 mmol) was added, and the mixture was stirred 16 hrs. The mixture was diluted with ethyl acetate (300 mL) washed with brine (2×300 mL), dried over sodium sulfate and concentrated. The resulting solid was purified by flash chromatography, eluting with 1-3% MeOH in DCM, to give benzyl (S)-(3-(hexylamino)-2-(octylamino)-3-oxopropyl) carbamate as a yellow oil (2.0 g, 57.02%). LCMs(Method-H): 88.34% (RT: 4.496, 202.00 nm) (MS: ESI +ve 434.4 [M+1]).

Step 4: Preparation of tert-butyl (S)-(3-(((benzyloxy)carbonyl)amino)-1-(hexylamino)-1-oxopropan-2-yl)(octyl)carbamate

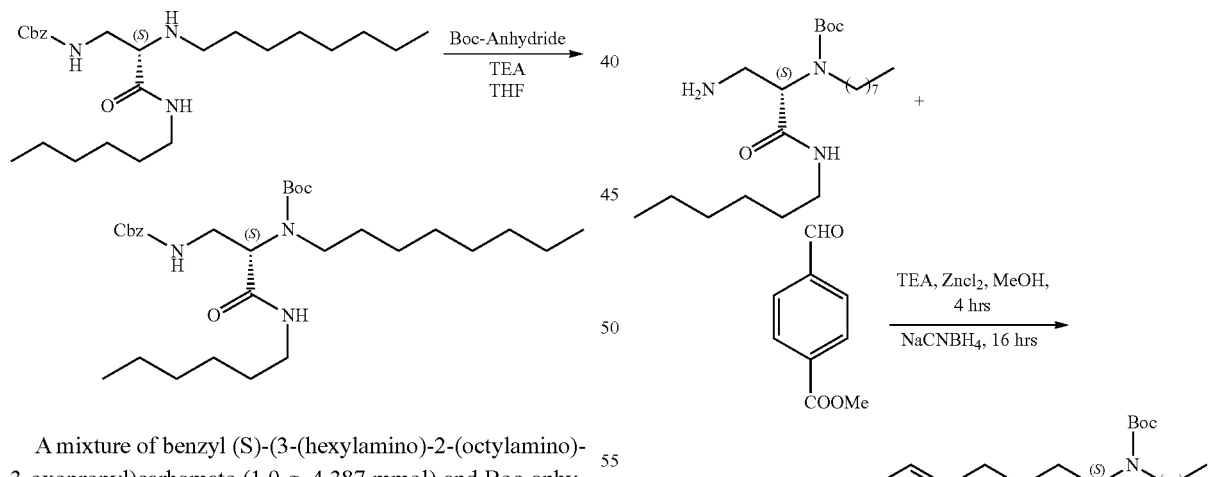

A mixture of benzyl (S)-(3-(hexylamino)-2-(octylamino)-3-oxopropyl)carbamate (1.9 g, 4.387 mmol) and Boc-anhydride(1.4 g, 6.581 mmol) was stirred for 16 hrs. The mixture was diluted with ethyl acetate (300 mL) and washed with brine (2×300 mL). The organic layer was dried over sodium sulfate and concentrated. The resulting solid was purified by flash chromatography, eluting with 30-40% EtOAc in hexane, to give tert-butyl (S)-(3-(((benzyloxy)carbonyl)amino)-1-(hexylamino)-1-oxopropan-2-yl)(octyl) carbamate (1.4 g, 59.86%). LCMS (Method-C FAST): 71.04% (RT: 2.698, 202.00 nm) (MS: ESI +ve 434.4 [M+1]).

Step 5: Preparation of tert-butyl (S)-(3-amino-1-(hexylamino)-1-oxopropan-2-yl)(octyl) carbamate

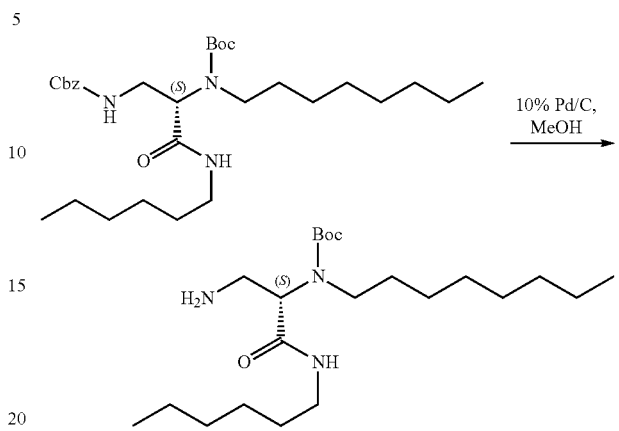

A mixture of tert-butyl (S)-(3-(((benzyloxy)carbonyl)amino)-1-(hexylamino)-1-oxopropan-2-yl)(octyl)carbamate (1.3 g, 2.439 mmol) and palladium/carbon (1.3 g) in MeOH (30 mL) was hydrogenated under balloon pressure for 16 h. The mixture was filtered through celite and the filtrate was concentrated to give tert-butyl (S)-(3-amino-1-(hexylamino)-1-oxopropan-2-yl)(octyl) carbamate. (0.65 g, 66.78%). LCMS (Method-C2): 92.07% (RT: 1.460, 202.00 nm) (MS: ESI +ve 400.53. [M+1]).

Step 6: Preparation of methyl (S)-4-(((2-((tert-butoxycarbonyl)(octyl) amino)-3-(hexylamino)-3-oxopropyl)amino)methyl)benzoate To a stirred solution of tert-butyl (S)-(3-amino-1-(hexylamino)-1-oxopropan-2-yl)(octyl) carbamate (0.65 g, 1.692 mmol) and methyl 4-formylbenzoate (0.26 g, 1.629 mmol) in MeOH (10 mL) at 0° C. was added TEA (0.8 mL) and zinc chloride (1.95 mL). The mixture was stirred for 4 h. Sodium cyanoborohydride (0.402 g, 6.768 mmol) was added and stirring was continued for 16 hrs. The mixture was diluted with ethyl acetate (200 mL) and washed with brine (2×200 mL). The organic layer was dried over sodium sulfate, concentrated, and the resulting solid was purified by flash chromatography, eluting with 1-3% MeOH and DCM, to give benzyl (S)-(3-(hexylamino)-2-(octylamino)-3-oxopropyl)carbamate, as a white solid (0.32 g, 35.92%). LCMs (Method-C2): 98.53% (RT: 1.461, 230.00 nm) (MS: ESI +ve 549.64 [M+2]).

Step 7: preparation of methyl (S)-4-(((3-(hexylamino)-2-(octylamino)-3-oxopropyl) amino)methyl) benzoate

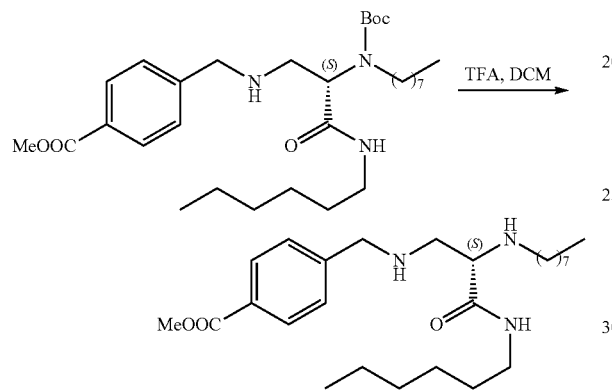

Prepare using General B Deprotection Procedure to give methyl (S)-4-(((3-(hexylamino)-2-(octylamino)-3-oxopropyl)amino) methyl)benzoate (0.2 g, 62.50%). LCMs (Method-C2): 100% (RT: 1.582, 202.00 nm) (MS: ESI +ve 448.5 [M+1]).

Step 8: preparation of methyl (S)-4-((4-(hexylcarbamoyl)-3-octyl-2-oxoimidazolidin-1-yl)methyl)benzoate

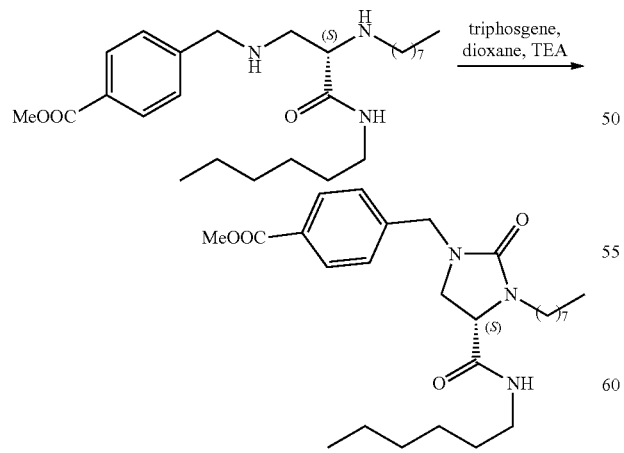

To a stirred solution of methyl (S)-4-(((3-(hexylamino)-2-(octylamino)-3-oxopropyl)amino) methyl)benzoate(0.2 g, 0.4469 mmol), in 1,4 dioxane (12 mL) was added TEA(0.09 mL) at 0° C. After 5 minutes, triphosgene (0.016, 0.2234 mmol) was added and stirring continued for 16 h. The mixture was diluted with ethyl acetate (100 mL) and washed with brine (2×100 mL). The organic layer was dried over sodium sulfate and concentrated. The crude product was purified by flash chromatography, eluting with 2-3% MeOH and DCM, to give methyl (S)-4-((4-(hexylcarbamoyl)-3-octyl-2-oxoimidazolidin-1-yl)methyl)benzoate as a white solid (0.1 g, 47.26%). LCMS (Method-C2): 100% (RT: 1.553, 235.00 nm) (MS: ESI +ve 474.92 [M+1]).

Step 9: preparation of (S)-4-((4-(hexylcarbamoyl)-3-octyl-2-oxoimidazolidin-1-yl methyl)benzoic acid

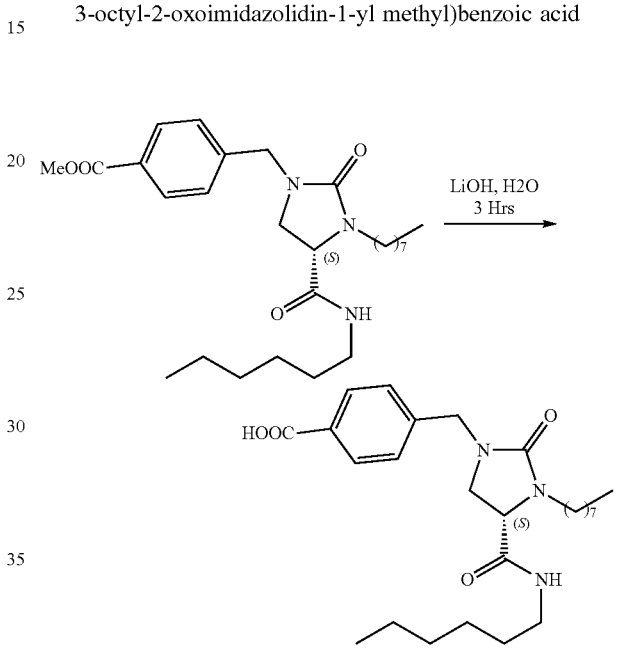

Prepared using General Ester Hydrolysis Procedure to give (S)-4-((4-(hexylcarbamoyl)-3-octyl-2-oxoimidazolidin-1-yl)methyl)benzoic acid, as a white solid (0.075 g, 77.29%). LCMS (Method-C2): 87.50% (RT: 1.438, 233.00 nm) (MS: ESI +ve 460.55 [M+1]).

Step 10: preparation of (3S,4S)-1-(4-(((S)-4-(hexylcarbamoyl)-3-octyl-2-oxoimidazolidin-1-yl)methyl) benzoyl)-N3,N4-bis((1S,2R)-2-phenylcyclopropyl) pyrrolidine-3,4-dicarboxamide, Compound 167

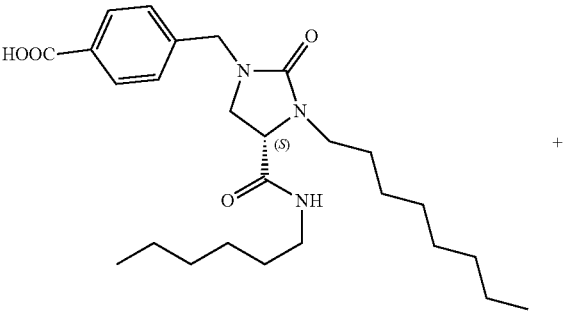

+

-continued

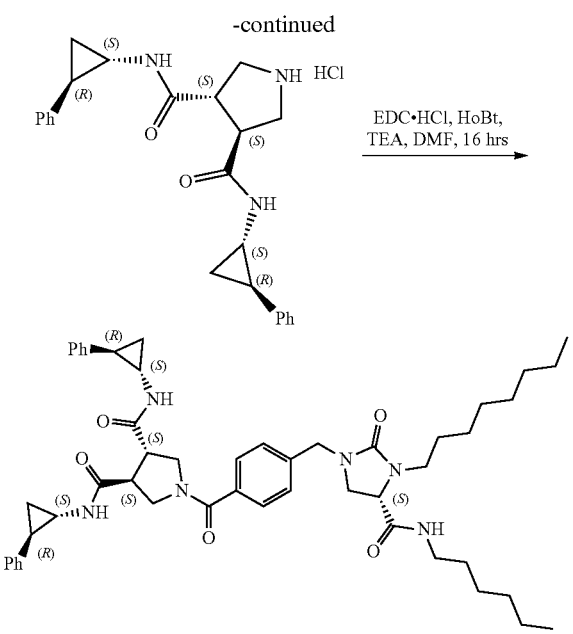

Prepared using General EDC, HOBT Coupling Procedure. The crude product was purified using Prep HPLC Method 1 to give (3S,4S)-1-(4-(((S)-4-(hexylcarbamoyl)-3-octyl-2-oxoimidazolidin-1-yl)methyl)benzoyl)-N3,N4-bis ((1S,2R)-2-phenylcyclopropyl) pyrrolidine-3,4-dicarboxamide (Compound 167)(0.025 g, 18.43%). LCMS (Method-J): 100% (RT: 4.971, 254 nm) (MS: ESI +ve 831.5[M+1]). ¹H NMR: (400 MHz, DMSO) 3 ppm: 0.83-0.88 (m, 7H), 1.10-1.39 (m, 20H), 1.87-1.97 (s, 2H), 2.68 (s, 4H), 2.68-2.85 (m, 4H), 3.00-3.21 (m, 7H), 3.34-3.53 (m, 3H), 3.65-3.79 (m, 2H), 4.04-4.07 (t, J=9.6 Hz, 1H), '4.31-4.32 (d, J=5.6 HZ, 2H), 7.07-7.31 (m, 12H), 7.48-7.50 (d, J=8 HZ, 2H), 8.22 (s, 1H), 8.28-8.29 (d, J=4 HZ, 1H), 8.42-8.43 (d, J=3.6 Hz, 11H).

Synthesis of (3S,4S)-1-(4-(((R)-4-(hexylcarbamoyl)-3-octyl-2-oxoimidazolidin-1-yl)methyl)benzoyl)-N3,N4-bis((1S,2R)-2-phenylcyclopropyl)pyrrolidine-3,4-dicarboxamide, Compound 168

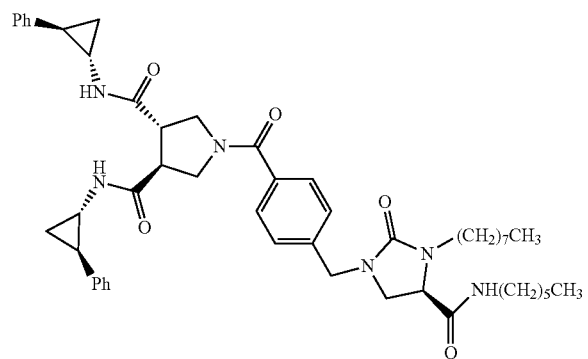

Prepared by a procedure similar to that reported for (3S,4S)-1-(4-(((S)-4-(hexylcarbamoyl)-3-octyl-2-oxoimidazolidin-1-yl)methyl)benzoyl)-N3,N4-bis((1S,2R)-2-phenylcyclopropyl) pyrrolidine-3,4-dicarboxamide (Compound 167), to give (3S,4S)-1-(4-(((R)-4-(hexylcarbamoyl)-3-octyl-2-oxoimidazolidin-1-yl)methyl)benzoyl)-N3,N4-bis ((1S,2R)-2-phenylcyclopropyl)pyrrolidine-3,4-dicarboxamide, Compound 168. LCMS (Method-J): 100% (RT: 4.971, 254 nm) (MS: ESI +ve 831.5[M+1]). ¹H NMR: (400 MHz, DMSO) δ ppm: 0.83-0.88 (m, 7H), 1.10-1.39 (m, 20H), 1.87-1.97 (s, 2H), 2.68 (s, 4H), 2.68-2.85 (m, 4H), 3.00-3.21 (m, 7H), 3.34-3.53 (m, 3H), 3.65-3.79 (m, 2H), 4.04-4.07 (t, J=9.6 Hz, 1H), '4.31-4.32 (d, J=5.6 HZ, 2H), 7.07-7.31 (m, 12H), 7.48-7.50 (d, J=8 HZ, 2H), 8.22 (s, 1H), 8.28-8.29 (d, J=4 HZ, 1H), 8.42-8.43 (d, J=3.6 Hz, 1H).

Synthesis of (3S,4S)-1-(4-(((((S)-3,6-dioxo-1-tetradecylpiperazin-2-yl)methyl)carbamoyl)benzoyl)-N3,N4-bis((1S,2R)-2-phenylcyclopropyl)pyrrolidine-3,4-dicarboxamide, Compound 147

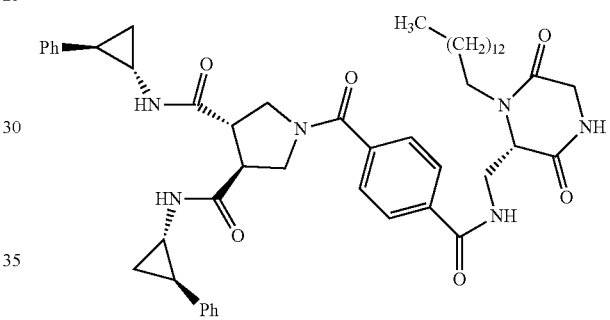

Step-1: Preparation of allyl (S)-3-amino-2-(((benzyloxy)carbonyl) amino)propanoate

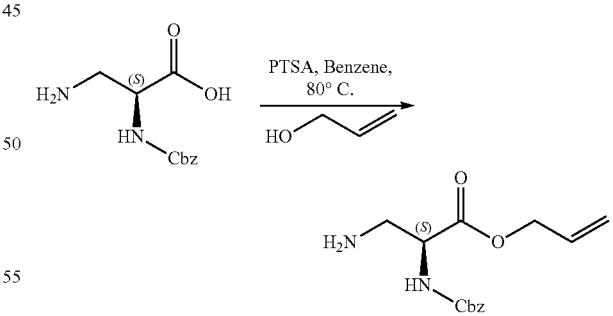

(S)-3-amino-2-(((benzyloxy)carbonyl)amino)propanoic acid (7.0 g, 29.38 mmol) and prop-2-en-1-ol (15.0 g, 258.6 mmol) were dissolved in dry benzene (175 mL). 4-methylbenzenesulfonic acid (6.7 g, 35.26 mmol) was added and the mixture was heated at 80° C. in a flask fitted with a Dean-Stark apparatus for 48 hrs. The mixture was concentrated to give allyl (S)-3-amino-2-(((benzyloxy)carbonyl)amino)propanoate (19.0 g, crude) which was used directly in the next step. LCMS (Method-C2): 34.32% (RT 1.006, 202.0 nm) (MS: ESI +ve 279.32 [M+1]).

Step-2: Preparation of methyl (S)-4-((3-(allyloxy)-2-(((benzyloxy)carbonyl)amino)-3-oxopropyl)carbamoyl)benzoate

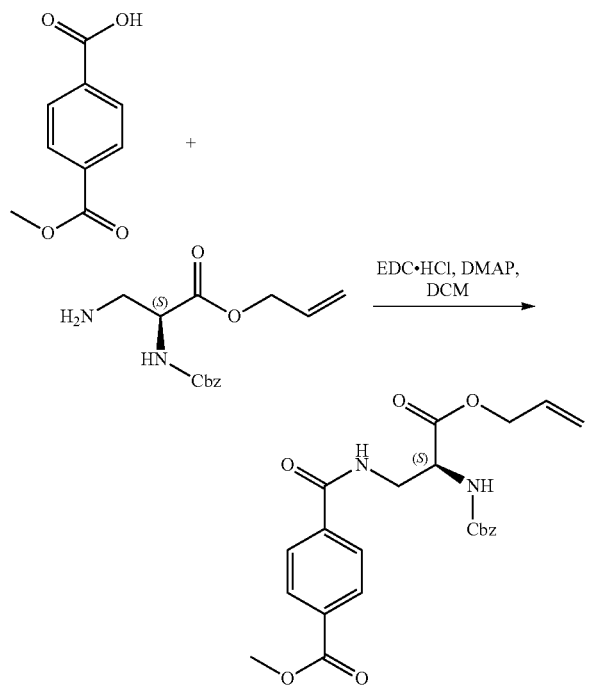

Prepared using General EDC, HOBT Coupling Procedure. The crude product was purified using flash chromatography, eluting with 50% EtOAc in hexane, to give methyl (S)-4-((3-(allyloxy)-2-(((benzyloxy)carbonyl)amino)-3-oxopropyl)carbamoyl)benzoate. (5.1 g, 40.2%). LCMS (Method-C3): 97.97% (RT 1.252, 241.0 nm) (MS: ESI +ve 441.35 [M+1]).

Step-3: Preparation of (S)-2-(((benzyloxy)carbonyl)amino)-3-(4-(methoxycarbonyl)benzamido)propanoic acid

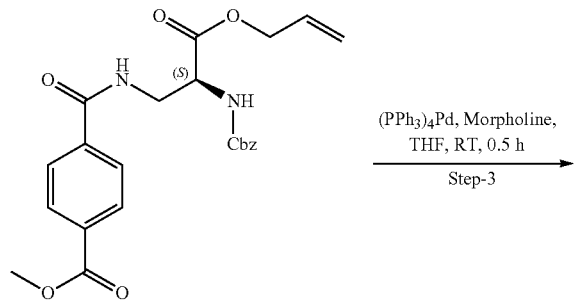

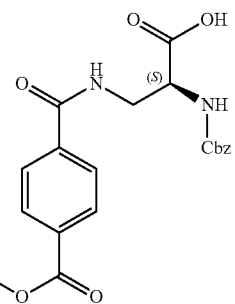

Methyl (S)-4-((3-(allyloxy)-2-(((benzyloxy)carbonyl)amino)-3-oxopropyl)carbamoyl)benzoate (5.1 g, 11.73 mmol) was dissolved in THF (50 mL). Morpholine (1.02 g, 11.73 mmol) and tetrakistriphenylphosphine palladium (1.35 g, 1.173 mmol) were added at room temperature and stirred for 30 min. The mixture was extracted in EtOAc (2×100 mL), washed with brine (100 mL), dried and concentrated to give (S)-2-(((benzyloxy)carbonyl)amino)-3-(4-(methoxycarbonyl)benzamido)propanoic acid. (3.81 g, 82.1%). LCMS (Method-C2): 93.91% (RT 1.168, 240.0 nm) (MS: ESI +ve 401.0 [M+1]).

Step-4: Preparation of methyl (S)-4-((2-(((benzyloxy)carbonyl)amino)-3-((2-(tert-butoxy)-2-oxoethyl)amino)-3-oxopropyl)carbamoyl)benzoate

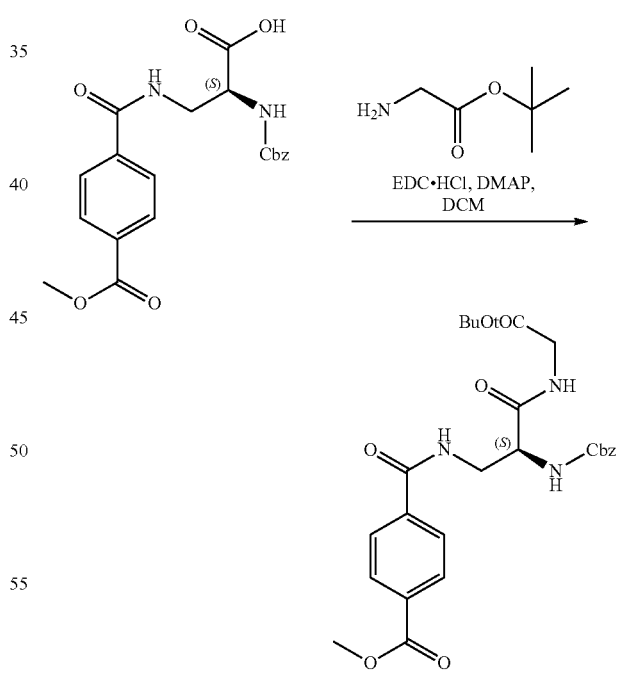

Prepared using General EDC, HOBT Coupling Procedure. The crude product was purified using flash chromatography, eluting with 50% EtOAc in hexane, to give methyl (S)-4-((2-(((benzyloxy)carbonyl)amino)-3-((2-(tert-butoxy)-2-oxoethyl)amino)-3-oxopropyl)carbamoyl)benzoate. (1.76 g, 36.11%). LCMS (Method-C3): 98.39% (RT 1.286, 242.0 nm) (MS: ESI +ve 514.71 [M+1]).

Step-5: Preparation of methyl (S)-4-((3-((2-(tert-butoxy)-2-oxoethyl)amino)-3-oxo-2-(tetradecylamino)propyl)carbamoyl)benzoate

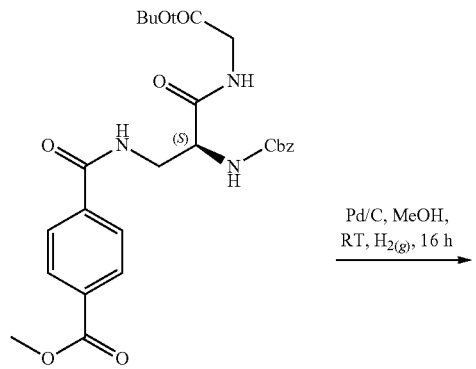

Pd/C, MeOH,
RT, H₂(g), 16 h
→

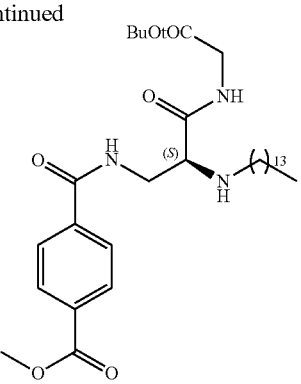

Methyl (S)-4-((2-(((benzyloxy)carbonyl)amino)-3-((2-(tert-butoxy)-2-oxoethyl)amino)-3-oxopropyl)carbamoyl)benzoate (0.5 g, 0.973 mmol) and tetradecanal (0.208 g, 0.973 mmol) was dissolved in MeOH (10 mL). Palladium on carbon was added (50% moisture) (0.5 g), and the reaction mixture was stirred at room temperature for 16 hr under H₂ (balloon). The mixture was filtered through a pad of celite and the filtrated was concentrated to give methyl (S)-4-((3-((2-(tert-butoxy)-2-oxoethyl)amino)-3-oxo-2-(tetradecylamino)propyl)carbamoyl)benzoate (0.5 g, 89.19%). LCMS (Method-H): 96.49% (RT 6.009, 230.0 nm) (MS: ESI +ve 574.5 [M+1]).

Step-6: Preparation of (S)-(3-(4-(methoxycarbonyl)benzamido)-2-(tetradecylamino)propanoyl)glycine (TFA Salt)

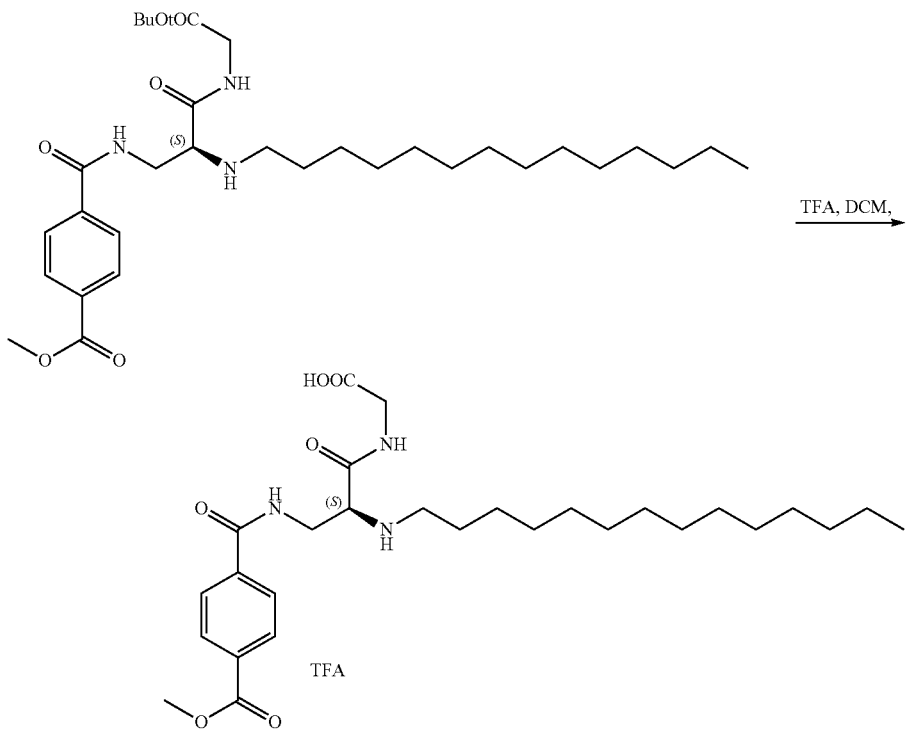

Prepared using General BOC Deprotection Procedure to give (S)-(3-(4-(methoxycarbonyl)benzamido)-2-(tetradecylamino)propanoyl)glycine (0.5 g, crude). LCMS (Method-X): 74.34% (RT 1.490, 225.0 nm) (MS: ESI +ve 520.9 [M+1]).

Step-7: Preparation of methyl (S)-4-(((3,6-dioxo-1-tetradecylpiperazin-2-yl)methyl)carbamoyl)benzoate

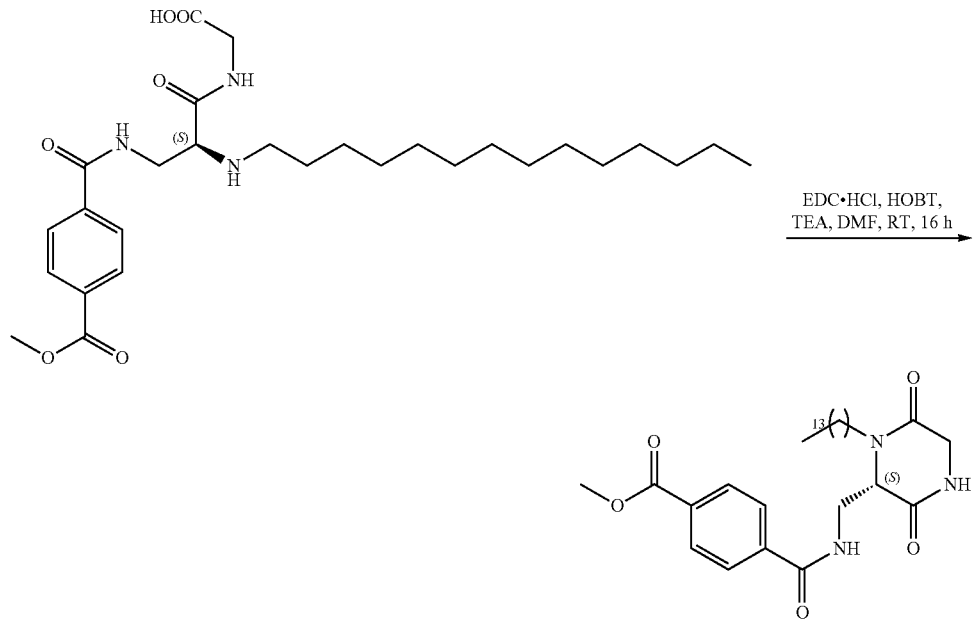

Prepared using General EDC, HOBT Coupling Procedure. The crude product was purified using flash chromatography, eluting with 3% MeOH in DCM, to give methyl (S)-4-(((3,6-dioxo-1-tetradecylpiperazin-2-yl)methyl)carbamoyl)benzoate (0.32 g, 99%). LCMS (Method-C3): 61.47% (RT 1.692, 215.0 nm) (MS: ESI +ve 502.82 [M+1]).

Step 8: Preparation of (S)-4-(((3,6-dioxo-1-tetradecylpiperazin-2-yl)methyl)carbamoyl)benzoic acid

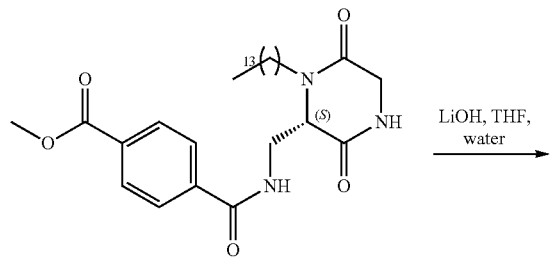

Prepared using General Ester Hydrolysis Procedure to give (S)-4-(((3,6-dioxo-1-tetradecylpiperazin-2-yl)methyl)carbamoyl)benzoic acid as an off white solid (0.3 g, 97%). LCMS (Method-C2): 64.62% (RT 1.564, 228 nm) (MS: ESI +ve 488.8 [M+H]).

Step-9: Preparation of (3S,4S)-1-(4-((((S)-3,6-dioxo-1-tetradecylpiperazin-2-yl)methyl)carbamoyl)benzoyl)-N3,N4-bis((1S,2R)-2-phenylcyclopropyl)pyrrolidine-3,4-dicarboxamide, Compound 147

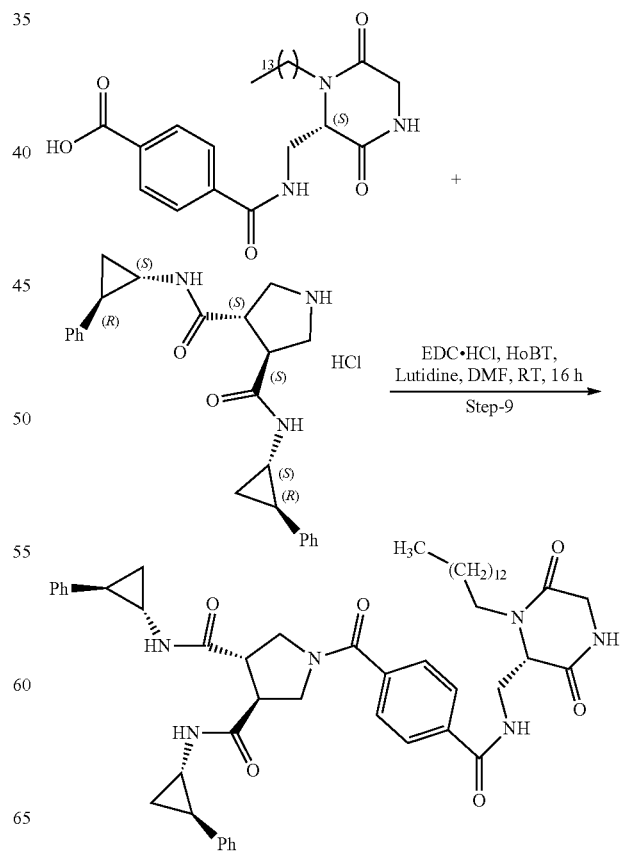

Prepare using General EDC, HOBT Coupling Procedure. The crude product was purified using Prep HPLC Method 1 to give (3S,4S)-1-(4-((((S)-3,6-dioxo-1-tetradecylpiperazin-2-yl)methyl)carbamoyl)benzoyl)-N3,N4-bis((1S,2R)-2-phenylcyclopropyl)pyrrolidine-3,4-dicarboxamide (Compound 147)(0.04 g, 6.2%). LCMS (Method-J): 95.25% (RT 6.297, 202.4 nm) (MS: ESI +ve 859.6 [M+H]). $^1$H NMR: (400 MHz, DMSO) δ ppm: 0.83-0.86 (m, 3H), 1.10-1.23 (m, 27H), 1.43-1.49 (m, 2H), 1.86 (s, 1H), 1.97 (s, 1H), 2.78 (s, 1H), 2.85-2.86 (m, 2H), 3.11-3.13 (m, 1H), 3.17-3.23 (m, 1H), 3.47-3.66 (m, 4H), 3.77-3.85 (m, 4H), 3.96 (s, 1H), 7.06-7.08 (d, J=7.6 Hz, 2H), 7.11-7.18 (m, 4H), 7.22-7.28 (m, 4H), 7.59-7.61 (d, J=8 Hz, 2H), 7.84-7.86 (d, J=7.6 Hz, 2H), 8.18 (s, 1H), 8.31-8.32 (d, J=3.6 Hz, 1H), 8.46-8.51 (m, 1H), 8.87 (m, 1H).

Synthesis of (3S,4S)-1-(4-((((S)-3,6-dioxo-4-tetradecylpiperazin-2-yl)methyl)carbamoyl)benzoyl)-N3,N4-bis((1S,2R)-2-phenylcyclopropyl)pyrrolidine-3,4-dicarboxamide, Compound 177

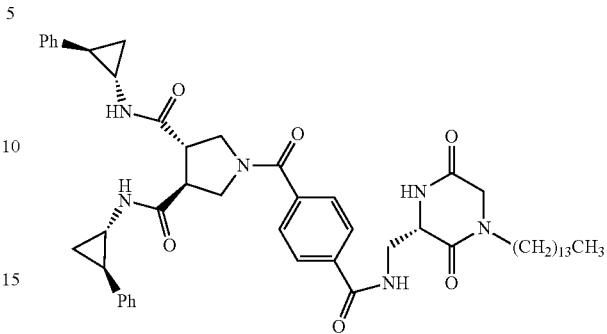

Step-1: Preparation of tert-butyl tetradecylglycinate

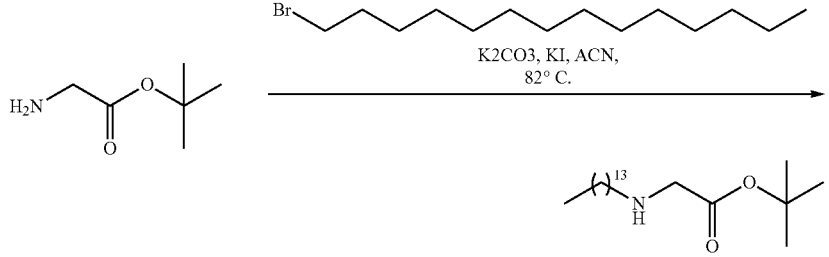

tert-Butyl glycinate (1.4 g, 5.307 mmol) was dissolved in acetonitrile (24 mL). 1-bromotetradecane (1.47 g, 2.653 mmol), potassium carbonate (1.46 g, 5.307 mmol) and potassium iodide (0.082 g, 0.249 mmol) were added and the reaction mixture was stirred at 82° C. for 7 hr. The mixture was extracted with EtOAc (2×150 mL), washed with brine, (150 mL), dried and concentrated. The crude product was purified using flash chromatography, eluting with 20% ethyl acetate in hexane, to give tert-butyl tetradecylglycinate. (1.0 g, 28.6%). (MS: ESI +ve 328 [M+1]).

Step-2: Preparation of methyl (S)-4-((2-(((benzyloxy)carbonyl)amino)-3-((2-(tert-butoxy)-2-oxoethyl)(tetradecyl)amino)-3-oxopropyl)carbamoyl)benzoate

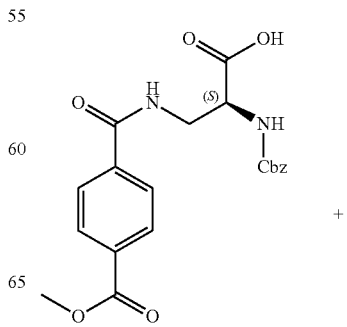

+

607

-continued

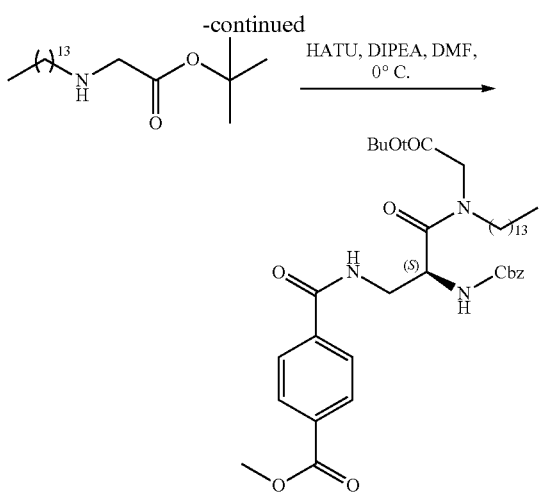

HATU, DIPEA, DMF,
0° C.

Prepared using General EDC, HOBT Coupling Procedure. The crude product was purified using flash chromatography, eluting with 50% ethyl acetate in hexane, to give methyl (S)-4-((2-(((benzyloxy)carbonyl)amino)-3-((2-(tert-butoxy)-2-oxoethyl)(tetradecyl)amino)-3-oxopropyl)carbamoyl)benzoate. (0.73 g, 44%). (MS: ESI +ve 710.74 [M+1]).

Step-3: Preparation of methyl (S)-4-((2-amino-3-((2-(tert-butoxy)-2-oxoethyl)(tetradecyl)amino)-3-oxopropyl)carbamoyl)benzoate

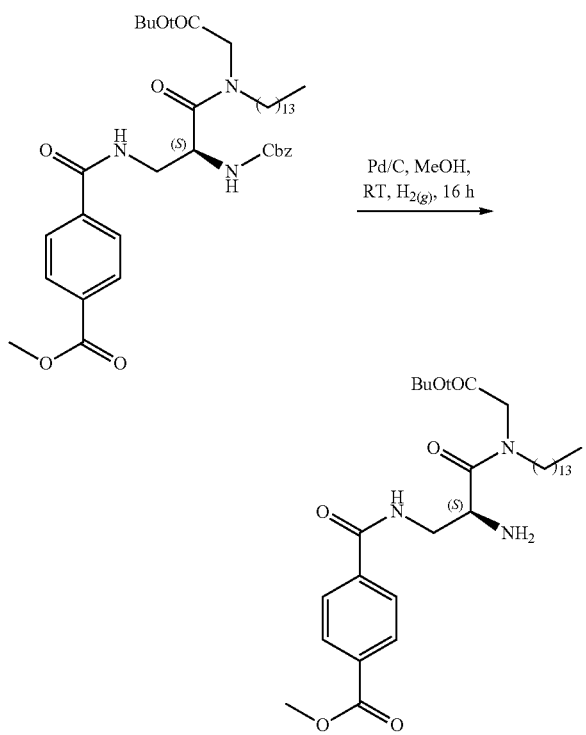

Pd/C, MeOH,
RT, H₂(g), 16 h

A mixture of methyl (S)-4-((2-(((benzyloxy)carbonyl)amino)-3-((2-(tert-butoxy)-2-oxoethyl)(tetradecyl)amino)-3-oxopropyl)carbamoyl)benzoate (0.73 g, 1.029 mmol) and palladium on carbon (50% moisture) (0.5 g) was dissolved

608 in MeOH (10 mL) and stirred for 16 hrs under H₂ (balloon). The mixture was filtered through a pad of celite and the filtrate was concentrated to give methyl (S)-4-((2-amino-3-((2-(tert-butoxy)-2-oxoethyl)(tetradecyl)amino)-3-oxopropyl)carbamoyl)benzoate (0.54 g, 91.3%). LCMS (Method-H): 93.24% (RT 5.272, 202.0 nm) (MS: ESI +ve 576.4 [M+1])

Step-4: Preparation of methyl (S)-4-(((3,6-dioxo-4-tetradecylpiperazin-2-yl)methyl)carbamoyl)benzoate (TFA Salt)

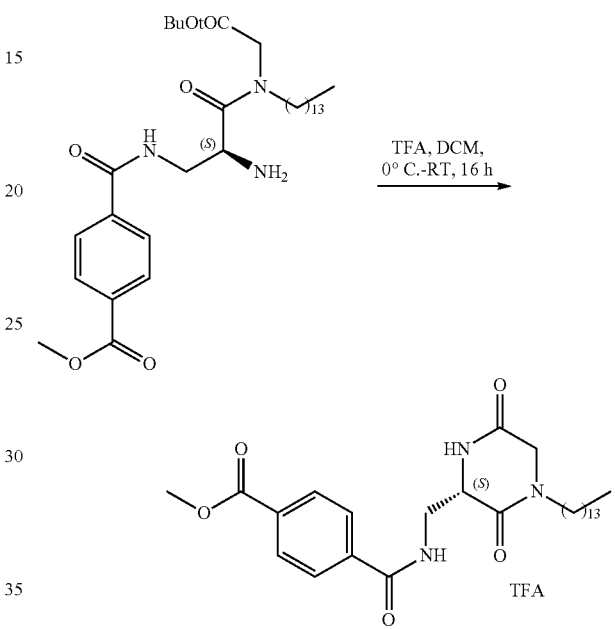

TFA, DCM,
0° C.-RT, 16 h

Methyl (S)-4-((2-amino-3-((2-(tert-butoxy)-2-oxoethyl)(tetradecyl)amino)-3-oxopropyl)carbamoyl)benzoate (0.54 g, 0.936 mmol) was dissolved in DCM (10 mL). Trifluoracetic acid (1 mL) was added dropwise at 0° C. The reaction mixture was stirred at room temperature for 16 hrs then concentrated under vacuum to remove the solvents. The mixture was extracted in DCM (2×150 mL) and aq. NaHCO₃ (150 mL). The organic layer was dried and concentrated. The crude product was purified using flash chromatography, eluting with 5% MeOH in DCM, to give methyl (S)-4-(((3,6-dioxo-4-tetradecylpiperazin-2-yl)methyl)carbamoyl)benzoate (0.17 g, 38.4%). LCMS (Method-C2): 100% (RT 1.592, 202.0 nm) (MS: ESI +ve 502.8 [M+1]).

Step 5: Preparation of (S)-4-(((3,6-dioxo-4-tetradecylpiperazin-2-yl)methyl)carbamoyl)benzoic acid

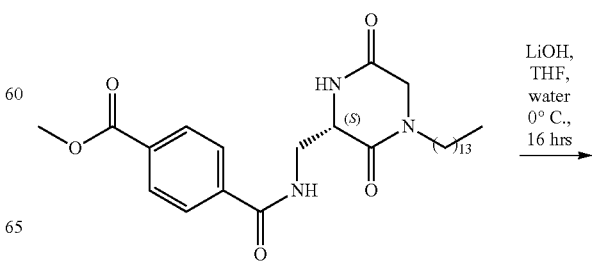

LiOH,
THF,
water
0° C.,
16 hrs

609

-continued

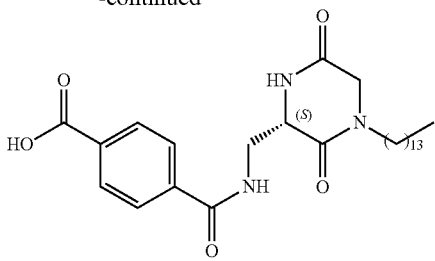

Prepared using General Ester Hydrolysis Procedure to give (S)-4-(((3,6-dioxo-4-tetradecylpiperazin-2-yl)methyl) carbamoyl)benzoic acid (0.16 g, 94%) LCMS (Method-C2): 86.07% (RT 1.520, 238 nm) (MS: ESI +ve 488.5 [M+H]).

Step-6: Preparation of (3S,4S)-1-(4-((((S)-3,6-dioxo-4-tetradecylpiperazin-2-yl)methyl)carbamoyl) benzoyl)-N3,N4-bis((1S,2R)-2-phenylcyclopropyl) pyrrolidine-3,4-dicarboxamide, Compound 177

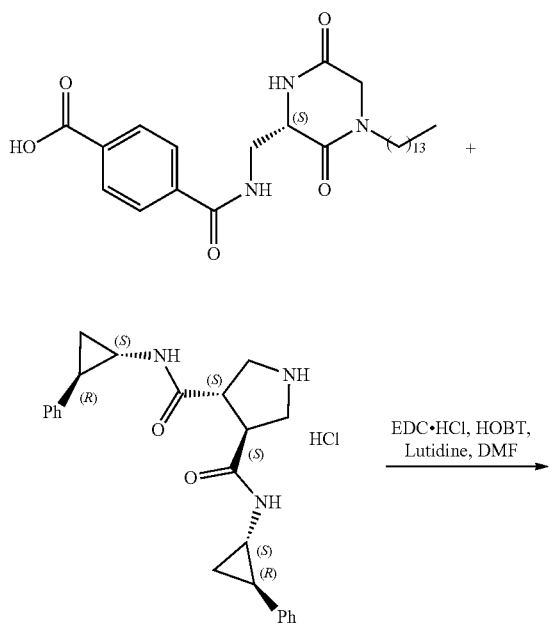

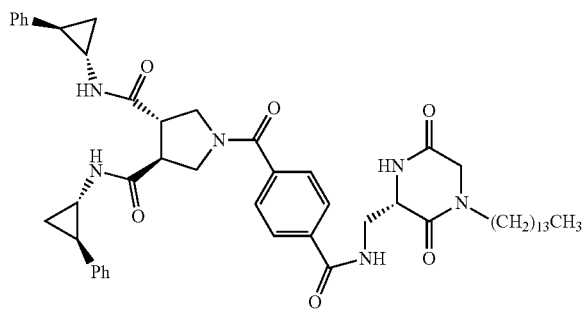

Prepared using General EDC, HOBT Coupling Procedure. The final product was purified using Prep HPLC Method 1 to give (3S,4S)-1-(4-((((S)-3,6-dioxo-4-tetradecylpiperazin-2-yl)methyl)carbamoyl)benzoyl)-N3,N4-bis ((1S,2R)-2-phenylcyclopropyl)pyrrolidine-3,4-dicarboxamide (Compound 177), as an off white solid (0.07 g, 24.8%). LCMS (Method-C2): 98.23% (RT 1.811, 225.0 nm) (MS: ESI +ve 859.6 [M+H]). $^1$H NMR: (400 MHz, DMSO) δ ppm: 0.83-0.86 (m, 3H), 1.08-1.23 (m, 26H), 1.44 (s, 2H), 1.83-1.86 (m, 1H), 1.94-1.98 (m, 1H), 2.76-2.79 (m, 1H), 2.83-2.86 (m, 1H), 3.10-3.19 (m, 1H), 3.21-3.28 (m, 3H), 3.47-3.54 (m, 3H), 3.61-3.65 (m, 1H), 3.70-3.73 (m, 1H), 3.81-3.83 (m, 2H), 3.91-3.96 (m, 2H), 7.06-7.07 (d, J=7.6 Hz, 2H), 7.11-7.18 (m, 4H), 7.22-7.28 (m, 4H), 7.59-7.61 (d, J=8.4 Hz, 2H), 7.88-7.90 (d, J=8.4 Hz, 2H), 8.29-8.31 (m, 2H), 8.44-8.45 (d, J=4 Hz, 1H), 8.66-8.69 (t, 1H).

Synthesis of (3S,4S)-1-(4-((((2S,5S)-4-hexyl-3,6-dioxo-5-pentylpiperazin-2-yl)methyl)carbamoyl) benzoyl)-N3,N4-bis((1S,2R)-2-phenylcyclopropyl) pyrrolidine-3,4-dicarboxamide, Compound 176

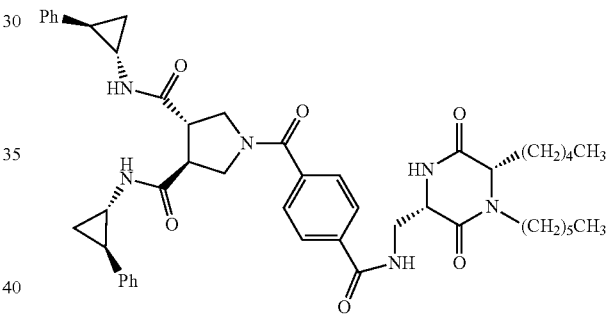

Prepared by a procedure similar to that reported for (3S,4S)-1-(4-((((S)-3,6-dioxo-4-tetradecylpiperazin-2-yl) methyl)carbamoyl)benzoyl)-N3,N4-bis((1S,2R)-2-phenylcyclopropyl)pyrrolidine-3,4-dicarboxamide (Compound 177), substituting the applicable starting materials in step 1. The crude product was purified using Prep HPLC Method 1 to give (3S,4S)-1-(4-((((2S,5S)-4-hexyl-3,6-dioxo-5-pentylpiperazin-2-yl)methyl)carbamoyl)benzoyl)-N3,N4-bis ((1S,2R)-2-phenylcyclopropyl)pyrrolidine-3,4-dicarboxamide (Compound 176)(0.062 g, 16.91%). LCMS (Method-J): 100% (RT 4.439, 202.0 nm) (MS: ESI +ve 817 [M+H]). $^1$H NMR: (400 MHz, DMSO) δ ppm: 0.82-0.84 (m, 6H), 1.08-1.25 (m, 16H), 1.35-1.55 (m, 2H), 1.76-1.87 (m, 3H), 1.94-1.97 (m, 1H), 2.67-2.78 (m, 1H), 2.83-2.88 (m, 2H), 3.09-3.21 (m, 2H), 3.34-3.42 (m, 3H), 3.48-3.64 (m, 2H), 3.78-3.83 (m, 2H), 4.16-4.18 (m, 2H), 7.05-7.07 (d, J=7.2 Hz, 2H), 7.11-7.22 (m, 4H), 7.24-7.28 (m, 4H), 7.57-7.61 (t, 2H), 7.89-7.91 (d, J=8 Hz, 2H), 8.16 (s, 1H), 8.30-8.31 (d, J=4 Hz, 1H), 8.45-8.46 (d, J=4.4 Hz, 1H), 8.55-8.58 (t, 1H).

Synthesis of (3S,4S)-1-(4-((5-(hexylcarbamoyl)-3-octyl-2-oxotetrahydropyrimidin-1 (2H)-yl)methyl) benzoyl)-N3,N4-bis((1S,2R)-2-phenylcyclopropyl) pyrrolidine-3,4-dicarboxamide, Compound 178

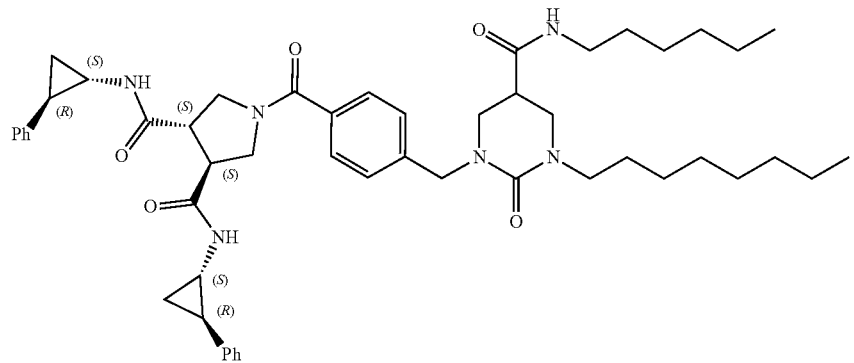

Step-1: Preparation of 1-isocyanatooctane

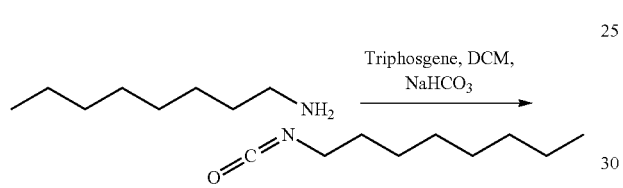

To a stirred solution of octan-1-amine (2.0 g, 15.47 mmol) in DCM (152 mL) at 0° C. was added sat. aq NaHCO₃ (152 mL) followed by triphosgene (1.69 g, 5.725 mmol). The mixture was stirred at 0° C. for 10 min. The organic layer was dried, concentrated and used without further purification in the next step.

Step-2: Preparation of 1-octylurea

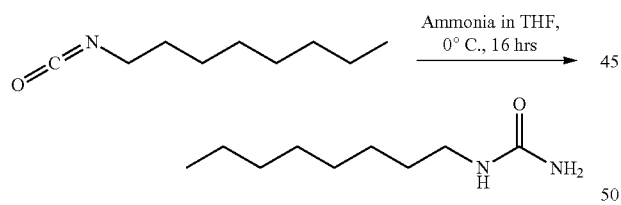

A mixture of 1-isocyanatooctane (152 mL) and ammonia in THF (30 mL) at 0° C. was stirred for 16 hrs, warming from 0° C. to room temperature. The reaction mixture was concentrated to give 1-octylurea (2.6 g, 94.6%). LCMS (Method-C2): 87.83% (RT: 1.183, 202.4 nm) (MS: ESI +ve 173.29 [M+H]).

Step-3: Preparation of ethyl (E)-2-(ethoxymethyl)-3-methoxyacrylate

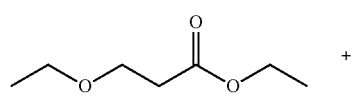

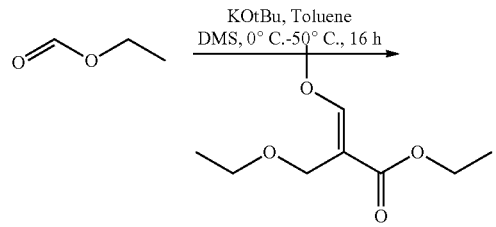

To a stirred solution of ethyl 3-ethoxypropanoate (5.0 g, 67.49 mmol) and ethyl formate (4.9 g, 33.74 mmol) at 0° C. in toluene (70 mL) was added a solution of 1M potassium t-butoxide in THF (67.4 mL, 67.49 mmol). The reaction mixture was stirred for 2 h then dimethyl sulfate (8.7 mL, 68.16 mmol) was added. Stirring was continued at 50° C. for 16 hr. The mixture was diluted with 2 N aq. NaOH (100 mL), extracted with EtOAc (2×150 mL), dried over sodium sulfate and concentrated to give ethyl (E)-2-(ethoxymethyl)-3-methoxyacrylate (2.3 g), which was used without further purification in the next step.

Step-4: Preparation of ethyl 1-octyl-2-oxo-1,2,3,4-tetrahydropyrimidine-5-carboxylate

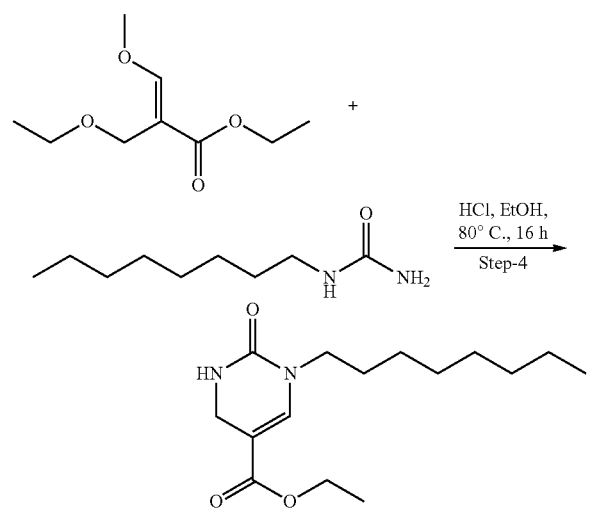

Conc. HCl (3.62 mL) was added to a stirred solution of ethyl (E)-2-(ethoxymethyl)-3-methoxyacrylate (1.4 g, 7.446 mmol) and 1-octylurea (1.28 g, 7.446 mmol) in EtOH (40 mL). The reaction was heated at 80° C. for 16 hr. The mixture was diluted with sat. aq. NaHCO₃ (100 mL), extracted with ethyl acetate (2×150 mL), dried over sodium sulfate and concentrated. The crude product was purified using flash chromatography on basic alumina, eluting with 1.5% MeOH in DCM, to yield ethyl 1-octyl-2-oxo-1,2,3,4-tetrahydropyrimidine-5-carboxylate (0.41 g, 14.7%). LCMS (Method-C2): 21.34% (RT: 1.594, 265.4 nm) (MS: ESI +ve 283.5 [M+H]).

Step-5: Preparation of ethyl 1-octyl-2-oxohexahydropyrimidine-5-carboxylate

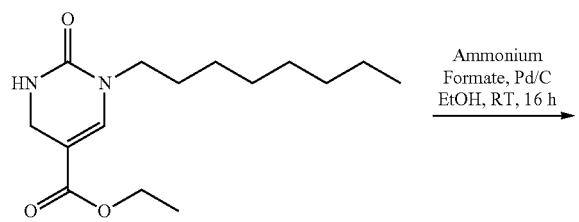

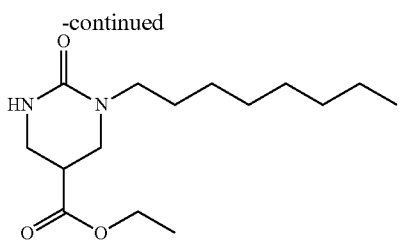

A mixture of ethyl 1-octyl-2-oxo-1,2,3,4-tetrahydropyrimidine-5-carboxylate (0.41 g, 1.452 mmol), ammonium formate (0.457 g, 7.263 mmol) and Pd/C (50% moisture, 0.41 g) in EtOH (20 mL) was heated at 80° C. for 16 hrs. The reaction mixture was filtered through a pad of celite and the filtrate was concentrated. The crude product was purified using flash chromatography on basic alumina, eluting with 1.5% MeOH in DCM, to yield ethyl 1-octyl-2-oxohexahydropyrimidine-5-carboxylate as a colorless gum (0.24 g, 58.12%). LCMS (Method-C2): 89.11% (RT: 1.345, 202.4 nm) (MS: ESI +ve 285.2 [M+H]).

Step-6: Preparation of 1-(4-(tert-butoxycarbonyl)benzyl)-3-octyl-2-oxohexahydropyrimidine-5-carboxylic acid

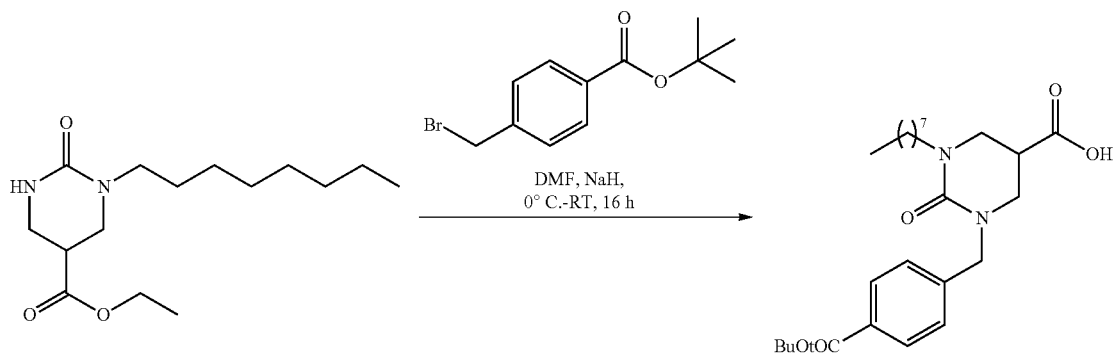

Sodium hydride (60% in mineral oil) (0.0646 g, 1.616 mmol) was added to a solution of ethyl 1-octyl-2-oxohexahydropyrimidine-5-carboxylate (0.22 g, 1.279 mmol) in DMF (5 mL) at 0° C. tert-butyl 4-(bromomethyl)benzoate (0.328 g, 1.212 mmol) was added and the reaction mixture was stirred at room temperature for 16 hrs. The mixture was diluted with 1 N HCl (50 mL), extracted with ethyl acetate (3×50 mL), dried over sodium sulfate and concentrated under vacuum to yield 1-(4-(tert-butoxycarbonyl)benzyl)-3-octyl-2-oxohexahydropyrimidine-5-carboxylic acid as a yellow gum (1.1 g, crude). LCMS (Method-C2): 25.91% (RT: 1.446, 235.0 nm) (MS: ESI +ve 447.67 [M+H]).

615

Step 7: Preparation of tert-butyl 4-((5-(hexylcarbamoyl)-3-octyl-2-oxotetrahydropyrimidin-1 (2H)-yl)methyl)benzoate

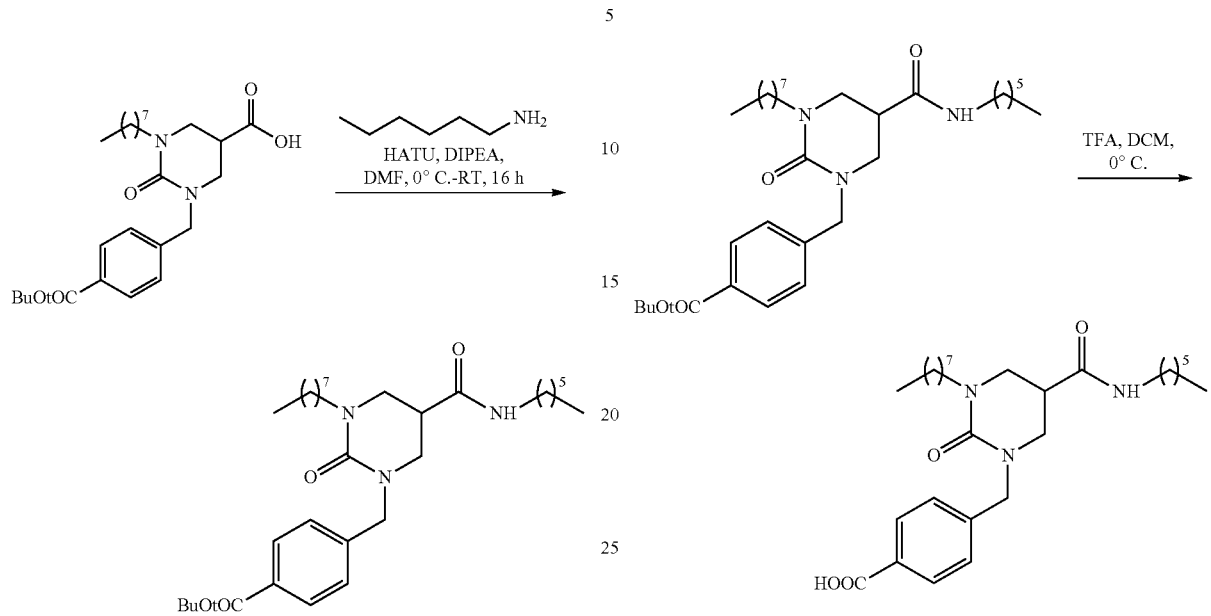

Prepared using General EDC, HOBT Coupling Procedure. The crude product was purified using flash chromatography, eluting with 3% MeOH in DCM, to give tert-butyl 4-((5-(hexylcarbamoyl)-3-octyl-2-oxotetrahydropyrimidin-1 (2H)-yl)methyl)benzoate (0.16 g, 24.8%). LCMS (Method-C2): 92.0% (RT 1.736, 225.0 nm) (MS: ESI +ve 530.6 [M+1]).

616

Step-8: Preparation of 4-((5-(hexylcarbamoyl)-3-octyl-2-oxotetrahydropyrimidin-1 (2H)-yl)methyl)benzoic acid Prepared using General BOC Deprotection Procedure to give 4-((5-(hexylcarbamoyl)-3-octyl-2-oxotetrahydropyrimidin-1 (2H)-yl)methyl)benzoic acid. (0.2 g). LCMS (Method-C2): 84.31% (RT 1.567, 235.0 nm) (MS: ESI +ve 474.5 [M+1]).

Step-9: Preparation of (3S,4S)-1-(4-((5-(hexylcarbamoyl)-3-octyl-2-oxotetrahydropyrimidin-1 (2H)-yl)methyl)benzoyl)-N3,N4-bis((1S,2R)-2-phenylcyclopropyl)pyrrolidine-3,4-dicarboxamide, Compound 178

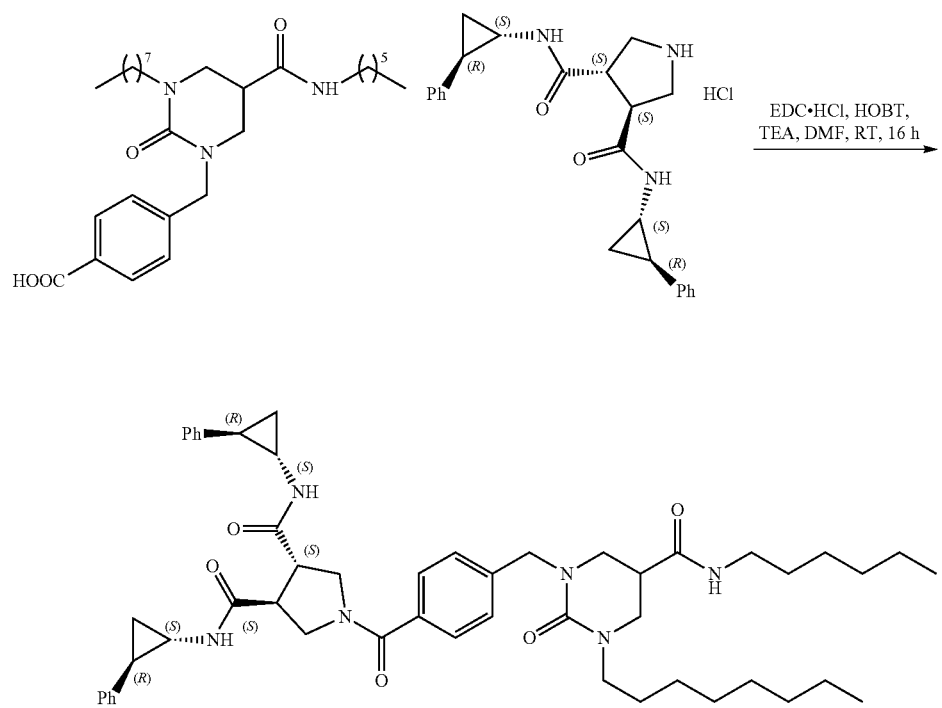

Prepared using General EDC, HOBT Coupling Procedure. The crude product was purified using Prep HPLC Method 1 to give (3S,4S)-1-(4-((5-(hexylcarbamoyl)-3-octyl-2-oxotetrahydropyrimidin-1 (2H)-yl)methyl)benzoyl)-N3,N4-bis((1S,2R)-2-phenylcyclopropyl)pyrrolidine-3,4-dicarboxamide (Compound 178), as an off white solid (0.06 g, 21%). LCMS (Method-J2): 100% (RT 4.833, 202.0 nm) (MS: ESI +ve 845.6 [M+H]). $^1$H NMR: (400 MHz, DMSO) δ ppm: 0.82-0.87 (m, 6H), 1.08-1.47 (m, 22H), 1.89-1.97 (m, 2H), 2.67-2.85 (m, 3H), 2.97-3.03 (m, 2H), 3.08-3.18 (m, 4H), 3.20-3.38 (m, 2H), 3.48-3.53 (m, 2H), 3.65-3.77 (m, 2H), 4.44-4.49 (m, 2H), 7.06-7.18 (m, 6H), 7.22-7.28 (m, 6H), 7.46-7.48 (d, J=8 Hz, 2H), 8.01-8.04 (t, 1H), 8.29-8.30 (d, J=4 Hz, 1H), 8.43-8.44 (d, J=4 Hz, 1H).

Synthesis of (3S,4S)—N3,N4-bis((1S,2R)-2-phenylcyclopropyl)-1-(4-((R)-3-(tetradecylcarbamoyl) piperidine-1-carbonyl) benzoyl) pyrrolidine-3,4-dicarboxamide, Compound 102

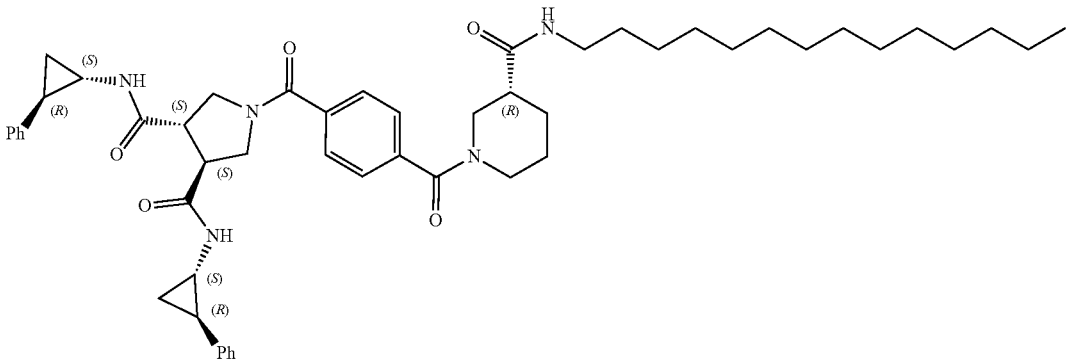

Step-1: Preparation of (3S,4S)—N3,N4-bis((1S,2R)-2-phenylcyclopropyl)-1-(4-((R)-3-(tetradecylcarbamoyl) piperidine-1-carbonyl) benzoyl) pyrrolidine-3,4-dicarboxamide, Compound 102

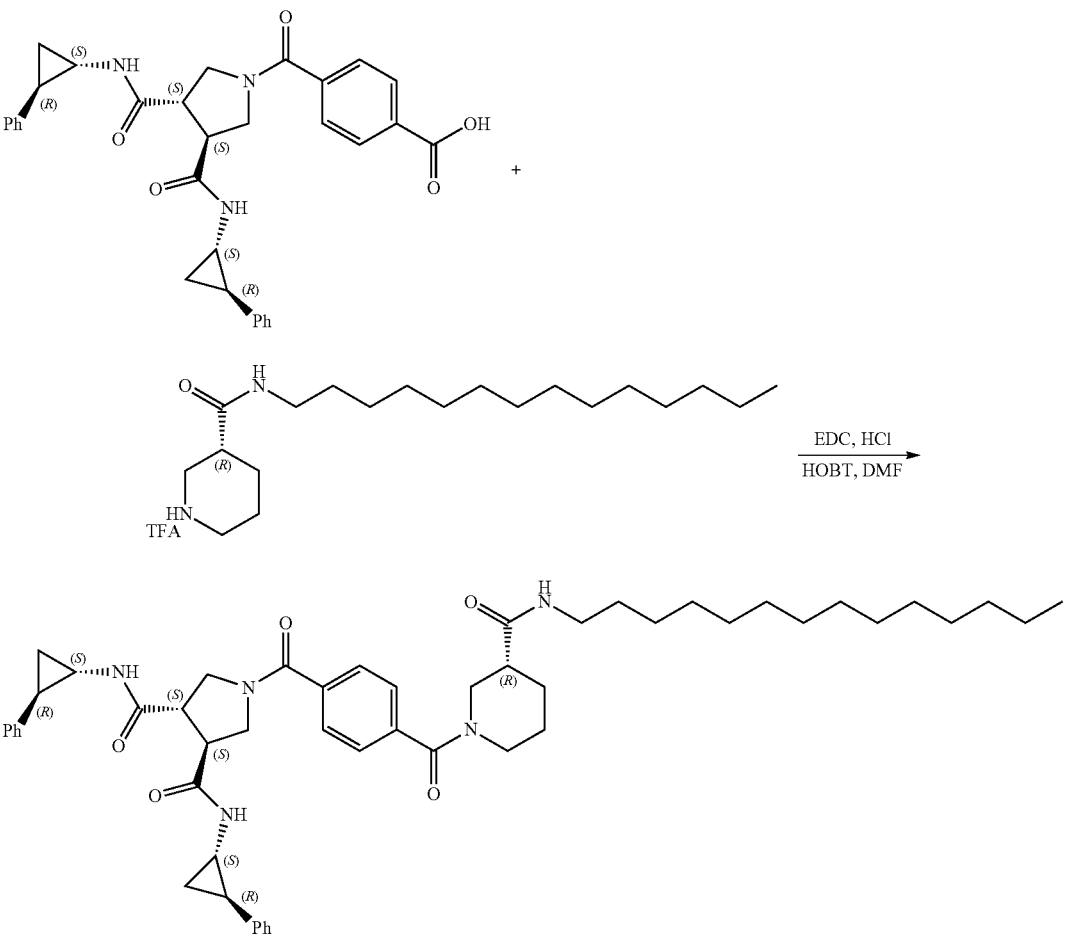

Prepared by a procedure similar to General EDC, HOBT Coupling Procedure using the applicable amine and carboxylic acid. The crude product was purified using Prep HPLC Method 1 to give (3S,4S)—N3,N4-bis((1S,2R)-2-phenylcyclopropyl)-1-(4-((R)-3-(tetradecylcarbamoyl) piperidine-1-carbonyl) benzoyl) pyrrolidine-3,4-dicarboxamide (Compound 102)(0.028 g, 11.5%). LCMS (Method-J): 98.3% (RT 6.831, 202.0 nm) (MS: ESI +ve 845 [M+H]). $^1$H NMR: (400 MHz, DMSO) δ ppm: 0.85-0.88 (t, 3H); 1.10 (s, 2H); 1.25 (s, 25H); 1.39 (s, 2H); 1.62-1.65 (d, J=10.4, 2H); 1.86 (s, 2H); 2.01 (s, 1H); 2.34-2.35 (m, 1H); 2.68-2.69 (m, 1H); 2.87 (s, 2H); 3.04 (s, 3H); 3.08 (s, 1H); 3.13-3.22 (m, 1H); 3.44-3.55 (m, 3H); 3.57-3.68 (m, 1H); 3.70-3.83 (m, 1H); 4.34 (s, 1H); 7.08-7.09 (d, J=7.2, 2H), 7.13-7.15 (d, J=7.6, 4H); 7.18-7.23 (m, 4H); 7.42-7.44 (d, J=8, 2H); 7.57-7.59 (d, J=8.4, 2H); 7.94 (s, 1H); 8.33 (s, 1H); 8.51 (s, 1H).

Synthesis of (3S,4S)—N3,N4-bis((1S,2R)-2-phenylcyclopropyl)-1-(4-((S)-3-(tetradecylcarbamoyl)piperidine-1-carbonyl)benzoyl)pyrrolidine-3,4-dicarboxamide, Compound 123

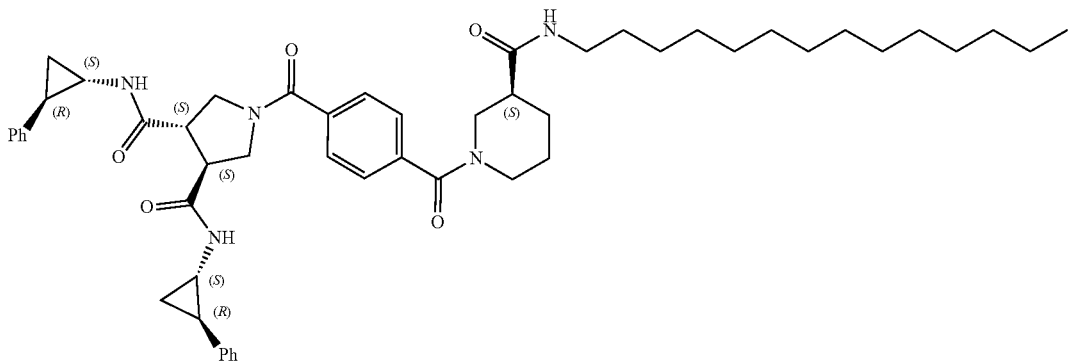

Step-1: Preparation of (3S,4S)—N3,N4-bis((1S,2R)-2-phenylcyclopropyl)-1-(4-((S)-3-(tetradecylcarbamoyl)piperidine-1-carbonyl)benzoyl)pyrrolidine-3,4-dicarboxamide, Compound 123

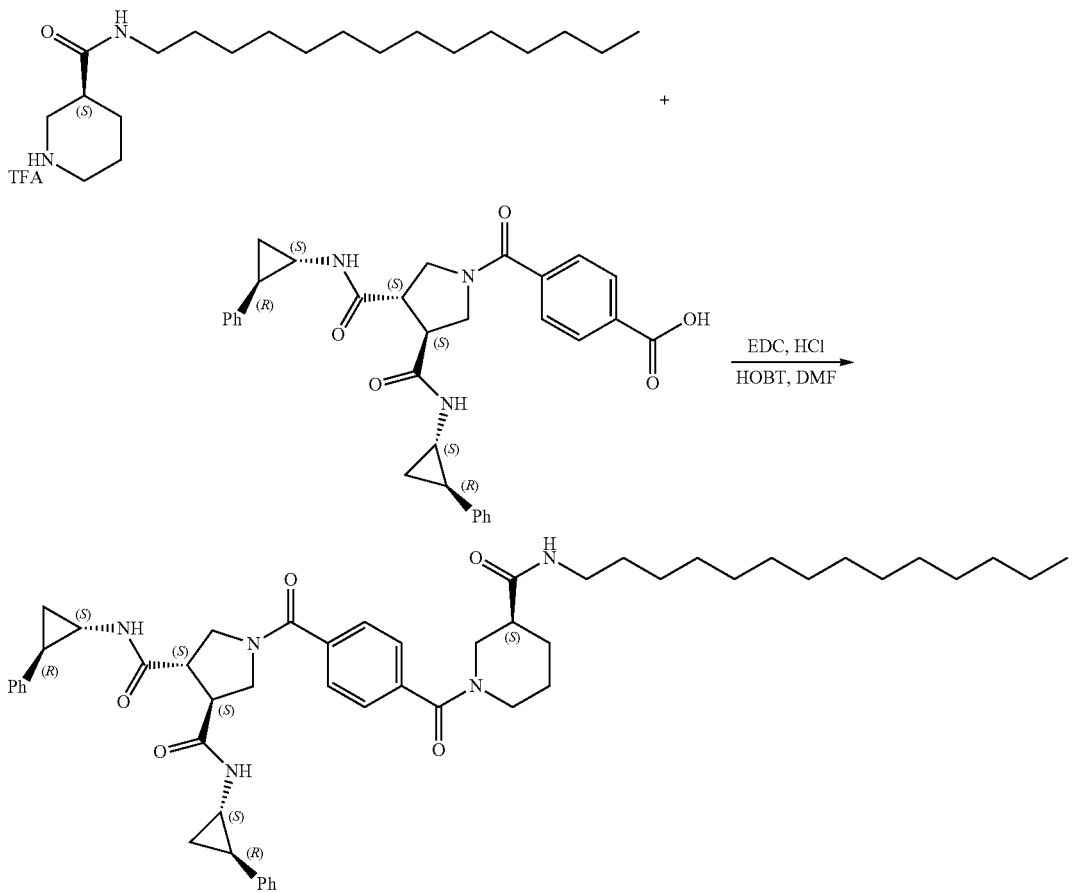

Prepared by a procedure similar to General EDC, HOBT Coupling Procedure using the applicable amine and carboxylic acid. The crude product was purified using Prep HPLC Method 12 to give (3S,4S)—N3,N4-bis((1S,2R)-2-phenylcyclopropyl)-1-(4-((S)-3-(tetradecylcarbamoyl)piperidine-1-carbonyl)benzoyl)pyrrolidine-3,4-dicarboxamide (Compound 123)(0.016 g, 7.1% yield), as a white solid. LCMS (Method-J): 100% (RT: 6.661, 202.0 nm) (MS: ESI +ve 844.6 [M−1]). $^1$H NMR: (400 MHz, DMSO) δ ppm: 0.853-0.873 (m, 4H), 1.222-1.255 (m, 27H), 1.385 (s, 2H), 1.623 (s, 3H), 1.865-1.968 (m, 4H), 2.356 (s, 4H), 2.656 (s, 5H), 3.027 (s, 5H), 3.318-3.370 (m, 7H), 3.521 (s, 3H), 3.669-3.688 (m, 1H), 3.794 (s, 1H), 7.103-7.141 (m, 5H), 7.251 (s, 4H), 7.425 (s, 2H), 7.582 (m, 2H), 7.770 (s, 1H), 7.933 (s, 1H), 8.317 (s, 1H), 8.417-8.446 (d, J=11.6 Hz, 1H).

Synthesis of (3S,4S)-1-(4-((S)-3-pentadecanamidopiperidine-1-carbonyl)benzoyl)-N3,N4-bis((1S,2R)-2-phenylcyclopropyl)pyrrolidine-3,4-dicarboxamide, Compound 124

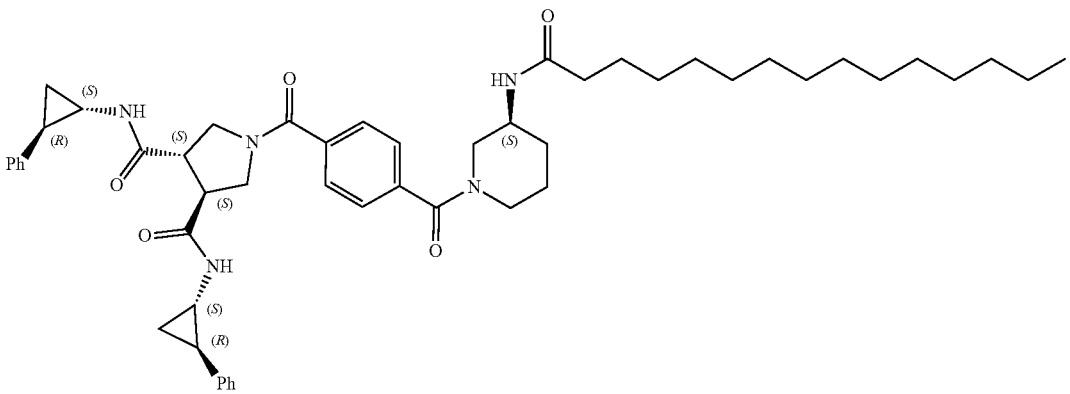

Step-1: Preparation of (3S,4S)-1-(4-((S)-3-pentadecanamidopiperidine-1-carbonyl) benzoyl)-N3,N4-bis((1S,2R)-2-phenylcyclopropyl)pyrrolidine-3,4-dicarboxamide

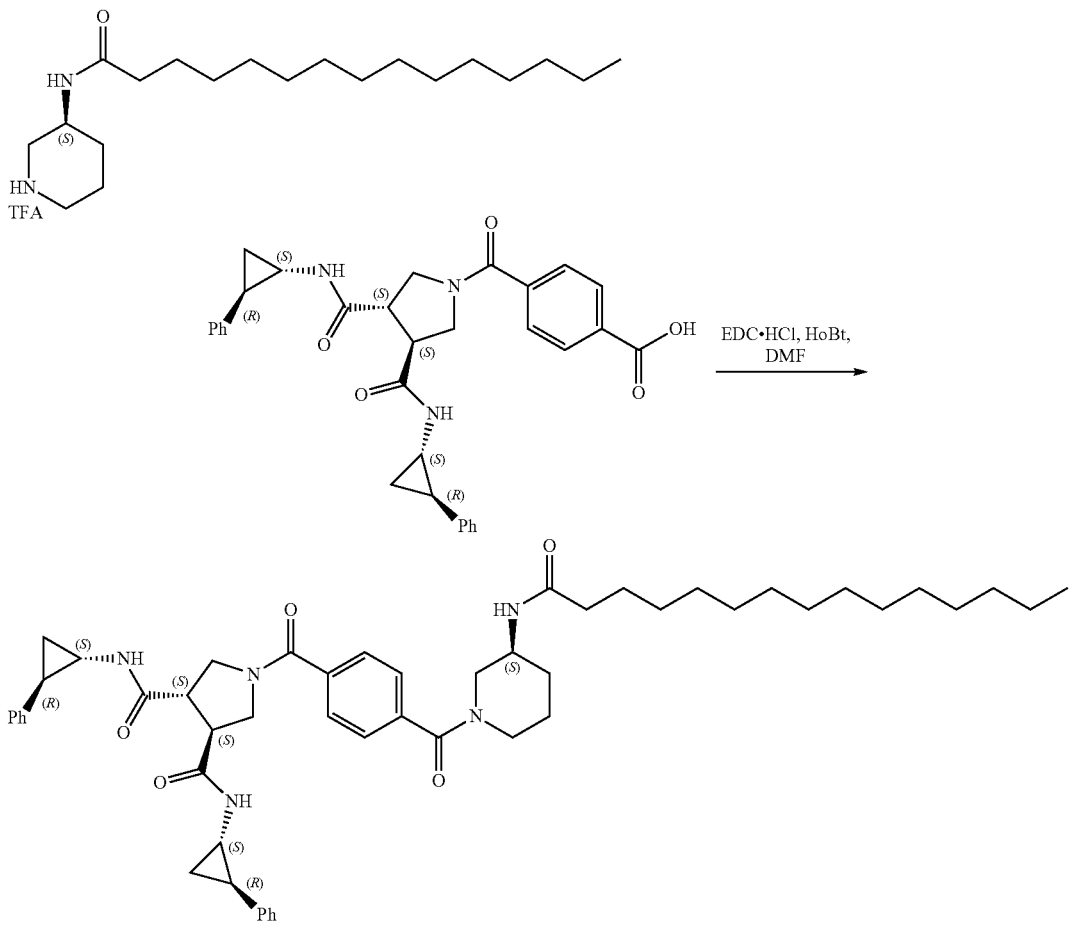

Prepared by a procedure similar to General EDC, HOBT Coupling Procedure using the applicable amine and carboxylic acid. The crude product was purified using Prep HPLC Method 12 to give (3S,4S)-1-(4-((S)-3-pentadecanamidopiperidine-1-carbonyl)benzoyl)-N3,N4-bis((1S,2R)-2-phenylcyclopropyl)pyrrolidine-3,4-dicarboxamide (Compound 124), (0.043 g, 15.2% yield), as a white solid. LCMS (Method-J): 100% (RT: 6.655, 202.0 nm) (MS: ESI +ve 843.5[M−1]). $^1$H NMR: (400 MHz, DMSO) δ ppm: 0.844-0.878 (m, 3H), 1.106-1.243 (m, 24H), 1.485 (s, 4H), 1.662 (s, 2H), 1.851-1.874 (m, 3H), 1.978-2.077 (m, 2H), 2.617 (s, 1H), 2.791-2.863 (m, 3H), 2.990-3.140 (m, 1H), 3.176-3.238 (m, 1H), 3.505-3.525 (m, 3H), 3.668 (s, 2H), 3.783-3.834 (m, 2H), 4.221 (s, 1H), 7.073-7.092 (d, 2H), 7.125-7.192 (m, 4H), 7.231-7.296 (m, 4H), 7.447 (s, 2H), 7.563 (s, 2H), 7.822 (s, 1H), 8.309-8.319 (d, J=4 Hz, 1H), 8.422-8.452 (d, J=12 Hz, 1H).

Synthesis of (3S,4S)-1-(4-((R)-3-pentadecanamidopiperidine-1-carbonyl)benzoyl)-N3,N4-bis((1S,2R)-2-phenylcyclopropyl)pyrrolidine-3,4-dicarboxamide, Compound 152

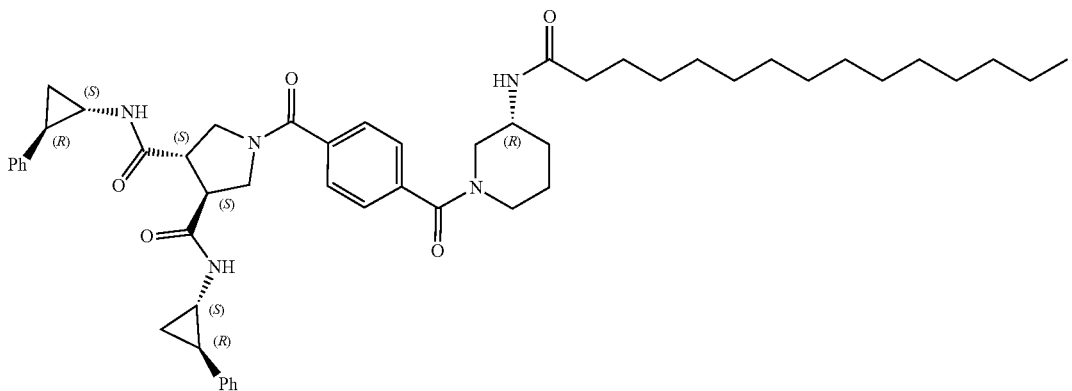

Step 1: Synthesis of (3S,4S)-1-(4-((R)-3-pentadecanamidopiperidine-1-carbonyl)benzoyl)-N3,N4-bis((1S,2R)-2-phenylcyclopropyl)pyrrolidine-3,4-dicarboxamide, Compound 152

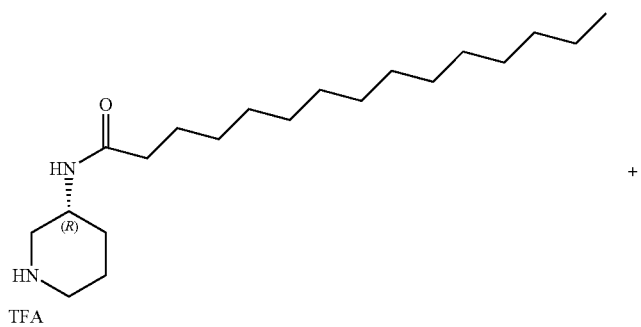

TFA

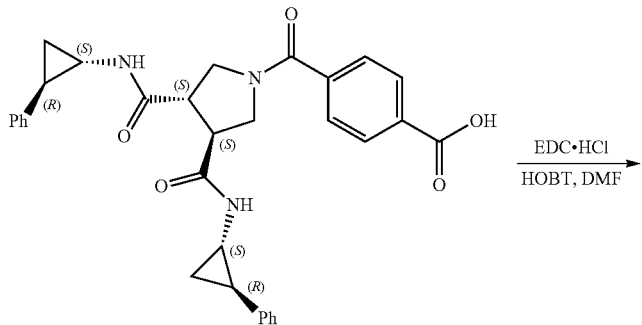

EDC·HCl
HOBT, DMF

-continued

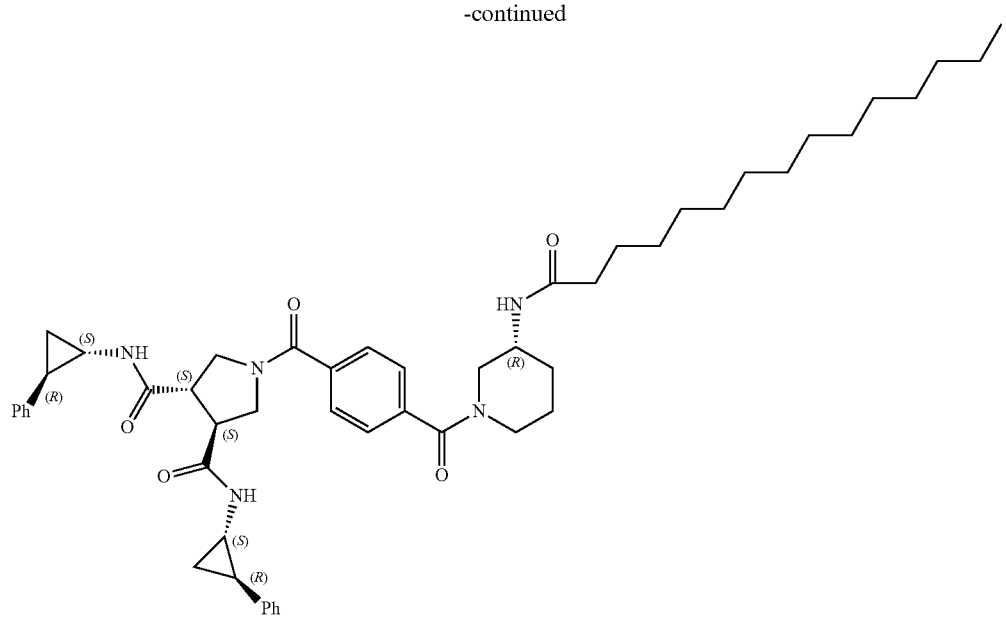

Prepared by a procedure similar to General EDC, HOBT Coupling Procedure using the applicable amine and carboxylic acid. The crude product was purified using Prep HPLC Method 1 to give (3S,4S)-1-(4-((R)-3-pentadecanamidopiperidine-1-carbonyl)benzoyl)-N3,N4-bis((1S,2R)-2-phenylcyclopropyl)pyrrolidine-3,4-dicarboxamide (Compound 152) (0.032 g, 14.95%), as an off white solid LCMS (Method-C3): 100% (RT 2.549, 225.0 nm) (MS: ESI +ve 844.86 [M+2]). (400 MHz, DMSO) δ ppm: 0.85-0.86 (d, J=6.8 Hz, 3H), 1.10-1.24 (m, 27H), 1.48 (s, 4H), 1.86-2.07 (m, 6H), 2.79-2.86 (m, 3H), 3.11-3.13 (d, J=8 Hz, 1H), 3.34 (s, 2H), 3.52-3.57 (t, J=9.2 Hz, 3H), 3.66 (s, 2H), 3.77-3.82 (s, 2H), 7.076-7.55 (m, 10H), 7.558 (s, 2H), 7.80 (s, 1H), 8.35 (s, 1H), 8.48-8.53 (d, J=20.4 Hz, 2H).

Synthesis of (3S,4S)—N3,N4-bis ((1S,2R)-2-phenylcyclopropyl)-1-(4-((R)-2-(tetradecylcarbamoyl) morpholine-4-carbonyl) benzoyl) pyrrolidine-3,4-dicarboxamide, Compound 150

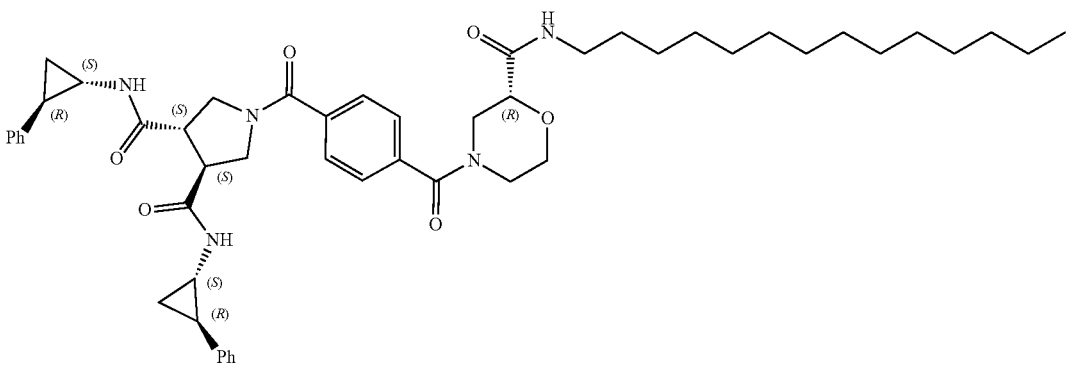

Step 1: Preparation of (3S,4S)—N3,N4-bis ((1S,2R)-2-phenylcyclopropyl)-1-(4-((R)-2-(tetradecylcarbamoyl) morpholine-4-carbonyl) benzoyl) pyrrolidine-3,4-dicarboxamide, Compound 150

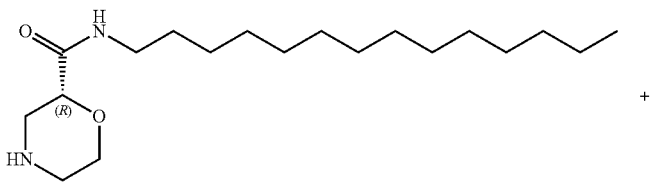

+

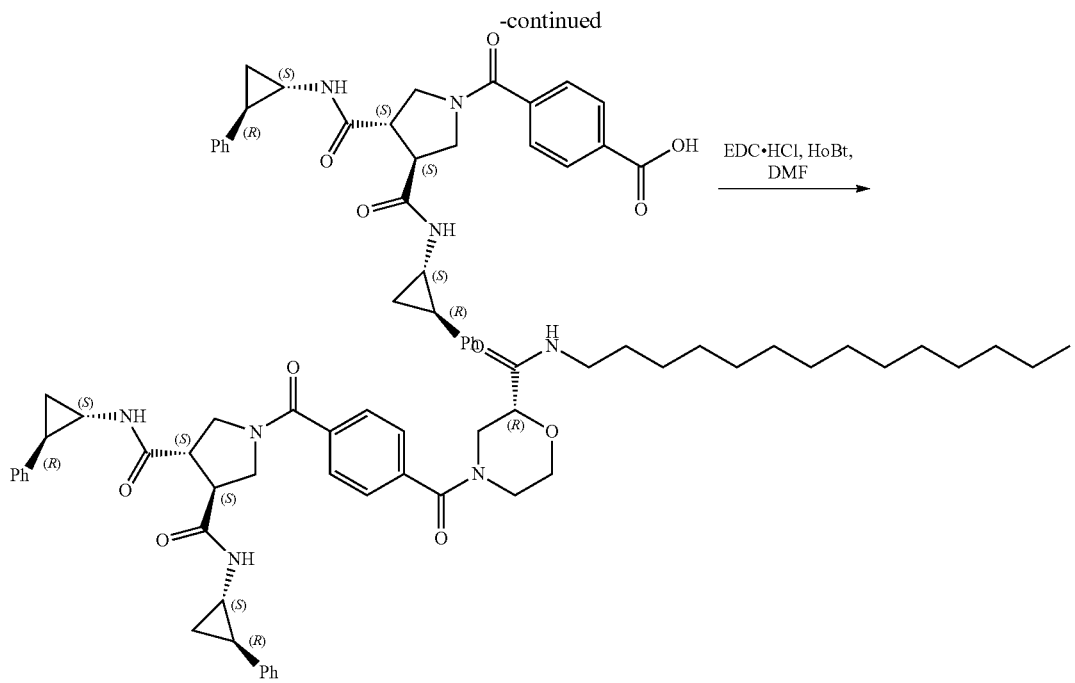

Prepared by a procedure similar to General EDC, HOBT Coupling Procedure using the applicable amine and carboxylic acid. The crude product was purified using Prep HPLC Method 1 to give (3S,4S)—N3,N4-bis ((1S,2R)-2-phenyl-cyclopropyl)-1-(4-((R)-2-(tetradecylcarbamoyl) morpholine-4-carbonyl) benzoyl) pyrrolidine-3,4-dicarboxamide (Compound 150), as a white solid (0.030 g, 12.75%). LCMS (Method-C3): 100% (RT 2.668, 222.0 nm) (MS: ESI +ve 847 [M+H]). $^1$H NMR: (400 MHz, DMSO) δ ppm: 0.83-0.87 (t, 4H); 1.09-1.12 (t, 3H); 1.23 (s, 28H); 1.36 (s, 2H); 1.86 (s, 1H); 2.04 (s, 1H); 2.78 (s, 1H); 2.84 (s, 1H); 3.10-3.12 (d, J=8, 2H); 3.53-3.55 (d, J=7.6, 3H); 3.64-3.66 (d, J=9.6, 2H); 3.78 (s, 1H); 3.95-3.97 (d, J=8.4, 1H); 7.06-7.16 (m, 6H); 7.22-7.28 (m, 4H); 7.48-7.50 (d, J=7.6, 2H); 7.58-7.60 (d, J=8, 2H); 7.87 (s, 1H); 8.31 (s, 1H); 8.43 (s, 1H).

Synthesis of (3S,4S)—N3,N4-bis((1S,2R)-2-phenyl-cyclopropyl)-1-(4-((S)-2-(tetradecylcarbamoyl)morpholine-4-carbonyl)benzoyl)pyrrolidine-3,4-dicarboxamide, Compound 151

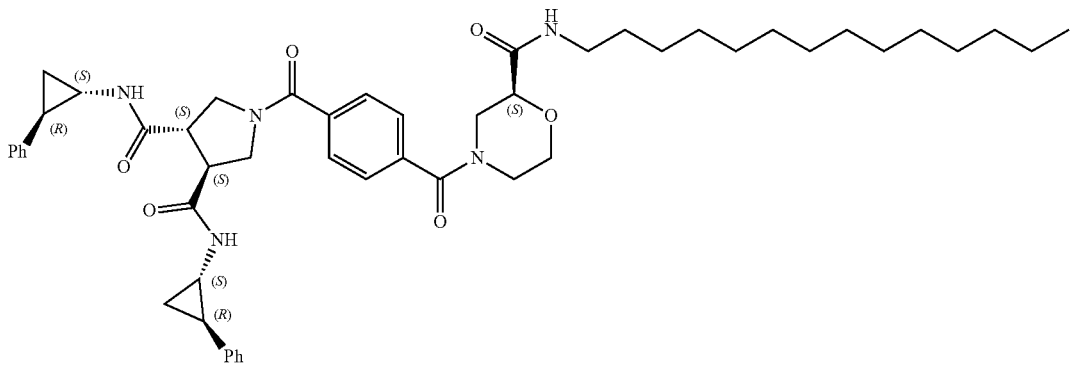

Step-1: Preparation of (3S,4S)—N3,N4-bis((1S,2R)-2-phenylcyclopropyl)-1-(4-((S)-2-(tetradecylcarbamoyl)morpholine-4-carbonyl)benzoyl)pyrrolidine-3,4-dicarboxamide, Compound 151

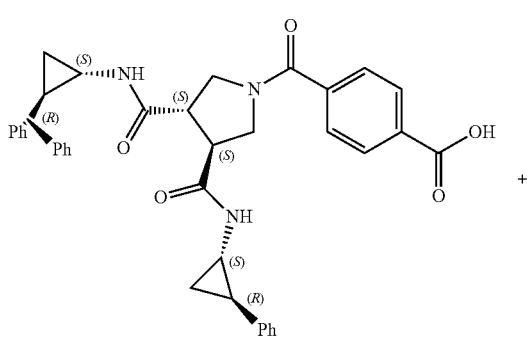

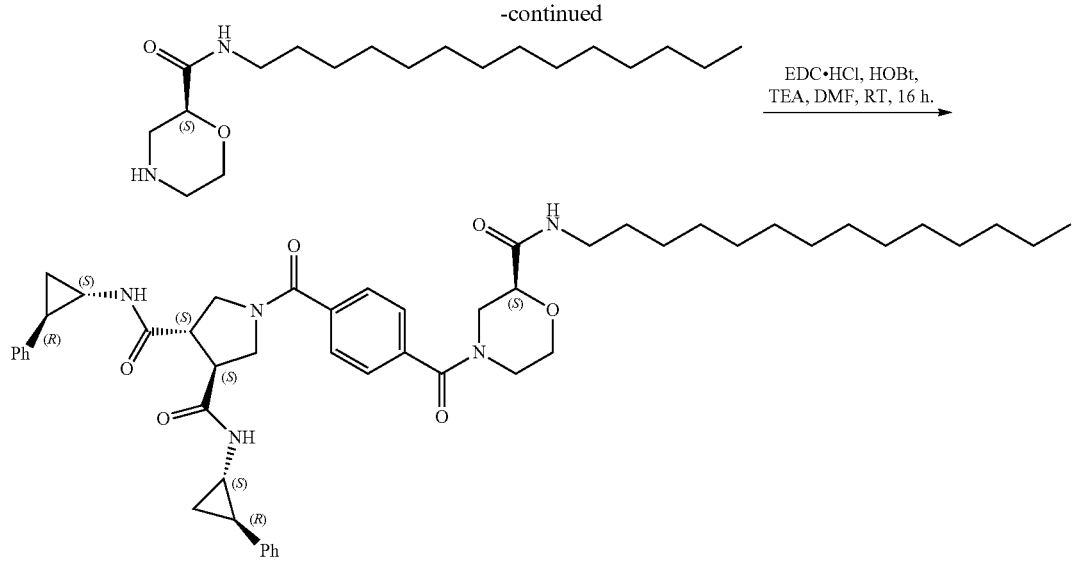

Prepared by a procedure similar to General EDC, HOBT Coupling Procedure using the applicable amine and carboxylic acid. The crude product was purified using Prep HPLC Method 7 to give (3S,4S)—N3,N4-bis((1S,2R)-2-phenylcyclopropyl)-1-(4-((S)-2-(tetradecylcarbamoyl)morpholine-4-carbonyl)benzoyl)pyrrolidine-3,4-dicarboxamide (Compound 151) (0.030 g, 16%), as an off white solid. LCMS (Method-J): 100% (RT 6.337, 202.0 nm) (MS: ESI +ve 846.9 [M+H]). $^1$H NMR: (400 MHz, DMSO) δ ppm: 0.85-0.86 (m, 3H), 1.10-1.24 (m, 28H), 1.39 (s, 3H), 1.88 (s, 1H), 1.98 (s, 1H), 2.80 (s, 1H), 2.85 (s, 1H), 3.11-3.13 (m, 3H), 3.20-3.23 (m, 2H), 3.53-3.55 (m, 3H), 3.65-3.67 (m, 1H), 3.79-3.84 (m, 1H), 3.96-3.98 (m, 1H), 4.20-4.50 (m, 1H), 7.08-7.19 (m, 6H), 7.23-7.30 (m, 4H), 7.49-4.51 (m, 2H), 7.60-7.61 (m, 2H), 7.81-7.87 (s, 1H), 8.32 (s, 1H), 8.44 (s, 1H).

Synthesis of (3S,4S)-1-(4-(((R)-1-pentadecanoylpiperidin-3-yl)carbamoyl)benzoyl)-N3,N4-bis((1S,2R)-2-phenylcyclopropyl)pyrrolidine-3,4-dicarboxamide, Compound 153

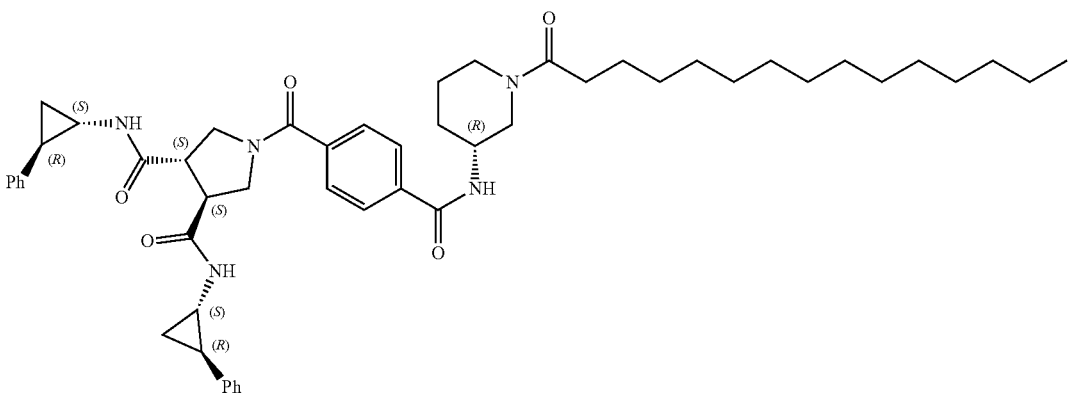

Step 1: Preparation of (3S,4S)-1-(4-(((R)-1-pentadecanoylpiperidin-3-yl)carbamoyl) benzoyl)-N3,N4-bis((1S,2R)-2-phenylcyclopropyl)pyrrolidine-3,4-dicarboxamide, Compound 153

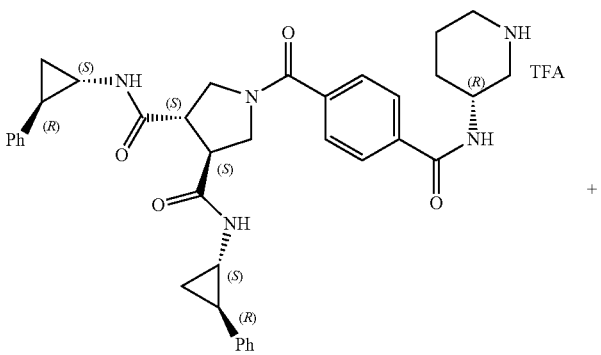

-continued

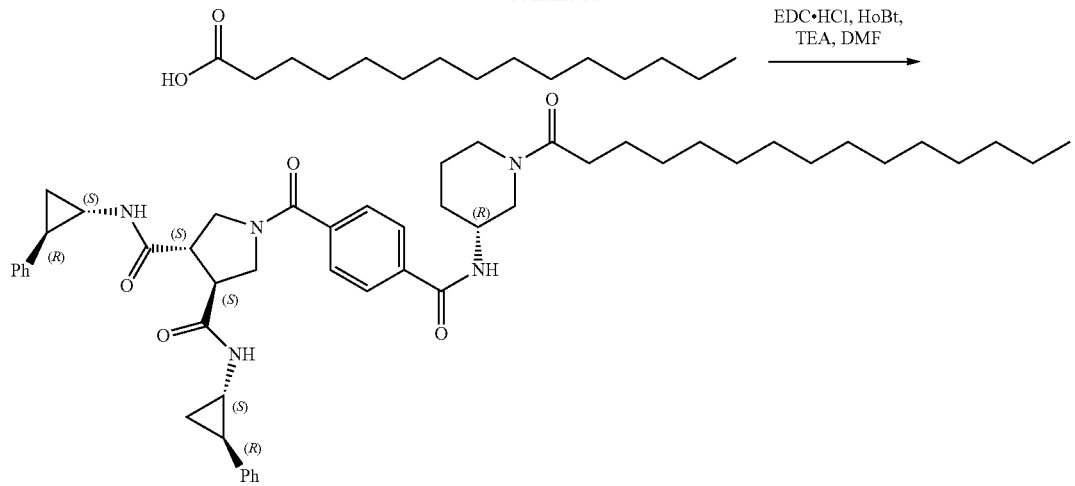

Prepared by a procedure similar to General EDC, HOBT Coupling Procedure using the applicable amine and carboxylic acid. The crude product was purified using Prep HPLC Method 13 to give (3S,4S)-1-(4-(((R)-1-pentadecanoylpiperidin-3-yl)carbamoyl)benzoyl)-N3,N4-bis((1S,2R)-2-phenylcyclopropyl)pyrrolidine-3,4-dicarboxamide (Compound 153)(22 mg, 12.42%). LCMS (Method-03): 100% (RT 6.840, 202.0 nm) (MS: ESI +ve 844.5 [M+2]). $^1$H NMR (400 MHz, DMSO) δ ppm: 0.84 (s, 3H), 0.85-1.24 (m, 27H), 1.48 (s, 2H), 1.57-1.97 (m, 4H), 3.83-4.37 (m, 4H), 2.22-2.33 (m, 3H), 2.78-2.85 (t, J=4 Hz, 2H), 2.98-3.19 (m, 4H), 3.45-3.75 (m, 2H), 4.24 (s, 1H), 7.06-7.28 (m, 10H), 7.58-7.60 (d, J=8 Hz, 2H), 7.87-7.91 (t, J=8.4 Hz, 2H), 8.33-8.50 (m, 4H).

Synthesis of (3S,4S)-1-(4-(((S)-1-pentadecanoylpiperidin-3-yl)carbamoyl) benzoyl)-N3,N4-bis((1S,2R)-2-phenylcyclopropyl)pyrrolidine-3,4-dicarboxamide, Compound 125

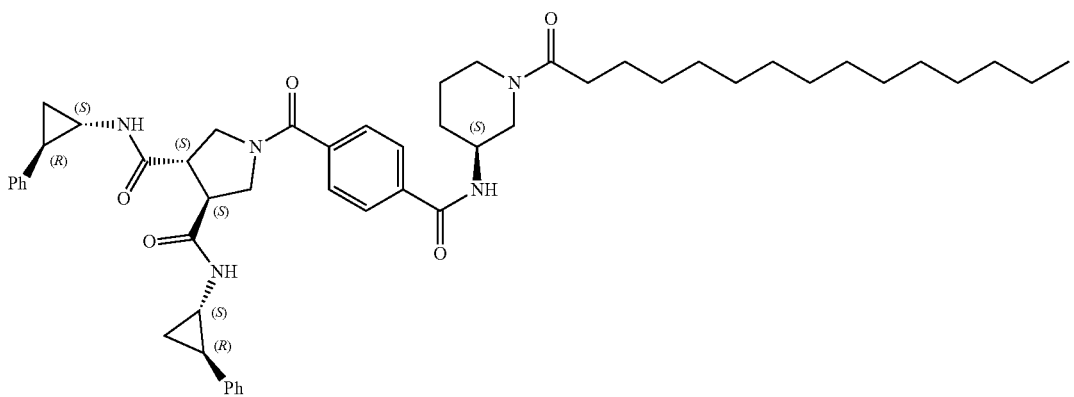

Step-1: Preparation of tert-butyl (S)-3-(4-((3S,4S)-3,4-bis(((1S,2R)-2-phenylcyclopropyl)carbamoyl)pyrrolidine-1-carbonyl)benzamido)piperidine-1-carboxylate, Compound 125

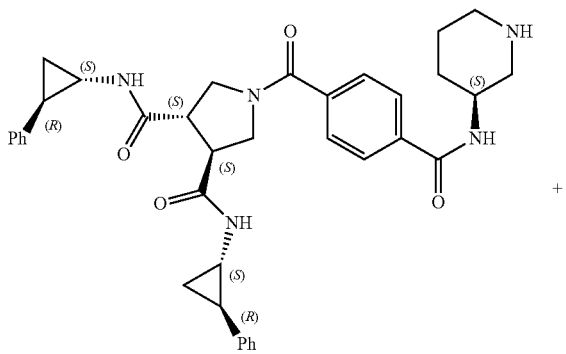

+

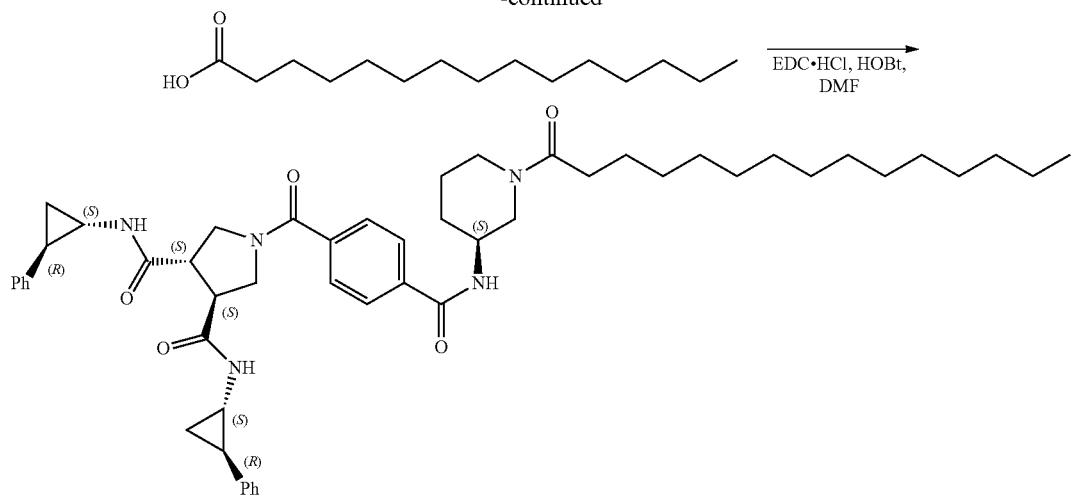

Prepared by a procedure similar to General EDC, HOBT Coupling Procedure using the applicable amine and carboxylic acid. The crude product was purified using Prep HPLC Method 12 to give (3S,4S)-1-(4-(((S)-1-pentadecanoylpiperidin-3-yl)carbamoyl)benzoyl)-N3,N4-bis((1S,2R)-2-phenylcyclopropyl)pyrrolidine-3,4-dicarboxamide (Compound 125) (0.020 g, 10.5% yield), as a white solid. LCMS (Method-J): 100% (RT: 6.760, 202.0 nm) (MS: ESI +ve 845.6 [M−1]). $^1$H NMR: (400 MHz, DMSO) δ ppm: 0.838-0.855 (m, 3H), 1.198-1.253 (m, 3H), 1.357-1.386 (m, 2H), 1.386-1.493 (m, 18H), 1.357-1.386 (m, 3H), 1.550 (m, 1H), 1.581 (m, 1H), 1.764 (m, 1H), 1.855-2.004 (m, 2H), 2.222-2.241 (m, 4H), 2.317 (m, 1H), 2.344 (m, 1H), 2.513 (m, 1H), 2.521-2.566 (m, 3H), 2.686-2.783 (m, 1H), 2.856-2.877 (m, 2H), 2.887 (m, 1H), 3.050-3.107 (m, 3H), 3.181-3.242 (m, 1H), 3.549-4.041 (m, 1H), 7.068-7.087 (m, 2H), 7.126-7.231 (m, 4H), 7.250-7.298 (m, 4H), 7.594-7.614 (d, 2H), 7.881-7.922 (t, J=16.4 Hz, 2H), 8.370-8.428 (m, 1H), 8.472-8.521 (t, J=19.6 Hz, 2H).

Synthesis of (3S,4S)-1-(4-(((S)-6-oxo-1-pentadecylpiperidin-3-yl)carbamoyl)benzoyl)-N3,N4-bis((1S,2R)-2-phenylcyclopropyl)pyrrolidine-3,4-dicarboxamide, Compound 180

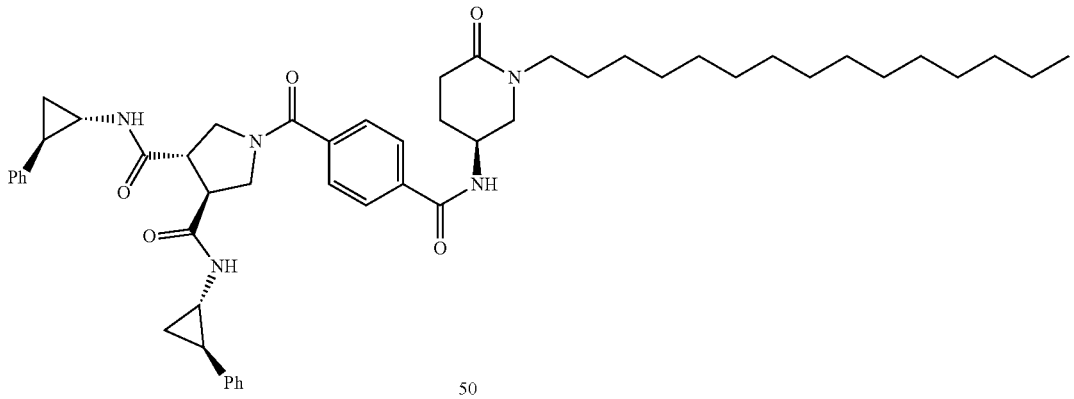

Step-1: Preparation of methyl (S)-4-((tert-butoxycarbonyl)amino)-5-hydroxypentanoate

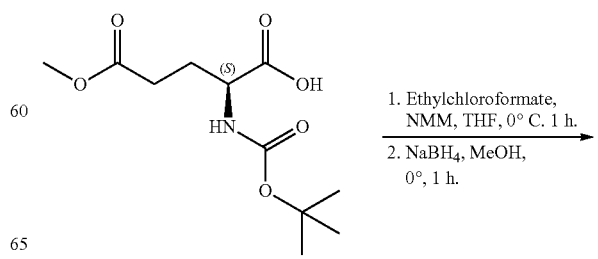

-continued

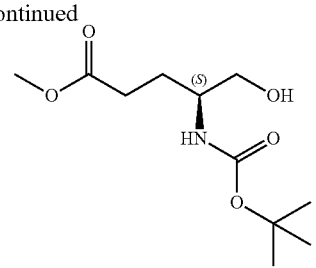

(S)-2-((tert-butoxycarbonyl)amino)-5-methoxy-5-oxopentanoic acid (5.0 g, 19.1 mmol) was dissolved in THF (75.0 mL) and cooled to 0° C. N-methyl morpholine (2.1 mL, 19.1 mmol) and ethyl chloroformate (2.07 mL, 19.1 mmol) were added and the mixture was stirred for 60 min. Sodiumborohydride (2.12 g, 57.3 mmol) and MeOH (175 ml) were added drop wise and the reaction mixture was stirred at room temperature for 1.5 hrs. The solvent was concentrated and the residue was dissolved in ethyl acetate (200 mL), washed with sat. aq. sodium bicarbonate (2×100 mL) followed by brine solution (2×100 mL). The organic layer was dried over sodium sulfate and concentrated under reduced pressure to give methyl (S)-4-((tert-butoxycarbonyl)amino)-5-hydroxypentanoate (5.3 g) as a semisolid material. LCMS (Method-C2): 46.09% (RT 1.052, 202.0 nm) (MS: ESI +ve 248.3[(M+H]).

Step-2: Preparation of methyl (S)-4-((tert-butoxycarbonyl)amino)-5-(tosyloxy)pentanoate

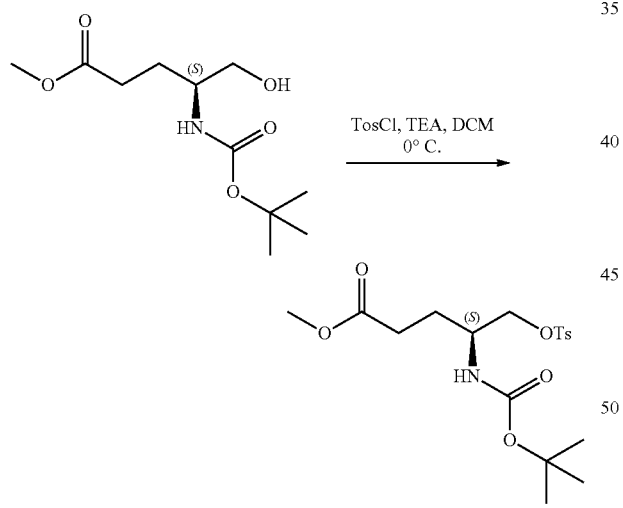

(S)-4-((tert-butoxycarbonyl)amino)-5-hydroxypentanoate (5.3 g, 21.43 mmol) was dissolved in dry DCM (50.0 mL) then cooled to 0° C. TEA (8.9 mL, 64.29 mmol) and tosyl chloride (4.9 g, 25.71 mmol) were added portion-wise. The mixture was stirred at room temperature for 16 h. The mixture was diluted with DCM (50 mL), washed with saturated aq. sodium bicarbonate (2×100 mL) then brine (2×100 mL). The organic layer was dried over sodium sulfate and concentrated under reduced pressure. The resulting solid was purified by flash chromatography, eluting with 0-50% ethyl acetate in hexane, to give (S)-4-((tert-butoxycarbonyl)amino)-5-(tosyloxy)pentanoate (4.2 g, 48%) as a semisolid material. LCMS (Method-C2): 92.25% (RT: 1.307, 230.0 nm) (MS: ESI +ve 302.3[M+100]).

Step-3: Preparation of methyl (S)-5-azido-4-((tert-butoxycarbonyl)amino)pentanoate

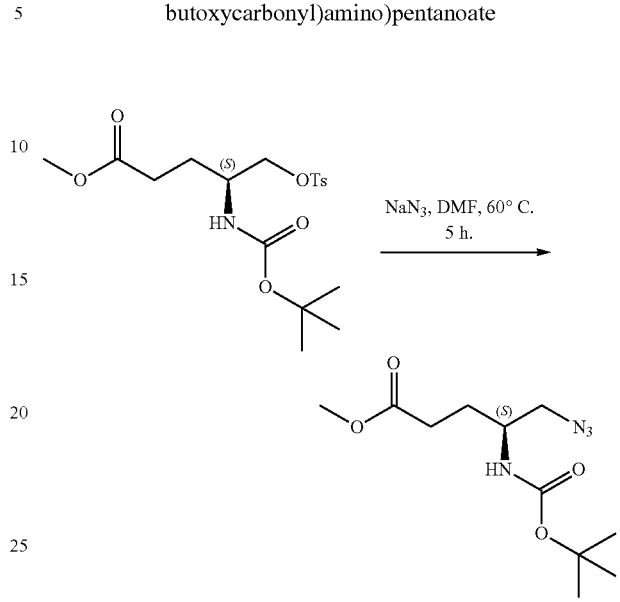

(S)-4-((tert-butoxycarbonyl)amino)-5-(tosyloxy)pentanoate (4.2 g, 10.46 mmol) and sodium azide (2.04 g, 31.38 mmol) in dry DMF (40 mL) were heated at 60° C. for 5 h. The reaction mixture was concentrated to give methyl (S)-5-azido-4-((tert-butoxycarbonyl)amino)pentanoate (1.2 g) as semisolid material. LCMS (Method-C2): 93.56% (RT: 1.243, 214.0 nm) (MS: ESI +ve 273.4[M+H]).

Step-4: Preparation of tert-butyl (S)-(6-oxopiperidin-3-yl)carbamate

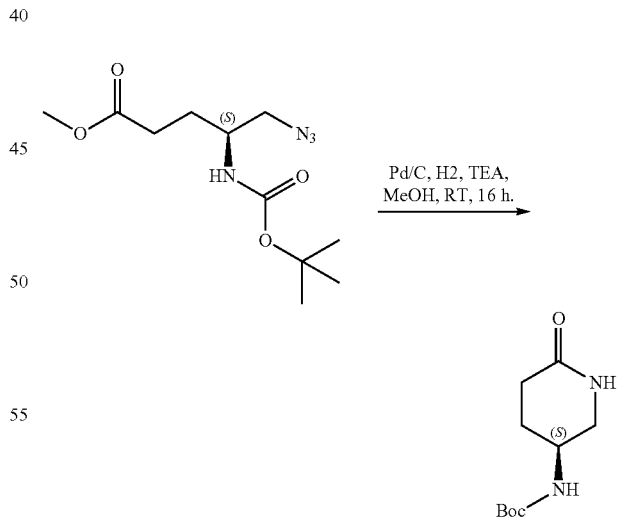

Methyl (S)-5-azido-4-((tert-butoxycarbonyl) amino)pentanoate (1.8 g) was dissolved in MeOH (50 mL). Pd/C (0.6 g, 10% with 50% moisture) and TEA (2 mL) were added and the mixture was stirred under hydrogen balloon pressure at room temperature for 16 hrs. The reaction mixture was filtered through a pad of celite and the filtrate was concentrated. The resulting solid was purified by flash chromatography, eluting with 0-5% MeOH in DCM, to give tert-butyl (S)-(6-oxopiperidin-3-yl) carbamate as a white solid (0.8 g, 56%). LCMS (Method-C3): 100% (RT 0.949, 202 nm) (MS: ESI +ve 215.1 [M+H]).

Step 5: Preparation of tert-butyl (S)-(6-oxo-1-pentadecylpiperidin-3-yl)carbamate

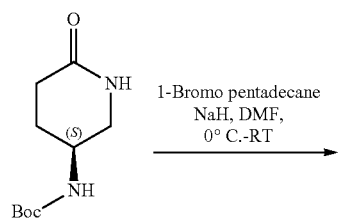

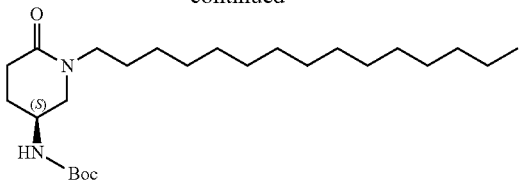

tert-Butyl (S)-(6-oxopiperidin-3-yl) carbamate (0.4 g, 1.86 mmol) was dissolved in dry DMF (10 mL) and cooled to 0° C. Sodium hydride (0.089 g, 2.24 mmol) was added in portions. After 15 min, 1-bromopentadecane (0.652 g, 2.24 mmol) was added and the mixture was stirred for 3.0 hrs at 0° C. The reaction was quenched with water then, extracted with ethyl acetate (3×50 mL). The combined organic layers were dried over anhydrous sodium sulfate and concentrated under reduced pressure. The resulting product was purified by flash chromatography, eluting with 0-2% MeOH in DCM, to give tert-butyl (S)-(6-oxo-1-pentadecylpiperidin-3-yl)carbamate (0.25 g, 31%), used without further purification in the next step.

Step-6: Preparation of (S)-5-amino-1-pentadecylpiperidin-2-one TFA Salt

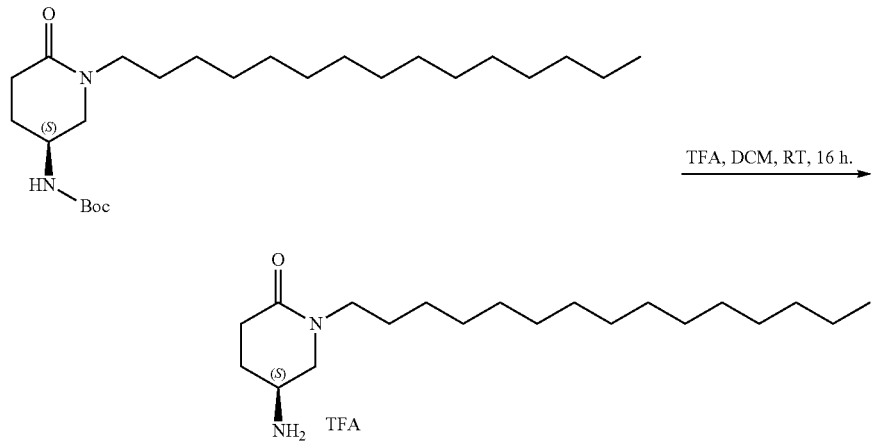

Prepared using General BOC Deprotection Procedure to give tert-butyl (S)-(6-oxo-1-pentadecylpiperidin-3-yl) carbamate TFA Salt (0.2 g). LCMS (Method-C2): 100% (RT: 1.539, 202.0 nm) (MS: ESI +ve 325.5[M+H]).

Step-7: Preparation of (3S,4S)-1-(4-(((S)-6-oxo-1-pentadecylpiperidin-3-yl)carbamoyl)benzoyl)-N3, N4-bis((1S,2R)-2-phenylcyclopropyl)pyrrolidine-3, 4-dicarboxamide, Compound 180

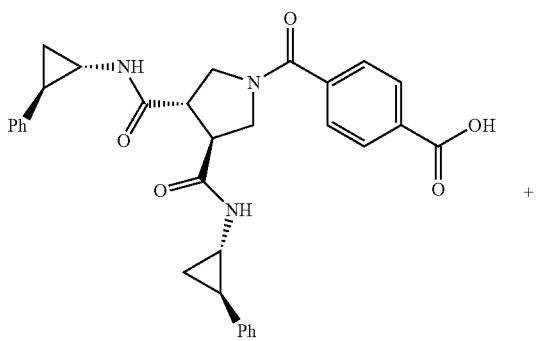

+

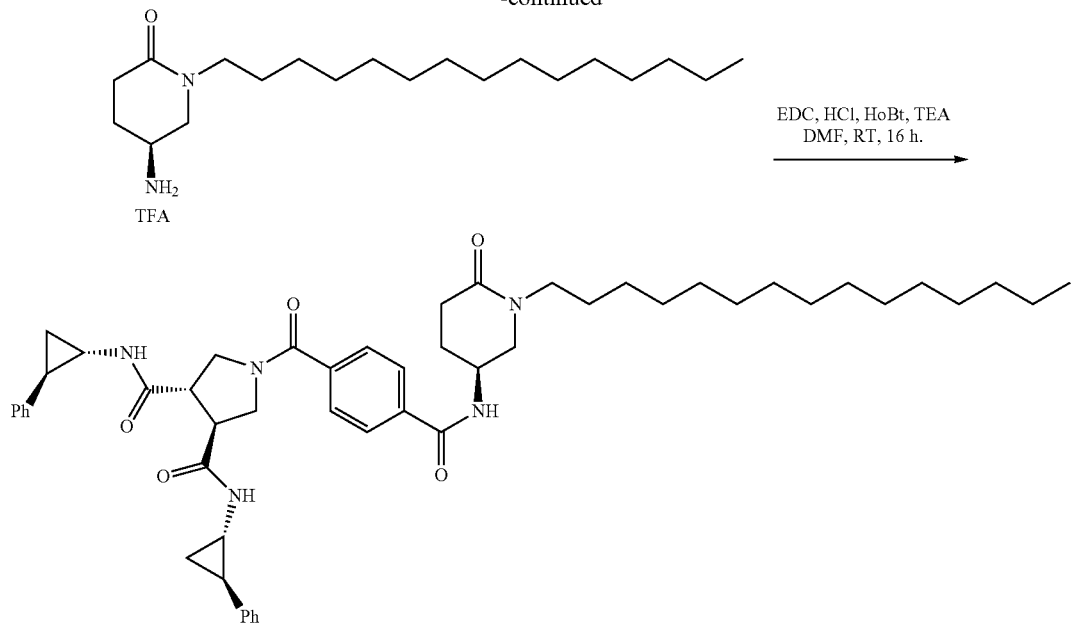

Prepared using General EDC, HOBT Coupling Procedure. The crude product was purified using Prep HPLC Method 1 to give (3S,4S)-1-(4-(((S)-6-oxo-1-pentadecylpiperidin-3-yl)carbamoyl)benzoyl)-N3,N4-bis((1S,2R)-2-phenylcyclopropyl)pyrrolidine-3,4-dicarboxamide (Compound 180)(0.046 g, 24%), as an off white solid. LCMS (Method-J): 100% (RT 5.377, 202.0 nm) (MS: ESI +ve 844.6 [M+H]). $^1$H NMR: (400 MHz, DMSO) δ ppm: 0.84-0.86 (m, 3H), 1.09-1.11 (m, 2H), 1.13-1.24 (m, 29H), 1.44 (s, 3H), 1.85-1.90 (m, 2H), 1.94-1.98 (m, 2H), 2.34-2.41 (m, 2H), 2.78 (s, 1H), 2.85 (s, 1H), 3.10-3.14 (m, 1H), 3.17-3.27 (m, 4H), 3.43-3.55 (m, 4H), 3.55-3.62 (m, 1H), 3.80-3.86 (m, 1H), 4.25 (s, 1H), 7.06-7.08 (m, 2H), 7.12-7.19 (m, 4H), 7.23-7.29 (m, 4H), 7.59-7.61 (m, 2H), 7.89-7.91 (m, 2H), 7.30-7.31 (m, 1H), 8.44-8.45 (d, 1H), 8.55-8.57 (d, 1H).

Synthesis of (3S,4S)-1-(4-(((R)-6-oxo-1-pentadecylpiperidin-3-yl)carbamoyl)benzoyl)-N3,N4-bis((1S,2R)-2-phenylcyclopropyl)pyrrolidine-3,4-dicarboxamide, Compound 169

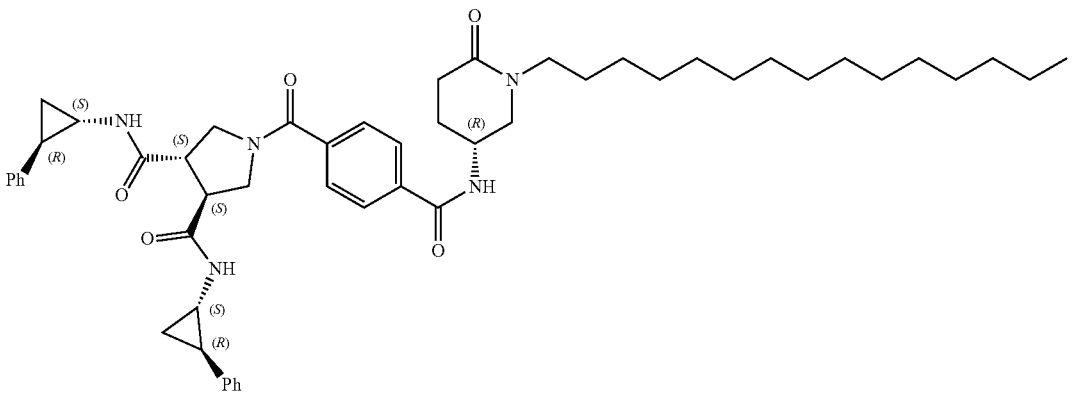

Prepared by a procedure similar to that reported for (3S,4S)-1-(4-(((S)-6-oxo-1-pentadecylpiperidin-3-yl)carbamoyl)benzoyl)-N3,N4-bis((1S,2R)-2-phenylcyclopropyl)pyrrolidine-3,4-dicarboxamide (Compound 180), substituting the applicable amino acid in step 1. The crude final product was purified using Prep HPLC Method 1 to give (3S,4S)-1-(4-(((R)-6-oxo-1-pentadecylpiperidin-3-yl)carbamoyl)benzoyl)-N3,N4-bis((1S,2R)-2-phenylcyclopropyl)pyrrolidine-3,4-dicarboxamide (Compound 169)(0.030 g, 30%), as an off white solid. LCMS (Method-J): 100% (RT 4.688, 254.0 nm) (MS: ESI +ve 844.6 [M+H]). ¹H NMR: (400 MHz, DMSO) δ ppm: 0.83-0.86 (m, 3H), 1.08-1.10 (m,2H), 1.22 (m, 24H), 1.41-1.44 (m, 3H), 1.82-1.99 (m, 4H), 2.33-2.40 (m, 2H), 2.77-2.86 (m, 2H), 3.07-3.25 (m, 6H), 2.42-3.53 (m, 4H), 3.59-3.64 (m, 1H), 3.78-3.83 (m, 1H), 4.24 (s, 1H), 7.05-7.07 (m, 2H), 7.11-7.18 (m, 4H), 7.22-7.28 (m, 4H), 7.59-7.61 (m, 2H), 7.88-7.90 (m, 2H), 8.31-7.32 (m, 1H), 8.46-8.47 (d, 1H), 8.56-8.58 (d, 1H).
Synthesis of (3S,4S)-1-(4-((S)-1,3-dioxo-2-tetradecyloctahydroimidazo [1,5-a]pyrazine-7-carbonyl) benzoyl)-N3,N4-bis((1S,2R)-2-phenylcyclopropyl) pyrrolidine-3,4-dicarboxamide, Compound 275
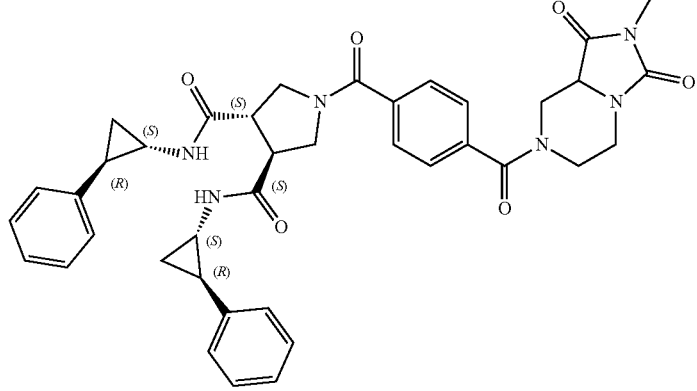
Step-1: Synthesis of 4-(tert-butyl) 2-methyl 1-(4-nitrophenyl) (S) piperazine-1,2,4-tricarboxylate
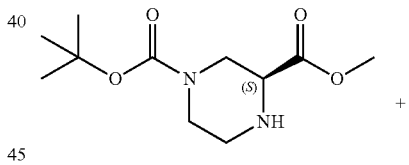
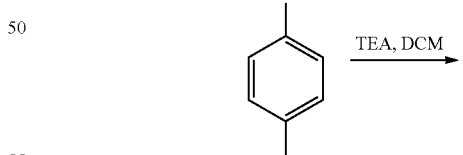
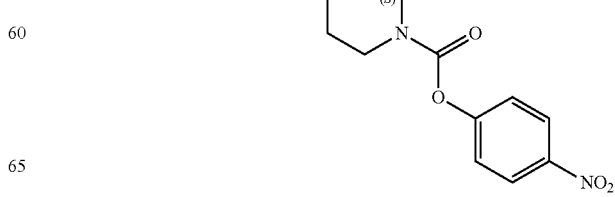

4-Nitrophenyl chloroformate (0.79 g, 3.27 mmol) was dissolved in DCM (5 mL) and a mixture of 1-(tert-butyl) 3-methyl (S)-piperazine-1,3-dicarboxylate (0.8 g, 3.92 mmol) and TEA (0.6 mL) in DCM (15 mL) was added dropwise. The reaction was stirred at room temperature for 16 h. The mixture was partitioned between DCM (50 mL) and water (50 mL). The aqueous layer was extracted with DCM (3×50 mL), the combined organic layers were concentrated, and the crude product was purified by flash chromatography, eluting with 2-3% MeOH:DCM, to give 4-(tert-butyl) 2-methyl 1-(4-nitrophenyl) (S)-piperazine-1,2,4-tricarboxylate, as an off white solid (0.5 g, 37.2%). LCMS (Method-C2): 96.66% (RT: 1.346, 270.00 nm) (MS: ESI +ve 310.1 [M+1]).

Step 2: Synthesis of tert-butyl 1,3-dioxo-2-tetradecylhexahydroimidazo[1,5-a]pyrazine-7 (1H)-carboxylate

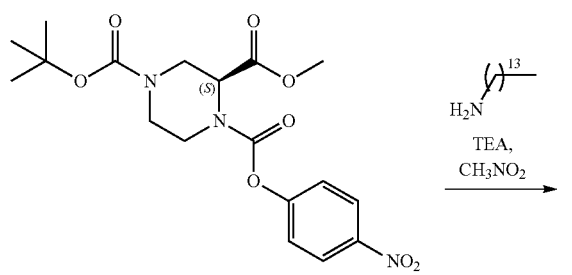

A mixture of 4-(tert-butyl) 2-methyl 1-(4-nitrophenyl) (S)-piperazine-1,2,4-tricarboxylate (0.5 g, 1.01 mmol), tetradecan-1-amine (1.45 g, 6.83 mmol), TEA (0.2 mL, 2.03 mmol) and nitromethane (10 mL) was heated at 130° C. in a microwave reactor for 3 h. The reaction mixture was concentrated then partitioned between water (50 mL) and EtOAc (3×50 mL). The combined organic layers were concentrated and the crude product was purified by flash chromatography, eluting with 10-12% EtOAc:Hexane, to give tert-butyl 1,3-dioxo-2-tetradecylhexahydroimidazo[1,5-a]pyrazine-7 (1H)-carboxylate (0.5 g, 85.2%). LCMS (Method-C_Fast): 94.14% (RT: 2.923, 225.0 nm) (MS: ESI +ve 396.4 [M−56]).

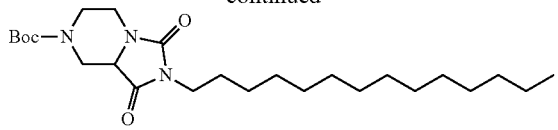

Step-3: Synthesis of 2-tetradecyltetrahydroimidazo[1,5-a]pyrazine-1,3 (2H,5H)-dione TFA salt

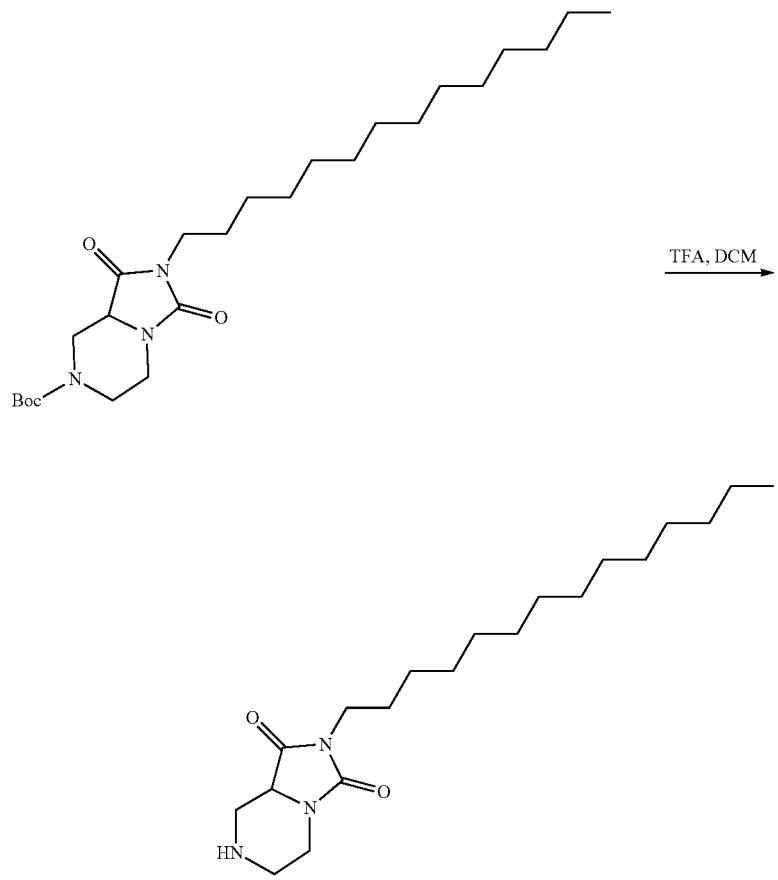

645

Prepared using General BOC Deprotection Procedure to give (S)-2-tetradecyltetrahydroimidazo[1,5-a]pyrazine-1,3 (2H,5H)-dione (0.23 g, 84.4%). LCMS (Method-C2): 100.0% (RT: 1.519, 202.0 nm) (MS: ESI +ve 352.4 [M+1]).

Step-5: Synthesis of (3S,4S)-1-(4-(1,3-dioxo-2-tetradecyloctahydroimidazo[1,5-a]pyrazine-7-carbonyl)benzoyl)-N3,N4-bis((1S,2R)-2-phenylcyclopropyl)pyrrolidine-3,4-dicarboxamide, Compound 275

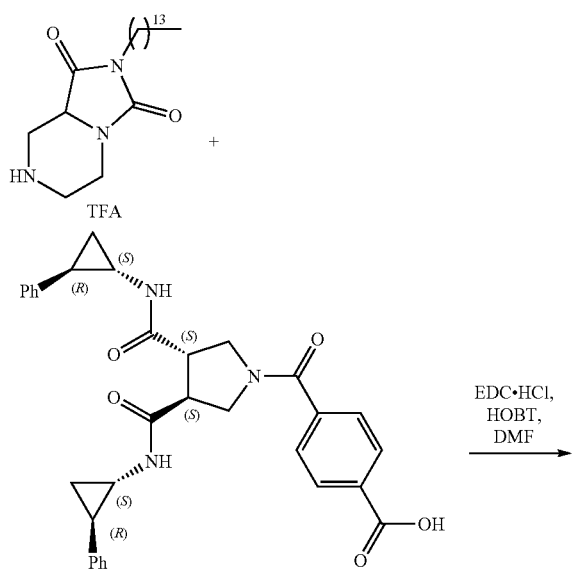

646

-continued

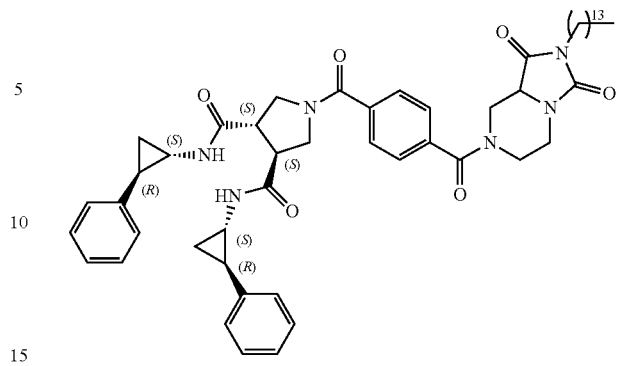

Prepared using General EDC, HOBT Coupling Procedure. The crude final product was purified using Prep HPLC Method 1 to give (3S,4S)-1-(4-((S)-1,3-dioxo-2-tetradecyloctahydroimidazo[1,5-a]pyrazine-7-carbonyl)benzoyl)-N3,N4-bis((1S,2R)-2-phenylcyclopropyl)pyrrolidine-3,4-dicarboxamide (Compound 275) (0.092 g), as a mixture of diastereomers. LCMS (Method-J): 100% (RT 5.010, 202.0 nm) (MS: ESI +ve 871.7 [M]). $^1$H NMR (400 MHz, DMSO) δ ppm: 0.84-0.88 (t, J=0.8, 311), 1.11-1.24 (m, 28H), 1.51 (s, 2H), 1.86-1.91 (m, 1H), 1.96-2.01 (m, 1H), 2.80-2.88 (m, 3H), 3.09-3.15 (m, 3H), 3.19-3.25 (m, 2H), 3.52-3.57 (m, 2H), 3.65-3.69 (t, J=2, 1H), 4.00 (s, 111), 4.29 (s, 111), 4.48-4.70 (t, J=72, 1H), 7.07-7.16 (m, 6H), 7.23-7.30 (m, 4H), 7.52-7.54 (d, J=8, 2H). 7.61-7.63 (d, J=8, 2H), 8.44 (bs, 111), 8.53-8.57 (t, J=8, 2H).

Synthesis of (3S,4S)-1-(2-((S)-2-decanamido-3-(hexylamino)-3-oxopropyl)imidazo[1,2-a]pyridine-7-carbonyl)-N3,N4-bis((1S,2R)-2-phenylcyclopropyl)pyrrolidine-3,4-dicarboxamide, Compound 274

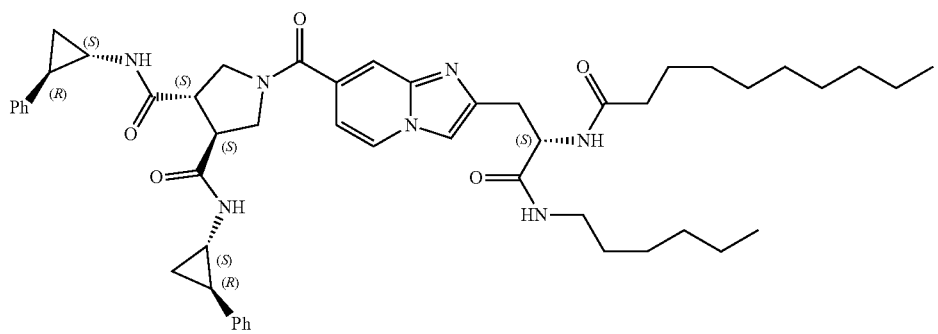

Step-1: Preparation of ethyl 7-bromoimidazo[1,2-a]pyridine-2-carboxylate

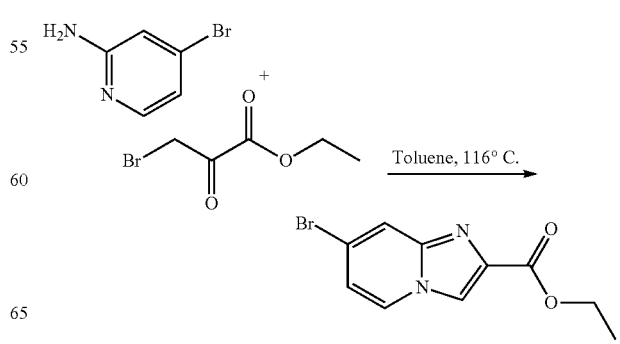

A mixture of 4-bromopyridin-2-amine (10.0 g, 57.80 mmol) and ethyl 3-bromo-2-oxopropanoate (11.24 g, 57.80 mmol) in toluene (200 mL) was heated to 116° C. for 16 h. The volatiles were removed and the crude product was purified using flash chromatography, eluting with 1.5% MeOH:DCM, to give ethyl 7-bromoimidazo[1,2-a]pyridine-2-carboxylate (8.2 g, 52%). LCMS (Method-C2): 100% (RT 1.122, 229.0 nm) (MS: ESI +ve 269.1 [M+1]).

Step-2: Preparation of (7-bromoimidazo[1,2-a]pyridin-2-yl)methanol

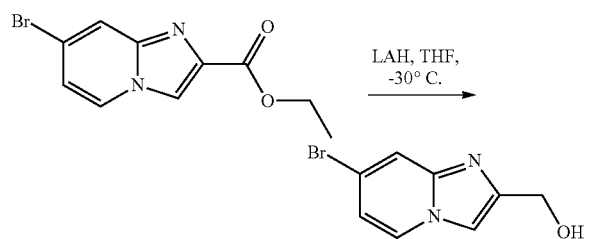

LiAlH₄ (21.26 mL, 21.26 mmol, 1M in THF) was added to a solution of ethyl 7-bromoimidazo[1,2-a]pyridine-2-carboxylate (5.2 g, 19.33 mmol) in THF (100 mL) at −30° C. The reaction was quenched with ethyl acetate (2×200 mL) and washed with brine (100 mL). The organic layers were filtered through celite, and the filtrate was concentrated. The crude product was purified using flash chromatography, eluting with 2.8% MeOH:DCM, to give (7-bromoimidazo[1,2-a]pyridin-2-yl)methanol (2.0 g, 52%). LCMS (Method-H): 98.80% (RT 1.947, 230.0 nm) (MS: ESI +ve 228.9 [M+1]).

Step-3: Preparation of 7-bromo-2-(bromomethyl)imidazo[1,2-a]pyridine

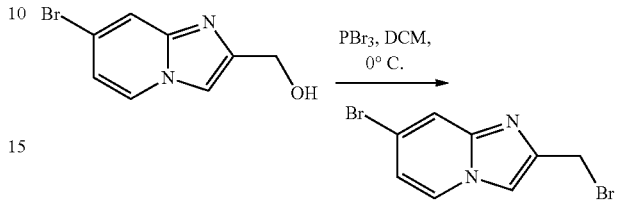

(7-bromoimidazo[1,2-a]pyridin-2-yl)methanol (3.0 g, 13.157 mmol) was dissolved in DCM (45 mL) and phosphorus tribromide (3.49 g, 12.89 mmol) was added at 0° C. The reaction mixture was stirred for 5 h, then diluted with DCM (150 mL) and washed with sat. aq. NaHCO₃ (100 mL). The organic layer was concentrated and purified using flash chromatography, eluting with 50% EtOAc:Hexane, to give 7-bromo-2-(bromomethyl)imidazo[1,2-a]pyridine (1.48 g, 39%). LCMS (Method-C2): 98.39% (RT 0.991, 254.0 nm) (MS: ESI +ve 292.99 [M+2]).

Step-4: Preparation of tert-butyl (S)-3-(7-bromoimidazo[1,2-a]pyridin-2-yl)-2-((diphenylmethylene)amino)propanoate

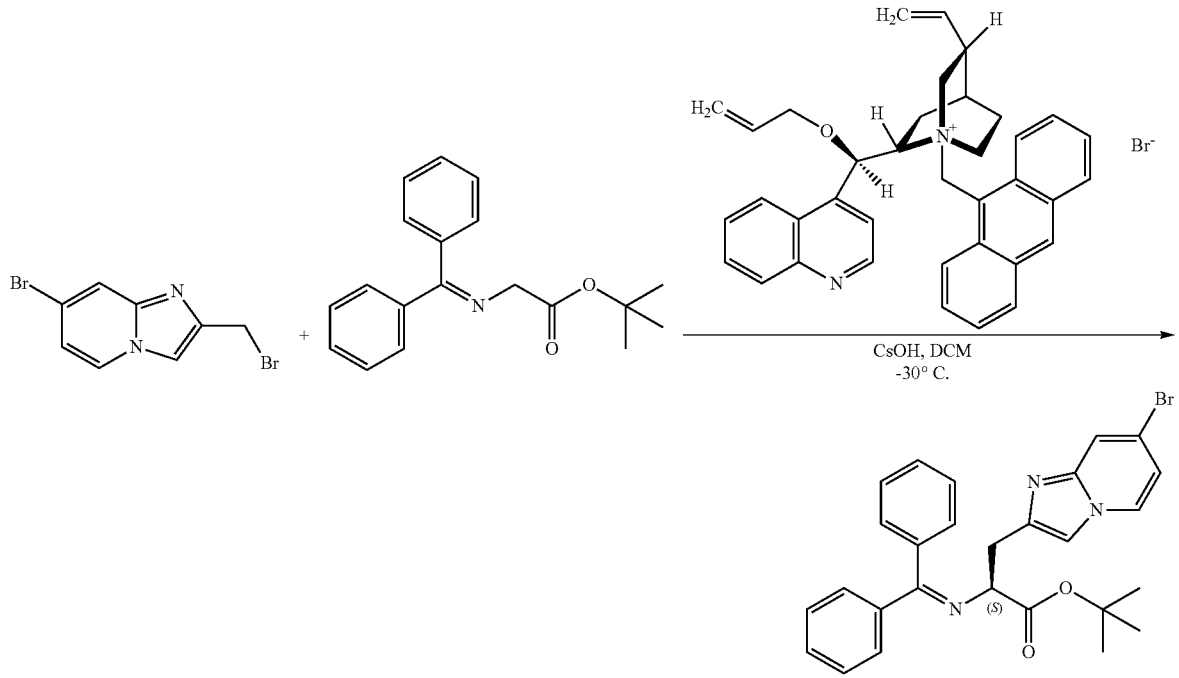

7-bromo-2-(bromomethyl)imidazo[1,2-a]pyridine (1.48 g, 5.085 mmol), tert-butyl 2-((diphenylmethylene)amino)acetate (1.80 g, 6.103 mmol) and O-Allyl-N-(9-anthracenylmethyl)cinchonidinium bromide (0.308 g, 0.508 mmol) were dissolved in DCM (38.9 mL). Cesium hydroxide (3.49 g, 12.89 mmol) was added at −30° C. and stirred for 18 h.

The mixture was then diluted with DCM (150 mL) and washed with water (100 mL). The organic layer was concentrated and purified using flash chromatography, eluting with 20% EtOAc:DCM, to give tert-butyl (S)-3-(7-bromoimidazo[1,2-a]pyridin-2-yl)-2-((diphenylmethylene) amino) propanoate (2.0 g, 82%). LCMS (Method-C2): 71.27% (RT 1.355, 202.0 nm) (MS: ESI +ve 504.41 [M+1]).

Step-5: Preparation of (S)-2-amino-3-(7-bromoimidazo[1,2-a]pyridin-2-yl)propanoic acid

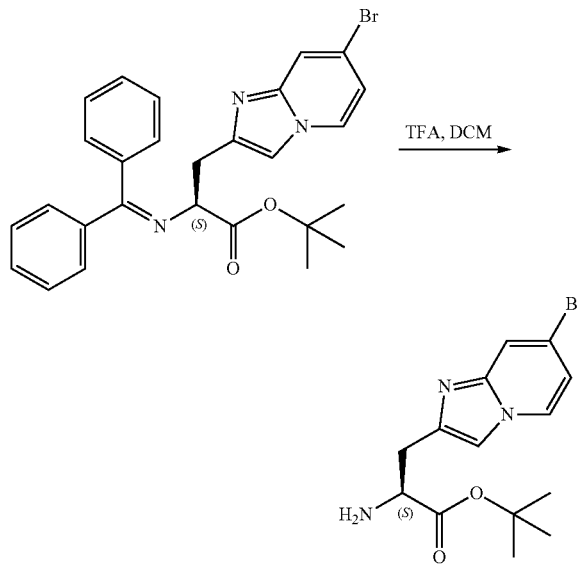

Prepared using General BOC Deprotection Procedure to give (S)-2-amino-3-(7-bromoimidazo[1,2-a]pyridin-2-yl)propanoic acid (1.7 g). TFA salt LCMS (Method-F): 88.97% (RT 3.344, 225.4 nm) (MS: ESI +ve 286.0[M+2]).

Step-6: Preparation of (S)-3-(7-bromoimidazo[1,2-a]pyridin-2-yl)-2-((tert-butoxycarbonyl)amino)propanoic acid

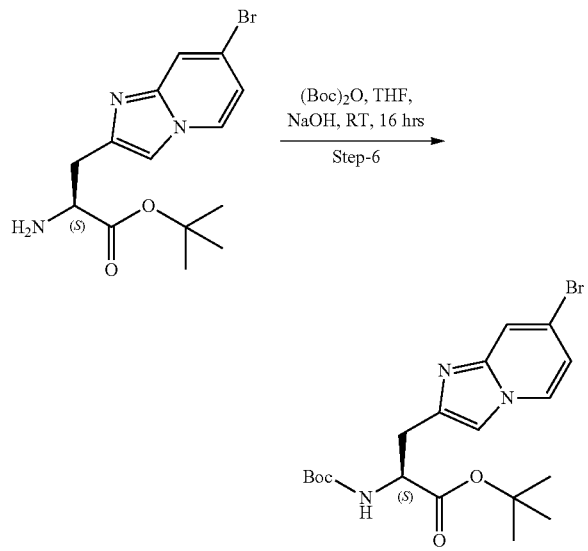

(S)-2-amino-3-(7-bromoimidazo[1,2-a]pyridin-2-yl)propanoic acid (1.7 g, 5.985 mmol) was dissolved in THF (26 mL). (Boc)$_2$O (1.56 g, 7.183 mmol) followed by 1M NaOH (23.9 mL, 23.94 mmol) were added and the mixture was stirred for 16 h at room temperature. The mixture was diluted with brine (100 mL), acidified with AcOH (10 mL) and extracted with ethyl acetate (2×100 mL). The organic layers were concentrated to give (S)-3-(7-bromoimidazo[1,2-a]pyridin-2-yl)-2-((tert-butoxycarbonyl)amino)propanoic acid (1.7 g, crude). LCMS (Method-C2): 82.30% (RT 0.964, 202.4 nm) (MS: ESI +ve 385.96[M+2]).

Step-7: Preparation of tert-butyl (S)-(3-(7-bromoimidazo[1,2-a]pyridin-2-yl)-1-(hexylamino)-1-oxopropan-2-yl)carbamate

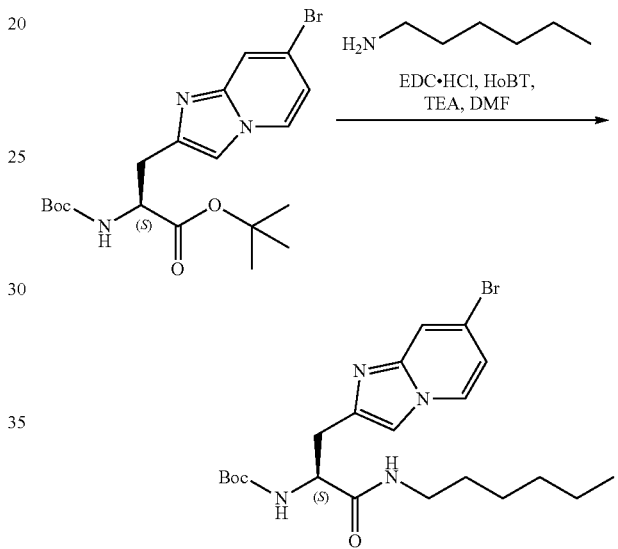

Prepared using General EDC, HOBT Coupling Procedure. The crude product was purified using flash chromatography, eluting with 3% MeOH:DCM, to give tert-butyl (S)-(3-(7-bromoimidazo[1,2-a]pyridin-2-yl)-1-(hexylamino)-1-oxopropan-2-yl)carbamate (0.9 g, 49.4%). LCMS (Method-C2): 100% (RT 1.272, 230.0 nm) (MS: ESI +ve 467.3 [M+1]).

Step-8: Preparation of methyl (S)-2-(2-((tert-butoxycarbonyl)amino)-3-(hexylamino)-3-oxopropyl)imidazo[1,2-a]pyridine-7-carboxylate

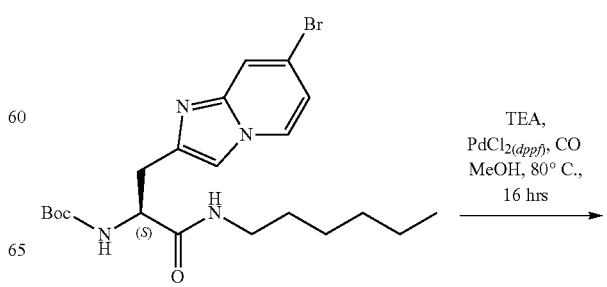

651
-continued

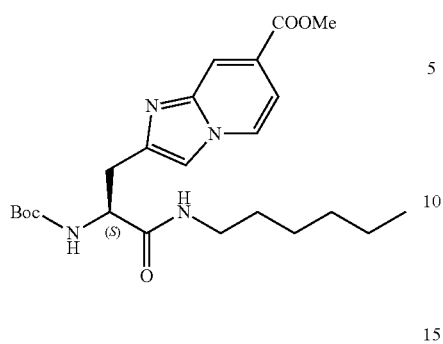

A mixture of tert-butyl (S)-(3-(7-bromoimidazo[1,2-a]pyridin-2-yl)-1-(hexylamino)-1-oxopropan-2-yl)carbamate (0.2 g, 0.426 mmol), MeOH (70 mL), TEA (0.889 mL, 6.396 mmol) and 1,1'-bis(diphenylphosphino)ferrocene]dichloropalladium(II) (0.093 g, 0.127 mmol) were heated at 80° C. for 3 h under 20 kg pressure of CO in an autoclave. The mixture was concentrated and purified using flash chromatography, eluting with 3% MeOH:DCM, to give methyl (S)-2-(2-((tert-butoxycarbonyl)amino)-3-(hexylamino)-3-oxopropyl)imidazo[1,2-a]pyridine-7-carboxylate (0.18 g, 94%). LCMS (Method-H): 89.72% (RT 3.103, 254.0 nm) (MS: ESI +ve 347.0 [M−100]).

652

Step-9: Preparation of methyl (S)-2-(2-amino-3-(hexylamino)-3-oxopropyl)imidazo[1,2-a]pyridine-7-carboxylate TFA salt

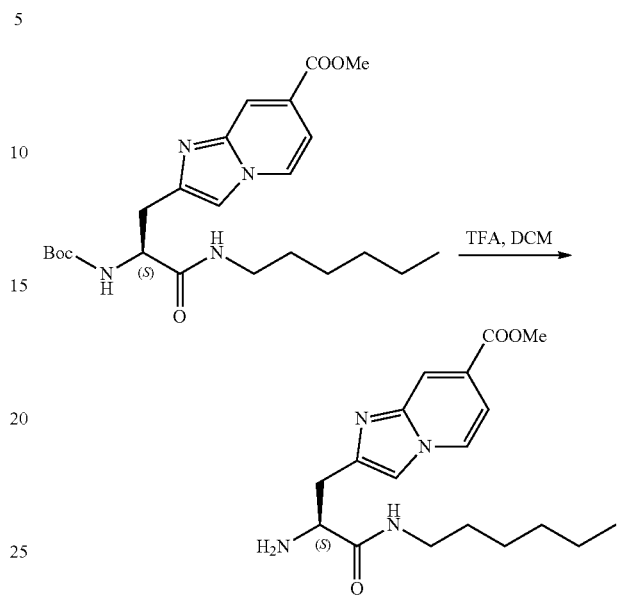

Prepared using General BOC Deprotection Procedure to give methyl (S)-2-(2-amino-3-(hexylamino)-3-oxopropyl)imidazo[1,2-a]pyridine-7-carboxylate as its TFA salt, as a brown gum (0.2 g, crude) LCMS (Method-C2): 49.56% (RT 1.027, 202.0 nm) (MS: ESI +ve 347.82 [M+1]).

Step-10: Preparation of methyl (S)-2-(2-decanamido-3-(hexylamino)-3-oxopropyl)imidazo[1,2-a]pyridine-7-carboxylate

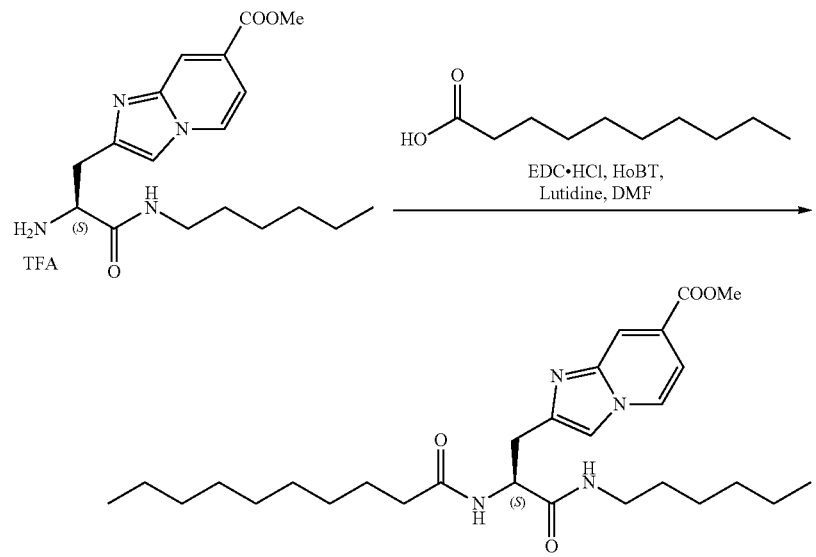

Prepared using General EDC, HOBT Coupling Procedure. The crude product was purified using flash chromatography, eluting with 2% MeOH:DCM, to give methyl (S)-2-(2-decanamido-3-(hexylamino)-3-oxopropyl)imidazo[1,2-a]pyridine-7-carboxylate (0.2 g, 93%). LCMS (Method-C2): 90.14% (RT 1.464, 242.0 nm) (MS: ESI +ve 501.49 [M+1]).

Step 11: Preparation of (S)-4-((4-(hexylcarbamoyl)-3-octyl-2-oxoimidazolidin-1-yl)methyl)benzoic acid

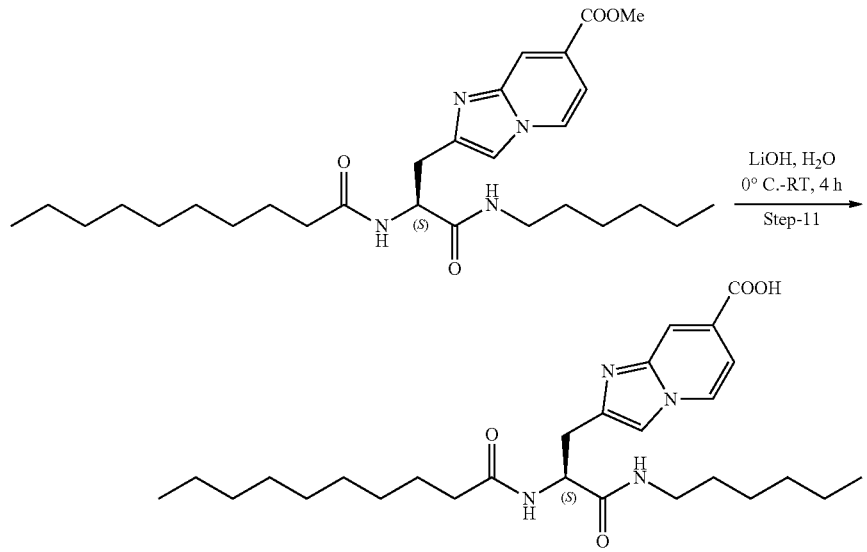

Prepared using General Ester Hydrolysis Procedure to give (S)-2-(2-decanamido-3-(hexylamino)-3-oxopropyl)imidazo[1,2-a]pyridine-7-carboxylic acid as a white solid (0.19 g, 98%). LCMS (Method-C2): 82.62% (RT: 1.315, 220.00 nm) (MS: ESI +ve 487.30 [M+1]).

Step-12: Preparation of (3S,4S)-1-(2-((S)-2-decanamido-3-(hexylamino)-3-oxopropyl)imidazo[1,2-a]pyridine-7-carbonyl)-N3,N4-bis((1S,2R)-2-phenylcyclopropyl)pyrrolidine-3,4-dicarboxamide, Compound 274

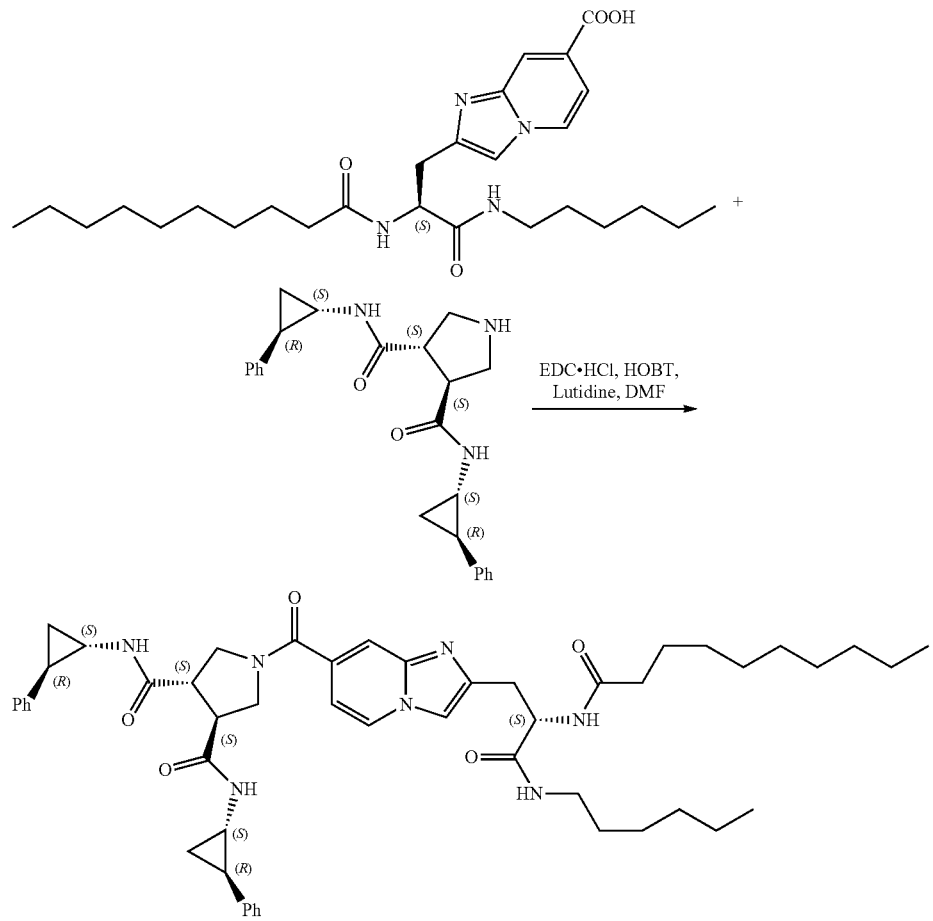

Prepared using General EDC, HOBT Coupling Procedure. The crude product was purified using Prep HPLC Method 10 to give (3S,4S)-1-(2-((S)-2-decanamido-3-(hexylamino)-3-oxopropyl)imidazo[1,2-a]pyridine-7-carbonyl)-N3,N4-bis((1S,2R)-2-phenylcyclopropyl)pyrrolidine-3,4-dicarboxamide (Compound 274), as an off white solid (0.085 g, 25.37%). LCMS (Method-C-Fast): 100% (RT 1.528, 225.0 nm) (MS: ESI +ve 858.89 [M+H]). ¹H NMR: (400 MHz, DMSO) δ ppm: 0.81-0.86 (m, 6H), 1.15-1.40 (m, 24H), 1.86-2.09 (m, 5H), 2.68-2.78 (m, 3H), 2.86-3.14 (m, 5H), 3.20-3.22 (m, 1H), 3.53-3.60 (m, 2H), 3.77-3.81 (m, 2H), 4.59-4.61 (m, 1H), 6.95-6.97 (d, J=6.8 Hz, 1H), 7.06-7.19 (m, 6H), 7.24-7.28 (m, 4H), 7.63 (s, 1H), 7.75 (s, 1H), 7.82-7.84 (m, 1H), 8.05-8.07 (d, J=8 Hz, 1H), 8.31 (s, 1H), 8.45 (s, 1H), 8.54-8.55 (d, J=6.8 Hz, 1H).

Synthesis of (3S,4S)-1-(4-((S)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, Compound 145 and (3S,4S)-1-(4-((R)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, Compound 146

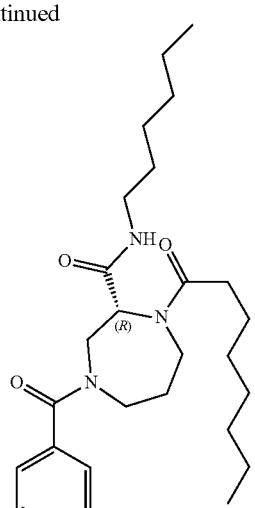

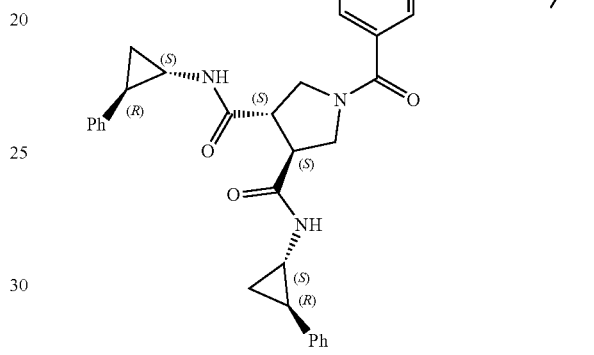

Step-1: Preparation of (3S,4S)-1-(4-(3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide diastereomers

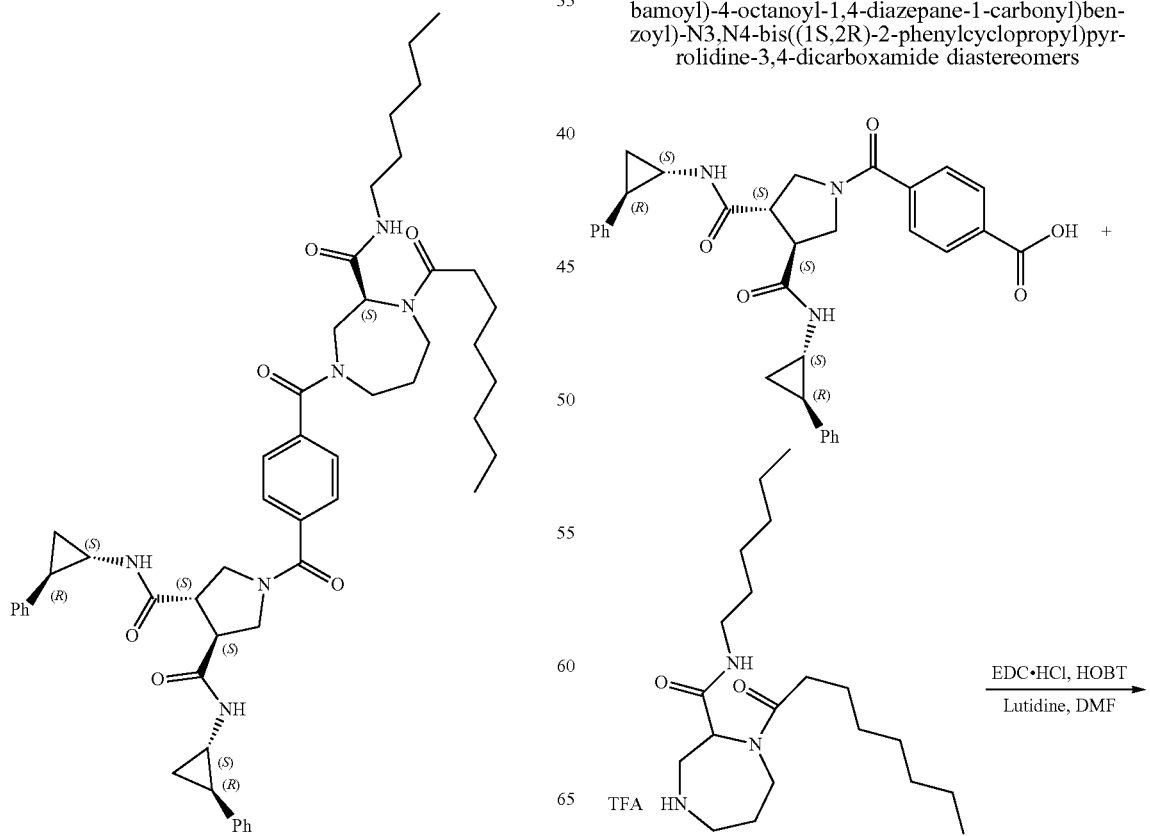

657

-continued

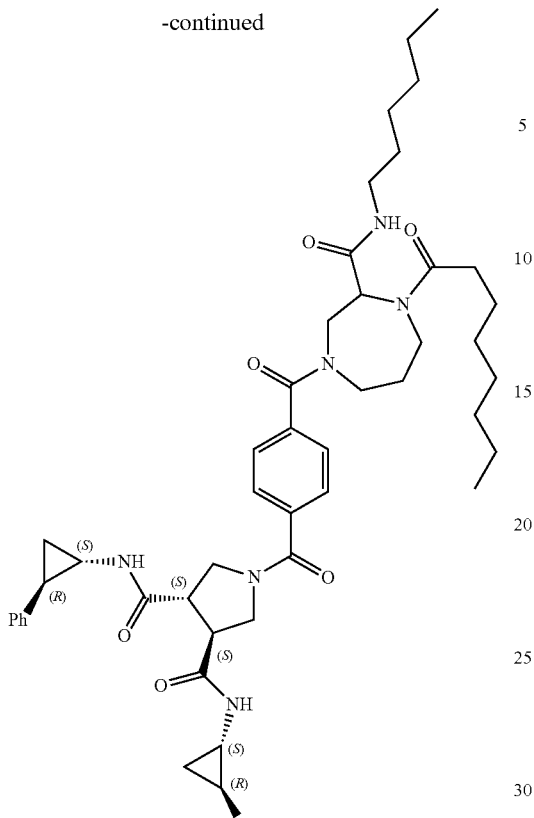

Prepared by a procedure similar to General EDC, HOBT Coupling Procedure using the applicable amine and carboxylic acid. The crude product was purified using Prep HPLC Method 1 to give (3S,4S)-1-(4-(3-(hexylcarbamoyl)-4-octanoyl-1,4-diazepane-1-carbonyl)benzoyl)-N3,N4-bis((1S, 2R)-2-phenylcyclopropyl)pyrrolidine-3,4-dicarboxamide (Racemic), as an off white solid (0.12 g, 21.11%). LCMS (Method-J): 98.60% (RT 5.779, 202.4 nm) (MS: ESI +ve 873.6 [M+H]).

Step-2: Chiral SFC Separation of (3S,4S)-1-(4-(3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide

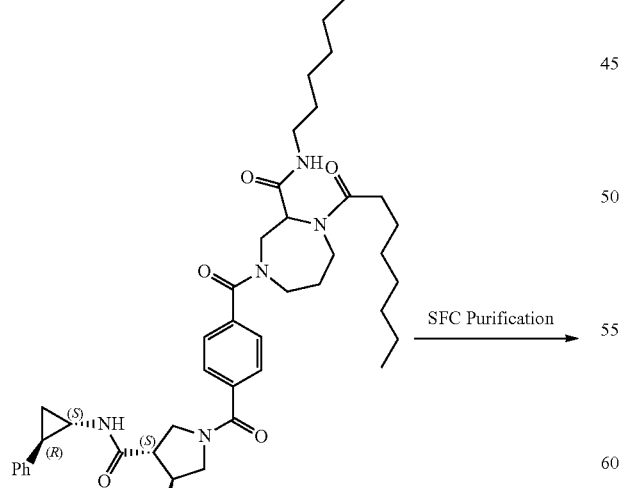

SFC Purification →

658

-continued

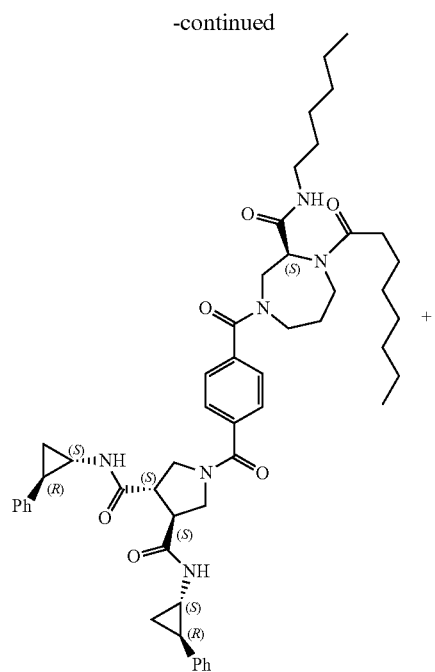

+

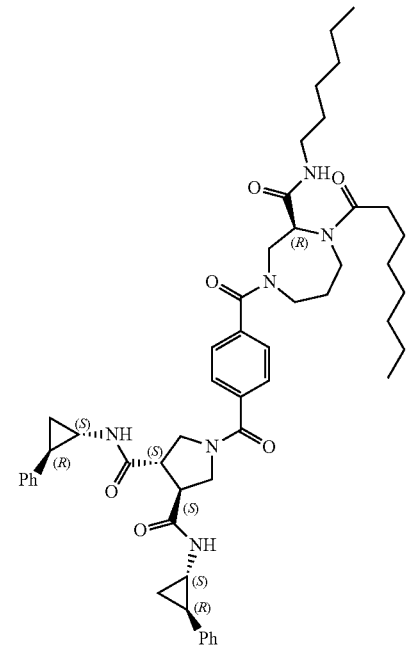

The diastereomers of (3S,4S)-1-(4-(3-(hexylcarbamoyl)-4-octanoyl-1,4-diazepane-1-carbonyl)benzoyl)-N3,N4-bis ((1S,2R)-2-phenylcyclopropyl)pyrrolidine-3,4-dicarboxamide (0.1 g) were separated on a Shimadzu LC-20AP chromatography system with UV detector. The column used was a CHIRALPAK IC (250*21.0) mm, 5 micron, column flow was 22.0 ml/min. Mobile phase, (A) 0.1% DEA IN hexane (B) 0.1% DEA in propan-1-ol:acetonitrile (70:30). The gradient solvent B was 55-45% over 30 min to give;

Fraction 1; (3S,4S)-1-(4-((S)-3-(hexylcarbamoyl)-4-octanoyl-1,4-diazepane-1-carbonyl)benzoyl)-N3,N4-bis((1S, 2R)-2-phenylcyclopropyl)pyrrolidine-3,4-dicarboxamide (0.045 g) which was repurified using Prep HPLC Method 1 to give (3S,4S)-1-(4-((S)-3-(hexylcarbamoyl)-4-octanoyl-1, 4-diazepane-1-carbonyl)benzoyl)-N3,N4-bis((1S,2R)-2-phenylcyclopropyl)pyrrolidine-3,4-dicarboxamide (Compound 145) (0.02 g, 20%) [absolute stereochemistry arbitrarily assigned]. LCMS (Method-J): 100% (RT 5.766, 202.0 nm) (MS: ESI +ve 874.6 [M+1]). $^1$H NMR: (400 MHz, DMSO) δ ppm: 0.81-0.87 (m, 6H), 1.10-1.16 (m, 20H), 1.42-1.54 (m, 6H), 1.85 (s, 1H), 1.97 (s, 1H), 2.13-2.19 (m, 1H), 2.24-2.29 (m, 2H), 2.78-2.84 (m, 2H), 3.02-3.04 (m, 2H), 3.18-3.20 (m, 2H), 3.38-3.42 (m, 3H), 3.63-3.67 (m, 1H), 3.77-3.82 (m, 1H), 4.12-4.16 (m, 1H), 4.50-4.57 (m, 1H), 4.82-5.13 (m, 1H), 7.06-7.18 (m, 6H), 7.22-7.33 (m, 6H), 7.55-7.59 (t, 2H), 7.87 (m, 1H), 8.30-8.43 (m, 2H). Chiral HPLC: 100% (RT: 13.24)

Fraction 2; (3S,4S)-1-(4-((R)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide (0.055 g) which was repurified using Prep HPLC Method 1 to give (3S,4S)-1-(4-((R)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide (Compound 146) (0.025 g, 25%) [absolute stereochemistry arbitrarily assigned]. LCMS (Method-J): 100% (RT 5.764, 254.0 nm) (MS: ESI +ve 875.5 [M+1]). $^1$H NMR: (400 MHz, DMSO) δ ppm: 0.78-0.84 (m, 6H), 1.09-1.26 (m, 21H), 1.43-1.62 (m, 6H), 1.86 (s, 1H), 0.97 (s, 1H), 2.08-2.09 (m, 2H), 2.78-2.85 (m, 2H), 3.02-3.19 (m, 5H), 3.38-3.50 (m, 3H), 3.65 (s, 1H), 3.78-3.83 (m, 1H), 4.12-4.16 (m, 1H), 4.50-4.86 (m, 1H), 7.06-7.18 (m, 6H), 7.22-7.33 (m, 6H), 7.55-7.59 (t, 2H), 7.87 (s, 1H), 8.30-8.43 (m, 2H). Chiral HPLC: 100% (RT: 15.95)

Synthesis of (3S,4S)-1-(3-((S)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, Compound 190 and (3S,4S)-1-(3-((R)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, Compound 191

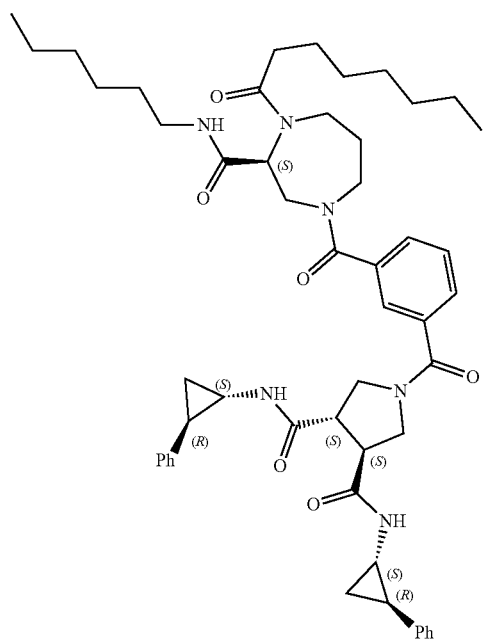

-continued

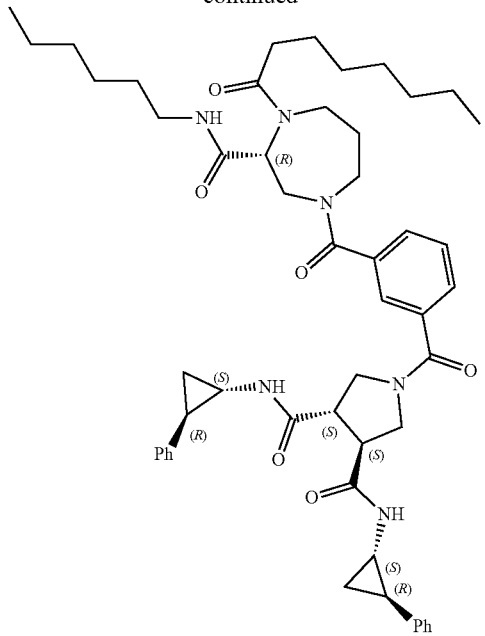

Prepared and separated by a procedure similar to that reported for (3S,4S)-1-(4-((S)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, (Compound 145) and (3S,4S)-1-(4-((R)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide, (Compound 146).

Fraction 1; (3S,4S)-1-(4-((S*)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide (Compound 190)(0.02 g, 20%) [absolute stereochemistry is arbitrarily assigned]. LCMS (Method-J2): 100% (RT 4.723, 202.0 nm) (MS: ESI +ve 872.5 [M−1]). $^1$H NMR: (400 MHz, DMSO) δ ppm: 0.82-0.86 (m, 6H), 1.11-1.25 (m, 19H), 1.42-1.52 (m, 6H), 1.75-1.96 (m, 2H), 2.17-2.33 (m, 2H), 2.67-2.84 (m, 2H), 3.03-3.13 (m, 2H), 3.18-3.20 (m, 2H), 3.33-3.49 (m, 3H), 3.63 (m, 1H), 3.78-3.81 (m, 2H), 4.11-4.14 (m, 1H), 4.54 (m, 1H), 4.84-5.13 (m, 1H), 7.06-7.08 (d, J=7.2 Hz, 2H), 7.11-7.18 (m, 4H), 7.22-7.30 (m, 4H), 7.34 (m, 2H), 7.50-7.53 (m, 1H), 7.59 (m, 1H), 7.85 (s, 1H), 8.28-8.35 (m, 2H), 7.42 (s, 1H). Chiral HPLC (Fr-1): 98.67% (RT: 6.35)

Fraction 2; (3S,4S)-1-(3-((R*)-3-(hexylcarbamoyl)-4-octanoyl-1,4-diazepane-1-carbonyl)benzoyl)-N3,N4-bis((1S,2R)-2-phenylcyclopropyl)pyrrolidine-3,4-dicarboxamide (Compound 191)(0.025 g, 25%) [absolute stereochemistry is arbitrarily assigned]. LCMS (Method-J2): 100% (RT 4.721, 202.0 nm) (MS: ESI +ve 872.5 [M−1]). $^1$H NMR: (400 MHz, DMSO) δ ppm: 0.80-0.86 (m, 6H), 1.10-1.25 (m, 16H), 1.40-1.53 (m, 4H), 1.61 (m, 3H), 1.85-1.96 (m, 2H), 2.67-2.77 (m, 2H), 3.02-3.20 (m, 5H), 3.38-3.48 (m, 4H), 3.63-3.68 (m, 1H), 3.79-3.82 (m, 2H), 4.10-1.13 (m, 2H), 4.49-4.51 (m, 2H), 4.85-5.12 (m, 2H), 7.06-7.08 (d, J=7.6 Hz, 2H), 7.11-7.18 (m, 4H), 7.22-7.31 (m, 4H), 7.34-7.37 (m, 2H), 7.49-7.53 (m, 1H), 7.58-7.60 (d, J=7.6 Hz, 1H), 7.86 (m, 1H), 8.28-8.35 (m, 1H), 8.42 (s, 1H). Chiral HPLC (Fr-2): 97.93% (RT: 22.09)

Synthesis of (3S,4S)-1-(3-(((S)-3-(hexylcarbamoyl)-4-octanoylpiperazin-1-yl)sulfonyl) benzoyl)-N3,N4-bis((1S,2R)-2-phenylcyclopropyl)pyrrolidine-3,4-dicarboxamide, Compound 170

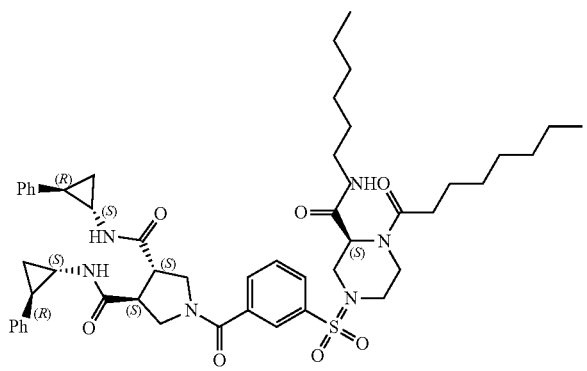

Step-1: Preparation of methyl (S)-3-((3-(hexylcarbamoyl)-4-octanoylpiperazin-1-yl)sulfonyl)benzoate

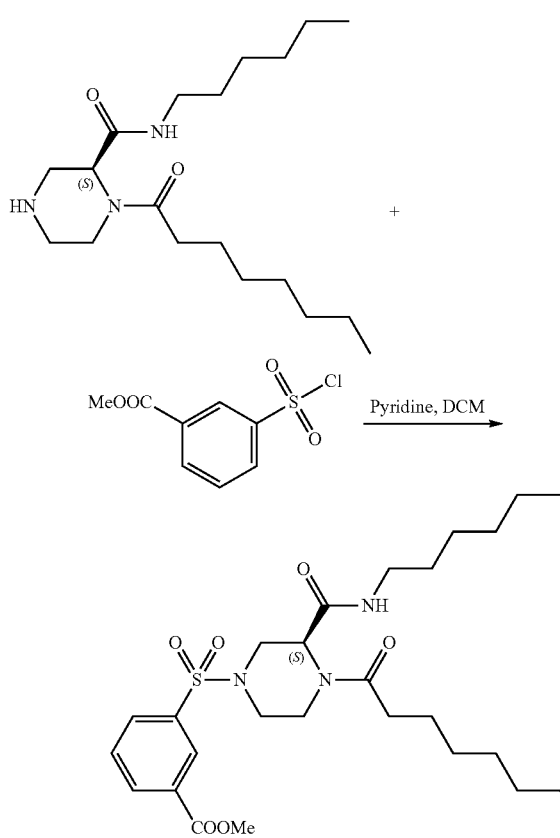

(S)—N-hexyl-1-octanoylpiperazine-2-carboxamide (0.300 g, 0.88 mmol) was dissolved in DCM (20 mL) and cooled to 0° C. Pyridine (0.27 mL) followed by methyl 3-(chlorosulfonyl)benzoate (0.248 g, 1.06 mmol) were added dropwise. The reaction mixture was stirred at room temperature for 6 hrs. The mixture was extracted in DCM (3×30 mL), washed with water (30 mL) then the organic layer was dried and concentrated. The crude product was purified using flash chromatography, eluting with 5-10% MeOH in DCM, to give methyl (S)-3-((3-(hexylcarbamoyl)-4-octanoylpiperazin-1-yl)sulfonyl)benzoate(0.420 g, 90.07%). LC-MS (Method-C2): 100% (RT 1.520, 230.0 nm) (MS: ESI +ve 538.5 [M+1]).

Step 2: Preparation of (S)-3-((3-(hexylcarbamoyl)-4-octanoylpiperazin-1-yl)sulfonyl)benzoic acid

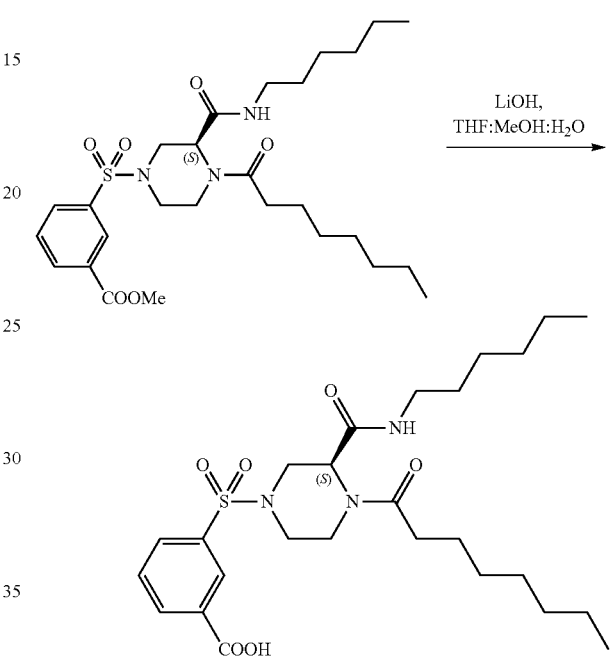

Prepared using General Ester Hydrolysis Procedure to give (S)-3-((3-(hexylcarbamoyl)-4-octanoylpiperazin-1-yl)sulfonyl)benzoic acid as a white solid (330 mg, 84.71%). LC-MS (Method-C2): 78% (RT: 1.460, 202.0 nm) (MS: ESI +ve 524.9[M+1]).

Step 3: Preparation of (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide, (Compound 170)

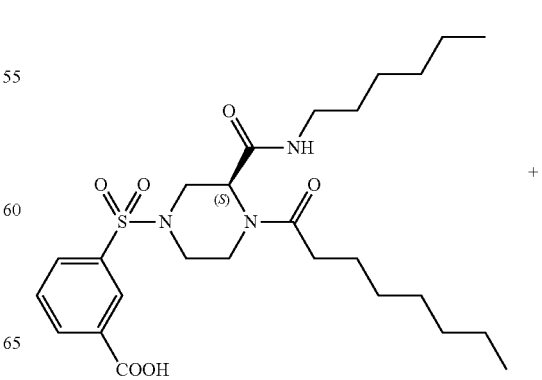

663

-continued

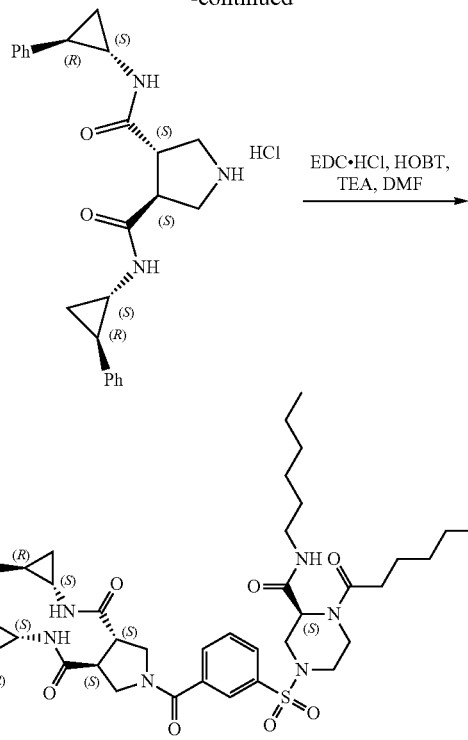

664

Synthesis of (3S,4S)-1-(3-(((R)-3-(hexylcarbamoyl)-4-octanoylpiperazin-1-yl)sulfonyl) benzoyl)-N3,N4-bis((1S,2R)-2-phenylcyclopropyl)pyrrolidine-3,4-dicarboxamide, Compound 171

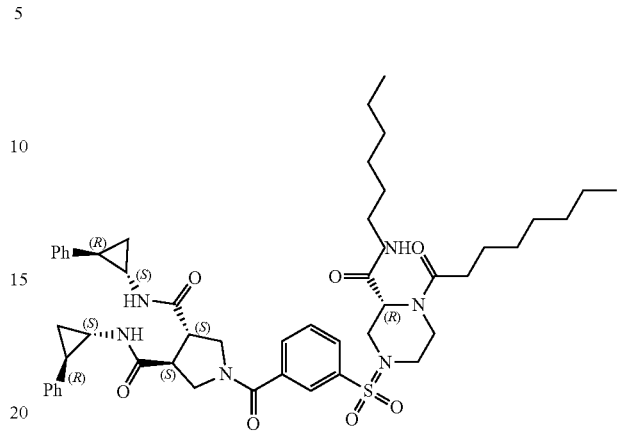

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The final product was purified using Prep HPLC Method 13 to give (3S,4S)-1-(3-(((R)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 171) (0.035 g, 17%). LCMS (Method-J): 100% (RT 4.968, 202.0 nm) (MS: ESI +ve 886.6 [M+H]). $^1$H NMR: (400 MHz, DMSO) δ ppm: 0.8-0.86 (m, 6H), 1.09-1.12 (m, 2H), 1.17-1.25 (m, 14H), 1.40 (s, 4H), 1.86 (s, 1H), 1.96 (s, 1H), 2.30-2.64 (m, 5H), 2.77 (s, 1H), 2.93 (s, 1H), 3.09-3.07-3.23 (m, 5H), 2.52-3.55 (m, 3H), 3.65-3.69 (m, 1H), 3.80-3.83 (m, 1H), 4.13-4.16 (m, 1H), 4.50 (s, 1H), 4.92 (s, 1H), 7.06-7.08 (m, 2H), 7.11-7.18 (m, 4H), 7.23-7.29 (m, 4H), 7.71-7.75 (m, 1H), 7.79-7.83 (m, 2H), 7.88-7.89 (m, 1H), 8.29-8.30 (d, 1H), 8.43-8.44 (d, 1H).

Prepared using General EDC, HOBT Coupling Procedure. The crude product was purified using Prep HPLC Method to give (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170)(0.015 g, 5.85%). LCMS (Method-J): 100% (RT 4.923, 202.0 nm) (MS: ESI +ve 896.6 [M+1]. $^1$H NMR: (400 MHz, DMSO) δ ppm: 0.81-0.86 (m, 6H), 1.11-1.25 (m, 16H), 1.40 (s, 4H), 1.86 (s, 1H), 1.97 (s, 1H), 2.28-2.50 (m, 6H), 2.67-2.93 (m, 2H), 3.08-3.20 (m, 5H), 3.52-3.55 (d, J=11.6 Hz, 3H), 3.64-3.69 (t, J=10 Hz, 1H), 3.79-3.82 (d, J=11.6 Hz, 2H), 4.13-4.16 (d, J=12.4 Hz, 1H), 4.92 (s, 1H), 7.06-7.28 (m, 10H), 7.71-7.81 (m, 5H), 7.87-7.89 (d, J=6.8 Hz, 1H), 8.30 (s, 1H), 8.43-8.44 (d, J=4 Hz, 1H).

Synthesis of (3S,4S)-1-(3-(((R)-4-acetyl-3-(tetradecylcarbamoyl)piperazin-1-yl)sulfonyl) benzoyl)-N3,N4-bis((1S,2R)-2-phenylcyclopropyl)pyrrolidine-3,4-dicarboxamide, Compound 192

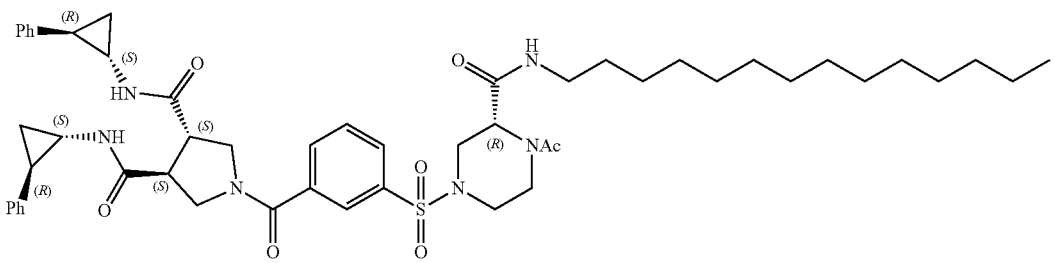

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The final product was purified using Prep HPLC Method 7 to give (3S,4S)-1-(3-(((R)-4-acetyl-3-(tetradecylcarbamoyl)piperazin-1-yl)sulfonyl)benzoyl)-N3,N4-bis((1S,2R)-2-phenylcyclopropyl)pyrrolidine-3,4-dicarboxamide (Compound 192)(0.135 g, 40.35%). LCMS (Method-C2): 100% (RT 1.703, 202.0 nm) (MS: ESI +ve 921.9 [M−H]). $^1$H NMR: (400 MHz, DMSO) δ ppm: 0.83-0.86 (m, 6H), 1.09-1.24 (m, 22H), 1.38 (s, 3H), 1.83-1.86 (m, 2H), 1.96-1.99 (m, 3H), 2.13-2.33 (m, 2H), 2.77-2.86 (m, 2H), 3.01-3.23 (m, 4H), 3.52-3.57 (m, 3H), 3.64-3.83 (m, 3H), 4.14-4.17 (m, 1H), 4.29-4.51 (m, 1H), 4.91 (s, 1H), 7.06-7.08 (d, J=7.2 Hz, 2H), 7.11-7.18 (m, 4H), 7.21-7.28 (m, 4H), 7.71-7.75 (m, 1H), 7.79-7.81 (d, J=9.2 Hz, 2H), 7.86-7.90 (m, 1H), 8.06 (m, 1H), 8.31-8.32 (d, J=4 Hz, 1H), 8.45-8.46 (d, J=4 Hz, 1H).

Synthesis of (3S,4S)-1-(3-(((S)-4-acetyl-3-(tetradecylcarbamoyl)piperazin-1-yl)sulfonyl) benzoyl)-N3,N4-bis((1S,2R)-2-phenylcyclopropyl)pyrrolidine-3,4-dicarboxamide, Compound 193

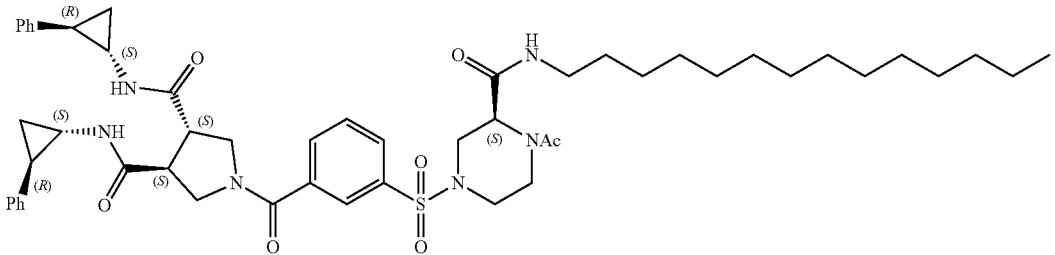

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The final product was purified using Prep HPLC Method 13 to give (3S,4S)-1-(3-(((S)-4-acetyl-3-(tetradecylcarbamoyl)piperazin-1-yl)sulfonyl)benzoyl)-N3,N4-bis((1S,2R)-2-phenylcyclopropyl)pyrrolidine-3,4-dicarboxamide (Compound 193), as an off white solid (0.065 g, 19.42%). LCMS (Method-J2): 98.79% (RT 1.703, 254.4 nm) (MS: ESI +ve 922.6 [M−H]). $^1$H NMR: (400 MHz, DMSO) δ ppm: 0.83-0.86 (m, 3H), 1.09-1.24 (m, 25H), 1.38 (m, 2H), 1.86 (s, 2H), 1.97 (s, 3H), 2.30-2.33 (m, 2H), 2.67-2.78 (m, 2H), 3.01-3.20 (m, 4H), 3.41-3.54 (m, 4H), 3.64-3.68 (m, 1H), 3.73-3.83 (m, 2H), 4.14-4.19 (m, 1H), 4.30-4.48 (m, 1H), 4.91 (s, 1H), 7.06-7.08 (d, J=7.6 Hz, 2H), 7.11-7.18 (m, 4H), 7.22-7.28 (m, 4H), 7.70-7.74 (m, 1H), 7.78-7.81 (m, 2H), 7.87 (m, 1H), 8.37-8.38 (d, J=4 Hz, 2H), 8.51 (s, 1H).

Synthesis of (3S,4S)-1-(3-((4-pentadecanamidopiperidin-1-yl)sulfonyl)benzoyl)-N3,N4-bis((1S,2R)-2-phenylcyclopropyl)pyrrolidine-3,4-dicarboxamide, Compound 194

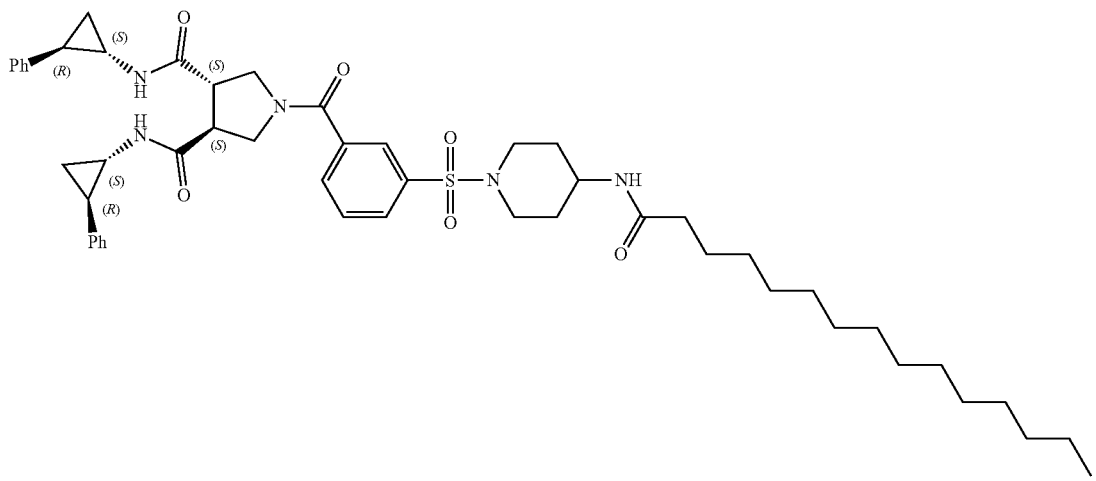

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170) substituting the applicable starting materials. The final product was purified using Prep HPLC Method 13 to give (3S,4S)-1-(3-((4-pentadecanamidopiperidin-1-yl)sulfonyl)benzoyl)-N3,N4-bis((1S,2R)-2-phenylcyclopropyl)pyrrolidine-3,4-dicarboxamide (Compound 194), as a white solid (0.12 g, 33%). LCMS (Method-C-Fast): 100% (RT: 2.644, 254.0 nm) (MS: ESI +ve 880.0 [M+H]). $^1$H NMR: (400 MHz, DMSO) δ ppm: 0.83-0.87 (t, 3H); 1.08-1.12 (t, 2H); 1.19 (s, 24H); 1.41 (s, 5H); 1.75 (s, 2H); 1.84 (s, 1H); 1.96-2.00 (t, 3H); 2.77 (s, 1H); 2.84 (s, 1H); 3.10-3.14 (m, 1H); 3.17-3.21 (m, 1H); 3.52-3.54 (d, J=8.4, 6H); 3.64-3.68 (m, 1H); 3.78-3.83 (m, 1H); 7.05-7.07 (d, J=7.2, 2H); 7.11-7.18 (m, 4H); 7.21-7.28 (m, 4H); 7.70-7.75 (m, 2H); 7.80-7.87 (m, 3H); 8.33 (s, 1H); 8.47 (s, 1H); 8.51 (s, 1H).

Synthesis of (3S,4S)-1-(4-(((R)-4-acetyl-3-(tetradecylcarbamoyl)piperazin-1-yl)sulfonyl) benzoyl)-N3,N4-bis((1S,2R)-2-phenylcyclopropyl)pyrrolidine-3,4-dicarboxamide, Compound 195

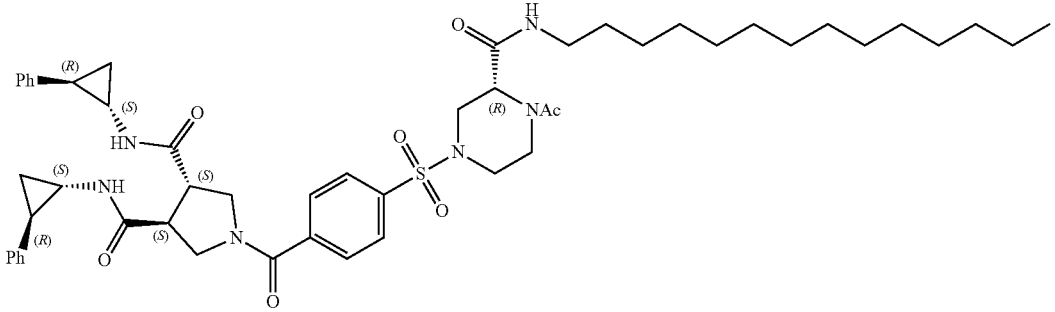

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The final product was purified using Prep HPLC Method 13 to give (3S,4S)-1-(4-(((R)-4-acetyl-3-(tetradecylcarbamoyl)piperazin-1-yl)sulfonyl)benzoyl)-N3,N4-bis((1S,2R)-2-phenylcyclopropyl)pyrrolidine-3,4-dicarboxamide (Compound 195), as an off white solid (0.085 g, 25.40%). LCMS (Method-J2): 100% (RT 5.360, 202.0 nm) (MS: ESI +ve 924.6 [M+H]). $^1$H NMR: (400 MHz, DMSO) δ ppm: 0.83-0.86 (m, 3H), 1.09-1.39 (m, 27H), 1.86 (s, 2H), 1.97-2.00 (m, 3H), 2.33-2.38 (m, 1H), 2.67-2.85 (m, 2H), 3.08-3.21 (m, 4H), 3.42-3.68 (m, 4H), 3.75-3.83 (m, 2H), 4.13-4.15 (m, 2H), 4.30-4.46 (m, 1H), 4.90 (s, 1H), 7.06-7.07 (d, J=7.2 Hz, 2H), 7.11-7.18 (m, 4H), 7.22-7.28 (m, 4H), 7.76 (s, 4H), 7.85-8.04 (m, 1H), 8.32 (s, 1H), 8.44-8.51 (m, 2H).

Synthesis of (3S,4S)-1-(4-(((S)-4-acetyl-3-(tetradecylcarbamoyl)piperazin-1-yl)sulfonyl)benzoyl)-N3,N4-bis((1S,2R)-2-phenylcyclopropyl)pyrrolidine-3,4-dicarboxamide, Compound 196

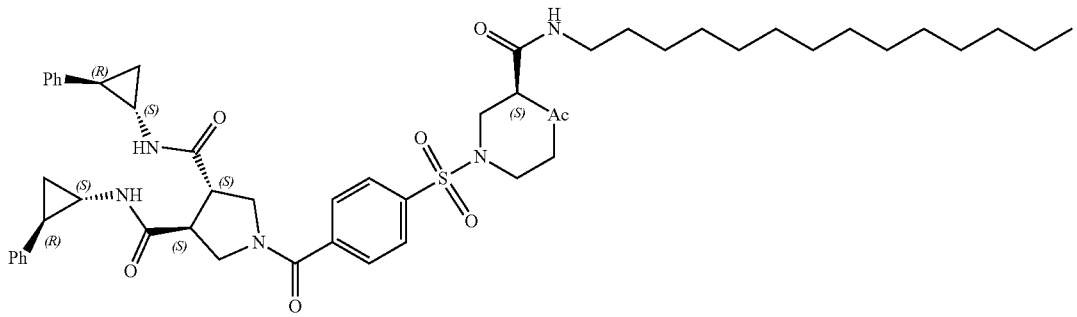

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The final product was purified using Prep HPLC Method 13 to give (3S,4S)-1-(4-(((S)-4-acetyl-3-(tetradecylcarbamoyl)piperazin-1-yl)sulfonyl)benzoyl)-N3,N4-bis((1S,2R)-2-phenylcyclopropyl)pyrrolidine-3,4-dicarboxamide (Compound 196), as an off white solid (0.075 g, 22.41%). LCMS (Method-J2): 100% (RT 5.282, 254.0 nm) (MS: ESI +ve 924.5 [M+H]). $^1$H NMR: (400 MHz, DMSO) δ ppm: 0.83-0.86 (m, 3H), 1.08-1.24 (m, 29H), 1.39 (s, 2H), 1.87 (s, 2H), 1.95-2.00 (m, 3H), 2.33-2.50 (m, 2H), 2.67-2.86 (m, 2H), 3.01-3.21 (m, 3H), 3.50-3.64 (m, 3H), 3.75-3.84 (m, 1H), 4.13-4.16 (m, 1H), 4.30-4.47 (m, 1H), 4.91 (s, 1H), 7.06-7.08 (d, J=7.6 Hz, 2H), 7.11-7.18 (m, 4H), 7.22-7.28 (m, 4H), 7.76 (s, 4H), 7.84-8.04 (m, 1H), 8.31-8.32 (d, J=4 Hz, 1H), 8.44-8.45 (d, J=4 Hz, 1H).

Synthesis of (3S,4S)-1-(4-(((S*)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Compound 202 and (3S,4S)-1-(4-(((R*)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Compound 203

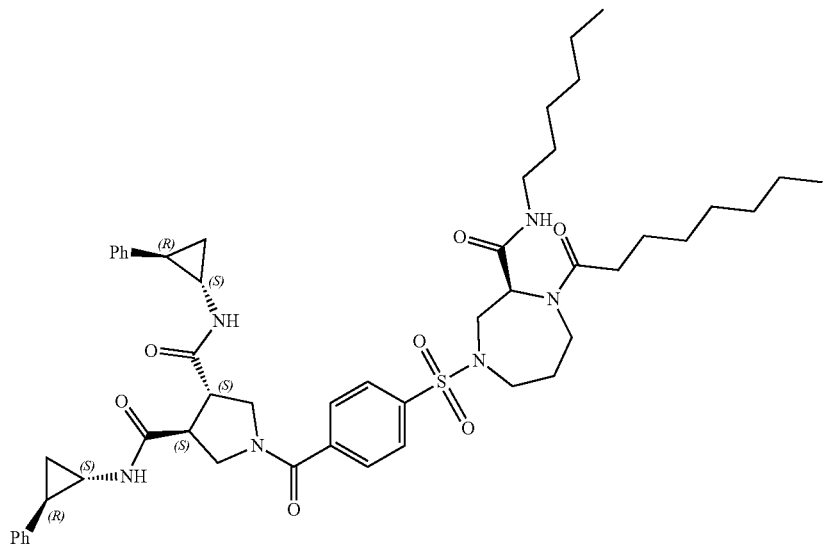

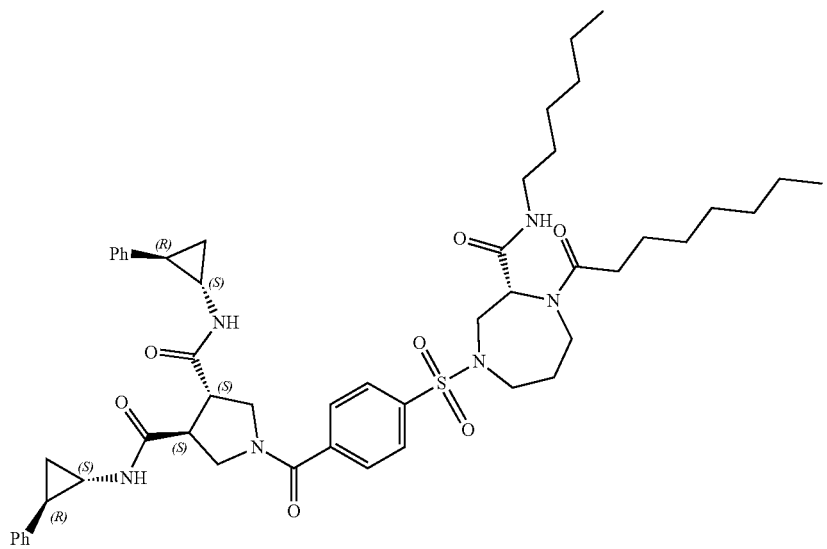

Step 1; Preparation of (3S,4S)-1-(4-((-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide.

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The crude final product was purified using Prep HPLC Method 1 to give (3S,4S)-1-(4-((3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide as a 1:1 mixture of diastereomers. (0.130 g, 20.11%). LCMS (Method-J2): 100% (RT 4.878, 202.4 nm) (MS: ESI +ve 910.6 [M+H]) Chiral HPLC: 50.06% (RT: 8.92), 45.71%, (RT: 9.87

Step-2: Chiral SFC Separation of (3S,4S)-1-(4-((3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Compound 202 and Compound 203

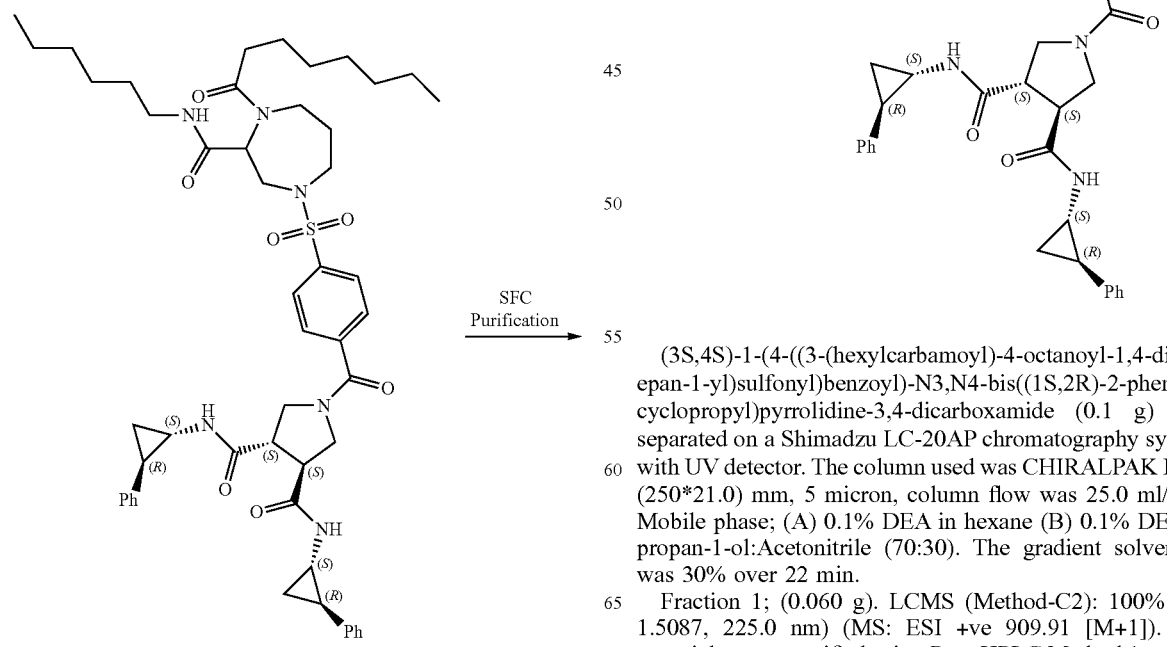

SFC Purification →

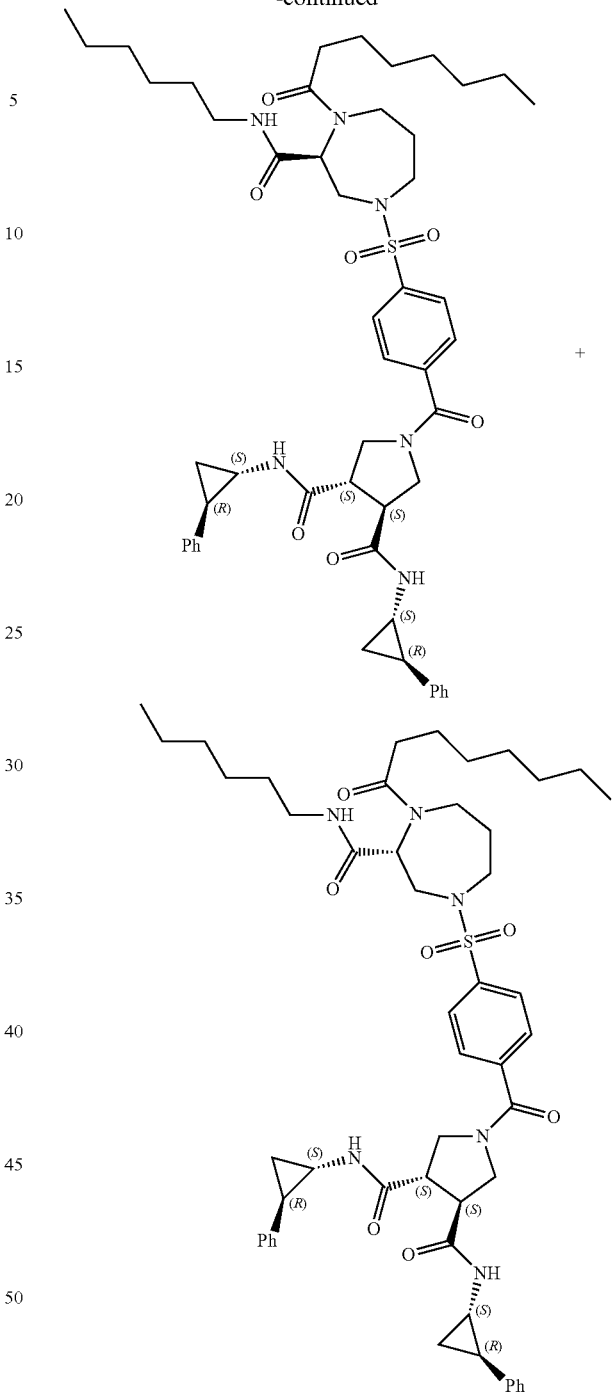

(3S,4S)-1-(4-((3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide (0.1 g) was separated on a Shimadzu LC-20AP chromatography system with UV detector. The column used was CHIRALPAK IB-N (250*21.0) mm, 5 micron, column flow was 25.0 ml/min. Mobile phase; (A) 0.1% DEA in hexane (B) 0.1% DEA in propan-1-ol:Acetonitrile (70:30). The gradient solvent B was 30% over 22 min.

Fraction 1; (0.060 g). LCMS (Method-C2): 100% (RT 1.5087, 225.0 nm) (MS: ESI +ve 909.91 [M+1]). The material was re-purified using Prep HPLC Method 1 to give

673

(3S,4S)-1-(4-(((S*)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide (Compound 202)(0.025 g, 25%). [Absolute stereochemistry arbitrarily assigned]. LCMS (Method-C2): 100% (RT 1.508, 202.0 nm) (MS: ESI +ve 907.8 [M−1]). ¹H NMR: (400 MHz, DMSO) δ ppm: 0.82-0.86 (m, 6H), 1.09-1.24 (m, 19H), 1.34-1.58 (m, 6H), 1.85-2.18 (m, 4H), 2.18-2.33 (m, 2H), 2.67-2.79 (m, 3H), 2.84-2.86 (m, 2H), 2.97-3.22 (m, 4H), 3.49-3.56 (m, 2H), 3.60-3.72 (m, 1H), 3.78-3.81 (m, 2H), 4.03-4.21 (m, 2H), 4.51-4.85 (m, 1H), 7.06-7.08 (d, J=7.6 Hz, 2H), 7.11-7.18 (m, 4H), 7.22-7.28 (m, 4H), 7.70-7.73 (t, 2H), 7.82-7.87 (q, 3H), 8.28-8.31 (t, 1H), 8.43-8.44 (d, J=4 Hz, 1H). Chiral HPLC (Fr-1): 95.63% (RT: 8.86)

Fraction 2; (0.055 g). LCMS (Method-J2): 100% (RT 4.794, 202.0 nm) (MS: ESI +ve 909.6 [M+1]). The material was re-purified Prep HPLC Method 1 to give (3S,4S)-1-(4-(((R*)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide (Compound 203)(0.023 g, 23%) [Absolute stereochemistry arbitrarily assigned]. LCMS (Method-J2): 100% (RT 4.778, 202.0 nm) (MS: ESI +ve 908.5 [M−1]). ¹H NMR: (400 MHz, DMSO) δ ppm: 0.83-0.86 (m, 6H), 1.09-1.25 (m, 19H), 1.33-1.58 (m, 6H), 1.86-1.99 (m, 3H), 2.15-2.19 (m, 2H), 2.67-2.78 (m, 3H), 2.97-3.28 (m, 6H), 3.51-3.62 (m, 3H), 3.74-3.83 (m, 3H), 4.03-4.20 (m, 2H), 4.55-4.85 (m, 1H), 7.06-7.08 (d, J=7.2 Hz, 2H), 7.11-7.18 (m, 4H), 7.22-7.28 (m, 4H), 7.70-7.73 (m, 2H), 7.82-7.88 (m, 3H), 8.28-8.30 (m, 1H), 8.43-8.44 (d, J=4 Hz, 1H). Chiral HPLC (Fr-2): 99.61% (RT: 9.82)

Synthesis of (3S,4S)-1-(3-(((S)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Compound 200 and (3S,4S)-1-(3-(((R)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Compound 201

674

-continued

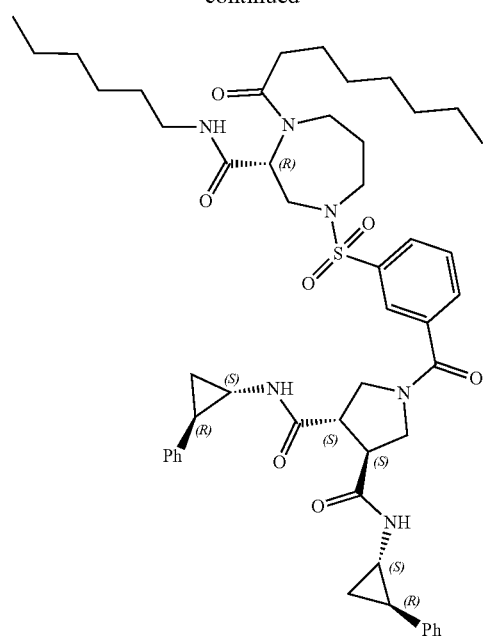

Step-1: Chiral SFC Separation of (3S,4)-1-(3-((3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide

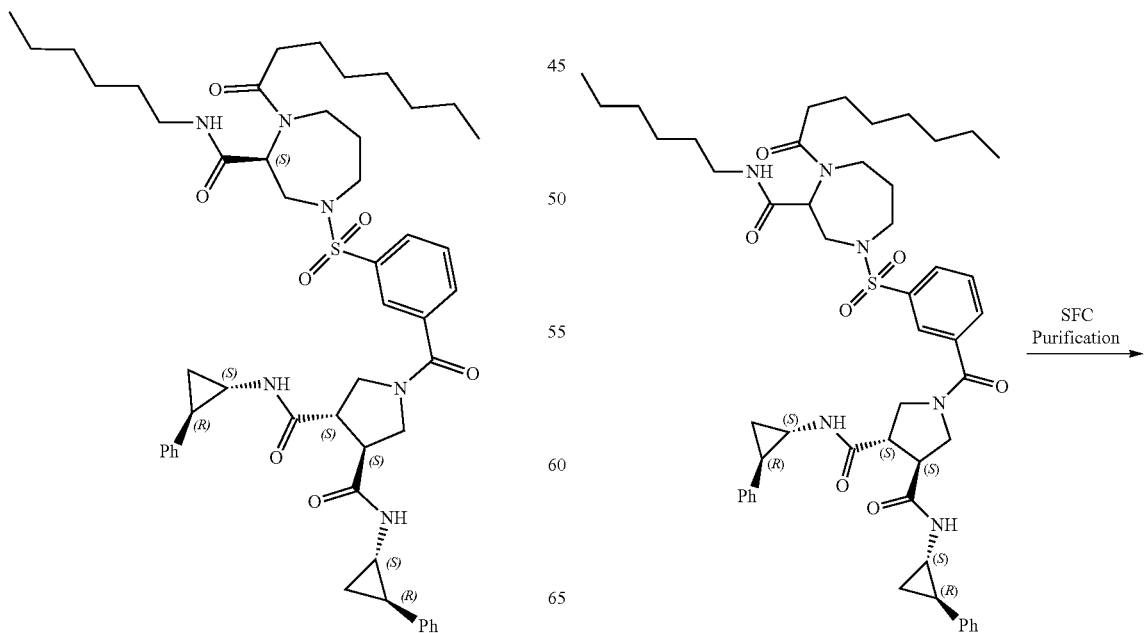

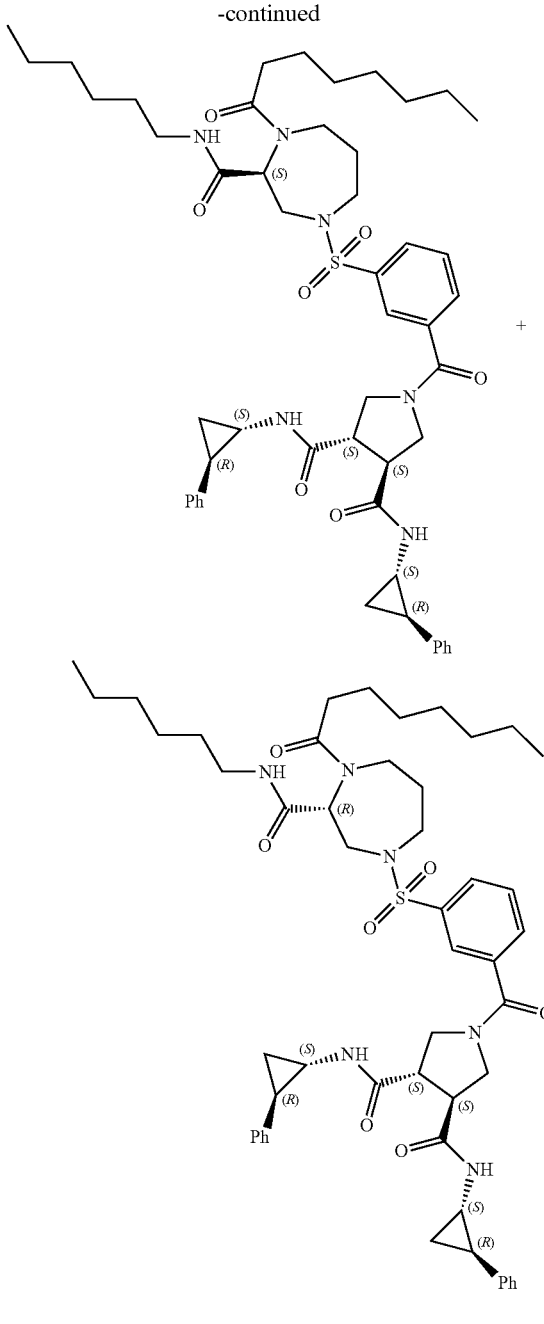

(3S,4S)-1-(3-((3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide, Chiral HPLC: 44.86% (RT: 4.67), 53.57%, (RT: 6.11) prepaired by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170) substituting the applicable starting materials. The column used was Chiralpak 111 (250*21.0) mm, 5 micron, column flow was 80.0 ml/min and ABPR was 100 bar. Mobile phase; (A) liquid carbon dioxide and (B) 0.1% DEA in MeOH. The gradient solvent B was 15% over 26 min to give;

Fraction 1; (0.050 g). LCMS (Method-C2): 100% (RT 1.508, 222.0 nm) (MS: ESI +ve 910.0 [M+1]). This material was re-purified by Prep HPLC Method 5 to give (3S,4S)-1-(3-(((S)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide (Compound 200)(0.012 g, 12%) [absolute stereochemistry of azepine is arbitrarily assigned (S)]. LCMS (Method-C2): 100% (RT 1.530, 202.0 nm) (MS: ESI +ve 909.85 [M+1]). $^1$H NMR: (400 MHz, DMSO) δ ppm: 0.83-0.86 (m, 6H), 1.10-1.19 (m, 21H), 1.24-1.46 (m, 6H), 1.57-1.71 (m, 1H), 1.86-1.97 (m, 2H), 2.09-2.18 (m, 2H), 2.67-2.84 (m, 4H), 2.95-3.20 (m, 3H), 3.50-3.67 (m, 2H), 3.70-3.84 (m, 2H), 4.01-4.05 (m, 1H), 4.50-4.85 (m, 1H), 7.06-7.08 (d, J=7.6 Hz, 2H), 7.11-7.18 (m, 4H), 7.22-7.28 (m, 4H), 7.61-7.71 (m, 1H), 7.80-7.92 (m, 4H), 8.28-8.29 (d, J=4 Hz, 1H), 8.43-8.44 (d, J=4 Hz, 1H). Chiral HPLC (Fraction-1): 100% (RT: 4.77)

Fraction 2; (0.055 g). LCMS (Method-C2): 100% (RT 1.509, 222.0 nm) (MS: ESI +ve 910.1 [M+1]). This material was re-purified by Prep HPLC Method 5 to give (3S,4S)-1-(3-(((R)-3-(hexylcarbamoyl)-4-octanoyl-1,4-diazepan-1-yl)sulfonyl)benzoyl)-N3,N4-bis((1S,2R)-2-phenylcyclopropyl)pyrrolidine-3,4-dicarboxamide (Compound 201) (0.030 g, 30%) [absolute stereochemistry of azepine is arbitrarily assigned (R)]. LCMS (Method-J2): 100% (RT 4.825, 202.0 nm) (MS: ESI +ve 909.6 [M+1]). $^1$H NMR: (400 MHz, DMSO) δ ppm: 0.80-0.86 (m, 6H), 1.09-1.39 (m, 19H), 1.47-1.57 (m, 6H), 1.70-1.97 (m, 2H), 2.08-2.18 (m, 3H), 2.78-2.84 (m, 3H), 3.00-3.28 (m, 4H), 3.50-3.54 (m, 2H), 3.63-3.65 (m, 2H), 3.73-3.82 (m, 2H), 3.98-4.06 (m, 1H), 4.48-4.86 (m, 1H), 7.06-7.08 (d, J=7.2 Hz, 2H), 7.11-7.18 (m, 4H), 7.22-7.28 (m, 4H), 7.65-7.71 (m, 1H), 7.82-7.92 (m, 4H), 8.29 (m, 1H), 7.43-7.44 (d, J=4 Hz, 1H). Chiral HPLC (Fraction-2): 100% (RT: 6.18)

Synthesis of (3S,4S)-1-(4-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide, Compound 160

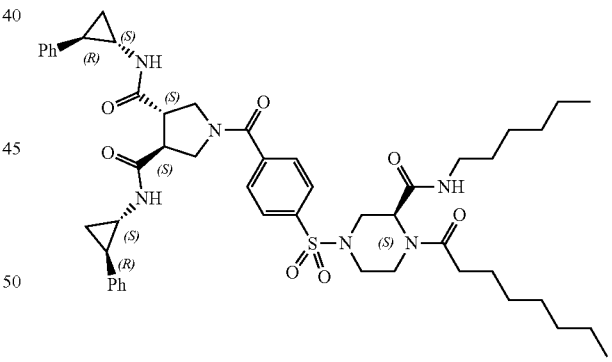

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170) substituting the applicable starting materials. The crude final product was purified using Prep HPLC Method 1 to give (3S,4S)-1-(4-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 160)(0.010 g, 4.88%). LCMS (Method-H): 100% (RT 3.92, 254.0 nm) (MS: ESI +ve 896.6 [M+1]. $^1$H NMR: (400 MHz, DMSO) δ ppm: 0.81-0.86 (m, 6H), 1.08-1.11 (t, J=1.6 Hz, 2H), 1.12-1.40 (m, 23H), 1.85 (s, 2H), 1.96-1.99 (t, J=0.8

Hz, 1H), 2.28-2.38 (m, 4H), 2.67-2.94 (m, 4H), 3.08-3.21 (m, 6H), 3.42-3.64 (m, 5H), 3.79-3.84 (m, 2H), 4.12-4.14 (d, J=11.2 Hz, 1H), 4.32 (s, 1H), 4.52 (s, 1H), 4.92 (s, 1H), 7.06-7.07 (d, J=7.6 Hz, 2H), 7.11-7.18 (m, 4H), 7.22-7.28 (m, 4H), 7.76-7.82 (m, 4H), 8.00 (s, 1H), 8.29-8.43 (m, 2H).

Synthesis of (3S,4S)-1-(4-(((R)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide, Compound 161

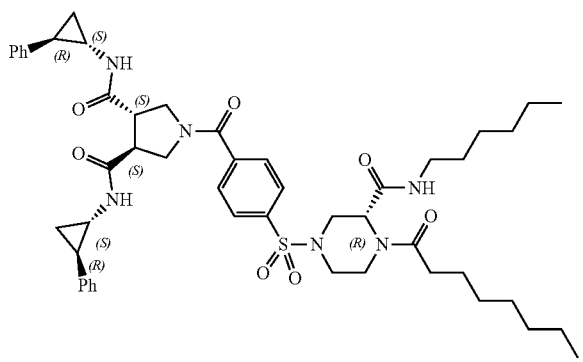

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The crude final product was purified using Prep HPLC Method 1 to give (3S,4S)-1-(4-(((R)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 161)(0.036 g, 14%), as an off white solid. LCMS (Method-J): 100% (RT 4.930, 202.0 nm) (MS: ESI +ve 895.5 [M+H]). $^1$H NMR: (400 MHz, DMSO) δ ppm: 0.85-0.87 (m, 6H), 1.09-1.13 (m, 2H), 1.18-1.26 (m, 18H), 1.41 (bs, 4H), 1.86 (s, 1H), 1.96 (s, 1H), 2.30-2.64 (m, 3H), 2.79 (s, 1H), 2.85 (s, 1H), 3.09-3.22 (m, 5H), 2.34-3.66 (m, 4H), 3.79-3.84 (m, 2H), 4.12-4.15 (m, 1H), 4.33-4.36 (m, 1H), 4.53 (s, 1H), 4.93 (s, 1H), 7.07-7.08 (m, 2H), 7.12-7.19 (m, 4H), 7.25-7.30 (m, 4H), 7.77 (s, 4H), 8.03 (s, 1H), 8.33-8.33 (m, 1H), 8.46-8.47 (m, 1H).

Synthesis of (3S,4S)-1-(4-((4-pentadecanamidopiperidin-1-yl)sulfonyl)benzoyl)-N3,N4-bis((1S,2R)-2-phenylcyclopropyl)pyrrolidine-3,4-dicarboxamide, Compound 165

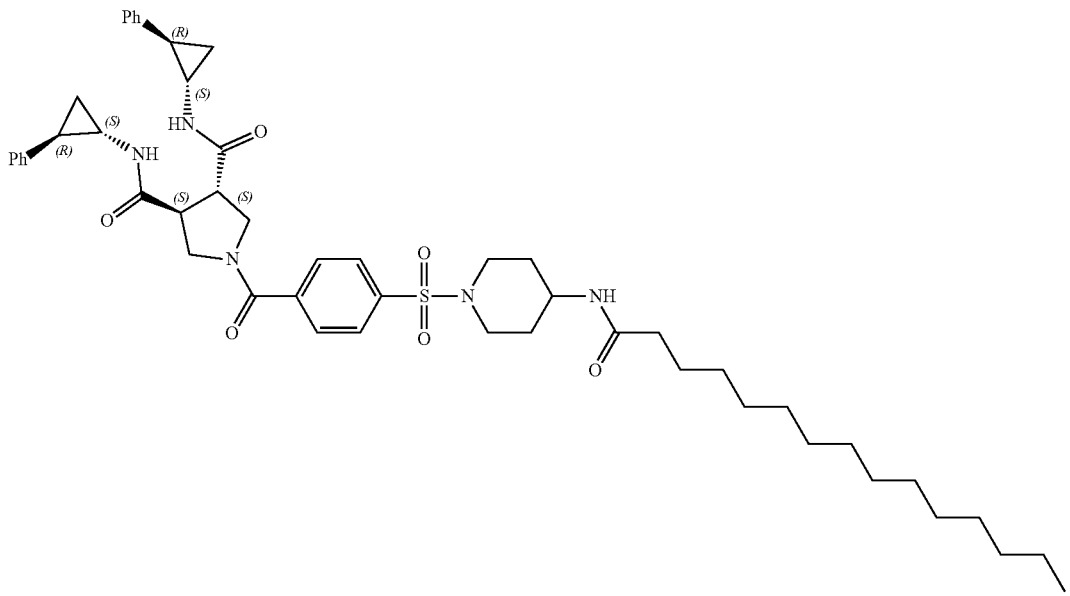

Prepared by a procedure similar to that reported for (3S,4S)-1-(3-(((S)-3-(hexylcarbamoyl)-4-octanoylpiperazin-1-yl)sulfonyl)benzoyl)-N3,N4-bis((1S,2R)-2-phenylcyclopropyl)pyrrolidine-3,4-dicarboxamide (Compound 170), substituting the applicable starting materials. The crude final product was purified using Prep HPLC Method 1 to give (3S,4S)-1-(4-((4-pentadecanamidopiperidin-1-yl)sulfonyl)benzoyl)-N3,N4-bis((1S,2R)-2-phenylcyclopropyl) pyrrolidine-3,4-dicarboxamide (Compound 165), as an off white solid (0.2 g, 66%) LCMS (Method-C-fast): 100%

(RT 2.823, 202.0 nm) (MS: ESI +ve 881 [M+H]). $^1$H NMR: (400 MHz, DMSO) δ ppm: 0.83-0.85 (d, J=6.8, 3H); 1.11-1.13 (d, J=6.4, 2H); 1.23 (s, 26H); 1.35-1.42 (m, 5H); 1.76 (s, 2H); 1.86 (s, 1H); 1.97-1.98 (d, J=6.4, 3H); 2.78 (s, 2H); 3.08-3.12 (t, 1H); 3.18-3.20 (d, J=7.6, 1H); 3.52 (s, 5H); 3.60-3.65 (t, 1H); 3.79-3.84 (t, 1H); 7.06-7.26 (m, 10H); 7.74-7.77 (m, 5H); 8.32 (s, 1H), 8.45 (s, 1H).

Synthesis of (3S,4S)—N3,N4-bis((1S,2R)-2-phenyl-cyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide, Compound 132

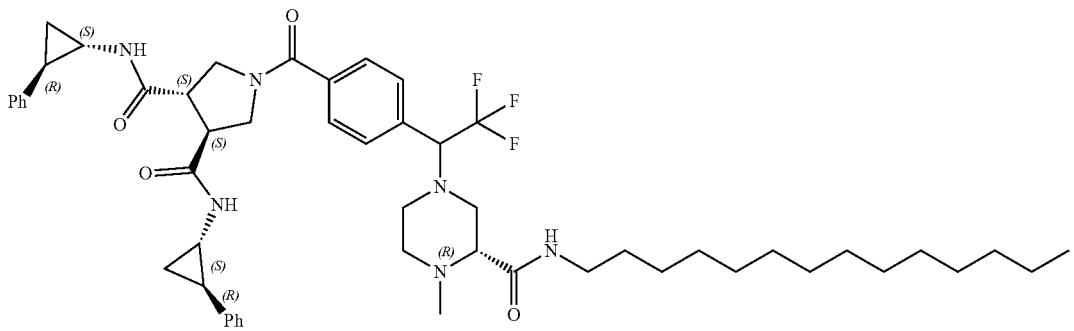

Step-1: Preparation of Methyl 4-(2,2,2-trifluoro-1-hydroxyethyl) benzoate

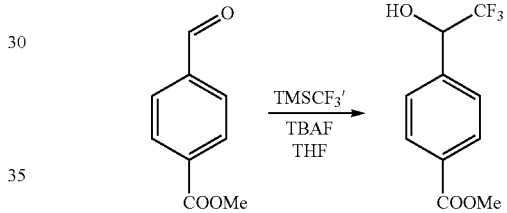

Methyl 4-formylbenzoate (2.0 g, 12.18 mmol) and tetra-n-butylammonium fluoride (1.21 mL, 1.21 mmol, 1M solution in THF) were cooled to 0° C. and trifluoromethyltrimethylsilane (1.8 g, 12.18 mmol) was added dropwise. The reaction mixture was stirred under a nitrogen atmosphere at room temperature for 16 hrs. The mixture was diluted with ethyl acetate (200 mL), washed with brine (2×100 mL), dried over sodium sulfate and concentrated under reduced pressure. The resulting solid was purified by flash chromatography, eluting with 5-10% ethyl acetate in hexane, to give methyl 4-(2,2,2-trifluoro-1-hydroxyethyl) benzoate (1.0 g, 22%). $^1$H NMR: (400 MHz, DMSO) δ ppm: 3.86 (s, 3H), 5.28-5.35 (m, 1H), 7.64-7.66 (m, 2H), 7.99-8.01 (m, 2H).

Step-2: Preparation of methyl 4-(2,2,2-trifluoro-1-(((trifluoromethyl)sulfonyl)oxy)ethyl)benzoate

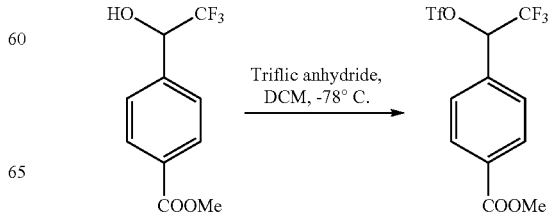

Methyl 4-(2,2,2-trifluoro-1-hydroxyethyl) benzoate (1.0 g, 4.26 mmol) dissolved in dry DCM (10 mL) and cooled to −78° C. N, N-Diisopropylethylamine (0.7 mL, 5.53 mmol) and trifluoromethanesulfonic anhydride (1.32 g, 4.69 mmol) were added dropwise. The reaction mixture was stirred at room temperature under nitrogen atmosphere for 16 h. The mixture was diluted with DCM (100 mL), washed with sodium bicarbonate (2×100 mL), dried over sodium sulfate and concentrated under reduced pressure. The crude product was purified using flash chromatography, eluting with 5-10% ethyl acetate in hexane, to give methyl 4-(2,2,2-trifluoro-1-(((trifluoromethyl)sulfonyl)oxy)ethyl)benzoate (1.3 g, 83%)material. $^1$H-NMR: (400 MHz, DMSO) δ ppm: 4.01 (s, 3H), 5.92-5.96 (m, 1H), 7.61-7.64 (m, 2H), 8.19.24 (m, 2H).

Step-3: Preparation of methyl 4-(2,2,2-trifluoro-1-((R)-4-methyl-3-(tetradecylcarbamoyl)piperazin-1-yl)ethyl)benzoate

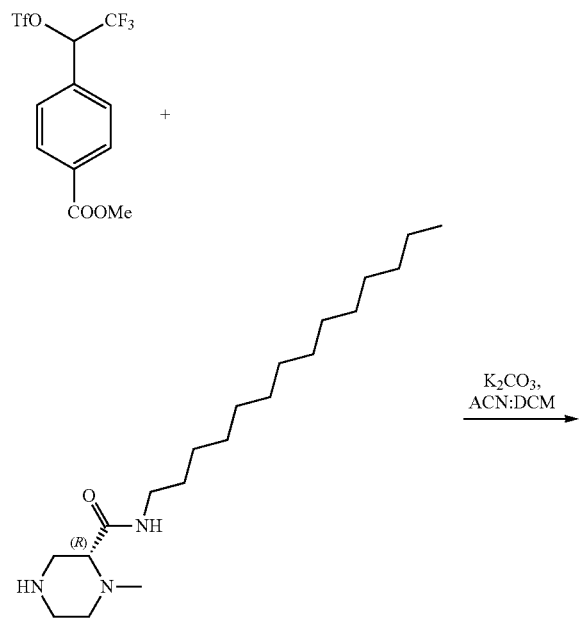

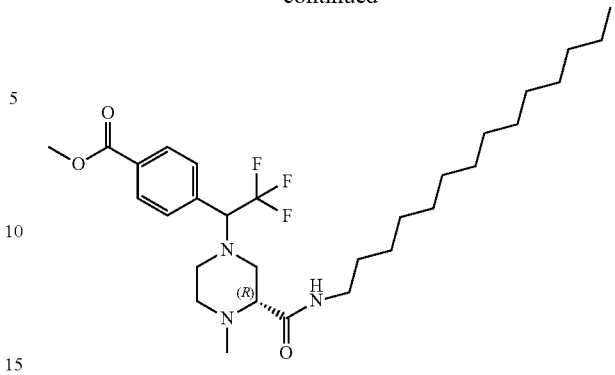

Methyl 4-(2,2,2-trifluoro-1-(((trifluoromethyl)sulfonyl)oxy)ethyl)benzoate (0.250 g, 0.682 mmol), (R)-1-methyl-N-tetradecylpiperazine-2-carboxamide (0.278 g, 0.819 mmol) and K$_2$CO$_3$ (0.140 g, 1.023 mmol) were dissolved in acetonitrile (20 mL). DCM (20 mL) was added and the reaction mixture was stirred for 48 hrs. The solvent was removed under reduced pressure and the crude product was purified using flash chromatography, eluting with 50% ethyl acetate in DCM, to give methyl 4-(2,2,2-trifluoro-1-((R)-4-methyl-3-(tetradecylcarbamoyl)piperazin-1-yl)ethyl)benzoate (0.22 g, 48%) as a mixture of diastereomers. LCMS (Method-J): 87.12% (RT: 6.108, 202.0 nm) (MS: ESI +ve 556.2[M+1]).

Step-4: Preparation of 4-(2,2,2-trifluoro-1-((R)-4-methyl-3-(tetradecylcarbamoyl)piperazin-1-yl)ethyl) benzoic acid

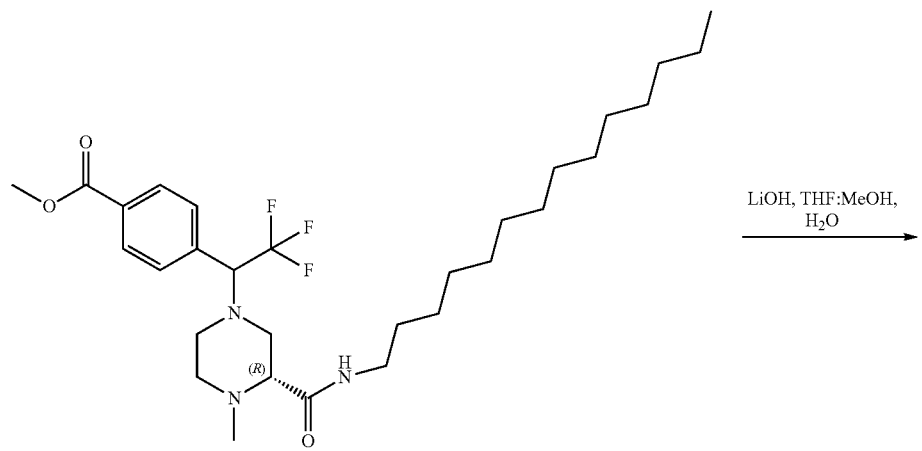

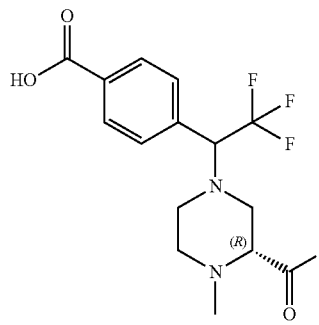
Prepared using the General Ester Hydrolysis Procedure to give 4-(2,2,2-trifluoro-1-((R)-4-methyl-3-(tetradecylcarbamoyl)piperazin-1-yl)ethyl)benzoic acid (0.150 g, 69%). LCMS (Method-C2): 88% (RT: 1.449, 230.0 nm) (MS: ESI +ve 542.6[M+1]).
Step-5: Preparation of (3S,4S)—N3,N4-bis((1S,2R)-2-phenylcyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide, Compound 132
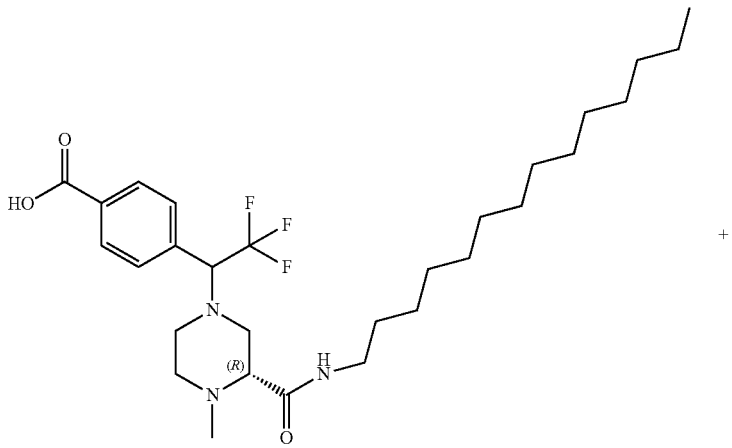
+
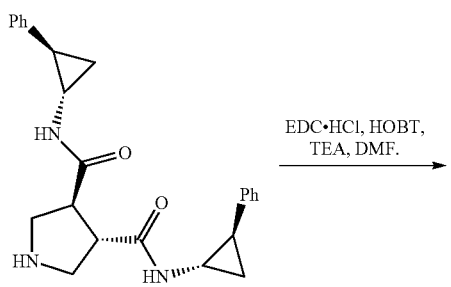
EDC·HCl, HOBT, TEA, DMF.

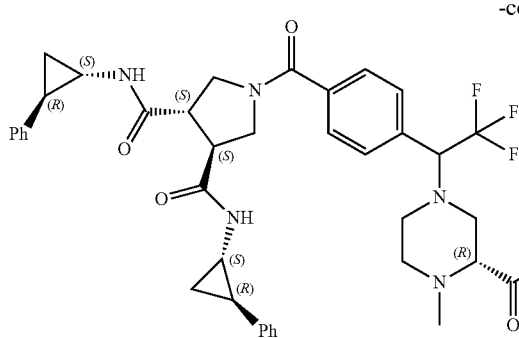

Prepared using General EDC, HOBT Coupling Procedure. The crude product was purified using Prep HPLC Method 1 to give (3S,4S)—N3,N4-bis((1S,2R)-2-phenylcyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide (Compound 132) (0.025 g, 10%), as an off white solid (mixture of diastereomers). LCMS (Method-J): 100% (RT 6.235, 202.0 nm) (MS: ESI +ve 913.6 [M+H]). $^1$H NMR: (400 MHz, DMSO) δ ppm: 0.84 (s, 3H), 1.10-1.12 (m, 2H), 1.23 (m, 26H), 1.33 (m, 2H), 1.87 (s, 1H), 1.97 (s, 1H), 2.08 (m, 3H), 2.10-2.15 (m, 2H), 2.29-2.32 (m, 1H), 2.67-2.85 (m, 4H), 2.95-2.99 (m, 2H), 3.09-3.10 (m, 1H), 3.19-3.21 (m, 1H), 3.50-3.55 (m, 1H), 3.64 (m, 1H), 3.75-3.80 (m, 1H), 4.72-4.74 (m, 1H), 7.06-7.08 (m, 2H), 7.11-7.18 (m, 4H), 7.22-7.26 (m, 4H), 7.43-7.44 (m, 2H), 7.57-7.59 (m, 2H), 8.38 (s, 1H), 8.48 (s, 2H).

Synthesis of (3S,4S)—N3,N4-bis((1S,2R)-2-phenylcyclopropyl)-1-(4-(2,2,2-trifluoro-1-(((S)-2-heptanamido-3-(hexylamino)-3-oxopropyl)amino)ethyl)benzoyl)pyrrolidine-3,4-dicarboxamide, Compound 148 and Compound 149

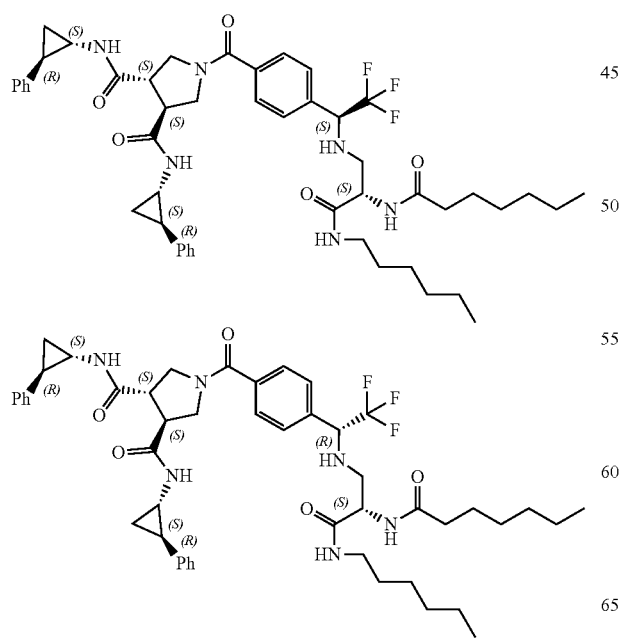

(3S,4S)—N3,N4-bis((1S,2R)-2-phenylcyclopropyl)-1-(4-(2,2,2-trifluoro-1-(((S)-2-heptanamido-3-(hexylamino)-3-oxopropyl)amino)ethyl)benzoyl)pyrrolidine-3,4-dicarboxamide was prepared as a 1:1 mixture of diastereomers by a procedure similar to that reported for (3S,4S)—N3,N4-bis((1S,2R)-2-phenylcyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide (Compound 132) substituting the applicable amine in step 3. The mixture was separated using Prep HPLC Method 13 to give;

Fraction 1; (3S,4S)—N3,N4-bis((1S,2R)-2-phenylcyclopropyl)-1-(4-((S)-2,2,2-trifluoro-1-(((S)-2-heptanamido-3-(hexylamino)-3-oxopropyl)amino)ethyl)benzoyl)pyrrolidine-3,4-dicarboxamide (Compound 148) (0.016 g, 10%) [absolute stereochemistry was arbitrarily assigned]. LCMS (Method-J): 100% (RT 5.769, 202.0 nm) (MS: ESI +ve 873.5 [M+H]). $^1$H NMR: (400 MHz, DMSO) δ ppm: 0.82-0.85 (m, 6H), 1.12 (m, 2H), 1.21-1.23 (m, 14H), 1.35-1.43 (m, 4H), 1.89 (s, 1H), 1.98 (s, 1H), 2.04-2.08 (m, 2H), 2.68-2.75 (m, 2H), 2.79 (s, 1H), 2.85 (s, 2H), 3.02-3.05 (m, 2H), 3.10-3.12 (m, 1H), 3.19-3.21 (m, 1H), 3.53 (s, 2H), 3.65-3.67 (m, 1H), 3.77-3.80 (m, 1H), 4.31-4.33 (m, 1H), 4.50-4.54 (m, 1H), 7.06-7.09 (m, 2H), 7.13-7.19 (m, 4H), 7.23-7.29 (m, 4H), 7.49-7.56 (m, 4H), 7.79-7.85 (m, 2H), 8.31 (s, 1H), 8.43 (s, 1H), 8.53 (s, 1H)

Fraction 2; (3S,4S)—N3,N4-bis((1S,2R)-2-phenylcyclopropyl)-1-(4-((R)-2,2,2-trifluoro-1-(((S)-2-heptanamido-3-(hexylamino)-3-oxopropyl)amino)ethyl)benzoyl)pyrrolidine-3,4-dicarboxamide (Compound 149)(0.019 g, 12%) [absolute stereochemistry was arbitrarily assigned]. LCMS (Method-J): 98.30% (RT 5.751, 202.0 nm) (MS: ESI +ve 873.4 [M+H]). $^1$H NMR: (400 MHz, DMSO) δ ppm: 0.83-0.86 (m, 6H), 1.10-1.12 (m, 2H), 1.22 (m, 14H), 1.35 (s, 2H), 1.36 (s, 2H), 1.88 (s, 1H), 1.98 (s, 1H), 2.09-2.13 (m, 2H), 2.62-2.68 (m, 2H), 2.78 (s, 1H), 2.85-2.86 (m, 2H), 3.00-3.03 (m, 2H), 3.10-3.14 (m, 1H), 3.18-3.24 (m, 1H), 3.51-3.56 (m, 2H), 3.65-3.67 (m, 1H), 3.77-3.79 (m, 1H), 4.33-4.34 (m, 1H), 4.49-4.53 (m, 1H), 7.07-7.09 (m, 2H), 7.12-7.19 (m, 4H), 7.23-7.29 (m, 4H), 7.51-7.58 (m, 4H), 7.83-7.92 (m, 2H), 8.33-8.34 (s, 1H), 8.45-8.46 (m, 1H).

Synthesis of (3S,4S)—N3,N4-bis((1S,2R)-2-phenyl-cyclopropyl)-1-(4-(2,2,2-trifluoro-1-((R)-4-heptanoyl-3-(hexylcarbamoyl)piperazin-1-yl)ethyl)benzoyl)pyrrolidine-3,4-dicarboxamide, Compound 158

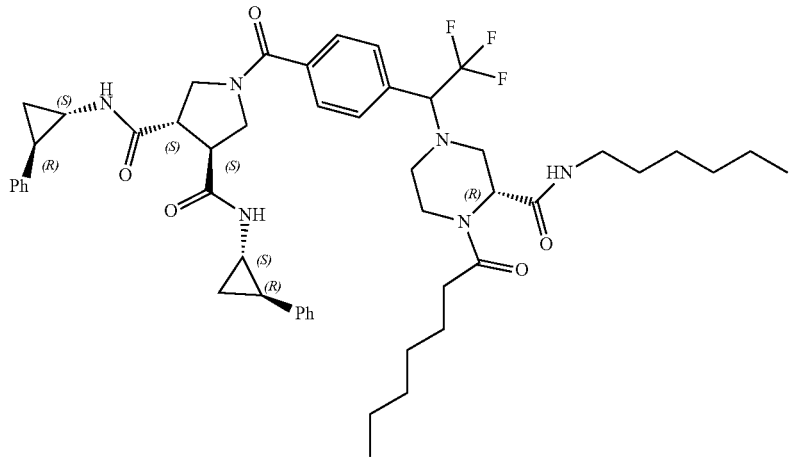

Prepare as a 1:1 mixture of diastereomers by a procedure similar to that reported for (3S,4S)—N3,N4-bis((1S,2R)-2-phenylcyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide (Compound 132), substituting the applicable amine in step 3. The final product was purified using Prep HPLC Method 10 to give (3S,4S)—N3,N4-bis((1S,2R)-2-phenylcyclopropyl)-1-(4-(2,2,2-trifluoro-1-((R)-4-heptanoyl-3-(hexylcarbamoyl)piperazin-1-yl)ethyl)benzoyl)pyrrolidine-3,4-dicarboxamide (Compound 158)(0.125 g, 48%), as an off white solid. LCMS (Method-J): 98.35% (RT 5.903, 254.0 nm) (MS: ESI +ve 899.5 [M+H]). $^1$H NMR: (400 MHz, DMSO) δ ppm: 0.83-0.85 (m, 6H), 1.09-1.23 (m, 17H), 1.40 (bs, 5H), 1.86 (s, 1H), 1.97 (s, 1H), 2.25-2.33 (m, 2H), 2.78-2.94 (m, 4H), 3.06-3.10 (m, 3H), 3.17-3.19 (m, 1H), 3.44-3.52 (m, 4H), 3.66 (m, 2H), 3.77-3.82 (m, 1H), 4.31-4.36 (m, 1H), 4.66-4.77 (m, 2H), 3.77-3.80 (m, 1H), 7.06-7.07 (m, 2H), 7.11-7.18 (m, 4H), 7.22-7.28 (m, 4H), 7.42-7.44 (m, 2H), 7.54-7.59 (m, 2H), 7.63 (s, 1H), 8.32 (s, 1H), 8.44 (s, 1H).

Synthesis of (3S,4S)—N3,N4-bis((1S,2R)-2-phenyl-cyclopropyl)-1-(4-(2,2,2-trifluoro-1-((3S,4S)-3-methoxy-4-(3-tridecylureido)pyrrolidin-1-yl)ethyl)benzoyl)pyrrolidine-3,4-dicarboxamide, Compound 189

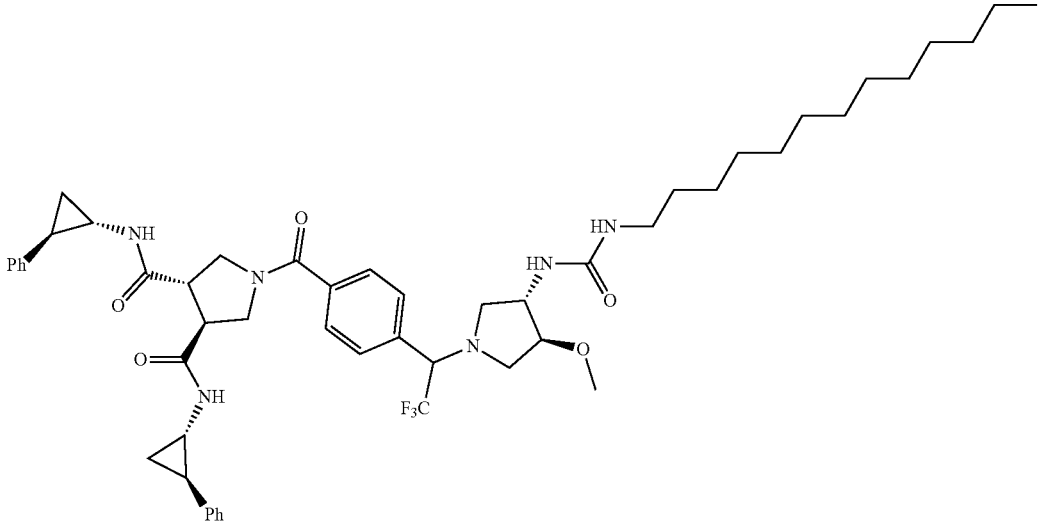 [SMILES: CCCCCCCCCCCCCNC(=O)N[C@H]1CN(C(c2ccc(C(=O)N3C[C@@H](C(=O)N[C@H]4C[C@@H]4c4ccccc4)[C@H](C(=O)N[C@H]4C[C@@H]4c4ccccc4)C3)cc2)C(F)(F)F)C[C@@H]1OC]

Prepared as a 1:1 mixture of diastereomers by a procedure similar to that reported for (3S,4S)—N3,N4-bis((1S,2R)-2-phenylcyclopropyl)-1-(4-(2,2,2-trifluoro-1-((R)-4-methyl-3-(tetradecylcarbamoyl)piperazin-1-yl)ethyl)benzoyl)pyrrolidine-3,4-dicarboxamide (Compound 132), substituting the applicable amine in step 3. The final product was purified using Prep HPLC Method 7 to give (3S,4S)—N3,N4-bis((1S,2R)-2-phenylcyclopropyl)-1-(4-(2,2,2-trifluoro-1-((3S,4S)-3-methoxy-4-(3-tridecylureido)pyrrolidin-1-yl)ethyl)benzoyl)pyrrolidine-3,4-dicarboxamide (Compound 189) (0.135 g, 26%). LCMS (Method-J): 100% (RT 4.873, 202.0 nm) (MS: ESI +ve 916.2 [M+H]). ¹H NMR: (400 MHz, DMSO) δ ppm: 0.83-0.87 (m, 3H), 1.08-1.32 (m, 24H), 1.86 (s, 1H), 1.97 (s, 1H), 2.27 (bs, 1H), 2.78-2.84 (m, 4H), 2.93-2.94 (m, 3H), 3.08-3.12 (m, 1H), 3.18-3.20 (m, 4H), 3.50-3.55 (m, 3H), 3.64-3.66 (m, 1H), 3.76-3.85 (m, 2H), 4.42-4.46 (m, 1H), 7.06-7.08 (m, 2H), 7.11-7.18 (m, 4H), 7.22-7.28 (m, 4H), 7.48-7.50 (m, 2H), 7.57-7.59 (m, 2H), 8.30-7.8.31 (m, 1H), 8.42-8.43 (m, 1H).

Synthesis of (3S,4S)—N3,N4-bis((1S,2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl)pyrrolidine-3,4-dicarboxamide, Compound 230

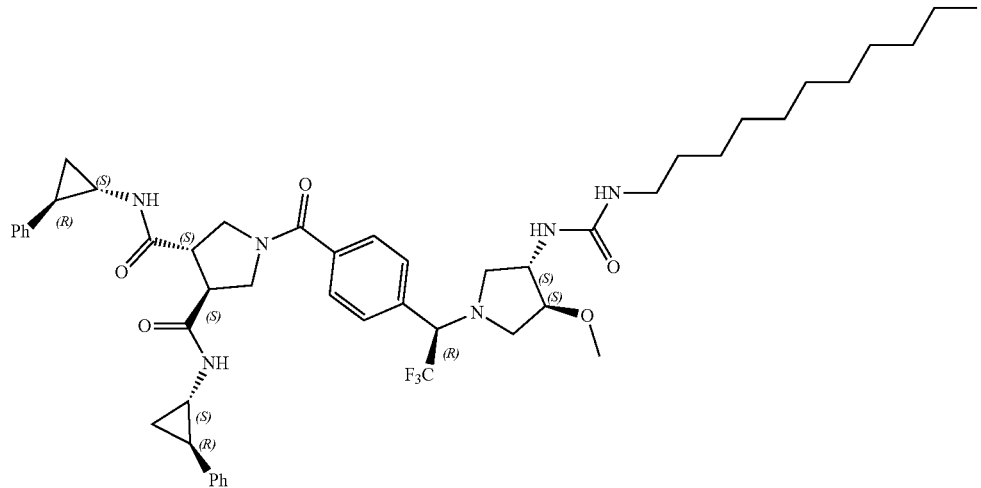

Step-1: Preparation of tert-butyl (3S,4S)-3-methoxy-4-(3-undecylureido)pyrrolidine-1-carboxylate

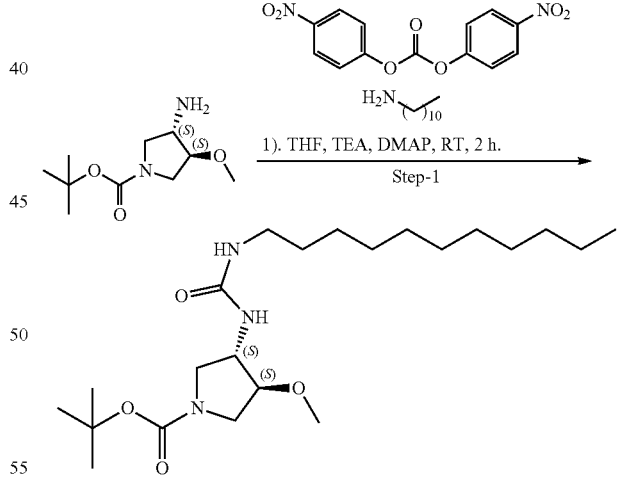

Bis(4-nitrophenyl) carbonate (1.4 g, 4.620 mmol), TEA (1.78 g, 13.8 mmol) and DMAP (0.056 g, 0.462 mmol) were dissolved in THF (10.0 mL) and cooled to 0° C. Undecan-1-amine (0.792 g, 4.62 mmol) in THF (5 mL) was added dropwise to the reaction mixture over a period of 30 min. The reaction mixture was stirred for 4 h, then tert-butyl (3S,4S)-3-amino-4-methoxypyrrolidine-1-carboxylate (1.0 g, 4.62 mmol) in THF (5 ml) was added and the mixture was stirred at room temperature for 16 h. The mixture was diluted with EtOAc (200 mL), washed with 1N aq. sodium hydroxide (5×100 mL) and brine (2×100 mL). The organic layer was dried over sodium sulfate and concentrated. The crude product was purified by flash chromatography, eluting with 0-2% MeOH:DCM, to give tert-butyl (3S,4S)-3-methoxy-4-(3-undecylureido) pyrrolidine-1-carboxylate (1.7 g, 89%), as a semisolid material. LCMS (Method-C2): 81.99% (RT 1.604, 202.0 nm) (MS: ESI +ve 414.5[(M+H]).

Step-2: Preparation of 1-((3S,4S)-4-methoxypyrrolidin-3-yl)-3-undecylurea

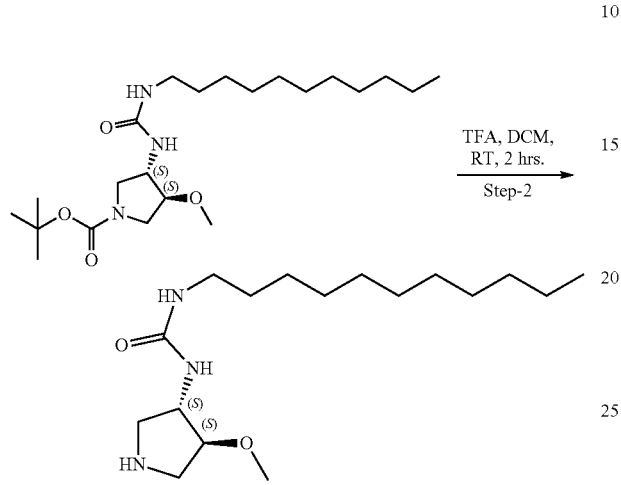

Prepared using General BOC Deprotection Procedure to give 1-((3S,4S)-4-methoxypyrrolidin-3-yl)-3-undecylurea (0.7 g, 54%) as a semisolid material. LCMS (Method-H): 95.96% (RT: 3.364, 202.0 nm) (MS: ESI +ve 314.2[M+H]).

Step-3: Preparation of methyl 4-((R*)-2,2,2-trifluoro-1-((3S,4S)-3-methoxy-4-(3-undecylureido) pyrrolidin-1-yl)ethyl)benzoate (Fraction-1) and methyl 4-((S*)-2,2,2-trifluoro-1-((3S,4S)-3-methoxy-4-(3-undecylureido)pyrrolidin-1-yl)ethyl) benzoate (Fraction-2)

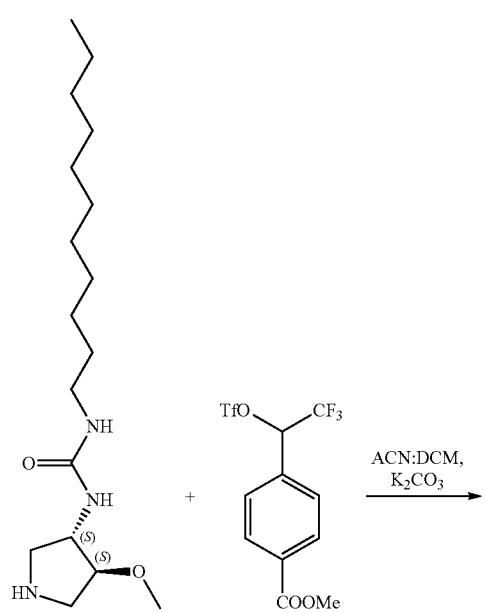

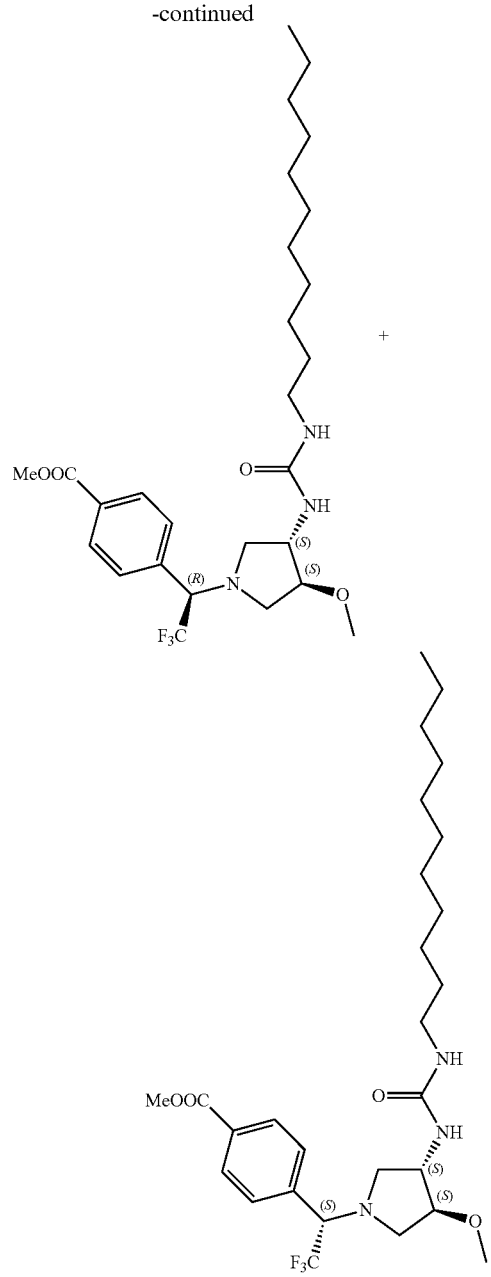

Methyl 4-(2,2,2-trifluoro-1-(((trifluoromethyl)sulfonyl) oxy)ethyl)benzoate (0.8 g, 2.18 mmol), 1-((3S,4S)-4-methoxypyrrolidin-3-yl)-3-undecylurea (0.821 g, 2.62 mmol) and K$_2$CO$_3$ (0.64 g, 4.36 mmol) were dissolved in acetonitrile (20 mL). DCM (20 mL) was added, and the reaction mixture was stirred for 48 hrs. The volatiles were removed and the resulting crude product was purified by flash chromatography, eluting with 50% EtOAc:DCM, to give a mixture of two isomers (0.86 g, 74%). LCMS (Method-J) Racemic: 94.39% (RT: 4.998, 202.0 nm) (MS: ESI +ve 530.2[M+H]). Chiral SFC of mixture: 49.64%, RT=8.22 and 50.35, RT=9.67, 230.0 nm). The mixture was separated on a Shimadzu LC-20AP chromatography system with UV detector. The column used was CHIRALPAK IC (250*21.0) mm, 5 micron, column flow was 20.0 ml/min. Mobile phase (A) 0.1% DEA in n-Hexane (B) 0.1% DEA in Propane-2-ol to give;

Fraction 1; (0.270 g) methyl 4-((R*)-2,2,2-trifluoro-1-((3S,4S)-3-methoxy-4-(3-undecylureido)pyrrolidin-1-yl)ethyl)benzoate (Fraction-1) Chiral SFC of Fraction-1: 100% (RT 12.63, 230.0 nm) absolute stereochemistry is arbitrarily assigned.

Fraction 2; 0.3 g of methyl 4-((S*)-2,2,2-trifluoro-1-((3S,4S)-3-methoxy-4-(3-undecylureido)pyrrolidin-1-yl)ethyl)benzoate (Fraction-2), Chiral SFC of Fraction-2: 100% (RT 16.47, 230.0 nm). absolute stereochemistry is arbitrarily assigned.

Step-4: Preparation of 4-((R*)-2,2,2-trifluoro-1-((3S,4S)-3-methoxy-4-(3-undecylureido)pyrrolidin-1-yl)ethyl)benzoic acid

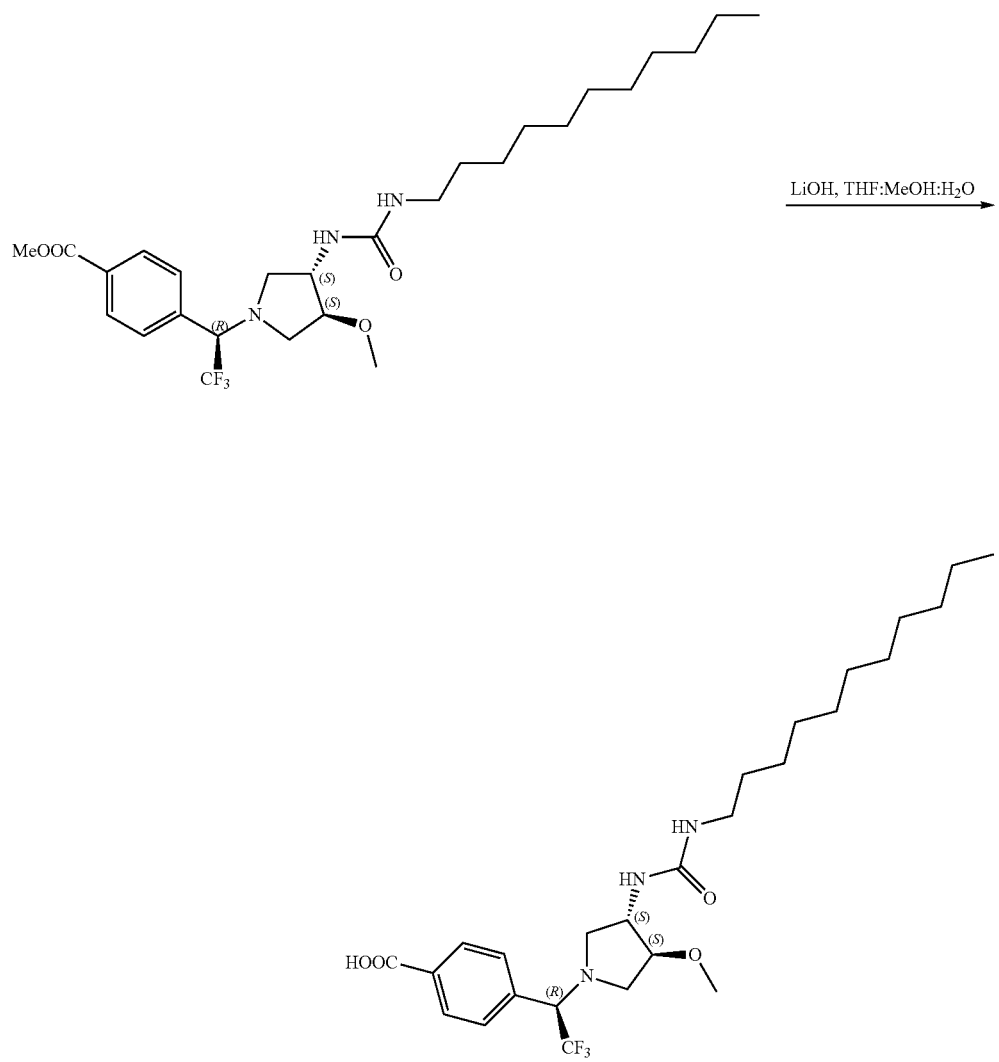

Prepared using General Ester Hydrolysis Procedure to give 4-((R*)-2,2,2-trifluoro-1-((3S,4S)-3-methoxy-4-(3-undecylureido)pyrrolidin-1-yl)ethyl)benzoic acid, as a white solid (0.2 g, 76%). LCMS (Method-C2): 100% (RT: 1.535, 230.0 nm) (MS: ESI +ve 516.5[M+1]).

Step-5: Preparation of (3S,4S)—N3,N4-bis((1S, 2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl) pyrrolidine-3,4-dicarboxamide, Compound 230

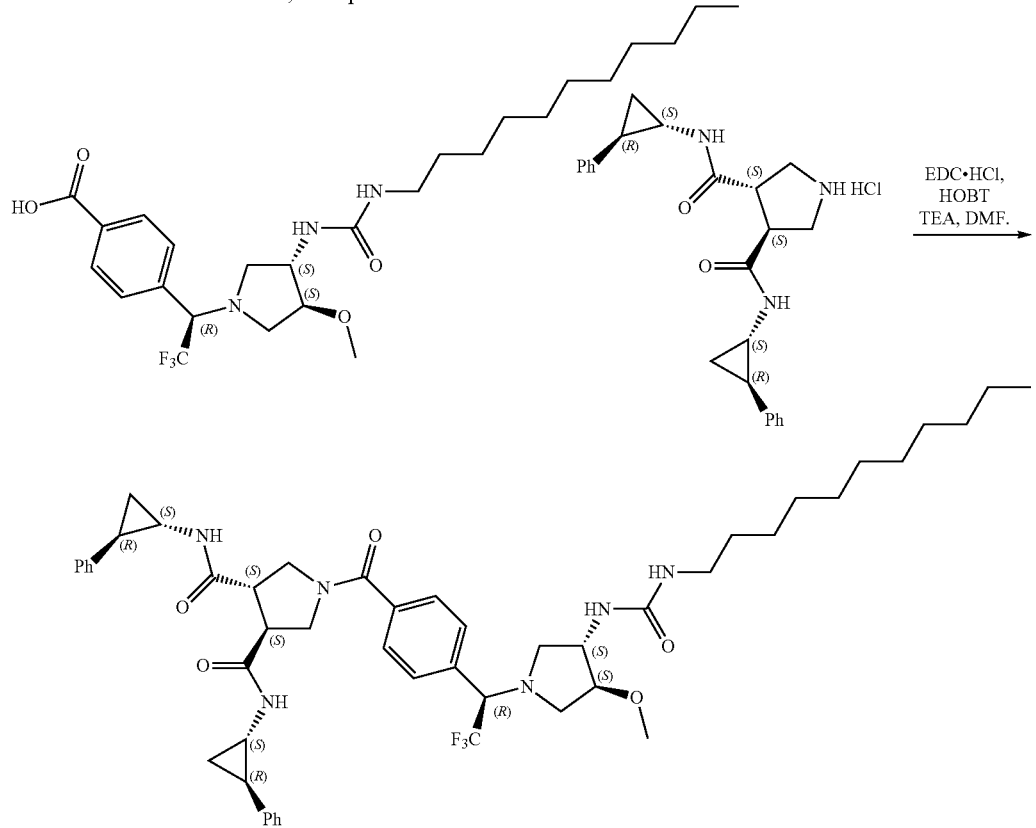

Prepared using General EDC, HOBT Coupling Procedure. The final product was purified using Prep HPLC Method 10 to give (3S,4S)—N3,N4-bis((1S,2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl) pyrrolidine-3,4-dicarboxamide (Compound 230) (0.035 g, 7%), as an off white solid; [stereochemistry arbitrarily assigned 4(R*)]. LCMS (Method-J): 100% (RT 5.042, 202.0 nm) (MS: ESI +ve 887.5 [M+H]). $^1$H NMR: (400 MHz, DMSO) δ ppm: 0.83-0.86 (m, 3H), 1.08-1.23 (m, 21H), 1.28-1.31 (m, 2H), 1.85-1.86 (m, 1H), 1.96-1.99 (m, 1H), 2.33-2.39 (m, 2H), 2.78-2.86 (m, 4H), 2.92-2.94 (m, 2H), 3.08-3.12 (m, 1H), 3.18-3.22 (m, 4H), 3.50-3.55 (m, 3H), 3.64-3.69 (m, 1H), 3.76-3.86 (m, 2H), 4.42-4.44 (m, 1H), 5.85-5.88 (m, 1H), 6.05-6.06 (m, 1H), 7.06-7.08 (m, 2H), 7.11-7.18 (m, 4H), 7.22-7.28 (m, 4H), 7.48-7.50 (m, 2H), 7.57-7.59 (m, 2H), 7.32-7.33 (m, 1H), 8.44-8.45 (m, 1H).

Synthesis of (3S,4S)—N3,N4-bis((1S,2R)-2-phenylcyclopropyl)-1-(4-((S*)-2,2,2-trifluoro-1-((3S,4S)-3-methoxy-4-(3-undecylureido)pyrrolidin-1-yl)ethyl)benzoyl)pyrrolidine-3,4-dicarboxamide, Compound 231

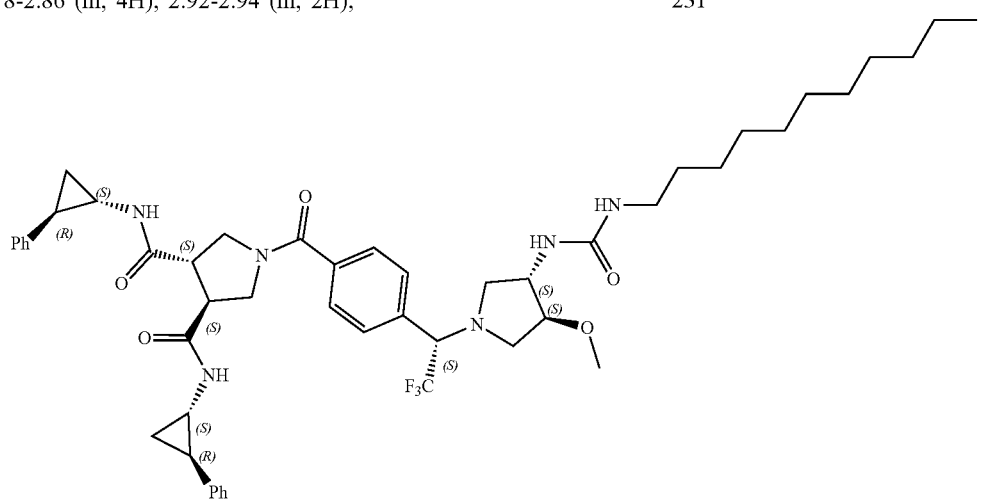

Prepared by a procedure similar to that reported for (3S,4S)—N3,N4-bis((1S,2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl)pyrrolidine-3,4-dicarboxamide (Compound 230), using Fraction 2 from step 3, methyl 4-((S)-2,2,2-trifluoro-1-((3S,4S)-3-methoxy-4-(3-undecylureido)pyrrolidin-1-yl)ethyl)benzoate (Fraction-2). The final product was purified using Prep HPLC Method 1 to give (3S,4S)—N3,N4-bis((1S,2R)-2-phenylcyclopropyl)-1-(4-((S*)-2,2,2-trifluoro-1-((3S,4S)-3-methoxy-4-(3-undecylureido)pyrrolidin-1-yl)ethyl)benzoyl)pyrrolidine-3,4-dicarboxamide (Compound 231)(0.035 g, 7%). LCMS (Method-J): 98.74% (RT 5.035, 202.0 nm) (MS: ESI +ve 887.6 [M+H]). ¹H NMR: (400 MHz, DMSO) δ ppm: 0.83-0.87 (m, 3H), 1.08-1.23 (m, 21H), 1.30-1.32 (m, 2H), 1.86 (s, 1H), 1.97-1.99 (m, 1H), 2.25-2.29 (m, 1H), 2.77-2.85 (m, 3H), 2.91-3.00 (m, 3H), 3.06-3.16 (m, 1H), 3.20 (m, 4H), 3.51-3.55 (m, 3H), 3.64-3.69 (m, 1H), 3.69-3.83 (m, 2H), 4.44-4.46 (m, 1H), 5.86-5.87 (m, 1H), 6.00-6.02 (m, 1H), 7.06-7.08 (m, 2H), 7.11-7.18 (m, 4H), 7.22-7.28 (m, 4H), 7.48-7.50 (m, 2H), 7.57-7.59 (m, 2H), 7.31-7.32 (m, 1H), 8.44-8.44 (m, 1H).

Synthesis of (3S,4S)-1-(4-((R*)-1-((3S,4S)-3-(3-dodecylureido)-4-methoxypyrrolidin-1-yl)-2,2,2-trifluoroethyl)benzoyl)-N3,N4-bis((1S,2R)-2-phenylcyclopropyl)pyrrolidine-3,4-dicarboxamide, Compound 232

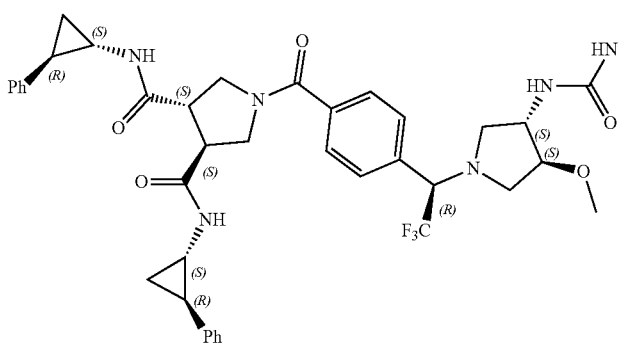

Prepared by a procedure similar to that reported for (3S,4S)—N3,N4-bis((S,2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl)pyrrolidine-3,4-dicarboxamide (Compound 230), using the applicable starting materials and Fraction 1 from step 3. The final product was purified using Prep HPLC Method 13 to give (3S,4S)-1-(4-((R)-1-((3S,4S)-3-(3-dodecylureido)-4-methoxypyrrolidin-1-yl)-2,2,2-trifluoroethyl)benzoyl)-N3,N4-bis((1S,2R)-2-phenylcyclopropyl)pyrrolidine-3,4-dicarboxamide (Compound 232) (0.016 g, 5%); [stereochemistry arbitrarily assigned 4(R*)]. LCMS (Method-J): 100% (RT 4.752, 225.0 nm) (MS: ESI +ve 902.6 [M+H]). ¹H NMR: (400 MHz, DMSO) δ ppm: 0.83-0.87 (m, 3H), 1.08-1.12 (m, 2H), 1.23-1.32 (m, 20H), 1.86 (s, 1H), 1.97 (s, 1H), 2.78-2.85 (m, 4H), 2.91-2.94 (m, 2H), 3.09-3.13 (m, 1H), 3.19 (m, 4H), 3.51-3.55 (m, 3H), 3.65-3.69 (m, 1H), 3.77-3.87 (m, 2H), 4.42-4.44 (m, 1H), 5.82-5.85 (m, 1H), 6.01-6.03 (m, 1H), 7.06-7.08 (m, 2H), 7.11-7.18 (m, 4H), 7.22-7.29 (m, 4H), 7.48-7.50 (m, 2H), 7.57-7.59 (m, 2H), 7.30-7.31 (m, 1H), 8.42-8.43 (m, 1H).

Synthesis of (3S,4S)-1-(4-((S*)-1-((3S,4S)-3-(3-dodecylureido)-4-methoxypyrrolidin-1-yl)-2,2,2-trifluoroethyl)benzoyl)-N3,N4-bis((1S,2R)-2-phenylcyclopropyl)pyrrolidine-3,4-dicarboxamide, Compound 233

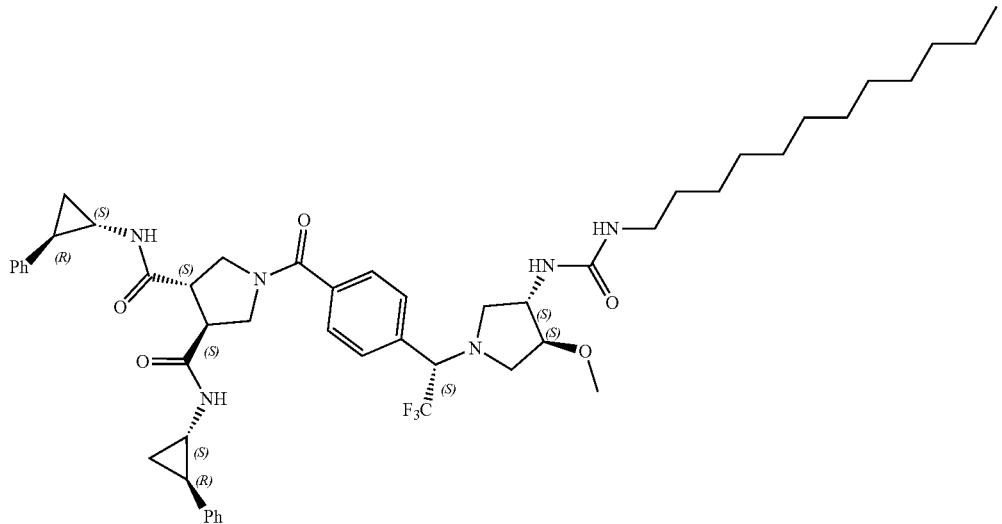

Prepared by a procedure similar to that reported for (3S,4S)—N3,N4-bis((1S,2R)-2-phenylcyclopropyl)-1-(4-((R*)-2,2,2-trifluoro-1-((3S,4S)-3-methoxy-4-(3-undecylureido)pyrrolidin-1-yl)ethyl)benzoyl)pyrrolidine-3,4-dicarboxamide (Compound 230), using the applicable starting materials and Fraction 2 from step 3. The final product was purified using Prep HPLC Method 13 to give (3S,4S)-1-(4-((S)-1-((3S,4S)-3-(3-dodecylureido)-4-methoxypyrrolidin-1-yl)-2,2,2-trifluoroethyl) benzoyl)-N3,N4-bis((1S,2R)-2-phenylcyclopropyl)pyrrolidine-3,4-dicarboxamide (Compound 233) (0.035 g, 7%); [stereochemistry arbitrarily assigned 4 (S*)]. LCMS (Method-J): 100% (RT 4.711, 214.0 nm) (MS: ESI +ve 901.7 [M+H]). $^1$H NMR: (400 MHz, DMSO) δ ppm: 0.83-0.87 (m, 3H), 1.09-1.12 (m, 2H), 1.17-1.32 (m, 20H), 1.86 (s, 1H), 1.97-1.99 (m, 1H), 2.25-2.27 (m, 1H), 2.67-2.85 (m, 3H), 2.93-3.00 (m, 3H), 3.08-3.12 (m, 1H), 3.25 (m, 4H), 3.51-3.55 (m, 3H), 3.64-3.76 (m, 1H), 3.79-3.86 (m, 2H), 4.44-4.46 (m, 1H), 5.87-5.88 (m, 1H), 6.01-6.03 (m, 1H), 7.06-7.08 (m, 2H), 7.11-7.18 (m, 4H), 7.22-7.28 (m, 4H), 7.48-7.50 (m, 2H), 7.56-7.58 (m, 2H), 7.32-7.33 (m, 1H), 8.44-8.45 (m, 1H).

Synthesis of (3S,4S)-1-(4-(3-((S)-2-decanamido-3-(hexylamino)-3-oxopropyl)ureido) benzoyl)-N3,N4-bis((1S,2R)-2-phenylcyclopropyl)pyrrolidine-3,4-dicarboxamide, Compound 235

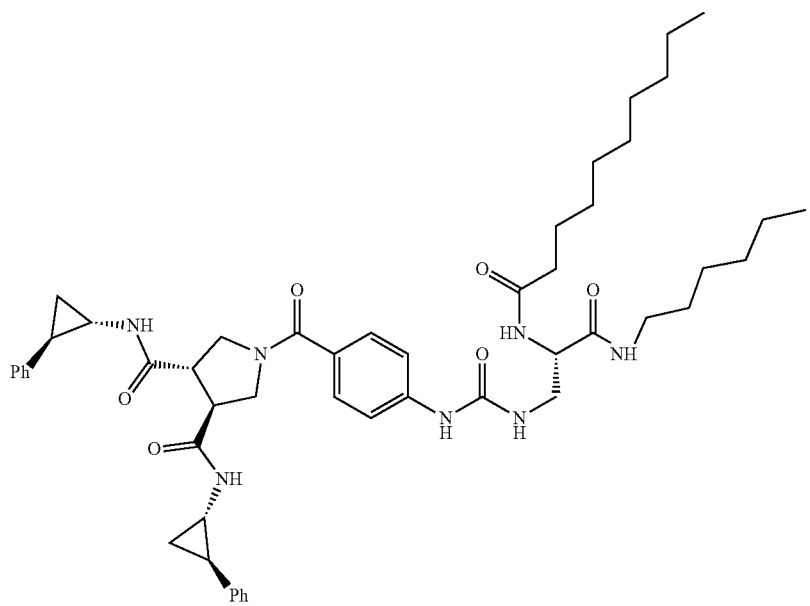 [SMILES: CCCCCCCCCC(=O)N[C@@H](CNC(=O)Nc1ccc(C(=O)N2C[C@@H](C(=O)N[C@H]3C[C@@H]3c3ccccc3)[C@H](C(=O)N[C@H]3C[C@@H]3c3ccccc3)C2)cc1)C(=O)NCCCCCC]

Step 1: Preparation of benzyl tert-butyl (3-(hexylamino)-3-oxopropane-1,2-diyl)(S)-dicarbamate

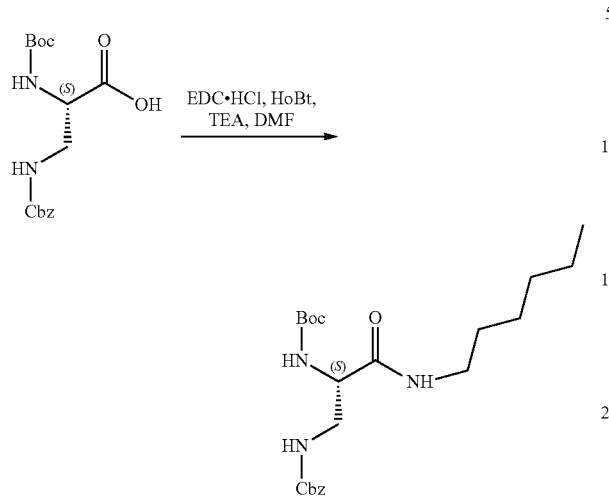

Prepared using General EDC, HOBT Coupling Procedure to give benzyl tert-butyl (3-(hexylamino)-3-oxopropane-1,2-diyl)(S)-dicarbamate, as a white solid (10.1 g, 90.08%). LCMS (Method-H): 79.23% (RT: 3.499, 202.00 nm) (MS: ESI +ve 366.2[M−56]).

Step 2: Preparation of benzyl (S)-(2-amino-3-(hexylamino)-3-oxopropyl)carbamate

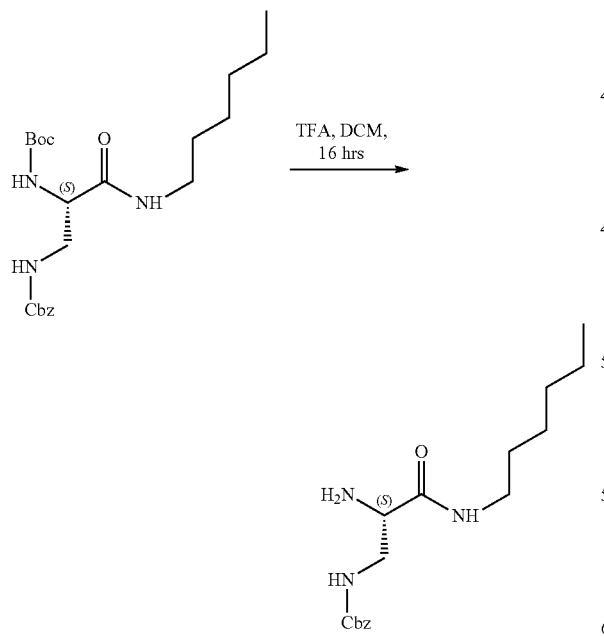

Prepared using General BOC Deprotection Procedure to give benzyl (S)-(2-amino-3-(hexylamino)-3-oxopropyl)carbamate (3.0 g, 78.69%) as a solid material. LCMS (Method-H): 89.75% (RT: 2.887, 202.0 nm) (MS: ESI +ve 322.2[M+H]).

Step 3: Preparation of benzyl (S)-(2-decanamido-3-(hexylamino)-3-oxopropyl)carbamate

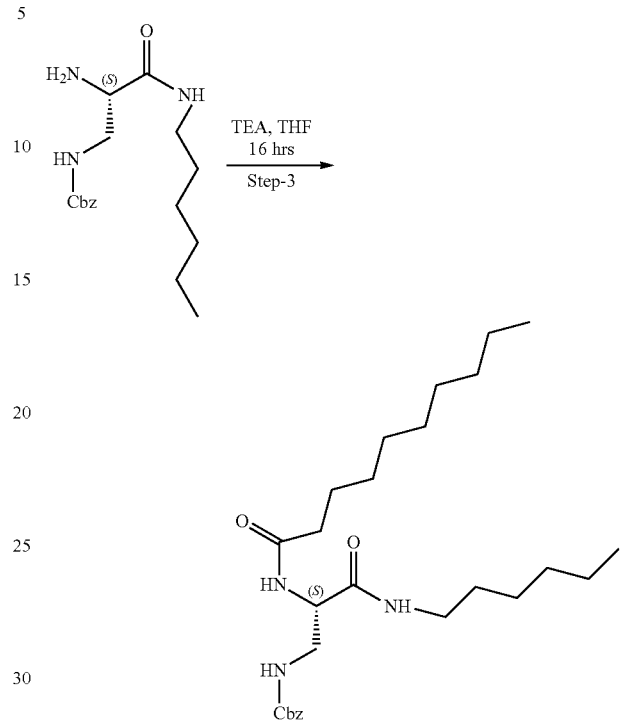

Benzyl (S)-(2-amino-3-(hexylamino)-3-oxopropyl)carbamate (0.25 g, 1.573 mmol) was dissolved in THF (10 mL) and cooled to 0° C. TEA (0.7 mL) was added followed by decanoyl chloride (0.25 g, 1.317 mmol). The reaction mixture was stirred for 16 hrs. The mixture was diluted with water (20 mL) and extracted with ethyl acetate (2×500 mL). The organic layer was dried over sodium sulfate and concentrated under reduced pressure to give benzyl (S)-(2-decanamido-3-(hexylamino)-3-oxopropyl)carbamate (0.36 g, 97.30%). LCMS (Method-C-FAST): 89.81% (RT: 2.131, 202.0 nm) (MS: ESI +ve 476.78[M+H]).

Step 4: Preparation of (S)—N-(3-amino-1-(hexylamino)-1-oxopropan-2-yl)decanamide

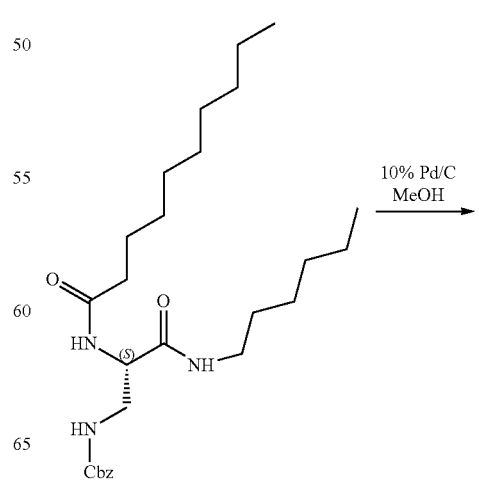

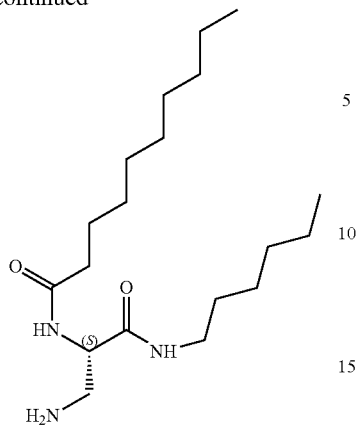

A mixture of benzyl (S)-(2-decanamido-3-(hexylamino)-3-oxopropyl)carbamate. ((0.360 g, 0.757 mmol) and palladium on carbon (0.360 g) in MeOH (20 mL) was stirred under a hydrogen gas filled balloon for 16 hours. The mixture filtered through celite and the filtrate was concentrated under reduced pressure to give (S)—N-(3-amino-1-(hexylamino)-1-oxopropan-2-yl)decanamide, as a brown solid (0.26 g, 100%). LCMS (Method-C-Fast): 91.78% (RT: 0.905, 202.00 nm) (MS: ESI +ve 342.6[M+1]).

Step 5: Preparation of methyl (S)-4-(3-(2-decanamido-3-(hexylamino)-3-oxopropyl) ureido)benzoate (S)—N-(3-amino-1-(hexylamino)-1-oxopropan-2-yl)decanamide (0.25 g, 0.7042 mmol) was dissolved in THF (10 mL) and cooled to 0° C. TEA (0.5 mL) was added followed by methyl 4-((phenoxycarbonyl)amino)benzoate (0.15 g, 0.7042 mmol) the reaction mixture was stirred for 16 hrs. The mixture was diluted water (20 mL) and extracted with ethyl acetate (2×50 mL). The organic layer was dried over sodium sulfate and concentrated under reduced pressure. The resulting solid was purified by flash chromatography, eluting with 1-3% MeOH in DCM, to give methyl (S)-4-(3-(2-decanamido-3-(hexylamino)-3-oxopropyl)ureido)benzoate. (0.15 g, 39.51%) as a white solid. LCMS (Method-C2): 100% (RT: 1.435, 202.0 nm) (MS: ESI +ve 519.53[M+H]).

Step 6: preparation of (S)-4-(3-(2-decanamido-3-(hexylamino)-3-oxopropyl)ureido) benzoic acid

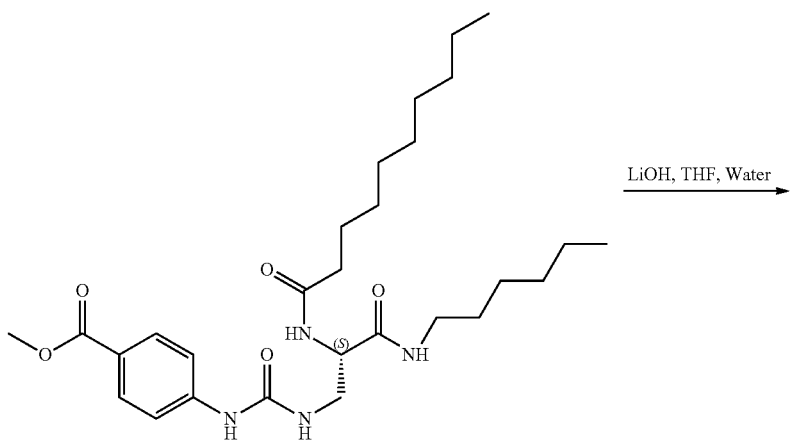

-continued
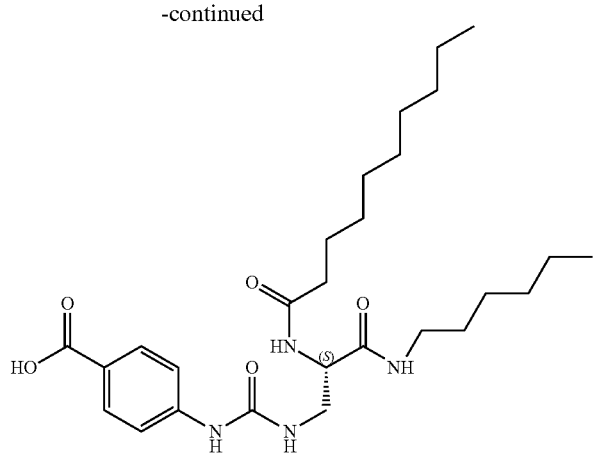
Prepared using General Ester Hydrolysis Procedure to give (S)-4-(3-(2-decanamido-3-(hexylamino)-3-oxopropyl)ureido)benzoic acid. (0.14, 95.93%) LCMS (Method-C2): 71.16% (RT: 1.333, 202.0 nm) (MS: ESI +ve 503.3[M−H]).
Step 7: preparation of (3S,4S)-1-(4-(3-((S)-2-decanamido-3-(hexylamino)-3-oxopropyl) ureido)benzoyl)-N3,N4-bis((1S,2R)-2-phenylcyclopropyl) pyrrolidine-3,4-dicarboxamide, Compound 235
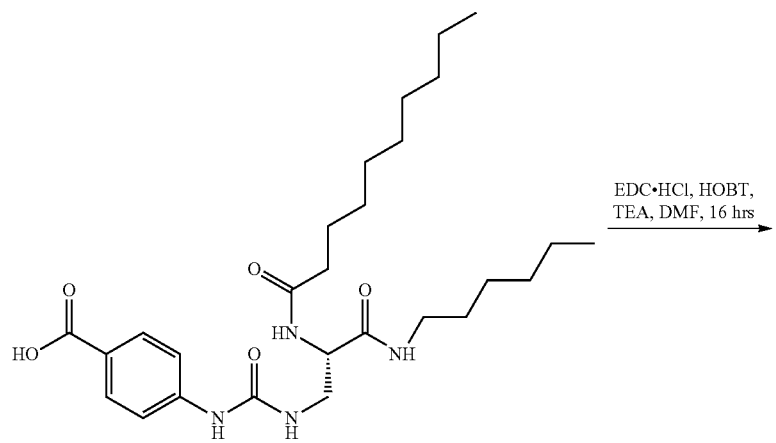
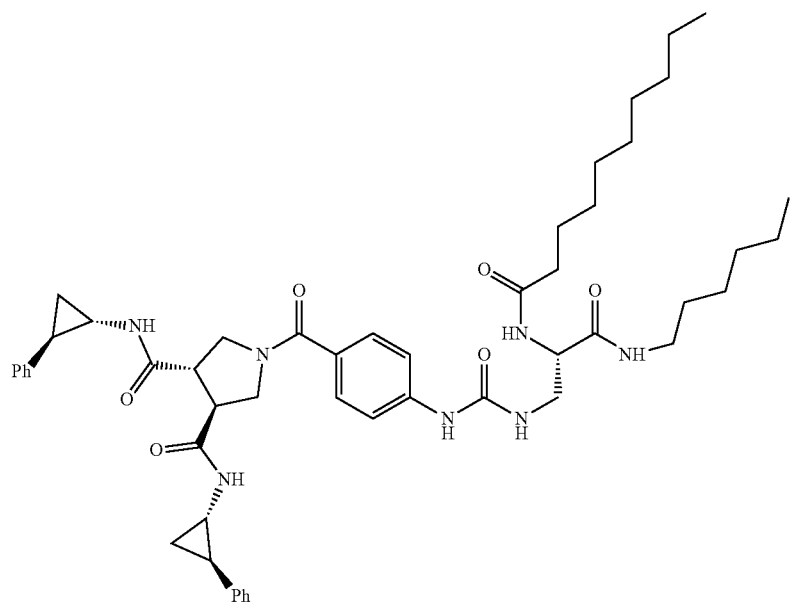

Prepared using General EDC, HOBT Coupling Procedure. The crude product was purified using Prep HPLC Method 3 to give (3S,4S)-1-(4-(3-((S)-2-decanamido-3-(hexylamino)-3-oxopropyl) ureido) benzoyl)-N3,N4-bis((1S,2R)-2-phenylcyclopropyl)pyrrolidine-3,4-dicarboxamide (Compound 235)(0.008 g, 3.07%), as an off white solid. LCMS (Method-J): 100% (RT 4.679, 254.0 nm) (MS: ESI +ve 874.3 [M–H]. $^1$H NMR: (400 MHz, DMSO) δ ppm: 0.82-0.84 (d, J=5.2 Hz, 6H), 1.20-1.47 (m, 26H), 1.86 (s, 1H), 1.95 (s, 2H), 2.10-2.14 (t, J=7.6 Hz, 2H), 2.79-3.51 (m, 9H), 3.73 (s, 3H), 4.29-4.31 (d, J=6.4 Hz, 1H), 6.53 (s, 1H), 7.08-7.15 (m, 6H), 7.24 (s, 4H), 7.39-7.45 (m, 4H), 7.87-7.90 (t, J=5.2 Hz, 1H), 7.97-7.99 (d, J=7.6 Hz, 1H), 8.31-8.42 (d, J=46 Hz, 2H), 9.17 (s, 1H).

Synthesis of (3S,4S)-1-(4-((3S,4S)-3-methoxy-4-(3-tridecylureido)pyrrolidine-1-carboxamido)benzoyl)-N3,N4-bis((1S,2R)-2-phenylcyclopropyl)pyrrolidine-3,4-dicarboxamide, Compound 238

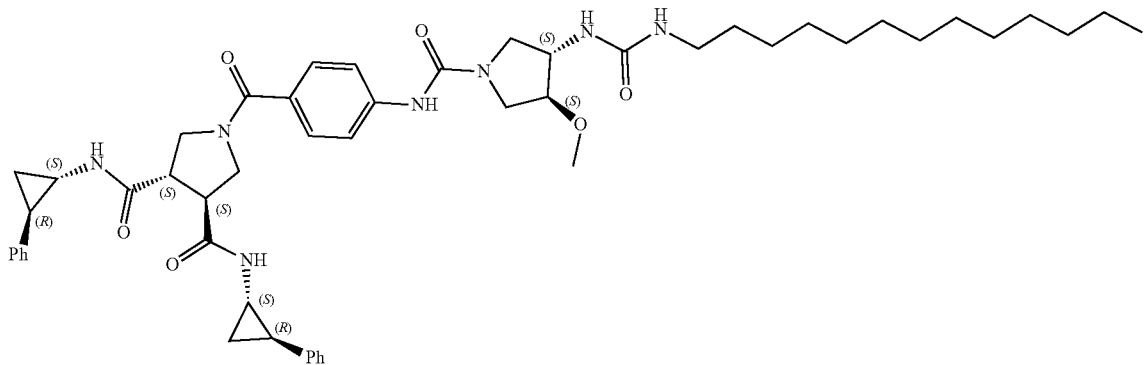

Prepared by a procedure similar to that reporter for (3S,4S)-1-(4-(3-((S)-2-decanamido-3-(hexylamino)-3-oxopropyl) ureido) benzoyl)-N3,N4-bis((1S,2R)-2-phenylcyclopropyl)pyrrolidine-3,4-dicarboxamide (Compound 235), substituting the applicable starting materials. The final product was purified using Prep HPLC Method 3 to give (3S,4S)-1-(4-((3S,4S)-3-methoxy-4-(3-tridecylureido)pyrrolidine-1-carboxamido)benzoyl)-N3,N4-bis((1S,2R)-2-phenylcyclopropyl)pyrrolidine-3,4-dicarboxamide (Compound 238)(0.008 g, 3.07%), as an off white solid. LCMS (Method-J): 100% (RT 4.549, 202.0 nm) (MS: ESI +ve 876.16 [M–H]. $^1$H NMR: (400 MHz, DMSO) δ ppm: 0.85-0.88 (t, J=6.4 Hz, 3H), 1.12-1.36 (m, 27H), 1.88 (s, 1H), 1.97 (s, 1H), 2.81-2.85 (d, J=18 Hz, 2H), 2.97-2.99 (d, J=7.6 Hz, 2H), 3.12-3.57 (m, 11H), 3.74 (s, 3H), 4.08 (s, 1H), 5.75-5.77 (t, J=5.2 Hz, 1H), 6.21-6.23 (d, J=6.8 Hz, 1H), 7.08-7.17 (m, 6H), 7.26-7.27 (d, J=7.2 Hz, 4H), 7.43-7.45 (d, J=8.8 Hz, 2H), 7.58-7.60 (d, J=8.8 Hz, 2H), 8.1 (s, 1H), 8.44 (s, 2H).

Synthesis of (3S,4S)-1-(4-((((S)-2-decanamido-3-(hexylamino)-3-oxopropyl) amino) methyl) benzoyl)-N3,N4-bis((1S,2R)-2-phenylcyclopropyl) pyrrolidine-3,4-dicarboxamide, Compound 266

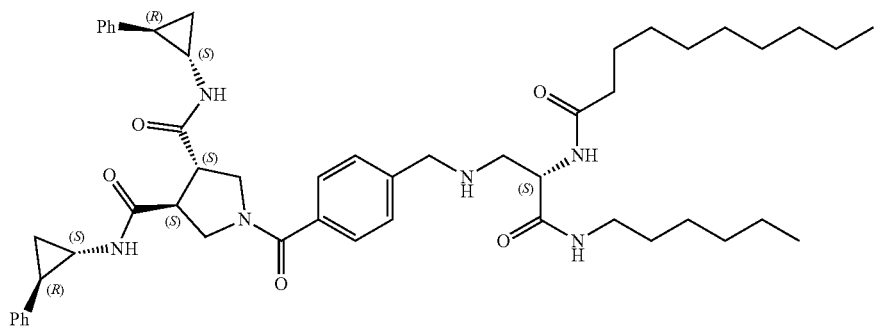

Step-1: Preparation of methyl (S)-4-(((2-decanamido-3-(hexylamino)-3-oxopropyl) amino) methyl) benzoate

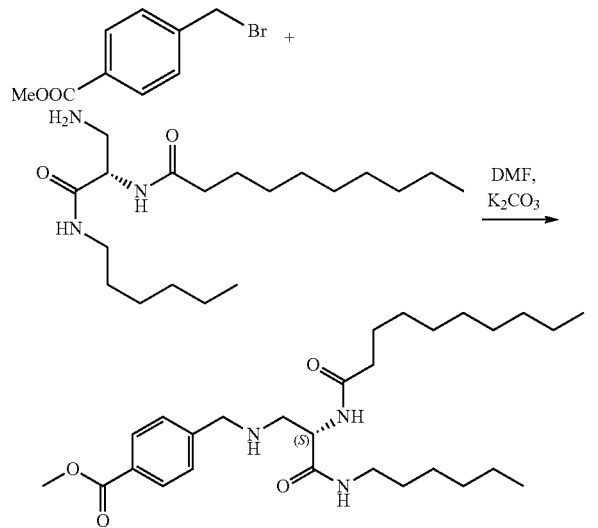

To a stirred solution of methyl 4-(bromomethyl) benzoate (0.25 g, 1.09 mmol) in DMF (5 mL), was added potassium carbonate (0.22 g, 1.63 mmol) at 0° C. followed by the addition of (S)—N-(3-amino-1-(hexylamino)-1-oxopropan-2-yl) decanamide (0.44 g, 1.30 mmol) in DMF (5 mL) dropwise. The reaction mixture was stirred for 16 h at room temperature then diluted with ice-cold water (25 mL). The resulting precipitate was collected by filtration and dried under vacuum. The crude product which was purified using flash chromatography, eluting with 0-6% DCM:MeOH, to give methyl (S)-4-(((2-decanamido-3-(hexylamino)-3-oxopropyl) amino) methyl) benzoate, as an off white solid (0.53 g, 99.1%) LCMS (Method-C-Fast): 47.4% (RT 1.833, 231.0 nm) (MS: ESI +ve 490 [M+H]).

Step-2: Preparation of (S)-4-(((2-decanamido-3-(hexylamino)-3-oxopropyl) amino) methyl) benzoic acid

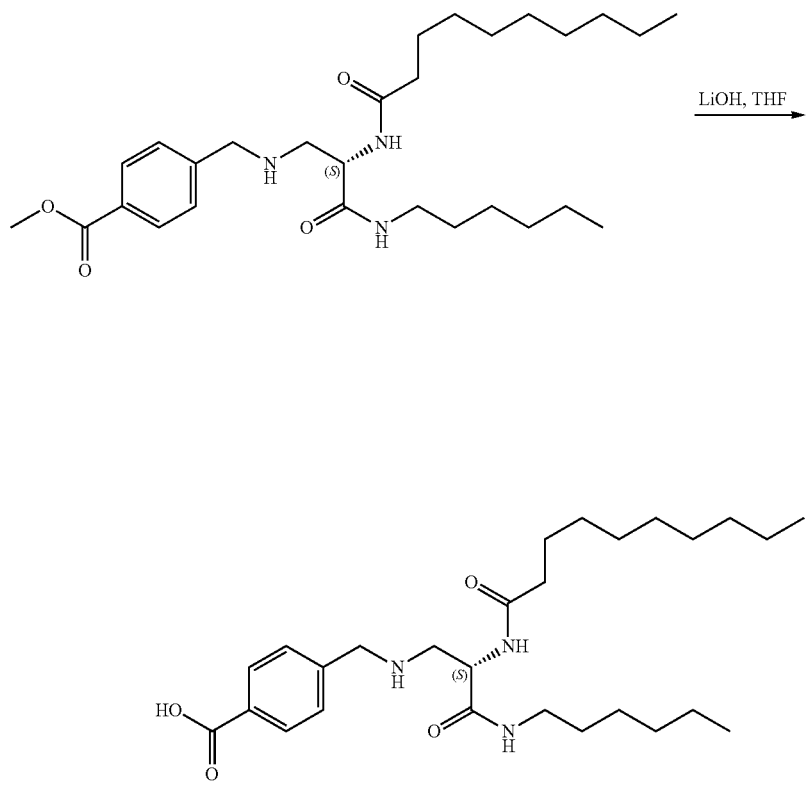

Prepared using General Ester Hydrolysis Procedure to give (S)-4-(((2-decanamido-3-(hexylamino)-3-oxopropyl) amino) methyl) benzoic acid as the HCl salt (0.3 g, 58.2%). LCMS (Method-C2): 57.94% (RT: 1.362, 202.0 nm) (MS: ESI +ve 476.0 [M+H]).

Step-3: Preparation of (3S,4S)-1-(4-((((S)-2-decanamido-3-(hexylamino)-3-oxopropyl) amino) methyl) benzoyl)-N3,N4-bis((1S,2R)-2-phenylcyclopropyl) pyrrolidine-3,4-dicarboxamide, Compound 266

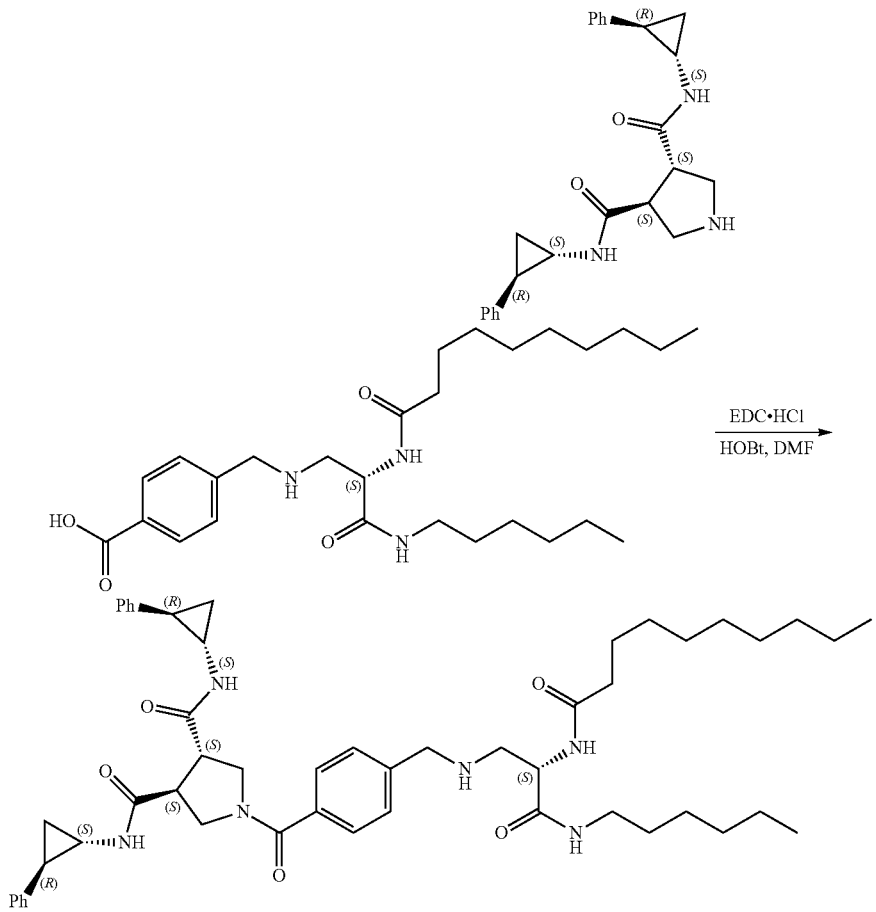

Prepared using General EDC, HOBT Coupling Procedure. The crude product was purified using Prep HPLC Method 7 to give (3S,4S)-1-(4-((((S)-2-decanamido-3-(hexylamino)-3-oxopropyl) amino) methyl) benzoyl)-N3,N4-bis((1S,2R)-2-phenylcyclopropyl) pyrrolidine-3,4-dicarboxamide (Compound 266)(0.04 g, 7.49%). LCMS (Method-H3): 100% (RT 4.037, 202.0 nm) (MS: ESI +ve 848[M+H]). $^1$H NMR: (400 MHz, DMSO) δ ppm: 0.86 (s, 6H); 1.22 (s, 3H); 1.23 (s, 18H); 1.37 (s, 2H); 1.48 (s, 2H); 2.11-2.13 (d, J=7.2, 3H); 2.68 (s, 2H); 3.03 (s, 4H); 3.51 (s, 3H); 4.32 (s, 1H); 7.07-7.09 (d, J=7.2, 2H); 7.12-7.17 (m, 4H); 7.25-7.27 (d, J=7.6, 4H); 7.36-7.37 (d, J=7.6, 2H); 7.45-7.50 (m, 2H); 7.86-7.91 (t, 2H); 8.32 (s, 1H); 8.46 (s, 1H).

Synthesis of (3S,4S)-1-(4-(((S)-2-decanamido-3-(hexylamino)-3-oxopropoxy) methyl) benzoyl)-N3, N4-bis((1S,2R)-2-phenylcyclopropyl) pyrrolidine-3, 4-dicarboxamide, Compound 263

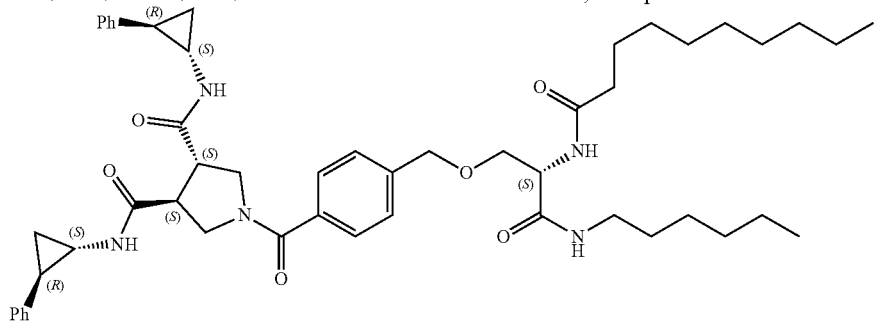

713

Step-1: Preparation of tert-butyl (3R,4S)-3-methoxy-4-pentadecanamidopyrrolidine-1-carboxylate

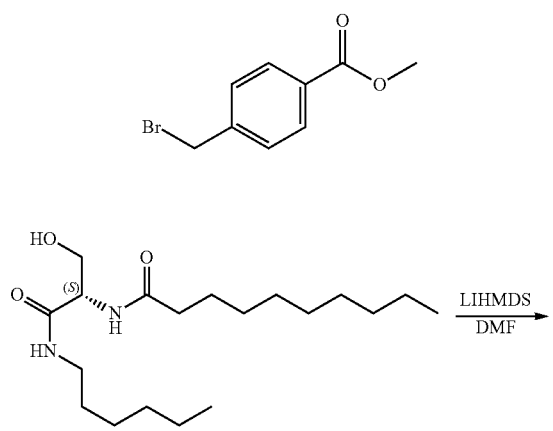

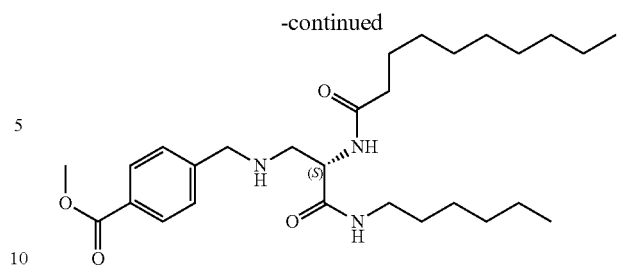

To a stirred solution of methyl 4-(bromomethyl) benzoate (0.2 g, 0.87 mmol) in DMF (5 mL), was added lithium bis(trimethylsilyl)amide (1.3 mL, 1.30 mmol) at 0° C. followed by (S)—N-(1-(hexylamino)-3-hydroxy-1-oxopropan-2-yl) decanamide (0.29 g, 0.87 mmol) in DMF (5 mL). The reaction mixture was stirred for 4 h at room temperature then diluted with ice-cold water (25 mL). The resulting precipitate was filtered and dried under vacuum. The crude product was purified using flash chromatography, eluting with 0-6% DCM:MeOH, to give tert-butyl (3R,4S)-3-methoxy-4-pentadecanamidopyrrolidine-1-carboxylate as an off white solid (0.41 g, 95.7%). LCMS (Method-C-Fast): 69.3% (RT 2.207, 236.0 nm) (MS: ESI +ve 491 [M+H]).

Step-2: Preparation of (S)-4-((2-decanamido-3-(hexylamino)-3-oxopropoxy) methyl) benzoic acid

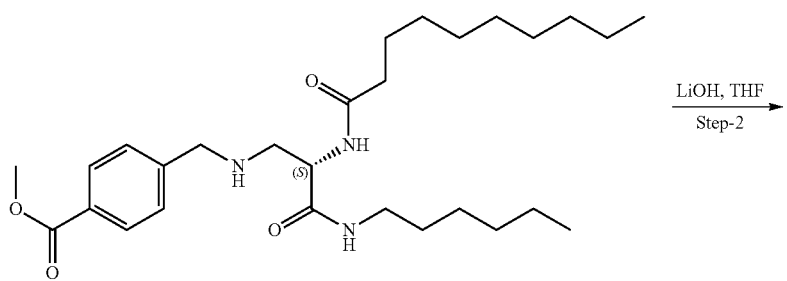

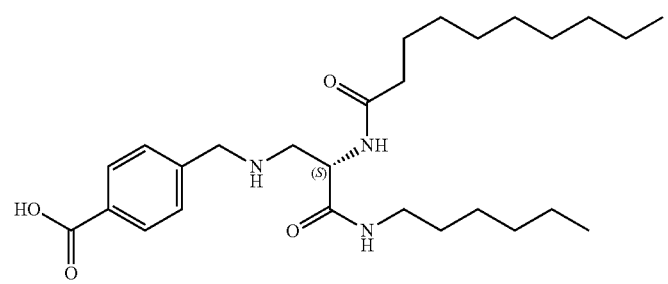

Prepared using General Ester Hydrolysis Procedure to give (S)-4-((2-decanamido-3-(hexylamino)-3-oxopropoxy) methyl) benzoic acid as a white solid (0.16 g, 40.17%). LCMS (Method-C2): 75.7% (RT: 1.428, 202.0 nm) (MS: ESI +ve 477.0 [M+H]).

Step-3: Preparation of (3S,4S)-1-(4-(((S)-2-decanamido-3-(hexylamino)-3-oxopropoxy) methyl) benzoyl)-N3,N4-bis((1S,2R)-2-phenylcyclopropyl) pyrrolidine-3,4-dicarboxamide, Compound 263

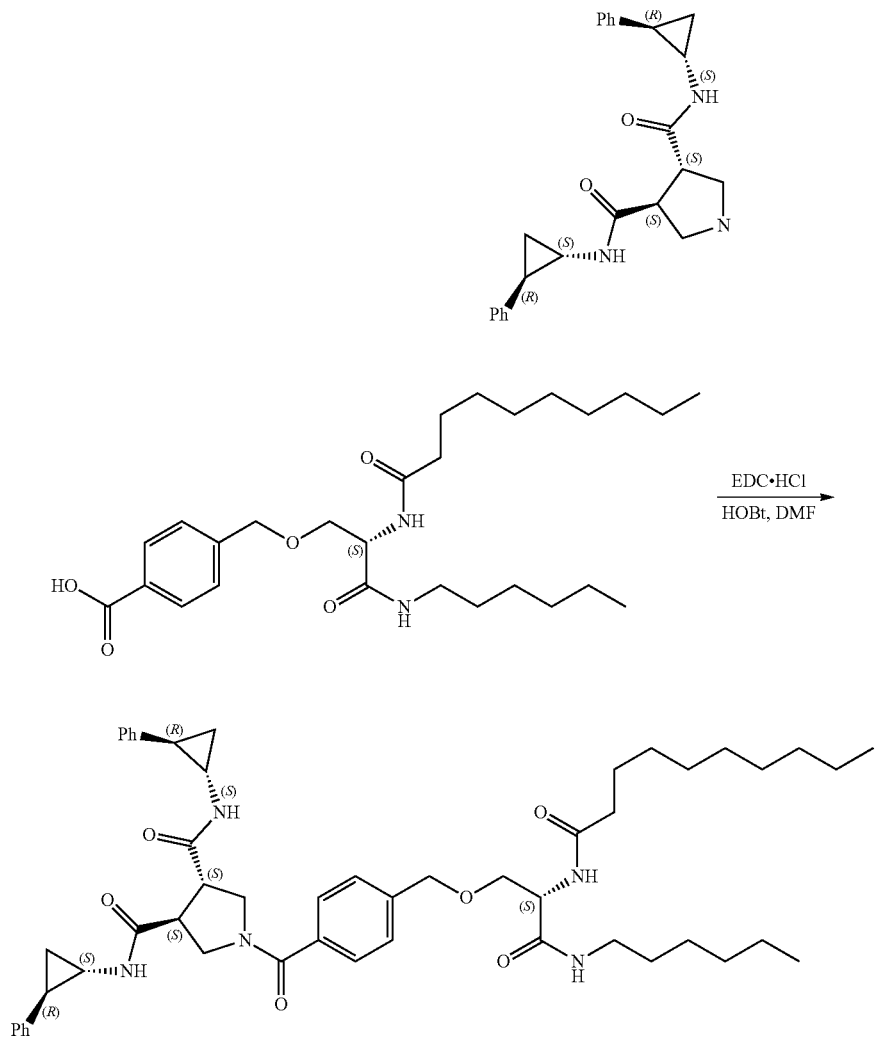

Prepared using General EDC, HOBT Coupling Procedure. The crude product was purified using Prep HPLC Method 10 to give (3S,4S)-1-(4-(((S)-2-decanamido-3-(hexylamino)-3-oxopropoxy) methyl) benzoyl)-N3,N4-bis ((1S,2R)-2-phenylcyclopropyl) pyrrolidine-3,4-dicarboxamide (Compound 263), as a white solid (0.02 g, 7.03%). LCMS (Method-J2): 100% (RT 4.507, 202.0 nm) (MS: ESI +ve 849[M+H]). $^1$H NMR: (400 MHz, DMSO) δ ppm: 0.82-0.87 (m, 6H); 1.10-1.13 (t, 2H); 1.18 (s, 21H); 1.37 (s, 2H); 1.47 (s, 2H); 1.86 (s, 1H); 1.97 (s, 1H); 2.12-2.16 (t, 2H); 2.68 (s, 2H); 3.05-3.13 (m, 3H); 3.17-3.23 (m, 1H); 3.49-3.52 (m, 4H); 3.63-3.68 (m, 1H); 3.76-3.81 (m, 1H); 4.52 (s, 3H); 7.07-7.08 (d, J=7.6, 2H); 7.12-7.19 (m, 4H); 7.23-7.29 (m, 4H); 7.35-7.37 (d, J=8, 2H); 7.48-7.50 (d, J=8, 2H); 7.96-8.01 (m, 2H); 8.34 (s, 1H); 8.47 (s, 1H).

Synthesis of (3S,4S)-1-(4-((((S)-2-decanamido-3-(hexylamino)-3-oxopropyl) thio)methyl)benzoyl)-N3,N4-bis((1S,2R)-2-phenylcyclopropyl)pyrrolidine-3,4-dicarboxamide, Compound 280

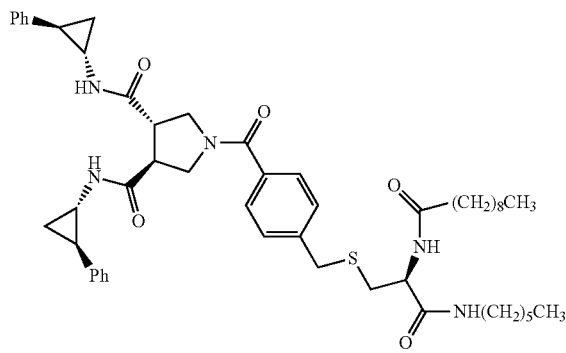

Step-1: Preparation of methyl (S)-4-(((3-(allyloxy)-2-((tert-butoxycarbonyl)amino)-3-oxopropyl)thio) methyl)benzoate

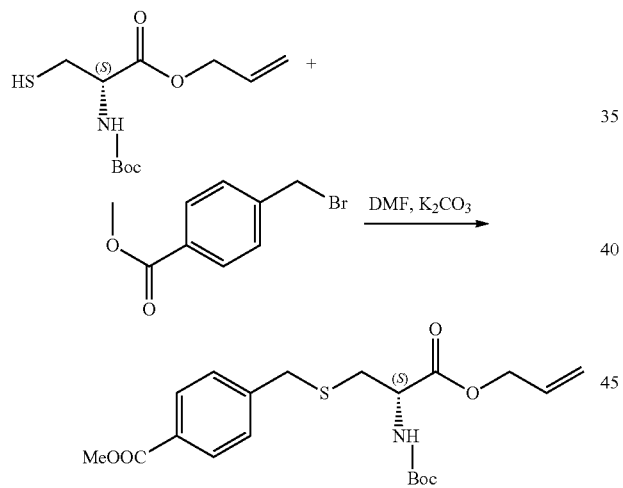

A mixture of allyl (tert-butoxycarbonyl)-D-cysteinate (0.5 g, 1.913 mmol), potassium carbonate (0.396 g, 2.869 mmol) and methyl 4-(bromomethyl)benzoate (0.438 g, 1.913 mmol) in DMF (10 mL) was stirred for 16 h at room temperature. The reaction mixture was diluted with water (20 mL) and extracted with ethyl acetate (3×100 mL). The organic layer was washed with brine (2×30 mL) and dried over anhydrous sodium sulfate then concentrated. The crude product was purified using flash chromatography, eluting with EtOAc:Hexanes 50-60%, to give methyl (S)-4-(((3-(allyloxy)-2-((tert-butoxycarbonyl)amino)-3-oxopropyl) thio)methyl)benzoate. (0.7 g, 89.35%). LCMS (Method-C-fast): 71.05% (RT: 1.622, 240.00 nm) (MS: ESI +ve 410 [M+1]).

Step-2: Preparation of N-(tert-butoxycarbonyl)-S-(4-(methoxycarbonyl)benzyl)-D-cysteine

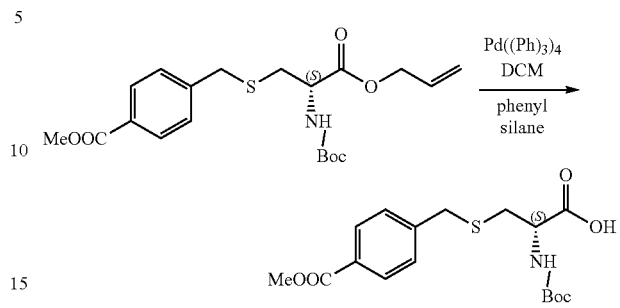

Methyl(S)-4-(((3-(allyloxy)-2-((tert-butoxy carbonyl) amino)-3-oxopropyl)thio)methyl) benzoate (0.7 g, 1.707 mmol) was dissolved in DCM (100 mL). Phenylsilane (0.370 g, 3.414 mmol) and tetrakistriphenylphosphine palladium(0.098 g, 0.085 mmol) were added, and the mixture was stirred for 16 h. The mixture was diluted with DCM (200 mL) and washed with water (2×200 mL). The organic layer was dried over sodium sulfate and concentrated to give N-(tert-butoxycarbonyl)-S-(4-(methoxycarbonyl)benzyl)-D-cysteine. (0.6 g, 95.01%) as a liquid. LCMS (Method-C2): 68.26% (RT 1.257, 254.0 nm) (MS: ESI +ve 270[(M−100]).

Step-3: Preparation of methyl (S)-4-(((2-((tert-butoxycarbonyl)amino)-3-(hexylamino)-3-oxopropyl) thio)methyl)benzoate

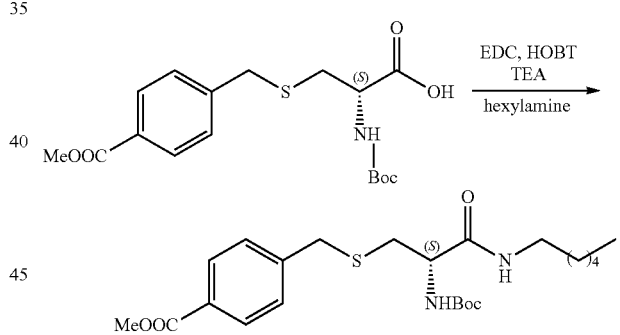

Prepared using General EDC, HOBT Coupling Procedure. The crude product was purified by using flash chromatography, eluting with 1-3% MeOH:DCM, to give methyl (S)-4-(((2-((tert-butoxycarbonyl)amino)-3-(hexylamino)-3-oxopropyl)thio)methyl)benzoate. as a semisolid (0.47 g, 63.94%) LCMS (Method-C2): 98.49% (RT 1.472, 236.0 nm) (MS: ESI +ve 453[(M+H]).

Step-4: Preparation of methyl (S)-4-(((2-amino-3-(hexylamino)-3-oxopropyl)thio) methyl) benzoate

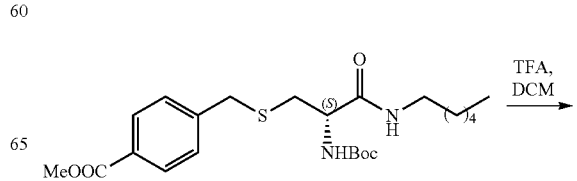

-continued

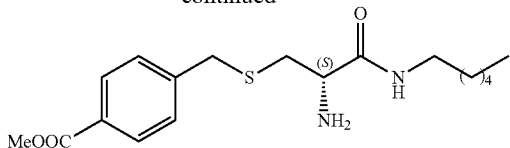

Prepared using General BOC Deprotection Procedure to give methyl (S)-4-(((2-amino-3-(hexylamino)-3-oxopropyl)thio)methyl)benzoate as its TFA salt (0.65 g). LCMS (Method-C2): 98.07% (RT: 1.137, 236.0 nm) (MS: ESI +ve 353[M+H]).

Step-5: Preparation of methyl (S)-4-(((2-decanamido-3-(hexylamino)-3-oxopropyl) thio) methyl) benzoate

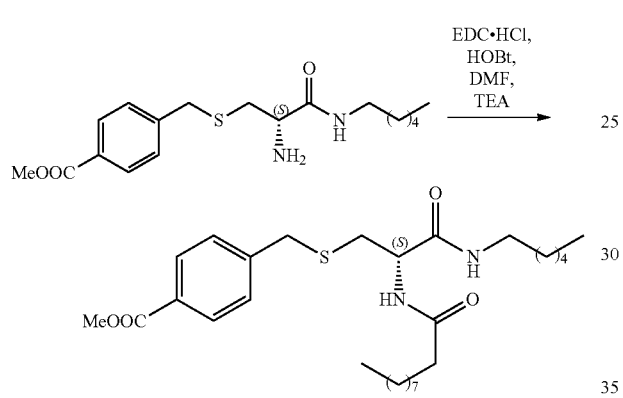

Prepared using General EDC, HOBT Coupling Procedure. The crude product was purified using flash chromatography, eluting with 1-3% MeOH:DCM, to give methyl (S)-4-(((2-decanamido-3-(hexylamino)-3-oxopropyl)thio)methyl)benzoate as a semisolid (0.4 g, 42.81%) LCMS (Method-C-Fast): 89.52% (RT 2.297, 235.0 nm) (MS: ESI +ve 507[(M+H]).

Step-6: Preparation of (S)-4-(((2-decanamido-3-(hexylamino)-3-oxopropyl) thio) methyl)benzoic acid

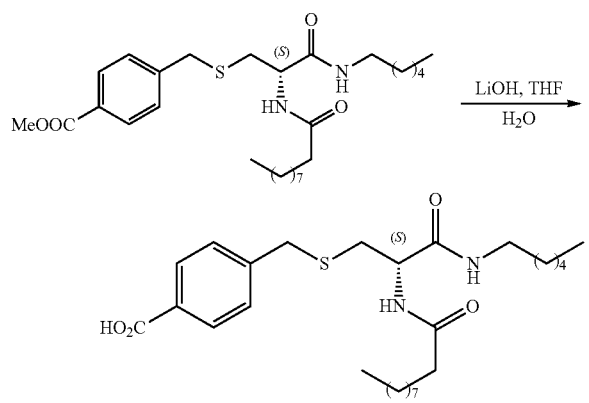

Prepared using General Ester Hydrolysis Procedure to give (R)-4-(((2-decanamido-3-(hexylamino)-3-oxopropyl)thio)methyl)benzoic acid. (0.2 g, 51.42%) LCMS (Method-C2): 75.10% (RT: 1.498, 254.0 nm) (MS: ESI +ve 494[M+H]).

Step-7: Preparation of (3S,4S)-1-(4-((((S)-2-decanamido-3-(hexylamino)-3-oxopropyl) thio)methyl)benzoyl)-N3,N4-bis((1S,2R)-2-phenylcyclopropyl)pyrrolidine-3,4-dicarboxamide, Compound 280

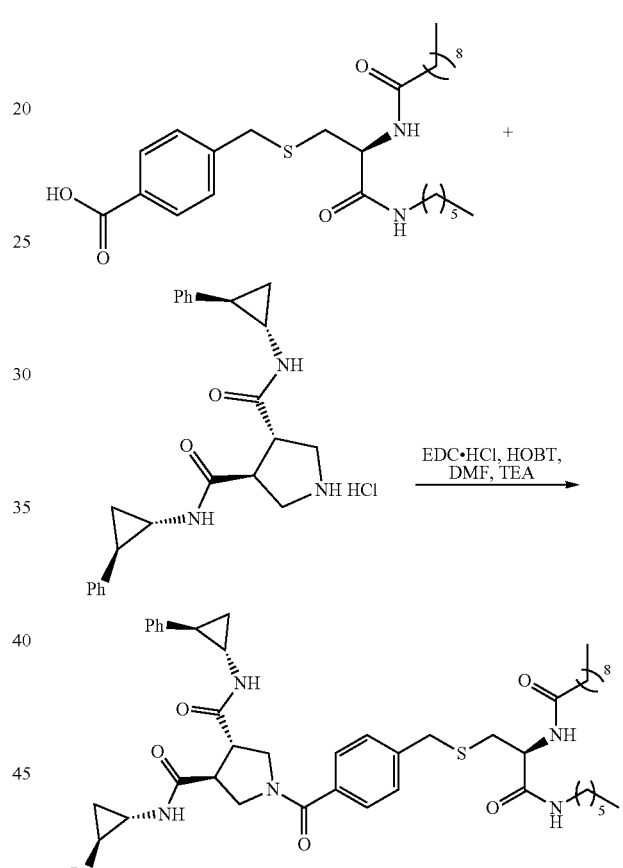

Prepared using General EDC, HOBT Coupling Procedure. The crude product was purified by using Prep HPLC Method 4 to give (3S,4S)-1-(4-((((S)-2-decanamido-3-(hexylamino)-3-oxopropyl) thio)methyl)benzoyl)-N3,N4-bis((1S,2R)-2-phenylcyclopropyl)pyrrolidine-3,4-dicarboxamide (Compound 280)(0.034 g, 9.69%). LCMS (Method-J2): 98.43% (RT 4.617, 225.0 nm) (MS: ESI +ve 864 [M+H]). $^1$H NMR: (400 MHz, DMSO) δ ppm: 0.85 (s, 6H), 1.11-1.48 (m, 27H), 1.87 (s, 1H), 1.97 (s, 1H), 2.10-2.12 (d, J=7.2 Hz, 2H), 2.65-2.85 (m, 3H), 3.05-3.21 (m, 4H), 3.49-3.54 (t, J=8.8 Hz, 2H), 3.67-3.85 (m, 4H), 4.48-4.50 (d, J=7.2 Hz, 1H), 7.07-7.27 (m, 6H), 7.23-7.27 (m, 4H), 7.37-7.39 (d, J=7.6 Hz, 2H), 7.45-7.47 (d, J=7.2 Hz, 2H), 8.09-8.10 (d, J=7.2 Hz, 2H), 8.36 (s, 1H), 8.49-8.52 (m, 1H).

Synthesis of (S)-2-decanamido-3-(hexylamino)-3-oxopropyl (4-((3S,4S)-3,4-bis(((1S,2R)-2-phenylcyclopropyl)carbamoyl)pyrrolidine-1-carbonyl)phenyl) carbamate, Compound 239

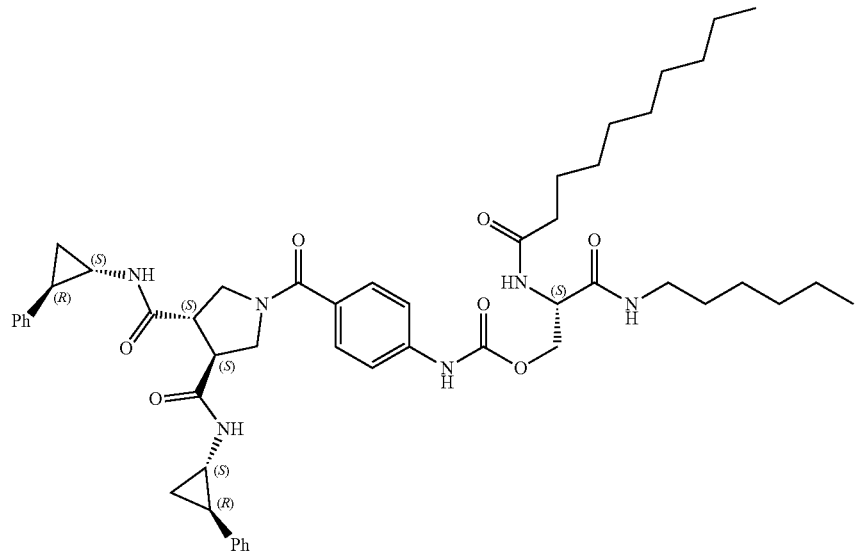

Step-1: Preparation of tert-butyl (S)-4-(((2-decanamido-3-(hexylamino)-3-oxopropoxy) carbonyl) amino)benzoate

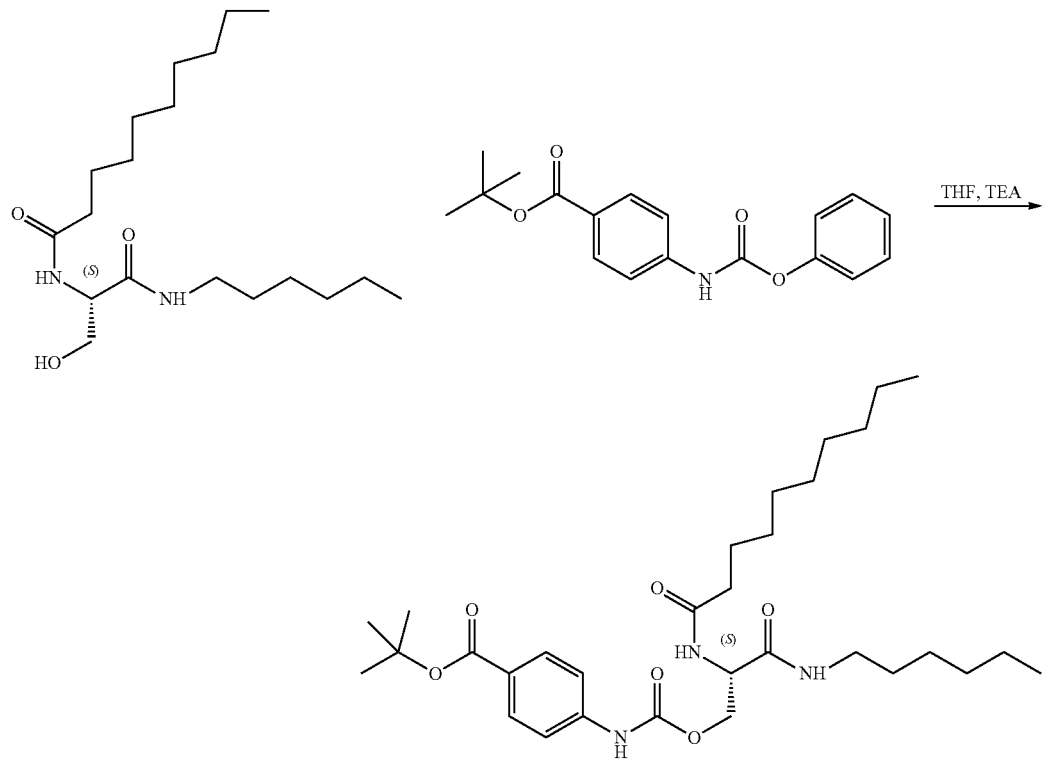

(S)—N-(1-(hexylamino)-3-hydroxy-1-oxopropan-2-yl) decanamide (0.500 g, 1.459 mmol) was dissolved in THF (10 mL) and cooled to 0° C. TEA (0.61 mL, 4.379 mmol) was added followed by tert-butyl 4-((phenoxycarbonyl)amino)benzoate (0.548 g, 1.751 mmol). The reaction mixture was stirred at room temperature for 16 h then heated at 70° C. for 4 h. Ice cold water was added and the resulting precipitate was collected by filtration then triturated with pentane to give tert-butyl (S)-4-(((2-decanamido-3-(hexylamino)-3-oxopropoxy)carbonyl)amino)benzoate. (0.678 g, 82.6% yield). LCMS (Method-H): 47.9% (RT: 4.400, 230.0 nm) (MS: ESI −ve 506.2 [M−56]).

Step-2: Preparation of (S)-4-(((2-decanamido-3-(hexylamino)-3-oxopropoxy) carbonyl)amino)benzoic acid

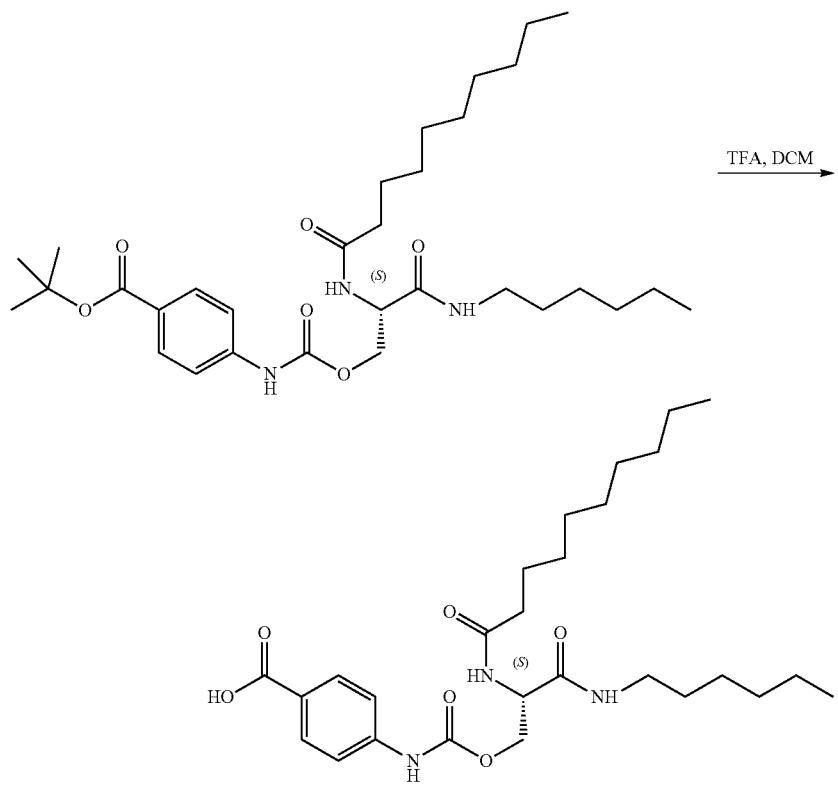

Prepared using General BOC Deprotection Procedure to give (S)-4-(((2-decanamido-3-(hexylamino)-3-oxopropoxy) carbonyl)amino)benzoic acid (0.210 g, 66.6% yield). LCMS (Method-C fast): 96.4% (RT: 1.699, 266 nm) (MS: ESI +ve 506.7 [M+1]).

Step-3: Preparation of (S)-2-decanamido-3-(hexylamino)-3-oxopropyl (4-((3S,4S)-3,4-bis(((1S,2R)-2-phenylcyclopropyl)carbamoyl)pyrrolidine-1-carbonyl)phenyl)carbamate, Compound 239

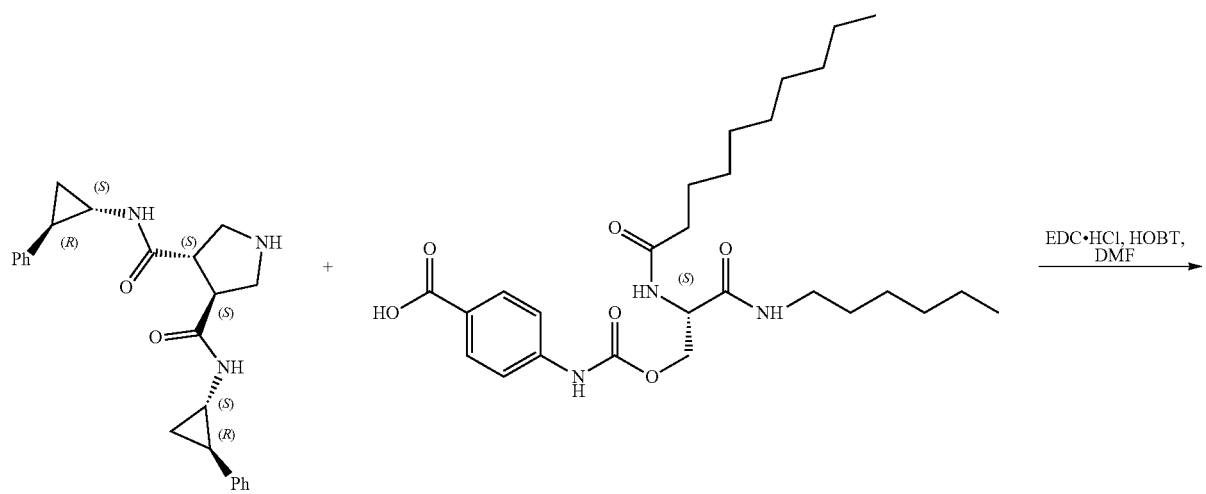

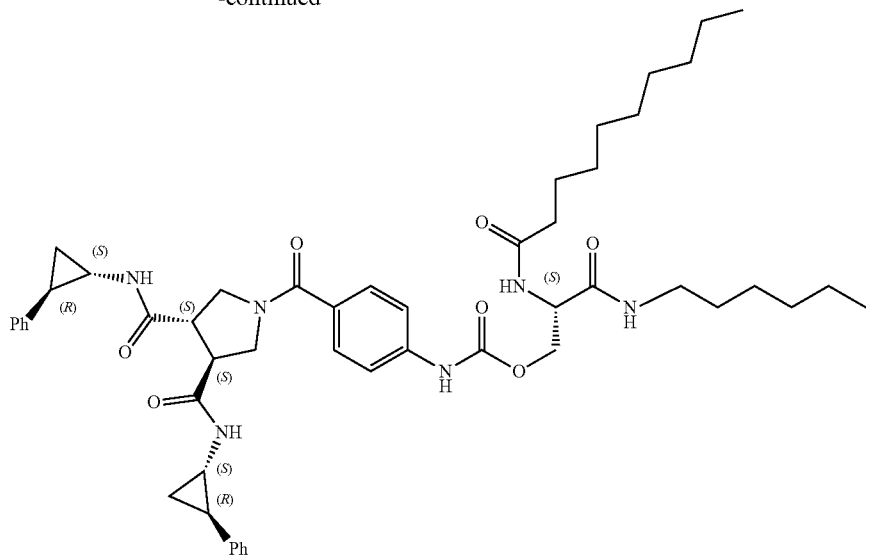

Prepared using General EDC, HOBT Coupling Procedure. The crude product was purified using Prep HPLC Method 10 to give (S)-2-decanamido-3-(hexylamino)-3-oxopropyl (4-((3S,4S)-3,4-bis(((1S,2R)-2-phenylcyclopropyl)carbamoyl)pyrrolidine-1-carbonyl)phenyl)carbamate (Compound 239)(0.059 g, 22.6%), as a white solid. LCMS (Method-H): 99.1% (RT: 3.940, 202.0 nm) (MS: ESI +ve 877.5 [M+1]). $^1$H NMR: (400 MHz, DMSO) δ ppm: 0.844-0.854 (m, 6H), 1.225 (m, 19H), 1.394-1.487 (m, 4H), 1.872-1.975 (m, 3H), 2.114-2.164 (m, 3H), 2.687 (m, 3H), 3.058-3.111 (m, 3H), 3.181-3.228 (m, 2H), 3.510-3.532 (m, 4H), 4.189-4.254 (m, 2H), 4.579-4.594 (m, 1H), 7.097-7.256 (m, 10H), 7.461-7.542 (m, 4H), 8.009-8.100 (t, J=36.4 Hz, 2H), 8.298-8.423 (m, 2H), 9.915 (s, 1H).

Synthesis of (3S,4S)-1-(4-(1-((S)-2-heptanamido-3-(hexylamino)-3-oxopropyl)-1H-1,2,3-triazol-4-yl)benzoyl)-N3,N4-bis((1S,2R)-2-phenylcyclopropyl)pyrrolidine-3,4-dicarboxamide, Compound 185

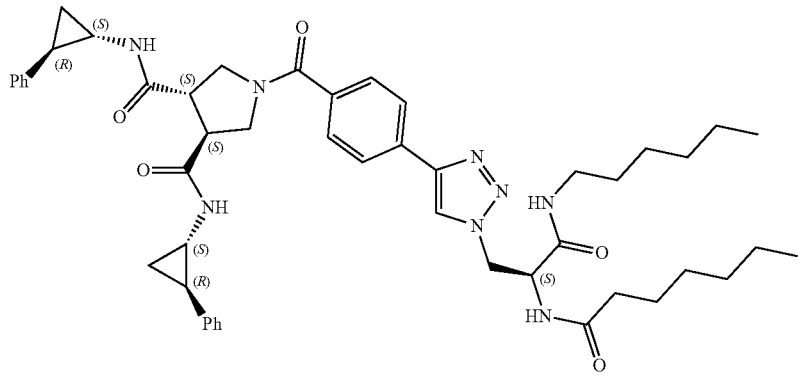

Step-1: Preparation of (S)—N-(3-azido-1-(hexylamino)-1-oxopropan-2-yl)heptanamide

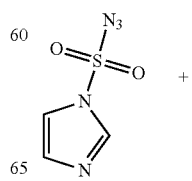

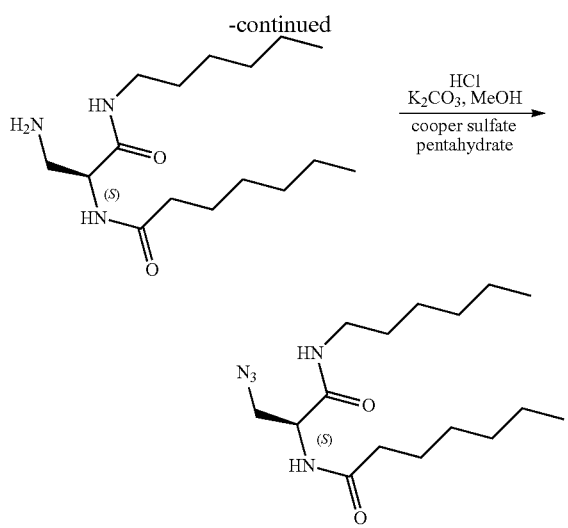

Imidazole-1-sulfonyl azide hydrochloride (0.41 g, 2.0 mmol) was added to a mixture of (S)—N-(3-amino-1-(hexylamino)-1-oxopropan-2-yl) heptanamide (0.5 g, 1.6 mmol), potassium carbonate (0.53 g, 3.8 mmol) and copper sulfate pentahydrate (0.004 mg, 0.01 mmol) in MeOH (10 mL). The resulting mixture was stirred at room temperature for 16 h. The reaction mixture was concentrated, and the residue was diluted with water (20 mL) then extracted into ethyl acetate (3×30 mL), dried over sodium sulfate and concentrated. The crude product was purified using flash chromatography on basic aluminium oxide, eluting with 10-30% EtOAc: hexane, to give (S)—N-(3-azido-1-(hexylamino)-1-oxopropan-2-yl) heptanamide, as a white solid (0.32 g, 59.6%).

Step-2: Preparation of (3S,4S)-1-(4-(1-((S)-2-heptanamido-3-(hexylamino)-3-oxopropyl)-1H-1, 2, 3-triazol-4-yl) benzoyl)-N3,N4-bis ((1S,2R)-2-phenylcyclopropyl) pyrrolidine-3,4-dicarboxamide, Compound 185

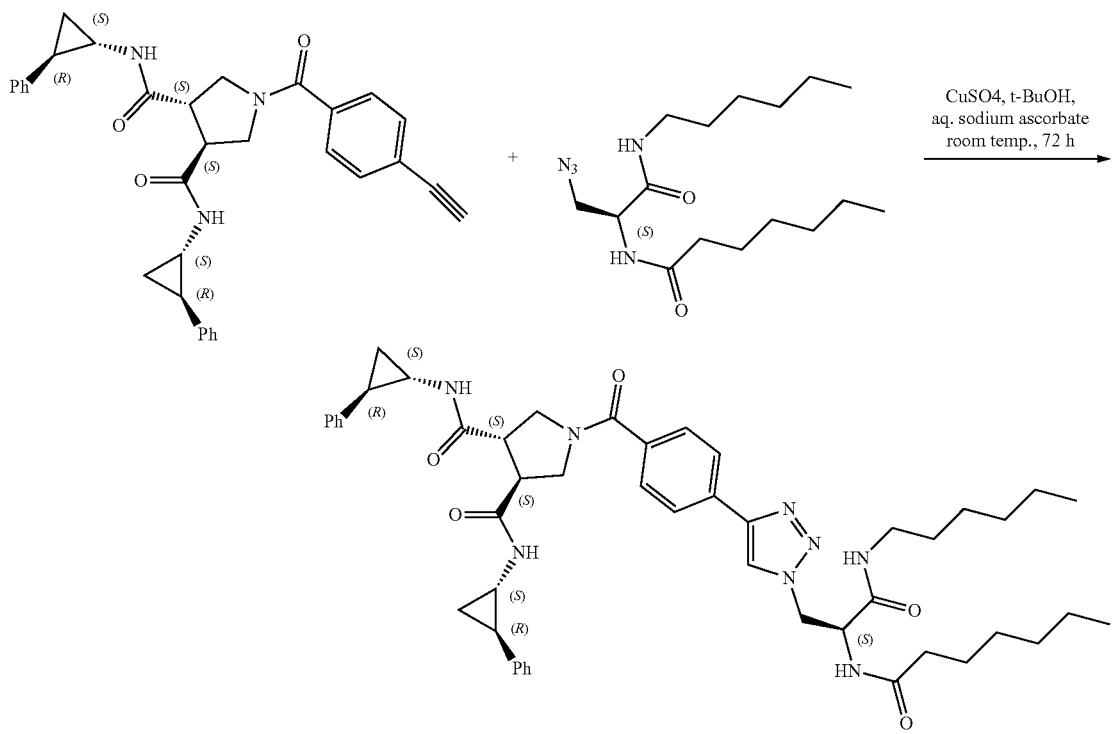

(3S,4S)-1-(4-ethynylbenzoyl)-N3,N4-bis ((1S,2R)-2-phenylcyclopropyl) pyrrolidine-3,4-dicarboxamide (0.2 g, 0.38 mmol) and (S)—N-(3-azido-1-(hexylamino)-1-oxopropan-2-yl) heptanamide (0.18 g, 0.58 mmol) were dissolved in t-butanol (5 mL). Sodium ascorbate (0.015 g, 0.07 mmol) in water (2.5 mL) was added to the mixture followed by copper sulfate (0.009 g, 0.038 mmol) in water (2.5 mL). The reaction mixture was stirred at room temperature for 3 days, and then was diluted with water (10 mL), extracted with EtOAc (3×10 mL), washed with brine (2×10 mL), dried over sodium sulfate and concentrated. The crude product was purified using flash chromatography, eluting with 0-5% MeOH:DCM, to give (3S,4S)-1-(4-(1-((S)-2-heptanamido-3-(hexylamino)-3-oxopropyl)-1H-1, 2, 3-triazol-4-yl) benzoyl)-N3,N4-bis ((1S,2R)-2-phenylcyclopropyl) pyrrolidine-3,4-dicarboxamide (Compound 185) (0.05 g, 15.3%), as a white solid. LCMS (Method-C-Fast): 97.5% (RT: 1.774, 263.0 nm) (MS: ESI +ve 842.0 [M−H]). ¹H NMR: (400 MHz, DMSO) 3 ppm: 0.75-0.84 (m, 6H); 1.18 (s, 15H); 1.33-1.37 (t, 4H); 1.57 (s, 1H); 1.85 (s, 1H); 1.98 (s, 1H); 2.09-2.34 (m, 2H); 2.87-2.98 (m, 1H); 2.99-3.03 (m, 1H); 3.05-3.15 (m, 3H); 3.18-3.24 (m, 1H); 3.54-3.56 (d, J=6.8, 2H); 3.68-3.73 (t, 1H); 4.01 (s, 1H); 4.49-4.55 (m, 1H); 4.69-4.73 (m, 1H); 4.81-4.84 (m, 1H); 7.06-7.08 (d, J=7.6, 2H); 7.13-7.19 (m, 4H); 7.23-7.30 (m, 4H); 7.60-7.62 (d, J=8, 2H); 7.87-7.89 (d, J=8, 2H); 8.09-8.12 (t, 1H); 8.21-8.23 (d, J=8.4, 1H); 8.30 (s, 1H); 8.44 (s, 1H); 8.49 (s, 1H).

Synthesis of (3S,4S)-1-(4-(1-((S)-3-(hexylamino)-2-nonanamido-3-oxopropyl)-1H-1, 2, 3-triazol-4-yl) benzoyl)-N3,N4-bis ((1S,2R)-2-phenylcyclopropyl) pyrrolidine-3,4-dicarboxamide, Compound 212

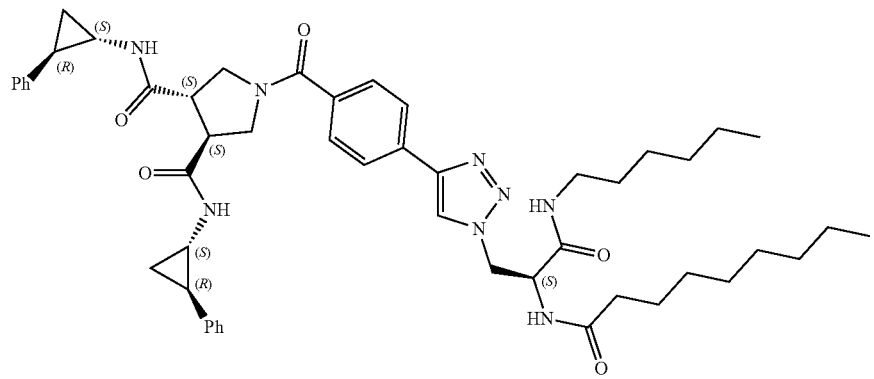

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude final product was purified using Prep HPLC Method 13 to give (3S,4S)-1-(4-(1-((S)-3-(hexylamino)-2-nonanamido-3-oxopropyl)-1H-1, 2, 3-triazol-4-yl) benzoyl)-N3,N4-bis ((1S,2R)-2-phenylcyclopropyl) pyrrolidine-3,4-dicarboxamide (Compound 212)(0.019 g, 5.87%). LCMS (Method-H): 100% (RT: 3.819, 254.0 nm) (MS: ESI +ve 872.0 [M+H]). ¹H NMR: (400 MHz, DMSO)3 ppm: 0.80-0.83 (m, 6H); 1.12 (s, 18H); 1.32-1.35 (t, 4H); 1.85 (s, 1H); 1.98 (s, 1H); 2.05-2.09 (t, 2H); 2.50 (s, 1H);2.55 (s, 1H); 2.86 (s, 2H); 3.04-3.12 (m, 3H); 3.18-3.22 (m, 1H); 3.54-3.56 (d, J=7.2, 2H); 3.79 (s, 2H); 4.52-4.55 (t, 1H); 4.67-4.72 (t, 1H); 4.80-4.82 (d, J=6, 1H); 7.05-7.07 (d, J=7.2, 2H); 7.12-7.18 (m, 4H); 7.23-7.27 (m, 4H); 7.58-7.60 (d, J=8.4, 2H); 7.85-7.87 (d, J=8.4, 2H); 8.16 (s, 1H); 8.34-8.37 (d, J=8.4, 1H); 8.40 (s, 1H); 8.50 (s, 3H).

Synthesis of (3S,4S)-1-(4-(1-((S)-2-decanamido-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide, Compound 213

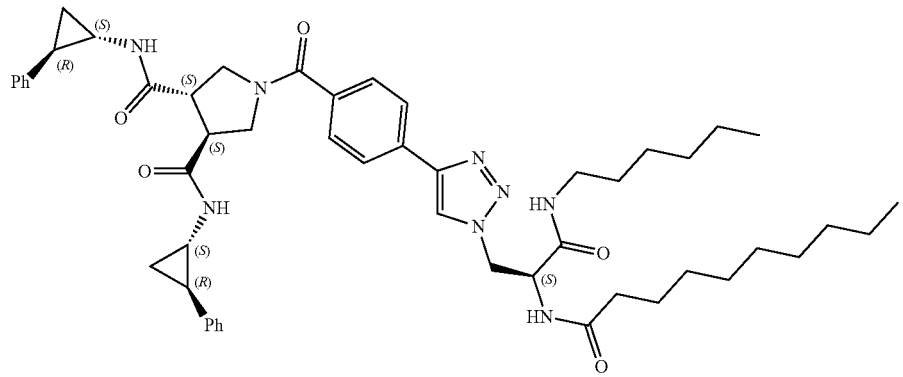

Prepared using a procedure similar to that reported for (3S,4S)-1-(4-(1-((2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude final product was purified using flash chromatography, eluting with 0-5% MeOH:DCM, to give (3S,4S)-1-(4-(1-((S)-2-decanamido-3-(hexylamino)-3-oxopropyl)-1H-1,2,3-triazol-4-yl)benzoyl)-N3,N4-bis((1S, 2R)-2-phenylcyclopropyl)pyrrolidine-3,4-dicarboxamide (Compound 213)(0.235 g, 69.9% yield), as a white solid. LCMS (Method-H): 98.8% (RT: 3.980, 254.0 nm) (MS: ESI +ve 884.6 [M−1]). $^1$H NMR: (400 MHz, DMSO) δ ppm: 0.795-0.852 (m, 6H), 1.121-1.166 (m, 7H), 1.220-1.240 (m, 13H), 1.302-1.139 (m, 4H), 1.341-1.361 (m, 4H), 1.847 (m, 2H), 1.975 (s, 2H), 2.078-2.334 (s, 2H), 2.970-3.018 (m, 2H), 3.036-3.142 (m, 4H), 3.330-3.380 (m, 2H), 3.539-3.684 (m, 1H), 3.726-3.841 (m, 1H), 4.489-4.545 (m, 1H), 4.673-7.721 (m, 1H), 4.797-4.833 (m, 1H), 7.055-7.074 (d, 2H), 7.121-7.219 (m, 4H), 7.237-7.289 (m, 4H), 7.585-7.606 (d, 2H), 7.858-7.878 (d, 2H), 8.078 (m, 1H), 8.196-8.217 (d, J=8.4 Hz, 1H), 8.290-8.299 (d, J=3.6 Hz, 1H), 8.424-8.481 (m, 2H).

Synthesis of (3S,4S)-1-(4-(1-((S)-3-(hexylamino)-2-octanamido-3-oxopropyl)-1H-1,2,3-triazol-4-yl)benzoyl)-N3,N4-bis((1S,2R)-2-phenylcyclopropyl)pyrrolidine-3,4-dicarboxamide, Compound 219

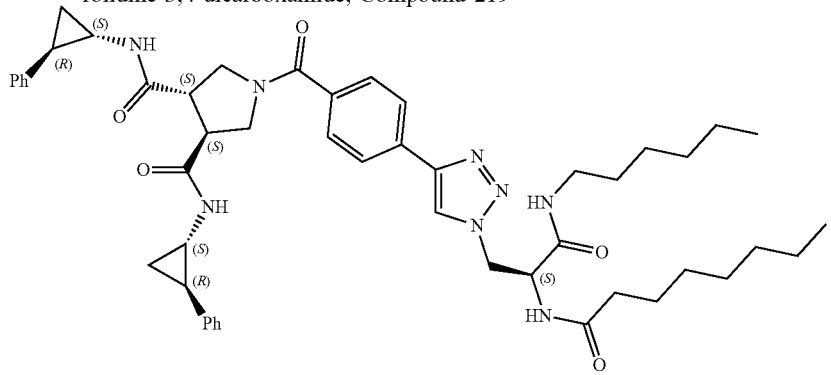

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude final product was purified using Prep HPLC Method 1 to give (3S,4S)-1-(4-(1-((S)-3-(hexylamino)-2-octanamido-3-oxopropyl)-1H-1,2,3-triazol-4-yl)benzoyl)-N3,N4-bis((1S,2R)-2-phenylcyclopropyl)pyrrolidine-3,4-dicarboxamide (Compound 219) as a white solid. (0.215 g, 32.7%) LCMS (Method-J): 100% (RT: 4.070, 263.0 nm) (MS: ESI +ve 857.9 [M+H]). $^1$H NMR: (400 MHz, DMSO) δ ppm: 0.77-0.82 (m, 6H), 1.11-1.16 (m, 19H), 1.32-1.37 (m, 4H), 1.84-1.97 (m, 2H), 2.05-2.09 (m, 2H), 2.77-2.97 (m, 2H), 2.97-3.38 (m, 4H), 3.50-3.53 (m, 2H), 3.67-3.72 (t, 1H), 3.78-3.84 (t, 1H), 4.48-4.54 (m, 1H), 4.67-4.72 (m, 1H), 4.79-4.85 (m, 1H), 7.05-7.07 (d, J=7.2 Hz, 2H), 7.12-7.18 (m, 3H), 7.21-7.28 (m, 4H), 7.58-7.60 (d, J=7.6 Hz, 2H), 7.85-7.87 (d, J=8 Hz, 2H), 8.08-8.11 (t, 1H), 8.22-8.24 (d, J=8.8 Hz, 1H), 8.30-3.31 (d, J=3.6 Hz, 1H), 8.44-8.48 (t, 2H).

Synthesis of (3S,4S)-1-(4-(1-((S)-2-(3-heptylureido)-3-(hexylamino)-3-oxopropyl)-1H-1,2,3-triazol-4-yl)benzoyl)-N3,N4-bis((1S,2R)-2-phenylcyclopropyl)pyrrolidine-3,4-dicarboxamide, Compound 220

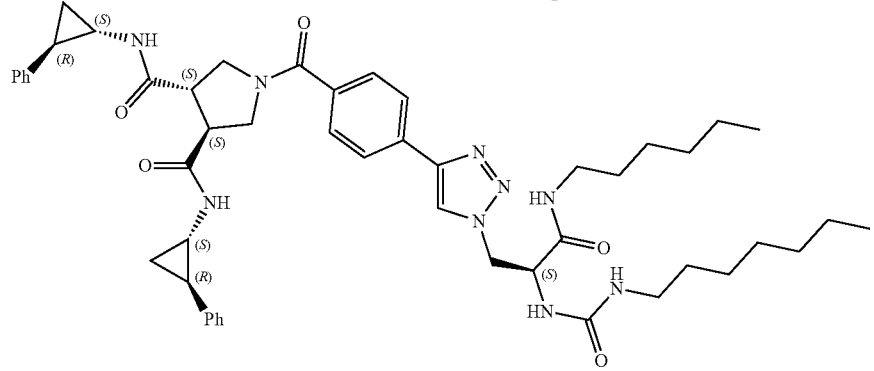

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude final product was purified using Prep HPLC Method 10 to give (3S,4S)-1-(4-(1-((S)-2-(3-heptylureido)-3-(hexylamino)-3-oxopropyl)-1H-1,2,3-triazol-4-yl)benzoyl)-N3,N4-bis((1S,2R)-2-phenylcyclopropyl)pyrrolidine-3,4-dicarboxamide (Compound 220), as a white solid. (0.035 g, 8.37%) LCMS (Method-C-Fast): 100% (RT: 1.877, 202.0 nm) (MS: ESI +ve 872.9 [M+H]).

$^1$H NMR: (400 MHz, DMSO) δ ppm: 0.77-0.85 (m, 6H), 1.09-1.29 (m, 23H), 1.84-1.97 (m, 2H), 2.78-2.85 (m, 2H), 2.92-2.98 (m, 7H), 3.52-3.54 (m, 2H), 3.69-3.81 (m, 2H), 4.57-4.69 (m, 3H), 6.35-6.32 (m, 2H), 7.05-7.07 (d, J=7.2 Hz, 2H), 7.12-7.18 (m, 4H), 7.21-7.28 (m, 4H), 7.58-7.60 (d, J=8 Hz, 2H), 7.86-7.88 (d, J=7.6 Hz, 2H), 8.09-8.12 (t, 1H), 8.33-8.47 (m, 3H).

Synthesis of (3S,4S)-1-(4-(1-((S)-3-(hexylamino)-2-(3-octylureido)-3-oxopropyl)-1H-1,2,3-triazol-4-yl) benzoyl)-N3,N4-bis((1S,2R)-2-phenylcyclopropyl) pyrrolidine-3,4-dicarboxamide, Compound 221

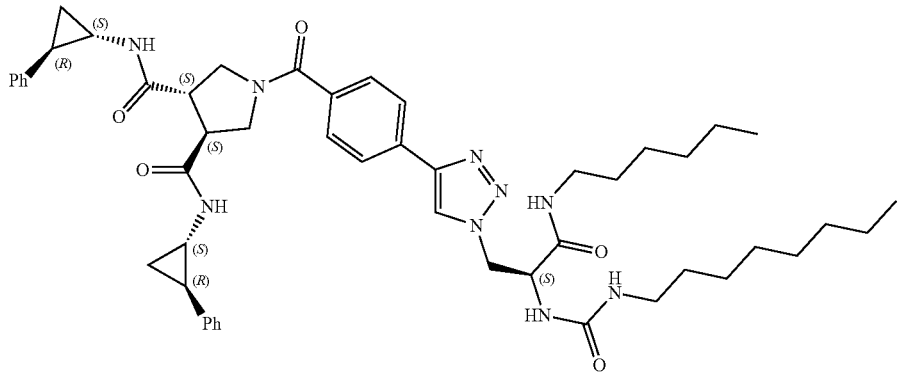

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude final product was purified using Prep HPLC Method 10 to give (3S,4S)-1-(4-(1-((S)-3-(hexylamino)-2-(3-octylureido)-3-oxopropyl)-1H-1,2,3-triazol-4-yl)benzoyl)-N3,N4-bis((1S,2R)-2-phenylcyclopropyl)pyrrolidine-3,4-dicarboxamide (Compound 221), as a white solid. (0.0065 g, 1.23%) LCMS (Method-C-Fast): 100% (RT: 1.916, 202.0 nm) (MS: ESI +ve 887.5 [M+H]).
$^1$H NMR: (400 MHz, DMSO) δ ppm: 0.78-0.85 (m, 6H), 1.09-1.29 (m, 22H), 1.978 (m, 2H), 2.67-2.78 (m, 3H), 2.92-3.12 (m, 6H), 3.20-3.35 (m, 2H), 3.54 (m, 2H), 3.69-3.75 (m, 2H), 4.57-4.63 (m, 2H), 6.34 (m, 1H), 6.43-6.45 (d, J=8 Hz, 1H), 7.05-7.18 (m, 6H), 7.21-7.26 (m, 3H), 7.58-7.60 (d, J=8 Hz, 2H), 7.86-7.88 (d, J=8 Hz, 2H), 8.13 (t, 1H), 8.39-8.53 (m, 4H).

Synthesis of (3S,4S)-1-(4-(1-((S)-3-(hexylamino)-3-oxo-2-(3-phenethylureido) propyl)-1H-1,2,3-triazol-4-yl) benzoyl)-N3,N4-bis((1S,2R)-2-phenylcyclopropyl) pyrrolidine-3,4-dicarboxamide, Compound 276

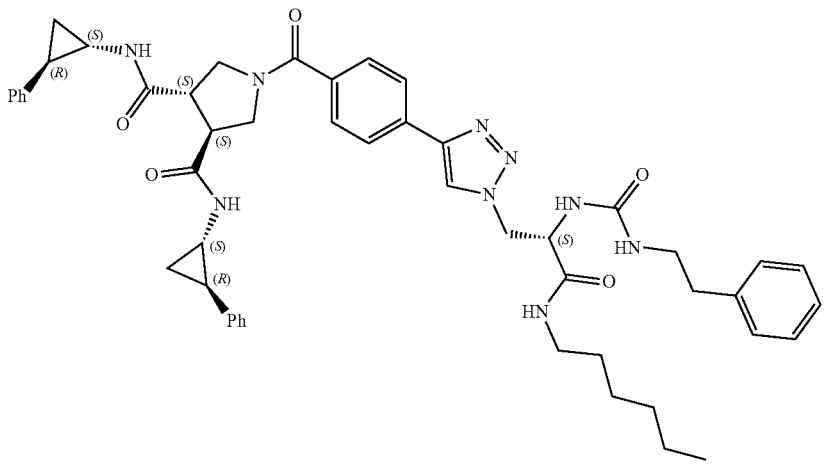

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified by flash chromatography, eluting with 3-4% MeOH:DCM, to give (3S,4S)-1-(4-(1-((S)-3-(hexylamino)-3-oxo-2-(3-phenethylureido) propyl)-1H-1,2,3-triazol-4-yl) benzoyl)-N3,N4-bis ((1S,2R)-2-phenylcyclopropyl) pyrrolidine-3,4-dicarboxamide (Compound 276), as a white solid. (0.04 g, 11.9%) LCMS (Method-C-Fast): 100% (RT: 1.570, 202.0 nm) (MS: ESI +ve 879 [M+H]). $^1$H NMR: (400 MHz, DMSO) δ ppm: 0.78-0.82 (t, 3H); 1.15-1.25 (m, 11H); 1.30 (s, 3H); 1.85 (s, 1H); 1.98 (s, 1H); 2.62-2.65 (m, 6H); 3.18-3.22 (m, 3H); 3.80-3.85 (m, 4H); 4.57-4.59 (d, J=5.2, 2H); 4.65-4.69 (t, 1H); 6.25-6.28 (t, 1H); 6.36-6.38 (d, J=8.8, 1H); 7.06-7.08 (d, J=7.2, 2H); 7.13-7.19 (m, 6H); 7.23-7.30 (m, 6H); 7.60-7.62 (d, J=8, 2H); 7.88-7.90 (d, J=8, 2H); 8.12 (s, 1H); 8.31 (s, 1H); 8.41 (s, 1H); 8.44 (s, 1H).

Synthesis of (3S,4S)-1-(4-(1-((S)-2-(3-(4-fluorophenethyl) ureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide, Compound 273

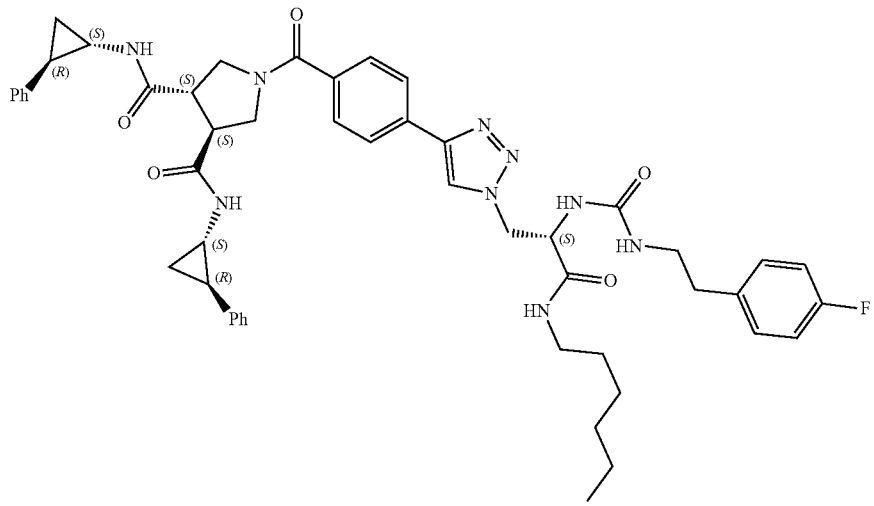

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified using Prep HPLC Method 10 to give (3S,4S)-1-(4-(1-((S)-2-(3-(4-fluorophenethyl) ureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide (Compound 273), as a white solid. (0.11 g, 33.5%) LCMS (Method-J2): 100% (RT: 4.170, 214.0 nm) (MS: ESI +ve 897 [M+H]). $^1$H NMR: (400 MHz, DMSO) δ ppm: 0.78-0.81 (t, 3H); 1.10-1.30 (m, 14H); 1.85 (s, 1H); 1.98 (s, 1H); 2.61-2.64 (m, 3H); 2.68 (s, 1H); 2.78 (s, 1H); 2.94-2.98 (m, 1H); 3.06-3.09 (m, 2H); 3.11-3.22 (m, 3H); 3.51-3.55 (t, 2H); 3.68-3.72 (t, 1H); 3.79-3.84 (t, 1H); 4.57-4.58 (d, J=5.6, 2H); 4.64-4.68 (t, 1H); 6.26-6.29 (t, 1H); 6.38-6.40 (d, J=8, 1H); 7.06-7.15 (m, 4H); 7.18-7.30 (m, 10H); 7.60-7.62 (d, J=8.4, 2H); 7.88-7.90 (d, J=8, 2H); 8.12-8.14 (t, 1H); 8.33 (s, 1H); 8.42 (s, 1H); 8.47 (s, 1H).

Synthesis of (3S,4S)-1-(4-(1-((S)-2-(3-(4-fluorobenzyl) ureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide, Compound 272

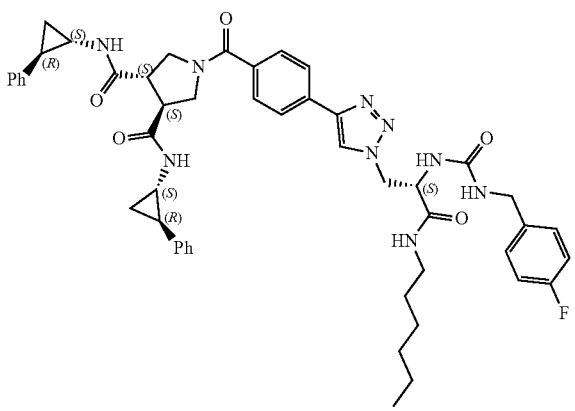

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified using Phase Prep HPLC Method 1 to give (3S,4S)-1-(4-(1-((S)-2-(3-(4-fluorobenzyl) ureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide (Compound 272) (0.060 g, 17.6%). LCMS (Method-J2): 97.25% (RT: 4.142, 202.0 nm) (MS: ESI +ve 883 [M+H]). ¹H NMR: (400 MHz, DMSO) δ ppm: 0.79-0.82 (t, 4H); 1.12-1.31 (m, 15H); 1.85 (s, 1H); 1.98 (s, 1H); 2.78 (s, 1H); 2.86 (s, 1H); 2.97-3.00 (m, 2H); 3.04-3.09 (m, 3H); 3.13-3.18 (m, 2H); 3.51-3.58 (m, 2H); 3.69-3.73 (m, 2H); 4.15-4.19 (m, 2H); 4.57-4.70 (m, 3H); 6.45-6.47 (d, J=8, 1H); 6.72-6.75 (t, 1H); 7.01-7.30 (m, 15H); 7.60-7.62 (d, J=8, 2H); 7.88-7.90 (d, J=8, 2H); 8.17 (s, 1H); 8.32 (s, 1H); 8.44 (s, 2H).

Synthesis of (3S,4S)-1-(4-(1-((S)-3-(hexylamino)-3-oxo-2-(3-(4-(trifluoromethyl) phenethyl) ureido) propyl)-1H-1,2,3-triazol-4-yl) benzoyl)-N3,N4-bis ((1S,2R)-2-phenylcyclopropyl) pyrrolidine-3,4-dicarboxamide, Compound 284

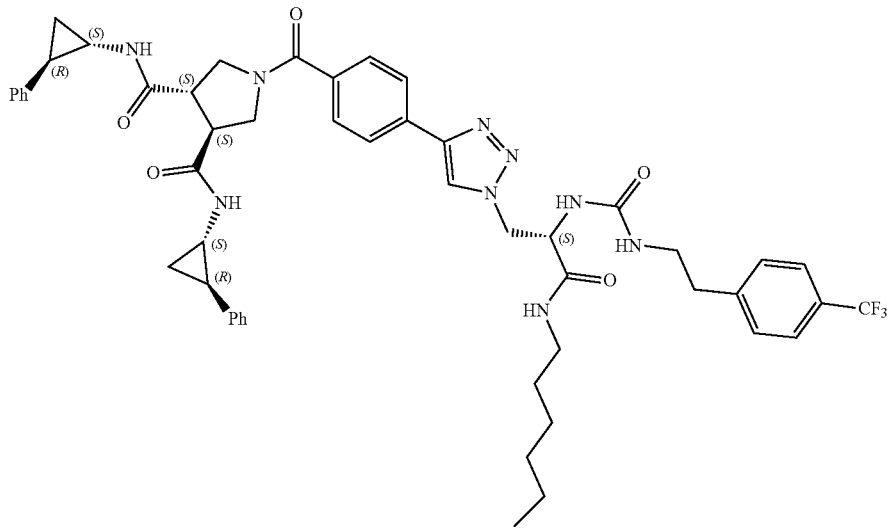

Prepared using a procedure similar to that reported or (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified using Prep HPLC Method 10 to give (3S,4S)-1-(4-(1-((S)-3-(hexylamino)-3-oxo-2-(3-(4-(trifluoromethyl) phenethyl) ureido) propyl)-1H-1,2,3-triazol-4-yl) benzoyl)-N3,N4-bis((1S, 2R)-2-phenylcyclopropyl) pyrrolidine-3,4-dicarboxamide (Compound 284), as a white solid. (0.033 g, 12.05%) LCMS (Method-J2): 100% (RT: 4.351, 202.0 nm) (MS: ESI +ve 948 [M+H]). ¹H NMR: (400 MHz, DMSO) δ ppm: 1.11 (s, 6H); 1.33 (s, 4H); 1.85 (s, 1H); 1.98 (s, 1H); 2.08 (s, 1H); 2.68-2.78 (m, 4H); 2.99-3.12 (m, 4H); 3.22-3.36 (t, 3H); 3.54 (s, 3H); 3.79-3.81 (d, J=9.2, 3H); 4.49-4.83 (m, 4H); 6.44-6.46 (d, J=6.8, 1H); 7.06-7.27 (m, 11H); 7.39-7.40 (d, J=7.2, 1H); 7.59-7.61 (d, J=6.8, 3H); 7.86-7.88 (d, J=6.8, 2H); 8.14 (s, 1H); 8.28-8.50 (m, 5H).

Synthesis of (3S,4S)-1-(4-(1-((S)-3-(hexylamino)-3-oxo-2-(3-(4-(trifluoromethyl) benzyl) ureido) propyl)-1H-1,2,3-triazol-4-yl) benzoyl)-N3,N4-bis((1S,2R)-2-phenylcyclopropyl) pyrrolidine-3,4-dicarboxamide, Compound 283

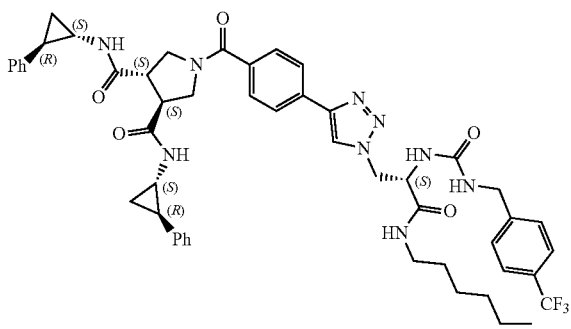

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide, (Compound 185). The crude product was purified using Prep HPLC Method 10 to give (3S,4S)-1-(4-(1-((S)-2-(3-(4-fluorophenethyl) ureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide (Compound 283), as a white solid. (0.057 g, 21.12%) LCMS (Method-C_Fast): 95.4% (RT: 1.667, 202.0 nm) (MS: ESI +ve 933 [M+H]). $^1$H NMR: (400 MHz, DMSO) δ ppm: 0.79-0.82 (t, 3H); 1.08-1.18 (m, 11H); 1.30 (s, 3H); 1.85 (s, 1H); 1.98 (s, 1H); 2.78 (s, 3H); 3.04-3.12 (m, 4H); 3.51-3.57 (m, 3H); 3.68-3.73 (t, 1H); 3.79-3.84 (t, 1H); 4.26-4.29 (t, 2H); 4.58-4.62 (t, 3H); 6.59-6.61 (d, J=8, 1H); 6.87-6.90 (t, J=8, 2H); 7.06-7.08 (d, J=7.2, 4H); 7.13-7.17 (m, 4H); 7.37-7.39 (d, J=8, 2H); 7.58-7.62 (t, 4H); 7.89-7.91 (d, J=8, 2H); 8.16-8.19 (t, 1H); 8.33 (s, 1H); 8.47 (s, 2H).

Synthesis of (3S,4S)-1-(4-(1-((S)-2-(3-benzylureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide, Compound 282

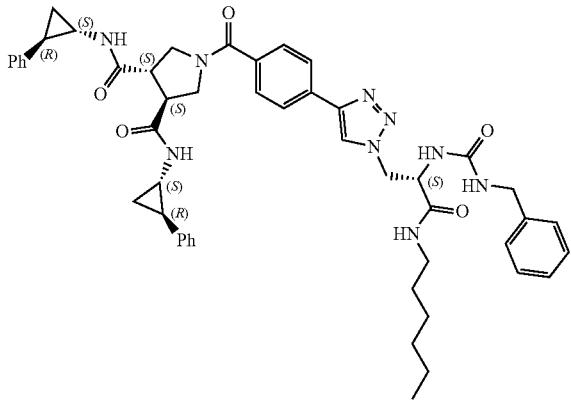

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified using Prep HPLC Method 10 to give (3S,4S)-1-(4-(1-((S)-2-(3-benzylureido)-3-(hexylamino)-3-oxopropyl)-1H-1,2,3-triazol-4-yl) benzoyl)-N3,N4-bis((1S,2R)-2-phenylcyclopropyl) pyrrolidine-3,4-dicarboxamide (Compound 282), as a white solid (0.031 g, 18.61%) LCMS (Method-C_Fast): 98.6% (RT: 1.474, 202.0 nm) (MS: ESI +ve 865 [M+H]). $^1$H NMR: (400 MHz, DMSO) δ ppm: 0.79-0.86 (t, 3H); 1.16 (m, 12H); 1.85 (s, 1H); 1.98 (s, 1H); 2.86 (s, 2H); 2.98-3.01 (m, 3H); 3.20-3.23 (d, J=8.4, 1H); 3.51-3.56 (t, 2H); 3.71 (s, 1H); 3.80-3.85 (t, 1H); 4.14-4.26 (m, 2H); 4.59-4.72 (t, 3H); 6.47-6.49 (d, J=8 1H); 6.73 (s, 1H); 7.06-7.28 (m, 15H); 7.60-7.62 (d, J=7.6, 2H); 7.88-7.90 (d, J=8, 2H); 8.18 (s, 1H); 8.35 (s, 1H); 8.44 (s, 2H).

Synthesis of (3S,4S)-1-(4-(1-((S)-3-(hexylamino)-3-oxo-2-(3-((1S,2R)-2-phenylcyclopropyl) ureido) propyl)-1H-1,2,3-triazol-4-yl) benzoyl)-N3,N4-bis ((1S,2R)-2-phenylcyclopropyl) pyrrolidine-3,4-dicarboxamide, Compound 281

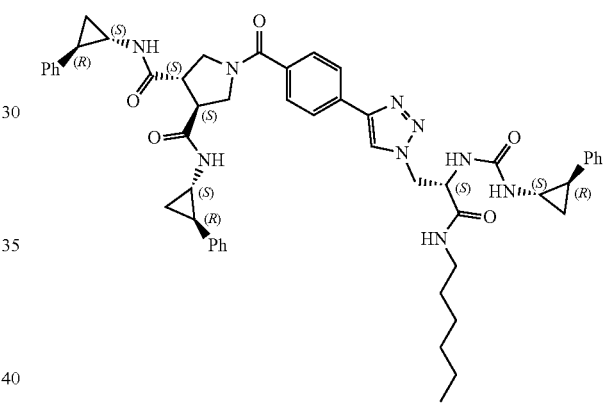

Prepared using a procedure similar to that reported for (3S,4S)-1-(4-(1-((S)-2-heptanamido-3-(hexylamino)-3-oxopropyl)-1H-1, 2, 3-triazol-4-yl) benzoyl)-N3,N4-bis ((1S, 2R)-2-phenylcyclopropyl) pyrrolidine-3,4-dicarboxamide (Compound 185). The crude product was purified using Prep HPLC Method 10 to give (3S,4S)-1-(4-(1-((S)-3-(hexylamino)-3-oxo-2-(3-((1S,2R)-2-phenylcyclopropyl) ureido) propyl)-1H-1,2,3-triazol-4-yl) benzoyl)-N3,N4-bis((1S, 2R)-2-phenylcyclopropyl) pyrrolidine-3,4-dicarboxamide (Compound 281), as a white solid (0.07 g, 29.9%). LCMS (Method-C_Fast): 100% (RT: 1.628, 202.0 nm) (MS: ESI +ve 891 [M+H]). $^1$H NMR: (400 MHz, DMSO) δ ppm: 0.78-0.81 (t, 5H); 1.09-1.16 (m, 10H); 1.25 (s, 1H); 1.35 (s, 2H); 1.57-1.69 (m, 1H); 1.85 (s, 1H); 1.97-1.98 (d, J=6, 1H); 2.65-2.68 (m, 1H); 2.79 (s, 1H); 2.86 (s, 1H); 2.98-3.01 (m, 2H); 3.04-3.13 (m, 2H); 3.13-3.22 (m, 1H); 3.45-3.55 (m, 3H); 3.66-3.68 (m, 1H); 3.79-3.85 (m, 2H); 4.57-4.64 (m, 2H); 4.65-4.68 (t, 1H); 6.19-6.24 (m, 1H); 7.06-7.08 (d, J=7.2, 2H); 7.11-7.19 (m, 7H); 7.21-7.30 (m, 5H); 7.57-7.61 (t, 2H); 7.87-7.89 (d, J=8, 2H); 8.12-8.15 (t, 1H); 8.32 (s, 1H); 8.37 (s, 1H); 8.43-8.45 (d, J=8.8, 2H).

Synthesis of (3S,4S)-1-(4-(1-(2-heptanamido-3-(hexylamino)-3-oxopropyl)-1H-imidazol-4-yl)benzoyl)-N3,N4-bis((1S,2R)-2-phenylcyclopropyl)pyrrolidine-3,4-dicarboxamide, Compound 214

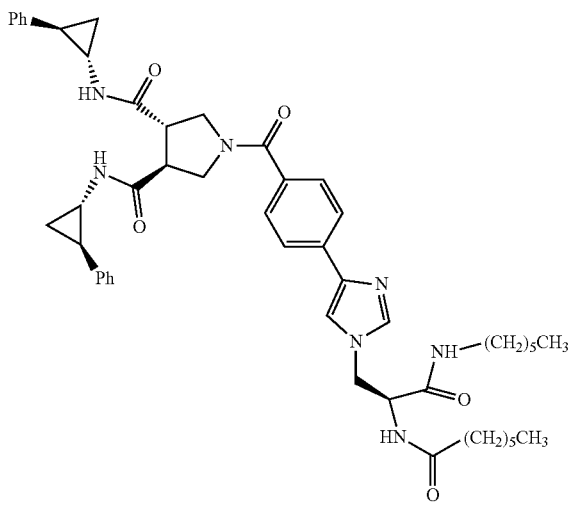

Step-1: Preparation of methyl 4-(2-bromoacetyl)benzoate

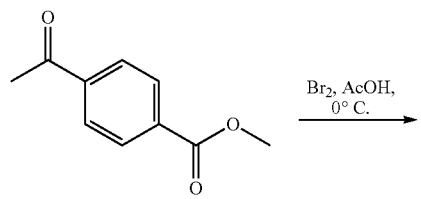

Bromine (1.48 mL, 28.0 mmol) was added dropwise at 0° C. to a solution of methyl 4-acetylbenzoate (5.0 g, 28.0 mmol) in acetic acid (50 mL). The reaction mixture was stirred for 1 h. The volatiles were removed under reduced pressure. Saturated aqueous sodium bicarbonate (100 mL) was added and the mixture was extracted with EtOAc (2×100 mL). The organic layer was dried over sodium sulfate and concentrated. The crude product was purified by flash chromatography, eluting with 20% ethyl acetate in hexane, to give methyl 4-(2-bromoacetyl) benzoate (6.2 g, 86%). $^1$H NMR: (400 MHz, DMSO) δ ppm: 3.91 (s, 3H), 5.01 (s, 2H), 8.07-8.15 (m, 4H).

Step-2: Preparation of methyl 4-(1H-imidazol-4-yl)benzoate

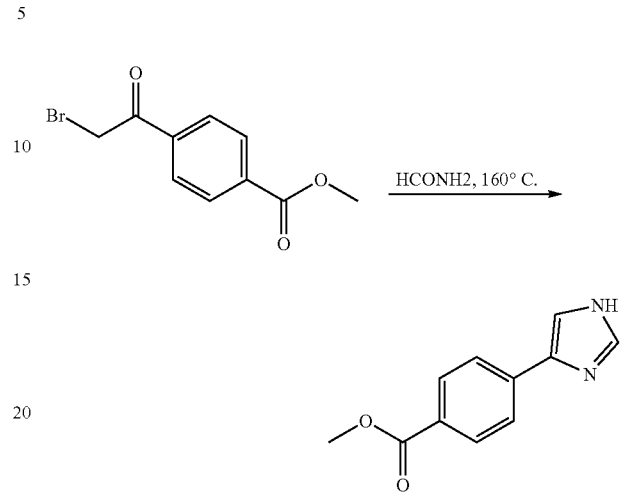

Methyl 4-(2-bromoacetyl) benzoate (4.3 g, 16.7 mmol) and formamide (45 mL) were heated at 160° C. for 2 h. The reaction mixture was diluted with water (100 mL) and extracted with EtOAc (2×100 mL). The organic phase was dried over sodium sulfate and concentrated. The crude product was purified by flash chromatography, eluting with 50-70% EtOAc in hexane, to give methyl 4-(1H-imidazol-4-yl) benzoate (0.890 g, 26%). LCMS (Method-H): 100% (RT: 2.213, 214.0 nm) (MS: ESI +ve 203.0[M+1]).

Step-3: Preparation of 4-(1H-imidazol-4-yl)benzoic acid

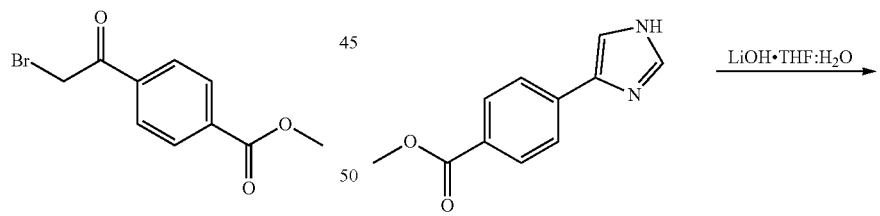

Prepared using General Ester Hydrolysis Procedure to give 4-(1H-imidazol-4-yl)benzoic acid as a white solid (0.52 g, 65%). LCMS (Method-C Fast): 100% (RT: 0.288, 254.0 nm) (MS: ESI +ve 189.2[M+1]).

Step-4: Preparation of (3S,4S)-1-(4-(1H-imidazol-4-yl)benzoyl)-N3,N4-bis((1S,2R)-2-phenylcyclopropyl)pyrrolidine-3,4-dicarboxamide

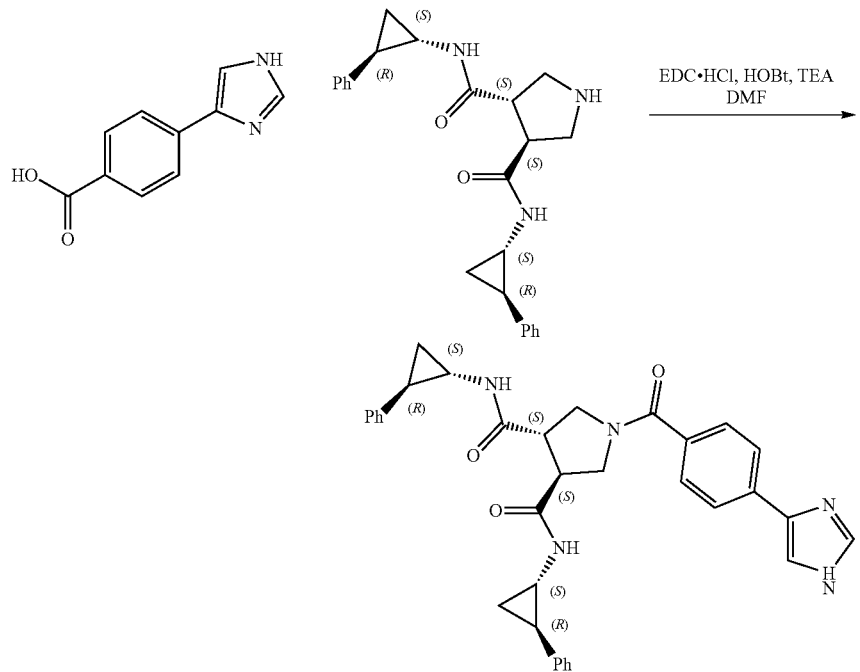

Prepared using General EDC, HOBT Coupling Procedure. The crude product was purified by flash chromatography, eluting with 0-5% MeOH:DCM, to give (3S,4S)-1-(4-(1H-imidazol-4-yl)benzoyl)-N3,N4-bis((1S,2R)-2-phenylcyclopropyl)pyrrolidine-3,4-dicarboxamide (0.7 g, 46%) as a white solid. LCMS (Method-C2): 92% (RT: 1.118, 264.0 nm) (MS: ESI +ve 560.4[M+H]).

Step-5: Preparation of methyl (S)-3-(4-(4-(((3S,4S)-3,4-bis(((1S,2R)-2-phenylcyclopropyl)carbamoyl)pyrrolidine-1-carbonyl)phenyl)-1H-imidazol-1-yl)-2-((tert-butoxycarbonyl)amino)propanoate

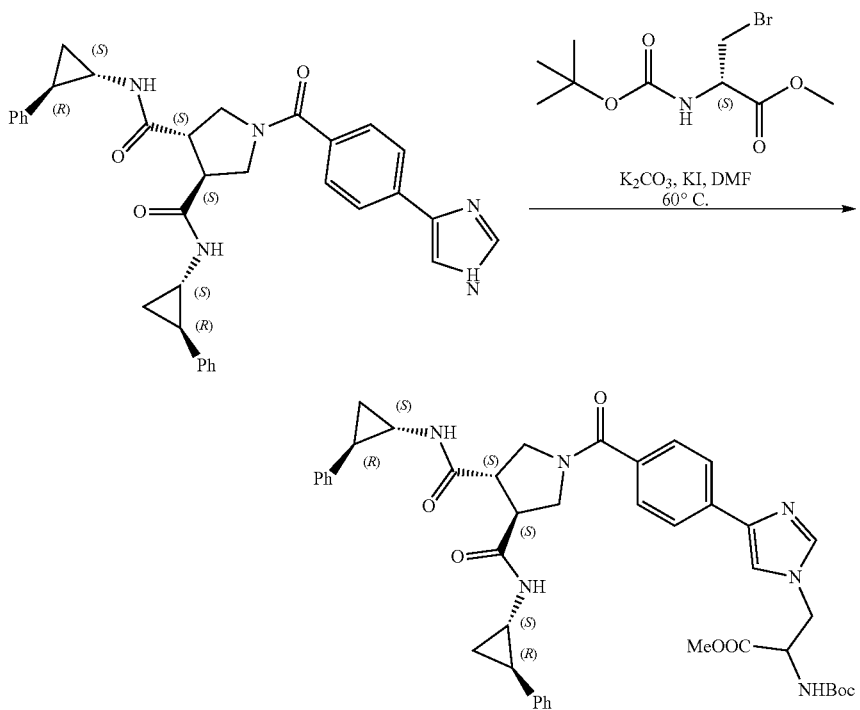

(3S,4S)-1-(4-(1H-imidazol-4-yl)benzoyl)-N3,N4-bis
((1S,2R)-2-phenylcyclopropyl)pyrrolidine-3,4-dicarboxamide (0.8 g, 1.47 mmol), methyl (S)-3-bromo-2-((tert-butoxycarbonyl)amino)propanoate (0.483 g, 1.78 mmol), potassium carbonate (0.392 g, 2.85 mmol) and potassium iodide (0.024 g, 0.147 mmol) in DMF (2.0 mL) was heated at 60° C. for 24 h. The reaction mixture was diluted with water (100 mL) and extracted with ethyl acetate (2×100 mL). The organic phase was dried over sodium sulfate and concentrated. The crude product was purified by flash chromatography, eluting with 0-7% MeOH:DCM, to give methyl (S)-3-(4-(4-((3S,4S)-3,4-bis(((1S,2R)-2-phenylcyclopropyl)carbamoyl)pyrrolidine-1-carbonyl)phenyl)-1H-imidazol-1-yl)-2-((tert-butoxycarbonyl)amino)propanoate (0.2 g, 18%) as semisolid. LCMS (Method-C2): 65.70% (RT 1.246, 270.0 nm) (MS: ESI +ve 761.7[(M+H]).

Step-6: Preparation of (S)-3-(4-(4-((3S,4S)-3,4-bis
(((1S,2R)-2-phenylcyclopropyl)carbamoyl)pyrrolidine-1-carbonyl)phenyl)-1H-imidazol-1-yl)-2-((tert-butoxycarbonyl)amino)propanoic acid

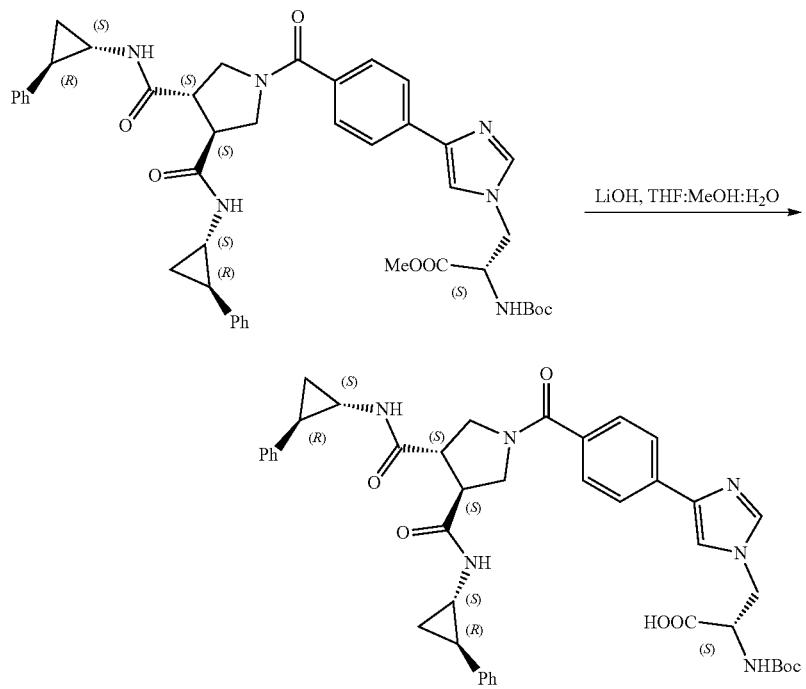

Prepared using General Ester Hydrolysis Procedure to give (S)-3-(4-(4-((3S,4S)-3,4-bis(((1S,2R)-2-phenylcyclopropyl)carbamoyl)pyrrolidine-1-carbonyl)phenyl)-1H-imidazol-1-yl)-2-((tert-butoxycarbonyl)amino)propanoic acid as a white solid (0.170 g, 86%). LCMS (Method-C2): 72.19% (RT: 1.208, 266.0 nm) (MS: ESI +ve 747.1[M+1]).

Step-7: Preparation of tert-butyl ((S)-3-(4-(4-((3S,4S)-3,4-bis(((1S,2R)-2-phenylcyclopropyl)carbamoyl)pyrrolidine-1-carbonyl)phenyl)-1H-imidazol-1-yl)-1-(hexylamino)-1-oxopropan-2-yl)carbamate

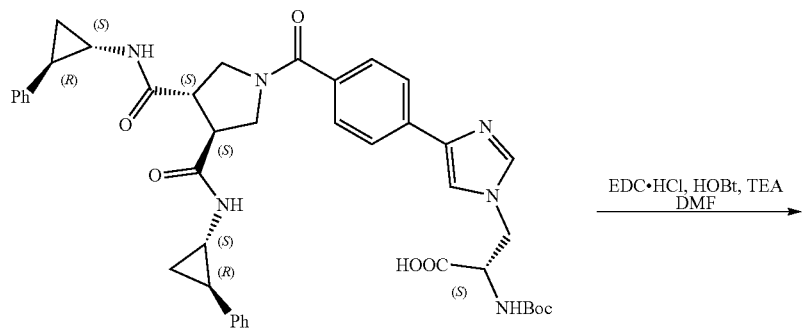

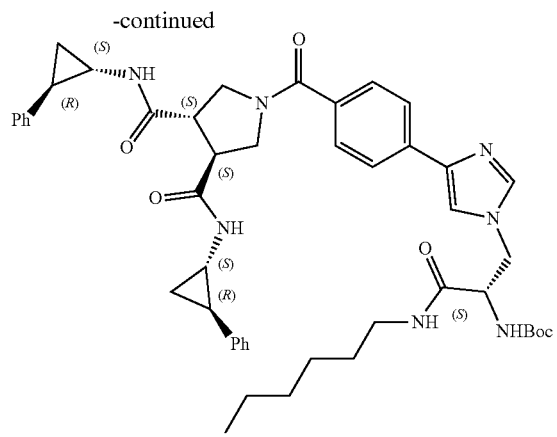

Prepared using General EDC, HOBT Coupling Procedure. The crude product was purified by flash chromatography, eluting with 0-5% MeOH:DCM, to give tert-butyl ((S)-3-(4-(4-((3S,4S)-3,4-bis(((1S,2R)-2-phenylcyclopropyl)carbamoyl)pyrrolidine-1-carbonyl)phenyl)-1H-imidazol-1-yl)-1-(hexylamino)-1-oxopropan-2-yl)carbamate (0.09 g, 40%) LCMS (Method-C2): 84.12% (RT: 1.301, 274.0 nm) (MS: ESI +ve 831.3[M+H]).

Step-8: Preparation of (3S,4S)-1-(4-(1-((S)-2-amino-3-(hexylamino)-3-oxopropyl)-1H-imidazol-4-yl)benzoyl)-N3,N4-bis((1S,2R)-2-phenylcyclopropyl)pyrrolidine-3,4-dicarboxamide

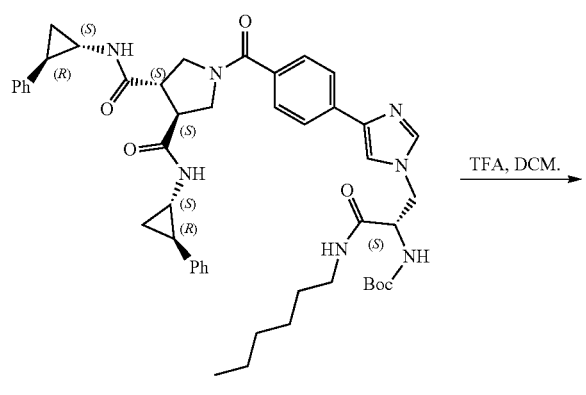 TFA, DCM.

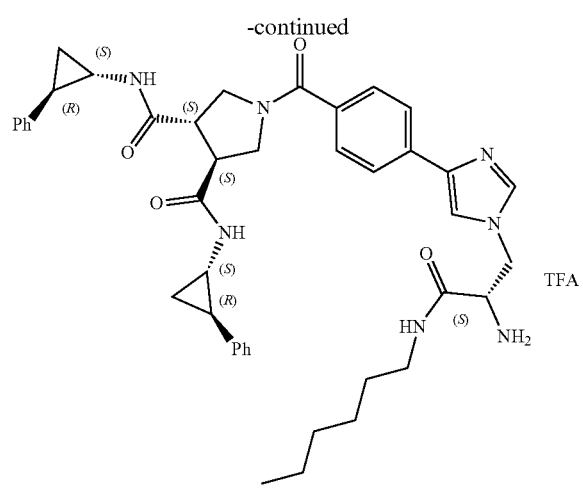

Prepared using General BOC Deprotection Procedure to give (3S,4S)-1-(4-(1-((S)-2-amino-3-(hexylamino)-3-oxopropyl)-1H-imidazol-4-yl)benzoyl)-N3,N4-bis((1S,2R)-2-phenylcyclopropyl)pyrrolidine-3,4-dicarboxamide as its TFA salt (0.13 g) LCMS (Method-C2): 85% (RT: 1.146, 274.0 nm) (MS: ESI +ve 731.2[M+H]).

Step-9: Preparation of (3S,4S)-1-(4-(1-((S)-2-heptanamido-3-(hexylamino)-3-oxopropyl)-1H-imidazol-4-yl)benzoyl)-N3,N4-bis((1S,2R)-2-phenylcyclopropyl)pyrrolidine-3,4-dicarboxamide

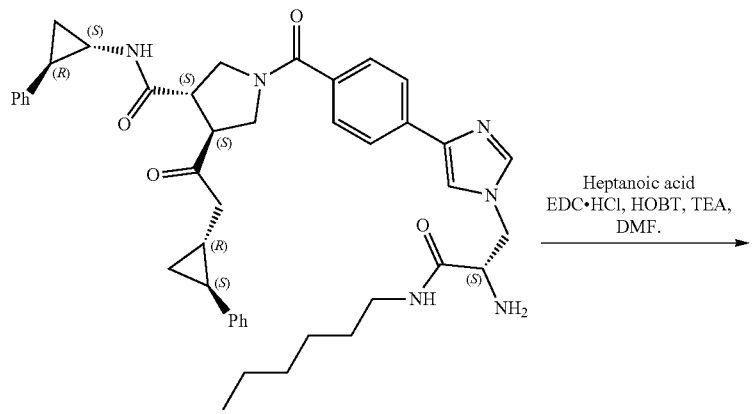 Heptanoic acid EDC·HCl, HOBT, TEA, DMF.

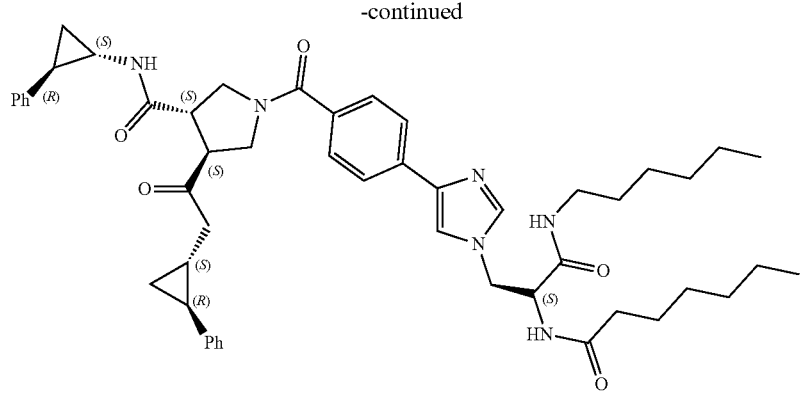

Prepared using General EDC, HOBT Coupling Procedure. The crude was purified by Prep HPLC Method 13 to give (3S,4S)-1-(4-(1-((S)-2-heptanamido-3-(hexylamino)-3-oxopropyl)-1H-imidazol-4-yl)benzoyl)-N3,N4-bis((1S,2R)-2-phenylcyclopropyl)pyrrolidine-3,4-dicarboxamide (Compound 214)(0.034 g, 24%), as an off white solid. LCMS (Method-J): 99.13% (RT 3.913, 270.0 nm) (MS: ESI +ve 843.8 [M+H]). $^1$H NMR: (400 MHz, DMSO) δ ppm: 0.76-0.85 (m, 6H), 1.11-1.23 (m, 17H), 1.35-1.36 (m, 4H), 1.85 (bs, 1H), 1.95-1.97 (m, 1H), 2.07-2.10 (m, 2H), 2.79-2.86 (m, 2H), 3.01-3.11 (m, 3H), 3.17-3.21 (m, 1H), 3.49-3.56 (m, 2H), 3.69-3.80 (m, 2H), 4.09-4.12 (m, 1H), 4.26-4.29 (m, 1H), 4.66-4.68 (m, 1H), 7.06-7.08 (m, 2H), 7.12-7.19 (m, 4H), 7.22-7.29 (m, 4H), 7.49-7.51 (m, 2H), 7.61 (m, 2H), 7.74-7.76 (m, 2H), 8.05-8.08 (m, 1H), 8.21-8.23 (m, 1H), 8.31-8.32 (m, 1H), 8.45-8.46 (m, 1H).

Synthesis of (3S,4S)-1-(4-(2-((3S,4S)-3-methoxy-4-(3-tridecylureido)pyrrolidin-1-yl)oxazol-5-yl)benzoyl)-N3,N4-bis((1S,2R)-2-phenylcyclopropyl)pyrrolidine-3,4-dicarboxamide, Compound 234

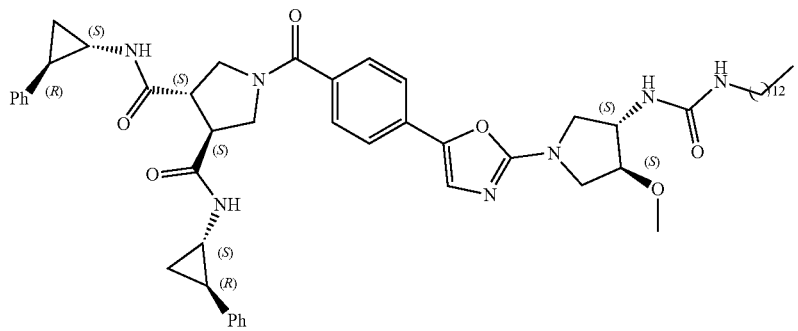

Step-1: Preparation of (tosylmethyl)carbonimidic dichloride

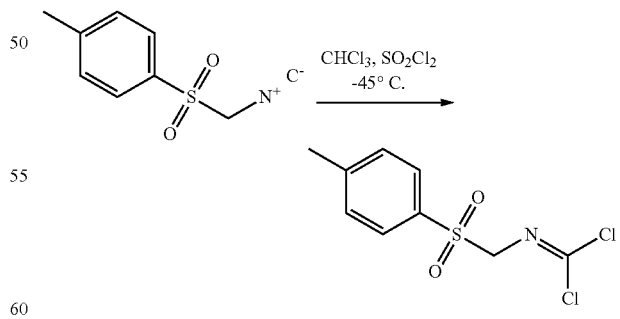

1-((isocyanomethyl)sulfonyl)-4-methylbenzene (0.140 g, 0.719 mmol) was dissolved in chloroform (2 mL) and cooled to −45° C. Sulphuryl chloride (0.097 g, 0.719 mmol) was added as a solution in chloroform (2 mL) over a period of 10 min. The mixture was stirred at room temperature then concentrated to remove the volatiles. The crude product was used in the next step.

Step-2: Preparation of methyl 4-(2-chloro-4-tosyl-4,5-dihydrooxazol-5-yl)benzoate

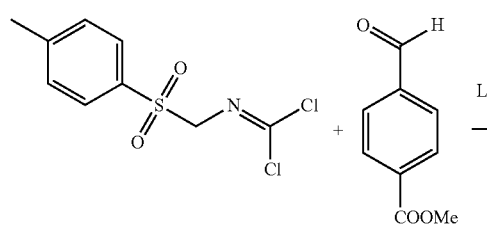

(Tosylmethyl)carbonimidic dichloride (0.4 g) was dissolved in THF (2 mL) and cooled to −79° C. Methyl 4-formylbenzoate (0.098 g, 0.6 mmol) was dissolved in THF (2 mL) and added followed by freshly prepared LDA (0.72 mL, 0.719 mmol). The reaction mixture was allowed to warm to room temperature for 16 hrs. The reaction mixture was used directly in the next step.

Step-3: Preparation of methyl 4-(2-((3S,4S)-3-methoxy-4-(3-tridecylureido)pyrrolidin-1-yl)oxazol-5-yl)benzoate

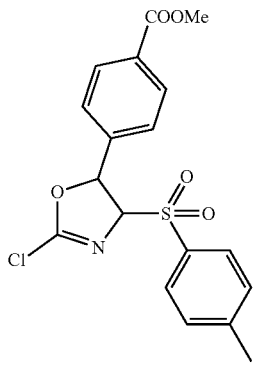

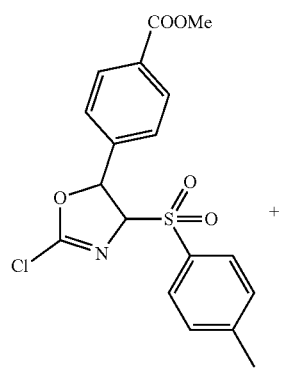

1-((3S,4S)-4-methoxypyrrolidin-3-yl)-3-tridecylurea (0.306 g, 0.9 mmol) in THF (2 mL) was added to the above reaction mixture. TEA (0.25 mL, 1.8 mmol) was added and the mixture was stirred at room temperature for 16 h. The mixture was diluted with water (50 mL) and extracted using ethyl acetate (3×50 mL), dried over sodium sulfate and concentrated. The crude was purified using by flash chromatography, eluting with MeOH: DCM, then eluting with 0-2% MeOH:DCM, to give methyl 4-(2-((3S,4S)-3-methoxy-4-(3-tridecylureido)pyrrolidin-1-yl)oxazol-5-yl)benzoate as a brown solid (0.3 g, 62.9%). LCMS (Method-C2): 86.78% (RT: 1.735, 345.0 nm) (MS: ESI +ve 543.86 [M+H]).

Step 4: Preparation of 4-(2-((3S,4S)-3-methoxy-4-(3-tridecylureido)pyrrolidin-1-yl)oxazol-5-yl)benzoic acid

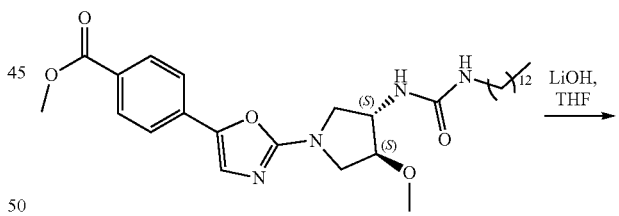

Prepared using General Ester Hydrolysis Procedure to give 4-(2-((3S,4S)-3-methoxy-4-(3-tridecylureido)pyrrolidin-1-yl)oxazol-5-yl)benzoic acid (0.27 g, 92%) LCMS (Method-C2): 86.71% (RT 1.571, 231 nm) (MS: ESI +ve 529.48 [M+H]).

Step-6: Preparation of (3S,4S)-1-(4-(2-((3S,4S)-3-methoxy-4-(3-tridecylureido)pyrrolidin-1-yl)oxazol-5-yl)benzoyl)-N3,N4-bis((1S,2R)-2-phenylcyclopropyl)pyrrolidine-3,4-dicarboxamide, Compound 234

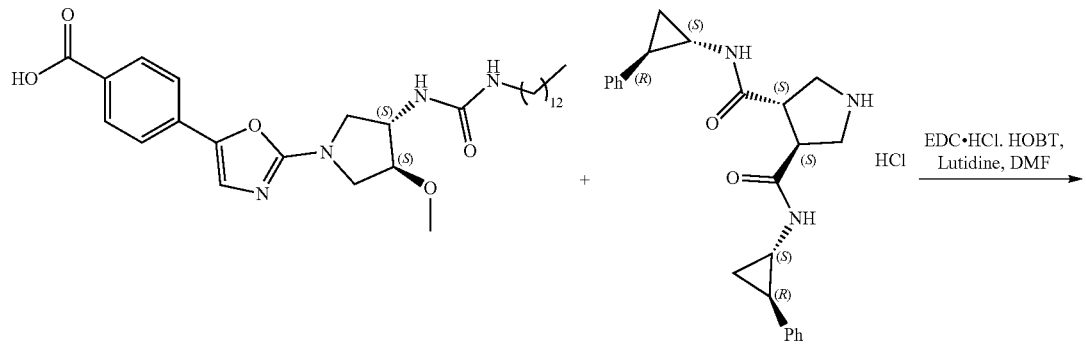

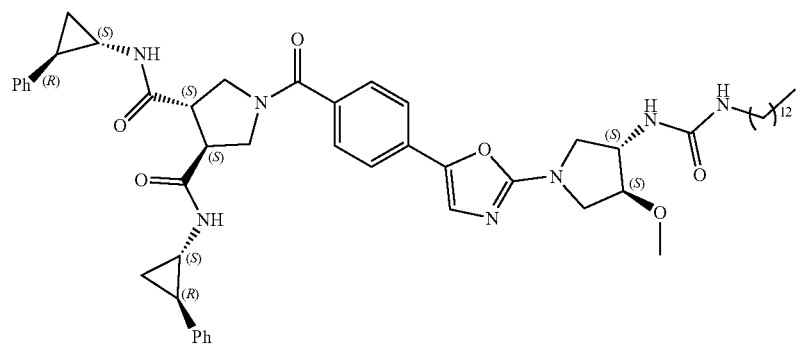

Prepared using General EDC, HOBT Coupling Procedure. The crude product was purified using Prep HPLC Method 10 to give (3S,4S)-1-(4-(2-((3S,4S)-3-methoxy-4-(3-tridecylureido)pyrrolidin-1-yl)oxazol-5-yl)benzoyl)-N3,N4-bis((1S,2R)-2-phenylcyclopropyl)pyrrolidine-3,4-dicarboxamide (Compound 234), as an off white solid (0.1 g, 18.59%). LCMS (Method-C-Fast): 100% (RT 2.377, 225.0 nm) (MS: ESI +ve 900.85 [M+H]). $^1$H NMR: (400 MHz, DMSO) δ ppm: 0.83-0.86 (m, 3H), 1.09-1.39 (m, 23H), 1.85-1.97 (m, 2H), 2.62-2.78 (m, 2H), 2.84-3.01 (m, 2H), 3.09-3.23 (m, 2H), 3.33-3.40 (m, 4H), 3.49-3.53 (m, 4H), 3.61-3.82 (m, 5H), 4.15 (m, 1H), 5.85-5.88 (t, 1H), 6.40-6.41 (d, J=6.8 Hz, 1H), 7.06-7.08 (d, J=7.2 Hz, 2H), 7.11-7.18 (m, 4H), 7.2-7.28 (m, 4H), 7.45 (s, 1H), 7.53-7.58 (m, 4H), 8.35-8.36 (d, J=3.6 Hz, 1H), 8.47-8.49 (m, 1H).

Synthesis of (3S,4S)-1-(4-(5-((3S,4S)-3-methoxy-4-(3-tridecylureido)pyrrolidin-1-yl)thiazol-2-yl)benzoyl)-N3,N4-bis((1S,2R)-2-phenylcyclopropyl)pyrrolidine-3,4-dicarboxamide, Compound 268

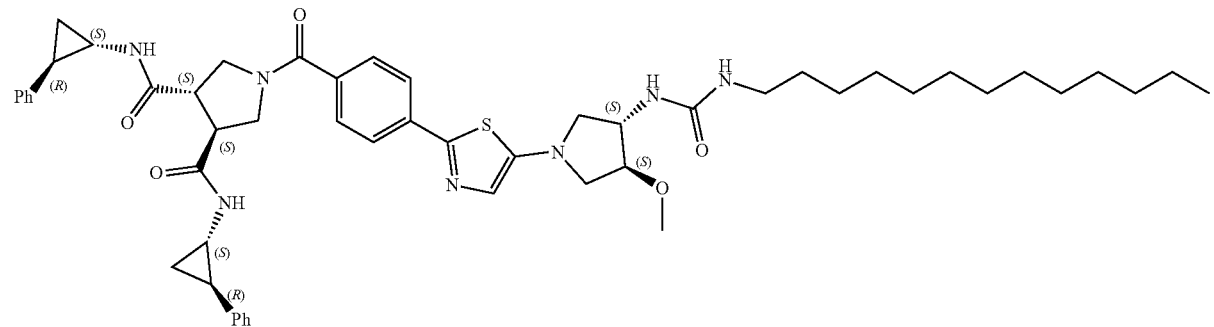

Step-1: Synthesis of tert-butyl (2-((3S,4S)-3-methoxy-4-(3-tridecylureido)pyrrolidin-1-yl)-2-oxoethyl)carbamate

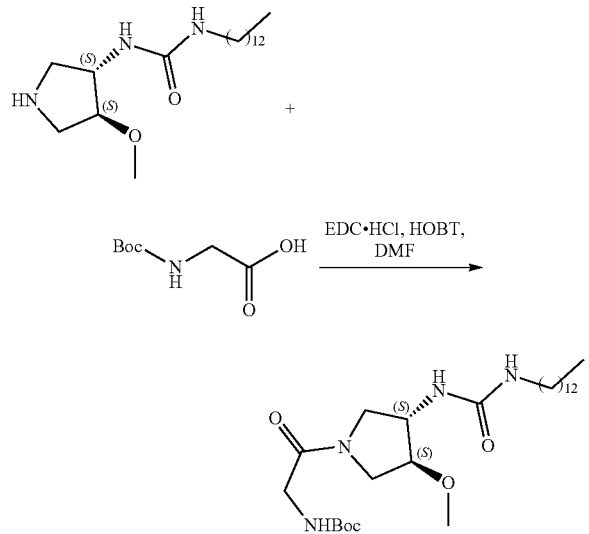

Prepared using General EDC, HOBT Coupling Procedure. The crude product was purified by flash chromatography, eluting with 5-6% MeOH:DCM, to give tert-butyl (2-((3S,4S)-3-methoxy-4-(3-tridecylureido)pyrrolidin-1-yl)-2-oxoethyl)carbamate, as an off white solid (0.5 g, 60.88%). LCMS (Method-C2): 98.10% (RT: 1.648, 202.00 nm) (MS: ESI +ve 499.7 [M+1]).

Step 2: Synthesis of 1-((3S,4S)-1-glycyl-4-methoxypyrrolidin-3-yl)-3-tridecylurea

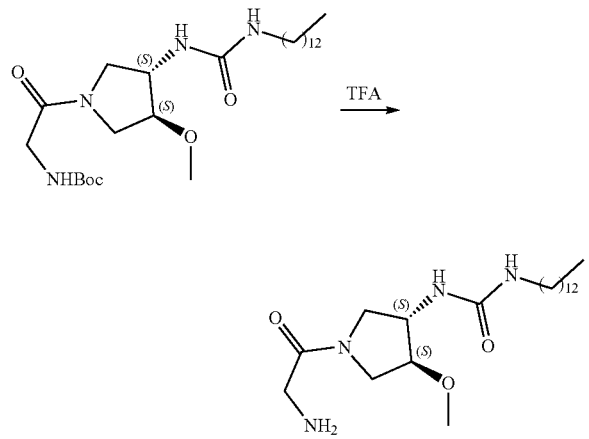

Prepared using General BOC Deprotection Procedure to give 1-((3S,4S)-1-glycyl-4-methoxypyrrolidin-3-yl)-3-tridecylurea (0.64 g, 98.88%). LCMS (Method-C2): 98.7% (RT: 3.745, 202.4 nm) (MS: ESI +ve 399.3 [M+1]).

Step-3: Preparation of methyl 4-((2-((3S,4S)-3-methoxy-4-(3-tridecylureido)pyrrolidin-1-yl)-2-oxoethyl)carbamoyl)benzoate

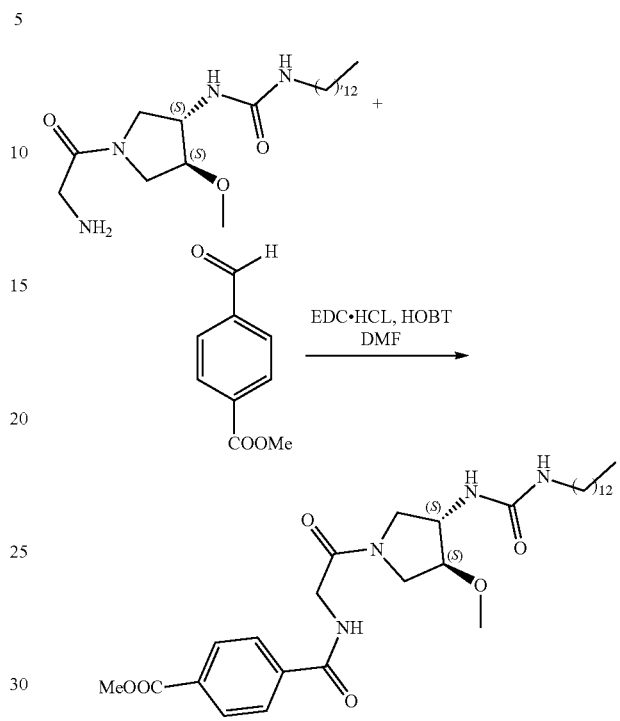

Prepared using General EDC, HOBT Coupling Procedure. The crude product was purified by flash chromatography, eluting with 5-6% MeOH:DCM, to give methyl 4-((2-((3S,4S)-3-methoxy-4-(3-tridecylureido)pyrrolidin-1-yl)2oxoethyl)carbamoyl)benzoate (0.47 g, 44.55%) LCMS (Method-C2): 100% (RT 1.584, 240.0 nm) (MS: ESI +ve 561.5 [M]).

Step-4: Synthesis of methyl 4-(5-((3S,4S)-3-methoxy-4-(3-tridecylureido)pyrrolidin-1-yl)thiazol-2-yl)benzoate

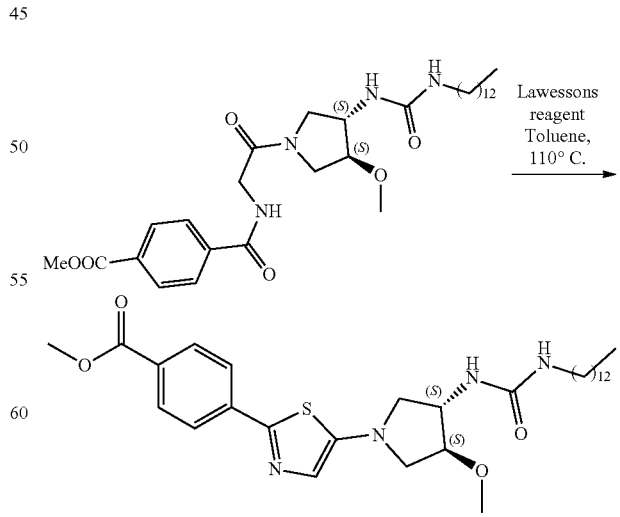

Methyl4-((2((3S,4S)3methoxy4 (3tridecylureido)pyrrolidinlyl) 2oxoethyl)carbamoyl)benzoate (0.35 g, 0.63 mmol)

was dissolved in Toluene (5 mL). Lawesson's reagent (0.252 g, 0.63) was added. The mixture was stirred at 60° C. for 6 h. The reaction mixture was then diluted with water (10 mL) and extracted with ethyl acetate (3×30 mL). The organic layer was washed with brine (2×20 mL), dried over anhydrous sodium sulfate, then concentrated. The crude product was purified by flash chromatography, eluting with 50-60% EtOAc; hexane, to give methyl 4-(5-((3S,4S)-3-methoxy-4-(3-tridecylureido)pyrrolidin-1-yl)thiazol-2-yl)benzoate, as a brown solid (0.15 g, 43.01%). LCMS (Method-C2): 50.45% (RT 1.817, 225 nm) (MS: ESI +ve 459.5 [M−100]).

Step-4: Synthesis of 4-(5-((3S,4S)-3-methoxy-4-(3-tridecylureido)pyrrolidin-1-yl)thiazol-2-yl)benzoic acid

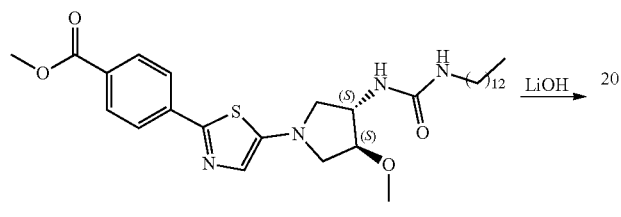

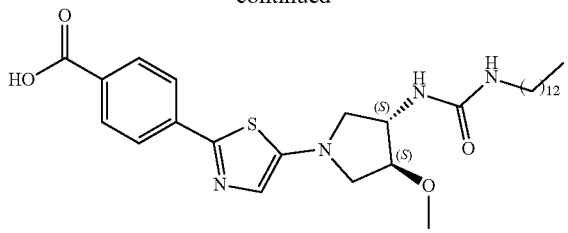

Prepared using General Ester Hydrolysis Procedure to give 4-(5-((3S,4S)-3-methoxy-4-(3-tridecylureido)pyrrolidin-1-yl)thiazol-2-yl)benzoic acid, as a brown solid (0.13 g). LCMS (Method-C2): 72.33% (RT 1.644, 202 nm) (MS: ESI +ve 543.5 [M−1]).

Step-5: Synthesis of (3S,4S)-1-(4-(5-((3S,4S)-3-methoxy-4-(3-tridecylureido)pyrrolidin-1-yl)thiazol-2-yl)benzoyl)-N3,N4-bis((1S,2R)-2-phenylcyclopropyl)pyrrolidine-3,4-dicarboxamide, Compound 268

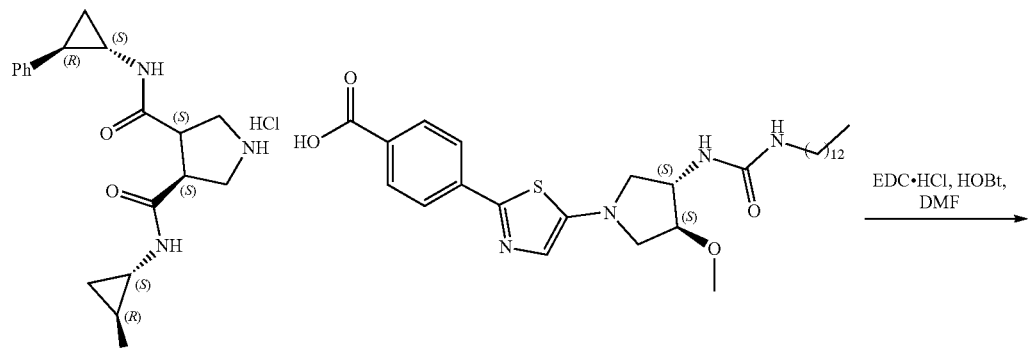

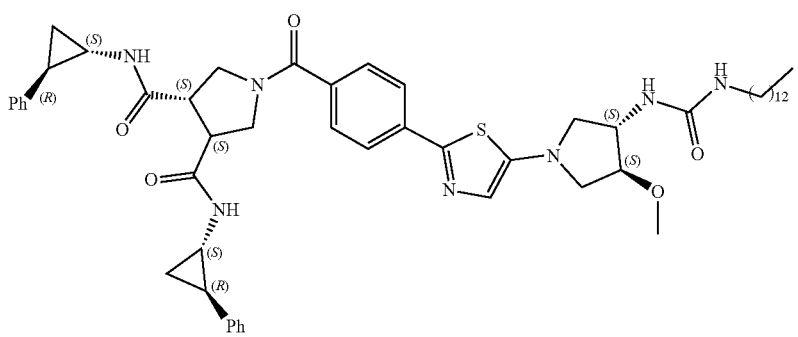

Prepared using General EDC, HOBT Coupling Procedure. The crude product was purified using Prep HPLC Method 10 to give (3S,4S)-1-(4-(5-((3S,4S)-3-methoxy-4-(3-tridecylureido)pyrrolidin-1-yl)thiazol-2-yl) benzoyl)-N3,N4-bis((1S,2R)-2-phenylcyclopropyl)pyrrolidine-3,4-dicarboxamide (Compound 268), as a yellow solid. (0.08 g, 19.07%) LCMS (Method-J2): 100% (RT: 4.781, 202.0 nm)

(MS: ESI +ve 916.1 [M+H]). $^1$H NMR (400 MHz, DMSO) δ ppm: 0.84-0.86 (d, J=8, 3H), 1.10-1.15 (m, 23H), 1.87 (bs, 1H), 1.98 (bs, 1H), 2.79-2.87 (d, 2H), 2.98-2.99 (d, J=4, 2H), 3.12-3.14 (m, 2H), 3.34-3.38 (d, J=14, 3H), 3.51-3.6 (m, 4H), 3.69-3.86 (m, 3H), 4.20 (s, 1H), 5.92 (s, 1H), 6.43-6.44 (d, J=4, 1H), 6.86 (s, 1H), 7.07-7.30 (m, 10H), 7.56-7.58 (d, J=8, 2H). 7.76-7.78 (d, J=8, 2H), 8.38 (s, 1H), 8.50 (s, 1H).

Synthesis of (3S,4S)-1-(4-(5-((3S,4S)-3-methoxy-4-(3-tridecylureido)pyrrolidin-1-yl)-1,3,4-oxadiazol-2-yl)benzoyl)-N3,N4-bis((1S,2R)-2-phenylcyclopropyl)pyrrolidine-3,4-dicarboxamide, Compound 260

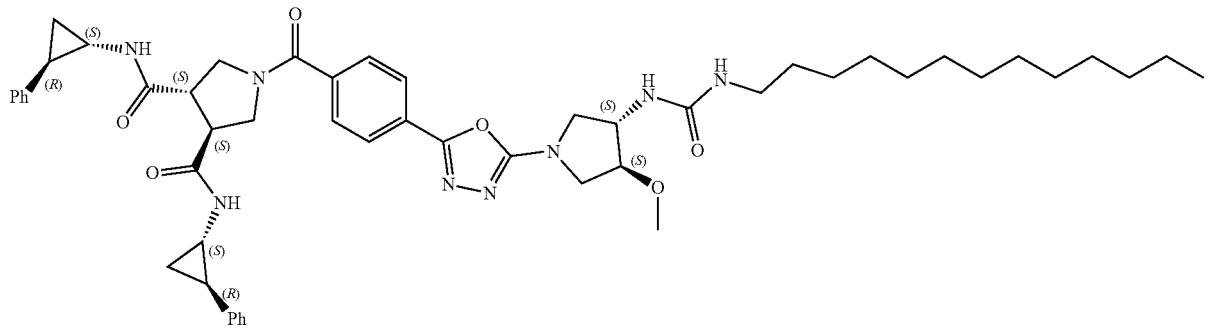

Step-1: Preparation of methyl 4-(1,3,4-oxadiazol-2-yl)benzoate

N-Isocyano-1,1,1-triphenyl-15-phosphanimine (2.0 g, 0.006 mmol) was dissolved in dry CHCl$_3$ (20 mL). 4-(Methoxycarbonyl)benzoic acid (1.2 g, 0.006 mmol) in CHCl$_3$ was added over 15 min. The mixture was stirred for 24 h then concentrated. The crude product was purified using flash chromatography, eluting with 0-40% EtOAc in hexane, to give methyl 4-(1,3,4-oxadiazol-2-yl)benzoate. (0.790 g, 58.5% yield). LCMS (Method-H): 99.2% (RT: 2.407, 254 nm) (MS: ESI +ve 204.9 [M+1]).

Step-2: Preparation of methyl 4-(2-((E)-((3S,4S)-3-methoxy-4-(3-tridecylureido) pyrrolidin-1-yl)methylene)hydrazine-1-carbonyl)benzoate

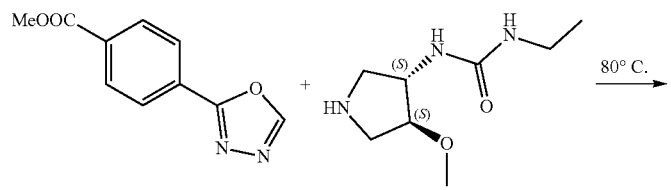

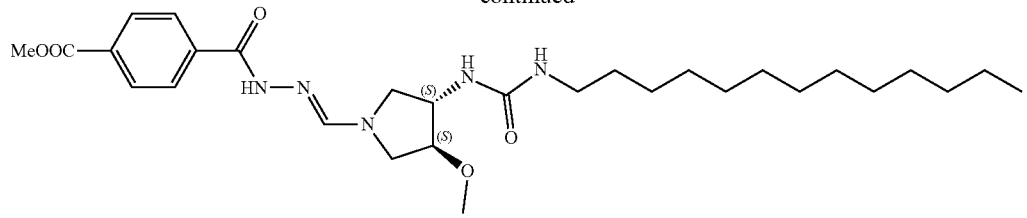

1-((3S,4S)-4-methoxypyrrolidin-3-yl)-3-tridecylurea (0.500 g, 1.470 mmol) and methyl 4-(1,3,4-oxadiazol-2-yl)benzoate (0.150 g, 0.734 mmol) were heated at 80° C. for 24 h, then cooled and diluted with DCM (20 mL) and concentrated to give methyl 4-(2-((E)-((3S,4S)-3-methoxy-4-(3-tridecylureido)pyrrolidin-1-yl)methylene)hydrazine-1-carbonyl)benzoate. (0.596 g, crude). LCMS (Method-C fast): 83% (RT: 1.956, 240 nm) (MS: ESI +ve 546.5 [M+1]).

Step-3: Preparation of methyl 4-(5-((3S,4S)-3-methoxy-4-(3-tridecylureido)pyrrolidin-1-yl)-1,3,4-oxadiazol-2-yl)benzoate

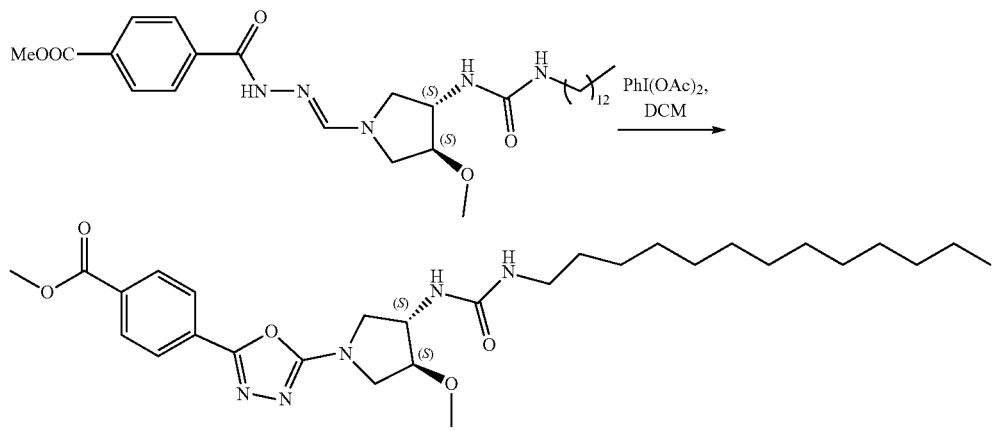

Methyl 4-(2-((E)-((3S,4S)-3-methoxy-4-(3-tridecylureido)pyrrolidin-1-yl)methylene)hydrazine-1-carbonyl)benzoate (0.596 g, 1.148 mmol) was dissolved in DCM (5 mL). Diacetoxyiodo benzene (0.386 g, 1.263 mmol) was added and the mixture was stirred for 5 min. Sat.aq sodium bicarbonate (25 mL) was added and the mixture was extracted in DCM (2×25 mL). The crude product was purified using flash chromatography, eluting with 0-5% MeOH:DCM, to give methyl 4-(5-((3S,4S)-3-methoxy-4-(3-tridecylureido)pyrrolidin-1-yl)-1,3,4-oxadiazol-2-yl)benzoate. (0.311 g, 52.4% yield). LCMS (Method-C fast): 21.2% (RT: 2.446, 202 nm) (MS: ESI +ve 544.5[M+1]).

Step-4: Preparation of 4-(5-((3S,4S)-3-methoxy-4-(3-tridecylureido)pyrrolidin-1-yl)-1,3,4-oxadiazol-2-yl)benzoic acid

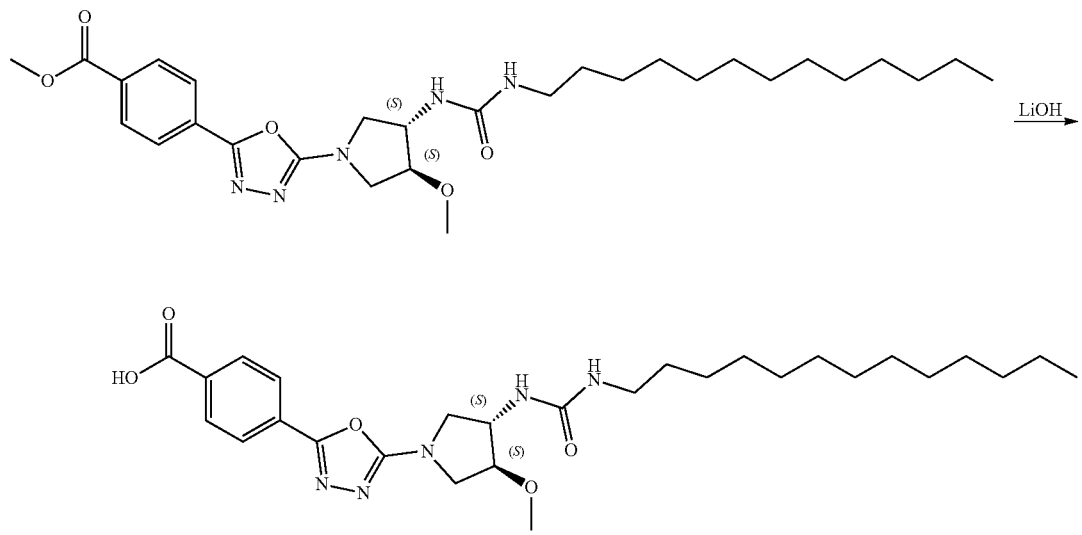

763

Prepared using General Ester Hydrolysis Procedure to give 4-(5-((3S,4S)-3-methoxy-4-(3-tridecylureido)pyrrolidin-1-yl)-1,3,4-oxadiazol-2-yl)benzoic acid. (0.249 g, 82.4% yield). LCMS (Method-J): 87% (RT: 4.598, 314.0 nm) (MS: ESI +ve 530.2 [M+1]).

764

Step-5: Preparation of (3S,4S)-1-(4-(5-((3S,4S)-3-methoxy-4-(3-tridecylureido) pyrrolidin-1-yl)-1,3,4-oxadiazol-2-yl)benzoyl)-N3,N4-bis((1S,2R)-2-phenylcyclopropyl)pyrrolidine-3,4-dicarboxamide, Compound 260

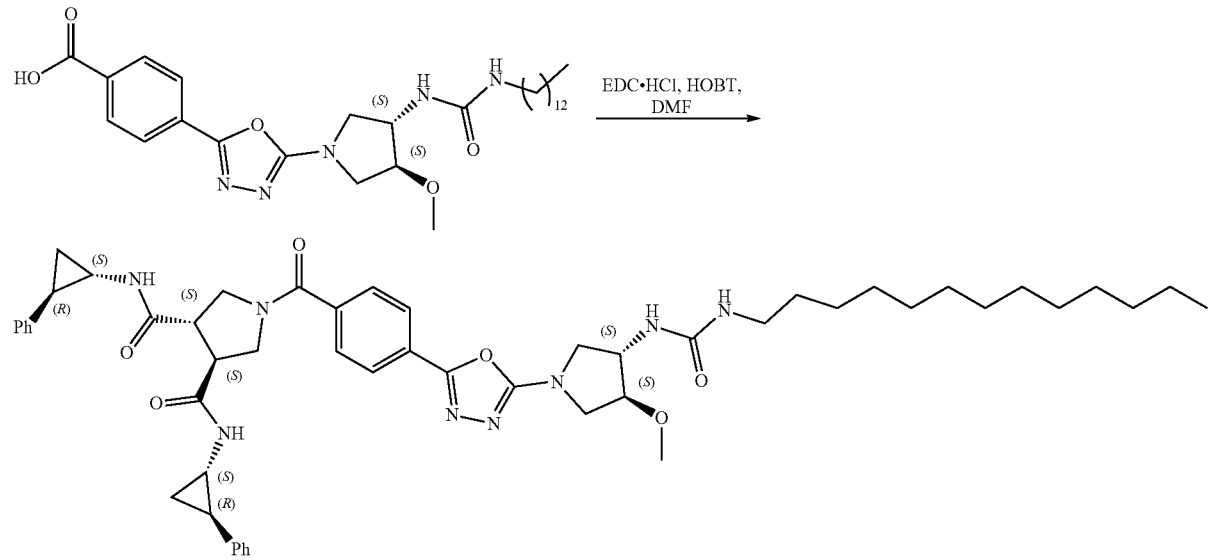

Prepared using General EDC, HOBT Coupling Procedure. The final product was purified using Prep HPLC Method 12 to give (3S,4S)-1-(4-(5-((3S,4S)-3-methoxy-4-(3-tridecylureido)pyrrolidin-1-yl)-1,3,4-oxadiazol-2-yl)benzoyl)-N3,N4-bis((1S,2R)-2-phenylcyclopropyl)pyrrolidine-3,4-dicarboxamide (Compound 260) (0.036 g, 8.6% yield), as a white solid. LCMS (Method-C fast): 98% (RT: 2.293, 225.0 nm) (MS: ESI +ve 902.5 [M+1]). $^1$H NMR: (400 MHz, DMSO, HT) δ ppm: 0.864-0.881 (m, 4H), 1.141-1.155 (m, 5H), 1.228-1.327 (m, 21H), 1.406 (m, 3H), 1.990 (s, 3H), 2.840 (s, 3H), 3.209 (s, 2H), 3.326 (s, 3H), 3.382-3.419 (m, 1H), 3.447 (m, 1H), 3.562 (m, 4H), 3.706-3.785 (m, 6H), 3.912 (s, 1H), 3.916 (s, 1H), 4.076 (s, 1H), 5.591 (s, 1H), 5.980 (m, 1H), 7.124-7.176 (m, 6H), 7.243-7.280 (m, 4H), 7.553 (s, 2H), 7.636-7.655 (d, J=7.6 Hz, 1H), 7.911-7.931 (d, 8 Hz, 1H), 8.026 (s, 2H).

Synthesis of (3S,4S)-1-(4-(5-((3S,4S)-3-methoxy-4-(3-tridecylureido)pyrrolidin-1-yl)-4H-1,2,4-triazol-3-yl)benzoyl)-N3,N4-bis((1S,2R)-2-phenylcyclopropyl)pyrrolidine-3,4-dicarboxamide, Compound 237

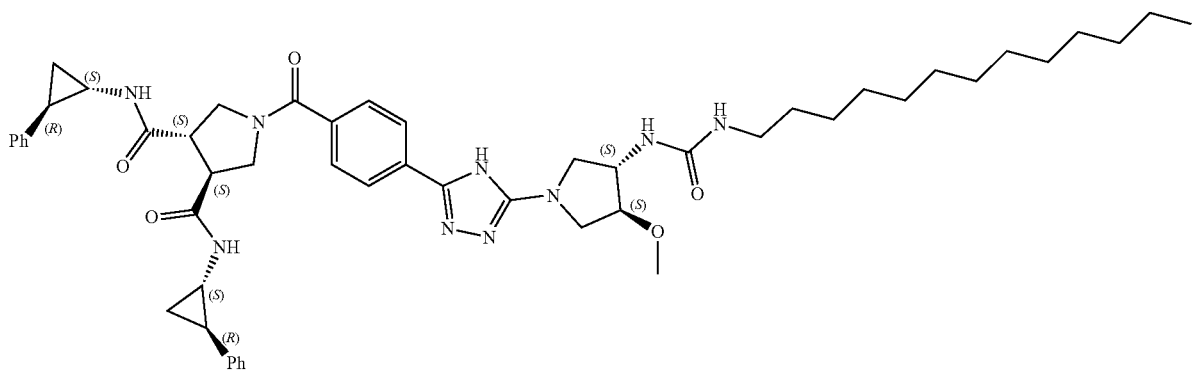

Step-1: Preparation of 1-((3S,4S)-1-cyano-4-methoxypyrrolidin-3-yl)-3-tridecylurea

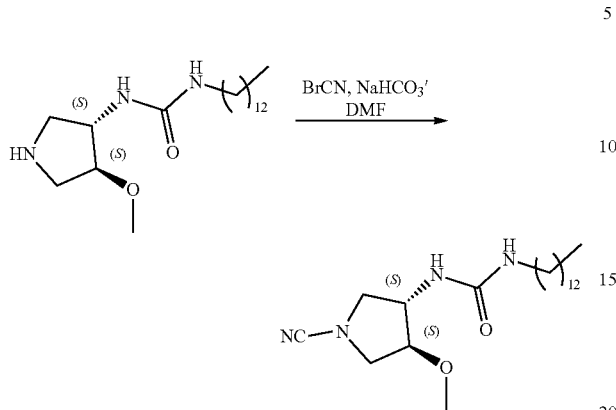

Sodium carbonate (0.118 g, 1.407 mmol) was added to a solution of 1-((3S,4S)-4-methoxypyrrolidin-3-yl)-3-tridecylurea (0.4 g, 1.173 mmol) in DMF (10 mL) and cooled to 0° C. for 5 minutes. Cyanogen bromide (0.124 g, 1.173 mmol) was added, with stirring continued for 3 h. The mixture was then diluted with EtOAc (300 mL), washed with brine (2×100 mL) dried over sodium sulfate and concentrated to give 1-((3S,4S)-1-cyano-4-methoxypyrrolidin-3-yl)-3-tridecylurea. as a white solid (0.3 g, 69.88%). LCMS (Method-C2): 100% (RT: 1.638, 202.0 nm) (MS: ESI +ve 367.29[M+1]).

Step-2: Preparation of tert-butyl 2-(4-(methoxycarbonyl)benzoyl)hydrazine-1-carboxylate

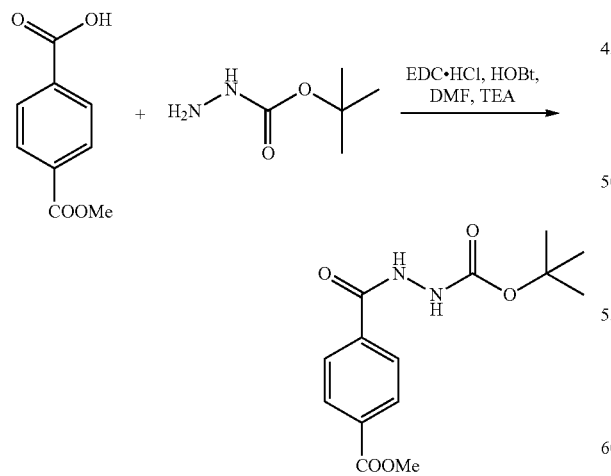

Prepared using General EDC, HOBT Coupling Procedure to give tert-butyl 2-(4-(methoxycarbonyl)benzoyl)hydrazine-1-carboxylate (5.5 g, 67.34%). LCMS (Method-H): 98.96% (RT: 2.583, 254.0 nm) (MS: ESI +ve 293[M−1]).

Step-3: Preparation of methyl 4-(hydrazinecarbonyl)benzoate

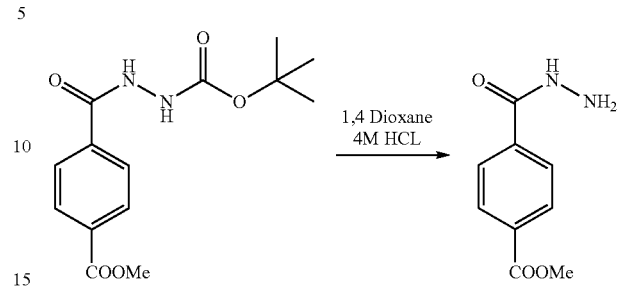

tert-Butyl 2-(4-(methoxycarbonyl)benzoyl)benzoyl)hydrazine-1-carboxylate (5.0 g, 16.999 mmol) was suspended in 1,4 dioxane (50 mL), then 4M HCL in dioxane (50 mL) was added dropwise and the mixture was stirred for 16 h. Saturated aqueous sodium bicarbonate solution (50 mL) was added, and the resulting precipitate was collected by filtration and dried to give methyl 4-(hydrazinecarbonyl)benzoate(5.5 g, 98.77%). LCMS (Method-H): 98.15% (RT: 1.812, 230.0 nm) (MS: ESI +ve 195 [M+H]).

Step-4: Preparation of methyl 4-(5-((3S,4S)-3-methoxy-4-(3-tridecylureido)pyrrolidin-1-yl)-4H-1,2,4-triazol-3-yl)benzoate

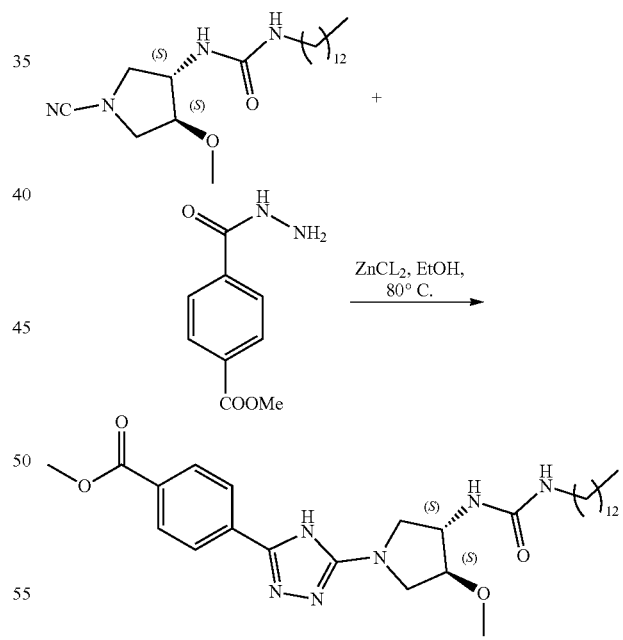

A mixture of 1-((3S,4S)-1-cyano-4-methoxypyrrolidin-3-yl)-3-tridecylurea (0.27 g, 0.735 mmol), methyl 4-(hydrazinecarbonyl)benzoate(0.114 g, 0.590 mmol) and zinc chloride (0.11 mL) in EtOH (5 mL) was heated at 80° C. for 16 h. The mixture was then cooled and concentrated to give methyl 4-(5-((3S,4S)-3-methoxy-4-(3-tridecylureido)pyrrolidin-1-yl)-4H-1,2,4-triazol-3-yl)benzoate (0.21 g, 52.53%), as a white solid. LCMS (Method-C2): 96.3% (RT: 1.618, 245.0 nm) (MS: ESI +ve 543[M+1]).

767

Step-5: Preparation of 4-(5-((3S,4S)-3-methoxy-4-(3-tridecylureido)pyrrolidin-1-yl)-4H-1,2,4-triazol-3-yl)benzoic acid

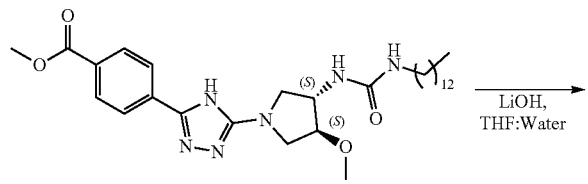

768

-continued

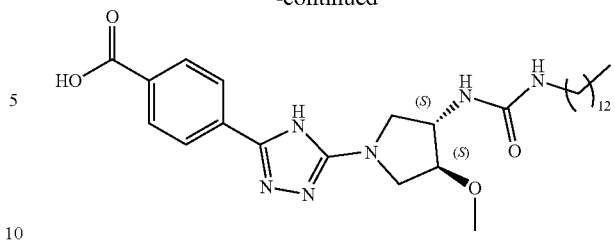

Prepared using General Ester Hydrolysis Procedure to give 4-(5-((3S,4S)-3-methoxy-4-(3-tridecylureido)pyrrolidin-1-yl)-4H-1,2,4-triazol-3-yl)benzoic acid. (0.18 g, 87.99%) LCMS (Method-C2): 93.23% (RT: 1.514, 245.0 nm) (MS: ESI +ve 529[M+H]).

Step-6: Preparation of (3S,4S)-1-(4-(5-((3S,4S)-3-methoxy-4-(3-tridecylureido) pyrrolidin-1-yl)-4H-1,2,4-triazol-3-yl)benzoyl)-N3,N4-bis((1S,2R)-2-phenylcyclopropyl)pyrrolidine-3,4-dicarboxamide, Compound 237

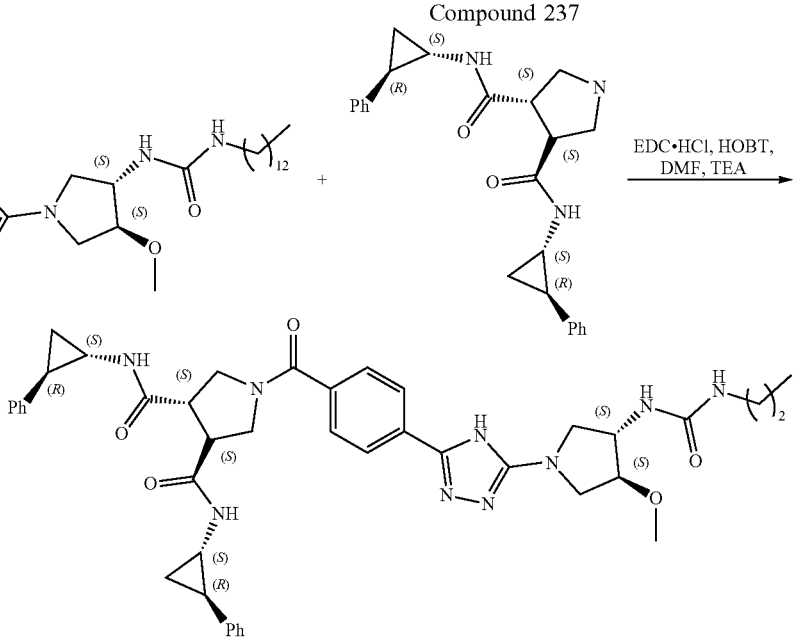

Prepared using General EDC, HOBT Coupling Procedure. The crude final product was purified using Prep HPLC Method 3 to give (3S,4S)-1-(4-(5-((3S,4S)-3-methoxy-4-(3-tridecylureido)pyrrolidin-1-yl)-4H-1,2,4-triazol-3-yl) benzoyl)-N3,N4-bis((1S,2R)-2-phenylcyclopropyl)pyrrolidine-3,4-dicarboxamide (Compound 237) (0.031 g, 12.14%), as an off white solid. LCMS (Method-J2): 100% (RT 4.520, 228.0 nm) (MS: ESI +ve 901 [M+1]. 1H NMR: (400 MHz, DMSO) δ ppm: 0.86 (s, 3H), 1.12-1.35 (m, 26H), 1.87 (s, 1H), 1.98 (s, 1H), 2.68-3.35 (m, 10H), 3.54-3.56 (d, J=7.2 Hz, 5H), 3.71 (s, 1H), 3.80 (s, 2H), 4.14 (s, 1H), 5.78 (s, 1H), 6.24-6.25 (d, J=6.8 Hz, 1H), 7.07-7.28 (m, 10H), 7.55-7.57 (d, J=7.2 Hz, 2H), 7.96-7.98 (d, J=7.2 Hz, 2H), 8.32 (s, 1H), 8.45 (s, 1H).

Synthesis of (3S,4S)-1-(4-(2-((3S,4S)-3-methoxy-4-(3-tridecylureido)pyrrolidin-1-yl)thiazol-5-yl)benzoyl)-N3,N4-bis((1S,2R)-2-phenylcyclopropyl)pyrrolidine-3,4-dicarboxamide, Compound 244

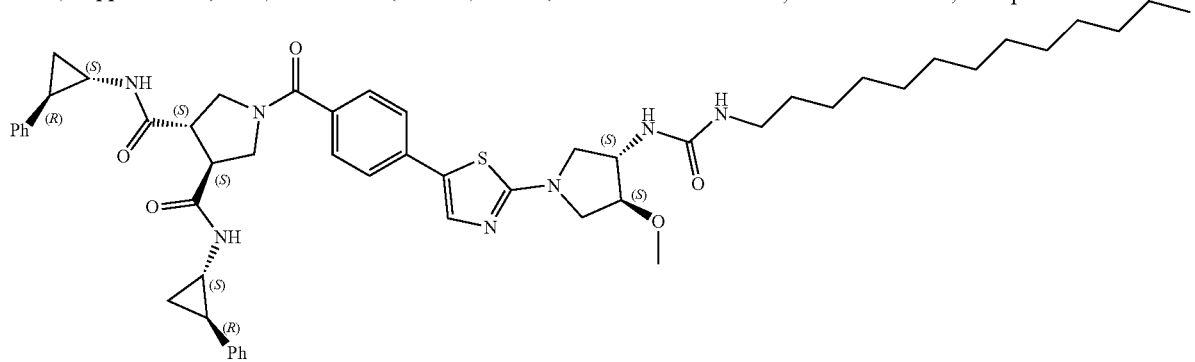

Step-1: Preparation of methyl (E)-4-(2-methoxyvinyl)benzoate

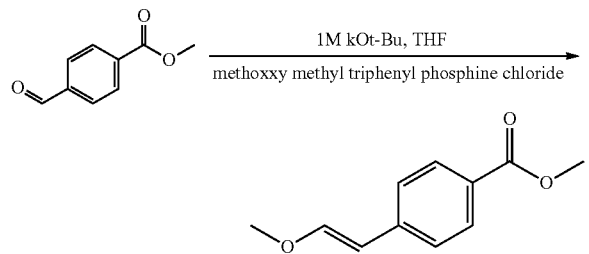

A mixture of methyl 4-formylbenzoate and methoxy methyl triphenyl phosphine chloride in THF was cooled to −60° C. 1M Potassium tert-butoxide 1M in THF was added dropwise and the reaction mixture was stirred for 3 h. The mixture was then diluted with water (100 mL) and extracted with ethyl acetate (2×200 mL). The organic layer was dried over sodium sulfate and concentrated. The crude product was purified using flash chromatography, eluting with 10-15% EtOAc:hexane, to give methyl (E)-4-(2-methoxyvinyl)benzoate. LCMS (Method-C2): 71.18% (RT 1.295, 254.0 nm) (MS: ESI +ve 193[(M+H]).

Step-2: Preparation of methyl 4-(2-oxoethyl)benzoate

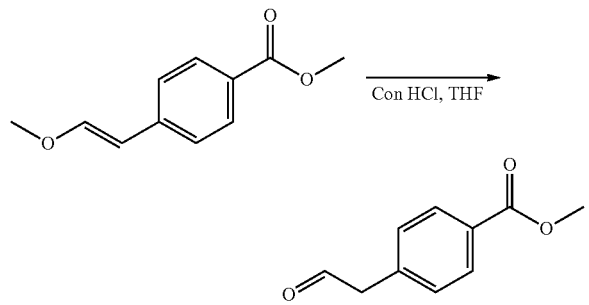

3N HCl (10 mL) was added to a solution of methyl (E)-4-(2-methoxyvinyl)benzoate(0.55 g, 2.849 mmol) in THF (10 mL). The mixture was stirred for 7 h. The mixture was diluted with water (100 mL) and extracted with ethyl acetate (2×200 mL). The organic layer was dried over sodium sulfate and concentrated to give methyl 4-(2-oxoethyl)benzoate, as a white solid (0.5 g, 98.07%). (MS: ESI +ve 178[(M+H]).

Step-3: Preparation of methyl 4-(1-bromo-2-oxoethyl)benzoate

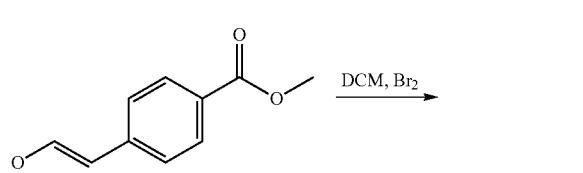

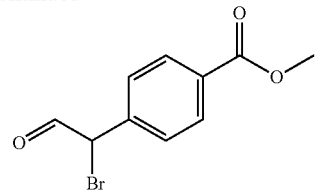

Methyl 4-(2-oxoethyl)benzoate(0.2 g, 1.123 mmol) was dissolved in DCM (5 mL) and cooled to 0° C. Bromine (0.05 mL, 1.123 mmol) was added, and the mixture was stirred for 1 h. The mixture was diluted with sodium bicarbonate (20 mL) and extracted with EtOAc (2×50 mL). The organic layer was dried over sodium sulfate and concentrated to give methyl 4-(1-bromo-2-oxoethyl)benzoate. as liquid (0.200 g, 69.31%). (MS: ESI +ve 256[(M+H]).

Step-4: Preparation of (3S,4S)-3-methoxy-4-(3-tridecylureido) pyrrolidine-1-carbothioamide

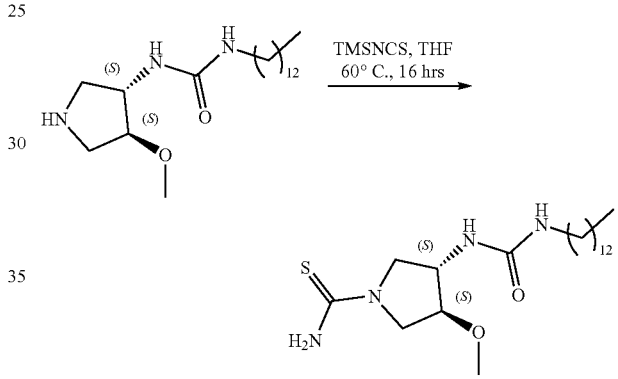

1-((3S,4S)-4-methoxypyrrolidin-3-yl)-3-tridecylurea (0.8 g, 2.346 mmol) was dissolved in THF (10 mL). Trimethylsilyl cyanide (0.307 g, 2.346 mmol) was added and the mixture was stirred at 60° C. for 16 h. The mixture was diluted with water (20 mL) and extracted with ethyl acetate (2×50 mL). The organic layer was dried over sodium sulfate and concentrated. The crude product was purified using flash chromatography, eluting with 1-3% MeOH:DCM, to give (3S,4S)-3-methoxy-4-(3-tridecylureido)pyrrolidine-1-carbothioamide. (0.13 g, 13.85%) LCMS (Method-C2): 79.20% (RT 1.554, 254.0 nm) (MS: ESI +ve 401[(M+H]).

Step-5: Preparation of methyl 4-(2-((3S,4S)-3-methoxy-4-(3-tridecylureido)pyrrolidin-1-yl)thiazol-5-yl)benzoate

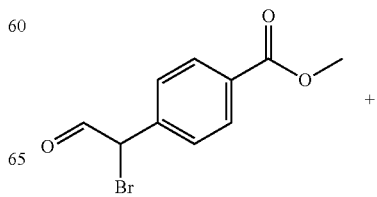 +

771
-continued

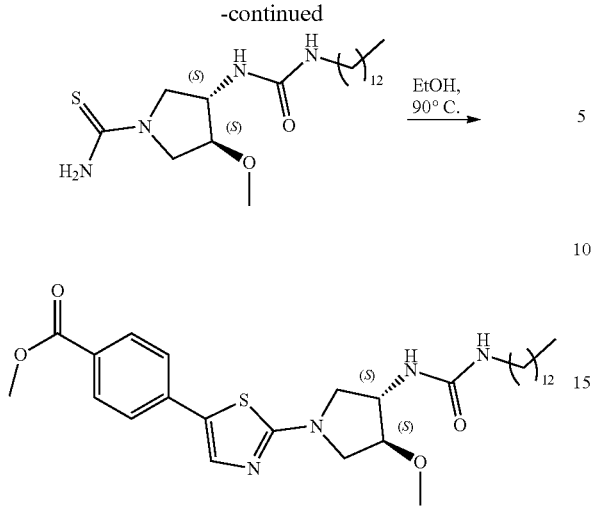

772
Step-6: Preparation of 4-(2-((3S,4S)-3-methoxy-4-(3-tridecylureido)pyrrolidin-1-yl)thiazol-5-yl)benzoic acid

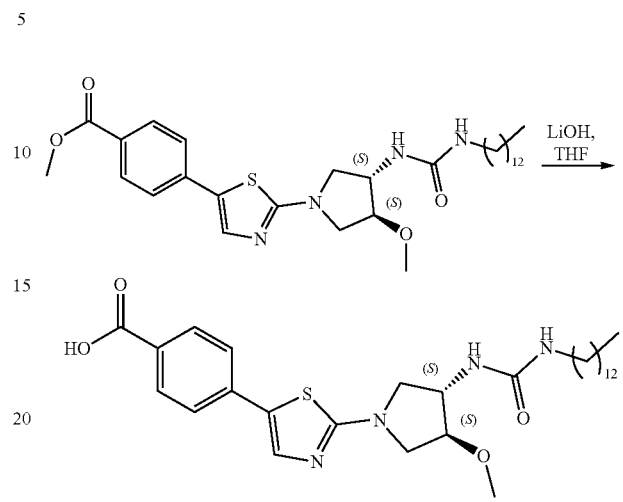

A mixture of methyl 4-(1-bromo-2-oxoethyl)benzoate (0.050, 0.195 mmol) and (3S,4S)-3-methoxy-4-(3-tridecylureido)pyrrolidine-1-carbothioamide (0.130 g, 0.325 mmol) in EtOH (5 mL) was heated at 90° C. for 5 h. The mixture was cooled, concentrated and the crude product was purified by flash chromatography, eluting with 1-3% MeOH: DCM, to give methyl 4-(2-((3S,4S)-3-methoxy-4-(3-tridecylureido)pyrrolidin-1-yl)thiazol-5-yl)benzoate, as a semi solid (0.11 g, 97.30%). LCMS (Method-CFast): 97.64% (RT 2.578, 355.0 nm) (MS: ESI +ve 559[(M+H]).

Prepared using General Ester Hydrolysis Procedure to give 4-(2-((3S,4S)-3-methoxy-4-(3-tridecylureido)pyrrolidin-1-yl)thiazol-5-yl)benzoic acid. (0.1 g, 93.25%) LCMS (Method-C2): 99.16% (RT: 1.683, 350.0 nm) (MS: ESI +ve 545[M+H]).

Step-7: Preparation of (3S,4S)-1-(4-(2-((3S,4S)-3-methoxy-4-(3-tridecylureido) pyrrolidin-1-yl)thiazol-5-yl)benzoyl)-N3,N4-bis((1S,2R)-2-phenylcyclopropyl) pyrrolidine-3,4-dicarboxamide, Compound 244

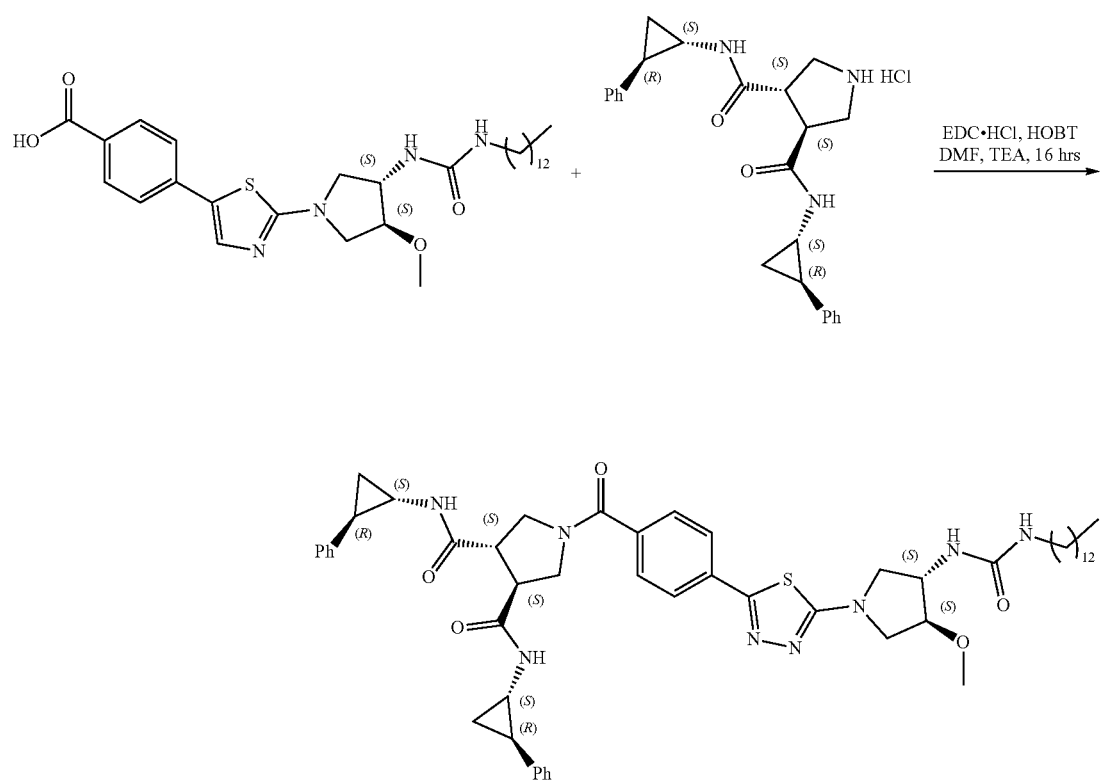

Prepared using General EDC, HOBT Coupling Procedure. The crude product was purified using flash chromatography, eluting with 1-3% MeOH:DCM, to give (3S,4S)-1-(4-(2-((3S,4S)-3-methoxy-4-(3-tridecylureido)pyrrolidin-1-yl)thiazol-5-yl)benzoyl)-N3,N4-bis((1S,2R)-2-phenylcyclopropyl) pyrrolidine-3,4-dicarboxamide (Compound 244)(0.033 g, 19.62%), as an off white solid. LCMS (Method-Cfast): 98.27% (RT: 2.418, 340.00 nm) (MS: ESI +ve 917[M+1]). $^1$H NMR: (400 MHz, DMSO) δ ppm: 0.67 (m, 3H), 1.11-1.34 (m, 27H), 1.55 (s, 1H), 1.86-1.96 (m, 2H), 2.67-2.68 (3, 2H), 2.84-2.99 (m, 2H), 3.09-4.19 (m, 14H), 5.73 (s, 1H), 6.29-6.31 (d, J=6.4 Hz, 1H), 7.06-7.26 (m, 9H), 7.51 (s, 4H), 7.73 (s, 1H), 8.29-8.43 (m, 2H).

Synthesis of (3S,4S)-1-(4-(2-((S)-2-decanamido-3-(hexylamino)-3-oxopropyl)oxazol-5-yl)benzoyl)-N3,N4-bis((1S,2R)-2-phenylcyclopropyl)pyrrolidine-3,4-dicarboxamide, Compound 267

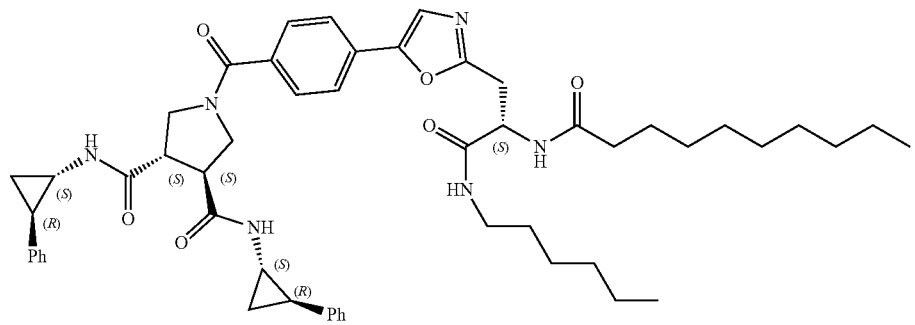

Step-1: Preparation of benzyl (S)-(2,5-dioxotetrahydrofuran-3-yl)carbamate

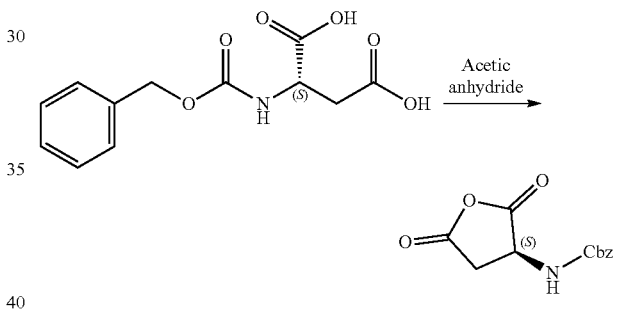

A mixture of ((benzyloxy)carbonyl)-L-aspartic acid (5.0 g) and acetic anhydride (50 mL) was stirred at room temperature for 16 h. The reaction mixture was concentrated then diluted with diethyl ether (100 mL). Then resulting white solid was filtered and dried to give benzyl (S)-(2,5-dioxotetrahydrofuran-3-yl)carbamate(3.5 g, 75%). $^1$H NMR: (400 MHz, DMSO) δ ppm: 2.91-2.97 (m, 1H), 3.24-3.32 (m, 1H), 4.69-4.75 (m, 1H), 5.08 (s, 2H), 7.32-7.41 (m, 5H), 8.16-8.18 (m, 1H).

Step-2: Preparation of (S)-3-(((benzyloxy)carbonyl)amino)-4-ethoxy-4-oxobutanoic acid

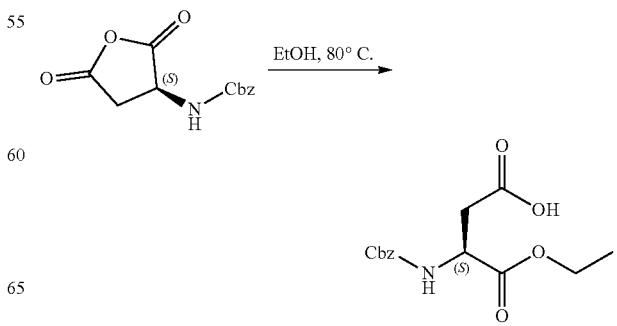

Benzyl (S)-(2,5-dioxotetrahydrofuran-3-yl)carbamate (14.0 g) was heated at reflux in ethanol (100 mL) for 16 h. The mixture was concentrated then dissolved in saturated sodium bicarbonate solution (200 mL). The aqueous layer was extracted with ethyl acetate (3×200 mL). The aqueous layer was acidified with 2M hydrochloric acid and extracted into ethyl acetate (3×200 mL). The organic layers were combined, dried over sodium sulfate and concentrated to give (S)-3-(((benzyloxy)carbonyl)amino)-4-ethoxy-4-oxobutanoic acid (12 g, 72%). LCMS (Method-C2): 82.15% (RT: 1.125, 202 nm) (MS: ESI +ve 296.5 [M+H]).

Step-3: Preparation of ethyl N2-((benzyloxy)carbonyl)-N4-(2-(4-bromophenyl)-2-oxoethyl)-L-asparaginate

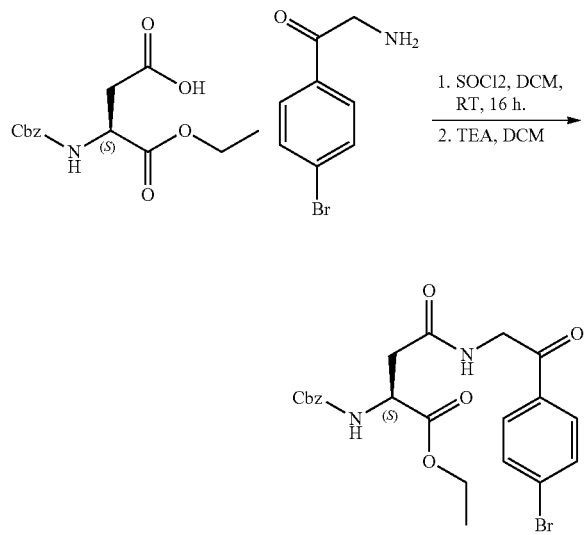

Thionyl chloride (11.7 mL, 162.57 mmol) and DMF (1 drop) were added to a solution of (S)-3-(((benzyloxy)carbonyl)amino)-4-ethoxy-4-oxobutanoic acid (12 g, 40.64 mmol) in DCM (120 mL). The reaction mixture was stirred at room temperature for 18 h then concentrated. The product was dissolved in DCM (50 mL) and added to a solution of 2-amino-1-(4-bromophenyl)ethan-1-one (11.1 g, 44.7 mmol) and TEA (34 mL, 243.84 mmol) in DCM (100 mL) which had been cooled to 0° C. The reaction mixture was stirred at room temperature for 1 h. The reaction mixture was diluted with DCM (300 mL), washed with 2M hydrochloric acid (40 mL) then saturated sodium bicarbonate (100 mL), dried over sodium sulfate and concentrated. The crude product was purified by flash chromatography, eluting with 35% EtOAc/hexane, to yield ethyl N2-((benzyloxy)carbonyl)-N4-(2-(4-bromophenyl)-2-oxoethyl)-L-asparaginate. LCMS (Method-C2): 100% (RT: 1.327, 258 nm) (MS: ESI +ve 491.2&493.2 [M+H]).

Step-4: Preparation of ethyl (S)-2-(((benzyloxy)carbonyl)amino)-3-(5-(4-bromophenyl)oxazol-2-yl)propanoate

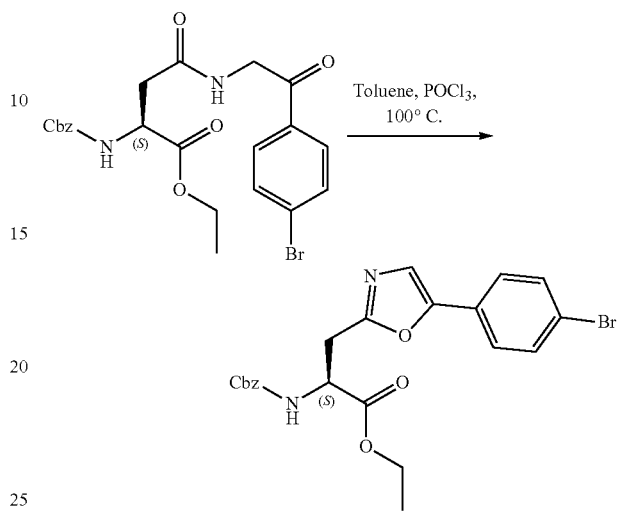

Phosphorous oxychloride (1.3 mL, 13.56 mmol) was added to a solution of ethyl N2-((benzyloxy)carbonyl)-N4-(2-(4-bromophenyl)-2-oxoethyl)-L-asparaginate (1.9 g, 3.87 mmol) in toluene (60 mL) and the reaction mixture was stirred at 100° C. for 90 minutes. The reaction mixture was poured onto ice (200 mL), extracted into DCM (2×50 mL), dried over sodium sulfate and concentrated. The crude product was purified by flash chromatography, eluting with 30% EtOAc/hexane, to give ethyl (S)-2-(((benzyloxy)carbonyl)amino)-3-(5-(4-bromophenyl)oxazol-2-yl)propanoate (1.7 g, 92). LCMS (Method-C2): 93.61% (RT: 1.455, 254 nm) (MS: ESI +ve 473.2&475.2 [M+H]).

Step-5: Preparation of (S)-2-(((benzyloxy)carbonyl)amino)-3-(5-(4-bromophenyl)oxazol-2-yl)propanoic acid

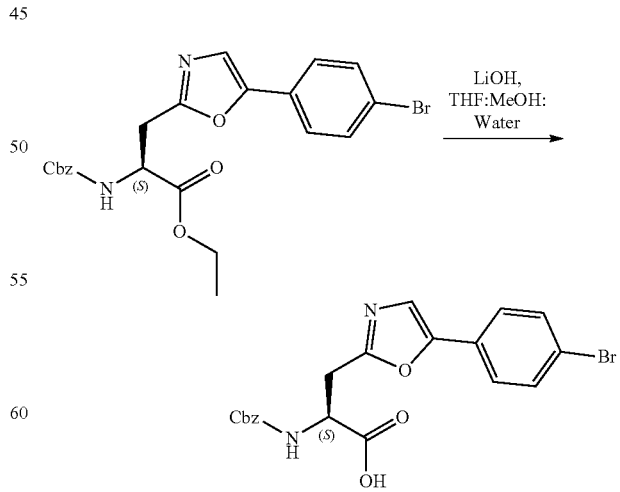

Prepared using General Ester Hydrolysis Procedure to give (S)-2-(((benzyloxy)carbonyl)amino)-3-(5-(4-bromophenyl)oxazol-2-yl)propanoic acid, as a white solid (1.3 g, 81%). LCMS (Method-C2): 92.23% (RT: 1.327, 254.0 nm) (MS: ESI +ve 445.1 & 447.1 [M–H]).

Step 6: Preparation of benzyl (S)-(3-(5-(4-bromophenyl)oxazol-2-yl)-1-(hexylamino)-1-oxopropan-2-yl)carbamate

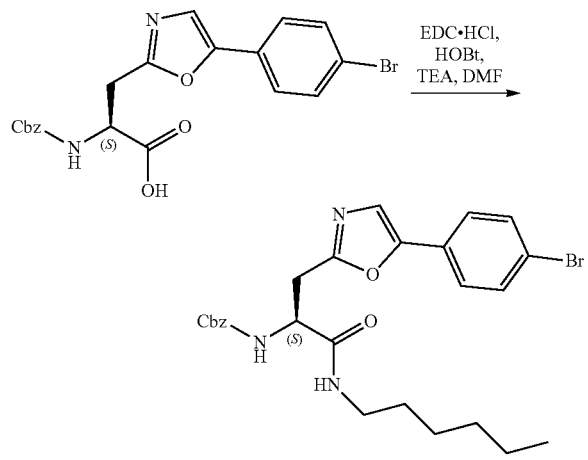

Prepared using General EDC, HOBT Coupling Procedure. The crude product was purified by flash chromatography, eluting with 0-2% MeOH/DCM, to give benzyl (S)-(3-(5-(4-bromophenyl)oxazol-2-yl)-1-(hexylamino)-1-oxopropan-2-yl)carbamate (1.3 g) as a white solid. LCMS (Method-C2): 95.38% (RT: 1.506, 254.0 nm) (MS: ESI +ve 528.3 & 530.3[M+H]).

Step-7: Preparation of methyl (S)-4-(2-(2-(((benzyloxy)carbonyl) amino)-3-(hexylamino)-3-oxopropyl)oxazol-5-yl)benzoate

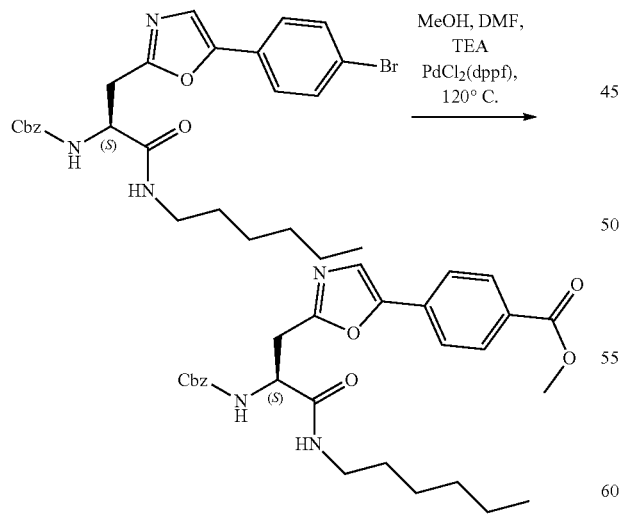

A mixture of benzyl (S)-(3-(5-(4-bromophenyl)oxazol-2-yl)-1-(hexylamino)-1-oxopropan-2-yl)carbamate (1.2 g), DMF (20 mL), TEA(10 mL) and MeOH (20 mL) were placed in an autoclave. Pd(Cl₂(dppf)) (0.4 g) was added and the mixture was heated at 120° C. under carbon monoxide gas pressure (35 kg). The mixture was concentrated then purified by flash chromatography, eluting with 50-100% EtOAc/hexane, to give methyl (S)-4-(2-(2-(((benzyloxy)carbonyl)amino)-3-(hexylamino)-3-oxopropyl)oxazol-5-yl)benzoate (0.7 g, 75%) as a brown solid. LCMS (Method-C2): 89.77% (RT 1.389, 295.0 nm) (MS: ESI +ve 508.4[M+1]).

Step-8: Preparation of methyl (S)-4-(2-(2-amino-3-(hexylamino)-3-oxopropyl)oxazol-5-yl)benzoate

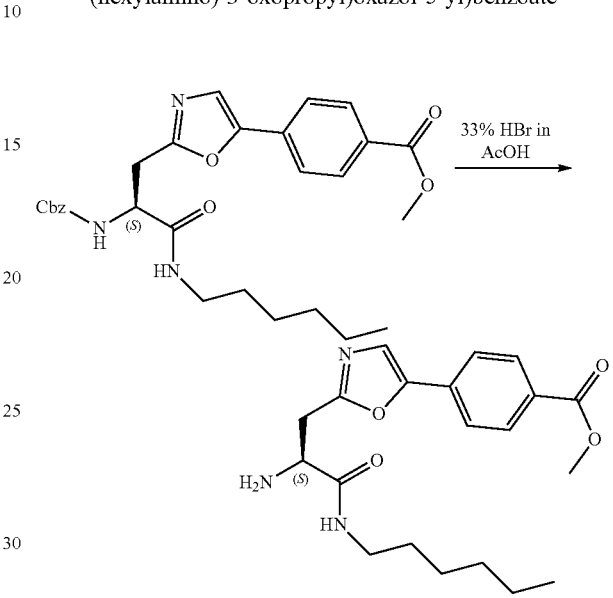

A mixture of methyl (S)-4-(2-(2-(((benzyloxy)carbonyl) amino)-3-(hexylamino)-3-oxopropyl)oxazol-5-yl)benzoate (0.65 g), 33% hydrogen bromide in acetic acid (1.5 mL) and acetic acid (1.5 mL) was stirred for 3 hrs. Volatiles were removed and ice cold water (20 mL) was added. The pH was adjusted with 10% sodium bicarbonate solution (20 mL), and the mixture was extracted with DCM (2×100 mL), dried over sodium sulfate and concentrated to give methyl (S)-4-(2-(2-amino-3-(hexylamino)-3-oxopropyl)oxazol-5-yl)benzoate (0.40 g, 90%) LCMS (Method-C2): 66.53% (RT 1.132, 215 nm) (MS: ESI +ve 374.3 [M+H]).

Step-9: Preparation of methyl (S)-4-(2-(2-decanamido-3-(hexylamino)-3-oxopropyl)oxazol-5-yl)benzoate

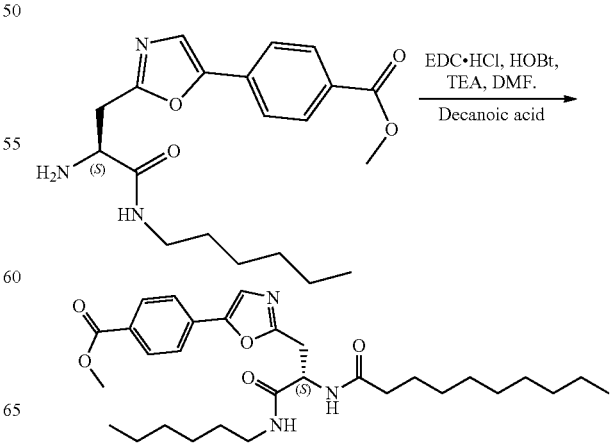

Prepared using General EDC, HOBT Coupling Procedure. The crude product was purified by flash chromatography, eluting with 0-2% MeOH/DCM, to give methyl (S)-4-(2-(2-decanamido-3-(hexylamino)-3-oxopropyl)oxazol-5-yl)benzoate (0.35 g, 63%), as a white solid. LCMS (Method-C2): 87.26% (RT: 1.565, 230.0 nm) (MS: ESI +ve 528.5[M+H]).

Step-10: Preparation of (S)-4-(2-(2-decanamido-3-(hexylamino)-3-oxopropyl)oxazol-5-yl)benzoic acid

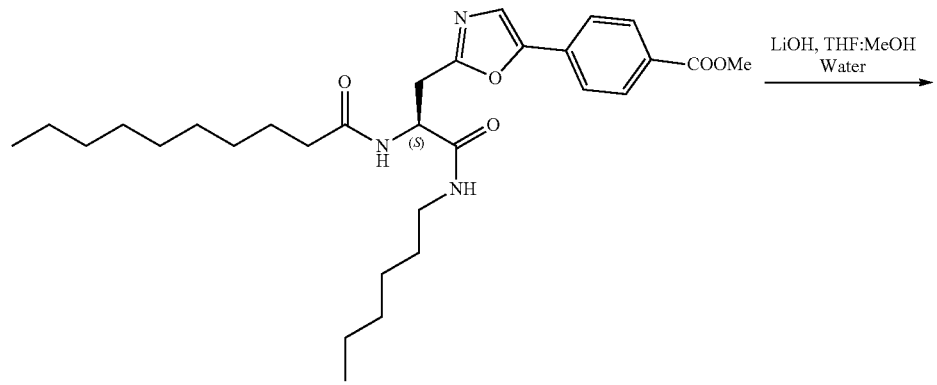

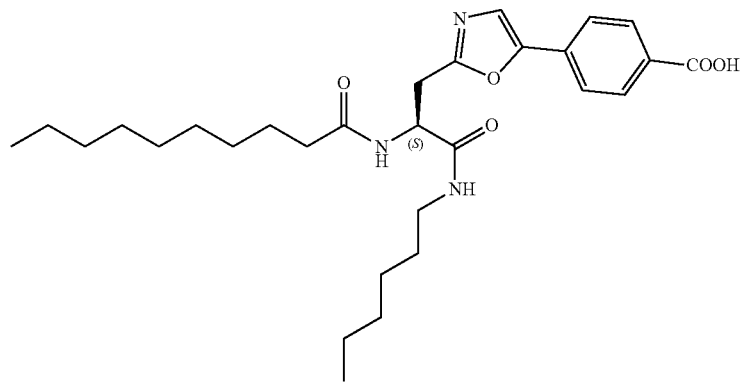

Prepared using General Ester Hydrolysis Procedure to give (S)-4-(2-(2-decanamido-3-(hexylamino)-3-oxopropyl)oxazol-5-yl)benzoic acid, as a white solid (0.3 g, 88%). LCMS (Method-C2): 74.44% (RT: 1.445, 293.0 nm) (MS: ESI +ve 514.4 [M−H]).

Step-11: Preparation of (3S,4S)-1-(4-(2-((S)-2-decanamido-3-(hexylamino)-3-oxopropyl)oxazol-5-yl)benzoyl)-N3,N4-bis((1S,2R)-2-phenylcyclopropyl)pyrrolidine-3,4-dicarboxamide, Compound 267

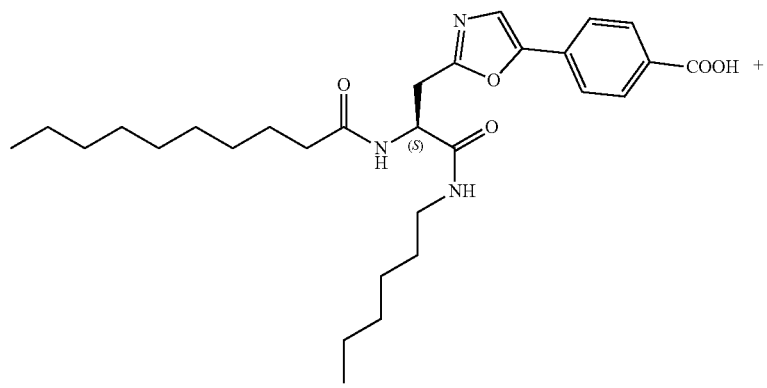

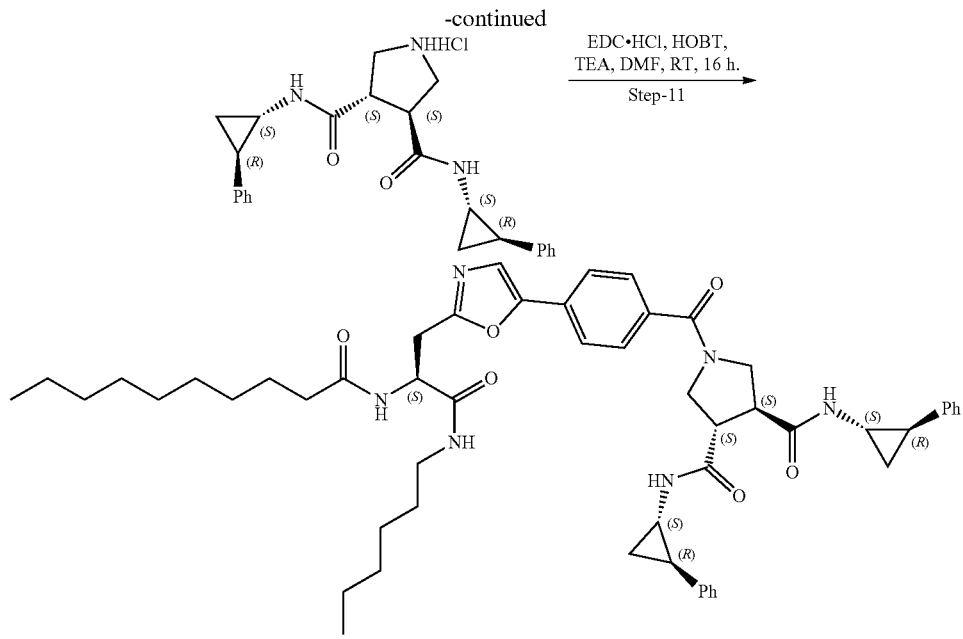

Prepared using General EDC, HOBT Coupling Procedure. The crude product was purified using Prep HPLC Method 10 to give (3S,4S)-1-(4-(2-((S)-2-decanamido-3-(hexylamino)-3-oxopropyl)oxazol-5-yl)benzoyl)-N3,N4-bis((1S,2R)-2-phenylcyclopropyl)pyrrolidine-3,4-dicarboxamide (Compound 267)(0.110 g, 11.59%). LCMS (Method-J): 100% (RT 4.422, 283.0 nm) (MS: ESI +ve 886.6 [M+H]). ¹H NMR: (400 MHz, DMSO) δ ppm: 0.79-0.84 (m, 6H), 1.11 (m, 8H), 1.17 (bs, 14H), 1.30-1.38 (m, 4H), 1.84 (s, 1H), 1.94-1.99 (m, 1H), 2.05-2.09 (m, 2H), 2.77 (m, 1H), 2.78 (m, 1H), 2.96-3.06 (m, 3H), 3.07-3.13 (m, 1H), 3.17-3.35 (s, 2H), 3.49-3.65 (m, 2H), 3.65-3.70 (m, 1H), 3.80-3.83 (m, 1H), 4.74-4.80 (m, 1H), 7.05-7.07 (m, 2H), 7.11-7.18 (m, 4H), 7.21-7.28 (m, 4H), 7.59-7.64 (m, 3H), 7.72.7.74 (m, 2H), 8.01-8.033 (m, 1H), 8.17-8.20 (m, 1H), 8.33-8.34 (m, 1H), 8.47-8.48 (m, 1H).

Synthesis of (3S,4S)-1-(4-(2-(2-decanamido-3-(hexylamino)-3-oxopropyl)oxazol-5-yl)benzoyl)-N3,N4-bis((1S,2R)-2-phenylcyclopropyl)pyrrolidine-3,4-dicarboxamide, Compound 278

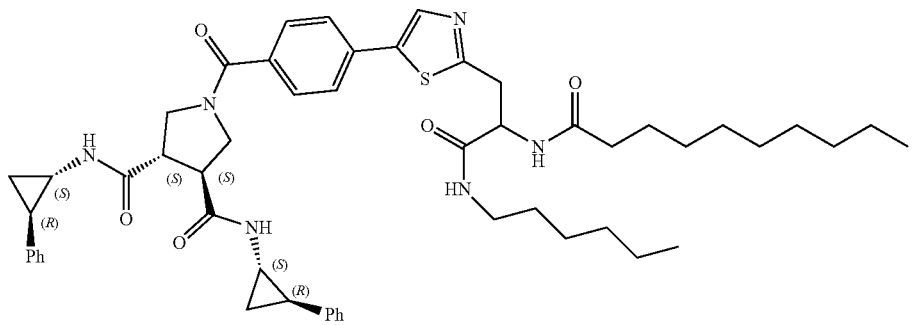

Step-1: Preparation of ethyl 2-(((benzyloxy)carbonyl)amino)-3-(5-(4-bromophenyl)thiazol-2-yl)propanoate

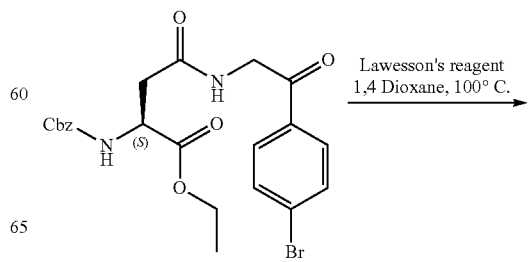

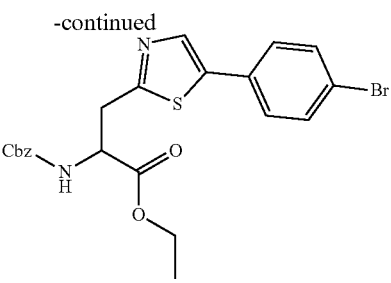

Ethyl N2-((benzyloxy) carbonyl)-N4-(2-(4-bromophenyl)-2-oxoethyl)-L-asparaginate (2.0 g, 4.07 mmol) and Lawesson's Reagent (2.1 g, 5.29 mmol) in 1,4 Dioxane (40 mL) were heated at 100° C. for 48 h. The reaction mixture was concentrated and the crude product was purified by flash chromatography eluting with 20% EtOAc:Hexane to give ethyl (S)-2-(((benzyloxy)carbonyl)amino)-3-(5-(4-bromophenyl)thiazol-2-yl)propanoate (1.8 g, 90%). LCMS (Method-C2): 100% (RT: 1.500, 283.0 nm) (MS: ESI +ve 489.2&491.2 [M+H]).

Step-2: Preparation of 2-(((benzyloxy)carbonyl)amino)-3-(5-(4-bromophenyl)thiazol-2-yl)propanoic acid

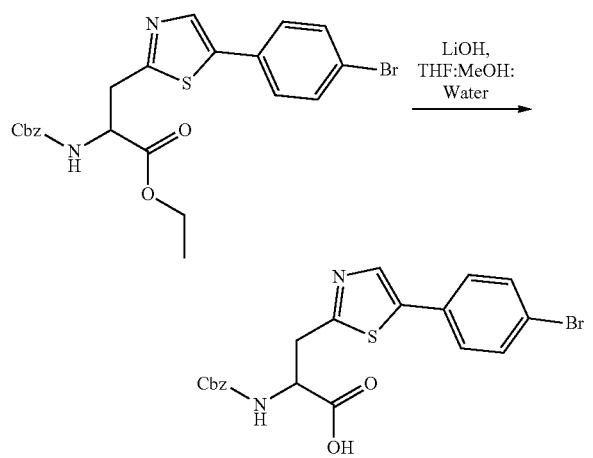

Prepared using General Ester Hydrolysis Procedure to give 2-(((benzyloxy)carbonyl)amino)-3-(5-(4-bromophenyl)thiazol-2-yl)propanoic acid as a white solid (1.5 g, 88.40%). LCMS (Method-C2): 100% (RT: 1.360, 280.0 nm) (MS: ESI +ve 461.2 & 463.2 [M−H]).

Step 3: Preparation of benzyl (3-(5-(4-bromophenyl)thiazol-2-yl)-1-(hexylamino)-1-oxopropan-2-yl) carbamate

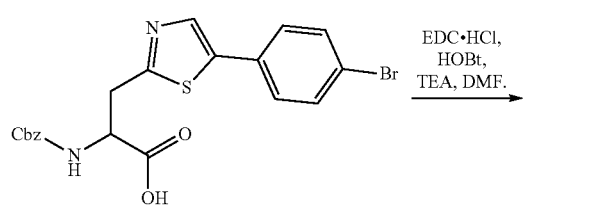

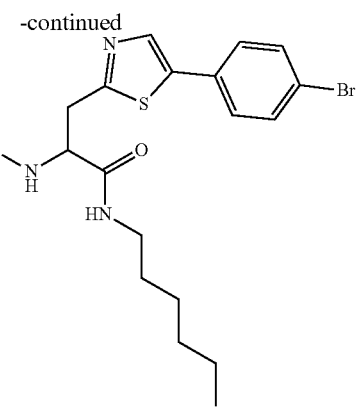

Prepared using General EDC, HOBT Coupling Procedure. The crude product was purified by flash chromatography, eluting with 0-2% MeOH:DCM, to give benzyl 3-(5-(4-bromophenyl)thiazol-2-yl)-1-(hexylamino)-1-oxopropan-2-yl)carbamate (1.5 g, 84%), as a white solid. LCMS (Method-C2): 96.74% (RT: 1.537, 270.0 nm) (MS: ESI +ve 544.3 & 546.3[M+H]).

Step-4: Preparation of methyl 4-(2-(2-(((benzyloxy)carbonyl)amino)-3-(hexylamino)-3-oxopropyl)thiazol-5-yl)benzoate Benzyl 3-(5-(4-bromophenyl)thiazol-2-yl)-1-(hexylamino)-1-oxopropan-2-yl)carbamate (1.3 g, 2.39 mmol), TEA (5.0 mL, 35.89 mmol) and PdCl₂(dppf)) (0.263 g, 0.358 mmol) in MeOH (20 mL) were heated at 120° C. under carbon monoxide gas pressure 35 kg in an autoclave. The mixture was concentrated and purified by flash chromatography, eluting with 50-100% EtOAc: hexane, to give methyl 4-(2-(2-(((benzyloxy)carbonyl)amino)-3-(hexylamino)-3-oxopropyl)thiazol-5-yl)benzoate (0.7 g, 56%), as a brown solid. LCMS (Method-C2): 96.52% (RT 1.450, 301.0 nm) (MS: ESI +ve 524.4[M+1]).

Step-5: Preparation of methyl 4-(2-(2-amino-3-(hexylamino)-3-oxopropyl)thiazol-5-yl)benzoate

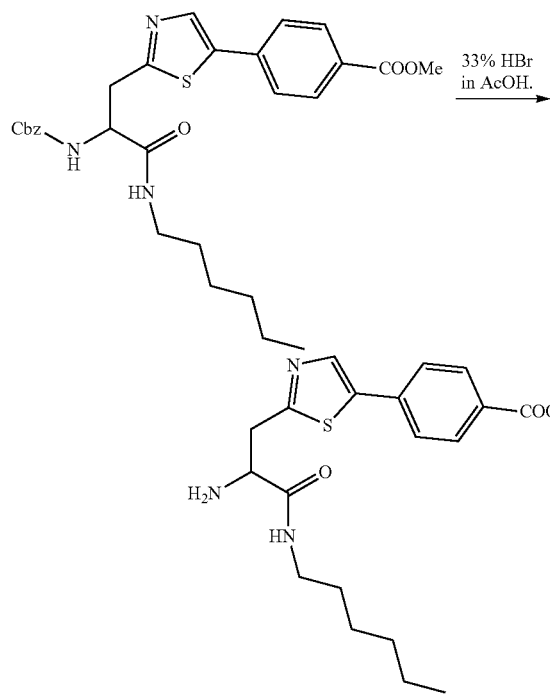

Methyl 4-(2-(2-(((benzyloxy)carbonyl)amino)-3-(hexylamino)-3-oxopropyl)thiazol-5-yl)benzoate (0.7 g) and 33% hydrogen bromide in AcOH (7.0 mL) in AcOH (7.0 mL) were stirred at room temperature for 3 h. The mixture was concentrated and ice cold water (20 mL) was added. 10% Sodium bicarbonate (20 mL) was added and the mixture was extracted into DCM (2×100 mL). The organic layer was dried over sodium sulfate and concentrated to give methyl 4-(2-(2-amino-3-(hexylamino)-3-oxopropyl)thiazol-5-yl)benzoate (0.3 g, 65%) LCMS (Method-C2): 65.34% (RT 1.137, 300 nm) (MS: ESI +ve 390.2 [M+H]).

Step-6: Preparation of methyl 4-(2-(2-decanamido-3-(hexylamino)-3-oxopropyl)thiazol-5-yl)benzoate

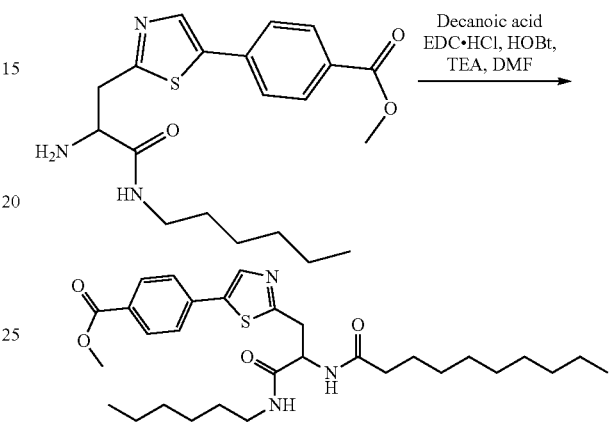

Prepared using General EDC, HOBT Coupling Procedure. The crude product was purified by flash chromatography, eluting with 0-2% MeOH:DCM, to give methyl 4-(2-(2-decanamido-3-(hexylamino)-3-oxopropyl)thiazol-5-yl)benzoate (0.3 g, 40%) as a white solid. LCMS (Method-C2): 95.48% (RT: 1.657, 301.0 nm) (MS: ESI +ve 542.25 [M+H]).

Step-7: Preparation of (S)-4-(2-(2-decanamido-3-(hexylamino)-3-oxopropyl)thiazol-5-yl)benzoic acid

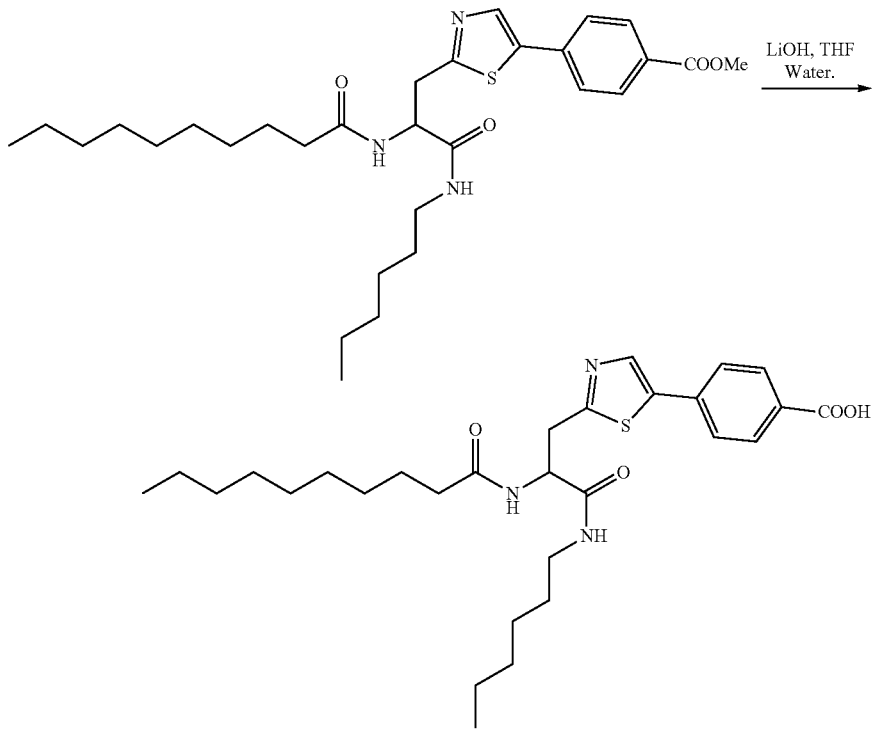

Prepared using General Ester Hydrolysis Procedure to give 4-(2-(2-decanamido-3-(hexylamino)-3-oxopropyl)thiazol-5-yl)benzoic acid as a white solid (0.2 g, 68%). LCMS (Method-C2): 92.22% (RT: 1.464, 297.0 nm) (MS: ESI +ve 530.7 [M−H]).

Step-8: Preparation of (3S,4S)-1-(4-(2-(2-decanamido-3-(hexylamino)-3-oxopropyl)thiazol-5-yl)benzoyl)-N3,N4-bis((1S,2R)-2-phenylcyclopropyl)pyrrolidine-3,4-dicarboxamide, Compound 278

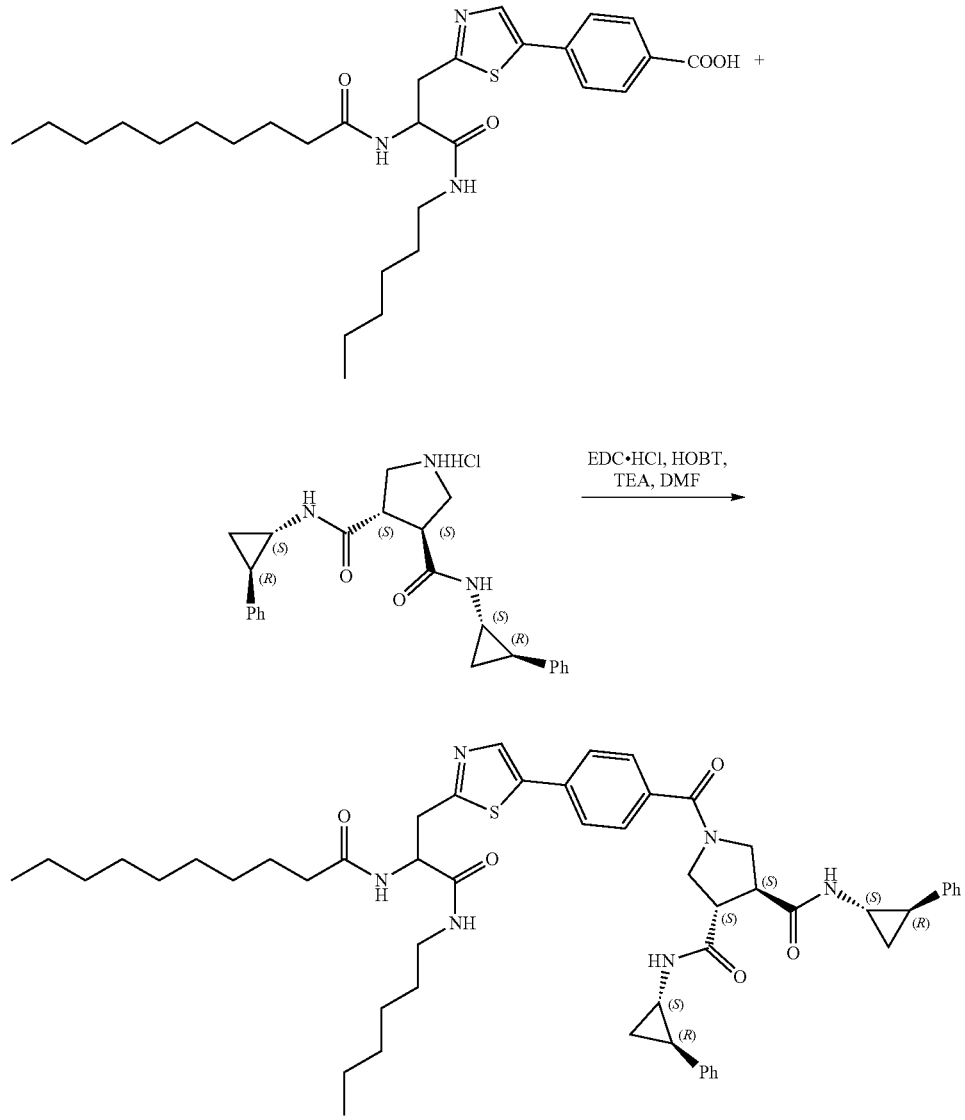

Prepared using General EDC, HOBT Coupling Procedure. The crude product was purified by Prep HPLC Method 13 to give (3S,4S)-1-(4-(2-(2-decanamido-3-(hexylamino)-3-oxopropyl)thiazol-5-yl)benzoyl)-N3,N4-bis((1S,2R)-2-phenylcyclopropyl)pyrrolidine-3,4-dicarboxamide (Compound 278), as a white solid (0.104 g, 40%). LCMS (Method-C2): 99.52% (RT 1.541, 220.0 nm) (MS: ESI +ve 901 7[M+H]). $^1$H NMR: (400 MHz, DMSO) δ ppm: 0.80-0.81 (m, 6H), 1.14-1.18 (m, 23H), 1.34-1.42 (m, 5H), 1.84 (s, 1H), 1.96 (s, 1H), 2.08-2.11 (m, 2H), 2.77 (s, 1H), 2.85 (s, 1H), 2.99-3.13 (m, 3H), 3.16-3.22 (m, 2H), 3.49-3.53 (s, 2H), 3.65-3.77 (m, 1H), 3.79-3.82 (m, 1H), 4.65-4.67 (m, 1H), 7.05-7.07 (m, 2H), 7.11-7.18 (m, 4H), 7.21-7.28 (m, 4H), 7.56-7.58 (m, 2H), 7.66-7.68 (m, 2H), 8.15 (bs, 1H), 8.17 (s, 1H), 8.23-8.26 (m, 1H), 8.36 (s, 1H), 8.49 (s, 1H).

Synthesis of (3S,4S)-1-(4-(5-((S)-2-decanamido-3-(hexylamino)-3-oxopropyl)-1,3,4-oxadiazol-2-yl)benzoyl)-N3,N4-bis((1S,2R)-2-phenylcyclopropyl)pyrrolidine-3,4-dicarboxamide, Compound 259

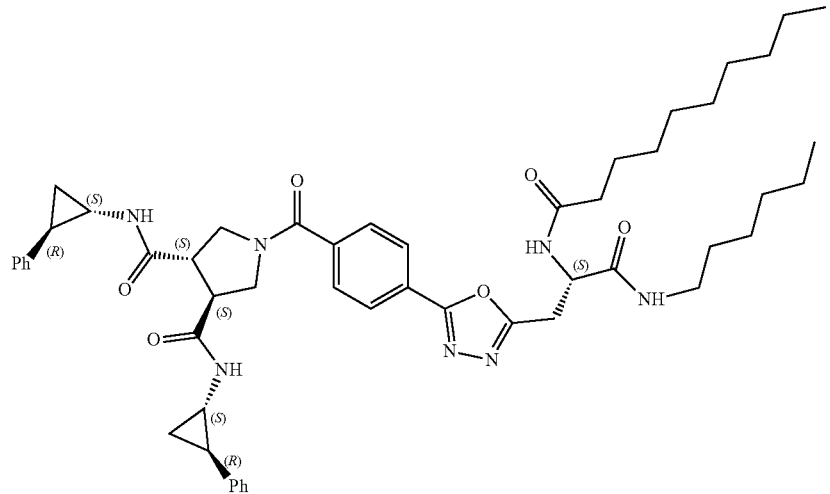

Step-1: Preparation of methyl (S)-4-(2-(3-((((9H-fluoren-9-yl)methoxy)carbonyl)amino)-4-(allyloxy)-4-oxobutanoyl)hydrazine-1-carbonyl)benzoate

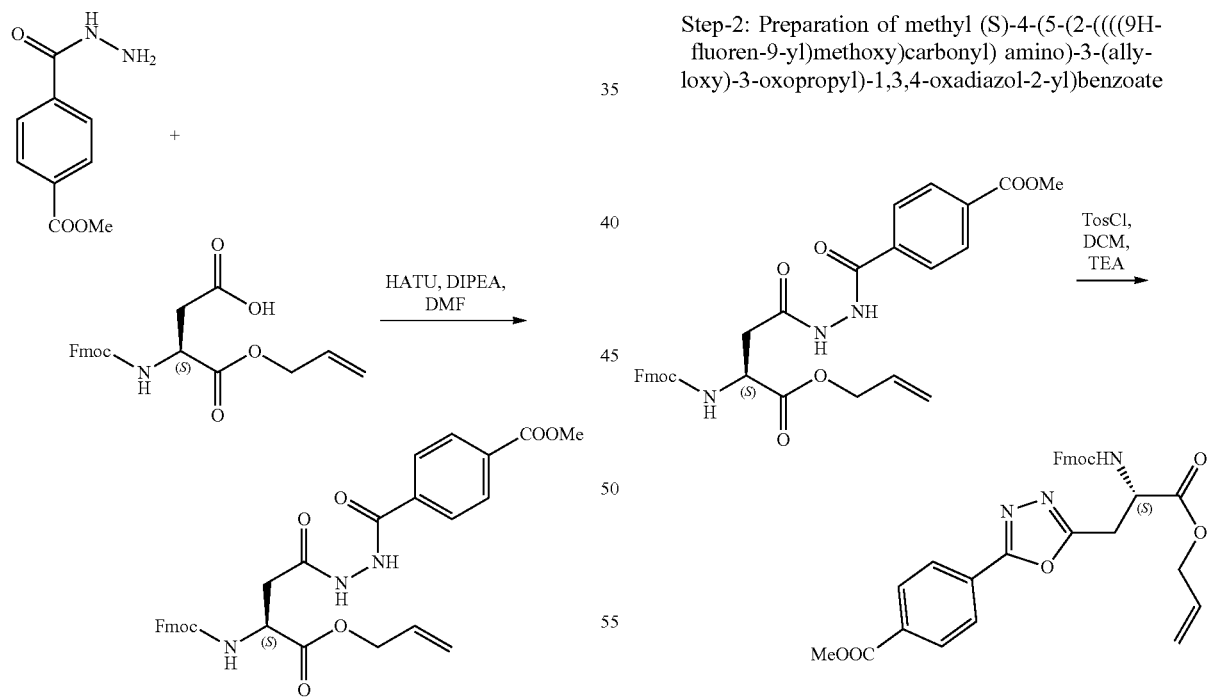

(S)-3-((((9H-fluoren-9-yl)methoxy)carbonyl)amino)-4-(allyloxy)-4-oxobutanoic acid (3.0 g, 7.587 mmol) was dissolved in DMF (50 mL). Methyl 4-(hydrazinecarbonyl)benzoate (1.47 g, 7.587 mmol) was added at 0° C. drop wise, then diisopropylethylamine (3.8 mL) and HATU (4.2 g, 11.380 mmol) were added and the mixture was stirred for 1 h. The mixture was then diluted with EtOAc (500 mL) and washed with water (2×200 mL). The organic layer was dried over sodium sulfate and concentrated to give methyl (S)-4-(2-(3-((((9H-fluoren-9-yl)methoxy)carbonyl)amino)-4-(allyloxy)-4-oxobutanoyl)hydrazine-1-carbonyl)benzoate. (4.0 g, 92.45%) as a white solid. LCMS (Method-C2): 74.83% (RT 1.306, 235.0 nm) (MS: ESI +ve 571[(M+H]).

Step-2: Preparation of methyl (S)-4-(5-(2-((((9H-fluoren-9-yl)methoxy)carbonyl) amino)-3-(allyloxy)-3-oxopropyl)-1,3,4-oxadiazol-2-yl)benzoate Methyl(S)-4-(2-(3-((((9H-fluoren-9-yl)methoxy)carbonyl)amino)-4-(allyloxy)-4-oxobutanoyl) hydrazine-1-carbonyl)benzoate (1.5 g, 1.049 mmol) was dissolved in DCM (30 mL) and cooled to 0° C. p-tosylchloride (0.5 g, 1.144 mmol) was added followed by TEA (0.5 mL), added dropwise. The reaction mixture was stirred for 16 h then diluted with DCM (200 mL) and washed with water (2×200 mL). The organic layer was dried over sodium sulfate, concentrated, and the crude product was purified using flash chromatography, eluting with 40-50 EtOAc:hexane, to give methyl (S)-4-(5-(2-((((9H-fluoren-9-yl)methoxy)carbonyl) amino)-3-(allyloxy)-3-oxopropyl)-1,3,4-oxadiazol-2-yl)benzoate, as a solid (0.7 g, 48.19%). LCMS (Method-C2): 77.05% (RT 1.446, 265.0 nm) (MS: ESI +ve 554[(M+H]).

Step-3: Preparation of (S)-2-((((9H-fluoren-9-yl)methoxy)carbonyl)amino)-3-(5-(4-(methoxycarbonyl)phenyl)-1,3,4-oxadiazol-2-yl)propanoic acid

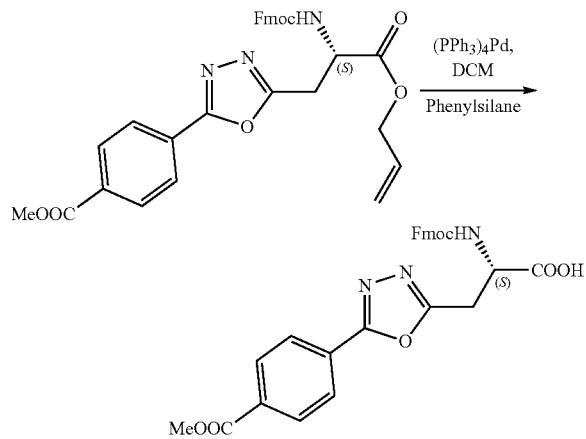

A mixture of methyl (S)-4-(5-(2-((((9H-fluoren-9-yl)methoxy)carbonyl) amino)-3-(allyloxy)-3-oxopropyl)-1,3,4-oxadiazol-2-yl)benzoate (1.0 g, 1.802 mmol), phenylsilane (0.39 g, 3.610 mmol) and tetrakistriphenylphosphine palladium (0.1 g, 0.090 mmol) in DCM (30 mL) was stirred for 16 h. The mixture was diluted with DCM (200 mL) and washed with water (2×200 mL). The organic layer was dried over sodium sulfate and concentrated to give (S)-2-((((9H-fluoren-9-yl)methoxy)carbonyl) amino)-3-(5-(4-(methoxycarbonyl)phenyl)-1,3,4-oxadiazol-2-yl)propanoic acid (0.8 g, 86.24%) as a liquid. LCMS (Method-C2): 96.56% (RT 1.283, 265.0 nm) (MS: ESI +ve 514[(M+H]).

Step-4: Preparation of methyl (S)-4-(5-(2-amino-3-(hexylamino)-3-oxopropyl)-1,3,4-oxadiazol-2-yl)benzoate

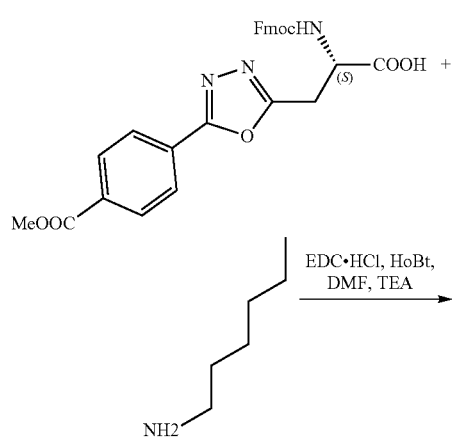

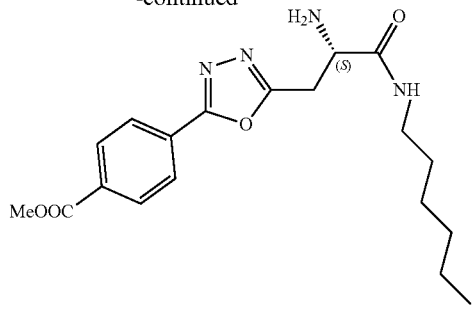

Prepared using General EDC, HOBT Coupling Procedure. The crude material was purified using flash chromatography, eluting with 1-3% MeOH:DCM, to give methyl (S)-4-(5-(2-amino-3-(hexylamino)-3-oxopropyl)-1,3,4-oxadiazol-2-yl)benzoate (0.2 g, 34.28%) LCMS (Method-C2): 79.21% (RT 1.065, 265.0 nm) (MS: ESI +ve 375[(M+H]).

Step-5: Preparation of methyl (S)-4-(5-(3-(hexylamino)-2-(nonylamino)-3-oxopropyl)-1,3,4-oxadiazol-2-yl)benzoate

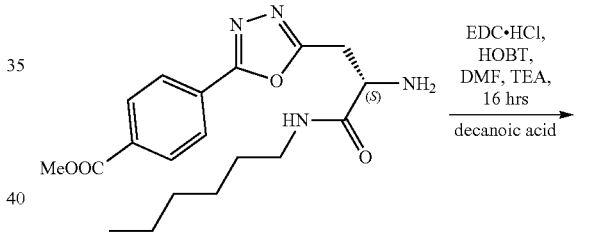

Prepared using General EDC, HOBT Coupling Procedure. The crude material was purified using flash chromatography, eluting with 1-3% MeOH:DCM, to give methyl (S)-4-(5-(3-(hexylamino)-2-(nonylamino)-3-oxopropyl)-1,3,4-oxadiazol-2-yl)benzoate, as a semisolid (0.2 g, 34.28%). LCMS (Method-C2): 98.30% (RT 1.530, 265.0 nm) (MS: ESI +ve 530[(M+H]).

793

Step-6: Preparation of (S)-4-(5-(2-decanamido-3-(hexylamino)-3-oxopropyl)-1,3,4-oxadiazol-2-yl)benzoic acid

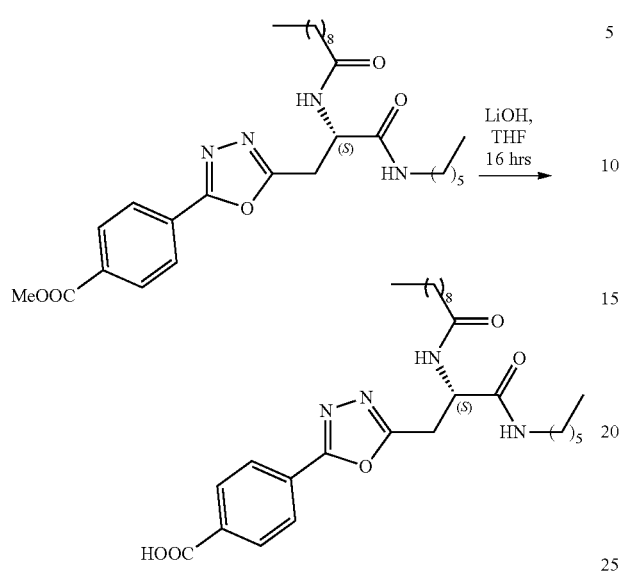

Prepared using General Ester Hydrolysis Procedure to give (S)-4-(5-(2-decanamido-3-(hexylamino)-3-oxopropyl)-1,3,4-oxadiazol-2-yl)benzoic acid (0.12 g, 61.64%.) LCMS (Method-C2): 57.72% (RT: 1.295, 254.0 nm) (MS: ESI +ve 515[M+H]).

Step-7: Preparation of (3S,4S)-1-(4-(5-((S)-2-decanamido-3-(hexylamino)-3-oxopropyl)-1,3,4-oxadiazol-2-yl)benzoyl)-N3,N4-bis((1S,2R)-2-phenylcyclopropyl)pyrrolidine-3,4-dicarboxamide, Compound 259

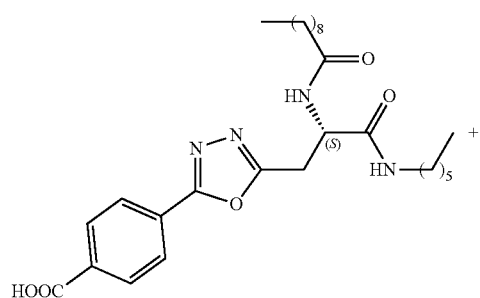

794

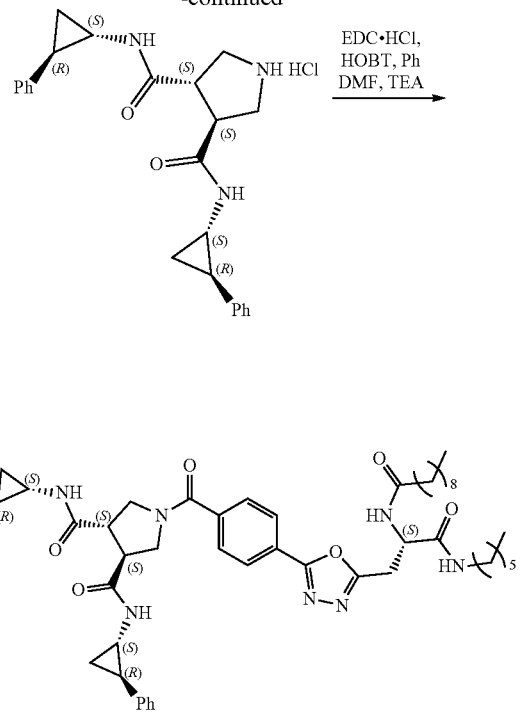

Prepared using General EDC, HOBT Coupling Procedure. The crude product was purified using Prep HPLC Method 1 to give (3S,4S)-1-(4-(5-((S)-2-decanamido-3-(hexylamino)-3-oxopropyl)-1,3,4-oxadiazol-2-yl)benzoyl)-N3,N4-bis((1S,2R)-2-phenylcyclopropyl) pyrrolidine-3,4-dicarboxamide (Compound 259)(0.01 g, 4.84%), as an off white solid. LCMS (Method-c-fast): 100% (RT 1.979, 202.0 nm) (MS: ESI +ve 886 [M+H]). $^1$H NMR: (400 MHz, DMSO) δ ppm: 0.82-0.87 (m, 6H), 1.11-1.35 (m, 24H), 1.46 (s, 2H), 1.59 (s, 2H), 1.85 (s, 1H), 1.97 (s, 1H), 2.05-2.09 (t, J=7.2 Hz, 2H), 2.76-2.85 (m, 3H), 3.10-3.64 (m, 7H), 3.79-3.84 (t, J=11.2 Hz, 1H), 4.34-4.36 (d, J=6.8 Hz, 1H), 7.06-7.28 (m, 10H), 7.58-7.60 (d, J=7.6 Hz, 2H), 7.86-7.88 (d, J=7.6 Hz, 2H), 8.30 (s, 1H), 8.45-8.47 (d, J=10.8 Hz, 2H).

Synthesis of (3S,4S)-1-(4-(5-((S)-2-decanamido-3-(hexylamino)-3-oxopropyl)-1,3,4-thiadiazol-2-yl)benzoyl)-N3,N4-bis((1S,2R)-2-phenylcyclopropyl) pyrrolidine-3,4-dicarboxamide, Compound 243

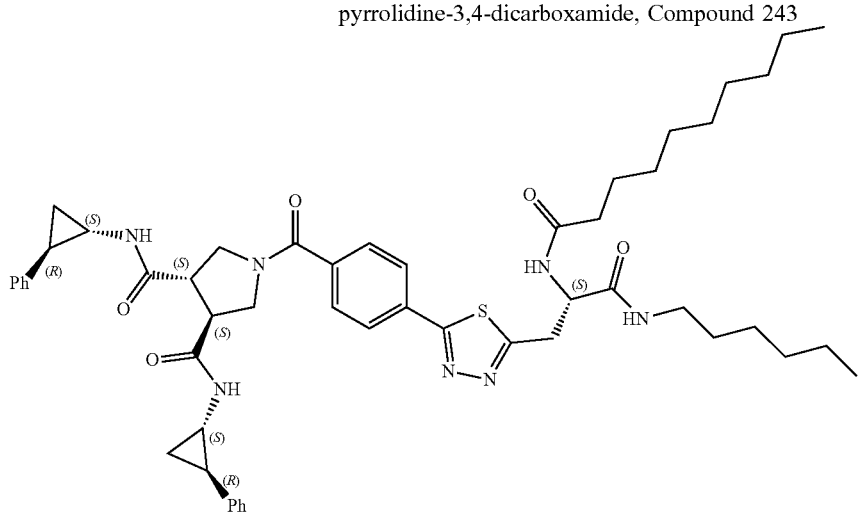

Step 1: Preparation of methyl (S)-4-(5-(2-((((9H-fluoren-9-yl)methoxy) carbonyl)amino)-3-(allyloxy)-3-oxopropyl)-1,3,4-thiadiazol-2-yl)benzoate

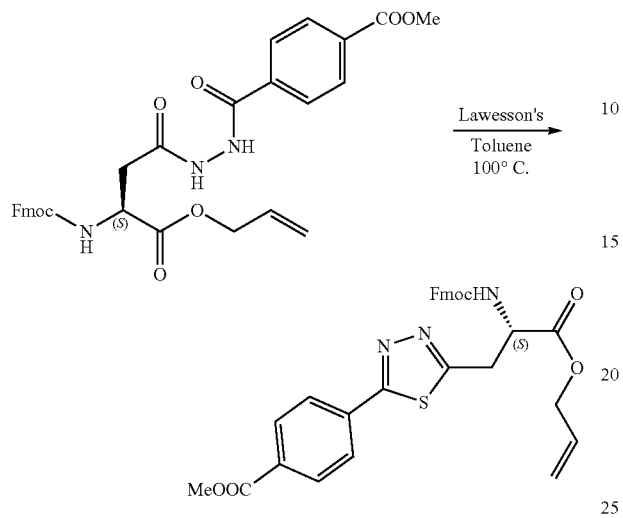

Methyl (S)-4-(2-(3-((((9H-fluoren-9-yl)methoxy)carbonyl)amino)-4-(allyloxy)-4-oxobutanoyl)hydrazine-1-carbonyl)benzoate (1.0 g, 1.748 mmol) was suspended in toluene (30 mL) and Lawesson's reagent (0.707 g, 1.748) was added. The mixture was stirred for 4 h at 100° C. The mixture was cooled, diluted with EtOAc (500 mL), washed with water (2×200 mL) dried over sodium sulfate and concentrated. The crude product was purified using flash chromatography, eluting with 10-20% EtOAc: hexane, to give methyl (S)-4-(5-(2-((((9H-fluoren-9-yl)methoxy)carbonyl)amino)-3-(allyloxy)-3-oxopropyl)-1,3,4-thiadiazol-2-yl)benzoate (1.0 g, 100%). LCMS (Method-C2): 85.79% (RT 1.464, 266.0 nm) (MS: ESI +ve 570.12[(M+H]).

Step 2: Preparation of (S)-2-((((9H-fluoren-9-yl)methoxy)carbonyl)amino)-3-(5-(4-(methoxycarbonyl)phenyl)-1,3,4-thiadiazol-2-yl)propanoic acid

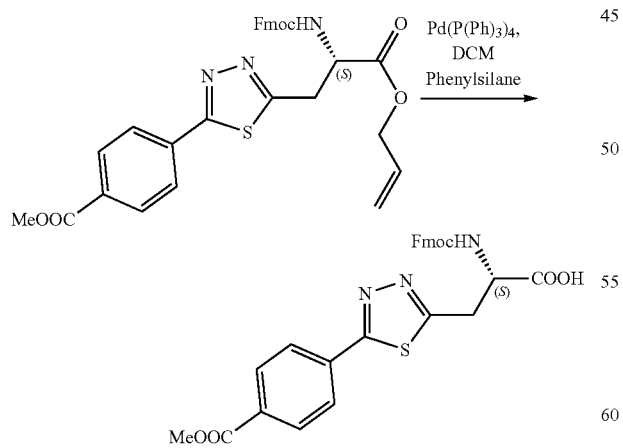

A mixture of methyl (S)-4-(5-(2-((((9H-fluoren-9-yl)methoxy) carbonyl)amino)-3-(allyloxy)-3-oxopropyl)-1,3,4-thiadiazol-2-yl)benzoate (0.9 g, 1.579 mmol), phenylsilane(0.341 g, 3.159 mmol) and tetrakistriphenylphosine palladium (0.091 g, 0.078 mmol) in DCM (20 mL) was stirred for 16 h. The mixture was diluted with DCM (200 mL), washed with water (2×200 mL) dried over sodium sulfate and concentrated to give (S)-2-((((9H-fluoren-9-yl)methoxy)carbonyl)amino)-3-(5-(4-(methoxycarbonyl)phenyl)-1,3,4-thiadiazol-2-yl)propanoic acid. (0.8 g, 95.61%) as a liquid. LCMS (Method-C2): 77.59% (RT 1.344, 266.0 nm) (MS: ESI +ve 530[(M+H]).

Step 3: Preparation of methyl (S)-4-(5-(2-amino-3-(hexylamino)-3-oxopropyl)-1,3,4-thiadiazol-2-yl)benzoate

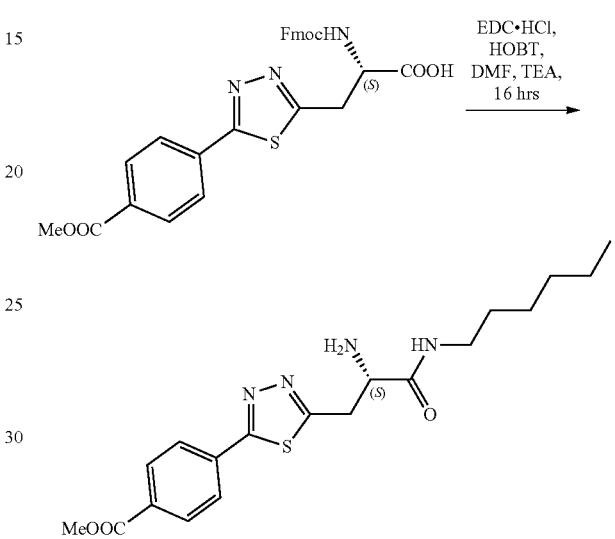

Prepared using General EDC, HOBT Coupling Procedure. The crude material was purified by using flash chromatography, eluting with 2-5% MeOH in DCM, to give methyl (S)-4-(5-(2-amino-3-(hexylamino)-3-oxopropyl)-1,3,4-thiadiazol-2-yl)benzoate (0.2 g, 33.90%) LCMS (Method-C2): 88.10% (RT 1.136, 281.0 nm) (MS: ESI +ve 390[(M+H]).

Step 4: Preparation of methyl (S)-4-(5-(3-(hexylamino)-2-nonanamido-3-oxopropyl)-1,3,4-thiadiazol-2-yl)benzoate

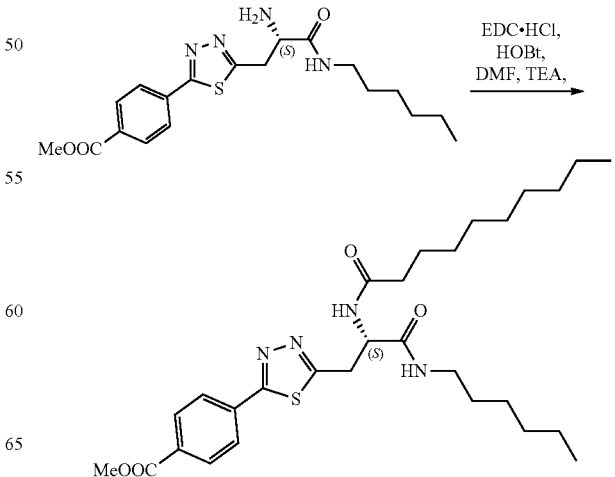

Prepared using General EDC, HOBT Coupling Procedure. The crude product was purified using flash chromatography, eluting with 1-3% MeOH:DCM, to give methyl (S)-4-(5-(3-(hexylamino)-2-nonanamido-3-oxopropyl)-1,3,4-thiadiazol-2-yl)benzoate, as a semisolid (0.2 g, 73.58%).

LCMS (Method-CFast): 88.96% (RT 2.128, 285.0 nm) (MS: ESI +ve 545[(M+H]).

Step 5: Preparation of (S)-4-(5-(3-(hexylamino)-2-nonanamido-3-oxopropyl)-1,3,4-thiadiazol-2-yl)benzoic acid

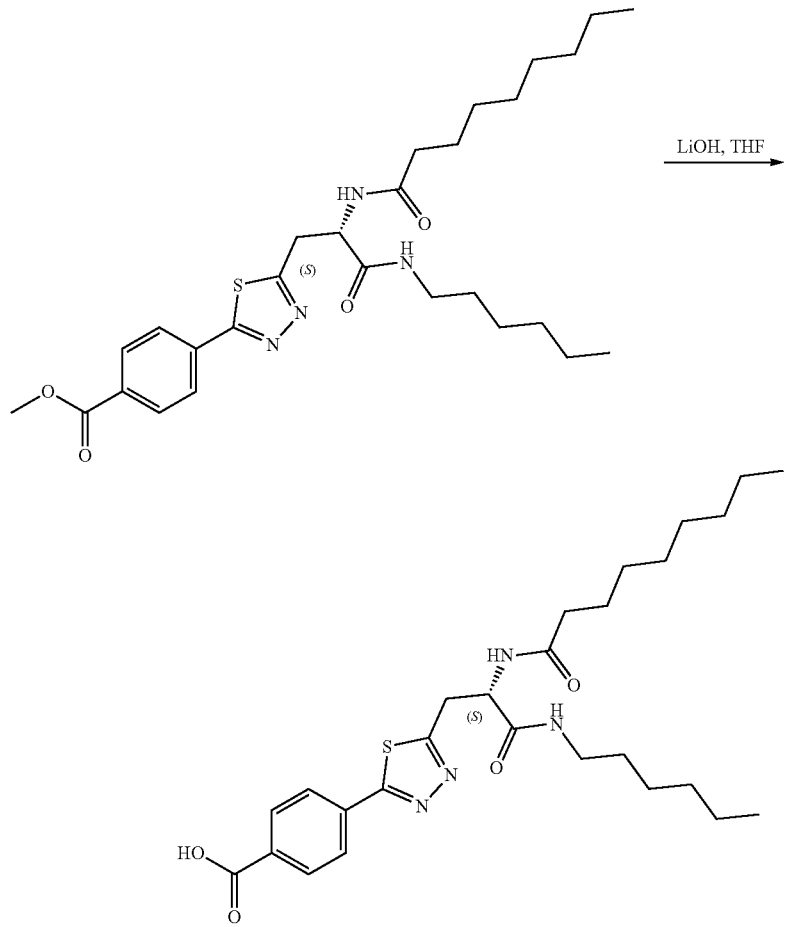

Prepare using General Ester Hydrolysis Procedure to give (S)-4-(5-(3-(hexylamino)-2-nonanamido-3-oxopropyl)-1,3,4-thiadiazol-2-yl)benzoic acid (0.15 g, 77.04%). LCMS (Method-C2): 92.96% (RT: 1.454, 282.0 nm) (MS: ESI +ve 531[M+H]).

Step 6: Preparation of (3S,4S)-1-(4-(5-((S)-2-decanamido-3-(hexylamino)-3-oxopropyl)-1,3,4-thiadiazol-2-yl)benzoyl)-N3,N4-bis((1S,2R)-2-phenylcyclopropyl)pyrrolidine-3,4-dicarboxamide, Compound 243

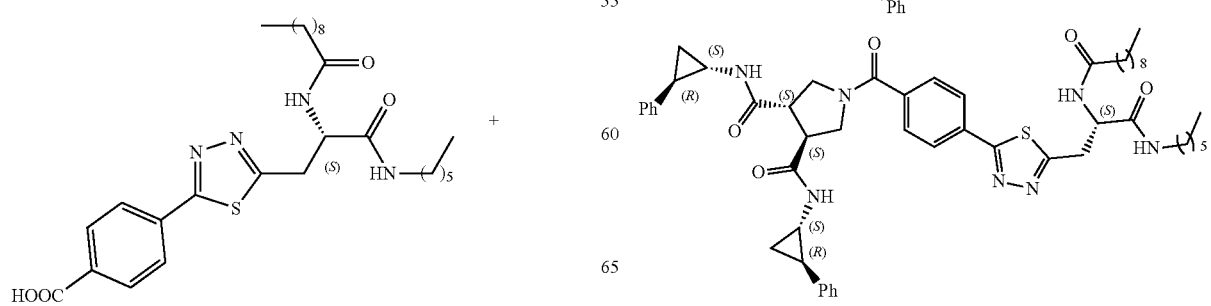

Prepared using General EDC, HOBT Coupling Procedure. The crude product was purified using Prep HPLC Method 10 to give (3S,4S)-1-(4-(5-((S)-2-decanamido-3-(hexylamino)-3-oxopropyl)-1,3,4-thiadiazol-2-yl)benzoyl)-N3,N4-bis((1S,2R)-2-phenylcyclopropyl) pyrrolidine-3,4-dicarboxamide (Compound 243)(0.034 g, 13.73%). LCMS (Method-c-fast): 100% (RT 2.106, 202.0 nm) (MS: ESI +ve 903 [M+H]. $^1$H NMR: (400 MHz, DMSO) δ ppm: 0.82-0.83 (m, 6H), 1.16-1.42 (m, 29H), 1.86 (s, 1H), 1.97-2.12 (m, 3H), 2.68-2.86 (m, 2H), 3.02-3.54 (m, 7H), 3.66-3.68 (d, J=8.4 Hz, 1H), 3.82-3.86 (t, J=9.2 HZ, 1H), 4.70-4.72 (d, J=6.4 Hz, 1H), 7.06-7.28 (m, 10H), 7.68-7.70 (d, J=10 Hz, 2H), 7.99-8.06 (m, 3H), 8.27-8.32 (m, 2H), 8.46 (s, 1H).

Synthesis of (3S,4S)-1-(4-(5-((S)-2-decanamido-3-(hexylamino)-3-oxopropyl)-1,2,4-oxadiazol-3-yl)benzoyl)-N3,N4-bis((1S,2R)-2-phenylcyclopropyl)pyrrolidine-3,4-dicarboxamide, Compound 249

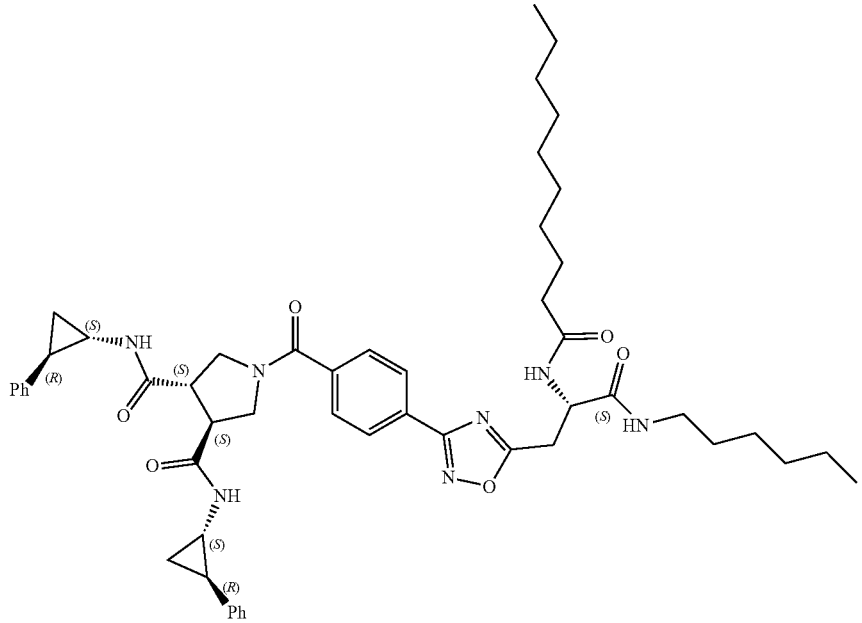

Step-1: Preparation of (3S,4S)-1-(4-cyanobenzoyl)-N3,N4-bis((1S,2R)-2-phenylcyclopropyl)pyrrolidine-3,4-dicarboxamide

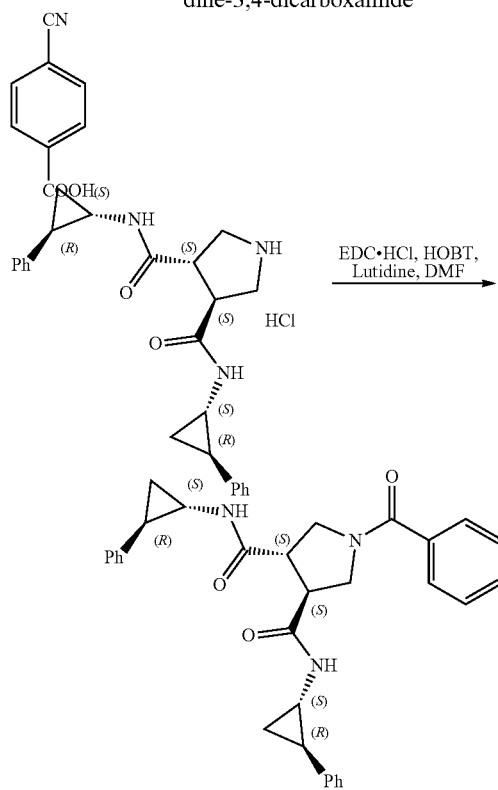

Prepared using General EDC, HOBT Coupling Procedure. The crude product was purified using flash chromatography, eluting with 3% MeOH:DCM, to give (3S,4S)-1-(4-cyanobenzoyl)-N3,N4-bis((1S,2R)-2-phenylcyclopropyl)pyrrolidine-3,4-dicarboxamide (1.1 g, 91.7%). LCMS (Method-C2): 98.49% (RT 1.294, 231.0 nm) (MS: ESI +ve 519.67 [M+1]).

Step-2: Preparation of (3S,4S)-1-(4-(N-hydroxycarbamimidoyl)benzoyl)-N3,N4-bis((1S,2R)-2-phenylcyclopropyl)pyrrolidine-3,4-dicarboxamide

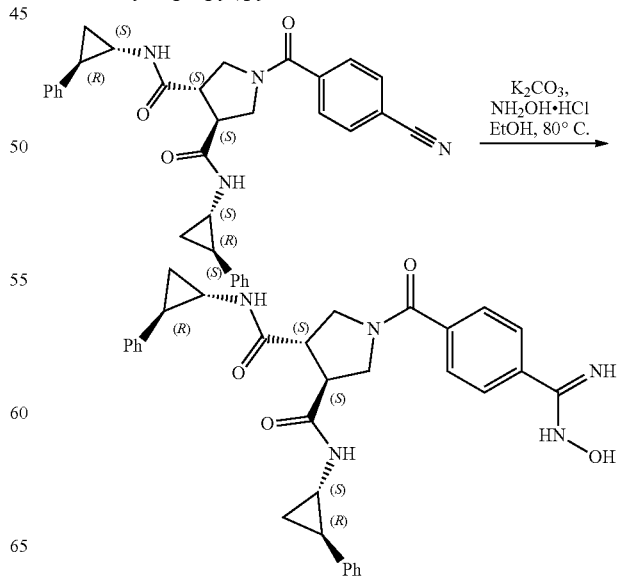

(3S,4S)-1-(4-cyanobenzoyl)-N3,N4-bis((1S,2R)-2-phenylcyclopropyl)pyrrolidine-3,4-dicarboxamide (1.1 g, 2.121 mmol) was dissolved in EtOH (70 mL). Potassium carbonate (1.75 g, 12.72 mmol) and hydroxyl amine hydrochloride (0.884 g, 12.72 mmol) were added and the mixture was heated at 80° C. for 20 h. The mixture was diluted with water (50 mL), extracted with EtOAc (3×100 mL), dried over sodium sulfate and concentrated to give (3S,4S)-1-(4-(N-hydroxycarbamimidoyl)benzoyl)-N3,N4-bis((1S,2R)-2-phenylcyclopropyl)pyrrolidine-3,4-dicarboxamide (1.3 g, crude). LCMS (Method-C2): 90.24% (RT 1.160, 236.0 nm) (MS: ESI +ve 552.24 [M+1]). The product was used directly in the next step.

Step-3: Preparation of allyl N2-(((9H-fluoren-9-yl)methoxy)carbonyl)-N4-((4-((3S,4S)-3,4-bis(((1S,2R)-2-phenylcyclopropyl)carbamoyl)pyrrolidine-1-carbonyl)phenyl)(imino)methyl)-N4-hydroxy-L-asparaginate

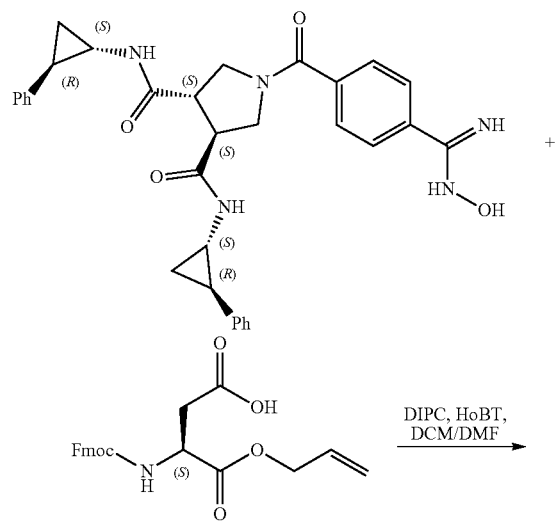

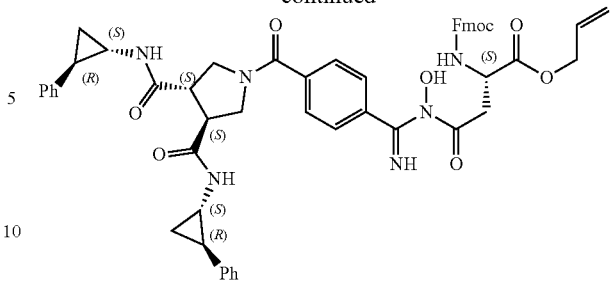

(3S,4S)-1-(4-(N-hydroxycarbamimidoyl)benzoyl)-N3,N4-bis((1S,2R)-2-phenylcyclopropyl)pyrrolidine-3,4-dicarboxamide (0.1.3 g, 2.359 mmol) was dissolved in a mixture of DCM:DMF (18:2 mL) and cooled to −10° C. HOBT (0.318 g, 2.359 mmol) and DIPC (0.297 mL, 2.359 mmol) were added, and the mixture was stirred at −10° C. for 20 min then warmed to ambient for 1.5 h. The mixture was concentrated then diluted with EtOAc (100 mL) and washed with sat. aq NaHCO₃ (2×50 mL), water (50 mL) and 0.5M KHSO₄ (2×50 mL). The organic layer was dried and concentrated then purified using flash chromatography, eluting with 3% MeOH:DCM, to give allyl N2-(((9H-fluoren-9-yl)methoxy)carbonyl)-N4-((4-((3S,4S)-3,4-bis(((1S,2R)-2-phenylcyclopropyl)carbamoyl)pyrrolidine-1-carbonyl)phenyl)(imino)methyl)-N4-hydroxy-L-asparaginate (1.2 g, 71.2%). LCMS (Method-C2): 91.21% (RT 1.423, 265.0 nm) (MS: ESI +ve 929.37 [M+1]).

Step-4: Preparation of allyl (S)-2-((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoate

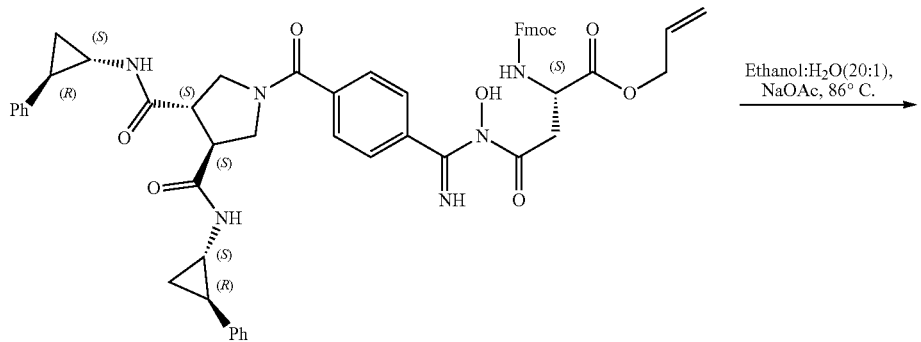

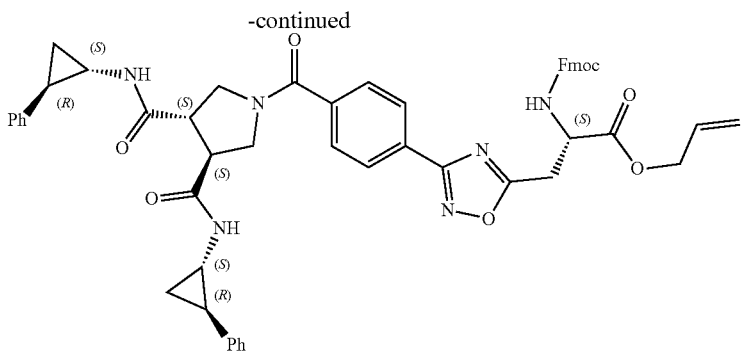

A mixture of allyl N2-(((9H-fluoren-9-yl)methoxy)carbonyl)-N4-((4-((3S,4S)-3,4-bis(((1S,2R)-2-phenylcyclopropyl)carbamoyl)pyrrolidine-1-carbonyl)phenyl)(imino)methyl)-N4-hydroxy-L-asparaginate (1.2 g, 1.292 mmol) and sodium acetate (0.116 g, 1.421 mmol) in EtOH:H$_2$O (20:1, 84 mL) was heated at 86° C. for 8 h. The mixture was cooled, concentrated, and the residue was diluted with water (100 mL), extracted with EtOAc (3×100 mL), dried over sodium sulfate and concentrated. The crude product was purified using flash chromatography, eluting with MeOH:DCM 0-5%, to give allyl (S)-2-((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoate (0.7 g, 59.4%) LCMS (Method-C2): 98.27% (RT: 1.452, 254.0 nm) (MS: ESI +ve 900.23 [M+H]).

Step 5: Preparation of (S)-2-((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoic acid

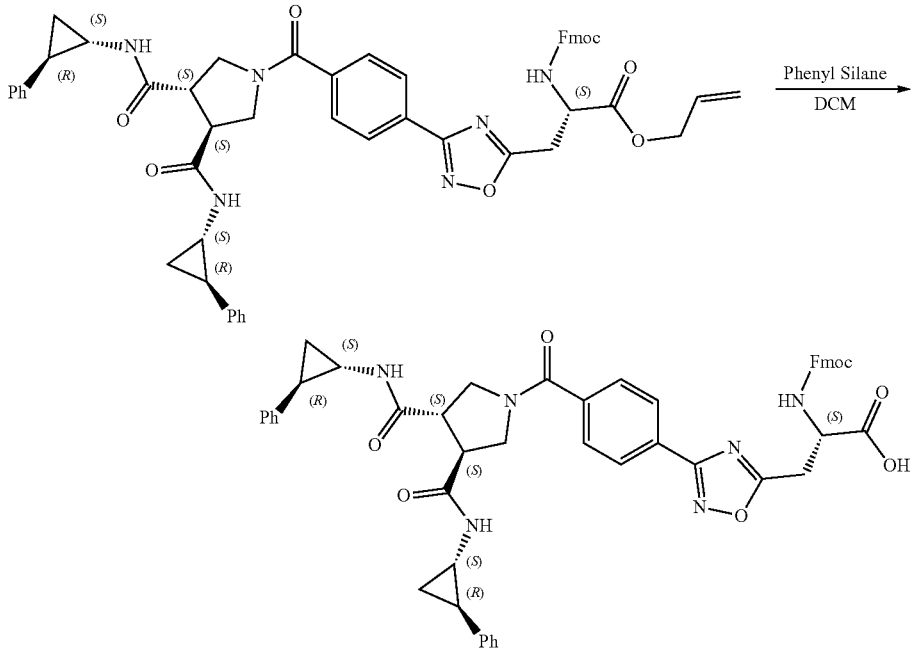

Allyl (S)-2-((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoate (0.47 g, 0.515 mmol), phenyl silane (0.111 g, 1.031 mmol) and tetrakistriphenyl phosphine palladium (0.0297 g, 0.0257 mmol) in DCM (20 mL) was stirred at room temperature for 24 h. The reaction mixture was diluted in DCM (2×50 mL), washed with water (50 mL) and concentrated to give (S)-2-((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoic acid (0.45 g, crude), which was used directly in the next step. LCMS (Method-C2): 34.08% (RT: 1.356, 220.0 nm) (MS: ESI +ve 871.48 [M−+H]).

Step-6: Preparation of (3S,4S)-1-(4-(5-((S)-2-amino-3-(hexylamino)-3-oxopropyl)-1,2,4-oxadiazol-3-yl)benzoyl)-N3,N4-bis((1S,2R)-2-phenylcyclopropyl)pyrrolidine-3,4-dicarboxamide

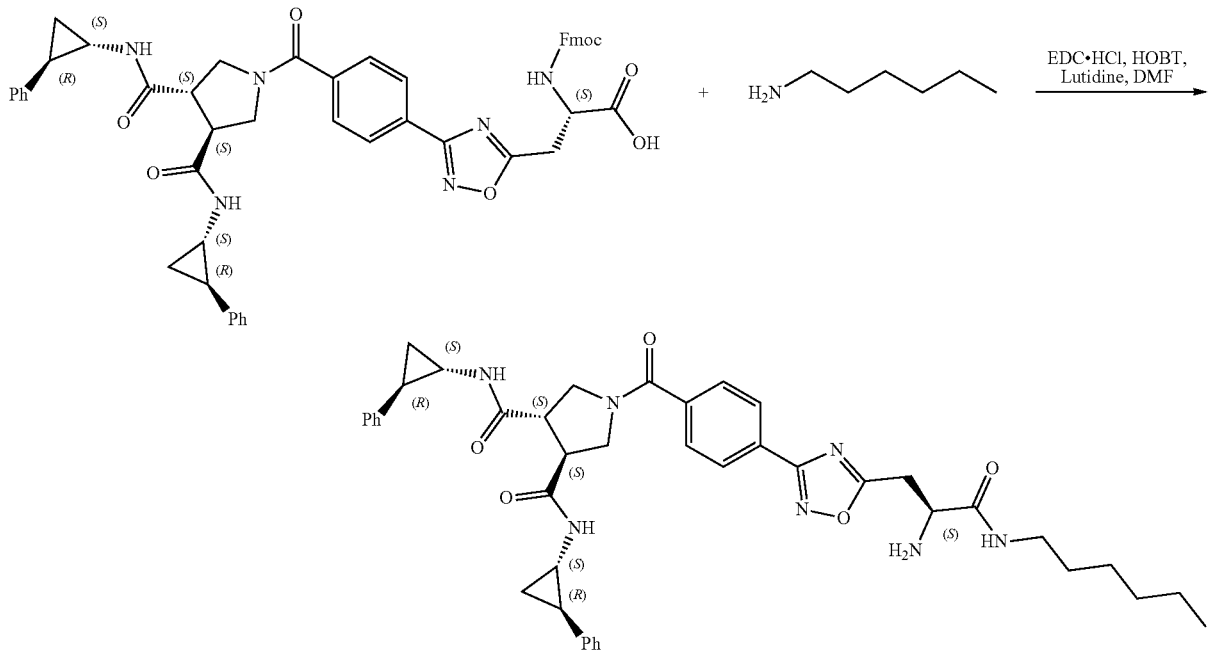

Prepared using General EDC, HOBT Coupling Procedure. The crude product was purified using flash chromatography, eluting with 6% e MeOH:DCM, to give (3S,4S)-1-(4-(5-((S)-2-amino-3-(hexylamino)-3-oxopropyl)-1,2,4-oxadiazol-3-yl)benzoyl)-N3,N4-bis((1S,2R)-2-phenylcyclopropyl)pyrrolidine-3,4-dicarboxamide (0.1 g, 25.5%). LCMS (Method-C2): 72.92% (RT 1.218, 225.0 nm) (MS: ESI +ve 732.59 [M+1]).

Step-7: Preparation of (3S,4S)-1-(4-(5-((S)-2-decanamido-3-(hexylamino)-3-oxopropyl)-1,2,4-oxadiazol-3-yl)benzoyl)-N3,N4-bis((1S,2R)-2-phenylcyclopropyl)pyrrolidine-3,4-dicarboxamide, Compound 249

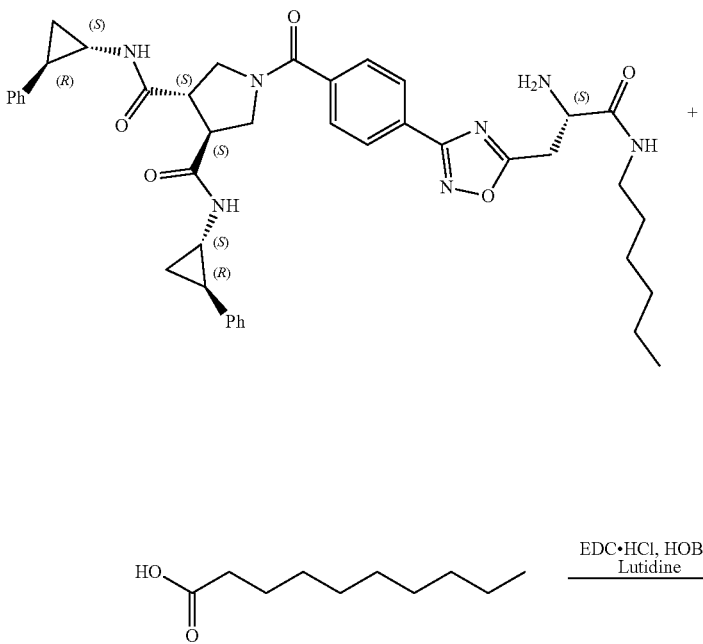

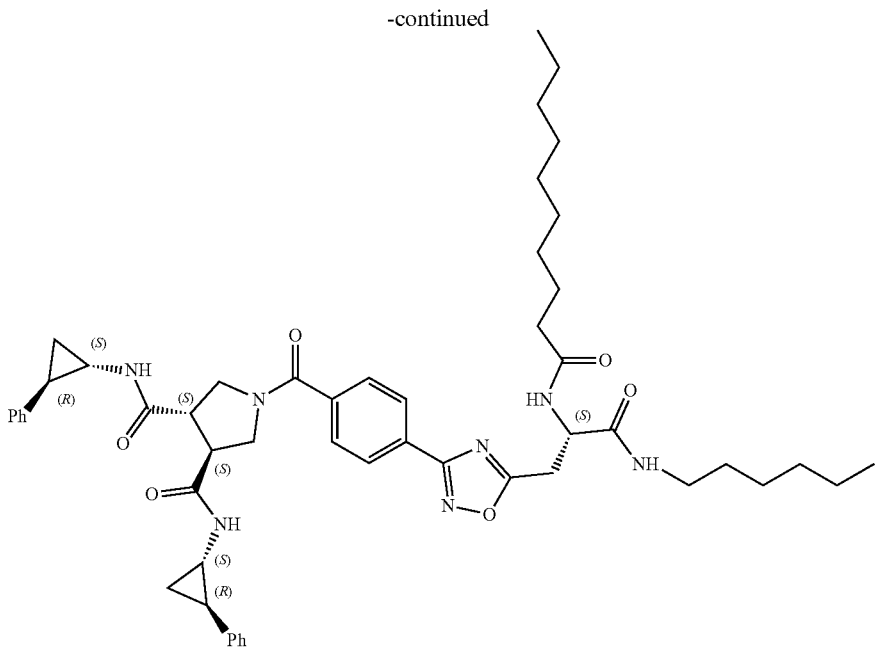

Prepared using General EDC, HOBT Coupling Procedure. The crude product was purified using Prep HPLC Method 10 to give (3S,4S)-1-(4-(5-((S)-2-decanamido-3-(hexylamino)-3-oxopropyl)-1,2,4-oxadiazol-3-yl)benzoyl)-N3,N4-bis((1S,2R)-2-phenylcyclopropyl)pyrrolidine-3,4-dicarboxamide (Compound 219), as an off white solid (0.017 g, 10.03%). LCMS (Method-C-Fast): 100% (RT 2.170, 225.0 nm) (MS: ESI +ve 886.69 [M+H]). $^1$H NMR: (400 MHz, DMSO) δ ppm: 0.80-0.84 (m, 6H), 1.14-1.19 (m, 18H), 1.35-1.41 (m, 4H), 1.84 (s, 1H), 1.97-2.10 (m, 3H), 2.67-2.85 (m, 2H), 3.00-3.14 (m, 4H), 3.19-3.27 (m, 3H), 3.37-3.42 (m, 3H), 3.49-3.56 (m, 2H), 3.64-3.69 (m, 1H), 3.80-3.85 (m, 1H), 4.82-4.83 (m, 1H), 7.05-7.29 (m, 10H), 7.68-7.70 (d, J=8.4 Hz, 2H), 8.02-8.04 (d, J=8 Hz, 3H), 8.23-8.29 (m, 2H), 8.42-8.43 (d, J=3.6 Hz, 1H).

Synthesis of (3S,4S)-1-(4-(3-((S)-2-decanamido-3-(hexylamino)-3-oxopropyl)-1,2,4-oxadiazol-5-yl)benzoyl)-N3,N4-bis((1S,2R)-2-phenylcyclopropyl)pyrrolidine-3,4-dicarboxamide, Compound 271

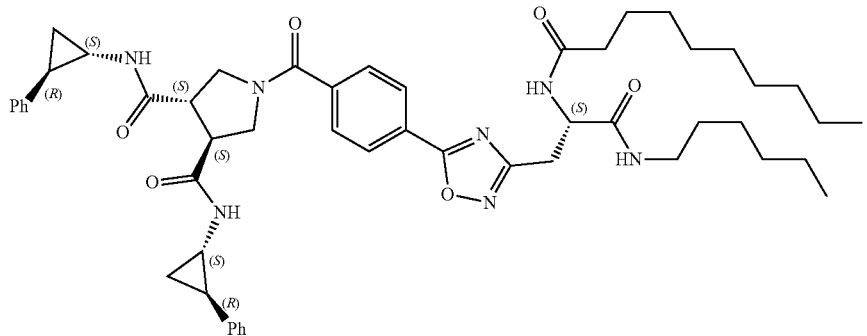

Step-1: Preparation of tert-butyl (S)-(3-cyano-1-(hexylamino)-1-oxopropan-2-yl)carbamate

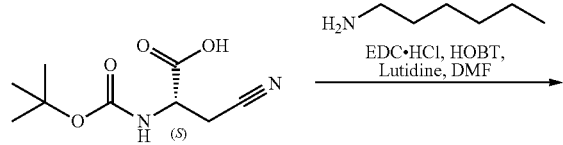 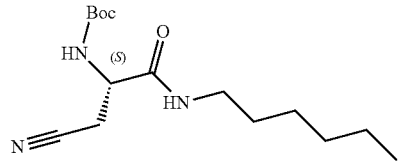

Prepared using General EDC, HOBT Coupling Procedure. The crude was purified using flash chromatography eluting with 3% MeOH:DCM to give tert-butyl (S)-(3-cyano-1-(hexylamino)-1-oxopropan-2-yl)carbamate (1.2 g, 86.44%). LCMS (Method-C2): 78.43% (RT 1.303, 202.0 nm) (MS: ESI +ve 298.3 [M+1]).

Step-2: Preparation of (S)-2-amino-3-cyano-N-hexylpropanamide

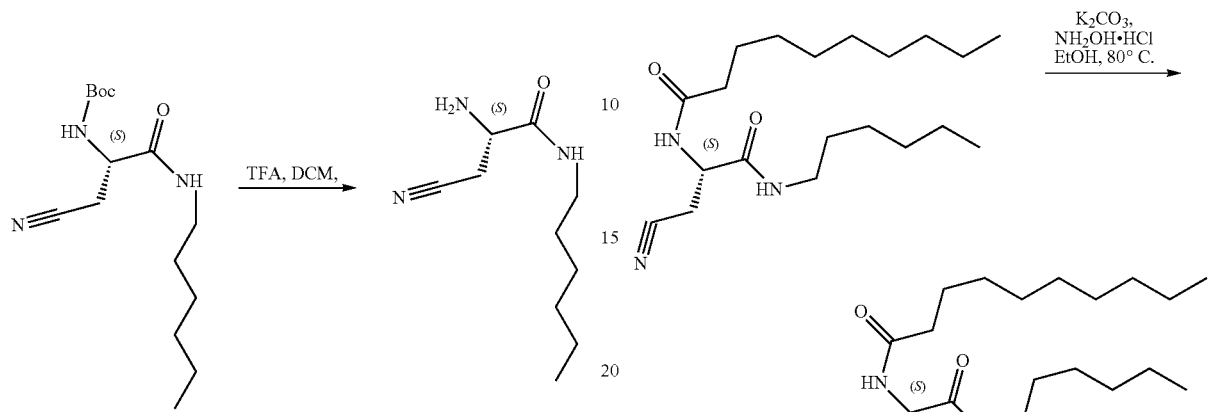

Prepared using General BOC Deprotection Procedure to give (S)-2-amino-3-cyano-N-hexylpropanamide as TFA salt, brown gum (0.9 g, Crude) LCMS (Method-C2): 29.38% (RT 0.924, 222.0 nm) (MS: ESI +ve 198.16 [M+1]).

Step-3: Preparation of (S)—N-(3-cyano-1-(hexylamino)-1-oxopropan-2-yl)decanamide

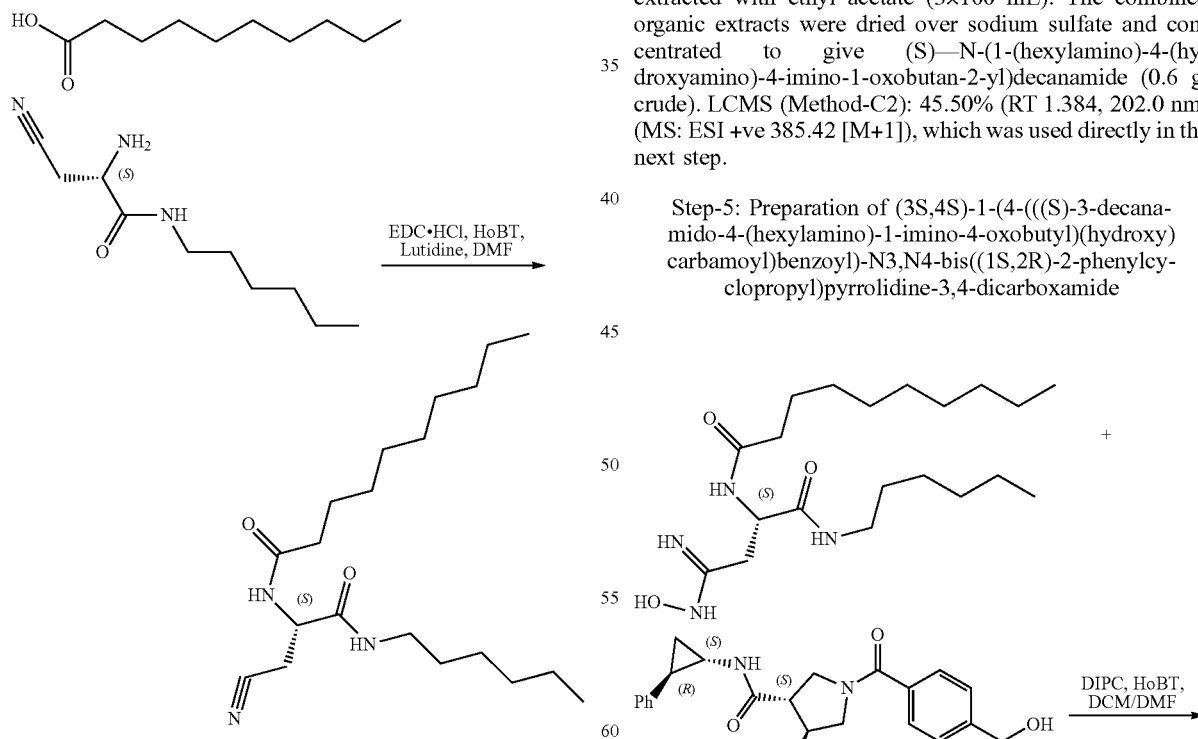

Prepared using General EDC, HOBT Coupling Procedure. The crude was purified using flash chromatography eluting with 3% MeOH:DCM to give (S)—N-(3-cyano-1-(hexylamino)-1-oxopropan-2-yl)decanamide (0.75 g, 46.77%). LCMS (Method-C2): 63.70% (RT 1.519, 202.0 nm) (MS: ESI +ve 352.25 [M+1]).

Step-4: Preparation of (S)—N-(1-(hexylamino)-4-(hydroxyamino)-4-imino-1-oxobutan-2-yl)decanamide

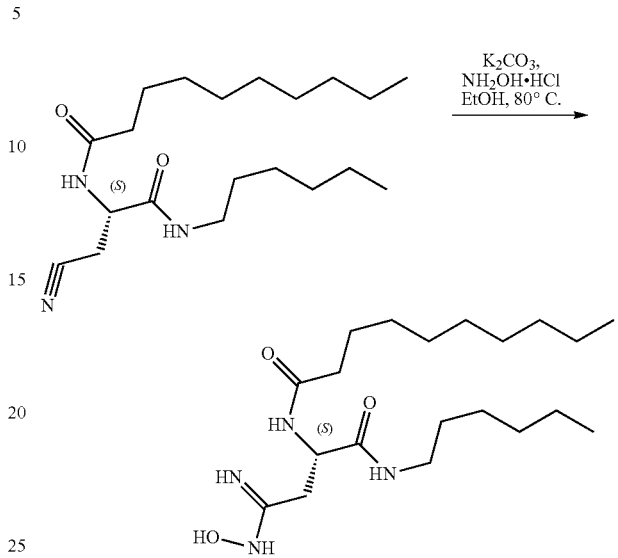

(S)—N-(3-cyano-1-(hexylamino)-1-oxopropan-2-yl) decanamide (0.7 g, 1.994 mmol), potassium carbonate (1.65 g, 11.965 mmol) and hydroxyl amine hydrochloride (0.831 g, 11.965 mmol) in EtOH (40 mL) was heated at 80° C. for 20 h. The mixture was diluted with water (50 mL) and extracted with ethyl acetate (3×100 mL). The combined organic extracts were dried over sodium sulfate and concentrated to give (S)—N-(1-(hexylamino)-4-(hydroxyamino)-4-imino-1-oxobutan-2-yl)decanamide (0.6 g, crude). LCMS (Method-C2): 45.50% (RT 1.384, 202.0 nm) (MS: ESI +ve 385.42 [M+1]), which was used directly in the next step.

Step-5: Preparation of (3S,4S)-1-(4-(((S)-3-decanamido-4-(hexylamino)-1-imino-4-oxobutyl)(hydroxy) carbamoyl)benzoyl)-N3,N4-bis((1S,2R)-2-phenylcyclopropyl)pyrrolidine-3,4-dicarboxamide

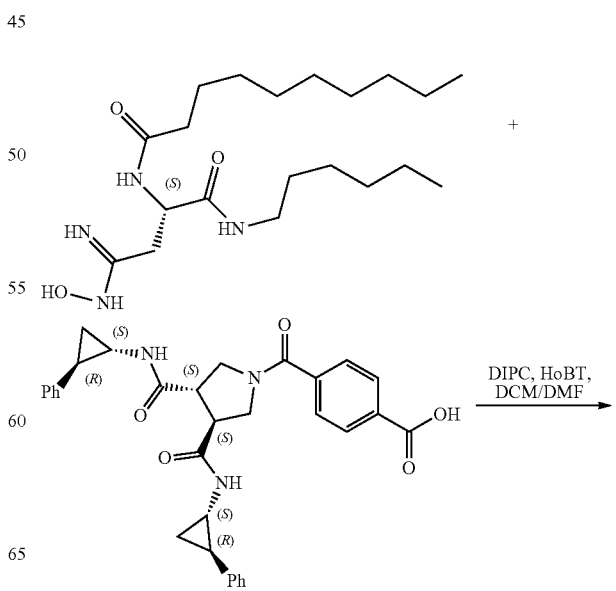

-continued

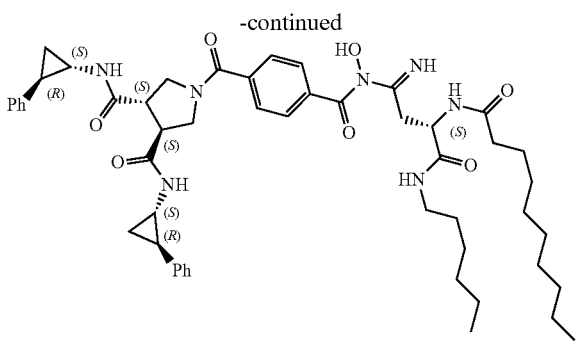

(S)—N-(1-(hexylamino)-4-(hydroxyamino)-4-imino-1-oxobutan-2-yl)decanamide (0.6 g, 1.562 mmol) and 4-((3S,4S)-3,4-bis(((1S,2R)-2-phenylcyclopropyl)carbamoyl)pyrrolidine-1-carbonyl)benzoic acid (0.550 g, 1.041 mmol) was dissolved in dry DCM: DMF (20:2 mL) and cooled to −10° C. HOBT (0.140 g, 1.041 mmol) and DIPC (0.131 g, 1.041 mmol) were added and stirred at −10° C. for 20 min, then warmed to room temperature for 1.5 h. The reaction mixture was evaporated, then diluted with ethyl acetate (100 mL), washed with sat. aq. NaHCO$_3$ solution (2×50 mL), water (50 mL) and 0.5M KHSO$_4$ (2×50 mL) then concentrated. The crude product was purified using flash chromatography, eluting with 6% MeOH:DCM, to give (3S,4S)-1-(4-(((S)-3-decanamido-4-(hexylamino)-1-imino-4-oxobutyl)(hydroxy)carbamoyl)benzoyl)-N3,N4-bis((1S,2R)-2-phenylcyclopropyl)pyrrolidine-3,4-dicarboxamide (0.32 g, 21.2%). LCMS (Method-C2): 55.93% (RT 1.502, 202.0 nm) (MS: ESI +ve 905.18 [M+1]).

Step-6: Preparation of (3S,4S)-1-(4-(3-((S)-2-decanamido-3-(hexylamino)-3-oxopropyl)-1,2,4-oxadiazol-5-yl)benzoyl)-N3,N4-bis((1S,2R)-2-phenylcyclopropyl)pyrrolidine-3,4-dicarboxamide, Compound 271

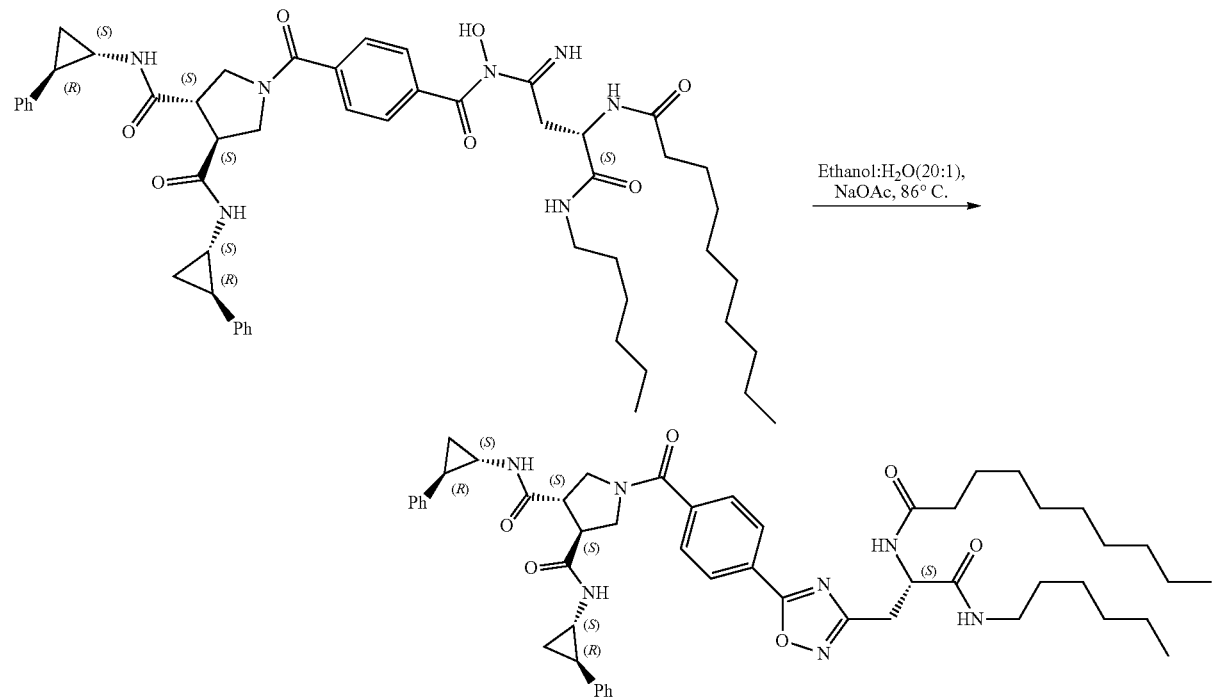

Prepared by a procedure similar to that reported for allyl (S)-2-(((((9H-fluoren-9-yl)methoxy)carbonyl)amino)-3-(3-(4-((3S,4S)-3,4-bis(((1S,2R)-2-phenylcyclopropyl)carbamoyl)pyrrolidine-1-carbonyl)phenyl)-1,2,4-oxadiazol-5-yl)propanoate. The crude product was purified using Prep HPLC Method 10 to give (3S,4S)-1-(4-(3-((S)-2-decanamido-3-(hexylamino)-3-oxopropyl)-1,2,4-oxadiazol-5-yl)benzoyl)-N3,N4-bis((1S,2R)-2-phenylcyclopropyl)pyrrolidine-3,4-dicarboxamide (Compound 271)(0.075 g, 25.51%). LCMS (Method-C2): 100% (RT 1.563, 265.0 nm) (MS: ESI +ve 886.7 [M+H]). $^1$H NMR: (400 MHz, DMSO) δ ppm: 0.84-0.85 (m, 6H), 1.10-1.41 (m, 26H), 1.84-1.85 (m, 1H), 1.96-1.99 (m, 1H), 2.07-2.10 (m, 2H), 2.68-2.78 (m, 2H), 3.01-3.25 (m, 6H), 3.49-3.57 (m, 2H), 3.63-3.67 (m, 1H), 3.79-3.86 (m, 1H), 4.76-4.77 (m, 1H), 7.06-7.08 (d, J=7.6 Hz, 2H), 7.13-7.19 (m, 4H), 7.23-7.30 (m, 4H), 7.75-7.77 (d, J=8.4 Hz, 2H), 7.99-8.02 (t, 1H), 8.13-8.19 (m, 3H), 8.36-8.52 (m, 2H).

Synthesis of (3S,4S)-1-(4-(5-((S)-2-decanamido-3-(hexylamino)-3-oxopropyl)-2H-tetrazol-2-yl)benzoyl)-N3,N4-bis((1S,2R)-2-phenylcyclopropyl)pyrrolidine-3,4-dicarboxamide, Compound 285

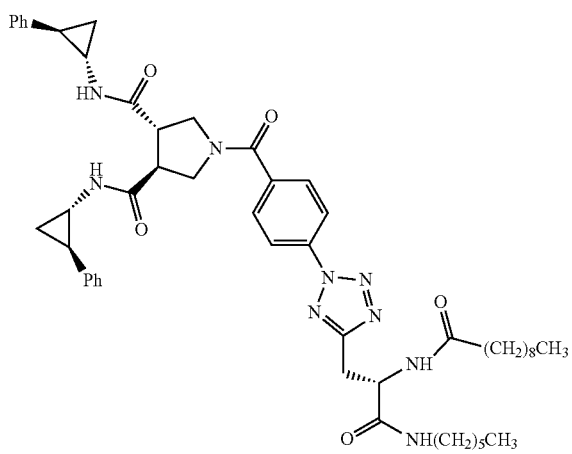

Step-1: Preparation of tert-butyl (S)-4-amino-2-(((benzyloxy)carbonyl)amino)-4-thioxobutanoate

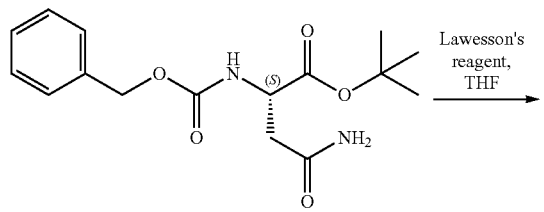

A mixture of Lawesson's reagent (1.8 g, 4.600 mmol) in THF (10 mL) was added dropwise to a solution of tert-butyl ((benzyloxy)carbonyl)-L-asparaginate (3 g, 9.300 mmol) in THF (15 mL). The mixture was stirred at room temperature for 16 h then concentrated. The solid was dissolved in EtOAc (100 mL) and washed with sat. aq. NaHCO₃ solution (2×50 mL). The organic layer was dried and concentrated. The crude product was purified using flash chromatography, eluting with 0-40% EtOAc:hexanes, to give tert-butyl (S)-4-amino-2-(((benzyloxy)carbonyl)amino)-4-thioxobutanoate. (1.3 g, 41.9% yield). LCMS (Method-C fast): 98.2% (RT: 0.818, 265 nm) (MS: ESI -ve 283.4 [M-56]).

Step-2: Preparation of tert-butyl (S)-2-(((benzyloxy)carbonyl)amino)-4-imino-4-(methylthio)butanoate

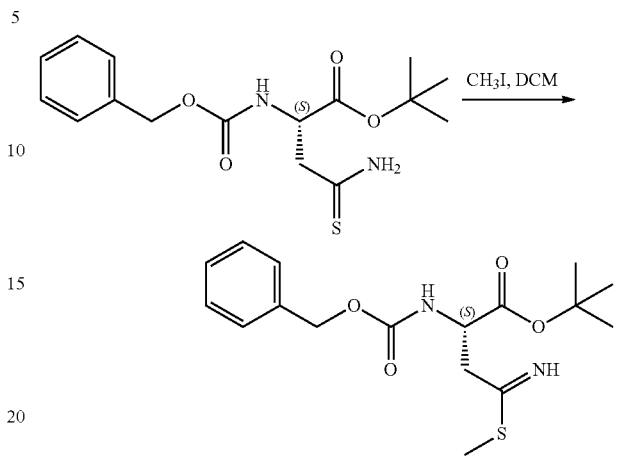

tert-Butyl (S)-4-amino-2-(((benzyloxy)carbonyl)amino)-4-thioxobutanoate (1.3 g, 3.800 mmol) was dissolved in DCM (10 mL) and cooled to 0° C. Methyl iodide (2.4 mL, 38.400 mmol) was added and the mixture was stirred at room temperature for 24 h. 10% aq K₂CO₃ solution (0.529 g, 3.800 mmol in 1.12 mL water) was added to the reaction mixture, with stirring for 5-10 mins at room temperature. The organic layer was separated and concentrated to give crude product, which was purified by flash chromatography, eluting with 0-40% Ethyl acetate in Hexane, to give tert-butyl (S)-2-(((benzyloxy)carbonyl)amino)-4-imino-4-(methylthio)butanoate. (1.1 g, 84.6% yield). LCMS (Method-H): 68% (RT: 3.374, 214 nm) (MS: ESI +ve 353.0 [M+1]).

Step-3: Preparation of tert-butyl (S)-4-amino-2-(((benzyloxy)carbonyl)amino)-4-iminobutanoate

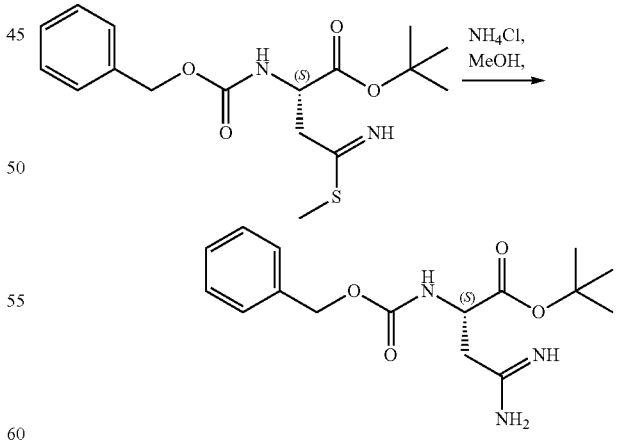

tert-Butyl (S)-2-(((benzyloxy)carbonyl)amino)-4-imino-4-(methylthio)butanoate (1.1 g, 3.100 mmol) was dissolved in MeOH (15 mL). Ammonium chloride (0.166 g, 3.100 mmol) was added, and the reaction mixture was heated at 70° C. for 3 h. The mixture was then concentrated to give tert-butyl (S)-4-amino-2-(((benzyloxy)carbonyl)amino)-4- iminobutanoate. (1.1 g, crude). LCMS (Method-J2): 74.4% (RT: 2.953, 214 nm) (MS: ESI +ve 322.0 [M+1]).

Step-4: Preparation of 2-(4-(methoxycarbonyl)phenyl)-1-(trifluoro-15-boraneylidene)diazen-1-ium fluoride

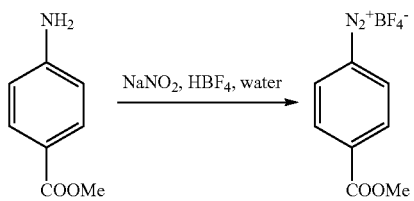

Methyl 4-aminobenzoate (2 g, 13.200 mmol) was added to a mixture of fluoroboric acid (7 mL) in water (10 mL) at 0° C. Sodium nitrite (0.912 g, 13.200 mmol) in water (1.98 mL) was added dropwise. The reaction mixture was stirred at 0° C. for 30 mins. The mixture was diluted with H₂O and the resulting precipitate was collected by filtration. The solid was dissolved in acetone (10 mL), diethyl ether was added and the precipitate was collected by filtration and dried to give 2-(4-(methoxycarbonyl)phenyl)-1-(trifluoro-15-boraneylidene)diazen-1-ium fluoride. (1.0 g, 30.3% yield). Mass m/z=249.05

Step-5: Preparation of methyl (S)-4-(5-(2-(((benzyloxy)carbonyl)amino)-3-(tert-butoxy)-3-oxopropyl)-2H-tetrazol-2-yl)benzoate

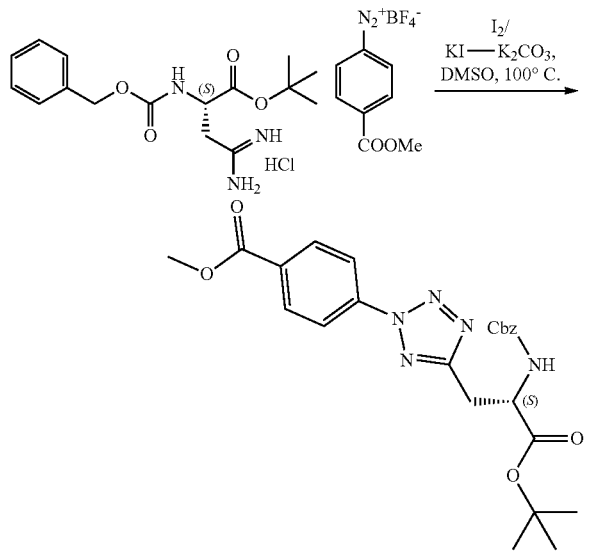

tert-Butyl (S)-4-amino-2-(((benzyloxy)carbonyl)amino)-4-iminobutanoate (0.900 g, 2.800 mmol) was dissolved in DMSO (10 mL). Potassium carbonate (1.93 g, 14.002 mmol) and 2-(4-(methoxycarbonyl)phenyl)-1-(trifluoro-15-boraneylidene)diazen-1-ium fluoride (0.699 g, 2.800 mmol) were added. The mixture was stirred at room temperature for 1 h. A solution of iodine (0.852 g, 3.360 mmol) and potassium iodide (0.697 g, 4.200 mmol) in DMSO was added dropwise. The mixture was stirred at room temperature for 1 h, concentrated then extracted with ethyl acetate (2×25 mL) and water (2×25 mL), concentrated again. The crude product was purified using flash chromatography eluting, with 0-20% EtOAc:hexanes, to give methyl (S)-4-(5-(2-(((benzyloxy)carbonyl)amino)-3-(tert-butoxy)-3-oxopropyl)-2H-tetrazol-2-yl)benzoate. (0.308 g, 23.6% yield). LCMS (Method-C fast): 74.8% (RT: 1.772, 268 nm) (MS: ESI +ve 482.5 [M+1]).

Step-6: Preparation of methyl (S)-4-(5-(2-amino-3-(tert-butoxy)-3-oxopropyl)-2H-tetrazol-2-yl)benzoate

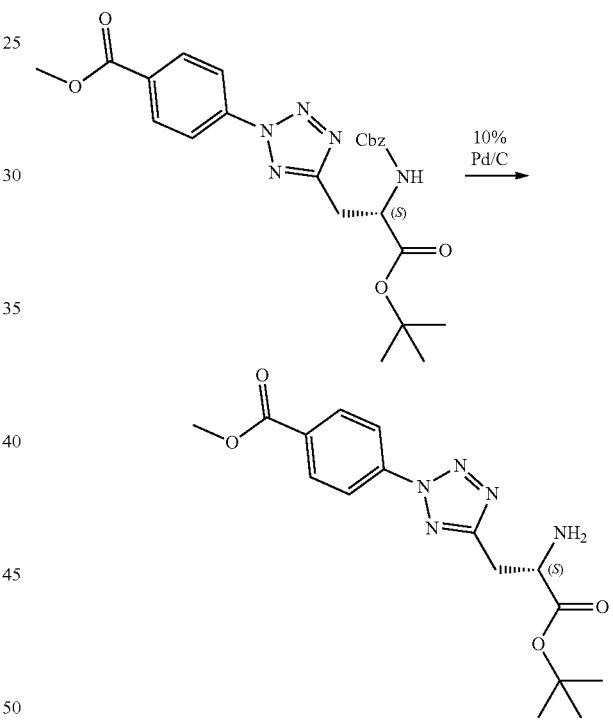

Methyl (S)-4-(5-(2-(((benzyloxy)carbonyl)amino)-3-(tert-butoxy)-3-oxopropyl)-2H-tetrazol-2-yl)benzoate (0.380 g, 0.789 mmol) was dissolved in MeOH (20 mL) and DCM (10 mL). Palladium on carbon (0.380 g) was added to the reaction mixture which was stirred under hydrogen (balloon) atmosphere for 2 h at room temperature. The mixture was filtered through celite and rinsed with MeOH then DCM (10 mL). The filtrate was concentrated and the crude product was purified using flash chromatography, eluting with 0-10% MeOH:DCM, to give methyl (S)-4-(5-(2-amino-3-(tert-butoxy)-3-oxopropyl)-2H-tetrazol-2-yl)benzoate (0.207 g, 75.5% yield). LCMS (Method-C fast): 73.2% (RT: 0.387, 265.0 nm) (MS: ESI +ve 348.3 [M+1]).

Step-7: Preparation of methyl (S)-4-(5-(3-(tert-butoxy)-2-decanamido-3-oxopropyl)-2H-tetrazol-2-yl)benzoate

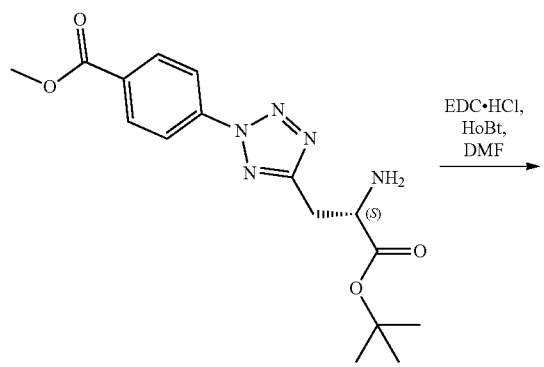

Prepared using General EDC, HOBT Coupling Procedure. The crude product was purified using flash chromatography, eluting with 0-30% EtOAc:hexanes, to give methyl (S)-4-(5-(3-(tert-butoxy)-2-decanamido-3-oxopropyl)-2H-tetrazol-2-yl)benzoate. (0.160 g, 66.6% yield). LCMS (Method-C Fast): 83.1% (RT: 2.275, 228 nm) (MS: ESI +ve 502.7 [M+1]).

Step-8: Preparation of (S)-2-decanamido-3-(2-(4-(methoxycarbonyl)phenyl)-2H-tetrazol-5-yl)propanoic acid

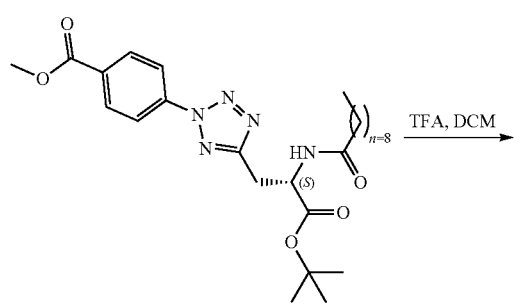

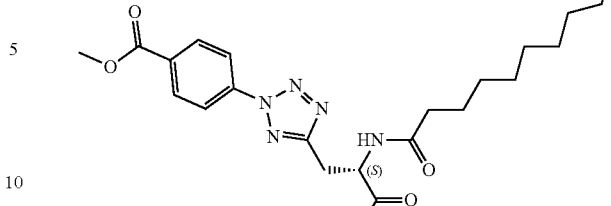

Prepared using General BOC Deprotection Procedure to give (S)-2-decanamido-3-(2-(4-(methoxycarbonyl)phenyl)-2H-tetrazol-5-yl)propanoic acid (0.167 g, crude). LCMS (Method-C fast): 88.6% (RT: 1.576, 257 nm) (MS: ESI +ve 446.7 [M+1]).

Step-9: Preparation of methyl (S)-4-(5-(2-decanamido-3-(hexylamino)-3-oxopropyl)-2H-tetrazol-2-yl)benzoate

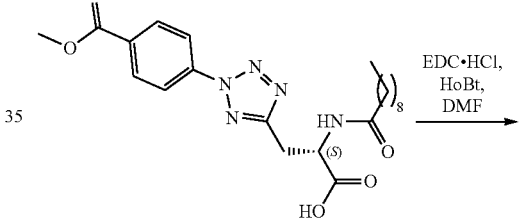

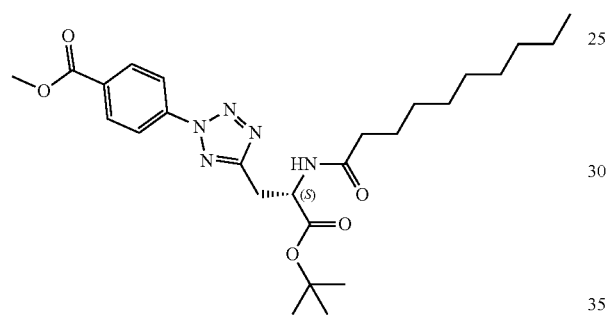

Prepared using General EDC, HOBT Coupling Procedure. The crude product was purified using flash chromatography, eluting with 0-60% EtOAc:hexane, to give methyl (S)-4-(5-(2-decanamido-3-(hexylamino)-3-oxopropyl)-2H-tetrazol-2-yl)benzoate. LCMS (Method-C fast): 96.9% (RT: 2.201, 268 nm) (MS: ESI +ve 529.8 [M+1]).

Step-10: Preparation of (S)-4-(5-(2-decanamido-3-(hexylamino)-3-oxopropyl)-2H-tetrazol-2-yl)benzoic acid
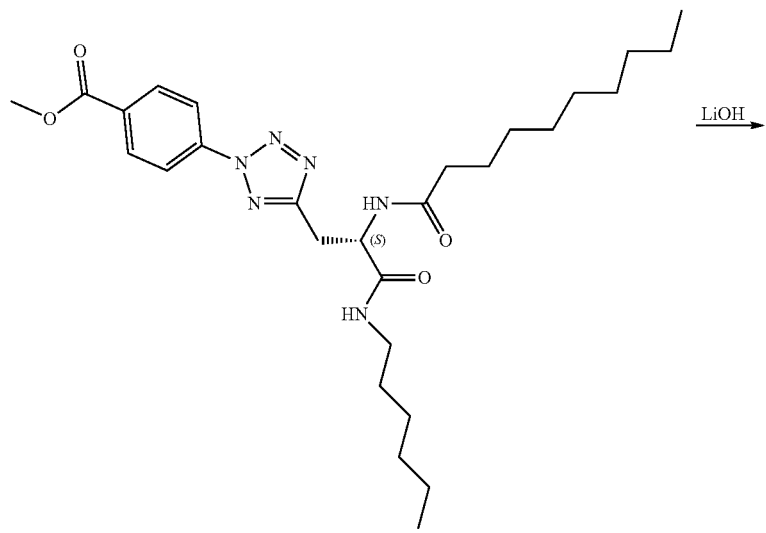
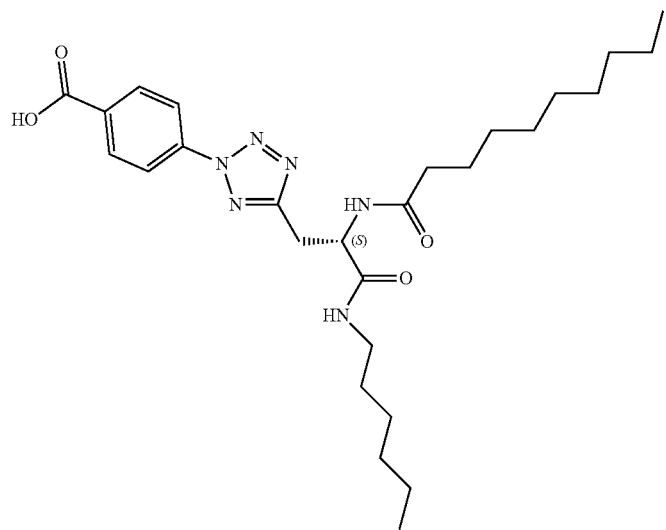
Prepared using General Ester Hydrolysis Procedure to give (S)-4-(5-(2-decanamido-3-(hexylamino)-3-oxopropyl)-2H-tetrazol-2-yl)benzoic acid. (0.136 g, 93.1% yield). LCMS (Method-C fast): 97.5% (RT: 1.815, 268.0 nm) (MS: ESI +ve 515.4 [M+1]).

Step-11: Preparation of (3S,4S)-1-(4-(5-((S)-2-decanamido-3-(hexylamino)-3-oxopropyl)-2H-tetrazol-2-yl)benzoyl)-N3,N4-bis((1S,2R)-2-phenylcyclopropyl)pyrrolidine-3,4-dicarboxamide, Compound 285

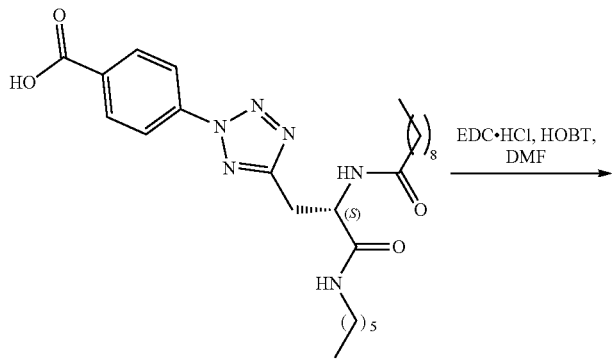

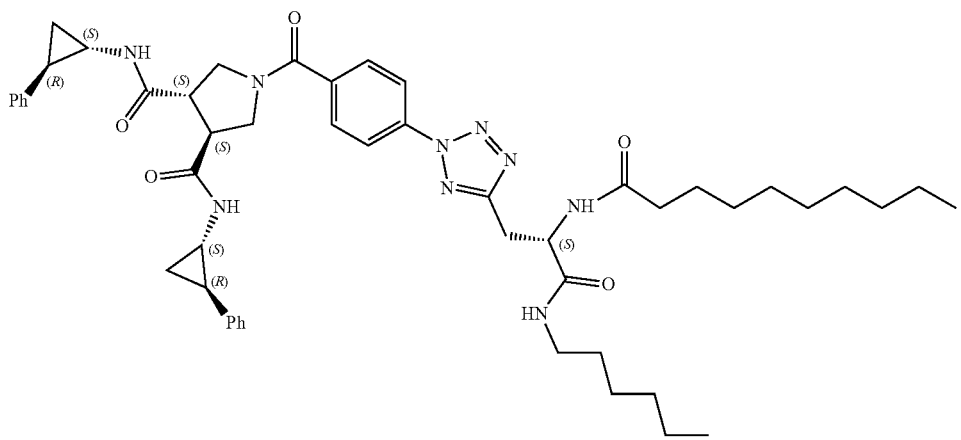

Prepared using General EDC, HOBT Coupling Procedure. The crude solid was purified by trituration in MeOH to give (3S,4S)-1-(4-(5-((S)-2-decanamido-3-(hexylamino)-3-oxopropyl)-2H-tetrazol-2-yl)benzoyl)-N3,N4-bis((1S,2R)-2-phenylcyclopropyl)pyrrolidine-3,4-dicarboxamide (Compound 285)(0.037 g, 16.1% yield), as a white solid. LCMS (Method-C fast): 100% (RT: 2.119, 266.0 nm) (MS: ESI −ve 885.9 [M−1]). $^1$H NMR: (400 MHz, DMSO) δ ppm: 0.799-0.857 (m, 6H), 1.124-1.166 (m, 22H), 1.318-1.376 (m, 4H), 1.854 (s, 1H), 1.989 (s, 1H), 2.059-2.094 (t, J=14 Hz, 2H), 2.687 (s, 1H), 2.798 (s, 1H), 2.991 (m, 1H), 3.084 (m, 1H), 3.125 (m, 3H), 3.227-3.305 (m, 2H), 3.558-3.579 (t, J=8 Hz, 2H), 3.677-3.697 (m, 1H), 3.824-3.845 (m, 1H), 4.785-4.802 (m, 1H), 7.062-7.081 (d, 2H), 7.132-7.228 (m, 4H), 7.264-7.301 (m, 4H), 7.813-7.834 (d, 2H), 8.009 (m, 1H), 8.116-8.171 (m, 3H), 8.327-8.336 (d, J=3.6 Hz, 1H), 8.461-8.470 (d, 3.6 Hz, 1H).

Synthesis of (3S,4S)-1-(2-((S)-2-decanamido-3-(hexylamino)-3-oxopropyl)-1,3-dioxoisoindoline-5-carbonyl)-N3,N4-bis((1S,2R)-2-phenylcyclopropyl)pyrrolidine-3,4-dicarboxamide, Compound 240

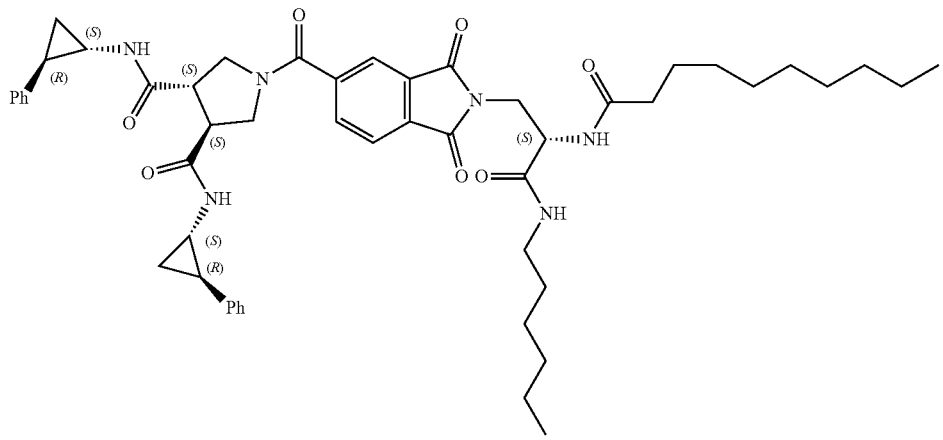

Step-1: Preparation of (S)-2-(2-decanamido-3-(hexylamino)-3-oxopropyl)-1,3-dioxoisoindoline-5-carboxylic acid

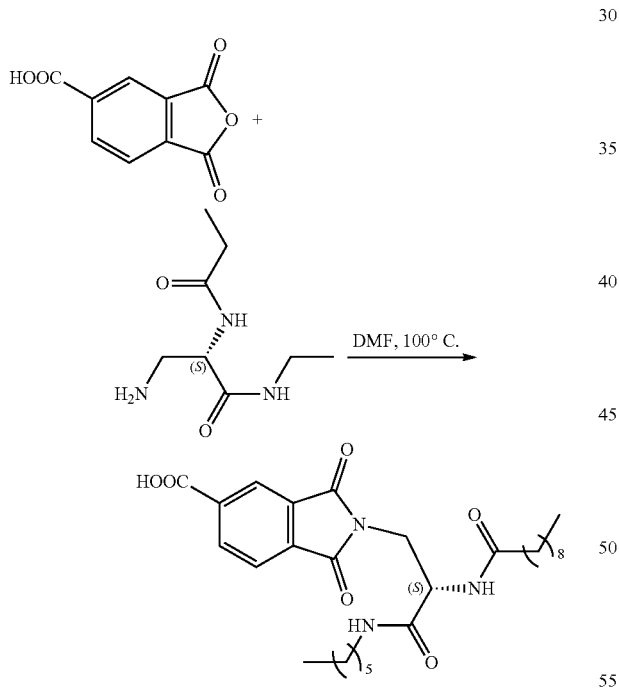

A mixture of (S)—N-(3-amino-1-(hexylamino)-1-oxo-propan-2-yl)decanamide (0.400 g, 1.171 mmol) and 1,3-dioxo-1,3-dihydroisobenzofuran-5-carboxylic acid (0.270 g, 1.405 mmol) in DMF (7 mL) was heated at 100° C. for 24 h. Cold water was added and the pH adjusted to 4 using 5% HCl. The resulting precipitate was collected by filtration and dried under vacuum to give (S)-2-(2-decanamido-3-(hexylamino)-3-oxopropyl)-1,3-dioxoisoindoline-5-carboxylic acid. (0.520 g, 86.2% yield). (Method-C3): 73.7% (RT: 1.780, 202.0 nm) (MS: ESI +ve 516.6 [M+1]).

Step-2: Preparation of (3S,4S)-1-(2-((S)-2-decanamido-3-(hexylamino)-3-oxopropyl)-1,3-dioxoisoindoline-5-carbonyl)-N3,N4-bis((1S,2R)-2-phenylcyclopropyl)pyrrolidine-3,4-dicarboxamide, Compound 240

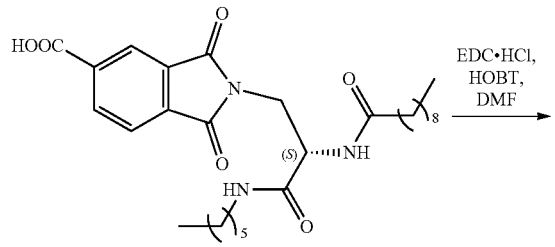

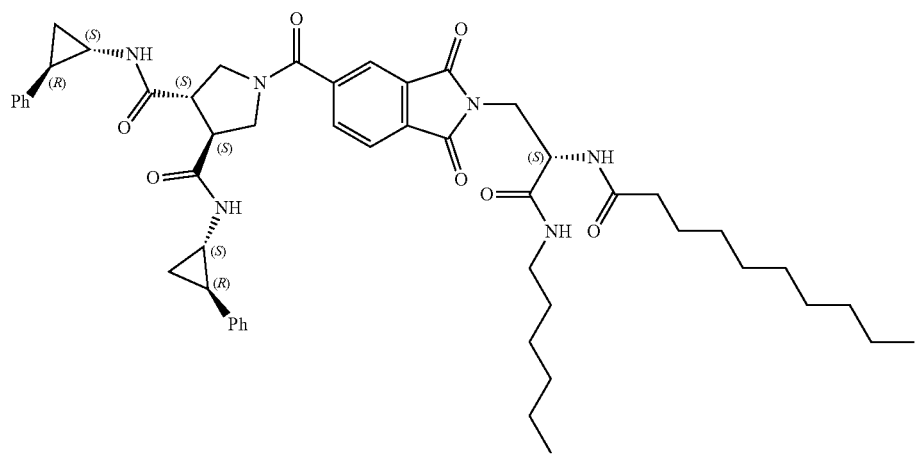

Prepared using General EDC, HOBT Coupling Procedure. The crude product was purified using flash chromatography, eluting with 0-10% MeOH:DCM, to give (3S,4S)-1-(2-((S)-2-decanamido-3-(hexylamino)-3-oxopropyl)-1,3-dioxoisoindoline-5-carbonyl)-N3,N4-bis((1S,2R)-2-phenylcyclopropyl)pyrrolidine-3,4-dicarboxamide (Compound 240)(0.256 g, 28.6% yield). LCMS (Method-J): 98.2% (RT: 4.475, 224.0 nm) (MS: ESI +ve 888.9 [M+1]). $^1$H NMR: (400 MHz, DMSO) δ ppm: 0.818-0.862 (m, 6H), 1.085-1.237 (m, 21H), 1.315-1.333 (m, 4H), 1.839 (s, 1H), 1.976-2.043 (m, 3H), 2.949-2.995 (m, 2H), 3.009-3.027 (m, 2H), 3.136-3.214 (m, 3H), 3.471-3.621 (m, 3H), 3.692-3.727 (m, 1H), 3.747-3.875 (m, 2H), 4.590-4.646 (m, 1H), 7.048-7.066 (d, 2H), 7.121-7.217 (m, 4H), 7.235-7.291 (m, 4H), 7.897-7.945 (t, 3H), 8.013-8.033 (d, 2H), 8.320-8.330 (d, J=4 Hz, 1H), 8.451-8.461 (d, J=4 Hz, 1H).

Synthesis of (3S,4S)-1-(2-((S)-2-decanamido-3-(hexylamino)-3-oxopropyl)-3-oxoisoindoline-5-carbonyl)-N3,N4-bis((1S,2R)-2-phenylcyclopropyl)pyrrolidine-3,4-dicarboxamide, Compound 241

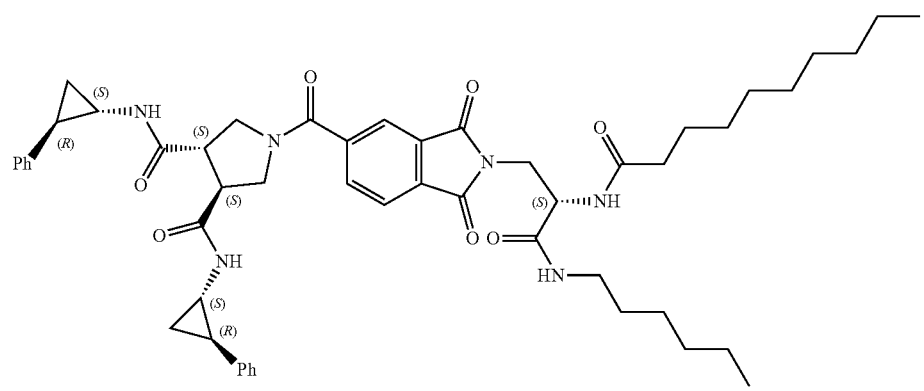

827

Step-1: Preparation of methyl (S)-2-(2-decanamido-3-(hexylamino)-3-oxopropyl)-3-oxoisoindoline-5-carboxylate

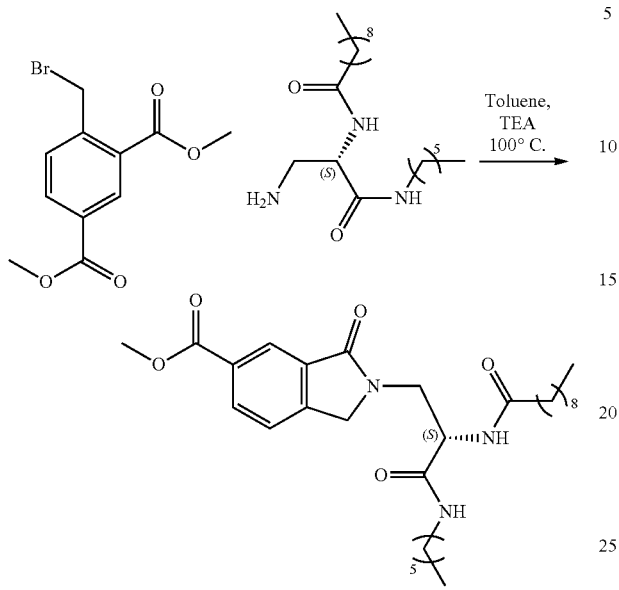

Dimethyl 4-(bromomethyl)isophthalate (0.5 g, 1.7414 mmol) was dissolved in toluene (7 mL). (S)—N-(3-amino-1-(hexylamino)-1-oxopropan-2-yl)decanamide (0.594 g, 1.7414 mmol) and TEA (0.73 mL, 5.224 mmol) were added and the mixture was heated at 110° C. for 4 h. The mixture was cooled, extracted with ethyl acetate (2×20 mL), washed with brine (2×20 mL), dried, and concentrated. The crude product was purified using flash chromatography, eluting with 0-60% EtOAc:hexane, to yield methyl (S)-2-(2-decanamido-3-(hexylamino)-3-oxopropyl)-3-oxoisoindoline-5-carboxylate (0.418 g, 46.5% yield). (Method-H): 95.5% (RT: 3.818, 214.0 nm) (MS: ESI +ve 516.2 [M+1]).

828

Step-2: Preparation of (S)-2-(2-decanamido-3-(hexylamino)-3-oxopropyl)-3-oxoiso indoline-5-carboxylic acid

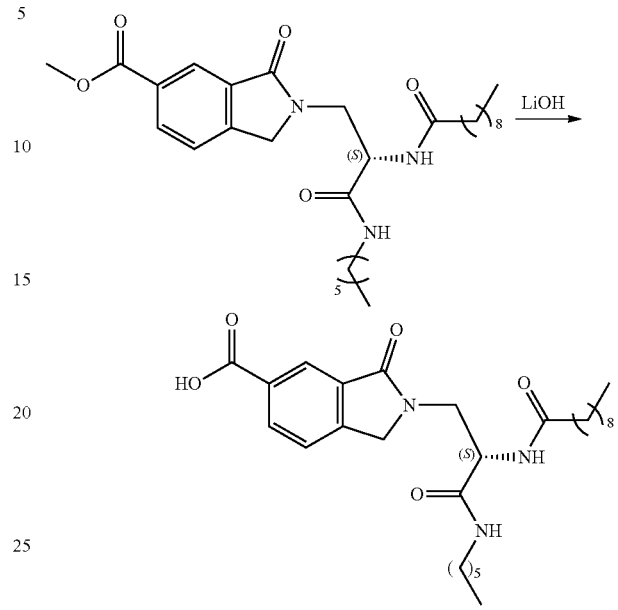

Prepared using General Ester Hydrolysis Procedure to give (S)-2-(2-decanamido-3-(hexylamino)-3-oxopropyl)-3-oxoisoindoline-5-carboxylic acid (0.379 g, 93.3% yield). LCMS (Method-C3): 96.5% (RT: 1.584, 228.0 nm) (MS: ESI +ve 502.4[M+1]).

Step-3: Preparation of (3S,4S)-1-(2-((S)-2-decanamido-3-(hexylamino)-3-oxopropyl)-3-oxoisoindoline-5-carbonyl)-N3,N4-bis((1S,2R)-2-phenylcyclopropyl)pyrrolidin-3,4-dicarboxamide, Compound 241

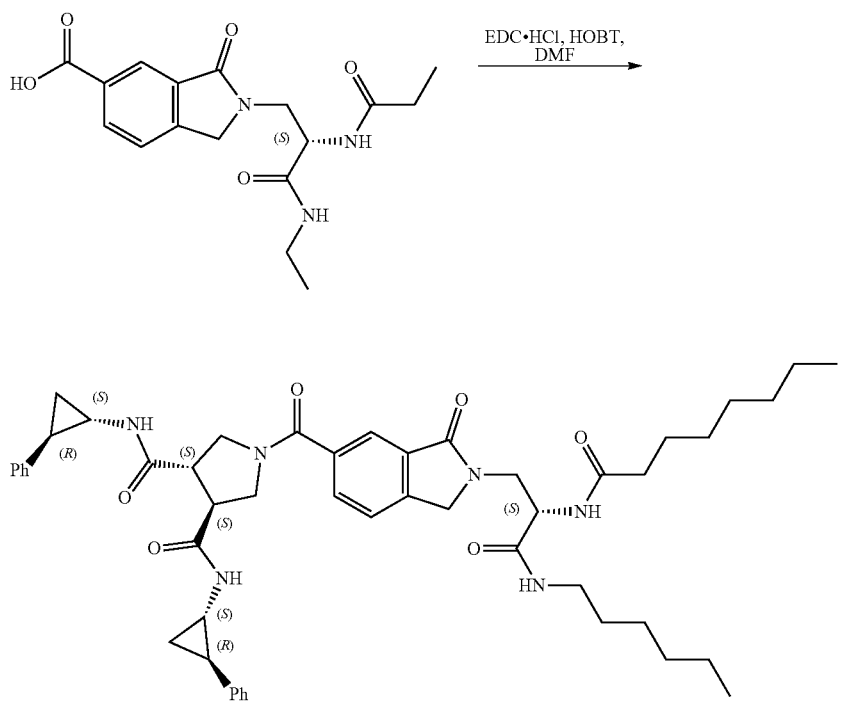

Prepared using General EDC, HOBT Coupling Procedure. The crude product was purified using Prep HPLC Method 12 to give (3S,4S)-1-(2-((S)-2-decanamido-3-(hexylamino)-3-oxopropyl)-3-oxoisoindoline-5-carbonyl)-N3,N4-bis((1S,2R)-2-phenylcyclopropyl)pyrrolidine-3,4-dicarboxamide (Compound 241) (0.106 g, 40.6% yield), as a white solid. LCMS (Method-H): 100% (RT: 3.911, 202.0 nm) (MS: ESI +ve 874.6 [M+1]). ¹H NMR: (400 MHz, DMSO) δ ppm: 0.813-0.872 (m, 6H), 1.121-1.177 (m, 18H), 1.324-1.375 (m, 2H), 1.855 (s, 1H), 1.987 (s, 1H), 2.058-2.093 (t, J=14 Hz, 2H), 2.863 (s, 1H), 2.993 (s, 1H), 3.025-3.054 (m, 2H), 3.089-3.134 (m, 1H), 3.152-3.217 (m, 1H), 3.486-3.533 (m, 2H), 3.564-3.649 (m, 1H), 3.736-3.752 (m, 2H), 3.840 (m, 1H), 4.539 (s, 2H), 4.659-4.679 (m, 1H), 7.064-7.082 (d, 2H), 7.131-7.228 (m, 4H), 7.246-7.298 (m, 4H), 7.681-7.732 (m, 3H), 8.015-8.068 (m, 1H), 8.309 (s, 1H), 8.452 (s, 1H).

Synthesis of (3S,4S)-1-(2-((S)-2-decanamido-3-(hexylamino)-3-oxopropyl)-1-oxoisoindoline-5-carbonyl)-N3,N4-bis((1S,2R)-2-phenylcyclopropyl)pyrrolidine-3,4-dicarboxamide, Compound 242

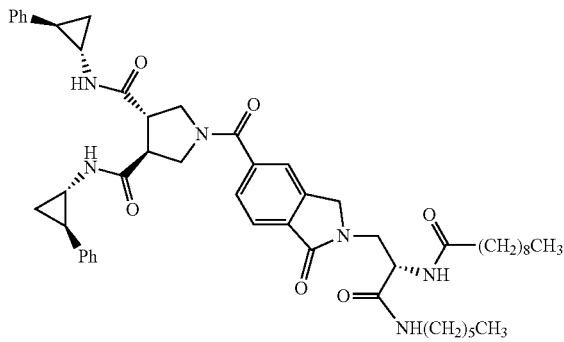

Prepared by a procedure similar to that reported for (3S,4S)-1-(2-((S)-2-decanamido-3-(hexylamino)-3-oxopropyl)-3-oxoisoindoline-5-carbonyl)-N3,N4-bis((1S,2R)-2-phenylcyclopropyl)pyrrolidine-3,4-dicarboxamide (Compound 241), substituting the applicable starting material. The final product was purified using Prep HPLC Method 12 to give (3S,4S)-1-(2-((S)-2-decanamido-3-(hexylamino)-3-oxopropyl)-1-oxoisoindoline-5-carbonyl)-N3,N4-bis((1S,2R)-2-phenylcyclopropyl)pyrrolidine-3,4-dicarboxamide (Compound 242)(0.107 g, 30.7% yield), as a white solid. LCMS (Method-H): 100% (RT: 3.880, 202.0 nm) (MS: ESI +ve 874.6 [M+1]). ¹H NMR: (400 MHz, DMSO) δ ppm: 0.804-0.857 (m, 6H), 1.100-1.160 (m, 23H), 1.312-1.328 (m, 4H), 1.832 (s, 1H), 1.975 (s, 1H), 2.054-2.063 (m, 3H), 3.044 (s, 1H), 3.061 (s, 1H), 3.076-3.115 (m, 2H), 3.135-3.170 (m, 1H), 3.170-3.209 (m, 1H), 3.448-3.555 (m, 2H), 3.588-3.609 (m, 1H), 3.632-3.752 (m, 2H), 3.805-3.856 (m, 1H), 4.463-4.563 (t, J=40 Hz, 2H), 4.653-4.671 (d, J=7.2 Hz, 1H), 7.047-7.065 (d, 2H), 7.120-7.218 (m, 4H), 7.237-7.271 (m, 4H), 7.567-7.586 (d, J=7.6 Hz, 1H), 7.680-7.735 (t, J=22 Hz, 2H), 8.013-8.049 (t, J=14.4 Hz, 2H), 8.319 (s, 1H), 8.448 (s, 1H).

Synthesis of (3S,4S)-1-(2-((S)-3-(hexylamino)-2-(nonylamino)-3-oxopropyl) benzo[d]oxazole-5-carbonyl)-N3,N4-bis((1S,2R)-2-phenylcyclopropyl)pyrrolidine-3,4-dicarboxamide, Compound 269

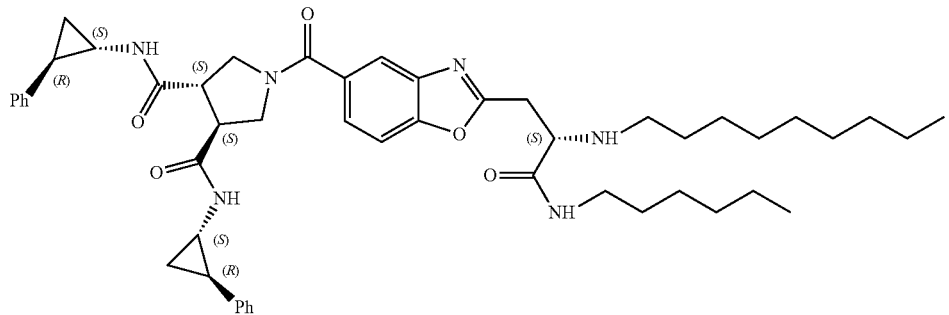

Step-1: Preparation of benzyl 3-amino-4-hydroxybenzoate

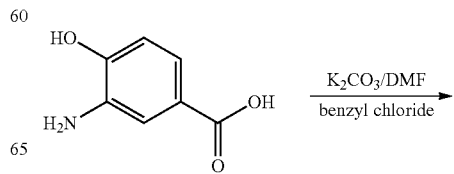

-continued

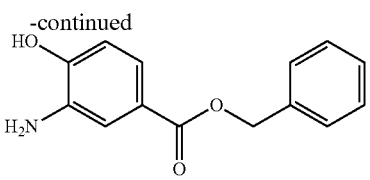

3-amino-4-hydroxybenzoic acid (5 g, 0.032 mmol) was dissolved in DMF (20 mL). Potassium carbonate (4.5 g, 0.032 mmol) was added to the reaction mixture and stirred for 10 min. Benzyl chloride (4.1 g, 0.032 mmol) was added dropwise and the reaction mixture was stirred at room temperature for 16 h, poured into ice cold water, extracted with EtOAc (2×70 mL), washed with brine (2×70 m L), dried and concentrated. The crude product was purified by flash chromatography, eluting with 0-30% EtOAc/hexane, to give benzyl 3-amino-4-hydroxybenzoate (1.4 g, 17.7% yield). LCMS (Method-C Fast): 100% (RT: 0.537, 230 nm) (MS: ESI +ve 244.2 [M+1]).

Step-2: Preparation of benzyl (S)-2-(2-((((9H-fluoren-9-yl)methoxy)carbonyl)amino)-3-(allyloxy)-3-oxopropyl)benzo[d]oxazole-5-carboxylate

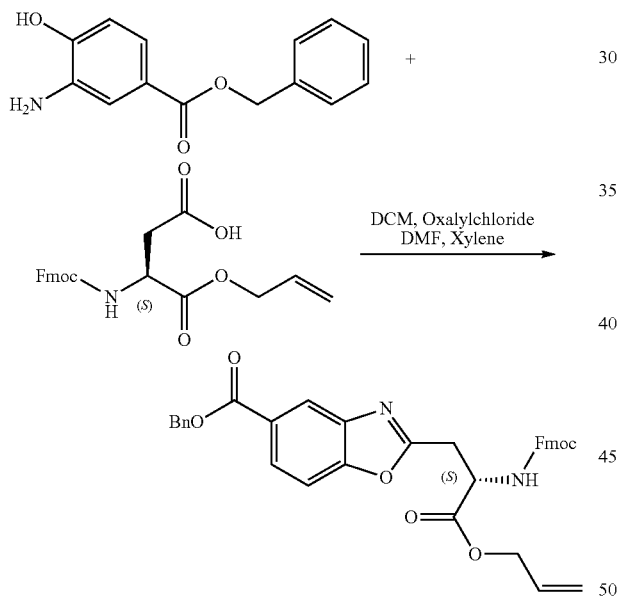

(S)-3-((((9H-fluoren-9-yl)methoxy)carbonyl)amino)-4-(allyloxy)-4-oxobutanoic acid (1.95 g, 0.004 mmol) was dissolved in DCM (10 mL) and cooled to 0° C. Oxalyl chloride (0.51 mL, 0.005 mmol) was added dropwise and the mixture was stirred at room temperature for 3 h. The volatiles were concentrated and azeotroped with toluene (2×30 mL). The crude product was dissolved in xylene (30 mL) and a solution of benzyl 3-amino-4-hydroxybenzoate (1.2 g, 0.004 mmol) in xylene was added to the mixture and heated at 140° C. for 48 h. The mixture was cooled, extracted with EtOAc (2×70 mL) and washed with water (2×70 mL). The organic layer was concentrated and purified by flash chromatography, eluting with 0-35% EtOAc/hexane, to give benzyl (S)-2-(2-((((9H-fluoren-9-yl)methoxy)carbonyl)amino)-3-(allyloxy)-3-oxopropyl)benzo[d]oxazole-5-carboxylate. (1.2 g, 41.3% yield). LCMS (Method-C Fast): 91.4% (RT: 2.129, 265 nm) (MS: ESI +ve 603.5 [M+1]).

Step-3: Preparation of (S)-2-((((9H-fluoren-9-yl)methoxy)carbonyl)amino)-3-(5-((benzyloxy)carbonyl)benzo[d]oxazol-2-~yl)propanoic acid

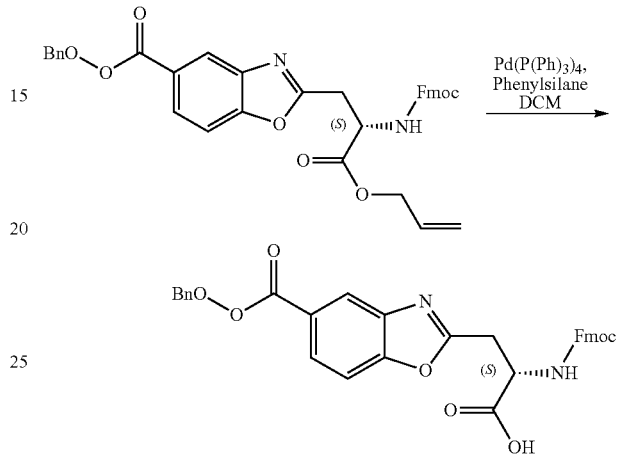

Benzyl (S)-2-(2-((((9H-fluoren-9-yl)methoxy)carbonyl)amino)-3-(allyloxy)-3-oxopropyl)benzo[d]oxazole-5-carboxylate (1.2 g, 0.001 mmol) was dissolved in DCM (15 mL). Phenylsilane (0.430 g, 0.003 mmol) was added followed by palladium tetrakistriphenylphosphine (0.115 g, 0.00009 mmol), and the mixture was stirred for 24 hrs then concentrated. The mixture was extracted with DCM (2×20 mL), washed with water (2×20 mL), dried and concentrated to give (S)-2-((((9H-fluoren-9-yl)methoxy)carbonyl)amino)-3-(5-((benzyloxy) carbonyl) benzo[d]oxazol-2-yl) propanoic acid. (1.4 g, crude). LCMS (Method-C Fast): 48.2% (RT: 1.765, 202 nm) (MS: ESI +ve 563.3 [M+1]).

Step-4: Preparation of benzyl (S)-2-(2-((((9H-fluoren-9-yl)methoxy)carbonyl)amino)-3-(hexylamino)-3-oxopropyl)benzo[d]oxazole-5-carboxylate

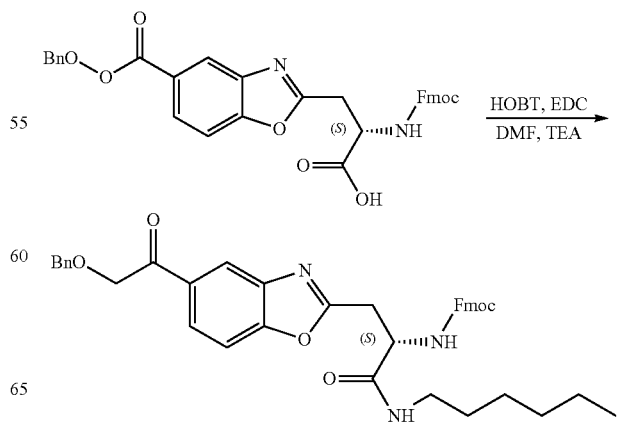

Prepared using General EDC, HOBT Coupling Procedure to give benzyl (S)-2-(2-((((9H-fluoren-9-yl)methoxy)carbonyl)amino)-3-(hexylamino)-3-oxopropyl)benzo[d]oxazole-5-carboxylate. (3 g, crude). LCMS (Method-C Fast): 5.6% (RT: 2.219, 225 nm) (MS: ESI +ve 646.3 [M+1]).

Step-5: Preparation of benzyl (S)-2-(2-amino-3-(hexylamino)-3-oxopropyl) benzo[d]oxazole-5-carboxylate benzyl (S)-2-(2-amino-3-(hexylamino)-3-oxopropyl)benzo[d]oxazole-5-carboxylate. (0.992 g, 52.2% yield). LCMS (Method-H: 59.1% (RT: 3.386, 214 nm) (MS: ESI +ve 424.2 [M+1]).

Step-6: Preparation of benzyl (S)-2-(2-decanamido-3-(hexylamino)-3-oxopropyl)benzo[d]oxazole-5-carboxylate

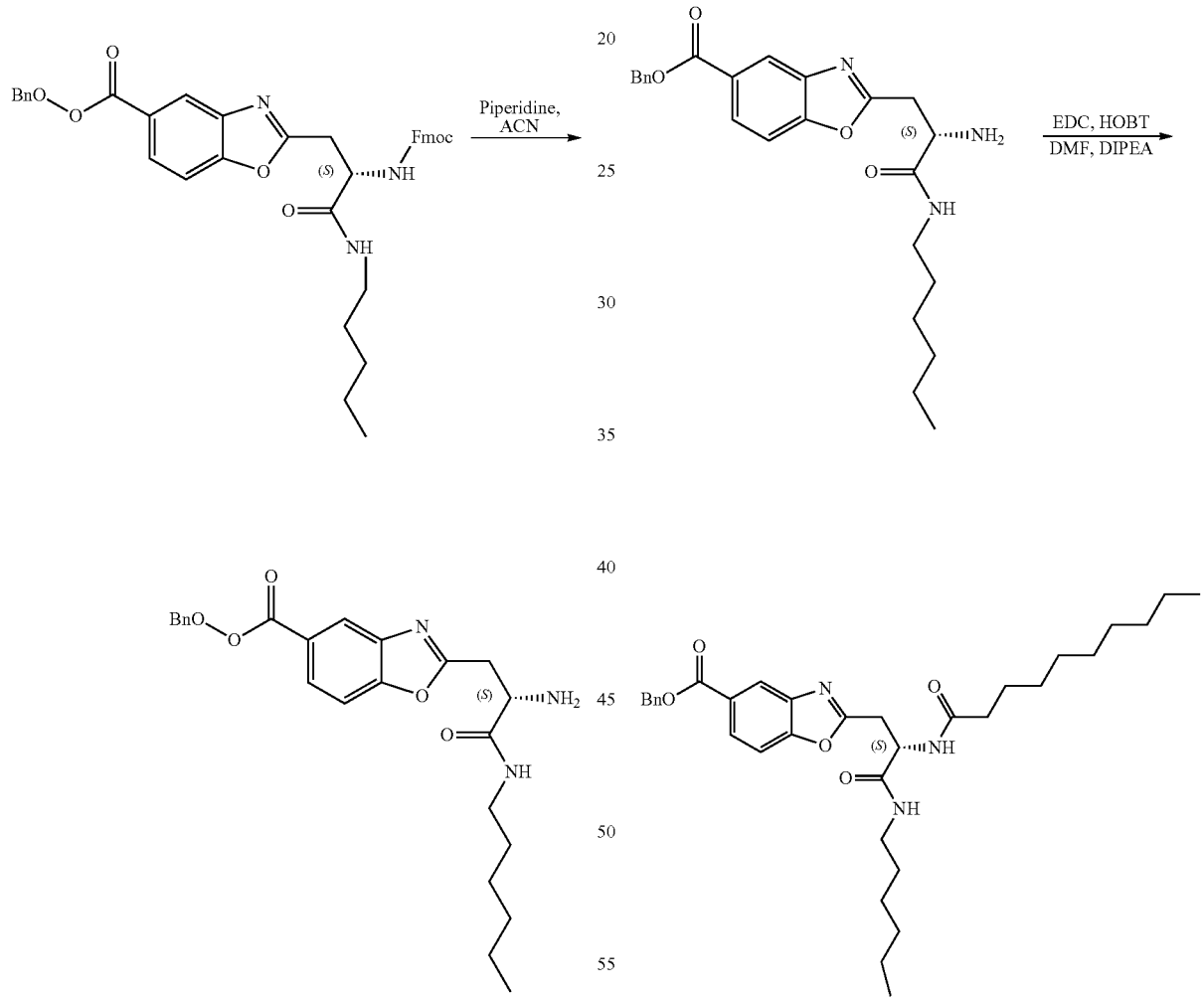

Benzyl (S)-2-(2-((((9H-fluoren-9-yl)methoxy)carbonyl)amino)-3-oxo-3-(pentylamino) propyl) benzo[d]oxazole-5-carboxylate (3 g, 0.004 mmol) was dissolved in acetonitrile (4 mL). Piperidine (1 mL) was added to the reaction mixture and stirred for 30 mins, followed by concentrated in vacuo to remove solvent. The crude product was purified by flash chromatography, eluting with 0-10% MeOH/DCM, to give Prepared using General EDC, HOBT Coupling Procedure. The crude product was purified using flash chromatography, eluting with 0-50% EtOAc/hexane gradient, to give benzyl (S)-2-(2-decanamido-3-(hexylamino)-3-oxopropyl)benzo[d]oxazole-5-carboxylate. LCMS (Method-C Fast): 99.1% (RT: 2.407, 221 nm) (MS: ESI +ve 578.6 [M+1]).

Step-7: Preparation of (S)-2-(2-decanamido-3-(hexylamino)-3-oxopropyl) benzo[d]oxazole-5-carboxylic acid

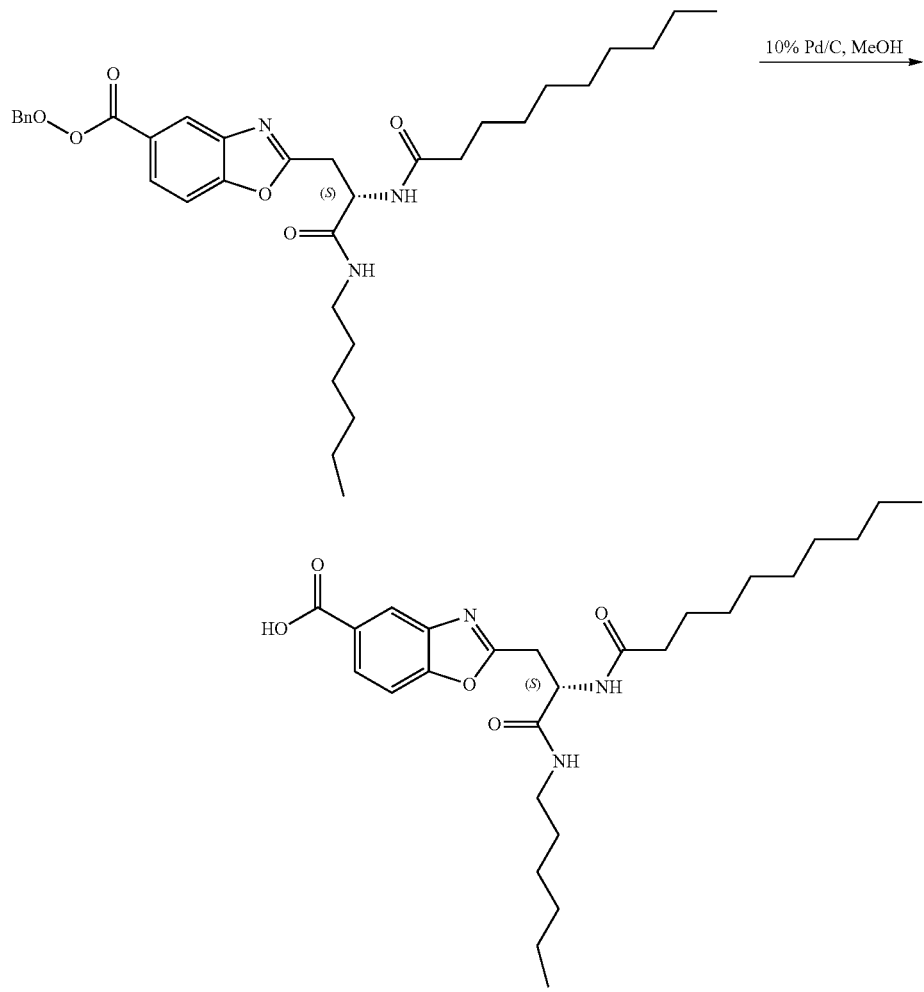

Benzyl (S)-2-(2-decanamido-3-(hexylamino)-3-oxopropyl)benzo[d]oxazole-5-carboxylate (0.300 g, 0.519 mmol) was dissolved in MeOH (20 mL) and DCM (10 mL). Palladium on carbon (0.300 g) was added, and the reaction mixture was stirred under hydrogen (balloon) atmosphere for 1 h at room temperature. The mixture was filtered through celite, rinsed with MeOH (15 mL), and the filtrate was concentrated to give (S)-2-(2-decanamido-3-(hexylamino)-3-oxopropyl)benzo[d]oxazole-5-carboxylic acid (0.213 g, 84.1% yield). LCMS (Method-C fast): 97.4% (RT: 1.781, 280.0 nm) (MS: ESI +ve 488.5 [M+1]).

Step-8: Preparation of (3S,4S)-1-(2-((S)-3-(hexylamino)-2-(nonylamino)-3-oxopropyl) benzo[d]oxazole-5-carbonyl)-N3,N4-bis((1S,2R)-2-phenylcyclopropyl)pyrrolidine-3,4-dicarboxamide, Compound 269

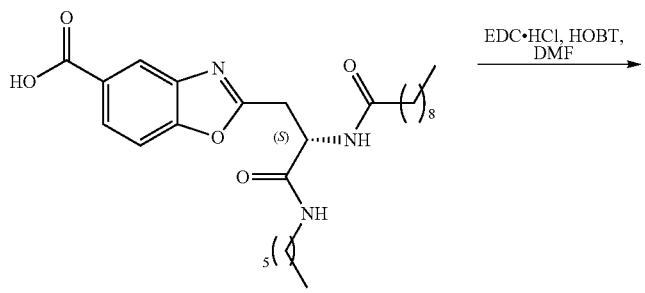

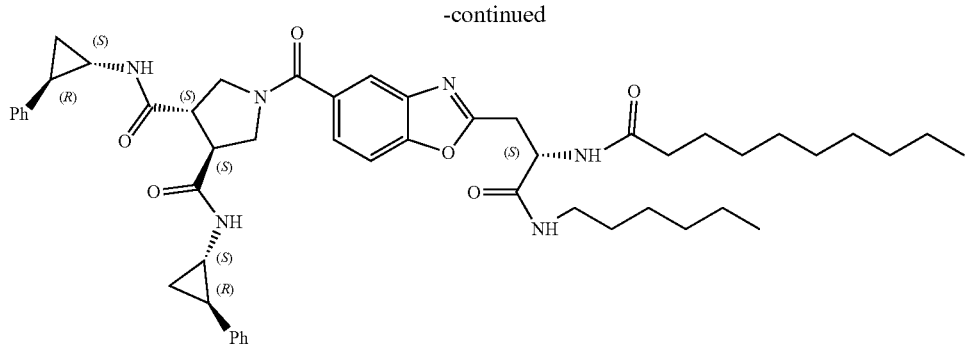

Prepared using General EDC, HOBT Coupling Procedure. The crude product was purified using Prep HPLC Method 12 to give (3S,4S)-1-(2-((S)-3-(hexylamino)-2-(nonylamino)-3-oxopropyl)benzo[d]oxazole-5-carbonyl)-N3,N4-bis((1S,2R)-2-phenylcyclopropyl)pyrrolidine-3,4-dicarboxamide (Compound 269)(0.063 g, 16.8% yield), as a white solid. LCMS (Method-J2): 100% (RT: 4.722, 202.0 nm) (MS: ESI +ve 860.6 [M+1]). $^1$H NMR: (400 MHz, DMSO, HT) δ ppm: 0.824-0.870 (m, 6H), 1.098-1.193 (m, 22H), 1.334-1.392 (m, 4H), 1.844 (s, 1H), 1.982 (s, 1H), 2.080-2.098 (t, J=7.2 Hz, 2H), 2.861 (s, 1H), 3.000 (s, 1H), 3.017-3.066 (m, 2H), 3.082-3.171 (m, 4H), 3.233-3.409 (m, 2H), 3.540-3.658 (m, 1H), 3.806-3.857 (m, 1H), 4.815-4.871 (s, 1H), 4.076 (m, 1H), 7.061-7.079 (d, 2H), 7.131-7.196 (m, 4H), 7.228-7.300 (m, 4H), 7.522-7.543 (d, J=8.4 Hz, 1H), 7.703-7.724 (d, J=8.4 Hz, 1H), 7.818 (s, 1 H), 8.005-8.032 (m, 1H), 8.249-8.270 (d, J=8.4 Hz, 1H), 8.304-8.313 (d, J=3.6 Hz, 1H), 8.463-8.472 (d, J=3.6 Hz, 1H).

Synthesis (3S,4S)-1-(2-((S)-2-decanamido-3-(hexylamino)-3-oxopropyl) benzo[d]oxazole-6-carbonyl)-N3,N4-bis((1S,2R)-2-phenylcyclopropyl) pyrrolidine-3,4-dicarboxamide, Compound 279

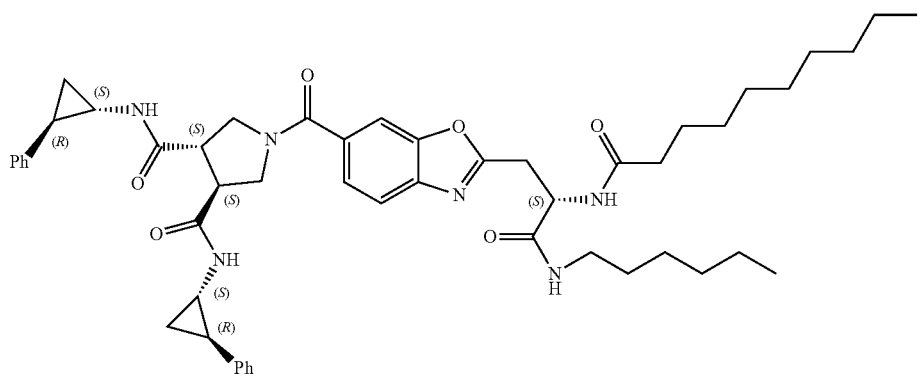

Prepared by a procedure similar to that reported for (3S,4S)-1-(2-((S)-3-(hexylamino)-2-(nonylamino)-3-oxopropyl) benzo[d]oxazole-5-carbonyl)-N3,N4-bis((1S,2R)-2-phenylcyclopropyl)pyrrolidine-3,4-dicarboxamide (Compound 269), substituting the applicable starting material. The final product was purified using flash chromatography, eluting with 0-10% MeOH:DCM, to give (3S,4S)-1-(2-((S)-2-decanamido-3-(hexylamino)-3-oxopropyl) benzo[d]oxazole-6-carbonyl)-N3,N4-bis((1S,2R)-2-phenylcyclopropyl) pyrrolidine-3,4-dicarboxamide (Compound 279), as an off white solid (0.073 g, 34.5%) LCMS (Method-C-Fast): 100% (RT 2.160, 202.0 nm) (MS: ESI +ve 860[M+H]). $^1$H NMR: (400 MHz, DMSO) δ ppm: 0.81-0.85 (m, 6H); 1.17 (s, 21H); 1.37 (s, 5H); 1.82 (s, 1H); 1.96 (s, 2H); 2.04-2.08 (t, 2H); 2.67 (s, 2H); 2.76 (s, 2H); 3.01-3.06 (t, 4H); 3.50-3.55 (t, 2H); 3.64-3.66 (d, J=8.4, 1H); 3.79-3.82 (d, J=9.6, 1H); 4.82-4.84 (d, J=7.2, 1H); 7.04-7.06 (d, J=7.2, 2H); 7.11-7.18 (m, 4H); 7.21-7.26 (m, 4H); 7.48-7.50 (d, J=8, 1H); 7.68-7.70 (d, J=8, 1H); 7.83 (s, 1H); 8.01 (s, 1H); 8.23-8.25 (d, J=8, 2H); 8.44 (s, 1H).

Synthesis of (3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide, Compound 245

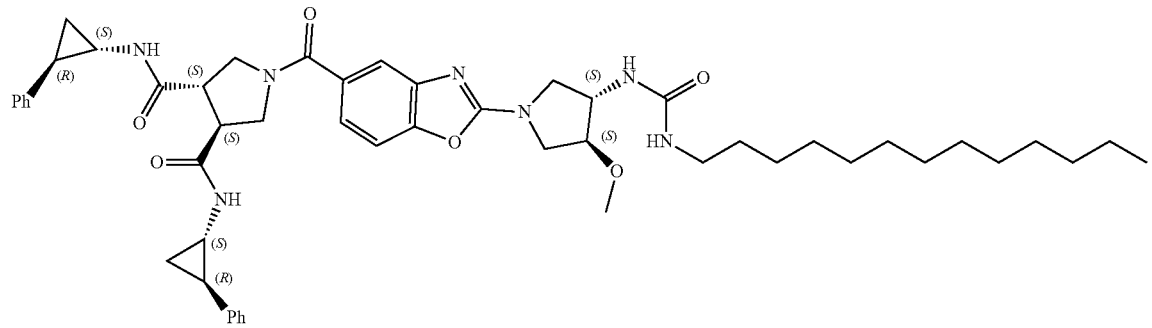

Step-1: Synthesis of methyl 2-mercaptobenzo[d]oxazole-5-carboxylate

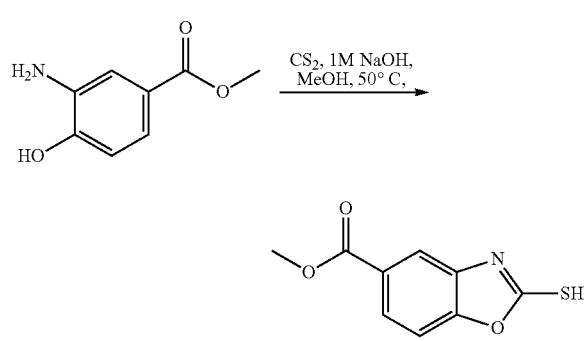

Carbon disulfide (3.6 mL, 59.8 mmol) and 1M NaOH (50 mL) were added to a solution of methyl 3-amino-4-hydroxybenzoate (5.0 g, 29.9 mmol) in MeOH (100 mL). The reaction was stirred at 50° C. for 72 h, then 2 N HCl (50 mL) was added and the mixture was extracted with EtOAc (3×100 mL), dried over sodium sulfate and concentrated. The crude product was purified using flash chromatography, eluting with 10-15% EtOAc/hexane, to give methyl 2-mercaptobenzo[d]oxazole-5-carboxylate as an off white solid (5.0 g, 79.90%). LCMS (Method-C2): 98.75% (RT: 1.128, 254.00 nm) (MS: ESI +ve 209.8 [M]).

Step 2: Synthesis of methyl 2-chlorobenzo[d]oxazole-5-carboxylate

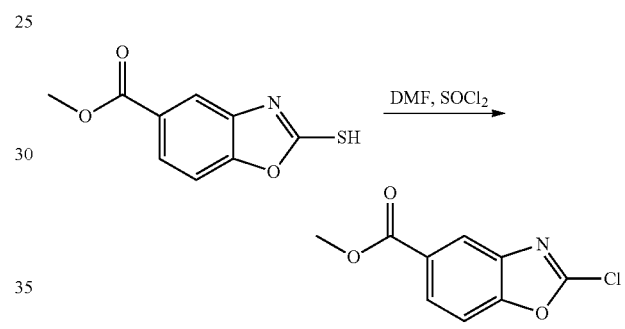

A mixture of methyl 2-mercaptobenzo[d]oxazole-5-carboxylate (1.0 g, 4.6 mmol) and thionyl chloride (10 mL) in DMF (0.5 mL) was stirred at RT for 16 h. The volatiles were evaporated, DCM (50 mL) was added, the mixture was washed with water (50 mL) and the organic layer was dried and concentrated. The crude product was purified by flash chromatography, eluting with 15-20% EtOAc/hexane, to give methyl 2-chlorobenzo[d]oxazole-5-carboxylate (0.45 g, 44.49%). LCMS (Method-C2): 100% (RT: 1.259, 230.0 nm) (MS: ESI +ve 212.1 [M+1]).

Step-3: Preparation of methyl 2-((3S,4S)-3-methoxy-4-(3-tridecylureido)pyrrolidin-1-yl)benzo[d]oxazole-5-carboxylate

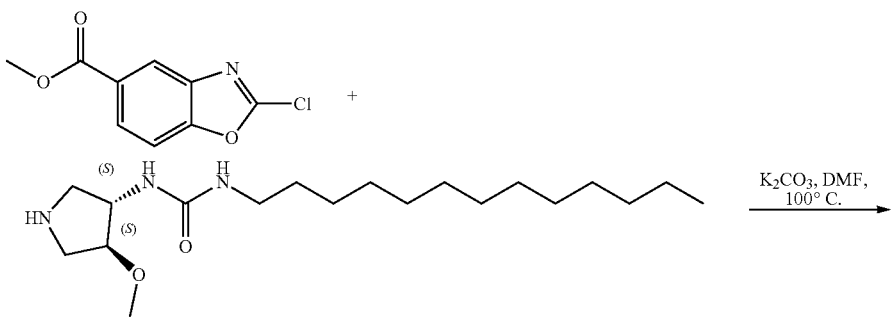

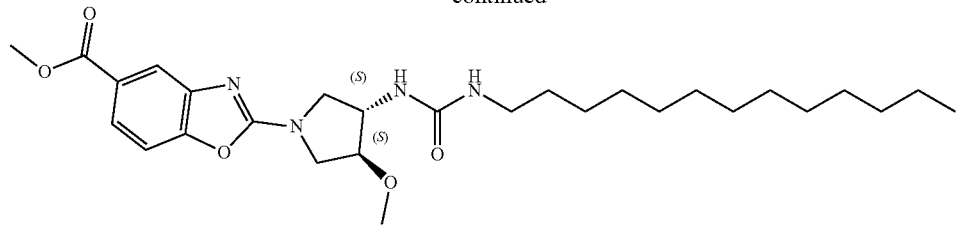

A mixture of methyl 2-chlorobenzo[d]oxazole-5-carboxylate (0.1 g, 0.47 mmol), 1-((3S,4S)-4-methoxypyrrolidin-3-yl)-3-tridecylurea (0.193 g, 0.56 mmol) and $K_2CO_3$ (0.129 g, 0.94 mmol). was dissolved in DMF (10 mL). The reaction mixture was heated at 100° C. for 4 h, then the reaction was quenched with water (10 mL) and the resulting precipitate was collected by filtration, dissolved in DCM, dried and concentrated to give methyl 2-((3S,4S)-3-methoxy-4-(3-tridecylureido)pyrrolidin-1-yl)benzo[d]oxazole-5-carboxylate (0.197 g, 68.54%). LCMs (Method-C2): 99.29% (RT 1.72, 240.0 nm) (MS: ESI +ve 517.4 [M+H]).

Step-4: Synthesis of 2-((3S,4S)-3-methoxy-4-(3-tridecylureido)pyrrolidin-1-yl)benzo[d]oxazole-5-carboxylic acid

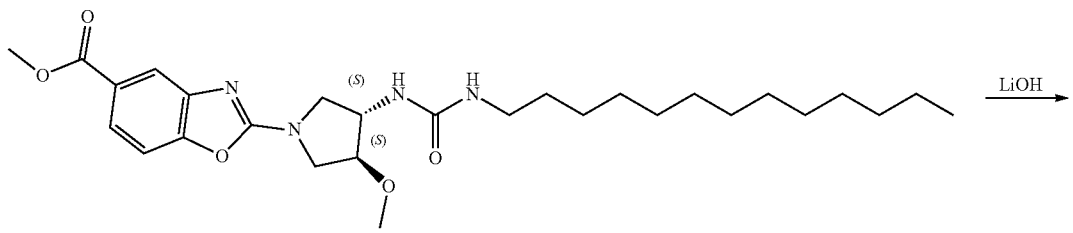

Prepared using General Ester Hydrolysis Procedure to give 2-((3S,4S)-3-methoxy-4-(3-tridecylureido)pyrrolidin-1-yl)benzo[d]oxazole-5-carboxylic acid, as a brown solid (0.18 g). LCMS (Method-C3): 98.56% (RT 1.547, 230 nm) (MS: ESI +ve 502.8 [M]).

Step-5: Synthesis of (3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide, Compound 245

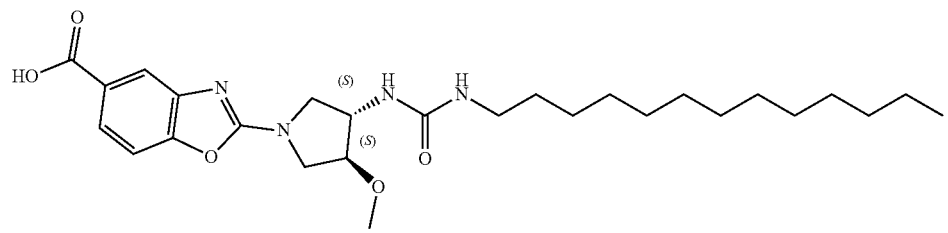

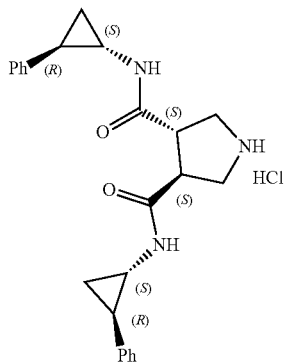

-continued

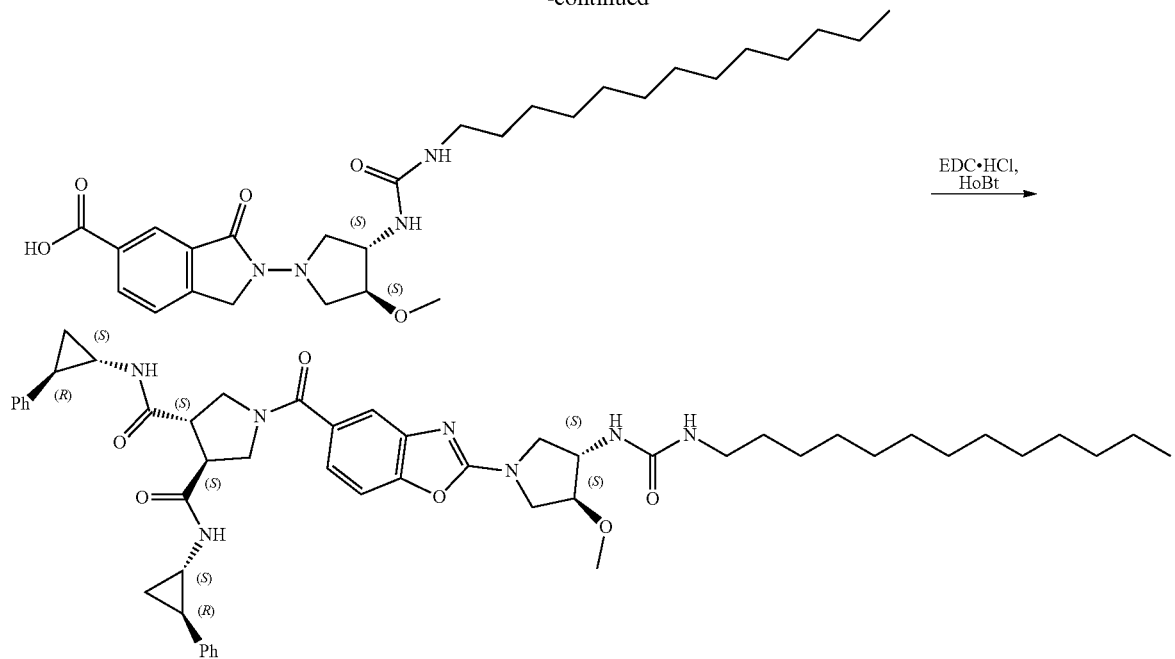

Prepared using General EDC, HOBT Coupling Procedure. The final product was purified using flash chromatography, eluting with 5-6% MeOH/DCM, to give (3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide (Compound 245)(0.12 g, 69.0%). LCMS (Method-J): 96.98% (RT 5.029, 254.0 nm) (MS: ESI +ve 874.5 [M]). $^1$H NMR (400 MHz, DMSO) δ ppm: 0.83-0.86 (t, J=0.8, 3H), 1.10-1.17 (m, 2H), 1.23-1.34 (m, 22H), 1.35-1.38 (m, 2H), 1.84 (bs, 11H), 1.96 (bs, 1H), 2.67 (s, 1H), 2.84 (s, 1H), 2.96-2.98 (m, 2H)', 3.08-3.12 (m, 1H), 3.17-3.23 (m, 1H), 3.29-3.34 (m, 3H), 3.48-3.52 (m, 3H), 3.58-3.60 (m, 1H), 3.64-3.66 (m, 1H), 3.73-3.80 (m, 3H), 3.85 (s, 1H), 4.18 (bs, 1H), 5.70-5.73 (t, J=4, 1H), 6.28-6.30 (d, J=8, 1H), 7.06-7.08 (m, 2H), 7.11-7.18 (m, 5H), 7.22-7.27 (m, 4H), 7.45-7.47 (d, J=8, 2H), 8.28 (s, 1H), 8.43 (s, 1H).

Synthesis of (3S,4S)-1-(2-((3S,4S)-3-methoxy-4-(3-tridecylureido)pyrrolidin-1-yl)benzo[d]oxazole-6-carbonyl)-N3,N4-bis((1S,2R)-2-phenylcyclopropyl)pyrrolidine-3,4-dicarboxamide, Compound 247

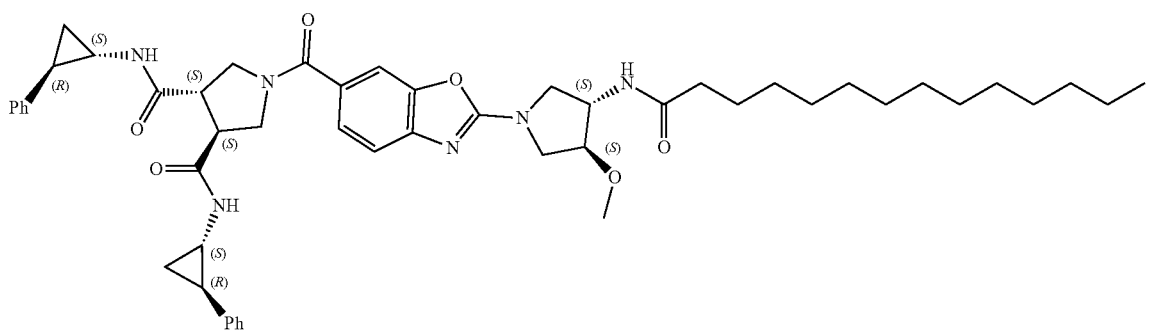

Prepared by a procedure similar to that reported for (3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide (Compound 245), substituting the applicable starting material. The crude product was purified by flash chromatography, eluting with 5-6% MeOH:DCM, to give (3S,4S)-1-(2-((3S,4S)-3-methoxy-4-(3-tridecylureido)pyrrolidin-1-yl)benzo[d]oxazole-6-carbonyl)-N3,N4-bis((1S,2R)-2-phenylcyclopropyl)pyrrolidine-3,4-dicarboxamide (Compound 247), (0.27 g, 99.3%). LCMS (Method-C FAST): 96.97% (RT 2.365, 298.0 nm) (MS: ESI +ve 874.8 [M]). ¹H NMR (400 MHz, DMSO) δ ppm: 0.83-0.87 (t, J=8, 3H), 1.11-1.23 (m, 28H), 1.34 (s, 3H), 1.96 (bs, 1H), 2.79-2.84 (d, J=20, 2H), 2.96-3.00 (t, J=0.4, 3H), 3.11 (s, 1H), 3.18 (s, 1H), 3.48-3.61 (m, 5H), 3.74-3.76 (m, 4H), 3.85 (s, 1H), 4.19 (s, 1H), 5.70-5.72 (t, J=5.6, 1H), 6.28-6.29 (d, J=4, 1H), 7.08-7.16 (m, 6H), 7.24-7.37 (m, 6H). 7.60 (s, 1H), 8.27-8.41 (d, J=56, 2H).

Synthesis of (3S,4S)-1-(2-(((S)-2-decanamido-3-(hexylamino)-3-oxopropyl)amino)benzo[d]oxazole-5-carbonyl)-N3,N4-bis((1S,2R)-2-phenylcyclopropyl)pyrrolidine-3,4-dicarboxamide, Compound 246

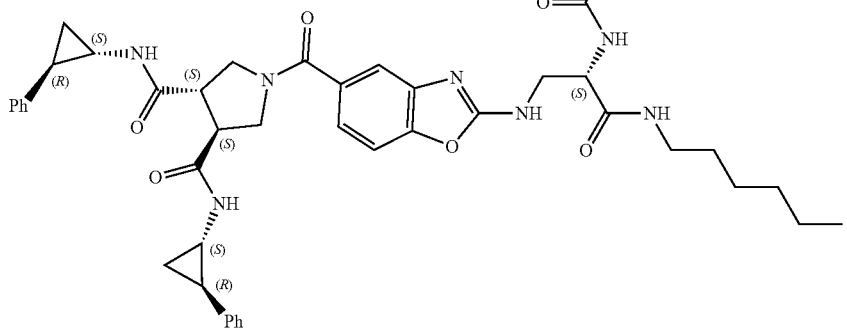

Prepared using a procedure similar to that reported for (3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide (Compound 245), using the applicable starting materials. The crude product was purified by flash chromatography, eluting with 5-6% MeOH/DCM, to give (3S,4S)-1-(2-(((S)-2-decanamido-3-(hexylamino)-3-oxopropyl)amino)benzo[d]oxazole-5-carbonyl)-N3,N4-bis((1S,2R)-2-phenylcyclopropyl)pyrrolidine-3,4-dicarboxamide (Compound 246) (0.078 g, 29.07%). LCMS (Method-J): 100% (RT 4.347, 220.0 nm) (MS: ESI +ve 874.4 [M]). ¹H NMR (400 MHz, DMSO) δ ppm: 0.67-0.85 (M, 6H), 1.10-1.23 (m, 24H), 1.33-1.37 (d, J=16, 4H), 1.83 (bs, 1H), 1.96-1.99 (d, J=12, 2H), 2.08-2.12 (t, J=0.4, 2H), 2.77-2.84 (d, J=28 2H), 3.01-3.03 (d, J=8, 2H), 3.08-3.28 (m, 2H)', 3.48-3.56 (m, 4H), 3.48-3.56 (m, 2H), 4.51-4.53 (d, J=8, 1H), 7.06-7.15 (m, 7H), 7.21-7.26 (m, 14H), 7.35-7.37 (d, J=8, 2H), 7.81 (s, 1H). 7.96-7.98 (d, J=8, 1H), 8.08 (bs, 1H), 8.28-8.42 (d, J=56, 2H).

Synthesis of (3S,4S)-1-(2-(((S)-2-decanamido-3-(hexylamino)-3-oxopropyl)amino)benzo[d]oxazole-6-carbonyl)-N3,N4-bis((1S,2R)-2-phenylcyclopropyl)pyrrolidine-3,4-dicarboxamide, Compound 261

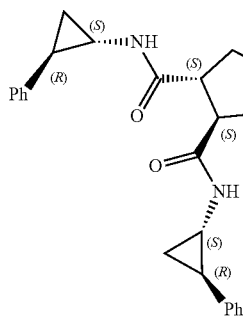

Prepared using a procedure similar to that reported for (3S,4S)-1-(2-((3S,4S)-3-methoxy-4-(3-tridecylureido)pyrrolidin-1-yl)benzo[d]oxazole-5-carbonyl)-N3,N4-bis((1S, 2R)-2-phenylcyclopropyl)pyrrolidine-3,4-dicarboxamide (Compound 245), using the applicable starting materials. The crude product was purified Prep HPLC Method 12 to give (3S,4S)-1-(2-(((S)-2-decanamido-3-(hexylamino)-3-oxopropyl)amino) benzo[d]oxazole-6-carbonyl)-N3,N4-bis ((1S,2R)-2-phenylcyclopropyl)pyrrolidine-3,4-dicarboxamide (Compound 261), as a white solid. (0.06 g, 19.07%) LCMS (Method-J2): 100% (RT: 4.322, 202.0 nm) (MS: ESI +ve 874.1 [M+H]). $^1$H NMR (400 MHz, DMSO) δ ppm: 0.81-0.87 (M, 6H), 1.19 (bs, 20H), 1.32-1.34 (d, J=8, 2H), 1.44 (bs, 2H), 1.86 (bs, 1H), 1.97-2.00 (d, J=12, 1H), 2.09-2.13 (t, J=7.2, 2H), 2.79-2.85 (d, J=24, 2H), 3.02-3.05 (m, 2H), 3.11 (s, 1H), 3.14 (s, 1H), 3.48-3.68 (m, 4H), 3.73-3.79 (m, 2H), 4.51-4.56 (m, 1H), 7.08-7.14 (d, J=24, 6H), 7.24-7.26 (d, J=8, 5H). 7.33-7.35 (d, J=4, 1H), 7.91-7.94 (t, J=4, 1H), 8.05-8.07 (d, J=4, 1H).

Synthesis of (3S,4S)-1-(2-(((S)-2-decanamido-3-(hexylamino)-3-oxopropyl) amino)benzo[d]thiazole-6-carbonyl)-N3,N4-bis((1S,2R)-2-phenylcyclopropyl) pyrrolidine-3,4-dicarboxamide, Compound 262

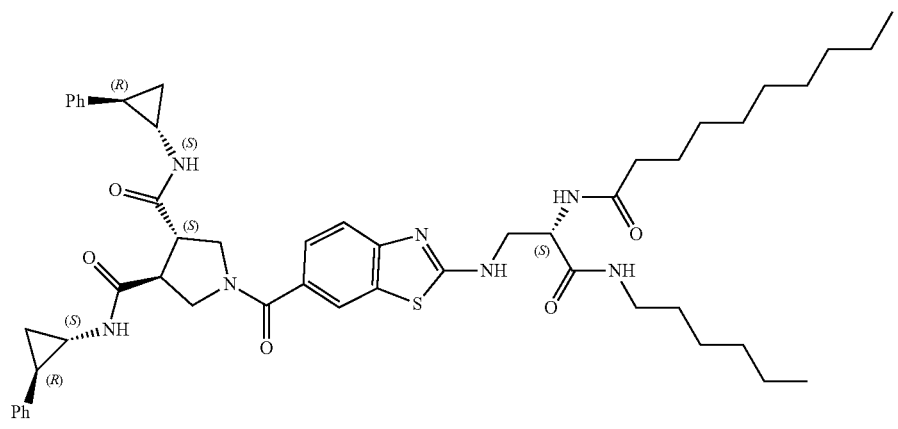

Step-1: Preparation of methyl 2-chlorobenzo[d]thiazole-6-carboxylate

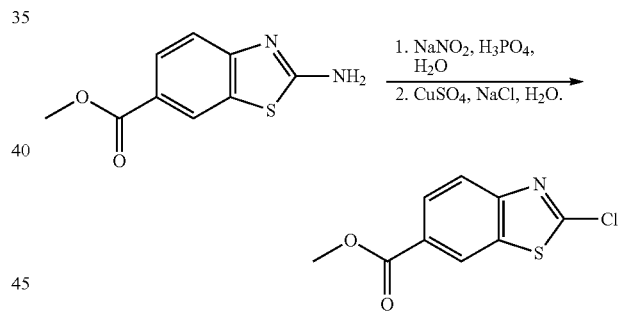

Methyl 2-aminobenzo[d]thiazole-6-carboxylate (1.0 g, 5.0 mmol) and H$_3$PO$_4$ (9.5 mL) were cooled to −5° C. A solution of NaNO$_2$ (1.0 g, 15.0 mmol) in water (2.4 mL) was added slowly maintaining the temperature below 0° C., with stirring for 2.5 h after the addition. A solution of CuSO$_4$ (2.4 g, 15.0 mmol) in water (2.4 mL) and a solution of NaCl (4.38 g, 75.0 mmol) in water (2.4 mL) were slowly added at −5° C. The ice salt bath was removed and the mixture was allowed to warm to room temperature over 1 h. The mixture was diluted with water and extracted with DCM three times. The organic layer was dried, concentrated and the crude product was purified using flash chromatography, eluting with 10% EtOAc/hexane, to give methyl 2-chlorobenzo[d]thiazole-6-carboxylate (7.0 g, yield: 62%), as a white solid. LCMS (Method-C2): 98.72% (RT: 1.425, 265.0 nm) (MS: ESI +ve 228.1 [M+H]). The remaining steps are similar to that reported for 3S,4S)-1-(2-((3S,4S)-3-methoxy-4-(3-tridecylureido)pyrrolidin-1-yl)benzo[d]oxazole-5-carbonyl)-N3,N4-bis((1S,2R)-2-phenylcyclopropyl)pyrrolidine-3,4-dicarboxamide (Compound 245) using the applicable starting materials.

Step 2: Preparation of (3S,4S)-1-(2-(((S)-2-decanamido-3-(hexylamino)-3-oxopropyl)amino)benzo[d]thiazole-6-carbonyl)-N3,N4-bis((1S,2R)-2-phenylcyclopropyl)pyrrolidine-3,4-dicarboxamide, Compound 262

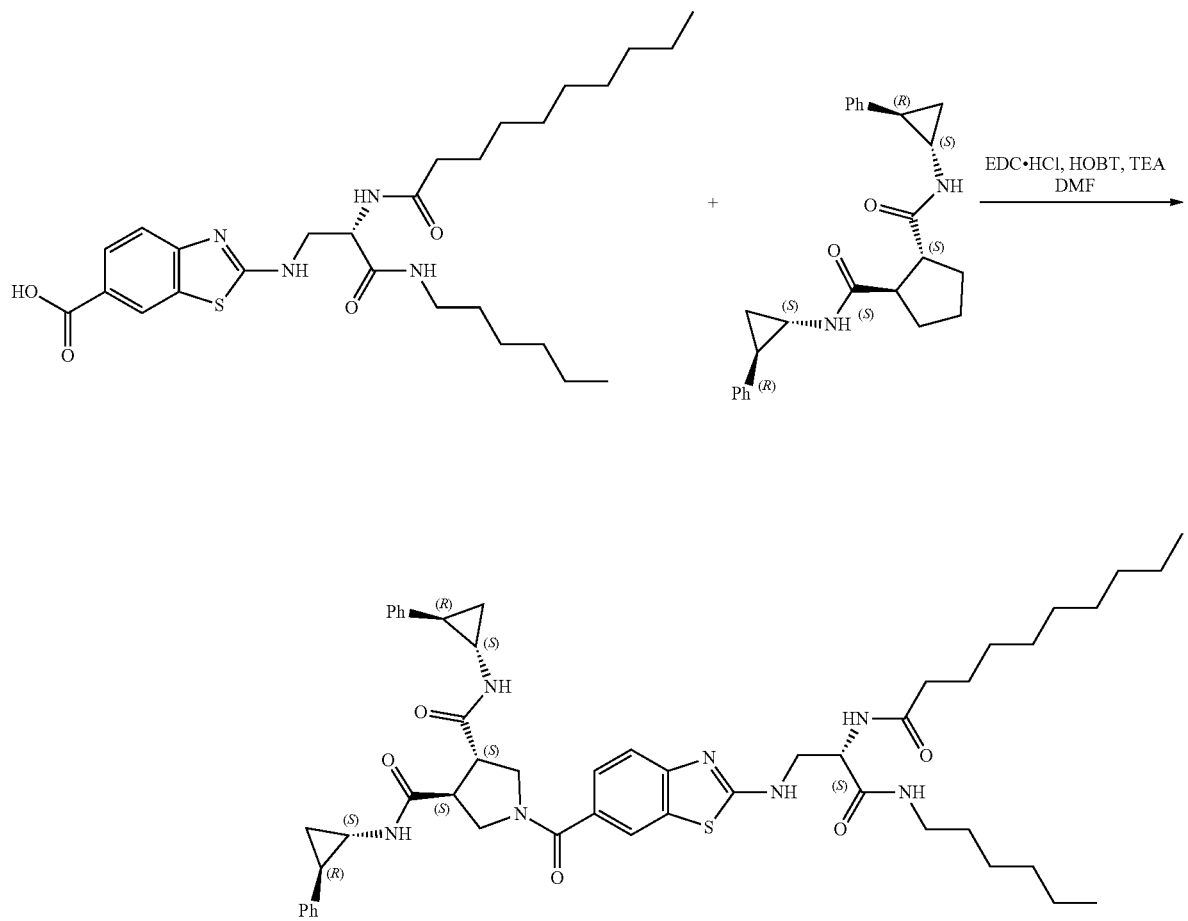

Prepared using General EDC, HOBT Coupling Procedure. The final product was purified using Prep HPLC Method 1 to give (3S,4S)-1-(2-(((S)-2-decanamido-3-(hexylamino)-3-oxopropyl)amino)benzo[d]thiazole-6-carbonyl)-N3,N4-bis((1S,2R)-2-phenylcyclopropyl)pyrrolidine-3,4-dicarboxamide (Compound 262)(0.040 g, 11%), as an off white solid. LCMS (Method-J): 100% (RT 4.378, 202.0 nm) (MS: ESI +ve 891.0 [M+H]). $^1$H NMR: (400 MHz, DMSO) δ ppm: 0.80-86 (m, 6H), 1.11-1.19 (m, 23H), 1.33-1.35 (m, 2H)1.45 (s, 2H), 2.85 (m, 1H), 2.96 (s, 1H), 2.09-2.13 (m, 2H), 2.78 (s, 1H), 2.84 (m, 1H), 3.00-3.03 (m, 2H), 3.10 (s, 1H), 3.18 (s, 1H), 3.54-3.59 (m, 3H), 3.64-3.66 (m, 1H), 3.73-3.75 (m, 2H), 4.48-4.53 (m, 1H), 7.07 (bs, 2H), 7.13 (bs, 4H), 7.24 (m, 4H), 7.36-7.41 (m, 2H), 7.88-7.91 (s, 2H), 8.06-8.08 (m, 1H), 8.28-8.30 (m, 2H), 8.44 (s, 1H).

Synthesis of (3S,4S)-1-(3-(2-decanamido-3-(hexylamino)-3-oxopropyl)-4-oxo-3,4-dihydroquinazoline-6-carbonyl)-N3,N4-bis((1S,2R)-2-phenylcyclopropyl)pyrrolidine-3,4-dicarboxamide, Compound 248

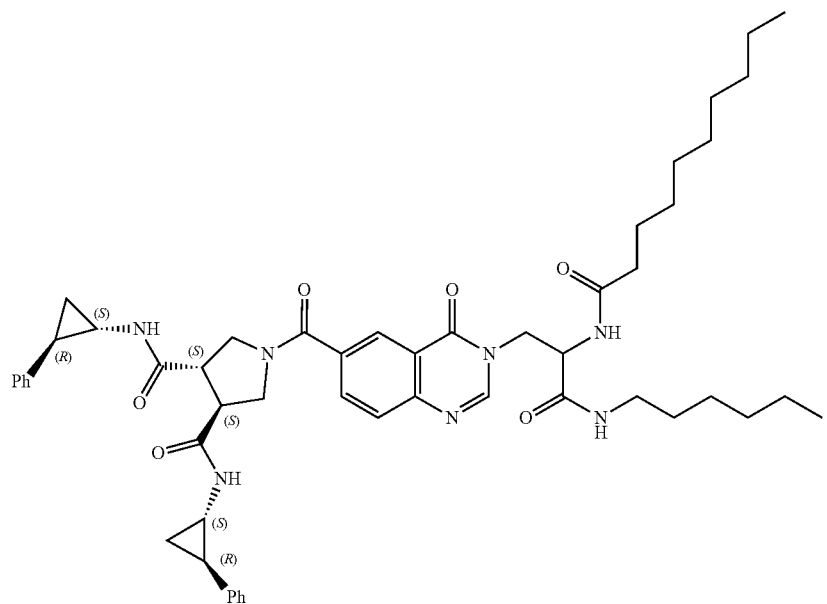

Step-1: Preparation of methyl 3-(6-bromo-4-oxoquinazolin-3(4H)-yl)-2-((tert-butoxycarbonyl)amino)propanoate

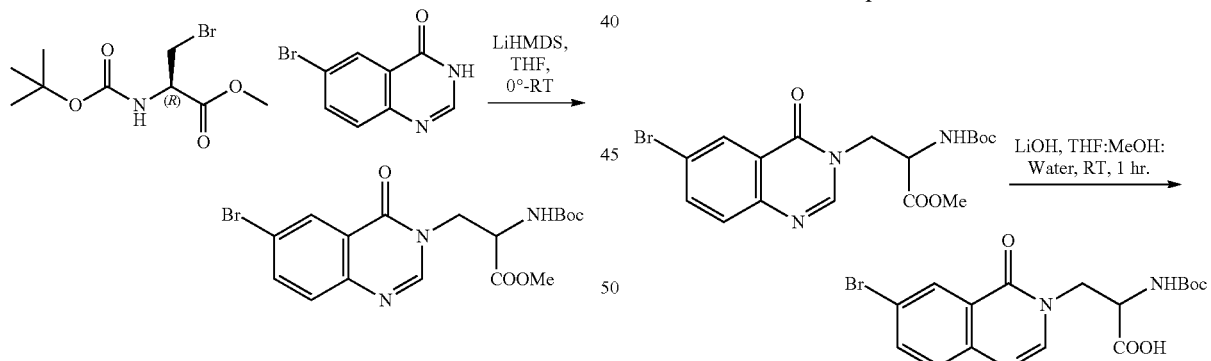

To a stirred solution of 6-bromoquinazolin-4(3H)-one (3.0 g, 13.33 mmol) in DMF (50 mL) was added LiHMDS (1M in THF) (19.9 mL, 19.9 mmol) at 0° C. After 10 min, methyl (R)-3-bromo-2-((tert-butoxycarbonyl)amino)propanoate (4.5 g, 15.99 mmol) in DMF (10 mL) was added, and the reaction was stirred at room temperature for 16 h. The mixture was diluted with water (150 mL) and extracted using EtOAc (3×150 mL). The organic layers were dried over sodium sulfate and concentrated. The crude product was purified using flash chromatography eluting, with 2% MeOH/DCM, to yield methyl (S)-3-(6-bromo-4-oxoquinazolin-3(4H)-yl)-2-((tert-butoxycarbonyl)amino)propanoate (2.7 g, 47%) LCMS (Method-C2): 92.72% (RT: 1.294, 235.0 nm) (MS: ESI +ve 426.2 [M+H]) as a mixture of diastereomers.

Step-2: Preparation of 3-(6-bromo-4-oxoquinazolin-3(4H)-yl)-2-((tert-butoxycarbonyl)amino)propanoic acid Methyl (S)-3-(6-bromo-4-oxoquinazolin-3(4H)-yl)-2-((tert-butoxycarbonyl)amino)propanoate (2.7 g, 6.34 mmol) was dissolved in THF:MeOH:H$_2$O (4:2:1, 70 mL) at RT, then LiOH·H$_2$O (1.3 g, 3.17 mmol) was added and stirred at room temperature for 3 hrs. Solvent was removed under reduced pressure, ice cold water (10 mL), and 10% citric acid solution (3-4 mL) was added, and precipitate was filtered dry under vacuum to give (S)-3-(6-bromo-4-oxoquinazolin-3(4H)-yl)-2-((tert-butoxycarbonyl)amino)propanoic acid (2.5 g, 95%). LCMS (Method-C2): 97.87% (RT 1.167, 275 nm) (MS: ESI +ve 412.3 [M+H]) as a mixture of diastereomers.

Step-3: Preparation of tert-butyl (3-(6-bromo-4-oxoquinazolin-3 (4H)-yl)-1-(hexylamino)-1-oxopropan-2-yl)carbamate

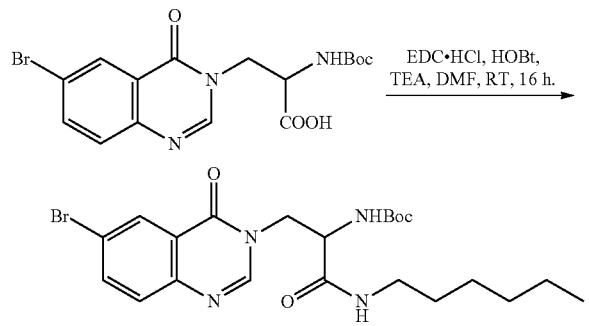

Prepared using General EDC, HOBT Coupling Procedure. The crude product was purified using flash chromatography, eluting with 0-5% MeOH/DCM, to give tert-butyl (S)-(3-(6-bromo-4-oxoquinazolin-3(4H)-yl)-1-(hexylamino)-1-oxopropan-2-yl)carbamate(1.4 g, 52%) as white solid. LCMS (Method-C2): 87.95% (RT: 1.421, 273.0 nm) (MS: ESI +ve 494.2[M+H]), as a mixture of diastereomers.

Step-4: Preparation of methyl 3-(2-((tert-butoxycarbonyl)amino)-3-(hexylamino)-3-oxopropyl)-4-oxo-3,4-dihydroquinazoline-6-carboxylate

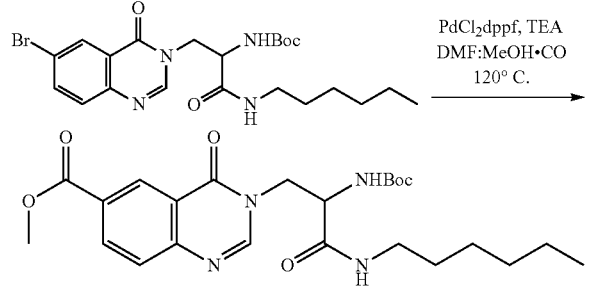

tert-Butyl (S)-(3-(6-bromo-4-oxoquinazolin-3 (4H)-yl)-1-(hexylamino)-1-oxopropan-2-yl)carbamate (1.4 g) and PdCl$_2$(dppf) (0.2 g) were dissolved in a mixture of DMF (15 mL), MeOH (15 mL), and TEA (5 mL) in an autoclave. The reaction mixture was stirred at 120° C. under carbon monoxide pressure (35 kg). The solvent was removed under reduced pressure and the resulting crude product was purified using flash chromatography, eluting with 60-100% EtOAc/hexane, to give methyl (S)-3-(2-((tert-butoxycarbonyl)amino)-3-(hexylamino)-3-oxopropyl)-4-oxo-3,4-dihydroquinazoline-6-carboxylate, as a white solid (0.9 g, 67%). LCMS (Method-C2): 89.40% (RT: 1.350, 254.0 nm) (MS: ESI +ve 475.4 [M+H]) as a mixture of diastereomers.

Step-5: Preparation of methyl 3-(3-(hexylamino)-3-oxo-2-((2,2,2-trifluoroacetyl)-14-azaneyl)propyl)-4-oxo-3,4-dihydroquinazoline-6-carboxylate

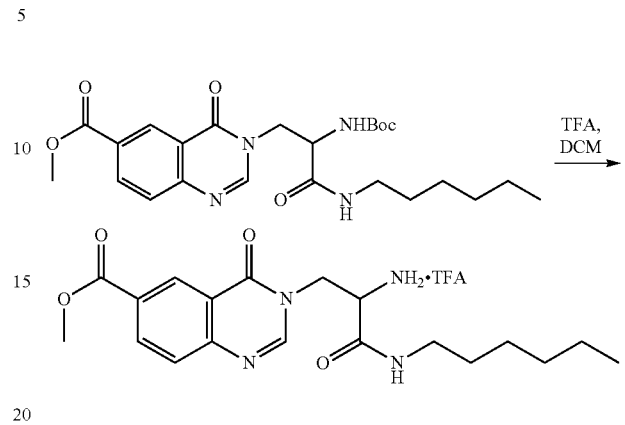

Prepared using General BOC Deprotection Procedure to give methyl (S)-3-(3-(hexylamino)-3-oxo-2-((2,2,2-trifluoroacetyl)-14-azaneyl)propyl)-4-oxo-3,4-dihydroquinazoline-6-carboxylate as its TFA salt (0.5 g, crude) LCMS (Method-C2): 94.16% (RT 1.074, 232.0 nm) (MS: ESI +ve 375.3[M+1]), as a mixture of diastereomers.

Step-6: Preparation of methyl 3-(2-decanamido-3-(hexylamino)-3-oxopropyl)-4-oxo-3,4-dihydroquinazoline-6-carboxylate

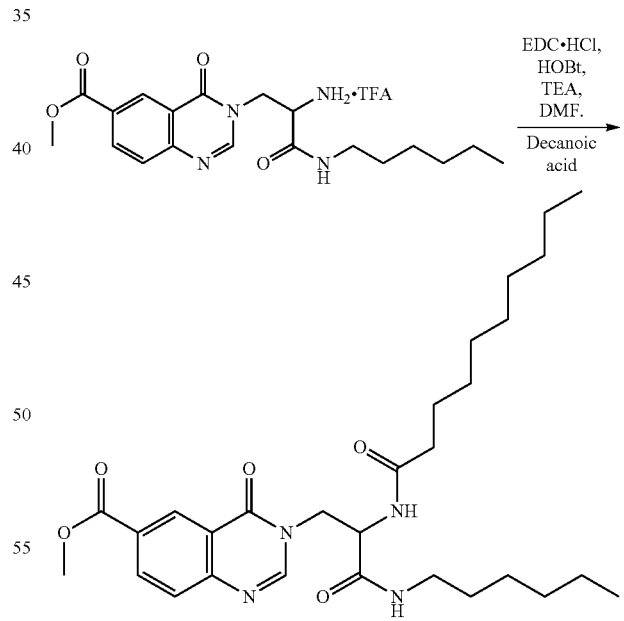

Prepared using General BOC Deprotection Procedure. The crude product was purified by flash chromatography, eluting with 0-2% MeOH/DCM, to give methyl (S)-3-(2-decanamido-3-(hexylamino)-3-oxopropyl)-4-oxo-3,4-dihydroquinazoline-6-carboxylate (0.42 g, 68%) as white solid. LCMS (Method-C2): 46.12% (RT: 1.618, 202.0 nm) (MS: ESI +ve 527.5[M−H]). Mixture of diastereomers.

Step 7: Preparation of 3-(2-decanamido-3-(hexylamino)-3-oxopropyl)-4-oxo-3,4-dihydroquinazoline-6-carboxylic acid

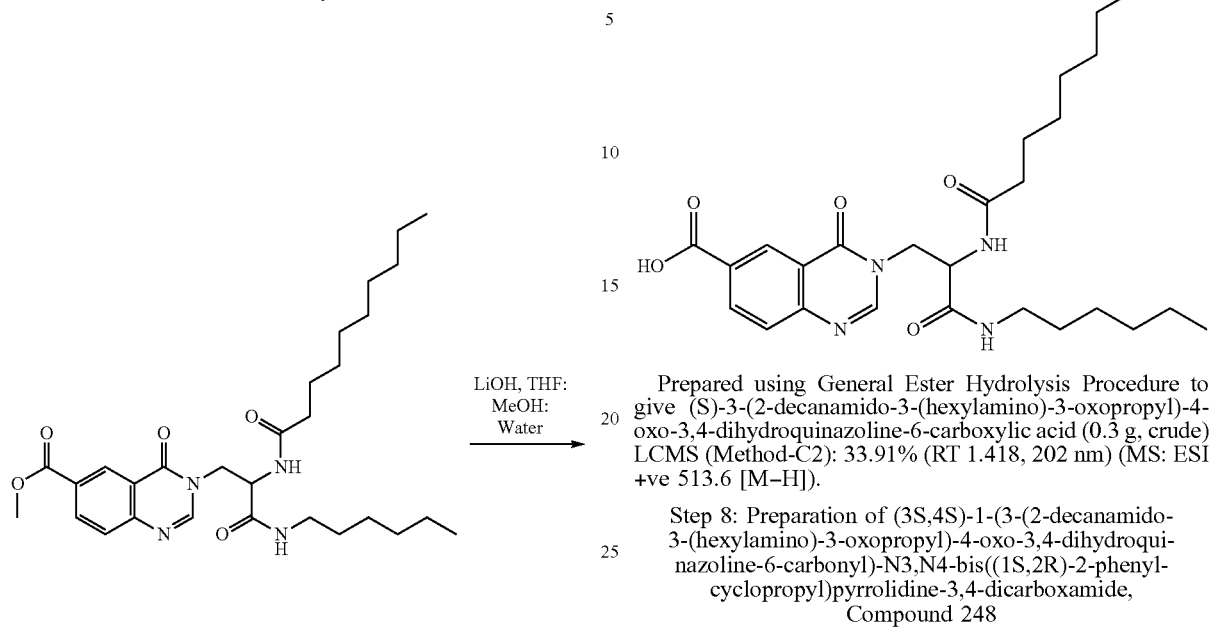

Prepared using General Ester Hydrolysis Procedure to give (S)-3-(2-decanamido-3-(hexylamino)-3-oxopropyl)-4-oxo-3,4-dihydroquinazoline-6-carboxylic acid (0.3 g, crude) LCMS (Method-C2): 33.91% (RT 1.418, 202 nm) (MS: ESI +ve 513.6 [M–H]).

Step 8: Preparation of (3S,4S)-1-(3-(2-decanamido-3-(hexylamino)-3-oxopropyl)-4-oxo-3,4-dihydroquinazoline-6-carbonyl)-N3,N4-bis((1S,2R)-2-phenylcyclopropyl)pyrrolidine-3,4-dicarboxamide, Compound 248

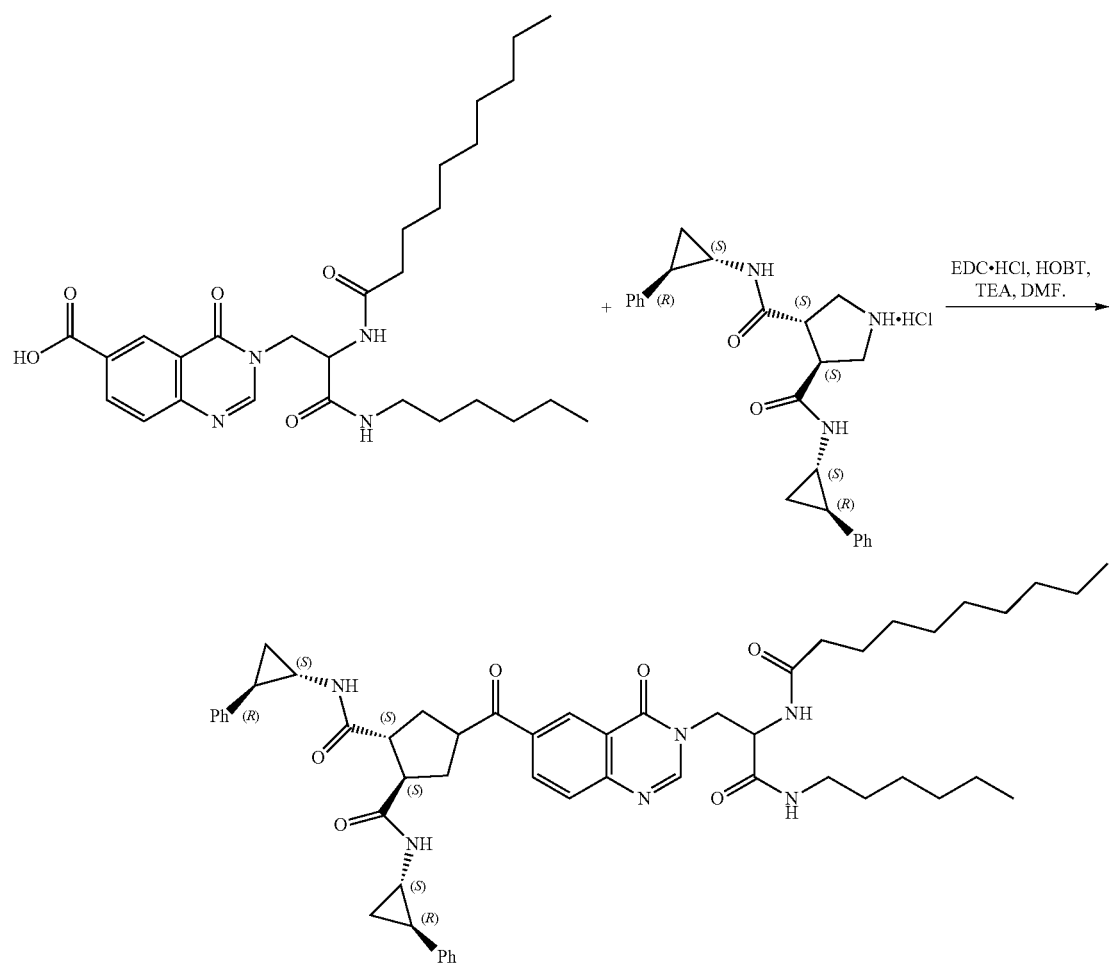

Prepared using General EDC, HOBT Coupling Procedure. The final product was purified using Prep HPLC Method 1 to give (S)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylic acid (Compound 248) (0.035 g, 8%), as an off white solid. LCMS (Method-J): 99.11% (RT 4.713, 220.0 nm) (MS: ESI +ve 886.6 [M+H]). ¹H NMR: (400 MHz, DMSO) δ ppm: 0.83 (bs, 6H), 1.10-1.18 (m, 20H), 1.32 (m, 3H), 1.85 (s, 1H), 1.98 (s, 1H), 2.02-2.05 (m, 2H), 2.77 (m, 1H), 2.85 (s, 1H), 3.03 (s, 2H), 3.10-3.12 (m, 1H), 3.19-3.22 (m, 1H), 3.53-3.58 (m, 2H), 3.67 (m, 1H), 3.81-3.84 (m, 1H), 3.92-3.95 (m, 1H), 4.36 (bs, 1H), 4.76 (m, 1H), 7.06-7.08 (m, 2H), 7.12-7.14 (m, 4H), 7.21-7.27 (m, 4H), 7.66-7.68 (m, 1H), 7.93-7.95 (m, 1H), 8.12-8.23 (m, 4H), 8.32 (s, 1H), 8.46 (s, 1H), as a mixture of diastereomers.

Synthesis of (3S,4S)-1-(3-(2-decanamido-3-(hexylamino)-3-oxopropyl)-4-oxo-3,4-dihydroquinazoline-7-carbonyl)-N3,N4-bis((1S,2R)-2-phenylcyclopropyl)pyrrolidine-3,4-dicarboxamide, Compound 270

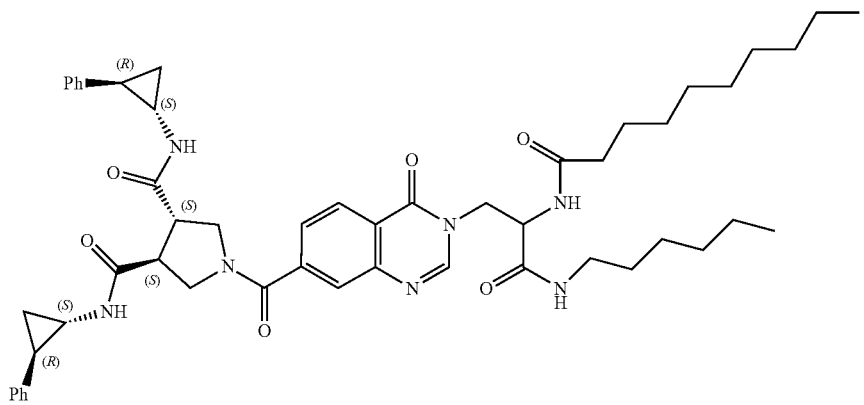

Prepared by a procedure similar to that reported for (S)-4-(4-((3S,4S)-3,4-bis(((1S,2R)-2-phenylcyclopropyl)carbamoyl)pyrrolidine-1-carbonyl)benzyl)-1-methyl-5-oxopiperazine-2-carboxylic acid (Compound 248), using the applicable starting materials. The crude product was purified using Prep HPLC Method 10 to give (3S,4S)-1-(3-((S)-2-decanamido-3-(hexylamino)-3-oxopropyl)-4-oxo-3,4-dihydroquinazoline-7-carbonyl)-N3,N4-bis((1S,2R)-2-phenylcyclopropyl)pyrrolidine-3,4-dicarboxamide (Compound 270)(0.035 g, 8%), as an off white solid. LCMS (Method-J): 99.62% (RT 4.669, 202.0 nm) (MS: ESI +ve 886.6 [M+H]). ¹H NMR: (400 MHz, DMSO) δ ppm: 0.83-86 (m, 6H), 1.11-1.35 (m, 24H), 1.85 (s, 1H), 1.98-2.05 (s, 4H), 2.78 (m, 1H), 2.87 (s, 1H), 3.04 (s, 2H), 3.11-3.15 (m, 1H), 3.21-3.23 (m, 1H), 3.46-3.57 (m, 2H), 3.64 (m, 1H), 3.82-3.87 (m, 1H), 3.92-3.97 (m, 1H), 4.36-4.39 (m, 1H), 4.77 (m, 1H), 7.06-7.08 (m, 2H), 7.13-7.19 (m, 4H), 7.22-7.30 (m, 4H), 7.66-7.68 (m, 1H), 7.71 (s, 1H), 8.15 (m, 1H), 8.19-8.22 (m, 3H), 8.33-8.34 (m, 1H), 8.49-8.50 (s, 1H).

Synthesis of (tert-butyl (R)-4-(4-methyl-3-(tetradecylcarbamoyl)piperazine-1-carbonyl)benzoate

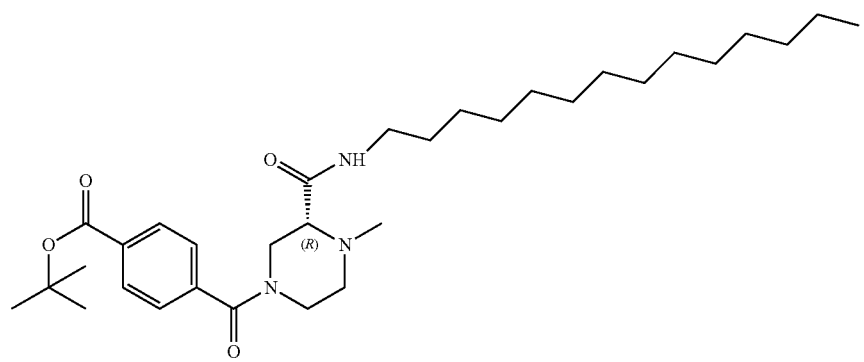

Step-1: Preparation of tert-butyl (R)-4-(4-methyl-3-(tetradecylcarbamoyl)piperazine-1-carbonyl)benzoate

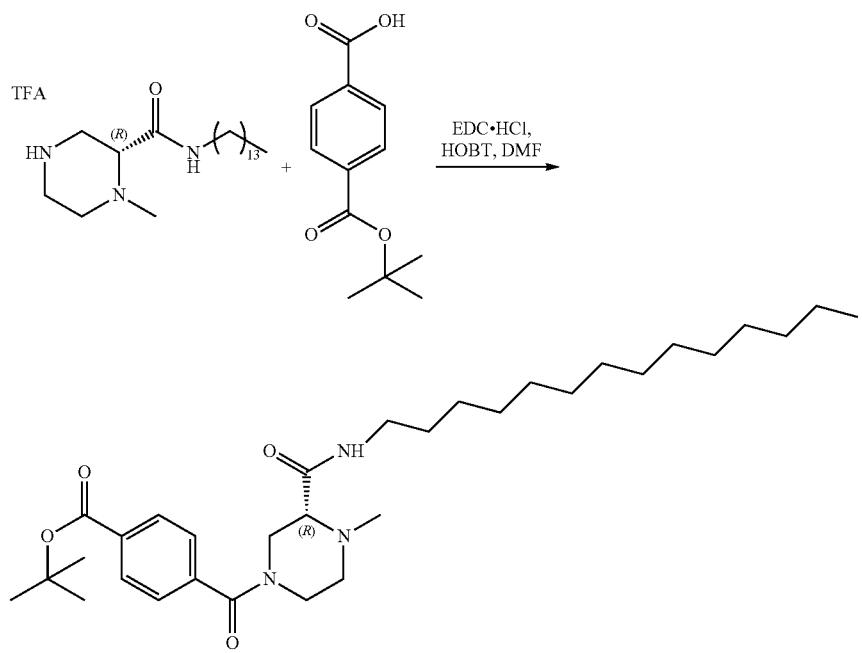

Prepared using General EDC, HOBT Coupling Procedure. The final product was purified using Prep HPLC Method 1 to give tert-butyl (R)-4-(4-methyl-3-(tetradecylcarbamoyl)piperazine-1-carbonyl)benzoate (0.007 g, 7%). LCMS (Method-J): 100% (RT: 6.494, 202.0 nm) (MS: ESI −+ve 544.3 [M+1]). $^1$H NMR: (400 MHz, DMSO) δ ppm: 0.837-0.869 (m, 3H), 1.236 (s, 21H), 1.558 (s, 9H), 2.144-2.161 (m, 6H), 2.978-3.228 (m, 7H), 3.341 (m, 2H), 7.495-7.515 (d, 2H), 7.947-7.962 (m, 3H).

Synthesis of (R)-4-(4-methyl-3-(tetradecylcarbamoyl) piperazine-1-carbonyl) benzoic acid

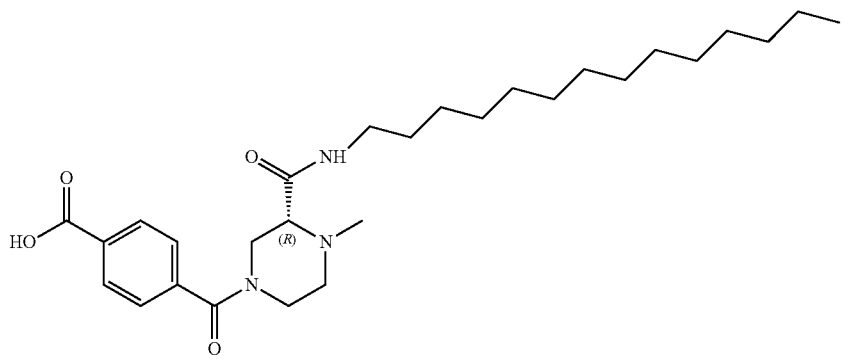

Step-1: Preparation of (R)-4-(4-methyl-3-(tetradecylcarbamoyl)piperazine-1-carbonyl)benzoic acid

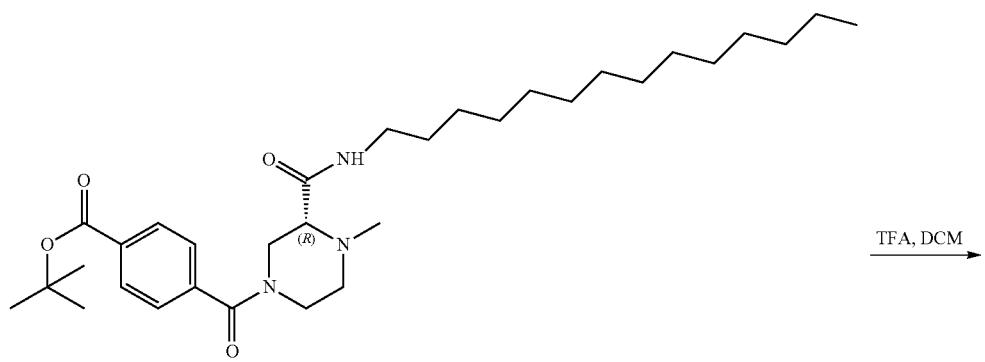

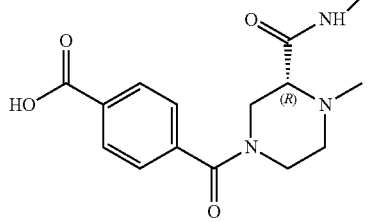

Prepared using General BOC Deprotection Procedure. The final product was purified using Prep HPLC Method 1 to give (R)-4-(4-methyl-3-(tetradecylcarbamoyl)piperazine-1-carbonyl)benzoic acid (0.008 g, 6.4%), as a white solid. LCMS (Method-J): 100% (RT: 5.404, 202.0 nm) (MS: ESI +ve 488.2 [M+1]). $^1$H NMR: (400 MHz, DMSO) δ ppm: 0.848-0.882 (t, 3H), 1.247 (s, 20H), 2.062 (s, 1H), 2.162 (s, 0.3H), 2.812 (s, 1H), 2.988 (s, 2H), 3.093 (s, 1H), 3.222-3.249 (m, 2H), 4.168-4.269 (m, 2H), 7.498-7.518 (s, 2H), 7.894-8.011 (s, 3H), 13.154-13.246 (s, 1H).

Synthesis of tert-butyl (R)-4-(3-(hexylcarbamoyl)-4-octanoylpiperazine-1-carbonyl) benzoate Step-1: Preparation of tert-butyl (R)-4-(3-(hexylcarbamoyl)-4-octanoylpiperazine-1-carbonyl)benzoate

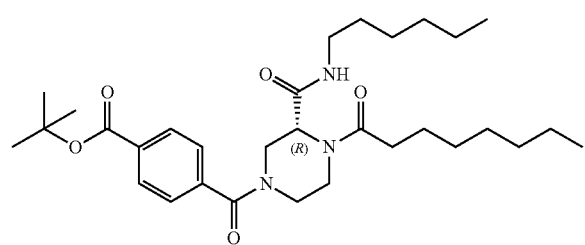

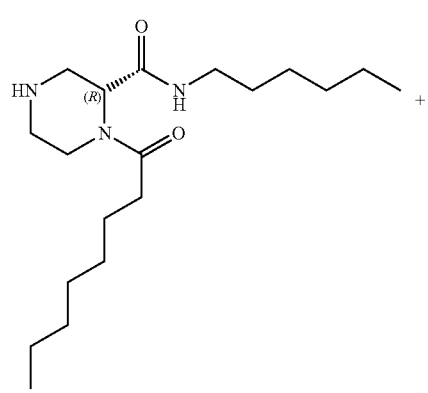

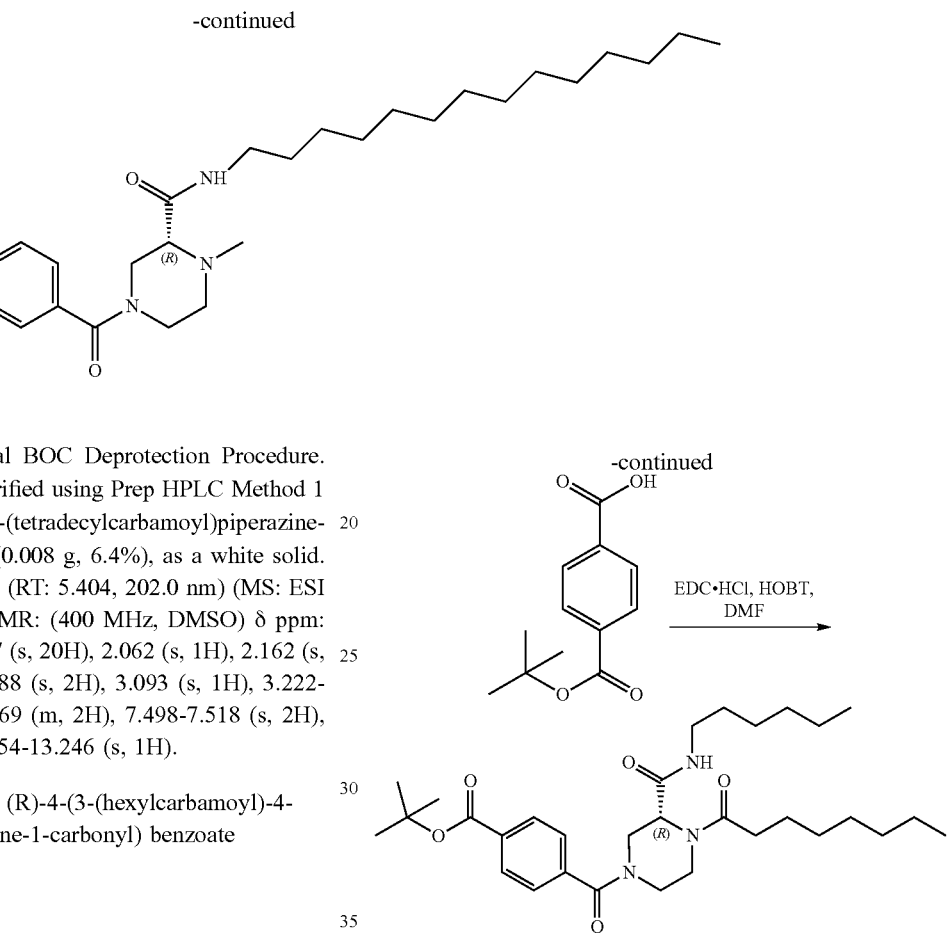

Prepared using General EDC, HOBT Coupling Procedure. The final product was purified using Prep HPLC Method 12 to give tert-butyl (R)-4-(3-(hexylcarbamoyl)-4-octanoylpiperazine-1-carbonyl)benzoate (0.036 g, 4.9% yield), as a white solid. LCMS (Method-J): 100% (RT: 5.968, 202.0 nm) (MS: ESI +ve 544.2[M+1]). $^1$H NMR: (400 MHz, DMSO) δ ppm: 0.852-0.865 (m, 6H), 1.225 (m, 15H), 1.483-1.561 (m, 11H), 2.337-2.507 (m, 5H), 3.018 (s, 2H), 3.345-3.582 (m, 2H), 3.841 (m, 1H), 4.218 (s, 1H), 4.598-4.672 (m, 1H), 7.421-7.440 (m, 2H), 7.677 (s, 1H), 7.941-7.957 (m, 2H).

Synthesis of (R)-4-(3-(hexylcarbamoyl)-4-octanoylpiperazine-1-carbonyl)benzoic acid Step-1: Preparation of (R)-4-(3-(hexylcarbamoyl)-4-octanoylpiperazine-1-carbonyl)benzoic acid

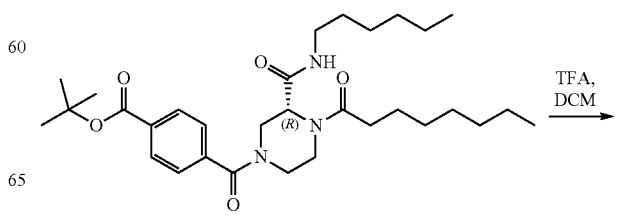

-continued

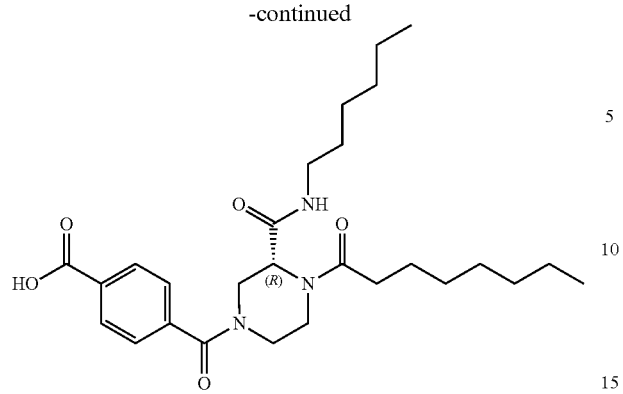

Prepared using General BOC Deprotection Procedure. The product was purified using Prep HPLC Method 12 to give (R)-4-(3-(hexylcarbamoyl)-4-octanoylpiperazine-1-carbonyl)benzoic acid (0.076 g, 40% yield), as a white solid. LCMS (Method-J): 100% (RT: 5.038, 202.0 nm) (MS: ESI +ve 488.2[M+1]). $^1$H NMR: (400 MHz, DMSO) δ ppm: 0.857-0.874 (m, 6H), 1.238-1.269 (m, 14H), 1.494 (s, 2H), 2.342-2.380 (m, 2H), 2.515-2.554 (m, 1H), 2.888-3.180 (m, 3H), 3.586-3.636 (m, 1H), 3.891-4.209 (m, 3H), 4.685 (s, 2H), 7.340-7.359 (d, 2H), 7.948-7.968 (d, 2H).

Synthesis of tert-Butyl 4-((3S,4S)-3,4-bis(((1S,2R)-2-phenylcyclopropyl)carbamoyl)pyrrolidine-1-carbonyl)benzoic acid

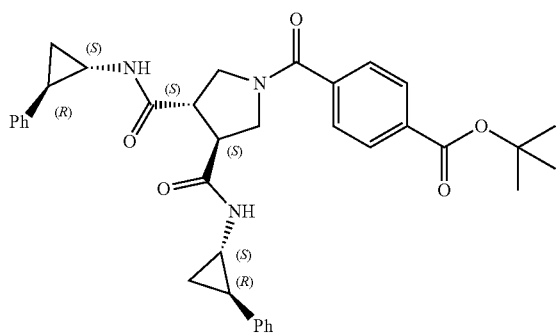

Step 1: Synthesis of tert-butyl 4-((3S,4S)-3,4-bis(((1S,2R)-2-phenylcyclopropyl) carbamoyl) pyrrolidine-1-carbonyl)benzoate

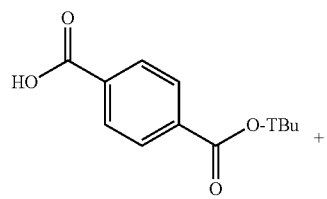

-continued

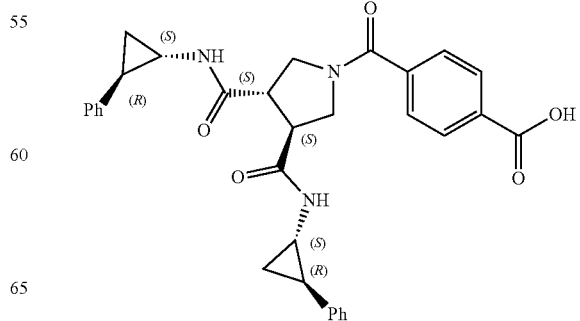

Prepared using General EDC, HOBT Coupling Procedure. The crude product was purified using flash chromatography, eluting with 3-5% MeOH/DCM, to give tert-butyl 4-((3S,4S)-3,4-bis(((1S,2R)-2-phenylcyclopropyl) carbamoyl) pyrrolidine-1-carbonyl)benzoate (0.035 g, 8.75%). LCMS (Method-C3): 100% (RT: 1.870, 226.00 nm) (MS: ESI +ve 594.33 [M+1]). $^1$H NMR:–1.09-1.17 (m, 4H), 1.55 (s, 9H), 1.84 (s, 1H), 1.96 (s, 1H), 2.76 (s, 1H), 2.85 (s, 1H), 3.07-3.20 (m, 2H), 3.42-3.62 (m, 3H), 3.79-3.84 (t, J=10.8 Hz, 1H), 7.06-7.28 (m, 10H), 7.61-7.63 (d, J=7.6 Hz, 2H) 7.94-7.96 (d, J=8 Hz, 2H), 8.29 (s, 1H), 8.44 (s, 1H).

Synthesis of 4-((3S,4S)-3,4-bis(((1S,2R)-2-phenylcyclopropyl)carbamoyl)pyrrolidine-1-carbonyl)benzoic acid Step 1: Synthesis of 4-((3S,4S)-3,4-bis(((1S,2R)-2-phenylcyclopropyl) carbamoyl) pyrrolidine-1-carbonyl)benzoic acid

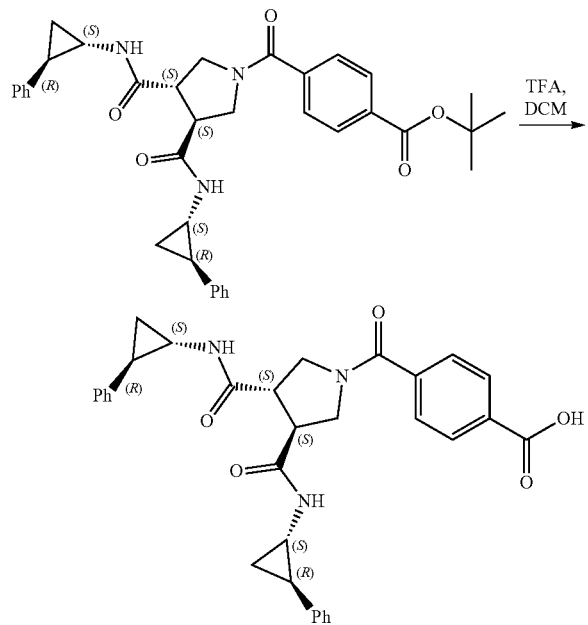

Prepared using General BOC Deprotection Procedure. The crude product was purified using Prep-HPLC Method 4 to give 4-((3S,4S)-3,4-bis(((1S,2R)-2-phenylcyclopropyl) carbamoyl) pyrrolidine-1-carbonyl)benzoic acid (0.030 g, 33.13%). LCMS (Method-03): 100% (RT 1.610, 226.0 nm) (MS: ESI +ve 538.31 [M+H]). $^1$H NMR:–1.09-1.01 (d, J=4.8 Hz, 2H), 1.17-1.18 (d, J=5.2 Hz, 2H), 1.85 (s, 1H), 1.96 (s, 1H), 2.77 (s, 1H), 2.84 (s, 1H), 3.09-3.20 (m, 2H), 3.44-3.62 (m, 3H), 3.79-3.81 (d, J=8.8 Hz, 1H), 7.06-7.28 (m, 10H), 7.61-7.63 (d, J=8 Hz, 2H), 7.98-8.00 (d, J=8 Hz, 2H), 8.30 (s, 1H), 8.44 (s, 1H), 13.15 (s, 1H).

Example 43: General Procedures

General EDC, HOBT Coupling Procedure

To a stirred solution carboxylic acid (1 eq) and amine (2 eq) in DMF was added 2,6-lutidine (5 eq) or TEA (5 eq), HOBT (2 eq) and EDC.HCl (2 eq). The reaction was stirred at room temperature for 12 hrs. Ice water was added and the mixture was extracted with ethyl acetate or dichloromethane. The organic layer was separated, dried over sodium sulphate and concentrated under reduced pressure to give the crude product.

General PyBroP Coupling Procedure

To a stirred solution of amine (1 eq) and carboxylic acid (1 eq) in DMF was added DIPEA (3 eq). The reaction mixture was stirred at room temperature for 5 minutes. PyBroP (1 eq) was added and stirring continued for 12 hrs. The reaction was quenched with ice cold water and the mixture was extracted by ethyl acetate (3×12 mL). The organic layer was dried over sodium sulphate to give the crude product.

General Boc Deprotection Procedure

The Boc protected amine in DCM was added to a 2:1 mixture of DCM:TFA at 0° C. The reaction was stirred for several hours slowly warming to room temperature then concentrated to dryness. The crude residue was chased with DCM or toluene (3X) and the crude amine trifluoroacetate salt was used in the next step without further purification unless otherwise specified.

General tert-Butyl Ester Deprotection Procedure

The tert-butyl ester in DCM was added to a 2:1 mixture of DCM:TFA at 0° C. The reaction was stirred for several hours slowly warming to room temperature then concentrated to dryness. The crude residue was chased with DCM or toluene (3X) to give the crude carboxylic acid.

General Ester Hydrolysis Procedure

Lithium hydroxide monohydrate (5 equiv) was added to a stirred solution of starting ester (1 equiv) in THF/MeOH/water (6:3:1, 0.1 mM). This mixture was stirred under nitrogen for 16 hours, then concentrated. The mixture was acidified with an aqueous solution of citric acid then extracted with ethyl acetate (3×100 mL). The organic layers were combined, dried over $Na_2SO_4$ and concentrated to give the product which was purified as described.

Prep HPLC Method 1:

Shimadzu LC-20AP and UV detector. The column used was ymc actus triart c18 (250*20) mm, 5 micron, Column flow was 16.0 ml/min. Mobile phase; (A) 0.1% formic acid in Water and (B) 100% Acetonitrile.

Prep HPLC Method 2:

Shimadzu LC-20AP and UV detector. The column used was ymc aqua c18 (150*20) mm, 5 micron, Column flow was 15.0 ml/min. Mobile phase; (A) 0.1% formic acid in Water and (B) 100% Acetonitrile.

Prep HPLC Method 3:

Shimadzu LC-20AP and UV detector. The column used was x-bridge c18 (250*19) mm, 5 micron, Column flow was 15.0 ml/min. Mobile phase; (A) 5 mm ammonium bicarbonate+0.1% ammonia in Water and (B) 100% Acetonitrile.

Prep HPLC Method 4:

Shimadzu LC-20AP and UV detector. The column used was x-bridge c18 (250*19) mm, 5 micron, Column flow was 17.0 ml/min. Mobile phase; (A) 0.1% formic acid in Water and (B) 100% Acetonitrile Prep HPLC Method 5:

Shimadzu LC-20AP and UV detector. The column used was Gemini nx c18 (150*21.2) mm, 5 micron, Column flow was 16.0 ml/min. Mobile phase; (A) 5 mm ammonium bicarbonate+0.1% ammonia in Water and (B) 100% Acetonitrile.

Prep HPLC Method 6:

Shimadzu LC-20AP and UV detector. The column used was Gemini nx c18 (150*21.2) mm, 5 micron, Column flow was 16.0 ml/min. Mobile phase; (A) 0.1% formic acid in Water and (B) 100% Acetonitrile.

Prep HPLC Method 7:

Shimadzu LC-20AP and UV detector. The column used was x-bridge c8 (250*19) mm, 5 micron, Column flow was 15.0 ml/min. Mobile phase; (A) 5 mm ammonium bicarbonate+0.1% ammonia in Water and (B) 100% Acetonitrile.

Prep HPLC Method 8:

Shimadzu LC-20AP and UV detector. The column used was x-bridge c8 (250*19) mm, 5 micron, Column flow was 16.0 ml/min. Mobile phase; (A) 0.1% formic acid in Water and (B) 100% Acetonitrile.

Prep HPLC Method 9:

Shimadzu LC-20AP and UV detector. The column used was x-select phenyl hexyl (250*19) mm, 5 micron, Column flow was 15.0 ml/min. Mobile phase; (A) 5 mm ammonium bicarbonate+0.1% ammonia in Water and (B) 100% Acetonitrile.

Prep HPLC Method 10:
Shimadzu LC-20AP and UV detector. The column used was sunfire c18 (250*19) mm, 5 micron, Column flow was 12.0 ml/min. Mobile phase; (A) 0.1% formic acid in Water and (B) 100% Acetonitrile.

Prep HPCL Method 11:
Shimadzu LC-20AP and UV detector. The column used was ymc actus triart c18 (250*20) mm, 5 micron, Column flow was 15.0 ml/min. Mobile phase; (A) 5 mm ammonium bicarbonate+0.1% ammonia in Water and (B) 100% Acetonitrile.

Prep HPLC Method 12:
Shimadzu LC-20AP and UV detector. The column used was x-select phenyl hexyl (250*19) mm, 5 micron, Column flow was 15.0 ml/min. Mobile phase were used (A) 0.1% formic acid in Water and (B) 100% Acetonitrile Prep HPLC Method 13:
Shimadzu LC-20AP and UV detector. The column used was phenomenex c8 (250*21.2) mm, 5 micron. Column flow was 15.0 ml/min. Mobile phase (A) 0.1% formic acid in Water and (B) 100% Acetonitrile.

Analytical LCMS Method-C3
Column: BEH C18 (50*2.1 mm) 1.7 um
Mobile phase: (A) 2 mM Ammonium Acetate followed by 0.1% Formic Acid in Water; (B) 0.1% Formic Acid Acetonitrile
Flow rate; 0.55 mL/min
Gradient:

| Time (min) | % A | % B |
|---|---|---|
| 0.01 | 98 | 2 |
| 0.30 | 98 | 2 |
| 0.60 | 50 | 50 |
| 1.10 | 25 | 75 |
| 2.00 | 0 | 100 |
| 2.70 | 0 | 100 |
| 2.71 | 98 | 2 |
| 3.0 | 98 | 2 |

Analytical LCMS Method-H2
Column: X-Bridge C18 (50*4.6 mm) 3.5 um
Mobile phase: (A) 5 mM Ammonium bicarbonate in Water; (B) 100% Acetonitrile
Flow rate; 1.0 mL/min
Gradient:

| Time (min) | % A | % B |
|---|---|---|
| 0.01 | 95 | 5 |
| 3.50 | 10 | 90 |
| 4.50 | 5 | 95 |
| 6.00 | 5 | 95 |
| 6.01 | 95 | 5 |
| 8.00 | 95 | 5 |

Analytical LCMS Method-DEV.M
Column: X-Select C8H (4.6×250 mm) 5 um
Mobile phase: (A) 10 mM Ammonium Acetate in Water; (B) 100% Acetonitrile
Flow rate; 1.0 mL/min
Gradient:

| Time (min) | % A | % B |
|---|---|---|
| 0.01 | 90 | 10 |
| 10 | 50 | 50 |
| 20 | 20 | 80 |
| 26 | 0 | 100 |
| 28 | 0 | 100 |
| 28.01 | 90 | 10 |
| 30 | 90 | 10 |

Analytical LCMS Method J
Column: BEH C18 (50*2.1 mm) 1.7 um
Mobile phase: (A) 2 mM Ammonium Acetate followed by 0.1% Formic Acid in Water; (B) 0.1% Formic Acid in Acetonitrile
Flow rate; 0.45 mL/min
Gradient:

| Time (min) | % A | % B |
|---|---|---|
| 0.01 | 98 | 2 |
| 0.50 | 98 | 2 |
| 5.00 | 10 | 90 |
| 6.00 | 5 | 95 |
| 7.00 | 5 | 95 |
| 7.01 | 98 | 2 |
| 8.00 | 98 | 2 |

Analytical LCMS Method X
Column: BEH C18 (50*2.1 mm) 1.7 um
Mobile phase: (A) 2 mM ammonium acetate followed by 0.1% formic acid in water; (B) Acetonitrile (90:10)
Flow rate; 0.6 mL/min
Gradient:

| Time (min) | % A | % B |
|---|---|---|
| 0.01 | 95 | 5 |
| 0.40 | 0 | 100 |
| 0.50 | 0 | 100 |
| 1.30 | 0 | 100 |
| 1.31 | 95 | 5 |
| 1.50 | 95 | 5 |
| 0.01 | 95 | 5 |

List of abbreviations:
ABPR Automatic Back Pressure Regulator
DCM Dichloromethane
DIPEA Diisopropylethylamine
DMF Dimethyl formamide
DIPC N,N'-Diisopropylcarbodiimide
DMSO Dimethylsulfoxide
EDC.HCl 3-(Ethyliminomethylideneamino)-N,N-dimethylpropan-1-amine hydrochloride
EtOH Ethanol
$^1$H NMR proton nuclear magnetic resonance spectrum
HOBT Hydroxybenzotriazole
LCMS Liquid chromatography mass spectrum
MeOH methanol
MS:ESI Mass Spectrum: electrospray ionization
Prep HPLC Preparatory high-pressure liquid chromatography
PyBroP Bromo-tris-pyrrolidino-phosphonium hexafluorophosphate
TEA Triethylamine
TFA Trifluoroacetic acid
THE Tetrahydrofuran
RT Retention time Example 44. TLR2 Agonist Screening Assay TLRs are a class of cell-surface receptors expressed on many different cell types that recognize conserved structural motifs present on pathogen-derived molecules. TLR2 recognizes bacteria-derived lipopeptides. One of the most potent agonists characterized to date is a synthetic lipopeptide known as Pam3CSK4, which consists of a peptide-like backbone with 3 lipophilic tails. More recently, Diprovocim, a dimeric molecule, was demonstrated to be a potent agonist of TLR2 despite possessing no extended lipid domains. Provided herein is an assay to identify and characterize the binding affinities of novel TLR2 agonists.

SUMMARY

The in vitro TLR2 assay consists of a cell line that responds to TLR2 engagement by producing a factor that elicits a color change in the culture media and can be readily measured by various colorimetric detection methods. This assay enables the identification of existing and novel compounds that engage TLR2 and, by virtue of compound dilution, to approximate the binding affinity of these compounds for eliciting a TLR2 signal.

Assay

The TLR2 screening assay was developed from the HEK-Blue TLR2 reporter cell line that is commercially available from Invivogen (San Diego, CA). The reporter cell line consists of HEK-293 embryonic kidney cells that have been engineered to express TLR2 and with an NF-kB promoter driving expression of Secreted Alkaline Phosphatase (SEAP). Upon engagement of TLR2, downstream signaling results in activation of NF-kB pathway activation and secretion of SEAR In the presence of the detection reagent in the tissue culture media, SEAP mediates a color change from clear to indigo that is readily assessed by measuring absorbance at 600 nm.

Procedure

HEK-Blue TLR2 reporter cells are cultured according to manufacturer's specifications until a confluence of 70-90%, at which point the cells are trypsinized, counted, and plated into 96-well plates at approximately 40,000 cells per well. Cells are cultured overnight and the TLR2 assay is performed 16-24 hours post-plating into 96 well plates.

For determining compound affinities, control or test compounds are assessed in a 7 point dilution scheme, comprising a top concentration of 10 microMolar and diluted 10-fold to 10 picoMolar. Compounds are diluted from stocks dissolved in DMSO and a 1% DMSO final concentration is maintained in all testing wells.

The assay consists of removing the cell culture media after cells have been cultured overnight and replacing the media with HEK-Blue Detection media with TLR2 agonists at indicated dilution schemes. The Detection media contains a chemical substrate that turns from clear to indigo when acted upon by SEAP. The HEK-Blue cells are then cultured overnight in Detection media with diluted compounds. After overnight culture with agonists, each well of the plate is assayed in a plate reader at 600 nanometer absorbance.

Protocol (1) HEK-Blue TLR2 cells are diluted in complete DME culture medium and plated into 96-well plates at 40,000 cells per well and cultured overnight.

(2) After 16-24 hours in culture, the media is removed and replaced with 200 microliters per well of HEK-Blue Detection media.
(3) TLR2 agonists are diluted 100-fold from DMSO stocks into each well, yielding a final DMSO concentration of 1% in all wells.
(3) Treated cells are cultured overnight and the following day are assayed in plate reader for Absorbance at 600 nanometer.

Example 45. TLR2 Functional Assay

Cells of the immune system respond to TLR agonists in part by secreting cytokines. Functional assays for TLR2 agonists measure cytokine release from purified immune cells or immortalized cell lines derived from immune cells. Cytokine release is measured by standard ELISA approaches or multiplexed analysis using the Meso Scale Discovery (MSD) platform.

Assay

Purified primary human peripheral blood mononuclear cells or RAW 264.7 mouse macrophage cell line cells are plated at approximately 40,000 cells per well. Cells are treated with agonist compounds and assays 6-24 hours post-treatment for cytokines released into the cell culture media.

Analysis

Following assay measurements utilizing either HEK-Blue detection or cytokine release, all data is analyzed with the GraphPad Prism8 statistical package to determine EC50, binding and activity metrics for the TLR2 modulators.

Example 46. TLR2 In Vitro Functional Assay

Many cell types can respond to TLR engagement. Primary immune cells are particularly well-suited to TLR studies, as they express a repertoire of TLRs and their primary function in vivo is to respond to infection that often detected through TLR engagement by pathogen-derived moieties. Primary peripheral blood mononuclear cells (PBMCs) purified from human, mouse and rat have been used to demonstrate TLR2 engagement by the compounds described herein.

PBMC Protocol

Purified cells were obtained from a cell preparatory lab. Briefly, the protocol requires either isolation of PBMC from blood by centrifugation onto a Ficoll buffer isolation gradient, or from spleen by positive sorting of the desired cell population with a population specific antibody that enables physical retrieval (magnetic sorting, for example). Purified PBMCs are kept on ice after purification, then plated into serum-free media in 96-well plates and incubated for one hour. After 1 hour, cells are treated individually with various TLR2-enganging compounds at varying concentrations. Twenty-four hours later, supernatants are collected and assayed for cytokine secretion into the media by multiplex immunodetection (Meso Scale Discovery plex inflammatory marker detection kits for human, mouse, or rat).

Cell Line Protocol

Numerous cell lines derived from various cell types can respond to TLR2 agonists with stereotyped cytokine and chemokine secretion. In particular, cell lines derived from macrophages respond robustly to TLR2 agonists by secreting a wide array of cytokines, including (but not limited to) TNF-alpha, IL-1, IL-10 and IL-12. The human monocytic cell line THP-1, the mouse macrophage line RAW-264.7, and the rat macrophage line NR8383 were used. For each assay, the respective cell lines were plated into 96-well plates overnight and then treated the following day with various TLR2-engaging compounds at varying concentrations. The next day, supernatants were collected and assayed by multiplex immunodetection for cytokines released (MSD detection kits for respective species).

Data is generated using protocol described in Example 44.

TABLE 3

| Compound | TLR2 (HEK-Blue) EC50 (nM)* |
| --- | --- |
| 001 | D |
| 002 | A |
| 003 | D |
| 004 | A |
| 005 | C |
| 006 | C |
| 007 | D |
| 008 | D |
| 009 | D |
| 010 | D |
| 011 | D |
| 012 | D |
| 013 | D |
| 014 | D |
| 015 | D |
| 016 | D |
| 017 | D |
| 018 | C |
| 019 | A |
| 020 | D |
| 021 | D |
| 022 | D |
| 023 | A |
| 024 | D |
| 025 | A |
| 026 | B |
| 027 | A |
| 028 | B |
| 029 | B |
| 030 | D |
| 031 | D |
| 032 | A |
| 033 | B |
| 034 | C |
| 035 | A |
| 036 | A |
| 037 | B |
| 038 | C |
| 039 | D |
| 040 | D |
| 041 | C |
| 042 | C |
| 043 | D |
| 044 | A |
| 045 | C |
| 046 | B |
| 047 | D |
| 048 | C |
| 049 | D |
| 050 | B |
| 051 | A |
| 052 | A |
| 053 | D |
| 054 | B |
| 055 | C |
| 056 | A |
| 057 | B |
| 058 | B |
| 059 | A |

TABLE 3-continued

| Compound | TLR2 (HEK-Blue) EC50 (nM)* |
| --- | --- |
| 060 | A |
| 061 | A |
| 062 | B |
| 063 | C |
| 064 | A |
| 065 | B |
| 066 | B |
| 067 | D |
| 068 | D |
| 069 | C |
| 070 | D |
| 071 | B |
| 072 | A |
| 073 | C |
| 074 | B |
| 075 | B |
| 076 | A |

*Reported values are an average of all runs. A: 0.1-50 nM; B: 51-350 nM; C: 351-1000 nM; D > 1000 nM.

TABLE 4

| Compound | TLR2 (HEK-Blue) EC50 (nM)* |
| --- | --- |
| 077 | D |
| 078 | B |
| 079 | A |
| 080 | B |
| 081 | C |
| 082 | D |
| 083 | D |
| 084 | D |
| 085 | A |
| 086 | D |
| 087 | D |
| 088 | D |
| 089 | D |
| 090 | D |
| 091 | D |
| 092 | B |
| 093 | B |
| 094 | B |
| 095 | C |
| 096 | A |
| 097 | B |
| 098 | A |
| 099 | D |
| 100 | D |
| 101 | A |
| 102 | A |
| 103 | C |
| 104 | A |
| 105 | B |
| 106 | B |
| 107 | C |
| 108 | A |
| 109 | A |
| 110 | A |
| 111 | A |
| 112 | B |
| 113 | B |
| 114 | B |
| 115 | D |
| 116 | C |
| 117 | D |
| 118 | D |
| 119 | D |
| 120 | D |
| 121 | C |
| 122 | D |
| 123 | A |
| 124 | D |
| 125 | D |
| 126 | D |

TABLE 4-continued

| Compound | TLR2 (HEK-Blue) EC50 (nM)* |
|---|---|
| 127 | B |
| 128 | D |
| 129 | B |
| 130 | C |
| 131 | C |
| 132 | B |
| 133 | D |
| 134 | A |
| 135 | D |
| 136 | A |
| 137 | B |
| 138 | A |
| 139 | A |
| 140 | A |
| 141 | A |
| 142 | D |
| 143 | B |
| 144 | C |
| 145 | D |
| 146 | C |
| 147 | D |
| 148 | C |
| 149 | B |
| 150 | B |
| 151 | D |
| 152 | A |
| 153 | D |
| 154 | C |
| 155 | D |
| 156 | B |
| 157 | C |
| 158 | D |
| 159 | C |
| 160 | D |
| 161 | D |
| 162 | D |
| 163 | C |
| 164 | D |
| 165 | D |
| 166 | D |
| 167 | A |
| 168 | B |
| 169 | D |
| 170 | D |
| 171 | D |
| 172 | D |
| 173 | A |
| 174 | C |
| 175 | A |
| 176 | D |
| 177 | D |
| 178 | C |
| 179 | D |
| 180 | D |
| 181 | A |
| 182 | D |
| 183 | B |
| 184 | A |
| 185 | A |
| 186 | A |
| 187 | A |
| 188 | A |
| 189 | A |
| 190 | C |
| 191 | C |
| 192 | C |
| 193 | B |
| 194 | D |
| 195 | D |
| 196 | D |
| 197 | A |
| 198 | D |
| 199 | A |
| 200 | D |
| 201 | C |
| 202 | B |
| 203 | D |
| 204 | A |
| 205 | A |
| 206 | A |
| 207 | A |
| 208 | A |
| 209 | A |
| 210 | A |
| 211 | A |
| 212 | A |
| 213 | A |
| 214 | B |
| 215 | B |
| 216 | A |
| 217 | A |
| 218 | C |
| 219 | A |
| 220 | A |
| 221 | A |
| 222 | A |
| 223 | D |
| 224 | D |
| 225 | C |
| 226 | D |
| 227 | A |
| 228 | A |
| 229 | A |
| 230 | A |
| 231 | A |
| 232 | A |
| 233 | A |
| 234 | D |
| 235 | D |
| 236 | A |
| 237 | D |
| 238 | C |
| 239 | A |
| 240 | D |
| 241 | B |
| 242 | B |
| 243 | A |
| 244 | C |
| 245 | D |
| 246 | D |
| 247 | D |
| 248 | D |
| 249 | D |
| 250 | D |
| 251 | D |
| 252 | D |
| 253 | D |
| 254 | D |
| 255 | D |
| 256 | D |
| 257 | C |
| 258 | D |
| 259 | C |
| 260 | A |
| 261 | D |
| 262 | D |
| 263 | C |
| 264 | D |
| 265 | D |
| 266 | C |
| 267 | N.D. |
| 268 | N.D. |
| 269 | N.D. |
| 270 | N.D. |
| 271 | N.D. |
| 272 | N.D. |
| 273 | N.D. |
| 274 | N.D. |
| 275 | N.D. |
| 276 | N.D. |
| 277 | D |

*Reported values are an average of all runs. A: 0.1-50 nM; B: 51-350 nM; C: 351-1000 nM; D > 1000 nM.

Data provided in Table 5 is generated using protocols described in Example 45 and 46.

TABLE 5

| Compound Number | RAW EC50 (nM) | THP-1 EC50 (nM) |
|---|---|---|
| 025 | | A |
| 026 | | B |
| 027 | | A |
| 032 | | A |
| 036 | | A |
| 044 | | A |
| 054 | | A |
| 059 | | A |
| 060 | | A |
| 063 | | A |
| 072 | | A |
| 075 | | A |
| 076 | | A |
| 101 | D | A |
| 102 | | A |
| 104 | | A |
| 108 | B | A |
| 109 | D | A |
| 110 | | A |
| 134 | C | |
| 138 | D | |
| 140 | B | |
| 141 | | |
| 142 | | |
| 152 | D | |
| 175 | B | |
| 181 | D | |
| 184 | B | |
| 185 | A | |
| 187 | B | |
| 188 | C | |
| 189 | C | |
| 190 | | |
| 197 | C | |
| 198 | D | |
| 199 | D | |
| 204 | D | |
| 205 | D | |
| 206 | D | |
| 207 | | |
| 208 | | |
| 209 | D | |
| 210 | D | |
| 211 | D | |
| 212 | C | |
| 213 | B | |
| 214 | A | |
| 215 | D | |
| 216 | D | |
| 217 | D | |
| 219 | A | |
| 220 | A | |
| 221 | A | |
| 222 | B | |
| 223 | C | |
| 224 | D | |
| 227 | D | |
| 228 | D | |
| 229 | D | |
| 230 | D | |
| 231 | B | |

* Reported values are an average of all runs. A: 0.1-50 nM; B: 51-350 nM; C: 351-1000 nM; D > 1000 nM.

Example 47. TLR2 Antagonist Screening Assay

TLRs signal through ligand-mediated dimerization or multimerization. TLR2 may partner with TLR1 or TLR6 to produce an agonist signal. Compounds that prevent agonist signaling, antagonists, may interfere with proper dimerization or with downstream signaling. The following assay was developed to identify and characterize novel TLR2 antagonists.

SUMMARY

The in vitro TLR2 assay consists of a cell line that responds to TLR2 engagement by producing a factor that elicits a color change in the culture media and can be readily measured by various colorimetric detection methods. This assay enables the identification of existing and novel compounds that engage TLR2. Treating reporter cells with putative TLR2 antagonists will diminish the reporter response to TLR2 agonists.

TLR2 HEK Blue assay for screening TLR2 antagonists:

TLR2 antagonists were screened for TLR2 binding and blocking with a competition assay. Briefly, a published TLR2 agonist, diprovocim, was dosed at its EC50 in the presence of increasing concentrations of antagonist. A dose response was generated for the antagonist, based on suppression of TLR2 activation elicited by diprovocim. The assay was performed with Invivogen HEK Blue cells, which express the human TLR2 receptor as well as NFkB-inducible secreted Alkaline Phosphatase. Alkaline Phosphatase activity was proportional to TLR2 activation, and thus served as a colorimetric reporter.

HEK Blue hTLR2 cells (Invivogen) were grown in DMEM with 10% FBS (Seradigm). Cells were seeded at 40,000 cells/well in 96-well plates and incubated overnight to adhere. Media was replaced with 200 uL/well HEK Blue Detection Medium (Invivogen). Cells were then dosed with TLR2 antagonists in log dilutions from 10 μM to 10 nM, followed by diprovocim at its EC50 concentration of 3 nM. Cells incubated for 16-24 hours, then absorbance at 600 nm was read on a SpectraMax M2 (Molecular Devices). To determine IC50s, absorbance values were normalized to 3 nM diprovocim alone, then entered in Prism 8 (Graphpad). Four parameter dose response curves were fit according to the following model, and IC50 values were reported:

$$Y = \text{Bottom} + (\text{Top} - \text{Bottom})/(1 + (IC50/X)^{\text{HillSlope}})$$

Where X is the antagonist concentration, Y is the normalized absorbance, Top and Bottom are the plateaus, IC50 is the concentration at half-maximal inhibition, and HillSlope is the slope factor.

Protocol

1. HEK-Blue TLR2 cells are diluted in complete DME culture medium and plated into 96-well plates at 40,000 cells per well and cultured overnight.
2. After 16-24 hours in culture, the media is removed and replaced with 200 microliters per well of HEK-Blue Detection media.
3. TLR2 antagonists are diluted 100-fold from DMSO stocks into each well, yielding a final DMSO concentration of 1% in all wells. Reporter cells are treated for 1-2 hours, then treated with TLR2 agonist diluted to the EC50-70 concentration.
4. Treated cells are cultured overnight and the following day are assayed in plate reader for Absorbance at 600 nanometer.

TABLE 6

| Compound | TLR2 (HEK-Blue) IC50 (nM)** |
|---|---|
| 007 | F |
| 008 | F |
| 024 | F |
| 053 | F |
| 077 | F |

TABLE 6-continued

| Compound | TLR2 (HEK-Blue) IC50 (nM)** |
|---|---|
| 160 | F |
| 162 | E |
| 176 | E |
| 177 | E |
| 203 | F |
| 277 | E |

**Reported values are an average of all runs. E: 1-350 nM; F: 351-1000 nM.

Example 48. In Vivo Functional Assays

The orthotopic tumor growth model is a highly sensitive method for determining cytotoxic T cell function. Mice are treated with potentially therapeutic compounds and a bolus of cultured cancer cell lines are implanted orthotopically into the animal, usually on the flank. Treatment may be initiated for some time before cancer cell implantation, after implantation, or both before and after. The rate and extent of tumor growth over time is a good indicator of the immune-potentiating and cancer-suppressive activities of the tested compounds.

Example 49. In Vivo Oncology/Tumor Models

To assess the efficacy of the disclosed compounds in cancer therapy, mice are treated orally with TLR2 modulator (e.g., an agonist or partial agonist for varying amounts of time before and/or after implantation of cancer cells. Tumor growth is monitored for alterations of progression from the control group. Antibiotics administration diminishes the efficacy of anti-PD1 therapy. Oncology experiments herein utilize this effect, and the potential ability of oral TLR2 modulators to rescue the impact of the loss of the microbiome on anti-PD1 therapy.

Protocol for Anti-Cancer Activity

The MC38 mouse adenocarcinoma cell line develops into a palpable tumor when implanted into syngeneic c57/Black6 mice. The MC38 cell line is also responsive to anti-PD1 checkpoint therapy, a monoclonal antibody therapy that blocks the T cell suppressive actions of the endogenous protein PD1. Antibiotics (ABX) have been shown to render anti-PD1 therapy largely ineffective, in part by depleting the intestinal microbiome. The assay described herein utilizes ABX to render MC38 tumor-bearing mice refractory to the effects of anti-PD1 checkpoint therapy, and then treating with an oral TLR2 agonist to restore anti-PD1 efficacy.

Method

C57/Black6 mice were treated with control or antibiotics (ABX)-containing water for the entirety of the tumor study. ABX treatment was initiated 14 days before tumor implant. Oral TLR2 agonists were initiated 12 days before tumor implant through 20 days post-implant of MC38 tumor cells.
Mice were dosed Q3D, with or without ABX treatment. MC38 tumor growth was measured by calipers every 2 or 3 days to follow tumor growth progression.

Example 50. Dosing and Pharmacodynamics Studies

Tumor growth is evaluated in an animal model by administering a TLR2 modulator compound disclosed herein on a dosing schedule of Q3D. Treatment of the TLR2 modulator is combined with an anti-PD1 agent administered on a separate dosing schedule described herein.

The invention claimed is:

1. A method for treating cancer in a subject in need thereof, comprising administering to the subject a compound of Formula (I):

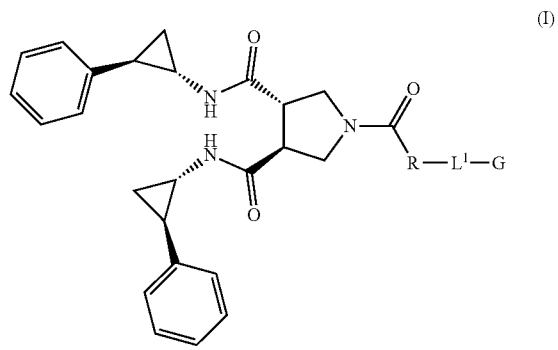

(I)

or a pharmaceutically acceptable salt thereof, wherein:
R is:

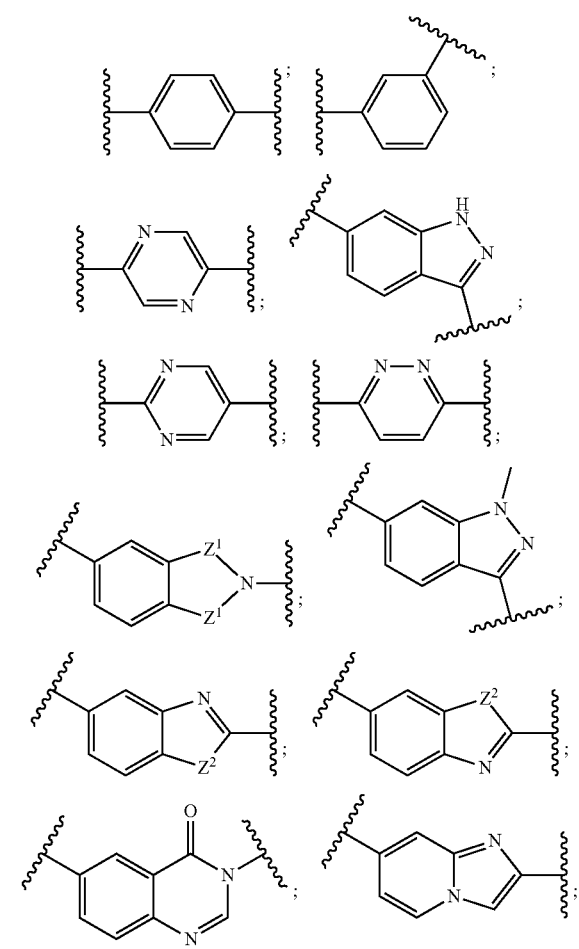

-continued
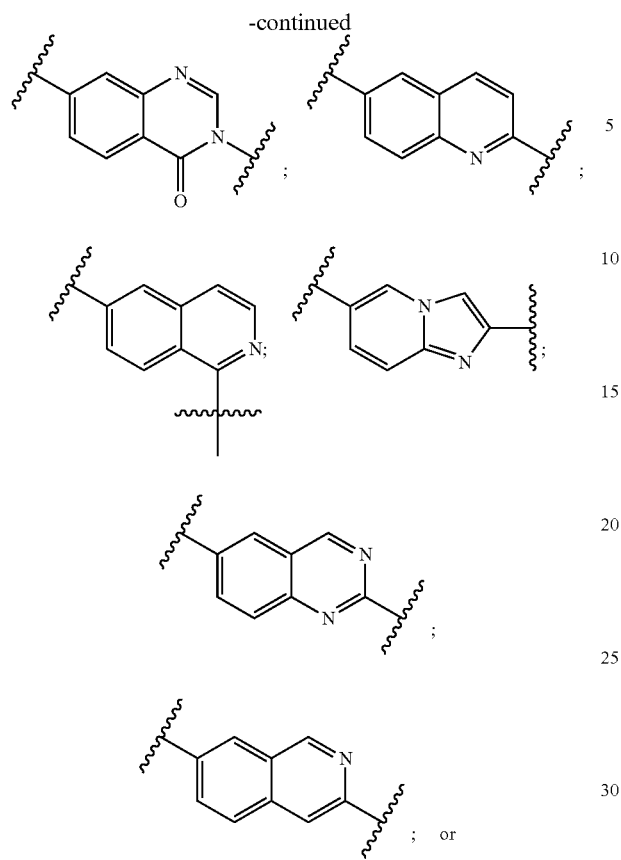
wherein each R is substituted or unsubstituted; or R is
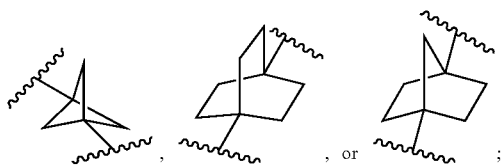 [SMILES: *C12CC(*)(C1)C2 ; *C12CCC(*)(CC1)CC2 ; *C12CCC(*)(CC1)C2]
L¹ is a five-membered heteroarylene, or a bond;
G is:
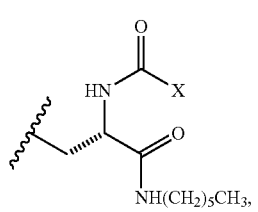
-continued
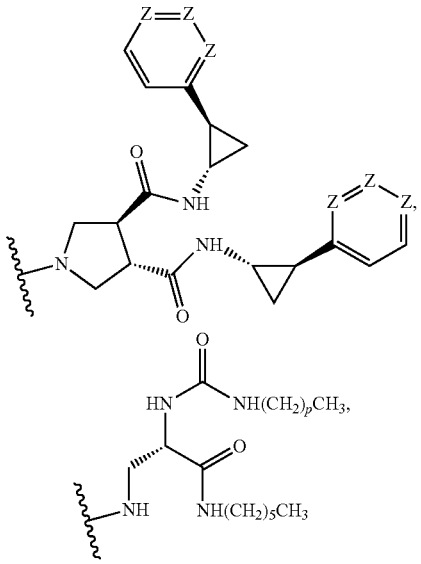
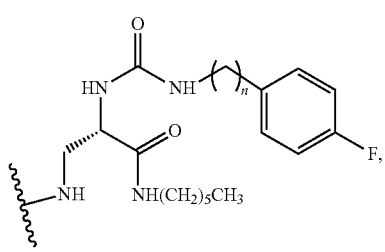
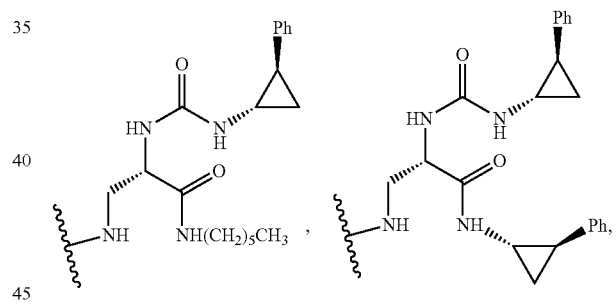
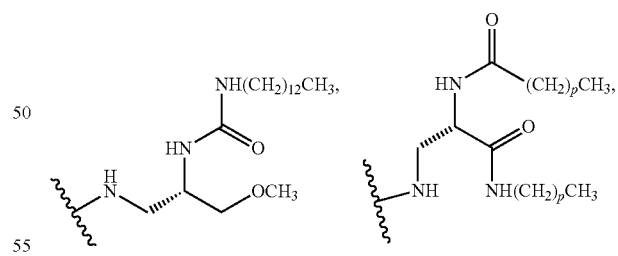
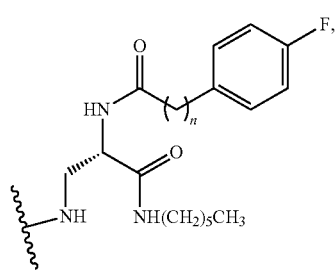

881
-continued
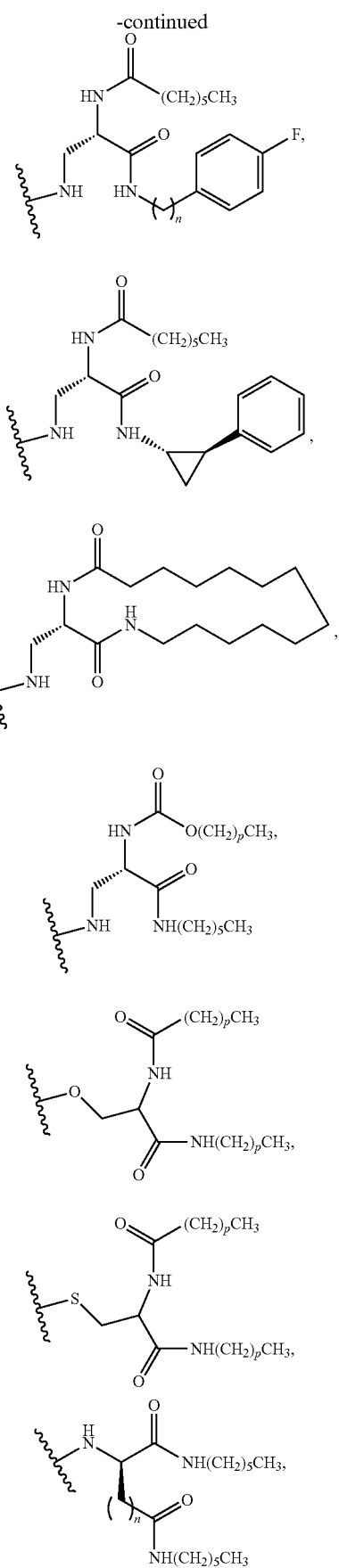
882
-continued
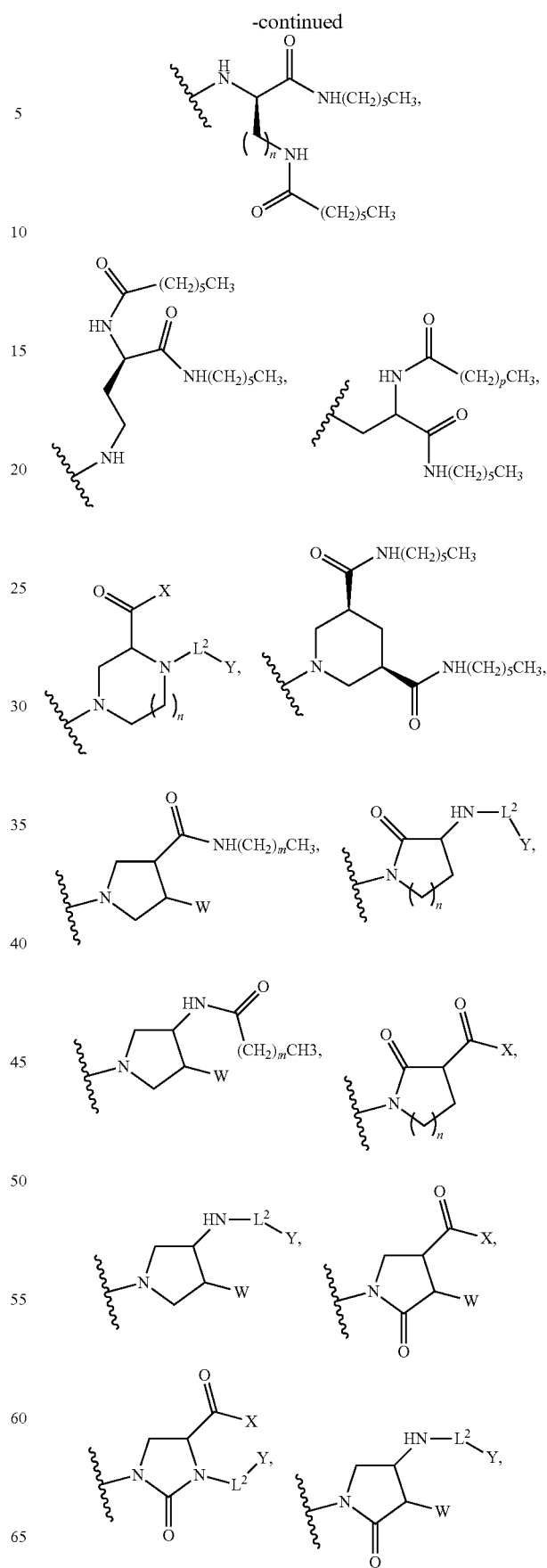

883
-continued

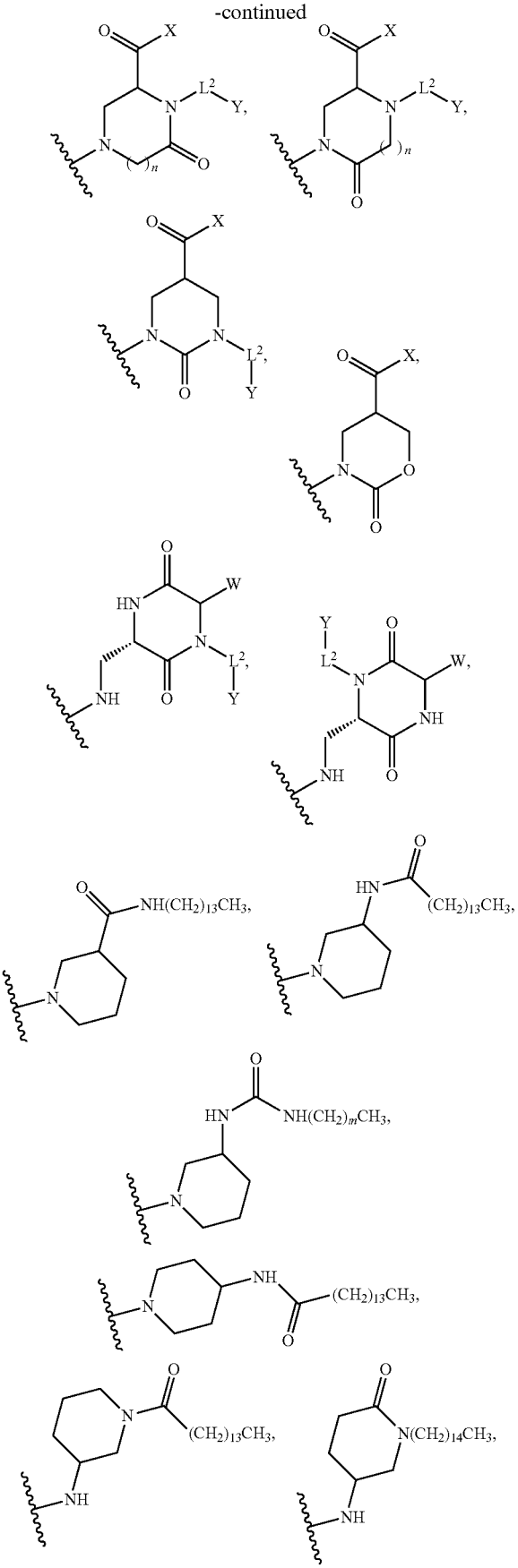

884
-continued

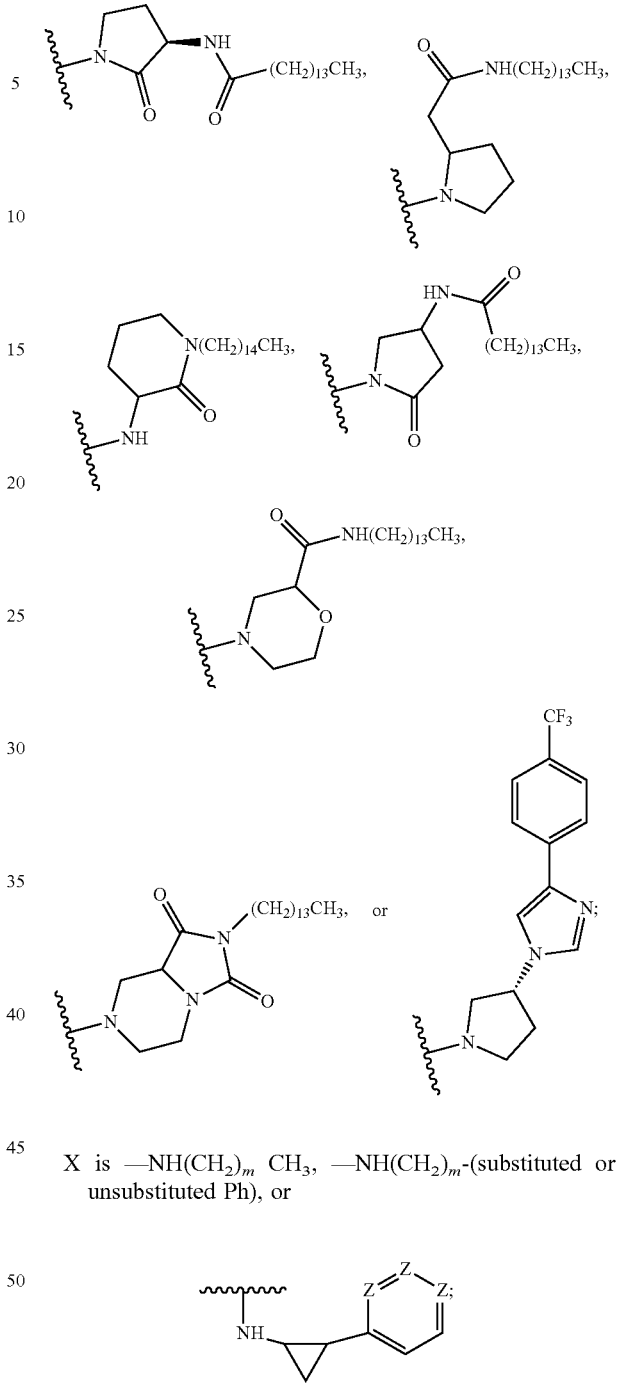

X is —NH(CH$_2$)$_m$CH$_3$, —NH(CH$_2$)$_m$-(substituted or unsubstituted Ph), or Z is CH or N, provided that no more than one Z on any one ring is N;

each Z$^1$ is independently —CH$_2$— or —C(=O)—;

each Z$^2$ is independently —O—, —S—, or —NH—;

L$^2$ is a bond, —(CH$_2$)$_m$—, —CO—, —SO$_2$—, —(C=O)NH—, or —(C=O)O—;

Y is —H, substituted or unsubstituted C$_{1-16}$ alkyl, C$_{1-16}$ alkyl-(substituted or unsubstituted Ph), —NH(CH$_2$)$_m$CH$_3$, —SO$_2$(CH$_2$)$_{13}$CH$_3$, or substituted or unsubstituted C$_{3-10}$ cycloalkyl;

W is H, hydroxyl, —OCH$_3$, —O(CH$_2$)$_m$CH$_3$, —NH(C=O)CH$_3$, —NH(C=O)(CH$_2$)$_m$CH$_3$, —(C=O)—NH(CH$_2$)$_m$CH$_3$, substituted or unsubstituted C$_{1-16}$ alkyl, C$_{1-16}$ alkyl-(substituted or unsubstituted Ph), —NH(CH$_2$)$_m$CH$_3$, —N((CH$_2$)$_m$CH$_3$)$_2$, —N(CH$_3$)(Y), or substituted or unsubstituted C$_{3-10}$ cycloalkyl;

each m is independently 1-16;

each n is independently 1-3; and each p is independently 3-8.

2. The method of claim 1, wherein the compound of Formula (I) has the following formula, or a salt thereof:

3. The method of claim 2, wherein the compound of Formula (I) has the structure of:

Formula (VI), wherein m is 10, 11, or 12.

4. The method of claim 1, wherein G is

5. The method of claim 1, wherein the compound of Formula (I) is selected from:

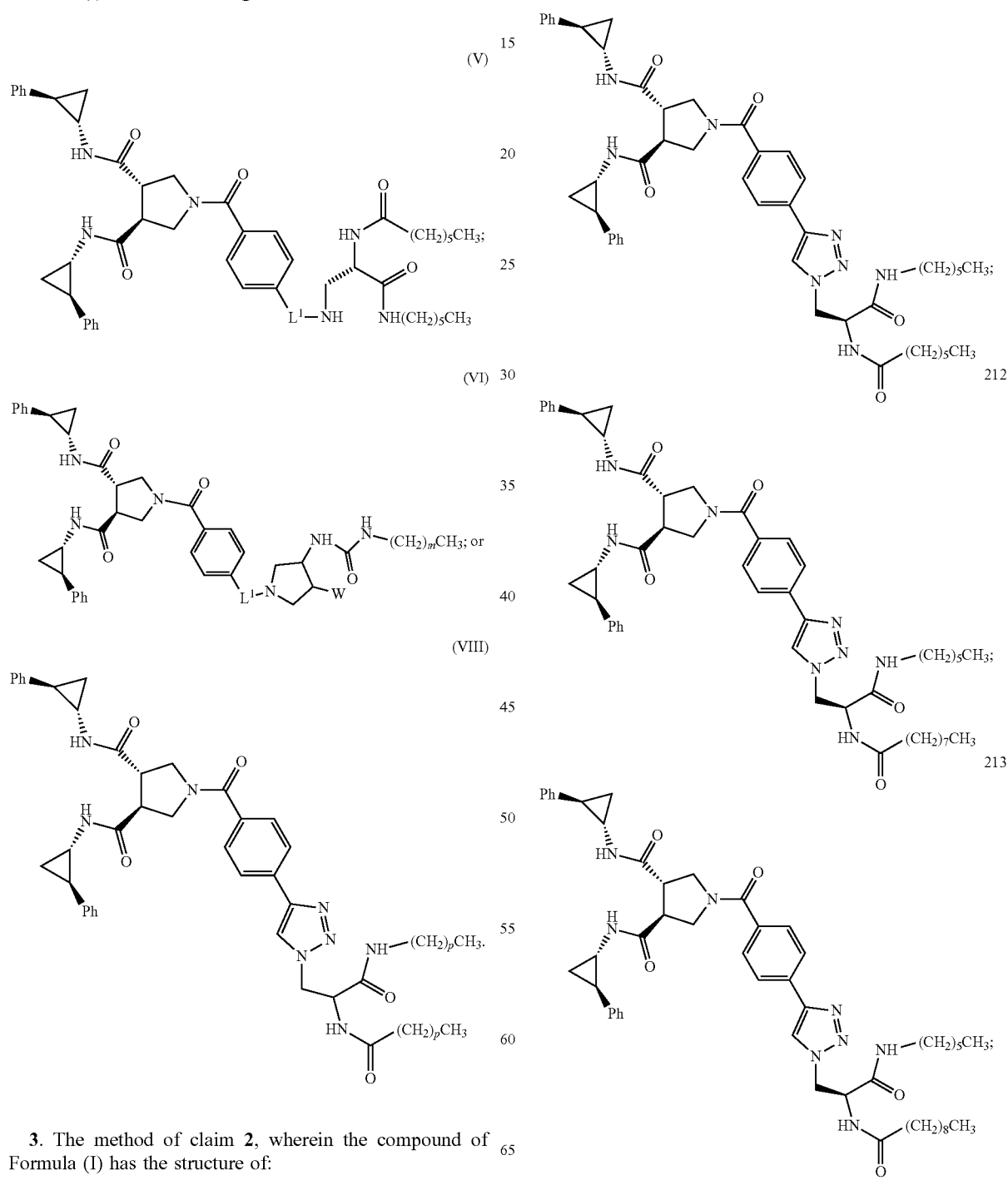

-continued

219

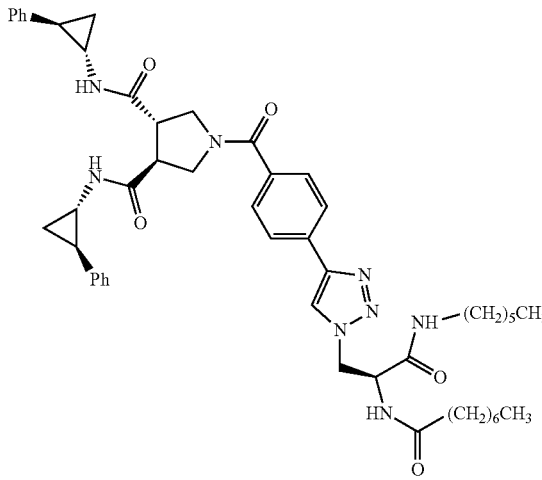

220

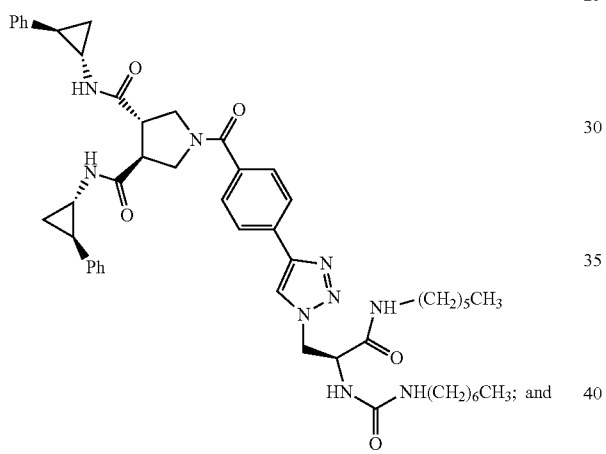

221

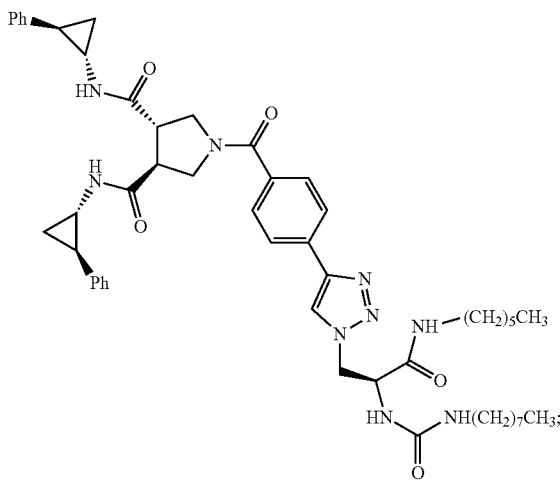

or a pharmaceutically acceptable salt thereof.

6. The method of claim 1, wherein:
G is

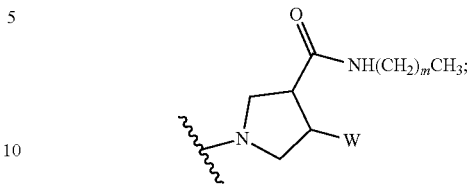

wherein

W is hydroxyl, —OCH$_3$, —O(CH$_2$)$_m$CH$_3$, —NH(C═O)CH$_3$—NH(C═O)(CH$_2$)$_m$CH$_3$, substituted or unsubstituted C$_{1-16}$ alkyl, C$_{1-16}$ alkyl-(substituted or unsubstituted Ph), —NH(CH$_2$)$_m$CH$_3$, —N((CH$_2$)$_m$CH$_3$)$_2$, —N(CH$_3$)(Y), or substituted or unsubstituted C$_{3-10}$ cycloalkyl;

Y is —H, substituted or unsubstituted C$_{1-16}$ alkyl, C$_{1-16}$ alkyl-(substituted or unsubstituted Ph), —NH(CH$_2$)$_m$CH$_3$, —SO$_2$(CH$_2$)$_{13}$CH$_3$, or substituted or unsubstituted C$_{3-10}$ cycloalkyl; and each m is independently 1-16.

7. A method for treating cancer in a subject in need thereof, comprising administering to the subject a compound of Formula (I):

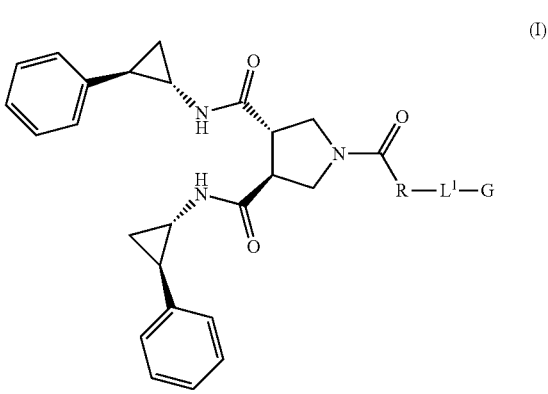

(I)

or a pharmaceutically acceptable salt thereof, wherein:
R is:

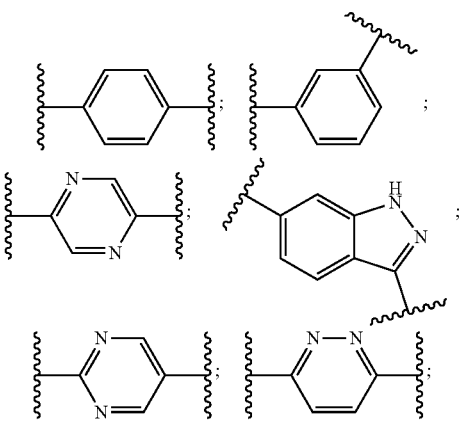

889
-continued

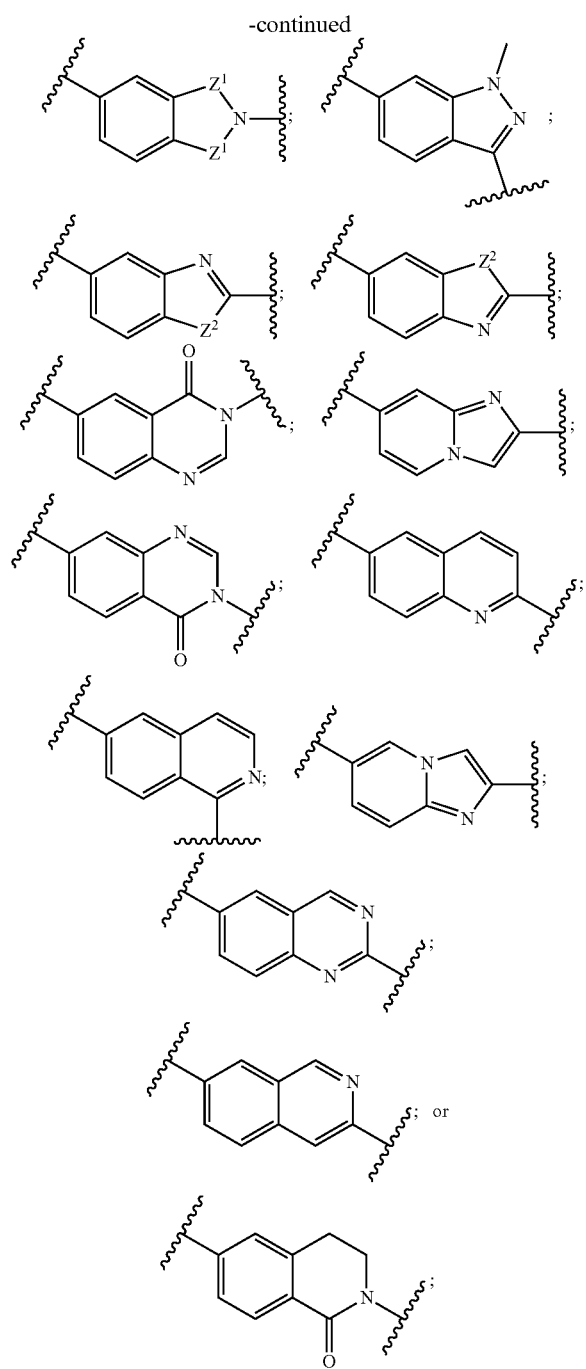

wherein each R is substituted or unsubstituted; or
R is

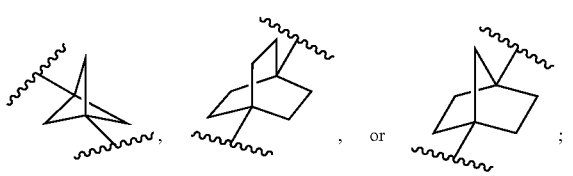 [SMILES: *C12CC(*)(C1)C2 ; *C12CCC(*)(CC1)CC2 ; *C12CCC(*)(CC1)C2]

$L^1$ is a five-membered heterocyclylene, a five-membered heteroarylene, a bond, —CO—, —SO$_2$—,

890

—(CH$_2$)$_m$—, —CH(CH$_3$)—, —CH(CF$_3$)—, —CF$_2$—, —NHC(=O)—, —NHCH$_2$—, or

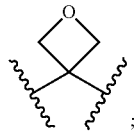 [SMILES: *C1(*)COC1]

G is

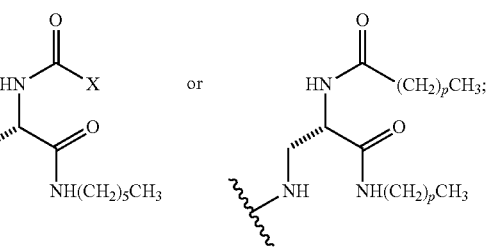

X is —NH(CH$_2$)m CH$_3$, —NH(CH$_2$)$_m$-(substituted or unsubstituted Ph), or

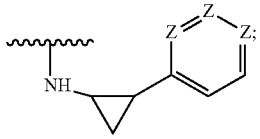

Z is CH or N, provided that no more than one Z on any one ring is N;
each $Z^1$ is independently -CH$_2$— or —C(=O)—;
each $Z^2$ is independently —O—, —S—, or —NH—;
each m is independently 1-16; and
each p is independently 3-8.

8. The method of claim 1 or 7, wherein:
R is

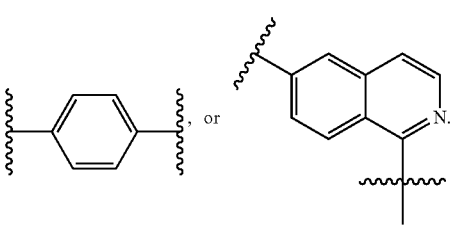 [SMILES: *c1ccc(*)cc1 ; *c1ccc2c(*)nccc2c1]

9. The method of claim 1 or 7, wherein $L^1$ is

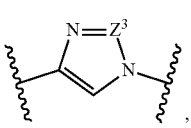

wherein $Z^3$ is N.

10. The method of claim 1 or 7, wherein:
R is

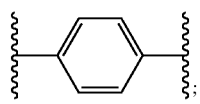 [SMILES: *c1ccc(*)cc1]

$L^1$ is

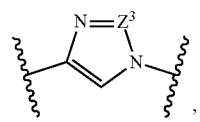

wherein $Z^3$ is N;
G is

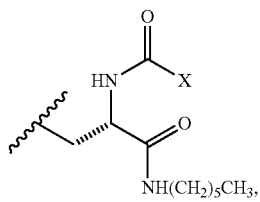

wherein X is —NH(CH$_2$)$_m$ CH$_3$; and
m is 5-10.

11. The method of claim 1 or 7, wherein:
R is

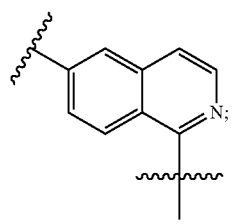 [SMILES: *c1ccc2c(*)nccc2c1]

$L^1$ is a bond;
G is

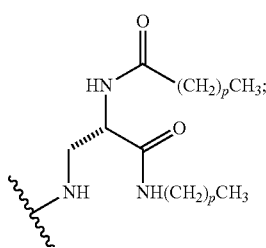

and
each p is independently 5-8.

12. The method of claim 1 or 7, wherein the cancer is a solid cancer, bladder cancer, breast cancer, cervical cancer, colon or rectal cancer, endometrial cancer, kidney cancer, lip cancer, liver cancer, melanoma, mesothelioma, non-small cell lung cancer, non-melanoma skin cancer, oral cancer, ovarian cancer, pancreatic cancer, prostate cancer, sarcoma, small cell lung cancer or thyroid cancer.

13. The method of claim 1 or 7, wherein the compound or pharmaceutically acceptable salt is co-administered with one or more oncolytic agents.

14. The method of claim 13, wherein the one or more oncolytic agents are selected from checkpoint inhibitors, immuno-oncology (TO) agents, protein kinase inhibitors, PARP inhibitors, nuclear receptor antagonists, degraders, and cytotoxic agents.

15. The method of claim 1 or 7, wherein the compound or pharmaceutically acceptable salt is co-administered with one or more hormone therapies, epigenetic therapies, or cellular therapies.

16. The method of claim 7, wherein the compound of Formula (I) has the following formula, or a salt thereof:

(V)

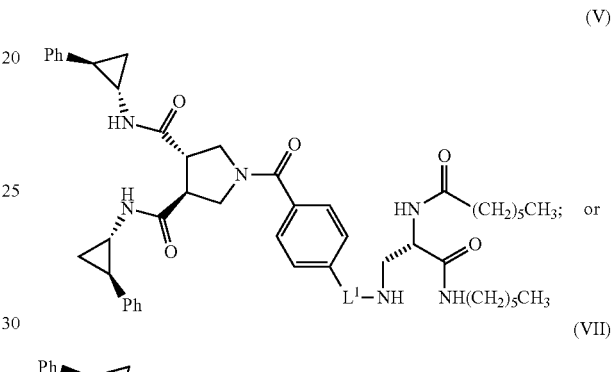

(VII)

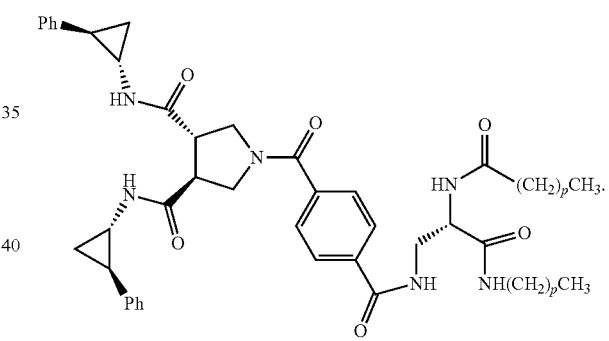

17. The method of claim 16, wherein the compound of Formula (I) has the structure of:
(a) Formula (V), wherein $L^1$ is —CO—, —SO$_2$—, (—CH$_2$—)$_m$ or —(CF$_2$)—; or
(b) Formula (VII), wherein p is 5, 6, 7, or 8.

18. The method of claim 7, wherein the compound of Formula (I) is selected from:

026

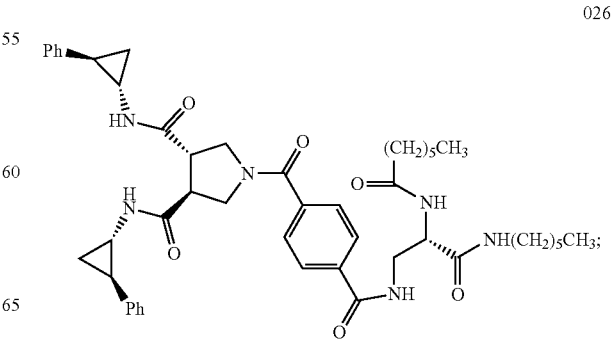

893
-continued
140
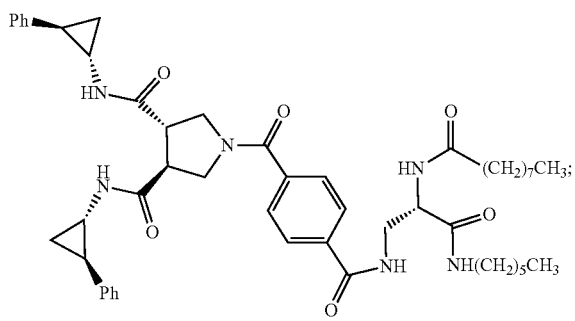
141
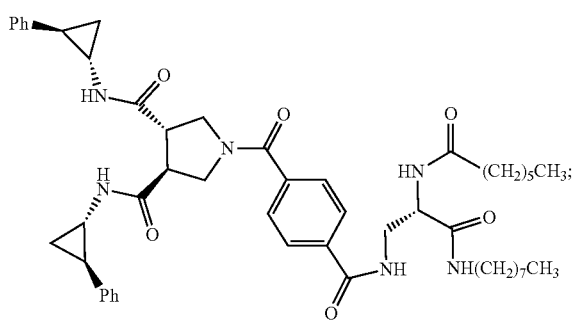
173
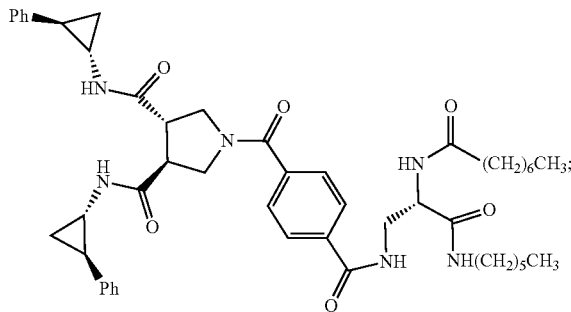
175
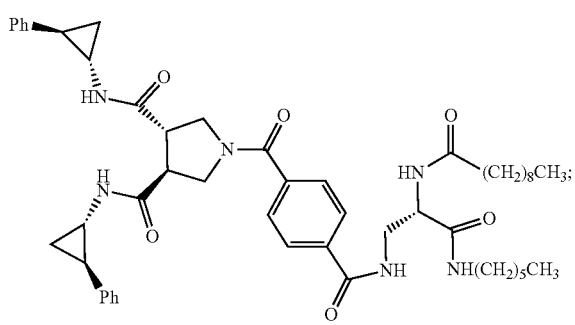
894
-continued
184
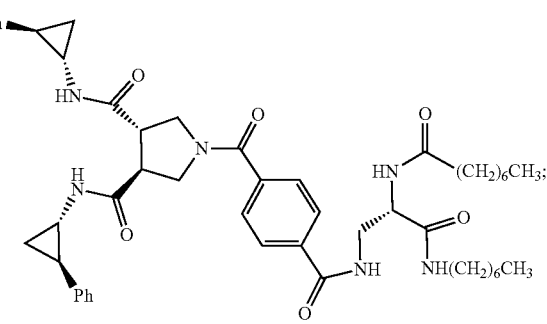
197
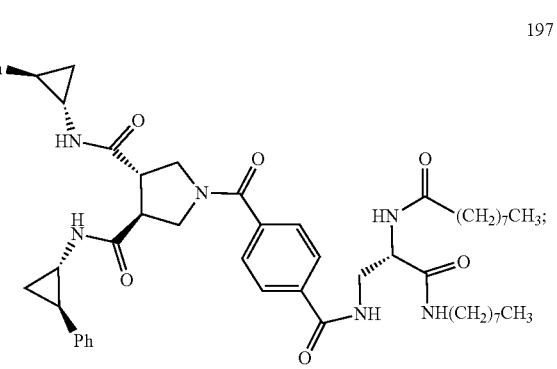
207
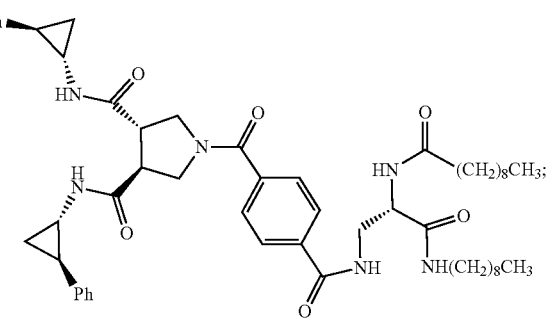
or a pharmaceutically acceptable salt thereof.
* * * * *

UNITED STATES PATENT AND TRADEMARK OFFICE
CERTIFICATE OF CORRECTION

PATENT NO. : 11,951,094 B2
APPLICATION NO. : 17/840952
DATED : April 9, 2024
INVENTOR(S) : Christopher J. Oalmann et al.

It is certified that error appears in the above-identified patent and that said Letters Patent is hereby corrected as shown below:

In the Claims

In Claim 6, at Column 888, Lines 15-16, the text: "-NH(C=O)CH$_3$ NH(C=O)(CH$_2$)$_m$CH$_3$," should be replaced with: -- -NH(C=O)CH$_3$, -NH(C=O)(CH$_2$)$_m$CH$_3$,--.

Signed and Sealed this
Twenty-eighth Day of May, 2024

*Katherine Kelly Vidal*
Katherine Kelly Vidal
*Director of the United States Patent and Trademark Office*